US008303944B2

(12) United States Patent
Bachand et al.

(10) Patent No.: US 8,303,944 B2
(45) Date of Patent: *Nov. 6, 2012

(54) HEPATITIS C VIRUS INHIBITORS

(75) Inventors: Carol Bachand, Candiac (CA); Makonen Belema, North Haven, CT (US); Daniel H. Deon, Brossard (CA); Andrew C. Good, Wallingford, CT (US); Jason Goodrich, Meriden, CT (US); Clint A. James, Longueuil (CA); Rico Lavoie, Candiac (CA); Omar D. Lopez, Wallingford, CT (US); Alain Martel, Delson (CA); Nicholas A. Meanwell, East Hampton, CT (US); Van N. Nguyen, Meriden, CT (US); Jeffrey Lee Romine, Meriden, CT (US); Edward H. Ruediger, Greenfield Park (CA); Lawrence B. Snyder, Killingworth, CT (US); Denis R. St. Laurent, Newington, CT (US); Fukang Yang, Madison, CT (US); David R. Langley, Meriden, CT (US); Gan Wang, Wallingford, CT (US); Lawrence G. Hamann, North Grafton, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 896 days.

This patent is subject to a terminal disclaimer.

(21) Appl. No.: 12/030,232

(22) Filed: Feb. 13, 2008

(65) Prior Publication Data

US 2009/0068140 A1    Mar. 12, 2009

Related U.S. Application Data

(63) Continuation-in-part of application No. 11/835,462, filed on Aug. 8, 2007.

(60) Provisional application No. 60/836,996, filed on Aug. 11, 2006.

(51) Int. Cl.
| | |
|---|---|
| *C07D 403/14* | (2006.01) |
| *A61K 31/4178* | (2006.01) |
| *A61K 31/506* | (2006.01) |
| *A61K 31/16* | (2006.01) |
| *A61K 31/7088* | (2006.01) |
| *A61K 38/20* | (2006.01) |
| *A61K 38/21* | (2006.01) |
| *A61K 38/43* | (2006.01) |
| *A61K 38/48* | (2006.01) |
| *A61P 31/12* | (2006.01) |

(52) U.S. Cl. ............... 424/85.2; 424/85.4; 424/85.7; 424/94.1; 424/94.63; 514/1.1; 514/269; 514/272; 514/397; 544/296; 548/313.1

(58) Field of Classification Search ............... None
See application file for complete search history.

(56) References Cited

U.S. PATENT DOCUMENTS

| | | | |
|---|---|---|---|
| 5,654,451 A | 8/1997 | Kari | |
| 7,659,270 B2 * | 2/2010 | Bachand et al. | ........... 514/235.8 |
| 2004/0142985 A1 | 7/2004 | Singh et al. | |
| 2005/0119318 A1 | 6/2005 | Hudyma et al. | |

FOREIGN PATENT DOCUMENTS

| | | |
|---|---|---|
| WO | WO 94/15909 | 7/1994 |
| WO | WO 2004/002940 A1 | 1/2004 |
| WO | WO2004/005264 | 1/2004 |
| WO | WO 2005/047288 A1 | 5/2005 |
| WO | WO 2005/105761 A1 | 11/2005 |
| WO | WO 2006/022442 A1 | 3/2006 |
| WO | WO 2006/093867 A1 | 9/2006 |
| WO | WO2006/133326 | 12/2006 |
| WO | WO 2007/031791 A1 | 3/2007 |
| WO | WO 2007/058384 A1 | 5/2007 |
| WO | WO 2007/077186 A1 | 7/2007 |
| WO | WO 2007/080401 A1 | 7/2007 |
| WO | WO 2007/081517 A2 | 7/2007 |
| WO | WO 2007/082554 A1 | 7/2007 |
| WO | WO2008021936 | * 8/2007 |
| WO | WO2007/138242 | 12/2007 |
| WO | WO2008/021927 | 2/2008 |
| WO | WO2008/021936 | 2/2008 |
| WO | WO2008021928 | 2/2008 |

OTHER PUBLICATIONS

Franciscus, 2012, HCV Advocate, www.hcvadvocate.org, Hepatitis C Treatments in Current Clinical Development.*
U.S. Appl. No. 12/120,494, filed May 14, 2008, Bachand, et al.
U.S. Appl. No. 12/029,680, filed Feb. 12, 2008, Bachand et al.

* cited by examiner

*Primary Examiner* — Sun Jae Loewe
(74) *Attorney, Agent, or Firm* — Pamela A. Mingo

(57) ABSTRACT

The present disclosure relates to compounds, compositions and methods for the treatment of hepatitis C virus (HCV) infection. Also disclosed are pharmaceutical compositions containing such compounds and methods for using these compounds in the treatment of HCV infection.

13 Claims, No Drawings

HEPATITIS C VIRUS INHIBITORS

CROSS REFERENCE TO RELATED APPLICATIONS

This application is a continuation-in-part of U.S. non-provisional application Ser. No. 11/835,462, filed Aug. 8, 2007, and claims the benefit of U.S. provisional application No. 60/836,996, filed Aug. 11, 2006.

The present disclosure is generally directed to antiviral compounds, and more specifically directed to compounds which can inhibit the function of the NS5A protein encoded by Hepatitis C virus (HCV), compositions comprising such compounds, and methods for inhibiting the function of the NS5A protein.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

Presently, the most effective HCV therapy employs a combination of alpha-interferon and ribavirin, leading to sustained efficacy in 40% of patients. Recent clinical results demonstrate that pegylated alpha-interferon is superior to unmodified alpha-interferon as monotherapy. However, even with experimental therapeutic regimens involving combinations of pegylated alpha-interferon and ribavirin, a substantial fraction of patients do not have a sustained reduction in viral load. Thus, there is a clear and long-felt need to develop effective therapeutics for treatment of HCV infection.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to herein as HCV polymerase) is a RNA-dependent RNA polymerase that is involved in the replication of HCV.

Compounds useful for treating HCV-infected patients are desired which selectively inhibit HCV viral replication. In particular, compounds which are effective to inhibit the function of the NS5A protein are desired. The HCV NS5A protein is described, for example, in Tan, S.-L., Katzel, M. G. *Virology* 2001, 284, 1-12; and in Park, K.-J.; Choi, S.-H, *J. Biological Chemistry* 2003.

In a first aspect the present disclosure provides a compound of Formula (I)

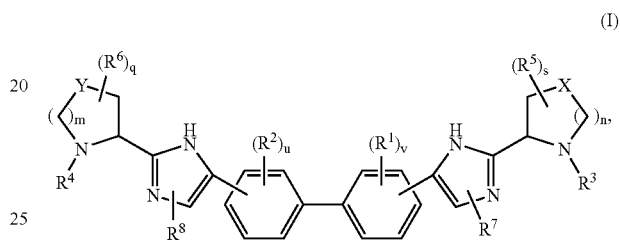

(I)

or a pharmaceutically acceptable salt thereof, wherein
m and n are independently 0, 1, or 2;
q and s are independently 0, 1, 2, 3, or 4;
u and v are independently 0, 1, 2, or 3;
X is selected from O, S, S(O), $SO_2$, $CH_2$, $CHR^5$, and $C(R^5)_2$;
provided that when n is 0, X is selected from $CH_2$, $CHR^5$, and $C(R^5)_2$;
Y is selected from O, S, S(O), $SO_2$, $CH_2$, $CHR^6$, and $C(R^6)_2$;
provided that when m is 0, Y is selected from $CH_2$, $CHR^6$, and $C(R^6)_2$;
each $R^1$ and $R^2$ is independently selected from alkoxy, alkoxyalkyl, alkoxycarbonyl, alkyl, arylalkoxycarbonyl, carboxy, formyl, halo, haloalkyl, hydroxy, hydroxyalkyl, —$NR^aR^b$, $(R^aR^b)$alkyl, and $(NR^aR^b)$carbonyl;
$R^3$ and $R^4$ are each independently selected from hydrogen, $R^9$—C(O)—, and $R^9$—C(S)—;
each $R^5$ and $R^6$ is independently selected from alkoxy, alkyl, aryl, halo, haloalkyl, hydroxy, and —$NR^aR^b$, wherein the alkyl can optionally form a fused three- to six-membered ring with an adjacent carbon atom, wherein the three- to six-membered ring is optionally substituted with one or two alkyl groups;
$R^7$ and $R^8$ are each independently selected from hydrogen, alkoxycarbonyl, alkyl, arylalkoxycarbonyl, carboxy, haloalkyl, $(NR^aR^b)$carbonyl, and trialkylsilylalkoxyalkyl; and
each $R^9$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —$NR^cR^d$, $R^cR^d$)alkenyl, $(R^cR^d)$alkyl, and $(NR^cR^d)$carbonyl.

In a first embodiment of the first aspect the present disclosure provides a compound of formula (I), or a pharmaceutically acceptable salt thereof, wherein m and n are each 1.

In a second embodiment of the first aspect the present disclosure provides a compound of formula (I), or a pharmaceutically acceptable salt thereof, wherein
u and v are each independently 0, 1, or 2; and
each $R^1$ and $R^2$ is independently selected from alkoxy, alkoxyalkyl, alkyl, arylalkoxycarbonyl, carboxy, formyl, halo, haloalkyl, hydroxyalkyl, $(NR^aR^b)$alkyl, and $(NR^aR^b)$carbonyl.

In a third embodiment of the first aspect the present disclosure provides a compound of formula (I), or a pharmaceutically acceptable salt thereof, wherein
u and v are each independently 0 or 1; and
when present, $R^1$ and/or $R^2$ are halo.

In a fourth embodiment of the first aspect the present disclosure provides a compound of formula (I), or a pharmaceutically acceptable salt thereof, wherein
u and v are each independently 0 or 1; and
when present, $R^1$ and/or $R^2$ are halo, wherein the halo is fluoro.

In a fifth embodiment of the first aspect the present disclosure provides a compound of formula (I), or a pharmaceutically acceptable salt thereof, wherein at least one of X and Y is S.

In a sixth embodiment of the first aspect the present disclosure provides a compound of formula (I), or a pharmaceutically acceptable salt thereof, wherein X and Y are each S.

In a seventh embodiment of the first aspect the present disclosure provides a compound of formula (I), or a pharmaceutically acceptable salt thereof, wherein X is selected from $CHR^5$, and $C(R^5)_2$; and Y is selected from $CH_2$, $CHR^6$, and $C(R^6)_2$.

In an eighth embodiment of the first aspect the present disclosure provides a compound of formula (I), or a pharmaceutically acceptable salt thereof, wherein $R^7$ and $R^8$ are independently selected from hydrogen, alkoxycarbonyl, alkyl, arylalkoxycarbonyl, carboxy, haloalkyl, and $(NR^aR^b)$carbonyl.

In a ninth embodiment of the first aspect the present disclosure provides a compound of formula (I), or a pharmaceutically acceptable salt thereof, wherein $R^7$ and $R^8$ are each hydrogen.

In a tenth embodiment of the first aspect the present disclosure provides a compound of formula (I), or a pharmaceutically acceptable salt thereof, wherein
q and s are independently 0, 1, or 2; and
each $R^5$ and $R^6$ is independently selected from alkyl, aryl, halo, and hydroxy, wherein the alkyl can optionally form a fused three- to six-membered ring with an adjacent carbon atom, wherein the three- to six-membered ring is optionally substituted with one or two alkyl groups.

In an eleventh embodiment of the first aspect the present disclosure provides a compound of formula (I), or a pharmaceutically acceptable salt thereof, wherein
q and s are independently 0 or 1; and
when present, $R^5$ and/or $R^6$ are each halo.

In a twelfth embodiment of the first aspect the present disclosure provides a compound of formula (I), or a pharmaceutically acceptable salt thereof, wherein
q and s are independently 0 or 1; and
when present, $R^5$ and/or $R^6$ are each halo, wherein the halo is fluoro.

In a thirteenth embodiment of the first aspect the present disclosure provides a compound of formula (I), or a pharmaceutically acceptable salt thereof, wherein at least one of $R^3$ and $R^4$ is hydrogen.

In a fourteenth embodiment of the first aspect the present disclosure provides a compound of formula (I), or a pharmaceutically acceptable salt thereof, wherein $R^3$ and $R^4$ are each $R^9$—C(O)—.

In a fifteenth embodiment of the first aspect the present disclosure provides a compound of formula (I), or a pharmaceutically acceptable salt thereof, wherein each $R^9$ is independently selected from alkoxy, alkoxyalkyl, alkyl, alkylcarbonylalkyl, aryl, arylalkenyl, arylalkoxy, arylalkyl, aryloxyalkyl, cycloalkyl, (cycloalkyl)alkyl, cycloalkyloxyalkyl, heterocyclyl, heterocyclylalkyl, hydroxyalkyl, —$NR^cR^d$, $(NR^cR^d)$alkenyl, $(NR^cR^d)$alkyl, and $(NR^cR^d)$carbonyl.

In a second aspect the present disclosure provides a compound of Formula (II)

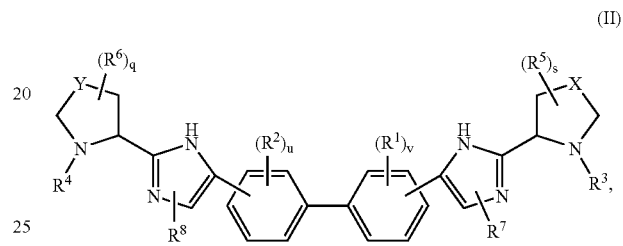

(II)

or a pharmaceutically acceptable salt thereof, wherein
q and s are independently 0, 1, or 2;
u and v are independently 0, 1, or 2;
X is selected from S, $CH_2$, $CHR^5$, and $C(R^5)_2$;
Y is selected from S, $CH_2$, $CHR^6$, and $C(R^6)_2$;
each $R^1$ and $R^2$ is independently selected from alkoxy, alkoxyalkyl, alkyl, arylalkoxycarbonyl, carboxy, formyl, halo, haloalkyl, hydroxyalkyl, $(NR^aR^b)$alkyl, and $(NR^aR^b)$carbonyl;
$R^3$ and $R^4$ are each independently selected from hydrogen and $R^9$—C(O)—;
each $R^5$ and $R^6$ is independently selected from alkyl, aryl, halo, and hydroxy, wherein the alkyl can optionally form a fused three- to six-membered ring with an adjacent carbon atom, wherein the three- to six-membered ring is optionally substituted with one or two alkyl groups;
$R^7$ and $R^8$ are each independently selected from hydrogen, alkoxycarbonyl, alkyl, arylalkoxycarbonyl, carboxy, haloalkyl, and $(NR^aR^b)$carbonyl; and
each $R^9$ is independently selected from alkoxy, alkoxyalkyl, alkyl, alkylcarbonylalkyl, aryl, arylalkenyl, arylalkoxy, arylalkyl, aryloxyalkyl, cycloalkyl, (cycloalkyl)alkyl, cycloalkyloxyalkyl, heterocyclyl, heterocyclylalkyl, hydroxyalkyl, —$NR^cR^d$, $(NR^cR^d)$alkenyl, $(NR^cR^d)$alkyl, and $(NR^cR^d)$carbonyl.

In a third aspect the present disclosure provides a compound of Formula (III)

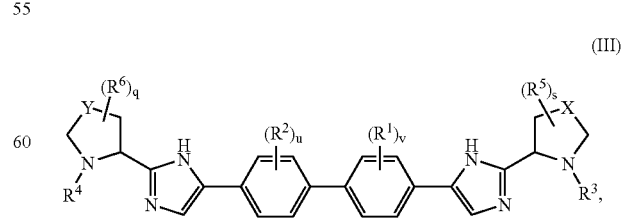

(III)

or a pharmaceutically acceptable salt thereof, wherein
q and s are independently 0, 1, or 2;
u and v are independently 0 or 1;

X is selected from CH$_2$, CHR$^5$, and C(R$^5$)$_2$;
Y is selected from CH$_2$, CHR$^6$, and C(R$^6$)$_2$;
when present, R$^1$ and/or R$^2$ are halo, wherein the halo is fluoro;
R$^3$ and R$^4$ are each R$^9$—C(O)—;
when present, R$^5$ and/or R$^6$ are halo, wherein the halo is fluoro; and
each R$^9$ is independently selected from alkoxy, alkoxyalkyl, alkoxycarbonyl, alkoxycarbonylalkyl, alkyl, alkylcarbonylalkyl, aryl, arylalkenyl, arylalkoxy, arylalkyl, aryloxyalkyl, cycloalkyl, (cycloalkyl)alkenyl, (cycloalkyl)alkyl, cycloalkyloxyalkyl, haloalkyl, heterocyclyl, heterocyclylalkenyl, heterocyclylalkoxy, heterocyclylalkyl, heterocyclyloxyalkyl, hydroxyalkyl, —NR$^c$R$^d$, (NR$^c$R$^d$)alkenyl, (NR$^c$R$^d$)alkyl, and (NR$^c$R$^d$)carbonyl.

In a fourth aspect the present disclosure provides a compound selected from
methyl((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate;
(1R,1'R)-2,2'-(4,4'-biphenyldiylbis(1H-imidazole-5,2-diyl (2S)-2,1-pyrrolidinediyl))bis(N,N-dimethyl-2-oxo-1-phenylethanamine);
methyl((1S)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-1-methyl-2-oxoethyl)carbamate;
methyl((1S)-1-(((2S)-2-(4-(4'-(2-((2S)-4,4-difluoro-1-((2S)-2-((methoxycarbonyl)amino)-3-methylbutanoyl)-2-pyrrolidinyl)-1H-imidazol-4-yl)-4-biphenylyl)-1H-imidazol-2-yl)-4,4-difluoro-1-pyrrolidinyl)carbonyl)-2-methylpropyl)carbamate;
methyl((1S)-1-(((1R,3R,5R)-3-(5-(4'-(2-((1R,3R,5R)-2-((2S)-2-((methoxycarbonyl)amino)-3-methylbutanoyl)-2-azabicyclo[3.1.0]hex-3-yl)-1H-imidazol-5-yl)-4-biphenylyl)-1H-imidazol-2-yl)-2-azabicyclo[3.1.0]hex-2-yl)carbonyl)-2-methylpropyl)carbamate;
methyl((1R)-2-oxo-1-phenyl-2-((2S)-2-(5-(4'-(2-((2S)-1-((2R)-tetrahydro-2-furanylcarbonyl)-2-pyrrolidinyl)-1H-imidazol-5-yl)-4-biphenylyl)-1H-imidazol-2-yl)-1-pyrrolidinyl)ethyl)carbamate;
methyl((1S)-2-methyl-1-(((2S)-2-(5-(4'-(2-((2S)-1-(N-2-pyrimidinyl-D-valyl)-2-pyrrolidinyl)-1H-imidazol-5-yl)-4-biphenylyl)-1H-imidazol-2-yl)-1-pyrrolidinyl)carbonyl)propyl)carbamate;
methyl((1R)-2-((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)-2-oxo-1-phenylethyl)carbamate;
dimethyl (4,4'-biphenyldiylbis(1H-imidazole-5,2-diyl(2S)-2,1-pyrrolidinediyl((1R)-2-oxo-1-phenyl-2,1-ethanediyl)))biscarbamate;
(1R)—N,N-dimethyl-2-oxo-1-phenyl-2-((2S)-2-(5-(4'-(2-((2S)-1-((2R)-tetrahydro-2-furanylcarbonyl)-2-pyrrolidinyl)-1H-imidazol-5-yl)-4-biphenylyl)-1H-imidazol-2-yl)-1-pyrrolidinyl)ethanamine;
methyl((1S)-2-((2S)-2-(5-(4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-1-methyl-2-oxoethyl)carbamate; and
methyl((1S)-1-(((2S)-2-(5-(4'-(2-((2S)-1-((2S)-2-((methoxycarbonyl)amino)-3,3-dimethylbutanoyl)-2-pyrrolidinyl)-1H-imidazol-5-yl)-4-biphenylyl)-1H-imidazol-2-yl)-1-pyrrolidinyl)carbonyl)-2,2-dimethylpropyl)carbamate;
or a pharmaceutically acceptable salt thereof.

In a first embodiment of the fifth aspect the pharmaceutically acceptable salt is a dihydrochloride salt.

In a sixth aspect the present disclosure provides a composition comprising a compound of formula (I), or a pharmaceutically acceptable salt thereof, and a pharmaceutically acceptable carrier.

In a first embodiment of the sixth aspect the composition further comprises one or two additional compounds having anti-HCV activity. In a second embodiment at least one of the additional compounds is an interferon or a ribavirin. In a third embodiment the interferon is selected from interferon alpha 2B, pegylated interferon alpha, consensus interferon, interferon alpha 2A, and lymphoblastoid interferon tau.

In a fourth embodiment of the sixth aspect the composition further comprises one or two additional compounds having anti-HCV activity wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment of the sixth aspect the composition further comprises one or two additional compounds having anti-HCV activity wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

In an seventh aspect the present disclosure provides a method of treating an HCV infection in a patient, comprising administering to the patient a therapeutically effective amount of a compound of formula (J), or a pharmaceutically acceptable salt thereof.

In a first embodiment of the seventh aspect the method further comprises administering one or two additional compounds having anti-HCV activity prior to, after or simultaneously with the compound of formula (I), or a pharmaceutically acceptable salt thereof. In a second embodiment at least one of the additional compounds is an interferon or a ribavirin. In a third embodiment the interferon is selected from interferon alpha 2B, pegylated interferon alpha, consensus interferon, interferon alpha 2A, and lymphoblastoid interferon tau.

In a fourth embodiment the method further comprises administering one or two additional compounds having anti-HCV activity prior to, after or simultaneously with the compound of formula (I), or a pharmaceutically acceptable salt thereof, wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

In a fifth embodiment the method further comprises administering one or two additional compounds having anti-HCV activity prior to, after or simultaneously with the compound of formula (I), or a pharmaceutically acceptable salt thereof, wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

Other embodiments of the present disclosure may comprise suitable combinations of two or more of embodiments and/or aspects disclosed herein.

Yet other embodiments and aspects of the disclosure will be apparent according to the description provided below.

The compounds of the present disclosure also exist as tautomers; therefore the present disclosure also encompasses all tautomeric forms.

The description of the present disclosure herein should be construed in congruity with the laws and principals of chemical bonding. In some instances it may be necessary to remove a hydrogen atom in order accommodate a substituent at any given location. For example, in the structure shown below

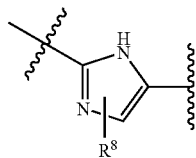

$R^8$ may be attached to either the carbon atom in the imidazole ring or, alternatively, $R^8$ may take the place of the hydrogen atom on the nitrogen ring to form an N-substituted imidazole.

It should be understood that the compounds encompassed by the present disclosure are those that are suitably stable for use as pharmaceutical agent.

It is intended that the definition of any substituent or variable (e.g., $R^1$, $R^2$, $R^5$, $R^6$, etc.) at a particular location in a molecule be independent of its definitions elsewhere in that molecule. For example, when u is 2, each of the two $R^1$ groups may be the same or different.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

Unless stated otherwise, all aryl, cycloalkyl, and heterocyclyl groups of the present disclosure may be substituted as described in each of their respective definitions. For example, the aryl part of an arylalkyl group may be substituted as described in the definition of the term 'aryl'.

The term "alkenyl," as used herein, refers to a straight or branched chain group of two to six carbon atoms containing at least one carbon-carbon double bond.

The term "alkenyloxy," as used herein, refers to an alkenyl group attached to the parent molecular moiety through an oxygen atom.

The term "alkenyloxycarbonyl," as used herein, refers to an alkenyloxy group attached to the parent molecular moiety through a carbonyl group.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylcarbonyl," as used herein, refers to an alkoxyalkyl group attached to the parent molecular moiety through a carbonyl group.

The term "alkoxycarbonyl," as used herein, refers to an alkoxy group attached to the parent molecular moiety through a carbonyl group.

The term "alkoxycarbonylalkyl," as used herein, refers to an alkyl group substituted with one, two, or three alkoxycarbonyl groups.

The term "alkyl," as used herein, refers to a group derived from a straight or branched chain saturated hydrocarbon containing from one to six carbon atoms. In the compounds of the present disclosure, when m and/or n is 1 or 2; X and/or Y is $CHR^5$ and/or $CHR^6$, respectively, and $R^5$ and/or $R^6$ is alkyl, each alkyl can optionally form a fused three- to six-membered ring with an adjacent carbon atom to provide one of the structures shown below:

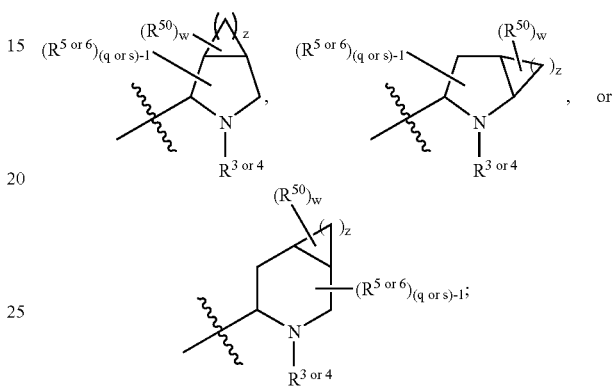

where z is 1, 2, 3, or 4, w is 0, 1, or 2, and $R^{50}$ is alkyl. When w is 2, the two $R^{50}$ alkyl groups may be the same or different.

The term "alkylcarbonyl," as used herein, refers to an alkyl group attached to the parent molecular moiety through a carbonyl group.

The term "alkylcarbonylalkyl," as used herein, refers to an alkyl group substituted with one, two, or three alkylcarbonyl groups.

The term "alkylcarbonyloxy," as used herein, refers to an alkylcarbonyl group attached to the parent molecular moiety through an oxygen atom.

The term "alkylsulfanyl," as used herein, refers to an alkyl group attached to the parent molecular moiety through a sulfur atom.

The term "alkylsulfonyl," as used herein, refers to an alkyl group attached to the parent molecular moiety through a sulfonyl group.

The term "aryl," as used herein, refers to a phenyl group, or a bicyclic fused ring system wherein one or both of the rings is a phenyl group. Bicyclic fused ring systems consist of a phenyl group fused to a four- to six-membered aromatic or non-aromatic carbocyclic ring. The aryl groups of the present disclosure can be attached to the parent molecular moiety through any substitutable carbon atom in the group. Representative examples of aryl groups include, but are not limited to, indanyl, indenyl, naphthyl, phenyl, and tetrahydronaphthyl. The aryl groups of the present disclosure are optionally substituted with one, two, three, four, or five substituents independently selected from alkoxy, alkoxyalkyl, alkoxycarbonyl, alkyl, alkylcarbonyl, a second aryl group, arylalkoxy, arylalkyl, arylcarbonyl, cyano, halo, haloalkoxy, haloalkyl, heterocyclyl, heterocyclylalkyl, heterocyclylcarbonyl, hydroxy, hydroxyalkyl, nitro, —$NR^xR^y$, ($NR^xR^y$) alkyl, oxo, and —$P(O)OR_2$, wherein each R is independently selected from hydrogen and alkyl; and wherein the alkyl part of the arylalkyl and the heterocyclylalkyl are unsubstituted and wherein the second aryl group, the aryl part of the arylalkyl, the aryl part of the arylcarbonyl, the heterocyclyl, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "arylalkenyl," as used herein, refers to an alkenyl group substituted with one, two, or three aryl groups.

The term "arylalkoxy," as used herein, refers to an aryl group attached to the parent molecular moiety through an alkoxy group.

The term "arylalkoxyalkyl," as used herein, refers to an alkyl group substituted with one, two, or three arylalkoxy groups.

The term "arylalkoxyalkylcarbonyl," as used herein, refers to an arylalkoxyalkyl group attached to the parent molecular moiety through a carbonyl group.

The term "arylalkoxycarbonyl," as used herein, refers to an arylalkoxy group attached to the parent molecular moiety through a carbonyl group.

The term "arylalkyl," as used herein, refers to an alkyl group substituted with one, two, or three aryl groups. The alkyl part of the arylalkyl is further optionally substituted with one or two additional groups independently selected from alkoxy, alkylcarbonyloxy, halo, haloalkoxy, haloalkyl, heterocyclyl, hydroxy, and —NR$^c$R$^d$, wherein the heterocyclyl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —NR$^x$R$^y$.

The term "arylalkylcarbonyl," as used herein, refers to an arylalkyl group attached to the parent molecular moiety through a carbonyl group.

The term "arylcarbonyl," as used herein, refers to an aryl group attached to the parent molecular moiety through a carbonyl group.

The term "aryloxy," as used herein, refers to an aryl group attached to the parent molecular moiety through an oxygen atom.

The term "aryloxyalkyl," as used herein, refers to an alkyl group substituted with one, two, or three aryloxy groups.

The term "aryloxycarbonyl," as used herein, refers to an aryloxy group attached to the parent molecular moiety through a carbonyl group.

The term "arylsulfonyl," as used herein, refers to an aryl group attached to the parent molecular moiety through a sulfonyl group.

The terms "Cap" and "cap" as used herein, refer to the group which is placed on the nitrogen atom of the terminal nitrogen-containing ring, i.e., the pyrrolidine rings of compound 1e. It should be understood that "Cap" or "cap" can refer to the reagent used to append the group to the terminal nitrogen-containing ring or to the fragment in the final product, i.e., "Cap-51" or "The Cap-51 fragment found in LS-19".

The term "carbonyl," as used herein, refers to —C(O)—.

The term "carboxy," as used herein, refers to —CO$_2$H.

The term "cyano," as used herein, refers to —CN.

The term "cycloalkyl," as used herein, refers to a saturated monocyclic, hydrocarbon ring system having three to seven carbon atoms and zero heteroatoms. Representative examples of cycloalkyl groups include, but are not limited to, cyclopropyl, cyclopentyl, and cyclohexyl. The cycloalkyl groups of the present disclosure are optionally substituted with one, two, three, four, or five substituents independently selected from alkoxy, alkyl, aryl, cyano, halo, haloalkoxy, haloalkyl, heterocyclyl, hydroxy, hydroxyalkyl, nitro, and —NR$^x$R$^y$, wherein the aryl and the heterocyclyl are further optionally substituted with one, two, or three substituents independently selected from alkoxy, alkyl, cyano, halo, haloalkoxy, haloalkyl, hydroxy, and nitro.

The term "(cycloalkyl)alkenyl," as used herein, refers to an alkenyl group substituted with one, two, or three cycloalkyl groups.

The term "(cycloalkyl)alkyl," as used herein, refers to an alkyl group substituted with one, two, or three cycloalkyl groups. The alkyl part of the (cycloalkyl)alkyl is further optionally substituted with one or two groups independently selected from hydroxy and —NR$^c$R$^d$.

The term "cycloalkyloxy," as used herein, refers to a cycloalkyl group attached to the parent molecular moiety through an oxygen atom.

The term "cycloalkyloxyalkyl," as used herein, refers to an alkyl group substituted with one, two, or three cycloalkyloxy groups.

The term "cycloalkylsulfonyl," as used herein, refers to a cycloalkyl group attached to the parent molecular moiety through a sulfonyl group.

The term "formyl," as used herein, refers to —CHO.

The terms "halo" and "halogen," as used herein, refer to F, Cl, Br, or I.

The term "haloalkoxy," as used herein, refers to a haloalkyl group attached to the parent molecular moiety through an oxygen atom.

The term "haloalkoxycarbonyl," as used herein, refers to a haloalkoxy group attached to the parent molecular moiety through a carbonyl group.

The term "haloalkyl," as used herein, refers to an alkyl group substituted by one, two, three, or four halogen atoms.

The term "heterocyclyl," as used herein, refers to a four-, five-, six-, or seven-membered ring containing one, two, three, or four heteroatoms independently selected from nitrogen, oxygen, and sulfur. The four-membered ring has zero double bonds, the five-membered ring has zero to two double bonds, and the six- and seven-membered rings have zero to three double bonds. The term "heterocyclyl" also includes bicyclic groups in which the heterocyclyl ring is fused to another monocyclic heterocyclyl group, or a four- to six-membered aromatic or non-aromatic carbocyclic ring; as well as bridged bicyclic groups such as 7-azabicyclo[2.2.1]hept-7-yl, 2-azabicyclo[2.2.2]oc-2-tyl, and 2-azabicyclo[2.2.2]oc-3-tyl. The heterocyclyl groups of the present disclosure can be attached to the parent molecular moiety through any carbon atom or nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, thiomorpholinyl, 7-azabicyclo[2.2.1]hept-7-yl, 2-azabicyclo[2.2.2]oc-2-tyl, and 2-azabicyclo[2.2.2]oc-3-tyl. The heterocyclyl groups of the present disclosure are optionally substituted with one, two, three, four, or five substituents independently selected from alkoxy, alkoxyalkyl, alkoxycarbonyl, alkyl, alkylcarbonyl, aryl, arylalkyl, arylcarbonyl, cyano, halo, haloalkoxy, haloalkyl, a second heterocyclyl group, heterocyclylalkyl, heterocyclylcarbonyl, hydroxy, hydroxyalkyl, nitro, —NR$^x$R$^y$, (NR$^x$R$^y$)alkyl, and oxo, wherein the alkyl part of the arylalkyl and the heterocyclylalkyl are unsubstituted and wherein the aryl, the aryl part of the arylalkyl, the aryl part of the arylcarbonyl, the second heterocyclyl group, and the heterocyclyl part of the heterocyclylalkyl and the heterocyclylcarbonyl are further optionally substituted with one, two, or three substituents independently selected from alkoxy, alkyl, cyano, halo, haloalkoxy, haloalkyl, and nitro.

The term "heterocyclylalkenyl," as used herein, refers to an alkenyl group substituted with one, two, or three heterocyclyl groups.

The term "heterocyclylalkoxy," as used herein, refers to a heterocyclyl group attached to the parent molecular moiety through an alkoxy group.

The term "heterocyclylalkoxycarbonyl," as used herein, refers to a heterocyclylalkoxy group attached to the parent molecular moiety through a carbonyl group.

The term "heterocyclylalkyl," as used herein, refers to an alkyl group substituted with one, two, or three heterocyclyl groups. The alkyl part of the heterocyclylalkyl is further optionally substituted with one or two additional groups independently selected from alkoxy, alkylcarbonyloxy, aryl, halo, haloalkoxy, haloalkyl, hydroxy, and —$NR^cR^d$, wherein the aryl is further optionally substituted with one or two substituents independently selected from alkoxy, alkyl, unsubstituted aryl, unsubstituted arylalkoxy, unsubstituted arylalkoxycarbonyl, halo, haloalkoxy, haloalkyl, hydroxy, and —$NR^xR^y$.

The term "heterocyclylalkylcarbonyl," as used herein, refers to a heterocyclylalkyl group attached to the parent molecular moiety through a carbonyl group.

The term "heterocyclylcarbonyl," as used herein, refers to a heterocyclyl group attached to the parent molecular moiety through a carbonyl group.

The term "heterocyclyloxy," as used herein, refers to a heterocyclyl group attached to the parent molecular moiety through an oxygen atom.

The term "heterocyclyloxyalkyl," as used herein, refers to an alkyl group substituted with one, two, or three heterocyclyloxy groups.

The term "heterocyclyloxycarbonyl," as used herein, refers to a heterocyclyloxy group attached to the parent molecular moiety through a carbonyl group.

The term "hydroxy," as used herein, refers to —OH.

The term "hydroxyalkyl," as used herein, refers to an alkyl group substituted with one, two, or three hydroxy groups.

The term "hydroxyalkylcarbonyl," as used herein, refers to a hydroxyalkyl group attached to the parent molecular moiety through a carbonyl group.

The term "nitro," as used herein, refers to —$NO_2$.

The term "—$NR^aR^b$," as used herein, refers to two groups, $R^a$ and $R^b$, which are attached to the parent molecular moiety through a nitrogen atom. $R^a$ and $R^b$ are independently selected from hydrogen, alkenyl, and alkyl.

The term "($NR^aR^b$)alkyl," as used herein, refers to an alkyl group substituted with one, two, or three —$NR^aR^b$ groups.

The term "($NR^aR^b$)carbonyl," as used herein, refers to an —$NR^aR^b$ group attached to the parent molecular moiety through a carbonyl group.

The term "—$NR^cR^d$," as used herein, refers to two groups, $R^c$ and $R^d$, which are attached to the parent molecular moiety through a nitrogen atom. $R^c$ and $R^d$ are independently selected from hydrogen, alkenyloxycarbonyl, alkoxyalkylcarbonyl, alkoxycarbonyl, alkyl, alkylcarbonyl, alkylsulfonyl, aryl, arylalkoxycarbonyl, arylalkyl, arylalkylcarbonyl, arylcarbonyl, aryloxycarbonyl, arylsulfonyl, cycloalkyl, cycloalkylsulfonyl, formyl, haloalkoxycarbonyl, heterocyclyl, heterocyclylalkoxycarbonyl, heterocyclylalkyl, heterocyclylalkylcarbonyl, heterocyclylcarbonyl, heterocyclyloxycarbonyl, hydroxyalkylcarbonyl, ($NR^eR^f$)alkyl, ($NR^eR^f$)alkylcarbonyl, ($NR^eR^f$)carbonyl, ($NR^eR^f$)sulfonyl, —C(NCN)OR', and —C(NCN)$NR^xR^y$, wherein R' is selected from alkyl and unsubstituted phenyl, and wherein the alkyl part of the arylalkyl, the arylalkylcarbonyl, the heterocyclylalkyl, and the heterocyclylalkylcarbonyl are further optionally substituted with one —$NR^eR^f$ group; and wherein the aryl, the aryl part of the arylalkoxycarbonyl, the arylalkyl, the arylalkylcarbonyl, the arylcarbonyl, the aryloxycarbonyl, and the arylsulfonyl, the heterocyclyl, and the heterocyclyl part of the heterocyclylalkoxycarbonyl, the heterocyclylalkyl, the heterocyclylalkylcarbonyl, the heterocyclylcarbonyl, and the heterocyclyloxycarbonyl are further optionally substituted with one, two, or three substituents independently selected from alkoxy, alkyl, cyano, halo, haloalkoxy, haloalkyl, and nitro.

The term "($NR^cR^d$)alkenyl," as used herein, refers to an alkenyl group substituted with one, two, or three —$NR^cR^d$ groups.

The term "($NR^cR^d$)alkyl," as used herein, refers to an alkyl group substituted with one, two, or three —$NR^cR^d$ groups. The alkyl part of the ($NR^cR^d$)alkyl is further optionally substituted with one or two additional groups selected from alkoxy, alkoxyalkylcarbonyl, alkoxycarbonyl, alkylsulfanyl, arylalkoxyalkylcarbonyl, carboxy, heterocyclyl, heterocyclylcarbonyl, hydroxy, and ($NR^eR^f$)carbonyl; wherein the heterocyclyl is further optionally substituted with one, two, three, four, or five substituents independently selected from alkoxy, alkyl, cyano, halo, haloalkoxy, haloalkyl, and nitro.

The term "($NR^cR^d$)carbonyl," as used herein, refers to an —$NR^cR^d$ group attached to the parent molecular moiety through a carbonyl group.

The term "—$NR^eR^f$," as used herein, refers to two groups, $R^e$ and $R^f$ which are attached to the parent molecular moiety through a nitrogen atom. $R^e$ and $R^f$ are independently selected from hydrogen, alkyl, unsubstituted aryl, unsubstituted arylalkyl, unsubstituted cycloalkyl, unsubstituted (cycloalkyl)alkyl, unsubstituted heterocyclyl, unsubstituted heterocyclylalkyl, ($NR^xR^y$)alkyl, and ($NR^xR^y$)carbonyl.

The term "($NR^eR^f$)alkyl," as used herein, refers to an alkyl group substituted with one, two, or three —$NR^eR^f$ groups.

The term "($NR^eR^f$)alkylcarbonyl," as used herein, refers to an ($NR^eR^f$)alkyl group attached to the parent molecular moiety through a carbonyl group.

The term "($NR^eR^f$)carbonyl," as used herein, refers to an —$NR^eR^f$ group attached to the parent molecular moiety through a carbonyl group.

The term "($NR^eR^f$)sulfonyl," as used herein, refers to an —$NR^eR^f$ group attached to the parent molecular moiety through a sulfonyl group.

The term "—$NR^xR^y$," as used herein, refers to two groups, $R^x$ and $R^y$, which are attached to the parent molecular moiety through a nitrogen atom. $R^x$ and $R^y$ are independently selected from hydrogen, alkoxycarbonyl, alkyl, alkylcarbonyl, unsubstituted aryl, unsubstituted arylalkoxycarbonyl, unsubstituted arylalkyl, unsubstituted cycloalkyl, unsubstituted heterocyclyl, and ($NR^{x'}R^{y'}$)carbonyl, wherein $R^{x'}$ and $R^{y'}$ are independently selected from hydrogen and alkyl.

The term "($NR^xR^y$)alkyl," as used herein, refers to an alkyl group substituted with one, two, or three —$NR^xR^y$ groups.

The term "oxo," as used herein, refers to =O.

The term "sulfonyl," as used herein, refers to —$SO_2$—.

The term "trialkylsilyl," as used herein, refers to —$SiR_3$, wherein R is alkyl. The R groups may be the same or different.

The term "trialkylsilylalkyl," as used herein, refers to an alkyl group substituted with one, two, or three trialkylsilyl groups.

The term "trialkylsilylalkoxy," as used herein, refers to a trialkylsilylalkyl group attached to the parent molecular moiety through an oxygen atom.

The term "trialkylsilylalkoxyalkyl," as used herein, refers to an alkyl group substituted with one, two, or three trialkylsilylalkoxy groups.

Asymmetric centers exist in the compounds of the present disclosure. These centers are designated by the symbols "R" or "S", depending on the configuration of substituents around the chiral carbon atom. It should be understood that the disclosure encompasses all stereochemical isomeric forms, or mixtures thereof, which possess the ability to inhibit NS5A. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, or direct separation of enantiomers on chiral chromatographic columns. Starting compounds of particular stereochemistry are either commercially available or can be made and resolved by techniques known in the art.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The term "compounds of the present disclosure", and equivalent expressions, are meant to embrace compounds of Formula (I), and pharmaceutically acceptable enantiomers, diastereomers, and salts thereof. Similarly, references to intermediates are meant to embrace their salts where the context so permits.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, dihydrobromide, dihydrochloride, dihydroiodide, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit, e.g., a reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing a compound of formula (I), or a pharmaceutically acceptable salt thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredient per unit dose. Dosage levels of between about 0.01 and about 250 milligram per kilogram ("mg/kg") body weight per day, preferably between about 0.05 and about 100 mg/kg body weight per day of the compounds of the present disclosure are typical in a monotherapy for the prevention and treatment of HCV mediated disease. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Treatment may be initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

When the compositions of this disclosure comprise a combination of a compound of the present disclosure and one or more additional therapeutic or prophylactic agent, both the compound and the additional agent are usually present at dosage levels of between about 10 to 150%, and more preferably between about 10 and 80% of the dosage normally administered in a monotherapy regimen.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s). Oral administration or administration by injection are preferred.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research* 1986, 3(6), 318.

Pharmaceutical formulations adapted for topical administration may be formulated as ointments, creams, suspensions, lotions, powders, solutions, pastes, gels, sprays, aerosols, or oils.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals.

The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

The compounds of the present disclosure can also be administered with a cyclosporin, for example, cyclosporin A. Cyclosporin A has been shown to be active against HCV in clinical trials (*Hepatology* 2003, 38, 1282; *Biochem. Biophys. Res. Commun.* 2004, 313, 42; *J. Gastroenterol.* 2003, 38, 567).

Table 1 below lists some illustrative examples of compounds that can be administered with the compounds of this disclosure. The compounds of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immunomodulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/ Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |

TABLE 1-continued

| Brand Name | Physiological Class | Type of Inhibitor or Target | Source Company |
|---|---|---|---|
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |

TABLE 1-continued

| Brand Name | Physiological Class | Type of Inhibitor or Target | Source Company |
|---|---|---|---|
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharmiceuticals Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/Valentis |
| Wellferon | Interferon | lymphoblastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc, San Diego, CA |
| ITMN-191 (R-7227) | Antiviral | serine protease inhibitor | InterMune Pharmaceuticals Inc., Brisbane, CA |

TABLE 1-continued

| Brand Name | Physiological Class | Type of Inhibitor or Target | Source Company |
|---|---|---|---|
| GL-59728 | Antiviral | NS5B Replicase Inhibitor | Genelabs |
| ANA-971 | Antiviral | TLR-7 agonist | Anadys |

The compounds of the present disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

This disclosure is intended to encompass compounds having formula (I) when prepared by synthetic processes or by metabolic processes including those occurring in the human or animal body (in vivo) or processes occurring in vitro.

The abbreviations used in the present application, including particularly in the illustrative schemes and examples which follow, are well-known to those skilled in the art. Some of the abbreviations used are as follows: HATU for O-(7-azabenzotriazol-1-yl)-N,N,N',N'-tetramethyluronium hexafluorophosphate; Boc or BOC for tert-butoxycarbonyl; NBS for N-bromosuccinimide; tBu or t-Bu for tert-butyl; SEM for -(trimethylsilyl)ethoxymethyl; DMSO for dimethylsulfoxide; MeOH for methanol; TFA for trifluoroacetic acid; RT for room temperature or retention time (context will dictate); $t_R$ for retention time; EDCI for 1-(3-dimethylaminopropyl)-3-ethylcarbodiimide hydrochloride; DMAP for 4-dimethylaminopyridine; THF for tetrahydrofuran; DBU for 1,8-diazabicyclo[5.4.0]undec-7-ene; t-Bu; DEA for diethylamine; HMDS for hexamethyldisilazide; DMF for N,N-dimethylformamide; Bzl for benzyl; EtOH for ethanol; iPrOH or i-PrOH for isopropanol; Me$_2$S for dimethylsulfide; Et$_3$N or TEA for triethylamine; Ph for phenyl; OAc for acetate; EtOAc for ethyl acetate; dppf for 1,1'-bis(diphenylphosphino)ferrocene; iPr$_2$EtN or DIPEA for diisopropylethylamine; Cbz for carbobenzyloxy; n-BuLi for n-butyllithium; ACN for acetonitrile; h or hr for hours; m or min for minutes; s for seconds; LiHMDS for lithium hexamethyldisilazide; DIBAL for diisobutyl aluminum hydride; TBDMSCl for tert-butyldimethylsilyl chloride; Me for methyl; ca. for about; OAc for acetate; iPr for isopropyl; Et for ethyl; Bn for benzyl; and HOAT for 1-hydroxy-7-azabenzotriazole.

The abbreviations used in the present application, including particularly in the illustrative schemes and examples which follow, are well-known to those skilled in the art. Some of the abbreviations used are as follows:

The compounds and processes of the present disclosure will be better understood in connection with the following synthetic schemes which illustrate the methods by which the compounds of the present disclosure may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reactants and agents in the syntheses shown below. It will also be readily apparent to one skilled in the art that the selective protection and deprotection steps, as well as the order of the steps themselves, can be carried out in varying order, depending on the nature of the variables to successfully complete the syntheses below. The variables are as defined above unless otherwise noted below.

Scheme 1

Symmetric or Asymmetric Biphenyls

Aryl halide 1 and boronic ester 2 can be coupled to produce biaryl 3 using standard Suzuki-Miayura coupling conditions (*Angew Chem. Int. Ed. Engl* 2001, 40, 4544). It should be noted that the boronic acid analog of 2 may be used in place of the ester. Mono-deprotection of the pyrrolidine moiety may be accomplished when $R^{12}$ and $R^{13}$ are different. When $R^{12}$=benzyl, and $R^{13}$=t-butyl treatment to hydrogenolytic conditions produces 4. For example, Pd/C catalyst in the presence of a base such as potassium carbonate can be used. Acylation of 4 can be accomplished under standard acylation conditions. A coupling reagent such as HATU in combination with an amine base such as Hunig's base can be used in this regard. Alternatively, 4 may be reacted with an isocyanate or carbamoyl chloride to provide compounds of formula 5 where $R^9$ is an amine. Further deprotection of 5 can be accomplished by treatment with strong acid such as HCl or trifluoroacetic acid. Standard conditions analogous to those used to convert 4 to 5 can be used to prepare 7 from 6. In another embodiment where $R^{12}$=$R^{13}$=t-Bu, direct conversion to 8 can be accomplished by treatment of 3 with strong acid such as HCl or trifluoroacetic acid. Conversion of 8 to 7 is accomplished in analogous fashion to the methods used to prepare 5 from 4 or 7 from 6. In this instance however, the caps in 7 will be identical.

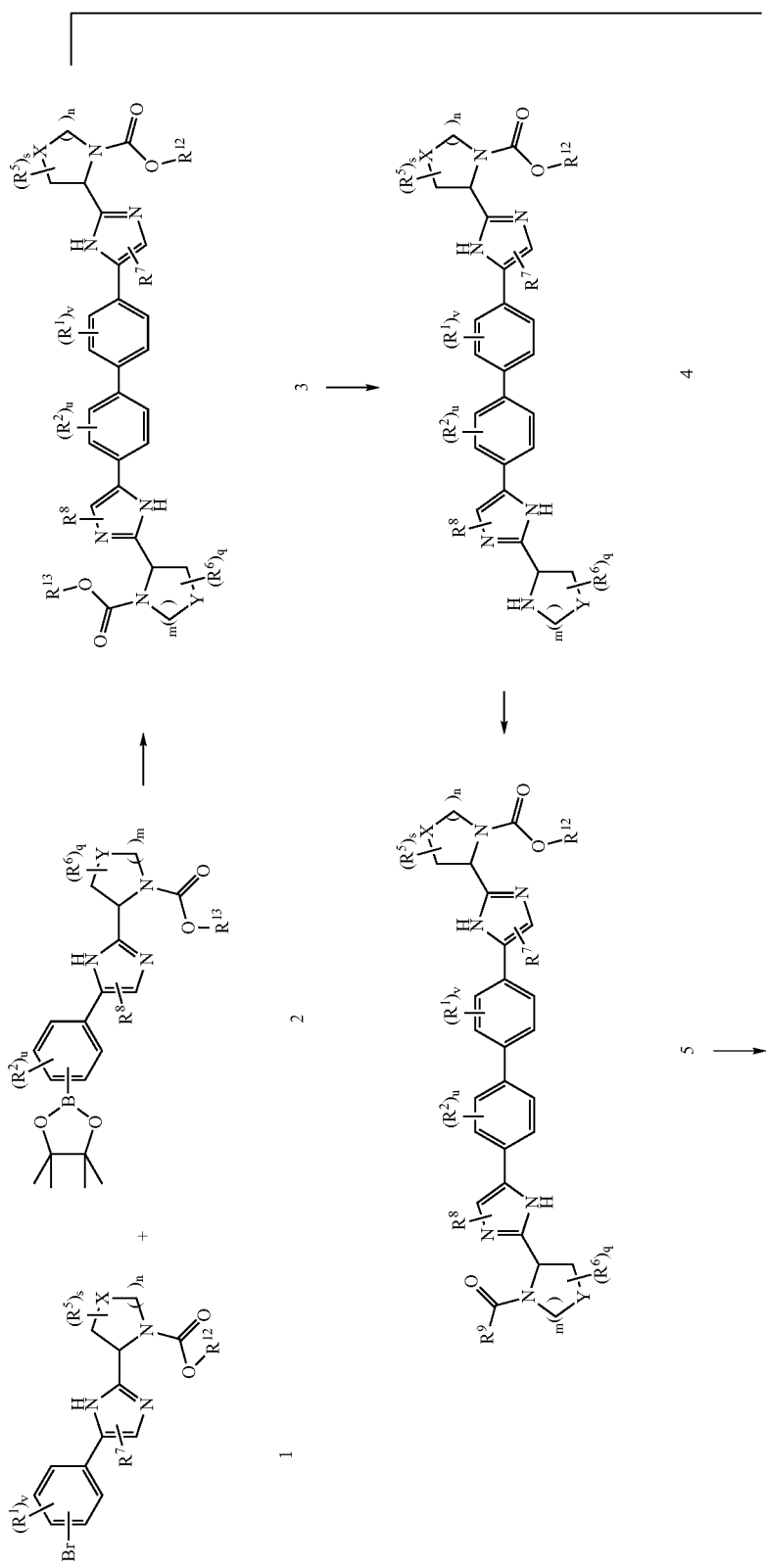

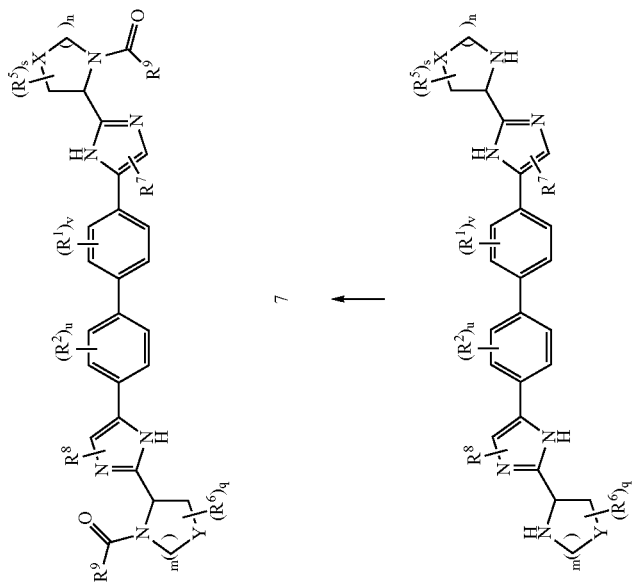
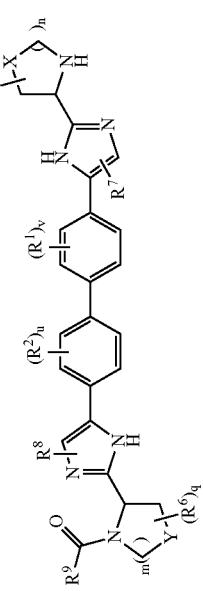

Scheme 2

Asymmetrically Capped Biphenyls

Conversion of 6 (from Scheme 1) to 10 can be done using standard amide coupling conditions such as HATU with an amine base, such as Hunig's base. Deprotection can be accomplished with strong acid such as HCl or trifluoroacetic acid affording 11. Compound 11 can then be converted to 12, 13, or 14 using an acid chloride, an isocyanate or carbamoyl chloride, or a chloroformate respectively.

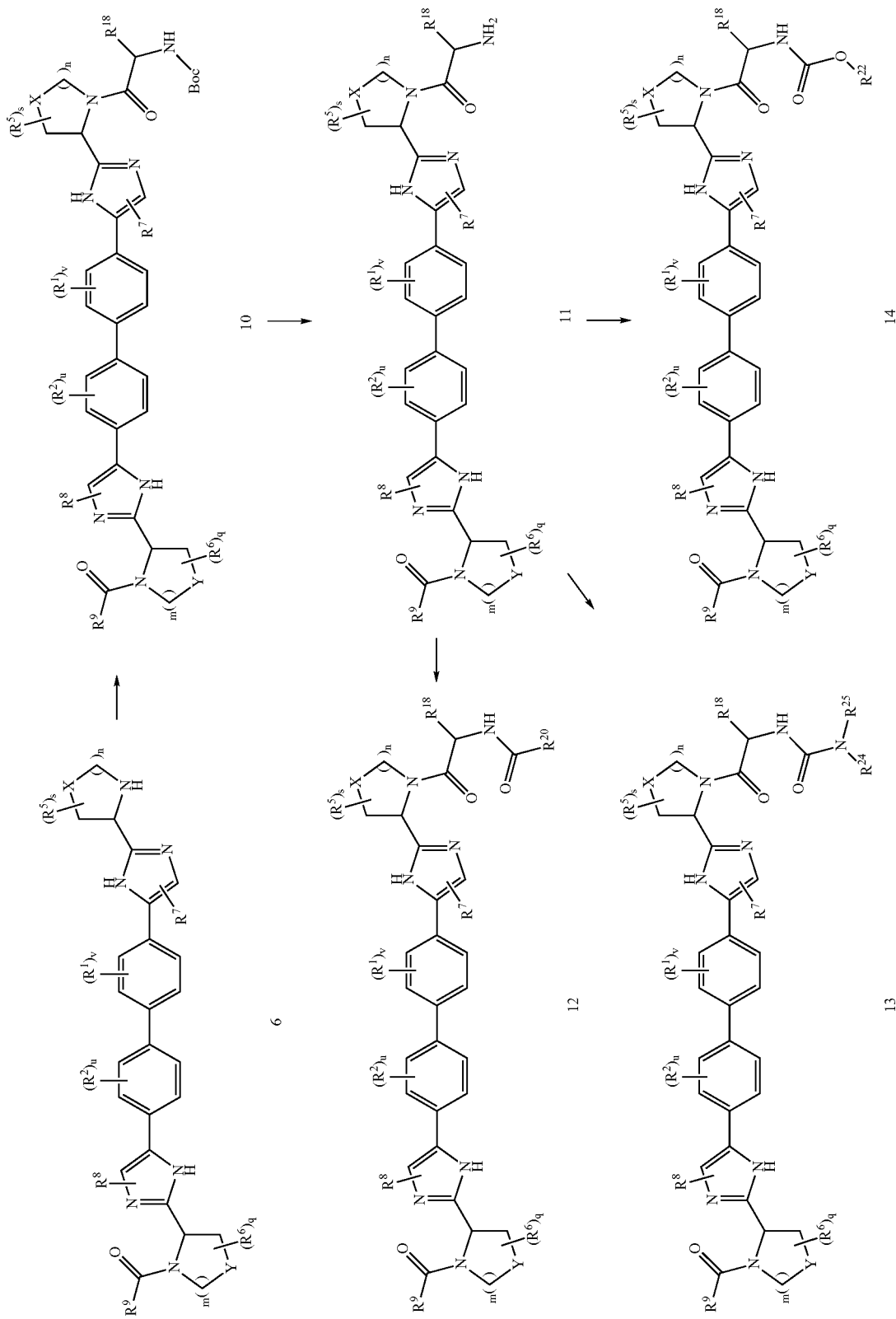

Scheme 3

Symmetric Cap Elaborated Biphenyls

Compound 15 (15=7 (Scheme 1) wherein each $R^9$ is —CH(NHBoc)$R^{18}$) can be converted to 16 via treatment with strong acid such as HCl or trifluoroacetic acid. Compounds 17, 18, and 19 can be prepared from 16 by treating 16 with an appropriate chloroformate, isocyanate or carbamoyl chloride, or an acid chloride respectively.

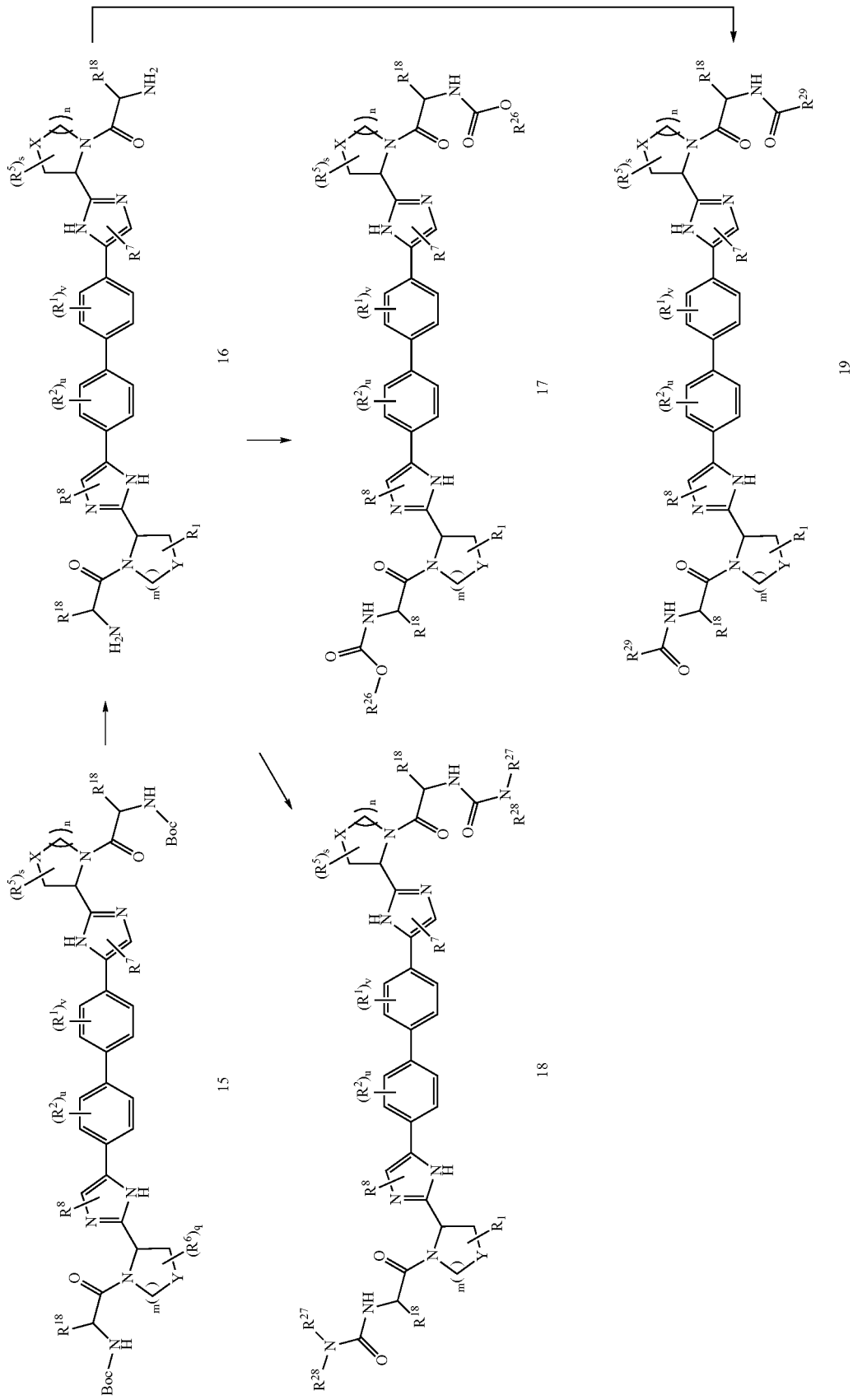

Scheme 4
Symmetric Biphenyls

Symmetrical biphenyl analogs (compounds of formula 7 where both halves of the molecule are equivalent) can be synthesized starting from bromoketone 20. Amination by displacement with a nucleophile such as azide, phthalimide or preferably sodium diformylamide (Yinglin and Hongwen, *Synthesis* 1990, 122) followed by deprotection affords 21. Condensation under standard amination conditions such as HATU and Hunig's base with an appropriately protected amino acid provides 22. Heating with ammonium acetate under thermal or microwave conditions results in the formation of 3 which can be deprotected with strong acid such as HCl or trifluoroacetic acid ($R^{12}$=$R^{13}$=t-Bu) or by hydrogenolysis with hydrogen gas and a transition metal catalyst such as Pd/C ($R^{12}$=$R^{13}$=benzyl). Acylation can be affected with a carboxylic acid ($R^9CO_2H$) in a manner similar to the conversion of 21 to 22. Urea formation can be accomplished by treatment with an appropriate isocycante ($R^9$=$R^{24}R^{25}N$; $R^{25}$=H) or carbamoyl chloride ($R^9$=$R^{24}R^{25}N$; $R^{25}$ is other than hydrogen).

Scheme 5
Starting Materials 25 and 2

Scheme 5 describes the preparation of some of the starting materials required for the synthetic sequences depicted in Schemes 1-4. Key intermediate 25 (analogous to 1 in Scheme 1) is prepared from keto-amide 24 or keto-ester 27 via heating with ammonium acetate under thermal or microwave conditions. Keto-amide 24 can be prepared from 23 via condensation with an appropriate cyclic or acyclic amino acid under standard amide formation conditions. Bromide 26 can give rise to 23 by treatment with a nucleophile such as azide, phthalimide or sodium diformylamide (*Synthesis* 1990, 122) followed by deprotection. Bromide 26 can also be converted to 27 by reacting with an appropriate cyclic or acyclic N-protected amino acid in the presence of base such as potassium carbonate or sodium bicarbonate. Bromination of 28 with a source of bromonium ion such as bromine, NBS, or $CBr_4$ results in the formation of 26. Bromide 25 can be converted to boronic ester 2 via treatment with bis-pinacalotodiboron under palladium catalysis according to the method described in *Journal of Organic Chemistry* 1995, 60, 7508, or variations thereof.

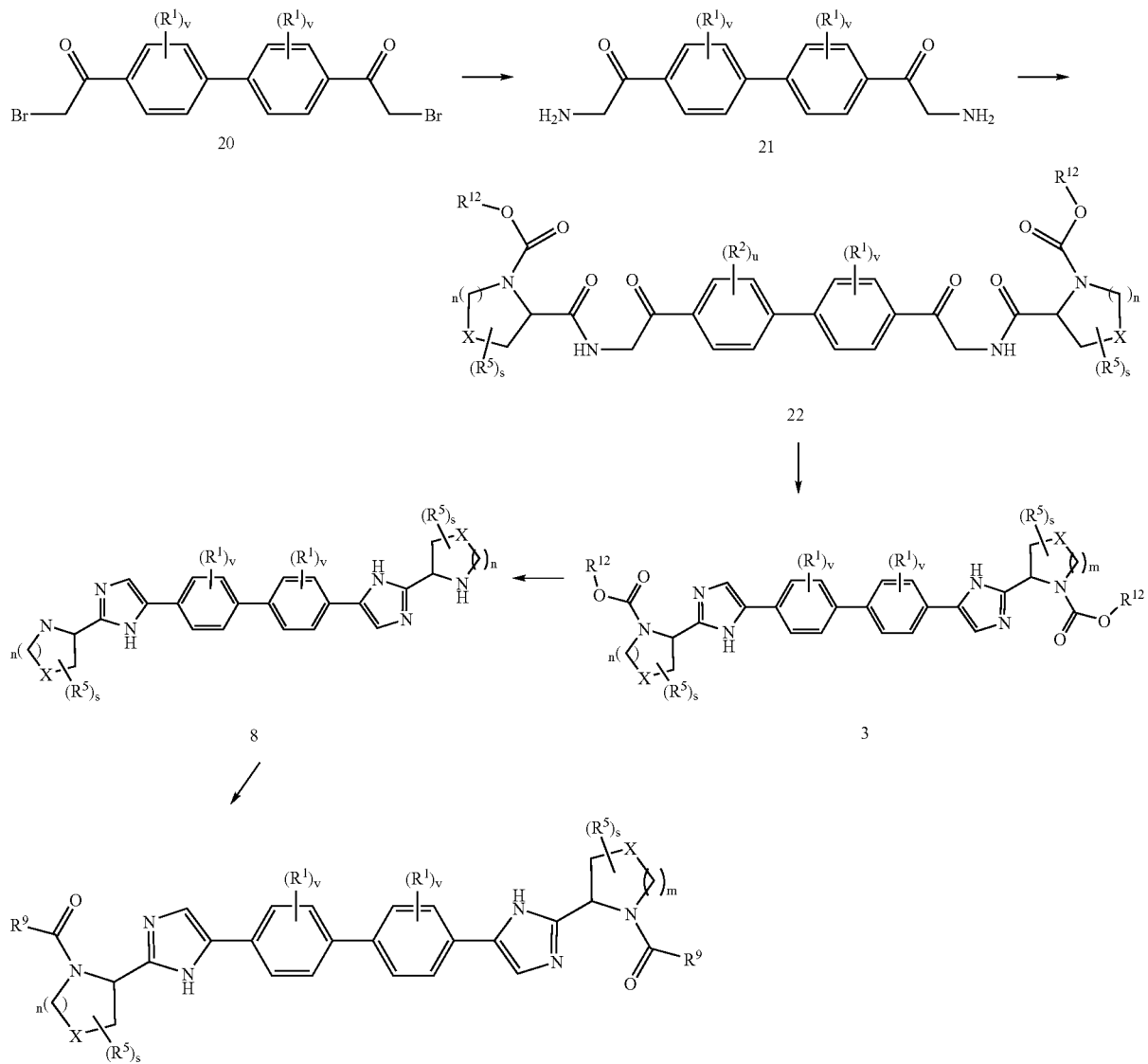

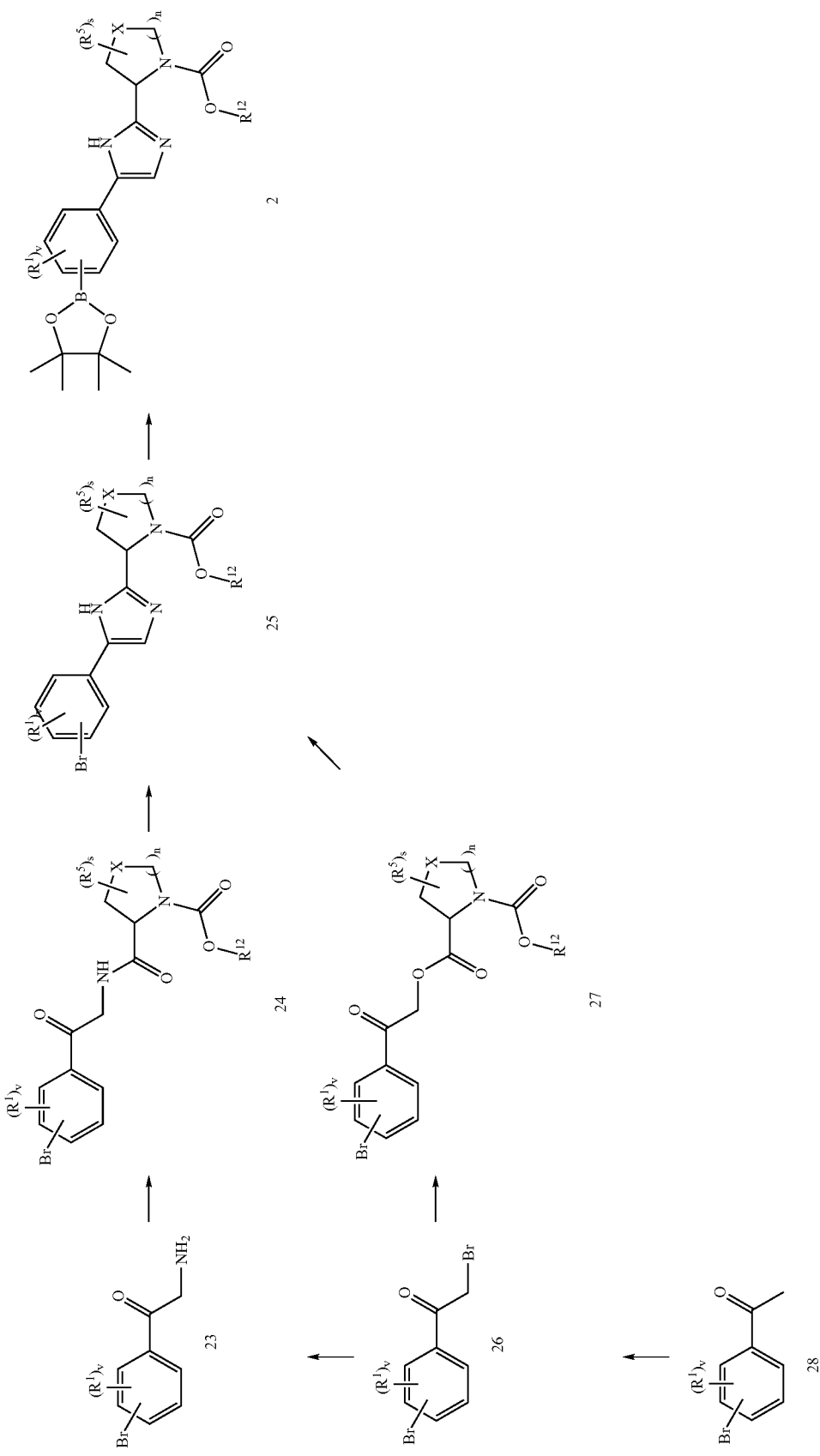

Scheme 6

Starting Material 31a

In another embodiment, starting materials such as 31a (analogous to 25 in Scheme 5 and 1 in Scheme 1) may be prepared by reacting bromoimidazole derivatives 31 under Suzuki-type coupling conditions with a variety of chloro-substituted aryl boronic acids which can either be prepared by standard methodologies (see, for example, *Organic Letters* 2006, 8, 305 and references cited therein) or purchased from commercial suppliers. Bromoimidazole 31 can be obtained by brominating imidazole 30 with a source of bromonium ion such as bromine, $CBr_4$, or N-bromosuccinimide. Imidazole 30 can be prepared from N-protected amino acids which are appropriately substituted by reacting with glyoxal in a methanolic solution of ammonium hydroxide.

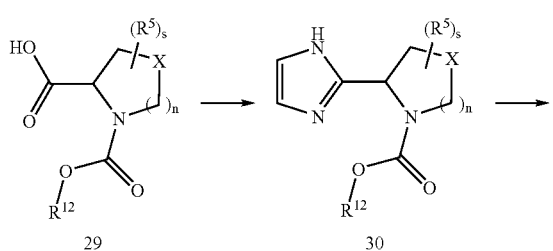

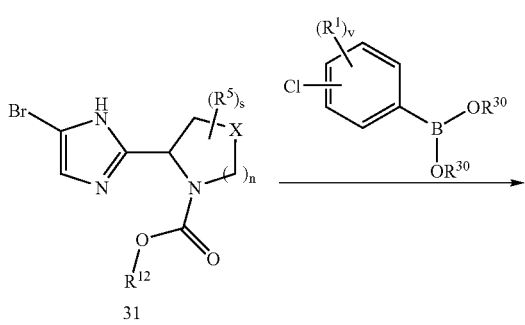

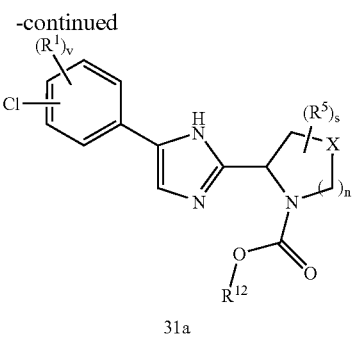

31a

Scheme 7

Heteroaryls

In yet another embodiment of the current disclosure, aryl halide 32 can be coupled under Suzuki-Miyaura palladium catalyzed conditions to form the heteroaryl derivative 34. Compound 34 can be elaborated to 35 by treatment to hydrogenolytic conditions with hydrogen and a transition metal catalyst such as palladium on carbon ($R^{13}$=benzyl). Acylation of 35 can be accomplished with an appropriate acid chloride ($R^9COCl$) in the presence of a base such as triethylamine, with an appropriately substituted carboxylic acid ($R^9CO_2H$) in the presence of a standard coupling reagent such as HATU, or with an isoscyanate ($R^{27}NCO$ wherein $R^9=R^{27}R^{28}N-$; $R^{28}=H$) or carbamoyl chloride ($R^{27}R^{28}NCOCl$ wherein $R^9=R^{27}R^{28}N-$). Compound 37 can be prepared from 36 ($R^{12}$=t-Bu) via treatment with strong acid such as HCl or trifluoroacetic acid. Acylation of the resulting amine in 37 to give 38 can be accomplished as in the transformation of 35 to 36. In cases where $R^{12}=R^{13}$, 34 can be directly transformed into 39 by treatment with strong acid such as HCl or trifluoroacetic acid ($R^{12}=R^{13}$=t-Bu) or by employing hydrogenolytic conditions with hydrogen and a transition metal catalyst such as palladium on carbon ($R^{12}=R^{13}$=benzyl). Acylation of 39 can be accomplished in analogous fashion to that described for the transformation of 35 to 36.

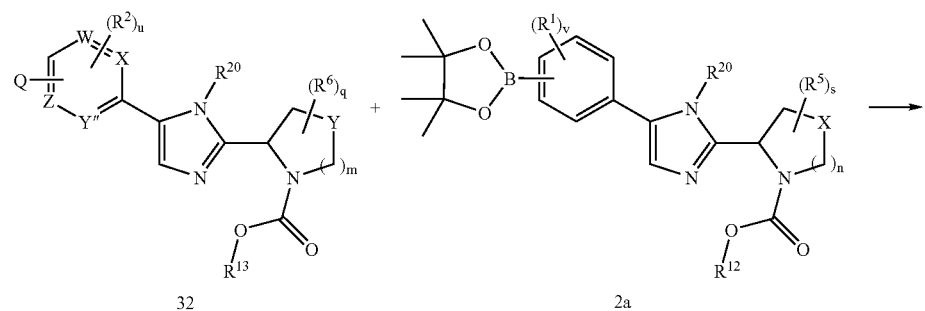

$R^{12}$ and $R^{13}$ are independently alkoxymethyl or H
Q = Cl or Br

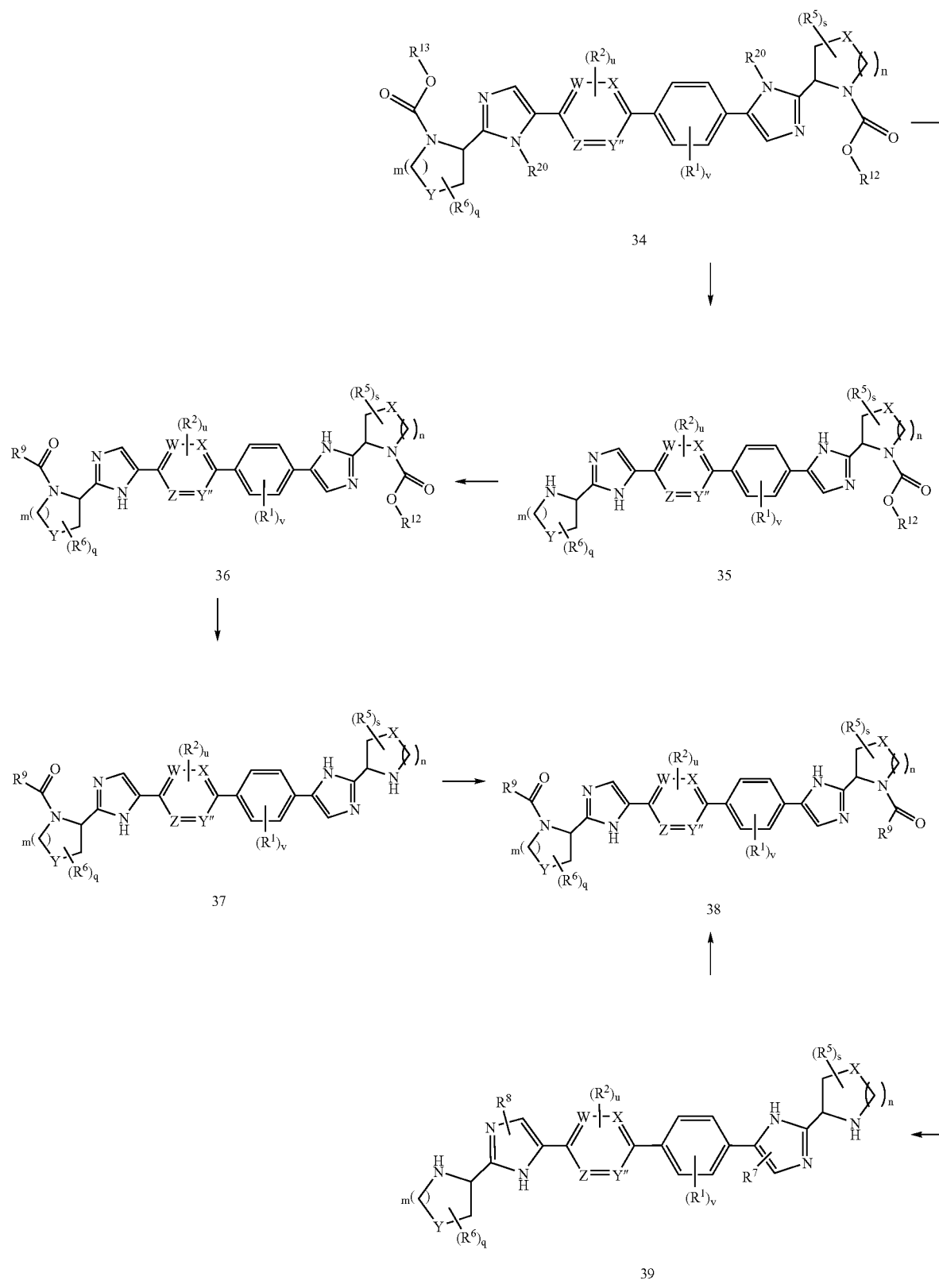
W, X, Y″, Z = C or N with at least one of W, X, Y, and Z must be C and at least one of W, X, Y″, and Z must be N each $R^9$ can be independently alkyl or $NR^{27}R^{28}$

Scheme 8

Heteroaryl chloride 29 can be converted to symmetrical analog 40 via treatment with a source of palladium such as dichlorobis(benzonitrile) palladium in the presence of tetrakis(dimethylamino)ethylene at elevated temperature. Removal of the SEM ether and Boc carbamates found in 40 can be accomplished in one step by treatment with a strong acid such as HCl or trifluoroacetic acid providing 41. Conversion to 42 can be accomplished in similar fashion to the conditions used to convert 38 to 39 in Scheme 7.

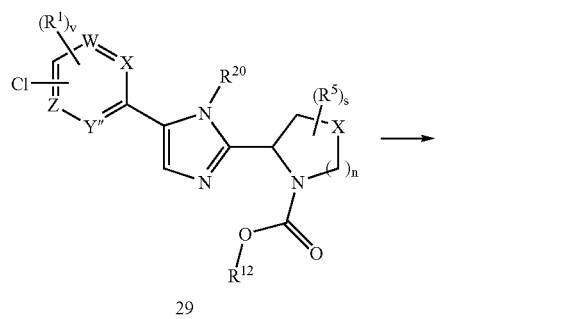

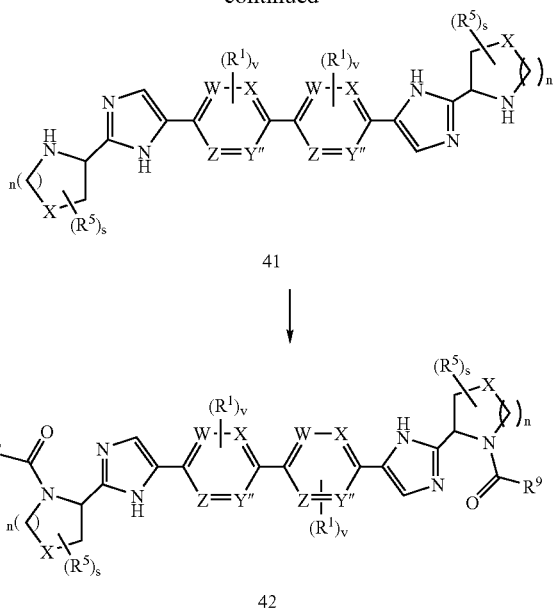

$R^{20}$ = alkoxymethyl or H
W, X, Y″, Z = C or N with at least one of W, X, Y″, and Z must be C
$R^9$ can be alkyl or $NR^{27}R^{28}$

Scheme 9

Symmetric Cap Substituted Heteroaryls

Compound 43 (analogous to 42 wherein $R_{23}$=—CH(NH-Boc)$R_{24}$) may be elaborated to 45, 46, and 47 via similar methodologies to those described in Scheme 3. In cases where $R_{20}$=alkoxymethyl (ie; SEM), removal can be accomplished simultaneously with removal of the Boc carbamate (cf; 43 to 44) using strong acid such as HCl or trifluoroacetic acid.

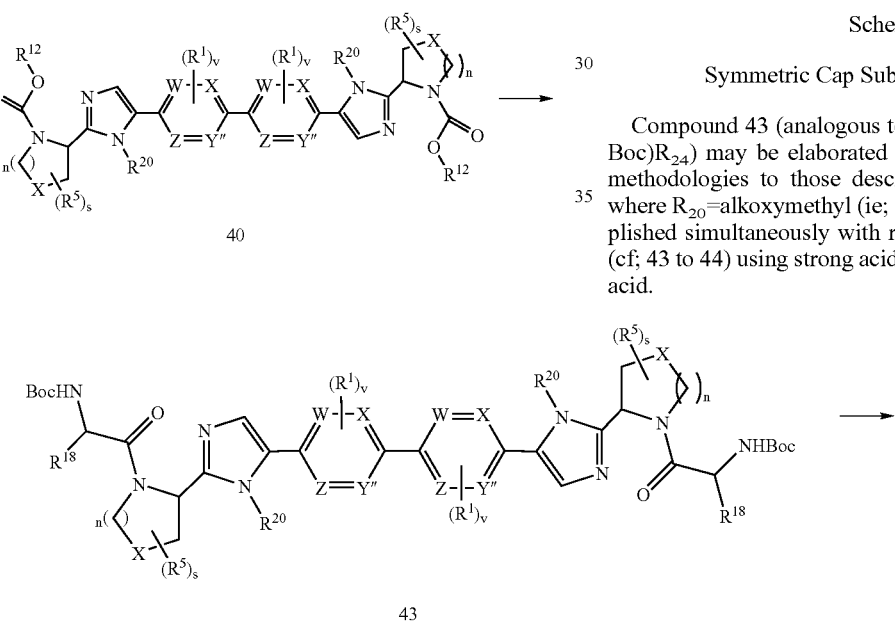

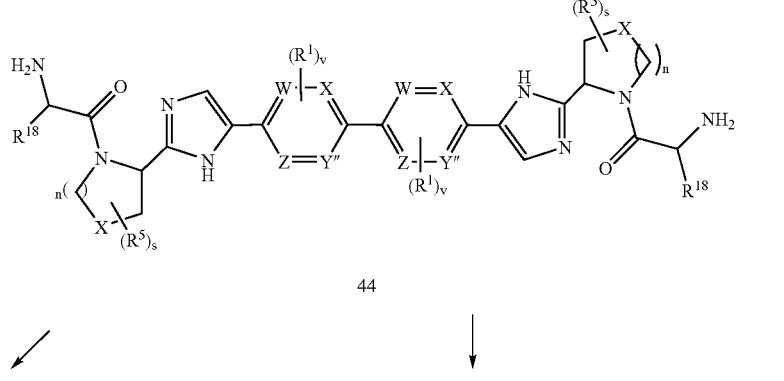

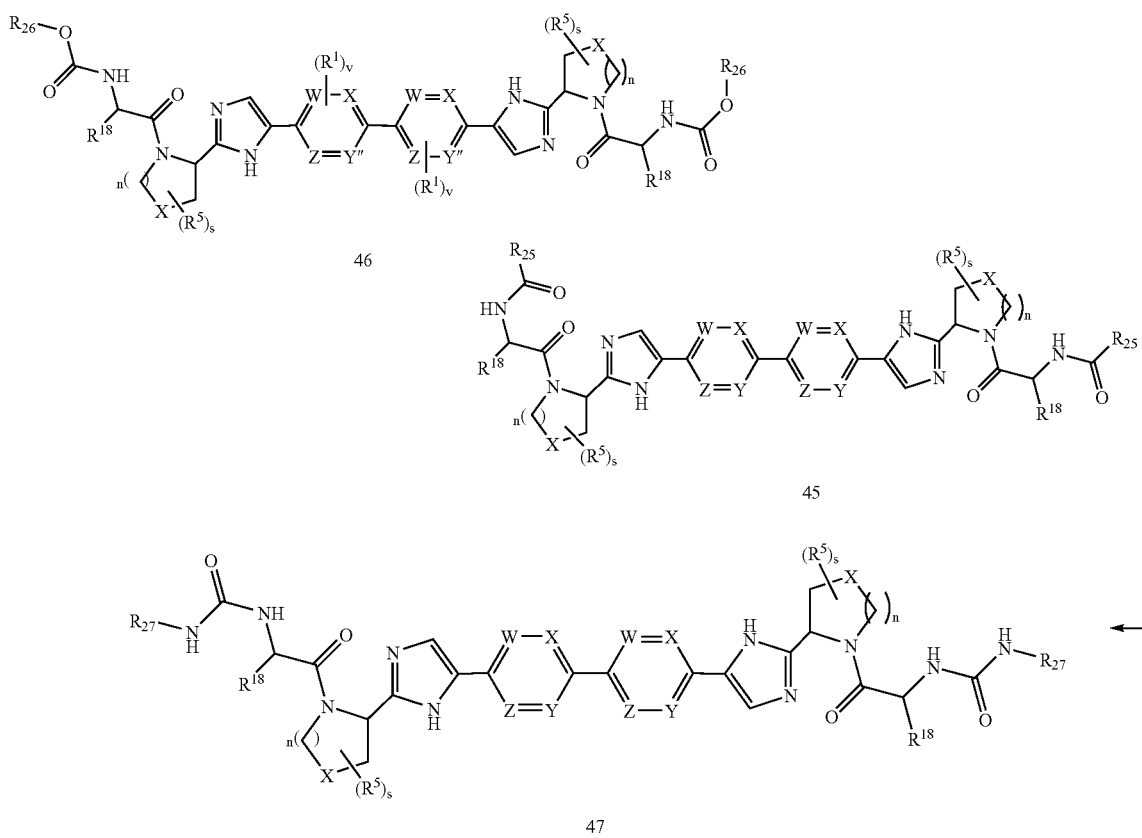

$R_{20}$ = alkoxymethyl or H
W, X, Y, Z = C or N with at least one of W, X, Y, and Z must be C; at least one of W, X, Y, and Z must be N Scheme 10

Starting Material 29

Heteroaryl bromides 54 may be reacted with a vinyl stannane such as tributyl(1-ethoxyvinyl)tin in the presence of a source of palladium such as dichlorobis(triphenylphosphine) palladium (II) to provide 55 which can be subsequently transformed into bromoketone 51 via treatment with a source of bromonium ion such as N-bromosuccinimide, CBr$_4$, or bromine. Alternatively, keto-substituted heteroaryl bromides 53 may be directly converted to 51 via treatment with a source of bromonium ion such as bromine, CBr$_4$, or N-bromosuccinimide. Bromide 51 can be converted to aminoketone 48 via addition of sodium azide, potassium phthalimide or sodium diformylamide (*Synthesis* 1990 122) followed by deprotection. Aminoketone 48 can then be coupled with an appropriately substituted amino acid under standard amide formation conditions (i.e.; a coupling reagent such as HATU in the presence of a mild base such as Hunig's base) to provide 49. Compound 49 can then be further transformed into imidazole 50 via reacting with ammonium acetate under thermal or microwave conditions. Alternatively, 51 can be directly reacted with an appropriately substituted amino acid in the presence of a base such as sodium bicarbonate or potassium carbonate providing 52 which can in turn be reacted with ammonium acetate under thermal or microwave conditions to provide 50. Imidazole 50 can be protected with an alkoxylmethyl group by treatment with the appropriate alkoxymethyl halide such as 2-(trimethylsilyl)ethoxymethyl chloride after first being deprotonated with a strong base such as sodium hydride.

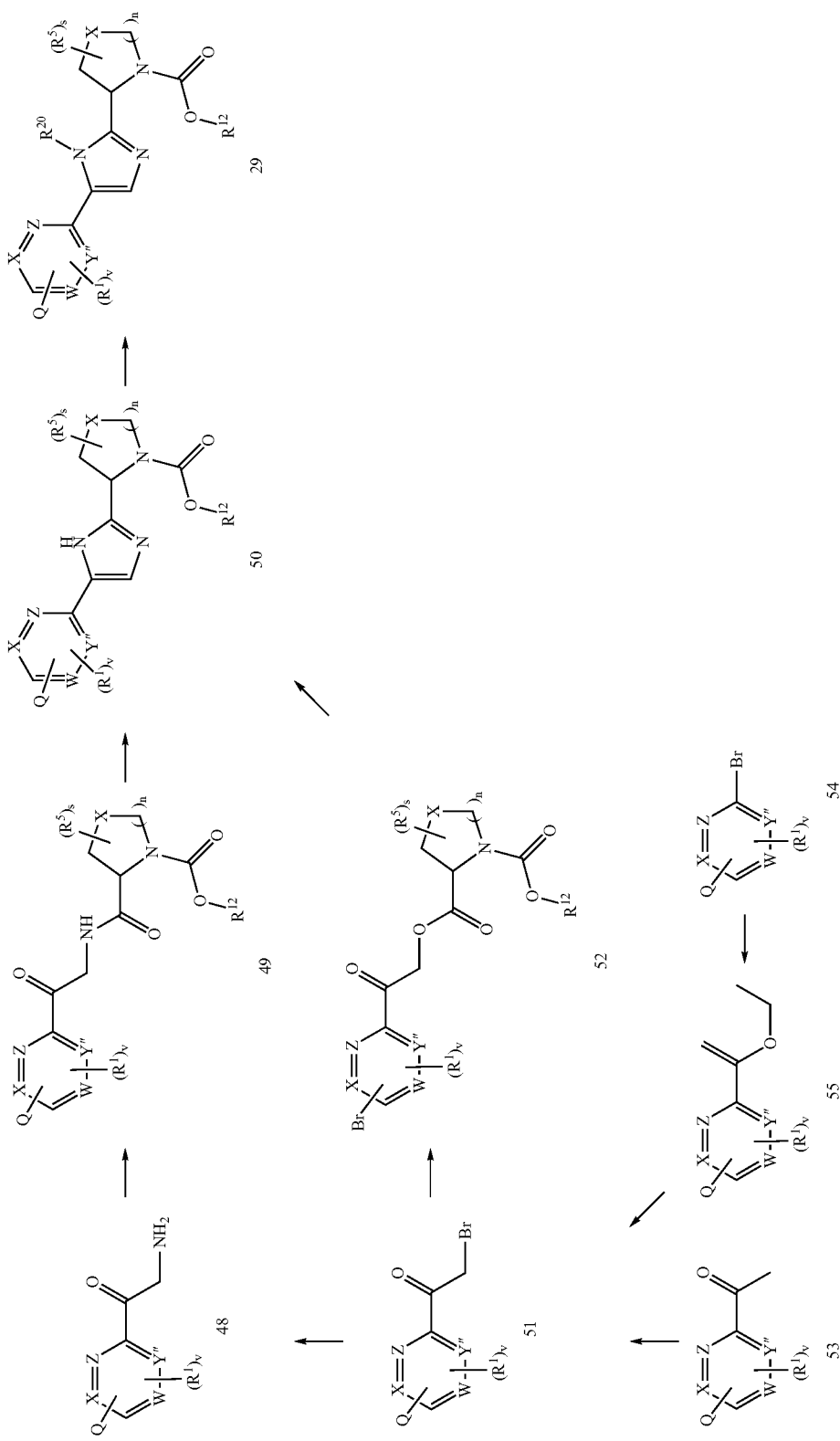

Scheme 11

Substituted Phenylglycine Derivatives

Substituted phenylglycine derivatives can be prepared by a number of methods shown below. Phenylglycine t-butyl ester can be reductively alkylated (pathway A) with an appropriate aldehyde and a reductant such as sodium cyanoborohydride in acidic medium. Hydrolysis of the t-butyl ester can be accomplished with strong acid such as HCl or trifluoroacetic acid. Alternatively, phenylglycine can be alkylated with an alkyl halide such as ethyl iodide and a base such as sodium bicarbonate or potassium carbonate (pathway B). Pathway C illustrates reductive alkylation of phenylglycine as in pathway A followed by a second reductive alkylation with an alternate aldehyde such as formaldehyde in the presence of a reducing agent and acid. Pathway D illustrates the synthesis of substituted phenylglycines via the corresponding mandelic acid analogs. Conversion of the secondary alcohol to a competent leaving group can be accomplished with p-toluensulfonyl chloride. Displacement of the tosylate group with an appropriate amine followed by reductive removal of the benzyl ester can provide substituted phenylglycine derivatives. In pathway E a racemic substituted phenylglycine derivative is resolved by esterification with an enantiomerically pure chiral auxiliary such as but not limited to (+)-1-phenylethanol, (−)-1-phenylethanol, an Evan's oxazolidinone, or enantiomerically pure pantolactone. Separation of the diastereomers is accomplished via chromatography (silica gel, HPLC, crystallization, etc) followed by removal of the chiral auxiliary providing enantiomerically pure phenylglycine derivatives. Pathway H illustrates a synthetic sequence which intersects with pathway E wherein the aforementioned chiral auxiliary is installed prior to amine addition. Alternatively, an ester of an arylacetic acid can be brominated with a source of bromonium ion such as bromine, N-bromosuccinimide, or $CBr_4$. The resultant benzylic bromide can be displaced with a variety of mono- or disubstituted amines in the presence of a tertiary amine base such as triethylamine or Hunig's base. Hydrolysis of the methyl ester via treatment with lithium hydroxide at low temperature or 6N HCl at elevated temperature provides the substituted phenylglycine derivatives. Another method is shown in pathway G. Glycine analogs can be derivatized with a variety of aryl halides in the presence of a source of palladium (0) such as palladium bis(tributylphosphine) and base such as potassium phosphate. The resultant ester can then be hydrolyzed by treatment with base or acid. It should be understood that other well known methods to prepare phenylglycine derivatives exist in the art and can be amended to provide the desired compounds in this description. It should also be understood that the final phenylglycine derivatives can be purified to enantiomeric purity greater than 98% ee via preparative HPLC.

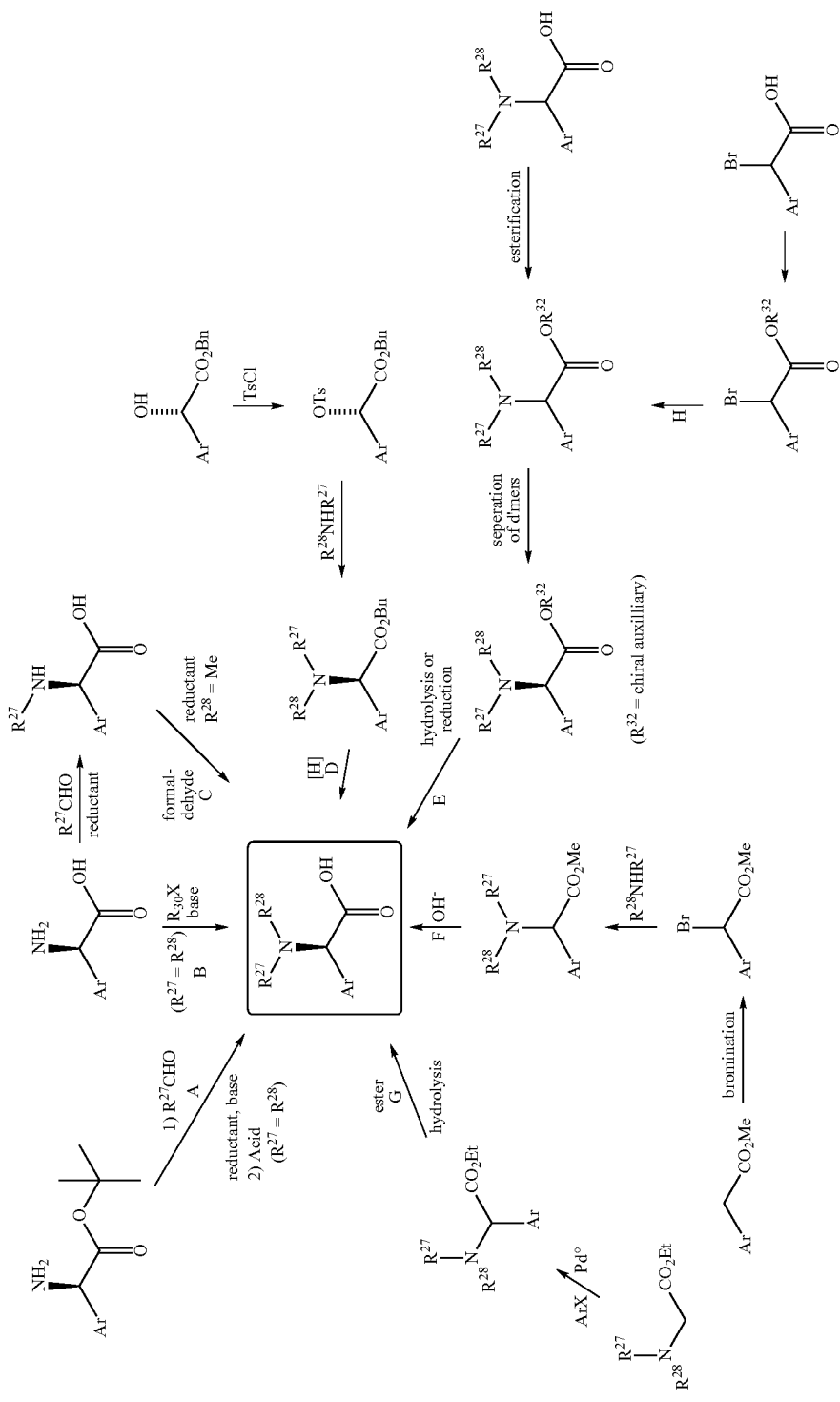

Scheme 12

Acylated Amino Acid Derivatives

In another embodiment of the present disclosure, acylated phenylglycine derivatives may be prepared as illustrated below. Phenylglycine derivatives wherein the carboxylic acid is protected as an easily removed ester, may be acylated with an acid chloride in the presence of a base such as triethylamine to provide the corresponding amides (pathway A). Pathway B illustrates the acylation of the starting phenylglycine derivative with an appropriate chloroformate while pathway C shows reaction with an appropriate isocyanate or carbamoyl chloride. Each of the three intermediates shown in pathways A-C may be deprotected by methods known by those skilled in the art (ie; treatment of the t-butyl ester with strong base such as HCl or trifluoroacetic acid).

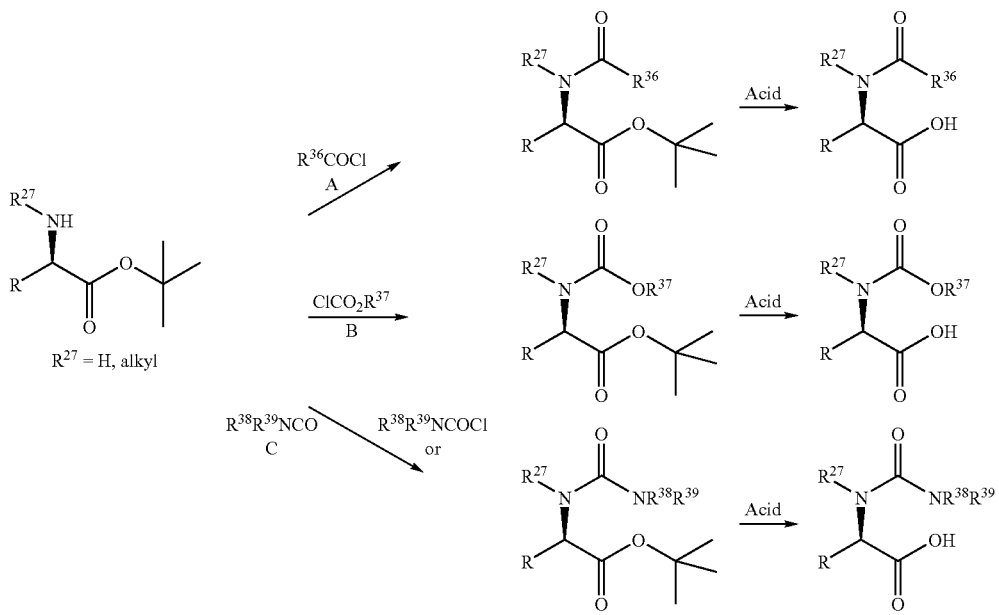

Scheme 13

Amino-substituted phenylacetic acids may be prepared by treatment of a chloromethylphenylacetic acid with an excess of an amine.

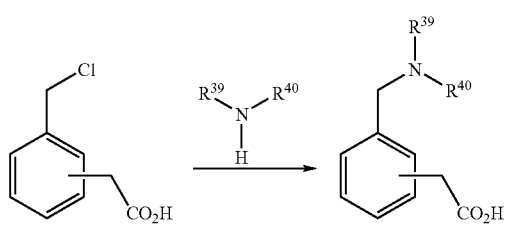

Compound Analysis Conditions

Purity assessment and low resolution mass analysis were conducted on a Shimadzu LC system coupled with Waters Micromass ZQ MS system. It should be noted that retention times may vary slightly between machines. The LC conditions employed in determining the retention time (RT) were:

Condition 1
Column=Phenomenex-Luna 3.0×50 mm S10
Start % B=0
Final % B=100
Gradient time=2 min
Stop time=3 min
Flow Rate=4 mL/min
Wavelength=220 nm
Solvent A=0.1% TFA in 10% methanol/90% $H_2O$
Solvent B=0.1% TFA in 90% methanol/10% $H_2O$
Condition 2
Column=Phenomenex-Luna 4.6×50 mm S10
Start % B=0
Final % B=100
Gradient time=2 min
Stop time=3 min
Flow Rate=5 mL/min
Wavelength=220 nm
Solvent A=0.1% TFA in 10% methanol/90% $H_2O$
Solvent B=0.1% TFA in 90% methanol/10% $H_2O$
Condition 3
Column=HPLC XTERRA C18 3.0×50 mm S7
Start % B=0
Final % B=100
Gradient time=3 min
Stop time=4 min
Flow Rate=4 mL/min
Wavelength=220 nm
Solvent A=0.1% TFA in 10% methanol/90% $H_2O$
Solvent B=0.1% TFA in 90% methanol/10% $H_2O$
Condition M1
Column: Luna 4.6×50 mm S10
Start % B=0
Final % B=100
Gradient time=3 min
Stop time=4 min
Flow rate=4 mL/min
Solvent A:=95% $H_2O$: 5% $CH_3CN$, 10 mm Ammonium acetate
Solvent B:=5% $H_2O$: 95% $CH_3CN$; 10 mm Ammonium acetate

Synthesis of Common Caps

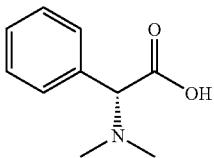

Cap-1

A suspension of 10% Pd/C (2.0 g) in methanol (10 mL) was added to a mixture of (R)-2-phenylglycine (10 g, 66.2 mmol), formaldehyde (33 mL of 37% wt. in water), 1N HCl (30 mL) and methanol (30 mL), and exposed to $H_2$ (60 psi) for 3 hours. The reaction mixture was filtered through diatomaceous earth (Celite®), and the filtrate was concentrated in vacuo. The resulting crude material was recrystallized from isopropanol to provide the HCl salt of Cap-1 as a white needle (4.0 g). Optical rotation: −117.1° [c=9.95 mg/mL in $H_2O$; λ=589 nm]. $^1H$ NMR (DMSO-$d_6$, δ=2.5 ppm, 500 MHz): δ 7.43-7.34 (m, 5H), 4.14 (s, 1H), 2.43 (s, 6H); LC (Cond. 1): RT=0.25; LC/MS: Anal. Calcd. for $[M+H]^+$ $C_{10}H_{14}NO_2$: 180.10. found 180.17; HRMS: Anal. Calcd. for $[M+H]^+$ $C_{10}H_{14}NO_2$ 180.1025. found 180.1017.

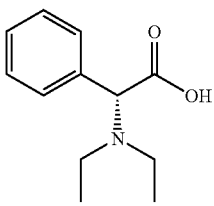

Cap-2

NaBH$_3$CN (6.22 g, 94 mmol) was added in portions over a few minutes to a cooled (ice/water) mixture of (R)-2-Phenylglycine (6.02 g, 39.8 mmol) and MeOH (100 mL), and stirred for 5 min. Acetaldehyde (10 mL) was added drop-wise over 10 min and stirring was continued at the same cooled temperature for 45 min and at ambient temperature for ~6.5 hr. The reaction mixture was cooled back with ice-water bath, treated with water (3 mL) and then quenched with a drop-wise addition of concentrated HCl over ~45 min until the pH of the mixture is ~1.5-2.0. The cooling bath was removed and the stirring was continued while adding concentrated HCl in order to maintain the pH of the mixture around 1.5-2.0. The reaction mixture was stirred over night, filtered to remove the white suspension, and the filtrate was concentrated in vacuo. The crude material was recrystallized from ethanol to afford the HCl salt of Cap-2 as a shining white solid in two crops (crop-1: 4.16 g; crop-2: 2.19 g). $^1H$ NMR (DMSO-$d_6$, δ=2.5 ppm, 400 MHz): 10.44 (1.00, br s, 1H), 7.66 (m, 2H), 7.51 (m, 3H), 5.30 (s, 1H), 3.15 (br m, 2H), 2.98 (br m, 2H), 1.20 (app br s, 6H). Crop-1: $[α]^{25}$-102.21° (c=0.357, $H_2O$); crop-2: $[α]^{25}$-99.7° (c=0.357, $H_2O$). LC (Cond. 1): RT=0.43 min; LC/MS: Anal. Calcd. for $[M+H]^+$ $C_{12}H_{18}NO_2$: 208.13. found 208.26

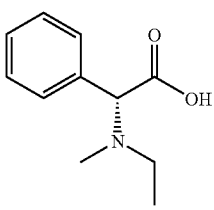

Cap-3

Acetaldehyde (5.0 mL, 89.1 mmol) and a suspension of 10% Pd/C (720 mg) in methanol/$H_2O$ (4 mL/1 mL) was sequentially added to a cooled (~15° C.) mixture of (R)-2-phenylglycine (3.096 g, 20.48 mmol), 1N HCl (30 mL) and methanol (40 mL). The cooling bath was removed and the reaction mixture was stirred under a balloon of $H_2$ for 17 hours. An additional acetaldehyde (10 mL, 178.2 mmol) was added and stirring continued under $H_2$ atmosphere for 24 hours [Note: the supply of $H_2$ was replenished as needed throughout the reaction]. The reaction mixture was filtered through diatomaceous earth (Celite®), and the filtrate was concentrated in vacuo. The resulting crude material was recrystallized from isopropanol to provide the HCl salt of (R)-2-(ethylamino)-2-phenylacetic acid as a shining white solid (2.846 g). $^1H$ NMR (DMSO-$d_6$, δ=2.5 ppm, 400 MHz): δ 14.15 (br s, 1H), 9.55 (br s, 2H), 7.55-7.48 (m, 5H), 2.88 (br m, 1H), 2.73 (br m, 1H), 1.20 (app t, J=7.2, 3H). LC (Cond. 1): RT=0.39 min; >95% homogeneity index; LC/MS: Anal. Calcd. for $[M+H]^+$ $C_{10}H_{14}NO_2$: 180.10. found 180.18.

A suspension of 10% Pd/C (536 mg) in methanol/$H_2O$ (3 mL/1 mL) was added to a mixture of (R)-2-(ethylamino)-2-phenylacetic acid/HCl (1.492 g, 6.918 mmol), formaldehyde (20 mL of 37% wt. in water), 1N HCl (20 mL) and methanol (23 mL). The reaction mixture was stirred under a balloon of $H_2$ for ~72 hours, where the $H_2$ supply was replenished as needed. The reaction mixture was filtered through diatomaceous earth (Celite®) and the filtrate was concentrated in vacuo. The resulting crude material was recrystallized from isopropanol (50 mL) to provide the HCl salt of Cap-3 as a white solid (985 mg). $^1H$ NMR (DMSO-$d_6$, δ=2.5 ppm, 400 MHz): δ 10.48 (br s, 1H), 7.59-7.51 (m, 5H), 5.26 (s, 1H), 3.08 (app br s, 2H), 2.65 (br s, 3H), 1.24 (br m, 3H). LC (Cond. 1): RT=0.39 min; >95% homogeneity index; LC/MS: Anal. Calcd. for $[M+H]^+$ $C_{11}H_{16}NO_2$: 194.12. found 194.18; HRMS: Anal. Calcd. for $[M+H]^+$ $C_{11}H_{16}NO_2$: 194.1180. found 194.1181.

Cap-4

ClCO$_2$Me (3.2 mL, 41.4 mmol) was added dropwise to a cooled (ice/water) THF (410 mL) semi-solution of (R)-tert-butyl 2-amino-2-phenylacetate/HCl (9.877 g, 40.52 mmol) and diisopropylethylamine (14.2 mL, 81.52 mmol) over 6 min, and stirred at similar temperature for 5.5 hours. The volatile component was removed in vacuo, and the residue was partitioned between water (100 mL) and ethyl acetate (200 mL). The organic layer was washed with 1N HCl (25 mL) and saturated NaHCO$_3$ solution (30 mL), dried (MgSO$_4$), filtered, and concentrated in vacuo. The resultant colorless oil was triturated from hexanes, filtered and washed with hexanes (100 mL) to provide (R)-tert-butyl 2-(methoxycarbonylamino)-2-phenylacetate as a white solid (7.7 g). $^1H$ NMR (DMSO-$d_6$, δ=2.5 ppm, 400 MHz): 7.98 (d, J=8.0, 1H), 7.37-7.29 (m, 5H), 5.09 (d, J=8, 1H), 3.56 (s, 3H), 1.33 (s, 9H). LC (Cond. 1): RT=1.53 min; ~90% homogeneity index; LC/MS: Anal. Calcd. for $[M+Na]^+$ $C_{14}H_{19}NNaO_4$: 288.12. found 288.15.

TFA (16 mL) was added dropwise to a cooled (ice/water) CH₂Cl₂ (160 mL) solution of the above product over 7 minutes, and the cooling bath was removed and the reaction mixture was stirred for 20 hours. Since the deprotection was still not complete, an additional TFA (1.0 mL) was added and stirring continued for an additional 2 hours. The volatile component was removed in vacuo, and the resulting oil residue was treated with diethyl ether (15 mL) and hexanes (12 mL) to provide a precipitate. The precipitate was filtered and washed with diethyl ether/hexanes (~1:3 ratio; 30 mL) and dried in vacuo to provide Cap-4 as a fluffy white solid (5.57 g). Optical rotation: −176.9° [c=3.7 mg/mL in H₂O; λ=589 nm]. ¹H NMR (DMSO-d₆, δ=2.5 ppm, 400 MHz): δ 12.84 (br s, 1H), 7.96 (d, J=8.3, 1H), 7.41-7.29 (m, 5H), 5.14 (d, J=8.3, 1H), 3.55 (s, 3H). LC (Cond. 1): RT=1.01 min; >95% homogeneity index; LC/MS: Anal. Calcd. for [M+H]⁺ C₁₀H₁₂NO₄ 210.08. found 210.17; HRMS: Anal. Calcd. for [M+H]⁺ C₁₀H₁₂NO₄ 210.0766. found 210.0756.

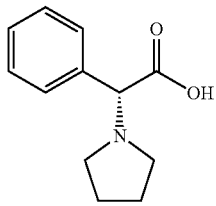

Cap-5

A mixture of (R)-2-phenylglycine (1.0 g, 6.62 mmol), 1,4-dibromobutane (1.57 g, 7.27 mmol) and Na₂CO₃ (2.10 g, 19.8 mmol) in ethanol (40 mL) was heated at 100° C. for 21 hours. The reaction mixture was cooled to ambient temperature and filtered, and the filtrate was concentrated in vacuo. The residue was dissolved in ethanol and acidified with 1N HCl to pH 3-4, and the volatile component was removed in vacuo. The resulting crude material was purified by a reverse phase HPLC (water/methanol/TFA) to provide the TFA salt of Cap-5 as a semi-viscous white foam (1.0 g). ¹H NMR (DMSO-d₆, δ=2.5, 500 MHz) δ 10.68 (br s, 1H), 7.51 (m, 5H), 5.23 (s, 1H), 3.34 (app br s, 2H), 3.05 (app br s, 2H), 1.95 (app br s, 4H); RT=0.30 min (Cond. 1); >98% homogeneity index; LC/MS: Anal. Calcd. for [M+H]⁺ C₁₂H₁₆NO₂: 206.12. found 206.25.

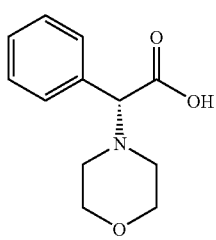

Cap-6

The TFA salt of Cap-6 was synthesized from (R)-2-phenylglycine and 1-bromo-2-(2-bromoethoxy)ethane by using the method of preparation of Cap-5. ¹H NMR (DMSO-d₆, δ=2.5, 500 MHz) δ 12.20 (br s, 1H), 7.50 (m, 5H), 4.92 (s, 1H), 3.78 (app br s, 4H), 3.08 (app br s, 2H), 2.81 (app br s, 2H); RT=0.32 min (Cond. 1); >98%; LC/MS: Anal. Calcd. for [M+H]⁺ C₁₂H₁₆NO₃: 222.11. found 222.20; HRMS: Anal. Calcd. for [M+H]⁺ C₁₂H₁₆NO₃: 222.1130. found 222.1121.

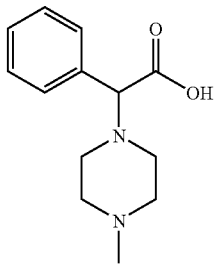

Cap-7
Cap-7a: enantiomer-1
Cap-7b: enantiomer-2

A CH₂Cl₂ (200 mL) solution of p-toluenesulfonyl chloride (8.65 g, 45.4 mmol) was added dropwise to a cooled (−5° C.) CH₂Cl₂ (200 mL) solution of (S)-benzyl 2-hydroxy-2-phenylacetate (10.0 g, 41.3 mmol), triethylamine (5.75 mL, 41.3 mmol) and 4-dimethylaminopyridine (0.504 g, 4.13 mmol), while maintaining the temperature between −5° C. and 0° C. The reaction was stirred at 0° C. for 9 hours, and then stored in a freezer (−25° C.) for 14 hours. It was allowed to thaw to ambient temperature and washed with water (200 mL), 1N HCl (100 mL) and brine (100 mL), dried (MgSO₄), filtered, and concentrated in vacuo to provide benzyl 2-phenyl-2-(tosyloxy)acetate as a viscous oil which solidified upon standing (16.5 g). The chiral integrity of the product was not checked and that product was used for the next step without further purification. ¹H NMR (DMSO-d₆, δ=2.5, 500 MHz) δ 7.78 (d, J=8.6, 2H), 7.43-7.29 (m, 10H), 7.20 (m, 2H), 6.12 (s, 1H), 5.16 (d, J=12.5, 1H), 5.10 (d, J=12.5, 1H), 2.39 (s, 3H). RT=3.00 (Cond. 3); >90% homogeneity index; LC/MS: Anal. Calcd. for [M+H]⁺ C₂₂H₂₀NaO₅S: 419.09. found 419.04.

A THF (75 mL) solution of benzyl 2-phenyl-2-(tosyloxy) acetate (6.0 g, 15.1 mmol), 1-methylpiperazine (3.36 mL, 30.3 mmol) and N,N-diisopropylethylamine (13.2 mL, 75.8 mmol) was heated at 65° C. for 7 hours. The reaction was allowed to cool to ambient temperature and the volatile component was removed in vacuo. The residue was partitioned between ethylacetate and water, and the organic layer was washed with water and brine, dried (MgSO₄), filtered, and concentrated in vacuo. The resulting crude material was purified by flash chromatography (silica gel, ethyl acetate) to provide benzyl 2-(4-methylpiperazin-1-yl)-2-phenylacetate as an orangish-brown viscous oil (4.56 g). Chiral HPLC analysis (Chiralcel OD-H) indicated that the sample is a mixture of enantiomers in a 38.2 to 58.7 ratio. The separation of the enantiomers were effected as follow: the product was dissolved in 120 mL of ethanol/heptane (1:1) and injected (5 mL/injection) on chiral HPLC column (Chiracel OJ, 5 cm ID×50 cm L, 20 μm) eluting with 85:15 Heptane/ethanol at 75 mL/min, and monitored at 220 nm. Enantiomer-1 (1.474 g) and enantiomer-2 (2.2149 g) were retrieved as viscous oil. ¹H NMR (CDCl₃, δ=7.26, 500 MHz) 7.44-7.40 (m, 2H), 7.33-7.24 (m, 6H), 7.21-7.16 (m, 2H), 5.13 (d, J=12.5, 1H), 5.08 (d, J=12.5, 1H), 4.02 (s, 1H), 2.65-2.38 (app br s, 8H), 2.25 (s, 3H). RT=2.10 (Cond. 3); >98% homogeneity index; LC/MS: Anal. Calcd. for [M+H]⁺ C₂₀H₂₅N₂O₂: 325.19. found 325.20.

A methanol (10 mL) solution of either enantiomer of benzyl 2-(4-methylpiperazin-1-yl)-2-phenylacetate (1.0 g, 3.1 mmol) was added to a suspension of 10% Pd/C (120 mg) in methanol (5.0 mL). The reaction mixture was exposed to a balloon of hydrogen, under a careful monitoring, for <50 min. Immediately after the completion of the reaction, the catalyst was filtered through diatomaceous earth (Celite®) and the filtrate was concentrated in vacuo to provide Cap-7, contaminated with phenylacetic acid as a tan foam (867.6 mg; mass is above the theoretical yield). The product was used for the next step without further purification. $^1$H NMR (DMSO-d$_6$, δ=2.5, 500 MHz) δ 7.44-7.37 (m, 2H), 7.37-7.24 (m, 3H), 3.92 (s, 1H), 2.63-2.48 (app. bs, 2H), 2.48-2.32 (m, 6H), 2.19 (s, 3H); RT=0.31 (Cond. 2); >90% homogeneity index; LC/MS: Anal. Calcd. for [M+H]$^+$ C$_{13}$H$_{19}$N$_2$O$_2$: 235.14. found 235.15; HRMS: Anal. Calcd. for [M+H]$^+$ C$_{13}$H$_{19}$N$_2$O$_2$: 235.1447. found 235.1440.

The synthesis of Cap-8 and Cap-9 was conducted according to the synthesis of Cap-7 by using appropriate amines for the SN$_2$ displacement step (i.e., 4-hydroxypiperidine for Cap-8 and (S)-3-fluoropyrrolidine for Cap-9) and modified conditions for the separation of the respective stereoisomeric intermediates, as described below.

Cap-8

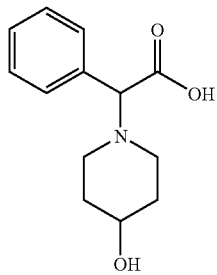

8a: enantiomer-1
8b: enantiomer-2

The enantiomeric separation of the intermediate benzyl 2-(4-hydroxypiperidin-1-yl)-2-phenyl acetate was effected by employing the following conditions: the compound (500 mg) was dissolved in ethanol/heptane (5 mL/45 mL). The resulting solution was injected (5 mL/injection) on a chiral HPLC column (Chiracel OJ, 2 cm ID×25 cm L, 10 μm) eluting with 80:20 heptane/ethanol at 10 mL/min, monitored at 220 nm, to provide 186.3 mg of enantiomer-1 and 209.1 mg of enantiomer-2 as light-yellow viscous oils. These benzyl ester was hydrogenolysed according to the preparation of Cap-7 to provide Cap-8: $^1$H NMR (DMSO-d$_6$, δ=2.5, 500 MHz) 7.40 (d, J=7, 2H), 7.28-7.20 (m, 3H), 3.78 (s 1H), 3.46 (m, 1H), 2.93 (m, 1H), 2.62 (m, 1H), 2.20 (m, 2H), 1.70 (m, 2H), 1.42 (m, 2H). RT=0.28 (Cond. 2); >98% homogeneity index; LC/MS: Anal. Calcd. for [M+H]$^+$ C$_{13}$H$_{18}$NO$_3$: 236.13. found 236.07; HRMS: Calcd. for [M+H]$^+$ C$_{13}$H$_{18}$NO$_3$: 236.1287. found 236.1283.

Cap-9

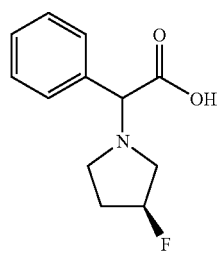

9a: diastereomer-1
9b: diastereomer-2

The diastereomeric separation of the intermediate benzyl 2-((S)-3-fluoropyrrolidin-1-yl)-2-phenylacetate was effected by employing the following conditions: the ester (220 mg) was separated on a chiral HPLC column (Chiracel OJ-H, 0.46 cm ID×25 cm L, 5 μm) eluting with 95% CO$_2$/5% methanol with 0.1% TFA, at 10 bar pressure, 70 mL/min flow rate, and a temperature of 35° C. The HPLC elute for the respective stereoisomers was concentrated, and the residue was dissolved in CH$_2$Cl$_2$ (20 mL) and washed with an aqueous medium (10 mL water+1 mL saturated NaHCO$_3$ solution). The organic phase was dried (MgSO$_4$), filtered, and concentrated in vacuo to provide 92.5 mg of fraction-1 and 59.6 mg of fraction-2. These benzyl esters were hydrogenolysed according to the preparation of Cap-7 to prepare Caps 9a and 9b. Cap-9a (diastereomer-1; the sample is a TFA salt as a result of purification on a reverse phase HPLC using H$_2$O/methanol/TFA solvent): $^1$H NMR (DMSO-d$_6$, δ=2.5, 400 MHz) 7.55-7.48 (m, 5H), 5.38 (d of m, J=53.7, 1H), 5.09 (br s, 1H), 3.84-2.82 (br m, 4H), 2.31-2.09 (m, 2H). RT=0.42 (Cond. 1); >95% homogeneity index; LC/MS: Anal. Calcd. for [M+H]$^+$ C$_{12}$H$_{15}$FNO$_2$: 224.11. found 224.14; Cap-9b (diastereomer-2): $^1$H NMR (DMSO-d$_6$, δ=2.5, 400 MHz) 7.43-7.21 (m, 5H), 5.19 (d of m, J=55.9, 1H), 3.97 (s, 1H), 2.95-2.43 (m, 4H), 2.19-1.78 (m, 2H). RT=0.44 (Cond. 1); LC/MS: Anal. Calcd. for [M+H]$^+$ C$_{12}$H$_{15}$FNO$_2$: 224.11. found 224.14.

Cap-10

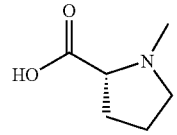

To a solution of D-proline (2.0 g, 17 mmol) and formaldehyde (2.0 mL of 37% wt. in H$_2$O) in methanol (15 mL) was added a suspension of 10% Pd/C (500 mg) in methanol (5 mL). The mixture was stirred under a balloon of hydrogen for 23 hours. The reaction mixture was filtered through diatomaceous earth (Celite®) and concentrated in vacuo to provide Cap-10 as an off-white solid (2.15 g). $^1$H NMR (DMSO-d$_6$, δ=2.5, 500 MHz) 3.42 (m, 1H), 3.37 (dd, J=9.4, 6.1, 1H), 2.85-2.78 (m, 1H), 2.66 (s, 3H), 2.21-2.13 (m, 1H), 1.93-1.84 (m, 2H), 1.75-1.66 (m, 1H). RT=0.28 (Cond. 2); >98% homogeneity index; LC/MS: Anal. Calcd. for [M+H]$^+$ C$_6$H$_{12}$NO$_2$: 130.09. found 129.96.

Cap-11

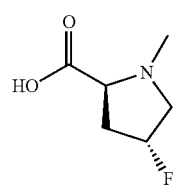

A mixture of (2S,4R)-4-fluoropyrrolidine-2-carboxylic acid (0.50 g, 3.8 mmol), formaldehyde (0.5 mL of 37% wt. in H$_2$O), 12 N HCl (0.25 mL) and 10% Pd/C (50 mg) in methanol (20 mL) was stirred under a balloon of hydrogen for 19 hours. The reaction mixture was filtered through diatomaceous earth (Celite®) and the filtrate was concentrated in vacuo. The residue was recrystallized from isopropanol to provide the HCl salt of Cap-11 as a white solid (337.7 mg). $^1$H NMR (DMSO-d$_6$, δ=2.5, 500 MHz) 5.39 (d m, J=53.7, 1H), 4.30 (m, 1H), 3.90 (ddd, J=31.5, 13.5, 4.5, 1H), 3.33 (dd, J=25.6, 13.4, 1H), 2.85 (s, 3H), 2.60-2.51 (m, 1H), 2.39-2.26 (m, 1H). RT=0.28 (Cond. 2); >98% homogeneity index; LC/MS: Anal. Calcd. for [M+H]$^+$ C$_6$H$_{11}$FNO$_2$: 148.08. found 148.06.

Cap-12

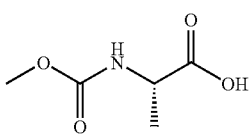

L-Alanine (2.0 g, 22.5 mmol) was dissolved in 10% aqueous sodium carbonate solution (50 mL), and a THF (50 mL) solution of methyl chloroformate (4.0 mL) was added to it. The reaction mixture was stirred under ambient conditions for 4.5 hours and concentrated in vacuo. The resulting white solid was dissolved in water and acidified with 1N HCl to a pH~2-3. The resulting solutions was extracted with ethyl acetate (3×100 mL), and the combined organic phase was dried ($Na_2SO_4$), filtered, and concentrated in vacuo to provide a colorless oil (2.58 g). 500 mg of this material was purified by a reverse phase HPLC ($H_2O$/methanol/TFA) to provide 150 mg of Cap-12 as a colorless oil. $^1$H NMR (DMSO-$d_6$, δ=2.5, 500 MHz) 7.44 (d, J=7.3, 0.8H), 7.10 (br s, 0.2H), 3.97 (m, 1H), 3.53 (s, 3H), 1.25 (d, J=7.3, 3H).

Cap-13

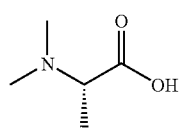

A mixture of L-alanine (2.5 g, 28 mmol), formaldehyde (8.4 g, 37 wt. %), 1N HCl (30 mL) and 10% Pd/C (500 mg) in methanol (30 mL) was stirred under a hydrogen atmosphere (50 psi) for 5 hours. The reaction mixture was filtered through diatomaceous earth (Celite®) and the filtrate was concentrated in vacuo to provide the HCl salt of Cap-13 as an oil which solidified upon standing under vacuum (4.4 g; the mass is above theoretical yield). The product was used without further purification. $^1$H NMR (DMSO-$d_6$, δ=2.5, 500 MHz) δ 12.1 (br s, 1H), 4.06 (q, J=7.4, 1H), 2.76 (s, 6H), 1.46 (d, J=7.3, 3H).

Cap-14

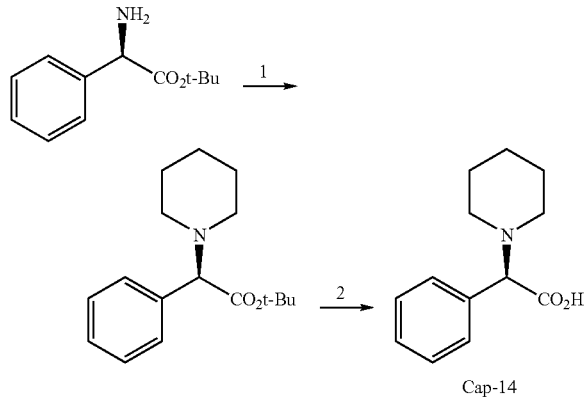

Step 1: A mixture of (R)-(−)-D-phenylglycine tert-butyl ester (3.00 g, 12.3 mmol), $NaBH_3CN$ (0.773 g, 12.3 mmol), KOH (0.690 g, 12.3 mmol) and acetic acid (0.352 mL, 6.15 mmol) were stirred in methanol at 0° C. To this mixture was added glutaric dialdehyde (2.23 mL, 12.3 mmol) dropwise over 5 minutes. The reaction mixture was stirred as it was allowed to warm to ambient temperature and stirring was continued at the same temperature for 16 hours. The solvent was subsequently removed and the residue was partitioned with 10% aqueous NaOH and ethyl acetate. The organic phase was separated, dried ($MgSO_4$), filtered and concentrated to dryness to provide a clear oil. This material was purified by reverse-phase preparative HPLC (Primesphere C-18, 30×100 mm; $CH_3CN$—$H_2O$-0.1% TFA) to give the intermediate ester (2.70 g, 56%) as a clear oil. $^1$HNMR (400 MHz, $CDCl_3$) δ 7.53-7.44 (m, 3H), 7.40-7.37 (m, 2H), 3.87 (d, J=10.9 Hz, 1H), 3.59 (d, J=10.9 Hz, 1H), 2.99 (t, J=11.2 Hz, 1H), 2.59 (t, J=11.4 Hz, 1H), 2.07-2.02 (m, 2H), 1.82 (d, J=1.82 Hz, 3H), 1.40 (s, 9H). LC/MS: Anal. Calcd. for $C_{17}H_{25}NO_2$: 275. found: 276 (M+H)$^+$.

Step 2: To a stirred solution of the intermediate ester (1.12 g, 2.88 mmol) in dichloromethane (10 mL) was added TFA (3 mL). The reaction mixture was stirred at ambient temperature for 4 hours and then it was concentrated to dryness to give a light yellow oil. The oil was purified using reverse-phase preparative HPLC (Primesphere C-18, 30×100 mm; $CH_3CN$—$H_2O$-0.1% TFA). The appropriate fractions were combined and concentrated to dryness in vacuo. The residue was then dissolved in a minimum amount of methanol and applied to applied to MCX LP extraction cartridges (2×6 g). The cartridges were rinsed with methanol (40 mL) and then the desired compound was eluted using 2M ammonia in methanol (50 mL). Product-containing fractions were combined and concentrated and the residue was taken up in water. Lyophilization of this solution provided the title compound (0.492 g, 78%) as a light yellow solid. $^1$HNMR (DMSO-$d_6$) δ 7.50 (s, 5H), 5.13 (s, 1H), 3.09 (br s, 2H), 2.92-2.89 (m, 2H), 1.74 (m, 4H), 1.48 (br s, 2H). LC/MS: Anal. Calcd. for $C_{13}H_{17}NO_2$: 219. found: 220 (M+H)$^+$.

Cap-15

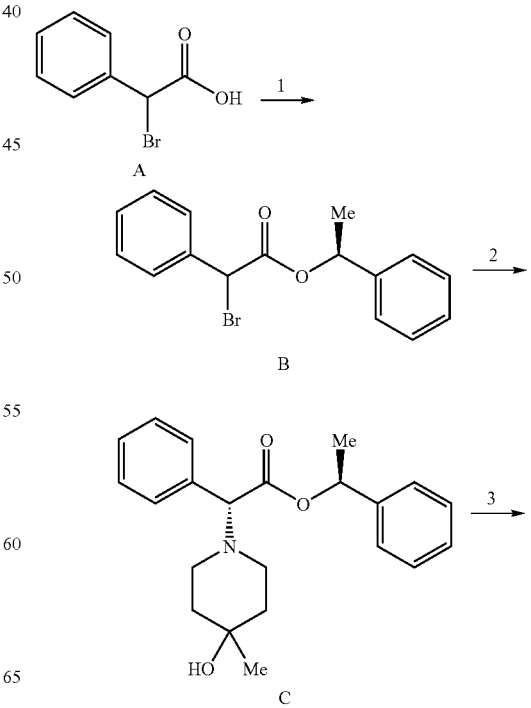

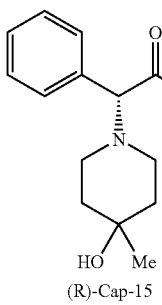

(R)-Cap-15

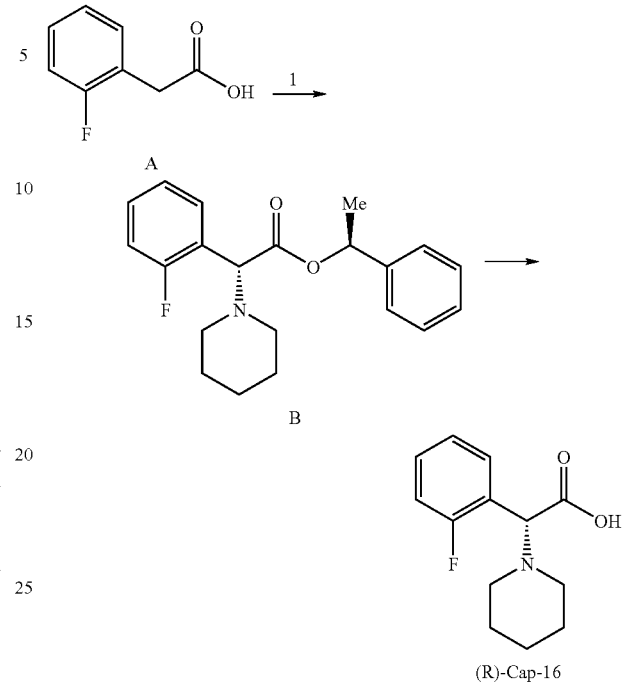

(R)-Cap-16

Step 1; (S)-1-Phenylethyl 2-bromo-2-phenylacetate: To a mixture of α-bromophenylacetic acid (10.75 g, 0.050 mol), (S)-(−)-1-phenylethanol (7.94 g, 0.065 mol) and DMAP (0.61 g, 5.0 mmol) in dry dichloromethane (100 mL) was added solid EDCI (12.46 g, 0.065 mol) all at once. The resulting solution was stirred at room temperature under Ar for 18 hours and then it was diluted with ethyl acetate, washed ($H_2O \times 2$, brine), dried ($Na_2SO_4$), filtered, and concentrated to give a pale yellow oil. Flash chromatography ($SiO_2$/hexane-ethyl acetate, 4:1) of this oil provided the title compound (11.64 g, 73%) as a white solid. $^1$HNMR (400 MHz, $CDCl_3$) δ 7.53-7.17 (m, 10H), 5.95 (q, J=6.6 Hz, 0.5H), 5.94 (q, J=6.6 Hz, 0.5H), 5.41 (s, 0.5H), 5.39 (s, 0.5H), 1.58 (d, J=6.6 Hz, 1.5H), 1.51 (d, J=6.6 Hz, 1.5H).

Step 2; (S)-1-Phenylethyl (R)-2-(4-hydroxy-4-methylpiperidin-1-yl)-2-phenylacetate: To a solution of (S)-1-phenylethyl 2-bromo-2-phenylacetate (0.464 g, 1.45 mmol) in THF (8 mL) was added triethylamine (0.61 mL, 4.35 mmol), followed by tetrabutylammonium iodide (0.215 g, 0.58 mmol). The reaction mixture was stirred at room temperature for 5 minutes and then a solution of 4-methyl-4-hydroxypiperidine (0.251 g, 2.18 mmol) in THF (2 mL) was added. The mixture was stirred for 1 hour at room temperature and then it was heated at 55-60° C. (oil bath temperature) for 4 hours. The cooled reaction mixture was then diluted with ethyl acetate (30 mL), washed ($H_2O \times 2$, brine), dried ($MgSO_4$), filtered and concentrated. The residue was purified by silica gel chromatography (0-60% ethyl acetate-hexane) to provide first the (S,R)-isomer of the title compound (0.306 g, 60%) as a white solid and then the corresponding (S,S)-isomer (0.120 g, 23%), also as a white solid. (S,R)-isomer: $^1$HNMR ($CD_3OD$) δ 7.51-7.45 (m, 2H), 7.41-7.25 (m, 8H), 5.85 (q, J=6.6 Hz, 1H), 4.05 (s, 1H), 2.56-2.45 (m, 2H), 2.41-2.29 (m, 2H), 1.71-1.49 (m, 4H), 1.38 (d, J=6.6 Hz, 3H), 1.18 (s, 3H). LCMS: Anal. Calcd. for $C_{22}H_{27}NO_3$: 353. found: 354 (M+H)$^+$. (S,S)-isomer: $^1$HNMR ($CD_3OD$) δ 7.41-7.30 (m, 5H), 7.20-7.14 (m, 3H), 7.06-7.00 (m, 2H), 5.85 (q, J=6.6 Hz, 1H), 4.06 (s, 1H), 2.70-2.60 (m, 1H), 2.51 (dt, J=6.6, 3.3 Hz, 1H), 2.44-2.31 (m, 2H), 1.75-1.65 (m, 1H), 1.65-1.54 (m, 3H), 1.50 (d, J=6.8 Hz, 3H), 1.20 (s, 3H). LCMS: Anal. Calcd. for $C_{22}H_{27}NO_3$: 353. found: 354 (M+H)$^+$.

Step 3; (R)-2-(4-Hydroxy-4-methylpiperidin-1-yl)-2-phenylacetic acid: To a solution of (S)-1-phenylethyl (R)-2-(4-hydroxy-4-methylpiperidin-1-yl)-2-phenylacetate (0.185 g, 0.52 mmol) in dichloromethane (3 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; $CH_3CN$—$H_2O$-0.1% TFA) to give the title compound (as TFA salt) as a pale bluish solid (0.128 g, 98%). LCMS: Anal. Calcd. for $C_{14}H_{19}NO_3$: 249. found: 250 (M+H)$^+$.

Step 1; (S)-1-Phenylethyl 2-(2-fluorophenyl)acetate: A mixture of 2-fluorophenylacetic acid (5.45 g, 35.4 mmol), (S)-1-phenylethanol (5.62 g, 46.0 mmol), EDCI (8.82 g, 46.0 mmol) and DMAP (0.561 g, 4.60 mmol) in $CH_2Cl_2$ (100 mL) was stirred at room temperature for 12 hours. The solvent was then concentrated and the residue partitioned with $H_2O$-ethyl acetate. The phases were separated and the aqueous layer back-extracted with ethyl acetate (2×). The combined organic phases were washed ($H_2O$, brine), dried ($Na_2SO_4$), filtered, and concentrated in vacuo. The residue was purified by silica gel chromatography (Biotage/0-20% ethyl acetate-hexane) to provide the title compound as a colorless oil (8.38 g, 92%). $^1$HNMR (400 MHz, $CD_3OD$) δ 7.32-7.23 (m, 7H), 7.10-7.04 (m, 2), 5.85 (q, J=6.5 Hz, 1H), 3.71 (s, 2H), 1.48 (d, J=6.5 Hz, 3H).

Step 2; (R)—((S)-1-Phenylethyl) 2-(2-fluorophenyl)-2-(piperidin-1-yl)acetate: To a solution of (S)-1-phenylethyl 2-(2-fluorophenyl)acetate (5.00 g, 19.4 mmol) in THF (1200 mL) at 0° C. was added DBU (6.19 g, 40.7 mmol) and the solution was allowed to warm to room temperature while stirring for 30 minutes. The solution was then cooled to −78° C. and a solution of $CBr_4$ (13.5 g, 40.7 mmol) in THF (100 mL) was added and the mixture was allowed to warm to −10° C. and stirred at this temperature for 2 hours. The reaction mixture was quenched with saturated aq. $NH_4Cl$ and the layers were separated. The aqueous layer was back-extracted with ethyl acetate (2×) and the combined organic phases were washed ($H_2O$, brine), dried ($Na_2SO_4$), filtered, and concentrated in vacuo. To the residue was added piperidine (5.73 mL, 58.1 mmol) and the solution was stirred at room temperature for 24 hours. The volatiles were then concentrated in vacuo and the residue was purified by silica gel chromatography (Biotage/0-30% diethyl ether-hexane) to provide a pure mixture of diastereomers (2:1 ratio by $^1$HNMR) as a yellow oil (2.07 g, 31%), along with unreacted starting material (2.53 g, 51%). Further chromatography of the diastereomeric mixture (Biotage/0-10% diethyl ether-toluene) provided the title compound as a colorless oil (0.737 g, 11%). $^1$HNMR (400 MHz, CD$_3$OD) δ 7.52 (ddd, J=9.4, 7.6, 1.8 Hz, 1H), 7.33-7.40 (m, 1), 7.23-7.23 (m, 4H), 7.02-7.23 (m, 4H), 5.86 (q, J=6.6 Hz, 1H), 4.45 (s, 1H), 2.39-2.45 (m, 4H), 1.52-1.58 (m, 4H), 1.40-1.42 (m, 1H), 1.38 (d, J=6.6 Hz, 3H). LCMS: Anal. Calcd. for C$_{21}$H$_{24}$FNO$_2$: 341. found: 342 (M+H)$^+$.

Step 3; (R)-2-(2-fluorophenyl)-2-(piperidin-1-yl)acetic acid: A mixture of (R)—((S)-1-phenylethyl) 2-(2-fluorophenyl)-2-(piperidin-1-yl)acetate (0.737 g, 2.16 mmol) and 20% Pd(OH)$_2$/C (0.070 g) in ethanol (30 mL) was hydrogenated at room temperature and atmospheric pressure (H$_2$ balloon) for 2 hours. The solution was then purged with Ar, filtered through diatomaceous earth (Celite®), and concentrated in vacuo. This provided the title compound as a colorless solid (0.503 g, 98%). $^1$HNMR (400 MHz, CD$_3$OD) δ 7.65 (ddd, J=9.1, 7.6, 1.5 Hz, 1H), 7.47-7.53 (m, 1H), 7.21-7.30 (m, 2H), 3.07-3.13 (m, 4H), 1.84 (br s, 4H), 1.62 (br s, 2H). LCMS: Anal. Calcd. for C$_{13}$H$_{16}$FNO$_2$: 237. found: 238 (M+H)$^+$.

formed using supercritical fluid chromatography (Chiralcel OJ-H, 30×250 mm; 20% ethanol in CO$_2$ at 35° C.), to give first the (R)-isomer of the title compound (0.534 g, 27%) as a yellow oil and then the corresponding (S)-isomer (0.271 g, 14%), also as a yellow oil. (S,R)-isomer: $^1$HNMR (400 MHz, CD$_3$OD) δ 7.55-7.47 (m, 4H), 7.44-7.25 (m, 10H), 7.25-7.17 (m, 1H), 5.88 (q, J=6.6 Hz, 1H), 4.12 (s, 1H), 2.82-2.72 (m, 1H), 2.64 (dt, J=11.1, 2.5 Hz, 1H), 2.58-2.52 (m, 1H), 2.40 (dt, J=11.1, 2.5 Hz, 1H), 2.20 (dt, J=12.1, 4.6 Hz, 1H), 2.10 (dt, J=12.1, 4.6 Hz, 1H), 1.72-1.57 (m, 2H), 1.53 (d, J=6.5 Hz, 3H). LCMS: Anal. Calcd. for C$_{27}$H$_{29}$NO$_3$: 415. found: 416 (M+H)$^+$; (S,S)-isomer: $^1$HNMR (400 MHz, CD$_3$OD) δ 7.55-7.48 (m, 2H), 7.45-7.39 (m, 2H), 7.38-7.30 (m, 5H), 7.25-7.13 (m, 4H), 7.08-7.00 (m, 2H), 5.88 (q, J=6.6 Hz, 1H), 4.12 (s, 1H), 2.95-2.85 (m, 1H), 2.68 (dt, J=11.1, 2.5 Hz, 1H), 2.57-2.52 (m, 1H), 2.42 (dt, J=11.1, 2.5 Hz, 1H), 2.25 (dt, J=12.1, 4.6 Hz, 1H), 2.12 (dt, J=12.1, 4.6 Hz, 1H), 1.73 (dd, J=13.6, 3.0 Hz, 1H), 1.64 (dd, J=13.6, 3.0 Hz, 1H), 1.40 (d, J=6.6 Hz, 3H). LCMS: Anal. Calcd. for C$_{27}$H$_{29}$NO$_3$: 415. found: 416 (M+H)$^+$.

The following esters were prepared in similar fashion employing step 1 in the synthesis of Cap-17.

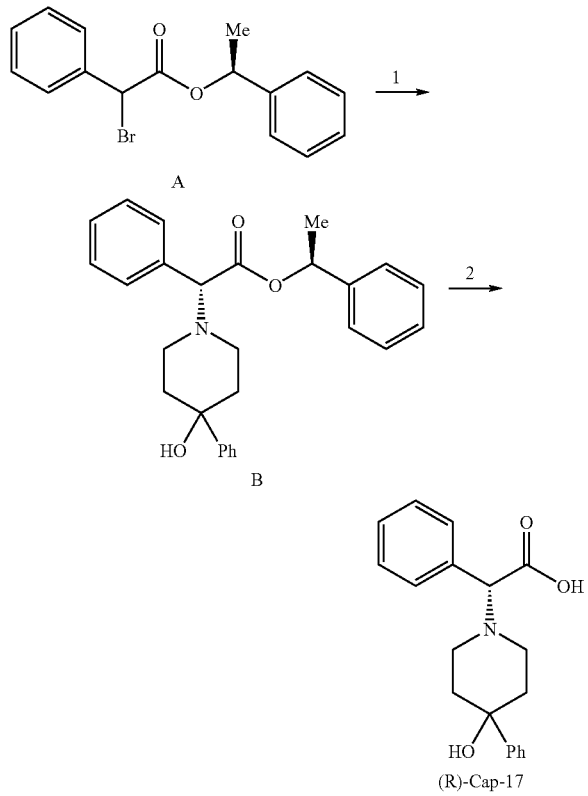

Cap-17

(R)-Cap-17

Step 1; (S)-1-Phenylethyl (R)-2-(4-hydroxy-4-phenylpiperidin-1-yl)-2-phenylacetate: To a solution of (S)-1-phenylethyl 2-bromo-2-phenylacetate (1.50 g, 4.70 mmol) in THF (25 mL) was added triethylamine (1.31 mL, 9.42 mmol), followed by tetrabutylammonium iodide (0.347 g, 0.94 mmol). The reaction mixture was stirred at room temperature for 5 minutes and then a solution of 4-phenyl-4-hydroxypiperidine (1.00 g, 5.64 mmol) in THF (5 mL) was added. The mixture was stirred for 16 hours and then it was diluted with ethyl acetate (100 mL), washed (H$_2$O 2, brine), dried (MgSO$_4$), filtered and concentrated. The residue was purified on a silica gel column (0-60% ethyl acetate-hexane) to provide an approximately 2:1 mixture of diastereomers, as judged by $^1$HNMR. Separation of these isomers was per-

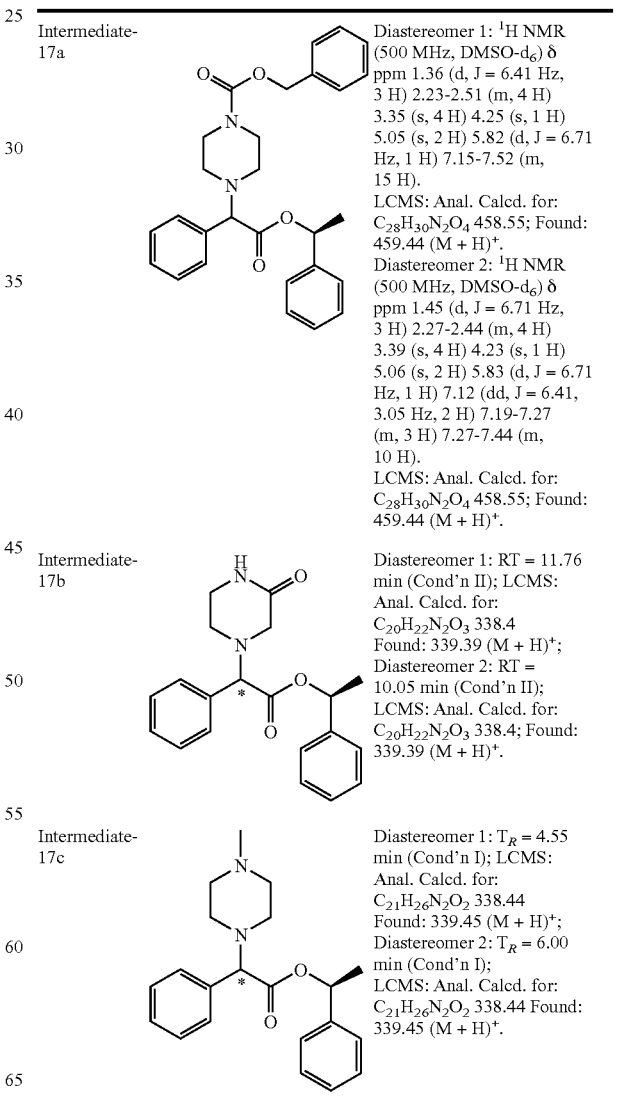

| | | |
|---|---|---|
| Intermediate-17a | | Diastereomer 1: $^1$H NMR (500 MHz, DMSO-d$_6$) δ ppm 1.36 (d, J = 6.41 Hz, 3 H) 2.23-2.51 (m, 4 H) 3.35 (s, 4 H) 4.25 (s, 1 H) 5.05 (s, 2 H) 5.82 (d, J = 6.71 Hz, 1 H) 7.15-7.52 (m, 15 H). LCMS: Anal. Calcd. for: C$_{28}$H$_{30}$N$_2$O$_4$ 458.55; Found: 459.44 (M + H)$^+$. Diastereomer 2: $^1$H NMR (500 MHz, DMSO-d$_6$) δ ppm 1.45 (d, J = 6.71 Hz, 3 H) 2.27-2.44 (m, 4 H) 3.39 (s, 4 H) 4.23 (s, 1 H) 5.06 (s, 2 H) 5.83 (d, J = 6.71 Hz, 1 H) 7.12 (dd, J = 6.41, 3.05 Hz, 2 H) 7.19-7.27 (m, 3 H) 7.27-7.44 (m, 10 H). LCMS: Anal. Calcd. for: C$_{28}$H$_{30}$N$_2$O$_4$ 458.55; Found: 459.44 (M + H)$^+$. |
| Intermediate-17b | | Diastereomer 1: RT = 11.76 min (Cond'n II); LCMS: Anal. Calcd. for: C$_{20}$H$_{22}$N$_2$O$_3$ 338.4 Found: 339.39 (M + H)$^+$; Diastereomer 2: RT = 10.05 min (Cond'n II); LCMS: Anal. Calcd. for: C$_{20}$H$_{22}$N$_2$O$_3$ 338.4; Found: 339.39 (M + H)$^+$. |
| Intermediate-17c | | Diastereomer 1: T$_R$ = 4.55 min (Cond'n I); LCMS: Anal. Calcd. for: C$_{21}$H$_{26}$N$_2$O$_2$ 338.44 Found: 339.45 (M + H)$^+$; Diastereomer 2: T$_R$ = 6.00 min (Cond'n I); LCMS: Anal. Calcd. for: C$_{21}$H$_{26}$N$_2$O$_2$ 338.44 Found: 339.45 (M + H)$^+$. |

| Intermediate-17d | 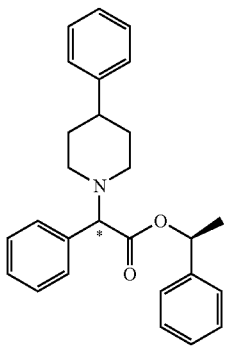 | Diastereomer 1: RT = 7.19 min (Cond'n I); LCMS: Anal. Calcd. for: $C_{27}H_{29}NO_2$ 399.52 Found: 400.48 (M + H)+; Diastereomer 2: RT = 9.76 min (Cond'n I); LCMS: Anal. Calcd. for: $C_{27}H_{29}NO_2$ 399.52 Found: 400.48 (M + H)+. |
|---|---|---|

Chiral SFC Conditions for Determining Retention Time for Intermediates 17b-17d

Condition 1
Column: Chiralpak AD-H Column, 4.6×250 mm, 5 μm
Solvents: 90% $CO_2$—10% methanol with 0.1% DEA
Temp: 35° C.
Pressure: 150 bar
Flow rate: 2.0 mL/min.
UV monitored @220 nm
Injection: 1.0 mg/3 mL methanol Condition 2
Column: Chiralcel OD-H Column, 4.6×250 mm, 5 μm
Solvents: 90% $CO_2$—10% methanol with 0.1% DEA
Temp: 35° C.
Pressure: 150 bar
Flow rate: 2.0 mL/min.
UV monitored @220 nm
Injection: 1.0 mg/mL methanol Cap-17, Step 2; (R)-2-(4-Hydroxy-4-phenylpiperidin-1-yl)-2-phenylacetic acid: To a solution of (S)-1-phenylethyl (R)-2-(4-hydroxy-4-phenylpiperidin-1-yl)-2-phenylacetate (0.350 g, 0.84 mmol) in dichloromethane (5 mL) was added trifluoroacetic acid (1 mL) and the mixture was stirred at room temperature for 2 hours. The volatiles were subsequently removed in vacuo and the residue was purified by reverse-phase preparative HPLC (Primesphere C-18, 20×100 mm; $CH_3CN$—$H_2O$-0.1% TFA) to give the title compound (as TFA salt) as a white solid (0.230 g, 88%). LCMS: Anal. Calcd. for $C_{19}H_{21}NO_3$: 311. found: 312 (M+H)+.

The following carboxylic acids were prepared in a similar fashion:

| Cap-17a | 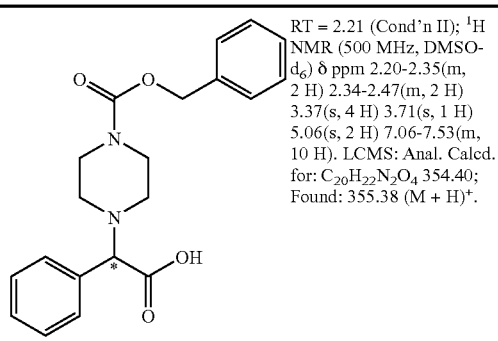 | RT = 2.21 (Cond'n II); $^1$H NMR (500 MHz, DMSO-$d_6$) δ ppm 2.20-2.35(m, 2 H) 2.34-2.47(m, 2 H) 3.37(s, 4 H) 3.71(s, 1 H) 5.06(s, 2 H) 7.06-7.53(m, 10 H). LCMS: Anal. Calcd. for: $C_{20}H_{22}N_2O_4$ 354.40; Found: 355.38 (M + H)+. |
|---|---|---|
| Cap-17b | 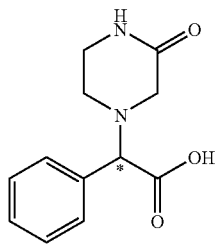 | RT = 0.27 (Cond'n III); LCMS: Anal. Calcd. for: $C_{12}H_{14}N_2O_3$ 234.25; Found: 235.22 (M + H)+. |
| Cap-17c | 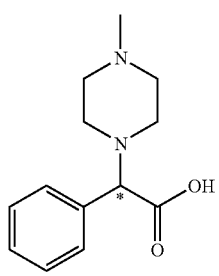 | RT = 0.48 (Cond'n II); LCMS: Anal. Calcd. for: $C_{13}N_{18}N_2O_2$ 234.29; Found: 235.31 (M + H)+. |
| Cap-17d | 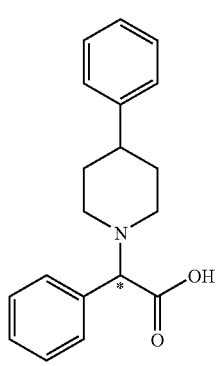 | RT = 2.21 (Cond'n I); LCMS: Anal. Calcd. for; $C_{19}H_{21}NO_2$ 295.38; Found: 296.33 (M + H)+. |

LCMS Conditions for Determining Retention Time for Caps 17a-17d

Condition 1
Column: Phenomenex-Luna 4.6×50 mm S10
Start % B=0
Final % B=100
Gradient Time=4 min
Flow Rate=4 mL/min
Wavelength=220
Solvent A=10% methanol—90% $H_2O$—0.1% TFA
Solvent B=90% methanol—10% $H_2O$—0.1% TFA Condition 2
Column: Waters-Sunfire 4.6×50 mm S5
Start % B=0
Final % B=100
Gradient Time=2 min
Flow Rate=4 mL/min
Wavelength=220
Solvent A=10% methanol—90% $H_2O$—0.1% TFA
Solvent B=90% methanol—10% $H_2O$—0.1% TFA Condition 3
Column: Phenomenex 10μ 3.0×50 mm
Start % B=0
Final % B=100
Gradient Time=2 min
Flow Rate=4 mL/min
Wavelength=220
Solvent A=10% methanol—90% $H_2O$—0.1% TFA
Solvent B=90% methanol—10% $H_2O$—0.1% TFA

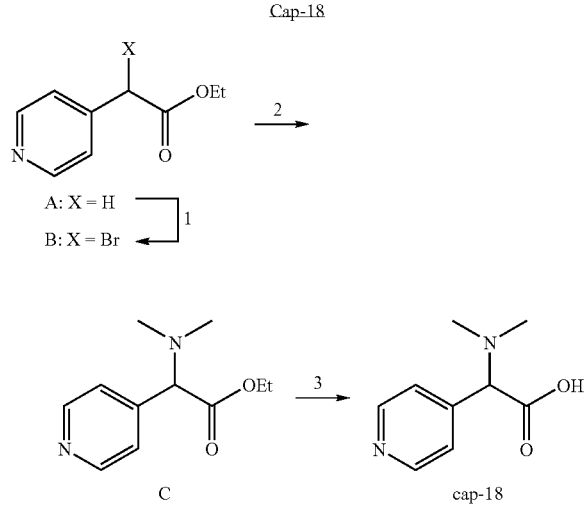

Cap-18

A: X = H
B: X = Br

C → cap-18

Step 1; (R,S)-Ethyl 2-(4-pyridyl)-2-bromoacetate: To a solution of ethyl 4-pyridylacetate (1.00 g, 6.05 mmol) in dry THF (150 mL) at 0° C. under argon was added DBU (0.99 mL, 6.66 mmol). The reaction mixture was allowed to warm to room temperature over 30 minutes and then it was cooled to −78° C. To this mixture was added $CBr_4$ (2.21 g, 6.66 mmol) and stirring was continued at −78° C. for 2 hours. The reaction mixture was then quenched with sat. aq. $NH_4Cl$ and the phases were separated. The organic phase was washed (brine), dried ($Na_2SO_4$), filtered, and concentrated in vacuo. The resulting yellow oil was immediately purified by flash chromatography ($SiO_2$/hexane-ethyl acetate, 1:1) to provide the title compound (1.40 g, 95%) as a somewhat unstable yellow oil. $^1$HNMR (400 MHz, $CDCl_3$) δ 8.62 (dd, J=4.6, 1.8 Hz, 2H), 7.45 (dd, J=4.6, 1.8 Hz, 2H), 5.24 (s, 1H), 4.21-4.29 (m, 2H), 1.28 (t, J=7.1 Hz, 3H). LCMS: Anal. Calcd. for $C_9H_{10}BrNO_2$: 242, 244. found: 243, 245 (M+H)$^+$.

Step 2; (R,S)-Ethyl 2-(4-pyridyl)-2-(N,N-dimethylamino) acetate: To a solution of (R,S)-ethyl 2-(4-pyridyl)-2-bromoacetate (1.40 g, 8.48 mmol) in DMF (10 mL) at room temperature was added dimethylamine (2M in THF, 8.5 mL, 17.0 mmol). After completion of the reaction (as judged by tlc) the volatiles were removed in vacuo and the residue was purified by flash chromatography (Biotage, 40+M $SiO_2$ column; 50%-100% ethyl acetate-hexane) to provide the title compound (0.539 g, 31%) as a light yellow oil. $^1$HNMR (400 MHz, $CDCl_3$) δ 8.58 (d, J=6.0 Hz, 2H), 7.36 (d, J=6.0 Hz, 2H), 4.17 (m, 2H), 3.92 (s, 1H), 2.27 (s, 6H), 1.22 (t, J=7.0 Hz). LCMS: Anal. Calcd. for $C_{11}H_{16}N_2O_2$: 208. found: 209 (M+H)$^+$.

Step 3; (R,S)-2-(4-Pyridyl)-2-(N,N-dimethylamino)acetic acid: To a solution of (R,S)-ethyl 2-(4-pyridyl)-2-(N,N-dimethylamino)acetate (0.200 g, 0.960 mmol) in a mixture of THF-methanol-$H_2O$ (1:1:1, 6 mL) was added powdered LiOH (0.120 g, 4.99 mmol) at room temperature. The solution was stirred for 3 hours and then it was acidified to pH 6 using 1N HCl. The aqueous phase was washed with ethyl acetate and then it was lyophilized to give the dihydrochloride of the title compound as a yellow solid (containing LiCl). The product was used as such in subsequent steps. $^1$HNMR (400 MHz, DMSO-$d_6$) δ 8.49 (d, J=5.7 Hz, 2H), 7.34 (d, J=5.7 Hz, 2H), 3.56 (s, 1H), 2.21 (s, 6H).

The following examples were prepared in similar fashion using the method described in Example 4;

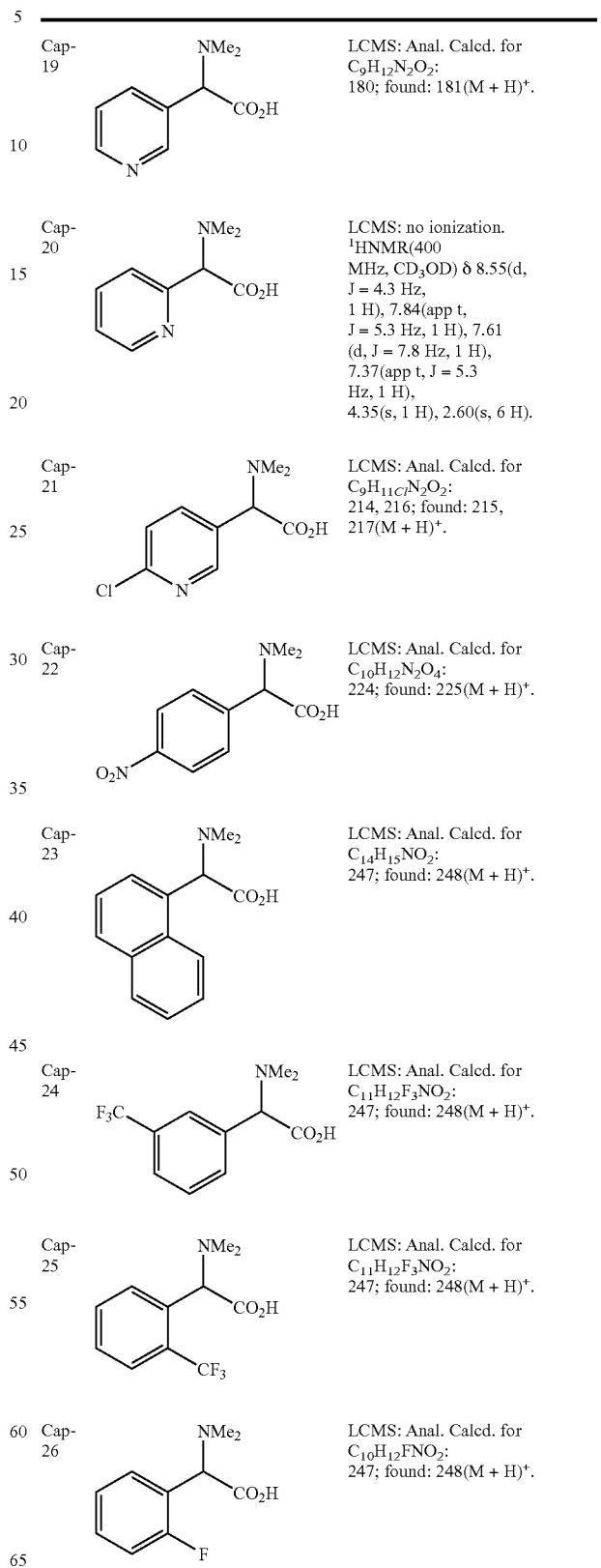

| Cap-19 | LCMS: Anal. Calcd. for $C_9H_{12}N_2O_2$: 180; found: 181(M + H)$^+$. |
|---|---|
| Cap-20 | LCMS: no ionization. $^1$HNMR(400 MHz, $CD_3OD$) δ 8.55(d, J = 4.3 Hz, 1 H), 7.84(app t, J = 5.3 Hz, 1 H), 7.61 (d, J = 7.8 Hz, 1 H), 7.37(app t, J = 5.3 Hz, 1 H), 4.35(s, 1 H), 2.60(s, 6 H). |
| Cap-21 | LCMS: Anal. Calcd. for $C_9H_{11}ClN_2O_2$: 214, 216; found: 215, 217(M + H)$^+$. |
| Cap-22 | LCMS: Anal. Calcd. for $C_{10}H_{12}N_2O_4$: 224; found: 225(M + H)$^+$. |
| Cap-23 | LCMS: Anal. Calcd. for $C_{14}H_{15}NO_2$: 247; found: 248(M + H)$^+$. |
| Cap-24 | LCMS: Anal. Calcd. for $C_{11}H_{12}F_3NO_2$: 247; found: 248(M + H)$^+$. |
| Cap-25 | LCMS: Anal. Calcd. for $C_{11}H_{12}F_3NO_2$: 247; found: 248(M + H)$^+$. |
| Cap-26 | LCMS: Anal. Calcd. for $C_{10}H_{12}FNO_2$: 247; found: 248(M + H)$^+$. |

-continued

| | | |
|---|---|---|
| Cap-27 | [structure: 3-F-C6H4-CH(NMe2)-CO2H] | LCMS: Anal. Calcd. for C10H12FNO2: 247; found: 248(M + H)+. |
| Cap-28 | [structure: 3-Cl-C6H4-CH(NMe2)-CO2H] | LCMS: Anal. Calcd. for C10H12ClNO2: 213, 215; found: 214, 217(M + H)+. |
| Cap-29 | [structure: 2-Cl-C6H4-CH(NMe2)-CO2H] | LCMS: Anal. Calcd. for C10H12ClNO2: 213, 215; found: 214, 217(M + H)+. |
| Cap-30 | [structure: 4-Cl-C6H4-CH(NMe2)-CO2H] | LCMS: Anal. Calcd. for C10H12ClNO2: 213, 215; found: 214, 217(M + H)+. |
| Cap-31 | [structure: 2-methylthiazol-4-yl-CH(NMe2)-CO2H] | LCMS: Anal. Calcd. for C8H11N2O2S: 200; found: 201(M + H)+. |
| Cap-32 | [structure: thiophen-2-yl-CH(NMe2)-CO2H] | LCMS: Anal. Calcd. for C8H11NO2S: 185; found: 186(M + H)+. |
| Cap-33 | [structure: thiophen-3-yl-CH(NMe2)-CO2H] | LCMS: Anal. Calcd. for C8H11NO2S: 185; found: 186(M + H)+. |
| Cap-34 | [structure: benzo[d]isoxazol-3-yl-CH(NMe2)-CO2H] | LCMS: Anal. Calcd. for C11H12N2O3: 220; found: 221(M + H)+. |
| Cap-35 | [structure: benzo[b]thiophen-3-yl-CH(NMe2)-CO2H] | LCMS: Anal. Calcd. for C12H13NO2S: 235; found: 236(M + H)+. |
| Cap-36 | [structure: 2-methylbenzothiazol-5-yl-CH(NMe2)-CO2H] | LCMS: Anal. Calcd. for C12H14N2O2S: 250; found: 251(M + H)+. |

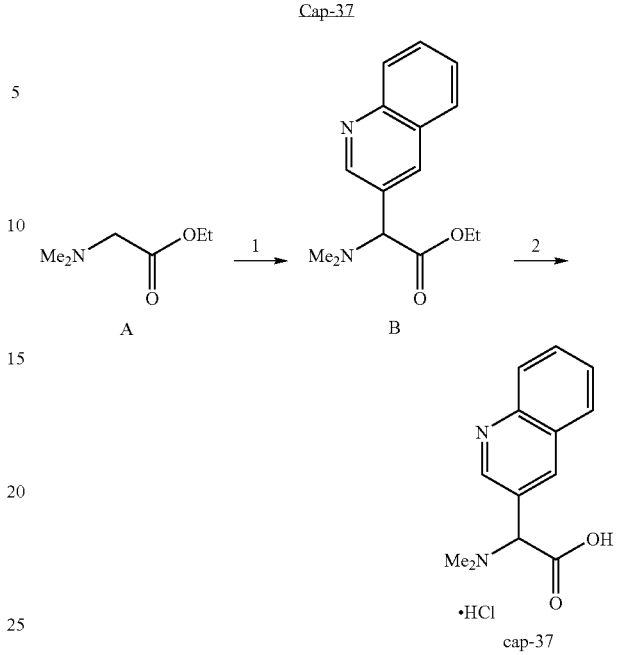

Cap-37

Step 1; (R,S)-Ethyl 2-(quinolin-3-yl)-2-(N,N-dimethylamino)-acetate: A mixture of ethyl N,N-dimethylaminoacetate (0.462 g, 3.54 mmol), $K_3PO_4$ (1.90 g, 8.95 mmol), $Pd(t-Bu_3P)_2$ (0.090 g, 0.176 mmol) and toluene (10 mL) was degassed with a stream of Ar bubbles for 15 minutes. The reaction mixture was then heated at 100° C. for 12 hours, after which it was cooled to room temperature and poured into $H_2O$. The mixture was extracted with ethyl acetate (2×) and the combined organic phases were washed ($H_2O$, brine), dried ($Na_2SO_4$), filtered, and concentrated in vacuo. The residue was purified first by reverse-phase preparative HPLC (Primesphere C-18, 30×100 mm; $CH_3CN$—$H_2O$-5 mM $NH_4OAc$) and then by flash chromatography ($SiO_2$/hexane-ethyl acetate, 1:1) to provide the title compound (0.128 g, 17%) as an orange oil. $^1HNMR$ (400 MHz, $CDCl_3$) δ 8.90 (d, J=2.0 Hz, 1H), 8.32 (d, J=2.0 Hz, 1H), 8.03-8.01 (m, 2H), 7.77 (ddd, J=8.3, 6.8, 1.5 Hz, 1H), 7.62 (ddd, J=8.3, 6.8, 1.5 Hz, 1H), 4.35 (s, 1H), 4.13 (m, 2H), 2.22 (s, 6H), 1.15 (t, J=7.0 Hz, 3H). LCMS: Anal. Calcd. for $C_{15}H_{18}N_2O_2$: 258. found: 259 (M+H)+.

Step 2; (R,S) 2-(Quinolin-3-yl)-2-(N,N-dimethylamino) acetic acid: A mixture of (R,S)-ethyl 2-(quinolin-3-yl)-2-(N,N-dimethylamino)acetate (0.122 g, 0.472 mmol) and 6M HCl (3 mL) was heated at 100° C. for 12 hours. The solvent was removed in vacuo to provide the dihydrochloride of the title compound (0.169 g, >100%) as a light yellow foam. The unpurified material was used in subsequent steps without further purification. LCMS: Anal. Calcd. for $C_{13}H_{14}N_2O_2$: 230. found: 231 (M+H)+.

Cap-38

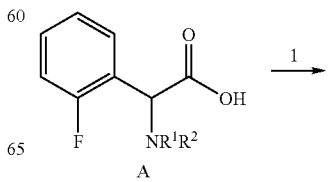

-continued

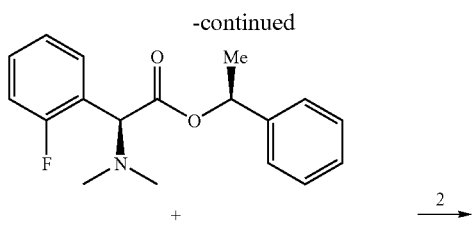

B

→ 2

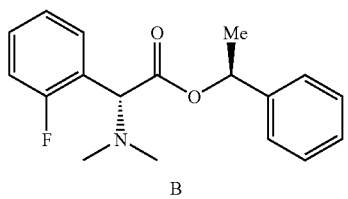

+

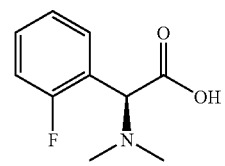

Cap-38

Step 1; (R)—((S)-1-phenylethyl) 2-(dimethylamino)-2-(2-fluorophenyl)acetate and (S)—((S)-1-phenylethyl) 2-(dimethylamino)-2-(2-fluorophenyl)acetate: To a mixture of (RS)-2-(dimethylamino)-2-(2-fluorophenyl)acetic acid (2.60 g, 13.19 mmol), DMAP (0.209 g, 1.71 mmol) and (S)-1-phenylethanol (2.09 g, 17.15 mmol) in CH$_2$Cl$_2$ (40 mL) was added EDCI (3.29 g, 17.15 mmol) and the mixture was allowed to stir at room temperature for 12 hours. The solvent was then removed in vacuo and the residue partitioned with ethyl acetate-H$_2$O. The layers were separated, the aqueous layer was back-extracted with ethyl acetate (2×) and the combined organic phases were washed (H$_2$O, brine), dried (Na$_2$SO$_4$), filtered, and concentrated in vacuo. The residue was purified by silica gel chromatography (Biotage/0-50% diethyl ether-hexane). The resulting pure diastereomeric mixture was then separated by reverse-phase preparative HPLC (Primesphere C-18, 30×100 mm; CH$_3$CN—H$_2$O-0.1% TFA) to give first (S)-1-phenethyl (R)-2-(dimethylamino)-2-(2-fluorophenyl)acetate (0.501 g, 13%) and then (S)-1-phenethyl (S)-2-(dimethylamino)-2-(2-fluorophenyl)-acetate (0.727 g. 18%), both as their TFA salts. (S,R)-isomer: $^1$HNMR (400 MHz, CD$_3$OD) δ 7.65-7.70 (m, 1H), 7.55-7.60 (ddd, J=9.4, 8.1, 1.5 Hz, 1H), 7.36-7.41 (m, 2H), 7.28-7.34 (m, 5H), 6.04 (q, J=6.5 Hz, 1H), 5.60 (s, 1H), 2.84 (s, 6H), 1.43 (d, J=6.5 Hz, 3H). LCMS: Anal. Calcd. for C$_{18}$H$_{20}$FNO$_2$: 301. found: 302 (M+H)$^+$; (S,S)-isomer: $^1$HNMR (400 MHz, CD$_3$OD) δ 7.58-7.63 (m, 1H), 7.18-7.31 (m, 6H), 7.00 (dd, J=8.5, 1.5 Hz, 2H), 6.02 (q, J=6.5 Hz, 1H), 5.60 (s, 1H), 2.88 (s, 6H), 1.54 (d, J=6.5 Hz, 3H). LCMS: Anal. Calcd. for C$_{18}$H$_{20}$FNO$_2$: 301. found: 302 (M+H)$^+$.

Step 2; (R)-2-(dimethylamino)-2-(2-fluorophenyl)acetic acid: A mixture of (R)—((S)-1-phenylethyl) 2-(dimethylamino)-2-(2-fluorophenyl)acetate TFA salt (1.25 g, 3.01 mmol) and 20% Pd(OH)$_2$/C (0.125 g) in ethanol (30 mL) was hydrogenated at room temperature and atmospheric pressure (H$_2$ balloon) for 4 hours. The solution was then purged with Ar, filtered through diatomaceous earth (Celite®), and concentrated in vacuo. This gave the title compound as a colorless solid (0.503 g, 98%). $^1$HNMR (400 MHz, CD$_3$OD) δ 7.53-7.63 (m, 2H), 7.33-7.38 (m, 2H), 5.36 (s, 1H), 2.86 (s, 6H). LCMS: Anal. Calcd. for C$_{10}$H$_{12}$FNO$_2$: 197. found: 198 (M+H)$^+$.

The S-isomer could be obtained from (S)—((S)-1-phenylethyl) 2-(dimethylamino)-2-(2-fluorophenyl)acetate TFA salt in similar fashion.

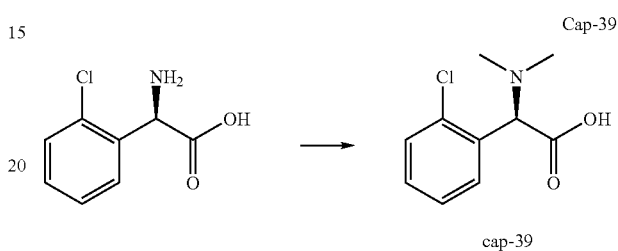

cap-39

A mixture of (R)-(2-chlorophenyl)glycine (0.300 g, 1.62 mmol), formaldehyde (35% aqueous solution, 0.80 mL, 3.23 mmol) and 20% Pd(OH)$_2$/C (0.050 g) was hydrogenated at room temperature and atmospheric pressure (H$_2$ balloon) for 4 hours. The solution was then purged with Ar, filtered through diatomaceous earth (Celite®) and concentrated in vacuo. The residue was purified by reverse-phase preparative HPLC (Primesphere C-18, 30×100 mm; CH$_3$CN—H$_2$O-0.1% TFA) to give the TFA salt of the title compound (R)-2-(dimethylamino)-2-(2-chlorophenyl)acetic acid as a colorless oil (0.290 g, 55%). $^1$H NMR (400 MHz, CD$_3$OD) δ 7.59-7.65 (m, 2H), 7.45-7.53 (m, 2H), 5.40 (s, 1H), 2.87 (s, 6H). LCMS: Anal. Calcd. for C$_{10}$H$_{12}$ClNO$_2$: 213, 215. found: 214, 216 (M+H)$^+$.

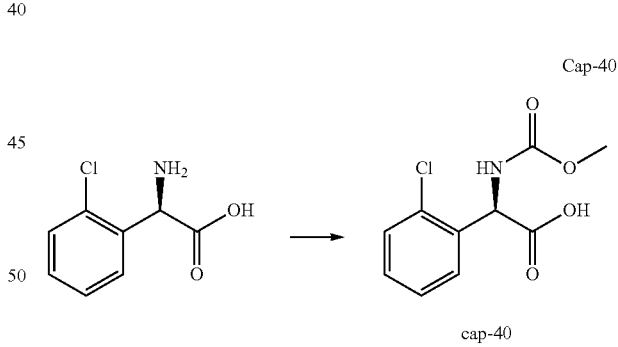

cap-40

To an ice-cold solution of (R)-(2-chlorophenyl)glycine (1.00 g, 5.38 mmol) and NaOH (0.862 g, 21.6 mmol) in H$_2$O (5.5 mL) was added methyl chloroformate (1.00 mL, 13.5 mmol) dropwise. The mixture was allowed to stir at 0° C. for 1 hour and then it was acidified by the addition of conc. HCl (2.5 mL). The mixture was extracted with ethyl acetate (2×) and the combined organic phase was washed (H$_2$O, brine), dried (Na$_2$SO$_4$), filtered, and concentrated in vacuo to give the title compound (R)-2-(methoxycarbonylamino)-2-(2-chlorophenyl)acetic acid as a yellow-orange foam (1.31 g, 96%). $^1$H NMR (400 MHz, CD$_3$OD) δ 7.39-7.43 (m, 2H), 7.29-7.31 (m, 2H), 5.69 (s, 1H), 3.65 (s, 3H). LCMS: Anal. Calcd. for C$_{10}$H$_{10}$ClNO$_4$: 243, 245. found: 244, 246 (M+H)$^+$.

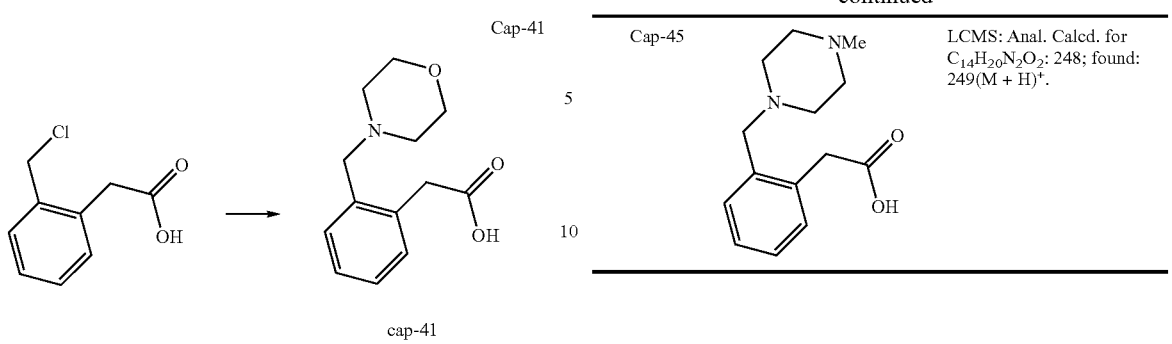

To a suspension of 2-(2-(chloromethyl)phenyl)acetic acid (2.00 g, 10.8 mmol) in THF (20 mL) was added morpholine (1.89 g, 21.7 mmol) and the solution was stirred at room temperature for 3 hours. The reaction mixture was then diluted with ethyl acetate and extracted with H₂O (2×). The aqueous phase was lyophilized and the residue was purified by silica gel chromatography (Biotage/0-10% methanol-CH₂Cl₂) to give the title compound 2-(2-(Morpholinomethyl)phenyl)acetic acid as a colorless solid (2.22 g, 87%). ¹HNMR (400 MHz, CD₃OD) δ 7.37-7.44 (m, 3H), 7.29-7.33 (m, 1H), 4.24 (s, 2H), 3.83 (br s, 4H), 3.68 (s, 2H), 3.14 (br s, 4H). LCMS: Anal. Calcd. for $C_{13}H_{17}NO_3$: 235. found: 236 (M+H)⁺.

The following examples were similarly prepared using the method described for Cap-41:

| Cap-42 |  | LCMS: Anal. Calcd. for $C_{14}H_{19}NO_2$: 233; found: 234(M+ H)⁺. |
|---|---|---|
| Cap-43 |  | LCMS: Anal. Calcd. for $C_{13}H_{17}NO_2$: 219; found: 220(M + H)⁺. |
| Cap-44 |  | LCMS: Anal. Calcd. for $C_{11}H_{15}NO_2$: 193; found: 194(M + H)⁺. |

| Cap-45 | 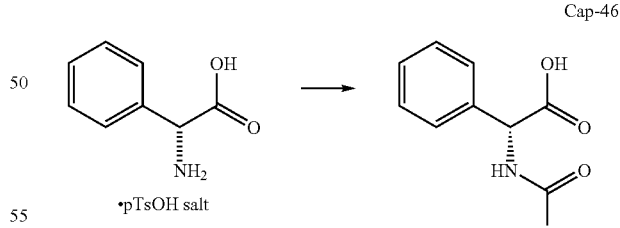 | LCMS: Anal. Calcd. for $C_{14}H_{20}N_2O_2$: 248; found: 249(M + H)⁺. |
|---|---|---|

Cap-45

HMDS (1.85 mL, 8.77 mmol) was added to a suspension of (R)-2-amino-2-phenylacetic acid p-toluenesulfonate (2.83 g, 8.77 mmol) in CH₂Cl₂ (10 mL) and the mixture was stirred at room temperature for 30 minutes. Methyl isocyanate (0.5 g, 8.77 mmol) was added in one portion stirring continued for 30 minutes. The reaction was quenched by addition of H₂O (5 mL) and the resulting precipitate was filtered, washed with H₂O and n-hexanes, and dried under vacuum. (R)-2-(3-methylureido)-2-phenylacetic acid (1.5 g; 82%) was recovered as a white solid and it was used without further purification. ¹H NMR (500 MHz, DMSO-d₆) δ ppm 2.54 (d, J=4.88 Hz, 3H) 5.17 (d, J=7.93 Hz, 1H) 5.95 (q, J=4.48 Hz, 1H) 6.66 (d, J=7.93 Hz, 1H) 7.26-7.38 (m, 5H) 12.67 (s, 1H). LCMS: Anal. Calcd. for $C_{10}H_{12}N_2O_3$ 208.08 found 209.121 (M+H)⁺; HPLC Phenomenex C-18 3.0×46 mm, 0 to 100% B over 2 minutes, 1 minute hold time, A=90% water, 10% methanol, 0.1% TFA, B=10% water, 90% methanol, 0.1% TFA, RT=1.38 min, 90% homogeneity index.

Cap-46

The desired product was prepared according to the method described for Cap-45. ¹H NMR (500 MHz, DMSO-d₆) δ ppm 0.96 (t, J=7.17 Hz, 3H) 2.94-3.05 (m, 2H) 5.17 (d, J=7.93 Hz, 1H) 6.05 (t, J=5.19 Hz, 1H) 6.60 (d, J=7.63 Hz, 1H) 7.26-7.38 (m, 5H) 12.68 (s, 1H). LCMS: Anal. Calcd. for $C_{11}H_{14}N_2O_3$ 222.10 found 209.121 (M+H)⁺.

HPLC XTERRA C-18 3.0×506 mm, 0 to 100% B over 2 minutes, 1 minutes hold time, A=90% water, 10% methanol, 0.2% H₃PO₄, B=10% water, 90% methanol, 0.2% H₃PO₄, RT=0.87 min, 90% homogeneity index.

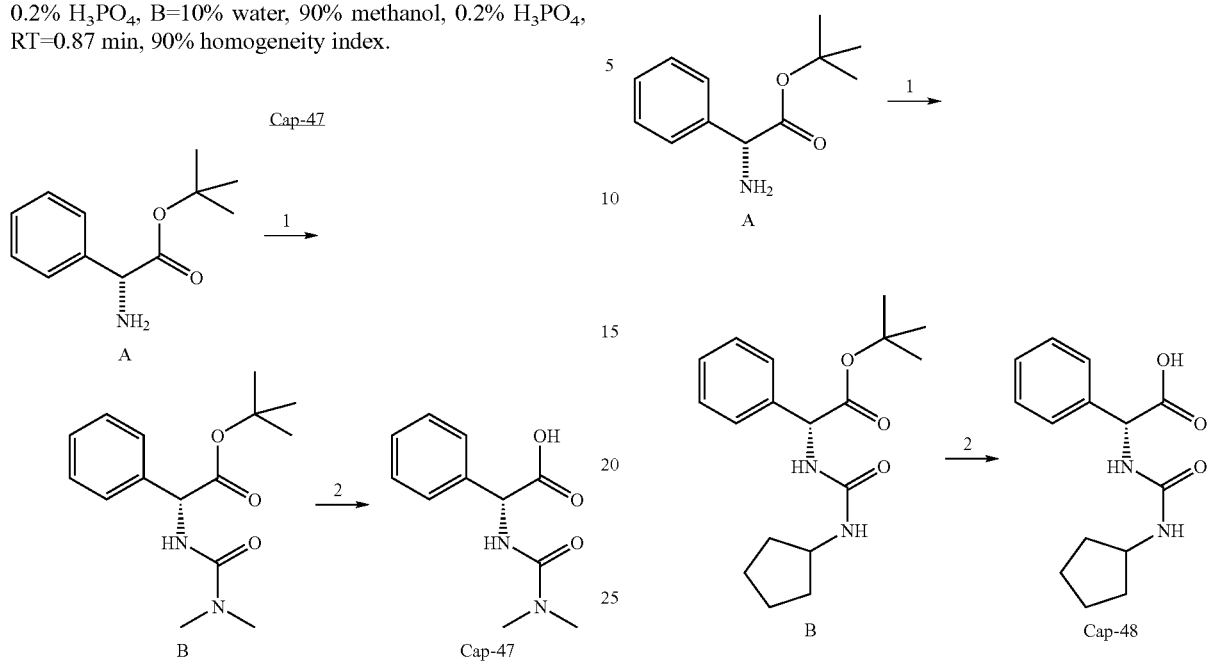

Step 1; (R)-tert-butyl 2-(3,3-dimethylureido)-2-phenylacetate: To a stirred solution of (R)-tert-butyl-2-amino-2-phenylacetate (1.0 g, 4.10 mmol) and Hunig's base (1.79 mL, 10.25 mmol) in DMF (40 mL) was added dimethylcarbamoyl chloride (0.38 mL, 4.18 mmol) dropwise over 10 minutes. After stirring at room temperature for 3 hours, the reaction was concentrated under reduced pressure and the resulting residue was dissolved in ethyl acetate. The organic layer was washed with H₂O, 1N aq. HCl and brine, dried (MgSO₄), filtered and concentrated under reduced pressure. (R)-tert-butyl 2-(3,3-dimethylureido)-2-phenylacetate was obtained as a white solid (0.86 g; 75%) and used without further purification. ¹H NMR (500 MHz, DMSO-d₆) δ ppm 1.33 (s, 9H) 2.82 (s, 6H) 5.17 (d, J=7.63 Hz, 1H) 6.55 (d, J=7.32 Hz, 1H) 7.24-7.41 (m, 5H). LCMS: Anal. Calcd. for C₁₅H₂₂N₂O₃ 278.16 found 279.23 (M+H)⁺; HPLC Phenomenex LUNA C-18 4.6×50 mm, 0 to 100% B over 4 minutes, 1 minutes hold time, A=90% water, 10% methanol, 0.1% TFA, B=10% water, 90% methanol, 0.1% TFA, RT=2.26 min, 97% homogeneity index.

Step 2; (R)-2-(3,3-dimethylureido)-2-phenylacetic acid: To a stirred solution of ((R)-tert-butyl 2-(3,3-dimethylureido)-2-phenylacetate (0.86 g, 3.10 mmol) in CH₂Cl₂ (250 mL) was added TFA (15 mL) dropwise and the resulting solution was stirred at rt for 3 h. The desired compound was then precipitated out of solution with a mixture of EtOAC:Hexanes (5:20), filtered off and dried under reduced pressure. (R)-2-(3,3-dimethylureido)-2-phenylacetic acid was isolated as a white solid (0.59 g, 86%) and used without further purification. ¹H NMR (500 MHz, DMSO-d₆) δ ppm 2.82 (s, 6H) 5.22 (d, J=7.32 Hz, 1H) 6.58 (d, J=7.32 Hz, 1H) 7.28 (t, J=7.17 Hz, 1H) 7.33 (t, J=7.32 Hz, 2H) 7.38-7.43 (m, 2H) 12.65 (s, 1H). LCMS: Anal. Calcd. for C₁₁H₁₄N₂O₃: 222.24. found: 223.21 (M+H)⁺. HPLC XTERRA C-18 3.0×50 mm, 0 to 100% B over 2 minutes, 1 minutes hold time, A=90% water, 10% methanol, 0.2% H₃PO₄, B=10% water, 90% methanol, 0.2% H₃PO₄, RT=0.75 min, 93% homogeneity index.

Step 1; (R)-tert-butyl 2-(3-cyclopentylureido)-2-phenylacetate: To a stirred solution of (R)-2-amino-2-phenylacetic acid hydrochloride (1.0 g, 4.10 mmol) and Hunig's base (1.0 mL, 6.15 mmol) in DMF (15 mL) was added cyclopentyl isocyanate (0.46 mL, 4.10 mmol) dropwise and over 10 minutes. After stirring at room temperature for 3 hours, the reaction was concentrated under reduced pressure and the resulting residue was taken up in ethyl acetate. The organic layer was washed with H₂O and brine, dried (MgSO₄), filtered, and concentrated under reduced pressure. (R)-tert-butyl 2-(3-cyclopentylureido)-2-phenylacetate was obtained as an opaque oil (1.32 g; 100%) and used without further purification. ¹H NMR (500 MHz, CD₃Cl-D) δ ppm 1.50-1.57 (m, 2H) 1.58-1.66 (m, 2H) 1.87-1.97 (m, 2H) 3.89-3.98 (m, 1H) 5.37 (s, 1H) 7.26-7.38 (m, 5H). LCMS: Anal. Calcd. for C₁₈H₂₆N₂O₃ 318.19 found 319.21 (M+H)⁺; HPLC XTERRA C-18 3.0×50 mm, 0 to 100% B over 4 minutes, 1 minutes hold time, A=90% water, 10% methanol, 0.1% TFA, B=10% water, 90% methanol, 0.1% TFA, RT=2.82 min, 96% homogeneity index.

Step 2; (R)-2-(3-cyclopentylureido)-2-phenylacetic acid: To a stirred solution of (R)-tert-butyl 2-(3-cyclopentylureido)-2-phenylacetate (1.31 g, 4.10 mmol) in CH₂Cl₂ (25 mL) was added TFA (4 mL) and trietheylsilane (1.64 mL; 10.3 mmol) dropwise, and the resulting solution was stirred at room temperature for 6 hours. The volatile components were removed under reduced pressure and the crude product was recrystallized in ethyl acetate/pentanes to yield (R)-2-(3-cyclopentylureido)-2-phenylacetic acid as a white solid (0.69 g, 64%). ¹H NMR (500 MHz, DMSO-d₆) δ ppm 1.17-1.35 (m, 2H) 1.42-1.52 (m, 2H) 1.53-1.64 (m, 2H) 1.67-1.80 (m, 2H) 3.75-3.89 (m, 1H) 5.17 (d, J=7.93 Hz, 1H) 6.12 (d, J=7.32 Hz, 1H) 6.48 (d, J=7.93 Hz, 1H) 7.24-7.40 (m, 5H) 12.73 (s, 1H). LCMS: Anal. Calcd. for C₁₄H₁₈N₂O₃: 262.31. found: 263.15 (M+H)⁺. HPLC XTERRA C-18 3.0×50 mm, 0 to 100% B over 2 minutes, 1 minutes hold time, A=90% water, 10% methanol, 0.2% H₃PO₄, B=10% water, 90% methanol, 0.2% H₃PO₄, RT=1.24 min, 100% homogeneity index.

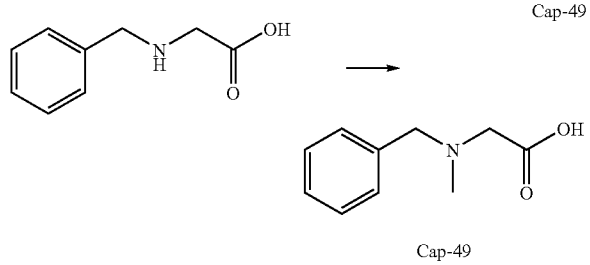

Cap-49

To a stirred solution of 2-(benzylamino)acetic acid (2.0 g, 12.1 mmol) in formic acid (91 mL) was added formaldehyde (6.94 mL, 93.2 mmol). After five hours at 70° C., the reaction mixture was concentrated under reduced pressure to 20 mL and a white solid precipitated. Following filtration, the mother liquors were collected and further concentrated under reduced pressure providing the crude product. Purification by reverse-phase preparative HPLC (Xterra 30×100 mm, detection at 220 nm, flow rate 35 mL/min, 0 to 35% B over 8 min; A=90% water, 10% methanol, 0.1% TFA, B=10% water, 90% methanol, 0.1% TFA) provided the title compound 2-(benzyl (methyl)-amino)acetic acid as its TFA salt (723 mg, 33%) as a colorless wax. $^1$H NMR (300 MHz, DMSO-d$_6$) δ ppm 2.75 (s, 3H) 4.04 (s, 2H) 4.34 (s, 2H) 7.29-7.68 (m, 5H). LCMS: Anal. Calcd. for: $C_{10}H_{13}NO_2$ 179.22. Found: 180.20 (M+H)$^+$.

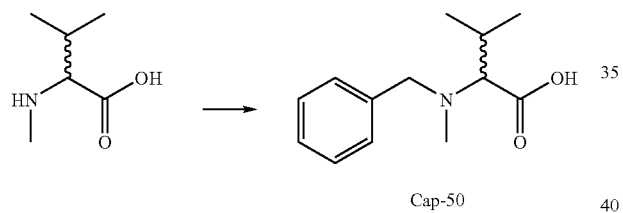

Cap-50

To a stirred solution of 3-methyl-2-(methylamino)butanoic acid (0.50 g, 3.81 mmol) in water (30 mL) was added K$_2$CO$_3$ (2.63 g, 19.1 mmol) and benzyl chloride (1.32 g, 11.4 mmol). The reaction mixture was stirred at ambient temperature for 18 hours. The reaction mixture was extracted with ethyl acetate (30 mL×2) and the aqueous layer was concentrated under reduced pressure providing the crude product which was purified by reverse-phase preparative HPLC (Xterra 30×100 mm, detection at 220 nm, flow rate 40 mL/min, 20 to 80% B over 6 min; A=90% water, 10% methanol, 0.1% TFA, B=10% water, 90% methanol, 0.1% TFA) to provide 2-(benzyl(methyl)amino)-3-methylbutanoic acid, TFA salt (126 mg, 19%) as a colorless wax. $^1$H NMR (500 MHz, DMSO-d$_6$) δ ppm 0.98 (d, 3H) 1.07 (d, 3H) 2.33-2.48 (m, 1H) 2.54-2.78 (m, 3H) 3.69 (s, 1H) 4.24 (s, 2H) 7.29-7.65 (m, 5H). LCMS: Anal. Calcd. for: $C_{13}H_{19}NO_2$ 221.30. Found: 222.28 (M+H)$^+$.

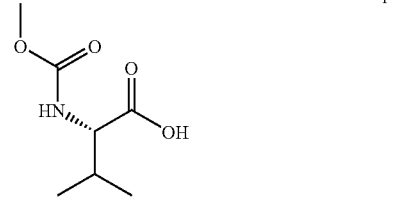

Cap-51

Na$_2$CO$_3$ (1.83 g, 17.2 mmol) was added to NaOH (33 mL of 1M/H$_2$O, 33 mmol) solution of L-valine (3.9 g, 33.29 mmol) and the resulting solution was cooled with ice-water bath. Methyl chloroformate (2.8 mL, 36.1 mmol) was added drop-wise over 15 min, the cooling bath was removed and the reaction mixture was stirred at ambient temperature for 3.25 hr. The reaction mixture was washed with ether (50 mL, 3×), and the aqueous phase was cooled with ice-water bath and acidified with concentrated HCl to a pH region of 1-2, and extracted with CH$_2$Cl$_2$ (50 mL, 3×). The organic phase was dried (MgSO$_4$), filtered, and concentrated in vacuo to afford Cap-51 as a white solid (6 g). $^1$H NMR for the dominant rotamer (DMSO-d$_6$, δ=2.5 ppm, 500 MHz): 12.54 (s, 1H), 7.33 (d, J=8.6, 1H), 3.84 (dd, J=8.4, 6.0, 1H), 3.54 (s, 3H), 2.03 (m, 1H), 0.87 (m, 6H). HRMS: Anal. Calcd. for [M+H]$^+$ $C_7H_{14}NO_4$: 176.0923. found 176.0922

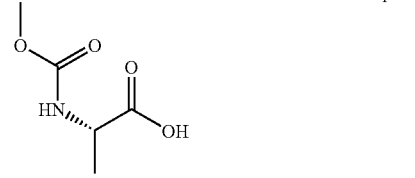

Cap-52

Cap-52 was synthesized from L-alanine according to the procedure described for the synthesis of Cap-51. For characterization purposes, a portion of the crude material was purified by a reverse phase HPLC (H$_2$O/MeOH/TFA) to afford Cap-52 as a colorless viscous oil. $^1$H NMR (DMSO-d$_6$, δ=2.5 ppm, 500 MHz): 12.49 (br s, 1H), 7.43 (d, J=7.3, 0.88H), 7.09 (app br s, 0.12H), 3.97 (m, 1H), 3.53 (s, 3H), 1.25 (d, J=7.3, 3H).

Cap-53 to -64 were prepared from appropriate starting materials according to the procedure described for the synthesis of Cap-51, with noted modifications if any.

| Cap | Structure | Data |
|---|---|---|
| Cap-53a: (R)<br>Cap-53b: (S) | ![structure] | $^1$H NMR(DMSO-d$_6$, δ = 2.5 ppm, 500 MHz): δ 12.51(br s, 1 H), 7.4(d, J = 7.9, 0.9 H), 7.06 (app s, 0.1 H), 3.86-3.82(m, 1 H), 3.53(s, 3 H), 1.75-1.67(m, 1 H), 1.62-1.54(m, 1 H), 0.88(d, J = 7.3, 3 H). RT = 0.77 minutes(Cond. 2); LC/MS: Anal. Calcd. for [M + Na]$^+$ $C_6H_{11}NNaO_4$: 184.06; found 184.07. HRMS Calcd. for [M + Na]$^+$ $C_6H_{11}NNaO_4$: 184.0586; found 184.0592. |

-continued

| Cap | Structure | Data |
|---|---|---|
| Cap-54a: (R) Cap-54b: (S) | 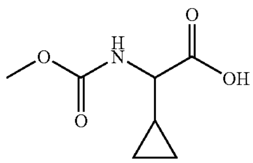 | $^1$H NMR(DMSO-d$_6$, δ = 2.5 ppm, 500 MHz): δ 12.48(s, 1 H), 7.58(d, J = 7.6, 0.9 H), 7.25 (app s, 0.1 H), 3.52(s, 3 H), 3.36-3.33(m, 1 H), 1.10-1.01(m, 1 H), 0.54-0.49(m, 1 H), 0.46-0.40(m, 1 H), 0.39-0.35(m, 1 H), 0.31-0.21(m, 1 H). HRMS Calcd. for [M + H]$^+$ C$_7$H$_{12}$NO$_4$: 174.0766; found 174.0771 |
| Cap-55 | 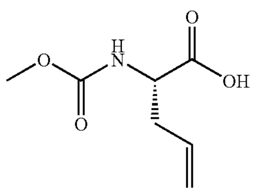 | $^1$H NMR(DMSO-d$_6$, δ = 2.5 ppm, 500 MHz): δ 12.62(s, 1 H), 7.42(d, J = 8.2, 0.9 H), 7.07 (app s, 0.1 H), 5.80-5.72(m, 1 H), 5.10(d, J = 17.1, 1 H), 5.04(d, J = 10.4, 1 H), 4.01-3.96 (m, 1 H), 3.53(s, 3 H), 2.47-2.42(m, 1 H), 2.35-2.29(m, 1 H). |
| Cap-56 | 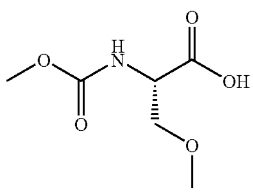 | $^1$H NMR(DMSO-d$_6$, δ = 2.5 ppm, 500 MHz): δ 12.75(s, 1 H), 7.38(d, J = 8.3, 0.9 H), 6.96 (app s, 0.1 H), 4.20-4.16(m, 1 H), 3.60-3.55(m, 2 H), 3.54(s, 3 H), 3.24(s, 3 H). |
| Cap-57 | 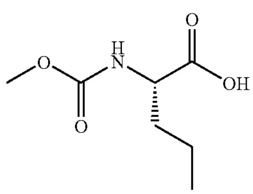 | $^1$H NMR(DMSO-d$_6$, δ = 2.5 ppm, 500 MHz): δ 12.50(s, 1 H), 8.02(d, J = 7.7, 0.08 H), 7.40 (d, J = 7.9, 0.76 H), 7.19(d, J = 8.2, 0.07 H), 7.07(d, J = 6.7, 0.09 H), 4.21-4.12(m, 0.08 H), 4.06-3.97(m, 0.07 H), 3.96-3.80(m, 0.85 H), 3.53(s, 3 H), 1.69-1.51(m, 2 H), 1.39-1.26(m, 2 H), 0.85(t, J = 7.4, 3 H). LC(Cond. 2): RT = 1.39 LC/MS: Anal. Calcd. for [M + H]$^+$ C$_7$H$_{14}$NO$_4$: 176.09; found 176.06. |
| Cap-58 | 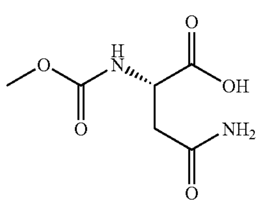 | $^1$H NMR(DMSO-d$_6$, δ = 2.5 ppm, 500 MHz): δ 12.63(bs, 1 H), 7.35(s, 1 H), 7.31(d, J = 8.2, 1 H), 6.92(s, 1 H), 4.33-4.29(m, 1 H), 3.54(s, 3 H), 2.54(dd, J = 15.5, 5.4, 1 H), 2.43(dd, J = 15.6, 8.0, 1 H). RT = 0.16 min (Cond. 2); LC/MS: Anal. Calcd. for [M + H]$^+$ C$_6$H$_{11}$N$_2$O$_5$: 191.07; found 191.14. |
| Cap-59a: (R) Cap-59b: (S) | 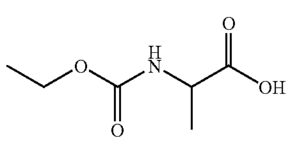 | $^1$H NMR(DMSO-d$_6$, δ = 2.5 ppm, 400 MHz): δ 12.49(br s, 1 H), 7.40(d, J = 7.3, 0.89 H), 7.04(br s, 0.11 H), 4.00-3.95(m, 3 H), 1.24(d, J = 7.3, 3 H), 1.15(t, J = 7.2, 3 H). HRMS: Anal. Calcd. for [M + H]$^+$ C$_6$H$_{12}$NO$_4$: 162.0766; found 162.0771. |
| Cap-60 | 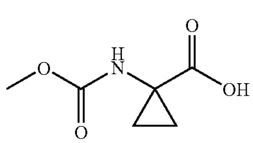 | The crude material was purified with a reverse phase HPLC(H$_2$O/MeOH/TFA) to afford a colorless viscous oil that crystallized to a white solid upon exposure to high vacuum. $^1$H NMR (DMSO-d$_6$, δ = 2.5 ppm, 400 MHz): δ 12.38 (br s, 1 H), 7.74(s, 0.82 H), 7.48(s, 0.18 H), 3.54/3.51(two s, 3 H), 1.30(m, 2 H), 0.98(m, 2 H). HRMS: Anal. Calcd. for [M + H]$^+$ C$_6$H$_{10}$NO$_4$: 160.0610; found 160.0604. |
| Cap-61 | 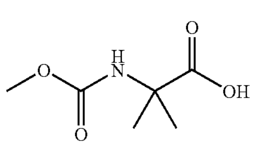 | $^1$H NMR(DMSO-d$_6$, δ = 2.5 ppm, 400 MHz): δ 12.27(br s, 1 H), 7.40(br s, 1 H), 3.50(s, 3 H), 1.32(s, 6 H). HRMS: Anal. Calcd. for [M + H]$^+$ C$_6$H$_{12}$NO$_4$: 162.0766; found 162.0765. |

| Cap | Structure | Data |
|---|---|---|
| Cap-62 | 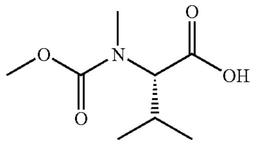 | $^1$H NMR(DMSO-d$_6$, δ = 2.5 ppm, 400 MHz): δ 12.74(br s, 1 H), 4.21(d, J = 10.3, 0.6 H), 4.05(d, J = 10.0, 0.4 H), 3.62/3.60(two singlets, 3 H), 3.0(s, 3 H), 2.14-2.05(m, 1 H), 0.95(d, J = 6.3, 3 H), 0.81(d, J = 6.6, 3 H). LC/MS: Anal. Calcd. for [M − H]$^-$ C$_8$H$_{14}$NO$_4$: 188.09; found 188.05. |
| Cap-63 | 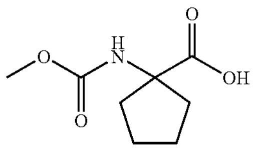 | [Note: the reaction was allowed to run for longer than what was noted for the general procedure.] $^1$H NMR(DMSO-d$_6$, δ = 2.5 ppm, 400 MHz): 12.21(br s, 1 H), 7.42(br s, 1 H), 3.50(s, 3 H), 2.02-1.85(m, 4 H), 1.66-1.58(m, 4 H). LC/MS: Anal. Calcd. for [M + H]$^+$ C$_8$H$_{14}$NO$_4$: 188.09; found 188.19. |
| Cap-64 | 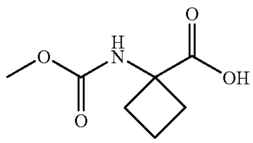 | [Note: the reaction was allowed to run for longer than what was noted for the general procedure.] $^1$H NMR(DMSO-d$_6$, δ = 2.5 ppm, 400 MHz): 12.35(br s, 1 H), 7.77(s, 0.82 H), 7.56/7.52(overlapping br s, 0.18 H), 3.50(s, 3 H), 2.47-2.40(m, 2 H), 2.14-2.07(m, 2 H), 1.93-1.82(m, 2 H). |

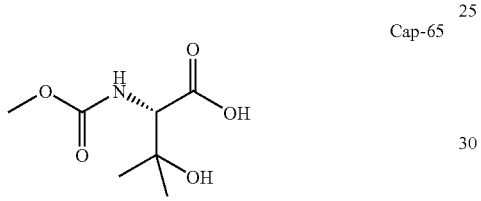

Cap-65

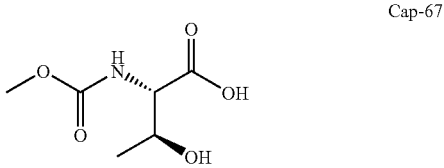

Cap-67

Methyl chloroformate (0.65 mL, 8.39 mmol) was added dropwise over 5 min to a cooled (ice-water) mixture of Na$_2$CO$_3$ (0.449 g, 4.23 mmol), NaOH (8.2 mL of 1M/H$_2$O, 8.2 mmol) and (s)-3-hydroxy-2-(methoxycarbonylamino)-3-methylbutanoic acid (1.04 g, 7.81 mmol). The reaction mixture was stirred for 45 min, and then the cooling bath was removed and stirring was continued for an additional 3.75 hr. The reaction mixture was washed with CH$_2$Cl$_2$, and the aqueous phase was cooled with ice-water bath and acidified with concentrated HCl to a pH region of 1-2. The volatile component was removed in vacuo and the residue was taken up in a 2:1 mixture of MeOH/CH$_2$Cl$_2$ (15 mL) and filtered, and the filterate was rotervaped to afford Cap-65 as a white semi-viscous foam (1.236 g). $^1$H NMR (DMSO-d$_6$, δ=2.5 ppm, 400 MHz): δ 6.94 (d, J=8.5, 0.9H), 6.53 (br s, 0.1H), 3.89 (d, J=8.8, 1H), 2.94 (s, 3H), 1.15 (s, 3H), 1.13 (s, 3H).

Cap-66 and -67 were prepared from appropriate commercially available starting materials by employing the procedure described for the synthesis of Cap-65.

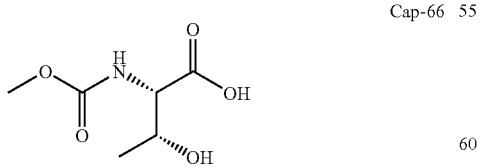

Cap-66

$^1$H NMR (DMSO-d$_6$, δ=2.5 ppm, 400 MHz): δ 12.58 (br s, 1H), 7.07 (d, J=8.3, 0.13H), 6.81 (d, J=8.8, 0.67H), 4.10-4.02 (m, 1.15H), 3.91 (dd, J=9.1, 3.5, 0.85H), 3.56 (s, 3H), 1.09 (d, J=6.2, 3H). [Note: only the dominant signals of NH were noted].

$^1$H NMR (DMSO-d$_6$, δ=2.5 ppm, 400 MHz): 12.51 (br s, 1H), 7.25 (d, J=8.4, 0.75H), 7.12 (br d, J=0.4, 0.05H), 6.86 (br s, 0.08H), 3.95-3.85 (m, 2H), 3.54 (s, 3H), 1.08 (d, J=6.3, 3H). [Note: only the dominant signals of NH were noted]

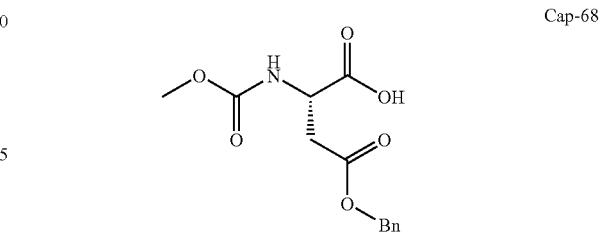

Cap-68

Methyl chloroformate (0.38 ml, 4.9 mmol) was added drop-wise to a mixture of 1N NaOH (aq) (9.0 ml, 9.0 mmol), 1M NaHCO$_3$ (aq) (9.0 ml, 9.0 mol), L-aspartic acid β-benzyl ester (1.0 g, 4.5 mmol) and Dioxane (9 ml). The reaction mixture was stirred at ambient conditions for 3 hr, and then washed with Ethyl acetate (50 ml, 3×). The aqueous layer was acidified with 12N HCl to a pH~1-2, and extracted with ethyl acetate (3×50 ml). The combined organic layers were washed with brine, dried (Na$_2$SO$_4$), filtered, and concentrated in vacuo to afford Cap-68 as a light yellow oil (1.37 g; mass is above theoretical yield, and the product was used without further purification). $^1$H NMR (DMSO-d$_6$, δ=2.5 ppm, 500 MHz): δ 12.88 (br s, 1H), 7.55 (d, J=8.5, 1H), 7.40-7.32 (m, 5H), 5.13 (d, J=12.8, 1H), 5.10 (d, J=12.9, 1H), 4.42-4.38 (m, 1H), 3.55 (s, 3H), 2.87 (dd, J=16.2, 5.5, 1H), 2.71 (dd, J=16.2, 8.3, 1H). LC (Cond. 2): RT=1.90 min; LC/MS: Anal. Calcd. For [M+H]$^+$ C$_{13}$H$_{16}$NO$_6$: 282.10. found 282.12.

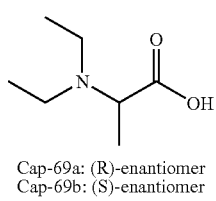

Cap-69a: (R)-enantiomer
Cap-69b: (S)-enantiomer

NaCNBH₃ (2.416 g, 36.5 mmol) was added in batches to a chilled (~15° C.) water (17 mL)/MeOH (10 mL) solution of alanine (1.338 g, 15.0 mmol). A few minutes later acetaldehyde (4.0 mL, 71.3 mmol) was added drop-wise over 4 min, the cooling bath was removed, and the reaction mixture was stirred at ambient condition for 6 hr. An additional acetaldehyde (4.0 mL) was added and the reaction was stirred for 2 hr. Concentrated HCl was added slowly to the reaction mixture until the pH reached ~1.5, and the resulting mixture was heated for 1 hr at 40° C. Most of the volatile component was removed in vacuo and the residue was purified with a Dowex® 50WX8-100 ion-exchange resin (column was washed with water, and the compound was eluted with dilute NH₄OH, prepared by mixing 18 ml of NH₄OH and 282 ml of water) to afford Cap-69 (2.0 g) as an off-white soft hygroscopic solid. $^1$H NMR (DMSO-$d_6$, δ=2.5 ppm, 400 MHz): δ 3.44 (q, J=7.1, 1H), 2.99-2.90 (m, 2H), 2.89-2.80 (m, 2H), 1.23 (d, J=7.1, 3H), 1.13 (t, J=7.3, 6H).

Cap-70 to −74 were prepared according to the procedure described for the synthesis of Cap-69 by employing appropriate starting materials.

| | | |
|---|---|---|
| Cap-70a: (R)<br>Cap-70b: (S) | 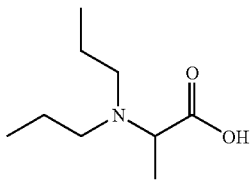 | $^1$H NMR(DMSO-$d_6$, δ = 2.5 ppm, 400 MHz):<br>δ 3.42(q, J = 7.1, 1 H), 2.68-2.60(m, 4 H),<br>1.53-1.44(m, 4 H), 1.19(d, J = 7.3, 3 H), 0.85<br>(t, J = 7.5, 6 H). LC/MS: Anal. Calcd. for<br>[M + H]⁺ C₉H₂₀NO₂: 174.15; found 174.13. |
| Cap-71a: (R)<br>Cap-71b: (S) | 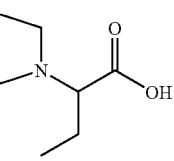 | $^1$H NMR(DMSO-$d_6$, δ = 2.5 ppm, 500 MHz):<br>δ 3.18-3.14(m, 1 H), 2.84-2.77(m, 2 H), 2.76-<br>2.68(m, 2 H), 1.69-1.54(m, 2 H), 1.05(t, J =<br>7.2, 6 H), 0.91(t, J = 7.3, 3 H). LC/MS: Anal.<br>Calcd. for [M + H]⁺ C₈H₁₈NO₂: 160.13; found<br>160.06. |
| Cap-72 | 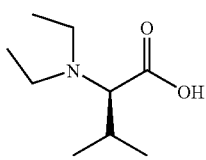 | $^1$H NMR(DMSO-$d_6$, δ = 2.5 ppm, 400 MHz):<br>δ 2.77-2.66(m, 3 H), 2.39-2.31(m, 2 H), 1.94-<br>1.85(m, 1 H), 0.98(t, J = 7.1, 6 H), 0.91(d, J =<br>6.5, 3 H), 0.85(d, J = 6.5, 3 H). LC/MS: Anal.<br>Calcd. for [M + H]⁺ C₉H₂₀NO₂: 174.15; found<br>174.15. |
| Cap-73 | 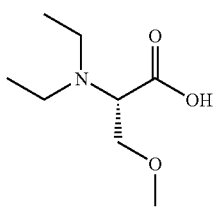 | $^1$H NMR(DMSO-$d_6$, δ = 2.5 ppm, 500 MHz):<br>δ 9.5(br s, 1 H), 3.77(dd, J = 1.8, 4.1, 1 H),<br>3.69-3.61(m, 2 H), 3.26(s, 3 H), 2.99-2.88(m,<br>4 H), 1.13(t, J = 7.2, 6 H). |
| Cap-74 | 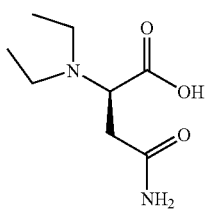 | $^1$H NMR(DMSO-$d_6$, δ = 2.5 ppm, 500 MHz):<br>δ 7.54(s, 1 H), 6.89(s, 1 H), 3.81(t, J = 6.6,<br>k, 1 H), 2.82-2.71(m, 4 H), 2.63(dd, J = 15.6,<br>7.0, 1 H), 2.36(dd, J = 15.4, 6.3, 1 H), 1.09(t, J =<br>7.2, 6 H). RT = 0.125 minutes (Cond. 2);<br>LC/MS: Anal. Calcd. for [M + H]⁺ C₈H₁₇N₂O₃:<br>189.12; found 189.13. |
| Cap-74x | 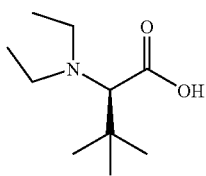 | LC/MS: Anal. Calcd. for [M + H]⁺ C₁₀H₂₂NO₂:<br>188.17; found 188.21 |

Cap-75

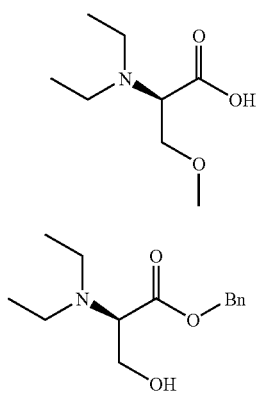

Cap-75, step a

NaBH₃CN (1.6 g, 25.5 mmol) was added to a cooled (ice/water bath) water (25 ml)/methanol (15 ml) solution of H-D-Ser-OBzl HCl (2.0 g, 8.6 mmol). Acetaldehyde (1.5 ml, 12.5 mmol) was added drop-wise over 5 min, the cooling bath was removed, and the reaction mixture was stirred at ambient condition for 2 hr. The reaction was carefully quenched with 12N HCl and concentrated in vacuo. The residue was dissolved in water and purified with a reverse phase HPLC (MeOH/H₂O/TFA) to afford the TFA salt of (R)-benzyl 2-(diethylamino)-3-hydroxypropanoate as a colorless viscous oil (1.9 g). ¹H NMR (DMSO-d₆, δ=2.5 ppm, 500 MHz): δ 9.73 (br s, 1H), 7.52-7.36 (m, 5H), 5.32 (d, J=12.2, 1H), 5.27 (d, J=12.5, 1H), 4.54-4.32 (m, 1H), 4.05-3.97 (m, 2H), 3.43-3.21 (m, 4H), 1.23 (t, J=7.2, 6H). LC/MS (Cond. 2): RT=1.38 min; LC/MS: Anal. Calcd. for [M+H]⁺ $C_{14}H_{22}NO_3$: 252.16. found 252.19.

Cap-75

NaH (0.0727 g, 1.82 mmol, 60%) was added to a cooled (ice-water) THF (3.0 mL) solution of the TFA salt (R)-benzyl 2-(diethylamino)-3-hydroxypropanoate (0.3019 g, 0.8264 mmol) prepared above, and the mixture was stirred for 15 min. Methyl iodide (56 μL, 0.90 mmol) was added and stirring was continued for 18 hr while allowing the bath to thaw to ambient condition. The reaction was quenched with water and loaded onto a MeOH pre-conditioned MCX (6 g) cartridge, and washed with methanol followed by compound elution with 2N NH₃/Methanol. Removal of the volatile component in vacuo afforded Cap-75, contaminated with (R)-2-(diethylamino)-3-hydroxypropanoic acid, as a yellow semisolid (100 mg). The product was used as is without further purification.

Cap-76

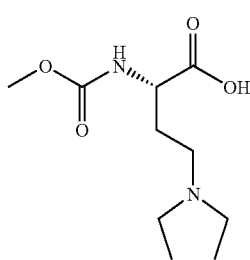

NaCNBH₃ (1.60 g, 24.2 mmol) was added in batches to a chilled (~15° C.) water/MeOH (12 mL each) solution of (S)-4-amino-2-(tert-butoxycarbonylamino) butanoic acid (2.17 g, 9.94 mmol). A few minutes later acetaldehyde (2.7 mL, 48.1 mmol) was added drop-wise over 2 min, the cooling bath was removed, and the reaction mixture was stirred at ambient condition for 3.5 hr. An additional acetaldehyde (2.7 mL, 48.1 mmol) was added and the reaction was stirred for 20.5 hr. Most of the MeOH component was removed in vacuo, and the remaining mixture was treated with concentrated HCl until its pH reached ~1.0 and then heated for 2 hr at 40° C. The volatile component was removed in vacuo, and the residue was treated with 4 M HCl/dioxane (20 mL) and stirred at ambient condition for 7.5 hr. The volatile component was removed in vacuo and the residue was purified with Dowex ® 50WX8-100 ion-exchange resin (column was washed with water and the compound was eluted with dilute NH₄OH, prepared from 18 ml of NH₄OH and 282 ml of water) to afford intermediate (S)-2-amino-4-(diethylamino) butanoic acid as an off-white solid (1.73 g).

Methyl chloroformate (0.36 mL, 4.65 mmol) was added drop-wise over 11 min to a cooled (ice-water) mixture of Na₂CO₃ (0.243 g, 2.29 mmol), NaOH (4.6 mL of 1M/H₂O, 4.6 mmol) and the above product (802.4 mg). The reaction mixture was stirred for 55 min, and then the cooling bath was removed and stirring was continued for an additional 5.25 hr. The reaction mixture was diluted with equal volume of water and washed with CH₂Cl₂ (30 mL, 2×), and the aqueous phase was cooled with ice-water bath and acidified with concentrated HCl to a pH region of 2. The volatile component was then removed in vacuo and the crude material was free-based with MCX resin (6.0 g; column was washed with water, and sample was eluted with 2.0 M NH₃/MeOH) to afford impure Cap-76 as an off-white solid (704 mg). ¹H NMR (MeOH-d₄, δ=3.29 ppm, 400 MHz): δ 3.99 (dd, J=7.5, 4.7, 1H), 3.62 (s, 3H), 3.25-3.06 (m, 6H), 2.18-2.09 (m, 1H), 2.04-1.96 (m, 1H), 1.28 (t, J=7.3, 6H). LC/MS: Anal. Calcd. for [M+H]⁺ $C_{10}H_{21}N_2O_4$: 233.15. found 233.24.

Cap-77a and -77b

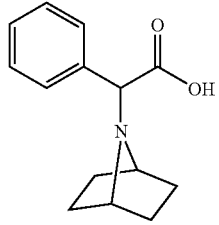

Cap-77a: enantiomer-1
Cap-77b: enantiomer-2

The synthesis of Cap-77 was conducted according to the procedure described for Cap-7 by using 7-azabicyclo[2.2.1]heptane for the SN₂ displacement step, and by effecting the enantiomeric separation of the intermediate benzyl 2-(7-azabicyclo[2.2.1]heptan-7-yl)-2-phenylacetate using the following condition: the intermediate (303.7 mg) was dissolved in ethanol, and the resulting solution was injected on a chiral HPLC column (Chiracel AD-H column, 30×250 mm, 5 um) eluting with 90% CO₂-10% EtOH at 70 mL/min, and a temperature of 35° C. to provide 124.5 mg of enantiomer-1 and 133.8 mg of enantiomer-2. These benzyl esters were hydrogenolysed according to the preparation of Cap-7 to provide Cap-77: ¹H NMR (DMSO-d₆, δ=2.5 ppm, 400 MHz): δ 7.55 (m, 2H), 7.38-7.30 (m, 3H), 4.16 (s, 1H), 3.54 (app br s, 2H), 2.08-1.88 (m, 4H), 1.57-1.46 (m, 4H). LC (Cond. 1): RT=0.67 min; LC/MS: Anal. Calcd. for [M+H]⁺

C₁₄H₁₈BrNO₂: 232.13. found 232.18. HRMS: Anal. Calcd. for [M+H]⁺ C₁₄H₁₈BrNO₂: 232.1338. found 232.1340.

Cap-78

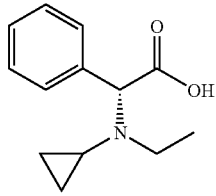

NaCNBH₃ (0.5828 g, 9.27 mmol) was added to a mixture of the HCl salt of (R)-2-(ethylamino)-2-phenylacetic acid (an intermediate in the synthesis of Cap-3; 0.9923 mg, 4.60 mmol) and (1-ethoxycyclopropoxy)trimethylsilane (1.640 g, 9.40 mmol) in MeOH (10 mL), and the semi-heterogeneous mixture was heated at 50° C. with an oil bath for 20 hr. More (1-ethoxycyclopropoxy)trimethylsilane (150 mg, 0.86 mmol) and NaCNBH₃ (52 mg, 0.827 mmol) were added and the reaction mixture was heated for an additional 3.5 hr. It was then allowed to cool to ambient temperature and acidified to a ~pH region of 2 with concentrated HCl, and the mixture was filtered and the filtrate was rotervaped. The resulting crude material was taken up in i-PrOH (6 mL) and heated to effect dissolution, and the non-dissolved part was filtered off and the filtrate concentrated in vacuo. About ⅓ of the resultant crude material was purified with a reverse phase HPLC (H₂O/MeOH/TFA) to afford the TFA salt of Cap-78 as a colorless viscous oil (353 mg). ¹H NMR (DMSO-d₆, δ=2.5 ppm, 400 MHz; after D₂O exchange): δ 7.56-7.49 (m, 5H), 5.35 (S, 1H), 3.35 (m, 1H), 3.06 (app br s, 1H), 2.66 (m, 1H), 1.26 (t, J=7.3, 3H), 0.92 (m, 1H), 0.83-0.44 (m, 3H). LC (Cond. 1): RT=0.64 min; LC/MS: Anal. Calcd. for [M+H]⁺ C₁₃H₁₈NO₂: 220.13. found 220.21. HRMS: Anal. Calcd. for [M+H]⁺ C₁₃H₁₈NO₂: 220.1338. found 220.1343.

Cap-79

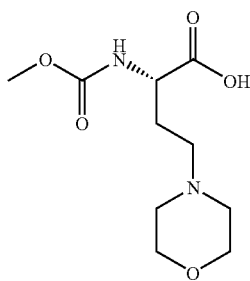

Ozone was bubbled through a cooled (−78° C.) CH₂Cl₂ (5.0 mL) solution Cap-55 (369 mg, 2.13 mmol) for about 50 min until the reaction mixture attained a tint of blue color. Me₂S (10 pipet drops) was added, and the reaction mixture was stirred for 35 min. The −78° C. bath was replaced with a −10° C. bath and stirring continued for an additional 30 min, and then the volatile component was removed in vacuo to afford a colorless viscous oil.

NaBH₃CN (149 mg, 2.25 mmol) was added to a MeOH (5.0 mL) solution of the above crude material and morpholine (500 μL, 5.72 mmol) and the mixture was stirred at ambient condition for 4 hr. It was cooled to ice-water temperature and treated with concentrated HCl to bring its pH to ~2.0, and then stirred for 2.5 hr. The volatile component was removed in vacuo, and the residue was purified with a combination of MCX resin (MeOH wash; 2.0 N NH₃/MeOH elution) and a reverse phase HPLC (H₂O/MeOH/TFA) to afford Cap-79 containing unknown amount of morpholine.

In order to consume the morpholine contaminant, the above material was dissolved in CH₂Cl₂ (1.5 mL) and treated with Et₃N (0.27 mL, 1.94 mmol) followed by acetic anhydride (0.10 mL, 1.06 mmol) and stirred at ambient condition for 18 hr. THF (1.0 mL) and H₂O (0.5 mL) were added and stirring continued for 1.5 hr. The volatile component was removed in vacuo, and the resultant residue was passed through MCX resin (MeOH wash; 2.0 N NH₃/MeOH elution) to afford impure Cap-79 as a brown viscous oil, which was used for the next step without further purification.

Cap-80a and -80b

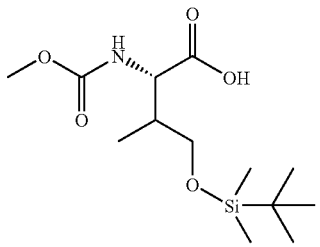

Cap-80a: S/S-diastereomer
Cap-80b: S/R-diastereomer

SOCl₂ (6.60 mL, 90.5 mmol) was added drop-wise over 15 min to a cooled (ice-water) mixture of (S)-3-amino-4-(benzyloxy)-4-oxobutanoic acid (10.04 g, 44.98 mmol) and MeOH (300 mL), the cooling bath was removed and the reaction mixture was stirred at ambient condition for 29 hr. Most of the volatile component was removed in vacuo and the residue was carefully partitioned between EtOAc (150 mL) and saturated NaHCO₃ solution. The aqueous phase was extracted with EtOAc (150 mL, 2×), and the combined organic phase was dried (MgSO₄), filtered, and concentrated in vacuo to afford (S)-1-benzyl 4-methyl 2-aminosuccinate as a colorless oil (9.706 g). ¹H NMR (DMSO-d₆, δ=2.5 ppm, 400 MHz): δ 7.40-7.32 (m, 5H), 5.11 (s, 2H), 3.72 (app t, J=6.6, 1H), 3.55 (s, 3H), 2.68 (dd, J=15.9, 6.3, 1H), 2.58 (dd, J=15.9, 6.8, 1H), 1.96 (s, 2H). LC (Cond. 1): RT=0.90 min; LC/MS: Anal. Calcd. for [M+H]⁺ C₁₂H₁₆NO₄: 238.11. found 238.22.

Pb(NO₃)₂ (6.06 g, 18.3 mmol) was added over 1 min to a CH₂Cl₂ (80 mL) solution of (S)-1-benzyl 4-methyl 2-aminosuccinate (4.50 g, 19.0 mmol), 9-bromo-9-phenyl-9H-fluorene (6.44 g, 20.0 mmol) and Et₃N (3.0 mL, 21.5 mmol), and the heterogeneous mixture was stirred at ambient condition for 48 hr. The mixture was filtered and the filtrate was treated with MgSO₄ and filtered again, and the final filtrate was concentrated. The resulting crude material was submitted to a Biotage purification (350 g silica gel, CH₂Cl₂ elution) to afford (S)-1-benzyl 4-methyl 2-(9-phenyl-9H-fluoren-9-ylamino)succinate as highly viscous colorless oil (7.93 g). ¹H NMR (DMSO-d₆, δ=2.5 ppm, 400 MHz): δ 7.82 (m, 2H), 7.39-7.13 (m, 16H), 4.71 (d, J=12.4, 1H), 4.51 (d, J=12.6, 1H), 3.78 (d, J=9.1, NH), 3.50 (s, 3H), 2.99 (m, 1H), 2.50-2.41 (m, 2H, partially overlapped with solvent). LC (Cond. 1): RT=2.16 min; LC/MS: Anal. Calcd. for [M+H]⁺ C₃₁H₂₈NO₄: 478.20. found 478.19.

LiHMDS (9.2 mL of 1.0 M/THF, 9.2 mmol) was added drop-wise over 10 min to a cooled (−78° C.) THF (50 mL) solution of (S)-1-benzyl 4-methyl 2-(9-phenyl-9H-fluoren-9-ylamino)succinate (3.907 g, 8.18 mmol) and stirred for 1 hr.

MeI (0.57 mL, 9.2 mmol) was added drop-wise over 8 min to the mixture, and stirring was continued for 16.5 hr while allowing the cooling bath to thaw to room temperature. After quenching with saturated NH$_4$Cl solution (5 mL), most of the organic component was removed in vacuo and the residue was partitioned between CH$_2$Cl$_2$ (100 mL) and water (40 mL). The organic layer was dried (MgSO$_4$), filtered, and concentrated in vacuo, and the resulting crude material was purified with a Biotage (350 g silica gel; 25% EtOAc/hexanes) to afford 3.65 g of a 2S/3S and 2S/3R diastereomeric mixtures of 1-benzyl 4-methyl 3-methyl-2-(9-phenyl-9H-fluoren-9-ylamino)succinate in ~1.0:0.65 ratio ($^1$H NMR). The stereochemistry of the dominant isomer was not determined at this juncture, and the mixture was submitted to the next step without separation. Partial $^1$H NMR data (DMSO-d$_6$, δ=2.5 ppm, 400 MHz): major diastereomer, δ 4.39 (d, J=12.3, 1H of CH$_2$), 3.33 (s, 3H, overlapped with H$_2$O signal), 3.50 (d, J=10.9, NH), 1.13 (d, J=7.1, 3H); minor diastereomer, δ 4.27 (d, J=12.3, 1H of CH$_2$), 3.76 (d, J=10.9, NH), 3.64 (s, 3H), 0.77 (d, J=7.0, 3H). LC (Cond. 1): RT=2.19 min; LC/MS: Anal. Calcd. for [M+H]$^+$ C$_{32}$H$_{30}$NO$_4$: 492.22. found 492.15.

Diisobutylaluminum hydride (20.57 ml of 1.0 M in hexanes, 20.57 mmol) was added drop-wise over 10 min to a cooled (−78° C.) THF (120 mL) solution of (2S)-1-benzyl 4-methyl 3-methyl-2-(9-phenyl-9H-fluoren-9-ylamino)succinate (3.37 g, 6.86 mmol) prepared above, and stirred at −78° C. for 20 hr. The reaction mixture was removed from the cooling bath and rapidly poured into ~1M H$_3$PO$_4$/H$_2$O (250 mL) with stirring, and the mixture was extracted with ether (100 mL, 2×). The combined organic phase was washed with brine, dried (MgSO$_4$), filtered and concentrated in vacuo. A silica gel mesh of the crude material was prepared and submitted to chromatography (25% EtOAc/hexanes; gravity elution) to afford 1.1 g of (2S,3S)-benzyl 4-hydroxy-3-methyl-2-(9-phenyl-9H-fluoren-9-ylamino)butanoate, contaminated with benzyl alcohol, as a colorless viscous oil and (2S,3R)-benzyl 4-hydroxy-3-methyl-2-(9-phenyl-9H-fluoren-9-ylamino)butanoate containing the (2S,3R) stereoisomer as an impurity. The later sample was resubmitted to the same column chromatography purification conditions to afford 750 mg of purified material as a white foam. [Note: the (2S,3S) isomer elutes before the (2S,3R) isomer under the above condition]. (2S,3S) isomer: $^1$H NMR (DMSO-d$_6$, δ=2.5 ppm, 400 MHz): 7.81 (m, 2H), 7.39-7.08 (m, 16H), 4.67 (d, J=12.3, 1H), 4.43 (d, J=12.4, 1H), 4.21 (app t, J=5.2, OH), 3.22 (d, J=10.1, NH), 3.17 (m, 1H), 3.08 (m, 1H), ~2.5 (m, 1H, overlapped with the solvent signal), 1.58 (m, 1H), 0.88 (d, J=6.8, 3H). LC (Cond. 1): RT=2.00 min; LC/MS: Anal. Calcd. for [M+H]$^+$ C$_{31}$H$_{30}$NO$_3$: 464.45. found 464.22. (2S,3R) isomer: $^1$H NMR (DMSO-d$_6$, δ=2.5 ppm, 400 MHz): 7.81 (d, J=7.5, 2H), 7.39-7.10 (m, 16H), 4.63 (d, J=12.1, 1H), 4.50 (app t, J=4.9, 1H), 4.32 (d, J=12.1, 1H), 3.59-3.53 (m, 2H), 3.23 (m, 1H), 2.44 (dd, J=9.0, 8.3, 1H), 1.70 (m, 1H), 0.57 (d, J=6.8, 3H). LC (Cond. 1): RT=1.92 min; LC/MS: Anal. Calcd. for [M+H]$^+$ C$_{31}$H$_{30}$NO$_3$: 464.45. found 464.52.

The relative stereochemical assignments of the DIBAL-reduction products were made based on NOE studies conducted on lactone derivatives prepared from each isomer by employing the following protocol: LiHMDS (50 μL of 1.0 M/THF, 0.05 mmol) was added to a cooled (ice-water) THF (2.0 mL) solution of (2S,3S)-benzyl 4-hydroxy-3-methyl-2-(9-phenyl-9H-fluoren-9-ylamino)butanoate (62.7 mg, 0.135 mmol), and the reaction mixture was stirred at similar temperature for ~2 hr. The volatile component was removed in vacuo and the residue was partitioned between CH$_2$Cl$_2$ (30 mL), water (20 mL) and saturated aqueous NH$_4$Cl solution (1 mL). The organic layer was dried (MgSO$_4$), filtered, and concentrated in vacuo, and the resulting crude material was submitted to a Biotage purification (40 g silica gel; 10-15% EtOAc/hexanes) to afford (3S,4S)-4-methyl-3-(9-phenyl-9H-fluoren-9-ylamino)dihydrofuran-2(3H)-one as a colorless film of solid (28.1 mg). (2S,3R)-benzyl 4-hydroxy-3-methyl-2-(9-phenyl-9H-fluoren-9-ylamino)butanoate was elaborated similarly to (3S,4R)-4-methyl-3-(9-phenyl-9H-fluoren-9-ylamino)dihydrofuran-2(3H)-one. (3S,4S)-lactone isomer: $^1$H NMR (DMSO-d$_6$, δ=2.5 ppm, 400 MHz), 7.83 (d, J=7.5, 2H), 7.46-7.17 (m, 11H), 4.14 (app t, J=8.3, 1H), 3.60 (d, J=5.8, NH), 3.45 (app t, J=9.2, 1H), ~2.47 (m, 1H, partially overlapped with solvent signal), 2.16 (m, 1H), 0.27 (d, J=6.6, 3H). LC (Cond. 1): RT=1.98 min; LC/MS: Anal. Calcd. for [M+Na]$^+$ C$_{24}$H$_{21}$NNaO$_2$: 378.15. found 378.42. (3S,4R)-lactone isomer: $^1$H NMR (DMSO-d$_6$, δ=2.5 ppm, 400 MHz), 7.89 (d, J=7.6, 1H), 7.85 (d, J=7.3, 1H), 7.46-7.20 (m, 11H), 3.95 (dd, J=9.1, 4.8, 1H), 3.76 (d, J=8.8, 1H), 2.96 (d, J=3.0, NH), 2.92 (dd, J=6.8, 3, NCH), 1.55 (m, 1H), 0.97 (d, J=7.0, 3H). LC (Cond. 1): RT=2.03 min; LC/MS: Anal. Calcd. for [M+Na]$^+$ C$_{24}$H$_{21}$NNaO$_2$: 378.15. found 378.49.

TBDMS-Cl (48 mg, 0.312 mmol) followed by imidazole (28.8 mg, 0.423 mmol) were added to a CH$_2$Cl$_2$ (3 ml) solution of (2S,3S)-benzyl 4-hydroxy-3-methyl-2-(9-phenyl-9H-fluoren-9-ylamino)butanoate (119.5 mg, 0.258 mmol), and the mixture was stirred at ambient condition for 14.25 hr. The reaction mixture was then diluted with CH$_2$Cl$_2$ (30 mL) and washed with water (15 mL), and the organic layer was dried (MgSO$_4$), filtered, and concentrated in vacuo. The resultant crude material was purified with a Biotage (40 g silica gel; 5% EtOAc/hexanes) to afford (2S,3S)-benzyl 4-(tert-butyldimethylsilyloxy)-3-methyl-2-(9-phenyl-9H-fluoren-9-ylamino)butanoate, contaminated with TBDMS based impurities, as a colorless viscous oil (124.4 mg). (2S,3R)-benzyl 4-hydroxy-3-methyl-2-(9-phenyl-9H-fluoren-9-ylamino)butanoate was elaborated similarly to (2S,3R)-benzyl 4-(tert-butyldimethylsilyloxy)-3-methyl-2-(9-phenyl-9H-fluoren-9-ylamino)butanoate. (2S,3S)-silyl ether isomer: $^1$H NMR (DMSO-d$_6$, δ=2.5 ppm, 400 MHz), 7.82 (d, J=4.1, 1H), 7.80 (d, J=4.0, 1H), 7.38-7.07 (m, 16H), 4.70 (d, J=12.4, 1H), 4.42 (d, J=12.3, 1H), 3.28-3.19 (m, 3H), 2.56 (dd, J=10.1, 5.5, 1H), 1.61 (m, 1H), 0.90 (d, J=6.8, 3H), 0.70 (s, 9H), −0.13 (s, 3H), −0.16 (s, 3H). LC (Cond. 1, where the run time was extended to 4 min): RT=3.26 min; LC/MS: Anal. Calcd. for [M+H]$^+$ C$_{37}$H$_{44}$NO$_3$Si: 578.31. found 578.40. (2S,3R)-silyl ether isomer: $^1$H NMR (DMSO-d$_6$, δ=2.5 ppm, 400 MHz), 7.82 (d, J=3.0, 1H), 7.80 (d, J=3.1, 1H), 7.39-7.10 (m, 16H), 4.66 (d, J=12.4, 1H), 4.39 (d, J=12.4, 1H), 3.61 (dd, J=9.9, 5.6, 1H), 3.45 (d, J=9.5, 1H), 3.41 (dd, J=10, 6.2, 1H), 2.55 (dd, J=9.5, 7.3, 1H), 1.74 (m, 1H), 0.77 (s, 9H), 0.61 (d, J=7.1, 3H), −0.06 (s, 3H), −0.08 (s, 3H).

A balloon of hydrogen was attached to a mixture of (2S,3S)-benzyl 4-(tert-butyldimethylsilyloxy)-3-methyl-2-(9-phenyl-9H-fluoren-9-ylamino)butanoate (836 mg, 1.447 mmol) and 10% Pd/C (213 mg) in EtOAc (16 mL) and the mixture was stirred at room temperature for ~21 hr, where the balloon was recharged with H$_2$ as necessary. The reaction mixture was diluted with CH$_2$Cl$_2$ and filtered through a pad of diatomaceous earth (Celite-545), and the pad was washed with EtOAc (200 mL), EtOAc/MeOH (1:1 mixture, 200 mL) and MeOH (750 mL). The combined organic phase was concentrated, and a silica gel mesh was prepared from the resulting crude material and submitted to a flash chromatography (8:2:1 mixture of EtOAc/i-PrOH/H$_2$O) to afford (2S,3S)-2-amino-4-(tert-butyldimethylsilyloxy)-3-methylbutanoic acid as a white fluffy solid (325 mg). (2S,3R)-benzyl 4-(tert-butyldimethylsilyloxy)-3-methyl-2-(9-phenyl-9H-fluoren-9- ylamino)butanoate was similarly elaborated to (2S,3R)-2-amino-4-(tert-butyldimethylsilyloxy)-3-methylbutanoic acid. (2S,3S)-amino acid isomer: ¹H NMR (Methanol-d₄, δ=3.29 ppm, 400 MHz), 3.76 (dd, J=10.5, 5.2, 1H), 3.73 (d, J=3.0, 1H), 3.67 (dd, J=10.5, 7.0, 1H), 2.37 (m, 1H), 0.97 (d, J=7.0, 3H), 0.92 (s, 9H), 0.10 (s, 6H). LC/MS: Anal. Calcd. for [M+H]⁺ C₁₁H₂₆NO₃Si: 248.17. found 248.44. (2S,3R)-amino acid isomer: ¹H NMR (Methanol-d₄, δ=3.29 ppm, 400 MHz), 3.76-3.75 (m, 2H), 3.60 (d, J=4.1, 1H), 2.16 (m, 1H), 1.06 (d, J=7.3, 3H), 0.91 (s, 9H), 0.09 (s, 6H). Anal. Calcd. for [M+H]⁺ C₁₁H₂₆NO₃Si: 248.17. found 248.44.

Water (1 mL) and NaOH (0.18 mL of 1.0 M/H₂O, 0.18 mmol) were added to a mixture of (2S,3S)-2-amino-4-(tert-butyldimethylsilyloxy)-3-methylbutanoic acid (41.9 mg, 0.169 mmol) and Na₂CO₃ (11.9 mg, 0.112 mmol), and sonicated for about 1 min to effect dissolution of reactants. The mixture was then cooled with an ice-water bath, methyl chloroformate (0.02 mL, 0.259 mmol) was added over 30 s, and vigorous stirring was continued at similar temperature for 40 min and then at ambient temperature for 2.7 hr. The reaction mixture was diluted with water (5 mL), cooled with ice-water bath and treated drop-wise with 1.0 N HCl aqueous solution (~0.23 mL). The mixture was further diluted with water (10 mL) and extracted with CH₂Cl₂ (15 mL, 2×). The combined organic phase was dried (MgSO₄), filtered, and concentrated in vacuo to afford Cap-80a as an off-white solid. (2S,3R)-2-amino-4-(tert-butyldimethylsilyloxy)-3-methylbutanoic acid was similarly elaborated to Cap-80b. Cap-80a: ¹H NMR (DMSO-d₆, δ=2.5 ppm, 400 MHz), 12.57 (br s, 1H), 7.64 (d, J=8.3, 0.3H), 7.19 (d, J=8.8, 0.7H), 4.44 (dd, J=8.1, 4.6, 0.3H), 4.23 (dd, J=8.7, 4.4, 0.7H), 3.56/3.53 (two singlets, 3H), 3.48-3.40 (m, 2H), 2.22-2.10 (m, 1H), 0.85 (s, 9H), ~0.84 (d, 0.9H, overlapped with t-Bu signal), 0.79 (d, J=7, 2.1H), 0.02/0.01/0.00 (three overlapping singlets, 6H). LC/MS: Anal. Calcd. for [M+Na]⁺ C₁₃H₂₇NNaO₅Si: 328.16. found 328.46. Cap-80b: ¹H NMR (CDCl₃, δ=7.24 ppm, 400 MHz), 6.00 (br d, J=6.8, 1H), 4.36 (dd, J=7.1, 3.1, 1H), 3.87 (dd, J=10.5, 3.0, 1H), 3.67 (s, 3H), 3.58 (dd, J=10.6, 4.8, 1H), 2.35 (m, 1H), 1.03 (d, J=7.1, 3H), 0.90 (s, 9H), 0.08 (s, 6H). LC/MS: Anal. Calcd. for [M+Na]⁺ C₁₃H₂₇NNaO₅Si: 328.16. found 328.53. The crude products were utilized without further purification.

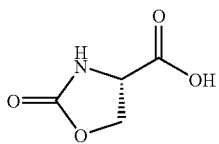

Cap-81

Prepared according to the protocol described by Falb et al. *Synthetic Communications* 1993, 23, 2839.

Cap-82 to Cap-85

Cap-82 to Cap-85 were synthesized from appropriate starting materials according to the procedure described for Cap-51. The samples exhibited similar spectral profiles as that of their enantiomers (i.e., Cap-4, Cap-13, Cap-51 and Cap-52, respectively)

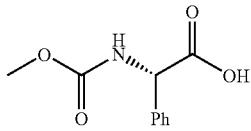

Cap-82

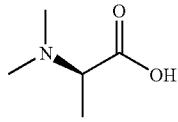

Cap-83

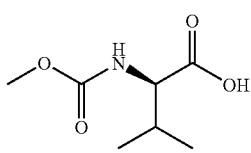

Cap-84

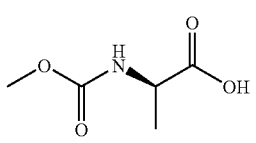

Cap-85

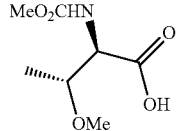

Cap-86

To a mixture of O-methyl-L-threonine (3.0 g, 22.55 mmol), NaOH (0.902 g, 22.55 mmol) in H₂O (15 mL) was added ClCO₂Me (1.74 mL, 22.55 mmol) dropwise at 0° C. The mixture was allowed to stir for 12 h and acidified to pH 1 using 1N HCl. The aqueous phase was extracted with EtOAc and (2×250 mL) and 10% MeOH in CH₂Cl₂ (250 mL) and the combined organic phases were concentrated under in vacuo to afford a colorless oil (4.18 g, 97%) which was of sufficient purity for use in subsequent steps. ¹HNMR (400 MHz, CDCl₃) δ 4.19 (s, 1H), 3.92-3.97 (m, 1H), 3.66 (s, 3H), 1.17 (d, J=7.7 Hz, 3H). LCMS: Anal. Calcd. for C₇H₁₃NO₅: 191. found: 190 (M−H)⁻.

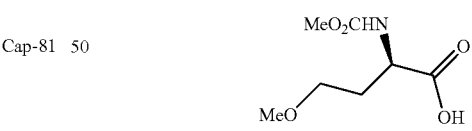

Cap-87

To a mixture of L-homoserine (2.0 g, 9.79 mmol), Na₂CO₃ (2.08 g, 19.59 mmol) in H₂O (15 mL) was added ClCO₂Me (0.76 mL, 9.79 mmol) dropwise at 0° C. The mixture was allowed to stir for 48 h and acidified to pH 1 using 1N HCl. The aqueous phase was extracted with EtOAc and (2×250 mL) and the combined organic phases were concentrated under in vacuo to afford a colorless solid (0.719 g, 28%) which was of sufficient purity for use in subsequent steps. ¹HNMR (400 MHz, CDCl₃) δ 4.23 (dd, J=4.5, 9.1 Hz, 1H), 3.66 (s, 3H), 3.43-3.49 (m, 2H), 2.08-2.14 (m, 1H), 1.82-1.89 (m, 1H). LCMS: Anal. Calcd. for C₇H₁₃NO₅: 191. found: 192 (M+H)⁺.

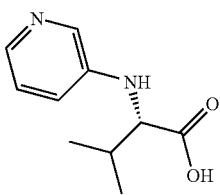
Cap-88

A mixture of L-valine (1.0 g, 8.54 mmol), 3-bromopyridine (1.8 mL, 18.7 mmol), $K_2CO_3$ (2.45 g, 17.7 mmol) and CuI (169 mg, 0.887 mmol) in DMSO (10 mL) was heated at 100° C. for 12 h. The reaction mixture was cooled to rt, poured into $H_2O$ (ca. 150 mL) and washed with EtOAc (×2). The organic layers were extracted with a small amount of $H_2O$ and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with $H_2O$ (200 mL), MeOH (200 mL), and then $NH_3$ (3M in MeOH, 2×200 mL). The appropriate fractions was concentrated in vacuo and the residue (ca. 1.1 g) was dissolved in $H_2O$, frozen and lyophilized. The title compound was obtained as a foam (1.02 g, 62%). $^1$HNMR (400 MHz, DMSO-$d_6$) δ 8.00 (s, br, 1H), 7.68-7.71 (m, 1H), 7.01 (s, br, 1H), 6.88 (d, J=7.5 Hz, 1H), 5.75 (s, br, 1H), 3.54 (s, 1H), 2.04-2.06 (m, 1H), 0.95 (d, J=6.0 Hz, 3H), 0.91 (d, J=6.6 Hz, 3H). LCMS: Anal. Calcd. for $C_{10}H_{14}N_2O_2$: 194. found: 195 (M+H)$^+$.

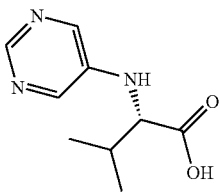
Cap-89

A mixture of L-valine (1.0 g, 8.54 mmol), 5-bromopyrimidine (4.03 g, 17.0 mmol), $K_2CO_3$ (2.40 g, 17.4 mmol) and CuI (179 mg, 0.94 mmol) in DMSO (10 mL) was heated at 100° C. for 12 h. The reaction mixture was cooled to RT, poured into $H_2O$ (ca. 150 mL) and washed with EtOAc (×2). The organic layers were extracted with a small amount of $H_2O$ and the combined aq phases were acidified to ca. pH 2 with 6N HCl. The volume was reduced to about one-third and 20 g of cation exchange resin (Strata) was added. The slurry was allowed to stand for 20 min and loaded onto a pad of cation exchange resin (Strata) (ca. 25 g). The pad was washed with $H_2O$ (200 mL), MeOH (200 mL), and then $NH_3$ (3M in MeOH, 2×200 mL). The appropriate fractions was concentrated in vacuo and the residue (ca. 1.1 g) was dissolved in $H_2O$, frozen and lyophilized. The title compound was obtained as a foam (1.02 g, 62%). $^1$HNMR (400 MHz, $CD_3OD$) showed the mixture to contain valine and the purity could not be estimated. The material was used as is in subsequent reactions. LCMS: Anal. Calcd. for $C_9H_{13}N_3O_2$: 195. found: 196 (M+H)$^+$.

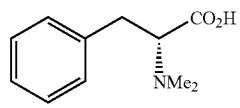
Cap-90

Cap-90 was prepared according to the method described for the preparation of Cap-1. The crude material was used as is in subsequent steps. LCMS: Anal. Calcd. for $C_{11}H_{15}NO_2$: 193. found: 192 (M−H)$^-$.

The following caps were prepared according to the method of example 51:

| Cap | Structure | LCMS |
| --- | --- | --- |
| Cap-91 | 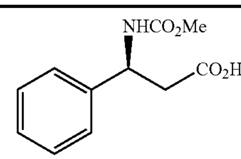 | LCMS: Anal. Calcd. for $C_{11}H_{13}NO_4$: 223; found: 222 (M − H)$^-$. |
| Cap-92 | 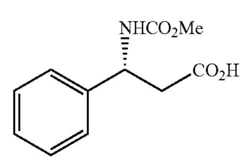 | LCMS: Anal. Calcd. for $C_{11}H_{13}NO_4$: 223; found: 222 (M − H)$^-$. |
| Cap-93 | 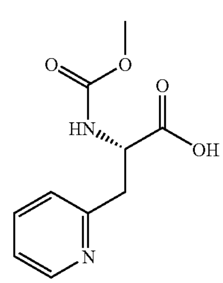 | LCMS: Anal. Calcd. for $C_{10}H_{12}N_2O_4$: 224; found: 225 (M + H)$^+$. |

| Cap | Structure | LCMS |
|---|---|---|
| Cap-94 | (histidine with methyl carbamate, L-configuration) | LCMS: Anal. Calcd. for $C_8H_{11}N_3O_4$: 213; found: 214 $(M + H)^+$. |
| Cap-95 | (methyl carbamate NH, 3-amino-5-phenylpentanoic acid derivative) | LCMS: Anal. Calcd. for $C_{13}H_{17}NO_4$: 251; found: 250 $(M - H)^-$. |
| Cap-96 | (methyl carbamate NH, 3-amino-4-phenylbutanoic acid derivative) | LCMS: Anal. Calcd. for $C_{12}H_{15}NO_4$: 237; found: 236 $(M - H)^-$. |
| Cap-97 | (methyl carbamate on cis-2-aminocyclohexanecarboxylic acid) | LCMS: Anal. Calcd. for $C_9H_{15}NO_4$: 201; found: 200 $(M - H)^-$. |
| Cap-98 | (methyl carbamate on cis-2-aminocyclohexanecarboxylic acid, other enantiomer) | LCMS: Anal. Calcd. for $C_9H_{15}NO_4$: 201; found: 202 $(M + H)^+$. |
| Cap-99 | (methyl carbamate on 3-aminocyclopentanecarboxylic acid) | $^1$HNMR(400 MHz, CD$_3$OD) δ 3.88-3.94(m, 1 H), 3.60, 3.61(s, 3 H), 2.80(m, 1 H), 2.20(m, 1 H), 1.82-1.94(m, 3 H), 1.45-1.71(m, 2 H). |

-continued

| Cap | Structure | LCMS |
|---|---|---|
| Cap-99a | 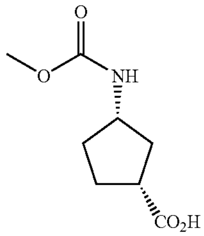 | ¹HNMR(400 MHz, CD₃OD) δ 3.88-3.94(m, 1 H), 3.60, 3.61(s, 3 H), 2.80(m, 1 H), 2.20(m, 1 H), 1.82-1.94(m, 3 H), 1.45-1.71(m, 2 H). |
| Cap-100 | 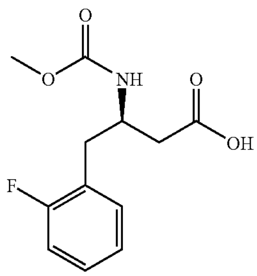 | LCMS: Anal. Calcd. for $C_{12}H_{14}NO_4F$: 255; found: 256(M + H)⁺. |
| Cap-101 | 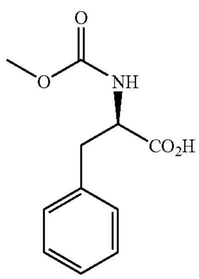 | LCMS: Anal. Calcd. for $C_{11}H_{13}NO_4$: 223; found: 222 (M − H)⁻. |
| Cap-102 | 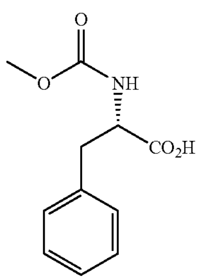 | LCMS: Anal. Calcd. for $C_{11}H_{13}NO_4$: 223; found: 222 (M − H)⁻ |
| Cap-103 | 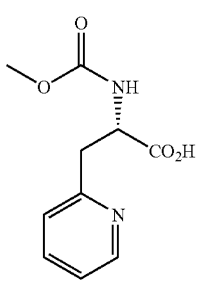 | LCMS: Anal. Calcd. for $C_{10}H_{12}N_2O_4$: 224; found: 225 (M + H)⁺. |
| Cap-104 | 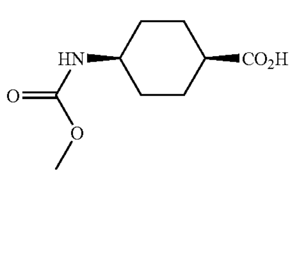 | ¹HNMR(400 MHz, CD₃OD) δ 3.60(s, 3 H), 3.50-3.53 (m, 1 H), 2.66-2.69 and 2.44-2.49(m, 1 H), 1.91-2.01 (m, 2 H), 1.62-1.74(m, 4 H), 1.51-1.62(m, 2 H). |

-continued

| Cap | Structure | LCMS |
|---|---|---|
| Cap-105 | (trans-4-(methoxycarbonylamino)cyclohexanecarboxylic acid) | ¹HNMR(400 MHz, CD₃OD) δ 3.60(s, 3 H), 3.33-3.35 (m, 1 H, partially obscured by solvent), 2.37-2.41 and 2.16-2.23(m, 1 H), 1.94-2.01(m, 4 H), 1.43-1.53(m, 2 H), 1.17-1.29(m, 2 H). |
| Cap-106 | (trans-4-(diethylamino)cyclohexanecarboxylic acid) | ¹HNMR(400 MHz, CD₃OD) δ 3.16(q, J = 7.3 Hz, 4 H), 2.38-2.41(m, 1 H), 2.28-2.31(m, 2 H), 1.79-1.89(m, 2 H), 1.74(app, ddd J = 3.5, 12.5, 15.9 Hz, 2 H), 1.46(app dt J = 4.0, 12.9 Hz, 2 H), 1.26 (t, J = 7.3 Hz, 6 H). |
| Cap-107 | (N-methoxycarbonyl-3-(thiazol-4-yl)-L-alanine) | LCMS: Anal. Calcd. for C₈H₁₀N₂O₄S: 230; found: 231(M + H)⁺. |
| Cap-108 | (N-methoxycarbonyl-1-benzyl-L-histidine) | LCMS: Anal. Calcd. for C₁₅H₁₇N₃O₄: 303; found: 304 (M + H)⁺. |
| Cap-109 | (N-methoxycarbonyl-3-(pyridin-3-yl)-L-alanine) | LCMS: Anal. Calcd. for C₁₀H₁₂N₂O₄: 224; found: 225 (M + H)⁺. |
| Cap-110 | (N-methoxycarbonyl-3-(pyridin-4-yl)-L-alanine) | LCMS: Anal. Calcd. for C₁₀H₁₂N₂O₄: 224; found: 225 (M + H)⁺. |

| Cap | Structure | LCMS |
|---|---|---|
| Cap-111 | (structure: methyl carbamate of tyrosine with methyl phosphate on phenol OH) | LCMS: Anal. Calcd. for $C_{12}H_{16}NO_8P$: 333; found: 334 $(M + H)^+$. |
| Cap-112 | (structure: N-methoxycarbonyl tryptophan) | LCMS: Anal. Calcd. for $C_{13}H_{14}N_2O_4$: 262; found: 263 $(M + H)^+$. |
| Cap-113 | (structure: N-methoxycarbonyl O-benzyl tyrosine) | LCMS: Anal. Calcd. for $C_{18}H_{19}NO_5$: 329; found: 330 $(M + H)^+$. |
| Cap-114 | (structure: N-methoxycarbonyl azetidine-2-carboxylic acid) | $^1$HNMR(400 MHz, CDCl$_3$) δ 4.82-4.84(m, 1 H), 4.00-4.05(m, 2 H), 3.77(s, 3 H), 2.56(s, br, 2 H) |
| Cap-115 | (structure: 3-(methoxycarbonylamino)butanoic acid) | $^1$HNMR(400 MHz, CDCl$_3$) δ 5.13(s, br, 1 H), 4.13(s, br, 1 H), 3.69(s, 3 H), 2.61(d, J = 5.0 Hz, 2 H), 1.28(d, J = 9.1 Hz, 3 H). |
| Cap-116 | (structure: 3-(methoxycarbonylamino)-4-methylpentanoic acid) | $^1$HNMR(400 MHz, CDCl$_3$) δ 5.10(d, J = 8.6 Hz, 1 H), 3.74-3.83(m, 1 H), 3.69(s, 3 H), 2.54-2.61(m, 2 H), 1.88(sept, J = 7.0 Hz, 1 H), 0.95(d, J = 7.0 Hz, 6 H). |

Cap-117 to Cap-123

For the preparation of caps Cap-117 to Cap-123 the Boc amino acids were commercially available and were deprotected by treatment with 25% TFA in CH$_2$Cl$_2$. After complete reaction as judged by LCMS the solvents were removed in vacuo and the corresponding TFA salt of the amino acid was carbamoylated with methyl chloroformate according to the procedure for Cap-51.

| Cap | Structure | LCMS |
|---|---|---|
| Cap-117 | (S)-methyl carbamate, benzyl side chain, β-amino acid | LCMS: Anal. Calcd. for $C_{12}H_{15}NO_4S$: 237; found: 238(M + H)+. |
| Cap-118 | (S)-methyl carbamate, 2-thienylmethyl side chain, β-amino acid | LCMS: Anal. Calcd. for $C_{10}H_{13}NO_4S$: 243; found: 244(M + H)+. |
| Cap-119 | (R)-methyl carbamate, 2-thienylmethyl side chain, β-amino acid | LCMS: Anal. Calcd. for $C_{10}H_{13}NO_4S$: 243; found: 244(M + H)+. |
| Cap-120 | methyl carbamate, 3-thienylmethyl side chain, β-amino acid | LCMS: Anal. Calcd. for $C_{10}H_{13}NO_4S$: 243; found: 244(M + H)+. |
| Cap-121 | methyl carbamate, cyclopentane with CO2H (cis) | ¹HNMR(400 MHz, CDCl₃) δ 4.06-4.16(m, 1 H), 3.63(s, 3 H), 3.43(s, 1 H), 2.82 and 2.66(s, br, 1 H), 1.86-2.10(m, 3 H), 1.64-1.76(m, 2 H), 1.44-1.53(m, 1 H). |
| Cap-122 | methyl carbamate, cyclopentane with CO2H (trans) | ¹HNMR(400 MHz, CDCl₃) δ 5.28 and 5.12 (s, br, 1 H), 3.66(s, 3 H), 2.64-2.74(m, 1 H), 1.86-2.12(m, 3 H), 1.67-1.74(m, 2 H), 1.39-1.54 (m, 1 H). |

| Cap | Structure | LCMS |
|---|---|---|
| Cap-123 | 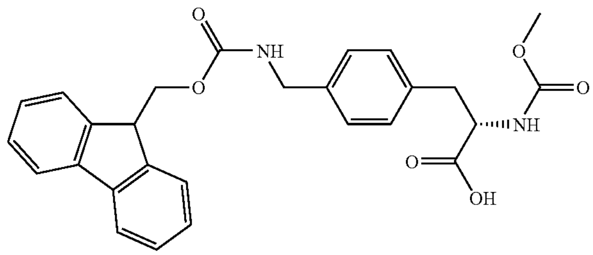 | LCMS: Anal. Calcd. for $C_{27}H_{26}N_2O_6$: 474; found: 475(M + H)$^+$. |

Preparation of Cap-124. (4S,5R)-5-methyl-2-oxooxazolidine-4-carboxylic acid

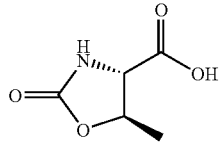

cap-124

The hydrochloride salt of L-threonine tert-butyl ester was carbamoylated according to the procedure for Cap-51. The crude reaction mixture was acidified with 1N HCl to pH~1 and the mixture was extracted with EtOAc (2×50 mL). The combined organic phases were concentrated in vacuo to give a colorless which solidified on standing. The aqueous layer was concentrated in vacuo and the resulting mixture of product and inorganic salts was triturated with EtOAc—CH$_2$Cl$_2$—MeOH (1:1:0.1) and then the organic phase concentrated in vacuo to give a colorless oil which was shown by LCMS to be the desired product. Both crops were combined to give 0.52 g of a solid. $^1$HNMR (400 MHz, CD$_3$OD) δ 4.60 (m, 1H), 4.04 (d, J=5.0 Hz, 1H), 1.49 (d, J=6.3 Hz, 3H). LCMS: Anal. Calcd. for $C_5H_7NO_4$: 145. found: 146 (M+H)$^+$.

Preparation of Cap-125. (S)-2-(tert-butoxycarbonylamino)-4-(dimethylamino)butanoic acid

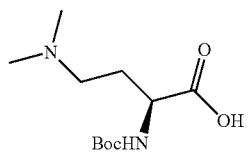

cap-125

Cap-125 was prepared according to the procedure for the preparation of Cap-1. The crude product was used as is in subsequent reactions. LCMS: Anal. Calcd. for $C_{11}H_{22}N_2O_4$: 246. found: 247 (M+H)$^+$.

Preparation of (S)-2-(methoxycarbonylamino)-3-(1-methyl-1H-imidazol-2-yl)propanoic acid (Cap-126)

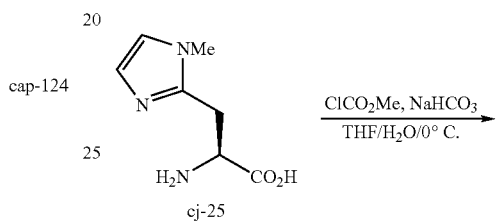

This procedure is a modification of that used to prepare Cap-51. To a suspension of (S)-2-amino-3-(1-methyl-1H-imidazol-2-yl)propanoic acid (0.80 g, 4.70 mmol) in THF (10 mL) and H$_2$O (10 mL) at 0° C. was added NaHCO$_3$ (0.88 g, 10.5 mmol). The resulting mixture was treated with ClCO$_2$Me (0.40 mL, 5.20 mmol) and the mixture allowed to stir at 0° C. After stirring for ca. 2 h LCMS showed no starting material remaining. The reaction was acidified to pH 2 with 6 N HCl.

The solvents were removed in vacuo and the residue was suspended in 20 mL of 20% MeOH in CH$_2$Cl$_2$. The mixture was filtered and concentrated to give a light yellow foam (1.21 g,). LCMS and $^1$H NMR showed the material to be a 9:1 mixture of the methyl ester and the desired product. This material was taken up in THF (10 mL) and H$_2$O (10 mL), cooled to 0° C. and LiOH (249.1 mg, 10.4 mmol) was added. After stirring ca. 1 h LCMS showed no ester remaining. Therefore the mixture was acidified with 6N HCl and the solvents removed in vacuo. LCMS and $^1$H NMR confirm the absence of the ester. The title compound was obtained as its HCl salt contaminated with inorganic salts (1.91 g, >100%). The compound was used as is in subsequent steps without further purification.

$^1$HNMR (400 MHz, CD$_3$OD) δ 8.84, (s, 1H), 7.35 (s, 1H), 4.52 (dd, J=5.0, 9.1 Hz, 1H), 3.89 (s, 3H), 3.62 (s, 3H), 3.35 (dd, J=4.5, 15.6 Hz, 1H, partially obscured by solvent), 3.12 (dd, J=9.0, 15.6 Hz, 1H).

LCMS: Anal. Calcd. for $C_{17}H_{15}NO_2$: 392. found: 393 (M+H)$^+$.

Preparation of (S)-2-(methoxycarbonylamino)-3-(1-methyl-1H-imidazol-4-yl)propanoic acid (Cap-127)

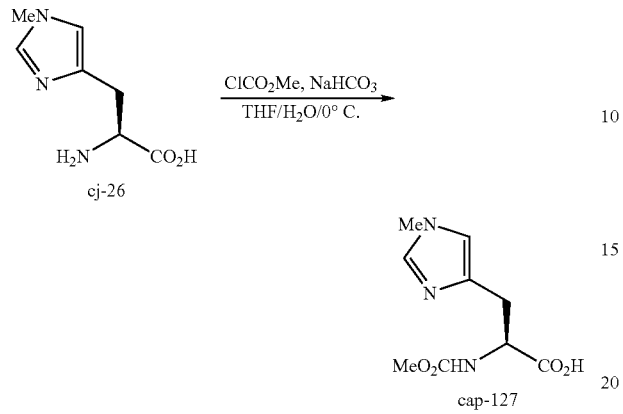

Cap-127 was prepared according to the method for Cap-126 above starting from (S)-2-amino-3-(1-methyl-1H-imidazol-4-yl)propanoic acid (1.11 g, 6.56 mmol), NaHCO$_3$ (1.21 g, 14.4 mmol) and ClCO$_2$Me (0.56 mL, 7.28 mmol). The title compound was obtained as its HCl salt (1.79 g, >100%) contaminated with inorganic salts. LCMS and $^1$H NMR showed the presence of ca. 5% of the methyl ester. The crude mixture was used as is without further purification.

$^1$HNMR (400 MHz, CD$_3$OD) δ 8.90 (s, 1H), 7.35 (s, 1H), 4.48 (dd, J=5.0, 8.6 Hz, 1H), 3.89 (s, 3H), 3.62 (s, 3H), 3.35 (m, 1H), 3.08 (m, 1H).

LCMS: Anal. Calcd. for C$_{17}$H$_{15}$NO$_2$: 392. found: 393 (M+H)$^+$.

Preparation of (S)-2-(methoxycarbonylamino)-3-(1H-1,2,3-triazol-4-yl)propanoic acid (Cap-128)

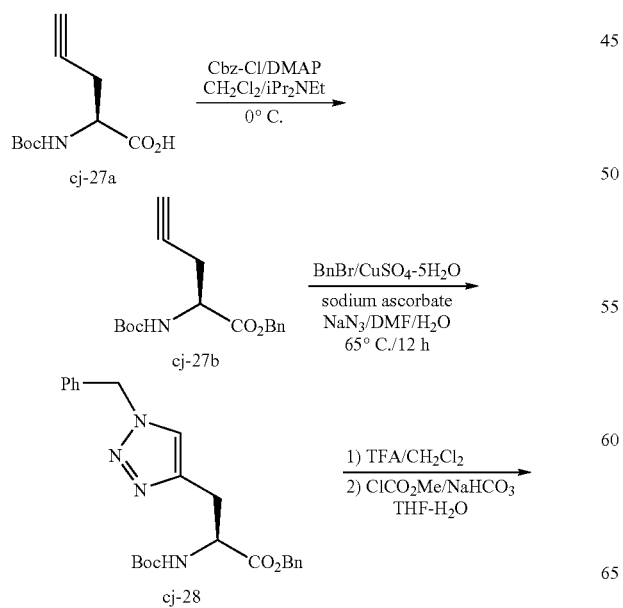

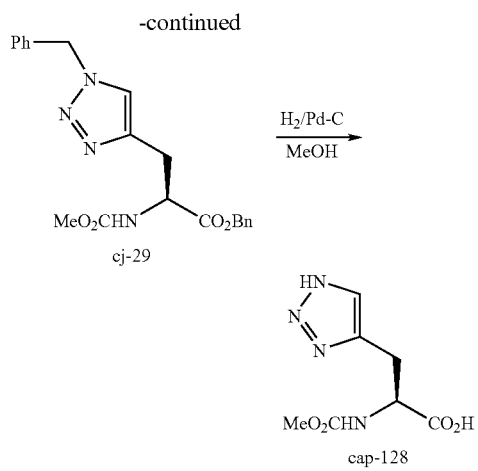

Step 1. Preparation of (S)-benzyl 2-(tert-butoxycarbonylamino)pent-4-ynoate (cj-27b)

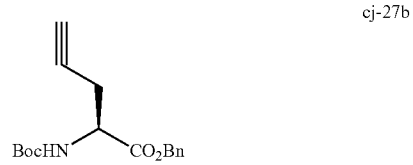

To a solution of cj-27a (1.01 g, 4.74 mmol), DMAP (58 mg, 0.475 mmol) and iPr$_2$NEt (1.7 mL, 9.8 mmol) in CH$_2$Cl$_2$ (100 mL) at 0° C. was added Cbz-Cl (0.68 mL, 4.83 mmol). The solution was allowed to stir for 4 h at 0° C., washed (1N KHSO$_4$, brine), dried (Na$_2$SO$_4$), filtered, and concentrated in vacuo. The residue was purified by flash column chromatography (TLC 6:1 hex:EtOAc) to give the title compound (1.30 g, 91%) as a colorless oil. $^1$HNMR (400 MHz, CDCl$_3$) δ 7.35 (s, 5H), 5.35 (d, br, J=8.1 Hz, 1H), 5.23 (d, J=12.2 Hz, 1H), 5.17 (d, J=12.2 Hz, 1H), 4.48-4.53 (m, 1H), 2.68-2.81 (m, 2H), 2.00 (t, J=2.5 Hz, 1H), 1.44 (s, 9H). LCMS: Anal. Calcd. for C$_{17}$H$_{21}$NO$_4$: 303. found: 304 (M+H)$^+$.

Step 2. Preparation of (S)-benzyl 3-(1-benzyl-1H-1,2,3-triazol-4-yl)-2-(tert-butoxycarbonylamino)propanoate (cj-28)

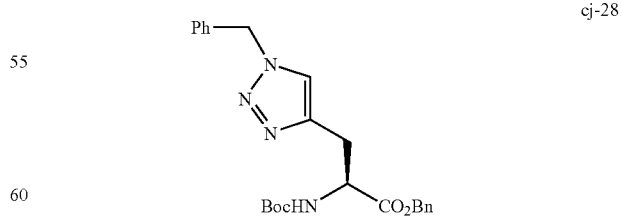

To a mixture of (S)-benzyl 2-(tert-butoxycarbonylamino)pent-4-ynoate (0.50 g, 1.65 mmol), sodium ascorbate (0.036 g, 0.18 mmol), CuSO$_4$·5H$_2$O (0.022 g, 0.09 mmol) and NaN$_3$ (0.13 g, 2.1 mmol) in DMF-H$_2$O (5 mL, 4:1) at rt was added BnBr (0.24 mL, 2.02 mmol) and the mixture was warmed to 65° C. After 5 h LCMS indicated low conversion. A further portion of NaN₃ (100 mg) was added and heating was continued for 12 h. The reaction was poured into EtOAc and H₂O and shaken. The layers were separated and the aqueous layer extracted 3× with EtOAc and the combined organic phases washed (H₂O×3, brine), dried (Na₂SO₄), filtered, and concentrated. The residue was purified by flash (Biotage, 40+M 0-5% MeOH in CH₂Cl₂; TLC 3% MeOH in CH₂Cl₂) to afford a light yellow oil which solidified on standing (748.3 mg, 104%). The NMR was consistent with the desired product but suggests the presence of DMF. The material was used as is without further purification. ¹HNMR (400 MHz, DMSO-d₆) δ 7.84 (s, 1H), 7.27-7.32 (m, 10H), 5.54 (s, 2H), 5.07 (s, 2H), 4.25 (m, 1H), 3.16 (dd, J=1.0, 5.3 Hz, 1H), 3.06 (dd, J=5.3, 14.7 Hz), 2.96 (dd, J=9.1, 14.7 Hz, 1H), 1.31 (s, 9H).

LCMS: Anal. Calcd. for C₂₄H₂₈N₄O₄: 436. found: 437 (M+H)⁺.

Step 2. Preparation of (S)-benzyl 3-(1-benzyl-1H-1,2,3-triazol-4-yl)-2-(methoxycarbonylamino)propanoate (cj-29)

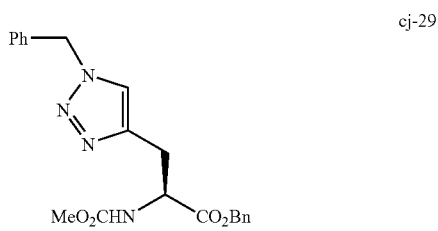

A solution of (S)-benzyl 3-(1-benzyl-1H-1,2,3-triazol-4-yl)-2-(tert-butoxycarbonylamino)propanoate (0.52 g, 1.15 mmol) in CH₂Cl₂ was added TFA (4 mL). The mixture was allowed to stir at room temperature for 2 h. The mixture was concentrated in vacuo to give a colorless oil which solidified on standing. This material was dissolved in THF—H₂O and cooled to 0° C. Solid NaHCO₃ (0.25 g, 3.00 mmol) was added followed by ClCO₂Me (0.25 mL, 3.25 mmol). After stirring for 1.5 h the mixture was acidified to pH~2 with 6N HCl and then poured into H₂O-EtOAc. The layers were separated and the aq phase extracted 2× with EtOAc. The combined org layers were washed (H₂O, brine), dried (Na₂SO₄), filtered, and concentrated in vacuo to give a colorless oil (505.8 mg, 111%, NMR suggested the presence of an unidentified impurity) which solidified while standing on the pump. The material was used as is without further purification. ¹HNMR (400 MHz, DMSO-d₆) δ 7.87 (s, 1H), 7.70 (d, J=8.1 Hz, 1H), 7.27-7.32 (m, 10H), 5.54 (s, 2H), 5.10 (d, J=12.7 Hz, 1H), 5.06 (d, J=12.7 Hz, 1H), 4.32-4.37 (m, 1H), 3.49 (s, 3H), 3.09 (dd, J=5.6, 14.7 Hz, 1H), 2.98 (dd, J=9.6, 14.7 Hz, 1H). LCMS: Anal. Calcd. for C₂₁H₂₂N₄O₄: 394. found: 395 (M+H)⁺.

Step 3. Preparation of (S)-2-(methoxycarbonylamino)-3-(1H-1,2,3-triazol-4-yl)propanoic acid (Cap-128)

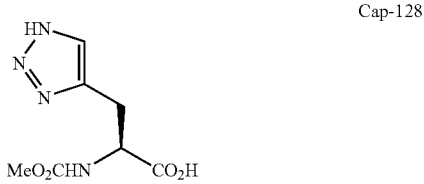

(S)-benzyl 3-(1-benzyl-1H-1,2,3-triazol-4-yl)-2-(methoxycarbonylamino)propanoate (502 mg, 1.11 mmol) was hydrogenated in the presence of Pd—C (82 mg) in MeOH (5 mL) at atmospheric pressure for 12 h. The mixture was filtered through diatomaceous earth (Celite®) and concentrated in vacuo. (S)-2-(methoxycarbonylamino)-3-(1H-1,2,3-triazol-4-yl)propanoic acid was obtained as a colorless gum (266 mg, 111%) which was contaminated with ca. 10% of the methyl ester. The material was used as is without further purification.

¹HNMR (400 MHz, DMSO-d₆) δ 12.78 (s, br, 1H), 7.59 9s, 1H), 7.50 (d, J=8.0 Hz, 1H), 4.19-4.24 (m, 1H), 3.49 (s, 3H), 3.12 (dd, J=4.8 Hz, 14.9 Hz, 1H), 2.96 (dd, J=9.9, 15.0 Hz, 1H). LCMS: Anal. Calcd. for C₇H₁₀N₄O₄: 214. found: 215 (M+H)⁺.

Preparation of (S)-2-(methoxycarbonylamino)-3-(1H-pyrazol-1-yl)propanoic acid (Cap-129)

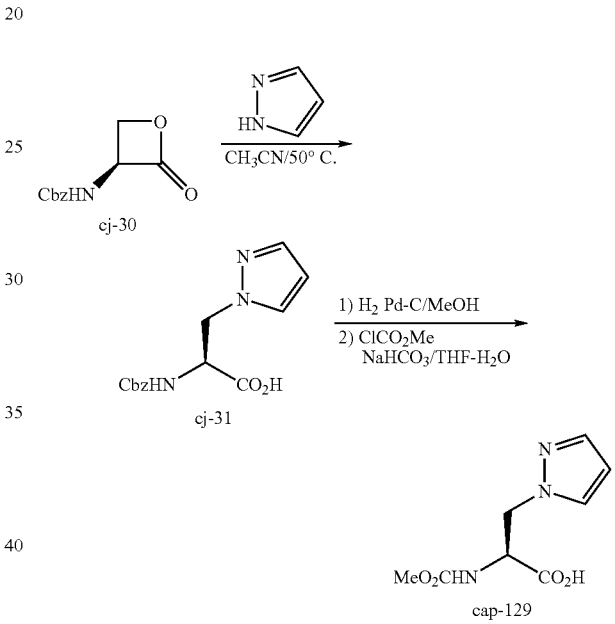

Step 1. Preparation of (S)-2-(benzyloxycarbonylamino)-3-(1H-pyrazol-1-yl)propanoic acid (cj-31)

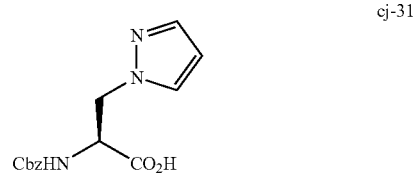

A suspension of (S)-benzyl 2-oxooxetan-3-ylcarbamate (0.67 g, 3.03 mmol), and pyrazole (0.22 g, 3.29 mmol) in CH₃CN (12 mL) was heated at 50° C. for 24 h. The mixture was cooled to rt overnight and the solid filtered to afford (S)-2-(benzyloxycarbonylamino)-3-(1H-pyrazol-1-yl)propanoic acid (330.1 mg). The filtrate was concentrated in vacuo and then triturated with a small amount of CH₃CN (ca. 4 mL) to afford a second crop (43.5 mg). Total yield 370.4 mg (44%).

m.p. 165.5-168° C. lit m.p. 168.5-169.5 Vederas et al. *J. Am. Chem. Soc.* 1985, 107, 7105.

$^1$HNMR (400 MHz, CD$_3$OD) δ 7.51 (d, J=2.0, 1H), 7.48 (s, J=1.5 Hz, 1H), 7.24-7.34 (m, 5H), 6.23 m, 1H), 5.05 (d, 12.7H, 1H), 5.03 (d, J=12.7 Hz, 1H), 4.59-4.66 (m, 2H), 4.42-4.49 (m, 1H). LCMS: Anal. Calcd. for C$_{14}$H$_{15}$N$_3$O$_4$: 289. found: 290 (M+H)$^+$.

Step 2. Preparation of (S)-2-(methoxycarbony-lamino)-3-(1H-pyrazol-1-yl)propanoic acid (Cap-129)

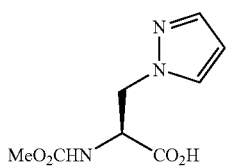

cap-129

(S)-2-(benzyloxycarbonylamino)-3-(1H-pyrazol-1-yl)propanoic acid (0.20 g, 0.70 mmol) was hydrogenated in the presence of Pd—C (45 mg) in MeOH (5 mL) at atmospheric pressure for 2 h. The product appeared to be insoluble in MeOH, therefore the rxn mixture was diluted with 5 mL H$_2$O and a few drops of 6N HCl. The homogeneous solution was filtered through diatomaceous earth (Celite®), and the MeOH removed in vacuo. The remaining solution was frozen and lyophilized to give a yellow foam (188.9 mg). This material was suspended in THF—H$_2$O (1:1, mL) and then cooled to 0° C. To the cold mixture was added NaHCO$_3$ (146.0 mg, 1.74 mmol) carefully (evolution of CO$_2$). After gas evolution had ceased (ca. 15 min) ClCO$_2$Me (0.06 mL, 0.78 mmol) was added dropwise. The mixture was allowed to stir for 2 h and was acidified to pH~2 with 6N HCl and poured into EtOAc. The layers were separated and the aqueous phase extract with EtOAC (×5). The combined organic layers were washed (brine), dried (Na$_2$SO$_4$), filtered, and concentrated to give the title compound as a colorless solid (117.8 mg, 79%).

$^1$HNMR (400 MHz, DMSO-d$_6$) δ 13.04 (s, 1H), 7.63 (d, J=2.6 Hz, 1H), 7.48 (d, J=8.1 Hz, 1H), 7.44 (d, J=1.5 Hz, 1H), 6.19 (app t, J=2.0 Hz, 1H), 4.47 (dd, J=3.0, 12.9 Hz, 1H), 4.29-4.41 (m, 2H), 3.48 (s, 3H). LCMS: Anal. Calcd. for C$_8$H$_{11}$N$_3$O$_4$: 213. found: 214 (M+H)$^+$.

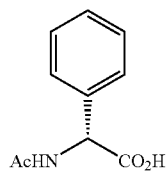

cap-130

Cap-130. N-Acetyl-(R)-Phenylglycine

Cap-130 was prepared by acylation of commercially available (R)-phenylglycine analogous to the procedure given in: Calmes, M.; Daunis, J.; Jacquier, R.; Verducci, J. *Tetrahedron,* 1987, 43(10), 2285.

EXAMPLES

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Solution percentages express a weight to volume relationship, and solution ratios express a volume to volume relationship, unless stated otherwise. Nuclear magnetic resonance (NMR) spectra were recorded either on a Bruker 300, 400, or 500 MHz spectrometer; the chemical shifts (δ) are reported in parts per million. Flash chromatography was carried out on silica gel (SiO$_2$) according to Still's flash chromatography technique (*J. Org. Chem.* 1978, 43, 2923).

Purity assessment and low resolution mass analysis were conducted on a Shimadzu LC system coupled with Waters Micromass ZQ MS system. It should be noted that retention times may vary slightly between machines. The LC conditions employed in determining the retention time (RT) were:
Condition 1
Column=Phenomenex-Luna 3.0×50 mm S10
Start % B=0
Final % B=100
Gradient time=2 min
Stop time=3 min
Flow Rate=4 mL/min
Wavelength=220 nm
Solvent A=0.1% TFA in 10% methanol/90% H$_2$O
Solvent B=0.1% TFA in 90% methanol/10% H$_2$O
Condition 2
Column=Phenomenex-Luna 4.6×50 mm S10
Start % B=0
Final % B=100
Gradient time=2 min
Stop time=3 min
Flow Rate=5 mL/min
Wavelength=220 nm
Solvent A=0.1% TFA in 10% methanol/90% H$_2$O
Solvent B=0.1% TFA in 90% methanol/10% H$_2$O
Condition 3
Column=HPLC XTERRA C18 3.0×50 mm S7
Start % B=0
Final % B=100
Gradient time=3 min
Stop time=4 min
Flow Rate=4 mL/min
Wavelength=220 nm
Solvent A=0.1% TFA in 10% methanol/90% H$_2$O
Solvent B=0.1% TFA in 90% methanol/10% H$_2$O
Method A: LCMS—Xterra MS C-18 3.0×50 mm, 0 to 100% B over 30.0 minute gradient, 1 minute hold time, A=5% acetonitrile, 95% water, 10 mm ammonium acetate, B=95% acetonitrile, 5% water, 10 mm ammonium acetate.
Method B: HPLC—X-Terra C-18 4.6×50 mm, 0 to 100% B over 10.0 minute gradient, 1 minute hold time, A=10% methanol 90% water 0.1% TFA, B=90% methanol 10% water 0.1% TFA
Method C: HPLC—YMC C-18 4.6×50 mm, 0 to 100% B over 10.0 minute gradient, 1 minute hold time, A=10% methanol 90% water 0.2% H$_3$PO$_4$, B=90% methanol 10% water 0.2% H$_3$PO$_4$.

Method D: HPLC—Phenomenex C-18 4.6×150 mm, 0 to 100% B over 10.0 minute gradient, 1 minute hold time, A=10% methanol 90% water 0.2% $H_3PO_4$, B=90% methanol 10% water 0.2% $H_3PO_4$ Method E: LCMS—Gemini C-18 4.6×50 mm, 0 to 100% B over 10.0 minute gradient, 1 minute hold time, A=5% acetonitrile, 95% water, 10 mm ammonium acetate, B=95% acetonitrile, 5% water, 10 mm ammonium acetate.

Method F: LCMS—Luna C-18 3.0×50 mm, 0 to 100% B over 7.0 minute gradient, 1 minute hold time, A=5% acetonitrile, 95% water, 10 mm ammonium acetate, B=95% acetonitrile, 5% water, 10 mm ammonium acetate.

Example 1

(1R,1'R)-2,2'-(4,4'-biphenyldiylbis(1H-imidazole-5,2-diyl(2S)-2,1-pyrrolidinediyl))bis(N,N-dimethyl-2-oxo-1-phenylethanamine)

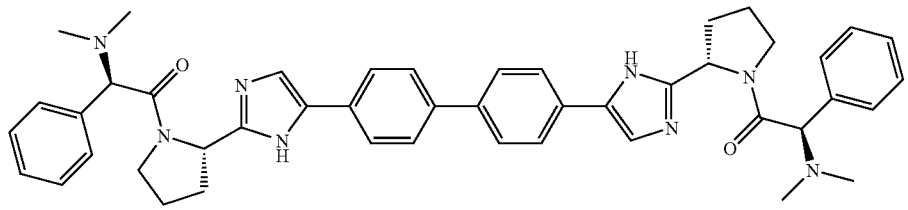

Example 1

Step a

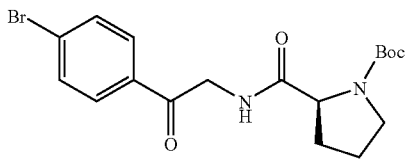

1a

N,N-Diisopropylethylamine (18 mL, 103.3 mmol) was added dropwise, over 15 minutes, to a heterogeneous mixture of N-Boc-L-proline (7.139 g, 33.17 mmol), HATU (13.324 g, 35.04 mmol), the HCl salt of 2-amino-1-(4-bromophenyl) ethanone (8.127 g, 32.44 mmol), and DMF (105 mL), and stirred at ambient condition for 55 minutes. Most of the volatile component was removed in vacuo, and the resulting residue was partitioned between ethyl acetate (300 mL) and water (200 mL). The organic layer was washed with water (200 mL) and brine, dried ($MgSO_4$), filtered, and concentrated in vacuo. A silica gel mesh was prepared from the residue and submitted to flash chromatography (silica gel; 50-60% ethyl acetate/hexanes) to provide ketoamide 1a as a white solid (12.8 g). $^1$H NMR (DMSO-$d_6$, δ=2.5 ppm, 400 MHz): δ 8.25-8.14 (m, 1H), 7.92 (br d, J=8.0, 2H), 7.75 (br d, J=8.6, 2H), 4.61 (dd, J=18.3, 5.7, 1H), 4.53 (dd, J=18.1, 5.6, 1H), 4.22-4.12 (m, 1H), 3.43-3.35 (m, 1H), 3.30-3.23 (m, 1H), 2.18-2.20 (m, 1H), 1.90-1.70 (m, 3H), 1.40/1.34 (two app br s, 9H). LC (Cond. 1): RT=1.70 min; LC/MS: Anal. Calcd. for [M+Na]$^+$ $C_{18}H_{23}BrN_2NaO_4$: 433.07. found 433.09.

Analogous compounds such as intermediate 1-1a to 1-5a can be prepared by incorporating the appropriately substituted amino acid and aryl bromide isomer.

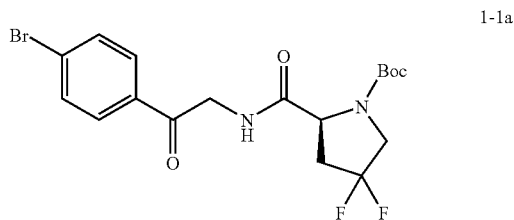

1-1a $^1$H NMR (500 MHz, DMSO-$d_6$) δ ppm 1.35/1.40 (two br s, 9H), 2.27-2.42 (m, 1H), 2.73-2.95 (m, 1H), 3.62-3.89 (m, 2H), 4.36-4.50 (m, 1H), 4.51-4.60 (m, 1H), 4.62-4.73 (m, 1H), 7.75 (d, J=8.24 Hz, 2H), 7.92 (d, J=7.63 Hz, 2H), 8.31-8.49 (m, 1H). HPLC XTERRA C-18 4.6×30 mm, 0 to 100% B over 4 minutes, 1 minute hold time, A=90% water, 10% methanol, 0.2% $H_3PO_4$, B=10% water, 90% methanol, 0.2% $H_3PO_4$, RT=1.59 minutes, 99% homogeneity index. LCMS: Anal. Calcd. for $C_{18}H_{21}BrF_2N_2O_4$: 446.06. found: 445.43 (M–H)$^-$.

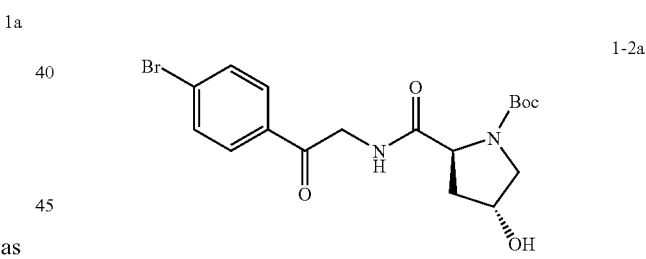

1-2a $^1$H NMR (500 MHz, DMSO-$d_6$) δ ppm (8.25 1H, s), 7.91 (2H, d, J=8.24 Hz), 7.75 (2H, d, J=8.24 Hz), 4.98 (1H, s), 4.59-4.63 (1H, m), 4.46-4.52 (1H, m), 4.23 (1H, m), 3.37 (1H, s), 3.23-3.28 (1H, m), 2.06 (1H, m), 1.88 (1H, s), 1.38 (3H, s), 1.33 (6H, s). LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA mobile phase, RT=3.34 minutes, Anal Calcd. for $C_{18}H_{23}BrN_2O_5$ 427.30. found 428.08 (M+H)$^+$.

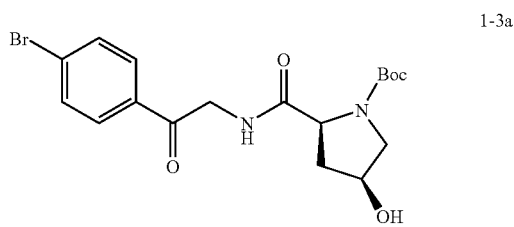

1-3a

¹H NMR (500 MHz, DMSO-d₆) δ ppm 8.30 (1H, s) 7.93-7.96 (2H, m) 7.76 (2H d, J=8.24 Hz) 5.13 (1H, s) 4.66-4.71 (1H, m) 4.52-4.55 (1H, m) 4.17 (1H, m) 3.51 (1H, s) 3.16-3.19 (1H, m) 2.36 (1H, m) 1.78 (1H, s) 1.40 (s, 3H), 1.34 (s, 6H). LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA, RT=3.69 minutes, Anal Calcd. for C$_{18}$H$_{23}$BrN$_2$O$_5$ 427.30. found 428.16 (M+H)⁺.

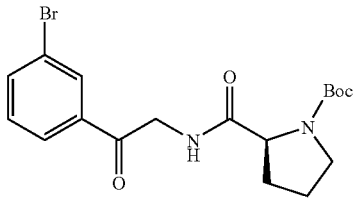

1-4a

¹H NMR (500 MHz, DMSO-d₆) δ ppm 1.29-1.47 (m, 9H), 1.67-1.90 (m, 3H), 2.00-2.20 (m, 1H), 3.23-3.30 (m, 1H), 3.34-3.44 (m, 1H), 4.16 (dd, 1H), 4.57 (q, 2H), 7.51 (t, J=7.78 Hz, 1H), 7.86 (dd, J=7.93, 1.22 Hz, 1H), 7.98 (d, J=7.63 Hz, 1H), 8.11 (s, 1H), 8.15-8.29 (m, 1H). LC/MS (M+Na)⁺= 433.12/435.12.

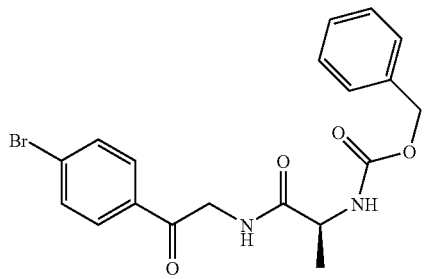

1-5a

LCMS conditions: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume. RT=1.93 min; LRMS: Anal. Calcd. for C$_{19}$H$_{18}$BrN$_2$O$_4$ 418.05. found: 419.07 (M+H)⁺.

Example 1

Step b

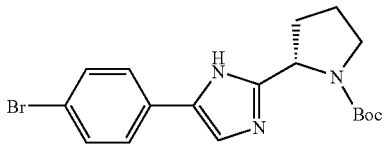

1b

A mixture of ketoamide 1a (12.8 g, 31.12 mmol) and NH₄OAc (12.0 g, 155.7 mmol) in xylenes (155 mL) was heated in a sealed tube at 140° C. for 2 hours. The volatile component was removed in vacuo, and the residue was partitioned carefully between ethyl acetate and water, whereby enough saturated NaHCO₃ solution was added so as to make the pH of the aqueous phase slightly basic after the shaking of the biphasic system. The layers were separated, and the aqueous layer was extracted with an additional ethyl acetate. The combined organic phase was washed with brine, dried (MgSO₄), filtered, and concentrated in vacuo. The resulting material was recrystallized from ethyl acetate/hexanes to provide two crops of imidazole 1b as a light-yellow dense solid, weighing 5.85 g. The mother liquor was concentrated in vacuo and submitted to a flash chromatography (silica gel; 30% ethyl acetate/hexanes) to provide an additional 2.23 g of imidazole 1b. ¹H NMR (DMSO-d₆, δ=2.5 ppm, 400 MHz): δ 12.17/11.92/11.86 (m, 1H), 7.72-7.46/7.28 (m, 5H), 4.86-4.70 (m, 1H), 3.52 (app br s, 1H), 3.36 (m, 1H), 2.30-1.75 (m, 4H), 1.40/1.15 (app br s, 9H). LC (Cond. 1): RT=1.71 min; >98% homogeneity index; LC/MS: Anal. Calcd. for [M+H]⁺ C$_{18}$H$_{23}$BrN$_3$O$_2$: 392.10. found 391.96; HRMS: Anal. Calcd. for [M+H]⁺ C$_{18}$H$_{23}$BrN$_3$O$_2$: 392.0974. found 392.0959

The optical purity of the two samples of 1b were assessed using the chiral HPLC conditions noted below (ee>99% for the combined crops; ee=96.7% for the sample from flash chromatography):
Column: Chiralpak AD, 10 um, 4.6×50 mm
Solvent: 2% ethanol/heptane (isocratic)
Flow rate: 1 mL/min
Wavelength: either 220 or 254 nm
Relative retention time: 2.83 minutes (R), 5.34 minutes (S)

Analogous compounds such as intermediates 1-1b to 1-4b can be prepared by incorporating the appropriate ketoamide.

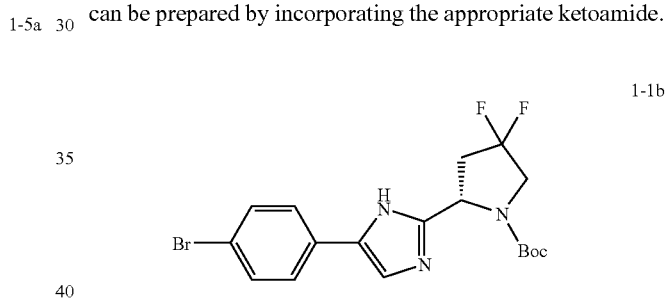

1-1b

¹H NMR (500 MHz, DMSO-d₆) δ ppm 1.17/1.40 (two br s, 9H), 2.50-2.74 (m, J=25.64 Hz, 1H), 2.84-3.07 (m, 1H), 3.88 (d, J=10.07 Hz, 2H), 5.03 (s, 1H), 7.50 (d, J=8.55 Hz, 2H), 7.60 (s, 1H), 7.70 (d, J=8.55 Hz, 2H), 12.10 (s, 1H). HPLC XTERRA C-18 4.6×30 mm, 0 to 100% B over 4 minutes, 1 minute hold time, A=90% water, 10% methanol, 0.2% H₃PO₄, B=10% water, 90% methanol, 0.2% H₃PO₄, RT=1.59 minutes, 99% homogeneity index; LCMS: Anal. Calcd. for C$_{18}$H$_{20}$BrF$_2$N$_3$O$_2$: 428.27. found: 428.02 (M)⁺.

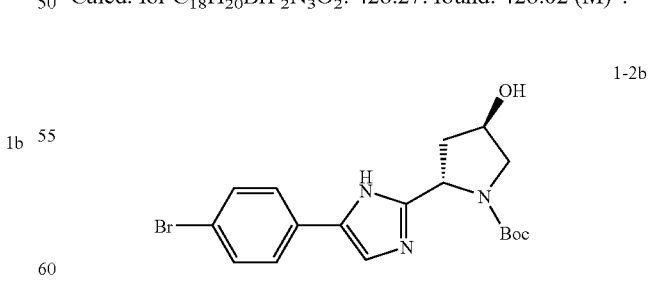

1-2b

¹H NMR (500 MHz, DMSO-d₆) δ ppm 11.89-11.99 (1H, m), 7.68 (2H, d, J=8.54 Hz), 7.52-7.59 (1H, m), 7.48 (2H, d, J=8.54 Hz), 4.80 (1H, m), 4.33 (1H, s), 3.51-3.60 (1H, m), 3.34 (1H, d, J=10.99 Hz), 2.14 (1H, s), 1.97-2.05 (1H, m), 1.37 (3H, s), 1.10 (6H, s); LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA, (RT=3.23 min) Anal Calcd. for C$_{18}$H$_{22}$BrN$_3$O$_3$ 408.30. found 409.12 (M+H)$^+$.

1-3b

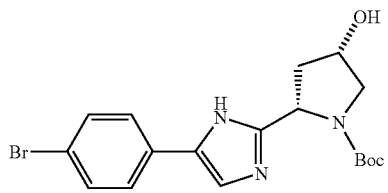

$^1$H NMR (500 MHz, DMSO-d$_6$) δ ppm 12.06-12.24 (1H, m), 7.58-7.69 (5H, m), 4.84-4.95 (1H, m), 4.34 (1H, s), 3.61 (1H, s), 3.34-3.40 (1H, m), 2.52 (1H, s), 1.92-2.20 (1H, m), 1.43 (3H, s), 1.22 (6H, s); LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA, (RT=3.41 min) Anal Calcd. for C$_{18}$H$_{22}$BrN$_3$O$_3$ 408.30. found 409.15 (M+H)$^+$.

1-4b

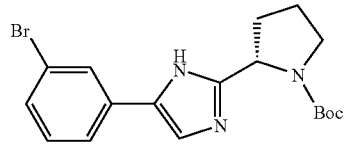

$^1$H NMR (500 MHz, DMSO-d$_6$) δ ppm 0.98-1.51 (m, 9H), 1.82-2.12 (m, 3H), 2.31-2.48 (m, 1H), 3.30-3.51 (m, 1H), 3.52-3.66 (m, 1H), 4.88-5.16 (m, 1H), 7.47 (t, J=7.93 Hz, 1H), 7.61 (d, J=7.93 Hz, 1H), 7.81 (d, J=7.93 Hz, 1H), 8.04 (s, 1H), 8.12 (d, J=28.38 Hz, 1H), 14.65 (s, 1H). LC/MS (M+H)$^+$=391.96/393.96.

Additional imidazole analogs made following procedures similar to those described above.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

| Example | Structure | Data |
|---|---|---|
| 1-5b | 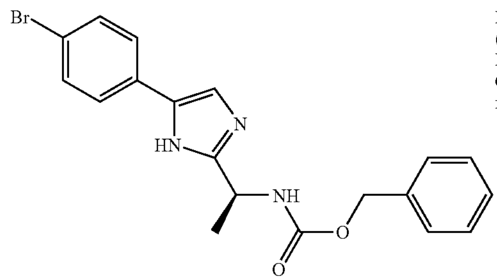 | RT = 1.70 minutes (condition 2, 98%); LRMS: Anal. Calcd. for C$_{19}$H$_{18}$BrN$_3$O$_2$ 399.05; found: 400.08(M + H)$^+$. |
| 1-6b | 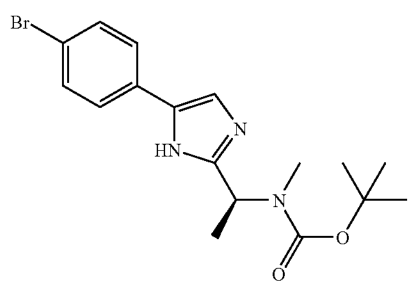 | RT = 1.64 minutes (condition 2, 98%); LRMS: Anal. Calcd. for C$_{17}$H$_{22}$N$_3$O$_2$ 379.09; found: 380.06(M + H)$^+$. |
| 1-7b | 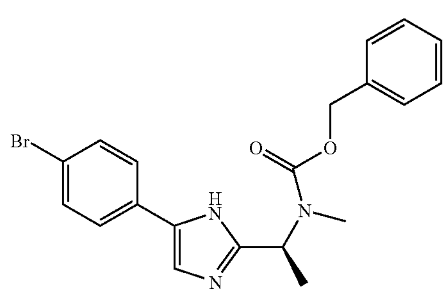 | RT = 2.28 minutes (95%); LRMS: Anal. Calcd. for C$_{20}$H$_{21}$BrN$_3$O$_2$ 414.08; found: 414.08 (M + H)$^+$; HRMS: Anal. Calcd. for C$_{20}$H$_{21}$BrN$_3$O$_2$ 414.0817; found: 414.0798(M + H)$^+$. |

Example 1

Step c

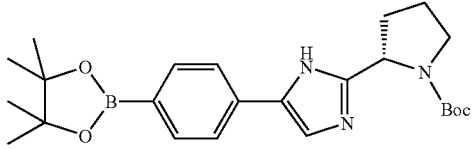

Pd(Ph$_3$P)$_4$ (469 mg, 0.406 mmol) was added to a pressure tube containing a mixture of bromide 1b (4.008 g, 10.22 mmol), bis(pinacolato)diboron (5.422 g, 21.35 mmol), potassium acetate (2.573 g, 26.21 mmol) and 1,4-dioxane (80 mL). The reaction flask was purged with nitrogen, capped and heated with an oil bath at 80° C. for 16.5 hours. The reaction mixture was filtered and the filtrate was concentrated in vacuo. The crude material was partitioned carefully between CH$_2$Cl$_2$ (150 mL) and an aqueous medium (50 mL water+10 mL saturated NaHCO$_3$ solution). The aqueous layer was extracted with CH$_2$Cl$_2$, and the combined organic phase was dried (MgSO$_4$), filtered, and concentrated in vacuo. The resulting material was purified with flash chromatography (sample was loaded with eluting solvent; 20-35% ethyl acetate/CH$_2$Cl$_2$) to provide boronate 1c, contaminated with pinacol, as an off-white dense solid; the relative mole ratio of 1c to pinacol was about 10:1 ($^1$H NMR). The sample weighed 3.925 g after ~2.5 days exposure to high vacuum. $^1$H NMR (DMSO-d$_6$, δ=2.5 ppm, 400 MHz): 12.22/11.94/11.87 (m, 1H), 7.79-7.50/7.34-7.27 (m, 5H), 4.86-4.70 (m, 1H), 3.52 (app br s, 1H), 3.36 (m, 1H), 2.27-1.77 (m, 4H), 1.45-1.10 (m, 21H). LC (Cond. 1): RT=1.64 min; LC/MS: Anal. Calcd. for [M+H]$^+$ C$_{24}$H$_{35}$BN$_3$O$_4$: 440.27. found 440.23.

Analogous compounds such as intermediates 1-1c to 1-4c can be prepared by incorporating the appropriate aryl bromide.

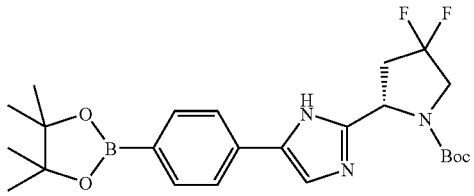

$^1$H NMR (500 MHz, DMSO-d$_6$) δ ppm 1.16 (s, 8H), 1.29 (s, 13H), 2.51-2.72 (m, 1H), 2.84-3.03 (m, 1H), 3.79-4.00 (m, 2H), 4.88-5.21 (m, 1H), 7.62 (d, J=7.93 Hz, 2H), 7.67 (s, 1H), 7.76 (d, J=7.93 Hz, 2H), 12.11/12.40 (two br s, 1H). HPLC GEMINI C-18 4.6×50 mm, 0 to 100% B over 4 minutes, 1 minute hold time, A=95% water, 5% acetonitrile, 0.1% NH$_4$OAc, B=5% water, 95% acetonitrile, 0.1% NH$_4$OAc, RT=1.62 minutes, 99% homogeneity index. LCMS: Anal. Calcd. for C$_{34}$H$_{32}$BF$_2$N$_3$O$_4$: 475.34. found: 474.78 (M−H)$^−$.

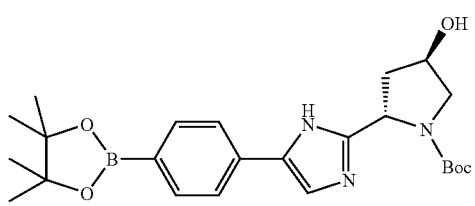

$^1$H NMR (500 MHz, DMSO-d$_6$) δ ppm 11.97 (1H, m), 7.62-7.75 (5H, m), 5.05 (1H d, J=3.36 Hz), 4.82 (m, 1H), 4.35 (m, 1H), 3.58 (1H, m), 2.389 (1H, s), 2.17 (1H, m), 1.38 (3H, s), 1.30 (12H, s), 1.1 (6H, s); LCMS—Phenomenex C-18 3.0×50 mm, 0 to 100% B over 4.0 minute gradient, 1 minute hold time, A=5% acetonitrile, 95% water, 10 mm ammonium acetate, B=95% acetonitrile, 5% water, 10 mm ammonium acetate, RT=3.63 minutes, Anal. Calcd. for C$_{24}$H$_{34}$BN$_3$O$_5$ 455.30. found 456.31 (M+H)$^+$.

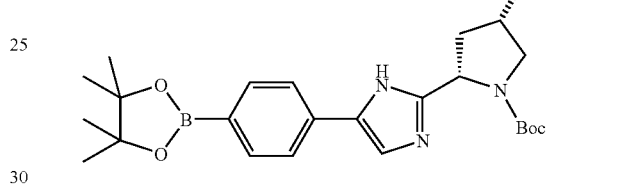

$^1$H NMR (500 MHz, DMSO-d$_6$) δ ppm 12.05-12.24 (1H, m), 7.61-7.73 (5H, m), 4.83-5.01 (1H, m), 4.33 (1H, s), 3.54-3.63 (1H, m), 3.39-3.80 (1H, m), 2.38-2.49 (1H, m), 1.98-2.01 (1H, m), 1.42 (3H, s), 1.34 (12H, s), 1.21 (6H, s); LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA, RT=3.64 minutes, Anal. Calcd. for C$_{24}$H$_{34}$BN$_3$O$_5$ 455.30. found 456.30 (M+H)$^+$.

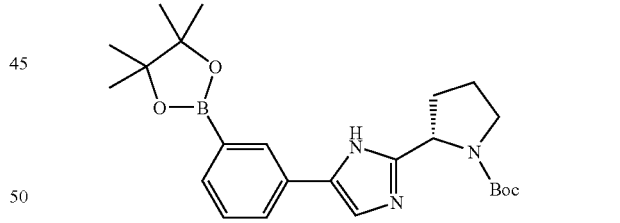

$^1$H NMR (500 MHz, DMSO-d$_6$) δ ppm 1.02-1.54 (m, 21H), 1.75-2.07 (m, 3H), 2.09-2.33 (m, 1H), 3.32-3.44 (m, 1H), 3.55 (s, 1H), 4.69-4.94 (m, 1H), 7.33 (t, J=7.32 Hz, 1H), 7.41-7.57 (m, 2H), 7.84 (d, J=7.32 Hz, 1H), 8.08 (s, 1H), 11.62-12.07 (m, 1H). LC/MS (M+H)$^+$=440.32.

Additional boronic esters: Conditions for 1-5c through 1-10c

LCMS conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

| | | |
|---|---|---|
| 1-5c | 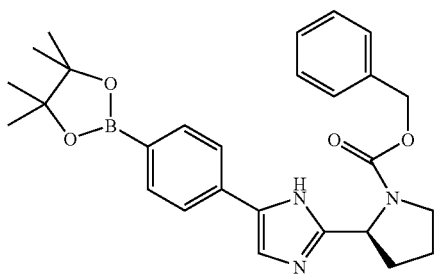 | RT = 1.84 minutes (condition 2); LCMS: Anal. Calcd. for $C_{27}H_{32}BN_3O_4$ 473; found: 474(M + H)$^+$. |
| 1-6c | 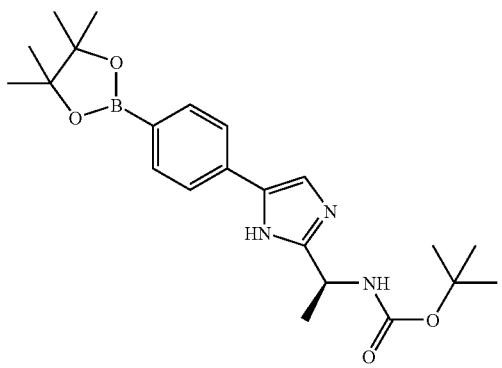 | RT = 1.84 minutes (condition 2); LCMS: Anal. Calcd. for $C_{22}H_{32}BN_3O_4$ 413; found: 414(M + H)$^+$. |
| 1-7c | 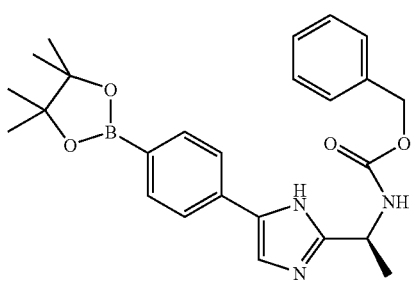 | RT = 1.85 minutes (condition 2); LRMS: Anal. Calcd. for $C_{25}H_{31}BN_3O_4$ 448; found: 448(M + H)$^+$. |
| 1-8c | 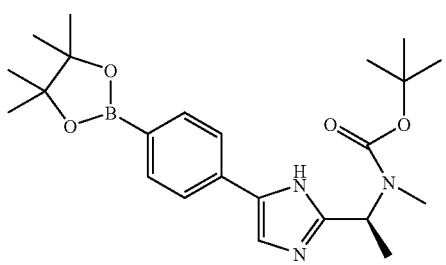 | RT = 2.49(76%, boronic ester) and 1.81(21.4%, boronic acid); LCMS: Anal. Calcd. for $C_{23}H_{35}N_3O_4B$ 428.27; found: 428.27(M + H)$^+$; HRMS: Anal. Calcd. for $C_{23}H_{35}N_3O_4B$ 428.2721; found: 428.2716(M + H)$^+$. |
| 1-9c | 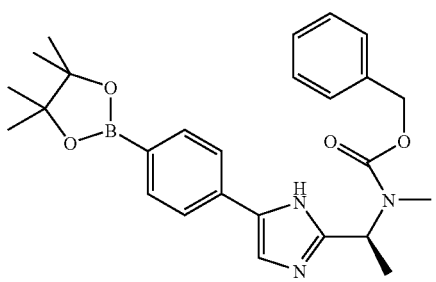 | RT = 2.54(74.2%, boronic ester) and 1.93 (25.8%, boronic acid); LRMS: Anal. Calcd. for $C_{26}H_{33}N_3O_4B$ 462.26; found: 462.25(M + H)$^+$; HRMS: Anal. Calcd. for $C_{26}H_{33}N_3O_4B$ 462.2564; found: 462.2570(M + H)$^+$. |

1-10c

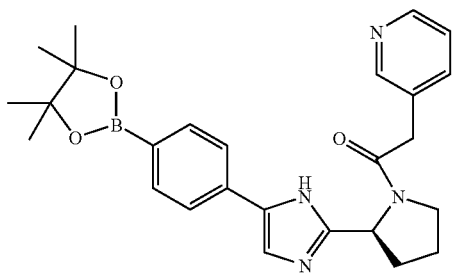

RT = 1.91(64.5%, boronic ester) and 1.02 (33.8%, boronic acid); LRMS: Anal. Calcd. for $C_{26}H_{32}N_4O_3{}^{10}B$ 458.26; found: 458.28(M + H)$^+$; HRMS: Anal. Calcd. for $C_{26}H_{32}N_4O_3{}^{10}B$ 458.2604; found: 458.2617(M + H)$^+$.

Example 1

Step d di-tert-butyl (2S,2'S)-2,2'-(4,4'-biphenyldiylbis(1H-imidazole-5,2-diyl))di(1-pyrrolidinecarboxylate)

1d

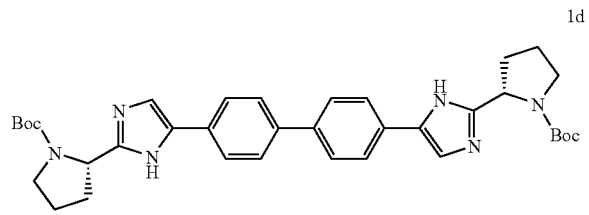

Pd(Ph$_3$P)$_4$ (59.9 mg, 0.0518 mmol) was added to a mixture of bromide 1b (576.1 mg, 1.469 mmol), boronate 1c (621.8 mg, 1.415 mmol), NaHCO$_3$ (400.4 mg, 4.766 mmol) in 1,2-dimethoxyethane (12 mL) and water (4 mL). The reaction mixture was flushed with nitrogen, heated with an oil bath at 80° C. for 5.75 hours, and then the volatile component was removed in vacuo. The residue was partitioned between 20% methanol/CHCl$_3$ (60 mL) and water (30 mL), and the aqueous phase was extracted with 20% methanol/CHCl$_3$ (30 mL). The combined organic phase was washed with brine, dried (MgSO$_4$), filtered, and concentrated in vacuo. A silica gel mesh was prepared from the resulting crude material and submitted to flash chromatography (ethyl acetate) to provide dimer 1d, contaminated with Ph$_3$PO, as an off-white solid (563 mg). $^1$H NMR (DMSO-d$_6$, δ=2.5 ppm, 400 MHz): δ 12.21-12-16/11.95-11.78 (m, 2H), 7.85-7.48/7.32-7.25 (m, 10H), 4.90-4.71 (m, 2H), 3.60-3.32 (m, 4H), 2.30-1.79 (m, 8H), 1.46-1.10 (m, 18H). LC (Cond. 1b): RT=1.77 min; LC/MS: Anal. Calcd. for [M+H]$^+$ C$_{36}$H$_{45}$BN$_6$O$_4$: 625.35. found 625.48.

Additional symmetric analogs can be prepared in similar fashion.

1-1d

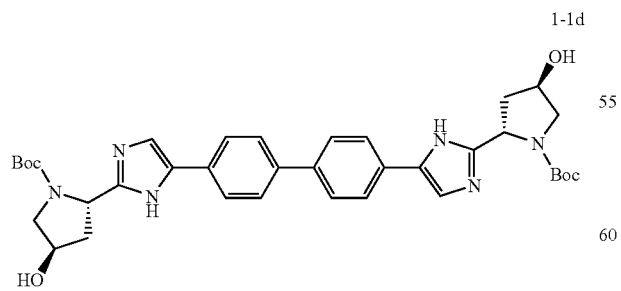

Example 1-1d was prepared using intermediates 1-2c and 1-2b. $^1$H NMR (500 MHz, DMSO-d$_6$) δ ppm 11.94-12.22 (2H, m) 7.53-7.82 (10H, m) 4.82-4.92 (2H, m) 4.34-4.43 (2H, m) 3.55-3.64 (2H, m) 3.36 (2H, d, J=11.29 Hz) 2.12-2.22 (2H, m) 2.02-2.11 (2H, m) 1.40 (6H, s) 1.14 (12H, s); LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA, RT=3.32 min, Anal. Calcd. for 656.79. found 657.40 (M+H)$^+$. Nominal/LRMS-(M+H)$^{+-}$657.42, (M−H)$^-$ 655.28.

1-2d

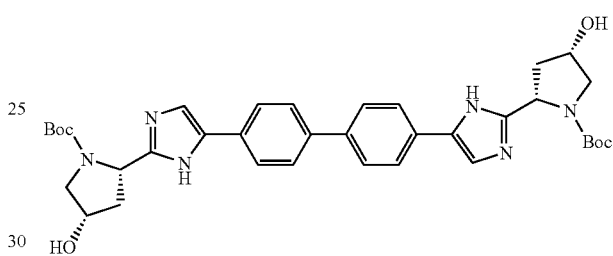

Example 1-2d was prepared using intermediates 1-3b and 1-3c. $^1$H NMR (500 MHz, DMSO-d$_6$) δ ppm 12.00-12.20 (2H, m) 7.56-7.76 (10H, m) 4.90 (1H, s) 4.82 (1H, s) 4.25-4.34 (2H, m) 3.56 (2H, s) 3.34-3.47 (2H, m) 1.97-2.13 (4H, m) 1.39 (9H, m) 1.20 (9H, s); LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA; RT=3.35 min, Anal. Calcd. for 656.79. found 657.30 (M+H)$^+$.

1-2d-1

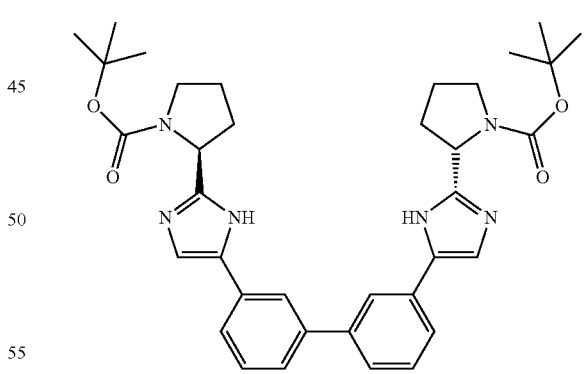

tert-butyl (2S)-2-(4-(3'-(2-((2S)-1-(tert-butoxycarbonyl)-2-pyrrolidinyl)-1H-imidazol-5-yl)-3-biphenylyl)-1H-imidazol-2-yl)-1-pyrrolidinecarboxylate Example 1-2d-1 was prepared using intermediates 1-4c and 1-4b. $^1$H NMR (500 MHz, DMSO-d$_6$) δ ppm 1.09-1.51 (m, 18H), 1.84-2.15 (m, 6H), 2.34-2.50 (m, 2H), 3.35-3.52 (m, 2H), 3.54-3.67 (m, 2H), 5.08 (d, J=5.49 Hz, 2H), 7.68 (t, J=7.78 Hz, 2H), 7.78-7.92 (m, 4H), 8.11-8.30 (m, 4H), 14.81 (s, 2H). LC/MS (M+H)$^+$=625.48.

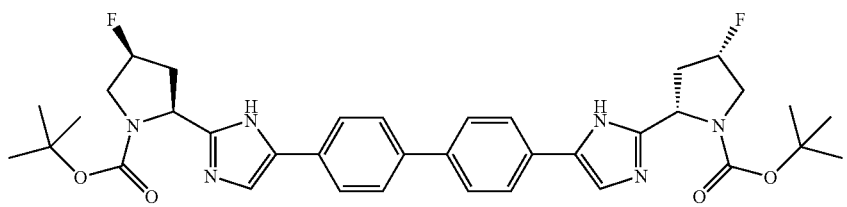

1-2d-2

Diol 1-1d (0.15 g, 0.23 mmol) was added as a solid to a solution of bis(2-methoxyethyl)aminosulfur trifluoride (0.1 mL, 0.51 mmol) in 11.0 mL CH$_2$Cl$_2$ cooled to −78° C. The reaction was stirred at −78° C. for two hours and then warmed to room temperature and stirred for 2 hours. The reaction was poured into saturated sodium bicarbonate solution and stirred until bubbling ceased. The layers were separated and the aqueous layer was extracted one time with CH$_2$Cl$_2$. The combined organics were washed with brine, dried (MgSO$_4$), filtered, and concentrated to give a yellow oil. The oil was triturated with CH$_2$Cl$_2$ and pentane to provide the desired product as a tan solid (0.092 g, 61%). $^1$H NMR (500 MHz, DMSO-d$_6$) δ ppm 11.76-11.94 (2H, m), 7.77-7.85 (4H, m), 7.66-7.72 (4H, m), 7.60-7.66 (2H, m, J=11.60 Hz), 5.39 (1H, s), 5.28 (1H, s), 5.03 (2H, s), 3.66-3.79 (4H, m), 2.61-2.70 (2H, m), 2.28-2.38 (2H, m), 1.42 (10H, s), 1.24 (8H, s). LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA, (t$_R$=3.58 min) Anal Calcd. for C$_{36}$H$_{42}$F$_2$N$_6$O$_4$ 660.70. found 661.68 (M+H)$^+$.

1-2d-3

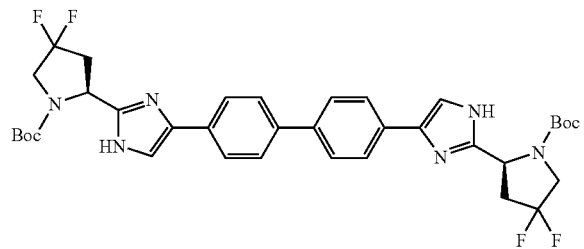

Prepared from 1-1b and 1-1c in the same manner as the preparation of 1d from 1b and 1c. $^1$H NMR (500 MHz, DMSO-d$_6$) δ ppm 1.18/1.40 (two br. s., 18H), 2.53-2.75 (m, J=25.94 Hz, 2H), 2.86-3.06 (m, 2H), 3.78-4.02 (m, 4H), 5.04 (br s, 2H), 7.17-8.24 (m, 10H), 12.07/12.37 (two br. s., 2H); HPLC XTERRA C-18 3.0×50 mm, 0 to 100% B over 2 minutes, 1 minutes hold time, A=90% water, 10% methanol, 0.2% H$_3$PO$_4$, B=10% water, 90% methanol, 0.2% H$_3$PO$_4$, RT=1.31 min, 99% homogeneity index. LCMS: Anal. Calcd. for C$_{36}$H$_{40}$F$_4$N$_6$O$_4$: 696.73. found: 967.64 (M+H)$^+$.

Dissymmetric compounds such as intermediate 1-3d and 1-4d can be prepared by the same method. For example, reaction of 1-1c with 1b in the same manner as described above for the preparation of 1d provided 1-3d. Similarly, reaction of 1-4c with 1b in the same manner as described above for the preparation of 1d provided 1-4d.

1-3d

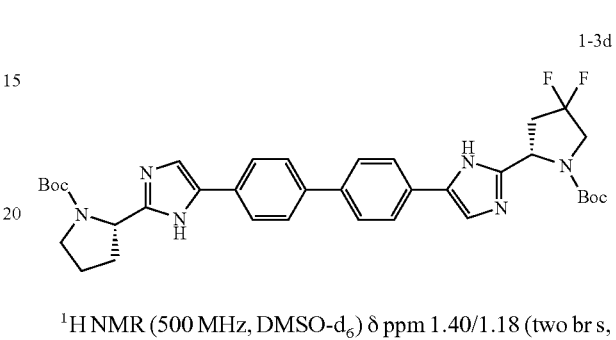

$^1$H NMR (500 MHz, DMSO-d$_6$) δ ppm 1.40/1.18 (two br s, 18H), 1.90-2.02 (m, 2H), 2.02-2.12 (m, 1H), 2.28-2.46 (m, 2H), 2.68-2.87 (m, 1H), 3.35-3.49 (m, 1H), 3.53-3.62 (m, 1H), 3.82-4.10 (m, 2H), 4.92-5.11 (m, 1H), 5.28 (s, 1H), 7.79-8.00 (m, 8H), 8.03-8.25 (m, 2H), 13.77-15.16 (m, 2H); HPLC XTERRA C-18 3.0×50 mm, 0 to 100% B over 4 minutes, 1 minute hold time, A=90% water, 10% methanol, 0.2% H$_3$PO$_4$, B=10% water, 90% methanol, 0.2% H$_3$PO$_4$, RT=1.22 minutes, 99% homogeneity index. LCMS: Anal. Calcd. for C$_{36}$H$_{42}$F$_2$N$_6$O$_4$: 660.75. found: 661.98 (M+H)$^+$.

1-4d

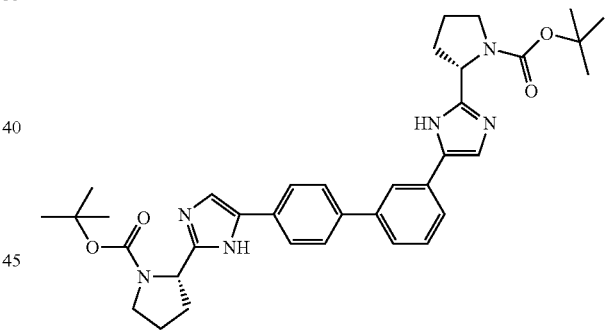

Example 1-4d was prepared from 1-4c and 1b in similar fashion to the preparation of 1d from 1b and 1c. $^1$H NMR (500 MHz, DMSO-d$_6$) δ ppm 0.99-1.60 (m, 18H) 1.75-2.11 (m, J=73.24 Hz, 6H) 2.12-2.32 (m, 2H) 3.32-3.41 (m, 2H) 3.56 (s, 2H) 4.63-5.02 (m, 2H) 6.98-8.28 (m, 10H) 11.67-12.33 (m, 2H); LC conditions: Phenomenex Luna 3.0×5.0 mm S10, Solvent A—0.1% TFA in 10% MeOH/90% H$_2$O, Solvent B—0.1% TFA in 90% MeOH/10% H$_2$O, 0 to 100% B over 2 min, Stop time=3 min, Flow rate=4 ml/min, Wavelength=220 nm, LC/MS (M+H)$^+$=625.32. Retention time=1.438 min Additional biphenyl analogs were prepared similarly.

LC conditions for Examples 1-5d through 1-7d: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

| Example | Compound Name | Structure | Characterization Data |
|---|---|---|---|
| 1-5d | di-tert-butyl(4,4'-biphenyldiylbis(1H-imidazole-5,2-diyl(1S)-1,1-ethanediyl))bis(methylcarbamte) | Prepared from 1-8c and 1-6b | RT = 1.64 minutes (>95%); Condition 2; LCMS: Anal. Calcd $C_{34}H_{45}N_6O_4$ 601.35; found: 601.48(M + H)$^+$; LRMS: Anal. Calcd. for $C_{34}H_{44}N_6O_4$ 600.34; found: 601.32(M + H)$^+$. |
| 1-6d | tert-butyl (2S)-2-(5-(4'-(2-((1S)-1-((tert-butoxycarbonyl)(methyl)amino)ethyl)-1H-imidazol-5-yl)-4-biphenylyl)-1H-imidazol-2-yl)-1-pyrrolidinecarboxylate | Prepared from 1-8c and 1b | RT = 1.63 minutes (>95%); Condition 2; LCMS: Anal. Calcd $C_{35}H_{45}N_6O_4$ 613.34; found: 613.56(M + H)$^+$; LRMS: Anal. Calcd. for $C_{35}H_{44}N_6O_4$ 612.34; found: 613.33(M + H)$^+$. |
| 1-7d | benzyl (2S)-2-(5-(4'-(2-((1S)-1-((tert-butoxycarbonyl)(methyl)amino)ethyl)-1H-imidazol-5-yl)-4-biphenylyl)-1H-imidazol-2-yl)-1-pyrrolidinecarboxylate | Prepared from 1-6b and 1-5c | RT = 1.65 minutes (>95%); Condition 2; LCMS: Anal. Calcd $C_{38}H_{43}N_6O_4$ 647.33; found: 647.44(M + H)$^+$; LRMS: Anal. Calcd. for $C_{38}H_{42}N_6O_4$ 646.33; found: 647.34(M + H)$^+$. |

Example 1

Step e 5,5'-(4,4'-biphenyldiyl)bis(2-((2S)-2-pyrrolidinyl)-1H-imidazole)

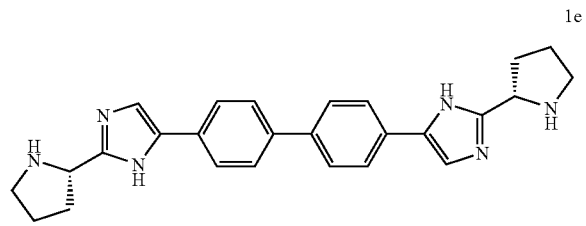

1e

A mixture of carbamate 1d (560 mg) and 25% TFA/CH$_2$Cl$_2$ (9.0 mL) was stirred at ambient condition for 3.2 hours. The volatile component was removed in vacuo, and the resulting material was free based using an MCX column (methanol wash; 2.0 M NH$_3$/methanol elution) to provide pyrrolidine 1e as a dull yellow solid (340 mg). $^1$H NMR (DMSO-d$_6$, δ=2.5 ppm, 400 MHz): δ 11.83 (br s, 2H), 7.80 (d, J=8.1, 4H), 7.66 (d, J=8.3, 4H), 7.46 (br s, 2H), 4.16 (app t, J=7.2, 2H), 2.99-2.69 (m, 6H), 2.09-2.00 (m, 2H), 1.94-1.66 (m, 6H). LC (Cond. 1): RT=1.27 min; >98% homogeneity index; LC/MS: Anal. Calcd. for [M+H]$^+$ C$_{26}$H$_{29}$N$_6$: 425.25. found 425.25; HRMS: Anal. Calcd. for [M+H]$^+$ C$_{26}$H$_{29}$N$_6$: 425.2454. found 425.2448

Additional analogs such as 1-1e to 1-4e can be prepared in a similar fashion.

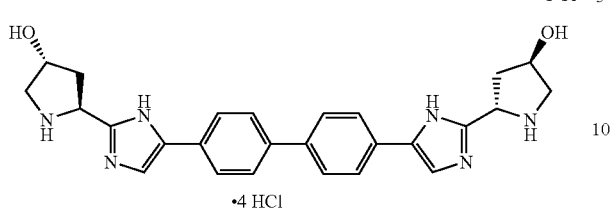

1-1e

·4 HCl

To a solution of 1-1d (3R,3'R,5S,5'S)-tert-butyl 5,5'-(5,5'-(biphenyl-4,4'-diyl)bis(1H-imidazole-5,2-diyl))bis(3-hydroxypyrrolidine-1-carboxylate) in 3 mL dioxane was added 0.8 mL of a 4.0M solution of HCl in dioxane. The reaction was stirred for 2 hours at room temperature and concentrated under reduced pressure. The resulting tan solid was dried under vacuum to give 1-1e (3R,3'R,5S,5'S)-5,5'-(5,5'-(biphenyl-4,4'-diyl)bis(1H-imidazole-5,2-diyl))dipyrrolidin-3-oltetrahydrochloride (0.55 g, 100% yield). Used without further purification. $^1$H NMR (500 MHz, DMSO-$d_6$) δ ppm 10.33 (s, 2H), 9.85 (s, 2H), 8.09 (s, 2H), 8.01 (d, J=8.24 Hz, 4H), 7.88 (d, J=8.24 Hz, 4H), 5.14 (m, 2H), 4.62 (m, 2H), 3.61 (m, 2H), 3.23 (d, J=11.29 Hz, 2H), 2.64 (m, 2H), 2.44 (dd, J=13.43, 6.71 Hz, 2H); LCMS—Waters-Sunfire C-18 4.6×50 mm, 0 to 100% B over 4.0 minute gradient, 1 minute hold time, A=10% methanol 90% water 0.1% TFA, B=90% methanol 10% water 0.1% TFA, RT=1.35 minutes Anal. Calcd. for 456.30. found 457.25 (M+H)$^+$; Nominal/LRMS-(M+H)$^{+-}$457.35.

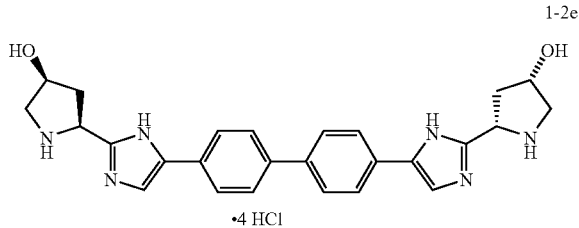

1-2e

·4 HCl

Example 1-2e was prepared in similar fashion to the method described for the preparation of 1-1e. $^1$H NMR (500 MHz, DMSO-$d_6$) δ ppm 10.32 (1H, s) 8.01 (2H, s) 7.97 (4H, d, J=8.24 Hz) 7.86 (4H, d, J=8.24 Hz) 5.01-5.10 (2H, m) 4.52-4.60 (2H, m) 3.36-3.45 (2H, m) 3.25 (2H, s) 2.60-2.68 (2H, m) 2.40-2.48 (2H, m); LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA, RT=2.10 min., Anal. Calcd. for 456.30. found 457.22 (M+H)$^+$

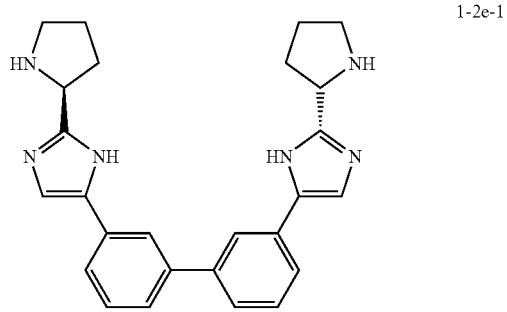

1-2e-1

2-((2S)-2-pyrrolidinyl)-4-(3'-(2-((2S)-2-pyrrolidinyl)-1H-imidazol-5-yl)-3-biphenylyl)-1H-imidazole Example 1-2e-1 was prepared from 1-2d-1 in similar fashion described for the preparation of 1-1e. $^1$H NMR (500 MHz, DMSO-$d_6$) δ ppm 1.74-2.44 (m, 12H), 4.83 (s, 2H), 7.37-7.72 (m, 4H), 7.74-8.03 (m, 4H), 8.10 (s, 2H), 9.14 (s, 2H), 9.81 (s, 2H). LC/MS (M+H)$^+$=425.30.

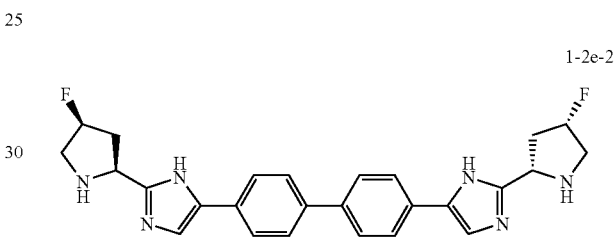

1-2e-2

To a solution of 1-2d-2 (0.084 g, 0.13 mmol) in 1 mL dioxane was added 0.5 mL of a 4.0M solution of HCl in dioxane. The reaction was stirred for 2 hours at room temperature and concentrated under reduced pressure. The resulting tan solid was dried under vacuum to give 1-2e-2 (0.077 g, 100% yield). The compound was used without further purification. $^1$H NMR (500 MHz, DMSO-$d_6$) δ ppm 8.00 (2H, s), 7.97 (4H, d, J=8.55 Hz), 7.85 (4H, d, J=8.24 Hz), 5.63 (1H, s), 5.52 (1H, s), 5.09-5.17 (2H, m), 3.67-3.74 (2H, m), 3.63-3.67 (2H, m), 3.07-3.14 (1H, m), 2.89-2.96 (1H, m), 2.81-2.87 (2H, m); LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA, ($t_R$=222 min) Anal Calcd. for $C_{26}H_{26}F_2N_6$ 460.53. found 461.37 (M+H)$^+$.

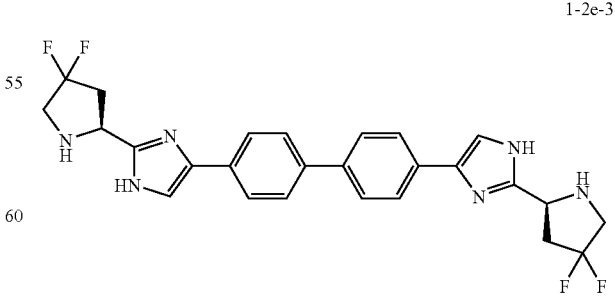

1-2e-3

Prepared from 1-2d-3 in the same manner as the preparation of 1-1e from 1-1d. $^1$H NMR (500 MHz, DMSO-$d_6$) δ ppm 2.97-3.13 (m, 4H), 3.64-3.91 (m, 4H), 5.16 (d, J=6.41

Hz, 2H), 7.84 (d, J=7.93 Hz, 4H), 7.96 (d, J=7.93 Hz, 4H), 8.00 (s, 2H); HPLC XTERRA C-18 3.0×50 mm, 0 to 100% B over 4 minutes, 1 minutes hold time, A=90% water, 10% methanol, 0.2% $H_3PO_4$, B=10% water, 90% methanol, 0.2% $H_3PO_4$, RT=1.66 min, 92% homogeneity index. LCMS: Anal. Calcd. for $C_{26}H_{24}F_4N_6$: 496.50. found: 495.53 $(M-H)^-$.

Analogous dissymmetric compounds such as intermediates 1-3e and 1-4e can be prepared by the same method.

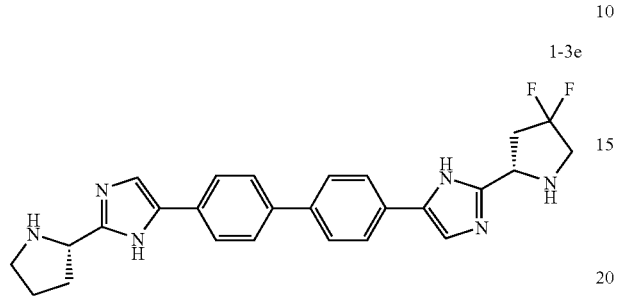

1-3e

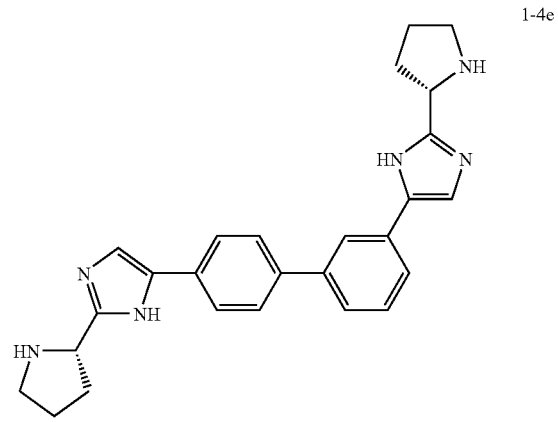

1-4e $^1$H NMR (500 MHz, DMSO-$d_6$) δ ppm 1.87-2.09 (m, 1H), 2.13-2.26 (m, 1H), 2.37-2.47 (m, 2H), 2.92-3.12 (m, 2H), 3.37 (s, 1H), 3.40-3.49 (m, 1H), 3.67-3.91 (m, 2H), 4.96-5.05 (m, 1H), 5.14 (t, J=8.70 Hz, 1H), 7.86 (t, J=9.00 Hz, 4H), 7.93-8.03 (m, 5H), 8.10 (s, 1H), 10.26/9.75 (two br s., 2H); HPLC XTERRA C-18 3.0×50 mm, 0 to 100% B over 4 minutes, 1 minute hold time, A=90% water, 10% methanol, 0.2% $H_3PO_4$, B=10% water, 90% methanol, 0.2% $H_3PO_4$, RT=0.8622 minutes, 99% homogeneity index; LCMS: Anal. Calcd. for $C_{26}H_{26}F_2N_6$: 460.52. found: 461.45 $(M+H)^+$.

Example 1-4e was prepared from 1-4d in similar fashion to that described for the preparation of 1-1e from 1-1d. $^1$H NMR (500 MHz, DMSO-$d_6$) δ ppm 1.90-2.13 (m, 2H) 2.12-2.31 (m, 2H) 2.36-2.60 (m, 4H) 3.29-3.55 (m, 4H) 5.00 (s, 2H) 7.35-8.50 (m, 10H) 9.76 (s, 2H) 10.12-10.45 (m, 2H). LC conditions: Phenomenex Luna 3.0×5.0 mm S10, Solvent A—0.1% TFA in 10% MeOH/90% $H_2O$, Solvent B—0.1% TFA in 90% MeOH/10% $H_2O$, 0 to 100% B over 2 min, Stop time=3 min, Flow rate=4 ml/min, Wavelength=220 nm, LC/MS $(M+H)^+$=425.28. Retention time=0.942 min Additional analogs were prepared similarly:

| Example | Compound Name | Structure | Data |
|---|---|---|---|
| 1-5e | | Prepared from 1-6d | RT = 1.37 min; LCMS: Anal. Calcd. for $C_{25}H_{28}N_6$ 412; found: 413 $(M + H)^+$. |
| 1-6e | | Prepared from 1-7d | RT = 1.43 min; LCMS: Anal. Calcd. for $C_{33}H_{35}N_6O_2$ 547; found: 547 $(M + H)^+$. |

| Example | Compound Name | Structure | Data |
|---|---|---|---|
| 1-7e | | 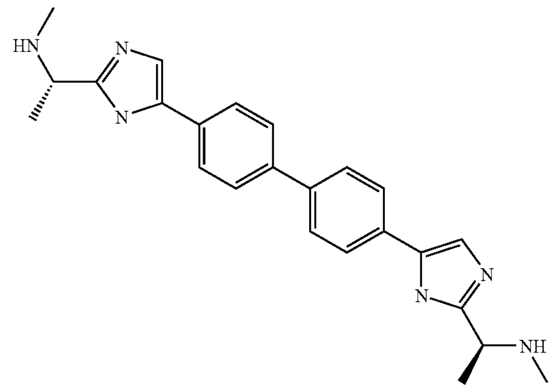 | RT = 1.12 min; LRMS: Anal. Calcd. for $C_{24}H_{28}N_6$ 400.24; found: 401.22 $(M + H)^+$. |

Prepared from 1-5d

LC Conditions for 1-5e through 1-7e; Phenomenex LUNA C-18 4.6 × 50 mm, 0 to 100% B over 2 minutes, 1 minute hold time, A = 90% water, 10% methanol, 0.1% TFA, B = 10% water, 90% methanol, 0.1% TFA, 220 nm, 5 μL injection volume.

Alternative Synthesis of Example 1

Step e 5,5'-(4,4'-biphenyldiyl)bis(2-((2S)-2-pyrrolidinyl)-1H-imidazole)

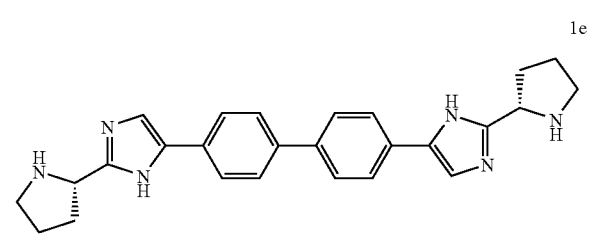

1e

Example A-1e-1

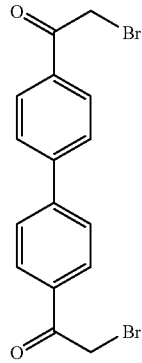

A 1 L, 3-neck round bottom flask, fitted with a nitrogen line, overhead stirrer and thermocouple was charged with 20 g (83.9 mmol, 1 equiv) 1,1'-(biphenyl-4,4'-diyl)diethanone, 200 mL $CH_2Cl_2$ and 8.7 mL (27.1 g, 169.3 mmol, 2.02 quiv) bromine. The mixture was allowed to stir under nitrogen for about 20 h under ambient conditions. The resulting slurry was charged with 200 mL $CH_2Cl_2$ and concentrated down to about 150 mL via vacuum distillation. The slurry was then solvent exchanged into THF to a target volume of 200 mL via vacuum distillation. The slurry was cooled to 20-25° C. over 1 h and allowed to stir at 20-25° C. for an additional hour. The off-white crystalline solids were filtered and washed with 150 mL $CH_2Cl_2$. The product was dried under vacuum at 60° C. to provide 27.4 g (69.2 mmol, 82%) of the desired product: $^1H$ NMR (400 MHz, $CDCl_3$) δ 7.95-7.85 (m, 4H), 7.60-7.50 (m, 4H), 4.26 (s, 4H); $^{13}C$ NMR (100 MHz, $CDCl_3$) δ 191.0, 145.1, 133.8, 129.9, 127.9, 30.8; IR (KBr, $cm^{-1}$) 3007, 2950, 1691, 1599, 1199; Anal calcd for $C_{16}H_{12}Br_2O_2$: C, 48.52; H, 3.05; Br, 40.34. Found: C, 48.53; H, 3.03; Br, 40.53. HRMS calcd for $C_{16}H_{13}Br_2O_2$ (M+H; $DCI^+$): 394.9282. Found: 394.9292. mp 224-226° C.

Example A-1e-2

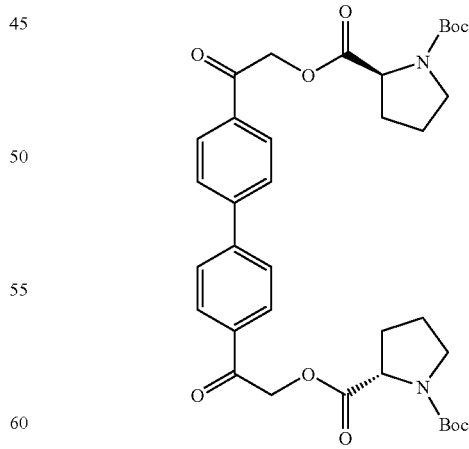

A 500 mL jacketed flask, fitted with a nitrogen line, thermocouple and overhead stirrer, was charged with 20 g (50.5 mmol, 1 equiv) of Example A-1e-1, 22.8 g (105.9 moles, 2.10 equiv) 1-(tert-butoxycarbonyl)-L-proline, and 200 mL acetonitrile. The slurry was cooled to 20° C. followed by the addition of 18.2 mL (13.5 g, 104.4 mmol, 2.07 equiv) DIPEA. The slurry was warmed to 25° C. and allowed to stir for 3 h. The resulting clear, organic solution was washed with 3×100 mL 13 wt % aqueous NaCl. The rich acetonitrile solution was solvent exchanged into toluene (target volume=215 mL) by vacuum distillation until there was less than 0.5 vol % acetonitrile.

Example A-1e-3

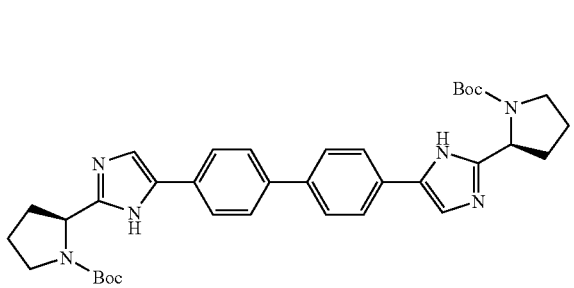

The above toluene solution of Example A-1e-2 was charged with 78 g (1.011 moles, 20 equiv) ammonium acetate and heated to 95-100° C. The mixture was allowed to stir at 95-100° C. for 15 h. After reaction completion, the mixture was cooled to 70-80° C. and charged with 7 mL acetic acid, 40 mL n-butanol, and 80 mL of 5 vol % aqueous acetic acid. The resulting biphasic solution was split while maintaining a temperature>50° C. The rich organic phase was charged with 80 mL of 5 vol % aqueous acetic acid, 30 mL acetic acid and 20 mL n-butanol while maintaining a temperature>50° C. The resulting biphasic solution was split while maintaining a temperature>50° C. and the rich organic phase was washed with an additional 80 mL of 5 vol % aqueous acetic acid. The rich organic phase was then solvent exchanged into toluene to a target volume of 215 mL by vacuum distillation. While maintaining a temperature>60° C., 64 mL MeOH was charged. The resulting slurry was heated to 70-75° C. and aged for 1 h. The slurry was cooled to 20-25° C. over 1 h and aged at that temperature for an additional hour. The slurry was filtered and the cake was washed with 200 mL 10:3 toluene:MeOH. The product was dried under vacuum at 70° C., resulting in 19.8 g (31.7 mmol, 63%) of the desired product: $^1$H NMR (400 MHz, DMSO-$d_6$) δ 13.00-11.00 (s, 2H), 7.90-7.75 (m, 4H), 7.75-7.60 (m, 4H), 7.60-7.30 (s, 2H), 4.92-4.72 (m, 2H), 3.65-3.49 (m, 2H), 3.49-3.28 (m, 2H), 2.39-2.1 (m, 2H), 2.10-1.87 (m, 6H), 1.60-1.33 (s, 8H), 1.33-1.07 (s, 10H); $^{13}$C NMR (100 MHz, DMSO-$d_6$) δ 154.1, 153.8, 137.5, 126.6, 125.0, 78.9, 78.5, 55.6, 55.0, 47.0, 46.7, 33.7, 32.2, 28.5, 28.2, 24.2, 23.5; IR (KBr, cm$^{-1}$) 2975, 2876, 1663, 1407, 1156, 1125; HRMS calcd for $C_{36}H_{45}N_6O_4$ (M+H; ESI$^+$): 625.3502. Found: 625.3502. mp 190-195° C. (decomposed).

Example A-1e-4

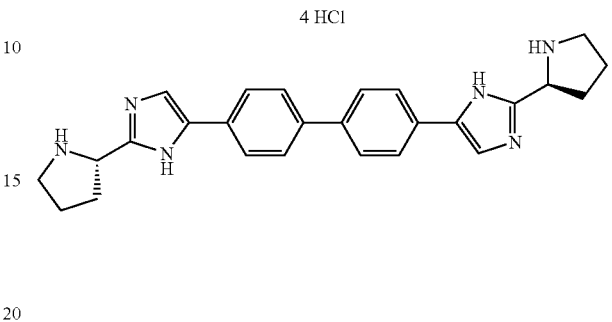

To a 250 ml reactor equipped with a nitrogen line and overhead stirrer, 25.0 g of Example A-1e-3 (40.01 mmol, 1 equiv) was charged followed by 250 mL methanol and 32.85 mL (400.1 mmol, 10 equiv) 6M aqueous hydrogen chloride. The temperature was increased to 50° C. and agitated at 50° C. for 5 h. The resulting slurry was cooled to 20-25° C. and held with agitation for ca. 18 h. Filtration of the slurry afforded a solid which was washed successively with 100 ml 90% methanol/water (V/V) and 2×100 ml of methanol. The wet cake was dried in a vacuum oven at 50° C. overnight to give 18.12 g (31.8 mmol, 79.4%) of the desired product.

Recrystallization of Example A-1e-4

To a 250 ml reactor equipped with a nitrogen line and an overhead stirrer, 17.8 g of crude Example A-1e-4 was charged followed by 72 mL methanol. The resulting slurry was agitated at 50° C. for 4 h, cooled to 20-25° C. and held with agitation at 20-25° C. for 1 h. Filtration of the slurry afforded a crystalline solid which was washed with 60 ml methanol. The resulting wet cake was dried in a vacuum oven at 50° C. for 4 days to yield 14.7 g (25.7 mmol, 82.6%) of the desired product: $^1$H NMR (400 MHz, DMSO-$d_6$) δ 10.5-10.25 (br, 2H), 10.1-9.75 (br, 2H), 8.19 (s, 2H), 7.05 (d, J=8.4, 4H), 7.92 (d, J=8.5, 4H), 5.06 (m, 2H), 3.5-3.35 (m, 4H), 2.6-2.3 (m, 4H), 2.25-2.15 (m, 2H), 2.18-1.96 (m, 2H); $^{13}$C NMR (100 MHz, DMSO-$d_6$) δ 156.6, 142.5, 139.3, 128.1, 127.5, 126.1, 116.9, 53.2, 45.8, 29.8, 24.3; IR (KBr, cm$^{-1}$) 3429, 2627, 1636, 1567, 1493, 1428, 1028. Anal calcd for $C_{26}H_{32}N_6Cl_4$: C, 54.75; H, 5.65; Cl, 24.86; Adjusted for 1.9% water: C, 53.71; H, 5.76; N, 14.46; Cl, 24.39. Found: C, 53.74; H, 5.72; N, 14.50; Cl, 24.49; KF=1.9. mp 240° C. (decomposed)

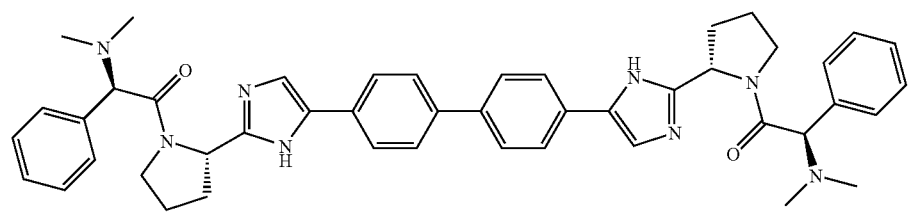

Example 1

(1R,1'R)-2,2'-(4,4'-biphenyldiylbis(1H-imidazole-5,2-diyl(2S)-2,1-pyrrolidinediyl))bis(N,N-dimethyl-2-oxo-1-phenylethanamine)

HATU (44.6 mg, 0.117 mmol) was added to a mixture of pyrrolidine 1e (22.9 mg, 0.054 mmol), diisopropylethylamine (45 μL, 0.259 mmol) and Cap-1 (28.1 mg, 0.13 mmol) in DMF (1.5 mL), and the resulting mixture was stirred at ambient for 90 minutes. The volatile component was removed in vacuo, and the residue was purified first by MCX (methanol wash; 2.0 M $NH_3$/methanol elution) and then by a reverse phase HPLC system ($H_2O$/methanol/TFA) to provide the TFA salt of Example 1 as an off-white foam (44.1 mg). $^1$H NMR (DMSO-$d_6$, δ=2.5 ppm, 400 MHz): δ 10.25 (br s, 2H), 8.20-7.10 (m, 20H), 5.79-5.12 (m, 4H), 4.05-2.98 (m, 4H), 2.98-2.62 (m, 6H), 2.50-1.70 (m, 14H), [Note: the signal of the imidazole NH was too broad to assign a chemical shift];

LC (Cond. 1): RT=1.40 min; >98% homogeneity index; LC/MS: Anal. Calcd. for [M+H]$^+$ $C_{46}H_{51}N_8O_2$: 747.41. found 747.58

Examples 2 to 24-4d

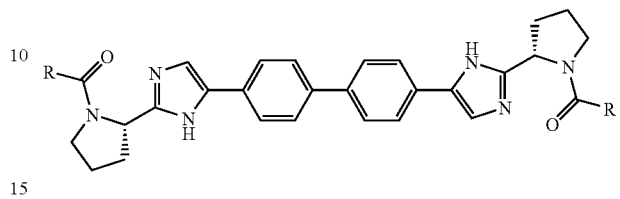

Examples 2 to 24-4 h were prepared as TFA salts by substituting the respective acids for Cap-1 using the same method described for Example 1. Caps in the following table without a number are commercially available.

| Example | Compound Name | R (acyl group) | RT(LC-Cond.); % homogeneity index; MS data |
|---|---|---|---|
| 2 | (1R,1'R)-2,2'-(4,4'-biphenyldiylbis(1H-imidazole-5,2-diyl(2S)-2,1-pyrrolidinediyl))bis(2-oxo-1-phenylethanol) | Ph-CH(OH)-C(O)- | 1.55 minutes(Cond. 1); >98%; LC/MS: Anal. Calcd. for [M + H]$^+$ $C_{42}H_{41}N_6O_4$: 693.32; found 693.46; HRMS: Anal. Calcd. for [M + H]$^+$ $C_{42}H_{41}N_6O_4$: 693.3189; found 693.3182 |
| 3 | (2S,2'S)-1,1'-(4,4'-biphenyldiylbis(1H-imidazole-5,2-diyl(2S)-2,1-pyrrolidinediyl))bis(1-oxo-2-phenyl-2-propanol) | Ph-C(OH)(CH3)-C(O)- | 1.77 minutes(Cond. 1); >98%; LC/MS: Anal. Calcd. for [M + H]$^+$ $C_{44}H_{45}N_6O_4$: 721.35; found 721.52; HRMS: Anal. Calcd. for [M + H]$^+$ $C_{44}H_{45}N_6O_4$: 721.3502; found 721.3515 |
| 4 | dimethyl (4,4'-biphenyldiylbis(1H-imidazole-5,2-diyl(2S)-2,1-pyrrolidinediyl((1R)-2-oxo-1-phenyl-2,1-ethanediyl)))biscarbamate | Cap-4 (Ph-CH(NHC(O)OMe)-C(O)-) | 1.64 minutes(Cond. 1); >98%; LC/MS: Anal. Calcd. for [M + H]$^+$ $C_{46}H_{47}N_8O_6$: 807.36; found 807.58 |
| 5 | (1S,1'S)-2,2'-(4,4'-biphenyldiylbis(1H-imidazole-5,2-diyl(2S)-2,1-pyrrolidinediyl))bis(N,N-dimethyl-2-oxo-1-phenylethanamine) | ent of Cap-1 (Ph-CH(NMe2)-C(O)-) | 1.33 minutes(Cond. 1); >98%; LC/MS: Anal. Calcd. for [M + H]$^+$ $C_{46}H_{51}N_8O_2$: 747.41; found 747.64; HRMS: Anal. Calcd. for [M + H]$^+$ $C_{46}H_{51}N_8O_2$: 747.4135; found 747.4103 |
| 6 | 5,5'-(4,4'-biphenyldiyl)bis(2-((2S)-1-benzoyl-2-pyrrolidinyl)-1H-imidazole) | Ph-C(O)- 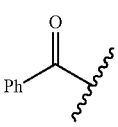 | 1.65 minutes(Cond. 1); >98%; LC/MS: Anal. Calcd. for [M + H]$^+$ $C_{40}H_{37}N_6O_2$: 633.30; found 633.51 |

-continued

| Example | Compound Name | R-C(O)- group | RT(LC-Cond.); % homogeneity index; MS data |
|---|---|---|---|
| 7 | 5,5'-(4,4'-biphenyldiyl)bis(2-((2)S-1-(phenylacetyl)-2-pyrrolidinyl)-1H-imidazole) | Ph-CH2-C(O)- | 1.71 minutes(Cond. 1); >98%; LCMS: Anal. Calcd. for [M + H]+ $C_{42}H_{41}N_6O_2$: 661.33; found 661.53; HRMS: Anal. Calcd. for [M + H]+ $C_{42}H_{41}N_6O_2$: 661.3291; found 661.3300 |
| 8 | 5,5'-(4,4'-biphenyldiyl)bis(2-((2S)-1-((2R)-2-methoxy-2-phenylacetyl)-2-pyrrolidinyl)-1H-imidaozle) | Ph-CH(OMe)-C(O)- | 1.63 minutes (Cond. 1); >98%; LC/MS: Anal. Calcd. for [M + H]+ $C_{44}H_{45}N_6O_4$: 721.35; found 721.59; HRMS: Anal. Calcd. for [M + H]+ $C_{44}H_{45}N_6O_4$: 721.3502; found 721.3536 |
| 9 | (2R,2'R)-1,1'-(4,4'-biphenyldiylbis(1H-imidazole-5,2-diyl(2S)-2,1-pyrrolidinediyl))bis(1-oxo-3-phenyl-2-propanol) | Ph-CH2-CH(OH)-C(O)- | 1.71 minutes(Cond. 1); >98%; LC/MS: Anal. Calcd. for [M + H]+ $C_{44}H_{45}N_6O_4$: 721.35; found 721.58; HRMS: Anal. Calcd. for [M + H]+ $C_{44}H_{45}N_6O_4$: 721.3502; found 721.3497 |
| 10 | 5,5'-(4,4'-biphenyldiyl)bis(2-((2S)-1-propionyl-2-pyrrolidinyl)-1H-imidazole) | CH3CH2-C(O)- | 1.47 minutes(Cond. 1); >98%; LC/MS: Anal. Calcd. for [M + H]+ $C_{32}H_{37}N_6O_2$: 537.30; found 537.40; HRMS: Anal. Calcd. for [M + H]+ $C_{32}H_{37}N_6O_2$: 537.2978; found 537.2952 |
| 11 | 5,5'-(4,4'-biphenyldiyl)bis(2-((2S)-1-(cyclopropylcarbonyl)-2-pyrrolidinyl)-1H-imidazole) | cyclopropyl-C(O)- | 1.48 minutes(Cond. 1); >98%; LC/MS: Anal. Calcd. for [M + H]+ $C_{34}H_{37}N_6O_2$: 561.30; found 561.44 |
| 12 | 5,5'-(4,4'-biphenyldiyl)bis(2-((2S)-1-(cyclopropylacetyl)-2-pyrrolidinyl)-1H-imidazole) | cyclopropyl-CH2-C(O)- | 1.57 minutes(Cond. 1); >98%; LC/MS: Anal. Calcd. for [M + H]+ $C_{36}H_{41}N_6O_2$: 589.33; found 589.48; HRMS: Anal. Calcd. for [M + H]+ $C_{36}H_{41}N_6O_2$: 589.3291; found 589.3268 |
| 13 | 5,5'-(4,4'-biphenyldiyl)bis(2-((2S)-1-((2R)-tetrahydro-2-furanylcarbonyl)-2-pyrrolidinyl)-1H-imidazole) | (tetrahydrofuran-2-yl)-C(O)- | 1.44 minutes(Cond. 1); >98%; LC/MS: Anal. Calcd. for [M + H]+ $C_{36}H_{41}N_6O_4$: 621.32; found 621.52; HRMS: Anal. Calcd. for [M + H]+ $C_{36}H_{41}N_6O_4$: 621.3189; found 621.3191 |
| 14 | 2,2'-(4,4'-biphenyldiylbis(1H-imidazole-5,2-diyl(2S)-2,1-pyrrolidinediyl))bis(N,N-dimethyl-2-oxoethanamine) | (CH3)2N-CH2-C(O)- | 1.27 minutes(Cond. 1); >98%; LC/MS: Anal. Calcd. for [M + H]+ $C_{34}H_{43}N_8O_2$: 595.35; found 595.54; HRMS: Anal. Calcd. for [M + H]+ $C_{34}H_{43}N_8O_2$: 595.3509; found 595.3503 |

-continued

| Example | Compound Name | R−C(=O)− group | RT(LC-Cond.); % homogeneity index; MS data |
|---|---|---|---|
| 15 | (2R,2'R)-1,1'-(4,4'-biphenyldiylbis(1H-imidazole-5,2-diyl(2S)-2,1-pyrrolidinediyl))bis(1-oxo-2-propanol) | CH₃-CH(OH)-C(=O)- | 1.36 minutes(Cond. 1); >98%; LC/MS: Anal. Calcd. for [M + H]⁺ C₃₂H₃₇N₆O₄: 569.29; found 569.44; HRMS: Anal. Calcd. for [M + H]⁺ C₃₂H₃₇N₆O₄: 569.2876; found 569.2872 |
| 16 | (2R,2'R)-1,1'-(4,4'-biphenyldiylbis(1H-imidazole-5,2-diyl(2S)-2,1-pyrrolidinediyl))bis(3-methyl-1-oxo-2-butanol) | (CH₃)₂CH-CH(OH)-C(=O)- | 1.51 minutes(Cond. 1); >98%; LC/MS: Anal. Calcd. for [M + H]⁺ C₃₆H₄₅N₆O₄: 625.35; found 625.50; HRMS: Anal. Calcd. for [M + H]⁺ C₃₆H₄₅N₆O₄: 625.3517 |
| 17 | 5,5'-(4,4'-biphenyldiyl)bis(2-((2S)-1-((2R)-2-phenyl-2-(1-pyrrolidinyl)acetyl)-2-pyrrolidinyl)-1H-imidazole) | Ph-CH(N-pyrrolidinyl)-C(=O)- Cap-5 | 1.13 minutes(Cond. 1); >98%; LC/MS: Anal. Calcd. for [M + H]⁺ C₅₀H₅₅N₈O₂: 799.45; found 799.67 |
| 18 | 4,4'-(4,4'-biphenyldiylbis(1H-imidaozle-5,2-diyl(2S)-2,1-pyrrolidinediyl((1R)-2-oxo-1-phenyl-2,1-ethanediyl)))dimorpholine | Ph-CH(N-morpholinyl)-C(=O)- Cap-6 | 1.11 minutes(Cond. 1); >98%; LC/MS: Anal. Calcd. for [M + H]⁺ C₅₀H₅₅N₈O₄: 831.44; found 831.71 |
| 19 | 5,5'-(4,4'-biphenyldiyl)bis(2-((2)S-1-(((3S)-3-fluoro-1-pyrrolidinyl)(phenyl)acetyl)-2-pyrrolidinyl)-1H-imdiazole) | Ph-CH(3-fluoropyrrolidinyl)-C(=O)- Diastereomer-1 Cap-9a | 1.17 minutes(Cond. 1); 97%; LC/MS: Anal. Calcd. for [M + H]⁺ C₅₀H₅₃F₂N₈O₂: 835.43; found 835.51; HRMS: Anal. Calcd. for [M + H]⁺ C₅₀H₅₃F₂N₈O₂: 835.4260; found 835.4261 |
| 20 | 5,5'-(4,4'-biphenyldiyl)bis(2-((2)S-1-(((3S)-3-fluoro-1-pyrrolidiny)(phenyl)acetyl)-2-pyrrolidinyl)-1H-imidazole) | Ph-CH(3-fluoropyrrolidinyl)-C(=O)- Diastereomer-2 Cap-9b | 1.03 minutes(Cond. 1); >98%; LC/MS: Anal. Calcd. for [M + H]⁺ C₅₀H₅₃F₂N₈O₂: 835.43; found 835.51; HRMS: Anal. Calcd. for [M + H]⁺ C₅₀H₅₃F₂N₈O₂: 835.4260; found 835.4261 |

| Example | Compound Name | R group (Cap) | RT(LC-Cond.); % homogeneity index; MS data |
|---|---|---|---|
| 21 | (1R,1'R)-2,2'-(4,4'-biphenyldiylbis(1H-imidazole-5,2-diyl(2S)-2,1-pyrrolidinediyl))bis(N,N-diethyl-2-oxo-1-phenylethanamine) | Cap-2 (Ph-CH, N(Et)₂, C=O) | 1.13 minutes(Cond. 1); >98%; LC/MS: Anal. Calcd. for [M + H]⁺ $C_{50}H_{59}N_8O_2$: 803.48; found 803.56; HRMS: Anal. Calcd. for [M + H]⁺ $C_{50}H_{59}N_8O_2$: 803.4761; found 803.4728 |
| 22 | (1R,1'R)-2,2'-(4,4'-biphenyldiylbis(1H-imidazole-5,2-diyl(2S)-2,1-pyrrolidinediyl))bis(N-ethyl-N-methyl-2-oxo-1-phenylethanamine) | Cap-3 | 1.10 minutes(Cond. 1); >98%; LC/MS: Anal. Calcd. for [M + H]⁺ $C_{48}H_{55}N_8O_2$: 775.45; found 775.52; HRMS: Anal. Calcd. for [M + H]⁺ $C_{50}H_{59}N_8O_2$: 775.4448; found 775.4456 |
| 23 | N,N'-(4,4'-biphenyldiylbis(1H-imidazole-5,2-diyl(2S)-2,1-pyrrolidinediyl((1R)-2-oxo-1-phenyl-2,1-ethanediyl)))diformamide | (Ph-CH, HN-CHO) | 1.22 minutes(Cond. 1); >98%; LC/MS: Anal. Calcd. for [M + H]⁺ $C_{44}H_{43}N_8O_4$: 747.34; found 747.38 |
| 24 | 1,1'-(4,4'-biphenyldiylbis(1H-imidazole-5,2-diyl(2S)-2,1-pyrrolidinediylcarbonyl))dicyclopropanol | (cyclopropyl-OH, C=O) | 1.77 minutes(Cond. 2); >98%; LC/MS: Anal. Calcd. for [M + H]⁺ $C_{34}H_{37}N_6O_4$: 593.29; found 593.16 |
| 24-1 | 1,1'-(4,4'-biphenyldiylbis(1H-imidazole-5,2-diyl(2S)-2,1-pyrrolidinediyl((1R)-2-oxo-1-phenyl-2,1-ethanediyl)))dipiperidine | Cap-14 | ¹HNMR(400 MHz, DMSO-d₆) δ 12.18(m, 0.4 H), 11.96 (m, 0.4 H), 11.79(m, 1.2 H), 7.84-7.70(m, 4 H), 7.69-7.65 (m, 4 H), 7.53-7.50(m, 2 H), 7.43-7.28(m, 4 H), 7.09-7.01 (m, 2 H), 6.87-6.85(m, 2 H), 5.51-5.48(m, 0.5 H), 5.01-4.98(m, 1.5 H), 4.29(m, 1.5 H), 4.16(m, 0.5 H), 3.98 (m, 2 H), 3.65-3.49(m, 2 H), 3.43-3.36(m, 2 H), 2.41-2.31 (m, 8 H), 2.14-1.82(m, 8 H), 1.47-1.31(m, 12 H); LCMS: Anal. Calcd. for $C_{52}H_{58}N_8O_2$: 826; found: 827(M + H)⁺. |
| 24-2 | 1,1'-(4,4'-biphenyldiylbis(1H-imidazole-5,2-diyl(2S)-2,1-pyrrolidinediyl((1R)-2-oxo-1-phenyl-2,1-ethanediyl)))bis(4-methyl-4-piperidinol) | Cap-15 | ¹HNMR(400 MHz, DMSO-d₆) δ 12.02(br s, 1 H), 11.82 (br s, 1 H), 7.90-7.79(m, 4 H), 7.79-7.65(m, 5 H), 7.55 (br s, 2 H), 7.45(d, J = 7.6 Hz, 2 H), 7.39-7.25(m, 3 H), 7.34(d, J = 7.6 Hz, 2 H), 7.04(t, J = 7.6 Hz, 2 H), 6.85(d, J = 8.1 Hz, 2 H), 5.15-4.96(m, 2 H), 4.31-3.96 (m, 6 H), 2.35-2.20(m, 2 H), 2.05-1.94(m, 4 H), 1.94-1.81 (m, 4 H), 1.50-1.35(m, 9 H), 1.35-1.20(m, 5 H), 1.09(s, 2 H), 1.05(s, 4 H); LCMS: Anal. Calcd. for $C_{54}H_{62}N_8O_4$: 886; found: 887(M + H)⁺. |

| Example | Compound Name | R group (Cap) | RT(LC-Cond.); % homogeneity index; MS data |
|---|---|---|---|
| 24-3 | dimethyl (4,4'-biphenyldiylbis(1H-imidazole-5,2-diyl(2S)-2,1-pyrrolidinediyl((1R)-1-(2-chlorophenyl)-2-oxo-2,1-ethanediyl)))biscarbamate | (2-chlorophenyl with NHCO$_2$Me) | LCMS: Anal. Calcd. for C$_{46}$H$_{44}$Cl$_2$N$_8$O$_6$: 874; found: 875(M + H)$^+$. |
| 24-4a | N',N'''-(4,4'-biphenyldiylbis(1H-imidazole-4,2-diyl(2S)-2,1-pyrrolidinediyl((1R)-2-oxo-1-phenyl-2,1-ethanediyl)))bis(1,1-dimethylurea) | Cap-47 | $^1$H NMR(500 MHz, DMSO-d$_6$) δ ppm 1.89-2.00 (m, J = 17.09, 7.02 Hz, 4 H), 2.06-2.13(m, J = 14.95, 3.97 Hz, 3 H), 2.24-2.33(m, J = 8.70, 6.56 Hz, 2 H), 2.79-2.84(m, 12 H), 3.29(q, 2 H), 3.95-4.03(m, 3 H), 5.26(dd, J = 8.55, 2.14 Hz, 3 H), 5.52 (d, J = 5.80 Hz, 3 H), 6.72(d, J = 6.10 Hz, 3 H), 7.02-7.07 (m, 1 H), 7.29-7.36(m, 3 H), 7.39(t, J = 7.17 Hz, 4 H), 7.46(d, J = 7.02 Hz, 3 H), 7.92(s, 8 H), 8.12(s, 2 H); HPLC XTERRA C-18 4.6 × 30 mm, 0 to 100% B over 4 minutes, 1 minute hold time, A = 90% water, 10% methanol, 0.2% H$_3$PO$_4$, B = 10% water, 90% methanol, 0.2% H$_3$PO$_4$, RT = 2.13 minutes, 96% homogeneity index; LCMS: Anal. Calcd. for C$_{48}$H$_{53}$N$_{10}$O$_4$: 832.42; found: 833.43(M + H)$^+$; HRMS: Anal. Calcd. for C$_{48}$H$_{54}$N$_{10}$O$_4$ 833.4251; found: 833.4267(M + H)$^+$. |
| 24-4b | N',N'''-(4,4'-biphenyldiylbis(1H-imidazole-5,2-diyl(2S)-2,1-pyrrolidinediyl((1R)-2-oxo-1-phenyl-2,1-ethanediyl)))bis(1-methylurea) | Cap-45 | RT = 4.45 minutes(Gemini C-18 4.6 × 50 mm, 0 to 100% B over 10.0 minute gradient, 1 minute hold time, A = 5% acetonitrile, 95% water, 10 mm ammonium acetate, B = 95% acetonitrile, 5% water, 10 mm ammonium acetate); LCMS: Anal. Calcd. for C$_{46}$H$_{48}$N$_{10}$O$_4$ 804.95; found: 805.41(M + H)$^+$; HRMS: Anal. Calcd. for C$_{46}$H$_{49}$N$_{10}$O$_4$ 805.3938; found: 805.3929(M + H)$^+$. |
| 24-4c | N',N'''-(4,4'-biphenyldiylbis(1H-imidazole-5,2-diyl(2S)-2,1-pyrrolidinediyl((1R)-2-oxo-1-phenyl-2,1-ethanediyl)))bis(1-ethylurea) | Cap-46 | RT = 4.20 minutes(Gemini C-18 4.6 × 50 mm, 0 to 100% B over 10.0 minute gradient, 1 minute hold time, A = 5% acetonitrile, 95% water, 10 mm ammonium acetate, B = 95% acetonitrile, 5% water, 10 mm ammonium acetate); LCMS: Anal. Calcd. for C$_{48}$H$_{52}$N$_{10}$O$_4$ 833.00; found: 833.48 (M + H)$^+$. |

| Example | Compound Name | | RT(LC-Cond.); % homogeneity index; MS data |
|---|---|---|---|
| 24-4d | N',N'''-(4,4'-biphenyldiylbis(1H-imidazole-5,2-diyl(2S)-2,1-pyrrolidinediyl((1R)-2-oxo-1-phenyl-2,1-ethanediyl)))bis(1-cyclopentylurea) | Cap-48 | RT = 4.92 minutes (Gemini C-18 4.6 × 50 mm, 0 to 100% B over 10.0 minute gradient, 1 minute hold time, A = 5% acetonitrile, 95% water, 0 mm ammonium acetate, B = 95%, acetonitrile, 5% water, 10 mm ammonium acetate); LCMS: Anal. Calcd. for $C_{54}H_{60}N_{10}O_4$ 912.49; found: 913.68 $(M + H)^+$; HRMS: Anal. Calcd. for $C_{54}H_{61}N_{10}O_4$ 913.4877; found: 913.4899 $(M + H)^+$. |
| 24-4e | 2,2'-(4,4'-bipenyldiylbis(1H-imidaozle-5,2-diyl(2S)-2,1-pyrrolidinediyl))bis(N-benzyl-N-methyl-2-oxoethanamine) | Cap-49 | $^1$H NMR(500 MHz, DMSO-$d_6$) δ ppm 1.97-2.43(m, 8 H), 2.64-2.91(m, 6 H), 3.45-3.63 (m, 2 H), 3.62-3.76(m, 2 H), 4.14(dd, 4 H), 4.22-4.45(m, 4 H), 5.29(s, 2 H), 7.28-7.65 (m, 10 H), 7.90(s, 8 H), 8.06 (s, 2 H), 14.62(s, 2 H); HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid. RT = 3.06 min; LCMS: Anal. Calcd. for: $C_{46}H_{50}N_8O_2$ 746.96; Found: 747.41 $(M + H)^+$. |
| 24-4f | (2S,2'S)-1,1'-(4,4'-biphenyldiylbis(1H-imidazole-5,2-diyl(2S)-2,1-pyrrolidinediyl))bis(N-benzyl-N-methyl-1-oxo-2-propanamine) | | RT = 2.95 minutes (99%); HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid; LCMS: Anal. Calcd. for: $C_{48}H_{54}N_8O_2$ 775.02; Found: 775.45$(M + H)^+$. |

-continued

| Example | Compound Name | R (acyl group) | RT(LC-Cond.); % homogeneity index; MS data |
|---|---|---|---|
| 24-4g | 1,1'-(4,4'-biphenyldiylbis(1H-imidaozle-5,2-diyl(2S)-2,1-pyrrolidinediyl))bis(N-benzyl-N,3-dimethyl-1-oxo-2-butanamine) | Cap-50 | RT = 3.86 minutes(100%); HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid; LCMS: Anal. Calcd. for: $C_{52}H_{62}N_8O_2$ 831.13; Found: 831.51(M + H)$^+$. |
| 24-4h | 1,1'-(4,4'-biphenyldiylbis(1H-imidazole-5,2-diyl(2S)-2,1-pyrrolidinediyl(2-oxo-1-phenyl-2,1-ethanediyl)))di(4-piperidinol) | Cap-8 | RT = 2.86 minutes(100%); HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid; LCMS: Anal. Calcd. for: $C_{52}H_{58}N_8O_4$ 859.09; Found: 859.45(M + H)$^+$. |

Examples 24-5 to 24-18

| Example | Compound Name | Structure | Data |
|---|---|---|---|
| 24-5 | 1,1'-(4,4'-biphenyldiylbis(1H-imidazole-5,2-diyl((2S,4S)-4-fluoro-2,1-pyrrolidinediyl)((1R)-2-oxo-1-phenyl-2,1-ethanediyl)))dipiperidine | from 1-2e-2 and Cap-1 | Gemini C-18 4.6 × 50 mm, 0 to 100% B over 10.0 minute gradient, 1 minute hold time, A = 5% acetonitrile, 95% water, 10 mm ammonium acetate, B = 95% acetonitrile, 5% water, 10 mm ammonium acetate. (RT = 4.163 min); Nominal/LRMS-Calcd. for $C_{46}H_{48}F_2N_8O_2$ 782.93; found 783.40 (M + H)$^+$; Accurate/HRMS-Calcd. for $C_{46}H_{49}F_2N_8O_2$ 783.3946; 783.3934 (M + H)$^+$. |

| Example | Compound Name | Structure | Data |
|---|---|---|---|
| 24-6 | (1R,1'R)-2,2'-(4,4'-biphenyldiylbis(1H-imidazole-5,2-diyl((2S,4S)-4-fluoro-2,1-pyrrolidinediyl))))bis(N,N-diethyl-2-oxo-1-phenylethanamine) | from 1-2e-2 and Cap-2 | Gemini C-18 4.6 × 50 mm, 0 to 100% B over 10.0 minute gradient, 1 minute hold time, A = 5% acetonitrile, 95% water, 10 mm ammonium acetate, B = 95% acetonitrile, 5% water, 10 mm ammonium acetate. (RT = 3.76 min); LCMS: Anal. Calcd. for $C_{50}H_{56}F_2N_8O_2$ 839.04; found: 839.49 $(M+H)^+$; HRMS: Anal. Calcd. for $C_{50}H_{57}F_2N_8O_2$ 839.4572; found: 839.4590 $(M+H)^+$. |
| 24-7 | (1R,1'R)-2,2'-(4,4'-biphenyldiylbis(1H-imidazole-5,2-diyl((2S,4S)-4-fluoro-2,1-pyrrolidinediyl))))bis(N,N-dimethyl-2-oxo-1-phenylethanamine) | from 1-2e-2 and Cap-14 | Gemini C-18 4.6 × 50 mm, 0 to 100% B over 10.0 minute gradient, 1 minute hold time, A = 5% acetonitrile, 95% water, 10 mm ammonium acetate, B = 95% acetonitrile, 5% water, 10 mm ammonium acetate. RT = 3.99 min; LCMS: Anal. Calcd. for $C_{52}H_{56}F_2N_8O_2$ 863.06; found: 863.47 $(M+H)^+$; HRMS: Anal. Calcd. for $C_{52}H_{57}F_2N_8O_2$ 863.4572; found: 863.4553 $(M+H)^+$. |
| 24-8 | 1,1'-(4,4'-biphenyldiylbis(1H-imidazole-4,2-diyl((2S)-4,4-difluoro-2,1-pyrrolidinediyl)((1R)-2-oxo-1-phenyl-2,1-ethanediyl)))dipiperidine | from 1-2e-3 and Cap-14 | RT = 1.64 minutes, method B; LCMS: Anal. Calcd. for $C_{52}H_{54}F_4N_8O_6$: 898.43; found: 899.46 $(M+H)^+$; HRMS: Anal. Calcd. for $C_{52}H_{55}F_4N_8O_6$ 899.4384; found: 899.4380 $(M+H)^+$. |
| 24-9 | dimethyl (4,4'-biphenyldiylbis(1H-imidazole-4,2-diyl((2S)-4,4-difluoro-2,1-pyrrolidinediyl)((1R)-2-oxo-1-phenyl-2,1-ethanediyl)))biscarbamate | from 1-2e-3 and Cap-4 | RT = 2.62 minutes, method C; LCMS: Anal. Calcd. for $C_{46}H_{42}F_4N_8O_6$: 878.88; found: 879.81 $(M+H)^+$; HRMS: Anal. Calcd. for $C_{46}H_{43}F_4N_8O_6$ 879.33242; found: 879.3273 $(M+H)^+$. |

| Example | Compound Name | Structure | Data |
|---|---|---|---|
| 24-10 | 1-((1R)-2-((2S)-2-(4-(4'-(2-((2S)-4,4-difluoro-1-((2R)-2-phenyl-2-(1-piperidinyl)acetyl)-2-pyrrolidinyl)-1H-imidazole-4-yl)-4-biphenylyl)-1H-imidazol-2-yl)-1-pyrrolidinyl)-2-oxo-1-phenylethyl)piperidine | from 1-3e and Cap-14. | RT = 1.54 minutes, method B; LCMS: Anal. Calcd. for $C_{52}H_{56}F_2N_8O_6$: 862.45; found: 863.46 (M + H)$^+$; HRMS: Anal. Calcd. for $C_{52}H_{57}F_2N_8O_6$ 863.4573; found: 863.4572 (M + H)$^+$. |
| 24-11 | dimethyl (4,4'-biphenyldiylbis(1H-imidazole-5,2-diyl((2S,4R)-4-hydroxy-2,1-pyrrolidinediyl)((1R)-2-oxo-1-phenyl-2,1-ethanediyl)))biscarbamate | from 1-1e and Cap-4 | RT = 8.54 minutes, method A; LCMS: Anal. Calcd. for $C_{46}H_{46}N_8O_8$ 838.93; found: 839.41 (M + H)$^+$; HRMS: Anal. Calcd. for $C_{46}H_{47}N_8O_8$ 839.9300; found: 839.3527 (M + H)$^+$. |
| 24-12 | (3R,5S,3'R,5'S)-5,5'-(4,4'-biphenyldiylbis(1H-imidazole-5,2-diyl))bis(1-((2R)-2-hydroxy-2-phenylacetyl)-3-pyrrolidinol) | from 1-1e and mandelic acid | RT = 6.92 minutes, method A; LCMS: Anal. Calcd. for $C_{42}H_{40}N_6O_6$ 724.81; found: 725.43 (M + H)$^+$; HRMS: Anal. Calcd. for $C_{42}H_{41}N_6O_6$ 725.3087; found: 725.3088 (M + H)$^+$. |
| 24-13 | N,N''-(4,4'-biphenyldiylbis(1H-imidazole-5,2-diyl((2S,4R)-4-hydroxy-2,1-pyrrolidinediyl)((1R)-2-oxo-1-phenyl-2,1-ethanediyl)))bis(3-methylurea) | Prepared from 1-1e and Cap-45 | RT = 3.80 minutes, method C; LCMS: Anal. Calcd. for $C_{46}H_{48}N_{10}O_6$ 836.95; found: 837.52 (M + H)$^+$; HRMS: Anal. Calcd. for $C_{46}H_{49}N_{10}O_6$ 837.3836; found: 837.3809 (M + H)$^+$. |
| 24-14 | N',N'''-(4,4'-biphenyldiylbis(1H-imidazole-5,2-diyl((2S,4R)-4-hydroxy-2,1-pyrrolidinediyl)((1R)-2-oxo-1-phenyl-2,1-ethanediyl)))bis(1-ethylurea) | Prepared from 1-1e and Cap-46 | RT = 4.39 minutes, method C; LRMS: Anal. Calcd. for $C_{48}H_{52}N_{10}O_6$ 865.003; found: 865.56 (M + H)$^+$; HRMS: Anal. Calcd. for $C_{48}H_{53}N_{10}O_6$ 865.4149; found: 865.4139 (M + H)$^+$. |

| Example | Compound Name | Structure | Data |
|---|---|---|---|
| 24-15 | N',N'''-(4,4'-biphenyldiylbis(1H-imidazole-5,2-diyl((2S,4R)-4-hydroxy-2,1-pyrrolidinediyl)((1R)-2-oxo-1-phenyl-2,1-ethanediyl)))bis(1-cyclopentylurea) | Prepared from 1-1e and Cap-48 | RT = 4.88 minutes, method B; LRMS: Anal. Calcd. for $C_{54}H_{60}N_{10}O_6$ 944.13; found: 945.65 $(M + H)^+$; HRMS: Anal. Calcd. for $C_{54}H_{61}N_{10}O_6$ 945.4775; found: 945.4769 $(M + H)^+$. |
| 24-16 | (3S,5S,3'S,5'S)-5,5'-(4,4'-biphenyldiylbis(1H-imidazole-5,2-diyl))bis(1-((2R)-2-(dimethylamino)-2-phenylacetyl)-3-pyrrolidinol) | Prepared from 1-2e and Cap-1 | RT = 3.66 minutes, method D; LRMS: Anal. Calcd. for $C_{46}H_{50}N_8O_4$ 778.39; found: 779.39 $(M + H)^+$; HRMS: Anal. Calcd. for $C_{46}H_{51}N_8O_4$ 779.4033; found: 779.4021 $(M + H)^+$. |
| 24-17 | dimethyl (4,4'-biphenyldiylbis(1H-imidazole-5,2-diyl((2S,4S)-4-hydroxy-2,1-pyrrolidinediyl)((1R)-2-oxo-1-phenyl-2,1-ethanediyl))) biscarbamate | Prepared from 1-2e and Cap-4 | RT = 5.75 minutes, method C; LRMS: Anal. Calcd. for $C_{46}H_{46}N_8O_8$ 838.93; found: 839.44 $(M + H)^+$; HRMS: Anal. Calcd. for $C_{46}H_{47}N_8O_8$ 839.3517; found: 839.3519 $(M + H)^+$. |
| 24-18 | (3S,5S,3'S,5'S)-5,5'-(4,4'-biphenyldiylbis(1H-imidazole-5,2-diyl))bis(1-((2R)-2-hydroxy-2-phenylacetyl)-3-pyrrolidinol) | from 1-2e and mandelic acid | RT = 4.41 minutes, method D; LRMS: Anal. Calcd. for $C_{42}H_{40}N_6O_6$ 724.81; found: 725.13 $(M + H)^+$. |
| 24-18-1 | dimethyl (4,4'-biphenyldiylbis(1H-imidazole-5,2-diyl((1S)-1,1-ethanediyl (methylimino)((1R)-2-oxo-1-phenyl-2,1-ethanediyl))) biscarbamate | from 1-7e and Cap-4 | RT = 1.55 min[1]; LRMS: Anal. Calcd. for $C_{44}H_{46}N_8O_6$ 782.35; found: 783.37 $(M + H)^+$; HRMS: Anal. Calcd. for $C_{44}H_{47}N_8O_6$ 783.3619 found: 783.3630 $(M + H)^+$. |

| Example | Compound Name | Structure | Data |
|---|---|---|---|
| 24-18-2 | (2R,2'R)-N,N'-(4,4'-biphenyldiylbis(1H-imidazole-5,2-diyl(1S)-1,1-ethanediyl))bis(2-(dimethylamino)-N-methyl-2-phenylacetamide) | from 1-7e and Cap-1 | RT = 1.16 min[1]; LRMS: Anal. Calcd. for $C_{44}H_{50}N_8O_2$ 722.41; found: 723.41 (M + H)+; HRMS: Anal. Calcd. for $C_{44}H_{51}N_8O_2$ 723.4135 found: 723.4152 (M + H)+. |
| 24-18-3 | (2R,2'R)-N,N'-(4,4'-biphenyldiylbis(1H-imidazole-5,2-diyl(1S)-1,1-ethandiyl))bis(N-methyl-2-phenyl-2-(1-piperidinyl)acetamide) | from 1-7e and Cap-14 | RT = 1.28 min[1]; LRMS: Anal. Calcd. for $C_{50}H_{58}N_8O_2$ 802.47; found: 803.50 (M + H)+; HRMS: Anal. Calcd. for $C_{50}H_{59}N_8O_2$ 803.4761 found: 803.4778 (M + H)+. |
| 24-18-4 | methyl ((1R)-2-((2S)-2-(5-(4'-(2-((1S)-1-(((2R)-2-((methoxycarbonyl)amino)-2-phenylacetyl)methyl)amino)ethyl)-1H-imidazol-5-yl)-4-biphenylyl)-1H-imidazol-2-yl)-1-pyrrolidinyl)-2-oxo-1-phenylethyl)carbamate | Prepared from 1-5e and Cap-4 | RT = 1.53 min[1]; LRMS: Anal. Calcd. for $C_{45}H_{46}N_8O_6$ 794.35; found: 795.39 (M + H)+; HRMS: Anal. Calcd. for $C_{45}H_{47}N_8O_6$ 795.3619 found: 795.3616 (M + H)+. |

-continued

| Example | Compound Name | Structure | Data |
|---|---|---|---|
| 24-18-5 | (2R)-2-(dimethylamino)-N-((1S)-1-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)ethyl)-N-methyl-2-phenylacetamide | Prepared from 1-5e and Cap-1 | RT = 1.21[1]; LRMS: Anal. Calcd. for $C_{45}H_{50}N_8O_2$ 734.41; found: 735.46 (M + H)[+]; HRMS: Anal. Calcd. for $C_{45}H_{51}N_8O_2$ 735.4135 found: 735.4136 (M + H)[+]. |
| 24-18-6 | (2R)-N-methyl-2-phenyl-N-((1S)-1-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)ethyl)-2-(1-piperidinyl)acetamide | Prepared from 1-5e and Cap-14 | RT = 1.30[1]; LRMS: Anal. Calcd. for $C_{51}H_{58}N_8O_2$ 814.47; found: 815.48 (M + H)[+]; HRMS: Anal. Calcd. for $C_{51}H_{59}N_8O_2$ 815.4761 found: 815.4744 (M + H)[+]. |

[1] LC Conditions for 24-18-1 through 24-18-6: Phenomenex LUNA C-18 4.6 × 50 mm, 0 to 100% B over 2 minutes, 1 minute hold time, A = 90% water, 10% methanol, 0.1% TFA, B = 10% water, 90% methanol, 0.1% TFA, 220 nm, 5 μL injection volume.

Examples 24-19 to 24-20

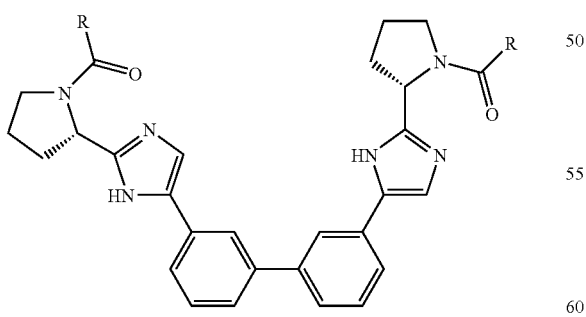

Example 24-19 and 24-20 were prepared as TFA salts from 1-2e-1 and the respective acids using the same method described for Example 1.

| Example | Compound Name | | Data |
|---|---|---|---|
| 24-19 | methyl ((1R)-2-((2S)-2-(4-(3'-(2-((2S)-1-((2R)-2-((methoxycarbonyl)amino)-2-phenylacetyl)-2-pyrrolidinyl)-1H-imidazol-5-yl)-3-biphenylyl)-1H-imidazol-2-yl)-1-pyrrolidinyl)-2-oxo-1-phenylethyl)carbamate | Cap-4 | $^1$H NMR (500 MHz, DMSO-d$_6$) δ ppm 1.82-1.97 (m, 2 H), 1.97-2.17 (m, 4 H), 2.18-2.37 (m, 2 H), 3.18 (d, J = 9.77 Hz, 2 H), 3.44-3.58 (m, 6 H), 3.79-4.04 (m, 2 H), 5.09-5.46 (m, 2 H), 5.45-5.84 (m, 2 H), 6.97-7.49 (m, 10 H), 7.61-7.74 (m, 4 H), 7.75-7.93 (m, 4 H), 8.10-8.32 (m, 4 H), 14.48 (app br s, 2 H); RT = 1.34 min; LC/MS: Anal. Calcd. for [M + H]$^+$ C$_{46}$H$_{47}$N$_8$O$_6$: 807.36; found 807.40 |
| 24-20 | (1R)-2-((2S)-2-(4-(3'-(2-((2S)-1-((2R)-2-(dimethylamino)-2-phenylacetyl)-2-pyrrolidinyl)-1H-imidazol-5-yl)-3-biphenylyl)-1H-imidazol-2-yl)-1-pyrrolidinyl)-N,N-dimethyl-2-oxo-1-phenylethanamine | Cap-1 | $^1$H NMR (500 MHz, DMSO-d$_6$) δ ppm 1.71-2.32 (m, 8 H), 3.33-3.68 (m, 2 H), 3.89-4.16 (m, J = 2.75 Hz, 2 H), 4.96 (app br s, 12 H), 5.26 (s, 2 H), 5.45 (s, 2 H), 7.03-7.78 (m, 12 H), 7.84 (s, 4 H), 8.07-8.43 (m, 4 H), 9.90-10.87 (m, 2 H); RT = 1.10 min; LC/MS: Anal. Calcd. for [M + H]$^+$ C$_{46}$H$_{51}$N$_8$O$_2$: 747.41; found 747.45 |

LC conditions for 24-19 and 24-20:
Column=Phenomenex-Luna 3.0×50 mm S10
Start % B=0
Final % B=100
Gradient time=2 min
Stop time=3 min
Flow Rate=4 mL/min
Wavelength=220 nm
Solvent A=0.1% TFA in 10% methanol/90% H$_2$O
Solvent B=0.1% TFA in 90% methanol/10% H$_2$O Examples 24-21 to 24-22

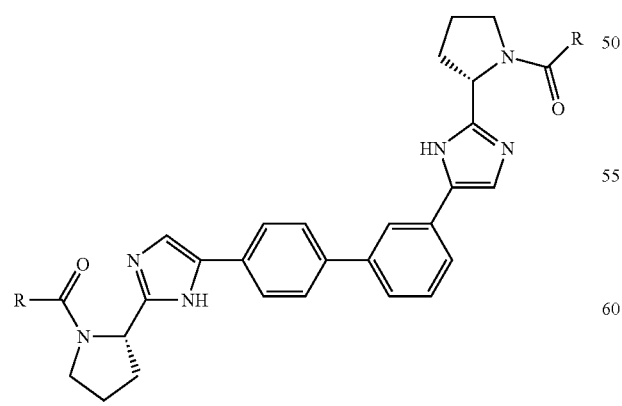

Example 24-21 and 24-22 were prepared as TFA salts from 1-4e and the respective carboxylic acids using the same method described for Example 1.

| Example | Compound Name | | Data |
|---|---|---|---|
| 24-21 | methyl ((1R)-2-((2R)-2-(4-(3'-(2-((2S)-1-((2R)-2-((methoxycarbonyl)amino)-2-phenylacetyl)-2-pyrrolidinyl)-1H-imidazol-4-yl)-4-biphenylyl)-1H-imidazol-2-yl)-1-pyrrolidinyl)-2-oxo-1-phenylethyl)carbamate | Cap-4 | $^1$H NMR (500 MHz, DMSO-$d_6$) δ ppm 1.73-2.37 (m, 8 H), 3.13 (s, 2 H), 3.36-4.29 (m, 8 H), 5.26 (s, 2 H), 5.53 (s, 2 H), 6.99-8.61 (m, 22 H), 14.51 (s, 2 H); RT = 1.33 min; LC/MS: Anal. Calcd. for [M + H]$^+$C$_{46}$H$_{47}$N$_8$O$_6$: 807.36; found 807.58 |
| 24-22 | (1R)-2-((2R)-2-(4-(3'-(2-((2S)-1-((2R)-2-(dimethylamino)-2-phenylacetyl)-2-pyrrolidinyl)-1H-imidazol-4-yl)-4-biphenylyl)-1H-imidazol-2-yl)-1-pyrrolidinyl)-N,N-dimethyl-2-oxo-1-phenylethanamine | Cap-1 | $^1$H NMR (500 MHz, DMSO-$d_6$) δ ppm 1.84-2.32 (m, 8 H), 2.92-3.10 (m, 2 H), 3.92-4.08 (m, 2 H), 4.43 (app br s, 12 H), 5.16-5.37 (m, 2 H), 5.39-5.58 (m, 2 H), 7.16-8.24 (m, 20 H), 9.60-10.46 (m, 2 H); RT = 1.08 min; LC/MS: Anal. Calcd. for [M + H]$^+$ C$_{46}$H$_{51}$N$_8$O$_2$: 747.41; found 747.45 |

LC conditions for 24-21 and 24-22:
Column=Phenomenex-Luna 3.0×50 mm S10
Start % B=0
Final % B=100
Gradient time=2 min
Stop time=3 min
Flow Rate=4 mL/min
Wavelength=220 nm
Solvent A=0.1% TFA in 10% methanol/90% H$_2$O
Solvent B=0.1% TFA in 90% methanol/10% H$_2$O Example 24-23

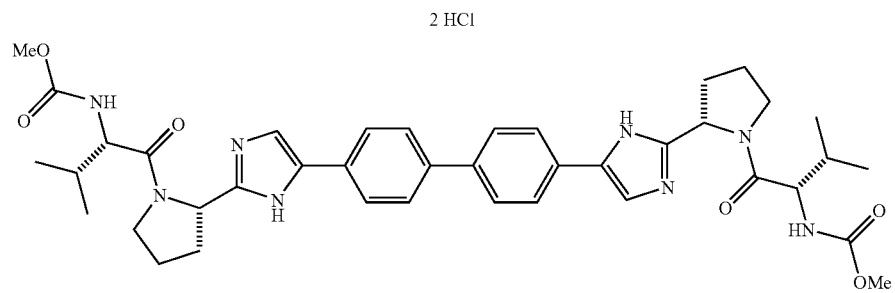

2 HCl methyl ((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate A 50 mL flask equipped with a stir bar was sequentially charged with 2.5 mL acetonitrile, 0.344 g (2.25 mmol, 2.5 equiv) hydroxy benzotriazole hydrate, 0.374 g (2.13 mmol, 2.4 equiv) N-(methoxycarbonyl)-L-valine, 0.400 g (2.09 mmol, 2.4 equiv) 1-(3-dimethyaminopropyl)-3-ethylcarbodiimide hydrochloride and an additional 2.5 mL acetonitrile. The resulting solution was agitated at 20° C. for 1 hour and charged with 0.501 g (0.88 mmol, 1 equiv) Example A-1e-4. The slurry was cooled to about 0° C. and 0.45 g (3.48 mmol, 4 equiv) diisopropylethylamine was added over 30 minutes while maintaining a temperature below 10° C. The solution was slowly heated to 15° C. over 3 hours and held at 15° C. for 16 hours. The temperature was increased to 20° C. and stirred for 3.25 hours. The resulting solution was charged with 3.3 g of 13 wt % aqueous NaCl and heated to 50° C. for 1 hour. After cooling to 20° C., 2.5 mL of isopropyl acetate was added. The rich organic phase was washed with 2×6.9 g of a 0.5 N NaOH solution containing 13 wt % NaCl followed by 3.3 g of 13 wt % aqueous NaCl. The mixture was then solvent exchanged into isopropyl acetate by vacuum distillation to a target volume of 10 mL. The resulting hazy solution was cooled to 20° C. and filtered through a 0.45 μm filter. The clear solution was then solvent exchanged into ethanol by vacuum distillation with a target volume of 3 mL. 1.67 mL (2.02 mmol, 2.3 equiv) of 1.21 M HCl in ethanol was added. The mixture was then stirred at 25° C. for 15 hours. The resulting slurry was filtered and the wet cake was washed with 2.5 mL of 2:1 acetone:ethanol. The solids were dried in a vacuum oven at 50° C. to give 0.550 g (0.68 mmol, 77%) of the desired product.

Recrystallization of Example 24-23

A solution of Example 24-23 prepared above was prepared by dissolving 0.520 g of the above product in 3.65 mL methanol. The solution was then charged with 0.078 g of type 3 Cuno Zeta loose carbon and allowed to stir for 0.25 hours. The mixture was then filtered and washed with 6 ml of methanol. The product rich solution was concentrated down to 2.6 mL by vacuum distillation. 7.8 mL acetone was added and allowed to stir at 25° C. for 15 h. The solids were filtered, washed with 2.5 mL 2:1 acetone:ethanol and dried in a vacuum oven at 70° C. to give 0.406 g (57.0%) of the desired product as white crystals: $^1$H NMR (400 MHz, DMSO-$d_6$, 80° C.): 8.02 (d, J=8.34 Hz, 4H), 7.97 (s, 2H), 7.86 (d, J=8.34 Hz, 4H), 6.75 (s, 2H), 5.27 (t, J=6.44 Hz, 2H), 4.17 (t, J=6.95 Hz, 2H), 3.97-4.11 (m, 2H), 3.74-3.90 (m, 2H), 3.57 (s, 6H), 2.32-2.46 (m, 2H), 2.09-2.31 (m, 6H), 1.91-2.07 (m, 2H), 0.88 (d, J=6.57 Hz, 6H), 0.79 (d, J=6.32 Hz, 6H); $^{13}$C NMR (75 MHz, DMSO-$d_6$): δ 170.9, 156.9, 149.3, 139.1, 131.7, 127.1, 126.5, 125.9, 115.0, 57.9, 52.8, 51.5, 47.2, 31.1, 28.9, 24.9, 19.6, 17.7; IR (neat, cm$^{-1}$): 3385, 2971, 2873, 2669, 1731, 1650. Anal. Calcd for $C_{40}H_{52}N_8O_6Cl_2$: C, 59.18; H, 6.45; N, 13.80; Cl, 8.73. Found C, 59.98; H, 6.80; N, 13.68; Cl, 8.77. mp 267° C. (decomposed). Characteristic diffraction peak positions (degrees 2θ±0.1)@RT, based on a high quality pattern collected with a diffractometer (CuKα) with a spinning capillary with 2θ calibrated with a NIST other suitable standard are as follows: 10.3, 12.4, 12.8, 13.3, 13.6, 15.5, 20.3, 21.2, 22.4, 22.7, 23.7.

Example 25

N,N'-(4,4'-biphenyldiylbis(1H-imidazole-5,2-diyl (2S)-2,1-pyrrolidinediyl((1R)-2-oxo-1-phenyl-2,1-ethanediyl)))diacetamide

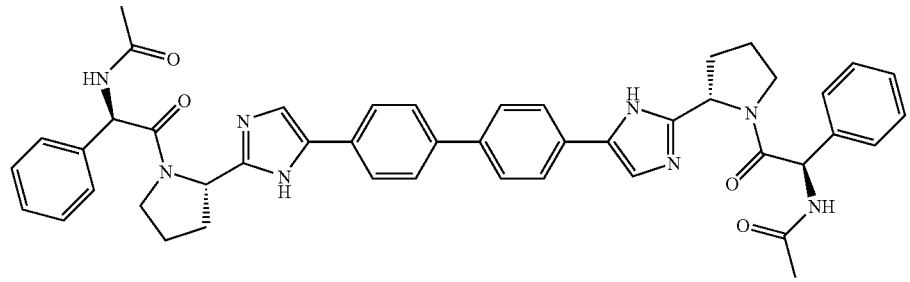

Example 25 Step a di-tert-butyl (4,4'-biphenyldiylbis(1H-imidazole-5,2-diyl(2S)-2,1-pyrrolidinediyl((1R)-2-oxo-1-phenyl-2,1-ethanediyl)))biscarbamate and

Example 25 Step b

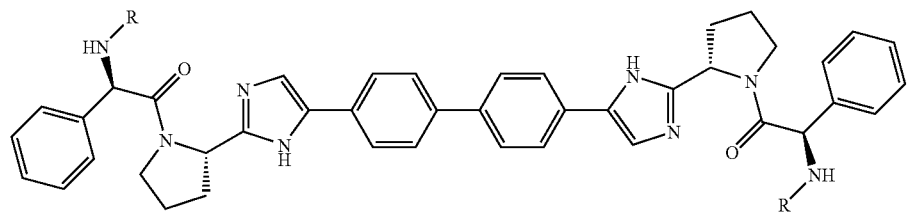

25a: R = Boc
25b: R = H

HATU (96.2 mg, 0.253 mmol) was added to a mixture of pyrrolidine 1e (52.6 mg, 0.124 mmol), diisopropylethylamine (100 μL, 0.57 mmol) and Boc-D-Phg-OH (69 mg, 0.275 mmol) in DMF (3.0 mL). The reaction mixture was stirred for 25 minutes, and then diluted with methanol and purified by a reverse phase HPLC system (H$_2$O/methanol/TFA). The HPLC elute was neutralized with excess 2.0 M/NH$_3$ in CH$_3$OH and the volatile component was removed in vacuo. The residue was carefully partitioned between CH$_2$Cl$_2$ and saturated NaHCO$_3$. The aqueous phase was extracted with more CH$_2$Cl$_2$ (2×). The combined organic phase was dried (MgSO$_4$), filtered, and concentrated in vacuo to provide 25a as a film of semisolid oil (78.8 mg). LC (Cond. 1): RT=1.99 min; >98% homogeneity index. LC/MS: Anal. Calcd. for [M+H]$^+$ $C_{52}H_{59}N_8O_6$: 891.46. found 891.55.

Carbamate 25a was converted to amine 25b according to the procedure described for the preparation of 1e. LC(Cond. 1): RT=1.44 min; 97% homogeneity index. LC/MS: Anal. Calcd. for [M+H]$^+$ $C_{42}H_{43}N_8O_2$: 691.35. found 691.32

Example 25

N,N'-(4,4'-biphenyldiylbis(1H-imidazole-5,2-diyl (2S)-2,1-pyrrolidinediyl((1R)-2-oxo-1-phenyl-2,1-ethanediyl)))diacetamide Acetic anhydride (20 μL, 0.21 mmol) was added to a DMF (1.5 mL) solution of amine 25b (29 mg, 0.042 mmol) and triethylamine (30 μL, 0.22 mmol) and stirred for 2.5 hours. The reaction mixture was then treated with NH$_3$/methanol (1 mL of 2 M) and stirred for an additional 1.5 hours. The volatile component was removed in vacuo and the residue was purified by a reverse phase HPLC system (H$_2$O/methanol/TFA) to provide the TFA salt of Example 25 as a white foam (28.1 mg). LC (Cond. 1): RT=1.61 min; >98% homogeneity index; LC/MS: Anal. Calcd. for [M+H]$^+$ $C_{46}H_{47}N_8O_4$: 775.37. found 775.40; HRMS: Anal. Calcd. for [M+H]$^+$ $C_{46}H_{47}N_8O_4$: 775.3720. found 775.3723

Example 25-1 to 25-5

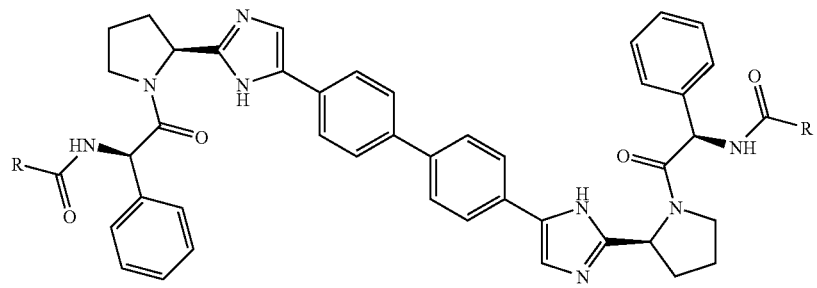

Examples 25-1 to 25-5 were prepared from 25b and the appropriate carboxylic acid using standard amide forming conditions similar to that described for the preparation of example 1 from 1e. Examples 25-6 to 25-8 were prepared from 25b and the appropriate carbamoyl chloride or isocyanate.

| Example Number | Compound Name | R | RT (LC-Cond.); % homogeneity index; MS data |
|---|---|---|---|
| 25-1 | (2R,2'R)-N,N'-(4,4'-biphenyldiylbis(1H-imidazole-5,2-diyl(2S)-2,1-pyrrolidinediyl((1R)-2-oxo-1-phenyl-2,1-ethanediyl)))ditetrahydro-2-furancarboxamide | | RT = 5.68 minutes; HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid; LCMS: Anal. Calcd. for: $C_{52}H_{54}N_8O_6$: 887.06; Found: 887.58 $(M + H)^+$ |
| 25-2 | N,N'-(4,4'-biphenyldiylbis(1H-imidazole-5,2-diyl(2S)-2,1-pyrrolidinediyl((1R)-2-oxo-1-phenyl-2,1-ethanediyl)))bis(1-methyl-1H-imidazole-5-carboxamide) | | RT = 3.54 minutes; HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid; LCMS: Anal. Calcd. for: $C_{52}H_{50}N_{12}O_4$: 907.06; Found: 907.42 $(M + H)^+$ |
| 25-3 | (2S,2'S)-N,N'-(4,4'-biphenyldiylbis(1H-imidazole-5,2-diyl(2S)-2,1-pyrrolidinediyl((1R)-2-oxo-1-phenyl-2,1-ethanediyl)))bis(1-methyl-2-pyrrolidinecarboxamide | | RT = 3.1 minutes; HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid; LCMS: Anal. Calcd. for: $C_{54}H_{60}N_{10}O_4$ 913.14; Found: 913.54 $(M + H)^+$ |
| 25-4 | N,N'-(4,4'-biphenyldiylbis(1H-imidazole-5,2-diyl(2S)-2,1-pyrrolidinediyl((1R)-2-oxo-1-phenyl-2,1-ethanediyl)))bis(2-(3-pyridinyl)acetamide) | | RT = 3.37 minutes; HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid; LCMS: Anal. Calcd. for: $C_{56}H_{52}N_{10}O_4$ 929.10 Found: 929.42 $(M + H)^+$ |
| 25-5 | N,N'-(4,4'-biphenyldiylbis(1H-imidazole-5,2-diyl(2S)-2,1-pyrrolidinediyl((1R)-2-oxo-1-phenyl-2,1-ethanediyl)))bis(2-dimethylamino)acetamide) (non-preferred name) | | RT = 7.07 minutes; HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid; LCMS: Anal. Calcd. for: $C_{50}H_{56}N_{10}O_4$ 861.07 Found: 859.69 $(M + H)^+$ |

| Example Number | Compound Name | R | RT (LC-Cond.); % homogeneity index; MS data |
|---|---|---|---|
| 25-6 | N,N'-(4,4'-biphenyldiylbis(1H-imidazole-5,2-diyl(2S)-2,1-pyrrolidinediyl((1R)-2-oxo-1-phenyl-2,1-ethanediyl)))di(4-morpholinecarboxamide) | 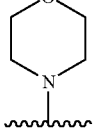 | $^1$H NMR (500 MHz, DMSO-d$_6$) δ ppm 1.86-2.18 (m, 6 H), 2.23-2.39 (m, 2 H), 3.20-3.40 (m, 8 H), 3.40-3.61 (m, 8 H), 3.90-4.19 (m, 4 H), 5.27 (dd, J = 8.09, 3.51 Hz, 2 H), 5.37-5.63 (m, 2 H), 6.92-7.11 (m, 3 H), 7.30-7.45 (m, 5 H), 7.44-7.56 (m, 4 H), 7.83-8.04 (m, 8 H), 8.15 (s, 2 H), 14.29 (s, 2 H); HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid, RT = 6.01 minutes; LCMS: Anal. Calcd. for: $C_{52}H_{56}N_{10}O_6$ 917.09; Found: 917.72 (M + H)$^+$. |
| 25-7 | N,N'-(4,4'-biphenyldiylbis(1H-imidazole-5,2-diyl(2S)-2,1-pyrrolidinediyl((1R)-2-oxo-1-phenyl-2,1-ethanediyl)))bis(4-methyl-1-piperazinecarboxamide) | 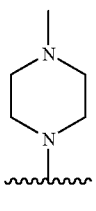 | RT = 3.74 minutes; HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid; LCMS: Anal. Calcd. for: $C_{54}H_{62}N_{12}O_4$ 943.17; Found: 943.84 (M + H)$^+$ |
| 25-8 | N,N''-(4,4'-biphenyldiylbis(1H-imidazole-5,2-diyl(2S)-2,1-pyrrolidinediyl((1R)-2-oxo-1-phenyl-2,1-ethanediyl)))bis(3-(3-pyridinyl)urea) | 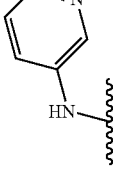 | $^1$H NMR (500 MHz, DMSO-d$_6$) δ ppm 1.79-2.17 (m, 6 H), 2.29 (d, J = 9.77 Hz, 2 H), 3.06-3.39 (m, 2 H), 3.72-4.14 (m, 2 H), 5.27 (dd, J = 8.24, 2.75 Hz, 2 H), 5.66 (d, J = 7.02 Hz, 2 H), 7.26-7.65 (m, 12 H), 7.82-8.11 (m, 12 H), 8.17 (s, 2 H), 8.23-8.45 (m, 2 H), 8.61-8.97 (m, 2 H), 9.38 (s, 2 H), 14.51 (s, 2 H); HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid, RT = 4.05 minutes; LCMS: Anal. Calcd. for: $C_{54}H_{50}N_{12}O_4$ 931.08; Found: 931.78 (M + H)$^+$. |

Example 26 methyl ((1R)-1-(((2S)-2-(5-(4'-(2-((2S)-1-((2R)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate

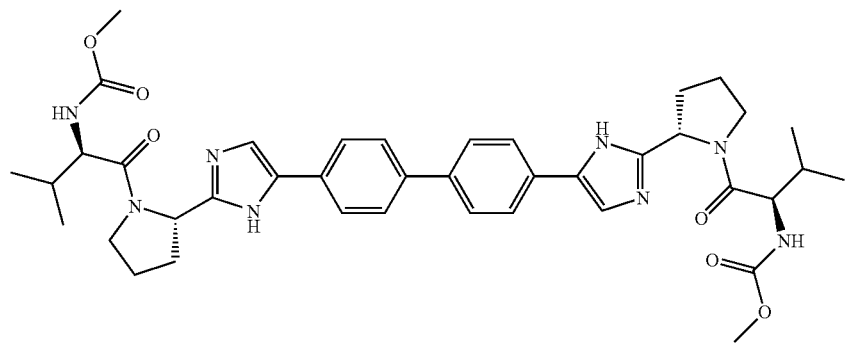

Example 26
Step a
(2R,2'R)-1,1'-(4,4'-biphenyldiylbis(1H-imidazole-5,2-diyl(2S)-2,1-pyrrolidinediyl))bis(3-methyl-1-oxo-2-butanamine)

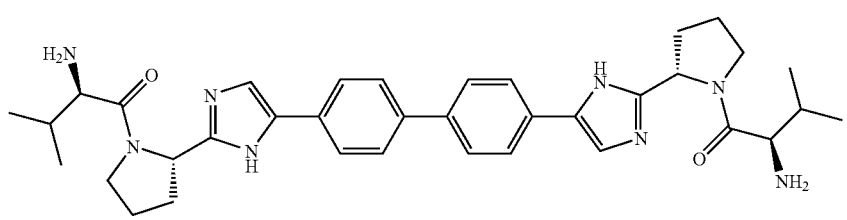

26a

Diamine 26a was prepared starting from pyrrolidine 1e and BOC-D-Val-OH according to the procedure described for the synthesis of diamine 25b.

Example 26
methyl ((1R)-1-(((2S)-2-(5-(4'-(2-((2S)-1-((2R)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate Methyl chloroformate (18 µL, 0.23 mmol) was added to a THF (1.5 mL) solution of diamine 26a (30 mg, 0.048 mmol) and triethylamine (30 µL, 0.22 mmol), and the reaction mixture was stirred at ambient condition for 3 hours. The volatile components was removed in vacuo, and the residue was treated with NH$_3$/methanol (2 mL of 2 M) and stirred at ambient conditions for 15 minutes. All the volatile component was removed in vacuo, and the crude product was purified by reverse phase prep-HPLC (H$_2$O/methanol/TFA) to provide the TFA salt of Example 26 as a white solid (13.6 mg). LC (Cond. 2): RT=2.00 min; >98% homogeneity index; LC/MS: Anal. Calcd. for [M+H]$^+$ C$_{40}$H$_{51}$N$_8$O$_6$: 739.39. found 739.67; HRMS: Anal. Calcd. for [M+H]$^+$ C$_{40}$H$_{51}$N$_8$O$_6$: 739.3932. found 739.3966.

Example 27
N-((1R)-1-(((2S)-2-(5-(4'-(2-((2S)-1-((2R)-2-acetamido-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)acetamide

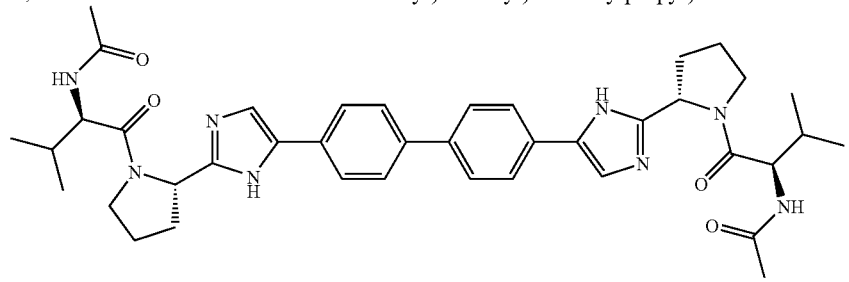

Diamine 26a was converted to Example 27 (TFA salt) according to a method described in the preparation of Example 25. LC (Cond. 2): RT=1.93 min; >98% homogeneity index; LC/MS: Anal. Calcd. for [M+H]$^+$ C$_{40}$H$_{51}$N$_8$O$_4$: 707.40. found 707.59; HRMS: Anal. Calcd. for [M+H]$^+$ C$_{40}$H$_{51}$N$_8$O$_4$: 707.4033. found 707.4054.

Example 28
methyl ((1R)-2-oxo-1-phenyl-2-((2S)-2-(5-(4'-(2-((2S)-1-(phenylacetyl)-2-pyrrolidinyl)-1H-imidazol-5-yl)-4-biphenylyl)-1H-imidazol-2-yl)-1-pyrrolidinyl)ethyl)carbamate

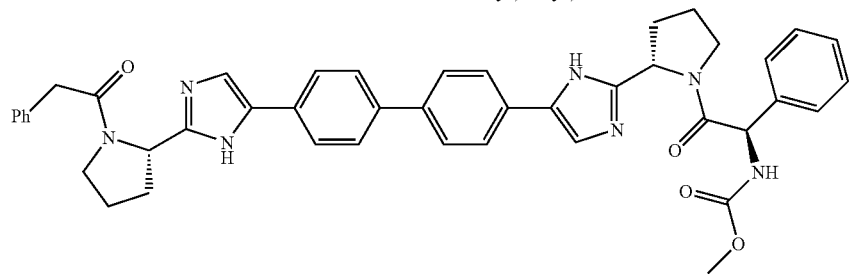

Example 28

Step a

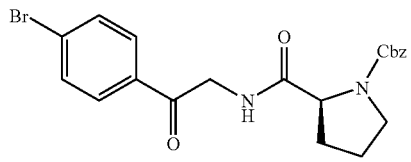

28a

HATU (19.868 g, 52.25 mmol) was added to a heterogeneous mixture of N-Cbz-L-proline (12.436 g, 49.89 mmol) and the HCl salt of 2-amino-1-(4-bromophenyl)ethanone (12.157 g, 48.53 mmol) in DMF (156 mL). The mixture was lowered in an ice-water bath, and immediately afterward N,N-diisopropylethylamine (27 mL, 155 mmol) was added dropwise to it over 13 minutes. After the addition of the base was completed, the cooling bath was removed and the reaction mixture was stirred for an additional 50 minutes. The volatile component was removed in vacuo; water (125 mL) was added to the resulting crude solid and stirred for about 1 hour. The off-white solid was filtered and washed with copious water, and dried in vacuo to provide ketoamide 28a as a white solid (20.68 g). $^1$H NMR (DMSO-$d_6$, δ=2.5 ppm, 400 MHz): δ 8.30 (m, 1H), 7.91 (m, 2H), 7.75 (d, J=8.5, 2H), 7.38-7.25 (m, 5H), 5.11-5.03 (m, 2H), 4.57-4.48 (m, 2H), 4.33-4.26 (m, 1H), 3.53-3.36 (m, 2H), 2.23-2.05 (m, 1H), 1.94-1.78 (m, 3H); LC (Cond. 1): RT=1.65 min; 98% homogeneity index; LC/MS: Anal. Calcd. for [M+H]$^+$ $C_{21}H_{22}BrN_2O_4$: 445.08. found 445.31.

Example 28

Step b

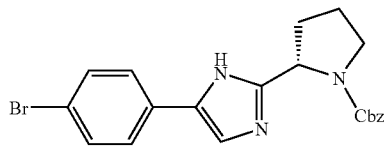

28b

Ketoamide 28a (10.723 g, 24.08 mmol) was converted to 28b according to the procedure described for the synthesis of carbamate 1b, with the exception that the crude material was purified by flash chromatography (sample was loaded with eluting solvent; 50% ethyl acetate/hexanes). Bromide 28b was retrieved as an off-white foam (7.622 g). $^1$H NMR (DMSO-$d_6$, δ=2.5 ppm, 400 MHz): δ 12.23/12.04/11.97 (m, 1H), 7.73-6.96 (m, 10H), 5.11-4.85 (m, 3H), 3.61 (m, 1H), 3.45 (m, 1H), 2.33-184 (m, 4H). LC (Cond. 1): RT=1.42 min; >95% homogeneity index; LC/MS: Anal. Calcd. for [M+H]$^+$ $C_{21}H_{21}BrN_3O_2$: 426.08. found 426.31; HRMS: Anal. Calcd. for [M+H]$^+$ $C_{21}H_{21}BrN_3O_2$: 426.0817. found: 426.0829. The optical purity of 28b was assessed using the following chiral HPLC methods, and an ee of 99% was observed.
Column: Chiralpak AD, 10 um, 4.6×50 mm
Solvent: 20% ethanol/heptane (isocratic)
Flow rate: 1 mL/min
Wavelength: 254 nm
Relative retention time: 1.82 minutes (R), 5.23 minutes (S)

Example 28

Step c benzyl tert-butyl (2S,2'S)-2,2'-(4,4'-biphenyldiylbis(1H-imidazole-5,2-diyl))di(1-pyrrolidinecarboxylate)

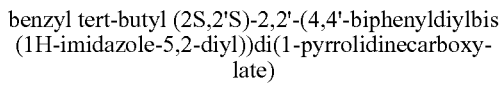

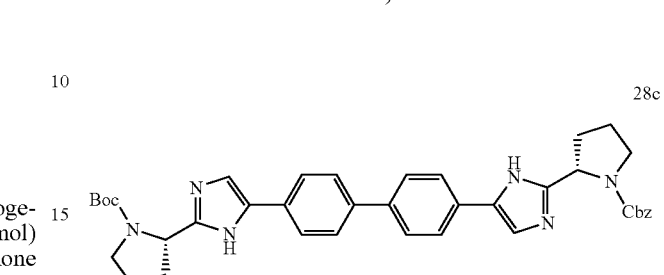

28c

Pd(Ph$_3$P)$_4$ (711.4 mg, 0.616 mmol) was added to a mixture of boronate ester 1c (7.582 g, ~17 mmol), bromide 28b (7.62 g, 17.87 mmol), NaHCO$_3$ (4.779 g, 56.89 mmol) in 1,2-dimethoxyethane (144 mL) and water (48 mL). The reaction mixture was purged with N$_2$ and heated with an oil bath at 80° C. for 15.5 hours, and then the volatile component was removed in vacuo. The residue was partitioned between CH$_2$Cl$_2$ and water, and the aqueous layer was extracted with CH$_2$Cl$_2$. The combined organic phase was dried (MgSO$_4$), filtered, and concentrated in vacuo. The resulting material was submitted to flash chromatography (sample was loaded as a silica gel mesh; ethyl acetate used as eluent) to provide biphenyl 28c as an off-white foam containing Ph$_3$PO impurity (7.5 g). $^1$H NMR (DMSO-$d_6$, δ=2.5 ppm, 400 MHz): δ 12.24-12.19 (m, 0.36H), 12.00-11.82 (m, 1.64H), 7.85-6.98 (15H), 5.12-4.74 (4H), 3.68-3.34 (4H), 2.34-1.79 (8H), 1.41/1.17 (two br S, 9H); LC (Cond. 1): RT=1.41 minutes; LC/MS: Anal. Calcd. for [M+H]$^+$ $C_{39}H_{43}N_6O_4$: 659.34. found 659.52; HRMS: Anal. Calcd. for [M+H]$^+$ $C_{39}H_{43}N_6O_4$: 659.3346. found 659.3374.

Example 28

Step d tert-butyl (2S)-2-(5-(4'-(2-((2S)-2-pyrrolidinyl)-1H-imidazol-5-yl)-4-biphenylyl)-1H-imidazol-2-yl)-1-pyrrolidinecarboxylate

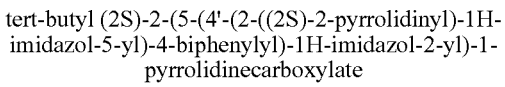

28d

K$_2$CO$_3$ (187.8 mg, 1.36 mmol) was added to a mixture of catalyst (10% Pd/C, 205.3 mg), carbamate 28c (1.018 g, ~1.5 mmol), methanol (20 mL) and 3 pipet-drops of water. A balloon of H$_2$ was attached and the mixture was stirred for 6 hours. Then, additional catalyst (10% Pd/C, 100.8 mg) and K$_2$CO$_3$ (101.8 mg, 0.738 mmol) were added and stirring continued for 3.5 hours. During the hydrogenation process, the balloon of H$_2$ was changed at intervals three times. The reaction mixture was filtered through a pad of diatomaceous earth (Celite® 521), and the filterate was removed in vacuo.

The resulting crude material was submitted to flash chromatography using a short column (sample was loaded as a silica gel mesh; 0-20% methanol/CH$_2$Cl$_2$ used as eluent) to provide 28d as a light-yellow foam (605.6 mg). $^1$H NMR (DMSO-d$_6$, δ=2.5 ppm, 400 MHz): δ 12.18/11.89/11.82 (three br s, 2H), 7.83-7.29 (m, 10H), 4.89-4.73 (m, 1H), 4.19 (app t, J=7.2, 1H), 3.55 (app br s, 1H), 3.40-3.35 (m, 1H), 3.02-2.96 (m, 1H), 2.91-2.84 (m, 1H), 2.30-1.69 (m, 8H), 1.41/1.16 (two br s, 9H). Note: the signal of pyrrolidine NH appears to have overlapped with signals in the 3.6-3.2 ppm region; LC (Cond. 1): RT=1.21 min; >95% homogeneity index; LC/MS: Anal. Calcd. for [M+H]$^+$ C$_{31}$H$_{37}$N$_6$O$_2$: 525.30. found 525.40.

Example 28

Step e-f

Example 28 Step e tert-butyl (2S)-2-(5-(4'-(2-((2S)-1-((2R)-2-((methoxycarbonyl)amino)-2-phenylacetyl)-2-pyrrolidinyl)-1H-imidazol-5-yl)-4-biphenylyl)-1H-imidazol-2-yl)-1-pyrrolidinecarboxylate

Example 28 Step f methyl ((1R)-2-oxo-1-phenyl-2-((2S)-2-(5-(4'-(2-((2S)-2-pyrrolidinyl)-1H-imidazol-5-yl)-4-biphenylyl)-1H-imidazol-2-yl)-1-pyrrolidinyl)ethyl)carbamate

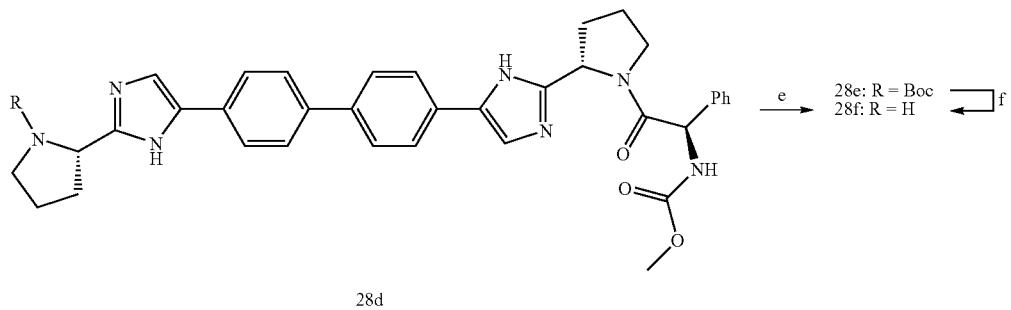

28d

Step e: HATU (316.6 mg, 0.833 mmol) was added to a DMF (7.0 mL) solution of pyrrolidine 28d (427 mg, 0.813 mmol), Cap-4 (177.6 mg, 0.849 mmol) and diisopropylethylamine (0.32 mL, 1.84 mmol), and the reaction mixture was stirred for 45 minutes. The volatile component was removed in vacuo, and the residue was partitioned between CH$_2$Cl$_2$ (50 mL) and an aqueous medium (20 mL H$_2$O+1 mL saturated NaHCO$_3$ solution). The aqueous phase was re-extracted with CH$_2$Cl$_2$, and the combined organic phase was dried (MgSO$_4$), filtered, and concentrated in vacuo. The resulting yellow oil was purified by flash chromatography (silica gel; ethyl acetate) to provide 28e as a yellow foam (336 mg). LC (Cond. 1): RT=1.68 min; 91% homogeneity index; LC/MS: Anal. Calcd. for [M+H]$^+$ C$_{41}$H$_{46}$N$_7$O$_5$: 716.35. found 716.53.

Step f: Carbamate 28e was elaborated to amine 28f by employing the procedure described in the conversion of 1d to 1e. LC (Cond. 1): RT=1.49 min; >98% homogeneity index. LC/MS: Anal. Calcd. for [M+H]$^+$ C$_{36}$H$_{38}$N$_7$O$_3$: 616.30. found 616.37; HRMS: Anal. Calcd. for [M+H]$^+$ C$_{36}$H$_{38}$N$_7$O$_3$: 616.3036. found 616.3046.

Example 28 methyl ((1R)-2-oxo-1-phenyl-2-((2S)-2-(5-(4'-(2-((2S)-1-(phenylacetyl)-2-pyrrolidinyl)-1H-imidazol-5-yl)-4-biphenylyl)-1H-imidazol-2-yl)-1-pyrrolidinyl)ethyl)carbamate

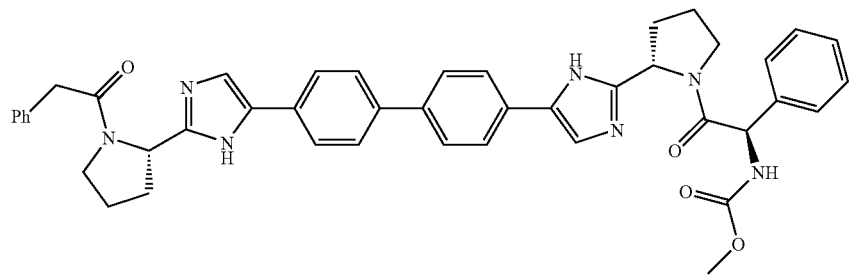

Amine 28f was converted to the TFA salt of Example 28 by employing the last step of the synthesis of Example 1. $^1$H NMR (DMSO-$d_6$, δ=2.5 ppm, 400 MHz): δ 8.21-7.03 (m, 21H), 5.78-5.14 (3H), 3.98-3.13 (m, 9H; includes the signal for OCH$_3$ at 3.54 & 3.53), 2.45-1.72 (m, 8H). LC (Cond. 1): RT=1.66 minutes, >98% homogeneity index; LC/MS: Anal. Calcd. for [M+H]$^+$ C$_{44}$H$_{44}$N$_7$O$_4$: 734.35. found 734.48; HRMS: Anal. Calcd. for [M+H]$^+$ C$_{44}$H$_{44}$N$_7$O$_4$: 734.3455; 734.3455.

Example 28-1 to 28-4

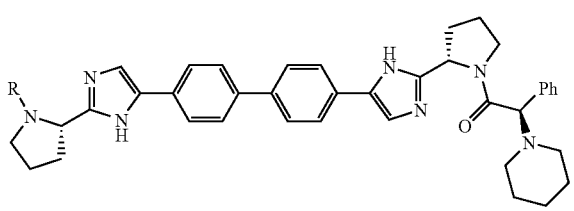

Examples 28-1 through 28-4 (R groups shown in the table below) were prepared in similar fashion to example 28 via the intermediacy of intermediate 28d.

Example 28-1

(1R)—N,N-dimethyl-2-oxo-1-phenyl-2-((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)ethanamine Cap-1 was appended, the Boc carbamate was removed with TFA or HCl, and Cap-14 was appended.

Example 28-2

1-((1R)-2-oxo-1-phenyl-2-((2S)-2-(5-(4'-(2-((2S)-1-((2R)-tetrahydro-2-furanylcarbonyl)-2-pyrrolidinyl)-1H-imidazol-5-yl)-4-biphenylyl)-1H-imidazol-2-yl)-1-pyrrolidinyl)ethyl)piperidine Tetrahydrofuroic acid was appended, the Boc carbamate was removed with TFA or HCl, and Cap-14 was appended.

Example 28-3 methyl ((1R)-1-(2-chlorophenyl)-2-oxo-2-((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)ethyl)carbamate Cap-40 was appended, the Boc carbamate was removed with TFA or HCl, and Cap-14 was appended.

Example 28-4

(1R)-1-(2-chlorophenyl)-N,N-dimethyl-2-oxo-2-((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)ethanamine Cap-39 was appended, the Boc carbamate was removed with TFA or HCl, and Cap-14 was appended.

Example 28-5

(1R)-1-(2-fluorophenyl)-N,N-dimethyl-2-oxo-2-((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)ethanamine Cap-38 was appended, the Boc carbamate was removed with TFA or HCl, and Cap-14 was appended.

| Example | Compound Name | R | Data |
|---|---|---|---|
| 28-1 | (1R)-N,N-dimethyl-2-oxo-1-phenyl-2-((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)ethanamine | | LCMS: Anal. Calcd. for C$_{49}$H$_{54}$N$_8$O$_2$: 786; found: 787 (M +H)$^+$. |
| 28-2 | 1-((1R)-2-oxo-1-phenyl-2-((2S)-2-(5-(4'-(2-((2S)-1-((2R)-tetrahydro-2-furanylcarbonyl)-2-pyrrolidinyl)-1H-imidazol-5-yl)-4-biphenylyl)-1H-imidazol-2-yl)-1-pyrrolidinyl)ethyl)piperidine | | LCMS: Anal. Calcd. for C$_{44}$H$_{49}$N$_7$O$_3$: 723; found: 724 (M +H)$^+$. |
| 28-3 | methyl ((1R)-1-(2-chlorophenyl)-2-oxo-2-((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)ethyl)carbamate | | LCMS: Anal. Calcd. for C$_{49}$H$_{51}$ClN$_8$O$_4$: 850; found: 851 (M +H)$^+$. |

-continued

| Example | Compound Name | R | Data |
|---|---|---|---|
| 28-4 | (1R)-1-(2-chlorophenyl)-N,N-dimethyl-2-oxo-2-((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)ethanamine | | LCMS: Anal. Calcd. for $C_{49}H_{53}ClN_8O_2$: 820; found: 821 $(M+H)^+$. |
| 28-5 | (1R)-1-(2-fluorophenyl)-N,N-dimethyl-2-oxo-2-((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)ethanamine | | LCMS: Anal. Calcd. for $C_{49}H_{53}FN_8O_2$: 804; found: 805 $(M+H)^+$. |

Example 29 methyl ((1R)-2-((2S)-2-(5-(4'-(2-((2S)-1-((4-methyl-1-piperazinyl)carbonyl)-2-pyrrolidinyl)-1H-imidazol-5-yl)-4-biphenylyl)-1H-imidazol-2-yl)-1-pyrrolidinyl)-2-oxo-1-phenylethyl)carbamate

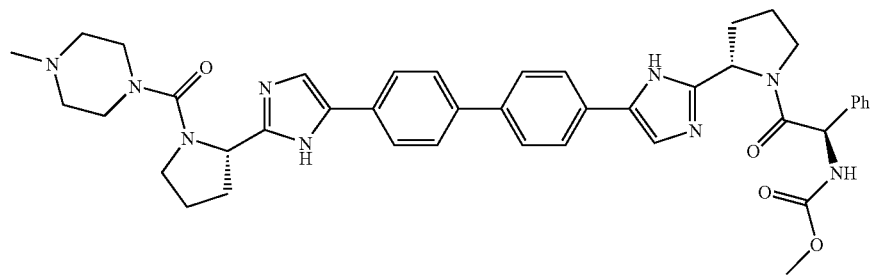

4-Methylpiperazine-1-carbonyl chloride/HCl (11.6 mg, 0.58 mmol) was added to a mixture of 28f (30 mg, 0.049 mmol), triethylamine (15 µl, 0.11 mmol) and THF (1.0 mL), and stirred at ambient conditions for 1 hour. The volatile component was removed in vacuo, and the residue was purified by a reverse phase HPLC (H₂O/methanol/TFA) to provide the TFA salt of Example 29 as a light yellow foam (29.3 mg). LC (Cond. 2): RT=1.82 minutes, >98% homogeneity index; LC/MS: Anal. Calcd. for $[M+H]^+$ $C_{42}H_{48}N_9O_4$: 742.38. found 742.49.

Example 30 methyl ((1R)-2-((2S)-2-(5-(4'-(2-((2S)-1-glycyl-2-pyrrolidinyl)-1H-imidazol-5-yl)-4-biphenylyl)-1H-imidazol-2-yl)-1-pyrrolidinyl)-2-oxo-1-phenylethyl)carbamate

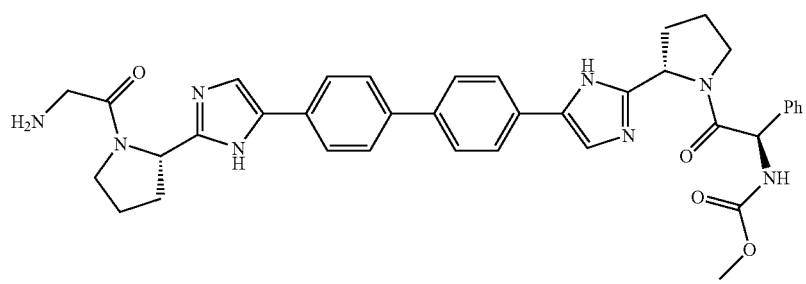

Example 30

Step a methyl ((1R)-2-((2S)-2-(5-(4'-(2-((2S)-1-(N-(tert-butoxycarbonyl)glycyl)-2-pyrrolidinyl)-1H-imidazol-5-yl)-4-biphenylyl)-1H-imidazol-2-yl)-1-pyrrolidinyl)-2-oxo-1-phenylethyl)carbamate

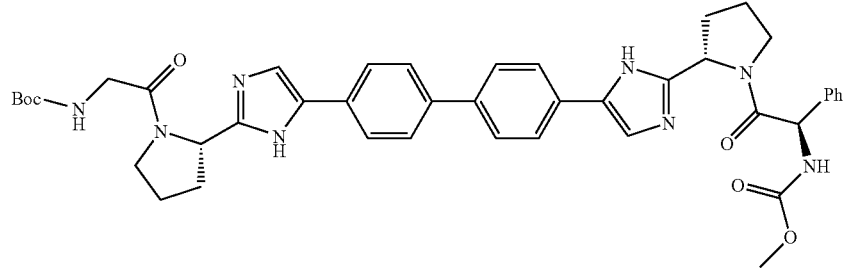

30a

Carbamate 30a was prepared from pyrrolidine 28f and Boc-Glycine by using the procedure described for the preparation of 25a from 1e. LC (Cond. 2): RT=2.12 minutes, >98% homogeneity index; LC/MS: Anal. Calcd. for [M+H]$^+$ $C_{43}H_{49}N_8O_6$: 773.38. found 773.46

Example 30 methyl ((1R)-2-((2S)-2-(5-(4'-(2-((2S)-1-glycyl-2-pyrrolidinyl)-1H-imidazol-5-yl)-4-biphenylyl)-1H-imidazol-2-yl)-1-pyrrolidinyl)-2-oxo-1-phenylethyl)carbamate Carbamate 30a was converted to Example 30 according to the procedure described for the preparation of 1e from 1d. LC (Cond. 2): RT=1.81 minutes, >98% homogeneity index; LC/MS: Anal. Calcd. for [M+H]$^+$ $C_{38}H_{41}N_8O_4$: 673.33. found 673.43

HRMS: Anal. Calcd. for [M+H]$^+$ $C_{38}H_{41}N_8O_4$: 673.3251. found 673.3262

Example 30-1 methyl ((1S)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-j-pyrrolidinyl)-1-methyl-2-oxoethyl)carbamate

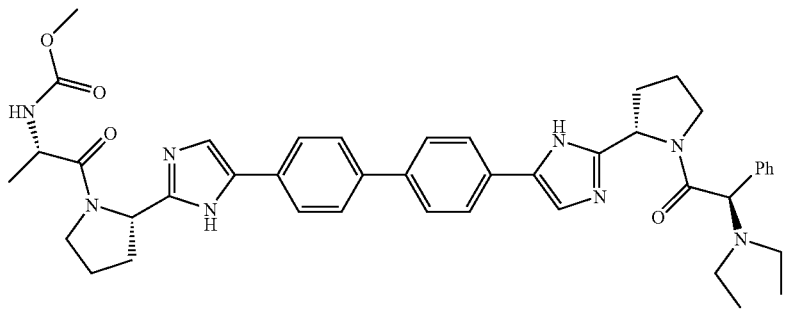

Example 30-1 was prepared in three steps from Example 28d. Step one: Append Cap-2 using the procedure describing the synthesis of 28e from 28d. Step two: Hydrolyze the Boc carbamate using the procedure describing the synthesis of 28f from 28e. Step three: Append Cap-52 using the procedure describing the synthesis of 28e from 28d. RT=1.70 min (Cond. 1b); >95% homogeneity index. LC/MS: Anal. Calcd. for [M+H]$^+$ $C_{43}H_{51}N_8O_4$: 743.40. found, 743.50. HRMS: Anal. Calcd. for [M+H]$^+$ $C_{43}H_{51}N_8O_4$: 743.4033. found, 743.4053

Substituting the appropriate acid chloride or carboxylic acid into Example 29 or 30, the following compounds (Example 31 to 84-87) were prepared as TFA salts.

Example 31 to 84-88

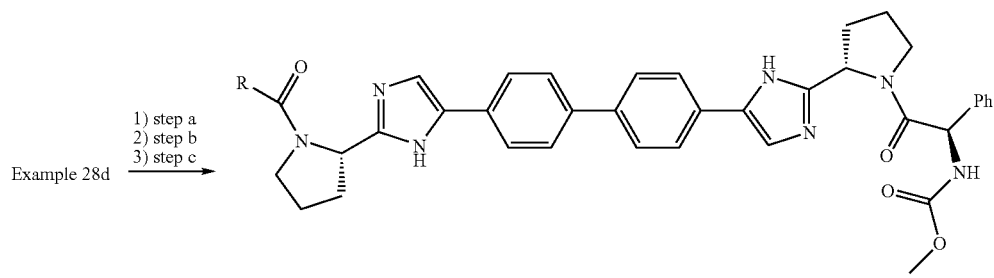

step a: Cap with cap-4 as in Example 28
step b: Same procedure as in conversion of Example 1d to 1e
step c: As in the last step of Example 1 using 1.1 equiv. of the appropriate carboxylic acid and HATU

| Example | Compound Name | R group | Retention time (LC-Condition); homogeneity index MS data |
|---|---|---|---|
| 31 | methyl ((1R)-2-((2S)-2-(5-(4'-(2-((2S)-1-acetyl-2-pyrrolidinyl)-1H-imidazol-5-yl)-4-biphenylyl)-1H-imidazol-2-yl)-1-pyrrolidinyl)-2-oxo-1-phenylethyl)carbamate | acetyl | 1.54 minutes (Cond. 1); >98%; LC/MS: Anal. Calcd. for [M + H]+ $C_{38}H_{40}N_7O_4$: 658.31; found 658.42; HRMS: Anal. Calcd. for [M + H]+ $C_{38}H_{40}N_7O_4$: 658.3142; found 658.3135 |
| 32 | methyl ((1R)-2-oxo-1-phenyl-2-((2S)-2-(5-(4'-(2-((2S)-1-propionyl-2-pyrrolidinyl)-1H-imidazol-5-yl)-4-biphenylyl)-1H-imidazol-2-yl)-1-pyrrolidinyl)ethyl)carbamate | propionyl | 1.57 minutes (Cond. 1); >98%; LC/MS: Anal. Calcd. for [M + H]+ $C_{39}H_{42}N_7O_4$: 672.33; found 672.46; HRMS: Anal. Calcd. for [M + H]+ $C_{39}H_{42}N_7O_4$: 672.3298; found 672.3299 |
| 33 | methyl ((1R)-2-((2S)-2-(5-(4'-(2-((2S)-1-(cyclopropylcarbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | cyclopropylcarbonyl | 1.59 minutes (Cond. 1); >98%; LC/MS: Anal. Calcd. for [M + H]+ $C_{40}H_{42}N_7O_4$: 684.33; found 684.44; HRMS: Anal. Calcd. for [M + H]+ $C_{40}H_{42}N_7O_4$: 684.3298; found 684.3324 |
| 34 | methyl ((1R)-2-((2S)-2-(5-(4'-(2-((2S)-1-(cyclopropylacetyl)-2-pyrrolidinyl)-1H-imidazol-5-yl)-4-biphenylyl)-1H-imidazol-2-yl)-1-pyrrolidinyl)-2-oxo-1-phenylethyl)carbamate | cyclopropylacetyl | 1.61 minutes (Cond. 1); >98%; LC/MS: Anal. Calcd. for [M + H]+ $C_{40}H_{42}N_7O_4$: 698.35; found 698.48; HRMS: Anal. Calcd. for [M + H]+ $C_{40}H_{42}N_7O_4$: 698.3455; found 698.3489 |
| 35 | methyl ((1R)-2-((2S)-2-(5-(4'-(2-((2S)-1-((2R)-2-hydroxypropanoyl)-2-pyrrolidinyl)-1H-imidazol-5-yl)-4-biphenylyl)-1H-imidazol-2-yl)-1-pyrrolidinyl)-2-oxo-1-phenylethyl)carbamate | (2R)-2-hydroxypropanoyl | 1.54 minutes (Cond. 1); >98%; LC/MS: Anal. Calcd. for [M + H]+ $C_{39}H_{42}N_7O_5$: 688.33; found 688.47 |

-continued

| Example | Compound Name |  | Retention time (LC-Condition); homogeneity index MS data |
|---|---|---|---|
| 36 | methyl ((1R)-2-oxo-1-phenyl-2-((2S)-2-(5-(4'-(2-((2S)-1-((2R)-tetrahydro-2-furanylcarbonyl)-2-pyrrolidinyl)-1H-imidazol-5-yl)-4-biphenylyl)-1H-imidazol-2-yl)-1-pyrrolidinyl)ethyl)carbamate | 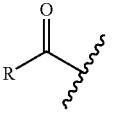 | 1.59 minutes (Cond. 1); >98%; LC/MS: Anal. Calcd. for [M + H]⁺ $C_{41}H_{44}N_7O_5$: 714.34; found 714.49; HRMS: Anal. Calcd. for [M + H]⁺ $C_{41}H_{44}N_7O_5$: 714.3404; found 714.3430 |
| 37 | methyl ((1R)-2-((2S)-2-(5-(4'-(2-((2S)-1-(N,N-dimethylglycyl)-2-pyrrolidinyl)-1H-imidazol-5-yl)-4-biphenylyl)-1H-imidazol-2-yl)-1-pyrrolidinyl)-2-oxo-1-phenylethyl)carbamate | 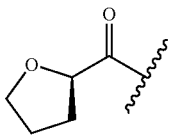 | 1.48 minutes (Cond. 1); >98%; LC/MS: Anal. Calcd. for [M + H]⁺ $C_{40}H_{45}N_8O_4$: 701.36; found 701.49; HRMS: Anal. Calcd. for [M + H]⁺ $C_{40}H_{45}N_8O_4$: 701.3564; found 701.3553 |
| 38 | methyl ((1R)-2-((2S)-2-(5-(4'-(2-((2S)-1-((2S)-2-(dimethylamino)-2-phenylacetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 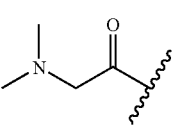<br>Cap-1 | 1.20 minutes (Cond. 1); >98%; LC/MS: Anal. Calcd. for [M + H]⁺ $C_{46}H_{49}N_8O_4$: 777.39; found 777.61; HRMS: Anal. Calcd. for [M + H]⁺ $C_{46}H_{49}N_8O_4$: 777.3877; found 777.3909 |
| 39 | methyl ((1R)-2-((2S)-2-(5-(4'-(2-((2S)-1-(4-morpholinylacetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 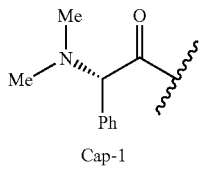 | 1.79 minutes (Cond. 2); >98%; LC/MS: Anal. Calcd. for [M + H]⁺ $C_{42}H_{47}N_8O_5$: 743.37; found 743.49; HRMS: Anal. Calcd. for [M + H]⁺ $C_{42}H_{47}N_8O_5$: 743.3669; found 743.3672 |
| 40 | methyl (2-((2S)-2-(5-(4'-(2-((2S)-1-((2R)-2-((methoxycarbonyl)amino)-2-phenylacetyl)-2-pyrrolidinyl)-1H-imidazol-5-yl)-4-biphenylyl)-1H-imidazol-2-yl)-1-pyrrolidinyl)-2-oxoethyl)carbamate | 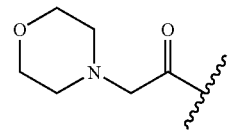 | 1.92 minutes (Cond. 2); >98%; LC/MS: Anal. Calcd. for [M + H]⁺ $C_{40}H_{43}N_8O_6$: 731.33; found 731.42; HRMS: Anal. Calcd. for [M + H]⁺ $C_{40}H_{43}N_8O_6$: 731.3306; found 731.3333 |
| 41 | methyl ((1R)-2-((2S)-2-(5-(4'-(2-((2S)-1-(N-acetylglycyl)-2-pyrrolidinyl)-1H-imidazol-5-yl)-4-biphenylyl)-1H-imidazol-2-yl)-1-pyrrolidinyl)-2-oxo-1-phenylethyl)carbamate | 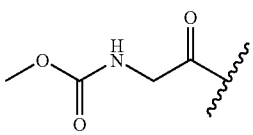 | 1.86 minutes (Cond. 2); >98%; LC/MS: Anal. Calcd. for [M + H]⁺ $C_{40}H_{43}N_8O_5$: 715.34; found 715.49; HRMS: Anal. Calcd. for [M + H]⁺ $C_{40}H_{43}N_8O_5$: 715.3356; found 715.3369 |
| 42 | methyl ((1R)-2-((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 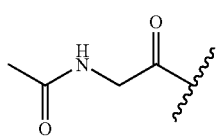 | 1.85 minutes (Cond. 2); >98%; LC/MS: Anal. Calcd. for [M + H]⁺ $C_{46}H_{49}N_8O_4$: 777.39; found 777.56 |

| Example | Compound Name | | Retention time (LC-Condition); homogeneity index MS data |
|---|---|---|---|
| | | 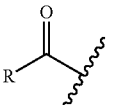 | |
| 43 | methyl ((1R)-2-((2S)-2-(5-(4'-(2-((2S)-1-((2R)-2-hydroxy-2-phenylacetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 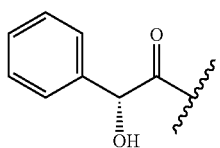 | 1.96 minutes (Cond. 2); >98%; LC/MS: Anal. Calcd. for [M + H]$^+$ C$_{44}$H$_{44}$N$_7$O$_5$: 750.34; found 750.51; HRMS: Anal. Calcd. for [M + H]$^+$ C$_{44}$H$_{44}$N$_7$O$_5$: 750.3404; found 750.3437 |
| 44 | methyl ((1R)-2-((2S)-2-(5-(4'-(2-((2S)-1-((1-methyl-4-piperidinyl)carbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | 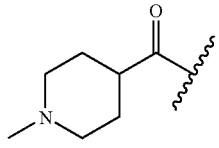 | 1.78 minutes (Cond. 2); >98%; LC/MS: Anal. Calcd. for [M + H]$^+$ C$_{43}$H$_{49}$N$_8$O$_4$: 741.39; found 741.55; HRMS: Anal. Calcd. for [M + H]$^+$ C$_{43}$H$_{49}$N$_8$O$_4$: 741.3877; found 741.3893 |
| 45 | methyl ((1R)-2-oxo-1-phenyl-2-((2S)-2-(5-(4'-(2-((2S)-1-(tetrahydro-2H-pyran-4-ylcarbonyl)-2-pyrrolidinyl)-1H-imidazol-5-yl)-4-biphenylyl)-1H-imidazol-2-yl)-1-pyrrolidinyl)ethyl)carbamate | 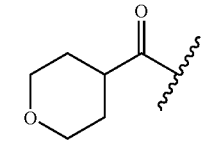 | 1.87 minutes (Cond. 2); >98%; LC/MS: Anal. Calcd. for [M + H]$^+$ C$_{42}$H$_{46}$N$_7$O$_5$: 728.36; found 728.52; HRMS: Anal. Calcd. for [M + H]$^+$ C$_{42}$H$_{46}$N$_7$O$_5$: 728.3560; found 728.3587 |
| 46 | methyl ((1R)-2-oxo-1-phenyl-2-((2S)-2-(5-(4'-(2-((2S)-1-(2-pyridinylacetyl)-2-pyrrolidinyl)-1H-imidazol-5-yl)-4-biphenylyl)-1H-imidazol-2-yl)-1-pyrrolidinyl)ethyl)carbamate | 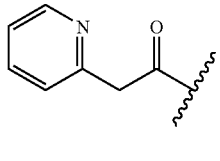 | 1.80 minutes (Cond. 2); >98%; LC/MS: Anal. Calcd. for [M + H]$^+$ C$_{43}$H$_{43}$N$_8$O$_4$: 735.34; found 735.51; HRMS: Anal. Calcd. for [M + H]$^+$ C$_{43}$H$_{43}$N$_8$O$_4$: 735.3407; found 735.3416 |
| 47 | methyl ((1R)-2-oxo-1-phenyl-2-((2S)-2-(5-(4'-(2-((2S)-1-(3-pyridinylacetyl)-2-pyrrolidinyl)-1H-imidazol-5-yl)-4-biphenylyl)-1H-imidazol-2-yl)-1-pyrrolidinyl)ethyl)carbamate | 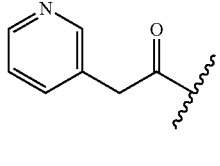 | 1.76 minutes (Cond. 2); >98%; LC/MS: Anal. Calcd. for [M + H]$^+$ C$_{43}$H$_{43}$N$_8$O$_4$: 735.34; found 735.52 |
| 48 | methyl ((1R)-2-oxo-1-phenyl-2-((2S)-2-(5-(4'-(2-((2S)-1-(4-pyridinylacetyl)-2-pyrrolidinyl)-1H-imidazol-5-yl)-4-biphenylyl)-1H-imidazol-2-yl)-1-pyrrolidinyl)ethyl)carbamate | 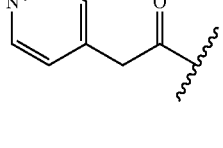 | 1.77 minutes (Cond. 2); >98%; LC/MS: Anal. Calcd. for [M + H]$^+$ C$_{43}$H$_{43}$N$_8$O$_4$: 735.34; found 735.50; HRMS: Anal. Calcd. for [M + H]$^+$ C$_{43}$H$_{43}$N$_8$O$_4$: 735.3407; found 735.3405 |
| 49 | methyl ((1R)-2-((2S)-2-(5-(4'-(2-((2S)-1-((1-methyl-1H-imidazol-5-yl)carbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | 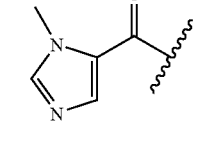 | 1.77 minutes (Cond. 2); >98%; LC/MS: Anal. Calcd. for [M + H]$^+$ C$_{41}$H$_{42}$N$_9$O$_4$: 724.34; found 724.51; HRMS: Anal. Calcd. for [M + H]$^+$ C$_{41}$H$_{42}$N$_9$O$_4$: 724.3360; found 724.3380 |

| Example | Compound Name | | Retention time (LC-Condition); homogeneity index MS data |
|---|---|---|---|
| 50 | methyl ((1R)-2-((2S)-2-(5-(4'-(2-((2S)-1-(dimethylcarbamoyl)-2-pyrrolidinyl)-1H-imidazol-5-yl)-4-biphenylyl)-1H-imidazol-2-yl)-1-pyrrolidinyl)-2-oxo-1-phenylethyl)carbamate | 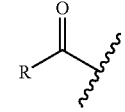 | 1.91 minutes (Cond. 2); >98%; LC/MS: Anal. Calcd. for [M + H]⁺ $C_{39}H_{43}N_8O_4$: 687.34; found 687.49; HRMS: Anal. Calcd. for [M + H]⁺ $C_{39}H_{43}N_8O_4$: 687.3407; found 687.3414 |
| 51 | methyl ((1R)-2-((2S)-2-(5-(4'-(2-((2S)-1-(1-methyl-D-prolyl)-2-pyrrolidinyl)-1H-imidazol-5-yl)-4-biphenylyl)-1H-imidazol-2-yl)-1-pyrrolidinyl)-2-oxo-1-phenylethyl)carbamate | <br>Cap-10 | 1.79 minutes (Cond. 2); >98%; LC/MS: Anal. Calcd. for [M + H]⁺ $C_{42}H_{47}N_8O_4$: 727.37; found 727.34; HRMS: Anal. Calcd. for [M + H]⁺ $C_{42}H_{47}N_8O_4$: 727.3720; found 727.3719 |
| 52 | methyl ((1R)-2-((2S)-2-(5-(4'-(2-((2S)-1-(1-methyl-L-prolyl)-2-pyrrolidinyl)-1H-imidazol-5-yl)-4-biphenylyl)-1H-imidazol-2-yl)-1-pyrrolidinyl)-2-oxo-1-phenylethyl)carbamate | <br>enantiomer of Cap-10 | 1.77 minutes (Cond. 2); >98%; LC/MS: Anal. Calcd. for [M + H]⁺ $C_{42}H_{47}N_8O_4$: 727.37; found 727.33; HRMS: Anal. Calcd. for [M + H]⁺ $C_{42}H_{47}N_8O_4$: 727.3720; found 727.3738 |
| 53 | methyl ((1R)-2-((2S)-2-(5-(4'-(2-((2S)-1-(N-acetyl-D-alanyl)-2-pyrrolidinyl)-1H-imidazol-5-yl)-4-biphenylyl)-1H-imidazol-2-yl)-1-pyrrolidinyl)-2-oxo-1-phenylethyl)carbamate | 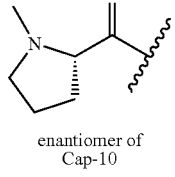 | 1.92 minutes (Cond. 2); >98%; LC/MS: Anal. Calcd. for [M + H]⁺ $C_{41}H_{45}N_8O_5$: 729.35; found 729.33; HRMS: Anal. Calcd. for [M + H]⁺ $C_{41}H_{45}N_8O_5$: 729.3513; found 729.3530 |
| 54 | methyl ((1R)-2-((2S)-2-(5-(4'-(2-((2S)-1-(N-acetyl-L-alanyl)-2-pyrrolidinyl)-1H-imidazol-5-yl)-4-biphenylyl)-1H-imidazol-2-yl)-1-pyrrolidinyl)-2-oxo-1-phenylethyl)carbamate | 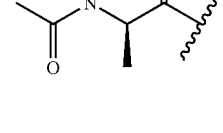 | 1.87 minutes (Cond. 2); >98%; LC/MS: Anal. Calcd. for [M + H]⁺ $C_{41}H_{45}N_8O_5$: 729.35; found 729.33 |
| 55 | methyl ((1R)-2-((2S)-2-(5-(4'-(2-((2S)-1-(methoxyacetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 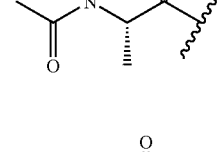 | 1.89 minutes (Cond. 2); >98%; LC/MS: Anal. Calcd. for [M + H]⁺ $C_{39}H_{42}N_7O_5$: 688.32; found 688.28; HRMS: Anal. Calcd. for [M + H]⁺ $C_{39}H_{42}N_7O_5$: 688.3247; found 688.3231 |
| 56 | methyl ((1R)-2-((2S)-2-(5-(4'-(2-((2S)-1-((2R)-2-hydroxybutanoyl)-2-pyrrolidinyl)-1H-imidazol-5-yl)-4-biphenylyl)-1H-imidazol-2-yl)-1-pyrrolidinyl)-2-oxo-1-phenylethyl)carbamate | 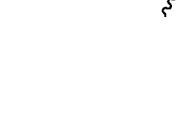 | 1.91 minutes (Cond. 2); >98%; LC/MS: Anal. Calcd. for [M + H]⁺ $C_{40}H_{44}N_7O_5$: 702.34; found 702.30; HRMS: Anal. Calcd. for [M + H]⁺ $C_{40}H_{44}N_7O_5$: 702.3404; found 702.3393 |

-continued

| Example | Compound Name |  | Retention time (LC-Condition); homogeneity index MS data |
|---|---|---|---|
| 57 | methyl ((1R)-2-((2S)-2-(5-(4'-(2-((2S)-1-((4-methyl-1-piperazinyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 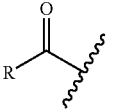 | 1.80 minutes (Cond. 2); >98%; LC/MS: Anal. Calcd. for [M + H]$^+$ C$_{43}$H$_{50}$N$_9$O$_4$: 756.40; found 756.36; HRMS: Anal. Calcd. for [M + H]$^+$ C$_{43}$H$_{50}$N$_9$O$_4$: 756.3986; found 756.3965 |
| 58 | methyl ((1R)-2-oxo-1-phenyl-2-((2S)-2-(5-(4'-(2-((2S)-1-(1-pyrrolidinylacetyl)-2-pyrrolidinyl)-1H-imidazol-5-yl)-4-biphenylyl)-1H-imidazol-2-yl)-1-pyrrolidinyl)ethyl)carbamate | 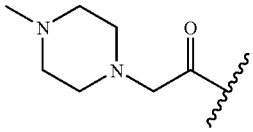 | 1.82 minutes (Cond. 2); >98%; LC/MS: Anal. Calcd. for [M + H]$^+$ C$_{42}$H$_{47}$N$_8$O$_4$: 727.37; found 727.33; HRMS: Anal. Calcd. for [M + H]$^+$ C$_{42}$H$_{47}$N$_8$O$_4$: 727.3720; found 727.3696 |
| 59 | methyl ((1R)-2-oxo-1-phenyl-2-((2S)-2-(5-(4'-(2-((2S)-1-((2S)-tetrahydro-2-furanylcarbonyl)-2-pyrrolidinyl)-1H-imidazol-5-yl)-4-biphenylyl)-1H-imidazol-2-yl)-1-pyrrolidinyl)ethyl)carbamate | 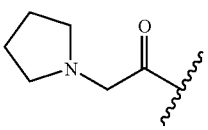 | 1.94 minutes (Cond. 2); >98%; LC/MS: Anal. Calcd. for [M + H]$^+$ C$_{41}$H$_{43}$N$_7$O$_5$: 714.34; found 714.24 |
| 60 | methyl ((1R)-2-((2S)-2-(5-(4'-(2-((2S)-1-((1-hydroxycyclopropyl)carbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | 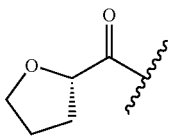 | 1.93 minutes (Cond. 2); >98%; LC/MS: Anal. Calcd. for [M + H]$^+$ C$_{40}$H$_{42}$N$_7$O$_5$: 700.32; found 700.23; HRMS: Anal. Calcd. for [M + H]$^+$ C$_{40}$H$_{42}$N$_7$O$_5$: 700.3247; found 700.3265 |
| 61 | methyl ((1R)-2-((2S)-2-(5-(4'-(2-((2S)-1-(1H-imidazol-5-ylacetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 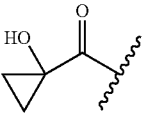 | 1.84 minutes (Cond. 2); >98%; LC/MS: Anal. Calcd. for [M + H]$^+$ C$_{41}$H$_{42}$N$_9$O$_4$: 724.34; found 724.21; HRMS: Anal. Calcd. for [M + H]$^+$ C$_{41}$H$_{42}$N$_9$O$_4$: 724.3360; found 724.3365 |
| 62 | methyl ((1R)-2-((2S)-2-(5-(4'-(2-((2S)-1-((1-methyl-1H-imidazol-4-yl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 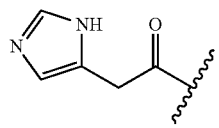 | 1.85 minutes (Cond. 2); >98%; LC/MS: Anal. Calcd. for [M + H]$^+$ C$_{42}$H$_{44}$N$_9$O$_4$: 738.35; found 738.22; HRMS: Anal. Calcd. for [M + H]$^+$ C$_{42}$H$_{44}$N$_9$O$_4$: 738.3516; found 738.3539 |
| 63 | methyl ((1R)-2-((2S)-2-(5-(4'-(2-((2S)-1-(1H-imidazol-2-ylcarbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | 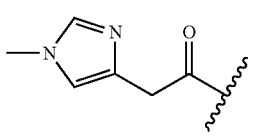 | 1.95 minutes (Cond. 2); >98%; LC/MS: Anal. Calcd. for [M + H]$^+$ C$_{40}$H$_{41}$N$_9$O$_4$: 710.32; found 710.17 |

| Example | Compound Name | R group | Retention time (LC-Condition); homogeneity index MS data |
|---|---|---|---|
| 64 | methyl ((1R)-2-((2S)-2-(5-(4'-(2-((2S)-1-((4-hydroxy-1-piperidinyl)(phenyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | Cap-8<br>A single diastereomer | 1.92 minutes (Cond. 2); >98%; LC/MS: Anal. Calcd. for [M + H]$^+$ C$_{49}$H$_{53}$N$_8$O$_5$: 833.41; found 833.32; HRMS: Anal. Calcd. for [M + H]$^+$ C$_{49}$H$_{53}$N$_8$O$_5$: 833.4139; found 833.4163 |
| 65 | methyl ((1R)-2-oxo-1-phenyl-2-((2S)-2-(5-(4'-(2-((2S)-1-(1H-tetrazol-5-ylacetyl)-2-pyrrolidinyl)-1H-imidazol-5-yl)-4-biphenylyl)-1H-imidazol-2-yl)-1-pyrrolidinyl)ethyl)carbamate | | 1.92 minutes (Cond. 2); >98%; LC/MS: Anal. Calcd. for [M + H]$^+$ C$_{39}$H$_{40}$N$_{11}$O$_4$: 726.33; found 726.22; HRMS: Anal. Calcd. for [M + H]$^+$ C$_{39}$H$_{40}$N$_{11}$O$_4$: 726.3265; found 726.3290 |
| 67 | methyl ((1R)-2-oxo-1-phenyl-2-((2S)-2-(5-(4'-(2-((2S)-1-(2-pyridinylcarbonyl)-2-pyrrolidinyl)-1H-imidazol-5-yl)-4-biphenylyl)-1H-imidazol-2-yl)-1-pyrrolidinyl)ethyl)carbamate | | 2.03 minutes (Cond. 2); >98%; LC/MS: Anal. Calcd. for [M + H]$^+$ C$_{42}$H$_{41}$N$_8$O$_4$: 721.33; found 721.31; HRMS: Anal. Calcd. for [M + H]$^+$ C$_{42}$H$_{41}$N$_8$O$_4$: 721.3251; found 721.3247 |
| 68 | methyl ((1R)-2-oxo-1-phenyl-2-((2S)-2-(5-(4'-(2-((2S)-1-(3-pyridinylcarbonyl)-2-pyrrolidinyl)-1H-imidazol-5-yl)-4-biphenylyl)-1H-imidazol-2-yl)-1-pyrrolidinyl)ethyl)carbamate | | 1.91 minutes (Cond. 2); >98%; LC/MS: Anal. Calcd. for [M + H]$^+$ C$_{42}$H$_{41}$N$_8$O$_4$: 721.33; found 721.31; HRMS: Anal. Calcd. for [M + H]$^+$ C$_{42}$H$_{41}$N$_8$O$_4$: 721.3251; found 721.3226 |
| 69 | methyl ((1R)-2-((2S)-2-(5-(4'-(2-((2S)-1-isonicotinoyl-2-pyrrolidinyl)-1H-imidazol-5-yl)-4-biphenylyl)-1H-imidazol-2-yl)-1-pyrrolidinyl)-2-oxo-1-phenylethyl)carbamate | | 1.89 minutes (Cond. 2); >98%; LC/MS: Anal. Calcd. for [M + H]$^+$ C$_{42}$H$_{41}$N$_8$O$_4$: 721.33; found 721.29; HRMS: Anal. Calcd. for [M + H]$^+$ C$_{42}$H$_{41}$N$_8$O$_4$: 721.3251; found 721.3251 |
| 70 | methyl ((1R)-2-((2S)-2-(5-(4'-(2-((2S)-1-((4R)-4-fluoro-1-methyl-L-prolyl)-2-pyrrolidinyl)-1H-imidazol-5-yl)-4-biphenylyl)-1H-imidazol-2-yl)-1-pyrrolidinyl)-2-oxo-1-phenylethyl)carbamate | Cap-11 | 1.84 minutes (Cond. 2); >98%; LC/MS: Anal. Calcd. for [M + H]$^+$ C$_{42}$H$_{46}$FN$_8$O$_4$: 745.36; found 745.27; HRMS: Anal. Calcd. for [M + H]$^+$ C$_{42}$H$_{46}$FN$_8$O$_4$: 745.3626; found 745.3658 |

-continued

| Example | Compound Name | R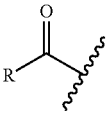 | Retention time (LC-Condition); homogeneity index MS data |
|---|---|---|---|
| 71 | methyl ((1R)-2-((2S)-2-(5-(4'-(2-((2S)-1-(1,3-oxazol-2-ylcarbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | 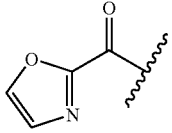 | 1.97 minutes (Cond. 2); >98%; LC/MS: Anal. Calcd. for [M + H]$^+$ C$_{40}$H$_{39}$N$_8$O$_5$: 711.30; found 711.27 |
| 72 | methyl ((1R)-2-((2S)-2-(5-(4'-(2-((2S)-1-(1,3-oxazol-5-ylcarbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | 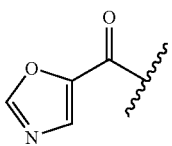 | 1.95 minutes (Cond. 2); >98%; LC/MS: Anal. Calcd. for [M + H]$^+$ C$_{40}$H$_{39}$N$_8$O$_5$: 711.30; found 711.27; HRMS: Anal. Calcd. for [M + H]$^+$ C$_{40}$H$_{39}$N$_8$O$_5$: 711.3043; found 711.3078 |
| 73 | methyl ((1R)-2-((2S)-2-(5-(4'-(2-((2S)-1-((dimethylamino)(oxo)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 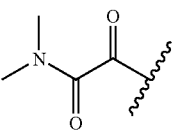 | 1.92 minutes (Cond. 2); >98%; LC/MS: Anal. Calcd. for [M + H]$^+$ C$_{40}$H$_{43}$N$_8$O$_5$: 715.34; found 715.40 |
| 74 | methyl ((1R)-2-oxo-1-phenyl-2-((2S)-2-(5-(4'-(2-((2S)-1-(tetrahydro-3-furanylcarbonyl)-2-pyrrolidinyl)-1H-imidazol-5-yl)-4-biphenylyl)-1H-imidazol-2-yl)-1-pyrrolidinyl)ethyl)carbamate | 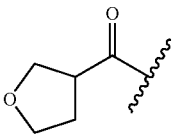 | 1.91 minutes (Cond. 2); >98%; LC/MS: Anal. Calcd. for [M + H]$^+$ C$_{41}$H$_{44}$N$_7$O$_5$: 714.34; found 714.39; HRMS: Anal. Calcd. for [M + H]$^+$ C$_{41}$H$_{44}$N$_7$O$_5$: 714.3404; found 714.3433 |
| 75 | methyl ((1R)-2-((2S)-2-(5-(4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-2-oxo-1-phenylethyl)carbamate | 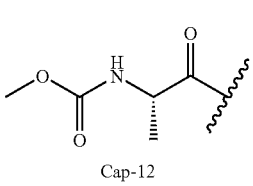<br>Cap-12 | 1.94 minutes (Cond. 2); >98%; LC/MS: Anal. Calcd. for [M + H]$^+$ C$_{41}$H$_{45}$N$_8$O$_6$: 745.35 found 745.34; HRMS: Anal. Calcd. for [M + H]$^+$ C$_{41}$H$_{45}$N$_8$O$_6$: 745.3462; found 745.3486 |
| 76 | methyl ((1R)-2-((2S)-2-(5-(4'-(2-((2S)-1-(N,N-dimethyl-L-alanyl)-2-pyrrolidinyl)-1H-imidazol-5-yl)-4-biphenylyl)-1H-imidazol-2-yl)-1-pyrrolidinyl)-2-oxo-1-phenylethyl)carbamate | 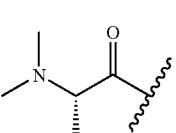 | 1.80 minutes (Cond. 2); >98%; LC/MS: Anal. Calcd. for [M + H]$^+$ C$_{41}$H$_{47}$N$_8$O$_4$: 715.37; found 715.35; HRMS: Anal. Calcd. for [M + H]$^+$ C$_{41}$H$_{47}$N$_8$O$_4$: 715.3720; found 715.3737 |
| 77 | methyl (2S)-2-(5-(4'-(2-((2S)-1-((2R)-2-((methoxycarbonyl)amino)-2-phenylacetyl)-2-pyrrolidinyl)-1H-imidazol-5-yl)-4-biphenylyl)-1H-imidazol-2-yl)-1-pyrrolidinecarboxylate | 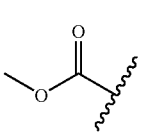 | 1.97 minutes (Cond. 2); >98%; LC/MS: Anal. Calcd. for [M + H]$^+$ C$_{38}$H$_{40}$N$_7$O$_5$: 674.31; found 674.66; HRMS: Anal. Calcd. for [M + H]$^+$ C$_{38}$H$_{40}$N$_7$O$_5$: 674.3091; found 674.3110 |

| Example | Compound Name | R group structure | Retention time (LC-Condition); homogeneity index MS data |
|---|---|---|---|
| 78 | methyl ((1R)-2-((2S)-2-(5-(4'-(2-((2S)-1-(4-morpholinylcarbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | morpholine-C(O)- | 1.95 minutes (Cond. 2); >98%; LC/MS: Anal. Calcd. for [M + H]$^+$ C$_{41}$H$_{45}$N$_8$O$_5$: 729.35; found 729.40; HRMS: Anal. Calcd. for [M + H]$^+$ C$_{41}$H$_{45}$N$_8$O$_5$: 729.3513; found 729.3502 |
| 79 | methyl ((1R)-2-((2S)-2-(5-(4'-(2-((2S)-1-((4S)-4-fluoro-L-prolyl)-2-pyrrolidinyl)-1H-imidazol-5-yl)-4-biphenylyl)-1H-imidazol-2-yl)-1-pyrrolidinyl)-2-oxo-1-phenylethyl)carbamate | (4S)-4-fluoro-prolyl | 1.80 minutes (Cond. 2); >98%; LC/MS: Anal. Calcd. for [M + H]$^+$ C$_{41}$H$_{44}$FN$_8$O$_4$: 731.84; found 731.26 |
| 80 | methyl ((1R)-2-oxo-1-phenyl-2-((2S)-2-(5-(4'-(2-((2S)-1-L-prolyl-2-pyrrolidinyl)-1H-imidazol-5-yl)-4-biphenylyl)-1H-imidazol-2-yl)-1-pyrrolidinyl)ethyl)carbamate | L-prolyl | 1.84 minutes (Cond. 2); >98%; LC/MS: Anal. Calcd. for [M + H]$^+$ C$_{41}$H$_{45}$N$_8$O$_4$: 713.36; found 713.36; HRMS: Anal. Calcd. for [M + H]$^+$ C$_{41}$H$_{45}$N$_8$O$_4$: 713.3564; found 713.3563 |
| 81 | methyl ((1R)-2-((2S)-2-(5-(4'-(2-((2S)-1-(4,4-difluoro-L-prolyl)-2-pyrrolidinyl)-1H-imidazol-5-yl)-4-biphenylyl)-1H-imidazol-2-yl)-1-pyrrolidinyl)-2-oxo-1-phenylethyl)carbamate | 4,4-difluoro-L-prolyl | 1.88 minutes (Cond. 2); >98%; LC/MS: Anal. Calcd. for [M + H]$^+$ C$_{41}$H$_{43}$F$_2$N$_8$O$_4$: 749.34; found 749.31; HRMS: Anal. Calcd. for [M + H]$^+$ C$_{41}$H$_{43}$F$_2$N$_8$O$_4$: 749.3375; found 749.3390 |
| 82 | methyl ((1R)-2-((2S)-2-(5-(4'-(2-((2S)-1-((4R)-4-fluoro-L-prolyl)-2-pyrrolidinyl)-1H-imidazol-5-yl)-4-biphenylyl)-1H-imidazol-2-yl)-1-pyrrolidinyl)-2-oxo-1-phenylethyl)carbamate | (4R)-4-fluoro-L-prolyl | 1.83 minutes (Cond. 2); >98%; LC/MS: Anal. Calcd. for [M + H]$^+$ C$_{41}$H$_{44}$FN$_8$O$_4$: 731.35; found 731.37; HRMS: Anal. Calcd. for [M + H]$^+$ C$_{41}$H$_{44}$FN$_8$O$_4$: 731.3470; found 731.3502 |
| 83 | methyl ((1R)-2-((2S)-2-(5-(4'-(2-((2S)-1-((1S,3S,5S)-2-azabicyclo[3.1.0]hex-3-ylcarbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | (1S,3S,5S)-2-azabicyclo[3.1.0]hex-3-ylcarbonyl | 1.82 minutes (Cond. 2); >98%; LC/MS: Anal. Calcd. for [M + H]$^+$ C$_{42}$H$_{45}$N$_8$O$_4$: 725.36; found 725.39; HRMS: Anal. Calcd. for [M + H]$^+$ C$_{42}$H$_{45}$N$_8$O$_4$: 725.3564; found 725.3574 |
| 84 | methyl ((1R)-2-((2S)-2-(5-(4'-(2-((2S)-1-L-alanyl-2-pyrrolidinyl)-1H-imidazol-5-yl)-4-biphenylyl)-1H-imidazol-2-yl)-1-pyrrolidinyl)-2-oxo-1-phenylethyl)carbamate | L-alanyl | 1.82 minutes (Cond. 2); >98%; LC/MS: Anal. Calcd. for [M + H]$^+$ C$_{39}$H$_{43}$N$_8$O$_4$: 687.34; found 687.32; HRMS: Anal. Calcd. for [M + H]$^+$ C$_{39}$H$_{43}$N$_8$O$_4$: 687.3407; found 687.3435 |

-continued

| Example | Compound Name | 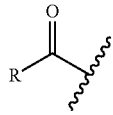 | Retention time (LC-Condition); homogeneity index MS data |
|---|---|---|---|
| 84-1 | methyl ((1R)-2-oxo-1-phenyl-2-((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)ethyl)carbamate | 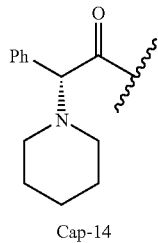<br>Cap-14 | $^1$HNMR (400 MHz, CD$_3$OD) δ 7.90-7.85 (m, 9 H), 7.81-7.79 (m, 1 H), 7.63-7.57 (m, 5 H), 7.45-7.32 (m, 6 H), 5.51 (s, 1 H), 5.45 (s, 1 H), 5.33-5.29 (m, 2 H), 4.06-4.01 (m, 2 H), 3.63 (d, J = 4.04 Hz, 3 H), 3.59-3.50 (m, 2 H), 3.19-3.12 (m, 1 H), 3.07-3.01 (m, 1 H), 2.93-2.76 (m, 2 H), 2.57-2.51 (m, 1 H), 2.40-2.31 (m, 2 H), 2.22-2.06 (m, 4 H), 2.00-1.90 (m, 3 H), 1.84-1.64 (m, 4 H), 1.52-1.43 (m, 2 H); LCMS: Anal. Calcd. for C$_{49}$H$_{52}$N$_8$O$_4$: 816; found: 817 (M + H)$^+$. |
| 84-2 | methyl ((1R)-2-((2S)-2-(5-(4'-(2-((2S)-1-((2S)-2-(2-fluorophenyl)-2-hydroxypropanoyl)-2-pyrrolidinyl)-1H-imidazol-5-yl)-4-biphenylyl)-1H-imidazol-2-yl)-1-pyrrolidinyl)-2-oxo-1-phenylethyl)carbamate | 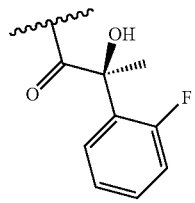 | $^1$HNMR (400 MHz, CD$_3$OD) δ 7.89-7.85 (m, 8 H), 7.81-7.73 (2 H), 7.67-7.65 (m, 1 H), 7.45-7.26 (m, 7H), 7.13-7.08 (m, 1 H), 6.94-6.89 (m, 0.5 H), 6.72-6.67 (0.5 H), 6.09-6.07 (m, 0.4 H), 5.51 (s, 1 H), 5.32-5.25 (m, 1.6 H), 4.08-3.95 (m, 2 H), 3.85-3.79 (1 H), 3.64-3.63 (m, 3 H), 3.56-3.49 (1 H), 3.09-3.03 (m, 1 H), 2.59-2.50 (m, 1 H), 2.42-2.33 (m, 2 H), 2.21-2.00 (m, 6 H), 1.82-1.74 (m, 1 H), 1.66 (d, J = 4.55 Hz, 3 H); LCMS: Anal. Calcd. for C$_{45}$H$_{46}$FN$_7$O$_3$: 781; found: 782 (M + H)$^+$. |
| 84-3 | methyl ((1R)-2-oxo-2-((2S)-2-(5-(4'-(2-((2S)-1-(5-oxo-D-prolyl)-2-pyrrolidinyl)-1H-imidazol-5-yl)-4-biphenylyl)-1H-imidazol-2-yl)-1-pyrrolidinyl)-1-phenylethyl)carbamate | 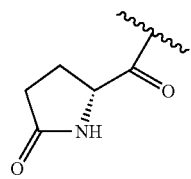 | LCMS: Anal. Calcd. for C$_{41}$H$_{42}$N$_8$O$_5$: 726; found: 727 (M + H)$^+$. |
| 84-4 | methyl ((1R)-2-((2S)-2-(5-(4'-(2-((2S)-1-((2R)-2-(4-hydroxy-4-methyl-1-piperidinyl)-2-phenylacetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 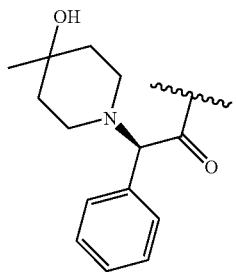<br>Cap-15 | LCMS: Anal. Calcd. for C$_{50}$H$_{54}$N$_8$O$_5$: 846; found: 847 (M + H)$^+$. |

-continued

| Example | Compound Name | R group structure | Retention time (LC-Condition); homogeneity index MS data |
|---------|---------------|-------------------|----------------------------------------------------------|
| 84-5 | tert-butyl (4R)-4-(((2S)-2-(5-(4'-(2-((2S)-1-((2R)-2-((methoxycarbonyl)amino)-2-phenylacetyl)-2-pyrrolidinyl)-1H-imidazol-5-yl)-4-biphenylyl)-1H-imidazol-2-yl)-1-pyrrolidinyl)carbonyl)-1,3-thiazolidine-3-carboxylate | (thiazolidine with Boc) | LCMS: Anal. Calcd. for $C_{45}H_{50}N_8O_6S$: 830; found: 831 $(M + H)^+$. |
| 84-6 | methyl ((1R)-2-((2S)-2-(5-(4'-(2-((2S)-1-((1-((tert-butoxycarbonyl)amino)cyclopentyl)carbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | (cyclopentyl with BocHN) | LCMS: Anal. Calcd. for $C_{47}H_{54}FN_8O_6$: 826; found: 827 $(M + H)^+$. |
| 84-7 | methyl ((1R)-2-((2S)-2-(5-(4'-(2-((2S)-1-(N-benzoylglycyl)-2-pyrrolidinyl)-1H-imidazol-5-yl)-4-biphenylyl)-1H-imidazol-2-yl)-1-pyrrolidinyl)-2-oxo-1-phenylethyl)carbamate | (Ph-C(O)-NH-CH2-C(O)-) | LCMS: Anal. Calcd. for $C_{45}H_{44}FN_8O_5$: 776; found: 777 $(M + H)^+$. |
| 84-8 | methyl ((1R)-2-((2S)-2-(5-(4'-(2-((2S)-1-(4-(4-methyl-1-piperazinyl)benzoyl)-2-pyrrolidinyl)-1H-imidazol-5-yl)-4-biphenylyl)-1H-imidazol-2-yl)-1-pyrrolidinyl)-2-oxo-1-phenylethyl)carbamate | (4-(4-methylpiperazinyl)benzoyl) | LCMS: Anal. Calcd. for $C_{48}H_{51}N_9O_4$: 817; found: 818 $(M + H)^+$. |
| 84-9 | methyl ((1R)-2-oxo-1-phenyl-2-((2S)-2-(5-(4'-(2-((2S)-1-((5-phenyl-2-thienyl)carbonyl)-2-pyrrolidinyl)-1H-imidazol-5-yl)-4-biphenylyl)-1H-imidazol-2-yl)-1-pyrrolidinyl)ethyl)carbamate | (5-phenyl-2-thienyl carbonyl) | LCMS: Anal. Calcd. for $C_{47}H_{43}N_7O_4S$: 801; found: 802 $(M + H)^+$. |
| 84-10 | methyl ((1R)-2-oxo-1-phenyl-2-((2S)-2-(5-(4'-(2-((2S)-1-((4-phenyl-1,2,3-thiadiazol-5-yl)carbonyl)-2-pyrrolidinyl)-1H-imidazol-5-yl)-4-biphenylyl)-1H-imidazol-2-yl)-1-pyrrolidinyl)ethyl)carbamate | (4-phenyl-1,2,3-thiadiazol-5-yl carbonyl) | LCMS: Anal. Calcd. for $C_{45}H_{41}N_9O_4S$: 803; found: 804 $(M + H)^+$. |
| 84-11 | methyl ((1R)-2-oxo-1-phenyl-2-((2S)-2-(5-(4'-(2-((2S)-1-((2-phenyl-1,3-thiazol-4-yl)carbonyl)-2-pyrrolidinyl)-1H-imidazol-5-yl)-4-biphenylyl)-1H-imidazol-2-yl)-1-pyrrolidinyl)ethyl)carbamate | (2-phenyl-1,3-thiazol-4-yl carbonyl) | LCMS: Anal. Calcd. for $C_{46}H_{42}N_8O_4S$: 802; found: 803 $(M + H)^+$. |
| 84-12 | tert-butyl 4-(((2S)-2-(5-(4'-(2-((2S)-1-((2R)-2-((methoxycarbonyl)amino)-2-phenylacetyl)-2-pyrrolidinyl)-1H-imidazol-5-yl)-4-biphenylyl)-1H-imidazol-2-yl)-1-pyrrolidinyl)carbonyl)-4-methyl-1-piperidinecarboxylate | (4-methyl-N-Boc-piperidinyl carbonyl) | LCMS: Anal. Calcd. for $C_{48}H_{56}N_8O_6$: 840; found: 841 $(M + H)^+$. |

-continued

| Example | Compound Name | 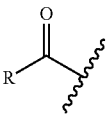 | Retention time (LC-Condition); homogeneity index MS data |
|---|---|---|---|
| 84-13 | methyl ((1R)-2-((2S)-2-(5-(4'-(2-((2S)-1-(4-(dimethylamino)butanoyl)-2-pyrrolidinyl)-1H-imidazol-5-yl)-4-biphenylyl)-1H-imidazol-2-yl)-1-pyrrolidinyl)-2-oxo-1-phenylethyl)carbamate | 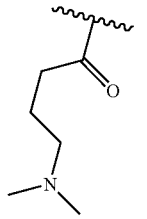 | LCMS: Anal. Calcd. for $C_{42}H_{48}N_8O_4$: 728; found: 729 $(M + H)^+$. |
| 84-14 | methyl ((1R)-2-((2S)-2-(5-(4'-(2-((2S)-1-((3-hydroxyphenyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 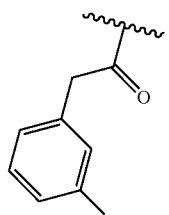 | LCMS: Anal. Calcd. for $C_{44}H_{43}N_7O_5$: 749; found: 750 $(M + H)^+$. |
| 84-15 | methyl ((1R)-2-((2S)-2-(5-(4'-(2-((2S)-1-(N,N-dimethyl-beta-alanyl)-2-pyrrolidinyl)-1H-imidazol-5-yl)-4-biphenylyl)-1H-imidazol-2-yl)-1-pyrrolidinyl)-2-oxo-1-phenylethyl)carbamate | 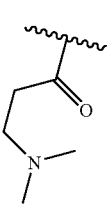 | LCMS: Anal. Calcd. for $C_{41}H_{46}N_8O_4$: 714; found: 715 $(M + H)^+$. |
| 84-16 | methyl ((1R)-2-((2S)-2-(5-(4'-(2-((2S)-1-(4-(hydroxymethyl)benzoyl)-2-pyrrolidinyl)-1H-imidazol-5-yl)-4-biphenylyl)-1H-imidazol-2-yl)-1-pyrrolidinyl)-2-oxo-1-phenylethyl)carbamate | 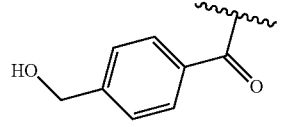 | LCMS: Anal. Calcd. for $C_{44}H_{43}N_7O_5$: 749; found: 750 $(M + H)^+$. |
| 84-17 | methyl ((1R)-2-((2S)-2-(5-(4'-(2-((2S)-1-(((3R)-1-benzyl-3-pyrrolidinyl)carbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | 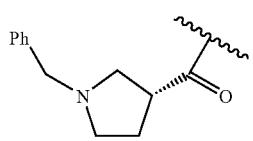 | LCMS: Anal. Calcd. for $C_{48}H_{50}N_8O_4$: 802; found: 803 $(M + H)^+$. |
| 84-18 | tert-butyl (2S)-2-(2-((2S)-2-(5-(4'-(2-((2R)-2-((methoxycarbonyl)amino)-2-phenylacetyl)-2-pyrrolidinyl)-1H-imidazol-5-yl)-4-biphenylyl)-1H-imidazol-2-yl)-1-pyrrolidinyl)-2-oxoethyl)-1-pyrrolidinecarboxylate | 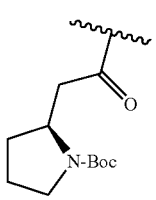 | LCMS: Anal. Calcd. for $C_{47}H_{54}N_8O_6$: 826; found: 827 $(M + H)^+$. |
| 84-19 | methyl ((1R)-2-((2S)-2-(5-(4'-(2-((2S)-1-((5-methyl-1H-pyrazol-3-yl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 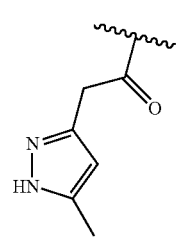 | LCMS: Anal. Calcd. for $C_{42}H_{43}N_9O_4$: 737; found: 738 $(M + H)^+$. |

-continued

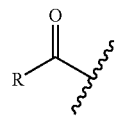

| Example | Compound Name | | Retention time (LC-Condition); homogeneity index MS data |
|---|---|---|---|
| 84-20 | methyl ((1R)-2-((2S)-2-(5-(4'-(2-((2S)-1-(((3S)-7-hydroxy-1,2,3,4-tetrahydro-3-isoquinolinyl)carbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | | LCMS: Anal. Calcd. for $C_{46}H_{46}N_8O_5$: 790; found: 791 (M + H)$^+$. |
| 84-21 | tert-butyl (2R)-2-(2-(((2S)-2-(5-(4'-(2-((2S)-1-((2R)-2-((methoxycarbonyl)amino)-2-phenylacetyl)-2-pyrrolidinyl)-1H-imidazol-5-yl)-4-biphenylyl)-1H-imidazol-2-yl)-1-pyrrolidinyl)carbonyl)-1-piperidinecarboxylate | | LCMS: Anal. Calcd. for $C_{47}H_{54}N_8O_6$: 826; found: 827 (M + H)$^+$. |
| 84-22 | methyl ((1R)-2-oxo-1-phenyl-2-((2S)-2-(5-(4'-(2-((2S)-1-((5-phenyl-4-isoxazolyl)carbonyl)-2-pyrrolidinyl)-1H-imidazol-5-yl)-4-biphenylyl)-1H-imidazol-2-yl)-1-pyrrolidinyl)ethyl)carbamate | | LCMS: Anal. Calcd. for $C_{46}H_{42}N_8O_5$: 786; found: 787 (M + H)$^+$. |
| 84-23 | methyl ((1R)-2-((2S)-2-(5-(4'-(2-((2S)-1-(((1R,3S)-3-((tert-butoxycarbonyl)amino)cyclopentyl)carbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | | LCMS: Anal. Calcd. for $C_{47}H_{54}N_8O_6$: 826; found: 827 (M + H)$^+$. |
| 84-24 | methyl ((1R)-2-oxo-1-phenyl-2-((2S)-2-(5-(4'-(2-((2S)-1-(3-(1-piperidinyl)propanoyl)-2-pyrrolidinyl)-1H-imidazol-5-yl)-4-biphenylyl)-1H-imidazol-2-yl)-1-pyrrolidinyl)ethyl)carbamate | | LCMS: Anal. Calcd. for $C_{44}H_{50}N_8O_4$: 754; found: 755 (M + H)$^+$. |
| 84-25 | methyl ((1R)-2-((2S)-2-(5-(4'-(2-((2S)-1-(2-benzoylbenzoyl)-2-pyrrolidinyl)-1H-imidazol-5-yl)-4-biphenylyl)-1H-imidazol-2-yl)-1-pyrrolidinyl)-2-oxo-1-phenylethyl)carbamate | | LCMS: Anal. Calcd. for $C_{50}H_{45}N_7O_5$: 823; found: 824 (M + H)$^+$. |
| 84-26 | methyl ((1R)-2-((2S)-2-(5-(4'-(2-((2S)-1-((2-methoxyphenoxy)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | | LCMS: Anal. Calcd. for $C_{45}H_{45}N_7O_6$: 779; found: 780 (M + H)$^+$. |

-continued

| Example | Compound Name | R group structure | Retention time (LC-Condition); homogeneity index MS data |
|---------|---------------|-------------------|----------------------------------------------------------|
| 84-27 | tert-butyl 3-(((2S)-2-(5-(4'-(2-((2S)-1-((2R)-2-((methoxycarbonyl)amino)-2-phenylacetyl)-2-pyrrolidinyl)-1H-imidazol-5-yl)-4-biphenylyl)-1H-imidazol-2-yl)-1-pyrrolidinyl)carbonyl)-1-azetidinecarboxylate | 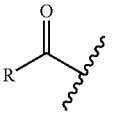 | LCMS: Anal. Calcd. for $C_{45}H_{50}N_8O_6$: 798; found: 799 $(M + H)^+$. |
| 84-28 | methyl ((1R)-2-((2S)-2-(5-(4'-(2-((2S)-1-(((3S)-1-benzyl-3-pyrrolidinyl)carbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | 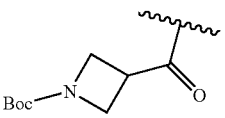 | LCMS: Anal. Calcd. for $C_{48}H_{50}N_8O_4$: 802; found: 803 $(M + H)^+$. |
| 84-29 | methyl ((1R)-2-oxo-1-phenyl-2-((2S)-2-(5-(4'-(2-((2S)-1-(3-(1-pyrrolidinyl)benzoyl)-2-pyrrolidinyl)-1H-imidazol-5-yl)-4-biphenylyl)-1H-imidazol-2-yl)-1-pyrrolidinyl)ethyl)carbamate | 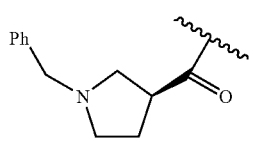 | LCMS: Anal. Calcd. for $C_{47}H_{48}N_8O_4$: 788; found: 789 $(M + H)^+$. |
| 84-30 | methyl ((1R)-2-((2S)-2-(5-(4'-(2-((2S)-1-(2-((tert-butoxycarbonyl)amino)benzoyl)-2-pyrrolidinyl)-1H-imidazol-5-yl)-4-biphenylyl)-1H-imidazol-2-yl)-1-pyrrolidinyl)-2-oxo-1-phenylethyl)carbamate | 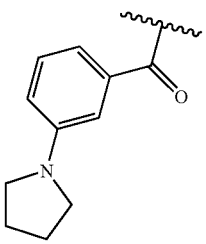 | LCMS: Anal. Calcd. for $C_{48}H_{50}N_8O_6$: 834; found: 835 $(M + H)^+$. |
| 84-31 | tert-butyl (3R)-3-(((2S)-2-(5-(4'-(2-((2S)-1-((2R)-2-((methoxycarbonyl)amino)-2-phenylacetyl)-2-pyrrolidinyl)-1H-imidazol-5-yl)-4-biphenylyl)-1H-imidazol-2-yl)-1-pyrrolidinyl)carbonyl)-1-piperidinecarboxylate | 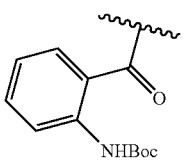 | LCMS: Anal. Calcd. for $C_{47}H_{54}N_8O_6$: 826; found: 827 $(M + H)^+$. |
| 84-32 | methyl ((1R)-2-oxo-1-phenyl-2-((2S)-2-(5-(4'-(2-((2S)-1-((1-trifluoromethyl)cyclopropyl)carbonyl)-2-pyrrolidinyl)-1H-imidazol-5-yl)-4-biphenylyl)-1H-imidazol-2-yl)-1-pyrrolidinyl)ethyl)carbamate | 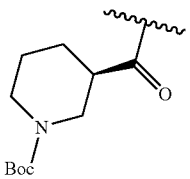 | LCMS: Anal. Calcd. for $C_{41}H_{40}F_3N_7O_4$: 751; found: 752 $(M + H)^+$. |
| 84-33 | methyl ((1R)-2-((2S)-2-(5-(4'-(2-((2S)-1-(4-(dimethylamino)benzoyl)-2-pyrrolidinyl)-1H-imidazol-5-yl)-4-biphenylyl)-1H-imidazol-2-yl)-1-pyrrolidinyl)-2-oxo-1-phenylethyl)carbamate | 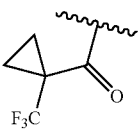 | LCMS: Anal. Calcd. for $C_{45}H_{46}N_8O_4$: 762; found: 763 $(M + H)^+$. |

-continued

| Example | Compound Name | R group (R-C(=O)-) | Retention time (LC-Condition); homogeneity index MS data |
|---|---|---|---|
| 84-34 | methyl ((1R)-2-((2S)-2-(5-(4'-(2-((2S)-1-(3-benzoylbenzoyl)-2-pyrrolidinyl)-1H-imidazol-5-yl)-4-biphenylyl)-1H-imidazol-2-yl)-1-pyrrolidinyl)-2-oxo-1-phenylethyl)carbamate | 3-benzoylbenzoyl | LCMS: Anal. Calcd. for $C_{50}H_{45}N_7O_5$: 823; found: 824 $(M+H)^+$. |
| 84-35 | methyl ((1R)-2-((2S)-2-(5-(4'-(2-((2S)-1-((cis-4-((tert-butoxycarbonyl)amino)cyclohexyl)carbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | cis-4-(BocNH)cyclohexyl | LCMS: Anal. Calcd. for $C_{48}H_{56}N_8O_6$: 840; found: 841 $(M+H)^+$. |
| 84-36 | tert-butyl 4-(((2S)-2-(5-(4'-(2-((2S)-1-((2R)-2-((methoxycarbonyl)amino)-2-phenylacetyl)-2-pyrrolidinyl)-1H-imidazol-5-yl)-4-biphenylyl)-1H-imidazol-2-yl)-1-pyrrolidinyl)carbonyl)-1-piperidinecarboxylate | 1-Boc-piperidin-4-yl | LCMS: Anal. Calcd. for $C_{47}H_{54}N_8O_6$: 826; found: 827 $(M+H)^+$. |
| 84-37 | methyl ((1R)-2-((2S)-2-(5-(4'-(2-((2S)-1-((cis-4-((tert-butoxycarbonyl)amino)cyclohexyl)carbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | 4-(BocNH)cyclohexyl | LCMS: Anal. Calcd. for $C_{48}H_{56}N_8O_6$: 840; found: 841 $(M+H)^+$. |
| 84-38 | methyl ((1R)-2-((2S)-2-(5-(4'-(2-((2S)-1-(diphenylacetyl)-2-pyrrolidinyl)-1H-imidazol-5-yl)-4-biphenylyl)-1H-imidazol-2-yl)-1-pyrrolidinyl)-2-oxo-1-phenylethyl)carbamate | diphenylmethyl | LCMS: Anal. Calcd. for $C_{50}H_{47}N_7O_4$: 809; found: 810 $(M+H)^+$. |
| 84-39 | methyl ((1R)-2-oxo-2-((2S)-2-(5-(4'-(2-((2S)-1-(4-oxopentanoyl)-2-pyrrolidinyl)-1H-imidazol-5-yl)-4-biphenylyl)-1H-imidazol-2-yl)-1-pyrrolidinyl)-1-phenylethyl)carbamate | 4-oxopentanoyl chain | LCMS: Anal. Calcd. for $C_{41}H_{43}N_7O_5$: 713; found: 714 $(M+H)^+$. |
| 84-40 | methyl ((1R)-2-((2S)-2-(5-(4'-(2-((2S)-1-(2-fluorobenzoyl)-2-pyrrolidinyl)-1H-imidazol-5-yl)-4-biphenylyl)-1H-imidazol-2-yl)-1-pyrrolidinyl)-2-oxo-1-phenylethyl)carbamate | 2-fluorobenzoyl | LCMS: Anal. Calcd. for $C_{43}H_{40}FN_7O_4$: 737; found: 738 $(M+H)^+$. |
| 84-41 | methyl ((1R)-2-((2S)-2-(5-(4'-(2-((2S)-1-(2-biphenylcarbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | 2-phenylbenzoyl | LCMS: Anal. Calcd. for $C_{49}H_{45}N_7O_4$: 795; found: 796 $(M+H)^+$. |

| Example | Compound Name | R group | Retention time (LC-Condition); homogeneity index MS data |
|---|---|---|---|
| 84-42 | methyl ((1R)-2-((2S)-2-(5-(4'-(2-((2S)-1-(2-benzylbenzoyl)-2-pyrrolidinyl)-1H-imidazol-5-yl)-4-biphenylyl)-1H-imidazol-2-yl)-1-pyrrolidinyl)-2-oxo-1-phenylethyl)carbamate | 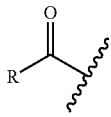 | LCMS: Anal. Calcd. for $C_{50}H_{47}N_7O_4$: 809; found: 810 $(M + H)^+$. |
| 84-43 | methyl ((1R)-2-((2S)-2-(5-(4'-(2-((2S)-1-((2E)-3-(4-(dimethylamino)phenyl)-2-propenoyl)-2-pyrrolidinyl)-1H-imidazol-5-yl)-4-biphenylyl)-1H-imidazol-2-yl)-1-pyrrolidinyl)-2-oxo-1-phenylethyl)carbamate | 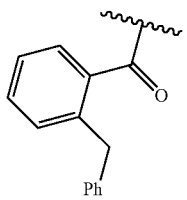 | LCMS: Anal. Calcd. for $C_{47}H_{48}N_8O_4$: 788; found: 789 $(M + H)^+$. |
| 84-44 | methyl ((1R)-2-oxo-1-phenyl-2-((2S)-2-(5-(4'-(2-((2S)-1-(1,3-thiazol-4-ylcarbonyl)-2-pyrrolidinyl)-1H-imidazol-5-yl)-4-biphenylyl)-1H-imidazol-2-yl)-1-pyrrolidinyl)ethyl)carbamate | 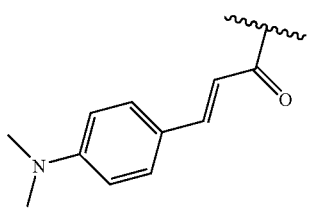 | LCMS: Anal. Calcd. for $C_{40}H_{38}N_8O_4S$: 726; found: 727 $(M + H)^+$. |
| 84-45 | methyl ((1R)-2-((2S)-2-(5-(4'-(2-((2S)-1-(((((1R,2S,5R)-2-isopropyl-5-methylcyclohexyl)oxy)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 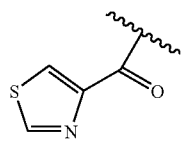 | LCMS: Anal. Calcd. for $C_{48}H_{57}N_7O_5$: 811; found: 812 $(M + H)^+$. |
| 84-46 | methyl ((1R)-2-((2S)-2-(5-(4'-(2-((2S)-1-((dimethylamino)(2-thienyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 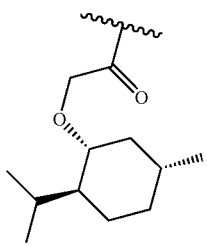<br>Cap-32 | LCMS: Anal. Calcd. for $C_{44}H_{46}N_8O_4S$: 782; found: 782 $(M + H)^+$. |
| 84-47 | methyl ((1R)-2-((2S)-2-(5-(4'-(2-((2S)-1-((dimethylamino)(3-thienyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | <br>Cap-33 | LCMS: Anal. Calcd. for $C_{44}H_{46}N_8O_4S$: 782; found: 782 $(M + H)^+$. |

| Example | Compound Name | R group structure | Retention time (LC-Condition); homogeneity index MS data |
|---------|---------------|-------------------|-----------------------------------------------------------|
| 84-48 | methyl ((1R)-2-((2S)-2-(5-(4'-(2-((2S)-1-((dimethylamino)(2-methyl-1,3-thiazol-4-yl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 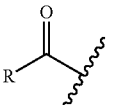<br>Cap-31 | LCMS: Anal. Calcd. for $C_{44}H_{47}N_9O_4S$: 797; found: 798 $(M+H)^+$. |
| 84-49 | methyl ((1R)-2-((2S)-2-(5-(4'-(2-((2S)-1-(1,2-benzisoxazol-3-yl(dimethylamino)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 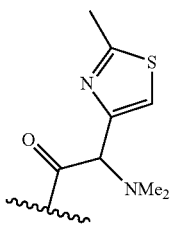<br>Cap-34 | LCMS: Anal. Calcd. for $C_{47}H_{47}N_9O_5$: 817; found: 818 $(M+H)^+$. |
| 84-50 | methyl ((1R)-2-((2S)-2-(5-(4'-(2-((2S)-1-(1-benzothiophen-3-yl(dimethylamino)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 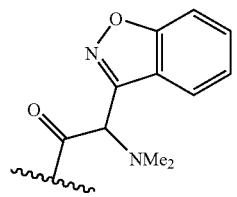<br>Cap-35 | LCMS: Anal. Calcd. for $C_{48}H_{48}N_8O_4S$: 832; found: 833 $(M+H)^+$. |
| 84-51 | methyl ((1R)-2-((2S)-2-(5-(4'-(2-((2S)-1-((dimethylamino)(1-naphthyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 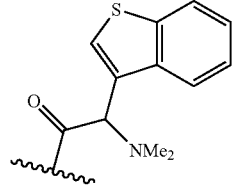<br>Cap-23 | LCMS: Anal. Calcd. for $C_{50}H_{50}N_8O_4$: 826; found: 827 $(M+H)^+$. |
| 84-52 | methyl ((1R)-2-((2S)-2-(5-(4'-(2-((2S)-1-((dimethylamino)(3-quinolinyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 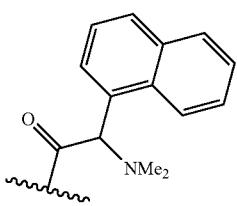<br>Cap-37 | LCMS: Anal. Calcd. for $C_{49}H_{49}N_9O_4$: 827; found: 828 $(M+H)^+$. |

-continued

| Example | Compound Name | R group structure | Retention time (LC-Condition); homogeneity index MS data |
|---|---|---|---|
| 84-53 | methyl ((1R)-2-((2S)-2-(5-(4'-(2-((2S)-1-((dimethylamino)(2-methyl-1,3-benzothiazol-5-yl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 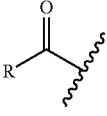<br>Cap-36 | LCMS: Anal. Calcd. for $C_{48}H_{49}N_9O_4S$: 847; found: 848 $(M + H)^+$. |
| 84-54 | methyl ((1R)-2-((2S)-2-(5-(4'-(2-((2S)-1-((dimethylamino)(3-(trifluoromethyl)phenyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 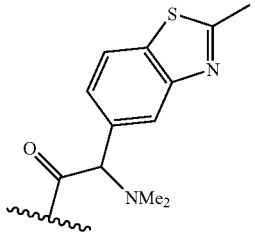<br>Cap-24 | LCMS: Anal. Calcd. for $C_{47}H_{47}F_3N_8O_4$: 844; found: 845 $(M + H)^+$. |
| 84-55 | methyl ((1R)-2-((2S)-2-(5-(4'-(2-((2S)-1-((dimethylamino)(2-(trifluoromethyl)phenyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 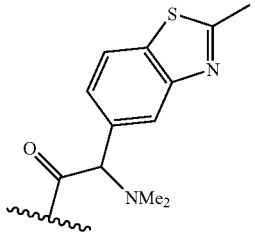<br>Cap-25 | LCMS: Anal. Calcd. for $C_{47}H_{47}F_3N_8O_4$: 844; found: 845 $(M + H)^+$. |
| 84-56 | methyl ((1R)-2-((2S)-2-(5-(4'-(2-((2S)-1-((2-chlorophenyl)(dimethylamino)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 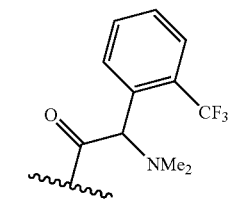<br>Cap-29 | LCMS: Anal. Calcd. for $C_{46}H_{47}ClN_8O_4$: 810; found: 811 $(M + H)^+$. |
| 84-57 | methyl ((1R)-2-((2S)-2-(5-(4'-(2-((2S)-1-((3-chlorophenyl)(dimethylamino)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | <br>Cap-28 | LCMS: Anal. Calcd. for $C_{46}H_{47}ClN_8O_4$: 810; found: 811 $(M + H)^+$. |

-continued

| Example | Compound Name | R group | Retention time (LC-Condition); homogeneity index MS data |
|---|---|---|---|
| 84-58 | methyl ((1R)-2-((2S)-2-(5-(4'-(2-((2S)-1-((4-chlorophenyl)(dimethylamino)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 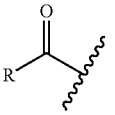<br>Cap-30 | LCMS: Anal. Calcd. for C$_{46}$H$_{47}$ClN$_8$O$_4$: 810; found: 811 (M + H)$^+$. |
| 84-59 | methyl ((1R)-2-((2S)-2-(5-(4'-(2-((2S)-1-((dimethylamino)(2-fluorophenyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 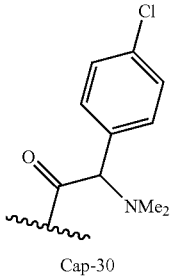<br>Cap-26 | LCMS: Anal. Calcd. for C$_{46}$H$_{47}$FN$_8$O$_4$: 794; found: 795 (M + H)$^+$. |
| 84-60 | methyl ((1R)-2-((2S)-2-(5-(4'-(2-((2S)-1-((dimethylamino)(3-fluorophenyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 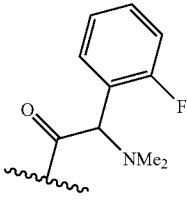<br>Cap-27 | LCMS: Anal. Calcd. for C$_{46}$H$_{47}$FN$_8$O$_4$: 794; found: 795 (M + H)$^+$. |
| 84-61 | methyl ((1R)-2-((2S)-2-(5-(4'-(2-((2S)-1-((dimethylamino)(2-pyridinyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 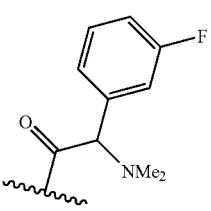<br>Cap-20 | LCMS: Anal. Calcd. for C$_{45}$H$_{47}$N$_9$O$_4$: 777; found: 778 (M + H)$^+$. |
| 84-62 | methyl ((1R)-2-((2S)-2-(5-(4'-(2-((2S)-1-((dimethylamino)(3-pyridinyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | <br>Cap-19 | LCMS: Anal. Calcd. for C$_{45}$H$_{47}$N$_9$O$_4$: 777; found: 778 (M + H)$^+$. |
| 84-63 | methyl ((1R)-2-((2S)-2-(5-(4'-(2-((2S)-1-((4-methoxyphenyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 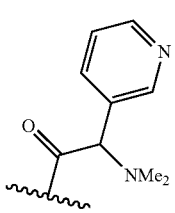 | LCMS: Anal. Calcd. for C$_{45}$H$_{45}$N$_7$O$_5$: 763; found: 764 (M + H)$^+$. |

-continued

| Example | Compound Name | | Retention time (LC-Condition); homogeneity index MS data |
|---|---|---|---|

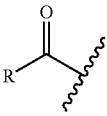

| 84-64 | methyl ((1R)-2-((2S)-2-(5-(4'-(2-((2S)-1-((3-methoxyphenyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | | LCMS: Anal. Calcd. for $C_{45}H_{45}N_7O_5$: 763; found: 764 $(M+H)^+$. |
| 84-65 | methyl ((1R)-2-((2S)-2-(5-(4'-(2-((2S)-1-((2-methoxyphenyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | | LCMS: Anal. Calcd. for $C_{45}H_{45}N_7O_5$: 763; found: 764 $(M+H)^+$. |
| 84-66 | methyl ((1R)-2-((2S)-2-(5-(4'-(2-((2S)-1-((2-chlorophenyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | | LCMS: Anal. Calcd. for $C_{44}H_{42}ClN_7O_4$: 767; found: 768 $(M+H)^+$. |
| 84-67 | methyl ((1R)-2-((2S)-2-(5-(4'-(2-((2S)-1-((3-chlorophenyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | | LCMS: Anal. Calcd. for $C_{44}H_{42}ClN_7O_4$: 767; found: 768 $(M+H)^+$. |
| 84-68 | methyl ((1R)-2-((2S)-2-(5-(4'-(2-((2S)-1-((4-chlorophenyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | | LCMS: Anal. Calcd. for $C_{44}H_{42}ClN_7O_4$: 767; found: 768 $(M+H)^+$. |
| 84-69 | methyl ((1R)-2-((2S)-2-(5-(4'-(2-((2S)-1-((2-methylphenyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | | LCMS: Anal. Calcd. for $C_{45}H_{45}N_7O_4$: 747; found: 748 $(M+H)^+$. |

| Example | Compound Name | R group | Retention time (LC-Condition); homogeneity index MS data |
|---|---|---|---|
| 84-70 | methyl ((1R)-2-((2S)-2-(5-(4'-(2-((2S)-1-((4-methylphenyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 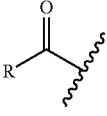 | LCMS: Anal. Calcd. for $C_{45}H_{45}N_7O_4$: 747; found: 748 $(M + H)^+$. |
| 84-71 | methyl ((1R)-2-((2S)-2-(5-(4'-(2-((2S)-1-((3-methylphenyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 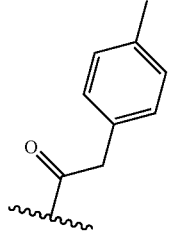 | LCMS: Anal. Calcd. for $C_{45}H_{45}N_7O_4$: 747; found: 748 $(M + H)^+$. |
| 84-72 | methyl ((1R)-2-((2S)-2-(5-(4'-(2-((2S)-1-((2-methyl-1,3-thiazol-4-yl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 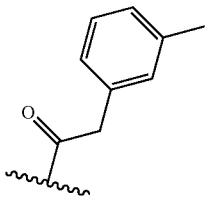 | LCMS: Anal. Calcd. for $C_{42}H_{42}N_8O_4S$: 754; found: 755 $(M + H)^+$. |
| 84-73 | methyl ((1R)-2-oxo-1-phenyl-2-((2S)-2-(5-(4'-(2-((2S)-1-(3-thienylacetyl)-2-pyrrolidinyl)-1H-imidazol-5-yl)-4-biphenylyl)-1H-imidazol-2-yl)-1-pyrrolidinyl)ethyl)carbamate | 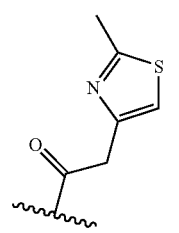 | LCMS: Anal. Calcd. for $C_{42}H_{41}N_7O_4S$: 739; found: 740 $(M + H)^+$. |
| 84-74 | methyl ((1R)-2-((2S)-2-(5-(4'-(2-((2S)-1-((3-methyl-5-isoxazolyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 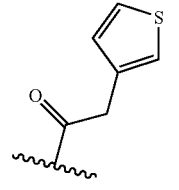 | LCMS: Anal. Calcd. for $C_{42}H_{42}N_8O_5$: 738; found: 739 $(M + H)^+$. |
| 84-75 | methyl ((1R)-2-((2S)-2-(5-(4'-(2-((2S)-1-(cyclohexylacetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 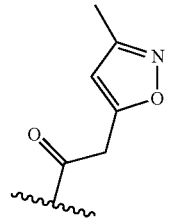 | LCMS: Anal. Calcd. for $C_{44}H_{49}N_7O_4$: 739; found: 740 $(M + H)^+$. |

-continued

| Example | Compound Name | R⤳⟨C=O⟩ group | Retention time (LC-Condition); homogeneity index MS data |
|---------|---------------|---|---|
| 84-76 | methyl ((1R)-2-oxo-1-phenyl-2-((2S)-2-(5-(4'-(2-((2S)-1-((2R)-2-phenylpropanoyl)-2-pyrrolidinyl)-1H-imidazol-5-yl)-4-biphenylyl)-1H-imidazol-2-yl)-1-pyrrolidinyl)ethyl)carbamate | 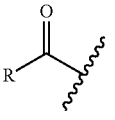 | LCMS: Anal. Calcd. for C$_{45}$H$_{45}$N$_7$O$_4$: 747; found: 748 (M + H)$^+$. |
| 84-77 | methyl ((1R)-2-oxo-1-phenyl-2-((2S)-2-(5-(4'-(2-((2S)-1-((1-phenylcyclopropyl)carbonyl)-2-pyrrolidinyl)-1H-imidazol-5-yl)-4-biphenylyl)-1H-imidazol-2-yl)-1-pyrrolidinyl)ethyl)carbamate | 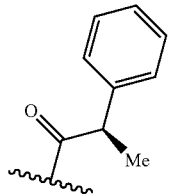 | LCMS: Anal. Calcd. for C$_{46}$H$_{45}$N$_7$O$_4$: 759; found: 760 (M + H)$^+$. |
| 84-78 | methyl ((1R)-2-((2S)-2-(5-(4'-(2-((2S)-1-((1-(4-chlorophenyl)cyclopropyl)carbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | 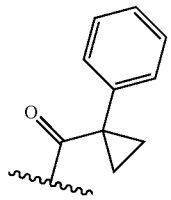 | LCMS: Anal. Calcd. for C$_{46}$H$_{44}$ClN$_7$O$_4$: 793; found: 794 (M + H)$^+$. |
| 84-79 | methyl ((1R)-2-((2S)-2-(5-(4'-(2-((2S)-1-(2-(4-chlorophenyl)-2-methylpropanoyl)-2-pyrrolidinyl)-1H-imidazol-5-yl)-4-biphenylyl)-1H-imidazol-2-yl)-1-pyrrolidinyl)-2-oxo-1-phenylethyl)carbamate | 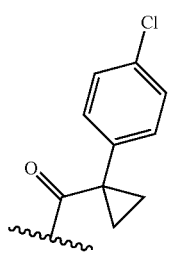 | LCMS: Anal. Calcd. for C$_{46}$H$_{46}$ClN$_7$O$_4$: 795; found: 796 (M + H)$^+$. |
| 84-80 | methyl ((1R)-2-((2S)-2-(5-(4'-(2-((2S)-1-((2R)-2-methoxy-2-phenylacetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 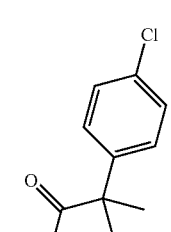 | LCMS: Anal. Calcd. for C$_{45}$H$_{45}$N$_7$O$_5$: 763; found: 764 (M + H)$^+$. |
| 84-81 | methyl ((1R)-2-oxo-1-phenyl-2-((2S)-2-(5-(4'-(2-((2S)-1-((2S)-3,3,3-trifluoro-2-methoxy-2-phenylpropanoyl)-2-pyrrolidinyl)-1H-imidazol-5-yl)-4-biphenylyl)-1H-imidazol-2-yl)-1-pyrrolidinyl)ethyl)carbamate | 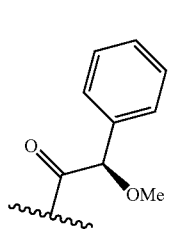 | LCMS: Anal. Calcd. for C$_{46}$H$_{44}$F$_3$N$_7$O$_5$: 831; found: 832 (M + H)$^+$. |

-continued

| Example | Compound Name | 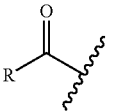 | Retention time (LC-Condition); homogeneity index MS data |
|---------|---------------|---|---|
| 84-82 | (1R)-2-((2S)-2-(5-(4'-(2-((2S)-1-((2R)-2-((methoxycarbonyl)amino)-2-phenylacetyl)-2-pyrrolidinyl)-1H-imidazol-5-yl)-4-biphenylyl)-1H-imidazol-2-yl)-1-pyrrolidinyl)-2-oxo-1-phenylethyl acetate | 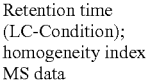 | LCMS: Anal. Calcd. for $C_{46}H_{45}N_7O_6$: 791; found: 792 $(M + H)^+$. |
| 84-83 | (1S)-2-((2S)-2-(5-(4'-(2-((2S)-1-((2R)-2-((methoxycarbonyl)amino)-2-phenylacetyl)-2-pyrrolidinyl)-1H-imidazol-5-yl)-4-biphenylyl)-1H-imidazol-2-yl)-1-pyrrolidinyl)-2-oxo-1-phenylethyl acetate | 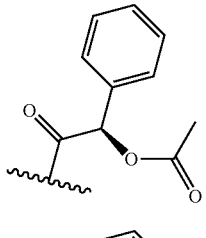 | LCMS: Anal. Calcd. for $C_{46}H_{45}N_7O_6$: 791; found: 792 $(M + H)^+$. |
| 84-84 | methyl ((1R)-2-((2S)-2-(5-(4'-2-((2S)-1-((2-(4-morpholinylmethyl)phenyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 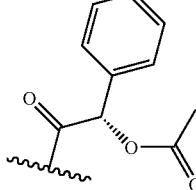<br>Cap-41 | LCMS: Anal. Calcd. for $C_{49}H_{52}N_8O_5$: 832; found: 833 $(M + H)^+$. |
| 84-85 | methyl ((1R)-2-oxo-1-phenyl-(2-((2S-2-(5-(4'-(2-((2S)-1-((2-(1-piperidinylmethyl)phenyl)acetyl)-2-pyrrolidinyl)-1H-imidazol-5-yl)-4-biphenylyl)-1H-imidazol-2-yl)-1-pyrrolidinyl)ethyl)carbamate | 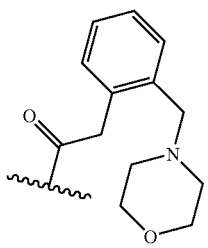<br>Cap-42 | LCMS: Anal. Calcd. for $C_{50}H_{54}N_8O_4$: 830; found: 831 $(M + H)^+$. |
| 84-86 | methyl ((1R)-2-oxo-1-phenyl-(2-((2S-2-(5-(4'-(2-((2S)-1-((2-(1-pyrrolidinylmethyl)phenyl)acetyl)-2-pyrrolidinyl)-1H-imidazol-5-yl)-4-biphenylyl)-1H-imidazol-2-yl)-1-pyrrolidinyl)ethyl)carbamate | 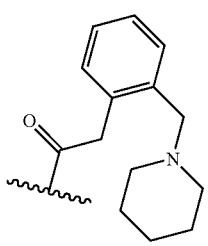<br>Cap-43 | LCMS: Anal. Calcd. for $C_{49}H_{52}N_8O_4$: 816; found: 816 $(M + H)^+$. |
| 84-87 | methyl ((1R)-2-((2S)-2-(5-(4'-(2-((2S)-1-((2-((dimethylamino)methyl)phenyl)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 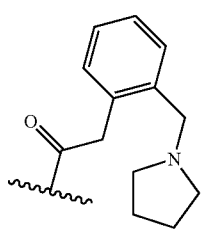<br>Cap-44 | LCMS: Anal. Calcd. for $C_{47}H_{50}N_8O_4$: 790; found: 791 $(M + H)^+$. |

Examples 85-94

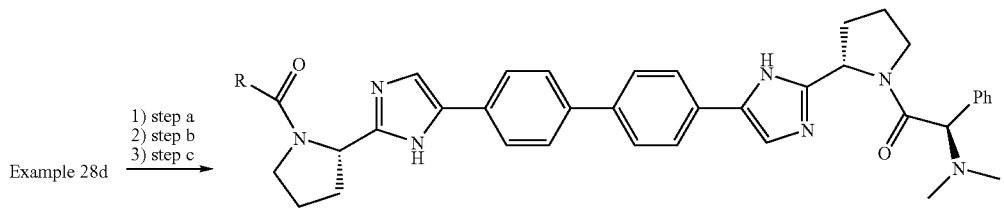

step a: Cap with cap-1 as in Example 28
step b: Same procedure as in conversion of Example 1d to 1e
step c: As in the last step of Example 1 using 1.1 equiv. of the appropriate carboxylic acid and HATU

| Example | Compound Name | R group | Retention time (LC-Condition); homogeneity index MS data |
|---|---|---|---|
| 85 | (1R)-N,N-dimethyl-2-oxo-1-phenyl-2-((2S)-2-(5-(4'-(2-((2S)-1-(3-pyridinylacetyl)-2-pyrrolidinyl)-1H-imidazol-5-yl)-4-biphenylyl)-1H-imidazol-2-yl)-1-pyrrolidinyl)ethanamine | 3-pyridinyl-CH$_2$-C(O)- | 1.64 minutes (Cond. 2); >98%; LC/MS: Anal. Calcd. for [M + H]$^+$ C$_{43}$H$_{45}$N$_8$O$_2$: 705.37; found 705.43; HRMS: Anal. Calcd. for [M + H]$^+$ C$_{43}$H$_{45}$N$_8$O$_2$: 705.3665; found 705.3675 |
| 86 | (1R)-N,N-dimethyl-2-oxo-1-phenyl-2-((2S)-2-(5-(4'-(2-((2S)-1-((2R)-tetrahydro-2-furanylcarbonyl)-2-pyrrolidinyl)-1H-imidazol-5-yl)-4-biphenylyl)-1H-imidazol-2-yl)-1-pyrrolidinyl)ethanamine | (2R)-tetrahydrofuran-2-yl-C(O)- | 1.73 minutes (Cond. 2); >98%; LC/MS: Anal. Calcd. for [M + H]$^+$ C$_{41}$H$_{46}$N$_7$O$_3$: 684.37; found 684.44; HRMS Anal. Calcd. for [M + H]$^+$ C$_{41}$H$_{46}$N$_7$O$_3$: 684.3662; found 684.3671 |
| 87 | (1R)-N,N-dimethyl-2-oxo-1-phenyl-2-((2S)-2-(5-(4'-(2-((2S)-1-((2S)-tetrahydro-2-furanylcarbonyl)-2-pyrrolidinyl)-1H-imidazol-5-yl)-4-biphenylyl)-1H-imidazol-2-yl)-1-pyrrolidinyl)ethanamine | (2S)-tetrahydrofuran-2-yl-C(O)- | 1.12 minutes (Cond. 2); >98%; LC/MS: Anal. Calcd. for [M + H]$^+$ C$_{41}$H$_{46}$N$_7$O$_3$: 684.37; found 684.68; HRMS Anal. Calcd. for [M + H]$^+$ C$_{41}$H$_{46}$N$_7$O$_3$: 684.3662; found 684.3692 |
| 88 | (1R)-N,N-dimethyl-2-((2S)-2-(5-(4'-(2-((2S)-1-((1-methyl-1H-imidazol-4-yl)acetyl)-2-pyrrolidinyl)-1H-imidazol-5-yl)-4-biphenylyl)-1H-imidazol-2-yl)-1-pyrrolidinyl)-2-oxo-1-phenylethanamine | 1-methyl-1H-imidazol-4-yl-CH$_2$-C(O)- | 1.66 minutes (Cond. 2); >98%; LC/MS: Anal. Calcd. for [M + H]$^+$ C$_{42}$H$_{46}$N$_9$O$_2$: 708.38; found 708.36 |
| 89 | (1R)-N,N-dimethyl-2-((2S)-2-(5-(4'-(2-((2S)-1-((2R)-2-(4-morpholinyl)-2-phenylacetyl)-2-pyrrolidinyl)-1H-imidazol-5-yl)-4-biphenylyl)-1H-imidazol-2-yl)-1-pyrrolidinyl)-2-oxo-1-phenylethanamine | (2R)-2-phenyl-2-morpholinyl-C(O)- | 1.70 minutes (Cond. 2); >98%; LC/MS: Anal. Calcd. for [M + H]$^+$ C$_{40}$H$_{45}$N$_8$O$_4$: 701.36; found 701.34; HRMS: Anal. Calcd. for [M + H]$^+$ C$_{40}$H$_{45}$N$_8$O$_4$: 701.3564; found 701.3576 |

Cap-6

| Example | Compound Name | R group structure | Retention time (LC-Condition); homogeneity index MS data |
|---|---|---|---|
| 90 | (1R)-N,N-dimethyl-2-oxo-1-phenyl-2-((2S)-2-(5-(4'-(2-((2S)-1-((2R)-2-phenyl-2-(1-pyrrolidinyl)acetyl)-2-pyrrolidinyl)-1H-imidazol-5-yl)-4-biphenylyl)-1H-imidazol-2-yl)-1-pyrrolidinyl)ethanamine | Cap-5 | 1.80 minutes (Cond. 2); >98%; LC/MS: Anal. Calcd. for [M + H]$^+$ C$_{48}$H$_{53}$N$_8$O$_2$: 773.43; found 773.42; HRMS: Anal. Calcd. for [M + H]$^+$ C$_{48}$H$_{53}$N$_6$O$_2$: 773.4291; found 773.4309 |
| 91 | methyl (2-((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)-2-oxoethyl)carbamate |  | 1.66 minutes (Cond. 2); >98%; LC/MS: Anal. Calcd. for [M + H]$^+$ C$_{42}$H$_{46}$N$_9$O$_2$: 708.38; found 708.36; HRMS: Anal. Calcd. for [M + H]$^+$ C$_{42}$H$_{46}$N$_9$O$_2$: 708.3774; found 708.3770 |
| 92 | methyl ((1S)-2-((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)-1-methyl-2-oxoethyl)carbamate | Cap-12 | 1.73 minutes (Cond. 2); >98%; LC/MS: Anal. Calcd. for [M + H]$^+$ C$_{41}$H$_{47}$N$_8$O$_4$: 715.37; found 715.41; HRMS: Anal. Calcd. for [M + H]$^+$ C$_{41}$H$_{47}$N$_8$O$_4$: 715.3720; found 715.3729 |
| 93 | (1R)-N,N-dimethyl-2-((2S)-2-(5-(4'-(2-((2S)-1-(4-morpholinylcarbonyl)-2-pyrrolidinyl)-1H-imidazol-5-yl)-4-biphenylyl)-1H-imidazol-2-yl)-1-pyrrolidinyl)-2-oxo-1-phenylethanamine |  | 1.76 minutes (Cond. 2); >98%; LC/MS: Anal. Calcd. for [M + H]$^+$ C$_{41}$H$_{47}$N$_8$O$_3$: 699.38; found 699.45; HRMS: Anal. Calcd. for [M + H]$^+$ C$_{41}$H$_{47}$N$_8$O$_3$: 699.3771; found 699.3803 |
| 94 | (1R)-N,N-dimethyl-2-oxo-1-phenyl-2-((2S)-2-(5-(4'-(2-((2S)-1-(1-pyrrolidinylcarbonyl)-2-pyrrolidinyl)-1H-imidazol-5-yl)-4-biphenylyl)-1H-imidazol-2-yl)-1-pyrrolidinyl)ethanamine |  | 1.86 minutes (Cond. 2); >98%; LC/MS: Anal. Calcd. for [M + H]$^+$ C$_{41}$H$_{47}$N$_8$O$_2$: 683.38; found 683.46; HRMS: Anal. Calcd. for [M + H]$^+$ C$_{41}$H$_{47}$N$_8$O$_2$: 683.3822; found 683.3835 |

-continued

| Example | Compound Name | R group (R-C(=O)-) | Retention time (LC-Condition); homogeneity index MS data |
|---|---|---|---|
| 94-1 | (2S)-1-((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)-2-(2-fluorophenyl)-1-oxo-2-propanol | (structure with OH, methyl, 2-fluorophenyl) | $^1$HNMR (400 MHz, CD$_3$OD) δ 7.90-7.84 (m, 9 H), 7.79-7.73 (m, 2 H), 7.67-7.65 (m, 1 H), 7.63-7.52 (m, 5 H), 7.39-7.36 (m, 1 H), 7.30-7.26 (m, 1 H), 7.13-7.08 (m, 1 H), 6.93-6.88 (m, 0.5 H), 6.72-6.67 (m, 0.5 H), 5.51 (s, 0.2 H), 5.46 (s, 0.8 H), 5.33-5.30 (m, 1 H), 5.28-5.24 (m, 1 H), 4.05-3.94 (m, 2 H), 3.84-3.73 (m, 1 H), 3.69-3.55 (m, 1 H), 3.21-3.04 (m, 2 H), 2.79 (br s, 6 H), 2.39-2.33 (m, 2 H), 2.21-1.93 (m, 5 H), 1.65 (d, J = 4.55 Hz, 3 H).; LCMS: Anal. Calcd. for C$_{45}$H$_{46}$FN$_7$O$_3$: 751; found: 752 (M + H)$^+$. |
| 94-2 | (5R)-5-(((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)carbonyl)-2-pyrrolidinone | (pyrrolidinone structure) | LCMS: Anal. Calcd. for C$_{41}$H$_{44}$N$_8$O$_3$: 696; found: 697 (M + H)$^+$. |
| 94-3 | 1-((1R)-2-((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)-2-oxo-1-phenylethyl)-4-methyl-4-piperidinol | (structure with 4-methyl-4-hydroxypiperidine, phenyl) Cap-15 | LCMS: Anal. Calcd. for C$_{50}$H$_{56}$N$_8$O$_3$: 816; found: 817 (M + H)$^+$. |
| 94-4 | tert-butyl (4R)-4-(((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)carbonyl)-1,3-thiazolidine-3-carboxylate | (N-Boc thiazolidine structure) | LCMS: Anal. Calcd. for C$_{45}$H$_{52}$N$_8$O$_4$S: 800; found: 801 (M + H)$^+$. |
| 94-5 | tert-butyl (1-(((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)carbonyl)cyclopentyl)carbamate | (BocHN-cyclopentyl structure) | LCMS: Anal. Calcd. for C$_{47}$H$_{56}$FN$_8$O$_4$: 796; found: 797 (M + H)$^+$. |

-continued

| Example | Compound Name | R (acyl group structure) | Retention time (LC-Condition); homogeneity index MS data |
|---|---|---|---|
| 94-6 | N-(2-((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)-2-oxoethyl)benzamide | Ph-C(O)-NH-CH2-C(O)- | LCMS: Anal. Calcd. for $C_{45}H_{46}FN_8O_3$: 746; found: 747 $(M + H)^+$. |
| 94-7 | (1R)-N,N-dimethyl-2-((2S)-2-(5-(4'-(2-((2S)-1-(4-(4-methyl-1-piperazinyl)benzoyl)-2-pyrrolidinyl)-1H-imidazol-5-yl)-4-biphenylyl)-1H-imidazol-2-yl)-1-pyrrolidinyl)-2-oxo-1-phenylethanamine | 4-(4-methylpiperazin-1-yl)benzoyl | LCMS: Anal. Calcd. for $C_{48}H_{53}N_9O_2$: 787; found: 788 $(M + H)^+$. |
| 94-8 | (1R)-N,N-dimethyl-2-oxo-1-phenyl-2-((2S)-2-(5-(4'-(2-((2S)-1-((5-phenyl-2-thienyl)carbonyl)-2-pyrrolidinyl)-1H-imidazol-5-yl)-4-biphenylyl)-1H-imidazol-2-yl)-1-pyrrolidinyl)ethanamine | 5-phenylthiophene-2-carbonyl | LCMS: Anal. Calcd. for $C_{47}H_{45}N_7O_2S$: 771; found: 772 $(M + H)^+$. |
| 94-9 | (1R)-N,N-dimethyl-2-((2S)-2-(5-(4'-(2-((2S)-1-(4-(4-morpholinyl)benzoyl)-2-pyrrolidinyl)-1H-imidazol-5-yl)-4-biphenylyl)-1H-imidazol-2-yl)-1-pyrrolidinyl)-2-oxo-1-phenylethanamine | 4-(morpholin-4-yl)benzoyl | LCMS: Anal. Calcd. for $C_{47}H_{50}N_8O_3$: 774; found: 775 $(M + H)^+$. |
| 94-10 | (1R)-N,N-dimethyl-2-oxo-1-phenyl-2-((2S)-2-(5-(4'-(2-((2S)-1-((4-phenyl-1,2,3-thiadiazol-5-yl)carbonyl)-2-pyrrolidinyl)-1H-imidazol-5-yl)-4-biphenylyl)-1H-imidazol-2-yl)-1-pyrrolidinyl)ethanamine | 4-phenyl-1,2,3-thiadiazole-5-carbonyl | LCMS: Anal. Calcd. for $C_{45}H_{43}N_9O_2S$: 773; found: 774 $(M + H)^+$. |
| 94-11 | (1R)-N,N-dimethyl-2-oxo-1-phenyl-2-((2S)-2-(5-(4'-(2-((2S)-1-((2-phenyl-1,3-thiazol-4-yl)carbonyl)-2-pyrrolidinyl)-1H-imidazol-5-yl)-4-biphenylyl)-1H-imidazol-2-yl)-1-pyrrolidinyl)ethanamine | 2-phenyl-1,3-thiazole-4-carbonyl | LCMS: Anal. Calcd. for $C_{46}H_{44}N_8O_2S$: 772; found: 773 $(M + H)^+$. |
| 94-12 | tert-butyl 4-(((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)carbonyl)-4-methyl-1-piperidinecarboxylate | 1-Boc-4-methylpiperidine-4-carbonyl | LCMS: Anal. Calcd. for $C_{48}H_{58}N_8O_4$: 810; found: 811 $(M + H)^+$. |
| 94-13 | 3-(2-((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)-2-oxoethyl)phenol | (3-hydroxyphenyl)acetyl | LCMS: Anal. Calcd. for $C_{44}H_{45}N_7O_3$: 719; found: 720 $(M + H)^+$. |

| Example | Compound Name | R group | Retention time (LC-Condition); homogeneity index MS data |
|---|---|---|---|
| 94-14 | 3-((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)-N,N-dimethyl-3-oxo-1-propanamine | | LCMS: Anal. Calcd. for $C_{41}H_{48}N_8O_2$: 684; found: 685 $(M + H)^+$. |
| 94-15 | (4-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)phenyl)methanol | | LCMS: Anal. Calcd. for $C_{44}H_{45}N_7O_3$: 719; found: 720 $(M + H)^+$. |
| 94-16 | (1R)-2-((2S)-2-(5-(4'-(2-((2S)-1-(1H-indol-3-ylcarbonyl)-2-pyrrolidinyl)-1H-imidazol-5-yl)-4-biphenylyl)-1H-imidazol-2-yl)-1-pyrrolidinyl)-N,N-dimethyl-2-oxo-1-phenylethanamine | | LCMS: Anal. Calcd. for $C_{45}H_{44}N_8O_2$: 728; found: 729 $(M + H)^+$. |
| 94-17 | (1R)-2-((2S)-2-(5-(4'-(2-((2S)-1-(((3R)-1-benzyl-3-pyrrolidinyl)carbonyl)-2-pyrrolidinyl)-1H-imidazol-5-yl)-4-biphenylyl)-1H-imidazol-2-yl)-1-pyrrolidinyl)-N,N-dimethyl-2-oxo-1-phenylethanamine | | LCMS: Anal. Calcd. for $C_{48}H_{52}N_8O$: 772; found: 773 $(M + H)^+$. |
| 94-18 | tert-butyl (2S)-2-(2-((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)-2-oxoethyl)-1-pyrrolidinecarboxylate | | LCMS: Anal. Calcd. for $C_{47}H_{56}N_8O_4$: 796; found: 797 $(M + H)^+$. |
| 94-19 | (1R)-N,N-dimethyl-2-((2S)-2-(5-(4'-(2-((2S)-1-((5-methyl-1H-pyrazol-3-yl)acetyl)-2-pyrrolidinyl)-1H-imidazol-5-yl)-4-biphenylyl)-1H-imidazol-2-yl)-1-pyrrolidinyl)-2-oxo-1-phenylethanamine | | LCMS: Anal. Calcd. for $C_{42}H_{45}N_9O_2$: 707; found: 708 $(M + H)^+$. |
| 94-20 | tert-butyl (2R)-2-(((2S)-2-(5-(4'-2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)carbonyl)-1-piperidinecarboxylate | | LCMS: Anal. Calcd. for $C_{47}H_{56}N_8O_4$: 796; found: 797 $(M + H)^+$. |
| 94-21 | tert-butyl ((1S,3R)-3-(((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)carbonyl)cyclopentyl)carbamate | | LCMS: Anal. Calcd. for $C_{47}H_{56}N_8O_4$: 796; found: 797 $(M + H)^+$. |

| Example | Compound Name | R group structure | Retention time (LC-Condition); homogeneity index MS data |
|---------|---------------|-------------------|----------------------------------------------------------|
| 94-22 | (1R)-N,N-dimethyl-2-oxo-1-phenyl-2-((2S)-2-(5-(4'-(2-((2S)-1-(3-(1-piperidinyl)propanoyl)-2-pyrrolidinyl)-1H-imidazol-5-yl)-4-biphenylyl)-1H-imidazol-2-yl)-1-pyrrolidinyl)ethanamine | 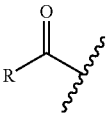 | LCMS: Anal. Calcd. for $C_{44}H_{52}N_8O_2$: 724; found: 725 $(M + H)^+$. |
| 94-23 | (2-(((2S)-2-(5-(4'-(2-((2S)-1-((2R)-1-(dimethylamino)-2-phenylacetyl)-2-pyrrolidinyl)-1H-imidazol-5-yl)-4-biphenylyl)-1H-imidazol-2-yl)-1-pyrrolidinyl)carbonyl)phenyl)phenyl)methanone | 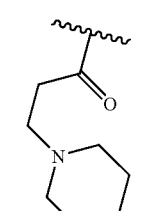 | LCMS: Anal. Calcd. for $C_{50}H_{47}N_7O_3$: 793; found: 794 $(M + H)^+$. |
| 94-24 | (1R)-2-((2S)-2-(5-(4'-(2-((2S)-1-((2-methoxyphenoxy)acetyl)-2-pyrrolidinyl)-1H-imidazol-5-yl)-4-biphenylyl)-1H-imidazol-2-yl)-1-pyrrolidinyl)-N,N-dimethyl-2-oxo-1-phenylethanamine | 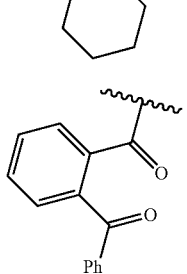 | LCMS: Anal. Calcd. for $C_{45}H_{47}N_7O_4$: 749; found: 750 $(M + H)^+$. |
| 94-25 | tert-butyl 3-(((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)carbonyl)-1-azetidinecarboxylate | 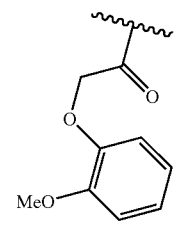 | LCMS: Anal. Calcd. for $C_{45}H_{52}N_8O_4$: 768; found: 769 $(M + H)^+$. |
| 94-26 | (1R)-2-((2S)-2-(5-(4'-(2-((2S)-1-(((3S)-1-benzyl-3-pyrrolidinyl)carbonyl)-2-pyrrolidinyl)-1H-imidazol-5-yl)-4-biphenylyl)-1H-imidazol-2-yl)-1-pyrrolidinyl)-N,N-dimethyl-2-oxo-1-phenylethanamine | 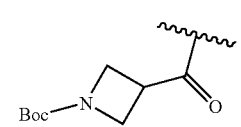 | LCMS: Anal. Calcd. for $C_{48}H_{52}N_8O_2$: 772; found: 773 $(M + H)^+$. |
| 94-27 | (1R)-N,N-dimethyl-2-oxo-1-phenyl-2-((2S)-2-(5-(4'-(2-((2S)-1-(3-(1-pyrrolidinyl)benzoyl)-2-pyrrolidinyl)-1H-imidazol-5-yl)-4-biphenylyl)-1H-imidazol-2-yl)-1-pyrrolidinyl)ethanamine | 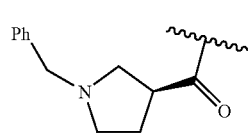 | LCMS: Anal. Calcd. for $C_{47}H_{50}N_8O_2$: 758; found: 759 $(M + H)^+$. |
| 94-28 | tert-butyl (2-(((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)carbonyl)phenyl)carbamate | 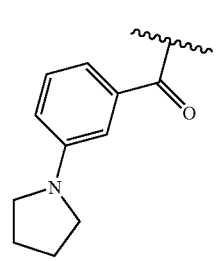 | LCMS: Anal. Calcd. for $C_{48}H_{52}N_8O_4$: 804; found: 805 $(M + H)^+$. |

| Example | Compound Name | R group | Retention time (LC-Condition); homogeneity index MS data |
|---|---|---|---|
| 94-29 | tert-butyl (3R)-3-(((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)carbonyl)-1-piperidinecarboxylate | N-Boc piperidin-3-yl | LCMS: Anal. Calcd. for $C_{47}H_{56}N_8O_4$: 796; found: 797 $(M + H)^+$. |
| 94-30 | (1R)-N,N-dimethyl-2-oxo-1-phenyl-2-((2S)-2-(5-(4'-(2-((2S)-(1-((1-(trifluoromethyl)cyclopropyl)carbonyl)-2-pyrrolidinyl)-1H-imidazol-5-yl)-4-biphenylyl)-1H-imidazol-2-yl)-1-pyrrolidinyl)ethanamine | 1-(trifluoromethyl)cyclopropyl | LCMS: Anal. Calcd. for $C_{41}H_{42}F_3N_7O_2$: 721; found: 722 $(M + H)^+$. |
| 94-31 | 4-(((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)carbonyl)-N,N-dimethylaniline | 4-(dimethylamino)phenyl | LCMS: Anal. Calcd. for $C_{45}H_{48}N_8O_2$: 732; found: 733 $(M + H)^+$. |
| 94-32 | (3-(((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)carbonyl)phenyl)(phenyl)methanone | 3-benzoylphenyl | LCMS: Anal. Calcd. for $C_{50}H_{47}N_7O_3$: 793; found: 794 $(M + H)^+$. |
| 94-33 | tert-butyl (cis-4-(((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)carbonyl)cyclohexyl)carbamate | cis-4-(BocNH)cyclohexyl | LCMS: Anal. Calcd. for $C_{48}H_{58}N_8O_4$: 810; found: 811 $(M + H)^+$. |
| 94-34 | tert-butyl 4-(((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)carbonyl)-1-piperidinecarboxylate | N-Boc piperidin-4-yl | LCMS: Anal. Calcd. for $C_{47}H_{56}N_8O_4$: 796; found: 797 $(M + H)^+$. |
| 94-35 | tert-butyl (cis-4-(((2S)-2-(5-(4'-(2-((2S)-1-((2R)-1-(dimethylamino)-2-phenylacetyl)-2-pyrrolidinyl)-1H-imidazol-5-yl)-4-biphenylyl)-1H-imidazol-2-yl)-1-pyrrolidinyl)carbonyl)cyclohexyl)carbamate | cis-4-(BocNH)cyclohexyl | LCMS: Anal. Calcd. for $C_{48}H_{58}N_8O_4$: 810; found: 811 $(M + H)^+$. |
| 94-36 | (1R)-2-((2S)-2-(5-(4'-(2-((2S)-1-(diphenylacetyl)-2-pyrrolidinyl)-1H-imidazol-5-yl)-4-biphenylyl)-1H-imidazol-2-yl)-1-pyrrolidinyl)-N,N-dimethyl-2-oxo-1-phenylethanamine | diphenylmethyl (CHPh$_2$) | LCMS: Anal. Calcd. for $C_{50}H_{49}N_7O_2$: 779; found: 780 $(M + H)^+$. |

-continued

| Example | Compound Name | 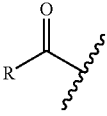 | Retention time (LC-Condition); homogeneity index MS data |
|---|---|---|---|
| 94-37 | 5-((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)-5-oxo-2-pentanone | 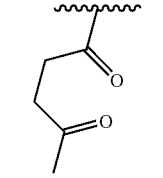 | LCMS: Anal. Calcd. for $C_{41}H_{45}N_7O_3$: 683; found: 684 $(M + H)^+$. |
| 94-38 | (1R)-2-((2S)-2-(5-(4'-(2-((2S)-1-(2-fluorobenzoyl)-2-pyrrolidinyl)-1H-imidazol-5-yl)-4-biphenylyl)-1H-imidazol-2-yl)-1-pyrrolidinyl)-N,N-dimethyl-2-oxo-1-phenylethanamine |  | LCMS: Anal. Calcd. for $C_{43}H_{42}FN_7O_2$: 707; found: 708 $(M + H)^+$. |
| 94-39 | (1R)-2-((2S)-2-(5-(4'-(2-((2S)-1-(2-biphenylylcarbonyl)-2-pyrrolidinyl)-1H-imidazol-5-yl)-4-biphenylyl)-1H-imidazol-2-yl)-1-pyrrolidinyl)-N,N-dimethyl-2-oxo-1-phenylethanamine | 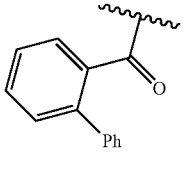 | LCMS: Anal. Calcd. for $C_{49}H_{47}N_7O_2$: 765; found: 766 $(M + H)^+$. |
| 94-40 | (1R)-2-((2S)-2-(5-(4'-(2-((2S)-1-(2-benzylbenzoyl)-2-pyrrolidinyl)-1H-imidazol-5-yl)-4-biphenylyl)-1H-imidazol-2-yl)-1-pyrrolidinyl)-N,N-dimethyl-2-oxo-1-phenylethanamine | 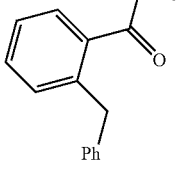 | LCMS: Anal. Calcd. for $C_{50}H_{49}N_7O_2$: 779; found: 780 $(M + H)^+$. |
| 94-41 | 4-((1E)-3-((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)-3-oxo-1-propen-1-yl)-N,N-dimethylaniline | 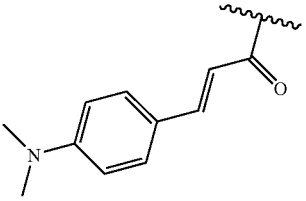 | LCMS: Anal. Calcd. for $C_{47}H_{50}N_8O_2$: 758; found: 759 $(M + H)^+$. |
| 94-42 | (1R)-N,N-dimethyl-2-oxo-1-phenyl-2-((2S)-2-(5-(4'-(2-((2S)-1-(1,3-thiazol-4-ylcarbonyl)-2-pyrrolidinyl)-1H-imidazol-5-yl)-4-biphenylyl)-1H-imidazol-2-yl)-1-pyrrolidinyl)ethanamine | 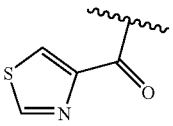 | LCMS: Anal. Calcd. for $C_{40}H_{40}N_8O_2S$: 696; found: 697 $(M + H)^+$. |
| 94-43 | (1R)-2-((2S)-2-(5-(4'-(2-((2S)-1-((((1R,2S,5R)-2-isopropyl-5-methylcylcohexyl)oxy)acetyl)-2-pyrrolidinyl)-1H-imidazol-5-yl)-4-biphenylyl)-1H-imidazol-2-yl)-1-pyrrolidinyl)-N,N-dimethyl-2-oxo-1-phenylethanamine | 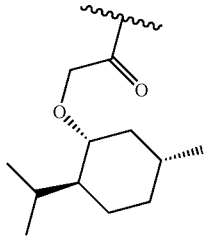 | LCMS: Anal. Calcd. for $C_{48}H_{59}N_7O_3$: 781; found: 782 $(M + H)^+$. |

| Example | Compound Name | R group (Cap) | Retention time (LC-Condition); homogeneity index MS data |
|---|---|---|---|
| 94-44 | 1-(6-chloro-3-pyridinyl)-2-((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)-N,N-dimethyl-2-oxoethanamine | Cap-21 | LCMS: Anal. Calcd. for $C_{45}H_{48}ClN_9O_2$: 781; found: 782 $(M+H)^+$. |
| 94-45 | 2-((2S)-2-(5-(4'-(2-((2S)-1-((2R)-1-(dimethylamino)-2-phenylacetyl)-2-pyrrolidinyl)-1H-imidazol-5-yl)-4-biphenylyl)-1H-imidazol-2-yl)-1-pyrrolidinyl)-N,N-dimethyl-2-oxo-1-(3-pyridinyl)ethanamine | Cap-19 | LCMS: Anal. Calcd. for $C_{45}H_{49}N_9O_2$: 747; found: 748 $(M+H)^+$. |
| 94-46 | 2-((2S)-2-(5-(4'-(2-((2S)-1-((2R)-1-(dimethylamino)-2-phenylacetyl)-2-pyrrolidinyl)-1H-imidazol-5-yl)-4-biphenylyl)-1H-imidazol-2-yl)-1-pyrrolidinyl)-N,N-dimethyl-2-oxo-1-(2-pyridinyl)ethanamine | Cap-20 | LCMS: Anal. Calcd. for $C_{45}H_{49}N_9O_2$: 747; found: 748 $(M+H)^+$. |
| 94-47 | (1R)-N,N-dimethyl-2-oxo-1-phenyl-2-((2S)-2-(5-(4'-(2-((2S)-1-(2-thienylacetyl)-2-pyrrolidinyl)-1H-imidazol-5-yl)-4-biphenylyl)-1H-imidazol-2-yl)-1-pyrrolidinyl)ethanamine | | LCMS: Anal. Calcd. for $C_{42}H_{43}N_7O_2S$: 709; found: 710 $(M+H)^+$. |
| 94-48 | (1R)-N,N-dimethyl-2-oxo-1-phenyl-2-((2S)-2-(5-(4'-(2-((2S)-1-(3-thienylacetyl)-2-pyrrolidinyl)-1H-imidazol-5-yl)-4-biphenylyl)-1H-imidazol-2-yl)-1-pyrrolidinyl)ethanamine | | LCMS: Anal. Calcd. for $C_{42}H_{43}N_7O_2S$: 709; found: 710 $(M+H)^+$. |
| 94-49 | (1R)-N,N-dimethyl-2-((2S)-2-(5-(4'-(2-((2S)-1-(1-naphthylacetyl)-2-pyrrolidinyl)-1H-imidazol-5-yl)-4-biphenylyl)-1H-imidazol-2-yl)-1-pyrrolidinyl)-2-oxo-1-phenylethanamine | | LCMS: Anal. Calcd. for $C_{48}H_{47}N_7O_2$: 753; found: 754 $(M+H)^+$. |

-continued

| Example | Compound Name | R | Retention time (LC-Condition); homogeneity index MS data |
|---|---|---|---|
| 94-50 | (1R)-2-((2S)-2-(5-(4'-(2-((2S)-1-(1H-imidazol-5-ylacetyl)-2-pyrrolidinyl)-1H-imidazol-5-yl)-4-biphenylyl)-1H-imidazol-2-yl)-1-pyrrolidinyl)-N,N-dimethyl-2-oxo-1-phenylethanamine | 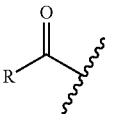 | LCMS: Anal. Calcd. for $C_{41}H_{43}N_9O_2$: 693; found: 694 $(M + H)^+$. |
| 94-51 | (1R)-2-((2S)-2-(5-(4'-(2-((2S)-1-((2-fluorophenyl)acetyl)-2-pyrrolidinyl)-1H-imidazol-5-yl)-4-biphenylyl)-1H-imidazol-2-yl)-1-pyrrolidinyl)-N,N-dimethyl-2-oxo-1-phenylethanamine | 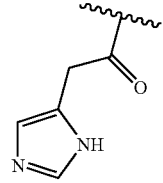 | LCMS: Anal. Calcd. for $C_{44}H_{44}FN_7O_2$: 721; found: 722 $(M + H)^+$. |
| 94-52 | (1R)-2-((2S)-2-(5-(4'-(2-((2S)-1-((3-fluorophenyl)acetyl)-2-pyrrolidinyl)-1H-imidazol-5-yl)-4-biphenylyl)-1H-imidazol-2-yl)-1-pyrrolidinyl)-N,N-dimethyl-2-oxo-1-phenylethanamine | 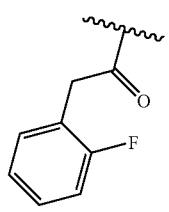 | LCMS: Anal. Calcd. for $C_{44}H_{44}FN_7O_2$: 721; found: 722 $(M + H)^+$. |
| 94-53 | (1R)-2-((2S)-2-(5-(4'-(2-((2S)-1-((4-fluorophenyl)acetyl)-2-pyrrolidinyl)-1H-imidazol-5-yl)-4-biphenylyl)-1H-imidazol-2-yl)-1-pyrrolidinyl)-N,N-dimethyl-2-oxo-1-phenylethanamine | 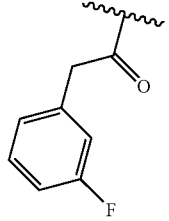 | LCMS: Anal. Calcd. for $C_{44}H_{44}FN_7O_2$: 721; found: 722 $(M + H)^+$. |
| 94-54 | (1R)-2-((2S)-2-(5-(4'-(2-((2S)-1-(1-benzothiophen-3-ylacetyl)-2-pyrrolidinyl)-1H-imidazol-5-yl)-4-biphenylyl)-1H-imidazol-2-yl)-1-pyrrolidinyl)-N,N-dimethyl-2-oxo-1-phenylethanamine | 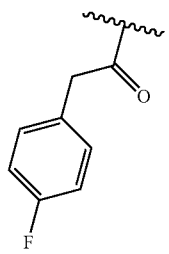 | LCMS: Anal. Calcd. for $C_{46}H_{45}N_7O_2S$: 759; found: 760 $(M + H)^+$. |
| 94-55 | (1R)-2-((2S)-2-(5-(4'-(2-((2S)-1-(1,2-benzisoxazol-3-ylacetyl)-2-pyrrolidinyl)-1H-imidazol-5-yl)-4-biphenylyl)-1H-imidazol-2-yl)-1-pyrrolidinyl)-N,N-dimethyl-2-oxo-1-phenylethanamine | 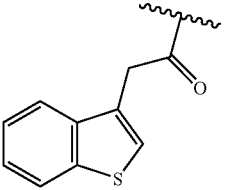 | LCMS: Anal. Calcd. for $C_{45}H_{44}N_8O_3$: 744; found: 745 $(M + H)^+$. |
| 94-56 | (1R)-2-((2S)-2-(5-(4'-(2-((2S)-1-(1H-indol-3-ylacetyl)-2-pyrrolidinyl)-1H-imidazol-5-yl)-4-biphenylyl)-1H-imidazol-2-yl)-1-pyrrolidinyl)-N,N-dimethyl-2-oxo-1-phenylethanamine | 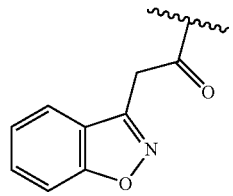 | LCMS: Anal. Calcd. for $C_{46}H_{46}N_8O_2$: 742; found: 743 $(M + H)^+$. |

Examples 95-103

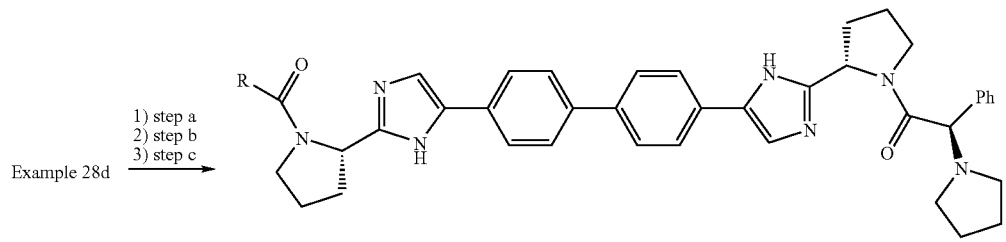

step a: Cap w/cap-5 as in Example 28
step b: Same procedure as in conversion of Example 1d to 1e
step c: As in the last step of Example 1 using 1.1 equiv. of the appropriate carboxylic acid and HATU

| Example | Compound Name | R⧸⧹O (structure) | Retention time (LC-Condition); homogeneity index MS data |
|---|---|---|---|
| 95 | 2-((2S)-1-((2R)-2-phenyl-2-(1-pyrrolidinyl)acetyl)-2-pyrrolidinyl)-5-(4'-(2-((2S)-1-((2S)-tetrahydro-2-furanylcarbonyl)-2-pyrrolidinyl)-1H-imidazol-5-yl)-4-biphenylyl)-1H-imidazol | (tetrahydrofuran-2-carbonyl) | 1.16 minutes (Cond. 1); >98%; LC/MS Anal. Calcd. for [M + H]$^+$ C$_{43}$H$_{48}$N$_7$O$_3$: 710.38; found 710.60 |
| 96 | 4-((1R)-2-oxo-1-phenyl-2-((2S)-2-(5-(4'-(2-((2S)-1-((2R)-2-phenyl-2-(1-pyrrolidinyl)acetyl)-2-pyrrolidinyl)-1H-imidazol-5-yl)-4-biphenylyl)-1H-imidazol-2-yl)-1-pyrrolidinyl)ethyl)morpholine | Cap-6 | 1.82 minutes (Cond. 1); >98%; LC/MS: Anal. Calcd. for [M + H]$^+$ C$_{50}$H$_{55}$N$_8$O$_3$: 815.44; found 815.45; HRMS: Anal. Calcd. for [M + H]$^+$ C$_{50}$H$_{55}$N$_8$O$_3$: 815.4397; found 815.4395 |
| 97 | 1-(2-oxo-1-phenyl-2-((2S)-2-(5-(4'-(2-((2S)-1-((2R)-2-phenyl-2-(1-pyrrolidinyl)acetyl)-2-pyrrolidinyl)-1H-imidazol-5-yl)-4-biphenylyl)-1H-imidazol-2-yl)-1-pyrrolidinyl)ethyl)-4-piperidinol | A single diastereomer Cap-8 | 1.79 minutes (Cond. 2); >98%; LC/MS: Anal. Calcd. for [M + H]$^+$ C$_{51}$H$_{57}$N$_8$O$_3$: 829.46; found 829.43; HRMS: Anal. Calcd. for [M + H]$^+$ C$_{51}$H$_{57}$N$_8$O$_3$: 829.4554; found 829.4585 |

| Example | Compound Name | R group structure | Retention time (LC-Condition); homogeneity index MS data |
|---------|---------------|-------------------|----------------------------------------------------------|
| 98 | 1-methyl-4-(2-oxo-1-phenyl-2-((2S)-2-(5-(4'-(2-((2S)-1-((2R)-2-phenyl-2-(1-pyrrolidinyl)acetyl)-2-pyrrolidinyl)-1H-imidazol-5-yl)-4-biphenylyl)-1H-imidazol-2-yl)-1-pyrrolidinyl)ethyl) piperazine | A single diastereomer Cap-17c | 1.84 minutes (Cond. 2); >98%; LC/MS: Anal. Calcd. for [M + H]$^+$ C$_{51}$H$_{58}$N$_9$O$_2$: 828.47; found 828.45; HRMS: Anal. Calcd. for [M + H]$^+$ C$_{51}$H$_{58}$N$_9$O$_2$: 828.4713; found 828.4722 |
| 99 | (1R)-N,N-diethyl-2-oxo-1-phenyl-2-((2S)-2-(5-(4'-(2-((2S)-1-((2R)-2-phenyl-2-(1-pyrrolidinyl)acetyl)-2-pyrrolidinyl)-1H-imidazol-5-yl)-4-biphenylyl)-1H-imidazol-2-yl)-1-pyrrolidinyl)ethanamine | Cap-2 | 1.86 minutes (Cond. 2); >98%; LC/MS: Anal. Calcd. for [M + H]$^+$ C$_{50}$H$_{57}$N$_8$O$_2$: 801.46; found 801.44; HRMS: Anal. Calcd. for [M + H]$^+$ C$_{50}$H$_{57}$N$_8$O$_2$: 801.4604; found 801.4595 |
| 100 | methyl ((1R)-2-oxo-1-phenyl-2-((2S)-2-(5-(4'-(2-((2S)-1-((2R)-2-phenyl-2-(1-pyrrolidinyl)acetyl)-2-pyrrolidinyl)-1H-imidazol-5-yl)-4-biphenylyl)-1H-imidazol-2-yl)-1-pyrrolidinyl)ethyl) carbamate | Cap-4 | 1.93 minutes (Cond. 2); LC/MS: Anal. Calcd. for [M + H]$^+$ C$_{48}$H$_{51}$N$_8$O$_4$: 803.40; found 803.47; HRMS: Anal. Calcd. for [M + H]$^+$ C$_{48}$H$_{51}$N$_8$O$_4$: 803.4033; found 803.4058 |
| 101 | methyl ((1S)-1-methyl-2-oxo-2-((2S)-2-(5-(4'-(2-((2S)-1-((2R)-2-phenyl-2-(1-pyrrolidinyl)acetyl)-2-pyrrolidinyl)-1H-imidazol-5-yl)-4-biphenylyl)-1H-imidazol-2-yl)-1-pyrrolidinyl)ethyl) carbamate | Cap-12 | 1.80 minutes (Cond. 2); LC/MS: Anal. Calcd. for [M + H]$^+$ C$_{43}$H$_{49}$N$_8$O$_4$: 741.39; found 741.33; HRMS: Anal. Calcd. for [M + H]$^+$ C$_{43}$H$_{49}$N$_8$O$_4$: 741.3877; found 741.3900 |
| 102 | methyl (2-oxo-2-((2S)-2-(5-(4'-(2-((2S)-1-((2R)-2-phenyl-2-(1-pyrrolidinyl)acetyl)-2-pyrrolidinyl)-1H-imidazol-5-yl)-4-biphenylyl)-1H-imidazol-2-yl)-1-pyrrolidinyl)ethyl) carbamate | | 1.80 minutes (Cond. 2); LC/MS: Anal. Calcd. for [M + H]$^+$ C$_{42}$H$_{47}$N$_8$O$_4$: 727.37; found 727.24; HRMS: Anal. Calcd. for [M + H]$^+$ C$_{42}$H$_{47}$N$_8$O$_4$: 727.3720; found 727.3743 |
| 103 | (2S)-N,N-dimethyl-1-oxo-1-((2S)-2-(5-(4'-(2-((2S)-1-((2R)-2-phenyl-2-(1-pyrrolidinyl)acetyl)-2-pyrrolidinyl)-1H-imidazol-5-yl)-4-biphenylyl)-1H-imidazol-2-yl)-1-pyrrolidinyl)-2-propanamine | Cap-13 | 1.69 minutes (Cond. 2); LC/MS: Anal. Calcd. for [M + H]$^+$ C$_{43}$H$_{51}$N$_8$O$_2$: 711.41; found 711.37; HRMS: Anal. Calcd. for [M + H]$^+$ C$_{43}$H$_{51}$N$_8$O$_2$: 711.4135; found 711.4154 |

Examples 103-1 to 103-12

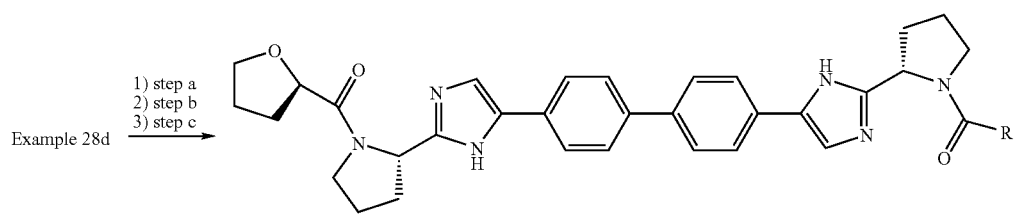

step a: Cap with (R)-2-tetrahydrofuroic acid as in Example 28
step b: Same procedure as in the conversion of Example 1d to 1e
step c: As in the last step of Example 1 using 1.1 equiv. of the appropriate carboxylic acid and HATU

| | | | |
|---|---|---|---|
| 103-1 | 1-(2-oxo-1-phenyl-2-((2S)-2-(5-(4'-(2-((2S)-1-((2R)-tetrahydro-2-furanylcarbonyl)-2-pyrrolidinyl)-1H-imidazol-4-yl)-4-biphenylyl)-1H-imidazol-2-yl)-1-pyrrolidinyl)ethyl)-4-phenylpiperidine | 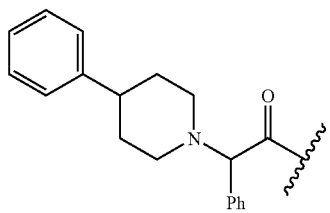<br>Diastereomer 1<br>Cap-17d | RT = 4.80 minutes; HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid; LCMS: Anal. Calcd. for: $C_{50}H_{53}N_7O_3$ 800.03 Found: 800.49 $(M + H)^+$ |
| 103-2 | 1-(2-oxo-1-phenyl-2-((2S)-2-(5-(4'-(2-((2S)-1-((2R)-tetrahydro-2-furanylcarbonyl)-2-pyrrolidinyl)-1H-imidazol-4-yl)-4-biphenylyl)-1H-imidazol-2-yl)-1-pyrrolidinyl)ethyl)-4-phenylpiperidine | 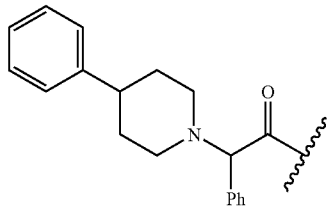<br>Diastereomer 2<br>Cap-17d | RT = 4.59 minutes; HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid; LCMS: Anal. Calcd. for: $C_{50}H_{53}N_7O_3$ 800.03 Found: 800.48 $(M + H)^+$ |
| 103-3 | 1-methyl-4-(2-oxo-1-phenyl-2-((2S)-2-(5-(4'-(2-((2S)-1-((2R)-tetrahydro-2-furanylcarbonyl)-2-pyrrolidinyl)-1H-imidazol-4-yl)-4-biphenylyl)-1H-imidazol-2-yl)-1-pyrrolidinyl)ethyl)piperazine | 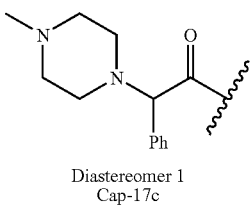<br>Diastereomer 1<br>Cap-17c | RT = 3.36; HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid; LCMS: Anal. Calcd. for: $C_{44}H_{50}N_8O_3$ 738.94 Found: 739.49 $(M + H)^+$ |

| | | | |
|---|---|---|---|
| 103-4 | 1-methyl-4-(2-oxo-1-phenyl-2-((2S)-2-(5-(4'-(2-((2S)-1-((2R)-tetrahydro-2-furanylcarbonyl)-2-pyrrolidinyl)-1H-imidazol-4-yl)-4-biphenylyl)-1H-imidazol-2-yl)-1-pyrrolidinyl)ethyl)piperazine | 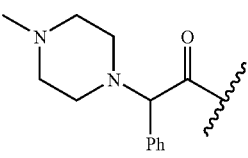<br>Diastereomer 2<br>Cap-17c | RT = 3.47 minutes; HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid; LCMS: Anal. Calcd. for: $C_{44}H_{50}N_8O_3$ 738.94 Found: 739.51 $(M + H)^+$ |
| 103-5 | benzyl 4-(2-oxo-1-phenyl-2-((2S)-2-(5-(4'-(2-((2S)-1-((2R)-tetrahydro-2-furanylcarbonyl)-2-pyrrolidinyl)-1H-imidazol-4-yl)-4-biphenylyl)-1H-imidazol-2-yl)-1-pyrrolidinyl)ethyl)-1-piperazinecarboxylate | 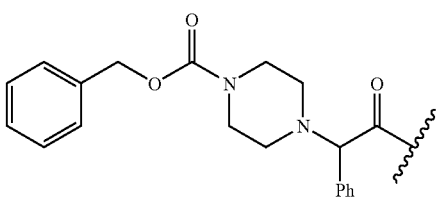<br>Diastereomer 1<br>Cap-17a | RT = 5.00 minutes; HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid; LCMS: Anal. Calcd. for: $C_{51}H_{54}N_8O_5$ 859.05 Found: 859.51 $(M + H)^+$ |
| 103-6 | benzyl 4-(2-oxo-1-phenyl-2-((2S)-2-(5-(4'-(2-((2S)-1-((2R)-tetrahydro-2-furanylcarbonyl)-2-pyrrolidinyl)-1H-imidazol-4-yl)-4-biphenylyl)-1H-imidazol-2-yl)-1-pyrrolidinyl)ethyl)-1-piperazinecarboxylate | 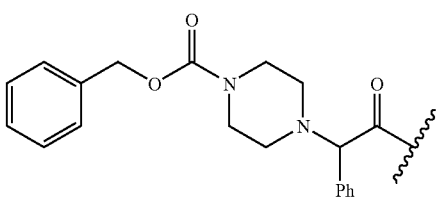<br>Diastereomer 2<br>Cap-17a | RT = 5.10 minutes; HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid; LCMS: Anal. Calcd. for: $C_{51}H_{54}N_8O_5$ 859.05 Found: 859.49 $(M + H)^+$ |
| 103-7 | 1-(2-oxo-1-phenyl-2-((2S)-2-(5-(4'-(2-((2S)-1-((2R)-tetrahydro-2-furanylcarbonyl)-2-pyrrolidinyl)-1H-imidazol-4-yl)-4-biphenylyl)-1H-imidazol-2-yl)-1-pyrrolidinyl)ethyl)piperazine | 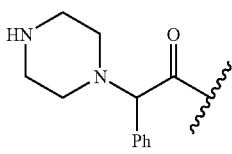<br>prepared by hydrogenolyzing 103-5 | RT = 3.61 minutes; HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid; LCMS: Anal. Calcd. for: $C_{43}H_{48}N_8O_3$ 724.91 Found: 725.47 $(M + H)^+$ |

| | | | |
|---|---|---|---|
| 103-8 | 4-(2-oxo-1-phenyl-2-((2S)-2-(5-(4'-(2-((2S)-1-((2R)-tetrahydro-2-furanylcarbonyl)-2-pyrrolidinyl)-1H-imidazol-4-yl)-4-biphenylyl)-1H-imidazol-2-yl)-1-pyrrolidinyl)ethyl)-2-piperazinone | <br>Cap-17b | RT = 3.97;<br>HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid; LCMS: Anal. Calcd. for: $C_{43}H_{46}N_8O_4$ 738.90 Found: 739.56 $(M + H)^+$ |
| 103-9 | 1-methyl-3-((1R)-2-oxo-1-phenyl-2-((2S)-2-(4-(4'-(2-((2S)-1-((2R)-tetrahydro-2-furanylcarbonyl)-2-pyrrolidinyl)-1H-imidazol-4-yl)-4-biphenylyl)-1H-imidazol-2-yl)-1-pyrrolidinyl)ethyl)urea | 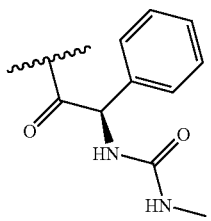 | HPLC XTERRA C-18 4.6 × 30 mm, 0 to 100% B over 4 minutes, 1 minute hold time, A = 90% water, 10% methanol, 0.2% $H_3PO_4$, B = 10% water, 90% methanol, 0.2% $H_3PO_4$, RT = 1.81 minutes, 96% homogeneity index.; LCMS: Anal. Calcd. for $C_{41}H_{44}N_8O_4$: 712.84; found: 713.37 $(M + H)^+$; HRMS: Anal. Calcd. for $C_{41}H_{45}N_8O_4$ 713.3564; found: 713.3564 $(M + H)^+$. |
| 103-10 | 1-ethyl-3-((1R)-2-oxo-1-phenyl-2-((2S)-2-(4-(4'-(2-((2S)-1-((2R)-tetrahydro-2-furanylcarbonyl)-2-pyrrolidinyl)-1H-imidazol-4-yl)-4-biphenylyl)-1H-imidazol-2-yl)-1-pyrrolidinyl)ethyl)urea | 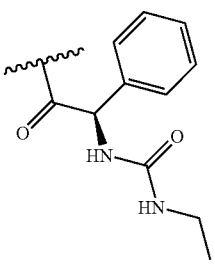<br>employed Cap-46 | HPLC XTERRA C-18 4.6 × 30 mm, 0 to 100% B over 2 minutes, 1 minute hold time, A = 90% water, 10% methanol, 0.2% $H_3PO_4$, B = 10% water, 90% methanol, 0.2% $H_3PO_4$, RT = 1.88 minutes, 95% homogeneity index; LCMS: Anal. Calcd. for $C_{42}H_{46}N_8O_4$: 726.87; found: 727.71 $(M + H)^+$; HRMS: Anal. Calcd. for $C_{42}H_{47}N_8O_4$ 727.3720; found: 727.3695 $(M + H)^+$. |

| | | | |
|---|---|---|---|
| 103-11 | 1-cyclopentyl-3-((1R)-2-oxo-1-phenyl-2-((2S)-2-(4-(4'-(2-((2S)-1-((2R)-tetrahydro-2-furanylcarbonyl)-2-pyrrolidinyl)-1H-imidazol-4-yl)-4-biphenylyl)-1H-imidazol-2-yl)-1-pyrrolidinyl)ethyl)urea | 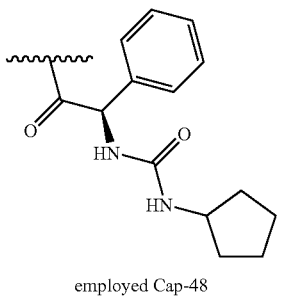  employed Cap-48 | HPLC XTERRA C-18 4.6 × 30 mm, 0 to 100% B over 2 minutes, 1 minute hold time, A = 90% water, 10% methanol, 0.2% $H_3PO_4$, B = 10% water, 90% methanol, 0.2% $H_3PO_4$, RT = 2.11 minutes, 96% homogeneity index; LCMS: Anal. Calcd. for $C_{45}H_{50}N_8O_4$: 766.93; found: 767.45 $(M + H)^+$; HRMS: Anal. Calcd. for $C_{45}H_{51}N_8O_4$ 767.4033; found: 767.4032 $(M + H)^+$. |
| 103-12 | 1,1-dimethyl-3-((1R)-2-oxo-1-phenyl-2-((2S)-2-(4-(4'-(2-((2S)-1-((2R)-tetrahydro-2-furanylcarbonyl)-2-pyrrolidinyl)-1H-imidazol-4-yl)-4-biphenylyl)-1H-imidazol-2-yl)-1-pyrrolidinyl)ethyl)urea | 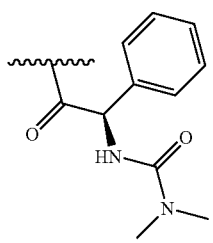  employed Cap-47 | HPLC XTERRA C-18 4.6 × 30 mm, 0 to 100% B over 2 minutes, 1 minute hold time, A = 90% water, 10% methanol, 0.2% $H_3PO_4$, B = 10% water, 90% methanol, 0.2% $H_3PO_4$, RT = 1.87 minutes, 97% homogeneity index; LCMS: Anal. Calcd. for $C_{42}H_{46}N_8O_4$: 726.87; found: 727.38 $(M + H)^+$; HRMS: Anal. Calcd. for $C_{42}H_{47}N_8O_4$ 727.3720; found: 727.3723 $(M + H)^+$. |

Examples 104-107

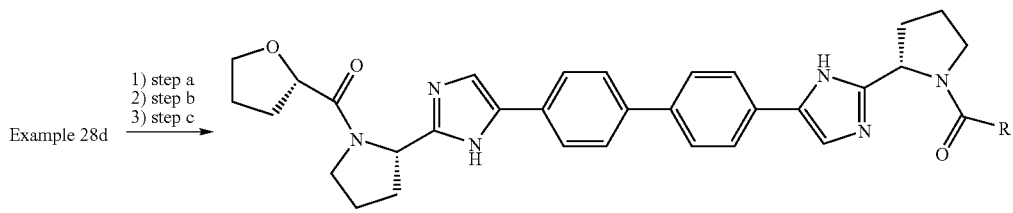

step a: Cap with (S)-2-tetrahydrofuroic acid as in Example 28
step b: Same procedure as in conversion of Example 1d to Example 1e
step c: As in the last step of Example 1 using 1.1 equiv. of the appropriate carboxylic acid and HATU

| Example | Compound Name | R (acyl group) | Retention time (LC-Condition); homogeneity index MS data |
|---|---|---|---|
| 104 | 1-methyl-4-(2-oxo-1-phenyl-2-((2S)-2-(5-(4'-(2-((2S)-1-((2S)-tetrahydro-2-furanylcarbonyl)-2-pyrrolidinyl)-1H-imidazol-5-yl)-4-biphenylyl)-1H-imidazol-2-yl)-1-pyrrolidinyl)ethyl)piperazine | A single diastereomer Cap-17c | 1.12 minutes (Cond. 1); >98%; LC/MS: Anal. Calcd. for [M + H]$^+$ C$_{44}$H$_{51}$N$_8$O$_3$: 739.41; found 739.63; HRMS: Anal. Calcd. for [M + H]$^+$ C$_{44}$H$_{51}$N$_8$O$_3$: 739.4084; found 739.4054 |
| 105 | 4-((1R)-2-oxo-1-phenyl-2-((2S)-2-(5-(4'-(2-((2S)-1-((2S)-tetrahydro-2-furanylcarbonyl)-2-pyrrolidinyl)-1H-imidazol-5-yl)-4-biphenylyl)-1H-imidazol-2-yl)-1-pyrrolidinyl)ethyl)morpholine | Cap-6 | 1.13 minutes (Cond. 1); >98%; LC/MS: Anal. Calcd. for [M + H]$^+$ C$_{43}$H$_{48}$N$_7$O$_4$: 726.38; found 726.63; HRMS: Anal. Calcd. for [M + H]$^+$ C$_{43}$H$_{48}$N$_7$O$_4$: 726.3768; found 726.3803 |
| 106 | (1R)-N,N-diethyl-2-oxo-1-phenyl-2-((2S)-2-(5-(4'-(2-((2S)-1-((2S)-tetrahydro-2-furanylcarbonyl)-2-pyrrolidinyl)-1H-imidazol-5-yl)-4-biphenylyl)-1H-imidazol-2-yl)-1-pyrrolidinyl)ethanamine | Cap-2 | 1.12 minutes (Cond. 1); >97%; LC/MS: Anal. Calcd. for [M + H]$^+$ C$_{43}$H$_{50}$N$_7$O$_3$: 712.40; found 712.45; HRMS: Anal. Calcd. for [M + H]$^+$ C$_{43}$H$_{50}$N$_7$O$_3$: 712.3975; found 712.3998 |
| 107 | (1R)-N-ethyl-N-methyl-2-oxo-1-phenyl-2-((2S)-2-(5-(4'-(2-((2S)-1-((2S)-tetrahydro-2-furanylcarbonyl)-2-pyrrolidinyl)-1H-imidazol-5-yl)-4-biphenylyl)-1H-imidazol-2-yl)-1-pyrrolidinyl)ethanamine | Cap-3 | 1.10 minutes (Cond. 1); >98%; LC/MS: Anal. Calcd. for [M + H]$^+$ C$_{42}$H$_{48}$N$_7$O$_3$: 698.38; found 698.45; HRMS: Anal. Calcd. for [M + H]$^+$ C$_{42}$H$_{48}$N$_7$O$_3$: 698.3819; 698.3823 |

Examples 107-1 to 107-30

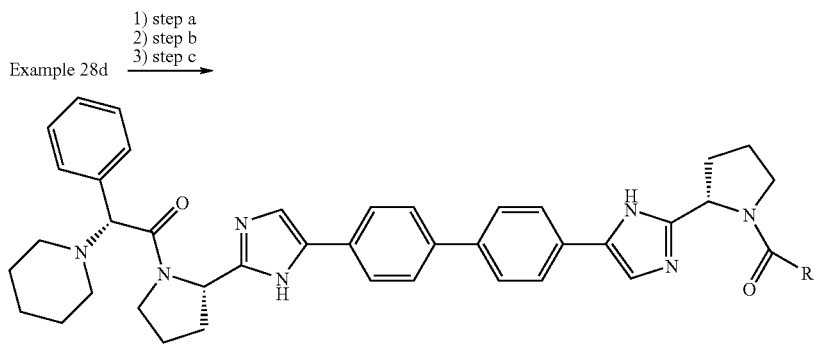

Example 28d →  1) step a  2) step b  3) step c step a: Cap with cap-14 as in Example 28
step b: Same procedure as in the conversion of Example 1d to 1e
step c: As in the last step of Example 1 using 1.1 equiv. of the appropriate carboxylic acid and HATU

| Example Number | Compound Name | Structure | Data |
|---|---|---|---|
| Example 107-1 | (1S)-2-oxo-1-phenyl-2-((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)ethyl acetate | 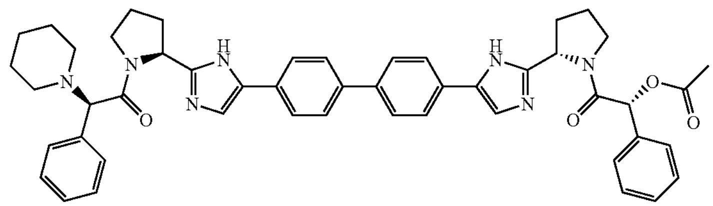 | ¹HNMR (400 MHz, CDCl₃) δ 7.63-7.85 (m, 8H), 7.48-7.54 (m, 2H), 7.26-7.46 (m, 7H), 6.94-7.17 (m, 3H), 6.22 and 6.18 (s, 1H, rotamers, 1:1), 5.99 and 5.68 (s, 1H, rotamers, 1:1), 5.61 and 5.54 (d, J = 7.8 Hz, 1H, rotamers, 1:1), 5.20-5.23 and 5.10-5.13 (m, 1H, rotamers, 1:1), 4.46 and 4.43 (s, 1H, rotamers, 1:1), 3.97-4.06 (m, 1H), 3.89-3.93 and 3.78-3.84 (m, 1H, rotamers, 1:1), 3.63-3.72 and 3.46-3.60 (m, 1H, rotamers, 1:1), 3.23-3.32 (m, 2H), 2.41-2.59 (m, 4H), 2.13-2.26 (m, 2H), 2.11 and 2.10 (s, 3H, rotamers, 1:1), 2.05-2.09 (m, 2H), 1.97-1.98 (m, 1H), 1.82-1.90 (m, 1H), 1.58 (br s, 4H), 1.45 (br s, 2H); LCMS: Anal. Calcd. for C₄₉H₅₁N₇O₄: 801; found: 802 (M + H)⁺. |
| Example 107-2 | 4-methyl-1-((1R)-2-oxo-1-phenyl-2-((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)ethyl)-4-piperidinol | 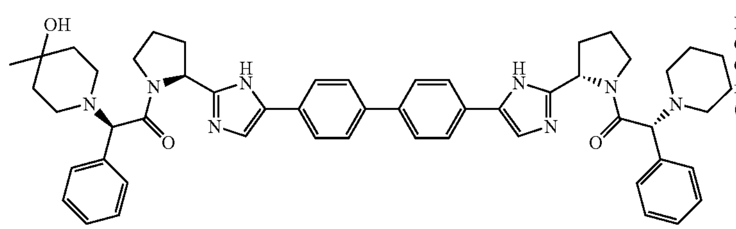 | LCMS: Anal. Calcd. for C₅₃H₆₀N₈O₃: 856; found: 857 (M + H)⁺. |
| Example 107-3 | 1-((1R)-2-((2S)-2-(5-(4'-(2-((2S)-1-(2-fluorobenzoyl)-2-pyrrolidinyl)-1H-imidazol-5-yl)-4-biphenylyl)-1H-imidazol-2-yl)-1-pyrrolidinyl)-2-oxo-1-phenylethyl)piperidine | 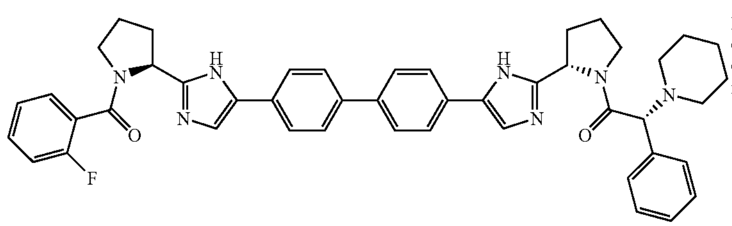 | LCMS: Anal. Calcd. for C₄₆H₅₆FN₇O₂: 747; found: 748 (M + H)⁺. |

| Example Number | Compound Name | Structure | Data |
|---|---|---|---|
| Example 107-4 | N,N-dimethyl-4-(((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)carbonyl)aniline | 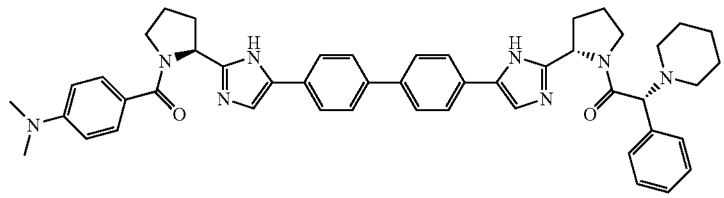 | LCMS: Anal. Calcd. for $C_{48}H_{52}N_8O_2$: 772; found: 773 $(M + H)^+$. |
| Example 107-5 | 5-oxo-5-((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)-2-pentanone | 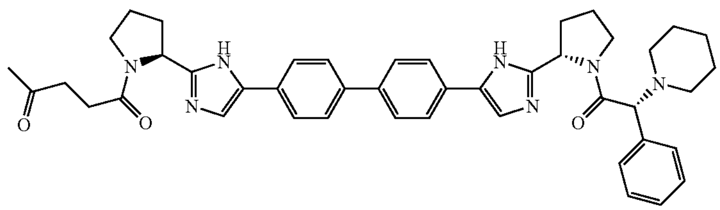 | LCMS: Anal. Calcd. for $C_{44}H_{49}N_7O_3$: 723; found: 724 $(M + H)^+$. |
| Example 107-6 | 1-((1R)-2-((2S)-2-(5-(4'-(2-((2S)-1-(diphenylacetyl)-2-pyrrolidinyl)-1H-imidazol-5-yl)-4-biphenylyl)-1H-imidazol-2-yl)-1-pyrrolidinyl)-2-oxo-1-phenylethyl)piperidine | 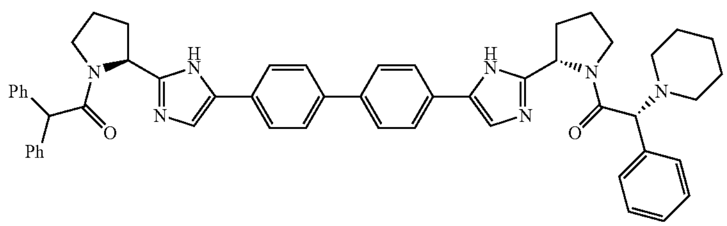 | LCMS: Anal. Calcd. for $C_{53}H_{53}N_7O_2$: 819; found: 820 $(M + H)^+$. |
| Example 107-7 | 1-(3-oxo-3-((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)propyl)piperidine | 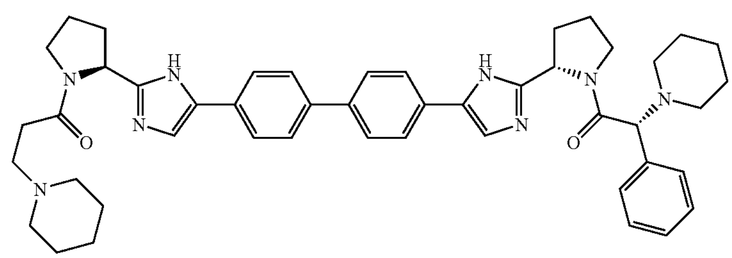 | LCMS: Anal. Calcd. for $C_{47}H_{56}N_8O_2$: 764; found: 765 $(M + H)^+$. |
| Example 107-8 | 1-((1R)-2-((2S)-2-(5-(4'-(2-((2S)-1-((2-methoxyphenoxy)acetyl)-2-pyrrolidinyl)-1H-imidazol-5-yl)-4-biphenylyl)-1H-imidazol-2-yl)-1-pyrrolidinyl)-2-oxo-1-phenylethyl)piperidine | 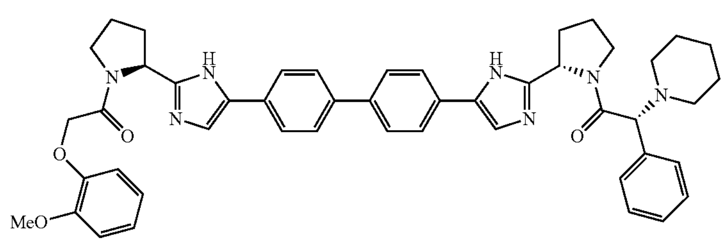 | LCMS: Anal. Calcd. for $C_{48}H_{51}N_7O_2$: 789; found: 790 $(M + H)^+$. |

| Example Number | Compound Name | Structure | Data |
|---|---|---|---|
| Example 107-9 | tert-butyl 4-(((2S)-2-(5-(4'-2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)carbonyl)-1-piperidine-carboxylate | 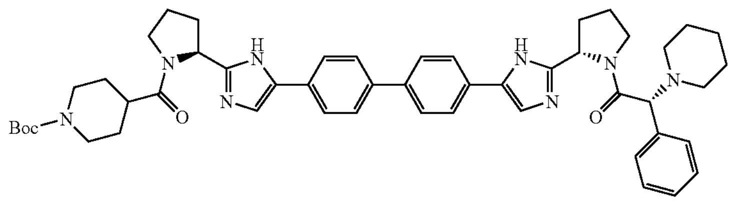 | LCMS: Anal. Calcd. for $C_{50}H_{60}N_8O_4$: 836; found: 837 $(M + H)^+$. |
| Example 107-10 | 4-(4-(((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)carbonyl)phenyl)morpholine | 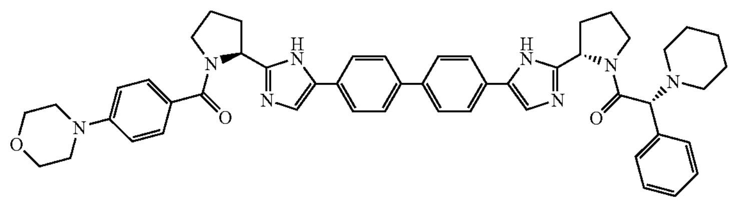 | LCMS: Anal. Calcd. for $C_{50}H_{54}N_8O_3$: 814; found: 815 $(M + H)^+$. |
| Example 107-11 | 1-((1R)-2-oxo-1-phenyl-2-((2S)-2-(5-(4'-(2-((2S)-1-(1,3-triazol-4-ylcarbonyl)-2-pyrrolidinyl)-1H-imidazol-5-yl)-4-biphenylyl)-1H-imidazol-2-yl)-1-pyrrolidinyl)ethyl)piperidine | 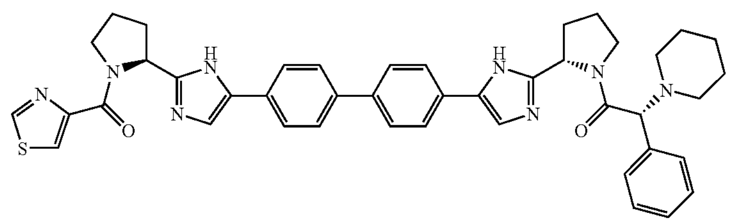 | LCMS: Anal. Calcd. for $C_{43}H_{44}N_8O_2S$: 736; found: 737 $(M + H)^+$. |
| Example 107-12 | tert-butyl 3-(((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)carbonyl)-1-azetidinecarboxylate | 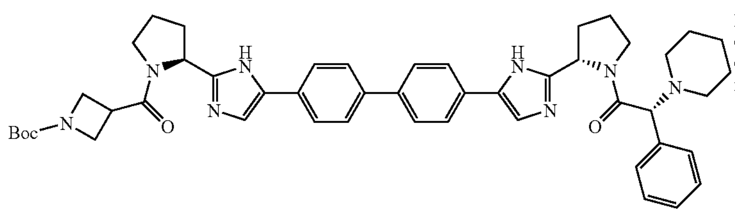 | LCMS: Anal. Calcd. for $C_{48}H_{56}N_8O_4$: 808; found: 809 $(M + H)^+$. |
| Example 107-13 | tert-butyl (cis-4-(((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)carbonyl)cyclohexyl)carbamate | 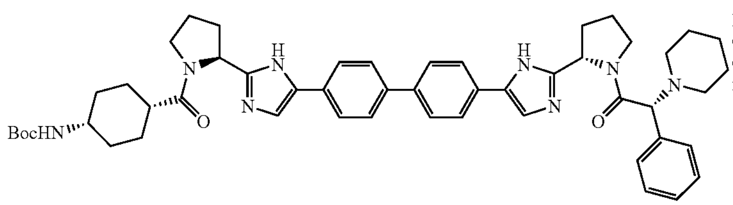 | LCMS: Anal. Calcd. for $C_{51}H_{62}N_8O_4$: 850; found: 851 $(M + H)^+$. |

-continued

| Example Number | Compound Name | Structure | Data |
|---|---|---|---|
| Example 107-14 | tert-butyl 4-methyl-4-(((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)carbonyl)-1-piperidinecarboxylate | 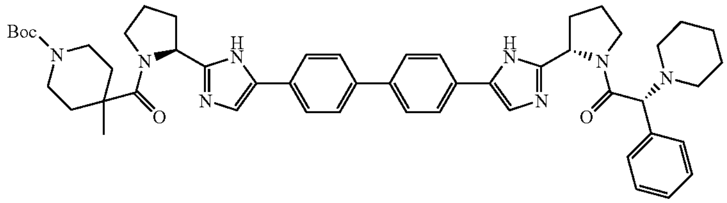 | LCMS: Anal. Calcd. for $C_{51}H_{62}N_8O_4$: 850; found: 851 $(M + H)^+$. |
| Example 107-15 | 1-((1R)-2-oxo-1-phenyl-2-((2S)-2-(5-(4'-(2-((2S)-1-((1-(trifluoromethyl)cyclopropyl)carbonyl)-2-pyrrolidinyl)-1H-imidazol-5-yl)-4-biphenylyl)-1H-imidazol-2-yl)-1-pyrrolidinyl)ethyl)piperidine | 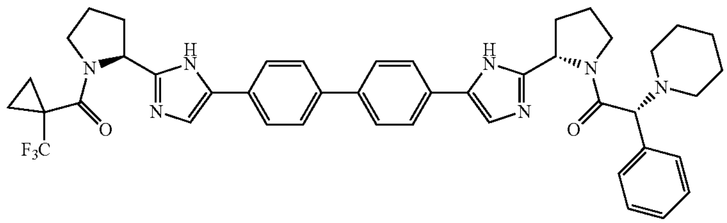 | LCMS: Anal. Calcd. for $C_{44}H_{46}F_3N_7O_2$: 761; found: 762 $(M + H)^+$. |
| Example 107-16 | 1-((1R)-2-((2S)-2-(5-(4'-(2-((2S)-1-((5-methyl-1H-pyrazol-3-yl)acetyl)-2-pyrrolidinyl)-1H-imidazol-5-yl)-4-biphenylyl)-1H-imidazol-2-yl)-1-pyrrolidinyl)-2-oxo-1-phenylethyl)piperidine | 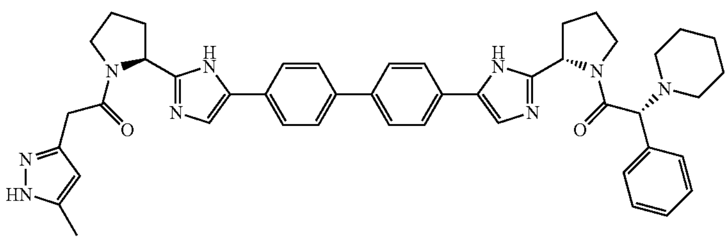 | LCMS: Anal. Calcd. for $C_{45}H_{49}N_9O_2$: 747; found: 748 $(M + H)^+$. |
| Example 107-17 | 1-((1R)-2-((2S)-2-(5-(4'-(2-((2S)-1-(((3R)-1-benzyl-3-pyrrolidinyl)carbonyl)-2-pyrrolidinyl)-1H-imidazol-5-yl)-4-biphenylyl)-1H-imidazol-2-yl)-1-pyrrolidinyl)-2-oxo-1-phenylethyl)piperidine | 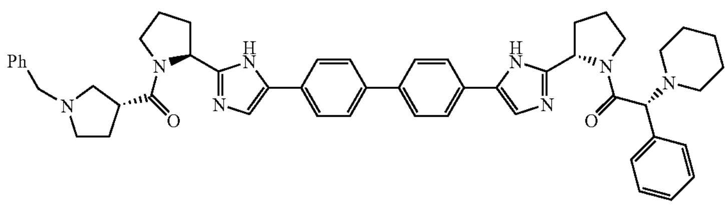 | LCMS: Anal. Calcd. for $C_{51}H_{56}N_8O_2$: 812; found: 813 $(M + H)^+$. |
| Example 107-18 | 1-((1R)-2-((2S)-2-(5-(4'-(2-((2S)-1-(((3S)-1-benzyl-3-pyrrolidinyl)carbonyl)-2-pyrrolidinyl)-1H-imidazol-5-yl)-4-biphenylyl)-1H-imidazol-2-yl)-1-pyrrolidinyl)-2-oxo-1-phenylethyl)piperidine | 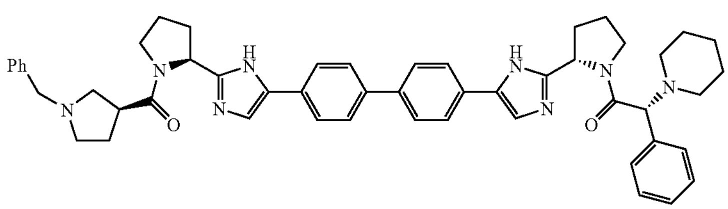 | LCMS: Anal. Calcd. for $C_{51}H_{56}N_8O_2$: 812; found: 813 $(M + H)^+$. |

-continued

| Example Number | Compound Name | Structure | Data |
|---|---|---|---|
| Example 107-19 | 1-((1R)-2-((2S)-2-(5-(4'-(2-((2S)-1-((2R)-2-methoxy-2-phenylacetyl)-2-pyrrolidinyl)-1H-imidazol-5-yl)-4-biphenylyl)-1H-imidazol-2-yl)-1-pyrrolidinyl)-2-oxo-1-phenylethyl) piperidine | 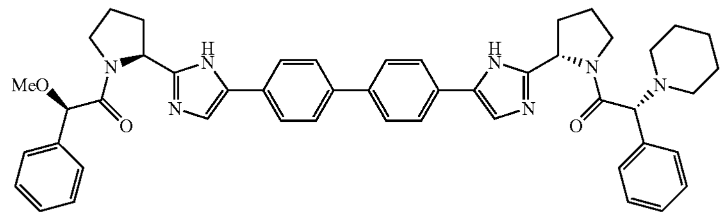 | LCMS: Anal. Calcd. for $C_{48}H_{51}N_7O_3$: 773; found: 774 $(M + H)^+$. |
| Example 107-20 | 1-((1R)-2-((2S)-2-(5-(4'-(2-((2S)-1-((2S)-2-methoxy-2-phenylacetyl)-2-pyrrolidinyl)-1H-imidazol-5-yl)-4-biphenylyl)-1H-imidazol-2-yl)-1-pyrrolidinyl)-2-oxo-1-phenylethyl) piperidine | 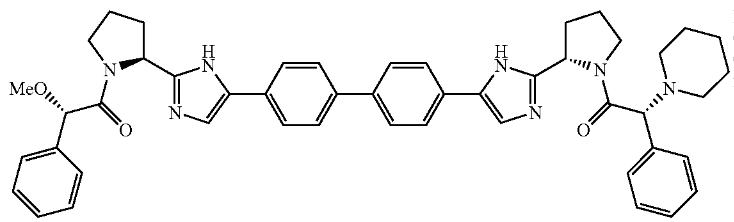 | LCMS: Anal. Calcd. for $C_{48}H_{51}N_7O_3$: 773; found: 774 $(M + H)^+$. |
| Example 107-21 | (1R)-2-oxo-1-phenyl-2-((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)ethyl acetate | 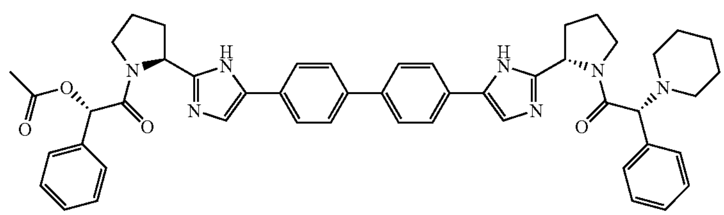 | LCMS: Anal. Calcd. for $C_{49}H_{51}N_7O_4$: 801; found: 802 $(M + H)^+$. |
| Example 107-22 | 1-((1R)-2-oxo-1-phenyl-2-((2S)-2-(5-(4'-(2-((2S)-1-((1-phenylcyclopropyl)carbonyl)-2-pyrrolidinyl)-1H-imidazol-5-yl)-4-biphenylyl)-1H-imidazol-2-yl)-1-pyrrolidinyl)ethyl) piperidine | 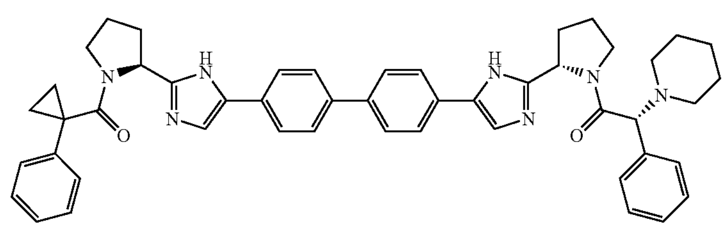 | LCMS: Anal. Calcd. for $C_{49}H_{51}N_7O_2$: 769; found: 770 $(M + H)^+$. |
| Example 107-23 | N,N-dimethyl-1-(2-(2-oxo-2-((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)ethyl)phenyl methanamine | 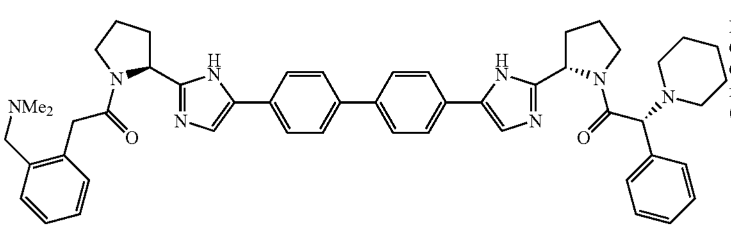 | LCMS: Anal. Calcd. for $C_{50}H_{56}N_8O_2$: 800; found: 801 $(M + H)^+$. |

| Example Number | Compound Name | Structure | Data |
|---|---|---|---|
| Example 107-24 | 1-((1R)-2-((2S)-2-(5-(4'-(2-((2S)-1-((3-methyl-5-isoxazolyl)acetyl)-2-pyrrolidinyl)-1H-imidazol-5-yl)-4-biphenylyl)-1H-imidazol-2-yl)-1-pyrrolidinyl)-2-oxo-1-phenylethyl)piperidine | 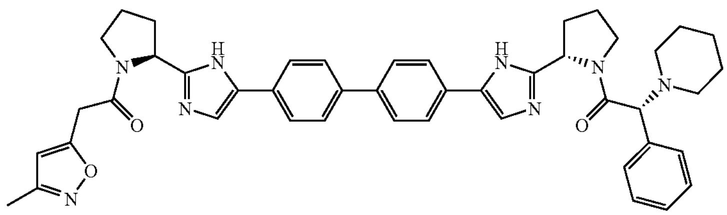 | LCMS: Anal. Calcd. for $C_{45}H_{48}N_8O_3$: 748; found: 749 $(M + H)^+$. |
| Example 107-25 | 1-((1R)-2-((2S)-2-(5-(4'-(2-((2S)-1-((2-methyl-1,3-thiazol-4-yl)acetyl)-2-pyrrolidinyl)-1H-imidazol-5-yl)-4-biphenylyl)-1H-imidazol-2-yl)-1-pyrrolidinyl)-2-oxo-1-phenylethyl)piperidine | 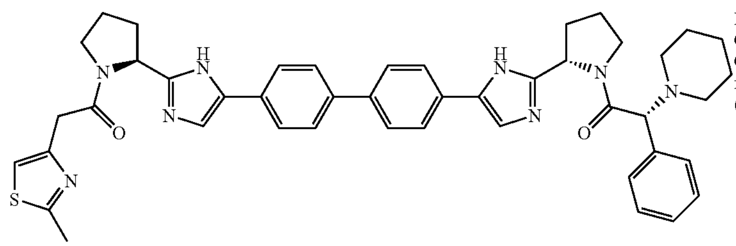 | LCMS: Anal. Calcd. for $C_{45}H_{48}N_8O_2S$: 764; found: 765 $(M + H)^+$. |
| Example 107-26 | 4-(2-(2-oxo-2-((2S)-2-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)ethyl)benzyl)morpholine | 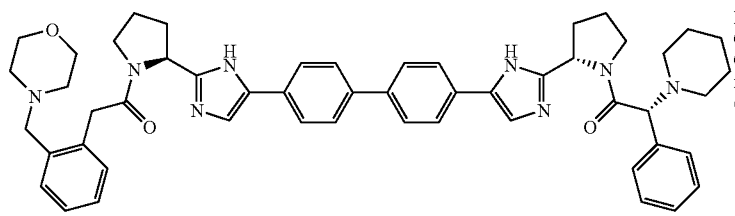 | LCMS: Anal. Calcd. for $C_{52}H_{58}N_8O_3$: 842; found: 843 $(M + H)^+$. |
| Example 107-27 | 1-((1R)-2-oxo-1-phenyl-2-((2S)-2-(5-(4'-(2-((2S)-1-((2-(1-pyrrolidinylmethyl)phenyl)acetyl)-2-pyrrolidinyl)-1H-imidazol-5-yl)-4-biphenylyl)-1H-imidazol-2-yl)-1-pyrrolidinyl)ethyl)piperidine | 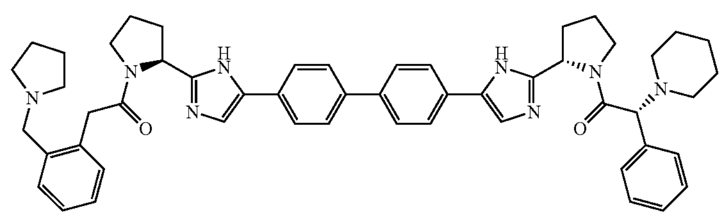 | LCMS: Anal. Calcd. for $C_{52}H_{58}N_8O_2$: 826; found: 827 $(M + H)^+$. |
| Example 107-28 | 1-((1R)-2-((2S)-2-(5-(4'-(2-((2S)-1-((2-fluorophenyl)acetyl)-2-pyrrolidinyl)-1H-imidazol-5-yl)-4-biphenylyl)-1H-imidazol-2-yl)-1-pyrrolidinyl)-2-oxo-1-phenylethyl)piperidine | 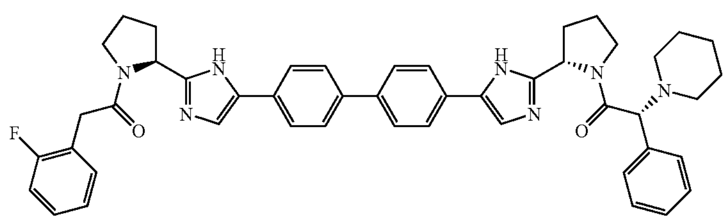 | LCMS: Anal. Calcd. for $C_{47}H_{48}FN_7O_2$: 800; found: 801 $(M + H)^+$. |

-continued

| Example Number | Compound Name | Structure | Data |
|---|---|---|---|
| Example 107-29 | 1-((1R)-2-((2S)-2-(5-(4'-(2-((2S)-1-acetyl-2-pyrrolidinyl)-1H-imidazol-5-yl)-4-biphenylyl)-1H-imidazol-2-yl)-1-pyrrolidinyl)-2-oxo-1-phenylethyl)piperidine | 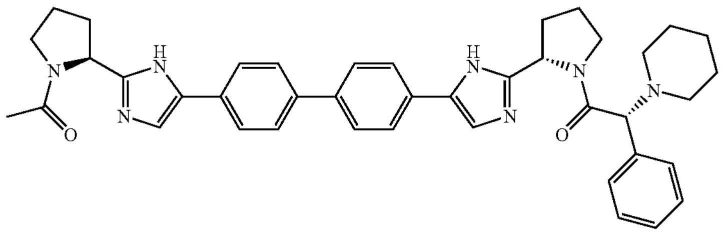 | LCMS: Anal. Calcd. for $C_{41}H_{45}FN_7O_2$: 667; found: 668 $(M + H)^+$. |
| Example 107-30 | 1-((1R)-2-oxo-1-phenyl-2-((2S)-2-(5-(4'-(2-((2S)-1-(2-thienylacetyl)-2-pyrrolidinyl)-1H-imidazol-5-yl)-4-biphenylyl)-1H-imidazol-2-yl)-1-pyrrolidinyl)ethyl)piperidine | 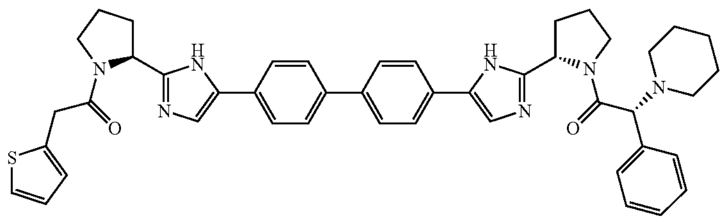 | LCMS: Anal. Calcd. for $C_{45}H_{47}N_7O_2S$: 749; found: 750 $(M + H)^+$. |

Example 107-31 to 107-34

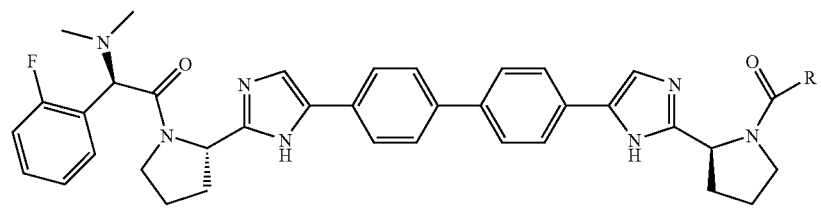

Examples 107-31 through 107-34 were prepared in similar fashion to example 28. Cap-38 was appended to intermediate 28d, the Boc carbamate was removed with TFA or HCl and the appropriate carboxylic acid was coupled.

| Example | Compound Name | Structure | Data |
|---|---|---|---|
| Example 107-31 | (1R)-2-((2S)-2-(5-(4'-(2-((2S)-1-((2R)-2-(dimethylamino)-2-(2-fluorophenyl)acetyl)-2-pyrrolidinyl)-1H-imidazol-5-yl)-4-biphenylyl)-1H-imidazol-2-yl)-1-pyrrolidinyl)-N,N-dimethyl-2-oxo-1-phenylethanamine | 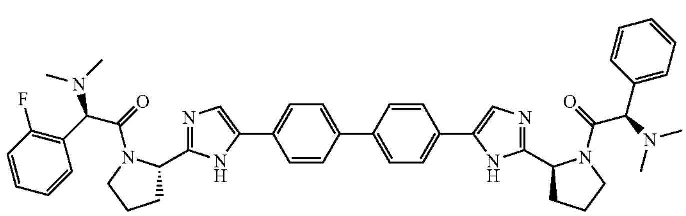 | LCMS: Anal. Calcd. for $C_{46}H_{49}FN_8O_2$: 764; found: 765 $(M + H)^+$. |
| Example 107-32 | (1R)-1-(2-fluorophenyl)-2-((2S)-2-(5-(4'-(2-((2S)-1-((2R)-2-methoxy-2-phenylacetyl)-2-pyrrolidinyl)-1H-imidazol-5-yl)-4-biphenylyl)-1H-imidazol-2-yl)-1-pyrrolidinyl)-N,N-dimethyl-2-oxoethanamine | 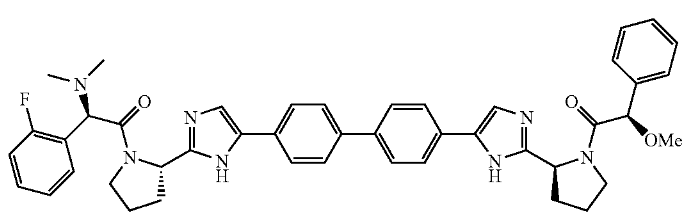 | LCMS: Anal. Calcd. for $C_{45}H_{46}FN_7O_3$: 751; found: 752 $(M + H)^+$. |

| Example | Compound Name | Structure | Data |
|---|---|---|---|
| Example 107-33 | (1R)-2-((2S)-2-(5-(4'-(2-((2S)-1-((2R)-2-(dimethylamino)-2-(2-fluorophenyl)acetyl)-2-pyrrolidinyl)-1H-imidazol-5-yl)-4-biphenylyl)-1H-imidazol-2-yl)-1-pyrrolidinyl)-2-oxo-1-phenylethyl acetate | 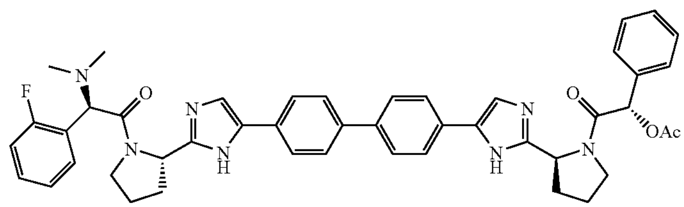 | LCMS: Anal. Calcd. for $C_{46}H_{46}FN_7O_4$: 779; found: 780 $(M + H)^+$. |
| Example 107-34 | (1R)-1-(2-fluorophenyl)-N,N-dimethyl-2-oxo-2-((2S)-2-(5-(4'-(2-((2S)-1-((1-phenylcyclopropyl)carbonyl)-2-pyrrolidinyl)-1H-imidazol-5-yl)-4-biphenylyl)-1H-imidazol-2-yl)-1-pyrrolidinyl)ethanamine | 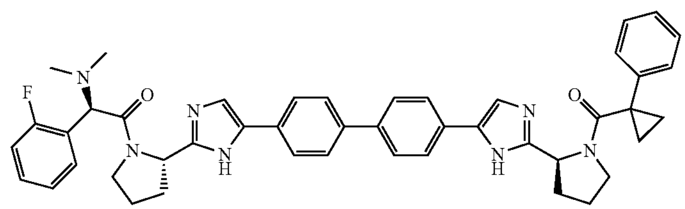 | LCMS: Anal. Calcd. for $C_{46}H_{46}FN_7O_2$: 747; found: 748 $(M + H)^+$. |

Example 107-35 to 107-38

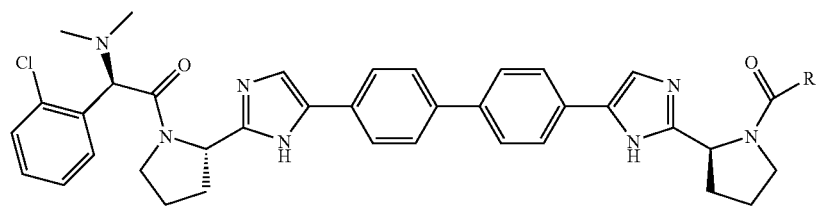

Examples 107-35 through 107-38 were prepared in similar fashion to example 28. Cap-39 was appended to intermediate 28d, the Boc carbamate was removed with TFA or HCl and the appropriate carboxylic acid was coupled.

| Example | Compound Name | Structure | Data |
|---|---|---|---|
| Example 107-35 | (1R)-1-(2-chlorophenyl)-2-((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)-N,N-dimethyl-2-oxoethanamine | 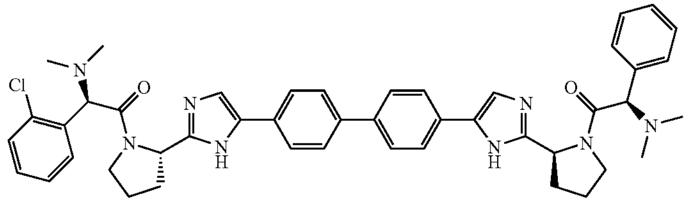 | LCMS: Anal. Calcd. for $C_{46}H_{49}ClN_8O_2$: 780; found: 781 $(M + H)^+$. |

| Example | Compound Name | Structure | Data |
|---|---|---|---|
| Example 107-36 | methyl ((1R)-2-((2S)-2-(5-(4'-(2-((2S)-1-((2R)-2-(2-chlorophenyl)-2-(dimethylamino)acetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 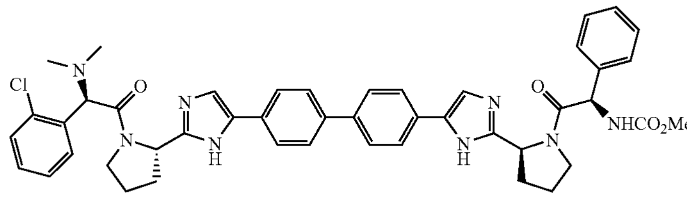 | LCMS: Anal. Calcd. for $C_{46}H_{47}ClN_8O_4$: 810; found: 811 $(M + H)^+$. |
| Example 107-37 | (1R)-1-(2-chlorophenyl)-2-((2S)-2-(5-(4'-(2-((2S)-1-((2R)-2-methoxy-2-phenylacetyl)-2-pyrrolidinyl)-1H-imidazol-5-yl)-4-biphenylyl)-1H-imidazol-2-yl)-1-pyrrolidinyl)-N,N-dimethyl-2-oxoethanamine | 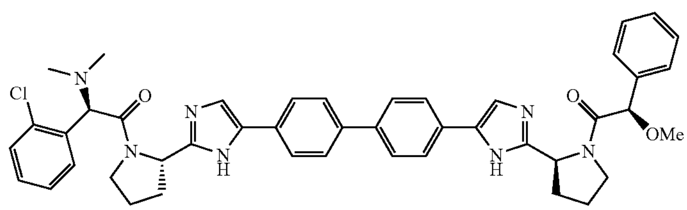 | LCMS: Anal. Calcd. for $C_{44}H_{46}ClN_7O_3$: 767; found: 768 $(M + H)^+$. |
| Example 107-38 | (1R)-1-(2-chlorophenyl)-N,N-dimethyl-2-oxo-2-((2S)-2-(5-(4'-(2-((2S)-1-((2R)-tetrahydro-2-furanylcarbonyl)-2-pyrrolidinyl)-1H-imidazol-5-yl)-4-biphenylyl)-1H-imidazol-2-yl)-1-pyrrolidinyl)ethanamine | 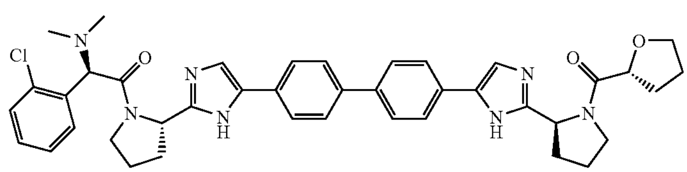 | LCMS: Anal. Calcd. for $C_{41}H_{44}ClN_7O_3$: 717; found: 718 $(M + H)^+$. |

Example 107-39 to 107-43

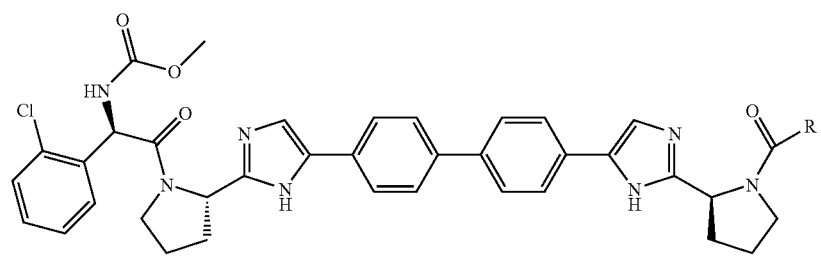

Examples 107-39 through 107-44 were prepared in similar fashion to example 28. Cap-40 was appended to intermediate 28d, the Boc carbamate was removed with TFA or HCl and the appropriate carboxylic acid was coupled.

| Example | Compound Name | Structure | Data |
|---|---|---|---|
| Example 107-39 | methyl ((1R)-1-(2-chlorophenyl)-2-oxo-2-((2S)-2-(5-(4'-(2-((2S)-1-((2R)-tetrahydro-2-furanylcarbonyl)-2-pyrrolidinyl)-1H-imidazol-5-yl)-4-biphenylyl)-1H-imidazol-2-yl)-1-pyrrolidinyl)ethyl)carbamate | 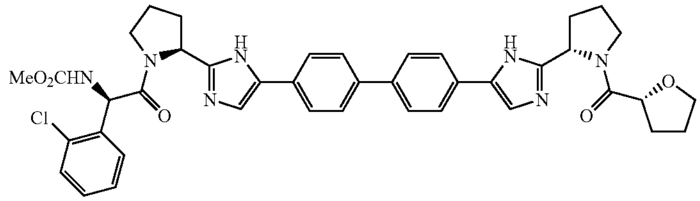 | ¹H NMR (400 MHz, CD₃OD) δ 7.58-7.77 (m, 8 H), 7.42-7.55 (m, 2 H), 7.19-7.39 (m, 4 H), 5.94 and 5.89 (s, 1 H, rotamers, 1:1), 5.80 and 5.61 (s, 1 H, rotamers, 1:1), 5.43-5.47 and 5.35-5.38 (m, 1 H, rotamers, 1:1), 5.20-5.24 (m, 1 H), 5.15-5.18 (m, 1 H), 4.67-4.70 and 4.39-4.42 (m, 1 H, rotamers, 1:1), 3.92-3.98 (m, 1 H), 3.85-3.90 (m, 1 H), 3.69-3.84 (m, 2 H), 3.64 and 3.63 (s, 3 H, rotamers, 1:1), 3.53-3.59 (m, 1 H), 2.35-2.46 (m, 1 H), 2.21-2.29 (m, 2 H), 2.06-2.17 (m, 3 H), 1.84-2.01 (m, 4 H), 1.66-1.76 and 1.41-1.47 (m, 1 H, rotamers, 1:1); LCMS: Anal. Calcd. for C₄₁H₄₂ClN₇O₅: 747; found 748 (M + H)⁺. |
| Example 107-40 | methyl ((1R)-1-(2-chlorophenyl)-2-((2S)-2-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)-1-pyrrolidinyl)-2-oxoethyl)carbamate | 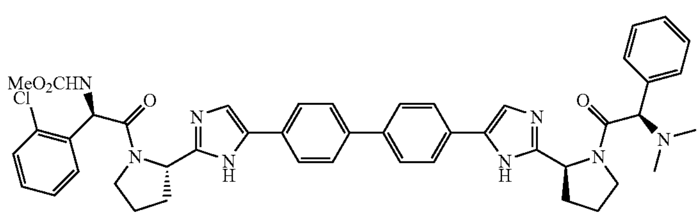 | LCMS: Anal. Calcd. for C₄₆H₄₇ClN₈O₄: 810; found: 811 (M + H)⁺. |
| Example 107-41 | methyl ((1R)-2-((2S)-2-(5-(4'-(2-((2S)-1-((2R)-2-(2-chlorophenyl)-2-((methoxycarbonyl)amino)acetyl)-2-pyrrolidinyl)-1H-imidazol-5-yl)-4-biphenylyl)-1H-imidazol-2-yl)-1-pyrrolidinyl)-2-oxo-1-phenyl)ethyl)carbamate | 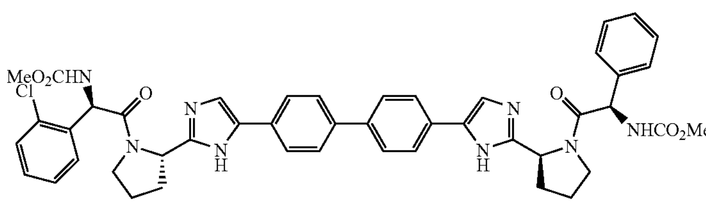 | LCMS: Anal. Calcd. for C₄₆H₄₅ClN₈O₆: 840; found: 841 (M + H)⁺. |
| Example 107-42 | methyl ((1R)-1-(2-chlorophenyl)-2-((2S)-2-(5-(4'-(2-((2S)-1-((2R)-2-(4-hydroxy-4-methyl-1-piperidinyl)-2-phenylacetyl)-2-pyrrolidinyl)-1H-imidazol-5-yl)-4-biphenylyl)-1H-imidazol-2-yl)-1-pyrrolidinyl)-2-oxoethyl)carbamate | 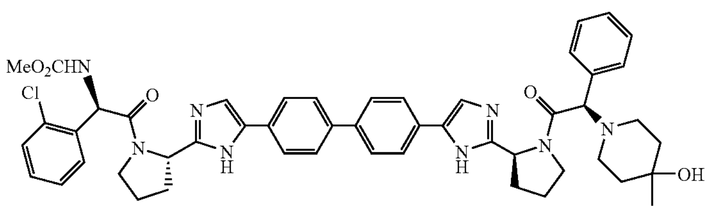 | LCMS: Anal. Calcd. for C₅₀H₅₃ClN₈O₅: 880; found: 881 (M + H)⁺. |

| Example | Compound Name | Structure | Data |
|---|---|---|---|
| Example 107-43 | methyl ((1R)-1-(2-chlorophenyl)-2-((2S)-2-(5-(4'-(2-((2S)-1-((2R)-2-methoxy-2-phenylacetyl)-2-pyrrolidinyl)-1H-imidazol-5-yl)-4-biphenylyl)-1H-imidazol-2-yl)-1-pyrrolidinyl)-2-oxoethyl)carbamate | 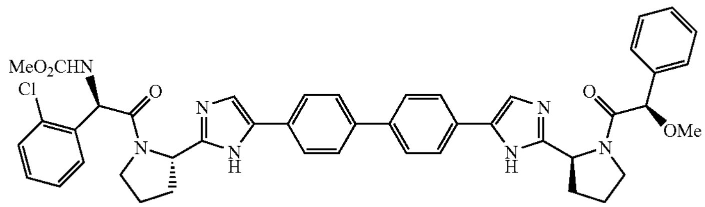 | LCMS: Anal. Calcd. for $C_{45}H_{44}ClN_7O_5$: 797; found: 798 $(M + H)^+$. |
| Example 107-44 | methyl ((1R)-1-(2-chlorophenyl)-2-((2S)-2-(5-(4'-(2-((2S)-1-((2R)-2-(2-chlorophenyl)-2-(dimethylamino)acetyl)-2-pyrrolidinyl)-1H-imidazol-5-yl)-4-biphenylyl)-1H-imidazol-2-yl)-1-pyrrolidinyl)-2-oxoethyl)carbamate | 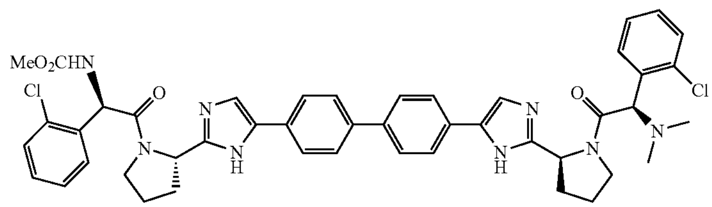 | LCMS: Anal. Calcd. for $C_{46}H_{46}Cl_2N_8O_4$: 844; found: 845 $(M + H)^+$. |

Example 108 methyl ((1R)-2-((2S)-2-(5-(4'-(2-((2S)-1-(ethylcarbamoyl)-2-pyrrolidinyl)-1H-imidazol-5-yl)-4-biphenylyl)-1H-imidazol-2-yl)-1-pyrrolidinyl)-2-oxo-1-phenylethyl)carbamate

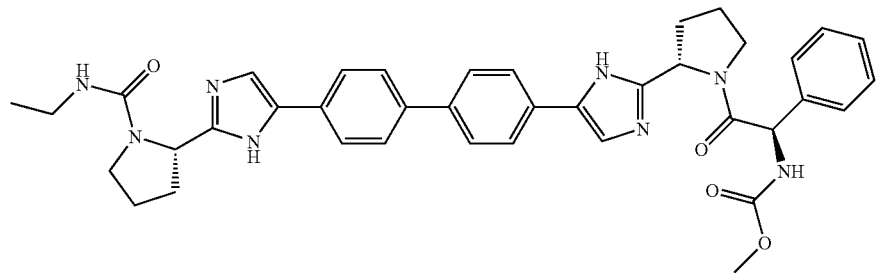

Ethyl isocyanate (5 μL, 0.063 mmol) was added to a methanol (1.0 mL) solution of 28f (30 mg, 0.049 mmol) and stirred at ambient condition for 1.8 hours. The residue was treated with 2.0 M $NH_3$/methanol (2 mL) and stirred for an additional 30 minutes, and all the volatile components were removed in vacuo. The resulting material was purified by a reverse phase HPLC ($H_2O$/methanol/TFA) to provide the TFA salt of Example 108 as a light yellow foam (16.7 mg) LC: 1.95 minutes (Cond. 2); >98% homogeneity index; LC/MS: Anal. Calcd. for [M+H]+ $C_{39}H_{43}N_8O_4$: 687.34. found 687.53; HRMS: Anal. Calcd. for $[M+H]^+$ $C_{39}H_{43}N_8O_4$: 687.3407. found 687.3417.

Example 109 dibenzyl (2S,2'S)-2,2'-(4,4'-biphenyldiylbis(1H-imidazole-5,2-diyl))di(1-pyrrolidinecarboxylate)

Example 109

Step a benzyl (2S)-2-(5-(4'-(2-((2S)-2-pyrrolidinyl)-1H-imidazol-5-yl)-4-biphenylyl)-1H-imidazol-2-yl)-1-pyrrolidinecarboxylate

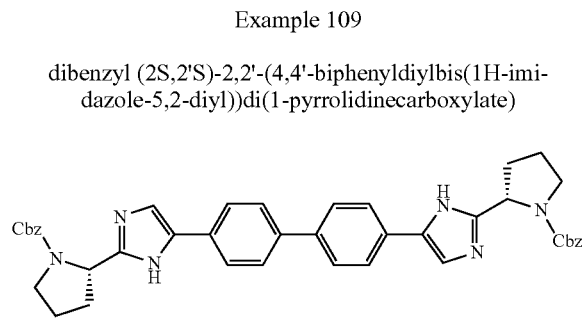

109a

The Boc-deprotection of 28c using the procedure described for the synthesis of pyrrolidine 1e from carbamate 1d provided 109a. RT=1.92 minutes (Cond 2); >98% homogeneity index; LC/MS: Anal. Calcd. $C_{34}H_{35}N_6O_2$: 559.28. found 559.44

Example 109 dibenzyl (2S,2'S)-2,2'-(4,4'-biphenyldiylbis(1H-imidazole-5,2-diyl))di(1-pyrrolidinecarboxylate)

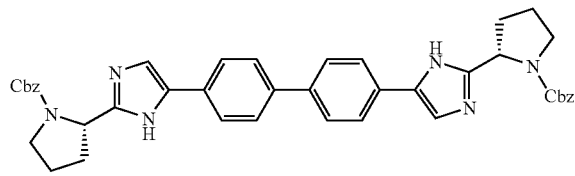

Benzyl chloroformate (10.5 μL, 0.0736 mmol) was added to a THF (2.0 mL) solution of 109a (37.1 mg, 0.664 mmol) and triethylamine (15 μl, 0.107 mmol), and stirred under ambient conditions for 6 hours. The volatile component was removed in vacuo, and the residue was treated with 2N $NH_3$/methanol (2 mL) and stirred for 15 minutes. The volatile component was removed in vacuo, and the residue purified by a reverse phase HPLC ($H_2O$/methanol/TFA) to provide the TFA salt of Example 109 as an off-white foam (37.9 mg). LC (Cond. 2): RT=2.25 min; >98% homogeneity index; LC/MS: Anal. Calcd. for $[M+H]^+$ $C_{42}H_{41}N_6O_4$: 693.32. found 693.59; HRMS: Anal. Calcd. for $[M+H]^+$ $C_{42}H_{41}N_6O_4$: 693.3189. found 693.3220.

Example 110

(2R)—N-((1R)-2-oxo-1-phenyl-2-((2S)-2-(5-(4'-(2-((2S)-1-((2S)-tetrahydro-2-furanylcarbonyl)-2-pyrrolidinyl)-1H-imidazol-5-yl)-4-biphenylyl)-1H-imidazol-2-yl)-1-pyrrolidinyl)ethyl)tetrahydro-2-furancarboxamide

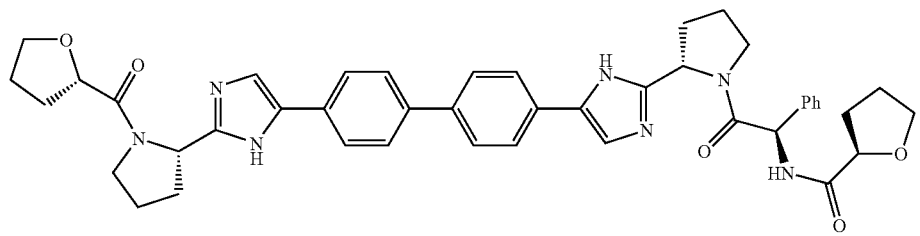

Example 110

Step a (1R)-2-oxo-1-phenyl-2-((2S)-2-(5-(4'-(2-((2S)-1-((2S)-tetrahydro-2-furanylcarbonyl)-2-pyrrolidinyl)-1H-imidazol-5-yl)-4-biphenylyl)-1H-imidazol-2-yl)-1-pyrrolidinyl)ethanamine

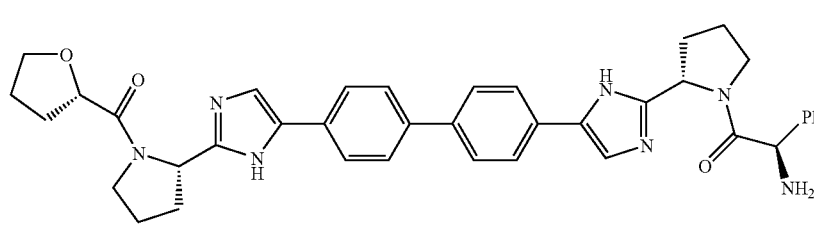

110a

Amine 110a was synthesized starting from 28d and (S)-tetrahydrofuran-2-carboxylic by sequentially employing procedures described in the preparation of 28f (from 28d) and 25b (from 1e). LC (Cond. 1): RT=1.13 min; >98% homogeneity index; LC/MS: Anal. Calcd. for $[M+H]^+$ $C_{39}H_{42}N_7O_3$: 656.34. found 656.49; HRMS: Anal. Calcd. for $[M+H]^+$ $C_{39}H_{42}N_7O_3$: 656.3349. found 656.3377.

Example 111

N-((1R)-2-oxo-1-phenyl-2-((2S)-2-(5-(4'-(2-((2S)-1-((2S)-tetrahydro-2-furanylcarbonyl)-2-pyrrolidinyl)-1H-imidazol-5-yl)-4-biphenylyl)-1H-imidazol-2-yl)-1-pyrrolidinyl)ethyl)4-morpholinecarboxamide

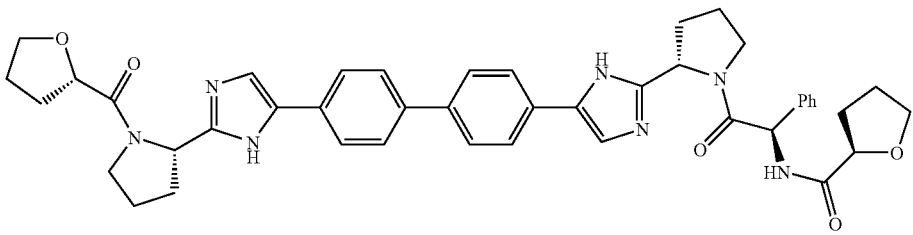

Example 110 (TFA salt) was prepared from Example 110a and (S)-tetrahydrofuran-2-carboxylic acid using the conditions described for the synthesis Example 1 from amine 1e. LC (Cond. 1): RT=1.28 min; >98% homogeneity index; LC/MS: Anal. Calcd. for $[M+H]^+$ $C_{44}H_{48}N_7O_5$: 754.37. found 754.60; HRMS: Anal. Calcd. for $[M+H]^+$ $C_{44}H_{48}N_7O_5$: 754.3717. found 754.3690.

Example 111

N-((1R)-2-oxo-1-phenyl-2-((2S)-2-(5-(4'-(2-((2S)-1-((2S)-tetrahydro-2-furanylcarbonyl)-2-pyrrolidinyl)-1H-imidazol-5-yl)-4-biphenylyl)-1H-imidazol-2-yl)-1-pyrrolidinyl)ethyl)-4-morpholinecarboxamide

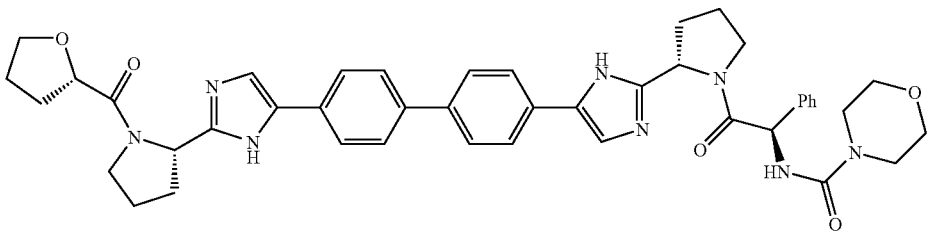

Example 111 (TFA salt) was prepared from amine 110a and morpholine 4-carbonyl chloride using the procedure described for the synthesis of Example 29 from amine 28f. LC (Cond. 1): RT=1.28 min; >98% homogeneity index; LC/MS: Anal. Calcd. for $[M+H]^+$ $C_{44}H_{49}N_8O_5$: 769.38. found 769.60.

Using similar methods described for the preparation of Example 111, the following compounds (Example 112-120) were synthesized as TFA salts.

Example 112-117

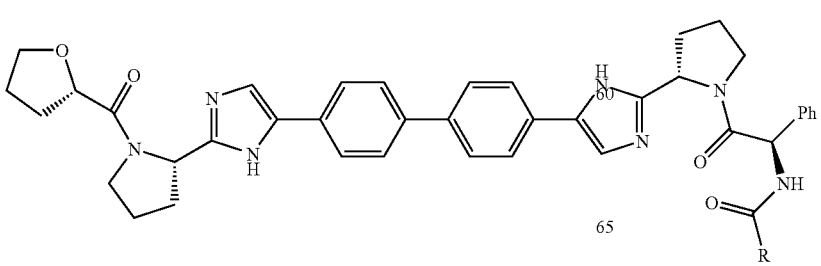

| Example | Compound Name | R group | Retention time (LC-Condition); homogeneity index; MS data |
|---|---|---|---|
| 112 | (2S)-N-((1R)-2-oxo-1-phenyl-2-((2S)-2-(5-(4'-(2-((2S)-1-((2S)-tetrahydro-2-furanylcarbonyl)-2-pyrrolidinyl)-1H-imidazol-5-yl)-4-biphenylyl)-1H-imidazol-2-yl)-1-pyrrolidinyl)ethyl)tetrahydro-2-furancarboxamide | 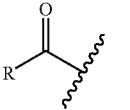 | 1.28 minutes (Cond. 1); >98%; LC/MS: Anal. Calcd. for [M + H]+ C44H48N7O5: 754.37; found 754.59; HRMS: Anal. Calcd. for [M + H]+ C44H48N7O5: 754.3717; found 754.3731 |
| 113 | 1-methyl-N-((1R)-2-oxo-1-phenyl-2-((2S)-2-(5-(4'-(2-((2S)-1-((2S)-tetrahydro-2-furanylcarbonyl)-2-pyrrolidinyl)-1H-imidazol-5-yl)-4-biphenylyl)-1H-imidazol-2-yl)-1-pyrrolidinyl)ethyl)-L-prolinamide | 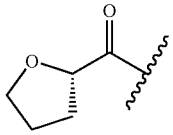 | 1.14 minutes (Cond. 1); >98%; LC/MS: Anal. Calcd. for [M + H]+ C44H51N8O4: 767.40; found 767.68; HRMS: Anal. Calcd. for [M + H]+ C44H51N8O4: 767.4033; found 767.4035 |
| 114 | 1-methyl-N-((1R)-2-oxo-1-phenyl-2-((2S)-2-(5-(4'-(2-((2S)-1-((2S)-tetrahydro-2-furanylcarbonyl)-2-pyrrolidinyl)-1H-imidazol-5-yl)-4-biphenylyl)-1H-imidazol-2-yl)-1-pyrrolidinyl)ethyl)-4-piperidinecarboxamide | 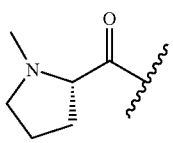 | 1.12 minutes (Cond. 1); >98%; LC/MS: Anal. Calcd. for [M + H]+ C46H53N8O4: 781.42; found 781.67; HRMS: Anal. Calcd. for [M + H]+ C46H53N8O4: 781.4190; found 781.4195 |
| 115 | N-((1R)-2-oxo-1-phenyl-2-((2S)-2-(5-(4'-(2-((2S)-1-((2S)-tetrahydro-2-furanylcarbonyl)-2-pyrrolidinyl)-1H-imidazol-5-yl)-4-biphenylyl)-1H-imidazol-2-yl)-1-pyrrolidinyl)ethyl)tetrahydro-2H-pyran-4-carboxamide | 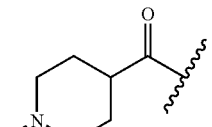 | 1.24 minutes (Cond. 1); >98%; LC/MS: Anal. Calcd. for [M + H]+ C45H50N7O5: 768.39; found 768.66; HRMS: Anal. Calcd. for [M + H]+ C45H50N7O5: 768.3873; found 768.3897 |
| 116 | (4R)-4-fluoro-1-methyl-N-((1R)-2-oxo-1-phenyl-2-((2S)-2-(5-(4'-(2-((2S)-1-((2S)-tetrahydro-2-furanylcarbonyl)-2-pyrrolidinyl)-1H-imidazol-5-yl)-4-biphenylyl)-1H-imidazol-2-yl)-1-pyrrolidinyl)ethyl)-L-prolinamide | 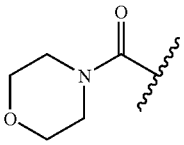<br>Cap-11 | 1.16 minutes (Cond. 1); >98%; LC/MS: Anal. Calcd. for [M + H]+ C45H50FN8O4: 785.39; found 785.63; HRMS: Anal. Calcd. for [M + H]+ C45H50FN8O4: 785.3939; found 785.3940 |
| 117 | 4-methyl-N-((1R)-2-oxo-1-phenyl-2-((2S)-2-(5-(4'-(2-((2S)-1-((2S)-tetrahydro-2-furanylcarbonyl)-2-pyrrolidinyl)-1H-imidazol-5-yl)-4-biphenylyl)-1H-imidazol-2-yl)-1-pyrrolidinyl)ethyl)-1-piperazinecarboxamide | 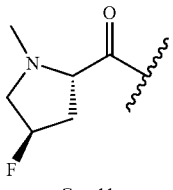 | 1.15 minutes (Cond. 1); 97.6%; LC/MS: Anal. Calcd. for [M + H]+ C45H52N9O4: 782.41; found 782.64; HRMS: Anal. Calcd. for [M + H]+ C45H52N9O4: 782.4142; found 782.4161 |

Examples 118 to 120-9

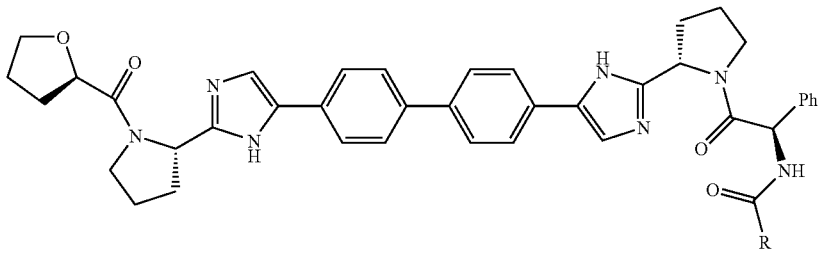

Examples 118 to 120-9 were prepared as described in the preparation of Example 110a substituting (R)-tetrahydrofuryl carboxylic acid and the appropriate carboxylic acid, carboxylic acid chloride, carbamoyl chloride, or isocyanate.

| Example | Compound Name | R group | Retention time (LC-Condition); homogeneity index; MS data |
|---|---|---|---|
| 118 | N-((1R)-2-oxo-1-phenyl-2-((2S)-2-(5-(4'-(2-((2S)-1-((2R)-tetrahydro-2-furanylcarbonyl)-2-pyrrolidinyl)-1H-imidazol-5-yl)-4-biphenylyl)-1H-imidazol-2-yl)-1-pyrrolidinyl)ethyl)acetamide | 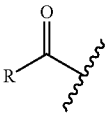 | 1.89 minutes (Cond. 2); >98%; LC/MS: Anal. Calcd. for $[M + H]^+$ $C_{41}H_{44}N_7O_4$: 698.35; found 698.25; HRMS: Anal. Calcd. for $[M + H]^+$ $C_{41}H_{44}N_7O_4$: 698.3455; found 698.3474 |
| 119 | (2R)-N-((1R)-2-oxo-1-phenyl-2-((2S)-2-(5-(4'-(2-((2S)-1-((2R)-tetrahydro-2-furanylcarbonyl)-2-pyrrolidinyl)-1H-imidazol-5-yl)-4-biphenyl)-1H-imidazol-2-yl)-1-pyrrolidinyl)ethyl)tetrahydro-2-furancarboxamide | 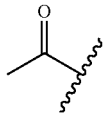 | 1.99 minutes (Cond. 2); >98%; LC/MS: Anal. Calcd. for $[M + H]^+$ $C_{44}H_{48}N_7O_5$: 754.37; found 754.28; $[M + H]^+$ $C_{44}H_{48}N_7O_5$: 754.3717; found 754.3705 |
| 120 | N-((1R)-2-oxo-1-phenyl-2-((2S)-2-(5-(4'-(2-((2S)-1-((2R)-tetrahydro-2-furanylcarbonyl)-2-pyrrolidinyl)-1H-imidazol-5-yl)-4-biphenylyl)-1H-imidazol-2-yl)-1-pyrrolidinyl)ethyl)-4-morpholinecarboxamide | 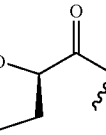 | 2.00 minutes (Cond. 2); >98%; LC/MS: Anal. Calcd. for $[M + H]^+$ $C_{44}H_{49}N_8O_5$: 769.38; found 769.32 |
| 120-5 | 1-methyl-N-((1R)-2-oxo-1-phenyl-2-((2S)-2-(5-(4'-(2-((2S)-1-((2R)-tetrahydro-2-furanylcarbonyl)-2-pyrrolidinyl)-1H-imidazol-4-yl)-4-biphenylyl)-1H-imidazol-2-yl)-1-pyrrolidinyl)ethyl)-1H-imidazole-5-carboxamide | 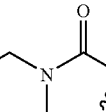 | RT = 4.02 (97%); HPLC XTERRA C-18 4.6 × 30 mm, 0 to 100% B over 2 minutes, 1 minute hold time, A = 90% water, 10% methanol, 0.2% $H_3PO_4$, B = 10% water, 90% methanol, 0.2% $H_3PO_4$, RT = 1.87 minutes, 97% homogeneity index; LCMS: Anal. Calcd. for: $C_{44}H_{45}N_9O_4$ 763.91; Found: 764.52 $(M + H)^-$ |

-continued

| Example | Compound Name | R (of R-C(=O)-) | Retention time (LC-Condition); homogeneity index; MS data |
|---|---|---|---|
| 120-6 | 1-methyl-N-((1R)-2-oxo-1-phenyl-2-((2S)-2-(5-(4'-(2-((2S)-1-((2R)-tetrahydro-2-furanylcarbonyl)-2-pyrrolidinyl)-1H-imidazol-4-yl)-4-biphenylyl)-1H-imidazol-2-yl)-1-pyrrolidinyl)ethyl)-L-prolinamide | (1-methylpyrrolidin-2-yl) | RT = 3.68 (99%); HPLC XTERRA C-18 4.6 × 30 mm, 0 to 100% B over 2 minutes, 1 minute hold time, A = 90% water, 10% methanol, 0.2% H$_3$PO$_4$, B = 10% water, 90% methanol, 0.2% H$_3$PO$_4$, RT = 1.87 minutes, 97% homogeneity index; LCMS: Anal. Calcd. for: C$_{45}$H$_{50}$N$_8$O$_4$ 766.95; Found: 767.47 (M + H)$^-$ |
| 120-7 | N-((1R)-2-oxo-1-phenyl-2-((2S)-2-(5-(4'-(2-((2S)-1-((2R)-tetrahydro-2-furanylcarbonyl)-2-pyrrolidinyl)-1H-imidazol-4-yl)-4-biphenylyl)-1H-imidazol-2-yl)-1-pyrrolidinyl)ethyl)-2-(3-pyridinyl)acetamide | (pyridin-3-ylmethyl) | RT = 3.81 (99%); HPLC XTERRA C-18 4.6 × 30 mm, 0 to 100% B over 2 minutes, 1 minute hold time, A = 90% water, 10% methanol, 0.2% H$_3$PO$_4$, B = 10% water, 90% methanol, 0.2% H$_3$PO$_4$, RT = 1.87 minutes, 97% homogeneity index; LCMS: Anal. Calcd. for: C$_{46}$H$_{46}$N$_8$O$_4$ 774.93; Found: 775.47 (M + H)$^-$ |
| 120-8 | N$^2$,N$^2$-dimethyl-N-((1R)-2-oxo-1-phenyl-2-((2S)-2-(5-(4'-(2-((2S)-1-((2R)-tetrahydro-2-furanylcarbonyl)-2-pyrrolidinyl)-1H-imidazol-4-yl)-4-biphenylyl)-1H-imidazol-2-yl)-1-pyrrolidinyl)ethyl)glycinamide | (dimethylaminomethyl) | $^1$H NMR (500 MHz, DMSO-d$_6$) δ ppm 1.71-2.44 (m, 12 H), 2.65-2.89 (m, 6 H), 3.04-3.21 (m, J = 8.55 Hz, 1 H), 3.46-3.68 (m, 1 H), 3.64-4.07 (m, 6 H), 4.64 (dd, J = 8.09, 5.34 Hz, 1 H), 5.09-5.30 (m, 2 H), 5.66-5.86 (m, 1 H), 7.32-7.49 (m, 4 H), 7.82-8.22 (m, 10 H), 9.15-9.38 (m, 1 H), 9.68 (s, 1 H), 14.60 (s, 2 H); HPLC Xterra 4.6 × 50 mm, 0 to 100% B over 10 minutes, one minute hold time A = 90% water, 10% methanol, 0.2% phosphoric acid, B = 10% water, 90% methanol, 0.2% phosphoric acid, RT = 3.61 min; LCMS: Anal. Calcd. for: C$_{52}$H$_{56}$N$_{10}$O$_6$ 740.91; Found: 741.48 (M + H)$^-$. |
| 120-9 | 1-((1R)-2-oxo-1-phenyl-2-((2S)-2-(5-(4'-(2-((2S)-1-((2R)-tetrahydro-2-furanylcarbonyl)-2-pyrrolidinyl)-1H-imidazol-4-yl)-4-biphenylyl)-1H-imidazol-2-yl)-1-pyrrolidinyl)ethyl)-3-(3-pyridinyl)urea | (pyridin-3-ylamino) | $^1$H NMR (500 MHz, DMSO-d$_6$) δ ppm 1.64-2.40 (m, 12 H), 3.11-3.27 (m, 1 H), 3.51-3.65 (m, 1 H), 3.80 (dd, J = 18.46, 6.87 Hz, 3 H), 3.96-4.11 (m, 1 H), 4.64 (dd, J = 7.78, 5.34 Hz, 1 H), 5.13-5.23 (m, 1 H), 5.21-5.35 (m, 1 H), 5.66 (d, J = 7.02 Hz, 1 H), 7.29-7.57 (m, 7 H), 7.82-8.07 (m, 10 H), 8.14 (s, 1 H), 8.22 (d, J = 4.58 Hz, 1 H), 8.68 (s, 1 H), 9.32 (s, 1 H), 14.46 (s, 2 H); HPLC Xterra 4.6 × 50 mm, 0 to 100% B over 10 minutes, one minute hold time, A = 90% water, 10% methanol, 0.2% phosphoric acid, B = 10% water, 90% methanol, 0.2% phosphoric acid, RT = 3.83 min; LCMS: Anal. Calcd. for: C$_{45}$H$_{45}$N$_9$O$_4$ 775.92; Found: 776.53 (M + H)$^-$. |

Example 121

(1R,1'R)-2,2'-((2,2'-dimethyl-4,4'-biphenyldiyl)bis
(1H-imidazole-5,2-diyl(2S)-2,1-pyrrolidinediyl))bis
(N,N-dimethyl-2-oxo-1-phenylethanamine)

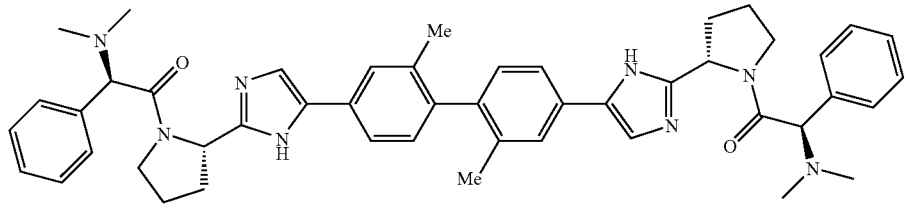

Example 121

Step a-b

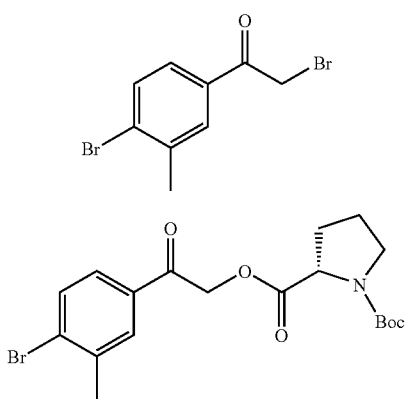

PdCl$_2$(Ph$_3$P)$_2$ (257 mg, 0.367 mmol) was added to a dioxane (45 mL) solution of 1-bromo-4-iodo-2-methylbenzene (3.01 g, 10.13 mmol) and tri-n-butyl(1-ethoxyvinyl)stannane (3.826 g, 10.59 mmol) and heated at 80° C. for 17 hours. The reaction mixture was treated with water (15 mL), cooled to ~0° C. (ice/water), and then NBS (1.839 g, 10.3 mmol) was added in batches over 7 minutes. After about 25 minutes of stirring, the volatile component was removed in vacuo, and the residue was partitioned between CH$_2$Cl$_2$ and water. The aqueous layer was extracted with CH$_2$Cl$_2$, and the combined organic phase was dried (MgSO$_4$), filtered, and concentrated in vacuo. The resulting crude material was purified by a gravity chromatography (silica gel; 4% ethyl acetate/hexanes) to provide bromide 121a as a brownish-yellow solid (2.699 g); the sample is impure and contains stannane-derived impurities, among others. $^1$H NMR (CDCl$_3$, δ=7.24, 400 MHz): 7.83 (s, 1H), 7.63 (s, 2H), 4.30 (s, 2H), 2.46 (s, 3H).

A CH$_3$CN (15 mL) solution of 121a (2.69 g, <9.21 mmol) was added dropwise over 3 minutes to a CH$_3$CN (30 mL) solution of (S)-Boc-proline (2.215 g, 10.3 mmol) and triethylamine (1.40 mL, 10.04 mmol), and stirred for 90 minutes. The volatile component was removed in vacuo, and the residue was partitioned between water and CH$_2$Cl$_2$, and the organic phase was dried (MgSO$_4$), filtered, and concentrated in vacuo. The resulting crude material was purified by a flash chromatography (silica gel; 15-20% ethyl acetate/hexanes) to provide 121b as a colorless viscous oil (2.74 g). $^1$H NMR (DMSO-d$_6$, δ=2.50, 400 MHz): δ 7.98 (m, 1H), 7.78 (d, J=8.3, 1H), 7.72-7.69 (m, 1H), 5.61-5.41 (m, 2H), 4.35-4.30 (m, 1H), 3.41-3.30 (m, 2H), 2.43 (s, 3H), 2.33-2.08 (m, 2H), 1.93-1.83 (m, 2H), 1.40/1.36 (s, 9H); LC (Cond. 1): RT=1.91 min; >95% homogeneity index; LC/MS: Anal. Calcd. for [M+Na]$^+$ C$_{19}$H$_{24}$BrNNaO$_5$ 448.07. found 448.10.

Additional keto-esters can be prepared in analogous fashion.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

| Example | Structure | Data |
|---|---|---|
| 121b-1 | ![structure] | RT = 2.15 minutes (condition 2, 98%); LRMS: Anal. Calcd. for C$_{17}$H$_{22}$NO$_5$ 399.07; found: 400.10 (M + H)$^+$. |

-continued

| Example | Structure | Data |
|---|---|---|
| 121b-2 | 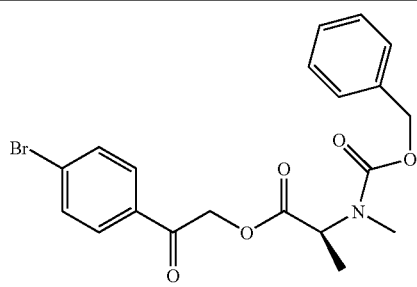 | RT = 2.78 minutes (condition 1, 90%); LRMS: Anal. Calcd. for $C_{20}H_{20}{}^{37}BrNO_5$ 435.05 found: 458.02 (M + Na)$^+$. |

Example 121

Step c

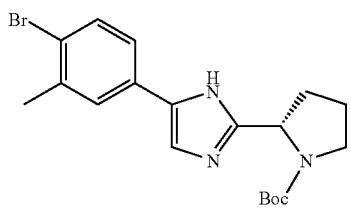

121c

A mixture of ketoester 121b (1.445 g, 3.39 mmol) and NH$_4$OAc (2.93 g, 38.0 mmol) in xylenes (18 mL) was heated with a microwave at 140° C. for 80 minutes. The volatile component was removed in vacuo, and the residue was carefully partitioned between CH$_2$Cl$_2$ and water, where enough saturated NaHCO$_3$ solution was added to neutralize the aqueous medium. The aqueous phase was extracted with CH$_2$Cl$_2$, and the combined organic phase was dried (MgSO$_4$), filtered, and concentrated in vacuo. The crude product was purified by a flash chromatography (silica gel, 40% ethyl acetate/hexanes) to provide imidazole 121c as an off-white solid (1.087 g). $^1$H NMR (DMSO-d$_6$, δ=2.50, 400 MHz): 12.15/11.91/11.84 (br s, 1H), 7.72-7.24 (m, 4H), 4.78 (m, 1H), 3.52 (m, 1H), 3.38-3.32 (m, 1H), 2.35 (s, 3H), 2.28-1.77 (m, 4H), 1.40/1.14 (s, 9H); LC (Cond. 1): RT=1.91 min; >98% homogeneity index; LC/MS: Anal. Calcd. for [M+H]$^+$ $C_{19}H_{25}BrN_3O_2$ 405.96. found 406.11.

Example 121

Step d

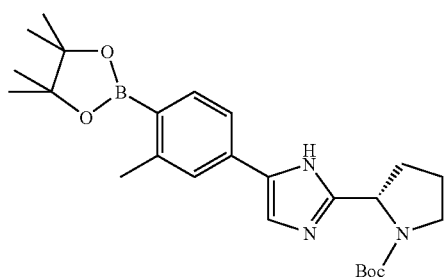

121d

PdCl$_2$dppf.CH$_2$Cl$_2$ (50.1 mg, 0.061 mmol) was added to a pressure tube containing a mixture of bromide 121c (538.3 mg, 1.325 mmol), bis(pinacolato)diboron (666.6 mg, 2.625 mmol), potassium acetate (365.8 mg, 3.727 mmol) and DMF (10 mL). The reaction mixture was flushed with N$_2$ and heated at 80° C. for 24.5 hours. The volatile component was removed in vacuo and the residue was partitioned between CH$_2$Cl$_2$ and water, where enough saturated NaHCO$_3$ solution was added to make the pH of the aqueous medium neutral. The aqueous phase was extracted with CH$_2$Cl$_2$, and the combined organic phase was dried (MgSO$_4$), filtered, and concentrated in vacuo. The resulting material was purified by a Biotage system (silica gel, 40-50% ethyl acetate/hexanes) to provide boronate 121d as a white foam (580 mg). According to $^1$H NMR the sample contains residual pinacol in a product/pinacol ratio of ~3. $^1$H NMR (DMSO-d$_6$, δ=2.50, 400 MHz): δ 12.16/11.91/11.83 (br s, 1H), 7.63-7.25 (m, 4H), 4.78 (m, 1H), 3.53 (m, 1H), 3.39-3.32 (m, 1H), 2.48/2.47 (s, 3H), 2.28-1.78 (m, 4H), 1.40/1.14/1.12 (br s, 9H), 1.30 (s, 12H); LC (Cond. 1): RT=1.62 min; LC/MS: Anal. Calcd. for [M+H]$^+$ $C_{25}H_{37}BN_3O_4$ 454.29. found 454.15

Example 121

Step e and

Example 121

Step f

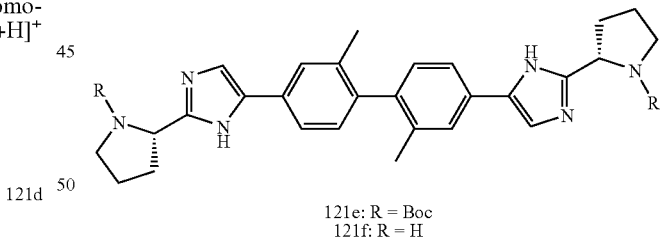

121e: R = Boc
121f: R = H

Carbamate 121e was prepared from bromide 121c and boronate 121d according to the preparation of dimer 1d; LC (Cond. 1): RT=1.43 min; LC/MS: Anal. Calcd. for [M+H]$^+$ $C_{38}H_{49}N_6O_4$ 653.38. found 653.65.

The deprotection of carbamate 121e, according to the preparation of pyrrolidine 1e, provided 121f as an off-white foam. $^1$H NMR (DMSO-d$_6$, s=2.50, 400 MHz): 11.79 (br s, 2H), 7.66 (s, 2H), 7.57 (d, J=7.8, 2H), 7.41 (br s, 2H), 7.02 (d, J=7.8, 2H), 4.15 (app t, J=7.2, 2H), 3.00-2.94 (m, 2H), 2.88-2.82 (m, 2H), 2.09-2.01 (m, 2H), 2.04 (s, 6H), 1.93-1.85 (m, 2H), 1.82-1.66 (m, 4H). Note: although broad signals corresponding to the pyrrolidine NH appear in the 2.8-3.2 ppm region, the actual range for their chemical shift could not be determined. LC (Cond. 1): RT=1.03 min; LC/MS: Anal. Calcd. for [M+H]$^+$ $C_{28}H_{33}N_6$ 453.28. found 453.53

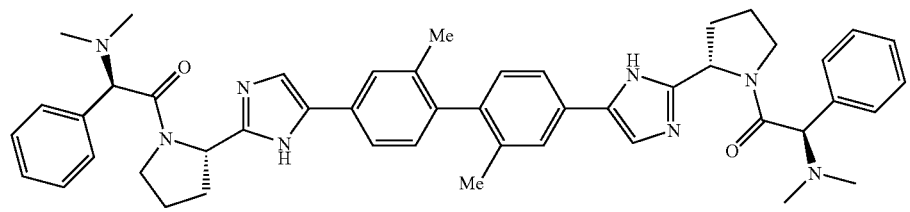

Example 121

(1R,1'R)-2,2'-((2,2'-dimethyl-4,4'-biphenyldiyl)bis(1H-imidazole-5,2-diyl(2S)-2,1-pyrrolidinediyl))bis(N,N-dimethyl-2-oxo-1-phenylethanamine)

Example 121 (TFA salt) was synthesized from 121f according to the preparation of Example 1 from 1e; LC (Cond. 1): RT=1.14 min; >98% homogeneity index; LC/MS: Anal. Calcd. for [M+H]+ C48H55N8O2 775.45; 775.75; HRMS: Anal. Calcd. for [M+H]+ C48H55N8O2 775.4448. found 775.4473

Example 122 dimethyl ((2,2'-dimethyl-4,4'-biphenyldiyl)bis(1H-imidazole-5,2-diyl(2S)-2,1-pyrrolidinediyl((1R)-2-oxo-1-phenyl-2,1-ethanediyl)))biscarbamate

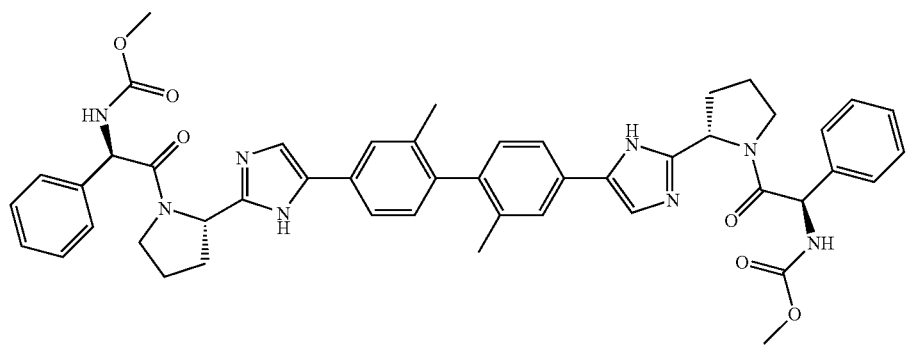

Example 122 (TFA salt) was prepared from pyrrolidine 121f and Cap-4 by using the procedure described for the preparation of Example 1 from pyrrolidine 1e. LC (Cond. 1): RT=1.35 min; >98% homogeneity index; HRMS: Anal. Calcd. for [M+H]+ C48H51N8O6 835.3932. found 835.3954

Example 123-125

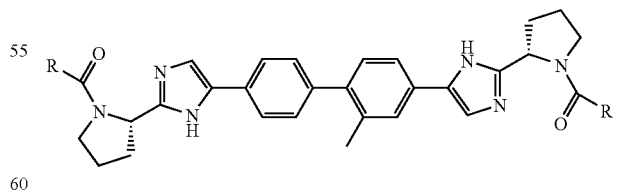

Example 123-125 were prepared starting from boronate 1c and bromide 121c by using the methods described in Example 1, step d, Example 1, step e, and in the step describing the final preparation of Example 1.

| Example | Compound Name | R (acyl group) | RT (LC-Cond.); % homogeneity index; MS data |
|---|---|---|---|
| 123 | (1R,1'R)-2,2'-((2-methyl-4,4'-biphenyldiyl)bis(1H-imidazole-5,2-diyl(2S)-2,1-pyrrolidinediyl))bis(N,N-dimethyl-2-oxo-1-phenylethanamine) | Cap-1 | 1.12 minutes (Cond. 1); >98%; LC/MS: Anal. Calcd. for $[M + H]^+$ $C_{47}H_{53}N_8O_2$: 761.43; found 761.49; HRMS: Anal. Calcd. for $[M + H]^+$ $C_{47}H_{53}N_8O_2$: 761.4291; found 761.4311 |
| 124 | dimethyl ((2-methyl-4,4'-biphenyldiyl)bis(1H-imidazole-5,2-diyl(2S)-2,1-pyrrolidinediyl((1R)-2-oxo-1-phenyl-2,1-ethanediyl)))biscarbamate | Cap-4 | 1.34 minutes (Cond. 1); >98%; LC/MS: Anal. Calcd. for $[M + H]^+$ $C_{47}H_{49}N_8O_6$: 821.38; found 821.45; HRMS: Anal. Calcd. for $[M + H]^+$ $C_{47}H_{49}N_8O_6$: 821.3775; found 821.3785 |
| 125 | (1R,1'R)-2,2'-((2-methyl-4,4'-biphenyldiyl)bis(1H-imidazole-5,2-diyl(2S)-2,1-pyrrolidinediyl))bis(2-oxo-1-phenylethanol) | | 1.23 minutes (Cond. 1); >98%; LC/MS: Anal. Calcd. for $[M + H]^+$ $C_{43}H_{43}N_6O_4$: 707.34; found 707.38; HRMS: Anal. Calcd. for $[M + H]^+$ $C_{43}H_{43}N_6O_4$: 707.3346; found 707.3356 |

Examples 126-128

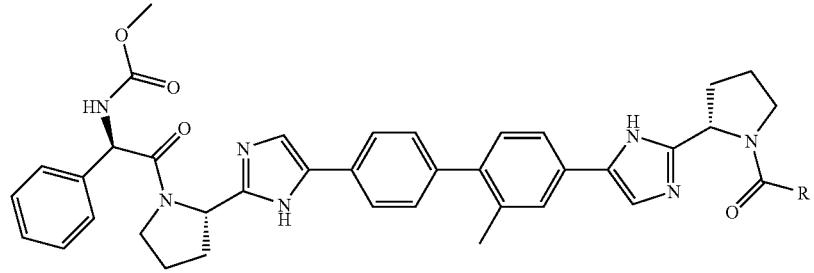

Example 126-128 were prepared starting from bromide 28b and boronate 121d by using the methods described in Example 28 starting with step c.

| Example | Compound Name | R | RT (LC-Cond.); % homogeneity index; MS data |
|---|---|---|---|
| 126 | methyl ((1R)-2-((2S)-2-(5-(4'-(2-((2S)-1-((2R)-2-(dimethylamino)-2-phenylacetyl)-2-pyrrolidinyl)-1H-imidazol-5-yl)-2'-methyl-4-biphenylyl)-1H-imidazol-2-yl)-1-pyrrolidinyl)-2-oxo-1-phenylethyl)carbamate | Cap-1 | 1.22 min (Cond. 1); >98%; LC/MS: Anal. Calcd. for $[M + H]^+$ $C_{47}H_{51}N_8O_4$: 791.40; found 791.70; HRMS: Anal. Calcd. for $[M + H]^+$ $C_{47}H_{51}N_8O_4$: 791.4033; found 791.4061 |

-continued

| Example | Compound Name | 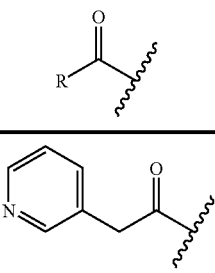 | RT (LC-Cond.); % homogeneity index; MS data |
|---|---|---|---|
| 127 | methyl ((1R)-2-((2S)-2-(5-(2'-methyl-4'-(2-((2S)-1-(3-pyridinylacetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 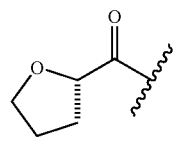 | 1.19 minutes (Cond. 1); >98%; LC/MS: Anal. Calcd. for [M + H]$^+$ C$_{44}$H$_{45}$N$_8$O$_4$: 749.36; found 749.62; HRMS: Anal. Calcd. for [M + H]$^+$ C$_{44}$H$_{45}$N$_8$O$_4$: 749.3564; found 749.3592 |
| 128 | methyl ((1R)-2-((2S)-2-(5-(2'-methyl-4'-(2-((2S)-1-((2S)-tetrahydro-2-furanylcarbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | | 1.27 minutes (Cond. 1); >98%; LC/MS: Anal. Calcd. for [M + H]$^+$ C$_{42}$H$_{46}$N$_7$O$_5$: 728.36; found 728.59; HRMS: Anal. Calcd. for [M + H]$^+$ C$_{42}$H$_{46}$N$_7$O$_5$: 728.3560; found 728.3593 |

Example 129 methyl ((1R)-2-((2S)-2-(5-(4'-(2-((2S)-1-((2R)-2-(dimethylamino)-2-phenylacetyl)-2-pyrrolidinyl)-1H-imidazol-5-yl)-2,2'-dimethyl-4-biphenylyl)-1H-imidazol-2-yl)-1-pyrrolidinyl)-2-oxo-1-phenylethyl)carbamate

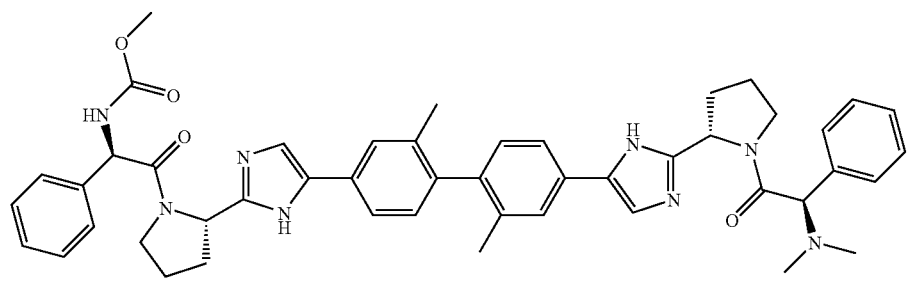

Example 129

Step a

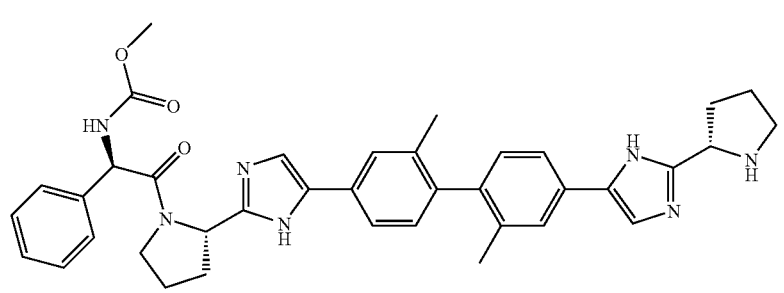

129a

HATU (104.3 mg, 0.274 mmol) was added to a mixture of 121f, Cap-4 (58.8 mg, 0.281 mmol) and diisopropylethylamine (110 µL, 0.631 mmol) in DMF (6.0 mL), and stirred for 90 minutes. The volatile component was removed in vacuo and the resulting crude material was purified by reverse phase HPLC (H$_2$O/methanol/TFA), and free-based by MCX column (methanol wash; 2.0 M NH$_3$/methanol) to provide 129a (89.9 mg). LC (Cond. 1): RT=1.22 min; 95% homogeneity index; LC/MS: Anal. Calcd. for [M+H]$^+$ C$_{38}$H$_{42}$N$_7$O$_3$ 644.34. found 644.55.

Example 129 methyl ((1R)-2-((2S)-2-(5-(4'-(2-((2S)-1-((2R)-2-(dimethylamino)-2-phenylacetyl)-2-pyrrolidinyl)-1H-imidazol-5-yl)-2,2'-dimethyl-4-biphenylyl)-1H-imidazol-2-yl)-1-pyrrolidinyl)-2-oxo-1-phenylethyl) carbamate

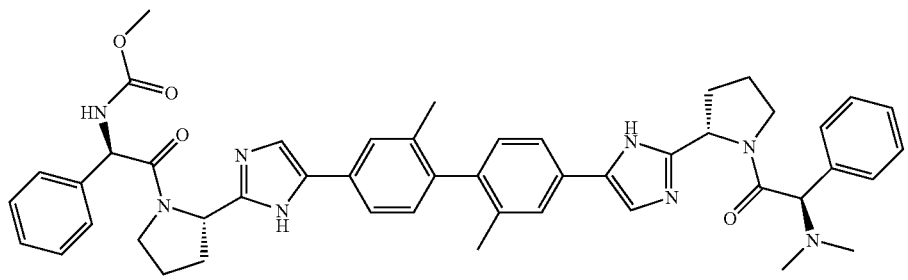

Example 129 (TFA salt) was prepared from 129a by the method used to convert Example 1e to Example 1. LC (Cond. 1): RT=1.27 min; 97% homogeneity index; LC/MS: Anal. Calcd. for [M+H]$^+$ C$_{48}$H$_{53}$N$_8$O$_4$ 805.42. found 805.61.

Example 130

(1R,1'R)-2,2'-((2-(trifluoromethyl)-4,4'-biphenyldiyl)bis(1H-imidazole-5,2-diyl(2S)-2,1-pyrrolidinediyl))bis(N,N-dimethyl-2-oxo-1-phenylethanamine)

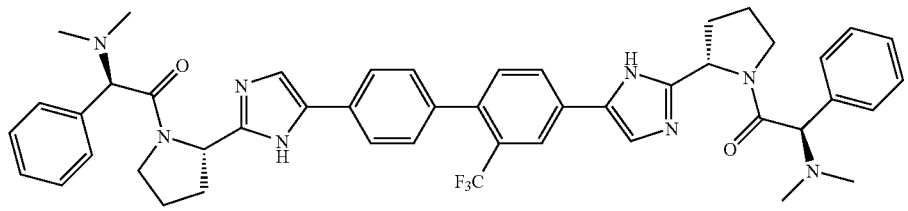

Example 130

Step a

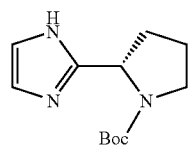

130a

Glyoxal (2.0 mL of 40% in water) was added dropwise over 11 minutes to a methanol solution of NH$_4$OH (32 mL) and (S)-Boc-prolinal (8.564 g, 42.98 mmol) and stirred at ambient temperature for 19 hours. The volatile component was removed in vacuo and the residue was purified by a flash chromatography (silica gel, ethyl acetate) followed by a recrystallization (ethyl acetate, room temperature) to provide imidazole 130a as a white fluffy solid (4.43 g). $^1$H NMR (DMSO-d$_6$, s=2.50, 400 MHz): 11.68/11.59 (br s, 1H), 6.94 (s, 1H), 6.76 (s, 1H), 4.76 (m, 1H), 3.48 (m, 1H), 3.35-3.29 (m, 1H), 2.23-1.73 (m, 4H), 1.39/1.15 (s, 9H). LC (Cond. 1): RT=0.87 min; >95% homogeneity index; LC/MS: Anal. Calcd. for [M+H]$^+$ C$_{12}$H$_{20}$N$_3$O$_2$ 238.16. found 238.22. Imidazole 130a had an ee of 98.9% when analyzed under chiral HPLC condition noted below.

Column: Chiralpak AD, 10 um, 4.6×50 mm

Solvent: 1.7% ethanol/heptane (isocratic)

Flow rate: 1 mL/min

Wavelength: either 220 or 256 nm

Relative retention time: 3.25 min (R), 5.78 minutes (S)

Example 130

Step b

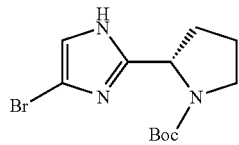

130b

N-Bromosuccinimide (838.4 mg, 4.71 mmol) was added in batches, over 15 minutes, to a cooled (ice/water) CH$_2$Cl$_2$ (20 mL) solution of imidazole 130a (1.0689 g, 4.504 mmol), and stirred at similar temperature for 75 minutes. The volatile component was removed in vacuo. The crude material was purified by a reverse phase HPLC system (H$_2$O/methanol/TFA) to separate bromide 130b from its dibromo-analog and the non-consumed starting material. The HPLC elute was neutralized with excess NH$_3$/methanol and the volatile component was removed in vacuo. The residue was partitioned between CH$_2$Cl$_2$ and water, and the aqueous layer was extracted with water. The combined organic phase was dried (MgSO$_4$), filtered, and concentrated in vacuo to provide 130b as a white solid (374 mg). $^1$H NMR (DMSO-d$_6$, δ=2.50, 400

MHz): 12.12 (br s, 1H), 7.10 (m, 1H), 4.70 (m, 1H), 3.31 (m, 1H; overlapped with water signal), 2.25-1.73 (m, 4H), 1.39/1.17 (s, 3.8H+5.2H). LC (Cond. 1): RT=1.10 min; >95% homogeneity index; LC/MS: Anal. Calcd. for [M+H]+ $C_{12}H_{19}BrN_3O_2$ 316.07. found 316.10.

Example 130

Step c

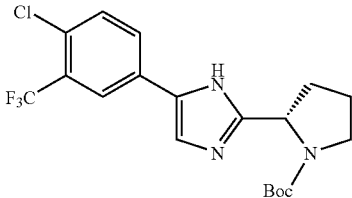

130c

Pd(Ph$_3$P)$_4$ (78.5 mg, 0.0679 mmol) was added to a mixture of bromide 130b (545 mg, 1.724 mmol), 2-(4-chloro-3-(trifluoromethyl)phenyl-4,4,5,5-tetramethyl-1,3,2-dioxaborolane (542.8 mg, 1.771 mmol) (commercially available), NaHCO$_3$ (477 mg, 5.678 mmol) in 1,2-dimethoxyethane (12.5 mL) and water (4.2 mL). The reaction mixture was purged with nitrogen, heated with an oil bath at 80° C. for 27 hours, and then the volatile component was removed in vacuo. The residue was partitioned between CH$_2$Cl$_2$ and water, and the organic layer was dried (MgSO$_4$), filtered, and concentrated in vacuo. The resulting crude material was purified by a Biotage system (silica gel, 40-50% ethyl acetate/hexanes) followed by a reverse phase HPLC (water/methanol/TFA). The HPLC elute was treated with excess NH$_3$/methanol and concentrated. The residue was partitioned between water and CH$_2$Cl$_2$, and the organic layer was dried (MgSO$_4$), filtered, and concentrated in vacuo to provide 130c as a white foam (317.4 mg). $^1$H NMR (DMSO-d$_6$, δ=2.50, 400 MHz): 12.36/12.09/12.03 (br s, 1H), 8.15 (d, J=1.8, 0.93H), 8.09 (br s, 0.07H), 8.01 (dd, J=8.3/1.3, 0.93H), 7.93 (m, 0.07H), 7.74 (m, 1H), 7.66 (d, J=8.3, 0.93H), 7.46 (m, 0.07H), 4.80 (m, 1H), 3.53 (m, 1H), 3.36 (m, 1H), 2.30-1.77 (m, 4 h), 1.40/1.15 (s, 3.8H+5.2H). LC (Cond. 1): RT=1.52 min; >95% homogeneity index; LC/MS: Anal. Calcd. for [M+H]+ $C_{19}H_{22}ClF_3N_3O_2$ 416.14. found 416.17.

Example 130

Step d-e

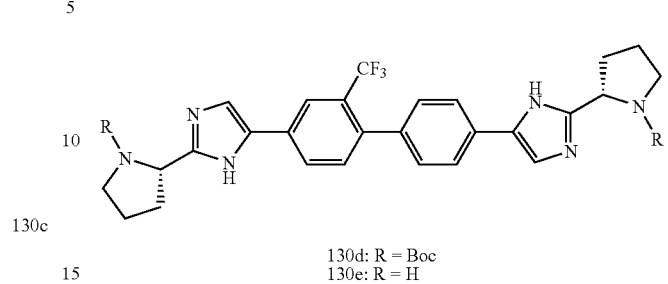

130d: R = Boc
130e: R = H

Pd[P(t-Bu)$_3$]$_2$ (48 mg, 0.094 mmol) was added to a mixture of chloride 130c (245 mg, 0.589 mmol), boronate 1c (277.1 mg, 0.631 mmol), KF (106.7 mg, 1.836 mmol) in DMF (6 mL), and heated at 110° C. for ~30 hours. The volatile component was removed in vacuo, and the residue was partitioned between CH$_2$Cl$_2$ (50 mL), water (20 mL) and saturated NaHCO$_3$ (1 mL). The aqueous layer was extracted with CH$_2$Cl$_2$ (2×), and the combined organic phase was dried (MgSO$_4$), filtered, and concentrated in vacuo. The resulting material was purified by a Biotage system (silica gel, ethyl acetate) to provide carbamate 130d as an off-white foam (297 mg). LC (Cond. 1): RT=1.44 min; >95% homogeneity index; LC/MS: Anal. Calcd. for [M+H]+ $C_{37}H_{44}F_3N_6O_4$ 693.34. found 693.34.

The deprotection of 130d, which was conducted according to the preparation of pyrrolidine 1e, provided 130e as a light yellow foam. $^1$H NMR (DMSO-d$_6$, s=2.50, 400 MHz): 11.88 (br s, 2H), 8.16 (d, J=1.5, 1H), 8.02 (d, J=7.8, 1H), 7.78 (d, J=8.1, 2H), 7.66 (br s, 1H), 7.48 (br s, 1H), 7.37 (d, J=8.1, 1H), 7.28 (d, J=8.3, 2H), 4.18 (m, 2H), 2.99-2.93 (m, 2H), 2.89-2.83 (m, 2H), 2.11-2.01 (m, 2H), 1.94-1.85 (m, 2H), 1.82-1.67 (m, 4H). Note: although broad signals corresponding to the pyrrolidine NH appear in the 2.8-3.2 ppm region, the actual range for their chemical shift could not be determined. LC (Cond. 1): RT=1.12 min; >95% homogeneity index; LC/MS: Anal. Calcd. for [M+H]+ $C_{27}H_{28}F_3N_6$ 493.23. found 493.14.

Example 130

(1R,1'R)-2,2'-((2-(trifluoromethyl)-4,4'-biphenyldiyl) bis(1H-imidazole-5,2-diyl(2S)-2,1-pyrrolidinediyl)) bis(N,N-dimethyl-2-oxo-1-phenylethanamine)

Example 130 (TFA salt) was prepared from 130e and Cap-1 according to the preparation of Example 1 from pyrrolidine 1e. LC (Cond. 1): RT=1.17 min; >98% homogeneity index; LC/MS: Anal. Calcd. for [M+H]+ $C_{47}H_{50}F_3N_8O_2$ 815.40. found 815.44; HRMS: Anal. Calcd. for [M+H]+ $C_{47}H_{50}F_3N_8O_2$ 815.4009. found 815.4013

Example 131

5,5'-(2-(trifluoromethyl)-4,4'-biphenyldiyl)bis(2-((2S)-1-((2R)-2-phenyl-2-(1-pyrrolidinyl)acetyl)-2-pyrrolidinyl)-1H-imidazole)

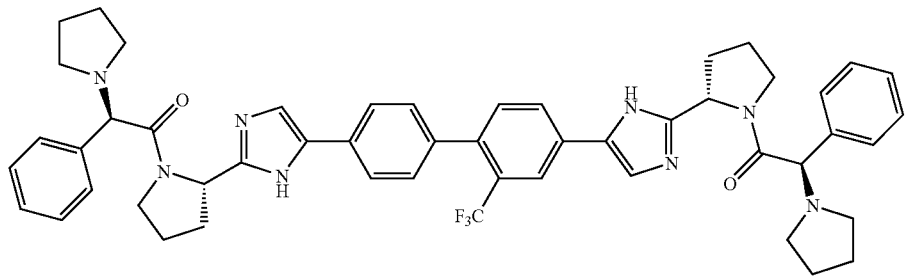

Example 131 (TFA salt) was synthesized from 130e and Cap-5 according to the preparation of Example 130.
LC (Cond. 1): RT=1.19 min; >98% homogeneity index
LC/MS: Anal. Calcd. for [M+H]$^+$ C$_{51}$H$_{54}$F$_3$N$_8$O$_2$ 867.43. found 867.51
HRMS: Anal. Calcd. for [M+H]$^+$ C$_{51}$H$_{54}$F$_3$N$_8$O$_2$ 867.4322. found 867.4315

Example 131.1-1 to 131.1-2

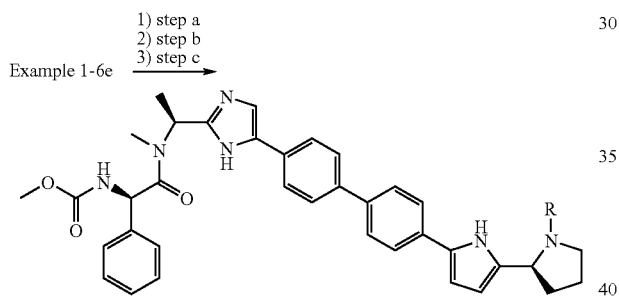

Example 1-6e →
1) step a
2) step b
3) step c step a: Couple cap-4 with HATU as in Example 28 step e
step b: Remove Cbz group with H$_2$, Pd/C
step c: Append appropriate cap Examples 131.1-1 through 131.1-2 were prepared in similar fashion to example 28 via the intermediacy of intermediate 1-6e after appending Cap-4.

Example 131.1-1 methyl ((1R)-2-(((1S)-1-(5-(4'-(2-((2S)-1-((2R)-2-(dimethylamino)-2-phenylacetyl)-2-pyrrolidinyl)-1H-imidazol-5-yl)-4-biphenylyl)-1H-imidazol-2-yl)ethyl)(methyl)amino)-2-oxo-1-phenylethyl)carbamate

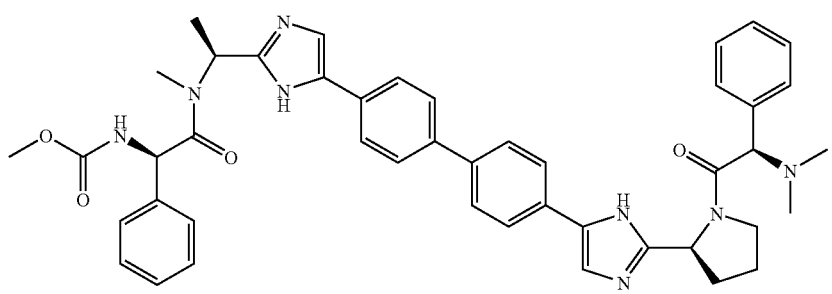

Cap-1 was appended after the CBz carbamate was removed from 1-6e with Pd/C/H$_2$.

LCMS conditions: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 µL injection volume. $t_R$=1.42 min LRMS: Anal. Calcd. for C$_{45}$H$_{49}$N$_8$O$_4$ 765.39. found: 765.38 (M+H)$^+$.

HRMS: Anal. Calcd. for C$_{45}$H$_{49}$N$_8$O$_4$ Calcd 765.3877 found: 765.3905 (M+H)$^+$.

Example 131.1-2 methyl ((1R)-2-(methyl((1S)-1-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)ethyl)amino)-2-oxo-1-phenylethyl)carbamate

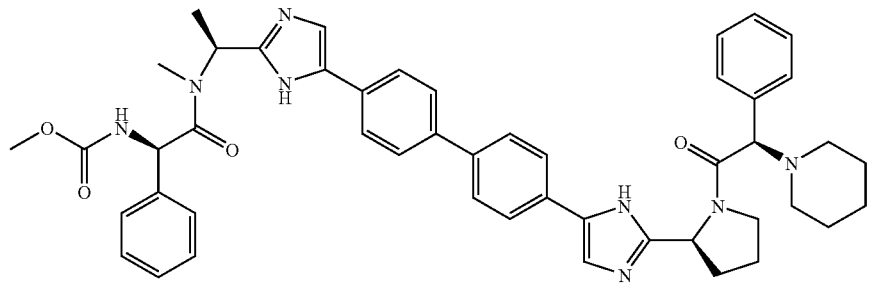

Cap-14 was appended after the CBz carbamate was removed from 1-6e with Pd/C/H$_2$.

LCMS conditions: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 µL injection volume. $t_R$=1.45 min (>95%)

LRMS: Anal. Calcd. for C$_{48}$H$_{52}$N$_8$O$_4$ 805.42. found: 805.41 (M+H)$^+$.

HRMS: Anal. Calcd. C$_{48}$H$_{52}$N$_8$O$_4$ Calcd 805.4190 found: 805.4214 (M+H)$^+$.

Example 131.2

(2R)-2-(dimethylamino)-N-methyl-2-phenyl-N-((1S)-1-(5-(4'-(2-((2S)-1-((2R)-2-phenyl-2-(1-piperidinyl)acetyl)-2-pyrrolidinyl)-1H-imidazol-5-yl)-4-biphenylyl)-1H-imidazol-2-yl)ethyl)acetamide

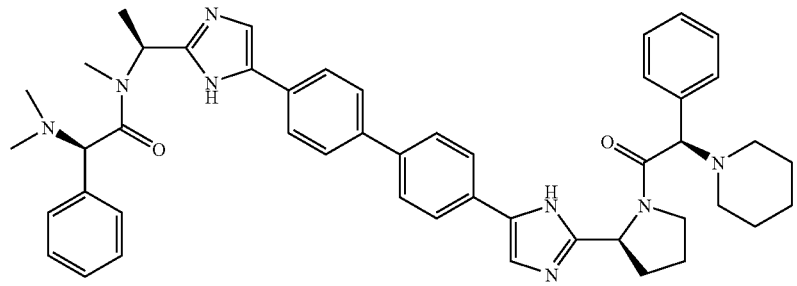

Example 131.2 was prepared in similar fashion to example 131.1-1 and example 131.1-2 via the intermediacy of intermediate 1-6e after appending Cap-1. Cap-14 was appended after the CBz carbamate was removed with Pd/C/H$_2$. LCMS conditions: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 µL injection volume. $t_R$=1.28 min LRMS: Anal. Calcd. for C$_{48}$H$_{54}$N$_8$O$_2$ 775.44. found: 775.45 (M+H)$^+$.

HRMS: Anal. Calcd. C$_{48}$H$_{54}$N$_8$O$_2$ Calcd 775.4448 found: 775.4460 (M+H)$^+$.

Example 132

(1R)-2-((2S)-2-(5-(6-(4-(2-((2S)-1-((2R)-2-(dimethylamino)-2-phenylacetyl)-2-pyrrolidinyl)-1H-imidazol-5-yl)phenyl)-3-pyridinyl)-1H-imidazol-2-yl)-1-pyrrolidinyl)-N,N-dimethyl-2-oxo-1-phenylethanamine

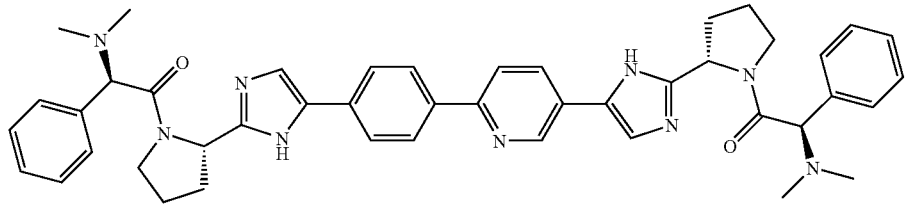

Example 132

Step a-b

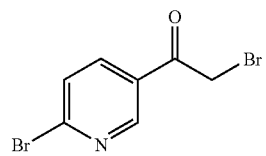

132a

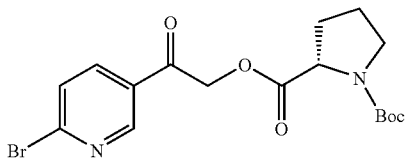

132b

A CH$_2$Cl$_2$ (10 mL) solution of Br$_2$ (7.63 g, 47.74 mmol) was added-drop wise over 5 min to a cooled (ice/water) CH$_2$Cl$_2$ (105 mL) solution of 1-(6-bromopyridine-3-yl)ethanone (9.496 g, 47.47 mmol) and 48% HBr (0.4 mL). The cooling bath was removed 40 min later, and stirring was continued at ambient temperature for about 66 hr. The cake of solid that formed was filtered, washed with CH$_2$Cl$_2$ and dried in vacuo to afford impure 132a as an off-white solid (15.94 g).

Boc-L-proline (9.70 g, 45.06 mmol) was added in one batch to a heterogeneous mixture of crude 132a (15.4 g) and CH$_3$CN (150 mL), and immediately afterward Et$_3$N (13.0 mL, 93.2 mmol) was added drop-wise over 6 min. The reaction mixture was stirred for 50 min, the volatile component was removed in vacuo and the residue was partitioned between CH$_2$Cl$_2$ and water. The CH$_2$Cl$_2$ layer was dried (MgSO$_4$), filtered and concentrated in vacuo, and the resultant material was purified by flash chromatography (silica gel; sample was loaded with eluting solvent; 25% EtOAc/hexanes) to afford 132b as a highly viscous yellow oil (11.44 g). $^1$H NMR (DMSO, δ=2.5 ppm; 400 MHz): 8.95 (m, 1H), 8.25-8.21 (m, 1H), 7.88 (d, J=8.3, 1H), 5.65-5.46 (m, 2H), 4.36-4.31 (m, 1H), 3.41-3.29 (m, 2H), 2.36-2.22 (m, 1H), 2.14-2.07 (m, 1H), 1.93-1.83 (m, 2H), 1.40 & 1.36 (two s, 9H).

LC (Cond. 1): RT=2.01 min; >90% homogeneity index

LC/MS: Anal. Calcd. for [M+Na]$^+$ C$_{17}$H$_{21}$NaBrN$_2$O$_5$: 435.05. found 435.15

HRMS: Anal. Calcd. for [M+H]$^+$ C$_{17}$H$_{22}$BrN$_2$O$_5$: 413.0712. found 413.0717

Example 132

Step c

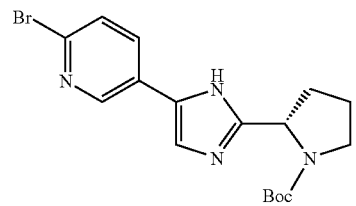

132c

A mixture of ketoester 132b (1.318 g, 3.19 mmol) and NH$_4$OAc (2.729 g, 35.4 mmol) in xylenes (18 mL) was heated with a microwave at 140° C. for 90 min. The volatile component was removed in vacuo and the residue was partitioned between CH$_2$Cl$_2$ and water, where enough saturated NaHCO$_3$ solution was added to neutralize the aqueous medium. The aqueous phase was extracted with CH$_2$Cl$_2$, and the combined organic phase was dried (MgSO$_4$), filtered, and concentrated in vacuo. The resulting crude material was purified by a Biotage system (silica gel; 50% EtOAc/hexanes) to afford imidazole 132c as an off-white foam (1.025 g). $^1$H NMR (DMSO, δ=2.5 ppm, 400 MHz): 12.33/12.09/12.02 (br m, 1H), 8.74 (d, J=2.3, 0.93H), 8.70 (app br s, 0.07H), 8.03/7.98 (dd for the first peak, J=8.3, 1H), 7.69/7.67 (br m, 1H), 7.58/7.43 (d for the first peak, J=8.3, 1H), 4.80 (m, 1H), 3.53 (m, 1H), 3.36 (m, 1H), 2.33-2.11 (m, 1H), 2.04-1.79 (m, 3H), 1.39/1.15 (app br s, 3.9H+5.1H).

LC (Cond. 1): RT=1.52 min; >98% homogeneity index

LC/MS: Anal. Calcd. for [M+H]$^+$ C$_{17}$H$_{22}$BrN$_4$O$_2$: 393.09. found 393.19

HRMS: Anal. Calcd. for [M+H]$^+$ C$_{17}$H$_{22}$BrN$_4$O$_2$: 393.0926. found 393.0909

Example 132

Step d-e

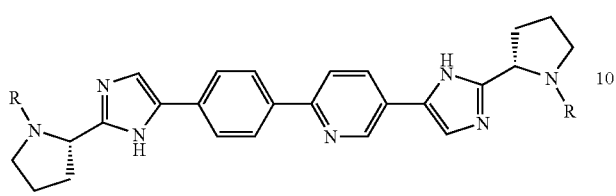

132d: R = Boc
132e: R = H

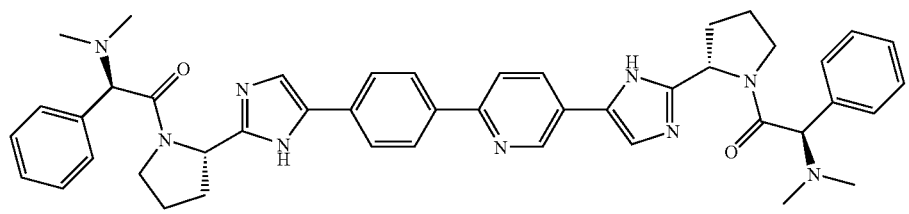

Pd(Ph₃P)₄ (115.1 mg, 0.10 mmol) was added to a mixture of bromide 132c (992 mg, 2.52 mmol), boronate 1c (1.207 g, 2.747 mmol), NaHCO₃ (698.8 mg, 8.318 mmol) in 1,2-dimethoxyethane (18 mL) and water (4 mL). The reaction mixture was flushed with nitrogen, heated with an oil bath at 90° C. for 37 hr and allowed to cool to ambient temperature. The suspension that formed was filtered and washed with water followed by 1,2-dimethoxyethane, and dried in vacuo. A silica gel mesh was prepared from the crude solid and submitted to flash chromatography (silica gel; EtOAc) to afford carbamate 132d as a white solid, which yellowed slightly upon standing at ambient conditions (1.124 g). $^1$H NMR indicated that the sample contains residual MeOH in a product/MeOH mole ratio of 1.3.

LC (Cond. 1): RT=1.71 min; >98% homogeneity index

LC/MS: Anal. Calcd. for [M+H]⁺ $C_{35}H_{44}N_7O_4$: 626.35. found 626.64

HRMS: Anal. Calcd. for [M+H]⁺ $C_{35}H_{44}N_7O_4$: 626.3455; 626.3479

Carbamate 132d (217 mg) was treated with 25% TFA/CH₂Cl₂ (3.6 mL) and stirred at ambient condition for 6 hr. The volatile component was removed in vacuo, and the resultant material was free based by MCX column (MeOH wash; 2.0 M NH₃/MeOH elution) to afford 132e as a dull yellow foam that solidified gradually upon standing (150.5 mg; mass is above theoretical yield). $^1$H NMR (DMSO, s=2.5 ppm; 400 MHz): 11.89 (very broad, 2H), 9.01 (d, J=1.8, 1H), 8.13 (dd, J=8.3, 2.2, 1H), 8.07 (d, J=8.6, 2H), 7.92 (d, J=8.3, 1H), 7.83 (d, J=8.5, 2H), 7.61 (br s, 1H), 7.50 (br s, 1H), 4.18 (m, 2H), 3.00-2.93 (m, 2H), 2.90-2.82 (m, 2H), 2.11-2.02 (m, 2H), 1.94-1.85 (m, 2H), 1.83-1.67 (m, 4H). [Note: the exchangeable pyrrolidine hydrogens were not observed]

LC (Cond. 1): RT=1.21 min; >98% homogeneity index

LC/MS: Anal. Calcd. for [M+H]⁺ $C_{25}H_{28}N_7$: 426.24. found 426.40

HRMS: Anal. Calcd. for [M+H]⁺ $C_{25}H_{28}N_7$: 426.2406. found 426.2425

Example 132

(1R)-2-((2S)-2-(5-(6-(4-(2-((2S)-1-((2R)-2-(dimethylamino)-2-phenylacetyl)-2-pyrrolidinyl)-1H-imidazol-5-yl)phenyl)-3-pyridinyl)-1H-imidazol-2-yl)-1-pyrrolidinyl)-N,N-dimethyl-2-oxo-1-phenylethanamine HATU (41.4 mg, 0.109 mmol) was added to a mixture of pyrrolidine 132e (23.1 mg, 0.054 mmol), (i-Pr)₂EtN (40 μL, 0.23 mmol) and Cap-1 (25.3 mg, 0.117 mmol) in DMF (1.5 mL), and the mixture was stirred at ambient for 1 hr. The volatile component was removed in vacuo, and the residue was purified first by MCX (MeOH wash; 2.0 M NH₃/MeOH elution) and then by a reverse phase HPLC (H₂O/MeOH/TFA) to afford the TFA salt of Example 132 as a yellow foam (39.2 mg).

LC (Cond. 1): RT=1.37 min; >98% homogeneity index

LC/MS: Anal. Calcd. for [M+H]⁺ $C_{45}H_{50}N_9O_2$: 748.41. found 748.53

HRMS: Anal. Calcd. for [M+H]⁺ $C_{45}H_{50}N_9O_2$: 748.4087. found 748.4090

Example 133-135 were prepared as TFA salts from 132e by using the same method of preparations as Example 132 and appropriate reagents.

Example 133-135

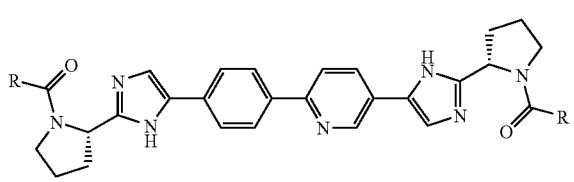

| Example | Compound Name | R (structure) | RT (LC-Cond.); % homogeneity index; MS data |
|---|---|---|---|
| 133 | (1R)-2-((2S)-2-(5-(6-(4-(2-((2S)-1-((2R)-2-hydroxy-2-phenylacetyl)-2-pyrrolidinyl)-1H-imidazol-5-yl)phenyl)-3-pyridinyl)-1H-imidazol-2-yl)-1-pyrrolidinyl)-2-oxo-1-phenylethanol | Ph, HO | 1.49 min (Cond. 1); >98%; LC/MS: Anal. Calcd. for [M + H]+ C41H40N7O4: 694.31; found 694.42 HRMS: Anal. Calcd. for [M + H]+ C41H40N7O4: 694.3142, found: 694.3164 |
| 134 | methyl ((1R)-2-((2S)-2-(5-(6-(4-(2-((2S)-1-((2R)-2-((methoxycarbonyl)amino)-2-phenylacetyl)-2-pyrrolidinyl)-1H-imidazol-5-yl)phenyl)-3-pyridinyl)-1H-imidazol-2-yl)-1-pyrrolidinyl)-2-oxo-1-phenylethyl)carbamate | Ph, HN-C(=O)-O-  Cap-4 | 1.60 min (Cond. 1); >98%; LC/MS: Anal. Calcd. for [M + H]+ C45H46N9O6: 808.36; found 808.51 HRMS: Anal. Calcd. for [M + H]+ C45H46N9O6: 808.3571; found 808.3576 |
| 135 | 5-(2-((2S)-1-((2R)-2-methoxy-2-phenylacetyl)-2-pyrrolidinyl)-1H-imidazol-5-yl)-2-(4-(2-((2S)-1-((2R)-2-methoxy-2-phenylacetyl)-2-pyrrolidinyl)-1H-imidazol-5-yl)phenyl)pyridine | Ph, OMe | 1.60 min (Cond. 1); >98%; LC/MS: Anal. Calcd. for [M + H]+ C43H44N7O4: 722.35; found 722.40 HRMS: Anal. Calcd. for [M + H]+ C43H44N7O4: 722.3455; found 722.3464 |

Example 136

(1R)-2-((2S)-2-(5-(6-(4-(2-((2S)-1-((2R)-2-(dimethylamino)-2-phenylacetyl)-2-pyrrolidinyl)-1H-imidazol-5-yl)-2-methylphenyl)-3-pyridinyl)-1H-imidazol-2-yl)-1-pyrrolidinyl)-N,N-dimethyl-2-oxo-1-phenylethanamine

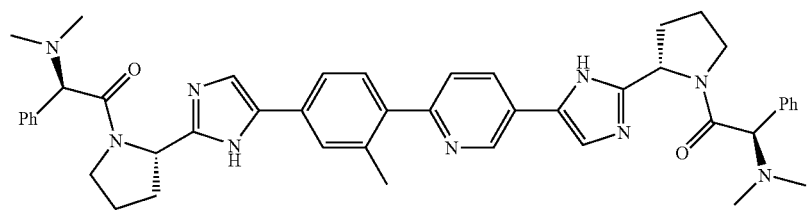

Example 136

Step a and b

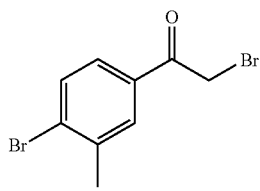

136a

-continued

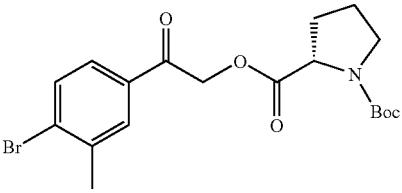

136b

PdCl$_2$(Ph$_3$P)$_2$ (257 mg, 0.367 mmol) was added to a dioxane (45 mL) solution of 1-bromo-4-iodo-2-methylbenzene (3.01 g, 10.13 mmol) and tri-n-butyl(1-ethoxyvinyl)stannane (3.826 g, 10.59 mmol) and heated at 80° C. for 17 hr. The reaction mixture was treated with water (15 mL), cooled to ~0° C. (ice/water), and then NBS (1.839 g, 10.3 mmol) was added in batches over 7 min. About 25 min of stirring, the volatile component was removed in vacuo, and the residue was partitioned between $CH_2Cl_2$ and water. The aqueous layer was extracted with $CH_2Cl_2$, and the combined organic phase was dried ($MgSO_4$), filtered, and concentrated in vacuo. The resulting crude material was purified by a gravity chromatography (silica gel; 4% EtOAc/hexanes) to afford bromide 136a as a brownish-yellow solid (2.699 g); the sample is impure and contains stannane-derived impurities, among others. $^1H$ NMR ($CDCl_3$, $\delta$=7.24, 400 MHz): 7.83 (s, 1H), 7.63 (s, 2H), 4.30 (s, 2H), 2.46 (s, 3H).

An $CH_3CN$ (15 mL) solution of 136a (2.69 g, <9.21 mmol) was added drop wise over 3 min to a $CH_3CN$ (30 mL) solution of (S)-Boc-proline (2.215 g, 10.3 mmol) and $Et_3N$ (1.40 mL, 10.04 mmol), and stirred for 90 min. The volatile component was removed in vacuo, and the residue was partitioned between water and $CH_2Cl_2$, and the organic phase was dried ($MgSO_4$), filtered, and concentrated in vacuo. The resultant crude material was purified by a flash chromatography (silica gel; 15-20% EtOAc/hexanes) to afford 136b as a colorless viscous oil (2.74 g). $^1H$ NMR (DMSO-$d_6$, $\delta$=2.50, 400 MHz): 7.98 (m, 1H), 7.78 (d, J=8.3, 1H), 7.72-7.69 (m, 1H), 5.61-5.41 (m, 2H), 4.35-4.30 (m, 1H), 3.41-3.30 (m, 2H), 2.43 (s, 3H), 2.33-2.08 (m, 2H), 1.93-1.83 (m, 2H), 1.40/1.36 (s, 9H).

LC (Cond. 1): RT=1.91 min; >95% homogeneity index

LC/MS: Anal. Calcd. for $[M+Na]^+$ $C_{19}H_{24}BrNNaO_5$ 448.07. found 448.10

Example 136

Step c

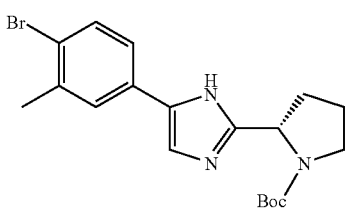

136c

A mixture of ketoester 136b (1.445 g, 3.39 mmol) and $NH_4OAc$ (2.93 g, 38.0 mmol) in xylenes (18 mL) was heated with a microwave at 140° C. for 80 min. The volatile component was removed in vacuo, and the residue was carefully partitioned between $CH_2Cl_2$ and water, where enough saturated $NaHCO_3$ solution was added to neutralize the aqueous medium. The aqueous phase was extracted with $CH_2Cl_2$, and the combined organic phase was dried ($MgSO_4$), filtered, and concentrated in vacuo. The crude was purified by a flash chromatography (silica gel, 40% EtOAc/hexanes) to afford imidazole 136c as an off-white solid (1.087 g). $^1H$ NMR (DMSO-$d_6$, $\delta$=2.50, 400 MHz): 12.15/11.91/11.84 (br s, 1H), 7.72-7.24 (m, 4H), 4.78 (m, 1H), 3.52 (m, 1H), 3.38-3.32 (m, 1H), 2.35 (s, 3H), 2.28-1.77 (m, 4H), 1.40/1.14 (s, 9H).

LC (Cond. 1): RT=1.91 min; >98% homogeneity index

LC/MS: Anal. Calcd. for $[M+H]^+$ $C_{19}H_{25}BrN_3O_2$ 405.96. found 406.11

Example 136

Step d

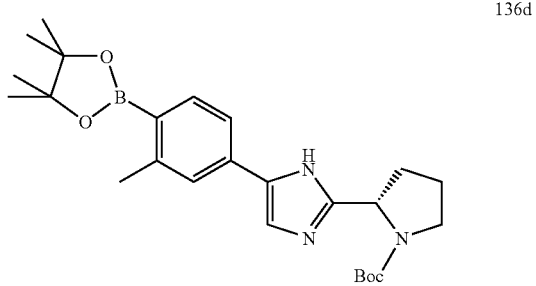

136d $PdCl_2dppf.CH_2Cl_2$ (50.1 mg, 0.061 mmol) was added to a pressure tube containing a mixture of bromide 136c (538.3 mg, 1.325 mmol), bis(pinacolato)diboron (666.6 mg, 2.625 mmol), KOAc (365.8 mg, 3.727 mmol) and DMF (10 mL). The reaction mixture was flushed with $N_2$ and heated at 80° C. for 24.5 hr. The volatile component was removed in vacuo and the residue was partitioned between $CH_2Cl_2$ and water, where enough saturated $NaHCO_3$ solution was added to make the pH of the aqueous medium neutral. The aqueous phase was extracted with $CH_2Cl_2$, and the combined organic phase was dried ($MgSO_4$), filtered, and concentrated in vacuo. The resulting material was purified by a Biotage system (silica gel, 40-50% EtOAc/hexanes) to afford boronate 136d as a white foam (580 mg). According to $^1H$ NMR the sample contains residual pinacol in a product/pinacol ratio of ~3. $^1H$ NMR (DMSO-$d_6$, $\delta$=2.50, 400 MHz): 12.16/11.91/11.83 (br s, 1H), 7.63-7.25 (m, 4H), 4.78 (m, 1H), 3.53 (m, 1H), 3.39-3.32 (m, 1H), 2.48/2.47 (s, 3H), 2.28-1.78 (m, 4H), 1.40/1.14/1.12 (br s, 9H), 1.30 (s, 12H).

LC (Cond. 1): RT=1.62 min

LC/MS: Anal. Calcd. for $[M+H]^+$ $C_{25}H_{37}BN_3O_4$ 454.29. found 454.15

Example 136

Step e-f

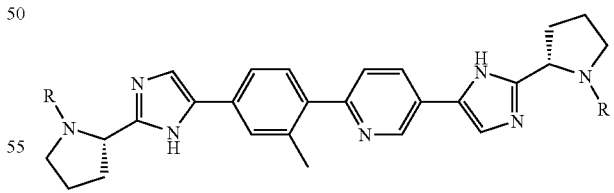

136e: R = Boc
136f: R = H

Biaryl 136e was prepared from bromide 132c and boronate 136d according to the coupling condition described for the preparation of biaryl 132d.

LC (Cond. 1a): RT=1.32 min; >90% homogeneity index

LC/MS: Anal. Calcd. for $[M+H]^+$ $C_{36}H_{45}N_7O_4$ 640.36. found 640.66

The deprotection of biaryl 136e was done according to the preparation of pyrrolidine 132e to afford 136f as a light yellow foam. $^1$H NMR (DMSO-$d_6$, δ=2.50, 400 MHz): 11.88 (br s, 2H), 9.02 (d, J=2, 1H), 8.12 (dd, J=8.4, 2.3, 1H), 7.67 (s, 1H), 7.64-7.62 (m, 2H), 7.50 (d, J=8.3, 1H), 7.46 (br s, 1H), 7.40 (d, J=7.8, 1H), 4.21-4.14 (m, 2H), 3.00-2.93 (m, 2H), 2.90-2.82 (m, 2H), 2.40 (s, 3H), 2.11-2.01 (m, 2H), 1.94-1.85 (m, 2H), 1.82-1.66 (m, 4H). [Note: the signal for the pyrrolidine NH appears in the region 3.22-2.80 and is too broad to make a chemical shift assignment.]

LC (Cond. 1): RT=0.84 min
LC/MS: Anal. Calcd. for [M+H]$^+$ $C_{26}H_{30}N_7$ 440.26. found 440.50

Example 136

(1R)-2-((2S)-2-(5-(6-(4-(2-((2S)-1-((2R)-2-(dimethylamino)-2-phenylacetyl)-2-pyrrolidinyl)-1H-imidazol-5-yl)-2-methylphenyl)-3-pyridinyl)-1H-imidazol-2-yl)-1-pyrrolidinyl)-N,N-dimethyl-2-oxo-1-phenylethanamine

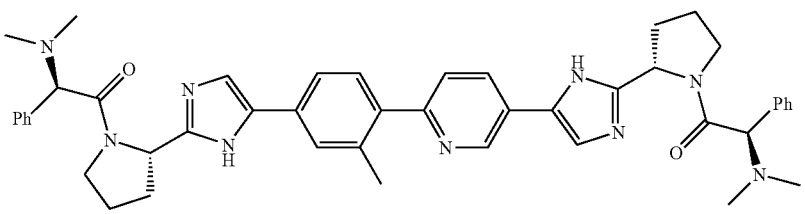

Example 136 (TFA salt) was synthesized from 136f according to the preparation of Example 132 from 132e.
1.05 min (Cond. 1); >98%
LC/MS: Anal. Calcd. for [M+H]$^+$ $C_{46}H_{52}N_9O_2$: 762.42. found: 762.77
HRMS: Anal. Calcd. for [M+H]$^+$ $C_{46}H_{52}N_9O_2$: 762.4244. found 762.4243

Example 138 methyl ((1R)-2-((2S)-2-(5-(6-(4-(2-((2S)-1-((2R)-2-((methoxycarbonyl)amino)-2-phenylacetyl)-2-pyrrolidinyl)-1H-imidazol-5-yl)-2-methylphenyl)-3-pyridinyl)-1H-imidazol-2-yl)-1-pyrrolidinyl)-2-oxo-1-phenylethyl)carbamate

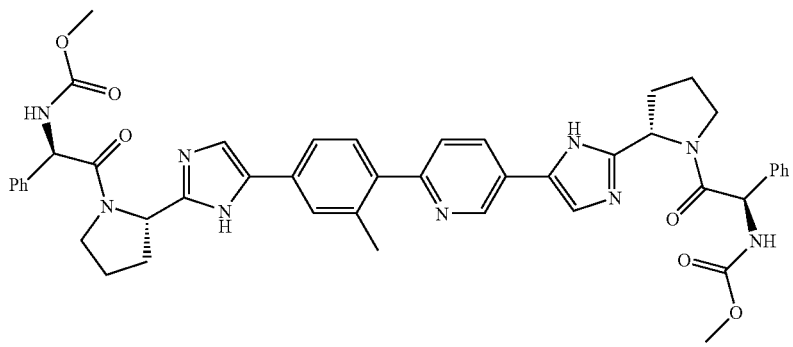

Example 138 was prepared similarly from pyrrolidine 136f and Cap-4.
1.60 min (Cond. 1); >98%
LC/MS: Anal. Calcd. for [M+H]$^+$ $C_{46}H_{48}N_9O_6$: 822.37. found 822.74
HRMS: Anal. Calcd. for [M+H]$^+$ $C_{46}H_{48}N_9O_6$: 822.3728. found 822.3760

Example 139

N-((1R)-2-((2S)-2-(5-(6-(4-(2-((2S)-1-((2R)-2-acetamido-2-phenylacetyl)-2-pyrrolidinyl)-1H-imidazol-5-yl)phenyl)-3-pyridinyl)-1H-imidazol-2-yl)-1-pyrrolidinyl)-2-oxo-1-phenylethyl)acetamide

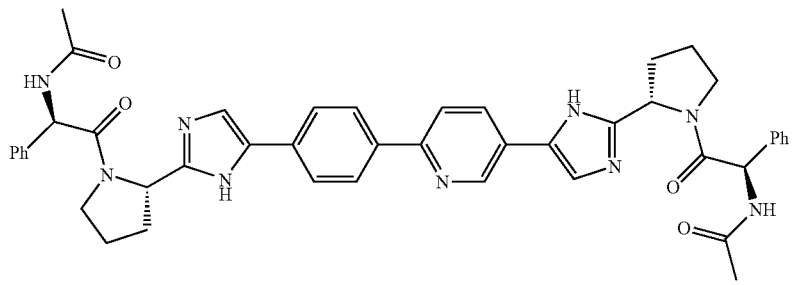

Example 139

Step a

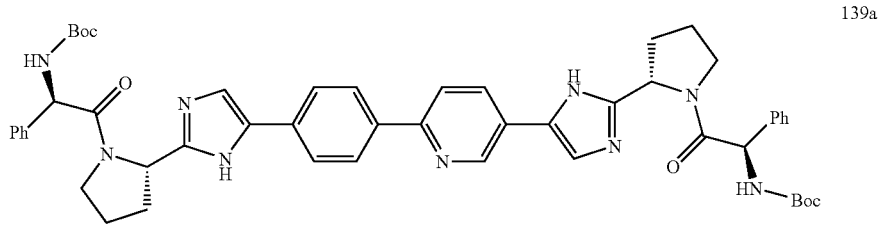

HATU (99.8 mg, 0.262 mmol) was added to a mixture of 132e (54.1 mg, 0.127 mmol), (R)-2-(t-butoxycarbonylamino)-2-phenylacetic acid (98.5 mg, 0.392 mmol) and i-Pr$_2$EtN (100 µL, 0.574 mol), and the reaction mixture was stirred for 70 min. The volatile component was removed in vacuo, and the residue was purified by a reverse phase HPLC (H$_2$O/MeOH/TFA), where the HPLC elute was treated with excess 2.0 N NH$_3$/MeOH before the removal of the volatile component in vacuo. The resulting material was partitioned between CH$_2$Cl$_2$ and water, and the aqueous phase was extracted with CH$_2$Cl$_2$ (2×). The combined organic phase was dried (MgSO$_4$), filtered, and concentrated in vacuo. Carbamate 139a was obtained as a white film of foam (82.3 mg).

LC (Cond. 1): RT=1.97 min; >95% homogeneity index.
LC/MS: Anal. Calcd. for [M+H]$^+$ C$_{51}$H$_{58}$N$_9$O$_6$: 892.45. found 892.72

Example 139b

Step b

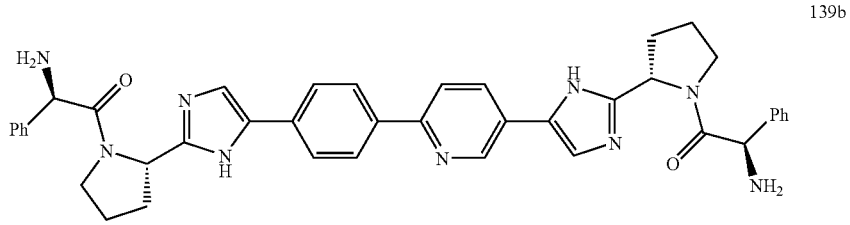

Carbamate 139a was deprotected to amine 139b by using the procedure described for the preparation of pyrrolidine 132e from 132d.

LC (Cond. 1): RT=1.37 min; >95% homogeneity index
LC/MS: Anal. Calcd. for [M+H]$^+$ C$_{41}$H$_{42}$N$_9$O$_2$: 692.35. found 692.32

Example 139

N-((1R)-2-((2S)-2-(5-(6-(4-(2-((2S)-1-((2R)-2-acetamido-2-phenylacetyl)-2-pyrrolidinyl)-1H-imidazol-5-yl)phenyl)-3-pyridinyl)-1H-imidazol-2-yl)-1-pyrrolidinyl)-2-oxo-1-phenylethyl)acetamide

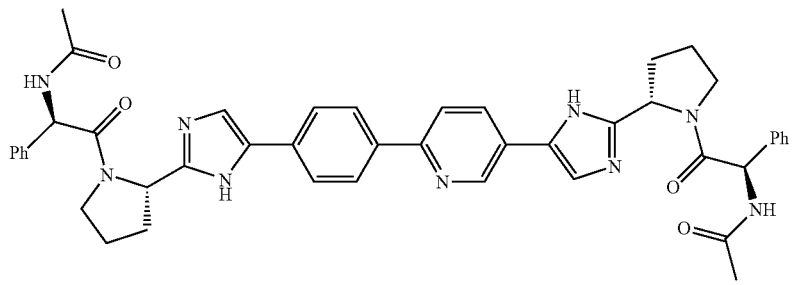

Acetic anhydride (20 µL, 0.212 mmol) was added to a DMF (1.5 mL) solution of 139b (31.2 mg, 0.045 mmol), and the reaction mixture was stirred for 1 hr. NH$_3$/MeOH (1.0 mL of 2N) was added to the reaction mixture and stirring continued for 100 min. The volatile component was removed in vacuo and the resulting crude material was purified by a reverse phase HPLC (H$_2$O/MeOH/TFA) to afford the TFA salt of Example 139 as a light yellow solid (24.1 mg).

LC (Cond. 1): RT=1.53 min; >98% homogeneity index
LC/MS: Anal. Calcd. for [M+H]$^+$ C$_{45}$H$_{46}$N$_9$O$_4$: 776.37. found 776.38
HRMS: Anal. Calcd. for [M+H]$^+$ C$_{45}$H$_{46}$N$_9$O$_4$: 776.3673. found 776.3680

Example 140 methyl ((1R)-2-((2S)-2-(5-(4-(5-(2-((2S)-1-((2R)-2-(dimethylamino)-2-phenylacetyl)-2-pyrrolidinyl)-1H-imidazol-5-yl)-2-pyridinyl)phenyl)-1H-imidazol-2-yl)-1-pyrrolidinyl)-2-oxo-1-phenylethyl)carbamate

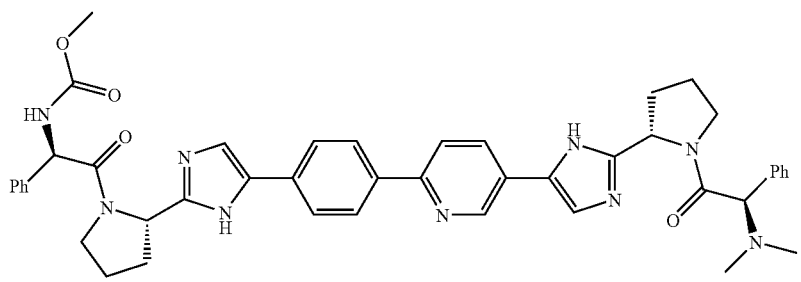

HATU (19.868 g, 52.25 mmol) was added to a heterogeneous mixture of N-Cbz-L-proline (12.436 g, 49.89 mmol) and the HCl salt of 2-amino-1-(4-bromophenyl)ethanone (12.157 g, 48.53 mmol) in DMF (156 mL). The mixture was lowered in an ice-water bath, and immediately afterward N,N-diisopropylethylamine (27 mL, 155 mmol) was added drop wise to it over 13 min. After the addition of the base was completed, the cooling bath was removed and the reaction mixture was stirred for an additional 50 min. The volatile component was removed in vacuo; water (125 mL) was added to the resultant crude solid and stirred for about 1 hr. The off-white solid was filtered and washed with copious water, and dried in vacuo to afford ketoamide 140a as a white solid (20.68 g). $^1$H NMR (DMSO-d$_6$, δ=2.5 ppm, 400 MHz): 8.30 (m, 1H), 7.91 (m, 2H), 7.75 (d, J=8.5, 2H), 7.38-7.25 (m, 5H), 5.11-5.03 (m, 2H), 4.57-4.48 (m, 2H), 4.33-4.26 (m, 1H), 3.53-3.36 (m, 2H), 2.23-2.05 (m, 1H), 1.94-1.78 (m, 3H).

LC (Cond. 1): RT=1.65 min; 98% homogeneity index
LC/MS: Anal. Calcd. for [M+H]$^+$ C$_{21}$H$_{22}$BrN$_2$O$_4$: 445.08. found 445.31

Example 140
Step a

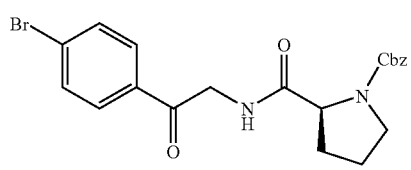

140a

Example 140
Step b

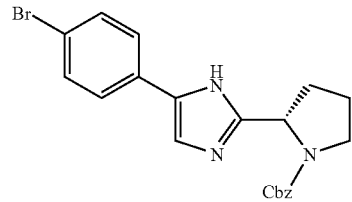

140b

329

Ketoamide 140a (10.723 g, 24.08 mmol) was converted to 140b according to the procedure described for the synthesis of carbamate 132c, with the exception that the crude material was purified by flash chromatography (silica gel; 50% EtOAc/hexanes). Bromide 140b was retrieved as an off-white foam (7.622 g). $^1$H NMR (DMSO-$d_6$, δ=2.5 ppm, 400 MHz): 12.23/12.04/11.97 (m, 1H), 7.73-6.96 (m, 10H), 5.11-4.85 (m, 3H), 3.61 (m, 1H), 3.45 (m, 1H), 2.33-184 (m, 4H).

LC (Cond. 1): RT=1.42 min; >95% homogeneity index

LC/MS: Anal. Calcd. for [M+H]$^+$ $C_{21}H_{21}BrN_3O_2$: 426.08. found 426.31

HRMS: Anal. Calcd. for [M+H]$^+$ $C_{21}H_{21}BrN_3O_2$: 426.0817. found: 426.0829

The optical purity of 140b was assessed using the following chiral HPLC methods, and an ee of 99% was observed.

Column: Chiralpak AD, 10 um, 4.6×50 mm

Solvent: 20% ethanol/heptane (isocratic)

Flow rate: 1 ml/min

Wavelength: 254 nm

Relative retention time: 1.82 min (R), 5.23 min (S)

Example 140

Step c

140c

Pd(Ph$_3$P)$_4$ (208 mg, 0.180 mmol) was added to a pressure tube containing a mixture of bromide 140b (1.80 g, 4.22 mmol), bis(pinacolato)diboron (2.146 g, 8.45 mmol), KOAc (1.8 g, 11.0 mmol) and 1,4-dioxane (34 mL). The reaction flask was purged with nitrogen, capped and heated with an oil bath at 80° C. for 23 hr. The volatile component was removed in vacuo, and the residue was partitioned carefully between CH$_2$Cl$_2$ (70 mL) and an aqueous medium (22 mL water+5 mL saturated NaHCO$_3$ solution). The aqueous layer was extracted with CH$_2$Cl$_2$, and the combined organic phase was dried (MgSO$_4$), filtered, and concentrated in vacuo. The oily reside was crystallized from EtOAc/hexanes to afford two crops of boronate 140c as a yellow solid (1.52 g). The mother liquor was evaporated in vacuo and the resulting material was purified by flash chromatography (silica gel; 20-35% EtOAc/CH$_2$Cl$_2$) to afford additional 140c as an off-white solid, containing residual pinacol (772 mg).

LC (Cond. 1): RT=1.95 min

LC/MS: Anal. Calcd. for [M+H]$^+$ $C_{27}H_{33}BN_3O_4$: 474.26. found 474.31

330

Example 140

Step d-e

140d: R = Cbz
140e: R = H

Arylbromide 132c was coupled with boronate 140c to afford 140d by using the same procedure described for the synthesis of biaryl 132d. The sample contains the desbromo version of 132c as an impurity. Proceeded to the next step without further purification.

LC (Cond. 1): RT=1.72 min; ~85% homogeneity index

LC/MS: Anal. Calcd. for [M+H]$^+$ $C_{38}H_{42}N_7O_4$: 660.33. found 660.30

A mixture of 10% Pd/C (226 mg), biaryl 140d (1.25 g) and MeOH (15 mL) was stirred under a balloon of hydrogen for ~160 hr, where the hydrogen supply was replenished periodically as needed. The reaction mixture was filtered through a pad of diatomaceous earth (Celite®), and the filtrate was evaporated in vacuo to afford crude 140e as a yellowish-brown foam (911 mg). Proceeded to the next step without further purification.

LC (Cond. 1): RT=1.53 min

LC/MS: Anal. Calcd. for [M+H]$^+$ $C_{30}H_{36}N_7O_2$: 526.29. found 526.23

Example 140

Step f-g

140f: R = Boc
140g: R = H

Pyrrolidine 140g was prepared from 140e and Cap-4, via the intermediacy of carbamate 140f, by sequentially employing the amide forming and Boc-deprotection protocols used in the synthesis of Example 132.

LC (Cond. 1): RT=1.09 min; ~94% homogeneity index

LC/MS: Anal. Calcd. for [M+H]$^+$ $C_{35}H_{37}N_8O_3$: 617.30. found 617.38

Example 140 methyl ((1R)-2-((2S)-2-(5-(4-(5-(2-((2S)-1-((2R)-2-(dimethylamino)-2-phenylacetyl)-2-pyrrolidinyl)-1H-imidazol-5-yl)-2-pyridinyl)phenyl)-1H-imidazol-2-yl)-1-pyrrolidinyl)-2-oxo-1-phenylethyl)carbamate

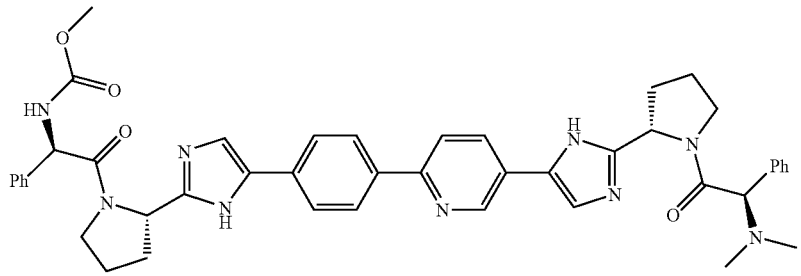

The TFA salt of Example 140 was synthesized from pyrrolidine 140g and Cap-1 by using the procedure described for the preparation of Example 132 from intermediate 132e.

1.15 min (Cond. 1); >98% homogeneity index
LC/MS: Anal. Calcd. for [M+H]$^+$ C$_{45}$H$_{40}$N$_7$O$_4$: 778.38. found 778.48
HRMS: Anal. Calcd. for [M+H]$^+$ C$_{45}$H$_{40}$N$_7$O$_4$: 778.3829. found 778.3849

The TFA salt of Example 141-143 were synthesized from intermediate 140g and appropriate reagents in a similar manner.

Example 141-143

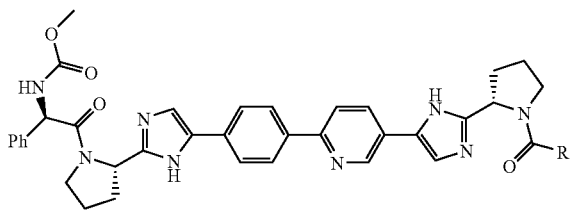

| Example | Compound Name | R (acyl group) | RT (LC-Cond.); % homogeneity index; MS data |
|---|---|---|---|
| 141 | methyl ((1R)-2-oxo-1-phenyl-2-((2S)-2-(5-(4-(5-(2-((2S)-1-((2R)-tetrahydro-2-furanylcarbonyl)-2-pyrrolidinyl)-1H-imidazol-5-yl)-2-pyridinyl)phenyl)-1H-imidazol-2-yl)-1-pyrrolidinyl)ethyl)carbamate | tetrahydrofuran-2-ylcarbonyl | 1.15 min (Cond. 1); >98% LC/MS: Anal. Calcd. for [M + H]$^+$ C$_{40}$H$_{43}$N$_8$O$_5$: 715.34; found 715.44 HRMS: Anal. Calcd. for [M + H]$^+$ C$_{40}$H$_{43}$N$_8$O$_5$: 715.3356; found 715.3381 |
| 142 | methyl ((1R)-2-((2S)-2-(5-(4-(5-(2-((2S)-1-((1-methyl-4-piperidinyl)carbonyl)-2-pyrrolidinyl)-1H-imidazol-5-yl)-2-pyridinyl)phenyl)-1H-imidazol-2-yl)-1-pyrrolidinyl)-2-oxo-1-phenylethyl)carbamate | 1-methylpiperidin-4-ylcarbonyl | 1.07 min (Cond. 1); >98% LC/MS: Anal. Calcd. for [M + H]$^+$ C$_{42}$H$_{48}$N$_9$O$_4$: 742.38; found 742.48 HRMS: Anal. Calcd. for [M + H]$^+$ C$_{42}$H$_{48}$N$_9$O$_4$: 742.3829; found 742.3859 |
| 143 | methyl ((1R)-2-oxo-1-phenyl-2-((2S)-2-(5-(4-(5-(2-((2S)-1-(3-pyridinylacetyl)-2-pyrrolidinyl)-1H-imidazol-5-yl)-2-pyridinyl)phenyl)-1H-imidazol-2-yl)-1-pyrrolidinyl)ethyl)carbamate | 3-pyridinylacetyl | 1.09 min (Cond. 1); >98% LC/MS: Anal. Calcd. for [M + H]$^+$ C$_{42}$H$_{42}$N$_9$O$_4$: 736.34; found 736.44 HRMS: Anal. Calcd. for [M + H]$^+$ C$_{42}$H$_{42}$N$_9$O$_4$: 736.3360; 736.3344 |

Example 144 methyl ((1R)-2-((2S)-2-(5-(4-(5-(2-((2S)-1-(4-morpholinylcarbonyl)-2-pyrrolidinyl)-1H-imidazol-5-yl)-2-pyridinyl)phenyl)-1H-imidazol-2-yl)-1-pyrrolidinyl)-2-oxo-1-phenylethyl)carbamate

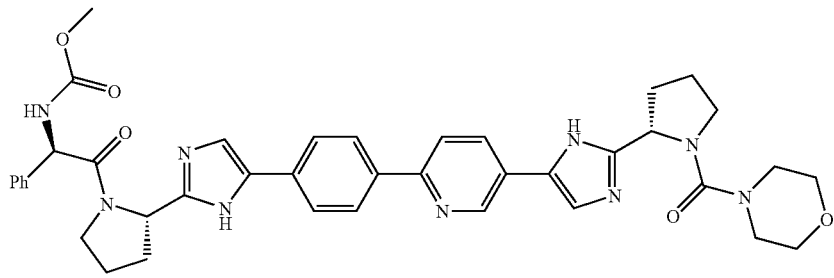

A DMF (1.5 mL) solution of morpholine-4-carbonyl chloride (8.5 mg, 0.057 mmol) was added to a mixture of i-Pr₂EtN (20 µL, 0.115 mmol) and 140g (27.3 mg, 0.044 mmol), and stirred for 100 min. The volatile component was removed in vacuo and the residue was purified by a reverse phase HPLC (H₂O/MeOH/TFA) to afford the TFA salt of Example 144 as a yellow foam (34.6 mg).

1.17 min (Cond. 1); >98%

LC/MS: Anal. Calcd. for [M+H]⁺ $C_{40}H_{44}N_9O_5$: 730.35. found 730.42

HRMS: Anal. Calcd. for [M+H]⁺ $C_{40}H_{44}N_9O_5$: 730.3465. found 730.3477

Example 145 dimethyl (2,2'-bipyridine-5,5'-diylbis(1H-imidazole-5,2-diyl(2S)-2,1-pyrrolidinediyl((1R)-2-oxo-1-phenyl-2,1-ethanediyl)))biscarbamate

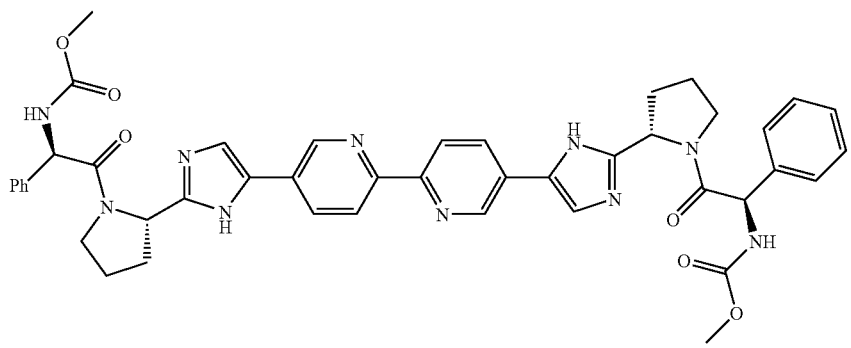

Example 145

Step a-b

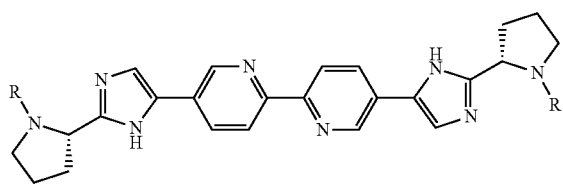

145a: R = Boc
145b: R = H

Pd(Ph₃P)₄ (9.6 mg, 0.008 mmol) and LiCl (28 mg, 0.67 mmol) were added to a mixture of arylbromide 132c (98.7 mg, 0.251 mmol) and hexamethylditin (51.6 mg, 0.158 mmol), and heated at 80° C. for ~3 days. The volatile component was removed in vacuo and the resultant crude material was purified by flash chromatography (silica gel; 0-10% MeOH/EtOAc) followed by a reverse phase HPLC (H₂O/MeOH/TFA). The HPLC elute was neutralized with excess 2.0 N NH₃/MeOH, and the volatile component was removed in vacuo. The residue was partitioned between CH₂Cl₂ and water, and the aqueous phase was washed with CH₂Cl₂ (2×).

The combined organic phase was dried (MgSO₄), filtered, and concentrated in vacuo to afford carbamate 145a as a film of oil (8.7 mg).

LC (Cond. 1): RT=1.68 min; >98% homogeneity index

LC/MS: Anal. Calcd. for [M+H]⁺ $C_{34}H_{43}N_8O_4$: 627.34. found 627.47

Carbamate 145a was elaborated to pyrrolidine 145b according to the preparation of 132e from 132d. ¹H NMR (DMSO, s=2.5 ppm; 400 MHz): 12.02 (br signal, 2H), 9.04 (d, J=1.6, 2H), 8.34 (d, J=8.3, 2H), 8.20 (dd, J=8.3, 2.3, 2H), 7.67 (br s, 1H), 4.21 (m, 2H), 3.00-2.85 (m, 4H), 2.12-2.04 (m, 2H), 1.95-1.68 (m, 6H). [Note: the pyrrolidine-NH signal was not observed].

LC (Cond. 1): RT=1.17 min; >98% homogeneity index

LC/MS: Anal. Calcd. for [M+H]⁺ $C_{24}H_{27}N_8$: 427.24. found 427.13

Example 145 dimethyl (2,2'-bipyridine-5,5'-diylbis(1H-imidazole-5,2-diyl(2S)-2,1-pyrrolidinediyl((1R)-2-oxo-1-phenyl-2,1-ethanediyl)))biscarbamate

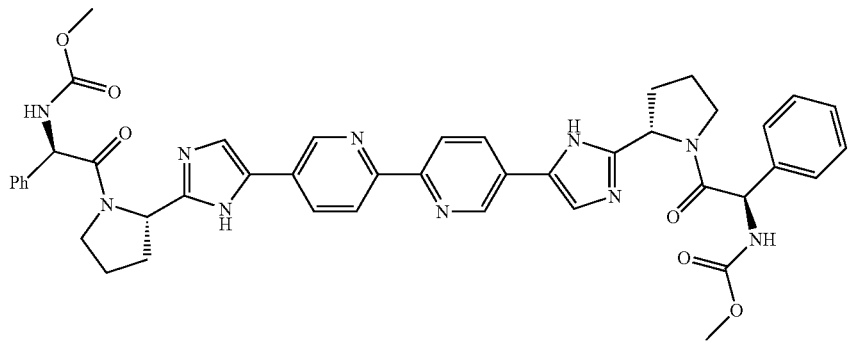

Example 145 (TFA salt) was synthesized from 145b according to the preparation of Example 132 from 132e.

LC (Cond. 1): RT=1.63 min; 98% homogeneity index
LC/MS: Anal. Calcd. for [M+H]$^+$ C$_{44}$H$_{45}$N$_{10}$O$_6$: 809.35. found 809.40

Example 146

(1R)-2-((2S)-2-(5-(5-(4-(2-((2S)-1-((2R)-2-(dimethylamino)-2-phenylacetyl)-2-pyrrolidinyl)-1H-imidazol-5-yl)phenyl)-2-pyridinyl)-1H-imidazol-2-yl)-1-pyrrolidinyl)-N,N-dimethyl-2-oxo-1-phenylethanamine

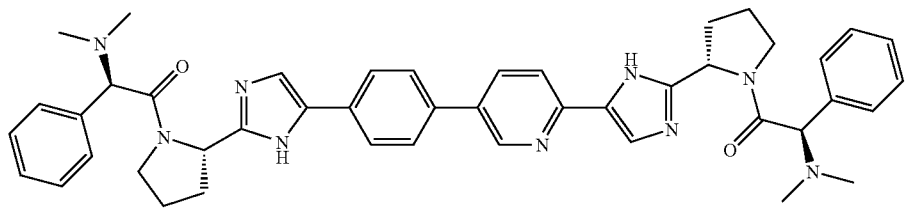

Example 146

Step a

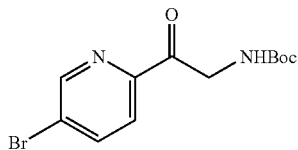

146a n-BuLi (12.0 mL of 2.5M/hexanes, 30 mmol) was added drop-wise over 15 min to a cooled (−78° C.) toluene (300 mL) semi-solution of 2,5-dibromopyridine (6.040 g, 25.5 mmol), and stirred for 2.5 hr. t-Butyl 2-(methoxy(methyl)amino)-2-oxoethylcarbamate (2.809 g, 12.87 mmol) was added in batches over 7 min, and stirring continued for 1.5 hr at −78° C. The −78° C. bath was replaced with −60° C. bath, which was allowed to warm up to −15° C. over 2.5 hr. The reaction was quenched with saturated NH$_4$Cl solution (20 mL), and the mixture was allowed to thaw to ambient temperature and the organic layer was separated and evaporated in vacuo. The resulting crude material was purified by flash chromatography (silica gel; 15% EtOAc/hexanes) to afford a reddish brown semisolid, which was washed with hexanes to removed the colored residue. Pyridine 146a was retrieved as an ash colored solid (842 mg). $^1$H NMR (DMSO, δ=2.5 ppm; 400 MHz): 8.89 (d, J=2.3, 1H), 8.30 (dd, J=8.4, 2.4, 1H), 7.90 (d, J=8.3, 1H), 7.03 (br t, J=5.7; 0.88H), 6.63 (app br s, 0.12H), 4.55 (d, J=5.8, 2H), 1.40/1.28 (two app s, 7.83H+ 1.17H).

LC (Cond. 1): RT=2.00 min; >95% homogeneity index
LC/MS: Anal. Calcd. for [M+Na]$^+$ C$_{12}$H$_{15}$BrNaN$_2$O$_3$: 337.02. found 337.13

Example 146

Step b

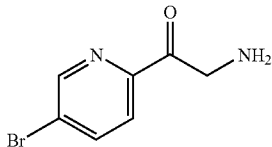

146b

48% HBr (1.0 mL) was added drop-wise to a dioxane (5.0 mL) solution of carbamate 146a (840 mg, 2.66 mmol) over 3 min, and the reaction mixture was stirred at ambient temperature for 17.5 hr. The precipitate was filtered and washed with dioxane, and dried in vacuo to afford amine the HBr salt of 146b as an off-white solid (672.4 mg; the exact mole equivalent of the HBr salt was not determined). $^1$H NMR (DMSO, δ=2.5 ppm; 400 MHz): 8.95 (d, J=2.3, 1H), 8.37 (dd, J=8.4, 2.3, 1H), 8.2 (br s, 3H), 8.00 (d, J=8.3, 1H), 4.61 (s, 2H).

LC (Cond. 1): RT=0.53 min

LC/MS: Anal. Calcd. for [M+H]$^+$ $C_7H_8BrN_2O$: 214.98. found 215.00

Example 146

Step c

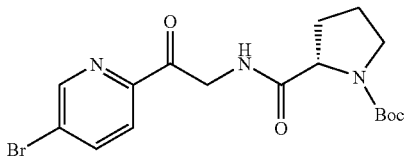

146c i-Pr$_2$EtN (2.3 mL, 13.2 mmol) was added drop-wise over 15 min to a heterogeneous mixture of amine 146b (1.365 g), (S)-Boc-proline (0.957 g, 4.44 mmol) and HATU (1.70 g, 4.47 mmol) in DMF (13.5 mL), and stirred at ambient temperature for 1 hr. The volatile component was removed in vacuo and the residue was partitioned between EtOAc (40 mL) and an aqueous medium (20 mL water+1 ml saturated NaHCO$_3$ solution). The aqueous layer was washed with EtOAc (20 mL), and the combined organic phase was dried (MgSO$_4$), filtered, and concentrated in vacuo. The resultant crude material was purified by flash chromatography (silica gel; 40-50% EtOAc/hexanes) to afford ketoamide 146c as a faint-yellow foam (1.465 g). $^1$H NMR (DMSO, δ=2.5 ppm; 400 MHz): 8.90 (d, J=2.3, 1H), 8.30 (dd, J=8.5, 2.4, 1H), 8.01-8.07 (m, 1H), 7.90 (d, J=8.3, 1H), 4.6 (m, 1H), 4.64 (dd, J=19.1, 5.5, 1H); 4.19 (m, 1H), 3.39 (m, 1H), 3.32-3.26 (m, 1H), 2.20-2.01 (m, 1H), 1.95-1.70 (m, 3H), 1.40/1.35 (two app s, 9H).

LC (Cond. 1): RT=1.91 min

LC/MS: Anal. Calcd. for [M+Na]$^+$ $C_{17}H_{22}BrN_3NaO_4$: 434.07. found 433.96.

Example 146

Step d

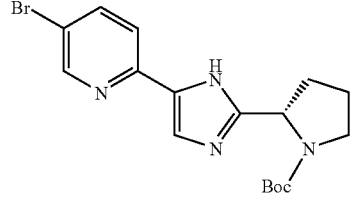

146d

A mixture of ketoamide 146c (782.2 mg, 1.897 mmol) and NH$_4$OAc (800 mg, 10.4 mmol) in xylenes was heated with a microwave (140° C.) for 90 min. The volatile component was removed in vacuo and the residue was carefully partitioned between CH$_2$Cl$_2$ and water, where enough saturated NaHCO$_3$ solution was added to neutralize it. The aqueous phase was extracted with CH$_2$Cl$_2$ (2×), and the combined organic phase was dried (MgSO$_4$), filtered, and concentrated in vacuo. The resultant crude material was purified by flash chromatography (silica gel; 50% CH$_2$Cl$_2$/EtOAc) to afford imidazole 146d as an off-white solid (552.8 mg). $^1$H NMR (DMSO, δ=2.5 ppm; 400 MHz): 12.49/12.39/12.15/12.06 (br s, 1H), 8.62 (app br s, 0.2H), 8.56 (d, J=2, 0.8H), 8.02 (br d, J=8.5, 0.2H), 7.97 (br d, J=7.8, 0.8H), 7.77 (d, J=8.6, 0.8H), 7.72 (d, J=8.6, 0.2H), 7.61-7.49 (m, 1H), 4.93-4.72 (m, 1H), 3.53 (m, 1H), 3.41-3.32 (m, 1H), 2.33-1.77 (m, 4H), 1.39/1.14 (app br s, 3.7H+5.3H).

LC (Cond. 1): RT=1.67 min; >95% homogeneity index

LC/MS: Anal. Calcd. for [M+Na]$^+$ $C_{17}H_{21}BrN_4NaO_2$: 415.08. found 415.12

Example 146

Step e

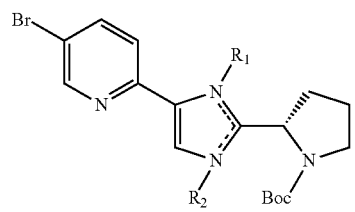

146e (R$_1$ = H, R$_2$ = SEM) or (R$_1$ = SEM, R$_2$ = H)

NaH (60%; 11.6 mg, 0.29 mmol) was added in one batch to a heterogeneous mixture of imidazole 146d (80 mg, 0.203 mmol) and DMF (1.5 mL), and stirred at ambient condition for 30 min. SEM-Cl (40 µL, 0.226 mmol) was added drop-wise over 2 min to the above reaction mixture, and stirring was continued for 14 hr. The volatile component was removed in vacuo and the residue was partitioned between water and CH$_2$Cl$_2$. The aqueous layer was extracted with CH$_2$Cl$_2$, and the combined organic phase was dried (MgSO$_4$), filtered, and concentrated in vacuo. The crude material was purified by a flash chromatography (silica gel; 20% EtOAc/hexanes) to afford 146e as a colorless viscous oil (87.5 mg). The exact regiochemistry of 146e was not determined. $^1$H NMR (CDCl$_3$, δ=7.4 ppm; 400 MHz): 8.53 (d, J=2.2, 1H), 7.90-7.72 (m, 2H), 7.52 (s, 1H), 5.87 (m, 0.46H), 5.41 (m, 0.54H), 5.16 (d, J=10.8, 1H), 5.03-4.85 (m, 1H), 3.76-3.42 (m, 4H), 2.54-1.84 (m, 4H), 1.38/1.19 (br s, 4.3H+4.7H), 0.97-0.81 (m, 2H), -0.03 (s, 9H).

LC (Cond. 1): RT=2.1 min

LC/MS: Anal. Calcd. for [M+H]$^+$ $C_{23}H_{36}BrN_4O_3Si$: 523.17. found 523.24

Example 146

Step f

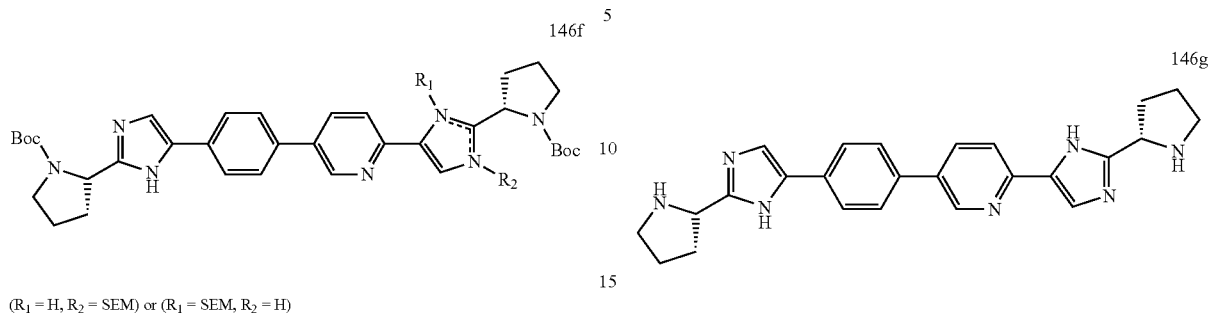

146f ($R_1$ = H, $R_2$ = SEM) or ($R_1$ = SEM, $R_2$ = H)

Pd(Ph$_3$P)$_4$ (24.4 mg, 0.021 mmol) was added to a mixture of imidazole 146e (280 mg, 0.535 mmol), 1c (241.5 mg, 0.55 mmol) and NaHCO$_3$ (148.6 mg, 1.769 mmol) in 1,2-dimethoxyethane (4.8 mL) and water (1.6 mL). The reaction mixture was flushed with nitrogen, heated with an oil bath at 80° C. for ~24 hr and then the volatile component was removed in vacuo. The residue was partitioned between CH$_2$Cl$_2$ and water, and the organic phase was dried (MgSO$_4$), filtered, and concentrated in vacuo. The crude material was purified by a Biotage system (silica gel; 75-100% EtOAc/hexanes) followed by a reverse phase HPLC (H$_2$O/MeOH/TFA). The HPLC elute was neutralized with 2M NH$_3$/MeOH and evaporated in vacuo, and the residue was partitioned between water and CH$_2$Cl$_2$. The organic layer was dried (MgSO$_4$), filtered, and concentrated in vacuo to afford 146f as a white foam (162 mg).

LC (Cond. 1): RT=2.1 min

LC/MS: Anal. Calcd. for [M+H]$^+$ C$_{41}$H$_{58}$N$_7$O$_5$Si: 756.43. found 756.55

Step g

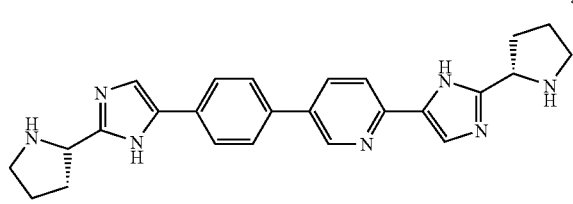

146g

Carbamate 146f (208 mg, 0.275 mmol) was treated with 25% TFA/CH$_2$Cl$_2$ (4.0 mL) and stirred at ambient temperature for 10 hr. The volatile component was removed in vacuo and the residue was first free-based by MCX (MeOH wash; 2.0 M NH$_3$/MeOH elution) and then purified by a reverse phase HPLC (H$_2$O/MeOH/TFA), and the resultant material was free-based again (MCX) to afford pyrrolidine 146g as a film of oil (53.7 mg). $^1$H NMR (DMSO, δ=2.5 ppm; 400 MHz): 1.88 (app br s, 2H), 8.83 (d, J=2.1, 1H), 8.07 (dd, J=8.3/2.3, 1H0, 7.87 (d, J=8.5, 1H), 7.84 (d, J=8.3, 2H), 7.71 (d, J=8.3, 2H), 7.55 (s, 1H), 7.50 (br s, 1H), 4.18 (m, 2H), 3.00-2.94 (m, 2H), 2.89-2.83 (m, 2H), 2.11-2.02 (m, 2H), 1.95-1.86 (m, 2H), 1.83-1.67 (m, 4H).

LC (Cond. 1): RT=0.95 min; >98% homogeneity index

LC/MS: Anal. Calcd. for [M+H]$^+$ C$_{25}$H$_{28}$N$_7$: 426.24. found 426.27

Example 146

(1R)-2-((2S)-2-(5-(5-(4-(2-((2S)-1-((2R)-2-(dimethylamino)-2-phenylacetyl)-2-pyrrolidinyl)-1H-imidazol-5-yl)phenyl)-2-pyridinyl)-1H-imidazol-2-yl)-1-pyrrolidinyl)-N,N-dimethyl-2-oxo-1-phenylethanamine

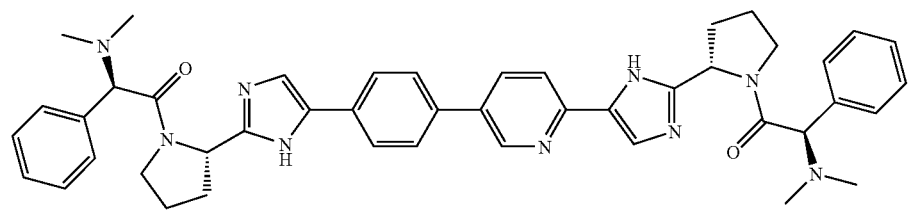

Example 146 (TFA salt) was synthesized from pyrrolidine 146g according to the preparation of Example 132 from intermediate 132e.

LC (Cond. 1): RT=1.42 min; 96.5% homogenity index

LC/MS: Anal. Calcd. for [M+H]$^+$ C$_{45}$H$_{50}$N$_9$O$_2$: 748.41. found 748.57

HRMS: Anal. Calcd. for [M+H]$^+$ C$_{45}$H$_{50}$N$_9$O$_2$: 748.4087. found 748.4100

Example 147 methyl ((1R)-2-((2S)-2-(5-(5-(4-(2-((2S)-1-((2R)-2-((methoxycarbonyl)amino)-2-phenylacetyl)-2-pyrrolidinyl)-1H-imidazol-5-yl)phenyl)-2-pyridinyl)-1H-imidazol-2-yl)-1-pyrrolidinyl)-2-oxo-1-phenylethyl) carbamate

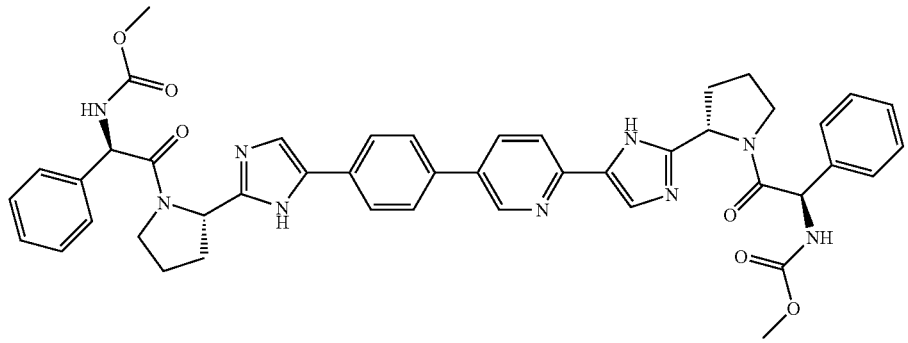

The TFA salt of Example 147 was prepared similarly from intermediate 146g by using Cap-4.

LC (Cond. 1): RT=1.66 min; 95% homogenity index
LC/MS: Anal. Calcd. for [M+H]$^+$ C$_{45}$H$_{46}$N$_9$O$_6$: 808.36. found 808.55

Example 148

(1R,1'R)-2,2'-(4,4'-biphenyldiylbis(1H-imidazole-5,2-diyl(4R)-1,3-thiazolidine-4,3-diyl))bis(N,N-dimethyl-2-oxo-1-phenylethanamine)

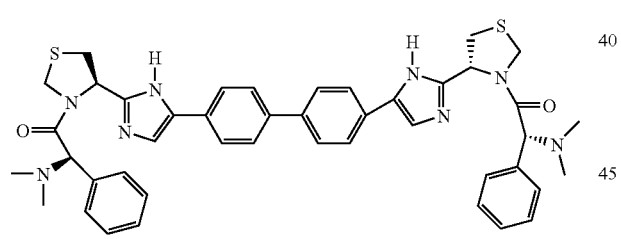

Example 148

Step a

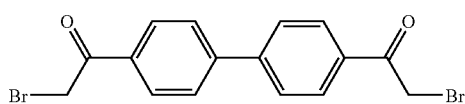

A solution of bromine (1.3 mL, 25.0 mmol) in 15 mL glacial acetic acid was added drop-wise to a solution of 4-4'-diacetylbiphenyl (3.0 g, 12.5 mmol) in 40 mL acetic acid at 50° C. Upon completion of addition the mixture was stirred at room temperature overnight. The precipitated product was filtered off and re-crystallized from chloroform to give 1,1'-(biphenyl-4,4'-diyl)bis(2-bromoethanone) (3.84 g, 77.5%) as a white solid.

$^1$H NMR (500 MHz, CHLOROFORM-D) δ ppm 8.09 (4H, d, J=7.93 Hz) 7.75 (4H, d, J=8.24 Hz) 4.47 (4H, s)

Nominal/LRMS—Anal. Calcd. for 369.07 found; (M+H)$^+$—397.33, (M−H)$^−$-395.14

Example 148

Step b

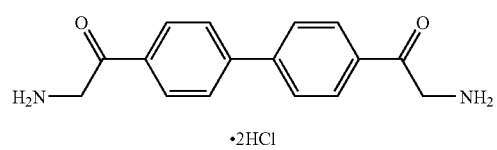

Sodium diformylamide (3.66 g, 38.5 mmol) was added to a suspension of 1,1'-(biphenyl-4,4'-diyl)bis(2-bromoethanone) (6.1 g, 15.4 mmol) in 85 mL acetonitrile. The mixture was heated at reflux for 4 hours and concentrated under reduced pressure. The residue was suspended in 300 mL 5% HCl in ethanol and heated at reflux for 3.5 hours. Reaction was cooled to room temperature and placed in the freezer for 1 hour. Precipitated solid was collected, washed with 200 mL 1:1 ethanol/ether followed by 200 mL pentane, and dried under vacuum to give 1,1'-(biphenyl-4,4'-diyl)bis(2-aminoethanone) dihydrochloride (4.85 g, 92%). Carried on without further purification.

$^1$H NMR (300 MHz, DMSO-d$_6$) δ ppm 8.47-8.55 (4H, m) 8.11-8.17 (4H, m) 8.00 (4H, d, J=8.42 Hz) 4.59-4.67 (4H, m).

LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA, $t_R$=0.44 minutes, Anal. Calcd. for $C_{16}H_{16}N_2O_2$ 268.31 found; 269.09 $(M+H)^+$.

Example 148

Step c

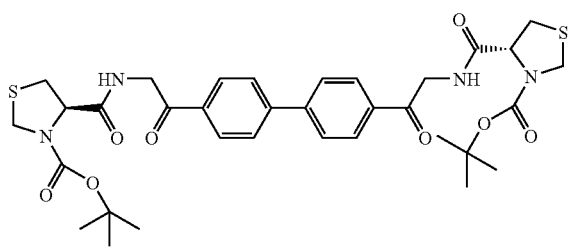

To a stirred solution of 1,1'-(biphenyl-4,4'-diyl)bis(2-aminoethanone) dihydrochloride (0.7 g, 2.1 mmol), N-(tert-butoxy carbonyl)-L-thioproline (0.96 g, 4.2 mmol), and HATU (1.68 g, 4.4 mmol) in 14 mL DMF was added diisopropylethyl amine (1.5 mL, 8.4 mmol) drop-wise over 5 minutes. The resulting clear yellow solution was stirred at room temperature overnight (14 hours) and concentrated under reduced pressure. The residue was partitioned between 20% methanol/chloroform and water. The aqueous phase was washed once with 20% methanol/chloroform. The combined organics were washed with brine, dried ($MgSO_4$), filtered, and concentrated under reduced pressure. The crude product was chromatographed on silica gel by gradient elution with 10-50% ethyl acetate/$CH_2Cl_2$ to give (4S,4'S)-tert-butyl 4,4'-(2,2'-(biphenyl-4,4'-diyl)bis(2-oxoethane-2,1-diyl))bis(azanediyl)bis(oxomethylene)dithiazolidine-3-carboxylate (0.39 g, 27%) as an orange foam.

$^1$H NMR (400 MHz, DMSO-$d_6$) δ ppm 8.38 (2H, s) 8.12 (4H, d, J=8.56 Hz) 7.94 (4H, d, J=8.56 Hz) 4.60-4.68 (4H, m) 4.33-4.38 (2H, m) 3.58-3.68 (2H, m) 3.38 (2H, s) 3.08-3.18 (2H, m) 1.40 (18H, s)

LCMS—Water-Sunfire C-18 4.6×50 mm, 0 to 100% B over 4.0 minute gradient, 1 minute hold time, A=10% methanol 90% water 0.1% TFA, B=90% methanol 10% water 0.1% TFA, $t_R$=3.69 min., Anal. Calcd. for $C_{34}H_{42}N_4O_8S_2$ 698.85 found; 699.12 $(M+H)^+$.

Example 148

Step d

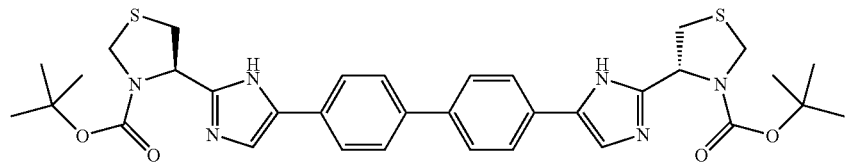

(4S,4'S)-tert-butyl 4,4'-(5,5'-(biphenyl-4,4'-diyl)bis(1H-imidazole-5,2-diyl))dithiazolidine-3-carboxylate (0.39 g, 0.56 mmol) and ammonium acetate (0.43 g, 5.6 mmol) were suspended in 8 mL o-xylene in a microwave reaction vessel. The mixture was heated under standard microwave conditions at 140° C. for 70 minutes and concentrated under reduced pressure. The residue was dissolved in 30 mL 20% methanol/chloroform and washed with 10% $NaHCO_3$(aq). The organic layer was washed with brine, dried ($MgSO_4$), filtered, and concentrated under reduced pressure. The crude product was chromatographed on silica gel by gradient elution with 1-6% methanol/$CH_2Cl_2$ to give (4S,4'S)-tert-butyl 4,4'-(5,5'-(biphenyl-4,4'-diyl)bis(1H-imidazole-5,2-diyl))dithiazolidine-3-carboxylate (0.15 g, 41%) as a yellow solid.

$^1$H NMR (500 MHz, DMSO-$d_6$) δ ppm 12.02 (2H, s) 7.70-7.88 (10H, m) 5.28-5.37 (2H, m) 4.68 (2H, d, J=9.16 Hz) 4.47-4.55 (2H, m) 3.46 (2H, s) 3.23 (2H, s) 1.26-1.43 (18H, m)

LCMS—Luna C-18 3.0×50 mm, 0 to 100% B over 3.0 minute gradient, 1 minute hold time, A=5% acetonitrile, 95% water, 10 mm ammonium acetate, B=95% acetonitrile, 5% water, 10 mm ammonium acetate, $t_R$=1.96 min., Anal. Calcd. for $C_{34}H_{40}N_6O_4S_2$ 660.85 found; 661.30 $(M+H)^+$, 659.34 $(M-H)^-$

Example 148

Step e

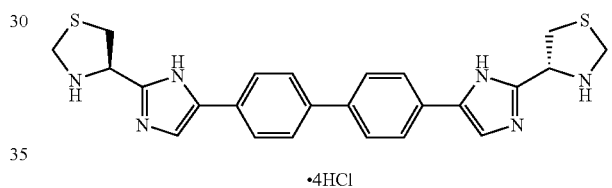

•4HCl

To a solution of (4S,4'S)-tert-butyl 4,4'-(5,5'-(biphenyl-4,4'-diyl)bis(1H-imidazole-5,2-diyl))dithiazolidine-3-carboxylate in 1 mL dioxane was added 0.3 mL of a 4.0M solution of HCl in dioxane. The reaction was stirred for 3 hours at room temperature and concentrated under reduced pressure. The resulting tan solid was dried under vacuum to give 4,4'-bis(2-((S)-thiazolidin-4-yl)-1H-imidazol-5-yl)biphenyl tetrahydrochloride (0.12 g, 100%) as a yellow solid.

$^1$H NMR (500 MHz, DMSO-$d_6$) δ ppm 8.09 (2H, s) 8.01 (4H, d, J=8.55 Hz) 7.90 (4H, d, J=8.55 Hz) 5.08 (2H, t, J=6.10 Hz) 4.38 (2H, d, J=9.16 Hz) 4.23 (2H, d, J=9.46 Hz) 3.48-3.54 (2H, m,) 3.35-3.41 (2H, m)

LCMS—Luna C-18 3.0×50 mm, 0 to 100% B over 4.0 minute gradient, 1 minute hold time, A=5% acetonitrile, 95% water, 10 mm ammonium acetate, B=95% acetonitrile, 5% water, 10 mm ammonium acetate, $t_R$=1.70 min., Anal. Calcd. for $C_{24}H_{24}N_6S_2$ 460.62 found; 461.16 $(M+H)^+$, 459.31 $(M-H)^-$

Example 148

(1R,1'R)-2,2'-(4,4'-biphenyldiylbis(1H-imidazole-5,2-diyl(4R)-1,3-thiazolidine-4,3-diyl))bis(N,N-dimethyl-2-oxo-1-phenylethanamine)

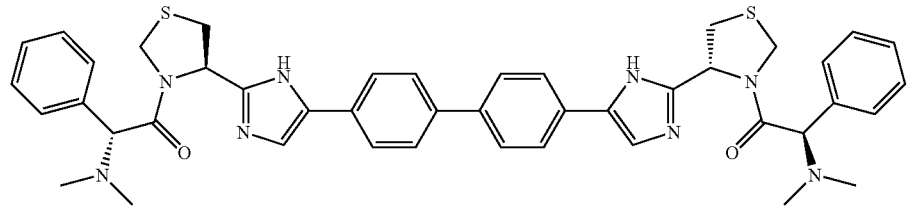

To a stirred solution of (4,4'-bis(2-((S)-thiazolidin-4-yl)-1H-imidazol-5-yl)biphenyl tetrahydrochloride (0.028 g, 0.046 mmol), (R)-2-(dimethylamino)-2-phenylacetic acid (Cap-1, 0.017 g, 0.0.10 mmol), and HATU (0.039 g, 0.10 mmol) in 2 mL DMF was added diisopropylethyl amine (0.05 mL, 0.28 mmol). The reaction was stirred at room temperature overnight (16 hours) and concentrated under reduced pressure. The crude product was purified by reverse-phase preparative HPLC to provide (2R,2'R)-1,1'-((4S,4'S)-4,4'-(5,5'-(biphenyl-4,4'-diyl)bis(1H-imidazole-5,2-diyl))bis(thiazolidine-4,3-diyl))bis(2-(dimethylamino)-2-phenylethanone), TFA salt (0.012 g, 21%)

$^1$H NMR (500 MHz, DMSO-d$_6$) δ ppm 7.59-7.91 (20H, m) 5.62 (2H, dd, J=6.56, 2.59 Hz) 4.99 (2H, d, J=8.85 Hz) 4.82/4.35 (2H, s) 4.22 (2H, s) 3.42 (2H, s) 3.25 (2H, s) 2.35-2.61 (12H, m)

LCMS—Luna C-18 3.0×50 mm, 0 to 100% B over 7.0 minute gradient, 1 minute hold time, A=5% acetonitrile, 95% water, 10 mm ammonium acetate, B=95% acetonitrile, 5% water, 10 mm ammonium acetate mobile phase t$_R$=3.128 min.

Nominal/LRMS—Calcd. for $C_{44}H_{46}N_8O_2S_2$ 783.03. found 783.28 (M+H)$^+$

Accurate/HRMS—Calcd. for $C_{44}H_{47}N_8O_2S_2$ 783.3263; 783.3246 (M+H)$^+$

Examples 149 and 150 were prepared in similar fashion as described for the preparation of example 148.

| Example | Compound Name | Structure | Data |
| --- | --- | --- | --- |
| Example 149 | dimethyl (4,4'-biphenyldiylbis(1H-imidazole-5,2-diyl(4R)-1,3-thiazolidine-4,3-diyl((1R)-2-oxo-1-phenyl-2,1-ethanediyl))biscarbamate | from 148c and Cap-4 | t$_R$ = 3.36 min (LCMS-Luna C-18 3.0 × 50 mm, 0 to 100% B over 7.0 minute gradient, 1 minute hold time, A = 5% acetonitrile, 95% water, 10 mm ammonium acetate, B = 95% acetonitrile, 5% water, 10 mm ammonium acetate) LRMS: Anal. Calcd. for $C_{44}H_{42}N_8O_6S_2$ 842.99 found: 843.25 (M + H)$^+$ HRMS: Anal. Calcd. for $C_{44}H_{43}N_8O_6S_2$ 843.2747 found: 843.2724 (M + H)$^+$ |

| Example | Compound Name | Structure | Data |
|---|---|---|---|
| Example 150 | (4R,4'R)-4,4'-(4,4'-biphenyldiylbis(1H-imidazole-5,2-diyl))bis(3-((2R)-tetrahydro-2-furanylcarbonyl)-1,3-thiazolidine) | from 148c and tetrahydrofuroic acid | $t_R$ = 4.32 min (HPLC-X-Terra C-18 4.6 × 50 mm, 0 to 100% B over 10.0 minute gradient, 1 minute hold time, A = 10% methanol 90% water 0.1% TFA, B = 90% methanol 10% water 0.1% TFA) LRMS: Anal. Calcd. for $C_{34}H_{36}N_6O_4S_2$ 656.83 found: 657.32 $(M + H)^+$ |

Example 151

(1R,1'R)-2,2'-(4,4'-biphenyldiylbis((1-methyl-1H-imidazole-4,2-diyl)(2S)-2,1-pyrrolidinediyl))bis(N,N-dimethyl-2-oxo-1-phenylethanamine)

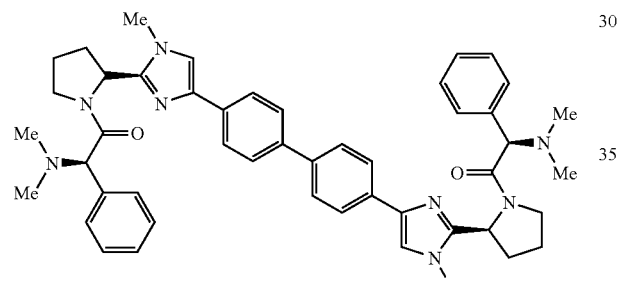

Example 151

Step a

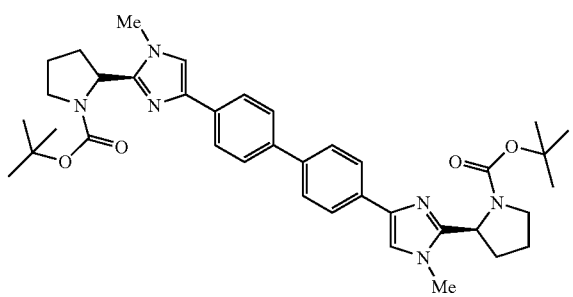

To a stirred solution of 1d, (2S,2'S)-tert-butyl 2,2'-(4,4'-(biphenyl-4,4'-diyl)bis(1H-imidazole-4,2-diyl))dipyrrolidine-1-carboxylate (100 mg, 0.16 mmole) and iodomethane (40 μL, 0.16 mmole) in $CH_2Cl_2$ (2 mL) was added sodium hydride (40%) (21.2 mg, 0.352 mmole). After five hours at ambient temperature, it was concentrated under reduced pressure. The crude reaction product 151a, (2S,2'S)-tert-butyl 2,2'-(4,4'-(biphenyl-4,4'-diyl)bis(1-methyl-1H-imidazole-4,2-diyl))dipyrrolidine-1-carboxylate (~90 mg) was moved onto next step without further purification (purity ~85%) LCMS: Anal. Calcd. for: $C_{38}H_{48}N_6O_4$ 652.83. Found: 653.51 $(M+H)^+$. It should be recognized that multiple methylation isomers are possible in this reaction and no attempt to assign these was made.

Example 151

Step b

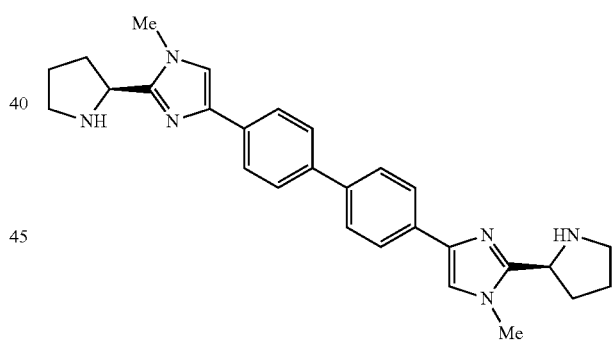

151a, (2S,2'S)-tert-butyl 2,2'-(4,4'-(biphenyl-4,4'-diyl)bis(1-methyl-1H-imidazole-4,2-diyl))dipyrrolidine-1-carboxylate (100 mg, 0.153 mmole) treated with 4 M HCl/dioxane (20 mL). After three hours at ambient temperature, it was concentrated under reduced pressure. The crude reaction product, 4,4'-bis(1-methyl-2-((S)-pyrrolidin-2-yl)-1H-imidazol-4-yl)biphenyl(~110 mg, HCl salt) was moved onto the next step without further purification (purity 85%) LCMS: Anal. Calcd. for: $C_{28}H_{32}N_6$ 452.59. Found: 453.38 $(M+H)^+$. Multiple imidazole isomers were present and carried forward.

Example 151

HATU (58.9 mg, 0.150 mmol) was added to a mixture of 151b, 4,4'-bis(1-methyl-2-((S)-pyrrolidin-2-yl)-1H-imidazol-4-yl)biphenyl (45.0 mg, 0.075 mmol), (i-Pr)$_2$EtN (78 μL, 0.451 mmol) and Cap-1, (R)-2-(dimethylamino)-2-phenylacetic acid (0.026 mg 0.150 mmol) in DMF (1.0 mL). The resultant mixture was stirred at ambient temperature until the coupling was complete as determined by LC/MS analysis. Purification was accomplished by reverse-phase preparative HPLC (Waters-Sunfire 30×100 mm S5, detection at 220 nm, flow rate 30 mL/min, 0 to 90% B over 14 min; A=90% water, 10% ACN, 0.1% TFA, B=10% water, 90% ACN, 0.1% TFA) to provide two isomer of 151, (2R,2'R)-1,1'-((2S,2'S)-2,2'-(4,4'-(biphenyl-4,4'-diyl)bis(1-methyl-1H-imidazole-4,2-diyl))bis(pyrrolidine-2,1-diyl))bis(2-(dimethylamino)-2-phenylethanone), TFA salts.

Isomer 1: (1R,1'R)-2,2'-(4,4'-biphenyldiylbis((1-methyl-1H-imidazole-4,2-diyl)(2S)-2,1-pyrrolidinediyl))bis(N,N-dimethyl-2-oxo-1-phenylethanamine)

(8 mg, 8.6%) as a colorless wax.
$^1$H NMR (500 MHz, DMSO-$d_6$) δ ppm 1.84-2.25 (m, 8H) 2.32-2.90 (m, 12H) 3.67-3.92 (m, 8H) 4.07 (s, 2H) 5.23 (s, 2H) 5.51 (s, 2H) 7.51-7.91 (m, 20H)

HPLC Xterra 4.6×50 mm, 0 to 100% B over 10 minutes, one minutes hold time, A=90% water, 10% methanol, 0.2% phosphoric acid, B=10% water, 90% methanol, 0.2% phosphoric acid, RT=2.74 min, 98%.

LCMS: Anal. Calcd. for: $C_{48}H_{54}N_8O_2$ 775.02. Found: 775.50 (M+H)$^+$.

Isomer 2: (1R,1'R)-2,2'-(4,4'-biphenyldiylbis((1-methyl-1H-imidazole-4,2-diyl)(2S)-2,1-pyrrolidinediyl))bis(N,N-dimethyl-2-oxo-1-phenylethanamine)

(10.2 mg, 11%) as a colorless wax.
$^1$H NMR (500 MHz, DMSO-$d_6$) δ ppm 1.83-2.26 (m, 8H) 2.30-2.92 (m, 12H) 3.68-3.94 (m, 8H) 4.06 (s, 2H) 5.25 (d, J=2.14 Hz, 2H) 5.50 (s, 2H) 7.52-7.91 (m, 20H).

HPLC Xterra 4.6×50 mm, 0 to 100% B over 10 minutes, one minutes hold time, A=90% water, 10% methanol, 0.2% phosphoric acid, B=10% water, 90% methanol, 0.2% phosphoric acid, RT=2.75 min, 90%.

LCMS: Anal. Calcd. for: $C_{48}H_{54}N_8O_2$ 775.02. Found: 775.52 (M+H)$^+$.

Example 152

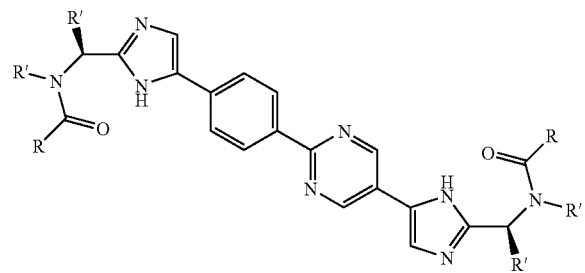

Example 152a-1 Step a

2-Chloro-5-(1-ethoxyvinyl)pyrimidine

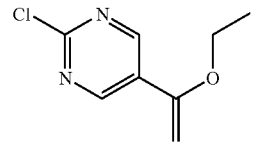

To a solution of 5-bromo-2-chloropyrimidine (12.5 g, 64.62 mmol) in dry DMF (175 mL) under $N_2$ was added tributyl(1-ethoxyvinyl)tin (21.8 mL, 64.62 mmol) and dichlorobis(triphenylphosphine)palladium (II) (2.27 g, 3.23 mmol). The mixture was heated at 100° C. for 3 h before being allowed to stir at room temperature for 16 hr. The mixture was then diluted with ether (200 mL) and treated with aqueous KF soln (55 g of potassium fluoride in 33 mL of water). The two phase mixture was stirred vigorously for 1 h at room temperature before being filtered through diatomaceous earth (Celite®). The filtrate was washed with sat'd $NaHCO_3$ soln and brine prior to drying ($Na_2SO_4$). The original aqueous phase was extracted with ether (2×) and the organic phase was treated as above. Repetition on 13.5 g of 5-bromo-2-chloropyrimidine and combined purification by Biotage™ flash chromatography on silica gel (gradient elution on a 65M column using 3% ethyl acetate in hexanes to 25% ethyl acetate in hexanes with 3.0 L) afforded the title compound as a white, crystalline solid (18.2 g, 73%).

$^1$H NMR (500 MHz, DMSO-$d_6$) δ 8.97 (s, 2H), 5.08 (d, J=3.7 Hz, 1H), 4.56 (d, J=3.4 Hz, 1H), 3.94 (q, J=7.0 Hz, 2H), 1.35 (t, J=7.0 Hz, 3H).

LCMS Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=2.53 min, 98.8% homogeneity index.

LCMS: Anal. Calcd. for $C_8H_{10}ClN_2O$ 185.05. found: 185.04 (M+H)$^+$.

HRMS: Anal. Calcd. for $C_8H_{10}ClN_2O$ 185.0482. found: 185.0490 (M+H)$^+$.

The same method was used for the preparation of Examples 152a-2 & 152a-3:

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

| Example 152a-2 | from dichloropyridazine | $t_R$ = 2.24 min 96.4%, condition 1 LRMS: Anal. Calcd. for $C_8H_{10}ClN_2O$ 185.05; found: 185.06 (M + H)$^+$. HRMS: Anal. Calcd for $C_8H_{10}ClN_2O$ 185.0482; found: 185.0476 (M + H)$^+$. |
|---|---|---|

| Example 152a-3 | 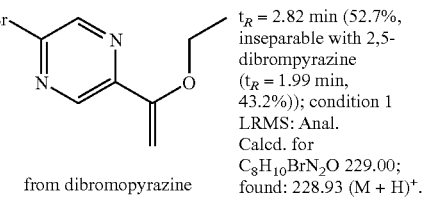<br>from dibromopyrazine | $t_R$ = 2.82 min (52.7%, inseparable with 2,5-dibrompyrazine ($t_R$ = 1.99 min, 43.2%)); condition 1 LRMS: Anal. Calcd. for $C_8H_{10}BrN_2O$ 229.00; found: 228.93 (M + H)$^+$. |
|---|---|---|

Example 152d-1 to 152d-6

Example 152b-1

Step b (S)-tert-Butyl 2-(5-(2-chloropyrimidin-5-yl)-1H-imidazol-2-yl)pyrrolidine-1-carboxylate or (S)-2-[5-(2-Chloro-pyrimidin-5-yl)-1H-imidazol-2-yl]-pyrrolidine-1-carboxylic acid tert-butyl ester

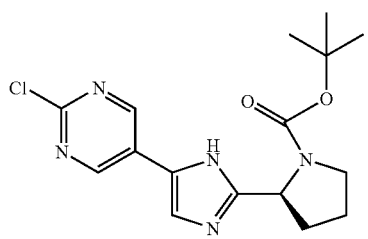

NBS (16.1 g, 90.7 mmol) was added in one portion to a stirred solution of 2-chloro-5-(1-ethoxyvinyl)pyrimidine (152a-1, 18.2 g, 98.6 mmol) in THF (267 mL) and H$_2$O (88 mL) at 0° C. under N$_2$. The mixture was stirred for 1 h at 0° C. before it was diluted with more H$_2$O and extracted with ethyl acetate (2×). The combined extracts were washed with sat'd NaHCO$_3$ soln and brine prior to drying (Na$_2$SO$_4$), filtration, and solvent evaporation. LCMS Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=1.52 min (unsymmetrical peak). LCMS: Anal. Calcd. for $C_6H_{14}BrClN_2O$ 235.92. found: 236.85 (M+H)$^+$.

Example 152c-1

Step c

Half of the crude residue (2-bromo-1-(2-chloropyrimidin-5-yl)ethanone, ~14.5 g) was dissolved into anhydrous acetonitrile (150 mL) and treated directly with N-Boc-L-proline (9.76 g, 45.35 mmol) and diisopropylethylamine (7.9 mL, 45.35 mmol). After being stirred for 3 h, the solvent was removed in vacuo and the residue was partitioned into ethyl acetate and water. The organic phase was washed with 0.1N hydrochloric acid, sat'd NaHCO$_3$ soln and brine prior to drying (Na$_2$SO$_4$), filtration, and concentration. LCMS Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=2.66 min.

The same method was used to prepare Examples 152c through 152c-6.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 µL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 µL injection volume.

| Example 152c-2 | 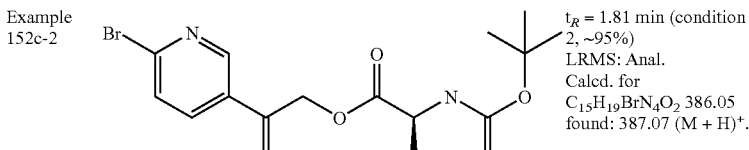 | $t_R$ = 1.81 min (condition 2, ~95%) LRMS: Anal. Calcd. for $C_{15}H_{19}BrN_4O_2$ 386.05 found: 387.07 (M + H)$^+$. |
|---|---|---|
| Example 152c-3 | 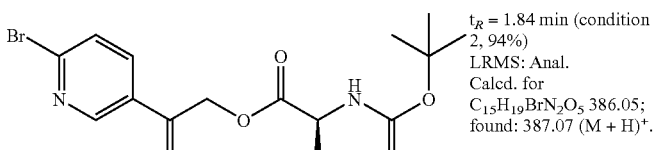 | $t_R$ = 1.84 min (condition 2, 94%) LRMS: Anal. Calcd. for $C_{15}H_{19}BrN_2O_5$ 386.05; found: 387.07 (M + H)$^+$. |
| Example 152c-3a | 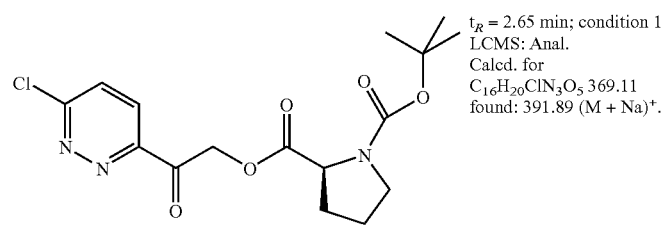 | $t_R$ = 2.65 min; condition 1 LCMS: Anal. Calcd. for $C_{16}H_{20}ClN_3O_5$ 369.11 found: 391.89 (M + Na)$^+$. |

| Example 152c-4 | 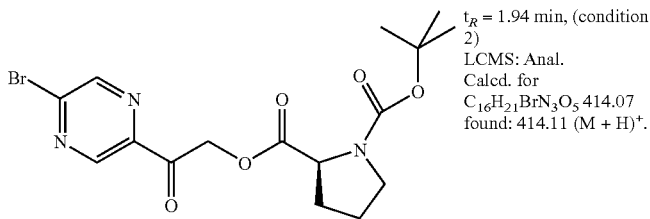 | $t_R$ = 1.94 min, (condition 2)<br>LCMS: Anal. Calcd. for $C_{16}H_{21}BrN_3O_5$ 414.07<br>found: 414.11 $(M + H)^+$. |
|---|---|---|
| Example 152c-5 | 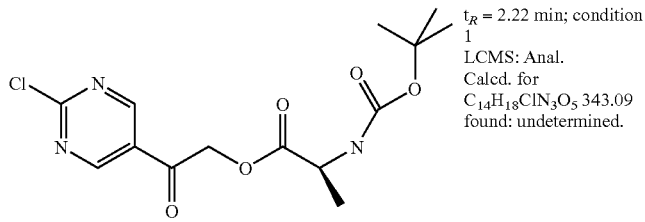 | $t_R$ = 2.22 min; condition 1<br>LCMS: Anal. Calcd. for $C_{14}H_{18}ClN_3O_5$ 343.09<br>found: undetermined. |
| Example 152c-6 | 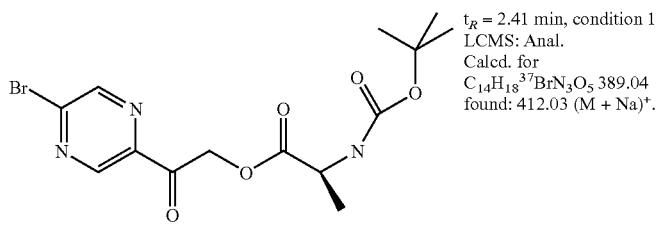 | $t_R$ = 2.41 min, condition 1<br>LCMS: Anal. Calcd. for $C_{14}H_{18}^{37}BrN_3O_5$ 389.04<br>found: 412.03 $(M + Na)^+$. |

Example 152d-1

Step d

This residue ((S)-1-tert-butyl 2-(2-(2-chloropyrimidin-5-yl)-2-oxoethyl)pyrrolidine-1,2-dicarboxylate) was taken up in xylenes (200 mL) and treated to NH₄OAc (17.5 g, 0.23 mol). The mixture was heated at 140° C. for 2 hr in a thick-walled, screw-top flask before it was cooled to ambient temperature and suction-filtered. The filtrate was then concentrated, partitioned into ethyl acetate and sat'd NaHCO₃ soln and washed with brine prior to drying (Na₂SO₄), filtration, and concentration The original precipitate was partitioned into aqueous NaHCO₃ soln and ethyl acetate and sonicated for 2 min before being suction-filtered. The filtrate was washed with brine, dried over (Na₂SO₄), filtered, and concentrated to dryness. Purification of the combined residues by Biotage™ flash chromatography on silica gel (65M column, preequilibration with 2% B for 900 mL followed by gradient elution with 2% B to 2% B for 450 ml followed by 2% B to 40% B for 300 mL where B=methanol and A=dichloromethane) afforded the title compound (7.0 g, 44% yield, 2 steps, pure fraction) as an yellowish orange foam. The mixed fractions were subjected to a second Biotage™ chromatography on silica gel (40M column, preequilibration with 1% B for 600 mL followed by gradient elution with 1% B to 1% B for 150 ml followed by 1% B to 10% B for 1500 mL where B=MeOH and A=CH₂Cl₂) afforded additional title compound (2.8 g, 18%) as a brownish-orange foam. ¹H NMR (500 MHz, DMSO-d₆) δ 12.24-12.16 (m, 1H), 9.05 (s, 2H), 7.84-7.73 (m, 1H), 4.90-4.73 (m, 1H), 3.59-3.46 (m, 1H), 3.41-3.31 (m, 1H), 2.32-2.12 (m, 1H), 2.03-1.77 (m, 3H), 1.39 and 1.15 (2s, 9H).

LCMS Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=1.92 min, 94.7% homogeneity index.

LRMS: Anal. Calcd. for $C_{16}H_{21}ClN_5O_2$ 350.14. found: 350.23 $(M+H)^+$.

HRMS: Anal. Calcd. for $C_{16}H_{21}ClN_5O_2$ 350.1384. found: 350.1398 $(M+H)^+$.

The same method was used to prepare Examples 152d-2 through 152d-6.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 µL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 µL injection volume.

| Example 152d-2 | 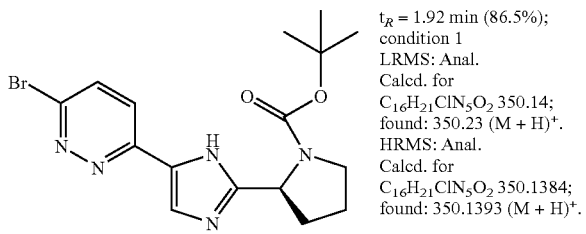 from 152c-3a | $t_R$ = 1.92 min (86.5%); condition 1 LRMS: Anal. Calcd. for $C_{16}H_{21}ClN_5O_2$ 350.14; found: 350.23 (M + H)+. HRMS: Anal. Calcd. for $C_{16}H_{21}ClN_5O_2$ 350.1384; found: 350.1393 (M + H)+. |
|---|---|---|
| Example 152d-3 | 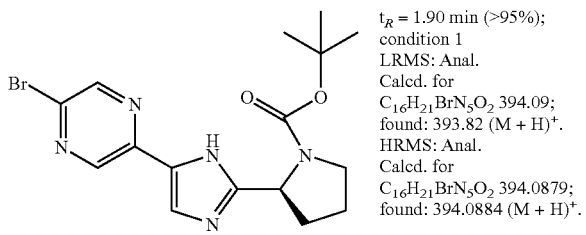 from 152c-4 | $t_R$ = 1.90 min (>95%); condition 1 LRMS: Anal. Calcd. for $C_{16}H_{21}BrN_5O_2$ 394.09; found: 393.82 (M + H)+. HRMS: Anal. Calcd. for $C_{16}H_{21}BrN_5O_2$ 394.0879; found: 394.0884 (M + H)+. |
| Example 152d-4 | 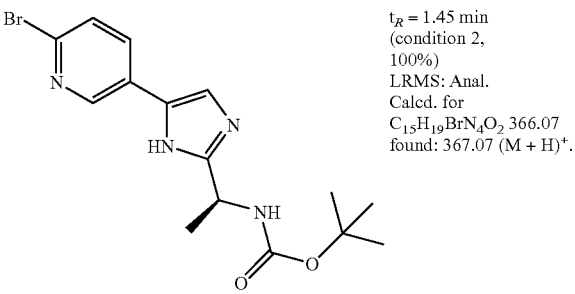 from 152c-3 | $t_R$ = 1.45 min (condition 2, 100%) LRMS: Anal. Calcd. for $C_{15}H_{19}BrN_4O_2$ 366.07 found: 367.07 (M + H)+. |
| Example 152d-5 | 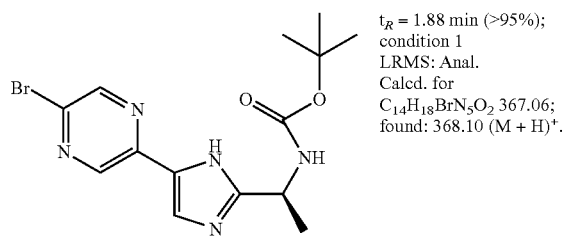 from 152c-6 | $t_R$ = 1.88 min (>95%); condition 1 LRMS: Anal. Calcd. for $C_{14}H_{18}BrN_5O_2$ 367.06; found: 368.10 (M + H)+. |
| Example 152d-6 | 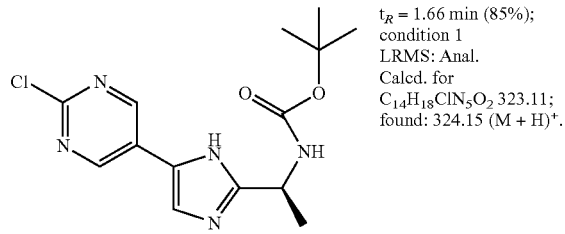 from 152c-5 | $t_R$ = 1.66 min (85%); condition 1 LRMS: Anal. Calcd. for $C_{14}H_{18}ClN_5O_2$ 323.11; found: 324.15 (M + H)+. |

Example 152e-1

Step e

Example 152e-1

(S)-tert-Butyl 2-(5-(2-chloropyrimidin-5-yl)-1-((2-(trimethyl-silyl)ethoxy)methyl)-1H-imidazol-2-yl)pyrrolidine-1-carboxylate

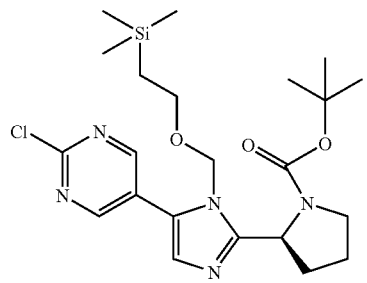

Sodium hydride (60% dispersion in mineral oil, 0.23 g, 5.72 mmol) was added in one portion to a stirred solution of (S)-tert-butyl 2-(5-(2-chloropyrimidin-5-yl)-1H-imidazol-2-yl)pyrrolidine-1-carboxylate (152d-1, 2.0 g, 5.72 mmol) in dry DMF (45 mL) at ambient temperature under $N_2$. The mixture was stirred for 5 min. before SEM chloride (1.01 mL, 5.72 mmol) was added in approx. 0.1 mL increments. The mixture was stirred for 3 h before being quenched with sat'd $NH_4Cl$ soln and diluted with ethyl acetate. The organic phase was washed with sat'd $NaHCO_3$ soln and brine, dried over ($Na_2SO_4$), filtered, and concentrated. The original aqueous phase was extracted twice more and the combined residue was purified by Biotage™ flash chromatography (40M column, 50 mL/min, preequilibration with 5% B for 750 mL, followed by step gradient elution with 5% B to 5% B for 150 mL, 5% B to 75% B for 1500 mL, then 75% B to 100% B for 750 mL where solvent B is ethyl acetate and solvent A is hexanes). Concentration of the eluant furnished the title compound as a pale yellow foam (2.35 g, 85%).

$^1$H NMR (500 MHz, DMSO-$d_6$) δ 9.04 (s, 2H), 7.98-7.95 (m, 1H), 5.70-5.31 (3m, 2H), 5.02-4.91 (m, 1H), 3.59-3.49 (m, 3H), 3.45-3.35 (m, 1H), 2.30-2.08 (m, 2H), 1.99-1.83 (m, 2H), 1.36 and 1.12 (2s, 9H), 0.93-0.82 (m, 2H), −0.02 (s, 9H).

LCMS Phenomenex LUNA C-18 4.6×50 mm, 0 to 100% B over 2 minutes, 2 minute hold time, A=90% water, 10% methanol, 0.1% TFA, B=10% water, 90% methanol, 0.1% TFA, RT=2.38 min, 95% homogeneity index.

LRMS: Anal. Calcd. for $C_{22}H_{35}ClN_5O_3Si$ 480.22. found: 480.23 (M+H)$^+$.

HRMS: Anal. Calcd. for $C_{22}H_{35}ClN_5O_3Si$ 480.2198. found: 480.2194 (M+H)$^+$.

The same method was used to prepare 152e-2 through 152e-4

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 µL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 µL injection volume.

Example 152e-2

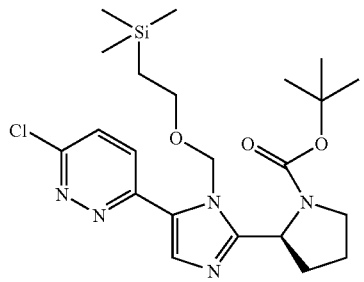

from 152d-2

$t_R$ = 2.34 min (85.7%); condition 1
LCMS: Anal. Calcd. for $C_{22}H_{35}ClN_5O_3Si$ 480.22; found: 480.22 (M + H)$^+$.
HRMS: Anal. Calcd. for $C_{22}H_{35}ClN_5O_3Si$ 480.2198 found: 480.2198 (M + H)$^+$.

Example 152e-3

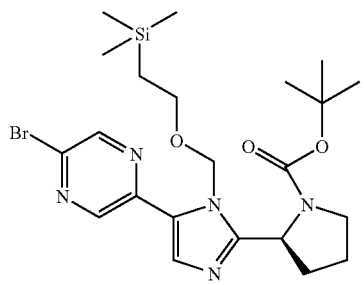

from 152d-3

$t_R$ = 3.18 min (>95%); condition 1
LCMS: Anal. Calcd. for $C_{22}H_{35}^{37}BrN_5O_3Si$ 526.17; found: 525.99 (M + H)$^+$.
HRMS: Anal. Calcd. for $C_{22}H_{35}^{37}BrN_5O_3Si$ 526.1692; found: 526.1674 (M + H)$^+$.

-continued

Example 152e-4

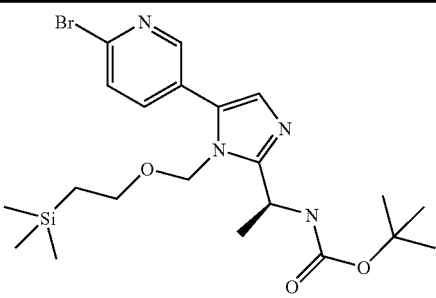

from 152d-4

$t_R$ = 2.14 min (condition 2, 96%)
LRMS: Anal. Calcd. For
$C_{21}H_{33}BrN_4O_3Si$ 496.15
found: 497.13 (M + H)$^+$.

Examples 152f-1 to 152f-2

Example 152f-1

(S)-1-(2-(5-(2-chloropyrimidin-5-yl)-1H-imidazol-2-yl)pyrrolidin-1-yl)-2-(pyridin-3-yl)ethanone

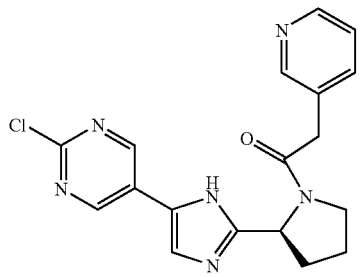

Cold (0° C.) 4 NHCl in dioxanes (5 mL) was added via syringe to (S)-tert-butyl 2-(5-(2-chloropyrimidin-5-yl)-1H-imidazol-2-yl)pyrrolidine-1-carboxylate (152d-1, 0.50 g, 1.43 mmol) in a 100 mL pear-shaped flask followed by MeOH (1.0 mL). The suspension was stirred at room temperature for 4 h before it was concentrated down to dryness and placed under high vacuum for 1 h. There was isolated intermediate (S)-2-chloro-5-(2-(pyrrolidin-2-yl)-1H-imidazol-5-yl)pyrimidine trihydrochloride as a pale yellow solid (with an orange tint) which was used without further purification.

HATU (0.60 g, 1.57 mmol) was added in one portion to a stirred solution of intermediate (S)-2-chloro-5-(2-(pyrrolidin-2-yl)-1H-imidazol-5-yl)pyrimidine trihydrochloride (0.46 g, 1.43 mmol, theoretical amount), 2-(pyridin-3-yl)acetic acid (0.25 g, 1.43 mmol) and DIEA (1.0 mL, 5.72 mmol) in anhydrous DMF (10 mL) at ambient temperature. The mixture was stirred at room temperature for 2 h before the DMF was removed in vacuo. The residue was taken up in $CH_2Cl_2$ and subjected to Biotage™ flash chromatography on silica gel (40M column, preequilibration with 0% B for 600 mL followed by step gradient elution with 0% B to 0% B for 150 mL followed by 0% B to 15% B for 1500 mL followed by 15% B to 25% B for 999 mL where B=MeOH and A=$CH_2Cl_2$). There was isolated the title compound (0.131 g, 25%, 2 steps) as a yellow solid.

$^1$H NMR (500 MHz, DMSO-d$_6$) δ 9.10-9.08 (2s, 2H), 8.72-8.55 (series of m, 2H), 8.21-8.20 and 8.11-8.10 (2m, 1H), 8.00 and 7.93 (2s, 1H), 7.84-7.77 (series of m, 1H), 5.43-5.41 and 5.17-5.15 (2m, 1H), 4.02-3.94 (3m, 2H), 3.90-3.58 (3m, 2H), 2.37-2.26 (m, 1H), 2.16-1.85 (2m, 3H).

LCRMS Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=0.92 min, 95.1% homogeneity index.

LRMS: Anal. Calcd. for $C_{18}H_{18}ClN_6O$ 369.12. found: 369.11 (M+H)$^+$.

HRMS: Anal. Calcd. for $C_{18}H_{18}ClN_6O$ 369.1231. found: 369.1246 (M+H)$^+$.

Example 152f-2 LCMS conditions: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 µL injection volume.

Example 152f-2

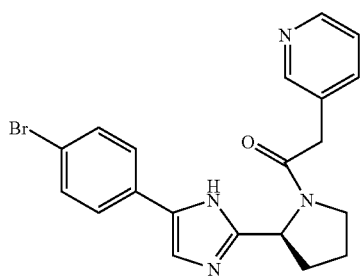

prepared from 1b with same procedure describing the preparation of 152f-1 from 152d-1

$t_R$ = 1.56 min (>95%)
LRMS: Anal. Calcd. for $C_{20}H_{20}BrN_4O$ 413.08; found: 412.99 (M + H)$^+$.

Examples 152g-1 to 152g-16

Example 152g-1 from 1c and 152e-1

(S)-2-[5-(2-{4-[2-((S)-1-tert-Butoxycarbonyl-pyrrolidin-2-yl)-3H-imidazol-4-yl]-phenyl}-pyrimidin-5-yl)-1-(2-trimethylsilanyl-ethoxymethyl)-1H-imidazol-2-yl]-pyrrolidine-1-carboxylic acid tert-butyl ester

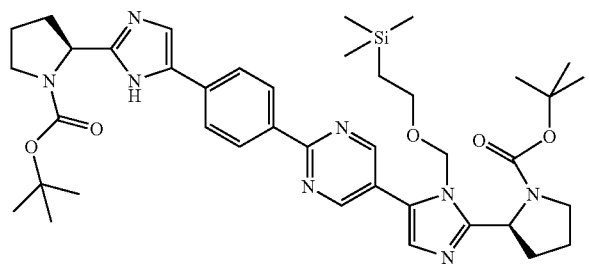

Pd(Ph$_3$)$_4$ (0.12 g, 0.103 mmol) was added in one portion to a stirred suspension of (S)-tert-butyl 2-(5-(4-(4,4,5,5-tetramethyl-1,3,2-dioxaborolan-2-yl)phenyl)-1H-imidazol-2-yl)pyrrolidine-1-carboxylate (1c, 1.00 g, 2.27 mmol), (S)-tert-butyl 2-(5-(2-chloropyrimidin-5-yl)-1-((2-(trimethylsilyl)ethoxy)methyl)-1H-imidazol-2-yl)pyrrolidine-1-carboxylate (152c-1, 0.99 g, 2.06 mmol) and NaHCO$_3$ (0.87 g, 10.3 mmol) in a solution of DME (20 mL) and H$_2$O (6 mL) at room temperature under N$_2$. The vessel was sealed and the mixture was placed into a preheated (80° C.) oil bath and stirred at 80° C. for 16 h before additional catalyst (0.12 g) was added. After heating the mixture for an additional 12 h at 80° C., the mixture was cooled to ambient temperature, diluted with ethyl acetate and washed with sat'd NaHCO$_3$ soln and brine prior to drying over anhydrous sodium sulfate and solvent concentration. Purification of the residue by Biotage™ flash chromatography on silica gel using a 40M column (preequilibrated with 40% B followed by step gradient elution with 40% B to 40% B for 150 mL, 40% B to 100% B for 1500 mL, 100% B to 100% B for 1000 mL where B=ethyl acetate and A=hexanes) furnished the title compound as a yellow foam (1.533 g, 98%). A small amount of the yellow foam was further purified for characterization purposes by pHPLC (Phenomenex GEMINI, 30×100 mm, S10, 10 to 100% B over 13 minutes, 3 minute hold time, 40 mL/min, A=95% water, 5% acetonitrile, 10 mM NH$_4$OAc, B=10% water, 90% acetonitrile, 10 mM NH$_4$OAc) to yield 95% pure title compound as a white solid.

$^1$HNMR (500 MHz, DMSO-d$_6$) δ 12.30-11.88 (3m, 1H), 9.17-9.16 (m, 2H), 8.43-8.31 (m, 2H), 7.99-7.35 (series of m, 4H), 5.72-5.30 (3m, 2H), 5.03-4.76 (2m, 2H), 3.64-3.50 (m, 4H), 3.48-3.31 (m, 2H), 2.36-2.07 (m, 2H), 2.05-1.80 (m, 4H), 1.46-1.08 (2m, 18H), 0.95-0.84 (m, 2H), −0.01 (s, 9H).

HPLC Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=2.91 min, 95% homogeneity index.

LRMS: Anal. Calcd. for C$_{40}$H$_{57}$N$_8$O$_5$Si 757.42. found: 757.42 (M+H)$^+$.

HRMS: Anal. Calcd. for C$_{40}$H$_{57}$N$_8$O$_5$Si 757.4221. found: 757.4191 (M+H)$^+$.

The same procedure was used to prepare Examples 152g-2 through 152g-17:

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 µL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 µL injection volume.

Example 152g-2

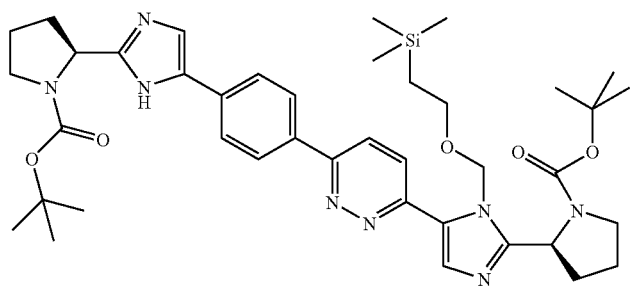

Prepared from 1c and 152e-2

$t_R$ = 2.81 min (79%); Condition 1
LRMS: Anal. Calcd. for C$_{40}$H$_{57}$N$_8$O$_5$Si 757.42; found: 758.05 (M + H)$^+$.
HRMS: Anal. Calcd. for C$_{40}$H$_{57}$N$_8$O$_5$Si 757.4221; found: 757.4196 (M + H)$^+$.

Example 152g-3

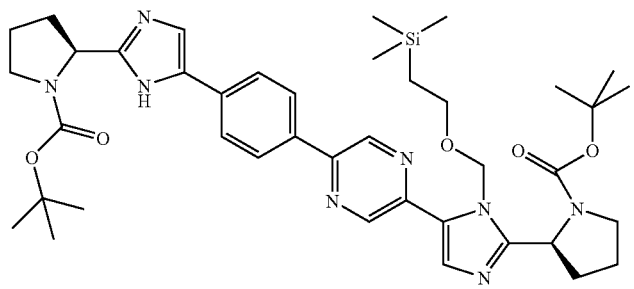

Prepared from 1c and 152e-3

$t_R$ = 2.89 min (>95%); Condition 1
LRMS: Anal. Calcd. for C$_{40}$H$_{57}$N$_8$O$_5$Si 757.42; found: 757.35 (M + H)$^+$.
HRMS: Anal. Calcd. for C$_{40}$H$_{57}$N$_8$O$_5$Si 757.4221; found: 757.4191 (M + H)$^+$.

Example 152g-4

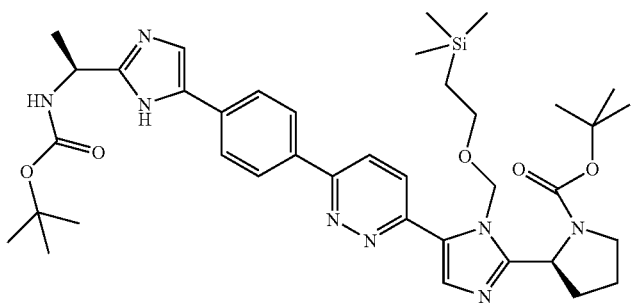

Prepared from 1-6c and 152e-2

$t_R$ = 2.87 min (97%); Condition 1
LRMS: Anal. Calcd. for
$C_{38}H_{55}N_8O_5Si$ 731.41; found:
731.26 (M + H)$^+$.
HRMS: Anal. Calcd. for
$C_{38}H_{55}N_8O_5Si$ 731.4065; found:
731.4070 (M + H)$^+$.

Example 152g-5

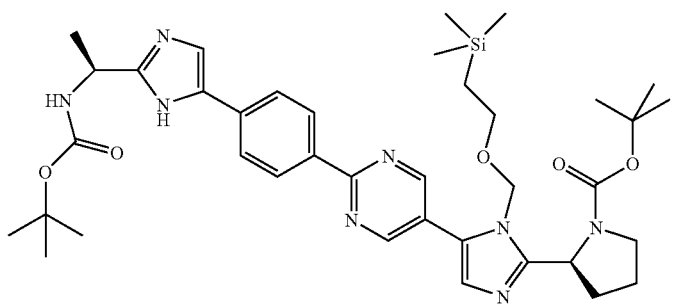

Prepared from 1-6c and 152e-1

$t_R$ = 2.94 min (>95%); Condition 1
LRMS: Anal. Calcd. for
$C_{38}H_{55}N_8O_5Si$ 731.41; found:
731.26 (M + H)$^+$.
HRMS: Anal. Calcd. for
$C_{38}H_{55}N_8O_5Si$ 731.4065; found:
731.4046 (M + H)$^+$.

Example 152g-6

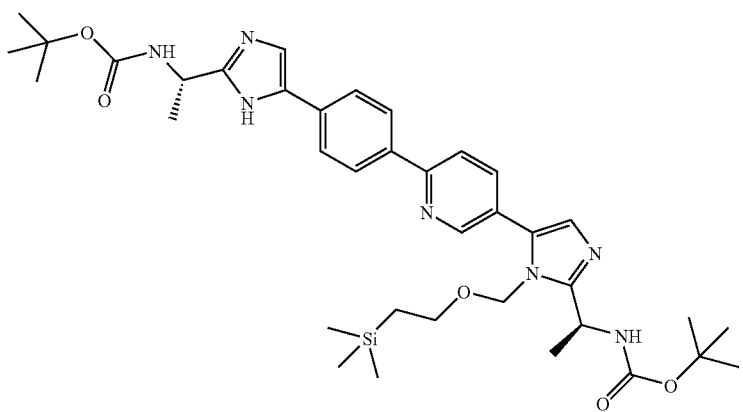

Prepared from 1-6c and 152e-4

$t_R$ = 1.99 min (condition 2, 96%)
LRMS: Anal. Calcd. for
$C_{37}H_{53}N_7O_2Si$ 703.39; found:
704.34 (M + H)$^+$.

| | | |
|---|---|---|
| Example 152g-7 | 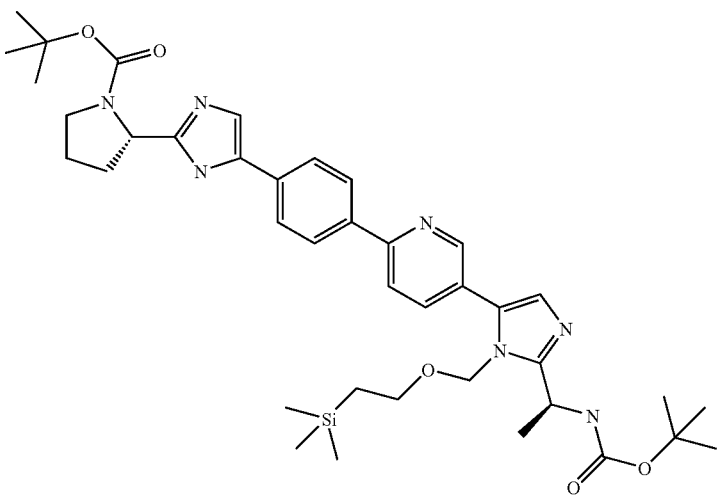<br>Prepared from 1c and 152e-4 | $t_R$ = 1.99 min (condition 2, 96%)<br>LRMS: Anal. Calcd. for<br>$C_{39}H_{55}N_7O_5Si$ 729.40; found:<br>730.42 $(M + H)^+$. |
| Example 152g-8 | 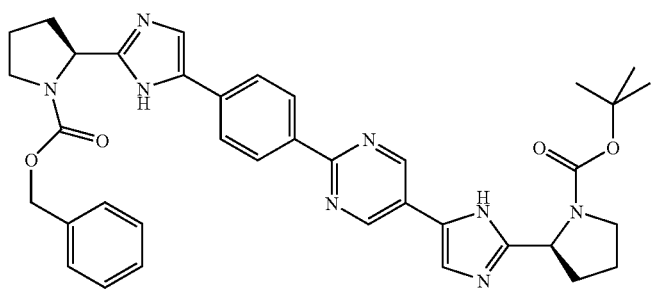<br>Prepared from 1-5c and 152d-1 | $t_R$ = 2.15 min (>95%); Condition 1<br>LRMS: Anal. Calcd. for<br>$C_{37}H_{41}N_8O_4$ 661.33; found:<br>661.39 $(M + H)^+$.<br>HRMS: Anal. Calcd. for<br>$C_{37}H_{41}N_8O_4$ 661.3251; found:<br>661.3268 $(M + H)^+$. |
| Example 152g-9 | 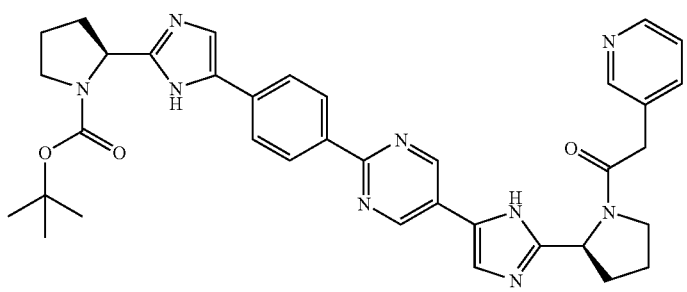<br>Prepared from 1c and 152f-1 | $t_R$ = 1.71 min (>95%); Condition 1<br>LRMS: Anal. Calcd. for<br>$C_{36}H_{40}N_9O_3$ 646.76; found:<br>646.47 $(M + H)^+$.<br>HRMS: Anal. Calcd. for<br>$C_{36}H_{40}N_9O_3$ not done found: not done $(M + H)^+$. |
| Example 152g-10 | 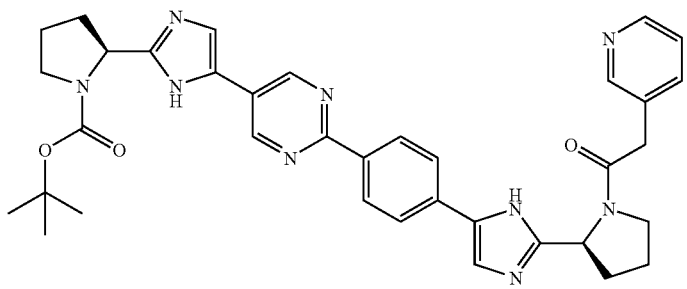<br>Prepared from 152d-1 and 1-10c | $t_R$ = 1.71 min (>95%); Condition 1<br>LRMS: Anal. Calcd. for<br>$C_{36}H_{40}N_9O_3$ 646.33; found:<br>646.37 $(M + H)^+$.<br>HRMS: Anal. Calcd. for<br>$C_{36}H_{40}N_9O_3$ 646.3254; found:<br>646.3240 $(M + H)^+$. |

| Example 152g-11 | 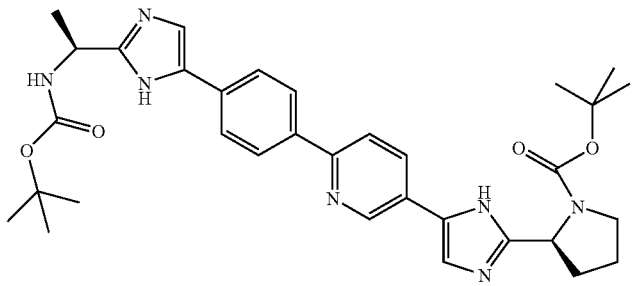<br>Prepared from 1-6c and 152e-4 | $t_R$ = 2.12 min (>93.9%); Condition 1<br>LRMS: Anal. Calcd. for $C_{33}H_{42}N_7O_4$ 600.33; found: 600.11 (M + H)$^+$.<br>HRMS: Anal. Calcd. for $C_{33}H_{42}N_7O_4$ 600.3298; found: 600.3312 (M + H)$^+$. |
|---|---|---|
| Example 152g-12 | 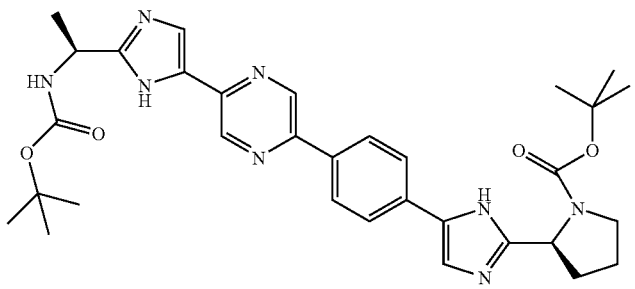<br>Prepared from 1c and 152d-5 | $t_R$ = 2.13 min (97.3%); Condition 1<br>LRMS: Anal. Calcd. for $C_{32}H_{41}N_8O_4$ 601.33; found: 601.36 (M + H)$^+$.<br>HRMS: Anal. Calcd. for $C_{32}H_{41}N_8O_4$ 601.3251; found: 601.3253 (M + H)$^+$. |
| Example 152g-13 | 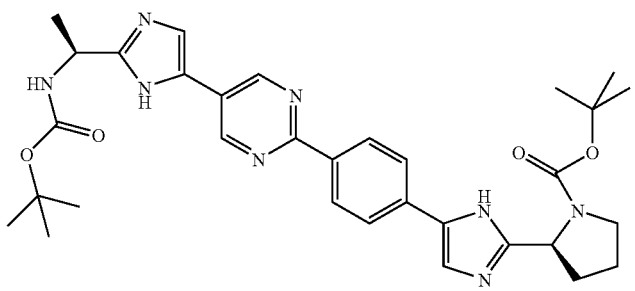<br>Prepared from 1c and 152d-6 | $t_R$ = 2.11 min (98.5%); Condition 1<br>LRMS: Anal. Calcd. for $C_{32}H_{41}N_8O_4$ 601.33; found: 601.36 (M + H)$^+$.<br>HRMS: Anal. Calcd. for $C_{32}H_{41}N_8O_4$ 601.3251; found: 661.3253 (M + H)$^+$. |
| Example 152g-14 | 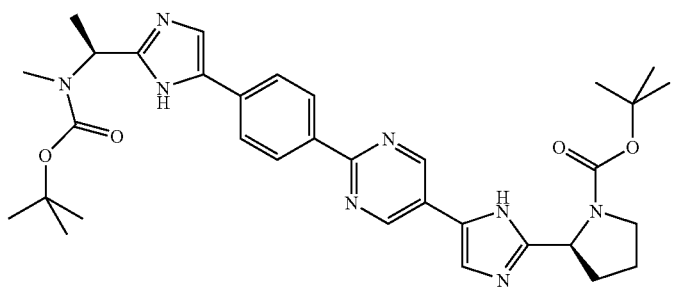<br>Prepared from 1-8c and 152d-1 | $t_R$ = 2.18 min (>95%); Condition 1<br>LRMS: Anal. Calcd. for $C_{33}H_{43}N_8O_4$ 615.38; found: 615.36 (M + H)$^+$.<br>HRMS: Anal. Calcd. for $C_{33}H_{43}N_8O_4$ 615.3407; found: 615.3433 (M + H)$^+$. |

Example 152g-15

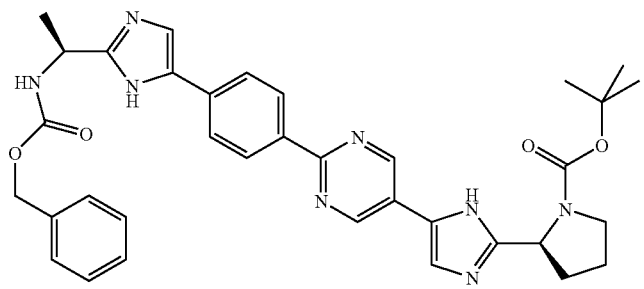

Prepared from 1c and 152d-1

$t_R$ = 2.20 min (97.7%); Condition 1
LRMS: Anal. Calcd. for
$C_{35}H_{39}N_8O_4$ 635.31; found:
635.36 (M + H)$^+$.
HRMS: Anal. Calcd. for
$C_{35}H_{39}N_8O_4$ 635.3094; found:
635.3119 (M + H)$^+$.

Example 152g-16

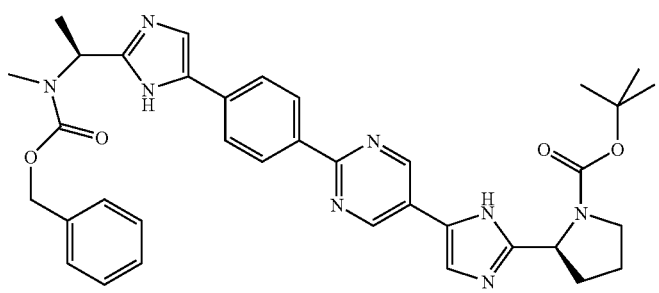

Prepared from 1-9c and 152d-1

$t_R$ = 2.26 min (>95%); Condition 1
LRMS: Anal. Calcd.
$C_{36}H_{41}N_8O_4$ 649.33; found:
649.39 (M + H)$^+$.
HRMS: Anal. Calcd. for
$C_{36}H_{41}N_8O_4$ 649.3251; found:
649.3276 (M + H)$^+$.

Example 152g-17

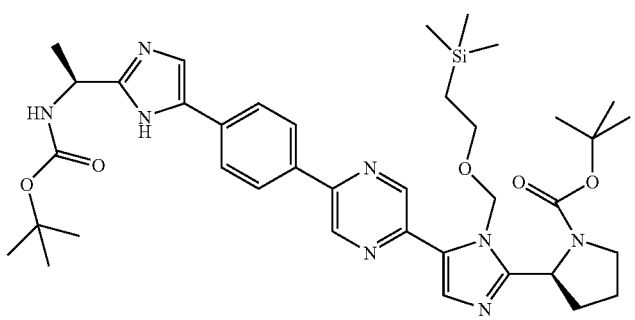

Prepared from 1-6c and 152e-3

$t_R$ = 2.98 min (98.5%); Condition 1
LRMS: Anal. Calcd. for
$C_{38}H_{54}N_8O_5Si$ 730.39; found:
731.40 (M + H)$^+$.
HRMS: Anal. Calcd. for
$C_{38}H_{54}N_8O_5Si$ 731.4065; found:
731.4045 (M + H)$^+$.

Example 152h-1-152h-7

Example 152h-1 from 152g-1

5-((S)-2-Pyrrolidin-2-yl-3H-imidazol-4-yl)-2-[4-((S)-2-pyrrolidin-2-yl-3H-imidazol-4-yl)-phenyl]-pyrimidine

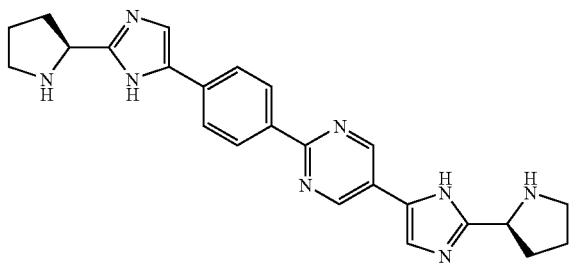

TFA (8 mL) was added in one portion to a stirred solution of (S)-2-[5-(2-{4-[2-((S)-1-tert-butoxycarbonyl-pyrrolidin-2-yl)-3H-imidazol-4-yl]-phenyl}-pyrimidin-5-yl)-1-(2-trimethylsilanyl-ethoxymethyl)-1H-imidazol-2-yl]-pyrrolidine-1-carboxylic acid tert-butyl ester (1.50 g, 1.98 mmol) in dry CH$_2$Cl$_2$ (30 mL) at room temperature. The flask was sealed and the mixture was stirred at room temperature for 16 h before the solvent(s) were removed in vacuo. The residue was taken up in methanol, filtered through a PVDF syringe filter (13 mm×0.45 μm), distributed to 8 pHPLC vials and chromatographed by HPLC (gradient elution from 10% B to 100% B over 13 min on a Phenomenex C18 column, 30×100 mm, 10 μm, where A=90% water, 10% methanol, 0.1% TFA, B=10% water, 90% methanol, 0.1% TFA). After concentration of the selected test tubes by speed vacuum evaporation, the product was dissolved in methanol and neutralized by passing the solution through an UCT CHQAX 110M75 anion exchange cartridge. There was isolated the title compound as a yellow mustard-colored solid (306.7 mg, 36% yield) upon concentration of the eluant.

$^1$H NMR (500 MHz, DMSO-d$_6$) μ 12.50-11.80 (br m, 2H), 9.18 (s, 2H), 8.36 (d, J=8.5 Hz, 2H), 7.89 (d, J=8.2 Hz, 2H), 7.77 (s, 1H), 7.61 (s, 1H), 4.34-4.24 (m, 2H), 3.09-2.89 (m, 4H), 2.18-2.07 (m, 2H), 2.02-1.89 (m, 2H), 1.88-1.72 (m, 4H).

LCMS Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=1.33 min, >95% homogeneity index.

LRMS: Anal. Calcd. for C$_{24}$H$_{27}$N$_8$ 427.24. found: 427.01 (M+H)$^+$.

HRMS: Anal. Calcd. for C$_{24}$H$_{27}$N$_8$ 427.2359. found: 427.2363 (M+H)$^+$.

The same conditions were used to prepare Examples 152h-2 through 152h-14.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

---

Example 152h-2

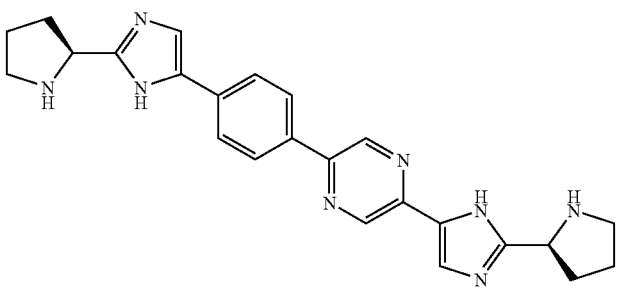

Prepared from 152g-3

$t_R$ = 1.36 min (98%); Condition 1
LRMS: Anal. Calcd. for C$_{24}$H$_{27}$N$_8$ 427.24; found: 427.48 (M + H)$^+$.
HRMS: Anal. Calcd. for C$_{24}$H$_{27}$N$_8$ 427.2359; found: 427.2339 (M + H)$^+$.

Example 152h-3

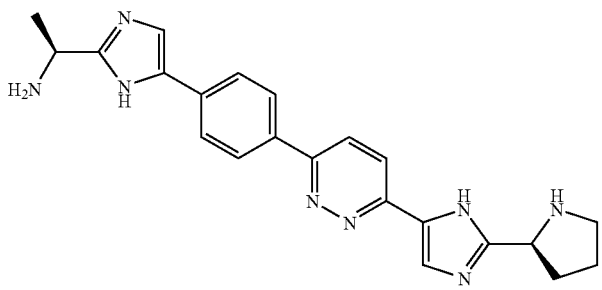

Prepared from 152g-4

$t_R$ = 1.17 min (>95%); Condition 1
LRMS: Anal. Calcd. for C$_{22}$H$_{25}$N$_8$ 401.22; found: 401.16 (M + H)$^+$.
HRMS: Anal. Calcd. for C$_{22}$H$_{25}$N$_8$ 401.2202; found: 401.2193 (M + H)$^+$.

| | | |
|---|---|---|
| Example 152h-4 | 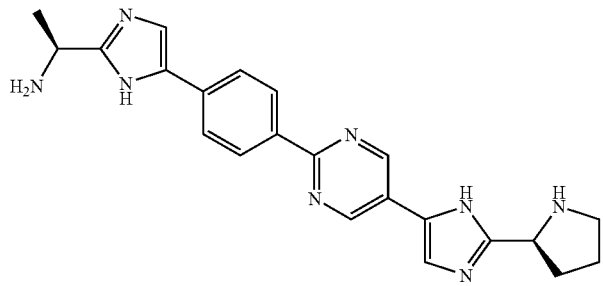<br>Prepared from 152g-5 | $t_R$ = 1.28 min (89.3%);<br>Condition 1<br>LRMS: Anal. Calcd.<br>for $C_{22}H_{25}N_8$ 401.22;<br>found: 401.16 $(M + H)^+$.<br>HRMS: Anal. Calcd.<br>for $C_{22}H_{25}N_8$ 401.2202;<br>found: 401.2201<br>$(M + H)^+$. |
| Example 152h-5 | 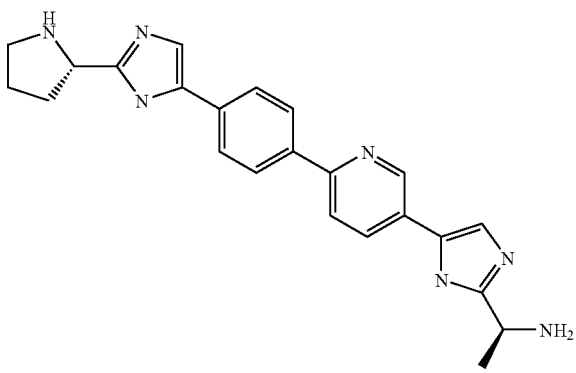<br>Prepared from 152g-7 | $t_R$ = 0.93 min;<br>Condition 2<br>LRMS: Anal. Calcd.<br>for $C_{23}H_{25}N_7$ 399;<br>found: 400 $(M + H)^+$. |
| Example 152h-6 | 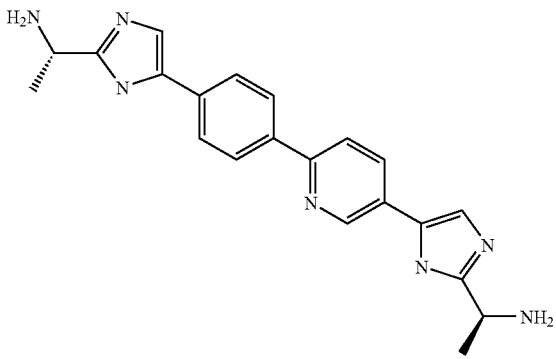<br>Prepared from 152g-6 | $t_R$ = 0.81 min;<br>Condition 2<br>LRMS: Anal. Calcd.<br>for $C_{21}H_{23}N_7$ 373;<br>found: 374 $(M + H)^+$. |
| Example 152h-7 | 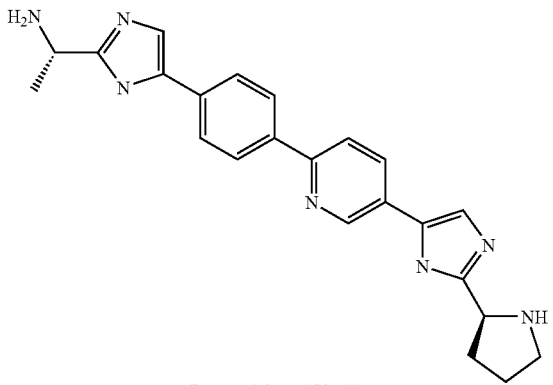<br>Prepared from 152g-11 | $t_R$ = 1.14 min (>95%);<br>Condition 1<br>LRMS: Anal. Calcd.<br>for $C_{23}H_{26}N_7$ 400.23;<br>found: 400.14 $(M + H)^+$.<br>HRMS: Anal. Calcd.<br>for $C_{23}H_{26}N_7$ 400.2250;<br>found: 400.2234<br>$(M + H)^+$. |

| | | |
|---|---|---|
| Example 152h-8 | 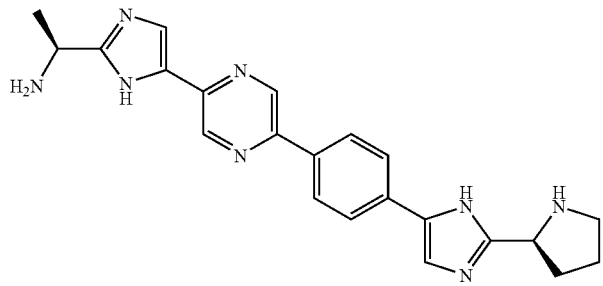  Prepared from 152g-12 | $t_R$ = 1.29 min (>95%); Condition 1 LRMS: Anal. Calcd. for $C_{22}H_{25}N_8$ 401.22; found: 401.21 $(M + H)^+$. HRMS: Anal. Calcd. for $C_{22}H_{25}N_8$ 401.2202; found: 401.2204 $(M + H)^+$. |
| Example 152h-9 | 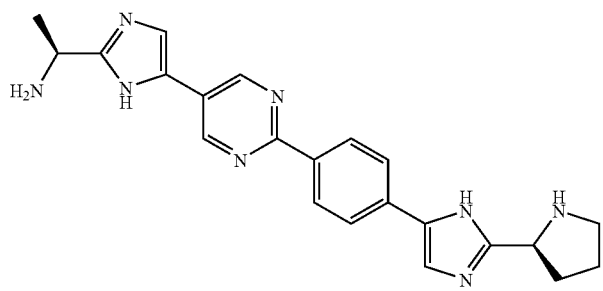  Prepared from 152g-13 | $t_R$ = 1.29 min (97.6%); Condition 1 LRMS: Anal. Calcd. for $C_{22}H_{25}N_8$ 401.22; found: 401.21 $(M + H)^+$. HRMS: Anal. Calcd. for $C_{22}H_{25}N_8$ 401.2202; found: 401.2220 $(M + H)^+$. |
| Example 152h-10 | 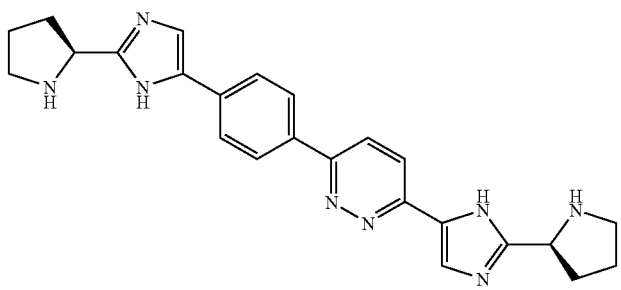  Prepared from 152g-2 | $t_R$ = 1.26 min (86.4%); Condition 1 LRMS: Anal. Calcd. for $C_{24}H_{27}N_8$ 427.24; found: 427.48 $(M + H)^+$. HRMS: Anal. Calcd. for $C_{24}H_{27}N_8$ 427.2359; found: 427.2339 $(M + H)^+$. |
| Example 152h-11 | 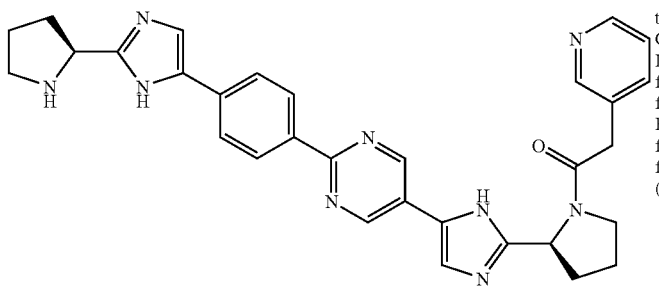  Prepared from 152g-9 | $t_R$ = 1.26 min (>95%); Condition 1 LRMS: Anal. Calcd. for $C_{31}H_{32}N_9O$ 546.27; found: 546.28 $(M + H)^+$. HRMS: Anal. Calcd. for $C_{31}H_{32}N_9O$ 546.2730 found: 546.2739 $(M + H)^+$. |

| Example 152h-12 | 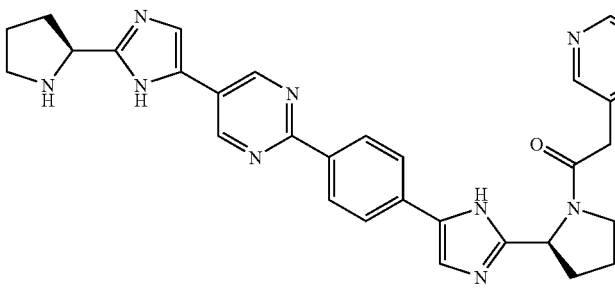 | $t_R$ = 1.39 min (95%); Condition 1 LRMS: Anal. Calcd. for $C_{31}H_{32}N_9O$ 546.27; found: 546.32 (M + H)$^+$. HRMS: Anal. Calcd. for $C_{31}H_{32}N_9O$ 546.2730; found: 546.2719 (M + H)$^+$. |
|---|---|---|
| | Prepared from 152g-10 | |
| Example 152h-13 | 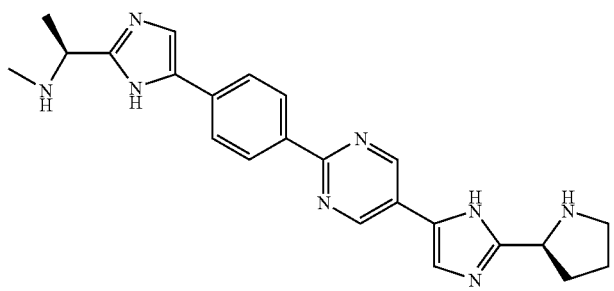 | $t_R$ = 1.42 min; Condition 1 LRMS: Anal. Calcd. for $C_{23}H_{26}N_8$ 414.24; found: 415.27 (M + H)$^+$. HRMS: Anal. Calcd. for $C_{23}H_{26}N_8$ 415.2359; found: 415.2371 (M + H)$^+$. |
| | Prepared from 152g-14 | |
| Example 152h-14 | 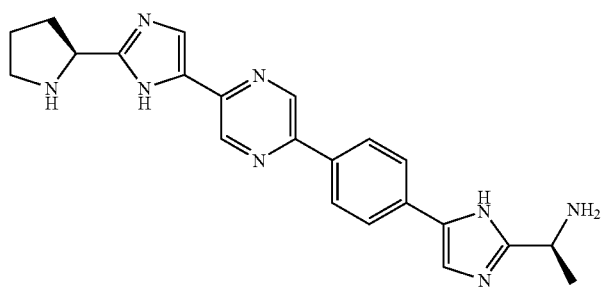 | $t_R$ = 1.30 min; Condition 1 LRMS: Anal. Calcd. for $C_{22}H_{24}N_8$ 400.21; found: 401.24 (M + H)$^+$. HRMS: Anal. Calcd. for $C_{22}H_{24}N_8$ 401.2202; found: 401.2198 (M + H)$^+$. |
| | Prepared from 152g-17 | |

Example 152i-1 to 152i-3

Example 152i-1 from 152g-8

(S)-2-(5-{2-[4-((S)-2-Pyrrolidin-2-yl-3H-imidazol-4-yl)-phenyl]-pyrimidin-5-yl}-1H-imidazol-2-yl)-pyrrolidine-1-carboxylic acid tert-butyl ester

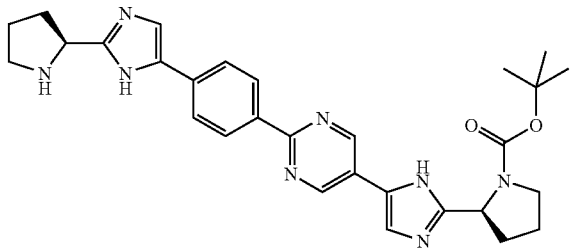

A solution of (S)-2-[5-(2-{4-[2-((S)-1-Benzyloxycarbonyl-pyrrolidin-2-yl)-3H-imidazol-4-yl]-phenyl}-pyrimidin-5-yl)-1H-imidazol-2-yl]-pyrrolidine-1-carboxylic acid tert-butyl ester (317.1 mg, 0.48 mmol) in MeOH (1 mL) was added to a stirred suspension of 10% palladium on carbon (60 mg) and $K_2CO_3$ (70 mg) in a solution of MeOH (5 mL) and $H_2O$ (0.1 mL) at room temperature under $N_2$. The flask was charged and evacuated three times with $H_2$ and stirred for 3 h at atmosphere pressure. Additional catalyst (20 mg) was then added and the reaction mixture was stirred further for 3 h before it was suction-filtered through diatomaceous earth (Celite®) and concentrated. The residue was diluted with MeOH, filtered through a PVDF syringe filter (13 mm×0.45 μm), distributed into 4 pHPLC vials and chromatographed (gradient elution from 20% B to 100% B over 10 min on a Phenomenex-Gemini C18 column (30×100 mm, 10 μm) where A=95% water, 5% acetonitrile, 10 mM $NH_4OAc$, B=10% water, 90% acetonitrile, 10 mM $NH_4OAc$). After concentration of the selected test tubes by speed vacuum evaporation, there was isolated the title compound as a yellow solid (142.5 mg, 56% yield).

$^1$H NMR (400 MHz, DMSO-$d_6$) δ 12.35-12.09 (br m, 1H), 9.17 (s, 2H), 8.35 (d, J=8.3 Hz, 2H), 7.87 (d, J=8.3 Hz, 2H), 7.80-7.72 (m, 1H), 7.56 (s, 1H), 4.92-4.77 (m, 1H), 4.21-4.13 (m, 1H), 3.61-3.05 (2m, 4H), 3.02-2.80 (2m, 2H), 2.37-1.67 (series of m, 6H), 1.41 and 1.17 (2s, 9H).

LCMS Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=1.77 min, >95% homogeneity index.

LRMS: Anal. Calcd. for $C_{29}H_{35}N_8O_2$ 527.29. found: 527.34 (M+H)$^+$.

HRMS: Anal. Calcd. for $C_{29}H_{35}N_8O_2$ 527.2883. found: 527.2874 (M+H)$^+$.

The same procedure was used to prepare Examples 152i-2 through 152i-3.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

Example 152i-2

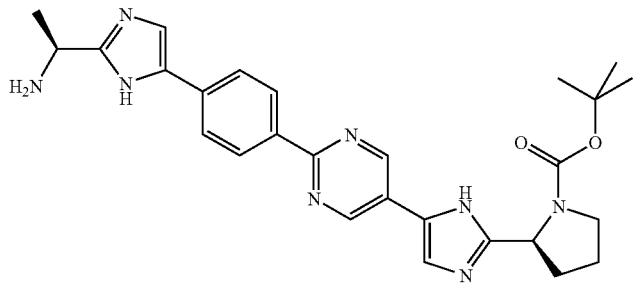

$t_R$ = 1.70 min (95.7%); Condition 1
LRMS: Anal. Calcd. for $C_{27}H_{33}N_8O_2$ 501.27; found: 501.35 (M + H)$^+$.
HRMS: Anal. Calcd. for $C_{27}H_{33}N_8O_2$ 501.27 found: 501.35 (M + H)$^+$.

Prepared from 152g-15

Example 152i-3

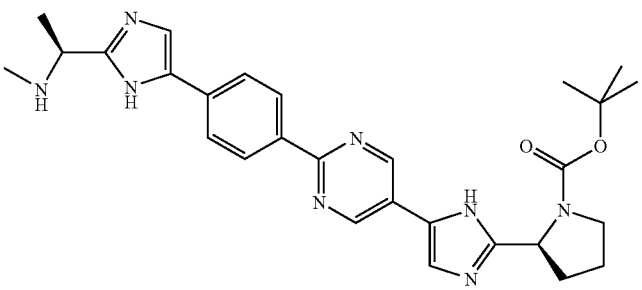

$t_R$ = 1.77 min (>95%); Condition 1
LRMS: Anal. Calcd. for $C_{28}H_{35}N_8O_2$ 515.29; found: 515.37 (M + H)$^+$.
HRMS: Anal. Calcd. for $C_{28}H_{35}N_8O_2$ 515.2883 found: 515.2869 (M + H)$^+$.

Prepared from 152g-16

Examples 152j-1 to 152j-28

Examples 152j were isolated as TFA or AcOH salts prepared using the procedure to convert Example 148e to 148.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

| Example | Compound Name | Structure | Data |
|---|---|---|---|
| Example 152j-1 | (1R)-2-((2S)-2-(5-(2-(4-(2-((2S)-1-((2R)-2-(dimethylamino)-2-phenylacetyl)-2-pyrrolidinyl)-1H-imidazol-5-yl)phenyl)-5-pyrimidinyl)-1H-imidazol-2-yl)-1-pyrrolidinyl)-N,N-dimethyl-2-oxo-1-phenylethanamine | 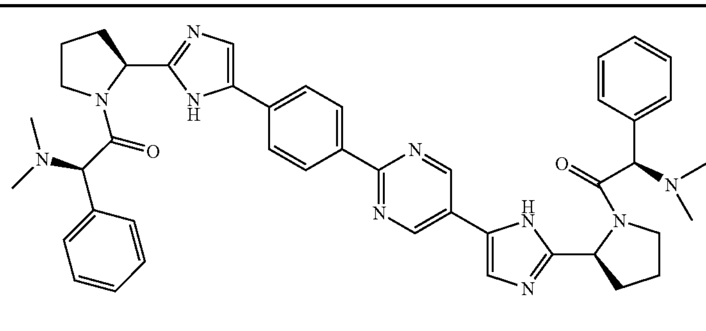 | $t_R$ = 1.61 min; (>95%); Condition 1 LRMS: Anal. Calcd. for $C_{44}H_{49}N_{10}O_2$ 749.40 found: 749.32 (M + H)$^+$ HRMS: Anal. Calcd. for $C_{44}H_{49}N_{10}O_2$ 749.4040 found: 749.4042 (M + H)$^+$ |

Prepared from 152h-1 and Cap-1.

| Example | Compound Name | Structure | Data |
|---|---|---|---|
| Example 152j-2 | methyl ((1R)-2-((2S)-2-(5-(2-(4-(2-((2S)-1-((2R)-2-((methoxycarbonyl)-amino)-2-phenylacetyl)-2-pyrrolidinyl)-1H-imidazol-5-yl)phenyl)-5-pyrimidinyl)-1H-imidazol-2-yl)-1-pyrrolidinyl)-2-oxo-1-phenylethyl)-carbamate | Prepared from 152h-1 and Cap-4 | $t_R$ = 1.99 min (>95%); Condition 1 LRMS: Anal. Calcd. for $C_{44}H_{45}N_{10}O_6$ 809.35 found: 809.17 (M + H)$^+$ HRMS: Anal. Calcd. for $C_{44}H_{45}N_{10}O_6$ 809.3524 found: 809.3505 (M + H)$^+$ |
| Example 152j-3 | methyl ((1R)-2-oxo-1-phenyl-2-((2S)-2-(5-(4-(5-(2-((2S)-1-(3-pyridinylacetyl)-2-pyrrolidinyl)-1H-imidazol-5-yl)-2-pyrimidinyl)phenyl)-1H-imidazol-2-yl)-1-pyrrolidinyl)ethyl)-carbamate | Prepared from 152h-11 and Cap-4 | $t_R$ = 1.65 min (92.3%); Condition 1 LRMS: Anal. Calcd. for $C_{41}H_{41}N_{10}O_2$ 737.33 found: 737.49 (M + H)$^+$ HRMS: Anal. Calcd. for $C_{41}H_{41}N_{10}O_4$ 737.3312 found: 737.3342 (M + H)$^+$ |
| Example 152j-4 | methyl ((1R)-2-oxo-1-phenyl-2-((2S)-2-(5-(2-(4-(2-((2S)-1-(3-pyridinylacetyl)-2-pyrrolidinyl)-1H-imidazol-5-yl)phenyl)-5-pyrimidinyl)-1H-imidazol-2-yl)-1-pyrrolidinyl)-ethyl)carbamate | Prepared from 152h-12 and Cap-4 | $t_R$ = 1.64 min (>95%); Condition 1 LRMS: Anal. Calcd. for $C_{41}H_{41}N_{10}O_4$ 737.33 found: 737.75 (M + H)$^+$ HRMS: Anal. Calcd. for $C_{41}H_{41}N_{10}O_4$ 737.3312 found: 737.3284 (M + H)$^+$ |
| Example 152j-5 | 5-(2-((2S)-1-((2R)-2-phenyl-2-(1-piperidinyl)acetyl)-2-pyrrolidinyl)-1H-imidazol-5-yl)-2-(4-(2-((2S)-1-((2R)-2-phenyl-2-(1-piperidinyl)acetyl)-2-pyrrolidinyl)-1H-imidazol-4-yl)phenyl)pyrimidine | Prepared from 152h-12 and Cap-14 | $t_R$ = 1.70 min (>95%); Condition 1 LRMS: Anal. Calcd. for $C_{50}H_{57}N_{10}O_2$ 829.47 found: 829.39 (M + H)$^+$ HRMS: Anal. Calcd. for $C_{50}H_{57}N_{10}O_2$ 829.4666 found: 829.4658 (M + H)$^+$ |

-continued

| Example | Compound Name | Structure | Data |
|---|---|---|---|
| Example 152j-6 | (2R)-N-methyl-2-phenyl-N-((1S)-1-(4-(4-(5-((2S)-1-((2R)-2-phenyl-2-(1-piperidinyl)acetyl)-2-pyrrolidinyl)-1H-imidazol-5-yl)-2-pyrimidinyl)phenyl)-1H-imidazol-2-yl)ethyl)-2-(1-piperidinyl)acetamide | Prepared from 152h-13 and Cap-14 | $t_R$ = 1.66 min (>95%); Condition 1 LRMS: Anal. Calcd. for $C_{49}H_{57}N_{10}O_2$ 817.47 found: 817.44 (M + H)$^+$ HRMS: Anal. Calcd. for $C_{49}H_{57}N_{10}O_2$ 817.4666 found: 817.4673 (M + H)$^+$ |
| Example 152j-7 | (1R)-2-((2S)-2-(5-(5-(4-(2-((2S)-1-((2R)-2-(dimethylamino)-2-phenylacetyl)-2-pyrrolidinyl)-1H-imidazol-5-yl)phenyl)-2-pyrazinyl)-1H-imidazol-2-yl)-1-pyrrolidinyl)-N,N-dimethyl-2-oxo-1-phenylethanamine | Prepared from 152h-2 and Cap-1 | $t_R$ = 1.60 min (>95%); Condition 1 LRMS: Anal. Calcd. for $C_{44}H_{49}N_{10}O_2$ 749.40 found: 749.31 (M + H)$^+$ HRMS: Anal. Calcd. for $C_{44}H_{49}N_{10}O_2$ 749.4040 found: 749.4031 (M + H)$^+$ |
| Example 152j-8 | methyl ((1R)-2-((2S)-2-(5-(5-(4-(2-((2S)-1-((2R)-2-((methoxycarbonyl)amino)-2-phenylacetyl)-2-pyrrolidinyl)-1H-imidazol-5-yl)phenyl)-2-pyrazinyl)-1H-imidazol-2-yl)-1-pyrrolidinyl)-2-oxo-1-phenylethyl)carbamate | Prepared from 152h-2 and Cap-4 | $t_R$ = 2.01 min (>95%); Condition 1 LRMS: Anal. Calcd. for $C_{44}H_{45}N_{10}O_6$ 809.35 found: 809.24 (M + H)$^+$ HRMS: Anal. Calcd. for $C_{44}H_{45}N_{10}O_6$ 809.3523 found: 809.3493 (M + H)$^+$ |
| Example 152j-9 | (1R)-2-((2S)-2-(5-(6-(4-(2-((2S)-1-((2R)-2-(dimethylamino)-2-phenylacetyl)-2-pyrrolidinyl)-1H-imidazol-5-yl)phenyl)-3-pyridazinyl)-1H-imidazol-2-yl)-1-pyrrolidinyl)-N,N-dimethyl-2-oxo-1-phenylethanamine | Prepared from 152h-10 and Cap-1 | $t_R$ = 1.76 min (>95%); Condition 1 LRMS: Anal. Calcd. for $C_{44}H_{49}N_{10}O_2$ 749.40 found: not obsd (M + H)$^+$ HRMS: Anal. Calcd. for $C_{44}H_{49}N_{10}O_2$ 749.4040 found: 749.4056 (M + H)$^+$ |

| Example | Compound Name | Structure | Data |
|---|---|---|---|
| Example 152j-10 | methyl ((1R)-2-((2S)-2-(5-(6-(4-(2-((2S)-1-((2R)-2-((methoxycarbonyl)-amino)-2-phenylacetyl)-2-pyrrolidinyl)-1H-imidazol-5-yl)phenyl)-3-pyridazinyl)-1H-imidazol-2-yl)-1-pyrrolidinyl)-2-oxo-1-phenylethyl)carbamate | Prepared from 152h-10 and Cap-4 | $t_R$ = 2.17 min (>95%); Condition 1 LRMS: Anal. Calcd. for $C_{44}H_{45}N_{10}O_6$ 809.35 found: 809.59 (M + H)$^+$ HRMS: Anal. Calcd. for $C_{44}H_{45}N_{10}O_6$ 809.3524 found: 809.3499 (M + H)$^+$ |
| Example 152j-11 | (2R)-2-(dimethylamino)-N-((1S)-1-(5-(4-(5-(2-((2S)-1-((2R)-2-(dimethylamino)-2-phenylacetyl)-2-pyrrolidinyl)-1H-imidazol-5-yl)-2-pyridinyl)phenyl)-1H-imidazol-2-yl)ethyl)-2-phenylacetamide | Prepared from 152h-7 and Cap-1 | $t_R$ = 1.56 min (>95%); Condition 1 LRMS: Anal. Calcd. for $C_{43}H_{48}N_9O_2$ 722.39 found: 722.89 (M + H)$^+$ HRMS: Anal. Calcd. for $C_{43}H_{48}N_9O_2$ 722.3931 found: 722.3930 (M + H)$^+$ |
| Example 152j-12 | methyl ((1R)-2-((2S)-2-(5-(6-(4-(2-((1S)-1-(((2R)-2-((methoxycarbonyl)-amino)-2-phenylacetyl)amino-ethyl)-1H-imidazol-5-yl)phenyl)-3-pyridinyl)-1H-imidazol-2-yl)-1-pyrrolidinyl)-2-oxo-1-phenylethyl)carbamate | Prepared from 152h-7 and Cap-4 | $t_R$ = 1.95 min (>95%); Condition 1 LRMS: Anal. Calcd. for $C_{43}H_{44}N_9O_6$ 782.34 found: 782.93 (M + H)$^+$ HRMS: Anal. Calcd. for $C_{43}H_{44}N_9O_6$ 782.3415 found: 782.3398 (M + H)$^+$ |
| Example 152j-13 | (2R)-2-(dimethylamino)-N-((1S)-1-(5-(4-(6-(2-((2S)-1-((2R)-2-(dimethylamino)-2-phenylacetyl)-2-pyrrolidinyl)-1H-imidazol-5-yl)-3-pyridazinyl)phenyl)-1H-imidazol-2-yl)ethyl)-2-phenylacetamide | Prepared from 152h-3 and Cap-1 | $t_R$ = 1.55 min (>95%); Condition 1 LRMS: Anal. Calcd. for $C_{42}H_{47}N_{10}O_2$ 723.39 found: 723.88 (M + H)$^+$ HRMS: Anal. Calcd. for $C_{42}H_{47}N_{10}O_2$ 723.3883 found: 723.3903 (M + H)$^+$ |

-continued

| Example | Compound Name | Structure | Data |
|---|---|---|---|
| Example 152j-14 | methyl ((1R)-2-((2S)-2-(5-(6-(4-(2-((1S)-1-(((2R)-2-((methoxycarbonyl)amino)-2-phenylacetyl)amino-ethyl)-1H-imidazol-5-yl)phenyl)-3-pyridazinyl)-1H-imidazol-2-yl)-1-pyrrolidinyl)-2-oxo-1-phenylethyl)carbamate | Prepared from 152h-3 and Cap-4 | $t_R$ = 1.95 min (>95%); Condition 1 LRMS: Anal. Calcd. for $C_{42}H_{43}N_{10}O_6$ 783.34 found: 783.95 (M + H)$^+$ HRMS: Anal. Calcd. for $C_{42}H_{43}N_{10}O_6$ 783.3367 found: 783.3337 (M + H)$^+$ |
| Example 152j-15 | methyl ((1R)-2-((2S)-2-(5-(2-(4-(2-((1S)-1-(((2R)-2-((methoxycarbonyl)amino)-2-phenylacetyl)amino)-ethyl)-1H-imidazol-5-yl)phenyl)-5-pyrimidinyl)-1H-imidazol-2-yl)-1-pyrrolidinyl)-2-oxo-1-phenylethyl)carbamate | Prepared from 152h-4 and Cap-4 | $t_R$ = 1.97 min (>95%); Condition 1 LRMS: Anal. Calcd. for $C_{42}H_{43}N_{10}O_6$ 783.34 found: 783.97 (M + H)$^+$ HRMS: Anal. Calcd. for $C_{42}H_{43}N_{10}O_6$ 783.3367 found: 783.3357 (M + H)$^+$ |
| Example 152j-16 | (2R)-2-(dimethylamino)-N-((1S)-1-(5-(2-(4-(2-((2S)-1-((2R)-2-(dimethylamino)-2-phenylacetyl)-2-pyrrolidinyl)-1H-imidazol-5-yl)-phenyl)-5-pyrimidinyl)-1H-imidazol-2-yl)ethyl)-2-phenylacetamide | Prepared from 152h-9 and Cap-1 | $t_R$ = 1.61 min (>95%); Condition 1 LRMS: Anal. Calcd. for $C_{42}H_{47}N_{10}O_2$ 723.39 found: 723.52 (M + H)$^+$ HRMS: Anal. Calcd. for $C_{42}H_{47}N_{10}O_2$ 723.3883 found: 723.3893 (M + H)$^+$ |
| Example 152j-17 | methyl ((1R)-2-((2S)-2-(5-(4-(5-(2-((1S)-1-(((2R)-2-((methoxycarbonyl)amino)-2-phenylacetyl)amino)-ethyl)-1H-imidazol-5-yl)-2-pyrimidinyl)phenyl)-1H-imidazol-2-yl)-1-pyrrolidinyl)-2-oxo-1-phenylethyl)carbamate | Prepared from 152h-9 and Cap-4 | $t_R$ = 1.99 min (95.6%); Condition 1 LRMS: Anal. Calcd. for $C_{42}H_{43}N_{10}O_6$ 783.34 found: 783.44 (M + H)$^+$ HRMS: Anal. Calcd. for $C_{42}H_{43}N_{10}O_6$ 783.3367 found: 783.3328 (M + H)$^+$ |

-continued

| Example | Compound Name | Structure | Data |
|---|---|---|---|
| Example 152j-18 | (2R)-2-(dimethylamino)-N-((1S)-1-(5-(5-(4-(2-((2S)-1-((2R)-2-(dimethylamino)-2-phenylacetyl)-2-pyrrolidinyl)-1H-imidazol-5-yl)-phenyl)-2-pyrazinyl)-1H-imidazol-2-yl)ethyl)-2-phenylacetamide | 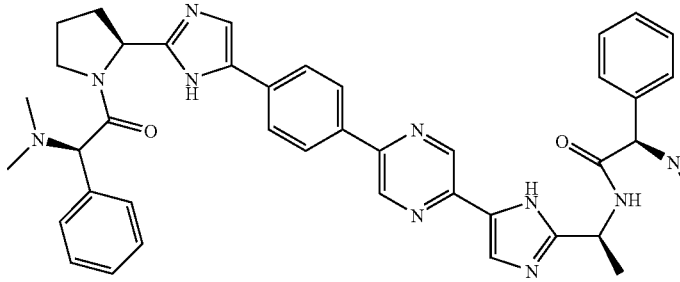<br>Prepared from 152h-8 and Cap-1 | $t_R$ = 1.60 min (>95%); Condition 1 LRMS: Anal. Calcd. for $C_{42}H_{47}N_{10}O_2$ 723.39 found: 723.47 (M + H)⁺ HRMS: Anal. Calcd. for $C_{42}H_{47}N_{10}O_2$ 723.3883 found: 723.3861 (M + H)⁺ |
| Example 152j-19 | methyl ((1R)-2-((2S)-2-(5-(4-(5-(2-((1S)-1-(((2R)-2-((methoxycarbonyl)-amino)-2-phenylacetyl)amino)-ethyl)-1H-imidazol-5-yl)-2-pyrazinyl)phenyl)-1H-imidazol-2-yl)-1-pyrrolidinyl)-2-oxo-1-phenylethyl)carbamate | 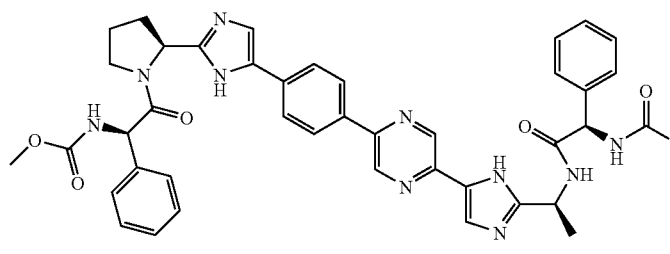<br>Prepared from 152h-8 and Cap-4 | $t_R$ = 1.97 min (94.7%); Condition 1 LRMS: Anal. Calcd. for $C_{42}H_{43}N_{10}O_6$ 783.34 found: 783.69 (M + H)⁺ HRMS: Anal. Calcd. for $C_{42}H_{43}N_{10}O_6$ 783.3367 found: 783.3345 (M + H)⁺ |
| Example 152j-20 | (2R)-2-(dimethylamino)-N-((1S)-1-(5-(4-(5-(2-((2S)-1-((2R)-2-(dimethylamino)-2-phenylacetyl)-2-pyrrolidinyl)-1H-imidazol-5-yl)-2-pyrimindinyl)phenyl)-1H-imidazol-2-yl)ethyl)-N-methyl-2-phenylacetamide | 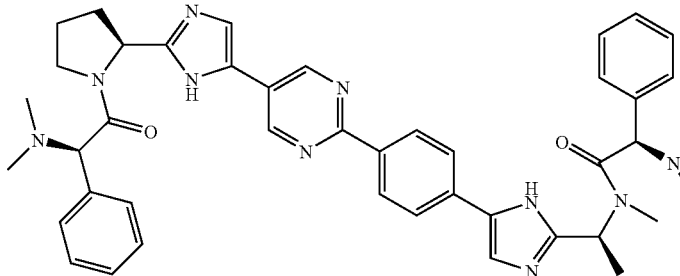<br>Prepared from 152h-13 and Cap-1 | $t_R$ = 1.54 min (>95%); Condition 1 LRMS: Anal. Calcd. for $C_{43}H_{49}N_{10}O_2$ 737.40 found: 737.54 (M + H)⁺ HRMS: Anal. Calcd. for $C_{43}H_{49}N_{10}O_2$ 737.4040 found: 7374066 (M + H)⁺ |
| Example 152j-21 | methyl ((1R)-2-((2S)-2-(5-(2-(4-(2-((1S)-1-(((2R)-2-((methoxycarbonyl)-amino)-2-phenylacetyl)(methyl)-amino)ethyl)-1H-imidazol-5-yl)phenyl)-5-pyrimidinyl)-1H-imidazol-2-yl)-1-pyrrolidinyl)-2-oxo-1-phenylethyl)carbamate | 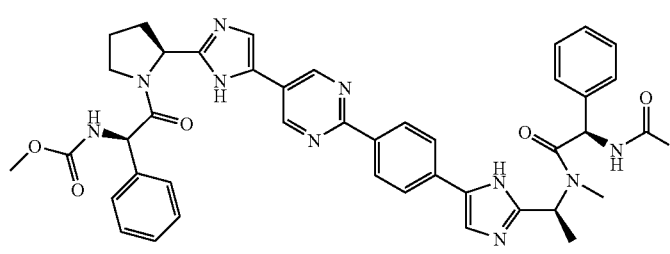<br>Prepared from 152h-13 and Cap-4 | $t_R$ = 2.00 min (>95%); Condition 1 LRMS: Anal. Calcd. for $C_{43}H_{45}N_{10}O_6$ 797.35 found: 797.38 (M + H)⁺ HRMS: Anal. Calcd. for $C_{43}H_{45}N_{10}O_6$ 797.3524 found: 797.3528 (M + H)⁺ |

| Example | Compound Name | Structure | Data |
|---|---|---|---|
| Example 152j-22 | methyl ((1R)-2-((2S)-2-(5-(4-(5-(2-((1S)-1-(((2R)-2-((methoxycarbonyl)amino)-2-phenylacetyl)amino)ethyl)-1H-imidazol-5-yl)-2-pyridinyl)phenyl)-1H-imidazol-2-yl)-1-pyrrolidinyl)-2-oxo-1-phenylethyl)carbamate | Prepared from 152h-5 and Cap-4 | $t_R$ = 1.46 min (condition 2, 98%) LRMS: Anal. Calcd. for $C_{43}H_{43}N_9O_6$ 781.33; found: 782.34 (M + H)$^+$. HRMS: Anal. Calcd. for $C_{43}H_{44}N_9O_6$ 782.3415 found: 782.3417 (M + H)$^+$ |
| Example 152j-23 | methyl ((1R)-2-(((1S)-1-(5-(6-(4-(2-((1S)-1-(((2R)-2-((methoxycarbonyl)amino)-2-phenylacetyl)amino)ethyl)-1H-imidazol-5-yl)phenyl)-3-pyridinyl)-1H-imidazol-2-yl)ethyl)amino)-2-oxo-1-phenylethyl)carbamate | Prepared from 152h-6 and Cap-4 | $t_R$ = 1.44 min condition 2, 90%) LRMS: Anal. Calcd. for $C_{41}H_{41}N_9O_6$ 755.32; found: 756.35 (M + H)$^+$. HRMS: Anal. Calcd. for $C_{41}H_{42}N_9O_6$ 756.3258 found: 756.3239 (M + H)$^+$. |

| Example | Compound Name | Structure | Data |
|---|---|---|---|
| Example 152j-24 | (2R)-2-(dimethylamino)-N-((1S)-1-(5-(6-(4-(2-((1S)-1-(((2R)-2-(dimethyl-amino)-2-phenylacetyl)amino)-ethyl)-1H-imidazol-5-yl)phenyl)-3-pyridinyl)-1H-imidazol-2-yl)-ethyl)-2-phenylacetamide | Prepared from 152h-6 and Cap 1 | $t_R$ = 1.18 min (condition 2, 91%) LRMS: Anal. Calcd. for $C_{41}H_{45}N_9O_2$ 695.37; found: 696.37 (M + H)$^+$. HRMS: Anal. Calcd. for $C_{41}H_{46}N_9O_2$ 696.3774 found: 696.3806 (M + H)$^+$. |
| Example 152j-25 | | Prepared from 152i-3 and Cap-4 | $t_R$ = 2.08 min (95.8%); Condition 1 LRMS: Anal. Calcd. for $C_{38}H_{44}N_9O_5$ 706.35; found: 706.53 (M + H)$^+$. HRMS: Anal. Calcd. for $C_{38}H_{44}N_9O_5$ 706.3465; found: 706.3492 (M + H)$^+$. |
| Example 152j-26 | | Prepared from 152i-2 and Cap-4 | $t_R$ = 2.04 min (96.4%); Condition 1 LRMS: Anal. Calcd. for $C_{37}H_{42}N_9O_5$ 692.33; found: 692.49 (M + H)$^+$. HRMS: Anal. Calcd. for $C_{37}H_{42}N_9O_5$ 692.3309; found: 692.3322 (M + H)$^+$. |
| Example 152j-27 | | Prepared from 152i-1 and Cap-4 | $t_R$ = 2.04 min (>95%); Condition 1 LRMS: Anal. Calcd. for $C_{39}H_{44}N_9O_5$ 718.35; found: 718.49 (M + H)$^+$. HRMS: Anal. Calcd. for $C_{39}H_{44}N_9O_5$ 718.3465; found: 718.3483 (M + H)$^+$. |

| Example | Compound Name | Structure | Data |
|---|---|---|---|
| Example 152j-28 | methyl ((1R)-2-((2S)-2-(5-(5-(4-(2-((1S)-1-(((2R)-2-((methoxycarbonyl)amino)-2-phenylacetyl)amino)-ethyl)-1H-imidazol-5-yl)phenyl)-2-pyazinyl)-1H-imidazol-2-yl)-1-pyrrolidinyl)-2-oxo-1-phenylethyl)carbamate | 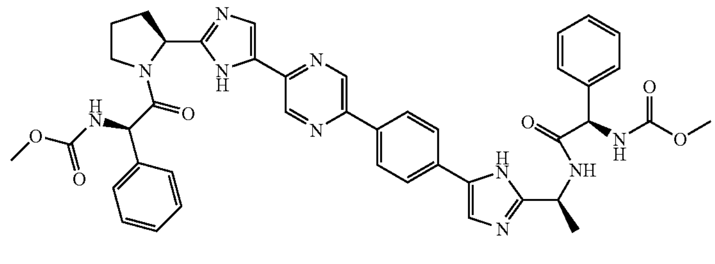 | $t_R$ = 2.00 min (>95%); Condition 1 LRMS: Anal. Calcd. for $C_{42}H_{43}N_{10}O_6$ 783.34 found: 783.96 (M + H)$^+$ HRMS: Anal. Calcd. for $C_{42}H_{43}N_{10}O_6$ 783.3367 found: 783.3375 (M + H)$^+$ |

Prepared from 152h-14 and Cap-4

Examples 152k-1 to 152k-

Example 152k-1 from 152j-27

{(R)-2-Oxo-1-phenyl-2-[(S)-2-(5-{4-[5-((S)-2-pyrrolidin-2-yl-3H-imidazol-4-yl)-pyrimidin-2-yl]-phenyl}-1H-imidazol-2-yl)-pyrrolidin-1-yl]-ethyl}-carbamic acid methyl ester

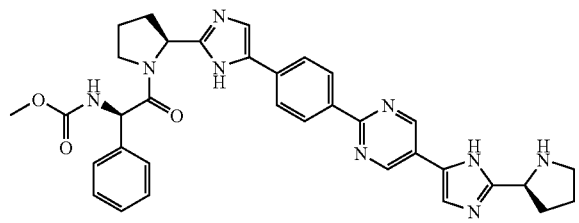

Cold (0° C.) 4 NHCl in dioxanes (4 mL) was added via syringe to (S)-2-{5-[2-(4-{2-[(S)-1-((R)-2-methoxycarbonylamino-2-phenyl-acetyl)-pyrrolidin-2-yl]-3H-imidazol-4-yl}-phenyl)-pyrimidin-5-yl]-1H-imidazol-2-yl}-pyrrolidine-1-carboxylic acid tert-butyl ester (104.6 mg, 0.146 mmol) in a 100 mL pear-shaped flask followed by MeOH (0.5 mL). The homogeneous mixture was stirred at room temperature for 15 min before a precipitate was observed. After stirring further for 1.75 h, the suspension was diluted with ether and hexanes. Suction-filtration of a small portion of the suspension yielded the title compound as a yellow solid which was used for characterization purposes. The balance of the suspension was concentrated down to dryness and placed under high vacuum for 16 h. There was isolated the rest of the title compound also as a yellow solid (137.7 mg, 123%) which was used without further purification.

$^1$H NMR (500 MHz, DMSO-$d_6$) δ 15.20 and 14.66 (2m, 1H), 10.29 (br s, 0.7H), 9.38-9.36 (m, 2H), 8.55-8.00 (series of m, 4H), 7.42-7.28 (2m, 3H), 5.53-4.00 (series of m, 7H), 3.99-3.13 (series of m, 4H), 3.57 and 3.52 (2s, 3H), 2.50-1.84 (series of m, 8H).

LCMS Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=1.79 min, >95% homogeneity index.

LRMS: Anal. Calcd. for $C_{34}H_{36}N_9O_3$ 618.29. found: 618.42 (M+H)$^+$.

HRMS: Anal. Calcd. for $C_{34}H_{36}N_9O_3$ 618.2921. found: 618.2958 (M+H)$^+$.

The same procedure was used to prepare Examples 152k-2 through 152k-3.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

| Example | Compound Name | Structure | Data |
|---|---|---|---|
| Example 152k-2 | | 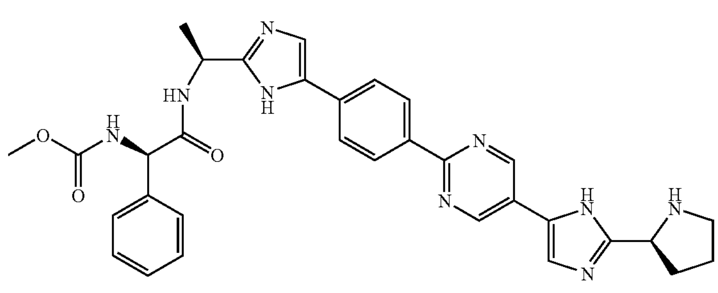 | $t_R$ = 1.74 min (>95%); Condition 1 LRMS: Anal. Calcd. for $C_{32}H_{34}N_9O_3$ 592.28; found: 592.41 (M + H)$^+$. HRMS: Anal. Calcd. for $C_{32}H_{34}N_9O_3$ 592.2785; found: 592.2775 (M + H)$^+$. |

Prepared from 152j-26

-continued

| Example | Compound Name | Structure | Data |
|---|---|---|---|
| Example 152k-3 | | 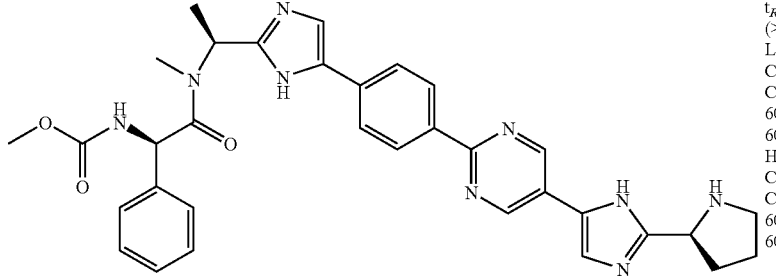<br>Prepared from 152j-25 | $t_R$ = 1.79 min (>95%); Condition 1<br>LRMS: Anal. Calcd. for $C_{33}H_{36}N_9O_3$ 606.29; found: 606.43 (M + H)$^+$.<br>HRMS: Anal. Calcd. for $C_{33}H_{36}N_9O_3$ 606.2941; found: 606.2925 (M + H)$^+$. |

Examples 152l-1 to 152l-

Examples 152l-1 through 152l-3 were isolated as TFA or AcOH salts prepared using the same procedure to convert Example 148e to 148.
LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 µL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 µL injection volume.

| Example | Compound Name | Structure | Data |
|---|---|---|---|
| Example 152l-1 | methyl ((1R)-2-(methyl((1S)-1-(4-(4-(5-(2-((2S)-1-((2R)-2-phenyl-2-(1-piperidinyl)acetyl)-2-pyrrolidinyl)-1H-imidazol-5-yl)-2-pyrimidinyl)phenyl-1H-imidazol-2-yl)ethyl)amino)-2-oxo-1-phenylethyl)carbamate | 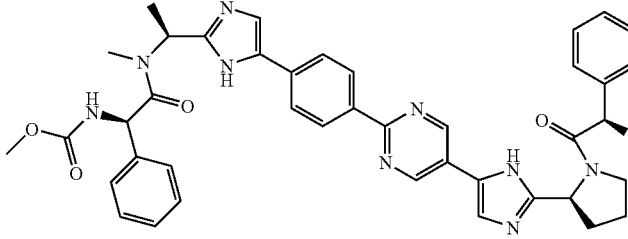<br>Prepared from 152k-3 and Cap-14 | $t_R$ = 1.87 min (>95%); Condition 1<br>LRMS: Anal. Calcd. for $C_{46}H_{51}N_{10}O_4$ 807.41 found: 807.57 (M + H)$^+$<br>HRMS: Anal. Calcd. for $C_{46}H_{51}N_{10}O_4$ 807.4095 found: 807.4128 (M + H)$^+$ |
| Example 152l-2 | methyl ((1R)-2-oxo-1-phenyl-2-(((1S)-1-(4-(4-(5-(2-((2S)-1-((2R)-2-phenyl-2-(1-piperidinyl)acetyl)-2-pyrrolidinyl)-1H-imidazol-5-yl)-2-pyrimidinyl)phenyl)-1H-imidazol-2-yl)ethyl)amino)ethyl)carbamate | 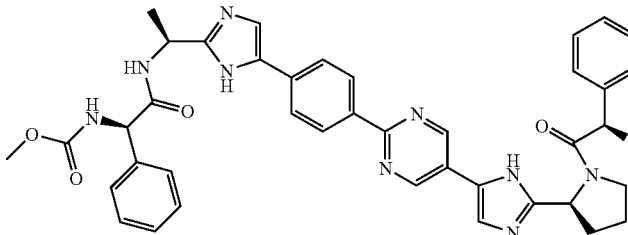<br>Prepared from 152k-2 and Cap-14 | $t_R$ = 1.83 min (>95%); Condition 1<br>LRMS: Anal. Calcd. for $C_{45}H_{49}N_{10}O_4$ 793.39 found: 793.52 (M + H)$^+$<br>HRMS: Anal. Calcd. for $C_{45}H_{49}N_{10}O_4$ 793.3938 found: 793.3934 (M + H)$^+$ |
| Example 152l-3 | methyl ((1R)-2-oxo-1-phenyl-2-((2S)-2-(4-(4-(5-(2-((2S)-1-((2R)-2-phenyl-2-(1-piperidinyl)acetyl)-2-pyrrolidinyl)-1H-imidazol-5-yl)-2-pyrimidinyl)phenyl)-1H-imidazol-2-yl)-1-pyrrolidinyl)ethyl)carbamate | 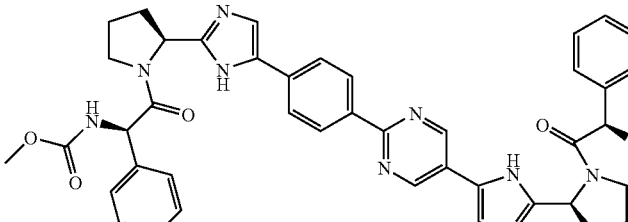<br>Prepared from 152k-1 and Cap-14 | $t_R$ = 1.87 min (>95%); Condition 1<br>LRMS: Anal. Calcd. for $C_{47}H_{51}N_{10}O_4$ 819.41 found: 819.50 (M + H)$^+$<br>HRMS: Anal. Calcd. for $C_{47}H_{51}N_{10}O_4$ 819.4095 found: 819.4127 (M + H)$^+$ |

Example 153a-1 from 153a-4

Example 153a-1 prepared from 152e-1

(S)-2-[5-{5'-[2-((S)-1-tert-Butoxycarbonyl-pyrrolidin-2-yl)-3-(2-trimethylsilanyl-ethoxymethyl)-3H-imidazol-4-yl]-[2,2']bipyrimidinyl-5-yl}-1-(2-trimethylsilanyl-ethoxymethyl)-1H-imidazol-2-yl]-pyrrolidine-1-carboxylic acid tert-butyl ester

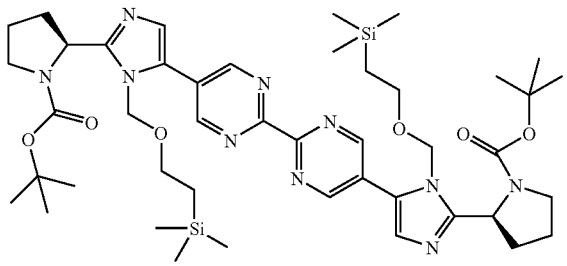

To a stirred solution of (S)-tert-butyl 2-(5-(2-chloropyrimidin-5-yl)-1-((2-(trimethylsilyl)ethoxy)methyl)-1H-imidazol-2-yl)pyrrolidine-1-carboxylate (1.0 g, 2.08 mmol) and dichlorobis(benzonitrile) palladium (40 mg, 0.104 mmol) in dry DMF (10 mL) at room temperature under argon was added neat tetrakis(dimethylamino)ethylene (1.0 mL, 4.16 mmol). The mixture was heated to 60° C. for 15 h before it was diluted with ethyl acetate and suction-filtered through diatomaceous earth (Celite®). The filtrate was washed with sat'd NaHCO$_3$ soln and brine prior to drying over Na$_2$SO$_4$ and solvent evaporation. Purification of the residue by Biotage™ flash chromatography on silica gel (step gradient elution with 15% B to 15% B for 150 mL, 15% B to 75% B for 1500 mL, 75% B to 100% B for 1000 mL, 100% B to 100% B for 1000 mL where B=ethyl acetate and A=hexane followed by a second gradient elution with 10% B to 100% B for 700 mL where B=methanol and A=ethyl acetate) furnished the title compound as a caramel-colored, viscous oil (487.8 mg, 26% yield).

$^1$H NMR (500 MHz, DMSO-d$_6$) δ 9.27 (s, 4H), 8.09-8.06 (m, 2H), 5.73-5.66 and 5.50-5.44 (2m, 2H), 5.06-4.93 (m, 2H), 3.60-3.39 (2m, 8H), 2.32-2.08 (3m, 4H), 2.00-1.85 (m, 4H), 1.37 and 1.14 (2s, 18H), 0.95-0.84 (m, 4H), −0.01 (s, 18H).

LCMS Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=3.37 min, >95% homogeneity index.

LRMS: Anal. Calcd. for C$_{44}$H$_{69}$N$_{10}$O$_6$S$_{i2}$ 889.49. found: 889.57 (M+H)$^+$.

HRMS: Anal. Calcd. for C$_{44}$H$_{69}$N$_{10}$O$_6$S$_{i2}$ 889.4940. found: 889.4920 (M+H)$^+$.

The same procedure was used to prepare Examples 153a-2 through 153a-4.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 µL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 µL injection volume.

| Example | Compound Name | Structure | Data |
|---|---|---|---|
| Example 153a-2 | | Prepared from 152e-2 | $t_R$ = 3.37 min (89.6%); Condition 1<br>LRMS: Anal. Calcd. for C$_{44}$H$_{69}$N$_{10}$O$_6$Si$_2$ 889.49; found: 889.56 (M + H)$^+$.<br>HRMS: Anal. Calcd. for C$_{44}$H$_{69}$N$_{10}$O$_6$Si$_2$ 889.494; found: 889.4951 (M + H)$^+$. |
| Example 153a-3 | | Prepared from 152e-3 | $t_R$ = 3.37 min (95%); Condition 1<br>LRMS: Anal. Calcd. for C$_{44}$H$_{69}$N$_{10}$O$_6$Si$_2$ 889.49; found: 889.51 (M + H)$^+$.<br>HRMS: Anal. Calcd. for C$_{44}$H$_{69}$N$_{10}$O$_6$Si$_2$ 889.4940; found: 889.4915 (M + H)$^+$. |

-continued

| Example | Compound Name | Structure | Data |
|---|---|---|---|
| Example 153a-4 | | 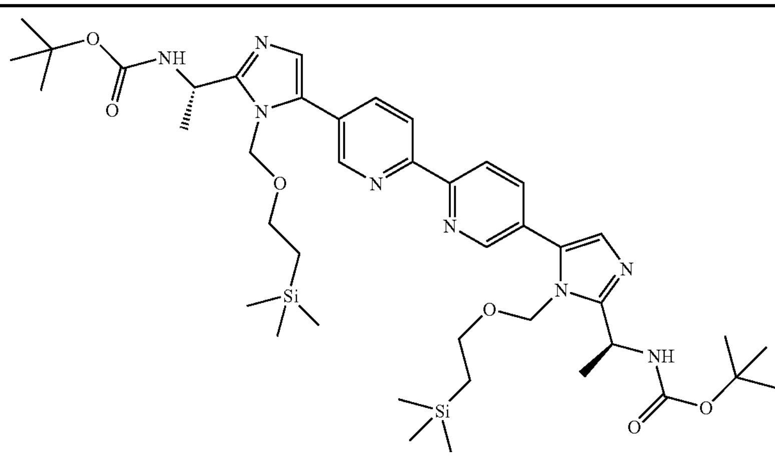 | $t_R$ = 2.3 min (condition 2) LRMS: Anal. Calcd. for $C_{42}H_{66}N_8Si_2$ 834; found: 835 $(M + H)^+$. |

Prepared from 152e-4

Example 153b-1-153b-3

The hydrolysis reactions was performed as above for Example 152h.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 µL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 µL injection volume.

| Example | Compound Name | Structure | Data |
|---|---|---|---|
| Example 153b-1 | | 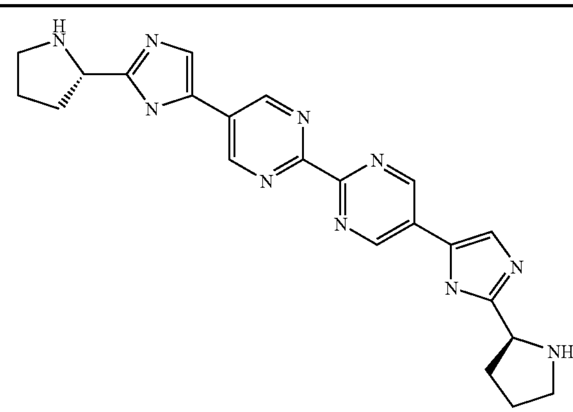 | $t_R$ = 1.18 min (>95%); Condition 1 LRMS: Anal. Calcd. for $C_{22}H_{25}N_{10}$ 429.23; found: 429.01 $(M + H)^+$. HRMS: Anal. Calcd. for $C_{22}H_{25}N_{10}$ 429.2264; found: 429.2259 $(M + H)^+$. |
| | | Prepared from 153a-1 | |
| Example 153b-2 | | 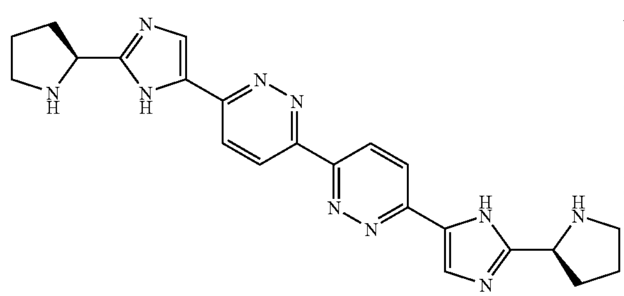 | $t_R$ = 1.26 min (>95%); Condition 1 LRMS: Anal. Calcd. for $C_{41}H_{41}N_{10}O_2$ 737.33 found: 737.49 $(M + H)^+$ HRMS: Anal. Calcd. for $C_{41}H_{41}N_{10}O_4$ 737.3312 found: 737.3342 $(M + H)^+$ |
| | | Prepared from 153a-2 | |

-continued

| Example | Compound Name | Structure | Data |
|---|---|---|---|
| Example 153b-3 | | Prepared from 153a-3 | $t_R$ = 1.40 min (>95%); Condition 1 LRMS: Anal. Calcd. for $C_{22}H_{25}N_{10}$ 429.23; found: 429.20 $(M + H)^+$. HRMS: Anal. Calcd. for $C_{22}H_{25}N_{10}$: 429.2264; Found: 429.2254 $(M + H)^+$ |
| Example 153b-4 | | Prepared from 153a-4 | $t_R$ = 0.85 min (condition 1) LCMS: Anal. Calcd. for $C_{20}H_{22}N_8$ 374; found 375 $(M + H)^+$. |

Examples 153c-1 to 153c-7

Examples 153c-1 through 153c-7 were isolated as TFA or AcOH salts using the procedure used to convert Example 148e to 148.

LC conditions: Condition 1: Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, 220 nm, 5 μL injection volume.

Condition 2: Phenomenex LUNA C-18 4.6×50 mm, 0 to 100% B over 2 minutes, 1 minute hold time, A=90% water, 10% methanol, 0.1% TFA, B=10% water, 90% methanol, 0.1% TFA, 220 nm, 5 μL injection volume.

| Example | Compound Name | Structure | Data |
|---|---|---|---|
| Example 153c-1 | (1R,1'R)-2,2'-(3,3'-bipyridazine-6,6'-diylbis(1H-imidazole-5,2-diyl(2S)-2,1-pyrrolidinediyl))bis(N,N-dimethyl-2-oxo-1-phenylethanamine) | Prepared from 153b-2 and Cap-1 | $t_R$ = 1.55 min (>95%); Condition 1 LRMS: Anal. Calcd. for $C_{42}H_{47}N_{12}O_2$ 751.39 found: 751.64 $(M + H)^+$ HRMS: Anal. Calcd. for $C_{42}H_{47}N_{12}O_2$ 751.3945 found: 751.3936 $(M + H)^+$ |

| Example | Compound Name | Structure | Data |
|---|---|---|---|
| Example 153c-2 | dimethyl (3,3'-bipyridazine-6,6'-diylbis(1H-imidazole-5,2-diyl(2S)-2,1-pyrrolidinediyl((1R)-2-oxo-1-phenyl-2,1-ethanediyl))) biscarbamate | Prepared from 153b-2 and Cap-4 | $t_R$ = 1.95 min (>95%); Condition 1 LRMS: Anal. Calcd. for $C_{42}H_{43}N_{12}O_6$ 811.34 found: 811.22 $(M + H)^+$ HRMS: Anal. Calcd. for $C_{42}H_{43}N_{12}O_6$ 811.3429 found: 811.3406 $(M + H)^+$ |
| Example 153c-3 | (1R,1'R)-2,2'-(2,2'-bipyrimidine-5,5'-diylbis(1H-imidazole-5,2-diyl(2S)-2,1-pyrrolidinediyl))bis(N,N-dimethyl-2-oxo-1-phenylethanamine) | Prepared from 153b-1 and Cap-1 | $t_R$ = 1.51 min (>90%*); Condition 1 LRMS: Anal. Calcd. for $C_{42}H_{47}N_{12}O_2$ 751.39 found: 751.21 $(M + H)^+$ HRMS: Anal. Calcd. for $C_{42}H_{47}N_{12}O_2$ 751.3945 found: 751.3921 $(M + H)^+$ |
| Example 153c-4 | dimethyl (2,2'-bipyrimidine-5,5'-diylbis(1H-imidazole-5,2-diyl(2S)-2,1-pyrrolidinediyl((1R)-2-oxo-1-phenyl-2,1-ethanediyl))) biscarbamate | Prepared from 153b-1 and Cap-4 | $t_R$ = 1.88 min (>95%); Condition 1 LRMS: Anal. Calcd. for $C_{42}H_{43}N_{12}O_6$ 811.34 found: 811.10 $(M + H)^+$ HRMS: Anal. Calcd. for $C_{42}H_{43}N_{12}O_6$ 811.3429 found: 811.3401 $(M + H)^+$ |
| Example 153c-5 | (1R,1'R)-2,2'-(2,2'-bipyrazine-5,5'-diylbis(1H-imidazole-5,2-diyl(2S)-2,1-pyrrolidinediyl))bis(N,N-dimethyl-2-oxo-1-phenyl-ethanamine) | Prepared from 153b-3 and Cap-1 | $t_R$ = 1.61 min (>95%); Condition 1 LRMS: Anal. Calcd. for $C_{42}H_{47}N_{12}O_2$ 751.39 found: 751.30 $(M + H)^+$ HRMS: Anal. Calcd. for $C_{42}H_{47}N_{12}O_2$ 751.3945 found: 751.3943 $(M + H)^+$ |

| Example | Compound Name | Structure | Data |
|---|---|---|---|
| Example 153c-6 | dimethyl (2,2'-bipyrazine-5,5'-diylbis(1H-imidazole-5,2-diyl(2S)-2,1-pyrrolidinediyl((1R)-2-oxo-1-phenyl-2,1-ethanediyl))) biscarbamate | 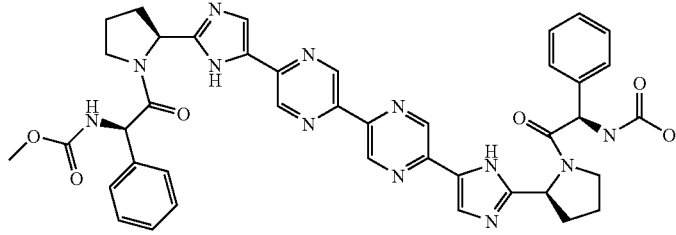<br>Prepared from 153b-3 and Cap-4 | $t_R$ = 2.00 min (>95%); Condition 1<br>LRMS: Anal. Calcd. for $C_{42}H_{43}N_{12}O_6$ 811.34 found: 811.23 $(M + H)^+$<br>HRMS: Anal. Calcd. for $C_{42}H_{43}N_{12}O_6$ 811.3429 found: 811.3407 $(M + H)^+$ |
| Example 153c-7 | dimethyl (2,2'-bipyridine-5,5'-diylbis(1H-imidazole-5,2-diyl(1S)-1,1-ethanediylimino((1R)-2-oxo-1-phenyl-2,1-ethanediyl))) biscarbamate | 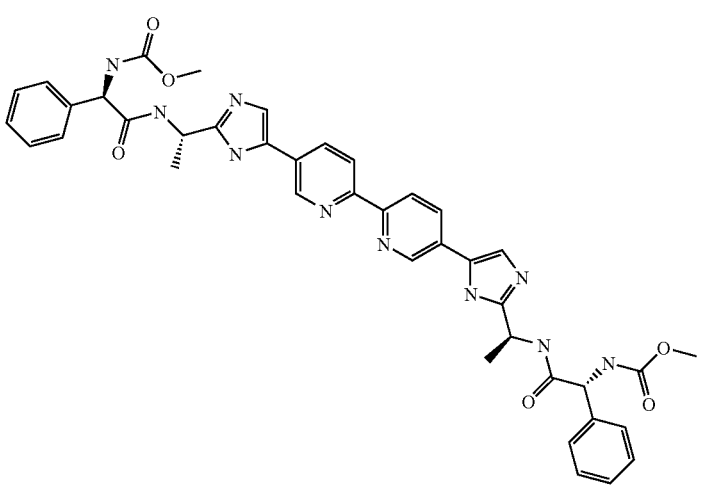<br>Prepared from 153b-4 and Cap-4 | $t_R$ = 1.42 min (condition 2, 94%)<br>LRMS: Anal. Calcd. for $C_{40}H_{40}N_{10}O_6$ 756.31; found: 757.34 $(M + H)^+$.<br>HRMS: Anal. Calcd. for $C_{40}H_{40}N_{10}O_6$ 757.3211 found: 757.3180 $(M + H)^+$. |

Section LS LC Conditions:

Condition 1: Solvent A: 10% methanol/90% water/0.1% TFA; Solvent B: 90% methanol/10% water/0.1% TFA; Column: Phenomenex-Luna 3.0×5.0 mm S10; Wavelength: 220 nM; Flow rate: 4 mL/min; 0% B to 100% B over 4 min with a 1 min hold time Condition 2: Solvent A: 10% methanol/90% water/0.1% TFA; Solvent B: 90% methanol/10% water/0.1% TFA; Column: Phenomenex 10u C18 3.0×5.0 mm; Wavelength: 220 nM; Flow rate: 4 mL/min; 0% B to 100% B over 4 min with a 1 min hold time Condition 3: Solvent A: 5% acetonitrile/95% water/10 mmol ammonium acetate; Solvent B: 95% acetonitrile/5% water/10 mmol ammonium acetate; Column: Phenomenex 10u C18 4.6×5.0 mm; Wavelength: 220 nM; Flow rate: 4 mL/min; 0% B to 100% B over 4 min with a 1 min hold time Condition 4: Solvent A: 5% acetonitrile/95% water/10 mmol ammonium acetate; Solvent B: 95% acetonitrile/5% water/10 mmol ammonium acetate; Column: Luna 4.6×50 mm S10; Wavelength: 220 nM; Flow rate: 4 mL/min; 0% B to 100% B over 3 min with a 1 min hold time Condition 5: Solvent A: 10% methanol/90% water/0.1% TFA; Solvent B: 90% methanol/10% water/0.1% TFA; Column: Phenomenex 10u C18 3.0×5.0 mm; Wavelength: 220 nM; Flow rate: 4 mL/min; 0% B to 100% B over 3 min with a 1 min hold time Condition 6: Solvent A: 5% acetonitrile/95% water/10 mmol ammonium acetate; Solvent B: 95% acetonitrile/5% water/10 mmol ammonium acetate; Column: Phenomenex-Luna 3.0×50 mm S10; Wavelength: 220 nM; Flow rate: 4 mL/min; 0% B to 100% B over 8 min with a 2 min hold time Condition 7: Solvent A: 10% methanol/90% water/0.1% TFA; Solvent B: 90% methanol/10% water/0.1% TFA; Column: Phenomenex-Luna 3.0×5.0 mm S10; Wavelength: 220 nM; Flow rate: 4 mL/min; 0% B to 100% B over 3 min with a 1 min hold time Condition 8: Solvent A: 10% methanol/90% water/0.2% $H_3PO_4$; Solvent B: 90% methanol/10% water/0.2% $H_3PO_4$; Column: YMC ODS-A 4.6×50 mm S5; Wavelength: 220 nM; Flow rate: 4 mL/min; 0% B to 100% B over 4 min with a 1 min hold time Condition 9: Solvent A: 10% methanol/90% water/0.2% $H_3PO_4$; Solvent B: 90% methanol/10% water/0.2% $H_3PO_4$; Column: YMC ODS-A 4.6×50 mm S5; Wavelength: 220 nM; Flow rate: 2.5 mL/min; 0% B to 50% B over 8 min with a 3 min hold time Condition 10: Xbridge C18, 150×4.6 mm I.D. S-3.5 um; Mobile Phase A: 95% Water-5% Acetonitrile with 10 mM ammonium acetate (pH=5); Mobile phase B: 95% Acetonitrile-5% Water with 10 mM ammonium acetate (pH=5); Isocratic 30% B for 20 min; Flow rate: 1 mL/min; UV detection: 220 nm Condition 11: Solvent A: 10% methanol/90% water/0.1% TFA; Solvent B: 90% methanol/10% water/0.1% TFA; Column: Phenomenex 10u C18 3.0×5.0 mm; Wavelength: 220 nM; Flow rate: 4 mL/min; 30% B to 100% B over 4 min with a 1 min hold time Condition 12: Solvent A: 10% methanol/90% water/0.1% TFA; Solvent B: 90% methanol/10% water/0.1% TFA; Column: Phenomenex 10u C18 3.0×5.0 mm; Wavelength: 220 nM; Flow rate: 4 mL/min; 20% B to 100% B over 4 min with a 1 min hold time Condition 13: Solvent A: 10% methanol/90% water/0.2% $H_3PO_4$; Solvent B: 90% methanol/10% water/0.2% $H_3PO_4$; Column: YMC ODS-A 4.6×50 mm S5; Wavelength: 220 nM; Flow rate: 2.5 mL/min; 0% B to 100% B over 8 min with a 3 min hold time Section LS Preparative HPLC Conditions:

Condition 1: Solvent A: 10% methanol/90% water/0.1% TFA; Solvent B: 90% methanol/10% water/0.1% TFA; Column: Phenomenex-Luna 30×100 mm S10; Wavelength: 220 nM; Flow rate: 30 mL/min; 0% B to 100% B over 10 min with a 2 min hold time Condition 2: Solvent A: 10% methanol/90% water/0.1% TFA; Solvent B: 90% methanol/10% water/0.1% TFA; Column: Xterra Prep MS C18 30×50 mm 5u; Wavelength: 220 nM; Flow rate: 30 mL/min; 0% B to 100% B over 8 min with a 3 min hold time Condition 3: Solvent A: 10% methanol/90% water/0.1% TFA; Solvent B: 90% methanol/10% water/0.1% TFA; Column: Xterra Prep MS C18 30×50 mm 5u; Wavelength: 220 nM; Flow rate: 25 mL/min; 10% B to 100% B over 8 min with a 2 min hold time Condition 4: Solvent A: 10% methanol/90% water/0.1% TFA; Solvent B: 90% methanol/10% water/0.1% TFA; Column: Xterra 19×100 mm S5; Wavelength: 220 nM; Flow rate: 20 mL/min; 30% B to 100% B over 5 min with a 3 min hold time Condition 5: Solvent A: 10% methanol/90% water/0.1% TFA; Solvent B: 90% methanol/10% water/0.1% TFA; Column: Phenomenex-Luna 30×100 mm S10; Wavelength: 220 nM; Flow rate: 30 mL/min; 10% B to 100% B over 8 min with a 2 min hold time Condition 6: Solvent A: 10% Acetonitrile/90% water/0.1% TFA; Solvent B: 90% Acetonitrile/10% water/0.1% TFA; Column: Phenomenex-Luna 21×100 mm S10; Wavelength: 220 nM; Flow rate: 25 mL/min; 0% B to 60% B over 10 min with a 5 min hold time Experimentals:

Compound LS2

(1S,1'S)-2,2'-(4,4'-biphenyldiylbis(1H-imidazole-5,2-diyl(2S)-2,1-pyrrolidinediyl))bis(1-cyclohexyl-2-oxoethanol)

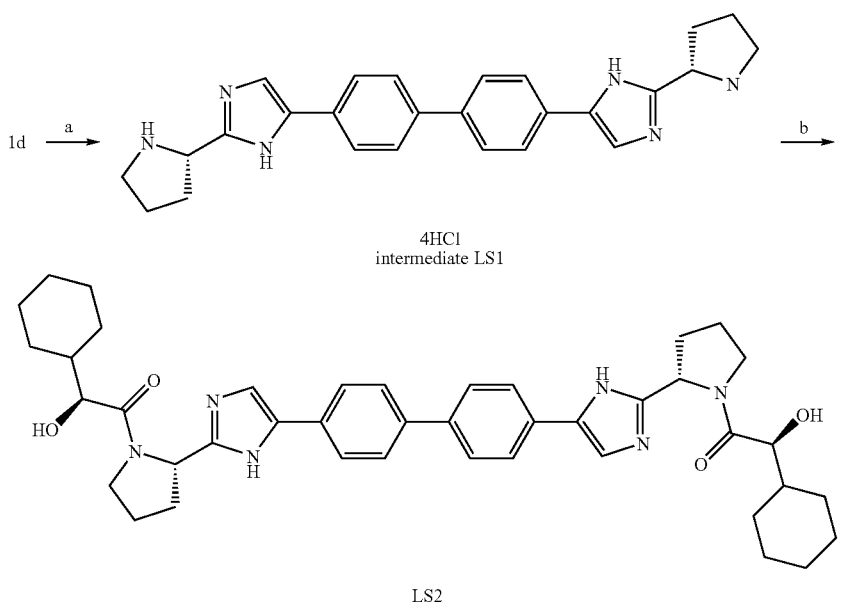

Step a: To 1d (1.4 g; 2.24 mmol) was added 30 mL 4N HCl in dioxane. After 3 h, 60 mL ether was added and the precipitate was filtered and dried under high vacuum providing 1.02 g (80%) intermediate LS1 as a pale yellow powder. $^1$H NMR (DMSO-$d_6$, δ=2.5 ppm, 500 MHz): δ 10.41 (s, 2H), 9.98 (s, 2H), 8.22 (s, 2H), 8.06 (d, J=8.54 Hz, 4H), 7.92 (d, J=8.55 Hz, 4H), 5.07 (s, 2H), 3.43-3.54 (m, 2H), 3.33-3.43 (m, 2H), 2.43-2.59 (m, 4H), 2.16-2.28 (m, 2H), 1.94-2.09 (m, 2H). LC (Cond. 1): RT=1.28 min; MS: Anal. Calcd. for [M+H]$^+$ $C_{26}H_{28}N_6$: 425.24. found 425.56.

Step b: To intermediate LS1 (200 mg; 0.35 mmol) in 2 mL DMF was added DIPEA (0.30 mL; 1.75 mmol), (S)-2-cyclohexyl-2-hydroxyacetic acid (61 mg; 0.39 mmol), followed by HATU (147 mg; 0.38 mmol). After stirring at ambient temperature for 18 h, the reaction mixture was split into two portions and purified via preparative HPLC (Cond'n 1). Fractions containing desired product were pooled and passed through an MCX cartridge (Oasis; 6 g; preconditioned with two column lengths of methanol). The cartridge was washed with two column lengths of methanol and product was eluted with ammonia/methanol. Concentration provided 65 mg of LS2 (26%) as a colorless powder. $^1$H NMR (500 MHz, DMSO-$d_6$) δ ppm 0.87-1.30 (m, 12H) 1.38-1.53 (m, J=24.72, 11.90 Hz, 4H) 1.54-1.75 (m, 8H) 1.95-2.21 (m, 6H) 3.72-3.86 (m, 6H) 5.13 (t, J=6.56 Hz, 2H) 7.87 (d, J=7.93 Hz, 4H) 7.96

(d, J=6.41 Hz, 4H) 8.13 (s, 2H) (imidazole NH and hydroxyl protons unaccounted for). LC (Cond'n 2): RT=3.07 min; MS: Anal. Calcd. for [M+H]$^+$ C$_{42}$H$_{52}$N$_6$O$_4$: 705.9. found 705.6.

The following analogs were prepared in similar fashion to the preparation of LS2 from intermediate LS1 employing the appropriate carboxylic acid:

| Example Number | Compound Name | Structure | Analytical Data |
|---|---|---|---|
| LS3 | (2S,2'S)-1,1'-(4,4'-biphenyldiylbis(1H-imidazole-5,2-diyl(2S)-2,1-pyrrolidinediyl))bis(4-methyl-1-oxo-2-pentanol) | 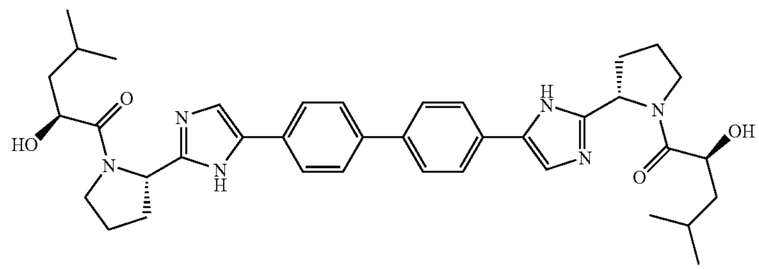 | LC/MS: 2.02 min (Cond'n 1); Anal. Calcd. for [M + H]$^+$ C$_{38}$H$_{48}$N$_6$O$_4$: 653.4; found 653.2. |
| LS4 | (2S,2'S)-1,1'-(4,4'-biphenyldiylbis(1H-imidazole-5,2-diyl(2S)-2,1-pyrrolidinediyl))bis(3-methyl-1-oxo-2-butanol) | 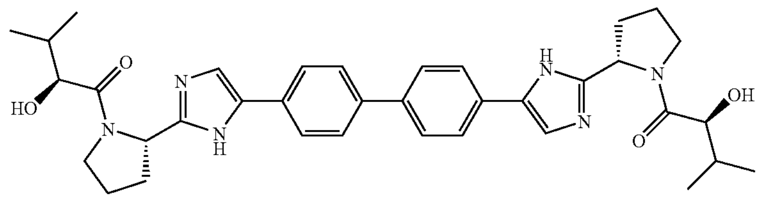 | LC/MS: 1.99 min (Cond'n 3); Anal. Calcd. for [M + H]$^+$ C$_{36}$H$_{44}$N$_6$O$_4$: 625.3; found 625.3. |
| LS16 | 3-buten-1-yl((1S)-1-(((2S)-2-(5-(4'-(2-((2S)-1-((2S)-2-(((3-buten-1-yloxy)carbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate | from intermediate LS1 and (S)-2-((but-3-enyloxy)carbonylamino)-3-methylbutanoic which was prepared from L-valine and butenylchloroformate in similar fashion to the preparation of Cap-51 | $^1$H NMR (500 MHz, CH$_3$OD) δ ppm 0.81-1.10 (m, 12 H) 1.90-2.15 (m, 4 H) 2.15-2.51 (m, 8 H) 3.82-3.96 (m, 2 H) 3.97-4.05 (m, 2 H) 4.05-4.19 (m, 4 H) 4.25 (d, J = 7.02 Hz, 2 H) 4.62 (s, 2 H) 5.00-5.17 (m, 4 H) 5.20 (t, J = 5.65 Hz, 2 H) 5.79-5.93 (m, 2 H) 7.20-7.47 (m, 2 H) 7.59-7.90 (m, 8 H) |

Example LS6

(2S,2'S)-1,1'-(4,4'-biphenyldiylbis(1H-imidazole-5,2-diyl(2S)-2,1-pyrrolidinediyl))bis(N-methyl-1-oxo-2-propanamine)

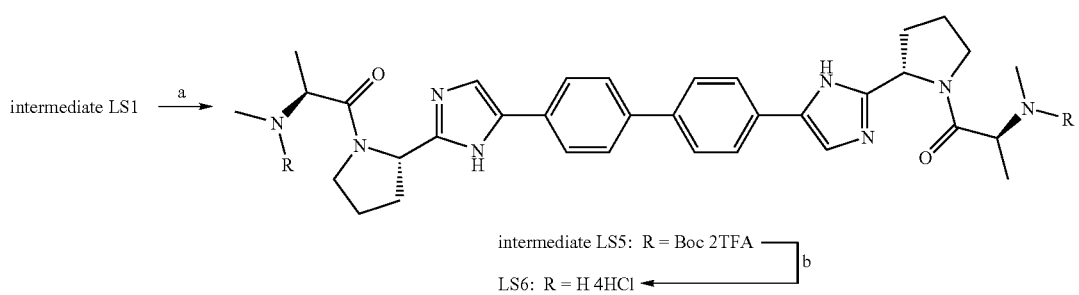

intermediate LS5: R = Boc 2TFA
LS6: R = H 4HCl

Step a: To intermediate LS1 (64 mg; 0.11 mmol) in 1 mL DMF was added (S)-2-(tert-butoxycarbonyl(methyl)amino)propanoic acid (48 mg; 0.24 mmol), Hunig's base (0.12 mL; 0.67 mmol) and HATU (90 mg; 0.24 mmol). After 3 h, the reaction was purified via preparative HPLC (Cond'n 2). Fractions containing intermediate LS5 were pooled and concentrated providing intermediate LS5 as a colorless powder (43 mg; 48%) after drying under high vacuum. LC (Cond'n 4): RT=2.12 min; MS: Anal. Calcd. for $[M+H]^+$ $C_{44}H_{58}N_8O_6$: 795.4. found 795.5.

Step b: Intermediate LS5 was allowed to stir in 2 mL HCl/Dioxane (4N) for 18 h at which time 10 mL ether was added and the resultant precipitate was filtered and dried under high vacuum providing LS6 (45 mg; 155%) as a colorless solid. $^1$H NMR (500 MHz, DMSO-$d_6$) δ ppm 2.00-2.11 (m, 2H) 2.12-2.27 (m, 4H) 2.38-2.47 (m, 2H) 2.39-2.48 (m, 2H) 2.58 (t, J=5.19 Hz, 2H) 3.78-3.85 (m, 2H) 3.91-4.02 (m, 2H) 4.21-4.32 (m, 2H) 5.26 (t, J=7.17 Hz, 2H) 7.93 (d, J=7.32 Hz, 4H) 8.02 (d, J=7.94 Hz, 4H) 8.12-8.21 (m, 2H) 8.69-8.81 (m, 2H) 9.09-9.17 (m, 2H); N-Me protons obscured by DMSO peak with 2 other protons unaccounted for. LC (Cond'n 5): RT=1.71 min; MS: Anal. Calcd. for $[M+H]^+$ $C_{34}H_{42}N_8O_2$: 595.3. found 595.6.

Example LS11

(4S,4'S)-4,4'-(4,4'-biphenyldiylbis(1H-imidazole-5,2-diyl(2S)-2,1-pyrrolidinediylcarbonyl))bis(1,3-oxazinan-2-one)

Step a: To intermediate LS1 (65 mg; 0.11 mmol) in 1 mL DMF was added HATU (91 mg; 0.24 mmol), (S)-2-oxo-1,3-oxazinane-4-carboxylic acid (intermediate LS10; mg; 0.24 mmol), followed by DIPEA (0.12 mL; 0.68 mmol. After 3 h, the reaction mixture was twice purified via preparative HPLC (Cond'n 3). Appropriate fractions were pooled and concentrated under high vacuum providing 8 mg (10%) bis TFA LS11 as a colorless oil. $^1$H NMR (500 MHz, CH$_3$OD) δ ppm $^1$H NMR (500 MHz, CH$_3$OD) δ ppm 1.99-2.43 (m, 10H) 2.48-2.66 (m, 1.98 Hz, 2H) 3.82-3.95 (m, 4H) 4.17-4.40 (m, 4H) 4.57 (t, J=5.80 Hz, 2H) 5.23-5.41 (m, 2H) 7.73-7.97 (m, 10H); imidazole and carbamate NH protons are unaccounted for. LC (Cond'n 6): RT=2.28 min; MS: Anal. Calcd. for $[M+H]^+$ $C_{34}H_{42}N_8O_2$: 679.3. found 679.4.

Step b: Performed as in Baldwin et al, *Tetrahedron* 1988, 44, 637

Step c: Performed as in Sakaitani and Ohfune, *J. Am. Chem. Soc.* 1990, 112, 1150 for the conversion of compound 1 to 5. Purification via Biotage (40M cartridge; 1:1 ether/ethyl acetate) then preparative HPLC (Cond'n 4) provided 77 mg (8%) intermediate LS9 as a viscous oil. $^1$H NMR (300 MHz, CDCl$_3$) δ ppm 2.02-2.21 (m, 1H) 2.23-2.41 (m, 1H) 4.11-4.38 (m, 3H) 5.11-5.31 (m, 2H) 6.15 (s, 1H) 7.27-7.46 (m, 5H). LC (Cond'n 7): RT=1.24 min; MS: Anal. Calcd. for $[M+H]^+$ $C_{34}H_{42}N_8O_2$: 236.1. found 236.4.

Step d: Intermediate LS9 was hydrogenated under 1 atm H$_2$ in 3 mL methanol with 10 mg Pd/C (10%) for 18 h. The reaction mixture was filtered through a pad of diatomaceous earth (Celite®) and concentrated to provide intermediate LS110 (40 mg; 83%) as a colorless powder. $^1$H NMR (500 MHz, CH$_3$OD) δ ppm 2.08-2.18 (m, 1H) 2.26-2.38 (m, 1H) 4.19 (t, J=5.95 Hz, 1H) 4.25-4.40 (m, 2H).

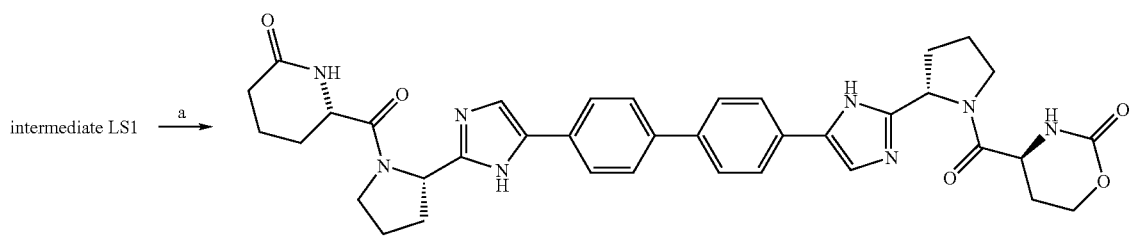

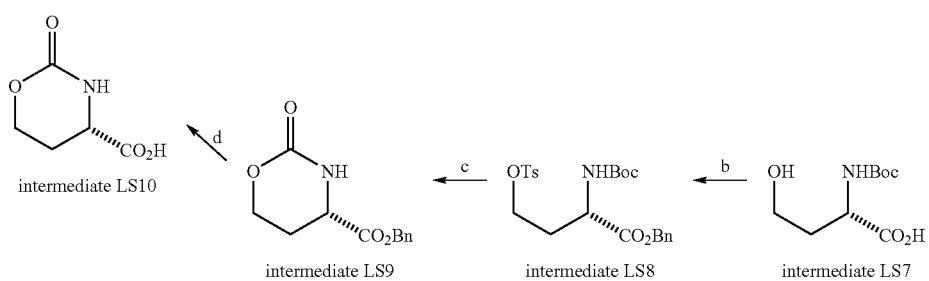

Example LS1-4 methyl ((1S)-2-((2S)-2-(5-(4'-(2-((2S)-1-((2R)-2-(diethylamino)-2-phenylacetyl)-2-oxo-1-(tetrahydro-2H-pyran-4-yl)ethyl)carbamate

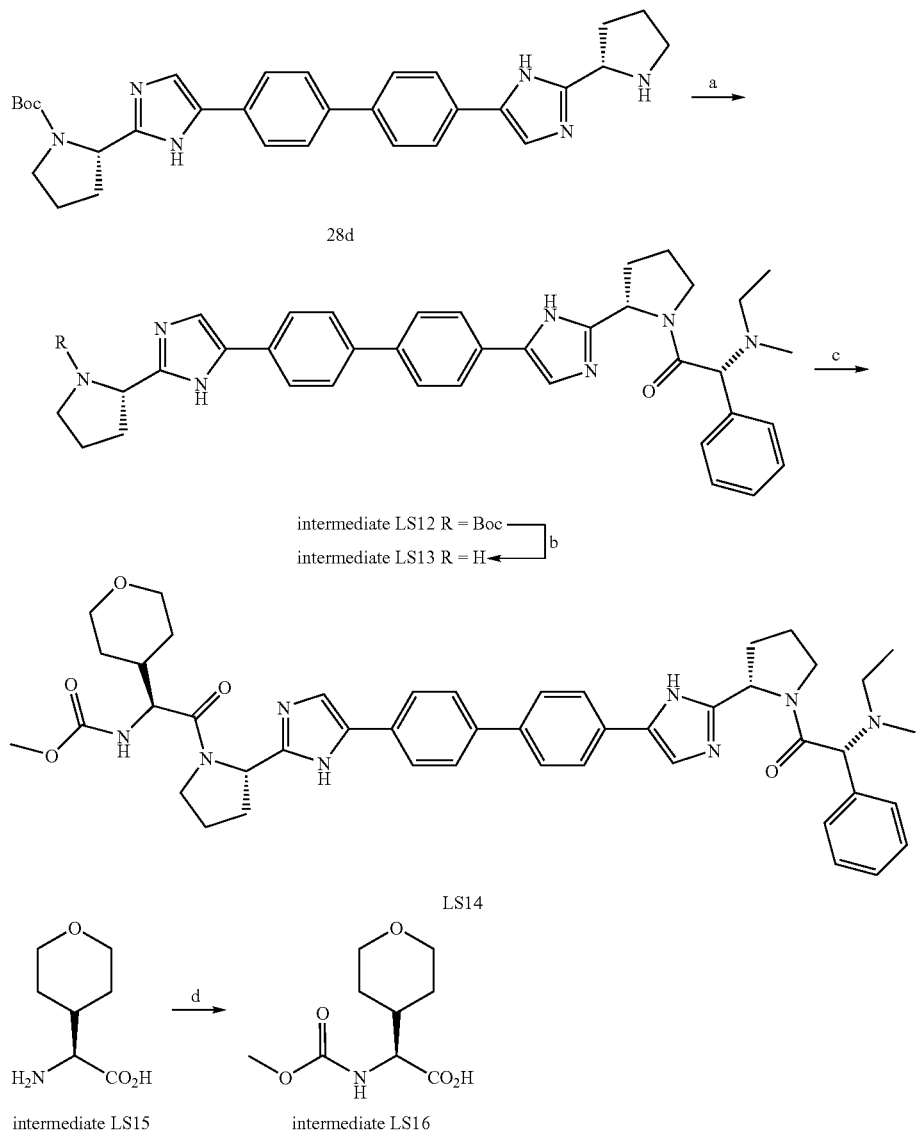

Step a: To 28 (1.5 g; 2.86 mmol) in 25 mL DMF was added sequentially Cap-2 (697 mg; 2.86 mmol), HATU (1.2 g; 3.14 mmol), and Hunig's base (1.5 mL; 8.57 mmol). After 3 h, the solution was concentrated to 10 mL and partitioned between chloroform and water. The organic layer was washed with brine, dried over magnesium sulfate, filtered, and concentrated in vacuo to an amber oil which was subjected to silica gel chromatography (Biotage; loaded on 40 samplet with dichloromethane; eluted on 40M cartridge with 0 to 12% dichloromethane/methanol over 1200 mL). Fractions containing intermediate LS12 were pooled and concentrated to provide material which contained residual DMF. This material was redissolved in dichloromethane and washed with water (3×50 mL) and then brine. The organic layer was dried over magnesium sulfate, filtered, and concentrated to 761 mg powder which was repurified via silica gel chromatography (Biotage; loaded on 40 samplet with dichloromethane; eluted on 40M cartridge with 0 to 80% 4:1 chloroform:methanol/ ethyl acetate over 1500 mL) to provide intermediate LS12 (501 mg; 25%) as a colorless powder. LC (Cond'n 8): RT=1.24 min.

Step b: To intermediate LS12 (490 mg; 0.69 mmol) was added 6 mL HCl/Dioxane followed by 25 mL dichloromethane. After 24 h, 75 mL ether was added, the reaction mixture was filtered and the precipitate was dried under vacuum providing intermediate LS13.4HCl (434 mg; quant) as a tan solid. $^1$H NMR (300 MHz, CH$_3$OD) δ ppm 1.16-1.29 (m, 3H) 1.37 (t, J=6.95 Hz, 3H) 1.89-2.06 (m, 6.95 Hz, 1H) 2.12-2.51 (m, 5H) 2.52-2.85 (m, 4H) 3.02-3.24 (m, 2H) 3.42-3.55 (m, 7.32 Hz, 1H) 3.58-3.71 (m, 2H) 4.26-4.41 (m, 1H) 5.18-5.37 (m, 2H) 5.65 (s, 1H) 7.57-7.66 (m, 3H) 7.67-7.75 (m, 1H) 7.86-8.04 (m, 10H) 8.14 (s, 1H). LC (Cond'n 8): RT=1.92 min.

Step c: To intermediate LS13.4HCl (75 mg; 0.099 mmol) in 0.7 mL DMF was added sequentially intermediate LS16

(26 mg; 0.118 mmol), HATU (45 mg; 0.118 mmol), and Hunig's base (0.10 mL; 0.591 mmol). After 2 h, the reaction mixture was filtered through diatomaceous earth (Celite®), the pad washed with 0.3 mL methanol and the resultant filtrate was purified via preparative HPLC (Cond'n 5) in two separate injections. The fractions containing desired product were passed through an MCX cartridge (Oasis; 1 g; preconditioned with two column lengths of methanol). The cartridge was washed with two column lengths of methanol and product was eluted with ammonia/methanol. Concentration provided 36 mg of LS14 as a colorless powder which was assayed to be of 82% diastereomeric purity (most likely epimeric at the stereogenic carbon in intermediate 16). Resubjected to preparative HPLC purification (2×) providing LS14 (13 mg; 16%) as a colorless solid. $^1$H NMR (500 MHz, CH$_3$OD) δ ppm 0.99 (q, J=6.92 Hz, 6H) 1.25-1.72 (m, 5H) 1.80-2.42 (m, 10H) 2.47-2.61 (m, 3H) 2.66-2.78 (m, 2H) 3.35-3.43 (m, 2H) 3.65-3.71 (m, 3H) 3.89-4.01 (m, 4H) 4.01-4.10 (m, 1H) 4.32 (d, J=8.24 Hz, 1H) 5.11-5.22 (m, 1H) 6.95-7.17 (m, 3H) 7.30-7.44 (m, 3H) 7.53 (d, J=7.02 Hz, 1H) 7.62-7.89 (m, 8H). LC (Cond'n 9): RT=5.31 min.

Step d: Intermediate LS16 was prepared in analogous fashion to the procedure describing the synthesis of Cap-51 substituting (S)-2-amino-2-(tetrahydro-2H-pyran-4-yl)acetic acid (available from Astatech) for L-Valine. $^1$H NMR (300 MHz, DMSO-d$_6$) δ ppm 1.15-1.63 (m, 5H) 1.75-2.03 (m, 1H) 3.54 (s, 3H) 3.76-3.98 (m, 4H) 7.45 (d, J=8.42 Hz, 1H); one proton obscured by water peak.

Example LS20 methyl ((1S)-2-methyl-1-(((2S)-2-(5-(4'-(2-((2S)-1-(N-methylglycyl)-2-pyrrolidinyl)-1H-imidazol-5-yl)-4-biphenylyl)-1H-imidazol-2-yl)-1-pyrrolidinyl)carbonyl)propyl)carbamate Step a & b: Intermediate LS18 was prepared in analogous fashion to the procedure describing the synthesis of intermediate LS13 substituting Cap-51 for Cap-2.

Step c: To intermediate LS18 (100 mg; 0.14 mmol) in 1.4 mL DMF was added sequentially N-Boc Sarcosine (30 mg; 0.16 mmol), Hunig's base (0.13 mL; 0.72 mmol) and HATU (60 mg; 0.16 mmol). After 2 h the reaction mixture was partitioned into dichloromethane, washed with NaHCO$_3$ (aq), brine, dried over magnesium sulfate, filtered and concentrated to crude intermediate LS19 which was used directly in the next step. LC (Cond'n 5): RT=2.42 min; MS: Anal. Calcd. for [M+H]$^+$ C$_{41}$H$_{52}$N$_8$O$_6$: 753.4. found 753.9.

Step d: Crude intermediate LS19 was dissolved in 0.5 mL methanol and 5 mL 4N HCl/Dioxane. After stirring for 1 h, the reaction was concentrated and purified via preparative HPLC (Cond'n 6) and the fractions containing desired product were passed through an MCX cartridge (Oasis; 1 g; preconditioned with two column lengths of methanol). The cartridge was washed with two column lengths of methanol and product was eluted with ammonia/methanol. Concentration provided LS20 (32 mg; 34%). $^1$H NMR (500 MHz, DMSO-d$_6$) δ ppm 0.74-0.98 (m, 6H) 1.79-2.24 (m, 9H) 2.29-2.38 (m, 2H) 3.19-3.51 (m, 8H) 3.50-3.56 (m, 3H) 3.59-3.71 (m, 1H) 3.81 (s, 1H) 3.97-4.17 (m, 1H) 5.01-5.16 (m, 2H) 7.30 (d, J=7.93 Hz, 1H) 7.51 (s, 1H) 7.59-7.74 (m, 4H) 7.79 (d, J=7.63 Hz, 4H) 11.78 (s, 1H). LC (Cond'n 5): RT=2.00 min; MS: Anal. Calcd. for [M+H]$^+$ C$_{36}$H$_{44}$N$_8$O$_4$: 653.4. found 653.7.

The following analogs were prepared in similar fashion to the preparation of LS20 from LS18 substituting the appropriate carboxylic acid for N-Boc Sarcosine:

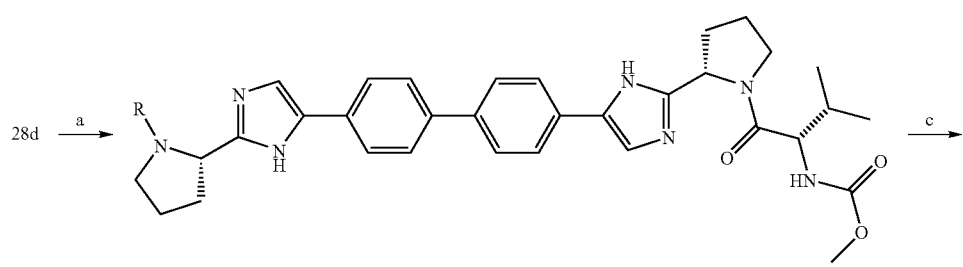

intermediate LS17 R = Boc
intermediate LS18 R = H

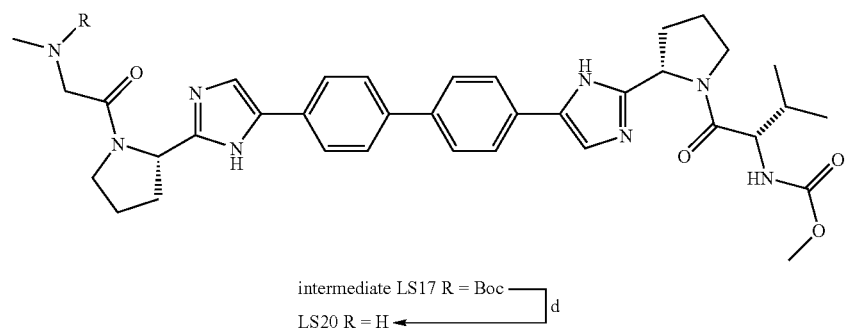

intermediate LS17 R = Boc
LS20 R = H

| Example Number | Compound Name | Structure | Analytical Data |
| --- | --- | --- | --- |
| LS21 | methyl ((1S)-1-(((2S)-2-(5-(4'-(2-((2S)-1-(N-ethylglycyl)-2-pyrrolidinyl)-1H-imidazol-5-yl)-4-biphenylyl)-1H-imidazol-2-yl)-1-pyrrolidinyl)carbonyl)-2-methylpropyl carbamate | 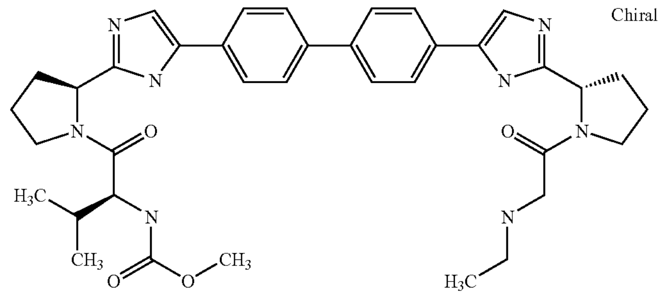 | LC/MS: 2.34 min (Cond'n 2); Anal. Calcd. for [M + H]$^+$ C$_{37}$H$_{46}$N$_8$O$_4$: 667.4; found 667.7. |
| LS22 | methyl ((1S)-1-(((2S)-2-(5-(4'-(2-((2S)-1-(N-benzylglycyl)-2-pyrrolidinyl)-1H-imidazol-5-yl)-4-biphenylyl)-1H-imidazol-2-yl)-1-pyrrolidinyl)carbonyl)-2-methylpropyl carbamate | 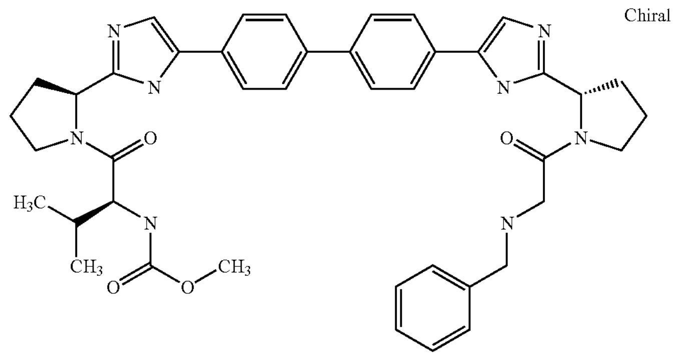 | LC/MS: 2.34 min (Cond'n 5); Anal. Calcd. for [M + H]$^+$ C$_{42}$H$_{48}$N$_8$O$_4$: 729.4; found 729.8. |
| LS23 | methyl ((1S)-1-(((2S)-2-(5-(4'-(2-((2S)-1-(N-isobutylglycyl)-2-pyrrolidinyl)-1H-imidazol-5-yl)-4-biphenylyl)-1H-imidazol-2-yl)-1-pyrrolidinyl)carbonyl)-2-methylpropyl carbamate | 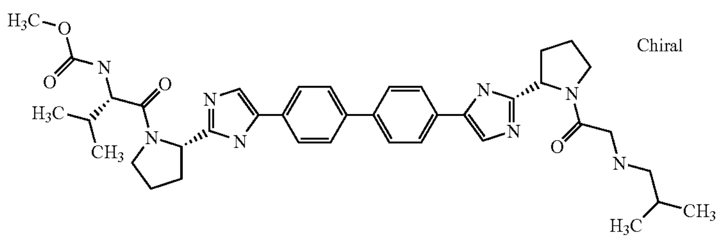 | LC/MS: 2.07 min (Cond'n 5); Anal. Calcd. for [M + H]$^+$ C$_{39}$H$_{50}$N$_8$O$_4$: 695.4; found 695.8. |
| LS24 | methyl ((1S)-1-(((2S)-2-(5-(4'-(2-((2S)-1-(N-sec-butylylglycyl)-2-pyrrolidinyl)-1H-imidazol-5-yl)-4-biphenylyl)-1H-imidazol-2-yl)-1-pyrrolidinyl)carbonyl)-2-methylpropyl carbamate | 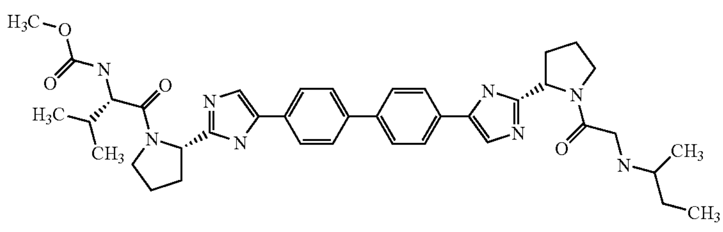 | LC/MS: 2.03 min (Cond'n 5); Anal. Calcd. for [M + H]$^+$ C$_{39}$H$_{50}$N$_8$O$_4$: 695.4; found 695.9. |
| LS25 | methyl ((1S)-1-(((2S)-2-(5-(4'-(2-((2S)-1-(N-isopropylglycyl)-2-pyrrolidinyl)-1H-imidazol-5-yl)-4-biphenylyl)-1H-imidazol-2-yl)-1-pyrrolidinyl)carbonyl)-2-methylpropyl carbamate | 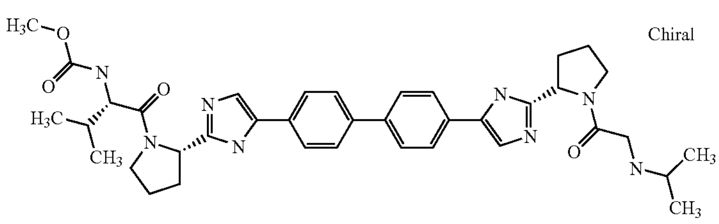 | LC/MS: 1.97 min (Cond'n 5); Anal. Calcd. for [M + H]$^+$ C$_{38}$H$_{48}$N$_8$O$_4$: 681.4; found 681.7. |

Example LS26 methyl ((1S)-1-(((2S)-2-(5-(4 (2-((2S)-1-(N,N-diisopropylglycyl)-2-pyrrolidinyl)-1H-imidazol-5-yl)-4-biphenylyl)-1H-imidazol-2-yl)-1-pyrrolidinyl)carbonyl)-2-methylpropyl)carbamate

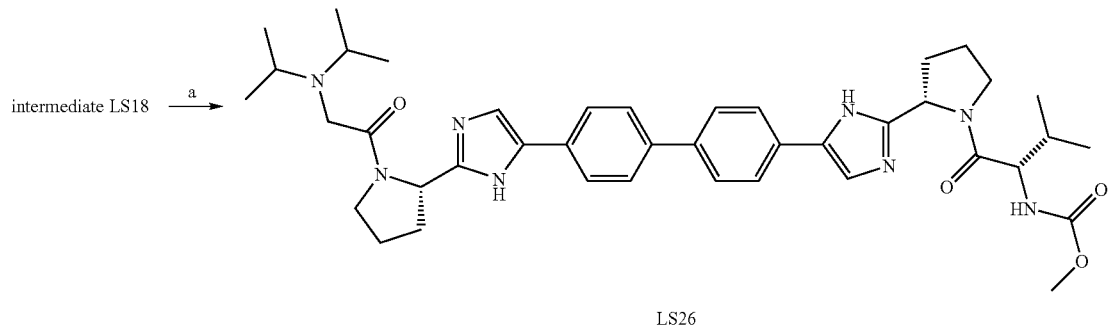

LS26

Step a: Compound LS26 was prepared in a similar fashion to the preparation of intermediate LS19 employing 2-(diisopropylamino)acetic acid as the carboxylic acid coupling partner. $^1$H NMR (500 MHz, DMSO-$d_6$) δ ppm 0.74-1.04 (m, 18H) 1.74-2.21 (m, 13H) 2.86-3.09 (m, 3H) 3.54 (s, 3H) 3.71-3.89 (m, 3H) 4.06 (t, J=8.55 Hz, 1H) 4.98-5.13 (m, 2H) 5.56 (d, J=8.55 Hz, 1H) 7.21-7.34 (m, 1H) 7.42-7.54 (m, 1H) 7.61-7.87 (m, 8H). LC (Cond'n 5): RT=1.98 min; MS: Anal. Calcd. for [M+H]$^+$ $C_{41}H_{54}N_8O_4$: 723.4. found 723.4.

Example LS27 Diastereomer 1 methyl ((1S)-1-(((2S)-2-(5-(4'-(2-((2S)-1-((2R)-2-((methoxycarbonyl)amino)-2-(3-oxetanyl)acetyl)-2-pyrrolidinyl)-1H-imidazol-5-yl)-4-biphenylyl)-1H-imidazol-2-yl)-1-pyrrolidinyl)carbonyl)-2-methylpropyl)carbamate

Example LS27 Diastereomer 2 methyl ((1S)-1-(((2S)-2-(5-(4'-(2-((2S)-1-((2S)-2-((methoxycarbonyl)amino)-2-(3-oxetanyl)acetyl)-2-pyrrolidinyl)-1H-imidazol-5-yl)-4-biphenylyl)-1H-imidazol-2-yl)-1-pyrrolidinyl)carbonyl)-2-methylpropyl)carbamate

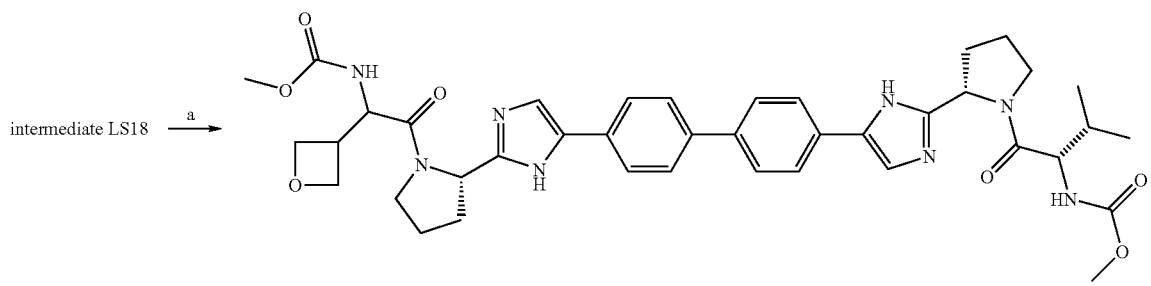

LS27

+

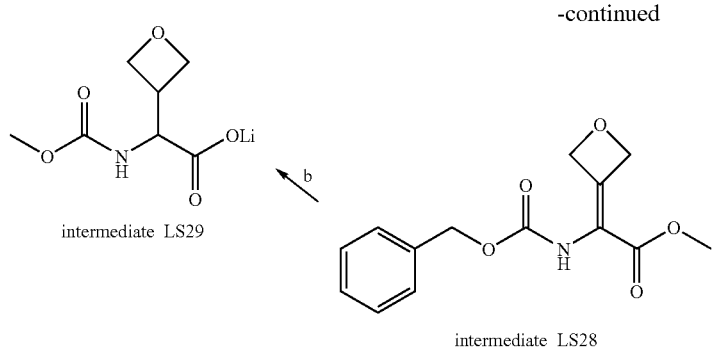

Step a: Compound LS27 was prepared in a similar fashion to the preparation of intermediate LS19 employing 2-(methoxycarbonylamino)-2-(oxetan-3-yl)acetic acid (intermediate LS29) as the carboxylic acid coupling partner. The two diastereomers of LS27 were separated via preparative HPLC (Xbridge C18, 100×19 mm I.D. S-5 µm; Mobile Phase A: 95% Water-5% Acetonitrile with 10 mM ammonium acetate (pH=5); Mobile phase B: 95% Acetonitrile-5% Water with 10 mM ammonium acetate (pH=5); Isocratic 30% B for 7 min; Flow rate: 25 mL/min; UV detection: 220 nm; Sample amount: ~5 mg/each injection, 300 µl sample solution in methanol (~17 mg/mL)). Diastereomer 1: $^1$H NMR (500 MHz, DMSO-$d_6$) δ ppm 0.80-0.96 (m, 6H) 1.91-2.06 (m, 6H) 2.09-2.21 (m, 3H) 3.54 (s, 3H) 3.59 (s, 3H) 3.77-3.83 (m, 2H) 3.87 (t, J=7.63 Hz, 1H) 4.06 (t, J=8.24 Hz, 1H) 4.31 (t, J=6.41 Hz, 1H) 4.43 (t, J=6.10 Hz, 1H) 4.49 (t, J=7.17 Hz, 1H) 4.51-4.57 (m, 1H) 4.80 (t, J=8.55 Hz, 1H) 5.00-5.05 (m, 1H) 5.06-5.11 (m, 1H) 7.30 (d, J=8.55 Hz, 1H) 7.50 (s, 1H) 7.58-7.89 (m, 8H) 11.77 (s, 2H). LC (Cond'n 10): RT=7.14 min; MS: Anal. Calcd. for [M+H]$^+$ $C_{40}H_{48}N_8O_7$: 753.4. found 753.9. Diastereomer 2: $^1$H NMR (500 MHz, DMSO-$d_6$) δ ppm 0.79-0.98 (m, 6H) 1.91-2.06 (m, 4H) 2.07-2.23 (m, 4H) 3.51-3.69 (m, 8H) 3.74-3.90 (m, 2H) 4.06 (t, J=7.48 Hz, 1H) 4.20-4.33 (m, 1H) 4.36-4.49 (m, 2H) 4.55 (s, 2H) 4.71 (s, 1H) 4.97-5.05 (m, 1H) 5.08 (s, 1H) 5.53 (s, 1H) 7.30 (d, J=7.93 Hz, 1H) 7.51 (s, 1H) 7.58-7.91 (m, 8H) 11.53 (s, 1H) 11.78 (s, 1H). LC (Cond'n 10): RT=8.79 min; MS: Anal. Calcd. for [M+H]$^+$ $C_{40}H_{48}N_8O_7$: 753.4. found 753.9.

Step b: A solution of methyl 2-(benzyloxycarbonylamino)-2-(oxetan-3-ylidene)acetate (intermediate LS28; Source: Moldes et al, *Il Farmaco*, 2001, 56, 609 and Wuitschik et al, *Ang. Chem. Int. Ed. Engl*, 2006, 45, 7736; 200 mg, 0.721 mmol) in ethyl acetate (7 mL) and $CH_2Cl_2$ (4.00 mL) was degassed by bubbling nitrogen for 10 min. Dimethyl dicarbonate (0.116 mL, 1.082 mmol) and Pd/C (20 mg, 0.019 mmol) were then added, the reaction mixture was fitted with a hydrogen balloon and allowed to stir at ambient temperature overnight. The reaction mixture was filtered through diatomaceous earth (Celite®) and concentrated. The residue was purified via Biotage (load with dichloromethane on 25 samplet; elute on 25S column with dichloromethane for 3CV then 0 to 5% methanol/dichloromethane over 250 mL then hold at 5% methanol/dichloromethane for 250 mL; 9 mL fractions). Fractions containing the desired product were concentrated to provide 167 mg methyl 2-(methoxycarbonylamino)-2-(oxetan-3-yl)acetate as a colorless oil which solidified on standing. $^1$H NMR (500 MHz, CHLOROFORM-D) δ ppm 3.29-3.40 (m, 1H) 3.70 (s, 3H) 3.74 (s, 3H) 4.55 (t, J=6.41 Hz, 1H) 4.58-4.68 (m, 2H) 4.67-4.78 (m, 2H) 5.31 (br s, 1H). MS: Anal. Calcd. for [M+H]$^+$ $C_8H_{13}NO_5$: 204.1. found 204.0. To methyl 2-(methoxycarbonylamino)-2-(oxetan-3-yl)acetate (50 mg, 0.246 mmol) in THF (2 mL) and Water (0.5 mL) was added lithium hydroxide monohydrate (10.33 mg, 0.246 mmol). The resultant solution was allowed to stir overnight at ambient temperature then concentrated to dryness to provide intermediate LS29 as a colorless powder. $^1$H NMR (500 MHz, $CH_3OD$) δ ppm 3.38-3.50 (m, 1H) 3.67 (s, 3H) 4.28 (d, J=7.63 Hz, 1H) 4.57-4.79 (m, 4H).

Example LS36 methyl ((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-2-methyl-1-pyrrolidinyl)carbonyl)-2-methylpropyl)carbamate

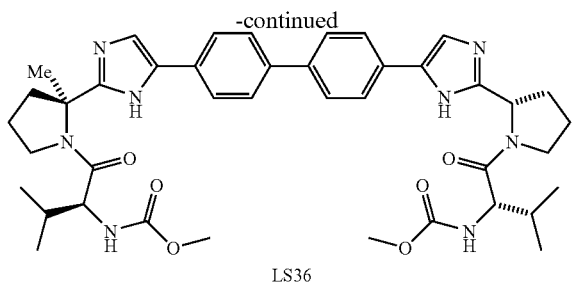

LS36

Step a: To (S)-1-(((9H-fluoren-9-yl)methoxy)carbonyl)-2-methylpyrrolidine-2-carboxylic acid (intermediate LS30; 1.5 g; 4.3 mmol) in 50 mL DMF was added sequentially 2-amino-1-(4-bromophenyl)ethanone hydrochloride (1.2 g; 4.7 mmol), HOAT (290 mg; 2.1 mmol), Hunig's base (0.7 mL; 4.3 mmol) and EDCI (1.2 g; 6.4 mmol). After 1 h, the reaction mixture was poured into 150 mL water and allowed to stir for 15 min before filtering the resultant precipitate which was dissolved in dichloromethane and dried over magnesium sulfate. The dichloromethane mixture was filtered and applied to a Biotage 40 samplet. Chromatography on a 40M column (25 to 60% ethyl acetate/hexane over 1200 mL) provided (S)-(9H-fluoren-9-yl)methyl 2-(2-(4-bromophenyl)-2-oxoethylcarbamoyl)-2-methylpyrrolidine-1-carboxylate (intermediate LS31; 2.4 g; quant) as a yellow foam. LC (Cond'n 11): RT=3.75 min; MS: Anal. Calcd. for $[M+H]^+$ $C_{29}H_{27}BrN_2O_4$: 547.1. found 547.0.

Step b: A mixture of ammonium acetate (844 mg; 10.97 mmol) and (S)-(9H-fluoren-9-yl)methyl 2-(2-(4-bromophenyl)-2-oxoethylcarbamoyl)-2-methylpyrrolidine-1-carboxylate (intermediate LS31; 1.00 g; 1.83 mmol) was heated to 140° C. in 25 mL xylene for 2.5 h at which time the reaction mixture was concentrated and loaded with dichloromethane onto a Biotage 40 samplet. Purification via Biotage (5 to 60% ethyl acetate/hexane over 100 mL with 400 mL hold time) provided (S)-(9H-fluoren-9-yl)methyl 2-(5-(4-bromophenyl)-1H-imidazol-2-yl)-2-methylpyrrolidine-1-carboxylate (intermediate LS32; 469 mg; 49%) as an amber liquid. LC (Cond'n 12): RT=3.09 min; MS: Anal. Calcd. for $[M+H]^+$ $C_{29}H_{26}BrN_3O_2$: 528.1. found 528.5.

Step c: To (S)-(9H-fluoren-9-yl)methyl 2-(5-(4-bromophenyl)-1H-imidazol-2-yl)-2-methylpyrrolidine-1-carboxylate (intermediate LS32; 329 mg; 0.62 mmol) in 3 mL DMF was added 1.5 mL piperidine. The reaction mixture was concentrated via a nitrogen stream overnight. The resultant residue was washed with hexane and passed through an MCX cartridge (Oasis; 6 g; preconditioned with two column lengths of methanol). The cartridge was washed with two column lengths of methanol and product was eluted with ammonia/methanol. Concentration provided 193 mg of (S)-5-(4-bromophenyl)-2-(2-methylpyrrolidin-2-yl)-1H-imidazole which was dissolved in 6 mL dichloromethane and combined with di-t-butyldicarbonate (413 mg; 1.89 mmol), DMAP (15 mg; 0.13 mmol) and TEA (0.17 mL; 1.30 mmol). After 48 h, the reaction mixture was concentrated and purified via chromatography on a Biotage system providing (S)-tert-butyl 5-(4-bromophenyl)-2-(1-(tert-butoxycarbonyl)-2-methylpyrrolidin-2-yl)-1H-imidazole-1-carboxylate (intermediate LS33; 150 mg; 48%) as an off white solid. LC (Cond'n 5): RT=3.75 min; MS: Anal. Calcd. for $[M+H]^+$ $C_{24}H_{32}BrN_3O_4$: 506.2. found 506.4

Step d: (S)-tert-butyl 2-(5-(4'-(2-((S)-1-(tert-butoxycarbonyl)pyrrolidin-2-yl)-1H-imidazol-5-yl)biphenyl-4-yl)-1H-imidazol-2-yl)-2-methylpyrrolidine-1-carboxylate (intermediate LS34) was prepared in a similar fashion to the preparation of 1d employing intermediate LS33 in place of 1b. $^1$H NMR (300 MHz, DMSO-$d_6$; 100° C.) δ ppm 1.18-1.29 (m, 9H) 1.29-1.40 (m, 9H) 1.75-1.82 (m, 3H) 1.81-2.39 (m, 8H) 3.35-3.75 (m, 4H) 4.81-4.92 (m, 1H) 7.36-7.45 (m, 1H) 7.57-7.74 (m, 5H) 7.76-7.89 (m, 4H) 11.29-11.63 (m, 2H). LC (Cond'n 5): RT=2.49 min; MS: Anal. Calcd. for $[M+H]^+$ $C_{37}H_{46}N_6O_4$: 639.4. found 639.9.

Step e: 2-((S)-2-methylpyrrolidin-2-yl)-5-(4'-(2-((S)-pyrrolidin-2-yl)-1H-imidazol-5-yl)biphenyl-4-yl)-1H-imidazole (intermediate LS35) was prepared in a similar fashion to the preparation of 1e employing intermediate LS34 in place of 1d. $^1$H NMR (500 MHz, DMSO-$d_6$) δ ppm 1.76-1.83 (m, 3H) 1.92-2.23 (m, 6H) 3.31-3.49 (m, 4H) 4.88-4.97 (m, 1H) 7.76-7.88 (m, 5H) 7.90-8.04 (m, 5H) 9.72-9.82 (m, 1H) 10.04-10.16 (m, 1H); imidazole and pyrrolidine NH protons unaccounted for. LC (Cond'n 5): RT=1.79 min; MS: Anal. Calcd. for $[M+H]^+$ $C_{27}H_{30}N_6$: 439.2. found 439.5.

Step f: Compound LS36 was prepared in a similar fashion to the preparation of example 1 employing intermediate LS35 in place of 1e and Cap-51 in place of Cap-1. $^1$H NMR (500 MHz, DMSO-$d_6$) δ ppm 0.72-0.97 (m, 12H) 1.77 (s, 3H) 1.86-2.08 (m, 8H) 2.09-2.19 (m, 2H) 2.25-2.39 (m, 2H) 3.49-3.59 (m, 6H) 3.81 (d, J=6.71 Hz, 4H) 4.06 (q, J=7.83 Hz, 2H) 5.08 (dd, J=7.02, 3.05 Hz, 1H) 7.12 (d, J=8.85 Hz, 1H) 7.27-7.34 (m, 1H) 7.46-7.55 (m, 1H) 7.59-7.73 (m, 4H) 7.75-7.86 (m, 3H) 11.66 (s, 1H) 11.77 (s, 1H). LC (Cond'n 5): RT=2.25 min; MS: Anal. Calcd. for $[M+H]^+$ $C_{41}H_{52}N_8O_6$: 753.4. found 754.0.

Example LS37 methyl ((1S,2R)-2-methoxy-1-(((2S)-2-(5-(4'-(2-((2S)-1-(N-(methoxycarbonyl)-O-methyl-L-threonyl)-2-pyrrolidinyl)-1H-imidazol-5-yl)-4-biphenylyl)-1H-imidazol-2-yl)-2-methyl-1-pyrrolidinyl)carbonyl)propyl)carbamate

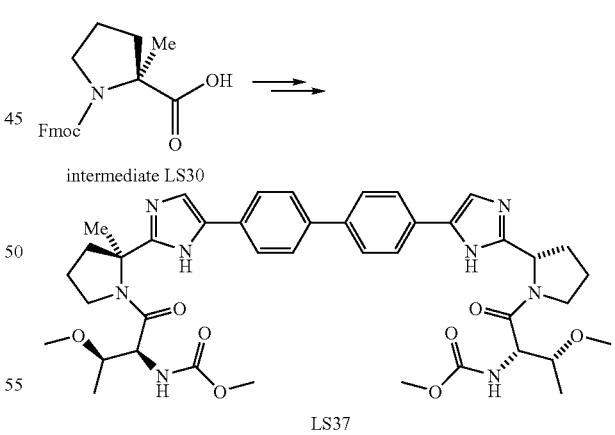

LS37

Compound LS37 was prepared in a similar fashion to the preparation of LS36 from intermediate LS30 using Cap-86 in place of Cap-51. $^1$H NMR (500 MHz, DMSO-$d_6$) δ ppm 0.99-1.17 (m, 6H) 1.76 (s, 3H) 1.87-2.09 (m, 4H) 2.10-2.23 (m, 2H) 2.34-2.38 (m, 2H) 2.56-2.60 (m, 1H) 2.63 (d, J=1.83 Hz, 1H) 3.17 (s, 3H) 3.19 (s, 3H) 3.54 (s, 6H) 3.75-3.96 (m, 4H) 4.13-4.36 (m, 2H) 5.07 (dd, J=7.48, 3.20 Hz, 1H) 7.20 (d, J=8.54 Hz, 1H) 7.24-7.34 (m, 1H) 7.50 (dd, J=7.17, 1.98 Hz, 1H) 7.59-7.73 (m, 4H) 7.76-7.86 (m, 3H) 11.65 (s, 1H) 11.77 (s, 1H). LC (Cond'n 13): RT=4.30 min; MS: Anal. Calcd. for [M+H]$^+$ $C_{41}H_{52}N_8O_8$: 785.4. found 785.4.

Section F LC Conditions for Determining Retention Time
Condition 1
Column: Phenomenex-Luna 4.6×50 mm S10
Start % B=0
Final % B=100
Gradient Time=4 min
Flow Rate=4 mL/Min
Wavelength=220
Solvent A=10% methanol—90% $H_2O$—0.1% TFA
Solvent B=90% methanol—10% $H_2O$—0.1% TFA
Condition 2
Column: Waters-Sunfire 4.6×50 mm S5
Start % B=0
Final % B=100
Gradient Time=2 min
Flow Rate=4 mL/Min
Wavelength=220
Solvent A=10% methanol—90% $H_2O$—0.1% TFA
Solvent B=90% methanol—10% $H_2O$—0.1% TFA
Condition 3
Column: Phenomenex 10u 3.0×50 mm
Start % B=0
Final % B=100
Gradient Time=2 min
Flow Rate=4 mL/Min
Wavelength=220
Solvent A=10% methanol—90% $H_2O$—0.1% TFA
Solvent B=90% methanol—10% $H_2O$—0.1% TFA
Condition 4
Column: Phenomenex-Luna 3.0×50 mm S10
Start % B=0
Final % B=100
Gradient Time=3 min
Flow Rate=4 mL/Min
Wavelength=220
Solvent A=10% methanol—90% $H_2O$—0.1% TFA
Solvent B=90% methanol—10% $H_2O$—0.1% TFA
Condition 5
Column: Phenomenex-Luna 4.6×50 mm S10
Start % B=0
Final % B=100
Gradient Time=3 min
Flow Rate=4 mL/Min
Wavelength=220
Solvent A=10% methanol—90% $H_2O$—0.1% TFA
Solvent B=90% methanol—10% $H_2O$—0.1% TFA
Condition 6
Column: Xbridge C18 4.6×50 mm S5
Start % B=0
Final % B=100
Gradient Time=3 min
Flow Rate=4 mL/Min
Wavelength=220
Solvent A=$H_2O$:ACN 95%:5% 10 mm Ammonium Acetate
Solvent B=$H_2O$:ACN 5%:95% 10 mm Ammonium Acetate
Condition 7
Column: Phenomenex C18 10u 4.6×30 mm
Start % B=0
Final % B=100
Gradient Time=3 min
Flow Rate=4 mL/Min
Wavelength=220
Solvent A=10% methanol—90% $H_2O$—0.1% TFA
Solvent B=90% methanol—10% $H_2O$—0.1% TFA
Condition 8
Column: Phenomenex LunaC18 10u 4.6×30 mm
Start % B=0
Final % B=100
Gradient Time=2 min
Flow Rate=5 mL/Min
Wavelength=220
Solvent A=10% methanol—90% $H_2O$—0.1% TFA
Solvent B=90% methanol—10% $H_2O$—0.1% TFA
Condition 9
Column: Phenomenex C18 10u 4.6×30 mm
Start % B=0
Final % B=100
Gradient Time=10 min
Flow Rate=4 mL/Min
Wavelength=220
Solvent A=$H_2O$:ACN 95%:5% 10 mm Ammonium Acetate
Solvent B=$H_2O$:ACN 5%:95% 10 mm Ammonium Acetate
Condition 10
Column: Phenomenex 10u 3.0×50 mm
Start % B=0
Final % B=100
Gradient Time=3 min
Flow Rate=4 mL/Min
Wavelength=220
Solvent A=10% methanol—90% $H_2O$—0.1% TFA
Solvent B=90% methanol—10% $H_2O$—0.1% TFA
Condition 11
Column: Xterra 4.6×30 mm S5
Start % B=0
Final % B=100
Gradient Time=2 min
Flow Rate=5 mL/Min
Wavelength=220
Solvent A=$H_2O$:ACN 95%:5% 10 mm Ammonium Acetate
Solvent B=$H_2O$:ACN 5%:95% 10 mm Ammonium Acetate

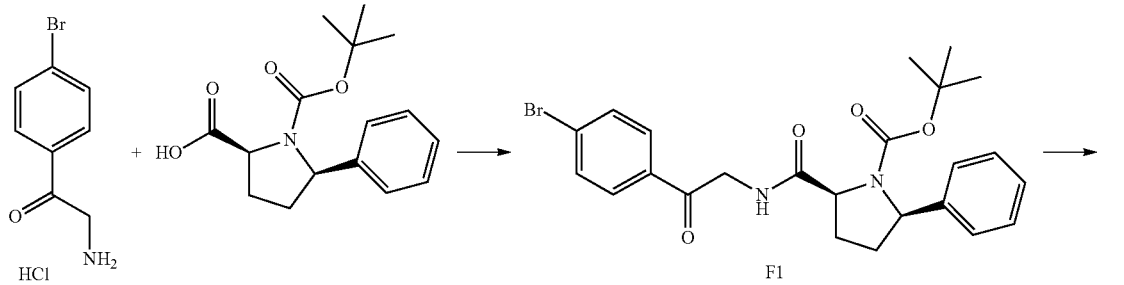

-continued
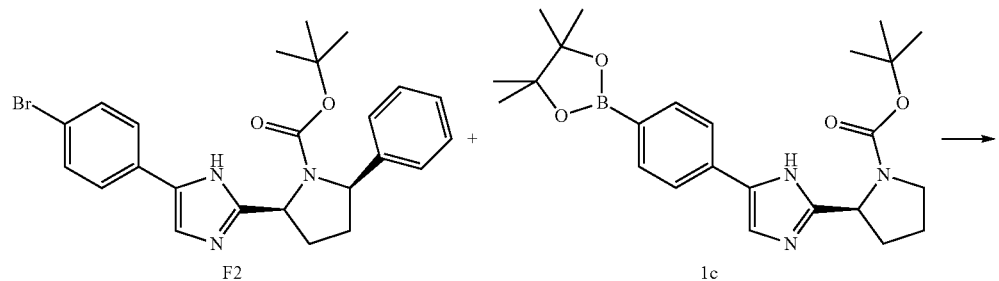
F2  1c
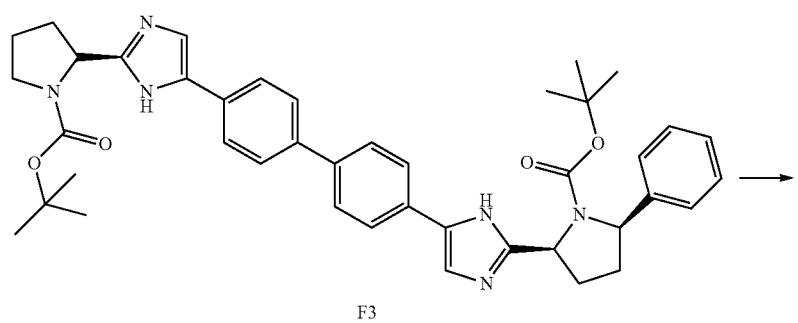
F3
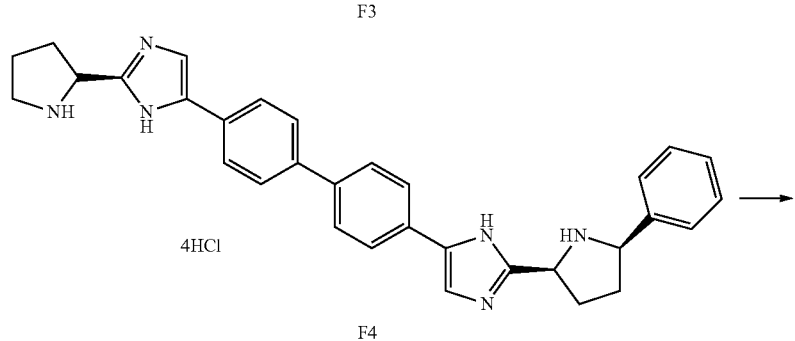
4HCl
F4
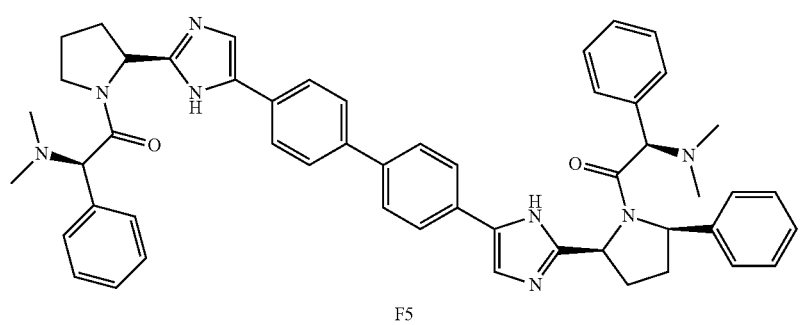
F5
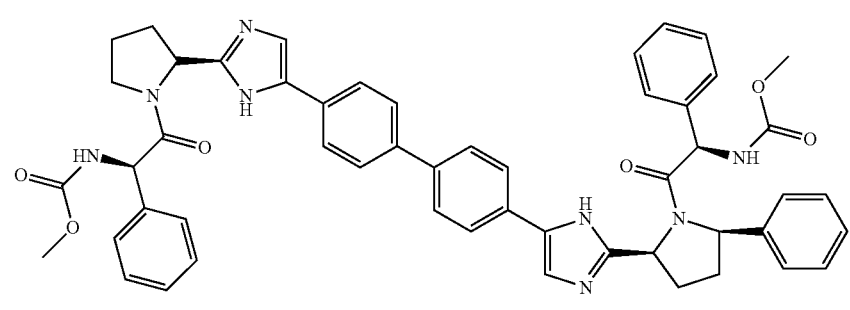
F6

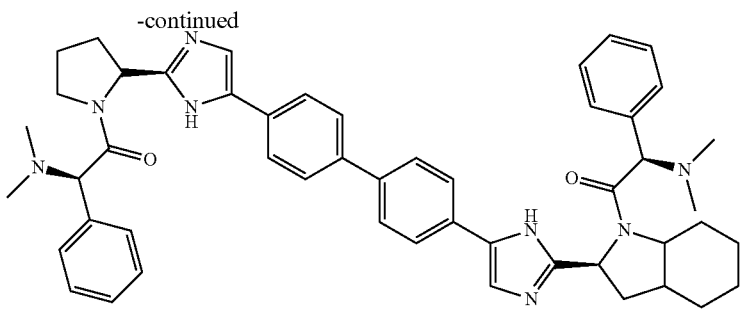

F7

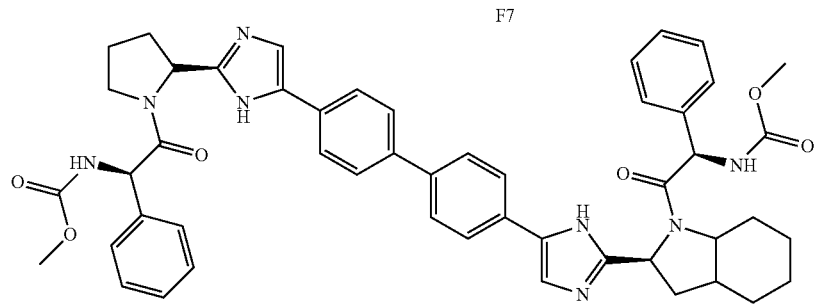

F8

Compound F1 was prepared in analogous fashion to the procedure used to synthesize 1a with following modification: (2S,5R)-1-(tert-butoxycarbonyl)-5-phenylpyrrolidine-2-carboxylic acid was used in place of N-Boc-L-proline.

Compound F2 was prepared in analogous fashion to the procedure used to synthesize 1b.

Compound F3 was prepared in analogous fashion to the procedure used to synthesize 1d.

Compound F4 was prepared in analogous fashion to the procedure used to synthesize 1e.

Compound F5, F6 was prepared in analogous fashion to the procedure used to synthesize example 1 from Compound F4.

Compound F7, F8 was prepared in analogous fashion to the procedure used to synthesize F5 with following modification: (2S)-1-(tert-butoxycarbonyl)octahydro-1H-indole-2-carboxylic acid was used in place of (2S,5R)-1-(tert-butoxycarbonyl)-5-phenylpyrrolidine-2-carboxylic acid.

| Entry | Compound Name | Retention time (LC-Condition); homogeneity index MS data |
|---|---|---|
| F1 | | RT = 3.838 minutes (condition 1, 94%); LRMS: Anal. Calcd. for C24H27BrN2O4 486.12; found: 487.26 (M + H)+. |
| F2 | | RT = 3.175 minutes (condition 1, 83%); LRMS: Anal. Calcd. for C24H27BrN2O4 467.12; found: 468.26 (M + H)+. |
| F3 | | RT = 2.965 minutes (condition 1, 93%); LRMS: Anal. Calcd. for C42H48N6O4 700.37; found: 701.49 (M + H)+. |
| F4 | | RT = 2.083 minutes (condition 1, 98%); LRMS: Anal. Calcd. for C32H32N6 500.27; found: 501.40 (M + H)+. |
| F5 | | RT = 1.222 minutes (condition 3, 98%); LRMS: Anal. Calcd. for C52H54N8O2 822.44; found: 823.5 (M + H)+. |
| F6 | methyl ((1R)-2-((2R)-2-(5-(4'-(2-((2S,5R)-1-((2R)-2-((methoxycarbonyl)amino)-2-phenylacetyl)-5-phenyl-2-pyrrolidinyl)-1H-imidazol-5-yl)-4-biphenylyl)-1H-imidazol-2-yl)-1-pyrrolidinyl)-2-oxo-1-phenylethyl)carbamate | RT = 1.512 minutes (condition 3, 98%); LRMS: Anal. Calcd. for C52H50N8O6 882.39; found: 883.45 (M + H)+. |
| F7 | rel-(1R)-2-((2S)-2-(4-(4'-(2-((2S)-1-((2R)-2-(dimethylamino)-2-phenylacetyl)octahydro-1H-indol-2-yl)-1H-imidazol-5-yl)-4-biphenylyl)-1H-imidazol-2-yl)-1-pyrrolidinyl)-N,N-dimethyl-2-oxo-1-phenylethanamine | RT = 1.223 minutes (condition 3, 98%); LRMS: Anal. Calcd. for C50H56N8O2 800.45; found: 801.51 (M + H)+. |
| F8 | methyl rel-((1R)-2-((2S)-2-(4-(4'-(2-((2S)-1-((2R)-2-((methoxycarbonyl)amino)-2-phenylacetyl)octahydro-1H-indol-2-yl)-1H-imidazol-5-yl)-4-biphenylyl)-1H-imidazol-2-yl)-1-pyrrolidinyl)-2-oxo-1-phenylethyl)carbamate | RT = 1.513 minutes (condition 3, 98%); LRMS: Anal. Calcd. for C50H56N8O2 860.40; found: 861.42 (M + H)+. |

433          434
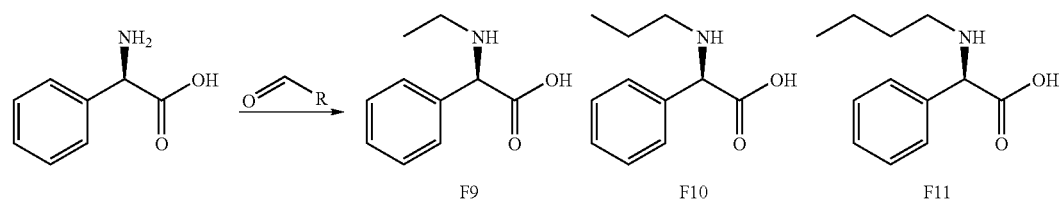
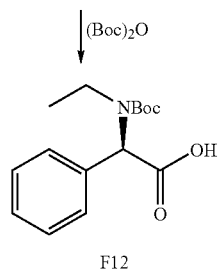
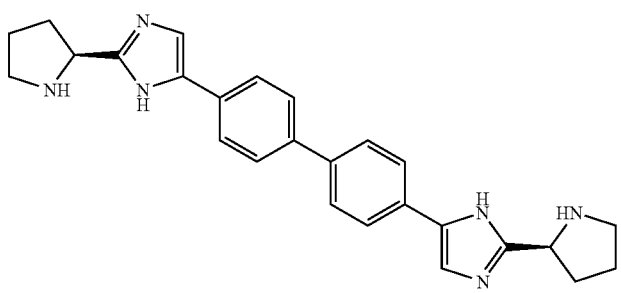
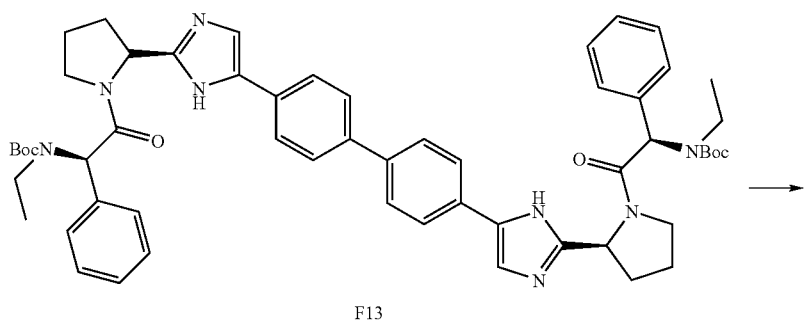
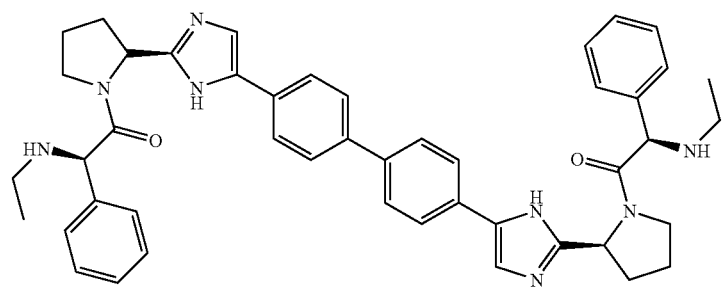

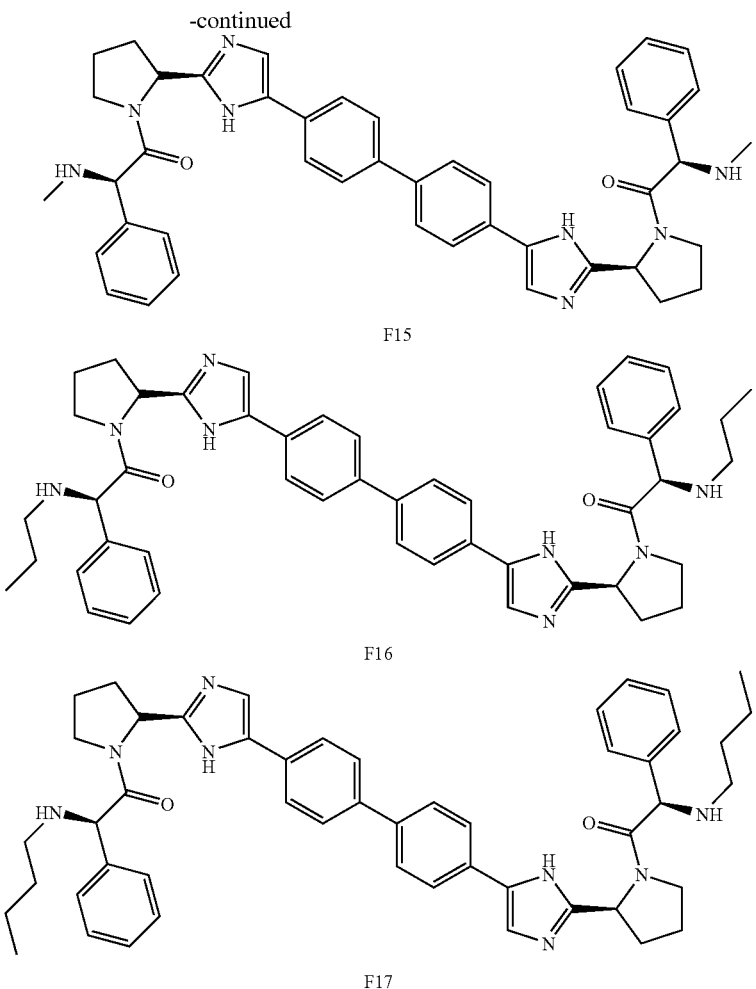

F15

F16

F17

Compound F9, F10, and F11 was prepared in analogous fashion to the procedure used to synthesize Cap-3 first half procedure using acetaldehyde, propionaldehyde, and butyraldehyde respectively.

Compound F12

(Boc)$_2$O (2.295 g, 10.20 mmol) was added to a mixture of compound F9 (1.0 g, 4.636 mmol), hunig's base (1.78 mL, 10.20 mmol) in CH$_2$Cl$_2$ (12 mL), and the resulting mixture was stirred over night. The volatile component was removed in vacuo, and the residue was purified by a reverse phase HPLC system (H$_2$O/methanol/TFA) to provide compound F12 as a clear wax (0.993 g).

LC (Cond. 3): RT=1.663 min; >95% homogeneity index; LC/MS: Anal. Calcd. for [M+H]$^+$ C15H21NO4: 279.33. found [M+Na]$^+$ 302.30

Compound F13 was prepared in analogous fashion to the procedure used to synthesized example 1 from Compound 1e and F12.

Compound F14 was prepared in analogous fashion to the procedure used to synthesized 132e.

Compound F15, F16, and F17 was prepared in analogous fashion to the procedure used to synthesize F14.

| Entry Compound Name | Retention time (LC-Condition); homogeneity index MS data |
|---|---|
| F9 | RT = 0.580 minutes (condition 1, 94%); LRMS: Anal. Calcd. for C10H13NO2 179.09; found: 180.26 (M + H)$^+$. |
| F10 | RT = 0.563 minutes (condition 3, 94%); LRMS: Anal. Calcd. for C11H15NO2 193.11; found: 194.26 (M + H)$^+$. |

-continued

| Entry | Compound Name | Retention time (LC-Condition); homogeneity index MS data |
|---|---|---|
| F11 | | RT = 1.023 minutes (condition 3, 94%); LRMS: Anal. Calcd. for C12H17NO2 207.13; found: 208.31 (M + H)⁺. |
| F12 | | RT = 1.663 minutes (condition 3, 95%); LRMS: Anal. Calcd. for C15H21NO4 279.15; found: 302.30 (Na + H)⁺. |
| F13 | | RT = 2.595 minutes (condition 4, 94%); LRMS: Anal. Calcd. for C56H66N8O6 946.51; found: 947.64 (M + H)⁺. |
| F14 | (1R)—N-ethyl-2-((2S)-2-(4-(4'-(2-((2S)-1-((2R)-2-(ethylamino)-2-phenylacetyl)-2-pyrrolidinyl)-1H-imidazol-5-yl)-4-biphenylyl)-1H-imidazol-2-yl)-1-pyrrolidinyl)-2-oxo-1-phenylethanamine | RT = 1.55 minutes (condition 5, 90%); LRMS: Anal. Calcd. for C46H50N8O2 746.41; found: 747.72 (M + H)⁺. |
| F15 | (1R)—N-methyl-2-((2S)-2-(4-(4'-(2-((2S)-1-((2R)-2-(methylamino)-2-phenylacetyl)-2-pyrrolidinyl)-1H-imidazol-5-yl)-4-biphenylyl)-1H-imidazol-2-yl)-1-pyrrolidinyl)-2-oxo-1-phenylethanamine | RT = 1.50 minutes (condition 5, 94%); LRMS: Anal. Calcd. for C44H46N8O2 718.37; found: 719.69 (M + H)⁺. |
| F16 | N-((1R)-2-oxo-1-phenyl-2-((2S)-2-(4-(4'-(2-((2S)-1-((2R)-2-phenyl-2-(propylamino)acetyl)-2-pyrrolidinyl)-1H-imidazol-5-yl)-4-biphenylyl)-1H-imidazol-2-yl)-1-pyrrolidinyl)ethyl)-1-propanamine | RT = 1.63 minutes (condition 5, 90%); LRMS: Anal. Calcd. for C48H54N8O2 774.43; found: 775.76 (M + H)⁺. |
| F17 | N-((1R)-2-((2S)-2-(4-(4'-(2-((2S)-1-((2R)-2-(butylamino)-2-phenylacetyl)-2-pyrrolidinyl)-1H-imidazol-5-yl)-4-biphenylyl)-1H-imidazol-2-yl)-1-pyrrolidinyl)-2-oxo-1-phenylethyl)-1-butanamine | RT = 1.81 minutes (condition 5, 85%); LRMS: Anal. Calcd. for C50H58N8O2 802.47; found: 803.79 (M + H)⁺. |

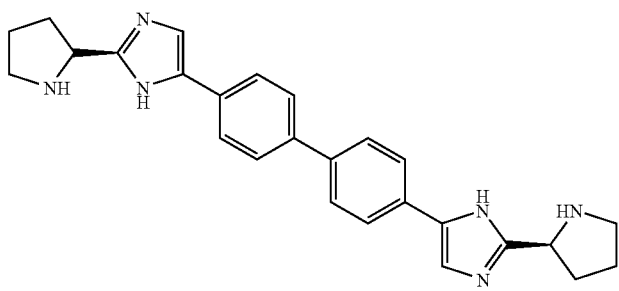

1e

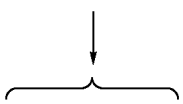

-continued
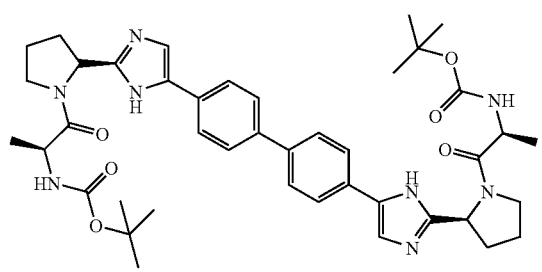
F18
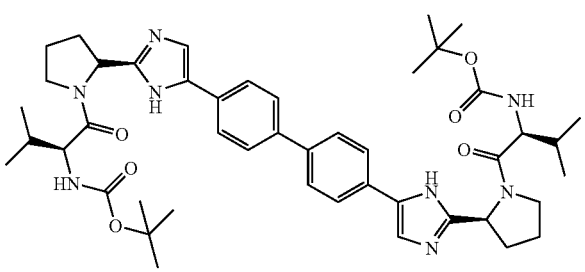
F23
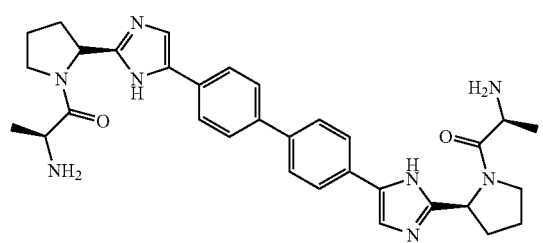
F19
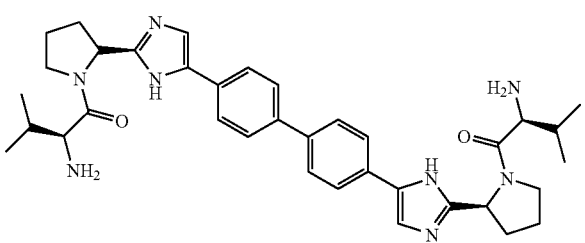
F24
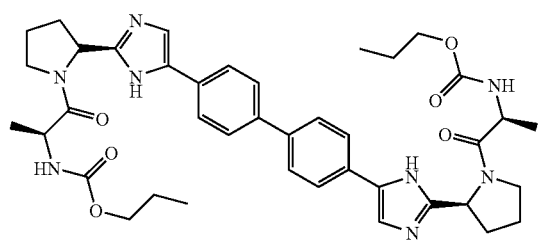
F20
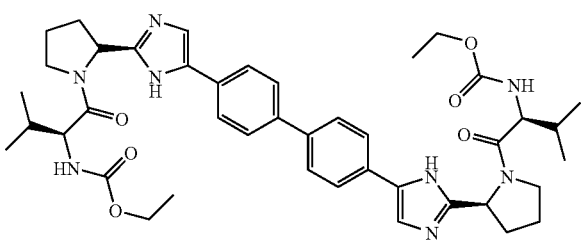
F25
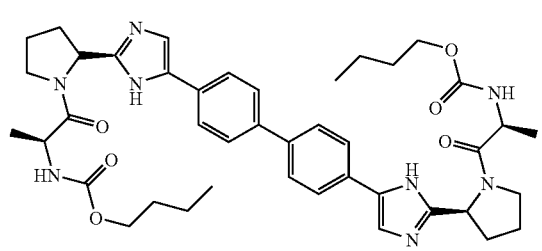
F21
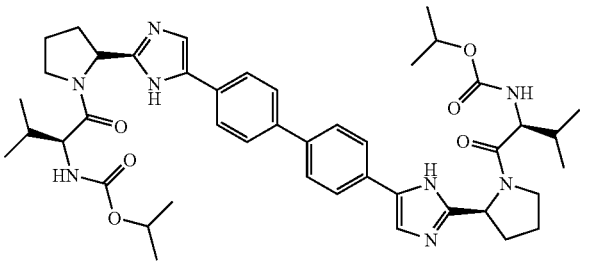
F26
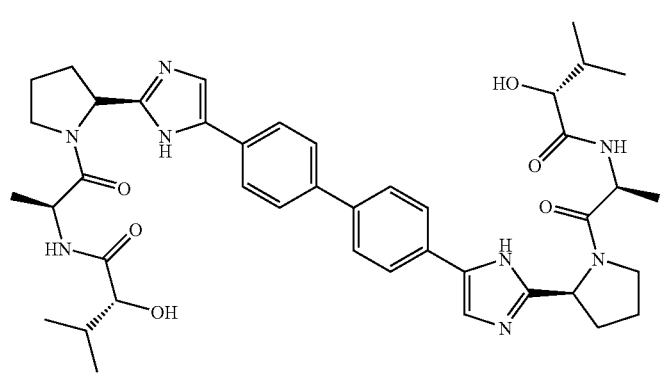
F22

Compound F18 and F23 was prepared in analogous fashion to the procedure used to synthesize example 1 with following modification: N-Boc-L-alanine and N-Boc-L-valine was used in place of N-Boc-L-proline respectively.

Compound F22 was prepared in analogous fashion to the procedure used to synthesize example 1 from Compound F19.

Compound F19, F24 was prepared in analogous fashion to the procedure used to synthesize 132e.

Compound F25 ethyl ((1S)-1-(((2S)-2-(4-(4'-(2-((2S)-1-((2S)-2-((ethoxycarbonyl)amino)-3-methylbutanoyl)-2-pyrrolidinyl)-1H-imidazol-4-yl)-4-biphenylyl)-1H-imidazol-2-yl)-1-pyrrolidinyl)carbonyl)-2-methylpropyl)carbamate To a solution of F24 (0.06 g, 0.074 mmol) in DMF (1 mL) was added Hunig's base (0.105 mL, 0.593 mmol) and ethyl carbonochloridate (0.016 mL, 0.163 mmol) then stirred it at room temperature. Two hours later, checked it by LCMS. There were three major peaks which indicated desired compound, tri-coupled, and tetra-coupled compound. Stopped reaction and concentrated it by reduced pressure to get light brown oil which was treated with 10 mL of 2 M $NH_3$ in methanol for 20 minutes then concentrated it again to a yellow solid which was purified by preparative LC to provide compound F25 as a white TFA salt (57.6 mg).

LC (Cond. 6): RT=1.932 min, LC/MS: Anal. Calcd. for $[M+H]^+$ $C_{42}H_{54}N_8O_6$: 766.42. found 767.55.

$^1H$ NMR (500 MHz, DMSO-$d_6$) δ ppm 0.69-0.94 (m, 12H) 1.16 (t, J=7.02 Hz, 6H) 1.90-2.26 (m, 8H) 2.40 (d, J=4.88 Hz, 2H) 3.73-3.92 (m, 4H) 3.94-4.08 (m, 4H) 4.12 (t, J=7.78 Hz, 2H) 5.15 (t, J=7.02 Hz, 2H) 7.26 (d, J=8.54 Hz, 2H) 7.85-7.93 (m, 4H) 7.93-8.01 (m, 4H) 8.13 (s, 2H) 14.68 (s, 2H)

Compound F20, F21, and F26 was prepared in analogous fashion to the procedure used to synthesize example 1.

| Entry | Compound Name | Retention time (LC-Condition); homogeneity index MS data |
|---|---|---|
| F18 | | RT = 2.257 minutes (condition 5, 96%); LRMS: Anal. Calcd. for C42H54N8O6 766.42; found: 767.88 (M + H)+. |
| F19 | | RT = 1.462 minutes (condition 5, 95%); LRMS: Anal. Calcd. for C32H38N8O2 566.31; found: 567.79 (M + H)+. |
| F20 | propyl ((1S)-1-methyl-2-oxo-2-((2S)-2-(4-(4'-(2-((2S)-1-(N-(propoxycarbonyl)-L-alanyl)-2-pyrrolidinyl)-1H-imidazol-5-yl)-4-biphenylyl)-1H-imidazol-2-yl)-1-pyrrolidinyl)ethyl)carbamate | RT = 1.338 minutes (condition 3, 89%); LRMS: Anal. Calcd. for C40H50N8O6 738.39; found: 739.95 (M + H)+. |
| F21 | butyl ((1S)-2-((2S)-2-(4-(4'-(2-((2S)-1-(N-(butoxycarbonyl)-L-alanyl)-2-pyrrolidinyl)-1H-imidazol-5-yl)-4-biphenylyl)-1H-imidazol-2-yl)-1-pyrrolidinyl)-1-methyl-2-oxoethyl)carbamate | RT = 1.447 minutes (condition 3, 96%); LRMS: Anal. Calcd. for C42H54N8O6 766.93; found: 768.02 (M + H)+. |
| F22 | (2S)-2-hydroxy-N-((1S)-2-((2S)-2-(5-(4'-(2-((2S)-1-(N-((2S)-2-hydroxy-3-methylbutanoyl)-L-alanyl)-2-pyrrolidinyl)-1H-imidazol-4-yl)-4-biphenylyl)-1H-imidazol-2-yl)-1-pyrrolidinyl)-1-methyl-2-oxoethyl)-3-methylbutanamide | RT = 1.703 minutes (condition 4, 98%); LRMS: Anal. Calcd. for C42H54N8O 766.93; found: 768.02 (M + H)+. |
| F23 | | RT = 2.881 minutes (condition 7, 93%); LRMS: Anal. Calcd. for C46H62N8O6 822.48; found: 823.95 (M + H)+. |
| F24 | | RT = 1.743 minutes (condition 7, 98%); LRMS: Anal. Calcd. for C36H46N8O2 622.37; found: 624.07 (M + H)+. |
| F25 | ethyl ((1S)-1-(((2S)-2-(4-(4'-(2-((2S)-1-((2S)-2-((ethoxycarbonyl)amino)-3-methylbutanoyl)-2-pyrrolidinyl)-1H-imidazol-4-yl)-4-biphenylyl)-1H-imidazol-2-yl)-1-pyrrolidinyl)carbonyl)-2-methylpropyl)carbamate | RT = 1.932 minutes (condition 6, 97%); LRMS: Anal. Calcd. for C42H54N8O6 766.42; found: 767.55 (M + H)+. |
| F26 | isopropyl ((1S)-1-(((2S)-2-(4-(4'-(2-((2S)-1-((2S)-2-((isopropoxycarbonyl)amino)-3-methylbutanoyl)-2-pyrrolidinyl)-1H-imidazol-4-yl)-4-biphenylyl)-1H-imidazol-2-yl)-1-pyrrolidinyl)carbonyl)-2-methylpropyl)carbamate | RT = 2.122 minutes (condition 6, 98%); LRMS: Anal. Calcd. for C44H58N8O6 794.45; found: 795.58 (M + H)+. |

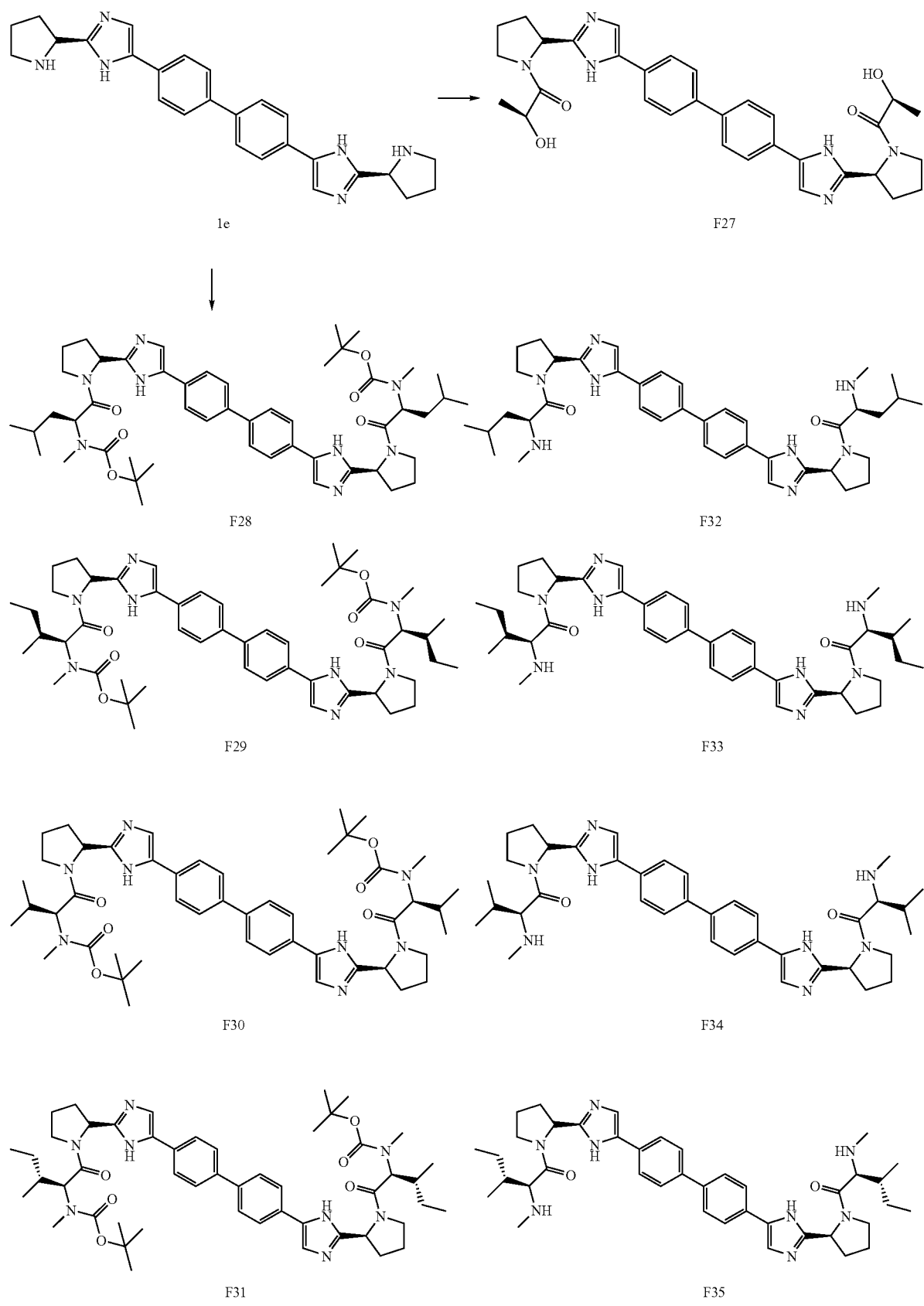

| Entry | Compound Name | Retention time (LC-Condition); homogeneity index MS data |
|---|---|---|
| F27 | (2S)-1-((2S)-2-(4-(4'-(2-((2S)-1-((2S)-2-hydroxypropanoyl)-2-pyrrolidinyl)-1H-imidazol-5-yl)-4-biphenylyl)-1H-imidazol-2-yl)-1-pyrrolidinyl)-1-oxo-2-propanol | RT = 1.03 minutes (condition 3, 98%); LRMS: Anal. Calcd. for C32H36N6O4 568.28; found: 569.76 (M + H)+. |
| F28 | tert-butyl ((1S)-1-(((2S)-2-(5-(4'-(2-((2S)-1-((2S)-2-((tert-butoxycarbonyl)(methyl)amino)-4-methylpentanoyl)-2-pyrrolidinyl)-1H-imidazol-4-yl)-4-biphenylyl)-1H-imidazol-2-yl)-1-pyrrolidinyl)carbonyl)-3-methylbutyl)methylcarbamate | RT = 1.847 minutes (condition 3, 95%); LRMS: Anal. Calcd. for C50H70N8O6 878.54; found: 879.53 (M + H)+. |
| F29 | tert-butyl ((1S)-1-(((2S)-2-(5-(4'-(2-((2S)-1-((2S)-2-((tert-butoxycarbonyl)(methyl)amino)-3-methylpentanoyl)-2-pyrrolidinyl)-1H-imidazol-4-yl)-4-biphenylyl)-1H-imidazol-2-yl)-1-pyrrolidinyl)carbonyl)-2-methylbutyl)methylcarbamate | RT = 2.202 minutes (condition 8, 98%); LRMS: Anal. Calcd. for C50H70N8O6 878.54; found: 879.57 (M + H)+. |
| F30 | tert-butyl ((1S)-1-(((2S)-2-(5-(4'-(2-((2S)-1-((2S)-2-((tert-butoxycarbonyl)(methyl)amino)-3-methylbutanoyl)-2-pyrrolidinyl)-1H-imidazol-4-yl)-4-biphenylyl)-1H-imidazol-2-yl)-1-pyrrolidinyl)carbonyl)-2-methylpropyl)methylcarbamate | RT = 1.743 minutes (condition 8, 96%); LRMS: Anal. Calcd. for C48H66N8O6 850.51; found: 851.52 (M + H)+. |
| F31 | tert-butyl ((1S,2R)-1-(((2S)-2-(4-(4'-(2-((2S)-1-(N-(tert-butoxycarbonyl)-N-methyl-L-alloisoleucyl)-2-pyrrolidinyl)-1H-imidazol-5-yl)-4-biphenylyl)-1H-imidazol-2-yl)-1-pyrrolidinyl)carbonyl)-2-methylbutyl)methylcarbamate | RT = 1.82 minutes (condition 8, 98%); LRMS: Anal. Calcd. for C50H70N8O6 878.54; found: 879.54 (M + H)+. |
| F32 | (2S)—N,4-dimethyl-1-((2S)-2-(4-(4'-(2-((2S)-1-((2S)-4-methyl-2-(methylamino)pentanoyl)-2-pyrrolidinyl)-1H-imidazol-5-yl)-4-biphenylyl)-1H-imidazol-2-yl)-1-pyrrolidinyl)-1-oxo-2-pentanamine | RT = 3.715 minutes (condition 9, 98%); LRMS: Anal. Calcd. for C40H54N8O2 678.44; found: 679.46 (M + H)+. |
| F33 | (2S)—N,3-dimethyl-1-((2S)-2-(4-(4'-(2-((2S)-1-((2S)-3-methyl-2-(methylamino)pentanoyl)-2-pyrrolidinyl)-1H-imidazol-5-yl)-4-biphenylyl)-1H-imidazol-2-yl)-1-pyrrolidinyl)-1-oxo-2-pentanamine | RT = 3.058 minutes (condition 9, 99%); LRMS: Anal. Calcd. for C36H46N8O2 678.44; found: 679.61 (M + H)+. |
| F34 | (2S)—N,3-dimethyl-1-((2S)-2-(4-(4'-(2-((2S)-1-((2S)-3-methyl-2-(methylamino)butanoyl)-2-pyrrolidinyl)-1H-imidazol-5-yl)-4-biphenylyl)-1H-imidazol-2-yl)-1-pyrrolidinyl)-1-oxo-2-butanamine | RT = 3.206 minutes (condition 9, 99%); LRMS: Anal. Calcd. for C38H50N8O2 650.41; found: 651.41 (M + H)+. |
| F35 | (2S,3R)-N,3-dimethyl-1-((2S)-2-(4-(4'-(2-((2S)-1-((2S,3R)-3-methyl-2-(methylamino)pentanoyl)-2-pyrrolidinyl)-1H-imidazol-5-yl)-4-biphenylyl)-1H-imidazol-2-yl)-1-pyrrolidinyl)-1-oxo-2-pentanamine | RT = 3.43 minutes (condition 9, 98%); LRMS: Anal. Calcd. for C40H54N8O2 678.44; found: 679.44 (M + H)+. |

Compound F27 to F31 was prepared in analogous fashion to the procedure used to synthesize example 1.

Compound F32 to F35 was prepared in analogous fashion to the procedure used to synthesize 1e.

Compound F36 was prepared in analogous fashion to the procedure used to synthesize Cap-52.

Compound F37, F38, and F39 was prepared in analogous fashion to the procedure used to synthesize example 1 from Compound F36 and LS16 respectively.

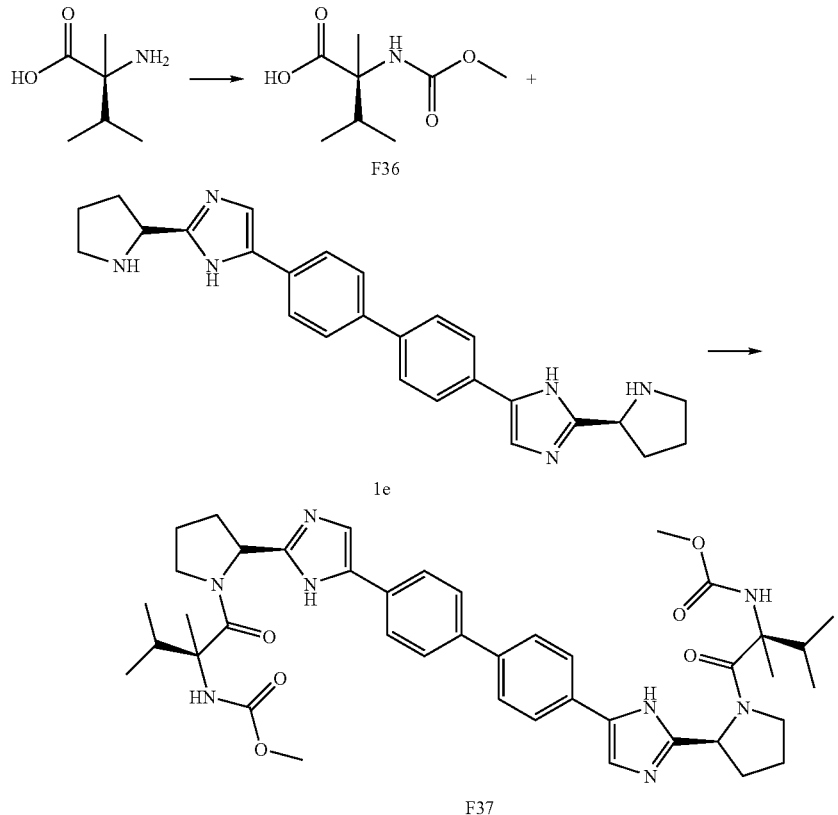

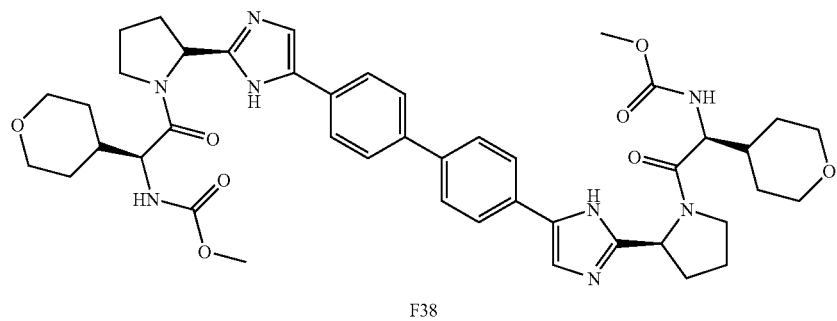

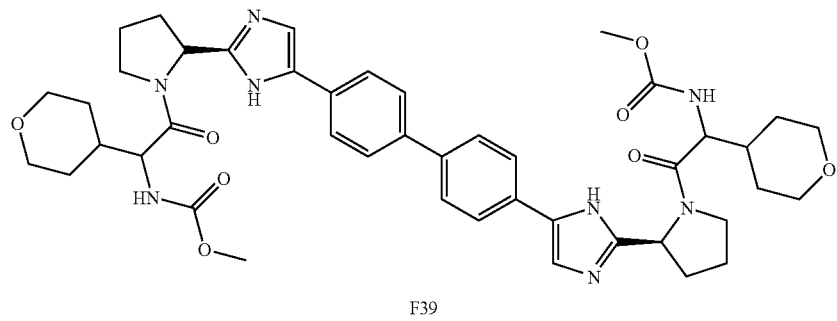

| Entry | Compound | Retention time (LC-Condition); homogeneity index MS data |
|---|---|---|
| F36 | | RT = 1.55 minutes (condition 10); LRMS: Anal. Calcd. for C10H13NO2 189.1; found: 190.13 (M + H)+. 1H NMR (500 MHz, DMSO-d6) δ ppm 0.71-1.00 (m, 6H) 1.16-1.41 (m, 3H) 1.75-2.09 (m, 1H) 3.39-3.64 (m, 3H) 7.13 (s, 1H) 12.27 (s, 1H) |
| F37 | methyl ((1S)-1-(((2S)-2-(4-(4'-(2-((2S)-1-((2S)-2-((methoxycarbonyl)amino)-2,3-dimethylbutanoyl)-2-pyrrolidinyl)-1H-imidazol-5-yl)-4-biphenylyl)-1H-imidazol-2-yl)-1-pyrrolidinyl)carbonyl)-1,2-dimethylpropyl)carbamate | RT = 2.572 minutes (condition 4, 98%); LRMS: Anal. Calcd. for C42H54N8O6 766.42; found: 767.48 (M + H)+. |
| F38 | methyl ((1S)-2-((2S)-2-(4-(4'-(2-((2S)-1-((2S)-2-((methoxycarbonyl)amino)-2-(tetrahydro-2H-pyran-4-yl)acetyl)-2-pyrrolidinyl)-1H-imidazol-5-yl)-4-biphenylyl)-1H-imidazol-2-yl)-1-pyrrolidinyl)-2-oxo-1-(tetrahydro-2H-pyran-4-yl)ethyl)carbamate | RT = 2.128 minutes (condition 7, 98%); LRMS: Anal. Calcd. for C44H54N8O8 822.41; found: 823.45 (M + H)+. |
| F39 | methyl (2-((2S)-2-(4-(4'-(2-((2S)-1-(((methoxycarbonyl)amino)(tetrahydro-2H-pyran-4-yl)acetyl)-2-pyrrolidinyl)-1H-imidazol-5-yl)-4-biphenylyl)-1H-imidazol-2-yl)-1-pyrrolidinyl)-2-oxo-1-(tetrahydro-2H-pyran-4-yl)ethyl)carbamate | RT = 2.162 minutes (condition 7, 98%); LRMS: Anal. Calcd. for C44H54N8O8 822.42; found: 823.49 (M + H)+. |

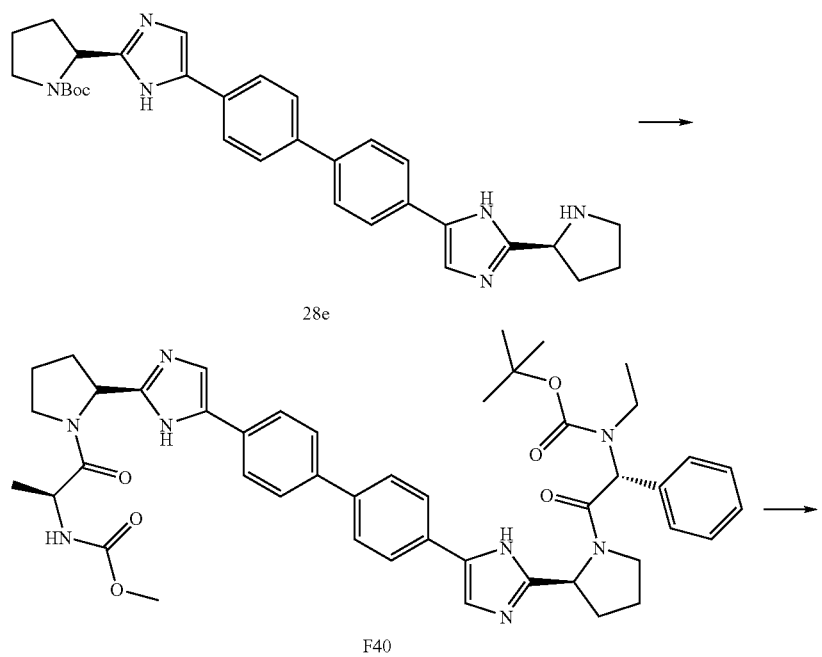

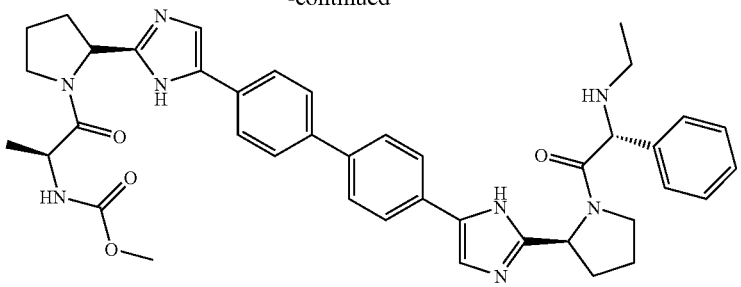

F41

Compound F41 was prepared in analogous fashion to the procedure used to synthesize example 1.

Compound F42 was prepared in analogous fashion to the procedure used to synthesize 1e.

| Entry | Compound Name | Retention time (LC-Condition); homogeneity index MS data |
|---|---|---|
| F40 | | RT = 2.72 minutes (condition 10); LRMS: Anal. Calcd. for C46H54N8O6 814.42; found: 815.98 (M + H)+. |
| F41 | methyl ((1S)-2-((2S)-2-(4-(4'-(2-((2S)-1-((2R)-2-(ethylamino)-2-phenylacetyl)-2-pyrrolidinyl)-1H-imidazol-5-yl)-4-biphenylyl)-1H-imidazol-2-yl)-1-pyrrolidinyl)-1-methyl-2-oxoethyl)carbamate | RT = 2.048 minutes (condition 10, 95%); LRMS: Anal. Calcd. for C41H46N8O4 714.36; found: 715.84 (M + H)+. |

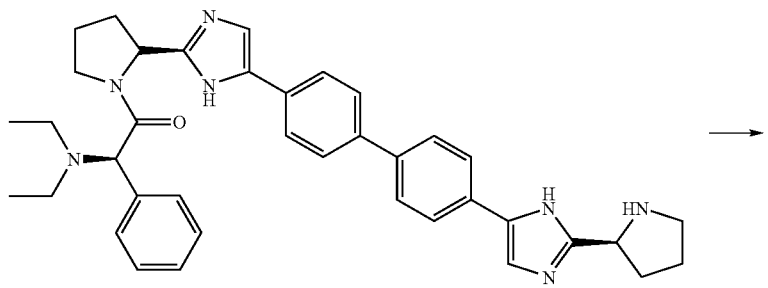

F42

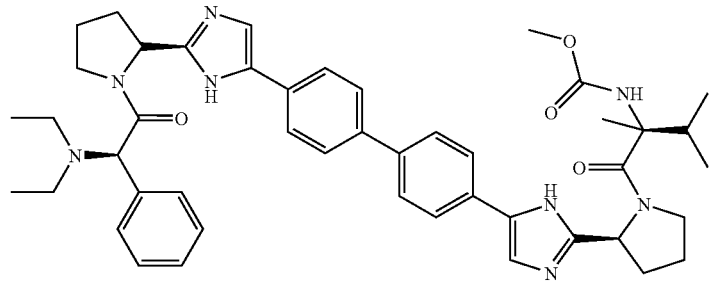

F43

Compound F42 was prepared in analogous fashion to the procedure used to synthesize example 28f employing Cap-2 in place of Cap-4.

Compound F43 was prepared in analogous fashion to the procedure used to synthesize 2 from Compound F42.

| Entry | Compound Name | Retention time (LC-Condition); homogeneity index MS data |
|---|---|---|
| F42 | | RT = 2.0 minutes (condition 10, 95%); LRMS: Anal. Calcd. for C38H43N7O 613.35; found: 614.40 (M + H)+. |
| F43 | methyl ((1S)-1-(((2S)-2-(5-(4'-(2-((2S)-1-((2R)-2-(diethylamino)-2-phenylacetyl)-2-pyrrolidinyl)-1H-imidazol-4-yl)-4-biphenylyl)-1H-imidazol-2-yl)-1-pyrrolidinyl)carbonyl)-1,2-dimethylpropyl)carbamate | RT = 2.308 minutes (condition 10, 98%); LRMS: Anal. Calcd. for C50H70N8O6 784.44; found: 785.49 (M + H)+. |

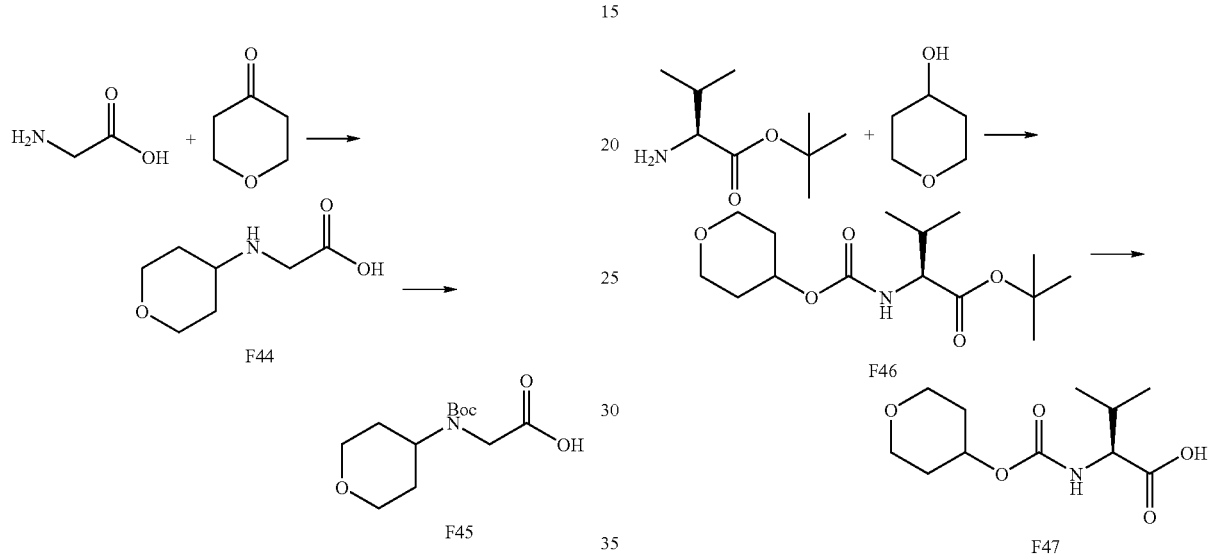

Compound F44 was prepared following below paper with following modification: glycine was used in place of leucine.

A simple method for preparation of N-mono- and N,N-dialkylated α-amino acids

Yuntao Song et al., *Tetrahedron Lett.* 41, October 2000, Pages 8225-8230.

¹H NMR (500 MHz, DMSO-d₆) δ ppm 1.37-1.62 (m, 2H) 1.86 (dd, J=12.36, 1.98 Hz, 2H) 3.01-3.12 (m, 1H) 3.15 (s, 2H) 3.25 (t, J=11.75 Hz, 2H) 3.86 (dd, J=11.44, 4.12 Hz, 2H) 7.67-8.48 (m, 1H).

Compound F45

2-(tetrahydro-2H-pyran-4-ylamino)acetic acid (0.2 g, 1.256 mmol) F44 was dissolved in DMF (22.5 mL) and Et₃N (2.5 mL, 17.94 mmol). After 5 minutes BOC₂O (0.583 mL, 2.51 mmol) was added and the reaction solution was heated to 60° C. for 1 h. The reaction was concentrated by reduced pressure providing a light yellow oil to which was added 20 mL HCl H₂O which was adjusted to PH3 at 0° C. and stirred for 10 minutes. The reaction mixture was extracted by ethyl acetate 3×20 mL, dried (MgSO₄), filtered, and concentrated to dryness. Ether was added and the mixture was sonicated and filtered providing a white solid F45 2-(tert-butoxycarbonyl(tetrahydro-2H-pyran-4-yl)amino)acetic acid (0.14 g, 0.540 mmol, 43.0% yield).

¹H NMR (300 MHz, DMSO-d₆) δ ppm 1.27-1.44 (m, 9H) 1.43-1.69 (m, 4H) 3.19-3.39 (m, 2H) 3.74 (s, 2H) 3.79-3.92 (m, 2H) 3.97-4.16 (m, 1H) 12.46 (s, 1H).

Compound F46 was prepared following the below referenced procedure with following modification: (S)-tert-butyl 2-amino-3-methylbutanoate was used in place of (S)-methyl 2-(((9H-fluoren-9-yl)methoxy)carbonylamino)-3-methylbutanoate.

Hans-Joachim Knolker, et al. *Synlett* 1997; 925-928

¹H NMR (500 MHz, DMSO-d₆) δ ppm 0.77-0.97 (m, 6H) 1.32-1.45 (m, 9H) 1.45-1.56 (m, 2H) 1.74-1.91 (m, 2H) 1.94-2.11 (m, 1H) 3.36-3.53 (m, 2H) 3.76 (dd, J=8.09, 6.26 Hz, 1H) 3.77-3.90 (m, 2H) 4.69 (dd, J=9.00, 4.73 Hz, 1H) 7.35 (d, J=8.24 Hz, 1H)

Compound F47

To a Compound 46 (S)-tert-butyl 3-methyl-2-((tetrahydro-2H-pyran-4-yloxy)carbonylamino)butanoate (0.21 g, 0.697 mmol) was added HCl in dioxane (15 mL, 60.0 mmol) and the mixture was stirred at room temperature under nitrogen for three hours. The reaction was done and concentrated under reduced pressure to provide F47(S)-3-methyl-2-((tetrahydro-2H-pyran-4-yloxy)carbonylamino)butanoic acid (0.1694 g, 0.691 mmol, 100% yield) as a clear wax.

¹H NMR (500 MHz, DMSO-d₆) δ ppm 0.88 (t, J=6.71 Hz, 6H) 1.41-1.60 (m, 2H) 1.85 (d, J=12.21 Hz, 2H) 1.97-2.08 (m, 1H) 3.41 (t, J=10.68 Hz, 1H) 3.45-3.52 (m, 1H) 3.64-3.74 (m, 1H) 3.77-3.89 (m, 2H) 4.63-4.72 (m, 1H) 7.32 (d, J=8.55 Hz, 1H) 12.52 (s, 1H)

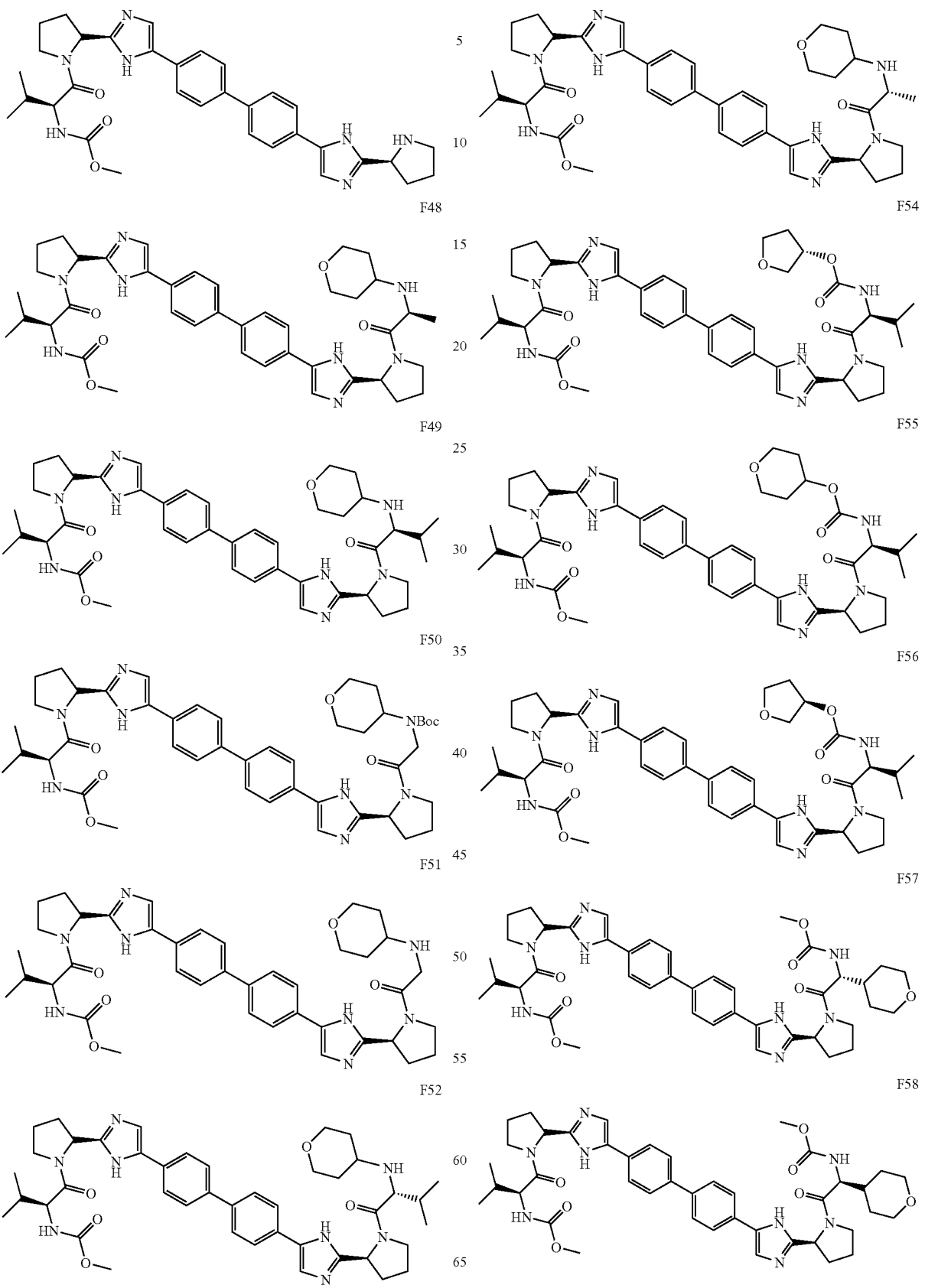

Compound F48 to F58 except F51 was prepared in analogous fashion to the procedure used to synthesize example 1 from LS18.

Compound F51 was prepared in analogous fashion to the procedure used to synthesize 1e from F50.

| Entry | Compound Name | Retention time (LC-Condition); homogeneity index MS data |
|---|---|---|
| F48 | methyl ((1S)-2-methyl-1-(((2S)-2-(4-(4'-(2-((2S)-1-(N-(tetrahydro-2H-pyran-4-yl)-L-alanyl)-2-pyrrolidinyl)-1H-imidazol-4-yl)-4-biphenylyl)-1H-imidazol-2-yl)-1-pyrrolidinyl)carbonyl)propyl)carbamate | RT = 2.103 minutes (condition 7, 98%); LRMS: Anal. Calcd. for C41H52N8O5 736.41; found: 737.07 (M + H)⁺. |
| F49 | methyl ((1S)-2-methyl-1-(((2S)-2-(4-(4'-(2-((2S)-1-(N-(tetrahydro-2H-pyran-4-yl)-L-valyl)-2-pyrrolidinyl)-1H-imidazol-4-yl)-4-biphenylyl)-1H-imidazol-2-yl)-1-pyrrolidinyl)carbonyl)propyl)carbamate | RT = 2.117 minutes (condition 7, 98%); LRMS: Anal. Calcd. for C43H56N8O5 764.44; found: 765.75 (M + H)⁺. |
| F50 | | RT = 2.547 minutes (condition 7, 98%); LRMS: Anal. Calcd. for C45H58N8O7 822.44; found: 823.17 (M + H)⁺. |
| F51 | methyl ((1S)-2-methyl-1-(((2S)-2-(4-(4'-(2-((2S)-1-(N-(tetrahydro-2H-pyran-4-yl)glycyl)-2-pyrrolidinyl)-1H-imidazol-4-yl)-4-biphenylyl)-1H-imidazol-2-yl)-1-pyrrolidinyl)carbonyl)propyl)carbamate | RT = 2.138 minutes (condition 7, 96%); LRMS: Anal. Calcd. for C40H50N8O5 722.39; found: 723.63 (M + H)⁺. |
| F52 | methyl ((1S)-2-methyl-1-(((2S)-2-(4-(4'-(2-((2S)-1-(N-(tetrahydro-2H-pyran-4-yl)-D-valyl)-2-pyrrolidinyl)-1H-imidazol-4-yl)-4-biphenylyl)-1H-imidazol-2-yl)-1-pyrrolidinyl)carbonyl)propyl)carbamate | RT = 2.083 minutes (condition 7, 98%); LRMS: Anal. Calcd. for C43H56N8O5 764.44; found: 765.78 (M + H)⁺. |
| F53 | methyl ((1S)-2-methyl-1-(((2S)-2-(4-(4'-(2-((2S)-1-(N-(tetrahydro-2H-pyran-4-yl)-D-alanyl)-2-pyrrolidinyl)-1H-imidazol-4-yl)-4-biphenylyl)-1H-imidazol-2-yl)-1-pyrrolidinyl)carbonyl)propyl)carbamate | RT = 0.963 minutes (condition 11, 95%); LRMS: Anal. Calcd. for C43H54N8O7 736.41; found: 737.54 (M + H)⁺. |
| F54 | (3S)-tetrahydro-3-furanyl ((1S)-1-(((2S)-2-(4-(4'-(2-((2S)-1-(N-(methoxycarbonyl)-L-valyl)-2-pyrrolidinyl)-1H-imidazol-4-yl)-4-biphenylyl)-1H-imidazol-2-yl)-1-pyrrolidinyl)carbonyl)-2-methylpropyl)carbamate | RT = 2.378 minutes (condition 7, 95%); LRMS: Anal. Calcd. for C43H54N8O7 794.41; found: 795.94 (M + H)⁺. |
| F55 | tetrahydro-2H-pyran-4-yl ((1S)-1-(((2S)-2-(4-(4'-(2-((2S)-1-(N-(methoxycarbonyl)-L-valyl)-2-pyrrolidinyl)-1H-imidazol-4-yl)-4-biphenylyl)-1H-imidazol-2-yl)-1-pyrrolidinyl)carbonyl)-2-methylpropyl)carbamate | RT = 2.447 minutes (condition 7, 99%); LRMS: Anal. Calcd. for C44H56N8O7 808.43; found: 809.42 (M + H)⁺. |
| F56 | (3R)-tetrahydro-3-furanyl ((1S)-1-(((2S)-2-(4-(4'-(2-((2S)-1-(N-(methoxycarbonyl)-L-valyl)-2-pyrrolidinyl)-1H-imidazol-4-yl)-4-biphenylyl)-1H-imidazol-2-yl)-1-pyrrolidinyl)carbonyl)-2-methylpropyl)carbamate | RT = 2.398 minutes (condition 7, 96%); LRMS: Anal. Calcd. for C43H54N8O7 794.41; found: 795.36 (M + H)⁺. |
| F57 | methyl ((1S)-1-(((2S)-2-(4-(4'-(2-((2S)-1-((2R)-2-((methoxycarbonyl)amino)-2-(tetrahydro-2H-pyran-4-yl)acetyl)-2-pyrrolidinyl)-1H-imidazol-5-yl)-4-biphenylyl)-1H-imidazol-2-yl)-1-pyrrolidinyl)carbonyl)-2-methylpropyl)carbamate | RT = 2.272 minutes (condition 7, 98%); LRMS: Anal. Calcd. for C42H52N8O7 780.40; found: 781.34 (M + H)⁺. |
| F58 | methyl ((1S)-1-(((2S)-2-(4-(4'-(2-((2S)-1-((2S)-2-((methoxycarbonyl)amino)-2-(tetrahydro-2H-pyran-4-yl)acetyl)-2-pyrrolidinyl)-1H-imidazol-5-yl)-4-biphenylyl)-1H-imidazol-2-yl)-1-pyrrolidinyl)carbonyl)-2-methylpropyl)carbamate | RT = 2.225 minutes (condition 7, 98%); LRMS: Anal. Calcd. for C42H52N8O7 780.40; found: 781.27 (M + H)⁺. |

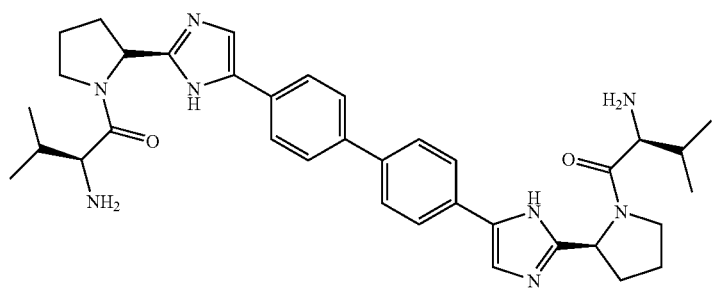

F59

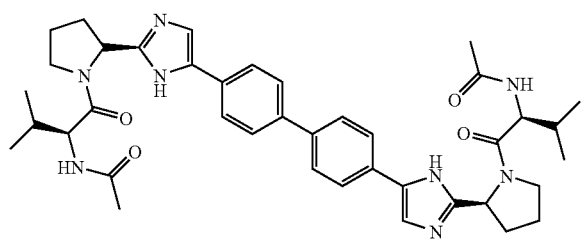

F60

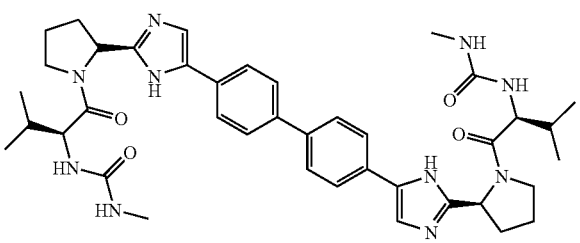

F63

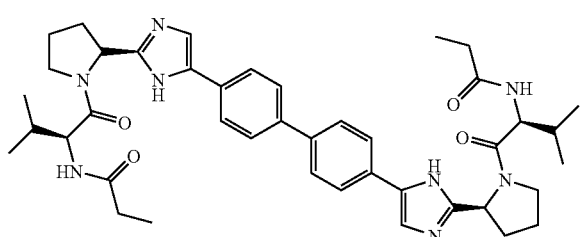

F61

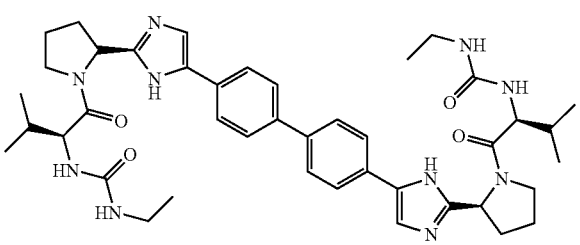

F64

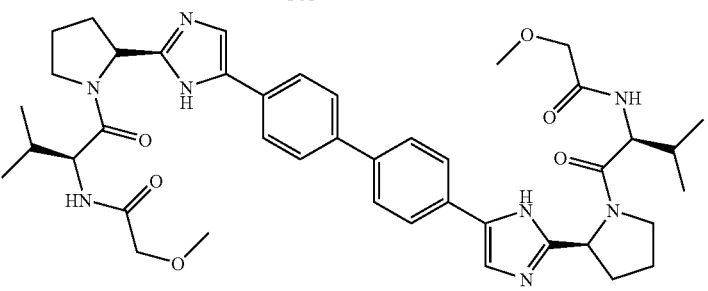

F62

Compound F59

Compound F59 was prepared in analogous fashion to the procedure used to synthesize 26a with following modification: Boc-L-val-OH was used in place of Boc-D-val-OH.

Compound F60 to F62 were prepared in analogous fashion to the procedure used to synthesize example 29 from F59.

Compound F63 and F64 were prepared in analogous fashion to the procedure used to synthesized Cap45.

| Entry | Compound Name | Retention time (LC-Condition); homogeneity index MS data |
|---|---|---|
| F59 | | RT = 1.743 minutes (condition 7, 98%); LRMS: Anal. Calcd. for C36H46N8O2 622.37; found: 624.07 (M + H)+. |
| F60 | N-((1S)-1-(((2S)-2-(4-(4'-(2-((2S)-1-((2S)-2-acetamido-3-methylbutanoyl)-2-pyrrolidinyl)-1H-imidazol-4-yl)-4-biphenylyl)-1H-imidazol-2-yl)-1-pyrrolidinyl)carbonyl)-2-methylpropyl)acetamide | RT = 2.047 minutes (condition 10, 98%); LRMS: Anal. Calcd. for C40H50N8O4 706.44; found: 707.77 (M + H)+. |
| F61 | N-((1S)-2-methyl-1-(((2S)-2-(4-(4'-(2-((2S)-1-((2S)-3-methyl-2-(propionylamino)butanoyl)-2-pyrrolidinyl)-1H-imidazol-4-yl)-4-biphenylyl)-1H-imidazol-2-yl)-1-pyrrolidinyl)carbonyl)propyl)propanamide | RT = 2.215 minutes (condition 10 98%); LRMS: Anal. Calcd. for C42H54N8O4 734.43; found: 735.87 (M + H)+. |
| F62 | 2-methoxy-N-((1S)-1-(((2S)-2-(4-(4'-(2-((2S)-1-((2S)-2-((methoxyacetyl)amino)-3-methylbutanoyl)-2-pyrrolidinyl)-1H-imidazol-4-yl)-4-biphenylyl)-1H-imidazol-2-yl)-1-pyrrolidinyl)carbonyl)-2-methylpropyl)acetamide | RT = 2.232 minutes (condition 10, 99%); LRMS: Anal. Calcd. for C42H54N8O6 766.93; found: 768.05 (M + H)+. |
| F63 | 1-methyl-3-((1S)-2-methyl-1-(((2S)-2-(4-(4'-(2-((2S)-1-(N-(methylcarbamoyl)-L-valyl)-2-pyrrolidinyl)-1H-imidazol-4-yl)-4-biphenylyl)-1H-imidazol-2-yl)-1-pyrrolidinyl)carbonyl)propyl)urea | RT = 2.082 minutes (condition 10, 95%); LRMS: Anal. Calcd. for C40H52N10O4 736.42; found: 737.86 (M + H)+. |
| F64 | 1-ethyl-3-((1S)-1-(((2S)-2-(4-(4'-(2-((2S)-1-((2S)-2-((ethylcarbamoyl)amino)-3-methylbutanoyl)-2-pyrrolidinyl)-1H-imidazol-4-yl)-4-biphenylyl)-1H-imidazol-2-yl)-1-pyrrolidinyl)carbonyl)-2-methylpropyl)urea | RT = 1.617 minutes (condition 12, 93%); LRMS: Anal. Calcd. for C42H56N10O4 764.45; found: 765.57 (M + H)+. |

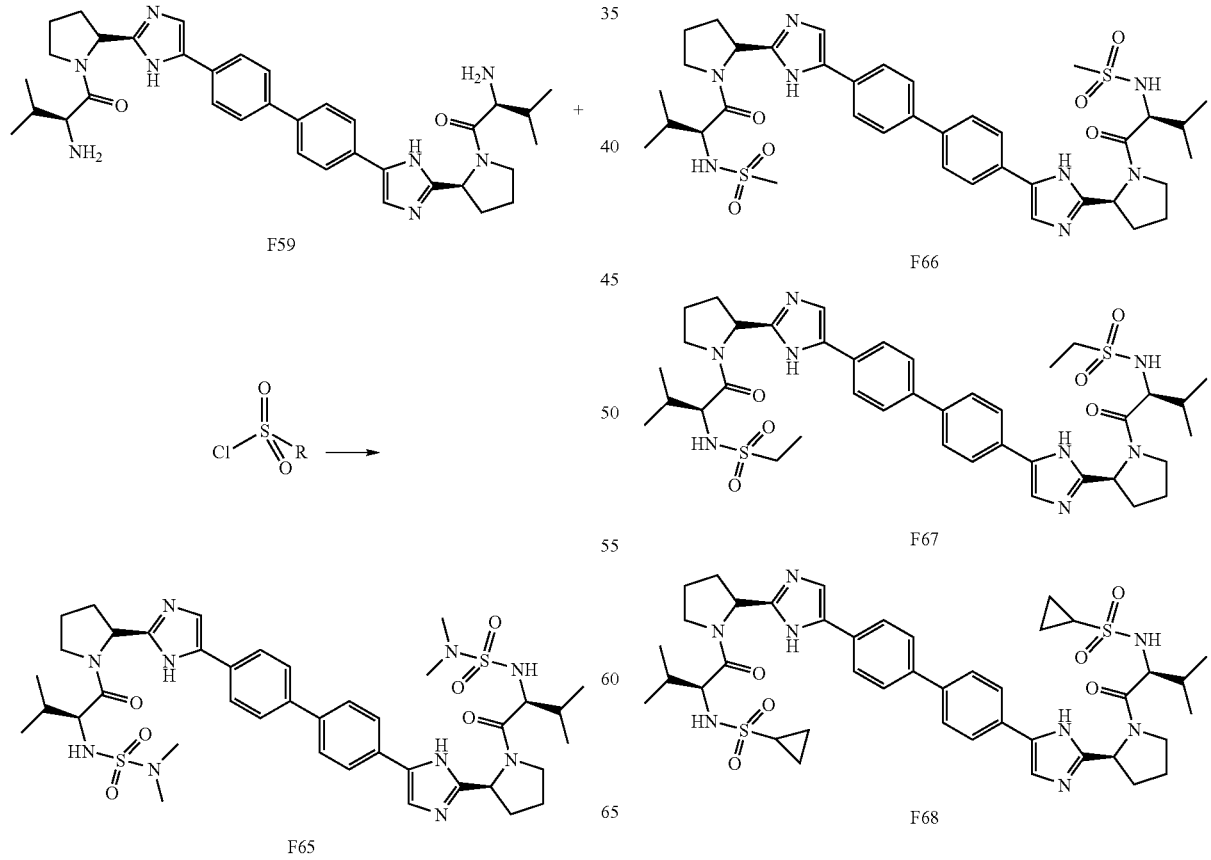

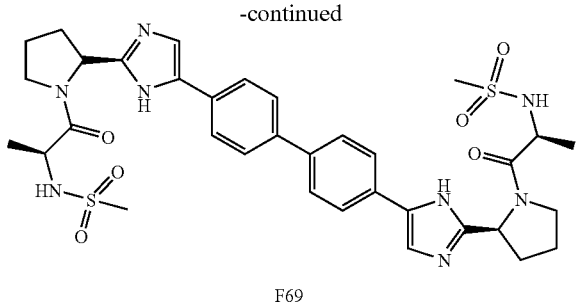

F69

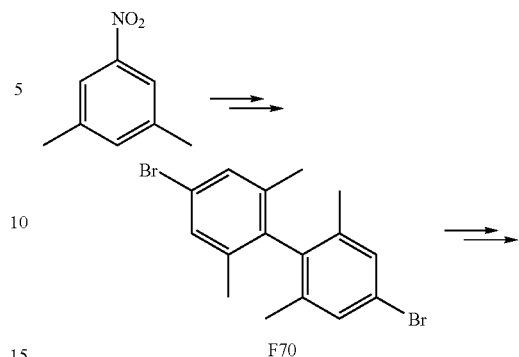

F70

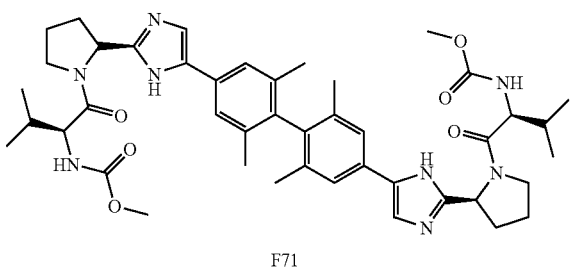

F71

Compound F65

To a solution of F59 (0.06 g, 0.074 mmol in DMF (1 mL) was added dimethylsulfamoyl chloride (0.016 mL, 0.148 mmol) and Hunig's Base (0.078 mL, 0.445 mmol) then stirred it at room temperature for 3 h. Solvent was removed by reduced pressure to get light brown oil which was purified by PreHPLC providing F65 N—((S)-1-((S)-2-(5-(4'-(2-((S)-1-((S)-2-(N,N-dimethylsulfamoylamino)-3-methylbutanoyl) pyrrolidin-2-yl)-1H-imidazol-5-yl)biphenyl-4-yl)-1H-imidazol-2-yl)pyrrolidin-1-yl)-3-methyl-1-oxobutan-2-yl) propane-2-sulfonamide (19.0 mg, 0.018 mmol, 24.08% yield)

$^1$H NMR (500 MHz, DMSO-d$_6$) δ ppm 0.65-1.03 (m, 12H) 1.87-2.08 (m, 4H) 2.06-2.27 (m, 4H) 2.37-2.46 (m, 2H) 2.56-2.69 (m, 12H) 3.66-3.92 (m, 6H) 5.14 (t, J=7.63 Hz, 2H) 7.49 (d, J=9.16 Hz, 2H) 7.89 (d, J=8.24 Hz, 4H) 7.96 (s, 4H) 8.14 (s, 2H) 14.72 (s, 2H)

RT=2.047 minutes (condition 10, 98%); LRMS: Anal. Calcd. for C$_{40}$H$_{50}$N$_8$O$_4$ 706.38. found: 707.77 (M+H)$^+$.

1b Fret (EC50,uM)=0.21

Compound F66 to F69 was prepared in analogous fashion to the procedure used to synthesize F65 from Compound F59.

Compound F70 was prepared following the procedure described in Anna Helms et al., *J. Am. Chem. Soc.* 1992 114(15) pp 6227-6238.

Compound F71 was prepared in analogous fashion to the procedure used to synthesize Example 1.

$^1$H NMR (500 MHz, DMSO-d$_6$) δ ppm 0.69-0.95 (m, 12H) 1.92 (s, 12H) 1.97-2.27 (m, 8H) 2.40 (s, 2H) 3.55 (s, 6H) 3.73-3.97 (m, 4H) 4.12 (t, J=7.78 Hz, 2H) 5.14 (t, J=7.02 Hz, 2H) 7.34 (d, J=8.24 Hz, 2H) 7.49-7.70 (m, 4H) 8.04 (s, 2H) 14.59 (s, 2H) RT=2.523 minutes (condition 7, 96%); LRMS: Anal. Calcd. for C$_{44}$H$_{58}$N$_8$O$_6$ 794.45. found: 795.48 (M+H)$^+$.

| Entry | Compound Name | Retention time (LC-Condition); homogeneity index MS data |
|---|---|---|
| F66 | N-((1S)-2-methyl-1-(((2S)-2-(4-(4'-(2-((2S)-1-((2S)-3-methyl-2-((methylsulfonyl)amino)butanoyl)-2-pyrrolidinyl)-1H-imidazol-4-yl)-4-biphenylyl)-1H-imidazol-2-yl)-1-pyrrolidinyl)carbonyl)propyl)methanesulfonamide | RT = 2.02 minutes (condition 10, 98%); LRMS: Anal. Calcd. for C38H50N8O6S2 778.38; found: 779.60 (M + H)$^+$. |
| F67 | N-((1S)-1-(((2S)-2-(4-(4'-(2-((2S)-1-((2S)-2-((ethylsulfonyl)amino)-3-methylbutanoyl)-2-pyrrolidinyl)-1H-imidazol-4-yl)-4-biphenylyl)-1H-imidazol-2-yl)-1-pyrrolidinyl)carbonyl)-2-methylpropyl)ethanesulfonamide | RT = 2.172 minutes (condition 10 98%); LRMS: Anal. Calcd. for C40H54N8O6S2 807.04; found: 808.42 (M + H)$^+$. |
| F68 | N-((1S)-1-(((2S)-2-(4-(4'-(2-((2S)-1-((2S)-2-((cyclopropylsulfonyl)amino)-3-methylbutanoyl)-2-pyrrolidinyl)-1H-imidazol-4-yl)-4-biphenylyl)-1H-imidazol-2-yl)-1-pyrrolidinyl)carbonyl)-2-methylpropyl)cyclopropanesulfonamide | RT = 2.217 minutes (condition 10, 93%); LRMS: Anal. Calcd. for C42H54N8O6S2 831.06; found: 832.49 (M + H)$^+$. |
| F69 | N-((1S)-1-methyl-2-((2S)-2-(5-(4'-(2-((2S)-1-(N-(methylsulfonyl)-L-alanyl)-2-pyrrolidinyl)-1H-imidazol-4-yl)-4-biphenylyl)-1H-imidazol-2-yl)-1-pyrrolidinyl)-2-oxoethyl)methanesulfonamide | RT = 1.983 minutes (condition 10, 95%); LRMS: Anal. Calcd. for C34H42N8O6S2 722.27; found: 723.68 (M + H)$^+$. |

Section cj

Synthesis of Carbamate Replacements

Example cj-2 and cj-3

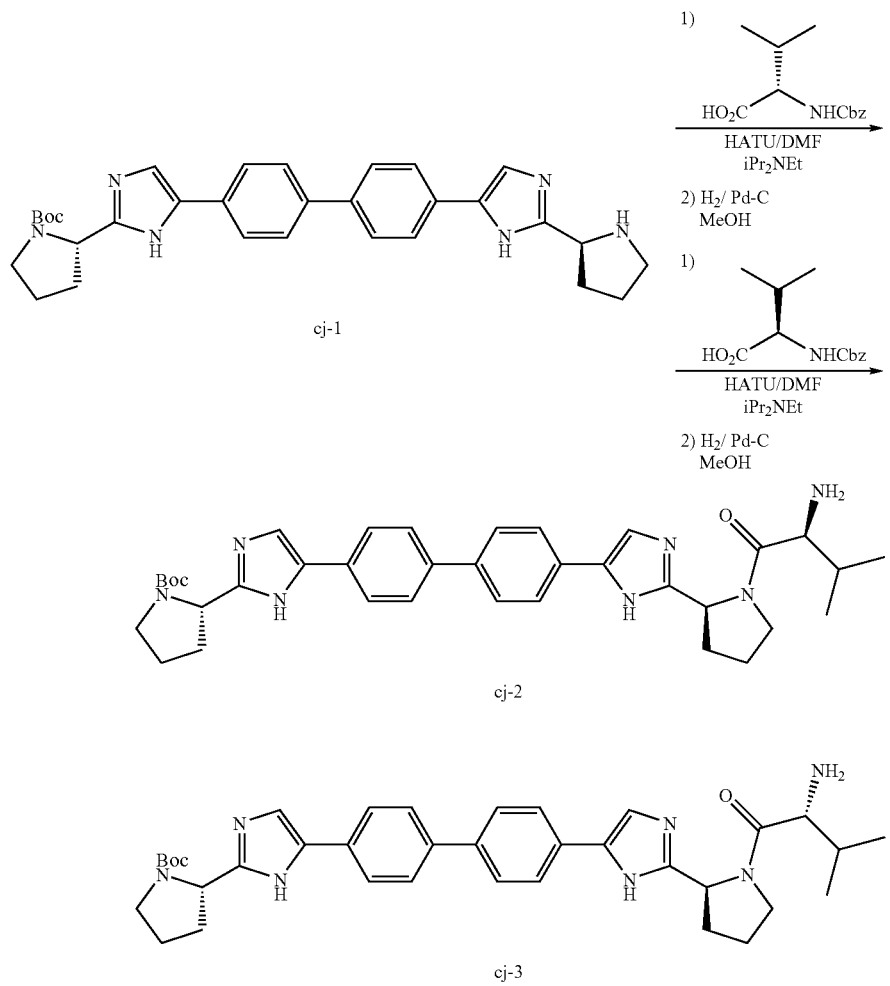

Preparation of (S)-tert-Butyl 2-(5-(4'-(2-((S)-1-((S)-2-amino-3-methylbutanoyl)pyrrolidin-2-yl)-1H-imidazol-5-yl)biphenyl-4-yl)-1H-imidazol-2-yl)pyrrolidine-1-carboxylate (cj-2)

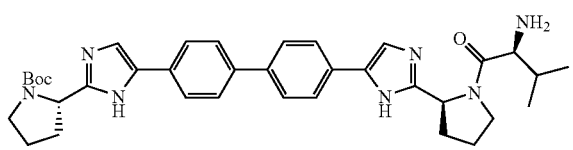

To a solution of (S)-tert-butyl 2-(5-(4'-(2-((S)-pyrrolidin-2-yl)-1H-imidazol-5-yl)biphenyl-4-yl)-1H-imidazol-2-yl)pyrrolidine-1-carboxylate (cj-1) (1.00 g, 1.91 mmol), iPr$_2$NEt (1.60 mL, 9.19 mmol) and N—Z-valine (0.62 g, 2.47 mmol) in DMF (10 mL) was added HATU (0.92 g, 2.42 mmol). The solution was allowed to stir at rt for 1 h and then it was poured into ice water (ca. 250 mL) and allowed to stand for 20 min. The mixture was filtered and the solid washed with water and then dried in vacuo overnight to afford a colorless solid (1.78 g) which was used as such in the next step. LCMS: Anal. Calcd. for $C_{44}H_{51}N_7O_5$: 757. found: 758 (M+H)$^+$. A mixture of this material (1.70 g) and 10% Pd—C (0.37 g) in MeOH (100 mL) was hydrogenated (balloon pressure) for 12 h. The mixture was then filtered and the solvent removed in vacuo. The residue was purified by silica gel chromatography (Biotage system/0-10% MeOH—CH$_2$Cl$_2$) to afford the title compound as a light yellow foam (0.90 g, 76%).

$^1$HNMR (400 MHz, DMSO-d$_6$) δ 12.18 (s, 0.35H), 11.73 (s, 0.65H), 11.89 (s, 0.65H), 11.82 (s, 0.35H), 7.77-7.81 (m, 3H), 7.57-7.71 (m, 5H), 7.50-7.52 (m, 2H), 5.17 (dd, J=3.6, 6.5 Hz, 0.3H), 5.08 (dd, J=3.6, 6.5 Hz, 0.7H), 4.84 (m, 0.3H), 4.76 (m, 0.7H), 3.67-3.69 (m, 1H), 3.50-3.62 (m, 1H), 3.34-3.47 (m, 2H), 2.22-2.28 (m, 2H), 2.10-2.17 (m, 2H), 1.74-2.05 (m, 6H), 1.40 (s, 4H), 1.15 (s, 5H), 0.85-0.91 (m, 4H), 0.79 (d, J=6.5 Hz, 2H).

LCMS: Anal. Calcd. for $C_{36}H_{45}N_7O_3$: 623. found: 624 (M+H)$^+$.

Preparation of (S)-tert-Butyl 2-(5-(4'-(2-((S)-1-((R)-2-amino-3-methylbutanoyl)pyrrolidin-2-yl)-1H-imidazol-5-yl)biphenyl-4-yl)-1H-imidazol-2-yl)pyrrolidine-1-carboxylate (cj-3)

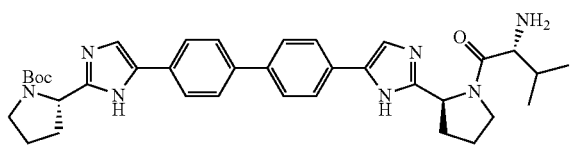

(S)-tert-Butyl 2-(5-(4'-(2-((S)-1-((R)-2-amino-3-methylbutanoyl)pyrrolidin-2-yl)-1H-imidazol-5-yl)biphenyl-4-yl)-1H-imidazol-2-yl)pyrrolidine-1-carboxylate (cj-3) was prepared using the same method used to prepare cj-2 to give a colorless foam (1.15 g, 76%). $^1$HNMR (400 MHz, DMSO-$d_6$) δ 12.17 (s, 0.35H), 12.04 (s, 0.65H), 11.89 (s, 0.65H), 11.81 (s, 0.35H), 7.78-7.83 (m, 3H), 7.60-7.71 (m, 5H), 7.43-7.52 (m, 2H), 5.22-5.25 (m, 0.4H), 5.05-5.07 (m, 0.6H), 4.83-4.86 (m, 0.5H), 4.72-4.78 (m, 0.5H), 3.78-3.84 (m, 1H), 3.49-3.64 (m, 2H), 3.35-3.43 (m, 2H), 2.19-2.32 (m, 1H), 2.04-2.17 (m, 3H), 1.95-2.04 (m, 2H), 1.76-1.90 (m, 3H), 1.40 (s, 4H), 1.15 (s, 5H), 0.85-0.91 (m, 4H), 0.67 (d, J=6.5 Hz, 1H), 0.35 (d, J=6.5 Hz, 1H). LCMS: Anal. Calcd. for $C_{36}H_{45}N_7O_3$: 623. found: 624 (M+H)$^+$.

Example cj-4 and cj-5

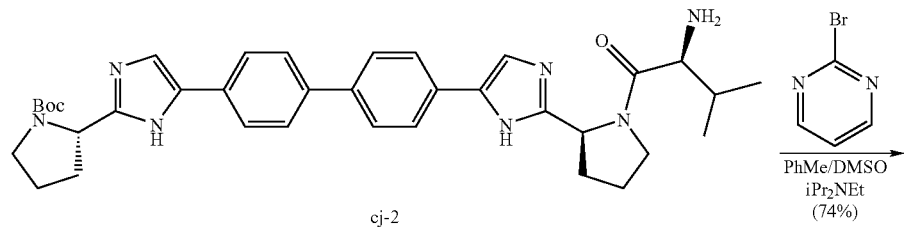

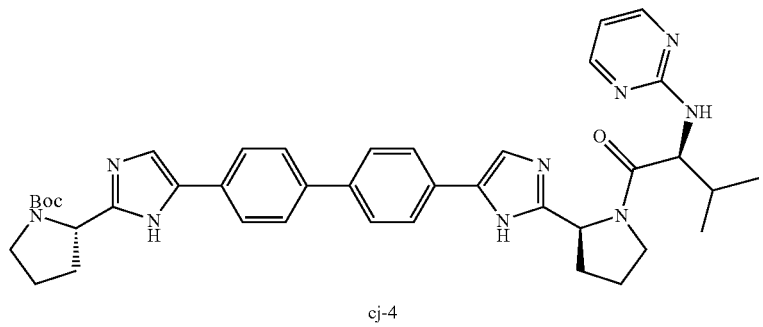

cj-4

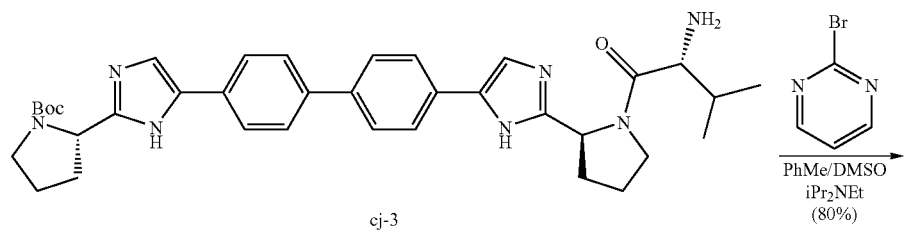

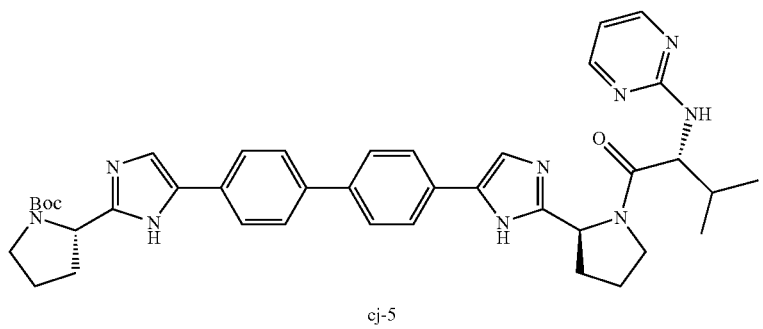

cj-5

Preparation of (S)-tert-Butyl 2-(5-(4'-(2-((S)-1-((S)-3-methyl-2-(pyrimidin-2-ylamino)butanoyl)pyrrolidin-2-yl)-1H-imidazol-5-yl)biphenyl-4-yl)-1H-imidazol-2-yl)pyrrolidine-1-carboxylate (cj-4)

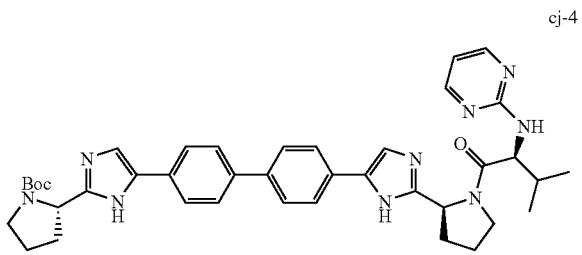

cj-4

A mixture of (S)-tert-butyl 2-(5-(4'-(2-((S)-1-((s)-2-amino-3-methylbutanoyl)pyrrolidin-2-yl)-1H-imidazol-5-yl)biphenyl-4-yl)-1H-imidazol-2-yl)pyrrolidine-1-carboxylate (cj-2) (0.45 g, 0.72 mmol), 2-bromopyrimidine (0.37 g, 2.34 mmol) and iPr$_2$NEt (0.20 mL, 1.18 mmol) in toluene-DMSO (4:1, 5 mL) was heated at 90° C. overnight. The volatiles were removed in vacuo and the residue was purified by preparative HPLC (YMC Pack C-1 8, 30×100 mm/MeCN—H$_2$O-TFA). The title compound (0.56 g, 74%), as its TFA salt, was obtained as a yellow-orange glass.

$^1$HNMR (400 MHz, DMSO-d$_6$) δ 14.56 (br s, 2H), 8.28 (d, J=5.0 Hz, 1H), 8.12-8.20 (m, 2H), 7.94-7.97 (m, 3H), 7.83-7.91 (m, 5H), 7.06 (d, J=8.1 Hz, 1H), 6.62 (app t, J=5.0 Hz, 1H), 4.99-5.10 (m, 2H), 4.50 (app t, J=7.7 Hz, 1H), 4.07-4.12 (m, 2H), 3.83-3.87 (m, 1H), 3.56-3.62 (m, 1H), 3.40-3.47 (m, 2H), 2.36-2.41 (m, 1H), 1.94-2.22 (m, 6H), 1.40 (s, 4H), 1.17 (s, 5H), 0.88 (app t, J=6.5 Hz, 6H).

LCMS: Anal. Calcd. for C$_{40}$H$_{47}$N$_9$O$_3$: 701. found: 702 (M+H)$^+$.

Preparation of (S)-tert-Butyl-2-(5-(4'-(2-((S)-1-((R)-3-methyl-2-(pyrimidin-2-ylamino)butanoyl)pyrrolidin-2-yl)-1H-imidazol-5-yl)biphenyl-4-yl)-1H-imidazol-2-yl)pyrrolidine-1-carboxylate (cj-5)

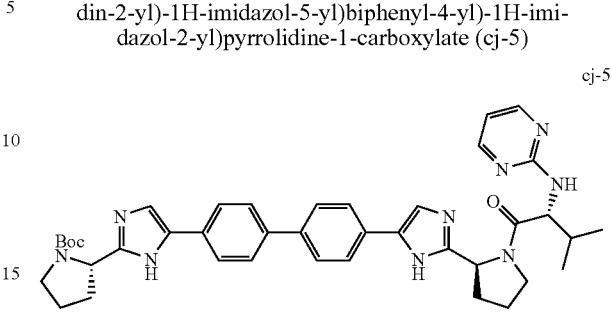

cj-5

The TFA salt of the title compound was prepared following the same method used to prepare cj-4 to give a light yellow solid (0.375 g, 59%).

$^1$HNMR (400 MHz, DMSO-d$_6$) δ 14.67 (br s, 2H), 8.30 (d, J=4.3 Hz, 1H), 8.04-8.19 (m, 2H), 7.84-7.96 (m, 8H), 6.88 (d, J=8.6 Hz, 1H), 6.61 (app t, J=4.5 Hz, 1H), 5.17 (dd, J=4.4, 8.0 Hz, 1H), 5.00-5.07 (m, 1H), 4.67 (dd, J=7.3, 8.1 Hz, 1H), 3.91-3.96 (m, 1H), 3.70-3.75 (m, 1H), 3.56-3.62 (m, 1H), 3.42-3.45 (m, 1H), 2.39-2.43 (m, 2H), 2.04-2.16 (m, 5H), 1.94-1.97 (m, 2H), 1.40 (s, 4H), 1.17 (s, 5H), 0.95 (d, J=6.6 Hz, 2.5H), 0.91 (d, J=6.6 Hz, 2.5H), 0.86 (d, J=6.6 Hz, 0.5H), 0.81 (d, J=6.6 Hz, 0.5H).

LCMS: Anal. Calcd. for C$_{40}$H$_{47}$N$_9$O$_3$: 701. found: 702 (M+H)$^+$.

Example cj-6 and cj-7

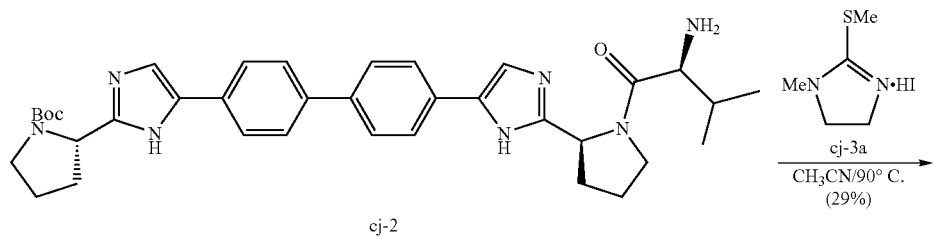

cj-2

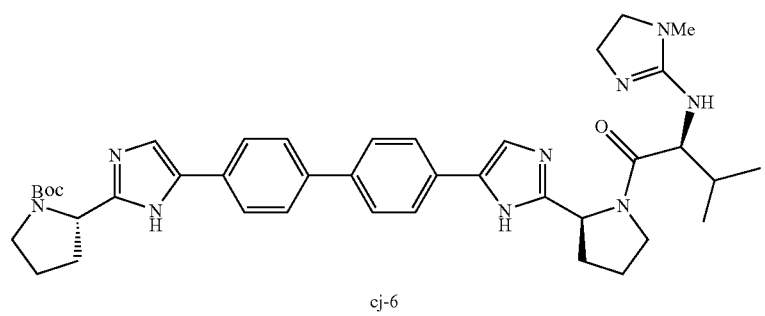

cj-6

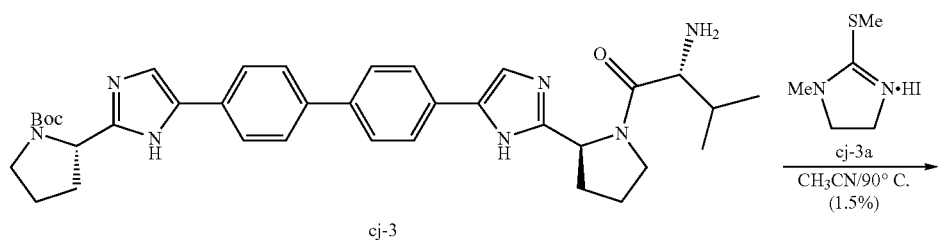

cj-3

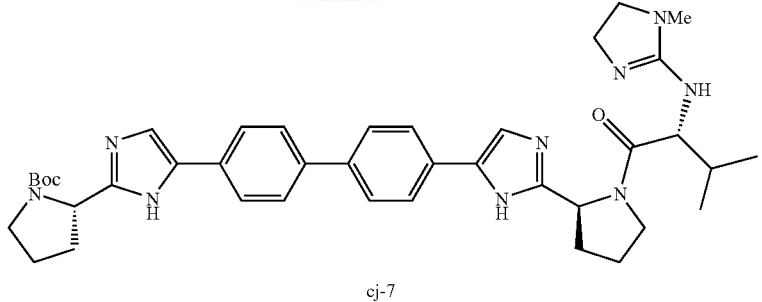

cj-7

Preparation of 1-Methyl-2-(methylthio)-4,5-dihydro-1H-imidazole hydroiodide

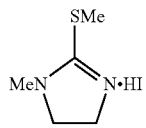

cj-3a

The title compound was prepared according to: Kister, J.; Assef, G.; Dou, H. J.-M.; Metzger, J. *Tetrahedron* 1976, 32, 1395. Thus, a solution of N-methylethylenediamine (10.8 g, 146 mmol) in EtOH—H$_2$O (1:1, 90 mL) was preheated to 60° C. and CS$_2$ (9.0 mL, 150 mmol) was added dropwise. The resulting mixture was heated at 60° C. for 3 h and then conc. HCl (4.7 mL) was slowly added. The temperature was raised to 90° C. and stirring was continued for 6 h. After the cooled mixture had been stored at −20° C., it was filtered and the resulting solid dried in vacuo to afford 1-methylimidazolidine-2-thione (8.43 g, 50%) as a beige solid.

$^1$HNMR (400 MHz, CDCl$_3$) δ 5.15 (s, br, 1H), 3.67-3.70 (m, 2H), 3.53-3.58 (m, 2H), 3.11 (s, 3H).

To a suspension of 1-methylimidazolidine-2-thione (5.17 g, 44.5 mmol) in acetone (50 mL) was added MeI (2.9 mL, 46.6 mmol). The solution was allowed to stir at room temperature for 4 h and the resulting solid was quickly filtered and then dried in vacuo to give 1-methyl-2-(methylthio)-4,5-dihydro-1H-imidazole hydroiodide (8.79 g, 77%) as beige solid.

$^1$HNMR (400 MHz, CDCl$_3$) δ 9.83 (s, br, 1H), 3.99-4.12 (m, 4H), 3.10 (s, 3H), 2.99 (s, 3H).

Preparation of (S)-tert-Butyl 2-(5-(4'-(2-((S)-1-((S)-3-methyl-2-(1-methyl-4-5-dihydroimidazol-2-ylamino)butanoyl)pyrrolidin-2-yl)-1H-imidazol-5-yl)biphenyl-4-yl)-1H-imidazol-2-yl)pyrrolidine-1-carboxylate (cj-6)

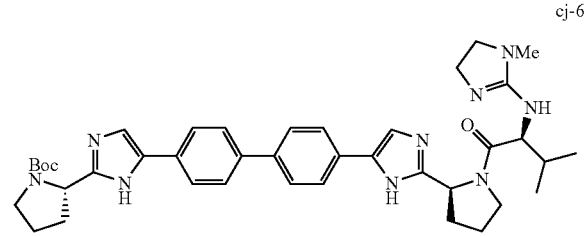

cj-6

A mixture of (S)-tert-butyl 2-(5-(4'-(2-((S)-1-((s)-2-amino-3-methylbutanoyl)pyrrolidin-2-yl)-1H-imidazol-5-yl)biphenyl-4-yl)-1H-imidazol-2-yl)-pyrrolidine-1-carboxylate (cj-2) (0.280 g, 0.448 mmol) and 1-methyl-2-(methylthio)-4,5-dihydro-1H-imidazole hydroiodide (cj-3a) (0.121 g, 0.468 mmol) in CH$_3$CN (5 mL) was heated at 90° C. for 12 h. Another 0.030 g of 1-methyl-2-(methylthio)-4,5-dihydro-1H-imidazole hydroiodide (cj-3a) was added and heating continued for a further 12 h. The crude reaction mixture was directly purified by prep HPLC (Luna C—18/MeCN—H$_2$O-TFA) to give the TFA salt of the title compound (0.089 g) as a light yellow solid which was used as such in the subsequent steps.

LCMS: Anal. Calcd. for C$_{40}$H$_{51}$N$_9$O$_3$: 705. found: 706 (M+H)$^+$.

Preparation of (S)-tert-Butyl 2-(5-(4'-(2-((S)-1-((R)-3-methyl-2-(1-methyl-4-5-dihydroimidazol-2-ylamino)butanoyl)pyrrolidin-2-yl)-1H-imidazol-5-yl)biphenyl-4-yl)-1H-imidazol-2-yl)pyrrolidine-1-carboxylate (cj-7)

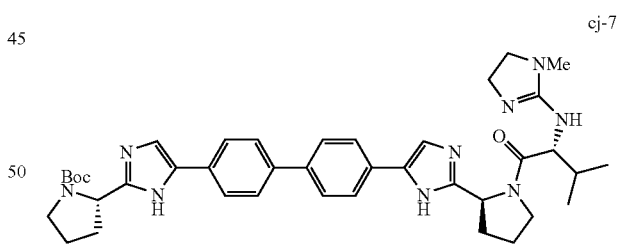

cj-7

The title compound was prepared from cj-3 according to the method described for the synthesis of cj-6, except that the reaction mixture was initially purified by prep HPLC (YMC-Pack 25×250 mm/MeCN—H$_2$O—NH$_4$OAc) and then repurified by prep HPLC (Luna Phenyl-hexyl/MeCN—H$_2$O—NH$_4$OAc). This gave the desired product (0.005 g) as a foam which was used as such in the subsequent steps.

LCMS: Anal. Calcd. for C$_{40}$H$_{51}$N$_9$O$_3$: 705. found: 706 (M+H)$^+$.

Example cj-8 and cj-9

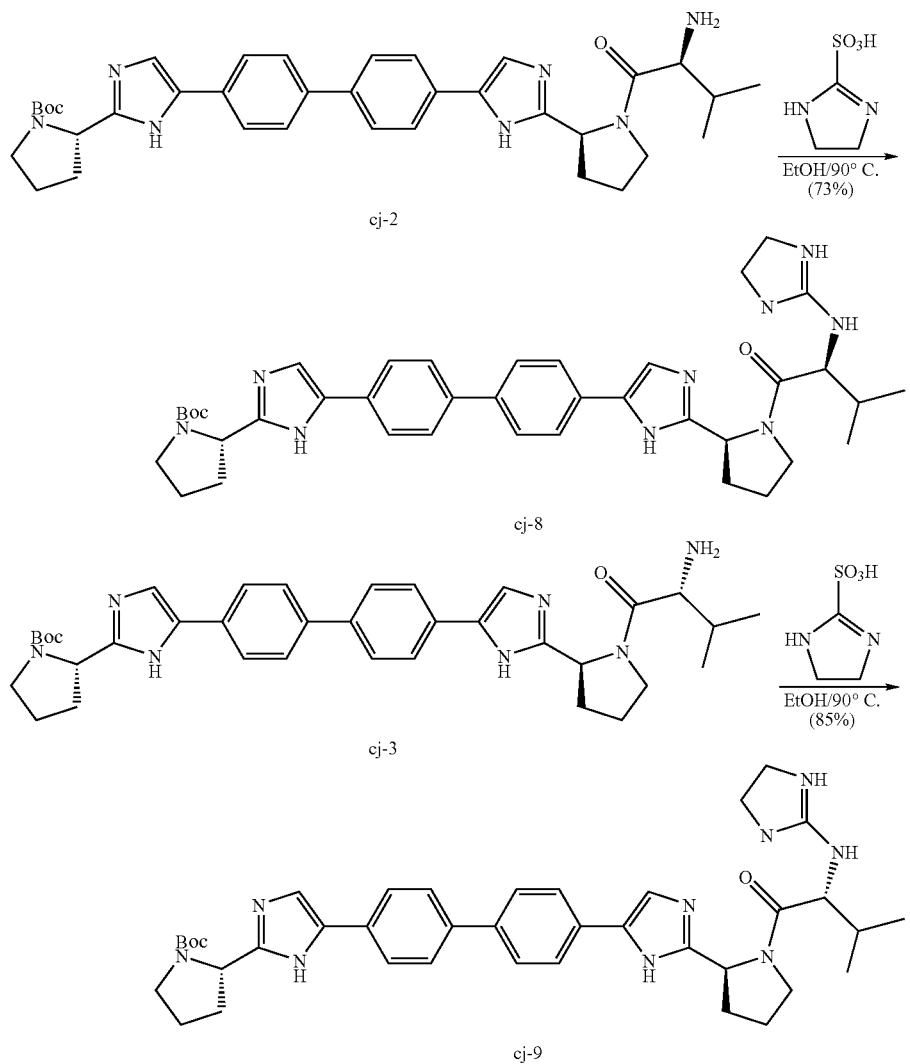

Preparation of (S)-tert-Butyl 2-(5-(4'-(2-((S)-1-((S)-3-methyl-2-(3,4-dihydroimidazol-2-ylamino)butanoyl)pyrrolidin-2-yl)-1H-imidazol-5-yl)biphenyl-4-yl)-1H-imidazol-2-yl)pyrrolidine-1-carboxylate (cj-8)

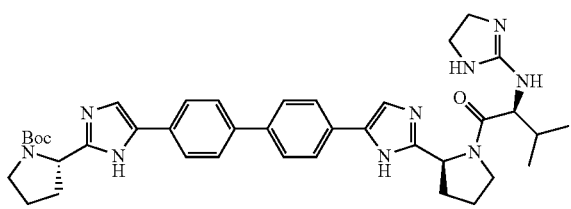

A mixture of (s)-tert-butyl 2-(5-(4'-(2-((S)-1-((s)-2-amino-3-methylbutanoyl)pyrrolidin-2-yl)-1H-imidazol-5-yl)biphenyl-4-yl)-1H-imidazol-2-yl)pyrrolidine-1-carboxylate (cj-2) (0.298 g, 0.480 mmol), 4,5-dihydro-1H-imidazole-2-sulfonic acid (AstaTech) (0.090 g, 0.60 mmol) and iPr$_2$NEt (0.083 mL, 0.48 mmol) in EtOH (4 mL) was heated at 100° C. for 12 h. The cooled mixture was evaporated to dryness and the residue was purified by prep HPLC (Luna 5u C18/ MeCN—H$_2$O-TFA, ×2) to afford the TFA salt of the title compound (0.390 g, 73%) as a light yellow solid.

$^1$HNMR (400 MHz, DMSO-d$_6$) δ 14.66 (br s, 2H), 8.51 (br s, 1H), 8.20 (d, J=10.1 Hz, 2H), 8.10 (br s, 1H), 7.82-7.91 (m, 7H), 7.30 (br s, 1H), 5.12 (t, J=7.1 Hz, 1H), 4.97-5.05 (m, 2H), 4.37 (dd, J=4.3, 10.1 Hz, 2H), 3.82-3.86 (m, 2H), 3.73-3.77 (m, 2H), 3.59 (s, 4H), 3.39-3.48 (m, 2H), 2.15-2.25 (m, 2H), 1.93-2.07 (m, 5H), 1.40 (s, 4H), 1.17 (s, 5H), 0.93 (d, J=6.6 Hz, 3H), 0.69 (br s, 3H).

LCMS: Anal. Calcd. for $C_{39}H_{49}N_9O_3$: 691. found: 692 (M+H)$^+$.

Preparation of (S)-tert-Butyl 2-(5-(4'-(2-((S)-1-((R)-3-methyl-2-(3,4-dihydroimidazol-2-ylamino)butanoyl)pyrrolidin-2-yl)-1H-imidazol-5-yl)biphenyl-4-yl)-1H-imidazol-2-yl)pyrrolidine-1-carboxylate (cj-9)

The title compound was prepared from cj-3 according to the same method used to prepare cj-8 to afford the TFA salt (0.199 g, 57%) as a yellow glass.

$^1$HNMR (400 MHz, DMSO-d$_6$) δ 14.58 (br s, 4H), 8.23 (d, J=9.6 Hz, 1H), 8.11 (s, 1H), 7.87-7.89 (m, 6H), 7.25 (br s, 1H), 5.17-5.20 (m, 1H), 4.96-5.04 (m, 1H), 4.37 (dd, J=5.5, 9.6 Hz, 1H), 3.91-3.95 (m, 2H), 3.37-3.46 (m, partially obscured by H$_2$O, 4H), 2.39-2.42 (m, partially obscured by solvent, 2H), 2.01-2.09 (m, 4H), 1.94-1.98 (m, 2H), 1.40 (s, 3H), 1.17 (s, 6H), 0.95 (d, J=6.5 Hz, 2.5H), 0.85 (d, J=6.5 Hz, 2.5H), 0.66 (d, J=7.0 Hz, 0.5H), 0.54 (d, J=6.5 Hz, 0.5H).

LCMS: Anal. Calcd. for C$_{39}$H$_{49}$N$_9$O$_3$: 691. found: 692 (M+H)$^+$.

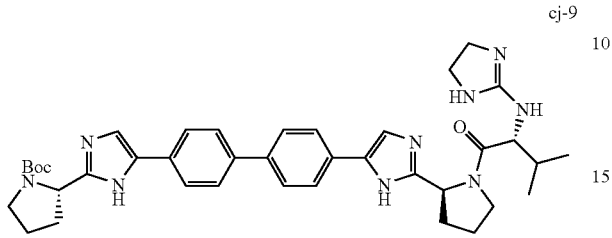

cj-9

Example cj-1

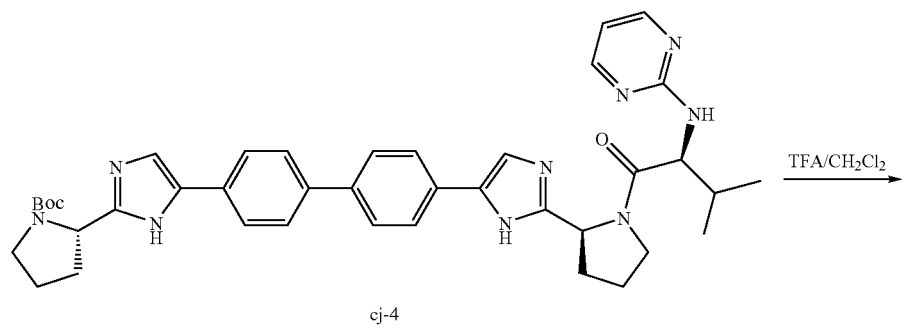

cj-4

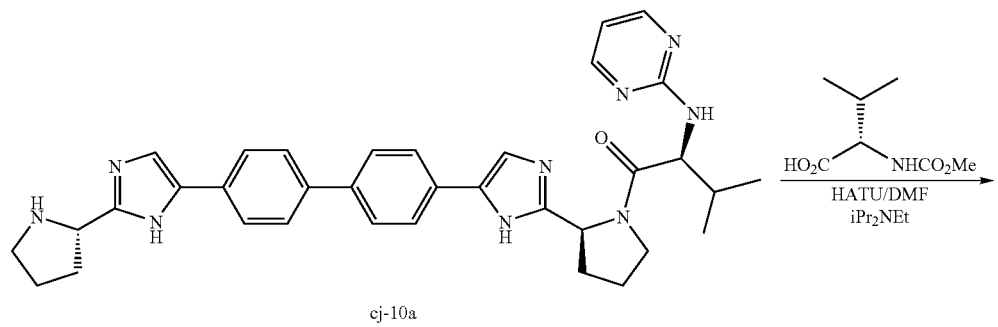

cj-10a

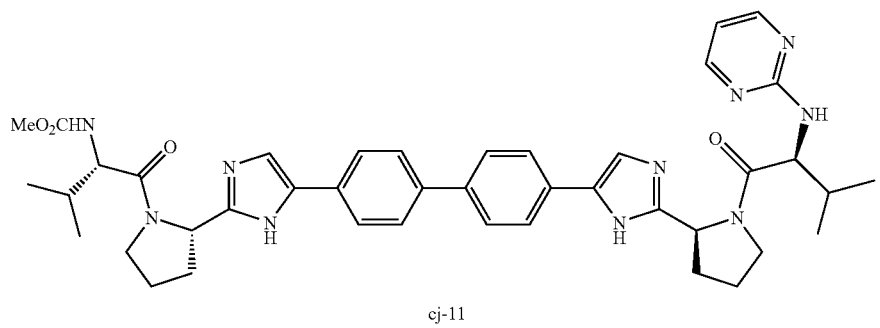

cj-11

Preparation of (S)-3-Methyl-2-(pyrimidin-2-ylamino)-1-((S)-2-(5-(4'-(2-((S)-pyrrolidin-2-yl)-1H-imidazol-5-yl)biphenyl-4-yl)-1H-imidazol-2-yl)pyrrolidin-1-yl)butan-1-one (cj-10a)

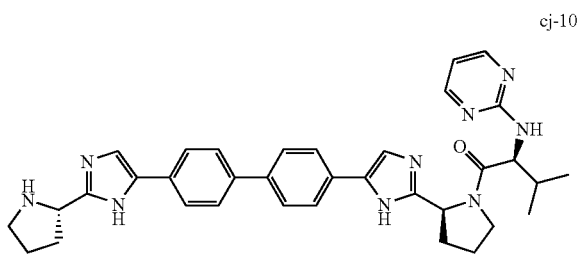

cj-10

Step 1: A solution of the TFA salt of (S)-tert-butyl 2-(5-(4'-(2-((S)-1-((S)-3-methyl-2-(pyrimidin-2-ylamino)butanoyl)pyrrolidin-2-yl)-1H-imidazol-5-yl)biphenyl-4-yl)-1H-imidazol-2-yl)pyrrolidine-1-carboxylate (cj-4) (0.208 g, 0.199 mmol) in a mixture $CH_2Cl_2$ (4 mL) and TFA (3 mL) was stirred at room temperature for 1.5 h. The solvents were then removed in vacuo and the residue was purified by prep HPLC (Luna 5u C18/MeCN—$H_2O$-TFA) to give the TFA salt of the title compound (0.391 g) as an orange gum.

$^1$HNMR (400 MHz, DMSO-$d_6$) δ 14.53 (br s, 3H), 9.52-9.57 (m, 2H), 8.98-9.04 (m, 2H), 8.28 (d, J=4.6 Hz, 2H), 8.13 (br s, 1H), 7.79-7.91 (m, 7H), 7.07 (d, J=8.1 Hz, 1H), 6.62 (app t, J=4.8 Hz, 1H), 5.07 (t, J=7.1 Hz, 1H), 4.72-4.78 (m, 2H), 4.48-4.51 (m, 1H), 4.08-4.12 (m, 2H), 3.28-3.36 (m, 2H), 2.37-2.42 (m, 2H), 1.97-2.22 (m, 6H), 0.88 (app t, J=4.5 Hz, 6H).

LCMS: Anal. Calcd. for $C_{35}H_{39}N_9O$: 601. found: 602 $(M+H)^+$.

Similarly, the following examples were prepared according to the representative method above;

| Example | Structure | LCMS |
| --- | --- | --- |
| cj-10a (from cj-3) | 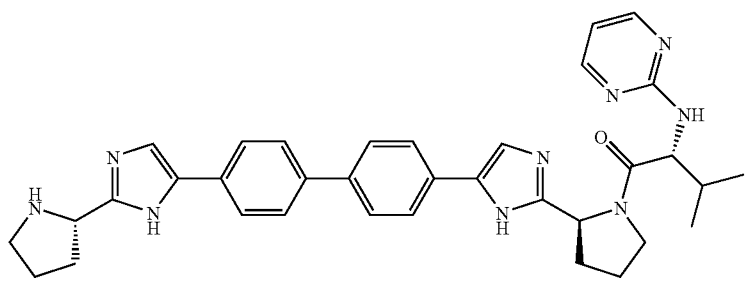 | LCMS: Anal. Calcd. for $C_{35}H_{39}N_9O$: 601; found: 602 $(M + H)^+$. |
| cj-10b (from cj-2) | 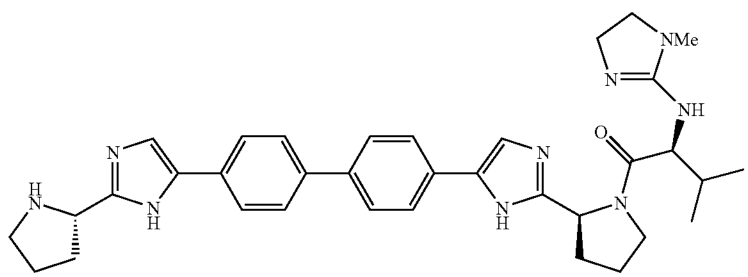 | LCMS: Anal. Calcd. for $C_{35}H_{43}N_9O$: 605; found: 606 $(M + H)^+$. |
| cj-10c (from cj-3) | 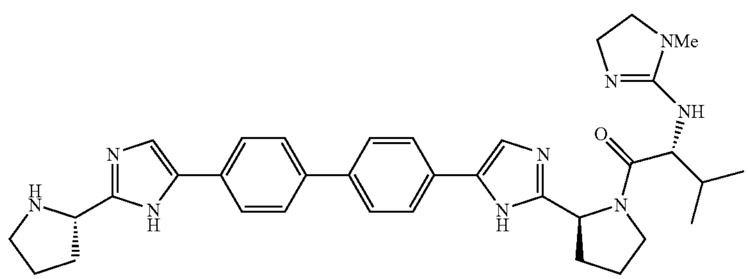 | LCMS: Anal. Calcd. for $C_{35}H_{43}N_9O$: 605; found: 606 $(M + H)^+$. |

| Example | Structure | LCMS |
|---|---|---|
| cj-10d (from cj-2) | 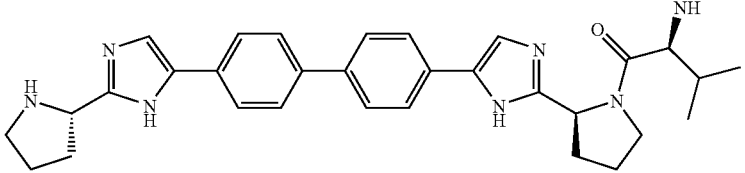 | LCMS: Anal. Calcd. for $C_{34}H_{41}N_9O$: 591; found: 592 $(M + H)^+$. |
| cj-10e (from cj-3) | 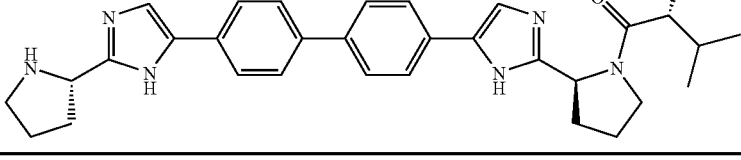 | LCMS: Anal. Calcd. for $C_{34}H_{41}N_9O$: 591; found: 592 $(M + H)^+$. |

Preparation of methyl ((1S)-2-methyl-1-(((2S)-2-(5-(4'-(2-((2S)-1-(N-2-pyrimidinyl-L-valyl)-2-pyrrolidinyl)-1H-imidazol-5-yl)-4-biphenylyl)-1H-imidazol-2-yl)-1-pyrrolidinyl)carbonyl)propyl)carbamate (cj-11)

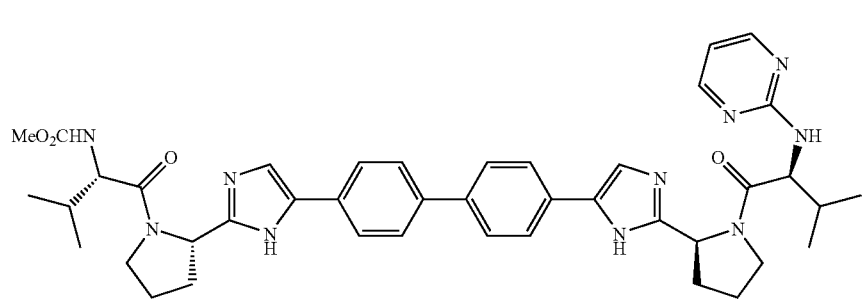

cj-11 methyl ((1S)-2-methyl-1-(((2S)-2-(5-(4'-(2-((2S)-1-(N-2-pyrimidinyl-L-valyl)-2-pyrrolidinyl)-1H-imidazol-5-yl)-4-biphenylyl)-1H-imidazol-2-yl)-1-pyrrolidinyl)carbonyl)propyl)carbamate Step 2: To a solution of the TFA salt of (S)-3-methyl-2-(pyrimidin-2-ylamino)-1-((S)-2-(5-(4'-(2-((S)-pyrrolidin-2-yl)-1H-imidazol-5-yl)biphenyl-4-yl)-1H-imidazol-2-yl)pyrrolidin-1-yl)butan-1-one (cj-10) (0.208 g, 0.197 mmol) in DMF (4 mL) was added iPr$_2$NEt (0.20 mL, 1.15 mmol), (S)-2-(methoxycarbonylamino)-3-methylbutanoic acid (0.049 g, 0.28 mmol) and HATU (0.105 g, 0.276 mmol). The solution was stirred for 1.5 h at room temperature, diluted with MeOH (2 mL) and purified directly by prep HPLC (Luna 5u C18/MeCN—H$_2$O—NH$_4$OAc). This material was repurified by flash chromatography (SiO$_2$/2-10% MeOH—CH$_2$Cl$_2$) to give a solid which was lyophilized from CH$_3$CN—H$_2$O to give the title compound (48.6 mg, 32%) as a colourless solid.

$^1$HNMR (400 MHz, DMSO-d$_6$) δ 11.78 (br s, 1H), 8.28 (d, J=4.5 Hz, 1H), 7.76-7.79 (m, 4H), 7.66-7.69 (m, 4H), 7.48-7.51 (m, 2H), 7.29 (d, J=8.6 Hz, 1H), 6.93 (d, J=8.1 Hz, 1H), 6.60 (app t, J=4.5 Hz, 1H), 5.03-5.09 (m, 2H), 4.48 (t. J=8.1 Hz, 1H), 3.99-4.08 (m, 2H), 3.78-3.85 (m, 2H) 3.53 (s, 3H), 2.12-2.21 (m, 4H), 1.87-2.05 (m, 7H), 0.83-0.97 (m, 12H).

LCMS: Anal. Calcd. for $C_{42}H_{50}N_{10}O_4$: 758. found: 759 (M+H)$^+$.

Similarly, the following examples were prepared according to the representative method above;

| Example | Compound Name | Structure | LCMS |
|---|---|---|---|
| cj-11a (from cj-10 and Cap-52) | methyl ((1S)-1-methyl-2-oxo-2-((2S)-2-(5-(4'-(2-((2S)-1-(N-2-pyrimidinyl-L-valyl)-2-pyrrolidinyl)-1H-imidazol-5-yl)-4-biphenylyl)-1H-imidazol-2-yl)-1-pyrrolidinyl)ethyl)carbamate | 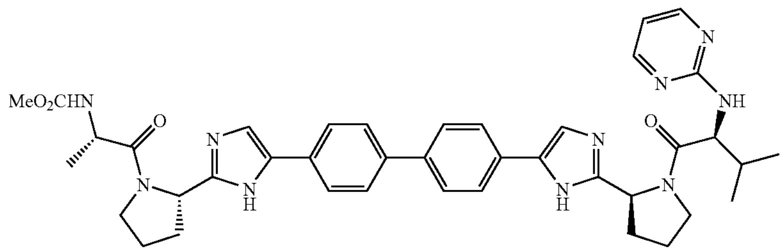 | LCMS: Anal. Calcd. for $C_{40}H_{46}N_{10}O_4$: 730; found: 731 $(M + H)^+$. |
| cj-11b (from cj-10 and Cap-4) | methyl ((1R)-2-oxo-1-phenyl-2-((2S)-2-(5-(4'-(2-((2S)-1-(N-2-pyrimidinyl-L-valyl)-2-pyrrolidinyl)-1H-imidazol-5-yl)-4-biphenylyl)-1H-imidazol-2-yl)-1-pyrrolidinyl)ethyl)carbamate | 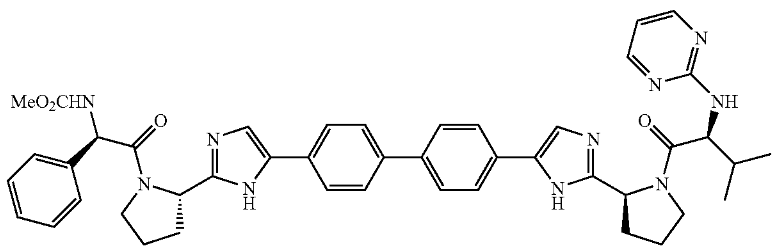 | LCMS: Anal. Calcd. for $C_{45}H_{48}N_{10}O_4$: 792; found: 793 $(M + H)^+$. |
| cj-11c (from cj-10 and Cap-2) | N-((1S)-1-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)-2-methylpropyl)-2-pyrimidinamine | 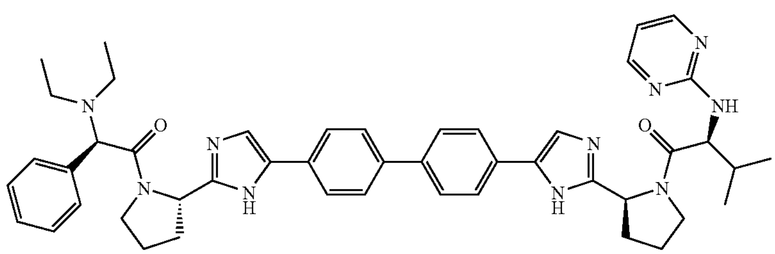 | LCMS: Anal. Calcd. for $C_{47}H_{54}N_{10}O_2$: 790; found: 791 $(M + H)^+$. |
| cj-11d (from cj-10b and Cap-51) | methyl ((1S)-2-methyl-1-(((2S)-2-(5-(4'-(2-((2S)-1-(N-(1-methyl-4,5-dihydro-1H-imidazol-2-yl)-L-valyl)-2-pyrrolidinyl)-1H-imidazol-5-yl)-4-biphenylyl)-1H-imidazol-2-yl)-1-pyrrolidinyl)carbonyl)propyl)carbamate | 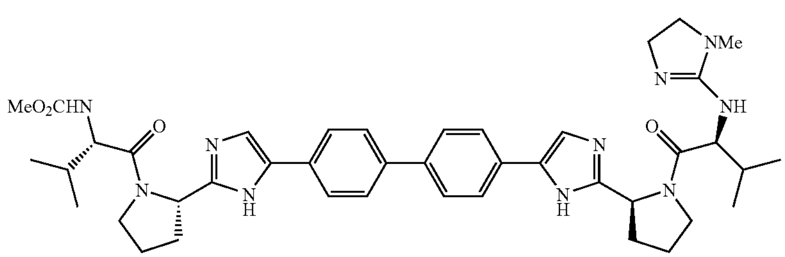 | LCMS: Anal. Calcd. for $C_{42}H_{54}N_{10}O_4$: 762; found: 763 $(M + H)^+$. |

| Example | Compound Name | Structure | LCMS |
|---|---|---|---|
| cj-11e (from cj-10d and Cap-51) | methyl ((1S)-1-(((2S)-2-(5-(4'-(2-((2S)-1-(N-(4,5-dihydro-1H-imidazol-2-yl)-L-valyl)-2-pyrrolidinyl)-1H-imidazol-5-yl)-4-biphenylyl)-1H-imidazol-2-yl)-1-pyrrolidinyl)carbonyl)-2-methylpropyl)carbamate | 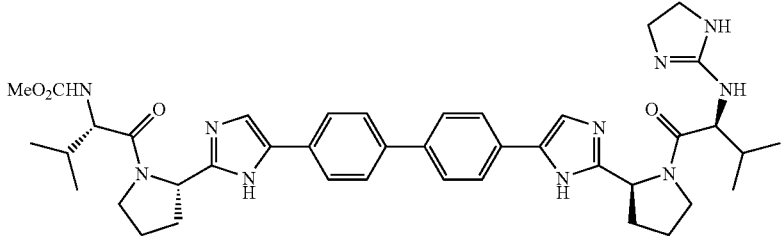 | LCMS: Anal. Calcd. for $C_{41}H_{52}N_{10}O_4$: 748; found: 749 $(M + H)^+$. |
| cj-11f (from cj-10d and Cap-52) | methyl ((1S)-2-((2S)-2-(5-(4'-(2-((2S)-1-(N-(4,5-dihydro-1H-imidazol-2-yl)-L-valyl)-2-pyrrolidinyl)-1H-imidazol-5-yl)-4-biphenylyl)-1H-imidazol-2-yl)-1-pyrrolidinyl)-1-methyl-2-oxoethyl)carbamate | 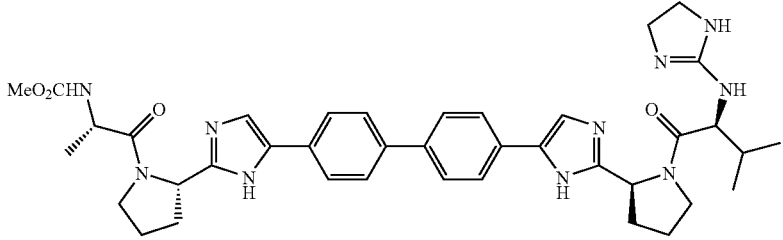 | LCMS: Anal. Calcd. for $C_{39}H_{48}N_{10}O_4$: 720; found: 721 $(M + H)^+$. |
| cj-11g (from cj-10d and Cap-2) | N-((1S)-1-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)-2-methylpropyl)-4,5-dihydro-1H-imidazol-2-amine | 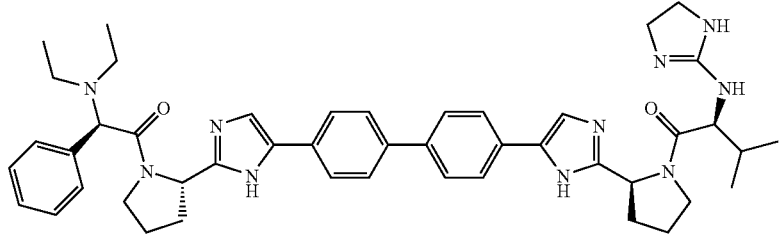 | LCMS: Anal. Calcd. for $C_{46}H_{56}N_{10}O_2$: 780; found: 781 $(M + H)^+$. |
| cj11h (from cj-10d and Cap-4) | methyl ((1R)-2-oxo-1-phenyl-2-((2S)-2-(5-(4'-(2-((2S)-1-(N-2-pyrimidinyl-D-valyl)-2-pyrrolidinyl)-1H-imidazol-5-yl)-4-biphenylyl)-1H-imidazol-2-yl)-1-pyrrolidinyl)ethyl)carbamate | 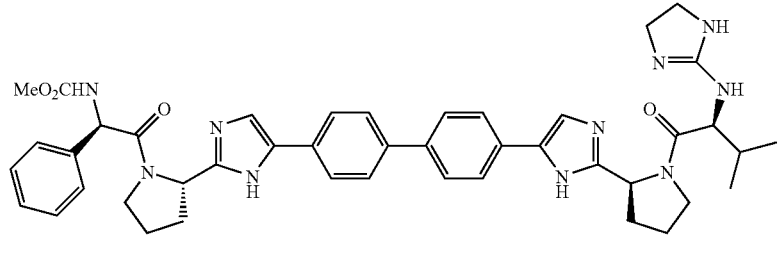 | LCMS: Anal. Calcd. for $C_{44}H_{50}N_{10}O_4$: 782; found: 783 $(M + H)^+$. |

| Example | Compound Name | Structure | LCMS |
|---|---|---|---|
| cj-11i (from cj-10a and Cap-51) | methyl ((1S)-2-methyl-1-(((2S)-2-(5-(4'-(2-((2S)-1-(N-2-pyrimidinyl-D-valyl)-2-pyrrolidinyl)-1H-imidazol-5-yl)-4-biphenylyl)-1H-imidazol-2-yl)-1-pyrrolidinyl)carbonyl)propyl)carbamate | 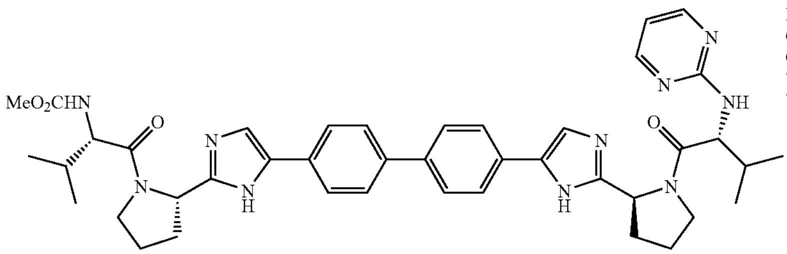 | LCMS: Anal. Calcd. for $C_{42}H_{50}N_{10}O_4$: 758; found: 759 $(M+H)^+$. |
| cj-11j (from cj-10a and Cap-52) | methyl ((1S)-1-methyl-2-oxo-2-((2S)-2-(5-(4'-(2-((2S)-1-(N-2-pyrimidinyl-D-valyl)-2-pyrrolidinyl)-1H-imidazol-5-yl)-4-biphenylyl)-1H-imidazol-2-yl)-1-pyrrolidinyl)ethyl)carbamate | 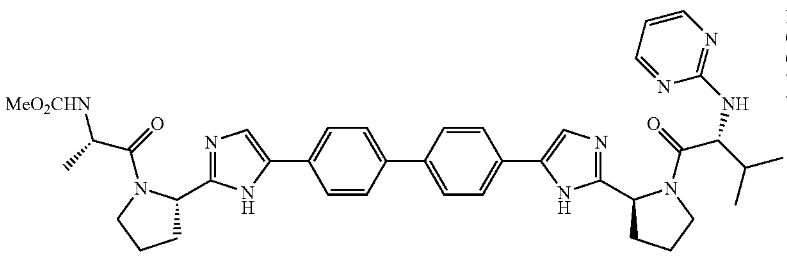 | LCMS: Anal. Calcd. for $C_{40}H_{46}N_{10}O_4$: 730; found: 731 $(M+H)^+$. |
| cj-11k (from cj-10a and Cap-2) | N-((1R)-1-(((2S)-2-(5-(4'-2-((2S)-1-((2R)-2-(diethylamino)-2-phenylacetyl)-2-pyrrolidinyl)-1H-imidazol-5-yl)-4-biphenylyl)-1H-imidazaol-2-yl)-1-pyrrolidinyl)carbonyl)-2-methylpropyl)-2-pyrimidinamine | 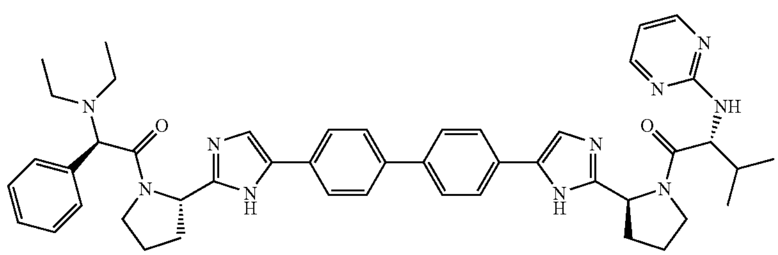 | LCMS: Anal. Calcd. for $C_{47}H_{54}N_{10}O_2$: 790; found: 791 $(M+H)^+$. |
| cj-11l (from cj-10a and Cap-4) | | 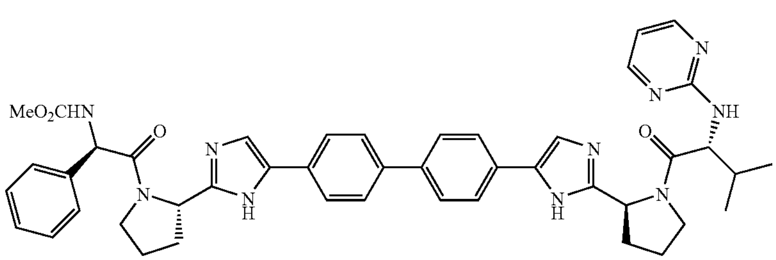 | LCMS: Anal. Calcd. for $C_{45}H_{48}N_{10}O_4$: 792; found: 793 $(M+H)^+$. |

| Example | Compound Name | Structure | LCMS |
|---|---|---|---|
| cf-11m (from cj-10c and Cap-51) | methyl ((1S)-2-methyl-1-(((2S)-2-(5-(4'-(2-((2S)-1-(N-(1-methyl-4,5-dihydro-1H-imidazol-2-yl)-D-valyl)-2-pyrrolidinyl)-1H-imidazol-5-yl)-4-biphenylyl)-1H-imidazol-2-yl)-1-pyrrolidinyl)carbonyl)propyl)carbamate | 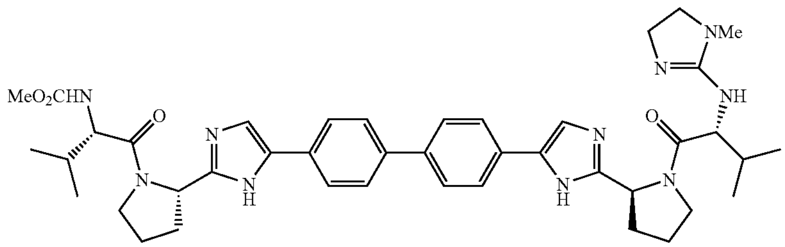 | LCMS: Anal. Calcd. for $C_{42}H_{54}N_{10}O_4$: 762; found: 763 (M + H)$^+$. |
| cj-11n (from cj-10e and Cap-51) | methyl ((1S)-1-(((2S)-2-(5-(4'-(2-((2S)-1-(N-(4,5-dihydro-1H-imidazol-2-yl)-D-valyl)-2-pyrrolidinyl)-1H-imidazol-5-yl)-4-biphenylyl)-1H-imidazol-2-yl)-1-pyrrolidinyl)carbonyl)-2-methyl)propyl)carbamate | 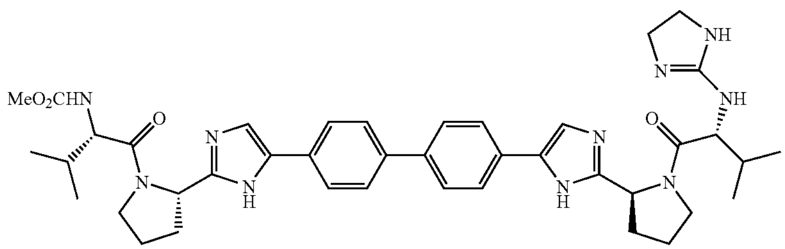 | LCMS: Anal. Calcd. for $C_{41}H_{52}N_{10}O_4$: 748; found: 749 (M + H)$^+$. |
| cj-11o (from cj-10e and Cap-54b) | methyl ((1S)-1-cyclopropyl-2-((2S)-2-(5-(4'-(2-((2S)-1-(N-(4,5-dihydro-1H-imidazol-2-yl)-D-valyl)-2-pyrrolidinyl)-1H-imidazol-5-yl)-4-biphenylyl)-1H-imidazol-2-yl)-1-pyrrolidinyl)-2-oxoethyl)carbamate | 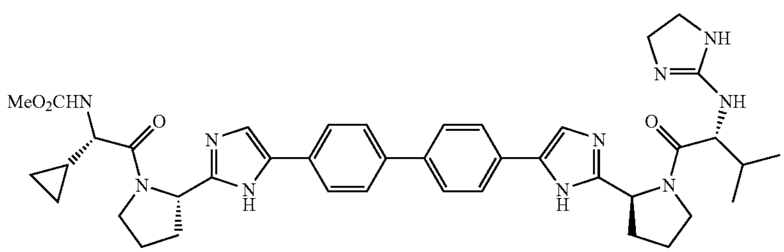 | LCMS: Anal. Calcd. for $C_{41}H_{50}N_{10}O_4$: 746; found: 747 (M + H)$^+$. |
| cj-11p (from cj-10e and Cap-2) | N-((1R)-1-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrrolidinyl)carbonyl)-2-methylpropyl)-4,5-dihydro-1H-imidazol-2-amine | 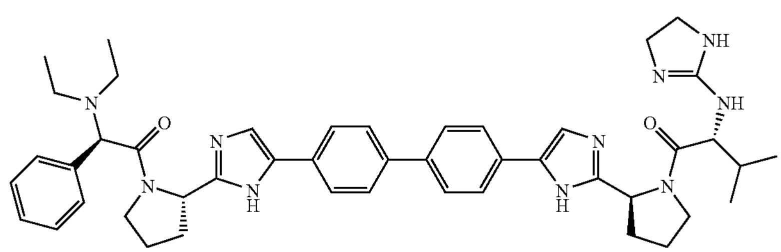 | LCMS: Anal. Calcd. for $C_{46}H_{56}N_{10}O_2$: 780; found: 781 (M + H)$^+$. |

Example-cj-13

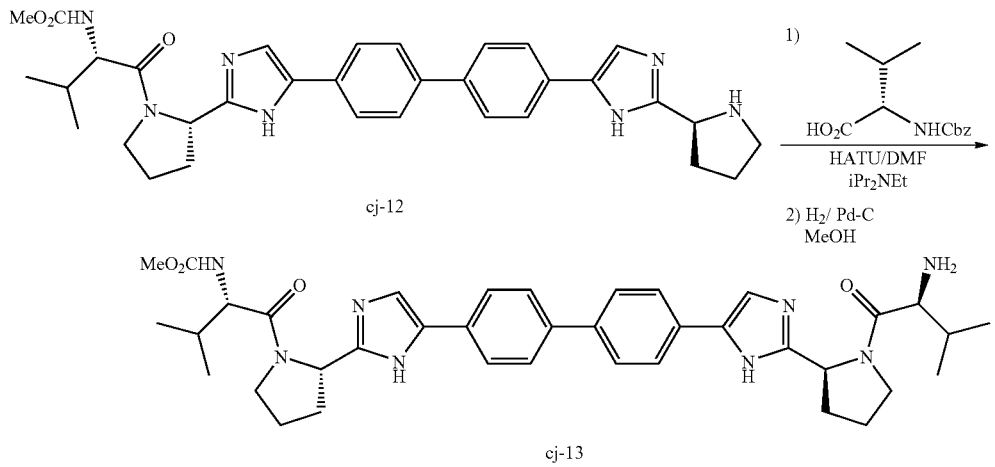

Preparation of Methyl (S)-1-((S)-2-(5-(4'-(2-((S)-1-((S)-2-amino-3-methylbutanoyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate (cj-13)

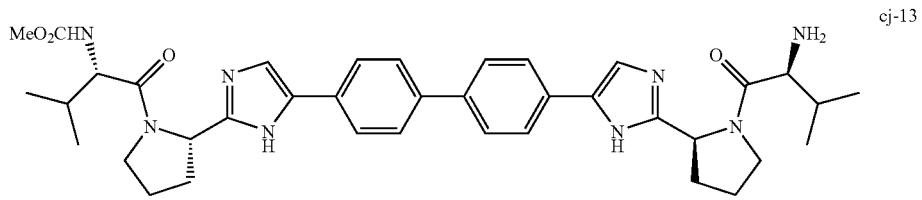

To a solution of methyl (S)-3-methyl-1-oxo-1-((S)-2-(5-(4'-(2-((S)-pyrrolidin-2-yl)-1H-imidazol-5-yl)biphenyl-4-yl)-1H-imidazol-2-yl)pyrrolidin-1-yl)butan-2-ylcarbamate (cj-12) (1.16 g, 1.99 mmol), Z-Val-OH (0.712 g, 2.83 mmol) and iPr$_2$NEt (0.70 mL, 5.42 mmol) in DMF (40 mL) was added HATU (1.10 g, 2.89 mmol) portionwise. The mixture was allowed to stir at room temperature for 1 h and was then poured into ice-water (400 mL) and allowed to stand for 20 min. The mixture was filtered and the solid washed with cold water and allowed to air dry overnight to give the Z-protected intermediate. LCMS: Anal. Calcd. for $C_{46}H_{54}N_8O_6$: 814. found: 815 (M+H)$^+$.

The obtained solid was dissolved in MeOH (80 mL), 10% Pd—C (1.0 g) was added and the mixture was hydrogenated at room temperature and atmospheric pressure for 3 h. The mixture was then filtered and the filtrate concentrated in vacuo. The resulting residue was purified by flash chromatography (SiO$_2$/5-20% MeOH—CH$_2$Cl$_2$) to afford the title compound (1.05 g, 77%) as a colorless foam. $^1$HNMR (400 MHz, DMSO-d$_6$) δ 11.75 (s, 1H), 7.75-7.79 (m, 3H), 7.61-7.67 (m, 5H), 7.49 (s, 1H), 7.26-7.28 (m, 1H), 5.05-5.09 (m, 2H), 4.03-4.09 (m, 2H), 3.77-3.80 (m, 1H), 3.66-3.70 (m, 1H), 3.52 (s, 3H), 3.40-3.47 (m, 2H), 2.21-2.26 (m, 1H), 2.10-2.17 (m, 3H), 1.81-2.02 (m, 6H), 0.77-0.92 (m, 12H).

LCMS: Anal. Calcd. for $C_{38}H_{48}N_8O_4$: 680. found: 681 (M+H)$^+$.

Example cj-15

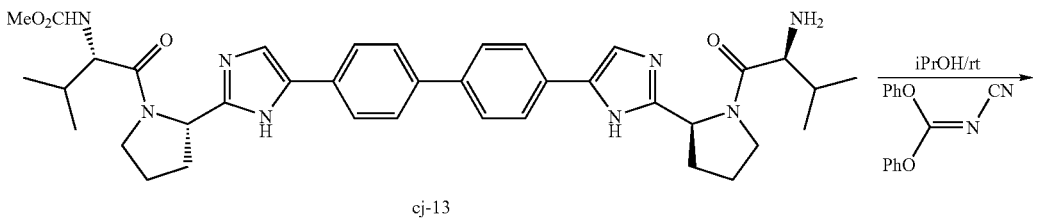

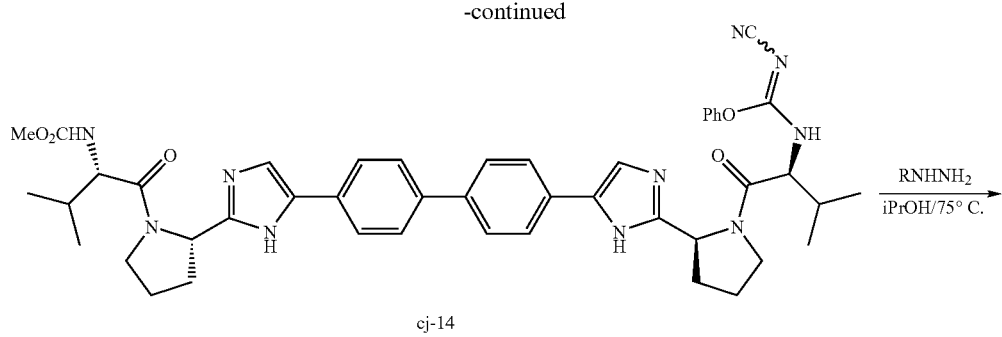

cj-14

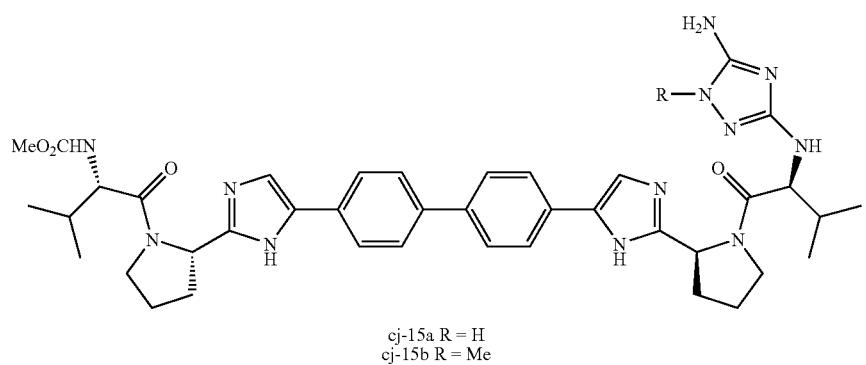

cj-15a R = H
cj-15b R = Me

Preparation of Methyl (S)-1-((S)-2-(5-(4'-(2-((S)-1-((S)-2-((Z/E)-(cyanoimino)(phenoxy)methylamino)-3-methylbutanoyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate (cj-14)

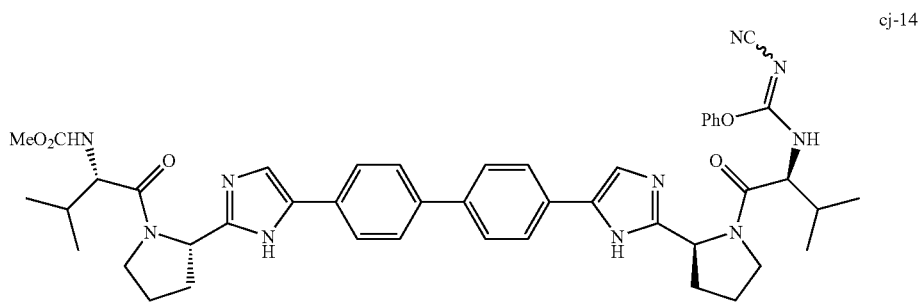

cj-14

A mixture of methyl (S)-1-((S)-2-(5-(4'-(2-((S)-1-((S)-2-amino-3-methylbutanoyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate (cj-13) (0.329 g, 0.527 mmol) and diphenyl cyanocarbonimidate (0.128 g, 0.537 mmol) in iPrOH (10 mL) was stirred at room temperature for 12 h. The resulting solid was filtered and air-dried to give the title compound (0.187 g, 43%) as a cream-colored solid. This material was used as such in the next step without further purification.

LCMS: Anal. Calcd. for $C_{46}H_{52}N_{10}O_5$: 824. found: 825 $(M+H)^+$.

Preparation of methyl ((1S)-1-(((2S)-2-(5-(4'-(2-((2S)-1-(N-(5-amino-1-methyl-1H-1,2,4-triazol-3-yl)-L-valyl)-2-pyrrolidinyl)-1H-imidazol-5-yl)-4-biphenylyl)-1H-imidazol-2-yl)-1-pyrrolidinyl)carbonyl)-2-methylpropyl)carbamate (cj-15a, R═H)

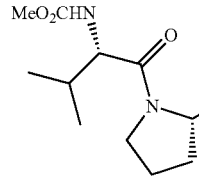
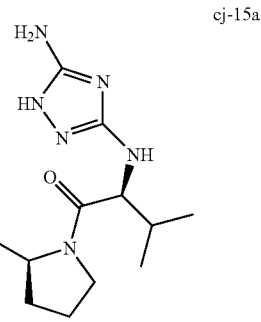

cj-15a

A solution of methyl (S)-1-((S)-2-(5-(4'-(2-((S)-1-((S)-2-((Z/E)-(cyanoimino)(phenoxy)methylamino)-3-methylbutanoyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate (cj-14) (0.074 g, 0.090 mmol) and hydrazine hydrate (0.05 mL, 0.88 mmol) in iPrOH (2 mL) was heated at 75° C. for 7 h. The solvent was then removed in vacuo and the residue was purified by prep HPLC (Luna 5u C18/MeCN—H$_2$O—NH$_4$OAc) to give foam which was lyophilized from CH$_3$CN—H$_2$O to give the title compound (0.032 g, 46%) as a colorless solid.

$^1$HNMR (400 MHz, DMSO-d$_6$) δ 12.17 (s, 1H), 11.75 (m, 2H), 10.66-10.84 (m, 2H), 7.76-7.79 (m, 3H), 7.62-7.74 (m, 4H), 7.49-7.51 (m, 1H), 7.24-7.29 (m, 2H), 5.28-5.32 (m, 1H), 5.05-5.08 (m, 2H), 4.04-4.09 (m, 3H), 3.87-3.94 (m, 2H), 3.72-3.81 (m, 2H), 3.53 (s, 3H), 2.09-2.17 (m, 2H), 1.90-2.02 (m, 6H), 0.81-0.99 (m, 12H).

LCMS: Anal. Calcd. for C$_{40}$H$_{50}$N$_{12}$O$_4$: 762. found: 763 (M+H)$^+$.

Preparation of Methyl (S)-1-((S)-2-(5-(4'-(2-((S)-1-((S)-2-(5-amino-1-methyl-1H-1,2,4-triazol-3-ylamino)-3-methylbutanoyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate (cj-15b, R═Me)

A solution of methyl (S)-1-((S)-2-(5-(4'-(2-((S)-1-((S)-2-((Z/E)-(cyanoimino)(phenoxy)methylamino)-3-methylbutanoyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate (cj-14) (0.105 g, 0.128 mmol) and N-methylhydrazine (0.010 mL, 0.188 mmol) in iPrOH (2 mL) was heated at 75° C. for 3 h. A second portion of N-methylhydrazine (0.010 mL, 0.188 mmol) was added and heating was continued for 7 h. The volatiles were then removed in vacuo and the residue was purified by prep HPLC (Luna 5u C18/MeCN—H$_2$O—NH$_4$OAc) to give a foam which was further purified by flash chromatography (SiO$_2$/0-20% MeOH—CH$_2$Cl$_2$). The resulting material was lyophilized from CH$_3$CN—H$_2$O to give the title compound (0.029 g, 29%) as a colorless solid.

$^1$HNMR (400 MHz, DMSO-d$_6$) δ 13.79 (s, 0.4H), 12.19 (s, 1H), 11.76 (m, 1.6H), 7.77-7.85 (m, 4H), 7.62-7.71 (m, 4H), 7.49-7.51 (m, 1H), 7.24-7.29 (m, 1H), 6.31 (d, J=9.1 Hz, 0.5H), 6.09 (d, J=9.1 Hz, 1.5H), 5.87 (s, 1H), 5.34-5.36 (m, 1H), 5.04-5.08 (m, 2H), 4.89 (s, 1H), 4.75 (s, 2H), 3.53 (s, 3H), 2.10-2.17 (m, 3H), 1.94-2.02 (m, 6H), 0.81-0.98 (m, 12H).

LCMS: Anal. Calcd. for C$_{41}$H$_{52}$N$_{12}$O$_4$: 776. found: 777 (M+H)$^+$.

HRMS: Anal. Calcd. for C$_{41}$H$_{52}$N$_{12}$O$_4$: 776.4234. found: 777.4305 (M+H)$^+$.

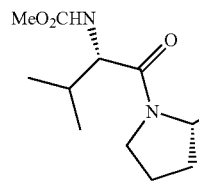
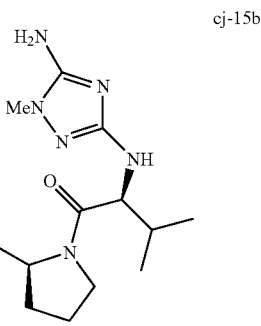

cj-15b

Example cj-15c methyl ((1S)-1-(((2S)-2-(5-(4'-(2-((2S)-1-(N-(4,5-dihydro-1,3-thiazol-2-yl)-L-valyl)-2-pyrrolidinyl)-1H-imidazol-5-yl)-4-biphenylyl)-1H-imidazol-2-yl)-1-pyrrolidinyl)carbonyl)-2-methylpropyl)carbamate

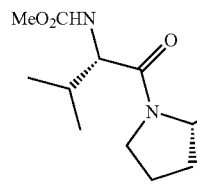
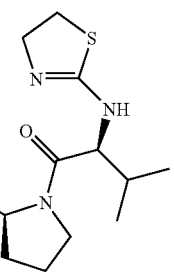

Example cj-15c was prepared by the condensation of Intermediate cj-13 with 2-(methylthio)-4,5-dihydrothiazole (Aldrich) using conditions analogous to those in the preparation of Intermediate cj-4. LCMS: Anal. Calcd. for $C_{41}H_{51}N_9O_4S$: 765. found: 766 $(M+H)^+$.

Example 15-d methyl ((1S)-2-methyl-1-(((2S)-2-(5-(4'-(2-((2S)-1-(N-4-pyrimidinyl-L-valyl)-2-pyrrolidinyl)-1H-imidazol-5-yl)-4-biphenylyl)-1H-imidazol-2-yl)-1-pyrrolidinyl)carbonyl)propyl)carbamate

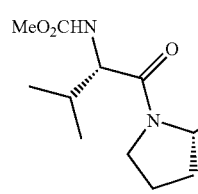
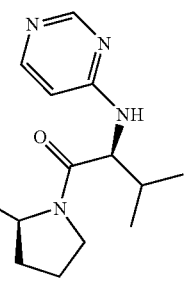

Example cj-15d was prepared by the condensation of Intermediate cj-13 with 4,6-dichloropyrimidine (Aldrich) using conditions analogous to those in the preparation of Intermediate cj-4, followed by hydrogenation with 10% Pd—C. LCMS: Anal. Calcd. for $C_{42}H_{50}N_{10}O_4$: 758. found: 759 $(M+H)^+$.

Example cj-16 and cj-17

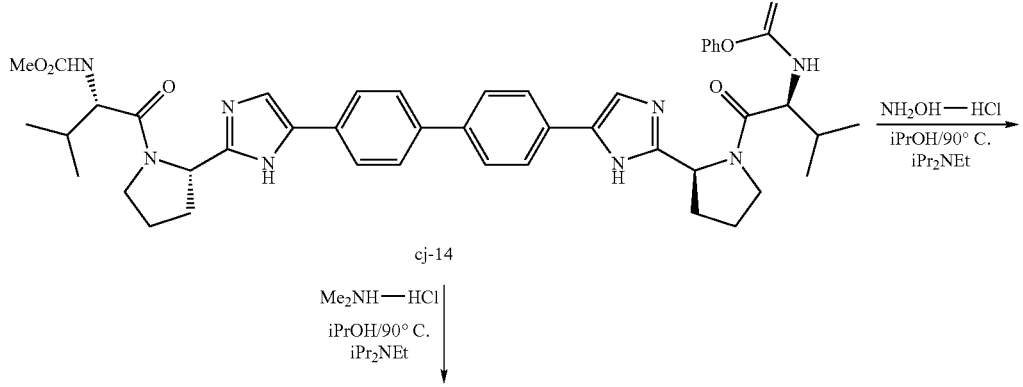

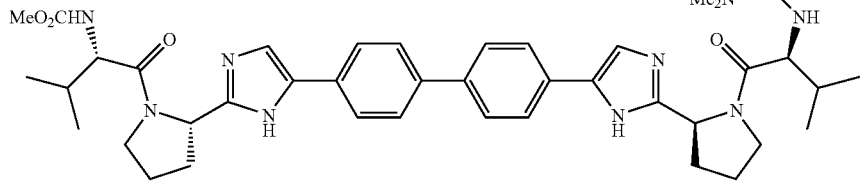

cj-17

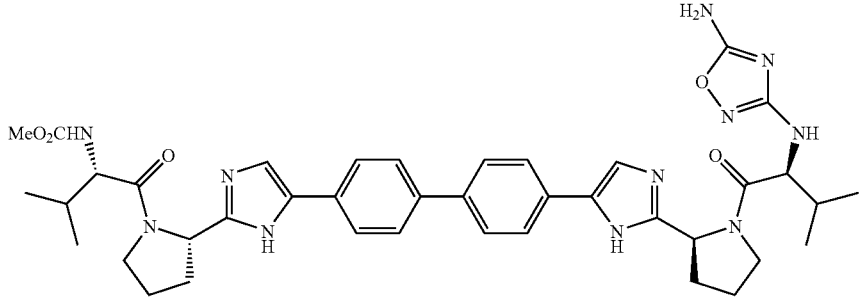

cj-16

Preparation of methyl ((1S)-1-(((2S)-2-(5-(4'-(2-((2S)-1-(N-(5-amino-1,2,4-oxadiazol-3-yl)-L-valyl)-2-pyrrolidinyl)-1H-imidazol-5-yl)-4-biphenylyl)-1H-imidazol-2-yl)-1-pyrrolidinyl)carbonyl)-2-methylpropyl)carbamate (cj-16)

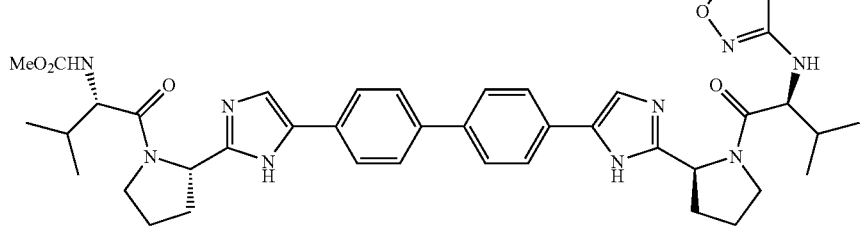

cj-16

A solution of methyl (S)-1-((S)-2-(5-(4'-(2-((S)-1-((S)-2-((Z/E)-(cyanoimino)(phenoxy)methylamino)-3-methylbutanoyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate (cj-14) (0.120 g, 0.205 mmol) and hydroxylamine hydrochloride (0.0213 g, 0.307 mmol) in iPrOH (5 mL) was heated at 75° C. for 3 h. A second portion of hydroxylamine hydrochloride (0.0213 g, 0.307 mmol) was added and heating continued for 7 h. The volatiles were then removed in vacuo and the residue was purified by prep HPLC (Luna 5u C18/MeCN—H$_2$O—NH$_4$OAc) to give a foam which was further purified by flash chromatography (SiO$_2$/ 5% MeOH—CH$_2$Cl$_2$). The resulting colorless wax was lyophilized from CH$_3$CN—H$_2$O to give the title compound (0.0344 g, 22%) as a colorless solid.

$^1$HNMR (400 MHz, DMSO-d$_6$) δ 12.18-12.22 (m, 1H), 11.80 (s, 1H), 11.75 (s, 1 h), 8.03-8.06 (m, 1H), 7.77 (app d, J=8.1 Hz, 2H), 7.62-7.73 (m, 4H), 7.50 (dd, J=2.0, 5.5 Hz, 1H), 7.24-7.29 (m, 2H), 5.69 (s, 1H), 5.06-5.11 (m, 2H), 4.14 (t, J=8.6 Hz, 1H), 4.06 (unresolved dd, J=8.0, 8.6 Hz, 1H), 3.78-3.90 (m, 3H), 3.53 (s, 3H), 3.01 (br s, 2H), 2.10-2.19 (m, 3H), 1.90-2.04 (m, 5H), 0.81-0.96 (m, 12H).

LCMS: Anal. Calcd. for C$_{40}$H$_{49}$N$_{11}$O$_5$: 763. found: 764 (M+H)$^+$.

Preparation of methyl ((1S)-1-(((2S)-2-(5-(4'-(2-((2S)-1-(N-(cyano(dimethyl)carbamimidoyl)-L-valyl)-2-pyrrolidinyl)-1H-imidazol-5-yl)-4-biphenylyl)-1H-imidazol-2-yl)-1-pyrrolidinyl)carbonyl)-2-methylpropyl)carbamate (cj-17)

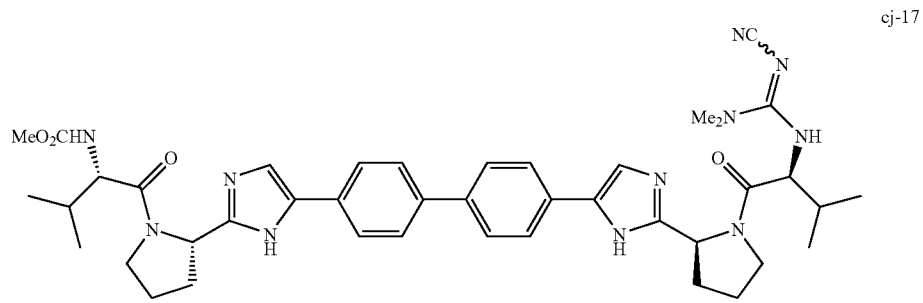

cj-17

A solution of methyl (S)-1-((S)-2-(5-(4'-(2-((S)-1-((S)-2-((Z/E)-(cyanoimino)(phenoxy)methylamino)-3-methylbutanoyl)pyrrolidin-2-yl)-1H-imidazol-5-yl)biphenyl-4-yl)-1H-imidazol-2-yl)pyrrolidin-1-yl)-3-methyl-1-oxobutan-2-ylcarbamate (cj-14) (0.115 g, 0.198 mmol) and dimethylamine hydrochloride (0.0257 g, 0.315 mmol) in iPrOH (5 mL) was heated at 90° C. for 12 h. A second portion of dimethylamine hydrochloride (0.0257 g, 0.315 mmol) was added and heating was continued for 48 h. The volatiles were then removed in vacuo and the residue was purified by prep HPLC (Luna 5u C18/MeCN—H$_2$O—NH$_4$OAc) and then repurified by flash chromatography (SiO$_2$/5% MeOH—CH$_2$Cl$_2$). The resulting colorless wax was lyophilized from CH$_3$CN—H$_2$O to give the title compound (0.0318 g, 21%) as a colorless solid.

$^1$HNMR (400 MHz, DMSO-d$_6$) δ 12.22 (m, 0.6H), 11.81 (s, 1H), 11.75 (s, 1H), 12.17-12.22 (m, 0.5H), 11.99-12.04 (m, 0.5H), 11.75-11.81 (m, 1H), 7.76-7.79 (m, 3H), 7.62-7.73 (m, 5H), 7.50 (t, J=2.0 Hz, 1H), 7.23-7.29 (m, 1H), 6.64 (d, J=8.1 Hz, 1H), 5.06-5.08 (m, 2H), 4.47 (t, J=8.1 Hz, 2H), 4.06 (unresolved dd, J=8.0, 8.6 Hz, 1H), 3.84-3.90 (m, 2H), 3.76-3.82 (m, 3H), 3.53 (s, 3H), 3.00 (s, 6H), 2.11-2.20 (m, 3H), 1.90-2.04 (m, 5H), 0.97 (d, J=6.5 Hz, 3H), 0.89-0.91 (m, 6H), 0.84 (d, J=6.5 Hz, 3H).

LCMS: Anal. Calcd. for C$_{42}$H$_{53}$N$_{11}$O$_4$: 775. found: 776 (M+H)$^+$

Example cj-20

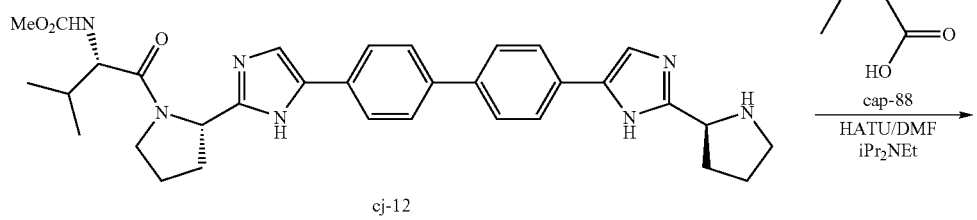

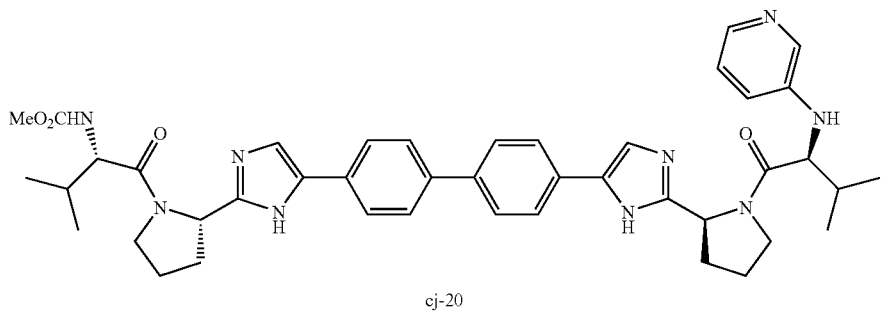

cj-20

Preparation of methyl ((1S)-2-methyl-1-(((2S)-2-(5-(4'-(2-((2S)-1-(N-3-pyridinyl-L-valyl)-2-pyrrolidinyl)-1H-imidazol-5-yl)-4-biphenylyl)-1H-imidazol-2-yl)-1-pyrrolidinyl)carbonyl)propyl)carbamate (cj-20)

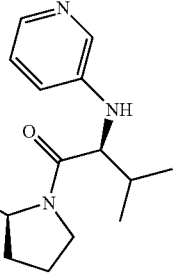

cj-20

To a solution of methyl (S)-3-methyl-1-oxo-1-((S)-2-(5-(4'-(2-((S)-pyrrolidin-2-yl)-1H-imidazol-5-yl)biphenyl-4-yl)-1H-imidazol-2-yl)pyrrolidin-1-yl)butan-2-ylcarbamate (cj-13) (0.060 g, 0.103 mmol) in DMF (2 mL) was added iPr$_2$NEt (0.18 mL, 1.02 mmol), (S)-3-methyl-2-(pyridin-3-ylamino)butanoic acid (Cap-88) (0.040 g, 0.206 mmol) and HATU (0.078 g, 0.205 mmol). The reaction mixture was stirred for 1.5 h at room temperature and then it was directly purified by prep HPLC (Luna 5u C18/MeCN—H$_2$O—NH$_4$OAc). The resulting solid was repurified by flash chromatography (SiO$_2$/0-10% MeOH—CH$_2$Cl$_2$) and the obtained product was lyophilized from CH$_3$CN—H$_2$O to give the title compound (0.044 g, 56%) as a solid.

$^1$HNMR (400 MHz, DMSO-d$_6$) δ 12.19 (s, 1H), 11.76 (s, 1H), 8.07 (d, J=2.6 Hz, 1H), 7.62-7.85 (m, 8H), 7.49-7.51 (m, 2H), 7.24-7.29 (m, 1H), 6.99-7.06 (m, 2H), 6.46-6.49 (m, 0.5H), 5.97-5.99 (m, 0.5H), 5.71 (d, J=9.0 Hz, 1H), 5.55 (d, J=10.6 Hz, 1H), 5.22-5.44 (m, 1H), 5.03-5.09 (m, 2H), 4.04-4.13 (m, 2H), 3.78-3.90 (m, 3H), 3.66-3.71 (m, 1H), 3.53 (s, 3H), 2.03-2.19 (m, 2H), 1.84-2.01 (m, 4H), 0.81-1.01 (m, 12H).

LCMS: Anal. Calcd. for C$_{43}$H$_{51}$N$_9$O$_4$: 757. found: 758 (M+H)$^+$.

Similarly, the following examples were prepared according to the representative method above;

| Example | Compound Name | Structure | LCMS |
|---|---|---|---|
| cj-20a (from cj-22 and Cap-88) | methyl ((1S)-1-methyl-2-oxo-2-((2S)-2-(5-(4'-(2-((2S)-1-(N-3-pyridinyl-L-valyl)-2-pyrrolidinyl)-1H-imidazol-5-yl)-4-biphenylyl)-1H-imidazol-2-yl)-1-pyrrolidinyl)ethyl)carbamate | 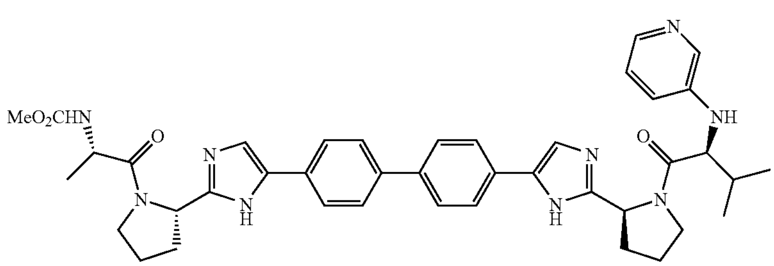 | LCMS: Anal. Calcd. for C$_{41}$H$_{47}$N$_9$O$_4$: 729; found: 730 (M + H)$^+$. |
| cj-20b (from cj-23 and Cap-88) | methyl ((1S,2R)-2-methoxy-1-(((2S)-2-(5-(4'-(2-((2S)-1-(N-3-pyridinyl-L-valyl)-2-pyrrolidinyl)-1H-imidazol-5-yl)-4-biphenylyl)-1H-imidazol-2-yl)-1-pyrrolidinyl)carbonyl)propyl)carbamate | 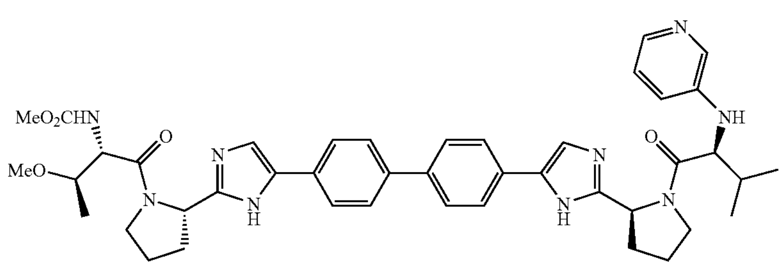 | LCMS: Anal. Calcd. for C$_{43}$H$_{51}$N$_9$O$_5$: 773; found: 774 (M + H)$^+$. |

-continued

| Example | Compound Name | Structure | LCMS |
|---|---|---|---|
| cj-20c (from cj-24 and Cap-88) | N-((1S)-1-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)-2-methylpropyl)-3-pyridinamine | 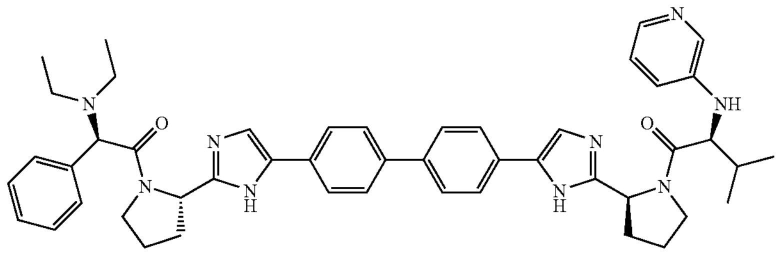 | LCMS: Anal. Calcd. for $C_{48}H_{55}N_9O_2$: 789; found: 790 (M + H)$^+$. |
| cj-20d (from cj-12 and Cap-88) | methyl ((1S)-2-methyl-1-(((2S)-2-(5-(4'-(2-((2S)-1-(N-5-pyrimidinyl-L-valyl)-2-pyrrolidinyl)-1H-imidazol-5-yl)-4-biphenylyl)-1H-imidazol-2-yl)-1-pyrrolidinyl)carbonyl)propyl)carbamate | 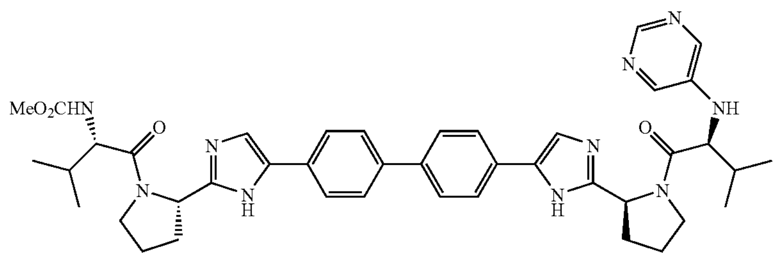 | LCMS: Anal. Calcd. for $C_{42}H_{50}N_{10}O_4$: 758; found: 759 (M + H)$^+$. |

Preparation of Methyl (S)-3-methyl-1-oxo-1-((S)-2-(5-(4'-(2-((S)-pyrrolidin-2-yl)-1H-imidazol-5-yl)biphenyl-4-yl)-1H-imidazol-2-yl)pyrrolidin-1-yl)butan-2-ylcarbamate (cj-12)

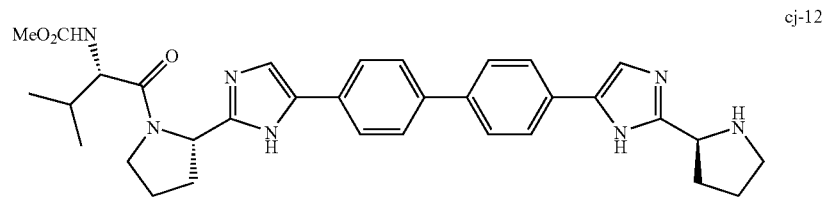

cj-12

Synthesized from Intermediate-28d and Cap-51 as in Example 28e, followed by Boc removal with TFA/CH$_2$Cl$_2$ and free base formation with MCX resin.

$^1$HNMR (400 MHz, MeOH-d$_4$) δ 7.79-7.82 (m, 3H), 7.65-7.75 (m, 5H), 7.48 (s, 1H), 7.32 (s, 1H), 5.19 (dd, J=5.5, 5.7 Hz, 1H), 4.75 (t, J=7.8 Hz, 1H), 4.25 (d, J=7.3 Hz, 1H), 3.88-4.04 (m, 2H), 3.67 (s, 3H), 3.35-3.51 (m, 3H), 2.43-2.51 (m, 1H), 2.02-2.38 (m, 7H), 0.97 (d, J=6.5 Hz, 3H), 0.92 (d, J=6.9 Hz, 3H).

LCMS: Anal. Calcd. for $C_{33}H_{39}N_7O_3$: 581. found: 582 (M+H)$^+$.

Preparation of Methyl (S)-1-oxo-1-((S)-2-(5-(4'-(2-((S)-pyrrolidin-2-yl)-1H-imidazol-5-yl)biphenyl-4-yl)-1H-imidazol-2-yl)pyrrolidin-1-yl)propan-2-ylcarbamate (cj-22)

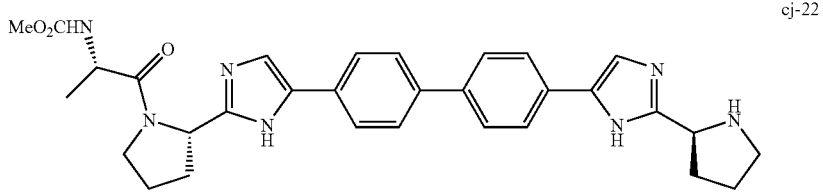

cj-22

Synthesized from Intermediate-28d and Cap-52 as in Example 28e, followed by Boc removal with TFA/CH$_2$Cl$_2$ and free base formation with MCX resin.

$^1$HNMR (400 MHz, MeOH-d$_4$) δ 7.68-7.79 (m, 4H), 7.59-7.65 (m, 4H), 7.44 (d, J=6.6 Hz, 1H), 7.37 (s, 0.3H), 7.27 (s, 0.7H), 5.18 (dd, J=4.0, 7.6 Hz, 1H), 4.74 (t, J=8.0 Hz, 1H), 4.46 (dd, J=6.8, 13.9 Hz, 1H), 3.84 (unresolved dd, J=6.1, 6.5 Hz, 1H), 3.62 (s, 3H), 3.54 (s, 1H), 3.32-3.46 (m, 3H), 2.40-2.46 (m, 1H), 2.26-2.39 (m, 2H), 2.14-2.24 (m, 2H), 2.01-2.12 (m, 2H), 0.32 (d, J=7.1 Hz, 3H).

LCMS: Anal. Calcd. for C$_{31}$H$_{35}$N$_7$O$_3$: 553. found: 554 (M+H)$^+$.

Preparation of Methyl (2S,3R)-3-methoxy-1-oxo-1-((S)-2-(5-(4'-(2-((S)-pyrrolidin-2-yl)-1H-imidazol-5-yl)biphenyl-4-yl)-1H-imidazol-2-yl)pyrrolidin-1-yl)butan-2-ylcarbamate (cj-23)

cj-23

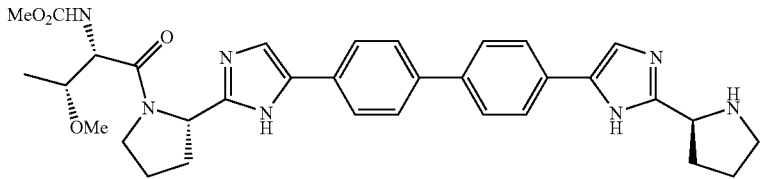

Synthesized from Intermediate-28d and Cap-86 as in Example 28e, followed by Boc removal with TFA/CH$_2$Cl$_2$ and free base formation with MCX resin.

$^1$HNMR (400 MHz, MeOH-d$_4$) δ 7.72 (m, 4H), 7.64-7.69 (m, 4H), 7.48 (d, J=4.1 Hz, 1H), 7.38 (s, 0.3H), 7.33 (s, 0.7H), 5.51-5.54 (m, 0.2H), 5.22 (dd, J=4.9, 7.6 Hz, 0.8H), 4.76 (t, J=8.0 Hz, 1H), 4.48 (d, J=5.1 Hz, 0.8H), 4.35-4.36 (m, 0.2H), 3.90-3.99 (m, 1H), 3.68 (s, 3H), 3.54 (s, 1H), 3.35-3.48 (m, 4H), 3.29 (s, 3H), 2.42-2.50 (m, 1H), 2.30-2.37 (m, 2H), 2.19-2.26 (m, 2H), 2.05-2.15 (m, 2H), 1.19 (d, J=6.1 Hz, 3H).

LCMS: Anal. Calcd. for C$_{33}$H$_{39}$N$_7$O$_4$: 597. found: 598 (M+H)$^+$.

Preparation of (R)-2-(Diethylamino)-2-phenyl-1-((S)-2-(5-(4'-(2-((S)-pyrrolidin-2-yl)-1H-imidazol-5-yl)biphenyl-4-yl)-1H-imidazol-2-yl)pyrrolidin-1-yl)ethanone (cj-24)

cj-24

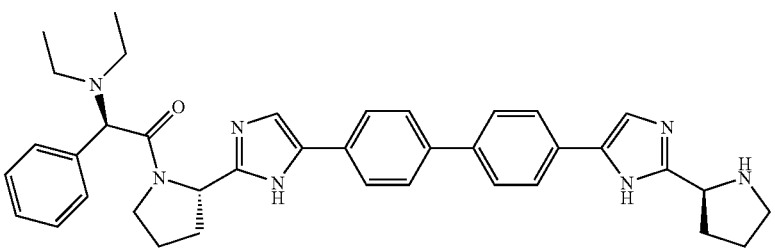

Synthesized from Intermediate-28d and Cap-2 as in Example 28e, followed by Boc removal with TFA/CH$_2$Cl$_2$ and free base formation with MCX resin.

$^1$HNMR (400 MHz, MeOH-d$_4$) δ 7.59-7.82 (m, 10H), 7.36-7.51 (m, 4H), 7.01-7.15 (m, 1H), 5.09-5.13 (m, 2H), 4.77 (t, J=8.5 Hz, 1H), 4.03-4.05 (m, 1H), 3.67-3.93 (m, 1H), 3.35-3.47 (m, 2H), 3.18-3.23 (m, 1H), 2.91-3.07 (m, 2H), 2.70-2.84 (m, 2H), 2.34-2.60 (m, 2H), 1.97-2.24 (m, 5H), 1.07-1.17 (m, 6H).

LCMS: Anal. Calcd. for C$_{38}$H$_{43}$N$_7$O: 613. found: 614 (M+H)$^+$.

The following were prepared according to the procedure in example 28 starting with 28d. The caps are given in the table in the order they were appended to 28d. Where a cap number is not given the corresponding carboxylic acid is commercially available.

| Example | Compound Name | Structure | LCMS | Cap |
|---|---|---|---|---|
| cj-32 | methyl ((1S)-2-((2S)-2-(5-(4'-(2-((2S)-1-((2R)-2-(diethylamino)-2-phenyl-acetyl)-2-pyrrolidinyl)-1H-imidazol-5-yl)-4-biphenylyl)-1H-imidazol-2-yl)-1-pyrrolidinyl)-2-oxo-1-(1H-1,2,3-triazol-4-ylmethyl)ethyl) carbamate | 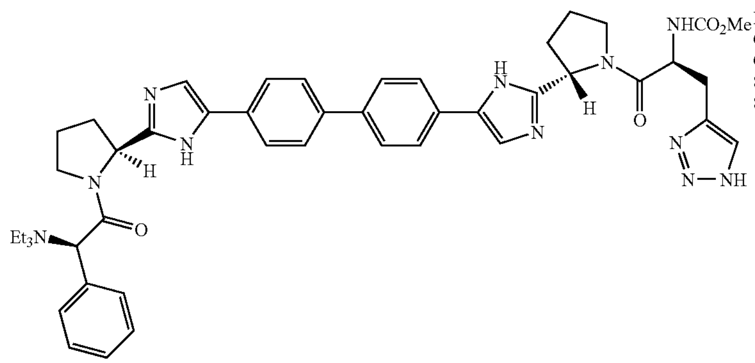 | LCMS: Anal. Calcd. for $C_{45}H_{51}N_{11}O_4$: 809; found: 810 (M + H)$^+$. | 2/128 |
| cj-33 | methyl ((1S)-2-((2S)-2-(5-(4'-(2-((2S)-1-(N-(methoxy-carbonyl)-L-alanyl)-2-pyrrolidinyl)-1H-imidazol-5-yl)-4-biphenylyl)-1H-imidazol-2-yl)-1-pyrrolidinyl)-2-oxo-1-(1H-1,2,3-traizol-4-ylmethyl)ethyl) carbamate | 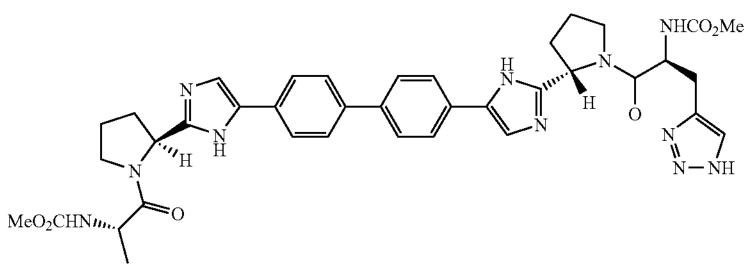 | LCMS: Anal. Calcd. for $C_{38}H_{43}N_{11}O_6$: 749; found: 750 (M + H)$^+$. | 52/128 |
| cj-34 | methyl ((1S)-1-(((2S)-2-(5-(4'-(2-((2S)-1-((2S)-2-((methoxy-carbonyl)amino)-3-(1H-1,2,3-triazol-4-yl)propanoyl)-2-pyrrolidinyl)-1H-imidazol-5-yl)-4-biphenylyl)-1H-imidazol-2-yl)-1-pyrrolidinyl)carbonyl)-2-methyl-propyl) carbamate | 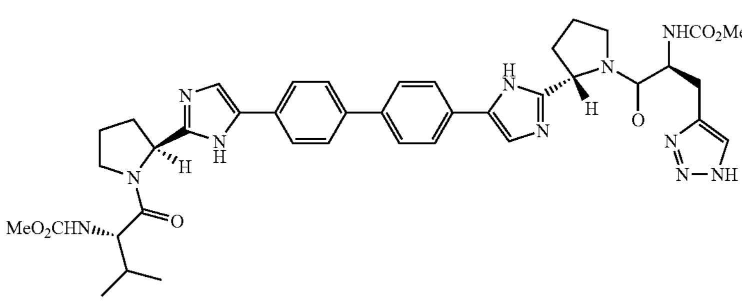 | LCMS: Anal. Calcd. for $C_{40}H_{47}N_{11}O_6$: 777; found: 777 (M + H)$^+$. | 51/128 |

| Example | Compound Name | Structure | LCMS | Cap |
|---|---|---|---|---|
| cj-35 | methyl ((1S)-2-((2S)-2-(5-(4'-(2-((2S)-1-((2S,3R)-3-methoxy-2-((methoxycarbonyl)amino)butanoyl)-2-pyrrolidinyl)-1H-imidazol-5-yl)-4-biphenylyl)-1H-imidazol-2-yl)-1-pyrrolidinyl)-2-oxo-1-(1H-1,2,3-triazol-4-ylmethyl)ethyl)carbamate | 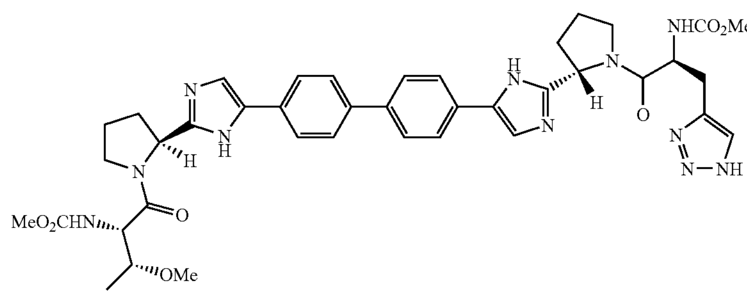 | LCMS: Anal. Calcd. for $C_{40}H_{47}N_{11}O_7$: 793; found: 794 $(M+H)^+$. | 86/128 |
| cj-36 | methyl ((1S)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-2-oxo-1-(1H-pyrazol-1-ylmethyl)ethyl)carbamate | 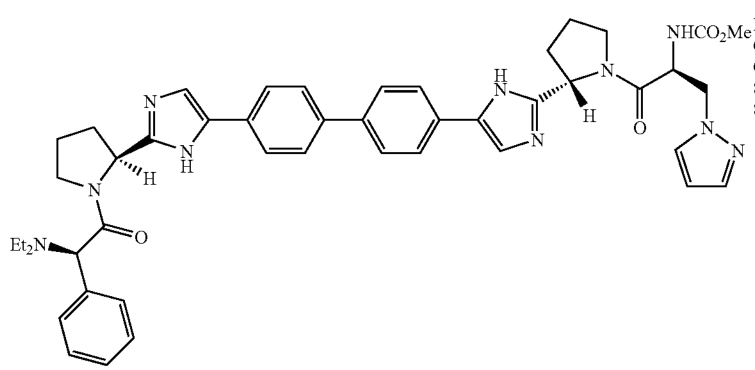 | LCMS: Anal. Calcd. for $C_{46}H_{52}N_{10}O_4$: 808; found: 809 $(M+H)^+$. | 2/129 |
| cj-37 | methyl ((1S)-2-((2S)-2-(5-(4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-2-oxo-1-(1H-pyrazol-1-ylmethyl)ethyl)carbamate | 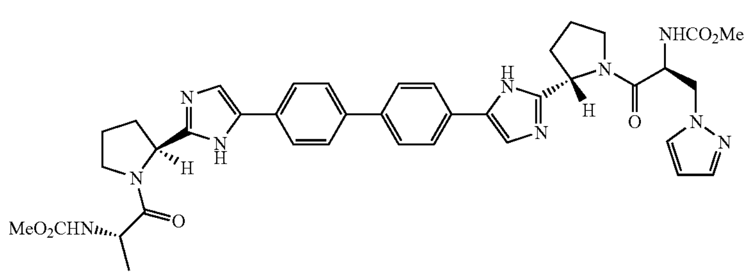 | LCMS: Anal. Calcd. for $C_{39}H_{44}N_{10}O_6$: 748; found: 749 $(M+H)^+$. | 52/129 |

| Example | Compound Name | Structure | LCMS | Cap |
|---|---|---|---|---|
| cj-38 | methyl ((1S)-1-(((2S)-2-(5-(4'-(2-((2S)-1-((2S)-2-((methoxycarbonyl)amino)-3-(1H-pyrazol-1-yl)propanoyl)-2-pyrrolidinyl)-1H-imidazol-5-yl)-4-biphenylyl)-1H-imidazol-2-yl)-1-pyrrolidinyl)carbonyl)-2-methylpropyl)carbamate | 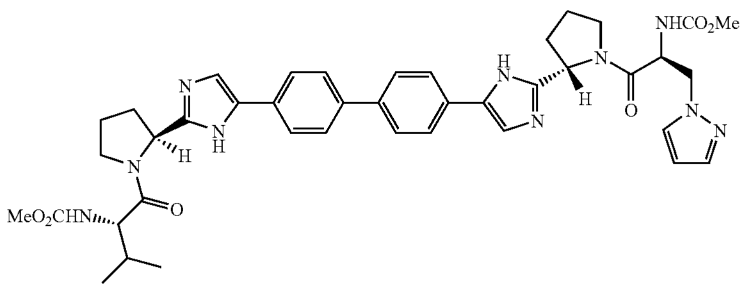 | LCMS: Anal. Calcd. for C₄₀H₄₇N₁₁O₇: 776; found: 777 (M + H)⁺. | 51/129 |
| cj-39 | methyl ((1S)-2-((2S)-2-(5-(4'-(2-((2S)-1-(N-(methoxycarbonyl)-O-methyl-L-threonyl)-2-pyrrolidinyl)-1H-imidazol-5-yl)-4-biphenylyl)-1H-imidazol-2-yl)-1-pyrrolidinyl)-2-oxo-1-(1H-pyrazol-1-ylmethyl)ethyl)carbamate | 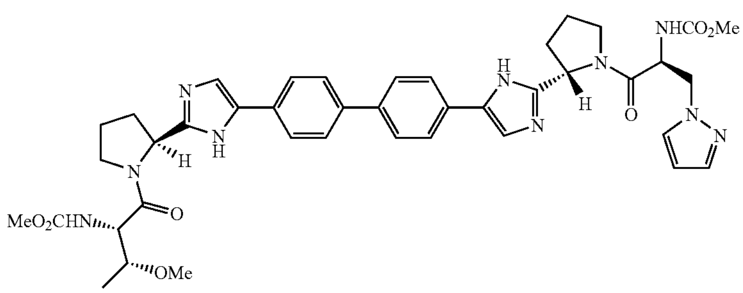 | LCMS: Anal. Calcd. for C₄₁H₄₈N₁₀O₇: 792; found: 793 (M + H)⁺. | 86/129 |
| cj-40 | methyl ((1S)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-1-((1-methyl-1H-imidazol-4-yl)methyl)-2-oxoethyl)carbamate | 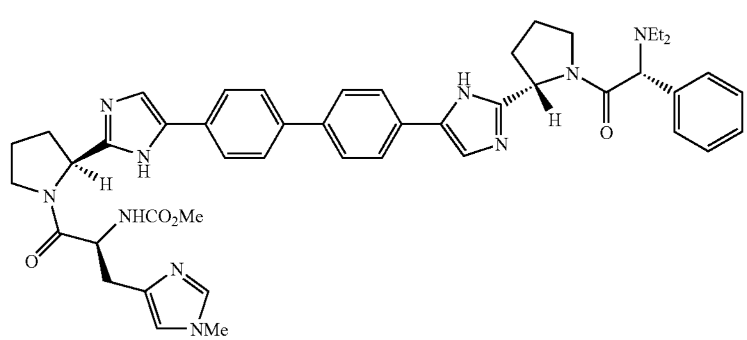 | LCMS: Anal. Calcd. for C₄₇H₅₄N₁₀O₄: 822; found: 823 (M + H)⁺. | 2/127 |

| Example | Compound Name | Structure | LCMS | Cap |
|---|---|---|---|---|
| cj-41 | methyl ((1S)-2-((2S)-2-(5-(4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-1-((1-methyl-1H-imidazol-4-yl)methyl)-2-oxoethyl) carbamate | 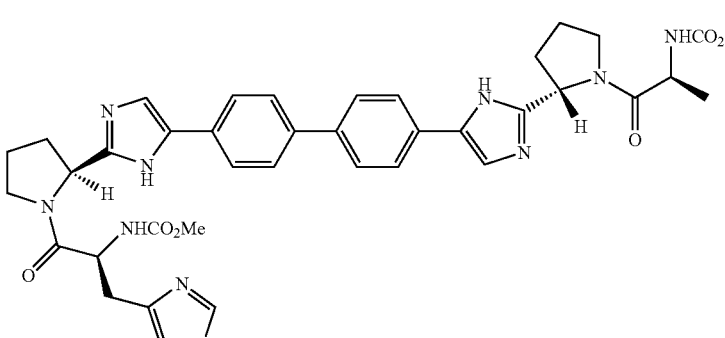 | LCMS: Anal. Calcd. for $C_{40}H_{46}N_{10}O_6$: 762; found: 763 (M + H)+. | 52/127 |
| cj-42 | methyl ((1S)-1-(((2S)-2-(5-(4'-(2-((2S)-1-((2S)-2-((methoxycarbonyl)amino)-3-(1-methyl-1H-imidazol-4-yl)propanoyl)-2-pyrrolidinyl)-1H-imidazol-5-yl)-4-biphenylyl)-1H-imidazol-2-yl)-1-pyrrolidinyl)carbonyl)-2-methylpropyl) carbamate | 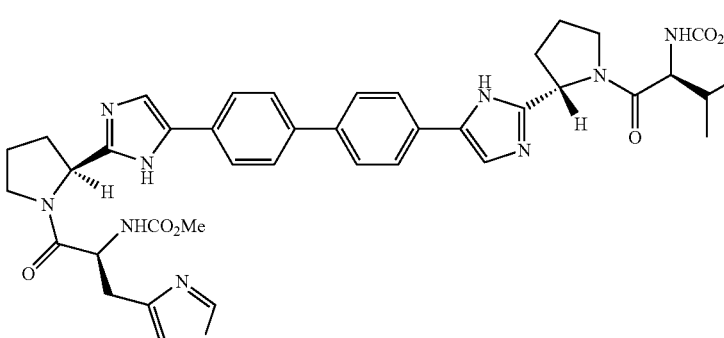 | LCMS: Anal. Calcd. for $C_{42}H_{50}N_{10}O_6$: 790; found: 791 (M + H)+. | 51/127 |
| cj-43 | methyl ((1S)-2-((2S)-2-(5-(4'-(2-((2S)-1-((2S,3R)-3-methoxy-2-((methoxycarbonyl)amino)butanoyl)-2-pyrrolidinyl)-1H-imidazol-5-yl)-4-biphenylyl)-1H-imidazol-2-yl)-1-pyrrolidinyl)-1-((1-methyl-1H-imidazol-4-yl)methyl)-2-oxoethyl) carbamate | 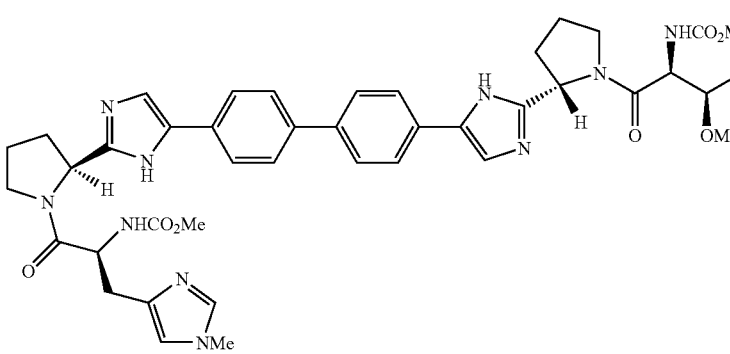 | LCMS: Anal. Calcd. for $C_{42}H_{50}N_{10}O_7$: 806; found: 806 (M + H)+. | 86/127 |

| Example | Compound Name | Structure | LCMS | Cap |
|---|---|---|---|---|
| cj-44 | methyl ((1S)-2-((2S)-2-(5-(4'-(2-((2S)-1-((2R)-2-(diethylamino)-2-phenyl-acetyl)-2-pyrrolidinyl)-1H-imidazol-5-yl)-4-biphenylyl)-1H-imidazol-2-yl)-1-pyrrolidinyl)-1-((1-methyl-1H-imidazol-5-yl)methyl)-2-oxoethyl) carbamate | 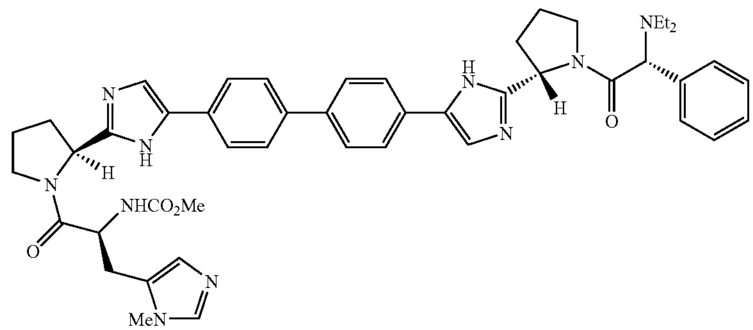 | LCMS: Anal. Calcd. for $C_{47}H_{54}N_{10}O_4$ 822; found: 823 $(M + H)^+$. | 2/126 |
| cj-45 | methyl ((1S)-2-((2S)-2-(5-(4'-(2-((2S)-1-(N-(methoxy-carbonyl)-L-alanyl)-2-pyrrolidinyl)-1H-imidazol-5-yl)-4-biphenylyl)-1H-imidazol-2-yl)-1-pyrrolidinyl)-1-((1-methyl-1H-imidazol-5-yl)methyl)-2-oxoethyl) carbamate | 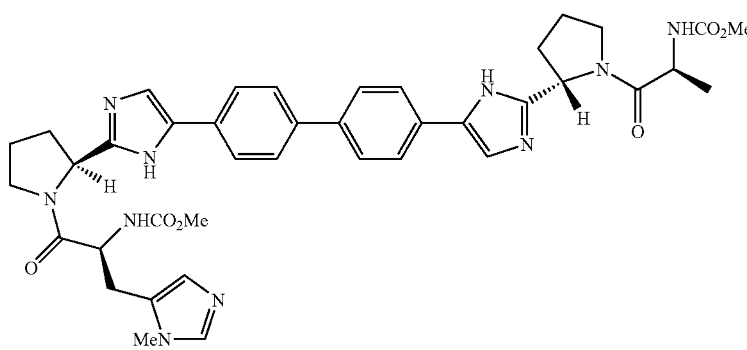 | LCMS: Anal. Calcd. for $C_{40}H_{46}N_{10}O_6$: 762; found: 763 $(M + H)^+$. | 52/126 |
| cj-46 | methyl ((1S)-1-(((2S)-2-(5-(4'-(2-((2S)-1-((2S)-2-((methoxy-carbonyl)amino)-3-(1-methyl-1H-imidazol-5-yl)propanoyl)-2-pyrrolidinyl)-1H-imidazol-5-yl)-4-biphenylyl)-1H-imidazol-2-yl)-1-pyrrolidinyl)carbonyl)-2-methylpropyl) carbamate | 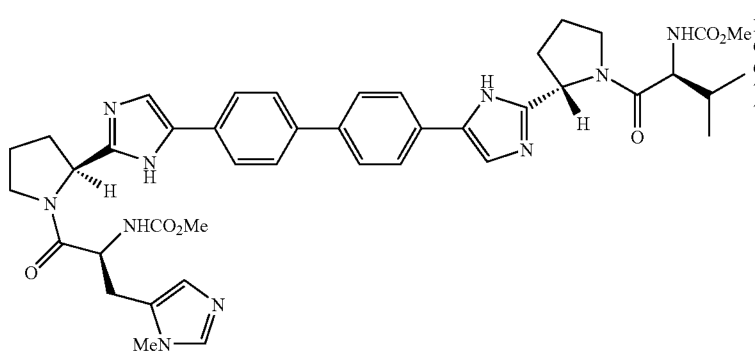 | LCMS: Anal. Calcd. for $C_{42}H_{50}N_{10}O_6$ 790; found: 791 | 51/126 |

| Example | Compound Name | Structure | LCMS | Cap |
|---|---|---|---|---|
| cj-47 | methyl ((1S)-2-((2S)-2-(5-(4'-(2-((2S)-1-((2S,3R)-3-methoxy-2-((methoxycarbonyl)amino)butanoyl)-2-pyrrolidinyl)-1H-imidazol-5-yl)-4-biphenylyl)-1H-imidazol-2-yl)-1-pyrrolidinyl)-1-((1-methyl-1H-imidazol-5-yl)methyl)-2-oxoethyl)carbamate | 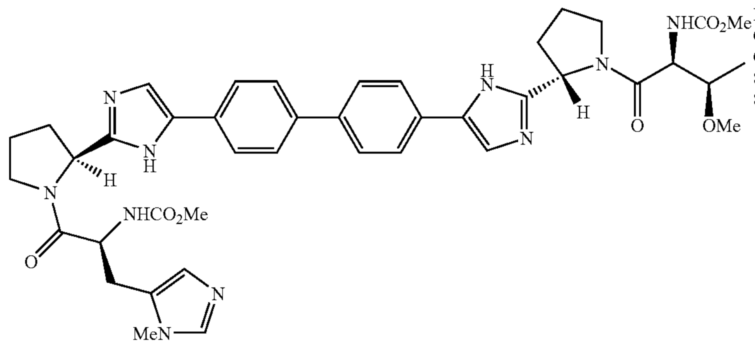 | LCMS: Anal. Calcd. for $C_{42}H_{50}N_{10}O_7$ 806; found: 807 (M + H)+. | 86/126 |
| cj-48 | methyl ((1S)-1-methyl-2-oxo-2-((2S)-2-(5-(4'-(2-((2S)-1-(((2S)-4-oxo-2-azetidinyl)carbonyl)-2-pyrrolidinyl)-1H-imidazol-5-yl)-4-biphenylyl)-1H-imidazol-2-yl)-1-pyrrolidinyl)ethyl)carbamate | 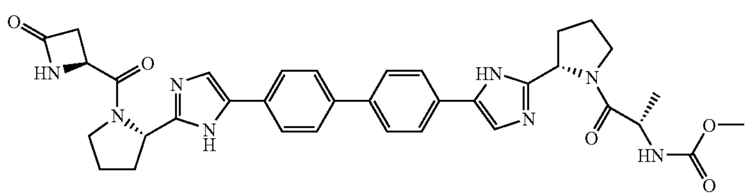 | LCMS: Anal. Calcd. for $C_{35}H_{38}N_8O_5$ 650; found: 651 (M + H)+. | 52/— |
| cj-49 | methyl (2S)-2-(((2S)-2-(5-(4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)carbonyl)-1-azetidinecarboxylate | 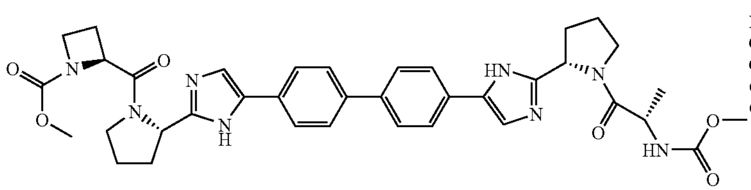 | LCMS: Anal. Calcd. for $C_{37}H_{42}N_8O_6$ 694; found: 695 (M + H)+. | 52/114 |
| cj-50 | methyl (2S)-2-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)-1-azetidinecarboxylate | 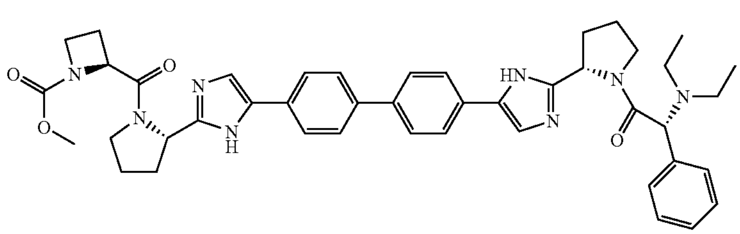 | LCMS: Anal. Calcd. for $C_{44}H_{50}N_8O_4$ 754; found: 755 (M + H)+. | 2/114 |

| Example | Compound Name | Structure | LCMS | Cap |
|---|---|---|---|---|
| cj-51 | methyl ((1S)-3-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-1-methyl-3-oxopropyl)carbamate | 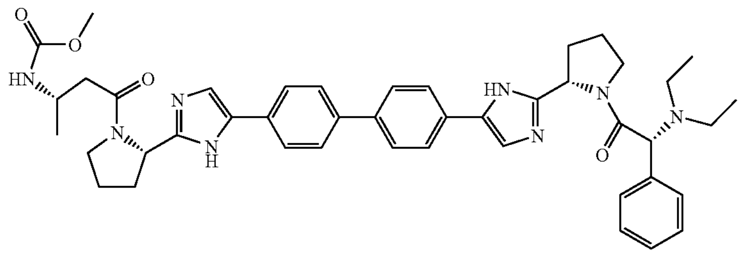 | LCMS: Anal. Calcd. for C$_{44}$H$_{52}$N$_8$O$_4$ 756; found: 757 (M + H)$^+$. | 2/115 |
| cj-52 | methyl ((1R)-3-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-1-isopropyl-3-oxopropyl)carbamate | 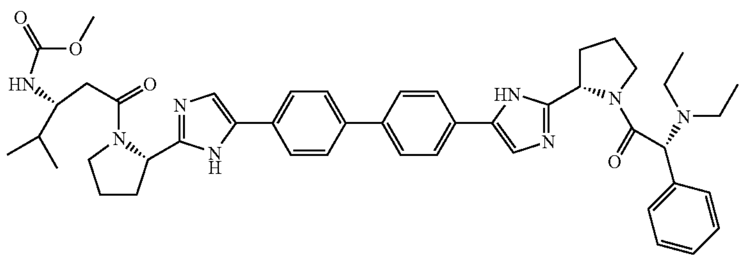 | LCMS: Anal. Calcd. for C$_{46}$H$_{56}$N$_8$O$_4$ 784; found: 785 (M + H)$^+$. | 2/116 |
| cj-53 | methyl ((1S)-1-benzyl-3-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-3-oxopropyl)carbamate | 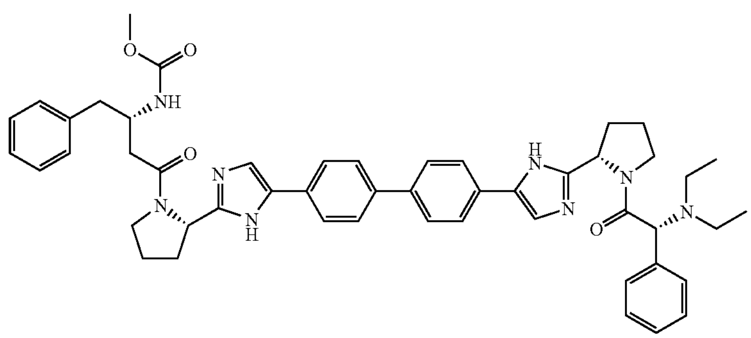 | LCMS: Anal. Calcd. for C$_{50}$H$_{56}$N$_8$O$_4$ 833; found: 834 (M + H)$^+$. | 2/96 |
| cj-54 | methyl ((1R)-3-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-3-oxo-1-(2-thienylmethyl)propyl)carbamate | 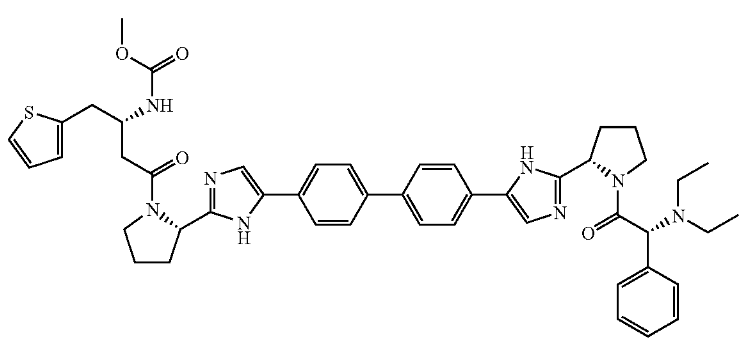 | LCMS: Anal. Calcd. for C$_{48}$H$_{54}$N$_8$O$_4$S 838; found: 839 (M + H)$^+$. | 2/119 |

| Example | Compound Name | Structure | LCMS | Cap |
|---|---|---|---|---|
| cj-55 | methyl ((1R)-3-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-3-oxo-1-(3-thienylmethyl)propyl) carbamate | 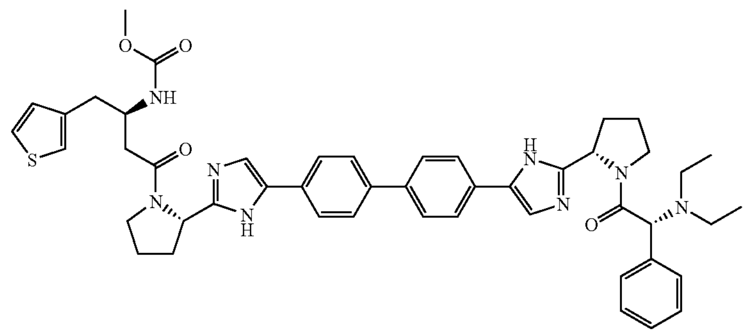 | LCMS: Anal. Calcd. for C₄₈H₅₄N₈O₄S 838; found: 839 (M + H)⁺. | 2/120 |
| cj-56 | methyl ((1S)-3-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-3-oxo-1-(2-thienylmethyl)propyl) carbamate | 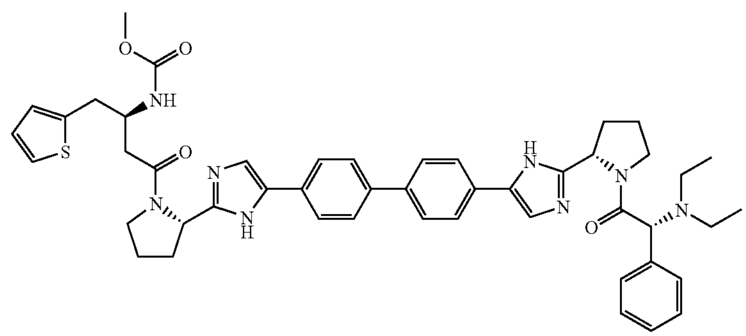 | LCMS: Anal. Calcd. for C₄₈H₅₄N₈O₄S 838; found: 839 (M + H)⁺. | 2/118 |
| cj-57 | methyl ((1S,3R)-3-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)cyclopenyl) carbamate | 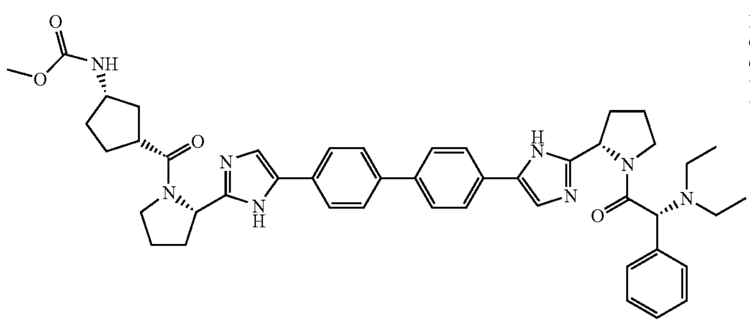 | LCMS: Anal. Calcd. for C₄₆H₅₄N₈O₄ 782; found: 783 (M + H)⁺. | 2/99a |
| cj-58 | methyl ((1R)-1-benzyl-3-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-3-oxopropyl) carbamate | 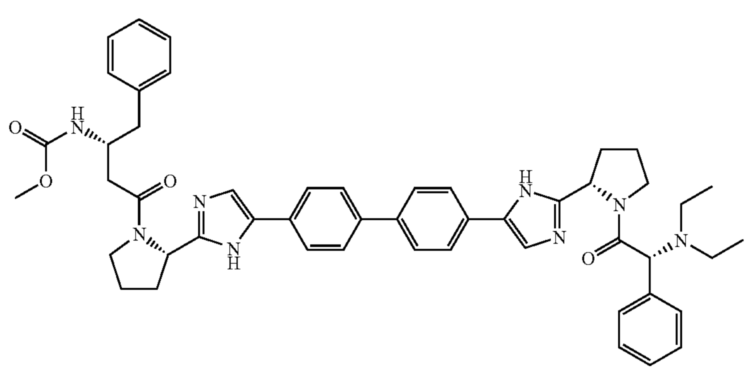 | LCMS: Anal. Calcd. for C₅₀H₅₆N₈O₄ 832; found: 833 (M + H)⁺. | 2/117 |

| Example | Compound Name | Structure | LCMS | Cap |
|---|---|---|---|---|
| cj-59 | methyl ((1R)-3-((2S)-2-(5-(4'-(2-((2S)-1-((2R)-2-(diethylamino)-2-phenylacetyl)-2-pyrrolidinyl)-1H-imidazol-5-yl)-4-biphenyl)-1H-imidazol-2-yl)-1-pyrrolidinyl)-1-(2-fluorobenzyl)-3-oxopropyl) carbamate | 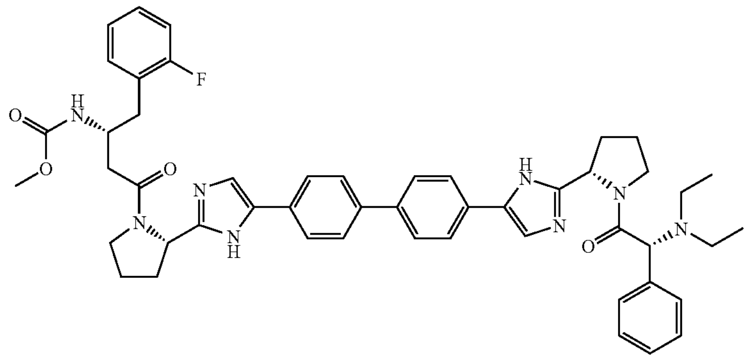 | LCMS: Anal. Calcd. for $C_{50}H_{55}N_8O_4F$ 850; found: 851 (M + H)$^+$. | 2/100 |
| cj-60 | methyl ((1R,3S)-3-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl) carbonyl) cyclopentyl) carbamate | 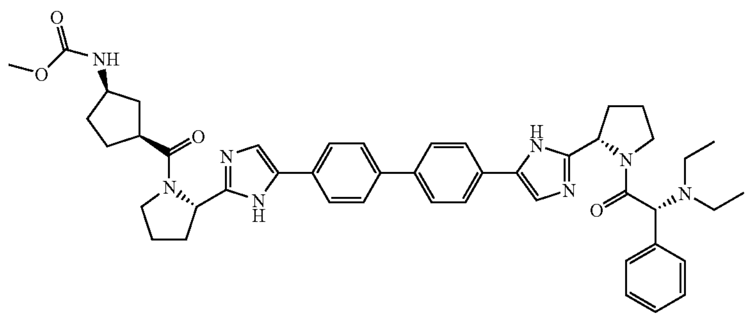 | LCMS: Anal. Calcd. for $C_{46}H_{54}N_8O_4$ 782; found: 783 (M + H)$^+$. | 2/99 |
| cj-61 | methyl ((1S)-1-(((2S)-2-(5-(4'-(2-((2S)-1-(((1R,3S)-3-((methoxycarbonyl)amino)cyclopentyl)carbonyl)-2-pyrrolidinyl)-1H-imidazol-5-yl)-4-biphenylyl)-1H-imidazol-2-yl)-1-pyrrolidinyl) carbonyl)-2-methylpropyl) carbamate | 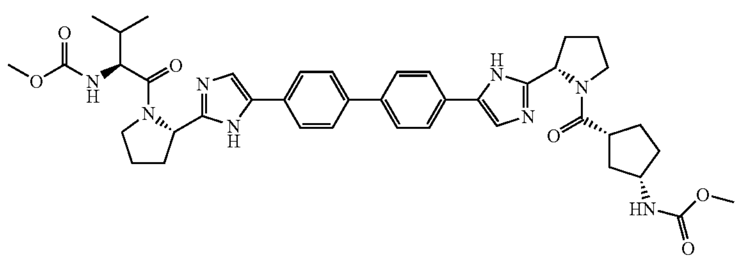 | LCMS: Anal. Calcd. for $C_{41}H_{50}N_8O_6$ 750; found: 751 (M + H)$^+$. | 52/99a |
| cj-62 | methyl ((1S)-1-(((2S)-2-(5-(4'-(2-((2S)-1-(((1S,3R)-3-((methoxycarbonyl)amino)cyclopentyl)carbonyl)-2-pyrrolidinyl)-1H-imidazol-5-yl)-4-biphenylyl)-1H-imidazol-2-yl)-1-pyrrolidinyl)carbonyl)-2-methylpropyl) carbamate | 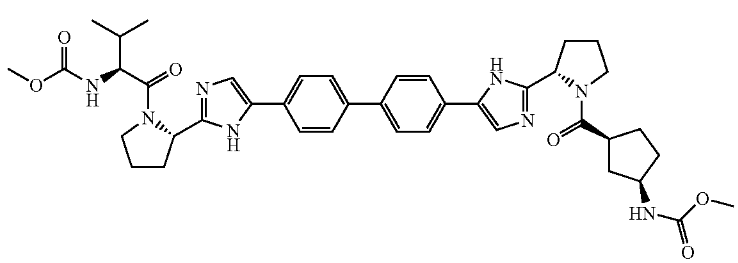 | LCMS: Anal. Calcd. for $C_{41}H_{50}N_8O_6$ 750; found: 751 (M + H)$^+$. | 52/99 |

| Example | Compound Name | Structure | LCMS | Cap |
|---|---|---|---|---|
| cj-63 | methyl ((1R)-2-((2S)-2-(5-(4'-(2-((2S)-1-(((1R,3S)-3-((methoxycarbonyl)amino)cyclopentyl)carbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | 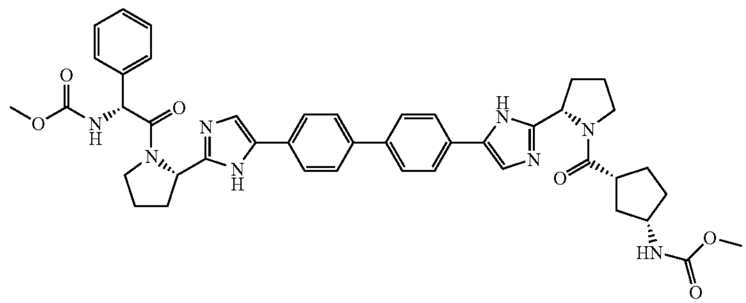 | LCMS: Anal. Calcd. for $C_{44}H_{48}N_8O_6$ 748; found: 785 (M + H)$^+$. | 4/99a |
| cj-64 | methyl ((1R)-2-((2S)-2-(5-(4'-(2-((2S)-1-(((1S,3R)-3-((methoxycarbonyl)amino)cyclopentyl)carbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | 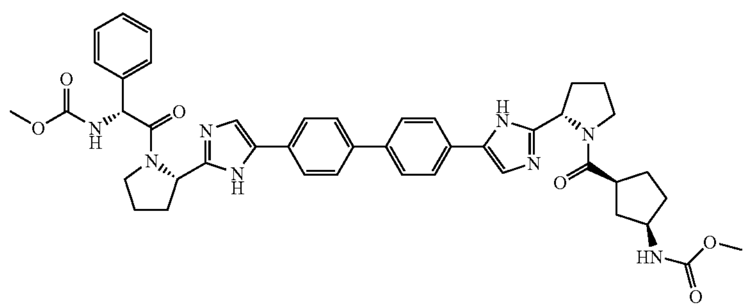 | LCMS: Anal. Calcd. for $C_{44}H_{48}N_8O_6$ 748; found: 785 (M + H)$^+$. | 4/99 |
| cj-65 | methyl ((1S)-1-(((2S)-2-(5-(4'-(2-((2S)-1-((2S)-2-((methoxycarbonyl)amino)-3-(2-pyridinyl)propanoyl)-2-pyrrolidinyl)-1H-imidazol-5-yl)-4-biphenylyl)-1H-imidazol-2-yl)-1-pyrrolidinyl)carbonyl)-2-methylpropyl)carbamate | 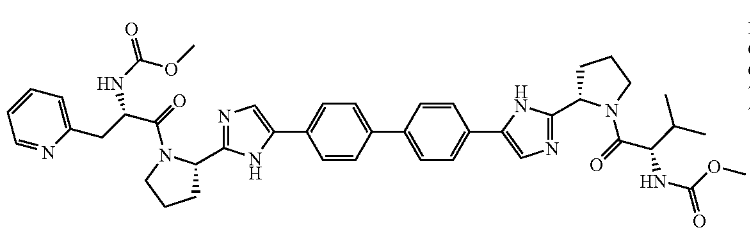 | LCMS: Anal. Calcd. for $C_{43}H_{49}N_9O_6$ 787; found: 788 (M + H)$^+$. | 51/93 |

| Example | Compound Name | Structure | LCMS | Cap |
|---|---|---|---|---|
| cj-66 | methyl ((1S)-2-((2S)-2-(5-(4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-2-oxo-1-(2-pyridinylmethyl)ethyl)carbamate | 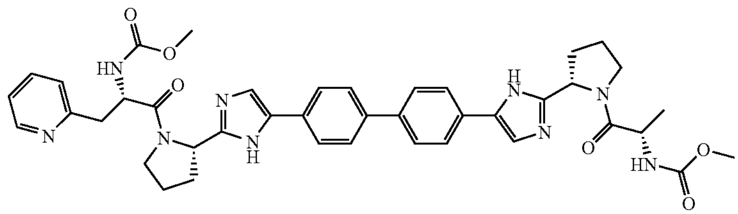 | LCMS: Anal. Calcd. for $C_{41}H_{45}N_9O_6$ 759; found: 760 (M + H)⁺. | 52/93 |
| cj-67 | methyl ((1S)-2-((2S)-2-(5-(4'-(2-((2S)-1-((2S,3R)-3-methoxy-2-((methoxycarbonyl)amino)butanonyl)-2-pyrrolidinyl)-1H-imidazol-5-yl)-4-biphenylyl)-1H-imidazol-2-yl)-1-pyrrolidinyl)-2-oxo-1-(2-pyridinylmethyl)ethyl)carbamate | 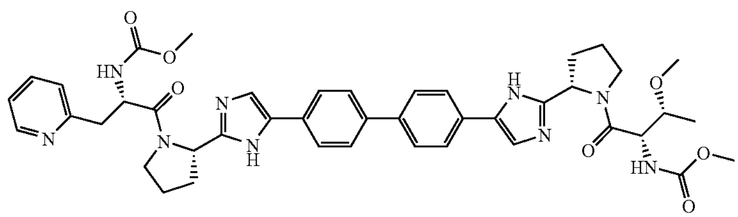 | LCMS: Anal. Calcd. for $C_{43}H_{49}N_9O_7$ 803; found: 804 (M + H)⁺. | 86/93 |
| cj-68 | methyl ((1S)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-2-oxo-1-(2-pyridinylmethyl)ethyl)carbamate | 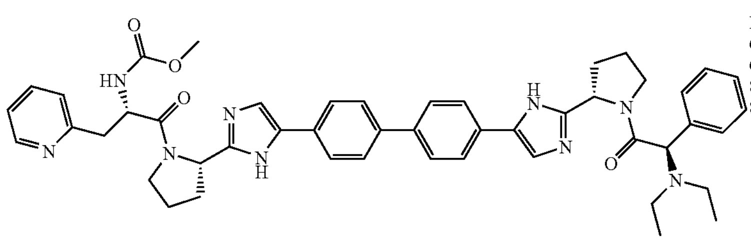 | LCMS: Anal. Calcd. for $C_{48}H_{53}N_9O_4$ 819; found: 820 (M + H)⁺. | 2/93 |

| Example | Compound Name | Structure | LCMS | Cap |
|---|---|---|---|---|
| cj-69 | methyl ((1S)-1-(((2S)-2-(5-(4'-(2-((2S)-1-((cis-4-((methoxycarbonyl)amino)cyclohexyl)carbonyl)-2-pyrrolidinyl)-1H-imidazol-5-yl)-4-biphenylyl)-1H-imidazol-2-yl)-1-pyrrolidinyl)carbonyl)-2-methylpropyl)carbamate | 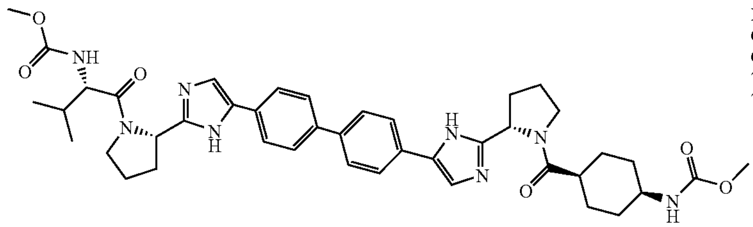 | LCMS: Anal. Calcd. for $C_{42}H_{52}N_8O_6$ 764; found: 765 $(M + H)^+$. | 51/104 |
| cj-70 | methyl ((1S)-1-(((2S)-2-(5-(4'-(2-((2S)-1-((trans-4-((methoxycarbonyl)amino)cyclohexyl)carbonyl)-2-pyrrolidinyl)-1H-imidazol-5-yl)-4-biphenylyl)-1H-imidazol-2-yl)-1-pyrrolidinyl)carbonyl)-2-methylpropyl)carbamate | 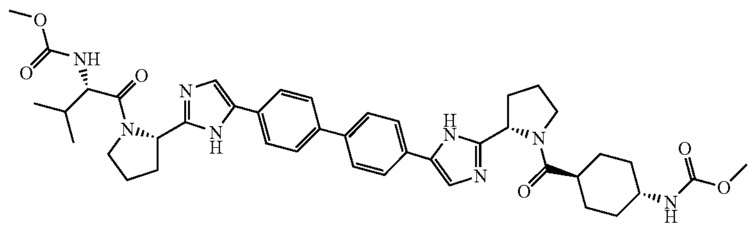 | LCMS: Anal. Calcd. for $C_{42}H_{52}N_8O_6$ 764; found: 765 $(M + H)^+$. | 51/105 |
| cj-71 | methyl ((1S)-1-(((2S)-2-(5-(4'-(2-((2S)-1-((cis-4-(diethylamino)cyclohexyl)carbonyl)-2-pyrrolidinyl)-1H-imidazol-5-yl)-4-biphenylyl)-1H-imidazol-2-yl)-1-pyrrolidinyl)carbonyl)-2-methylpropyl)carbamate | 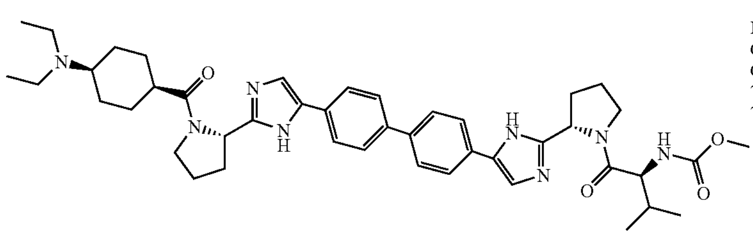 | LCMS: Anal. Calcd. for $C_{44}H_{58}N_8O_4$ 762; found: 763 $(M + H)^+$. | 51/106 |

| Example | Compound Name | Structure | LCMS | Cap |
|---|---|---|---|---|
| cj-72 | methyl ((1S,2R)-1-(((2S)-2-(5-(4'-(2-((2S)-1-((cis-4-(diethylamino)cyclohexyl)carbonyl)-2-pyrrolidinyl)-1H-imidazol-5-yl)-4-biphenylyl)-1H-imidazol-2-yl)-1-pyrrolidinyl)carbonyl)-2-methoxypropyl)carbamate | 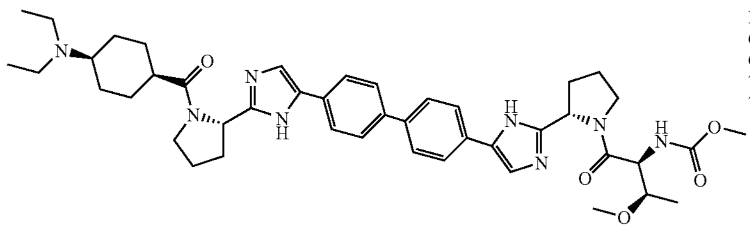 | LCMS: Anal. Calcd. for $C_{44}H_{58}N_8O_5$ 778; found: 779 $(M+H)^+$. | 86/106 |
| cj-73 | cis-4-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)-N,N-diethylcyclohexanamine | 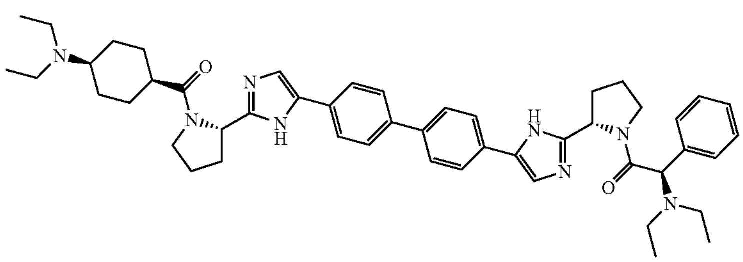 | LCMS: Anal. Calcd. for $C_{49}H_{62}N_8O_2$ 794; found: 795 $(M+H)^+$. | 2/106 |
| cj-74 | methyl ((1S)-2-((2S)-2-(5-(4'-(2-((2S)-1-((cis-4-(diethylamino)cyclohexyl)carbonyl)-2-pyrrolidinyl)-1H-imidazol-5-yl)-4-biphenylyl)-1H-imidazol-2-yl)-1-pyrrolidinyl)-1-methyl-2-oxoethyl)carbamate | 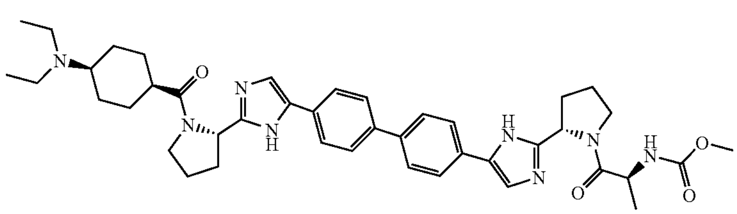 | LCMS: Anal. Calcd. for $C_{42}H_{54}N_8O_4$ 734; found: 735 $(M+H)^+$. | 52/106 |

| Example | Compound Name | Structure | LCMS | Cap |
|---|---|---|---|---|
| cj-75 | methyl ((1S)-1-((1-benzyl-1H-imidazol-4-yl)methyl)-2-((2S)-2-(5-(4'-(2-((2S)-1-((2S,3R)-3-methoxy-2-((methoxycarbonyl)amino)butanoyl)-2-pyrrolidinyl)-1H-imidazol-5-yl)-4-biphenylyl)-1H-imidazol-2-yl)-1-pyrrolidinyl)-2-oxoethyl)carbamate | 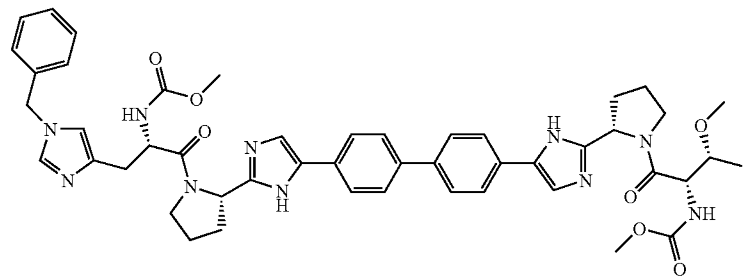 | LCMS: Anal. Calcd. for C<sub>48</sub>H<sub>54</sub>N<sub>10</sub>O<sub>7</sub> 882; found: 883 (M + H)<sup>+</sup>. | 86/108 |
| cj-76 | methyl ((1S)-1-(((2S)-2-(5-(4'-(2-((2S)-1-((2S)-3-(1-benzyl-1H-imidazol-4-yl)-2-((methoxycarbonyl)amino)propanoyl)-2-pyrrolidinyl)-1H-imidazol-5-yl)-4-biphenylyl)-1H-imidazol-2-yl)-1-pyrrolidinyl)carbonyl)-2-methylpropyl)carbamate | 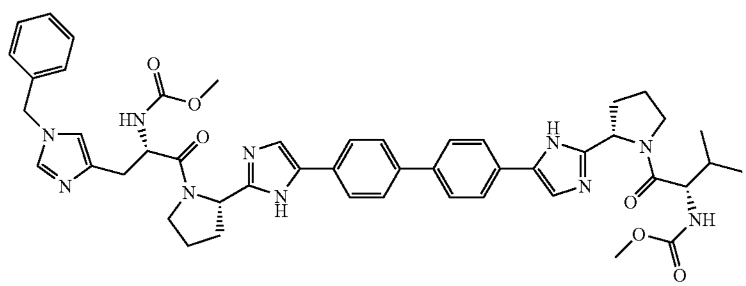 | LCMS: Anal. Calcd. for C<sub>48</sub>H<sub>54</sub>N<sub>10</sub>O<sub>6</sub> 866; found: 867 (M + H)<sup>+</sup>. | 51/108 |
| cj-77 | methyl ((1S)-2-((2S)-2-(5-(4'-(2-((2S)-1-((2S)-3-(1-benzyl-1H-imidazol-4-yl)-2-((methoxycarbonyl)amino)propanoyl)-2-pyrrolidinyl)-1H-imidazol-5-yl)-4-biphenylyl)-1H-imidazol-2-yl)-1-pyrrolidinyl)-1-methyl-2-oxoethyl)carbamate | 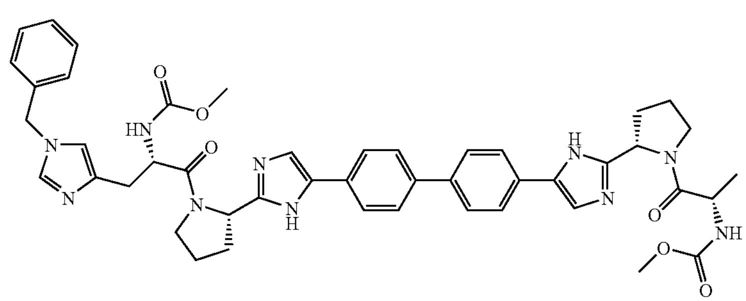 | LCMS: Anal. Calcd. for C<sub>46</sub>H<sub>50</sub>N<sub>10</sub>O<sub>6</sub> 838; found: 839 (M + H)<sup>+</sup>. | 52/108 |

| Example | Compound Name | Structure | LCMS | Cap |
|---|---|---|---|---|
| cj-78 | methyl ((1S)-2-((2S)-2-(5-(4'-(2-((2S)-1-((2S,3R)-3-methoxy-2-((methoxycarbonyl)amino)butanoyl)-2-pyrrolidinyl)-1H-imidazol-5-yl)-4-biphenylyl)-1H-imidazol-2-yl)-1-pyrrolidinyl)-2-oxo-1-(1,3-thiazol-4-ylmethyl)ethyl)carbamate | 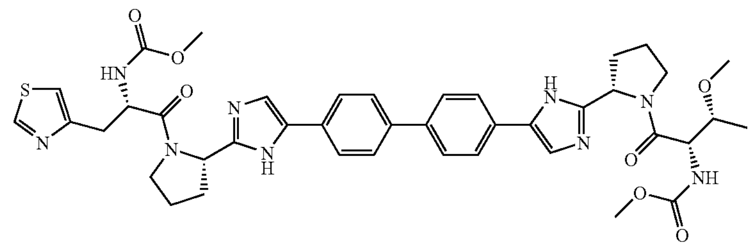 | LCMS: Anal. Calcd. for $C_{41}H_{47}N_9O_7S$ 809; found: 810 (M + H)⁺. | 86/107 |
| cj-79 | methyl ((1S)-1-(((2S)-2-(5-(4'-(2-((2S)-1-((2S)-2-((methoxycarbonyl)amino)-3-(1,3-thiazol-4-yl)propanoyl)-2-pyrrolidinyl)-1H-imidazol-5-yl)-4-biphenylyl)-1H-imidazol-2-yl)-1-pyrrolidinyl)carbonyl)-2-methylpropyl)carbamate | 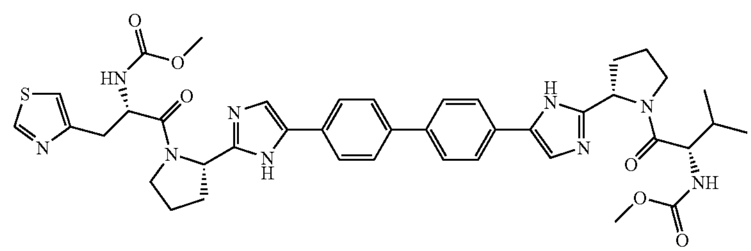 | LCMS: Anal. Calcd. for $C_{41}H_{47}N_9O_6S$ 793; found: 794 (M + H)⁺. | 51/107 |
| cj-80 | methyl ((1S)-2-((2)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-2-oxo-1-(1,3-thiazol-4-ylmethyl)ethyl)carbamate | 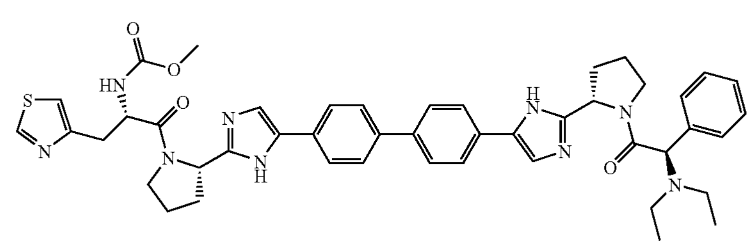 | LCMS: Anal. Calcd. for $C_{46}H_{51}N_9O_4S$ 825; found: 826 (M + H)⁺. | 2/107 |

| Example | Compound Name | Structure | LCMS | Cap |
|---|---|---|---|---|
| cj-81 | methyl ((1S)-2-((2S)-2-(5-(4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-2-oxo-1-(1,3-thiazol-4-ylmethyl)ethyl)carbamate | 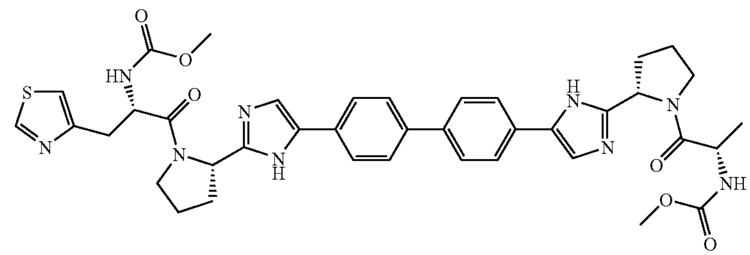 | LCMS: Anal. Calcd. for $C_{39}H_{43}N_9O_6S$ 765; found: 766 $(M+H)^+$. | 51/107 |
| cj-82 | methyl ((1S)-2-((2S)-2-(5-(4'-(2-((2S)-1-((2S,3R)-3-methoxy-2-((methoxycarbonyl)amino)butanoyl)-2-pyrrolidinyl)-1H-imidazol-5-yl)-4-biphenylyl)-1H-imidazol-2-yl)-1-pyrrolidinyl)-2-oxo-1-(3-pyridinylmethyl)ethyl)carbamate | 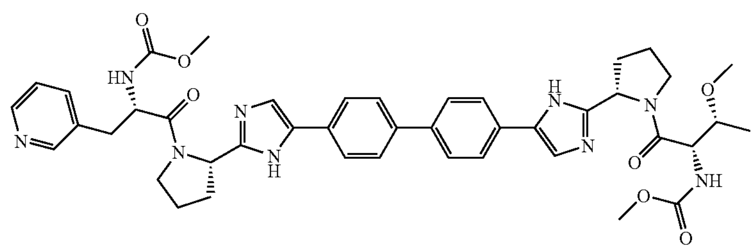 | LCMS: Anal. Calcd. for $C_{43}H_{49}N_9O_7$ 803; found: 804 $(M+H)^+$. | 86/109 |
| cj-83 | methyl ((1S)-2-((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)-2-oxo-1-(3-pyridinylmethyl)ethyl)carbamate | 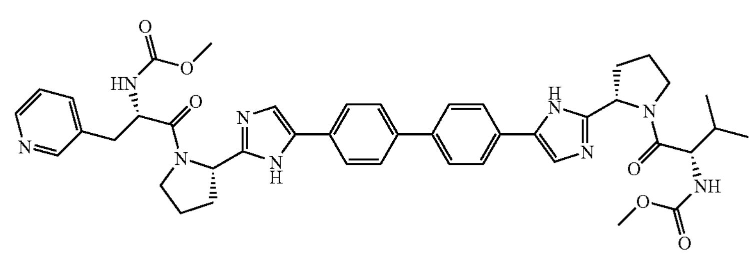 | LCMS: Anal. Calcd. for $C_{43}H_{49}N_9O_6$ 787; found: 788 $(M+H)^+$. | 51/109 |

| Example | Compound Name | Structure | LCMS | Cap |
|---|---|---|---|---|
| cj-84 | methyl ((1S)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-2-oxo-1-(3-pyridinylmethyl)ethyl) carbamate | 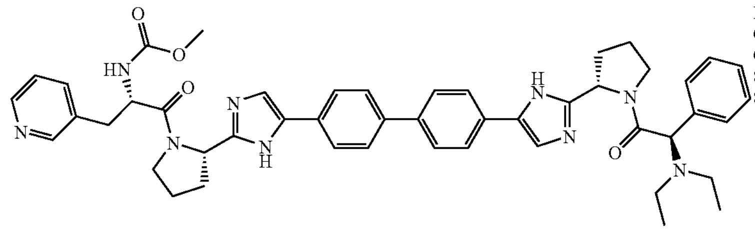 | LCMS: Anal. Calcd. for $C_{48}H_{53}N_9O_4$ 819; found: 820 (M + H)$^+$. | 2/109 |
| cj-85 | methyl ((1S)-2-((2S)-2-(5-(4'-(2-((2S)-1-N-(methoxycarbonyl)-L-alanyl)-2-pyrrolidinyl)-1H-imidazol-5-yl)-4-biphenylyl)-1H-imidazol-2-yl)-1-pyrrolidinyl)-2-oxo-1-(3-pyridinylmethyl)ethyl) carbamate | 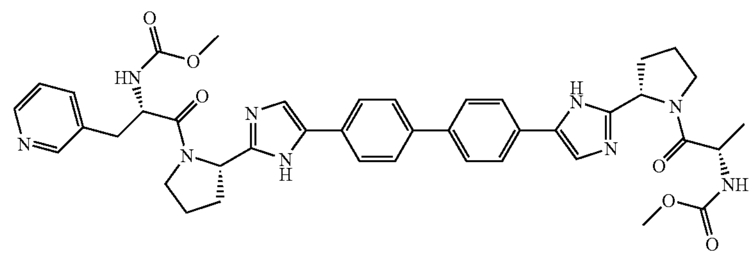 | LCMS: Anal. Calcd. for $C_{41}H_{45}N_9O_6$ 759; found: 760 (M + H)$^+$. | 52/109 |
| cj-86 | methyl ((1R,3S)-3-(((2S)-2-(5-(4'-(2-((2S)-1-((2S)-3-methoxy-2-((methoxycarbonyl)amino)butanoyl)-2-pyrrolidinyl)-1H-imidazol-5-yl)-4-biphenylyl)-1H-imidazol-2-yl)-1-pyrrolidinyl)carbonyl)cyclopentyl) carbamate | 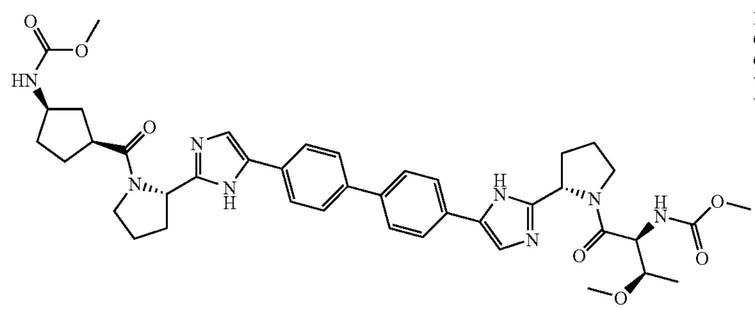 | LCMS: Anal. Calcd. for $C_{42}H_{50}N_8O_7$ 766; found: 767 (M + H)$^+$. | 86/99 |
| cj-87 | methyl ((1S)-2-((2S)-2-(5-(4'-(2-((2S)-1-((2S,3R)-3-methoxy-2-((methoxycarbonyl)amino)butanoyl)-2-pyrrolidinyl)-1H-imidazol-5-yl)-4-biphenylyl)-1H-imidazol-2-yl)-1-pyrrolidinyl)-2-oxo-1-(4-pyridinylmethyl)ethyl) carbamate | 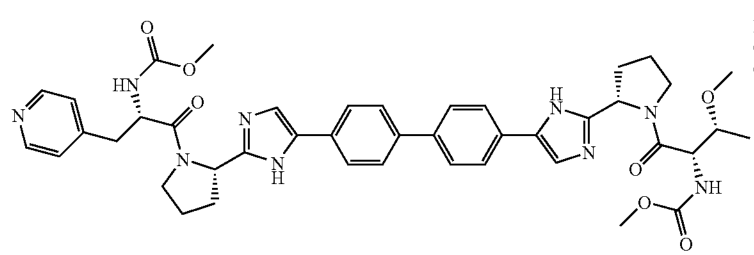 | LCMS: Anal. Calcd. for $C_{43}H_{49}N_9O_7$ 803; found: 804 (M + H)$^+$. | 86/110 |

| Example | Compound Name | Structure | LCMS | Cap |
|---|---|---|---|---|
| cj-88 | methyl ((1S)-2-((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)-2-oxo-1-(4-pyridinylmethyl)ethyl)carbamate | 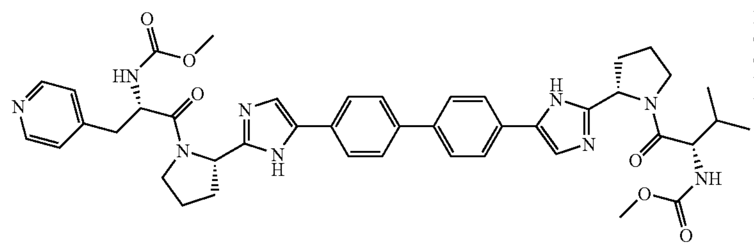 | LCMS: Anal. Calcd. for $C_{43}H_{49}N_9O_6$ 787; found: 788 (M + H)$^+$. | 51/110 |
| cj-89 | methyl ((1S)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-2-oxo-1-(4-pyridinylmethyl)ethyl)carbamate | 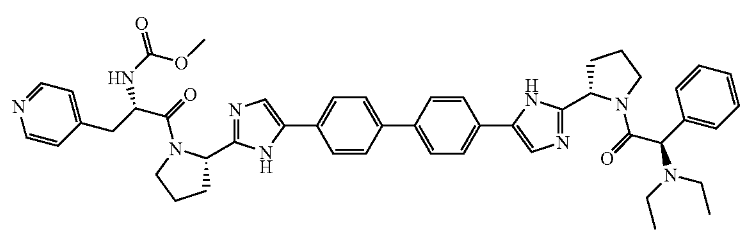 | LCMS: Anal. Calcd. for $C_{48}H_{53}N_9O_4$ 819; found: 820 (M + H)$^+$. | 2/110 |
| cj-90 | methyl ((1S)-2-((2S)-2-(5-(4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-2-oxo-1-(4-pyridinylmethyl)ethyl)carbamate | 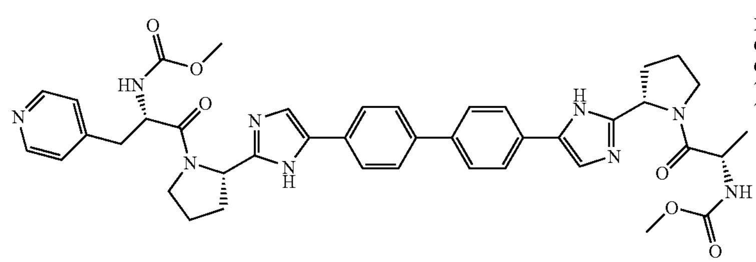 | LCMS: Anal. Calcd. for $C_{41}H_{45}N_9O_6$ 759; found: 760 (M + H)$^+$. | 52/110 |

-continued

| Example | Compound Name | Structure | LCMS | Cap |
|---|---|---|---|---|
| cj-91 | methyl ((1S)-1-(((2S)-2-(5-(4'-(2-((2S)-1-(O-hydroxy(methoxy)phosphoryl)-N-(methoxy-carbonyl)-L-tyrosyl)-2-pyrrolidinyl)-1H-imidazol-5-yl)-4-biphenylyl)-1H-imidazol-2-yl)-1-pyrrolidinyl)carbonyl)-2-methylpropyl)carbamate | 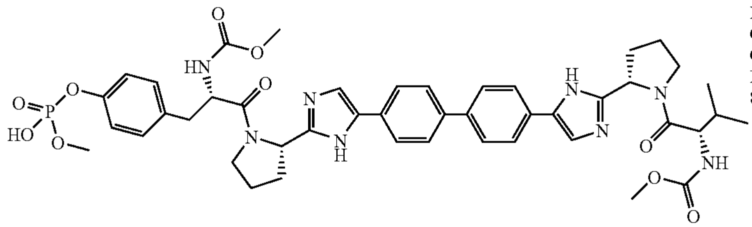 | LCMS: Anal. Calcd. for $C_{45}H_{53}N_8O_{10}P$ 896; found: 897 $(M+H)^+$. | 51/111 |
| cj-92 | methyl ((1S,2R)-1-(((2S)-2-(5-(4'-(2-((2S)-1-(O-hydroxy(methoxy)phosphoryl)-N-(methoxy-carbonyl)-L-tyrosyl)-2-pyrrolidinyl)-1H-imidazol-5-yl)-4-biphenylyl)-1H-imidazol-2-yl)-1-pyrrolidinyl)carbonyl)-2-methoxy-propyl)carbamate | 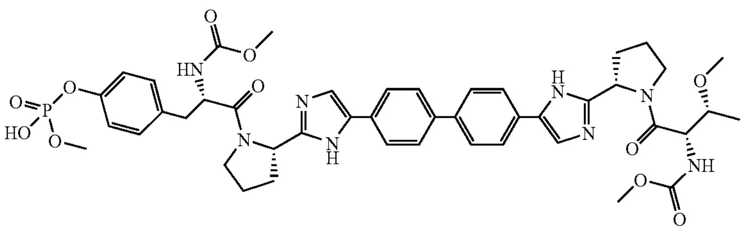 | LCMS: Anal. Calcd. for $C_{45}H_{53}N_8O_{11}P$ 912; found: 913 $(M+H)^+$. | 86/111 |
| cj-93 | methyl ((1S)-1-(((2S)-2-(5-(4'-(2-((2S)-1-(((1S,2R)-2-((methoxy-carbonyl)amino)cyclohexyl)carbonyl)-2-pyrrolidinyl)-1H-imidazol-5-yl)-4-biphenylyl)-1H-imidazol-2-yl)-1-pyrrolidinyl)carbonyl)-2-methyl-propyl)carbamate | 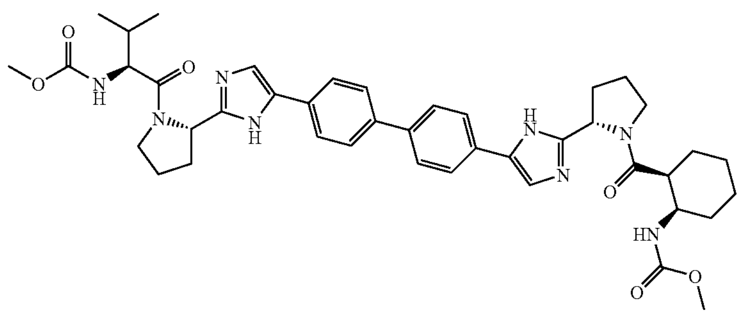 | LCMS: Anal. Calcd. for $C_{42}H_{52}N_8O_6$ 764; found: 765 $(M+H)^+$. | 98/51 |
| cj-94 | methyl ((1R,2S)-2-(((2S)-2-(5-(4'-(2-((2S)-1-((2R)-2-(diethyl-amino)-2-phenyl-acetyl)-2-pyrrolidinyl)-1H-imidazol-5-yl)-4-biphenylyl)-1H-imidazol-2-yl)-1-pyrrolidinyl)carbonyl)cyclohexyl)carbamate | 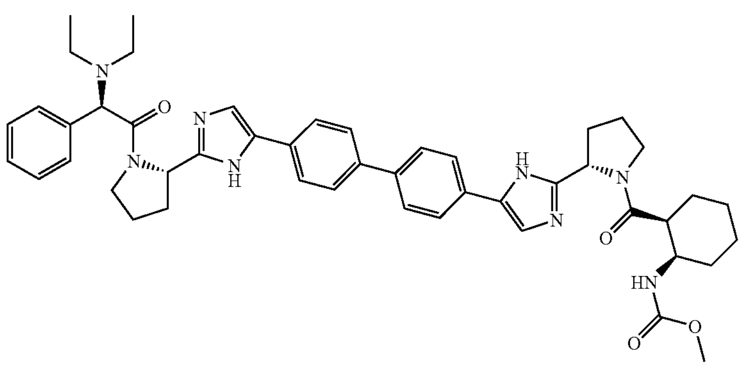 | LCMS: Anal. Calcd. for $C_{47}H_{56}N_8O_4$ 796; found: 797 $(M+H)^+$. | 98/2 |

| Example | Compound Name | Structure | LCMS | Cap |
|---|---|---|---|---|
| cj-95 | methyl ((1R)-2-((2S)-2-(5-(4'-(2-((2S)-1-(((1S,2R)-2-((methoxycarbonyl)amino)cyclohexyl)carbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | 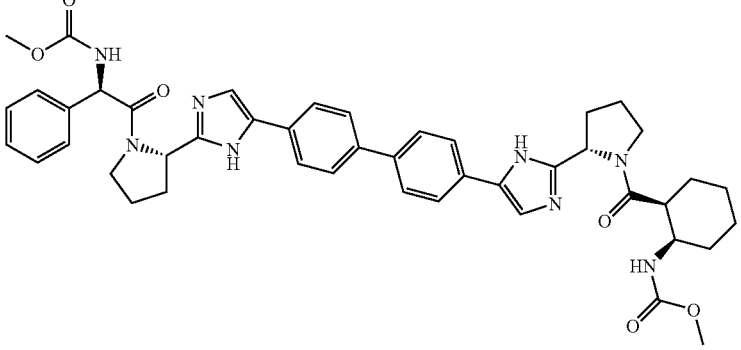 | LCMS: Anal. Calcd. for C$_{45}$H$_{50}$N$_8$O$_6$ 798; found: 799 (M + H)$^+$. | 98/4 |
| cj-96 | methyl ((1R,2S)-2-(((2S)-2-(5-(4'-(2-((2S)-1-N-(methoxycarbonyl)-L-alanyl)-2-pyrrolidinyl)-1H-imidazol-5-yl)-4-biphenylyl)-1H-imidazol-2-yl)-1-pyrrolidinyl)carbonyl)cyclohexyl)carbamate | 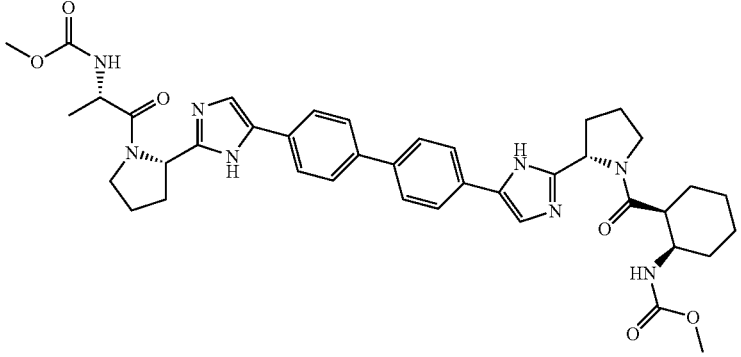 | LCMS: Anal. Calcd. for C$_{40}$H$_{48}$N$_8$O$_6$ 736; found: 737 (M + H)$^+$. | 98/51 |
| cj-97 | methyl ((1R,2S)-2-(((2S)-2-(5-(4'-(2-((2S)-1-((cis-4-(diethylamino)cyclohexyl)carbonyl)-2-pyrrolidinyl)-1H-imidazol-5-yl)-4-biphenylyl)-1H-imidazol-2-yl)-1-pyrrolidinyl)carbonyl)cyclohexyl)carbamate | 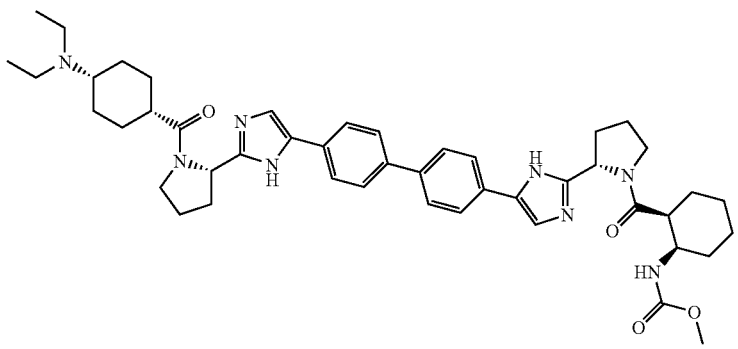 | LCMS: Anal. Calcd. for C$_{46}$H$_{60}$N$_8$O$_4$ 788; found: 789 (M + H)$^+$. | 98/106 |
| cj-98 | methyl ((1R,2S)-2-(((2S)-2-(5-(4'-(2-((2S)-1-((2R)-2-acetamido-2-phenylacetyl)-2-pyrrolidinyl)-1H-imidazol-5-yl)-4-biphenylyl)-1H-imidazol-2-yl)-1-pyrrolidinyl)carbonyl)cyclohexyl)carbamate | 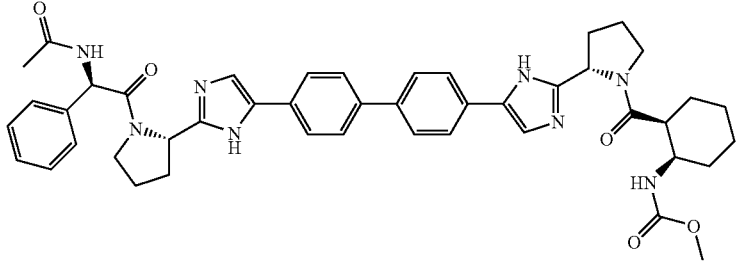 | LCMS: Anal. Calcd. for C$_{45}$H$_{50}$N$_8$O$_5$ 782; found: 783 (M + H)$^+$. | 98/130 |

-continued

| Example | Compound Name | Structure | LCMS | Cap |
|---|---|---|---|---|
| cj-99 | methyl ((1S)-1-(((2S)-2-(5-(4'-(2-((2S)-1-((2S)-3-(1H-indol-3-yl)-2-((methoxycarbonyl)amino)propanoyl)-2-pyrrolidinyl)-1H-imidazol-5-yl)-4-biphenylyl)-1H-imidazol-2-yl)-1-pyrrolidinyl)carbonyl)-2-methylpropyl)carbamate | 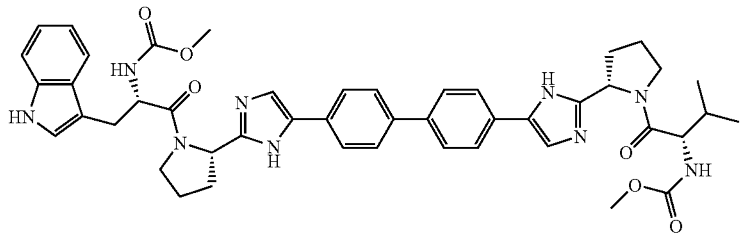 | LCMS: Anal. Calcd. for C₅₆H₆₁N₉O₆ 825; found: 826 (M + H)⁺. | 51/112 |
| cj-100 | methyl ((1S)-1-(1H-indol-3-ylmethyl)-2-((2S)-2-(5-(4'-(2-((2S)-1-((2S,3R)-3-methoxyl-2-((methoxycarbonyl)amino)butanoyl)-2-pyrrolidinyl)-1H-imidazol-5-yl)-4-biphenylyl)-1H-imidazol-2-yl)-1-pyrrolidinyl)-2-oxoethyl)carbamate | 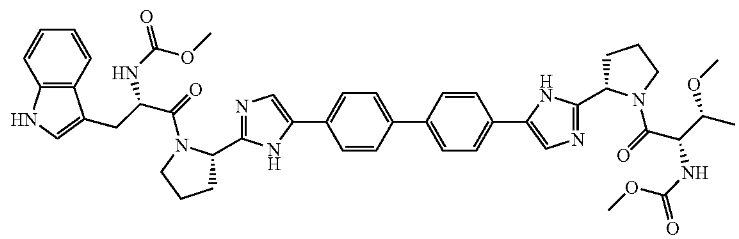 | LCMS: Anal. Calcd. for C₄₆H₅₁N₉O₇ 841; found: 842 (M + H)⁺. | 86/112 |
| cj-101 | methyl ((1S)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-1-(1H-indol-3-ylmethyl)-2-oxoethyl)carbamate | 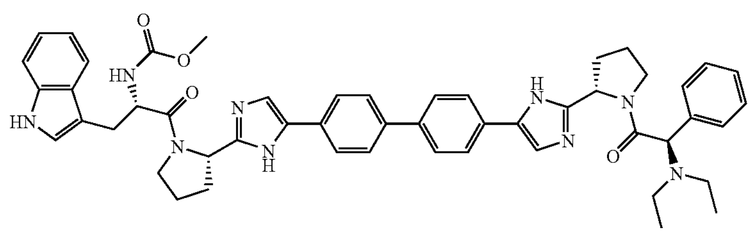 | LCMS: Anal. Calcd. for C₅₁H₅₅N₉O₄ 857; found: 858 (M + H)⁺. | 2/112 |
| cj-102 | methyl ((1S)-2-((2S)-2-(5-(4'-(2-((2S)-1-((2S)-3-(1H-indol-3-yl)-2-((methoxycarbonyl)amino)propanoyl)-2-pyrrolidinyl)-1H-imidazol-5-yl)-4-biphenylyl)-1H-imidazol-2-yl)-1-pyrrolidinyl)-1-methyl-2-oxoethyl)carbamate | 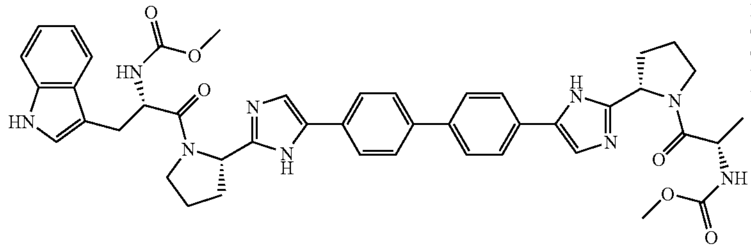 | LCMS: Anal. Calcd. for C₄₄H₄₇N₉O₆ 797; found: 798 (M + H)⁺. | 52/112 |

-continued

| Example | Compound Name | Structure | LCMS | Cap |
|---|---|---|---|---|
| cj-103 | methyl ((1S)-1-(4-(amino-methyl)benzyl)-2-((2S)-2-(5-(4'-(2-((2S)-1-((2S)-2-((methoxy-carbonyl)amino)-3-methyl)butanoyl)-2-pyrrolidinyl)-1H-imidazol-5-yl)-4-biphenylyl)-1H-imidazol-2-yl)-1-pyrrolidinyl)-2-oxoethyl) carbamate | 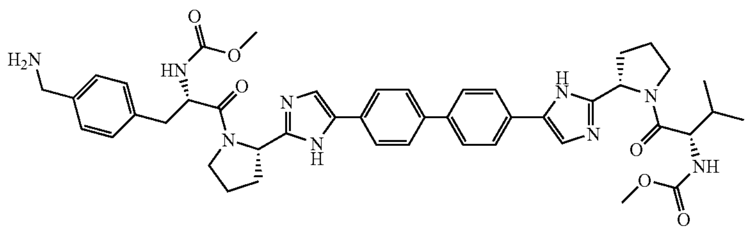 | LCMS: Anal. Calcd. for $C_{45}H_{53}N_9O_6$ 815; found: 816 (M + H)⁺. | see text |
| cj-104 | methyl ((1S)-1-(((2S)-2-(5-(4'-(2-((2S)-1-(O-benzyl-N-(methoxy-carbonyl)-L-tyrosyl)-2-pyrrolidinyl)-1H-imidazol-5-yl)-4-biphenylyl)-1H-imidazol-2-yl)-1-pyrrolidinyl)carbonyl)-2-methyl-propyl) carbamate | 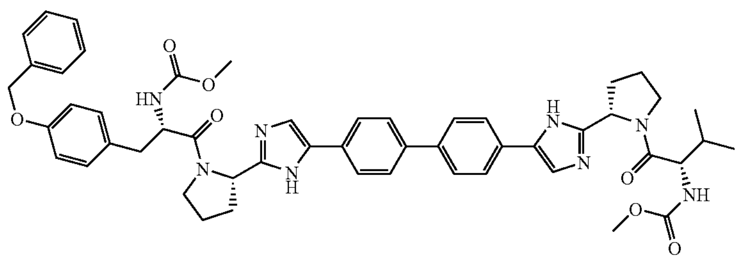 | LCMS: Anal. Calcd. for $C_{51}H_{56}N_8O_7$ 892; found: 893 (M + H)⁺. | 51/113 |
| cj-105 | methyl ((1S,2R)-1-(((2S)-2-(5-(4'-(2-((2S)-1-(O-benzyl-N-(methoxy-carbonyl)-L-tyrosyl)-2-pyrrolidinyl)-1H-imidazol-5-yl)-4-biphenylyl)-1H-imidazol-2-yl)-1-pyrrolidinyl)carbonyl)-2-methoxypropyl) carbamate | 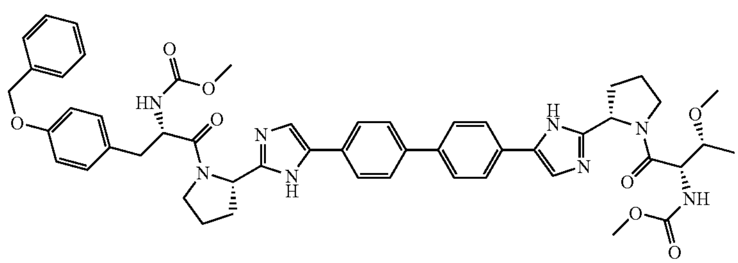 | LCMS: Anal. Calcd. for $C_{51}H_{56}N_8O_8$ 908; found: 909 (M + H)⁺. | 86/113 |
| cj-106 | methyl ((1S)-1-(4-(benzyloxy)benzyl)-2-((2S)-2-(5-(4'-(2-((2S)-1-((2R)-2-(diethyl-amino)-2-phenylacetyl)-2-pyrrolidinyl)-1H-imidazol-5-yl)-4-biphenylyl)-1H-imidazol-2-yl)-1-pyrrolidinyl)-2-oxoethyl) carbamate | 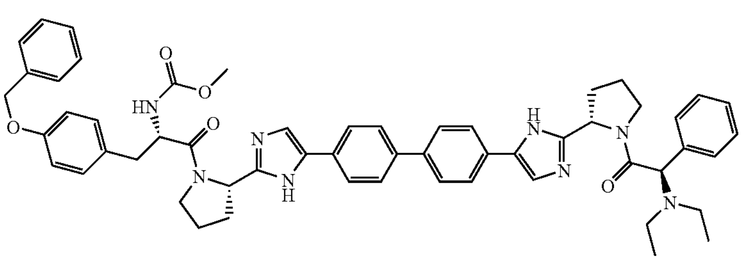 | LCMS: Anal. Calcd. for $C_{56}H_{60}N_8O_5$ 924; found: 925 (M + H)⁺. | 2/113 |

| Example | Compound Name | Structure | LCMS | Cap |
|---|---|---|---|---|
| cj-107 | methyl ((1S)-1-(4-(benzyloxy)benzyl)-2-((2S)-2-(5-(4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-2-oxoethyl)carbamate | 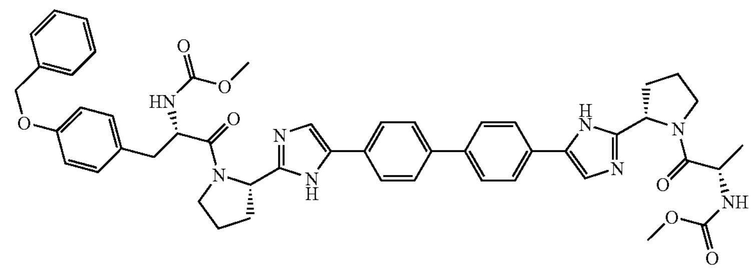 | LCMS: Anal. Calcd. for C$_{49}$H$_{52}$N$_8$O$_7$ 864; found: 865 (M + H)$^+$. | 52/113 |
| cj-108 | methyl ((1R,2R)-2-(((2S)-2-(5-(4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)carbonyl)cyclopentyl)carbamate | 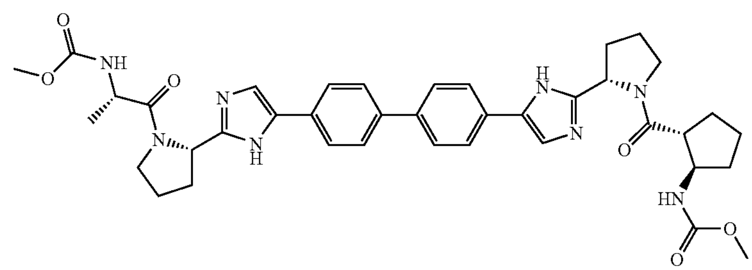 | LCMS: Anal. Calcd. for C$_{39}$H$_{46}$N$_8$O$_6$ 722; found: 723 (M + H)$^+$. | 122/52 |
| cj-109 | methyl ((1R,2R)-2-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)cyclopentyl)carbamate | 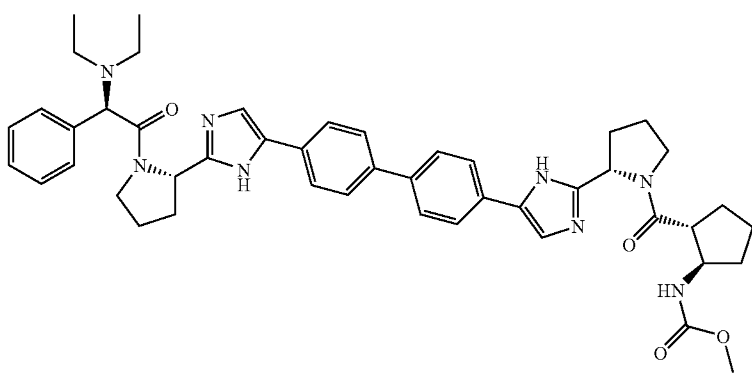 | LCMS: Anal. Calcd. for C$_{46}$H$_{54}$N$_8$O$_4$ 782; found: 783 (M + H)$^+$. | 122/2 |
| cj-110 | methyl ((1R)-2-((2S)-2-(5-(4'-(2-((2S)-1-(((1R,2R)-2-((methoxycarbonyl)amino)cyclopentyl)carbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | 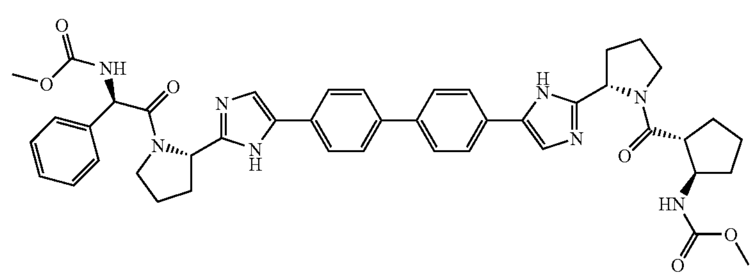 | LCMS: Anal. Calcd. for C$_{44}$H$_{48}$N$_8$O$_6$ 784; found: 785 (M + H)$^+$. | 122/4 |

| Example | Compound Name | Structure | LCMS | Cap |
|---|---|---|---|---|
| cj-111 | methyl ((1S)-1-(4-hydroxybenzyl)-2-((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)-2-oxoethyl)carbamate | 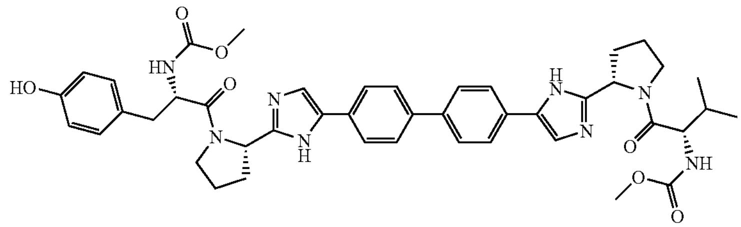 | LCMS: Anal. Calcd. for $C_{44}H_{50}N_8O_7$ 802; found: 803 (M + H)$^+$. | see text |
| cj-112 | methyl ((1S)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-1-(4-hydroxybenzyl)-2-oxoethyl)carbamate | 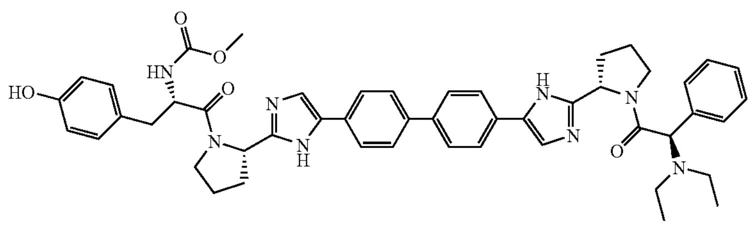 | LCMS: Anal. Calcd. for $C_{49}H_{54}N_8O_5$ 834; found: 835 (M + H)$^+$. | see text |
| cj-113 | methyl ((1S)-1-(4-hydroxybenzyl)-2-((2S)-2-(5-(4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-2-oxoethyl)carbamate | 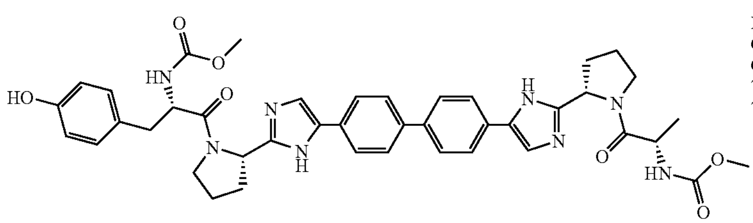 | LCMS: Anal. Calcd. for $C_{42}H_{46}N_8O_7$ 774; found: 775 (M + H)$^+$. | see text |

| Example | Compound Name | Structure | LCMS | Cap |
|---|---|---|---|---|
| cj-114 | methyl ((1S)-1-(4-(acetamidomethyl)benyzl)-2-((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)-2-oxoethyl)carbamate | 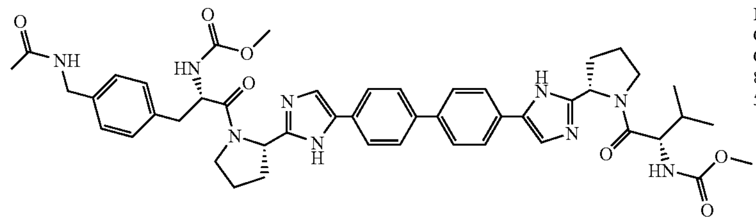 | LCMS: Anal. Calcd. for $C_{47}H_{55}N_9O_7$ 857; found: 585 (M + H)$^+$. | see text |
| cj-115 | methyl ((1S)-1-(4-(((ethylcarbamoyl)amino)methyl)benzyl)-2-((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)-2-oxoethyl)carbamate | 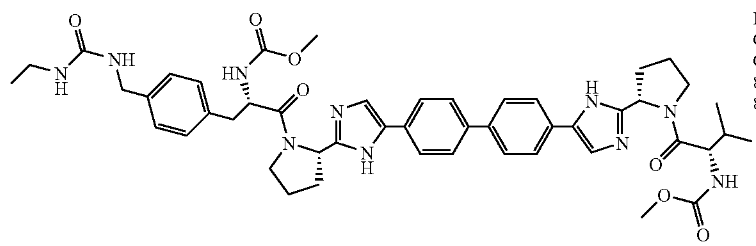 | LCMS: Anal. Calcd. for $C_{48}H_{58}N_{10}O_7$ 886; found: 887 (M + H)$^+$. | see text |
| cj-116 | methyl ((1S,2S)-2-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)cyclopentyl)carbamate | 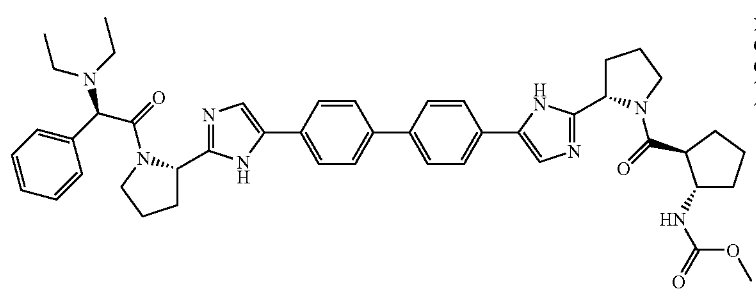 | LCMS: Anal. Calcd. for $C_{46}H_{54}N_8O_4$ 782; found: 783 (M + H)$^+$. | 121/2 |

| Example | Compound Name | Structure | LCMS | Cap |
|---|---|---|---|---|
| cj-117 | methyl ((1R)-2-((2S)-2-(5-(4'-(2-((2S)-1-(((1S,2S)-2-((methoxycarbonyl)amino)cyclopentyl)carbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | 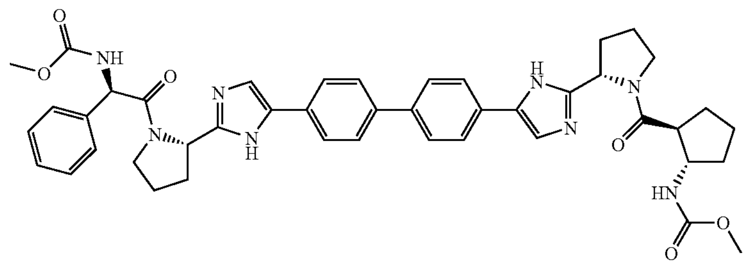 | LCMS: Anal. Calcd. for $C_{44}H_{48}N_8O_6$ 784; found: 785 $(M+H)^+$. | 121/4 |
| cj-118 | methyl ((1S,2S)-2-(((2S)-2-(5-(4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)carbonyl)cyclopentyl)carbamate | 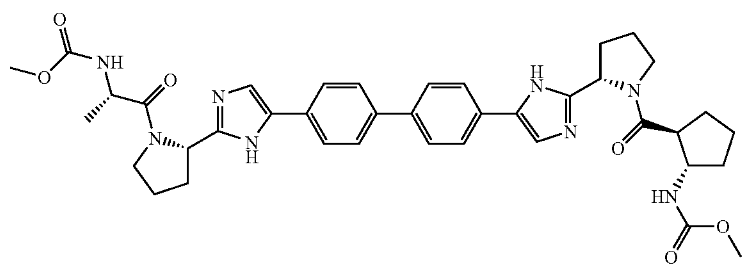 | LCMS: Anal. Calcd. for $C_{39}H_{46}N_8O_6$ 722; found: 723 $(M+H)^+$. | 121/52 |
| cj-119 | methyl ((1S)-1-(((2S)-2-(5-(4'-(2-((2S)-1-(N-(methoxycarbonyl)-O-methyl-L-homoseryl)-2-pyrrolidinyl)-1H-imidazol-5-yl)-4-biphenylyl)-1H-imidazol-2-yl)-1-pyrrolidinyl)carbonyl)-2-methylpropyl)carbamate | 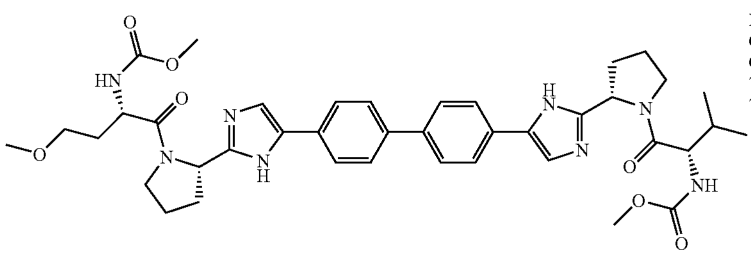 | LCMS: Anal. Calcd. for $C_{40}H_{50}N_8O_7$ 754; found: 755 $(M+H)^+$. | 51/87 |
| cj-120 | methyl ((1S)-3-methoxy-1-(((2S)-2-(5-(4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)carbonyl)propyl)carbamate | 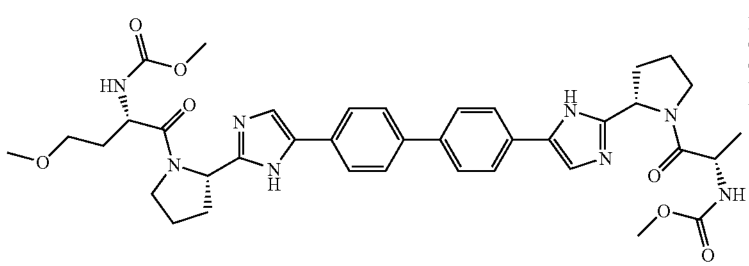 | LCMS: Anal. Calcd. for $C_{38}H_{46}N_8O_7$ 726; found: 727 $(M+H)^+$. | 52/87 |

| Example | Compound Name | Structure | LCMS | Cap |
|---|---|---|---|---|
| cj-121 | methyl ((1S,2R)-2-methoxy-1-(((2S)-2-(5-(4'-(2-((2S)-1-(N-(methoxycarbonyl)-O-methyl-L-homoseryl)-2-pyrrolidinyl)-1H-imidazol-5-yl)-4-biphenylyl)-1H-imidazol-2-yl)-1-pyrrolidinyl)carbonyl)propyl)carbamate | 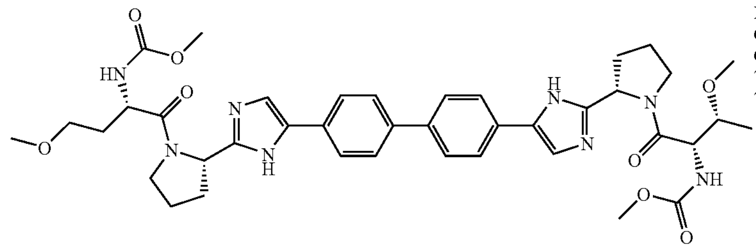 | LCMS: Anal. Calcd. for $C_{40}H_{50}N_8O_8$ 770; found: 771 (M + H)$^+$. | 86/87 |
| cj-122 | methyl ((1S,2S)-2-(((2S)-2-(5-(4'-(2-((2S)-1-(N-(methoxycarbonyl)-O-methyl-L-homoseryl)-2-pyrrolidinyl)-1H-imidazol-5-yl)-4-biphenylyl)-1H-imidazol-2-yl)-1-pyrrolidinyl)carbonyl)cyclopentyl)carbamate | 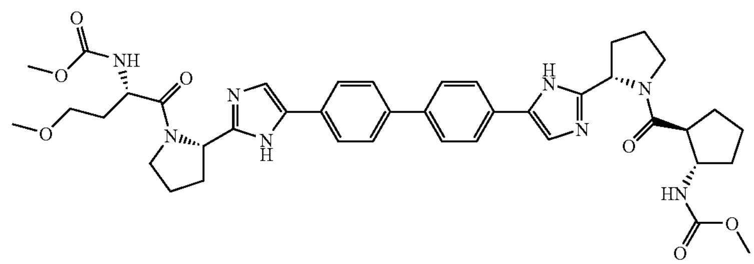 | LCMS: Anal. Calcd. for $C_{41}H_{50}N_8O_7$ 766; found: 767 (M + H)$^+$. | 121/87 |

Examples cj-111 to cj-113

For Examples cj-111 to cj-113 the compounds of Examples cj-105 to cj-107 were hydrogenated under conditions analogous to those used in Example 28, step d (with the exception that $K_2CO_3$ was not employed).

Preparation of examples cj-103, cj-114 and cj-115

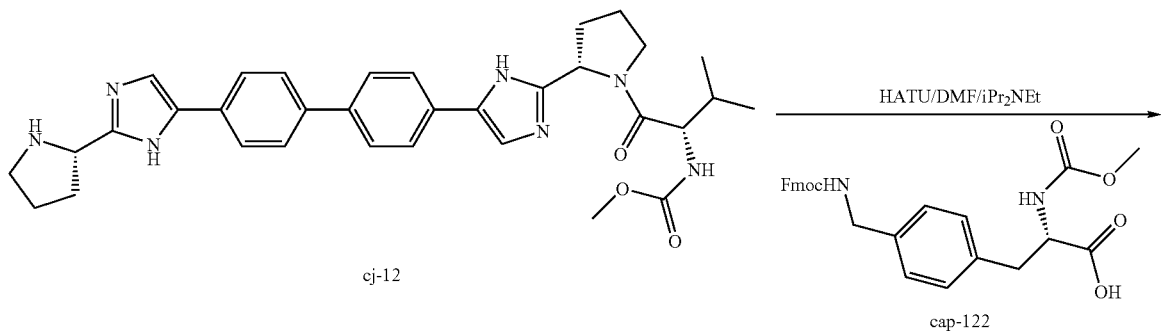

-continued

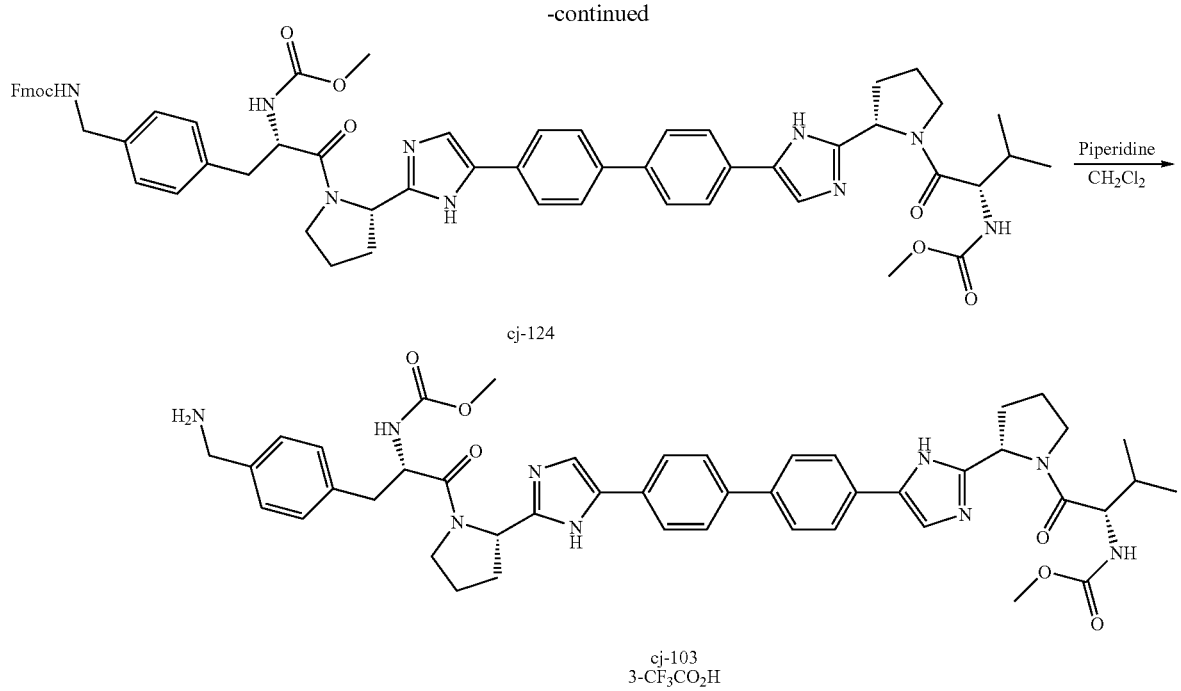

cj-124 cj-103
3-CF$_3$CO$_2$H

Intermediate cj-124 was prepared by coupling of intermediate cj-12 and Cap-122, as described in Example 28, step e. LCMS: Anal. Calcd. for C$_{60}$H$_{63}$N$_9$O$_8$ 1037. found: 520 (½M+H)$^+$. This corresponds to the doubly charged molecular ion.

Example cj-103

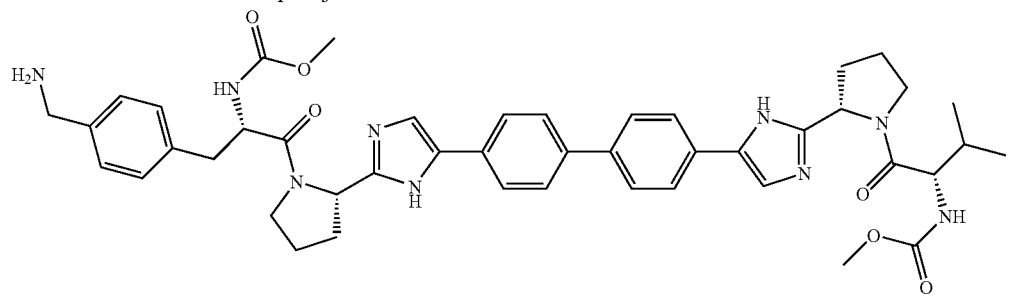

Intermediate cj-124 (83.0 mg, 0.08 mmol) was dissolved in DMF (5 mL) and piperidine (1 mL) was added at room temperature. After 2 h the volatiles were removed in vacuo and the residue was purified by preparative HPLC (YMC-Pack C-18, 30×100 mm, CH$_3$CN—H$_2$O-TFA) to give the TFA salt of the amine (87.0 mg, 94%). LCMS: Anal. Calcd. for C$_{45}$H$_{53}$N$_9$O$_6$ 815. found: 816 (M+H)$^+$.

Examples cj-114 to cj-115

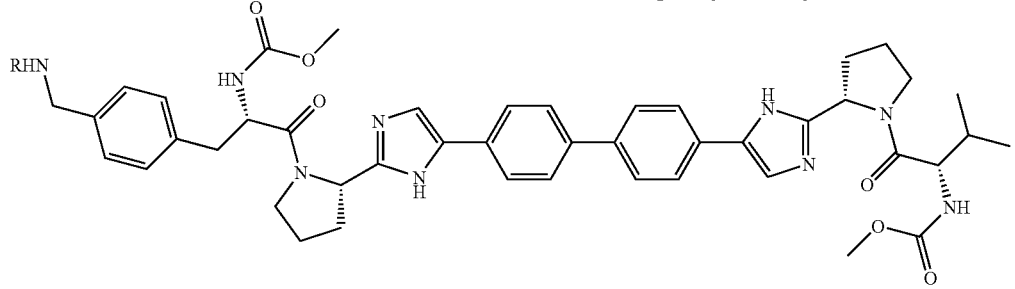

2-TFA

Example cj-114, R = Ac
Example cj-115, R = CONHEt

The product from Example cj-103 was acylated with either acetic anhydride or ethyl isocyanate as shown in scheme under conditions analogous to those in Example 25.

Example cj-114, LCMS: Anal. Calcd. for $C_{47}H_{55}N_9O_7$ 857. found: 858 $(M+H)^+$.

Example cj-115, LCMS: Anal. Calcd. for $C_{48}H_{58}N_{10}O_7$ 886. found: 887 $(M+H)^+$.

The following examples were prepared from intermediate 1e using a procedure analogous to Example 1. The appended cap is indicated in the Table and where no cap number is give the carboxylic acid was commercially available.

| Example | Compound Name | Structure | Cap | LCMS |
|---|---|---|---|---|
| cj-125 | methyl ((1S)-2-((2S)-2-(5-(4'-(2-((2S)-2-((methoxycarbonyl)amino)-3-(1H-1,2,3-triazol-4-yl)propanoyl)-2-pyrrolidinyl)-1H-imidazol-5-yl)-4-biphenylyl)-1H-imidazol-2-yl)-1-pyrrolidinyl)-2-oxo-1-(1H-1,2,3-triazol-4-ylmethyl)ethyl)carbamate | 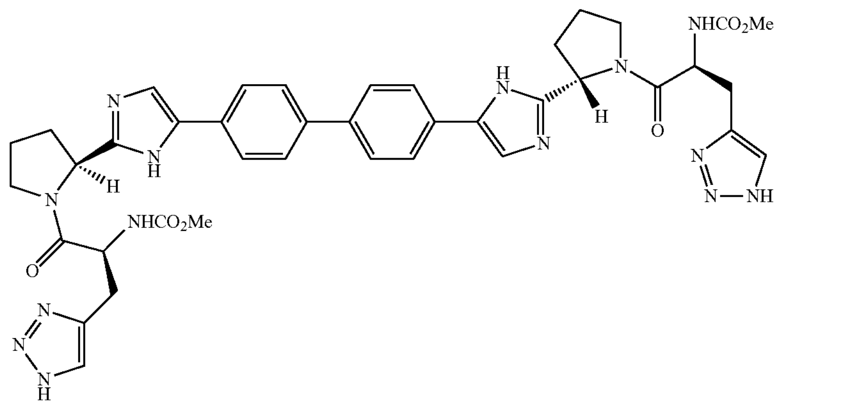 | 128 | LCMS: Anal. Calcd. for $C_{40}H_{44}N_{14}O_6$: 816; found: 817 $(M+H)^+$. |
| cj-126 | dimethyl (4,4'-biphenyldiylbis(1H-imidazole-5,2-diyl(2S)-2,1-pyrrolidinediyl((2S)-4-oxo-4,2-butanediyl)))-biscarbamate | 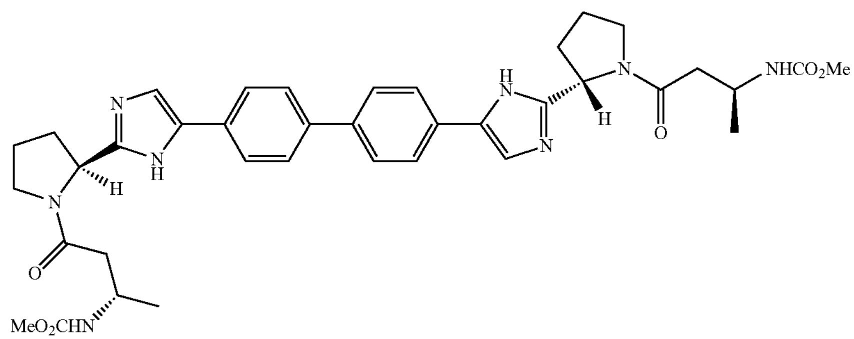 | 115 | LCMS: Anal. Calcd. for $C_{38}H_{46}N_8O_6$: 710; found: 711 $(M+H)^+$. |

| Example | Compound Name | Structure | Cap | LCMS |
|---|---|---|---|---|
| cj-127 | dimethyl (4,4'-biphenyldiylbis(1H-imidazole-5,2-diyl(2S)-2,1-pyrrolidinediyl((3R)-4-methyl-1-oxo-1,3-pentanediyl)))-biscarbamate | 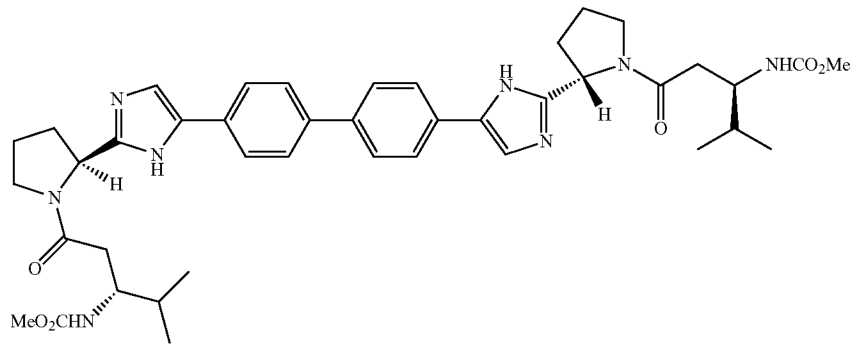 | 116 | LCMS: Anal. Calcd. for $C_{42}H_{54}N_8O_6$ 766; found: 777 $(M+H)^+$. |
| cj-128 | methyl ((1R)-3-((2S)-2-(5-(4'-(2-((3R)-1-((methoxycarbonyl)amino)-3-phenylpropanoyl)-1H-2-pyrrolidinyl)-1H-imidazol-5-yl)-4-biphenylyl)-1H-imidazol-2-yl)-1-pyrrolidinyl)-3-oxo-1-phenylpropyl)-carbamate | 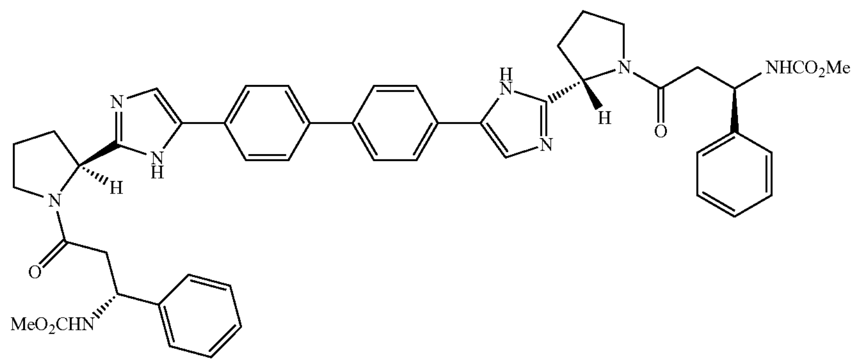 | 92 | LCMS: Anal. Calcd. for $C_{48}H_{50}N_8O_6$ 834; found: 835 $(M+H)^+$. |
| cj-129 | methyl ((1S)-3-((2S)-2-(5-(4'-(2-((3S)-1-((methoxycarbonyl)amino)-3-phenylpropanoyl)-1H-2-pyrrolidinyl)-1H-imidazol-5-yl)-4-biphenylyl)-1H-imidazol-2-yl)-1-pyrrolidinyl)-3-oxo-1-phenylpropyl)-carbamate | 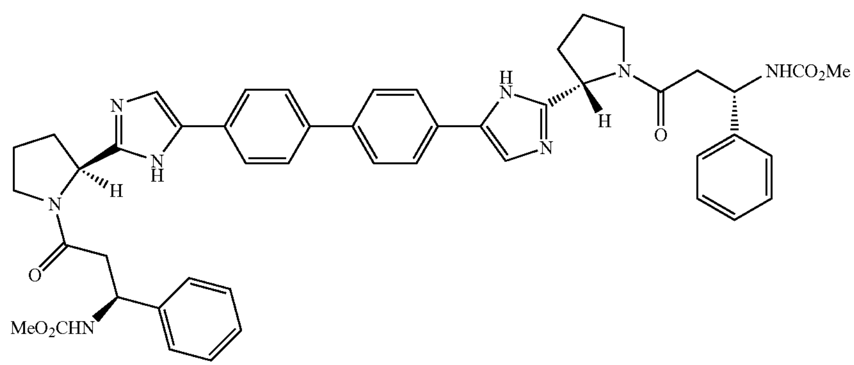 | 91 | LCMS: Anal. Calcd. for $C_{48}H_{50}N_8O_6$ 834; found: 835 $(M+H)^+$. |

| Example | Compound Name | Structure | Cap | LCMS |
|---|---|---|---|---|
| cj-130 | methyl ((1S)-2-((2S)-2-(5-(4'-(2-((2S)-1-((2S)-2-((methoxycarbonyl)amino)-3-(2-pyridinyl)propanoyl)-2-pyrrolidinyl)-1H-imidazol-5-yl)-4-biphenylyl)-1H-imidazol-2-yl)-1-pyrrolidinyl)-2-oxo-1-(2-pyridinylmethyl)ethyl)carbamate | 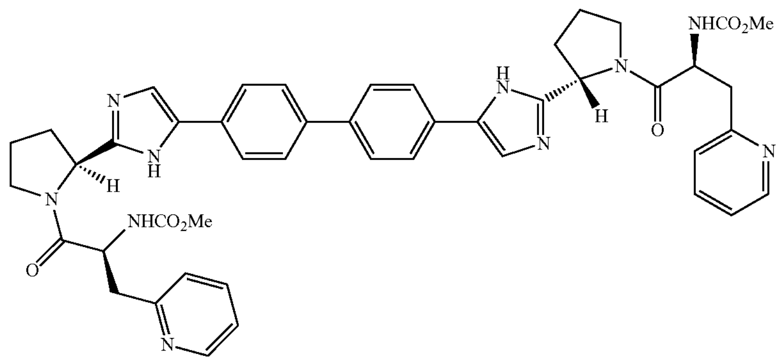 | 93 | LCMS: Anal. Calcd. for $C_{46}H_{48}N_{10}O_6$ 836; found: 837 $(M+H)^+$. |
| cj-131 | methyl ((1S)-2-((2S)-2-(5-(4'-(2-((2S)-1-((2S)-3-(1H-imidazol-4-yl)-2-((methoxycarbonyl)amino)propanoyl)-1H-2-pyrrolidinyl)-1H-imidazol-5-yl)-4-biphenylyl)-1H-imidazol-2-yl)-1-pyrrolidinyl)-1-(1H-imidazol-4-ylmethyl)-2-oxoethyl)carbamate | 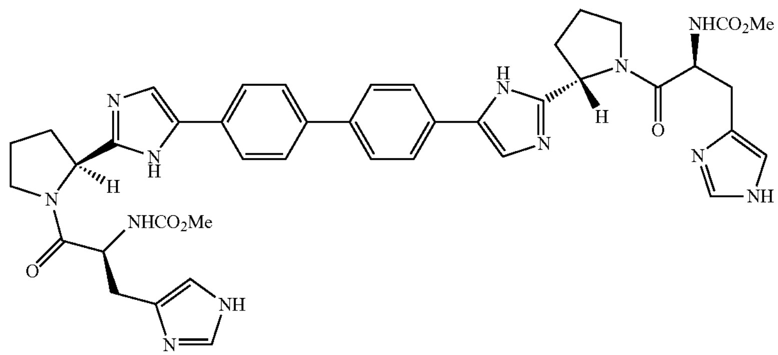 | 94 | LCMS: Anal. Calcd. for $C_{42}H_{46}N_{12}O_6$ 814; found: 815 $(M+H)^+$. |

| Example | Compound Name | Structure | Cap | LCMS |
|---|---|---|---|---|
| cj-132 | (6S,6'S)-6,6'-(4,4'-biphenyldiylbis(1H-imidazole-5,2-diyl(2S)-2,1-pyrrolidinediyl)dicarbonyl))didihydro-2,4(1H,3H)-pyrimidinedione) | 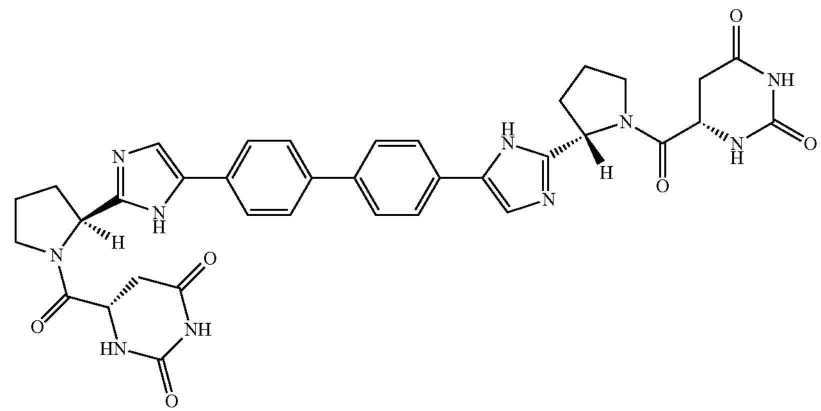 | — | LCMS: Anal. Calcd. for $C_{36}H_{36}N_{10}O_6$ 704; found: 705 $(M+H)^+$. |
| cj-133 | (4S,5R,4'S,5'R)-4,4'-(4,4'-biphenyldiylbis(1H-imidazole-5,2-diyl(2S)-2,1-pyrrolidinediyl-carbonyl))bis(5-methyl-1,3-oxazolidin-2-one) | 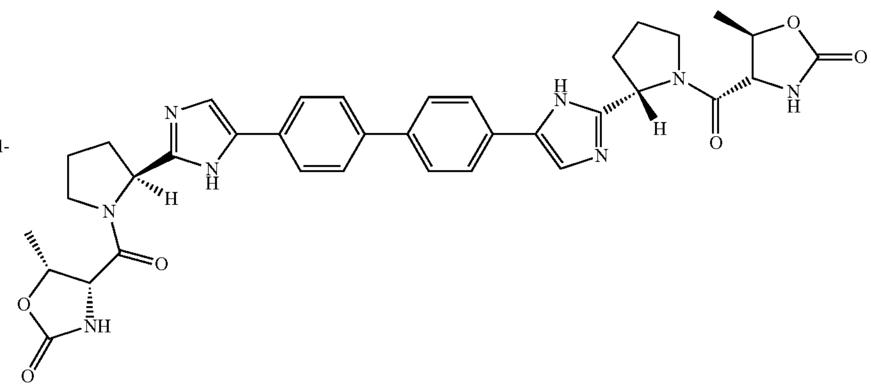 | 124 | LCMS: Anal. Calcd. for $C_{37}H_{40}N_8O_5$ 676; found: 677 $(M+H)^+$. |

| Example | Compound Name | Structure | Cap | LCMS |
|---|---|---|---|---|
| cj-134 | N-(3-((2S)-2-(5-(4'-(2-((2S)-1-(3-acetamidopropanoyl)-2-pyrrolidinyl)-1H-imidazol-5-yl)-4-biphenylyl)-1H-imidazol-2-yl)-1-pyrrolidinyl)-3-oxopropyl)acetamide | 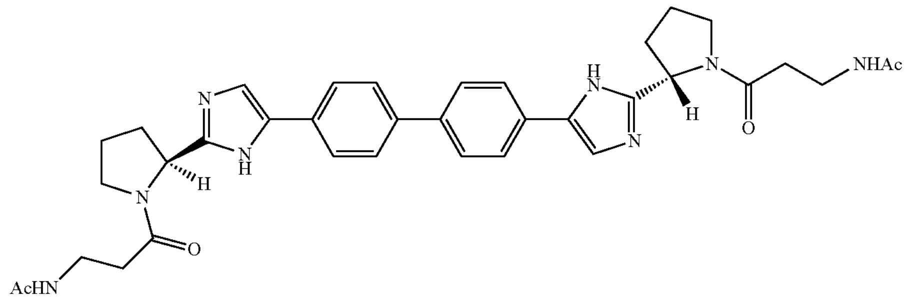 | — | LCMS: Anal. Calcd. for C$_{36}$H$_{42}$N$_8$O$_4$ 650; found: 651 (M + H)$^+$. |
| cj-135 | dimethyl (4,4'-biphenyldiylbis(1H-imidazole-5,2-diyl(2S)-2,1-pyrrolidinediyl((3R)-1-oxo-5-phenyl-1,3-pentanediyl))-biscarbamate | 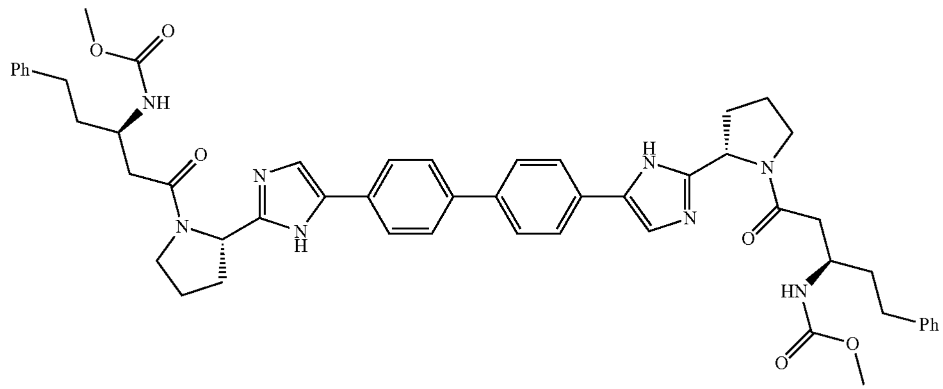 | 95 | LCMS: Anal. Calcd. for C$_{52}$H$_{58}$N$_8$O$_6$ 890; found: 890 (M + H)$^+$. |

| Example | Compound Name | Structure | Cap | LCMS |
|---|---|---|---|---|
| cj-136 | dimethyl (4,4'-biphenyldiylbis(1H-imidazole-5,2-diyl(2S)-2,1-pyrrolidinediyl((2R)-4-oxo-1-(2-thienyl)-4,2-butanediyl)))-biscarbamate | 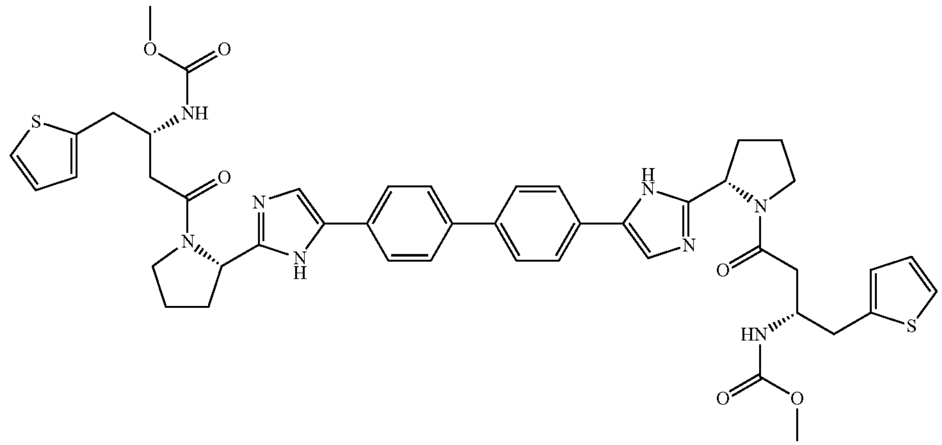 | 119 | LCMS: Anal. Calcd. for C₄₆H₅₀N₈O₆S₂ 874; found: 875 (M+H)⁺. |
| cj-137 | dimethyl (4,4'-biphenyldiylbis(1H-imidazole-5,2-diyl(2S)-2,1-pyrrolidinediyl((2R)-4-oxo-1-(3-thienyl)-4,2-butanediyl)))-biscarbamate | 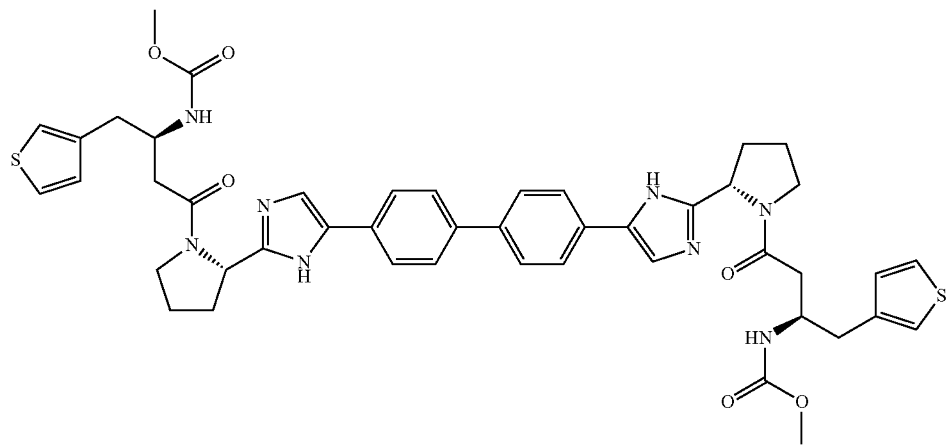 | 120 | LCMS: Anal. Calcd. for C₄₆H₅₀N₈O₆S₂ 874; found: 875 (M+H)⁺. |

| Example | Compound Name | Structure | Cap | LCMS |
|---|---|---|---|---|
| cj-138 | dimethyl (4,4'-biphenyldiylbis(1H-imidazole-5,2-diyl(2S)-2,1-pyrrolidinediyl((2S)-4-oxo-1-(2-thienyl)-4,2-butanediyl)))-biscarbamate | 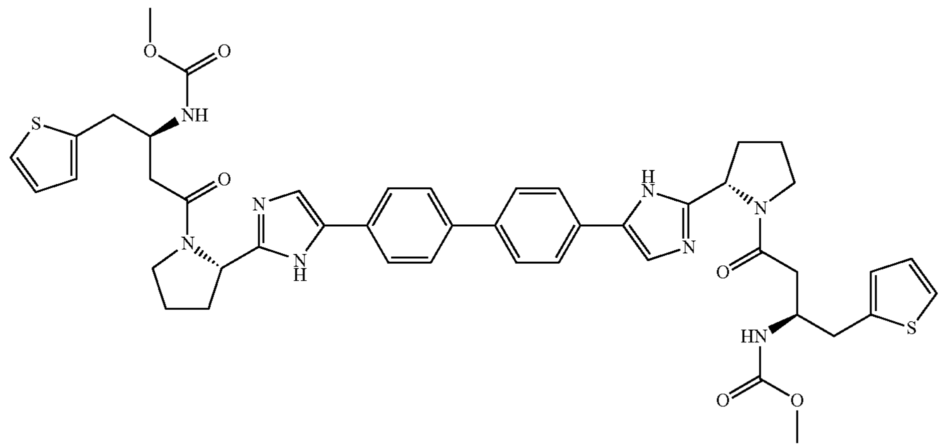 | 118 | LCMS: Anal. Calcd. for $C_{46}H_{50}N_8O_6S_2$ 874; found: 875 $(M+H)^+$. |
| cj-139 | dimethyl (4,4'-biphenyldiylbis(1H-imidazole-5,2-diyl(2S)-2,1-pyrrolidinediyl-carbonyl(1R,2R)-2,1-cyclohexanediyl))biscarbamate | 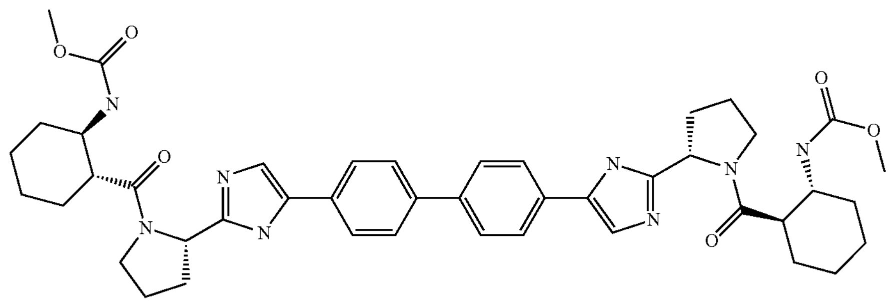 | 97 | LCMS: Anal. Calcd. for $C_{44}H_{54}N_8O_6$ 790; found: 791 $(M+H)^+$. |
| cj-140 | di-tert-butyl (4,4'-biphenyldiylbis(1H-imidazole-5,2-diyl(2S)-2,1-pyrrolidinediyl((2S)-4-(dimethylamino)-1-oxo-1,2-butanediyl)))-biscarbamate | 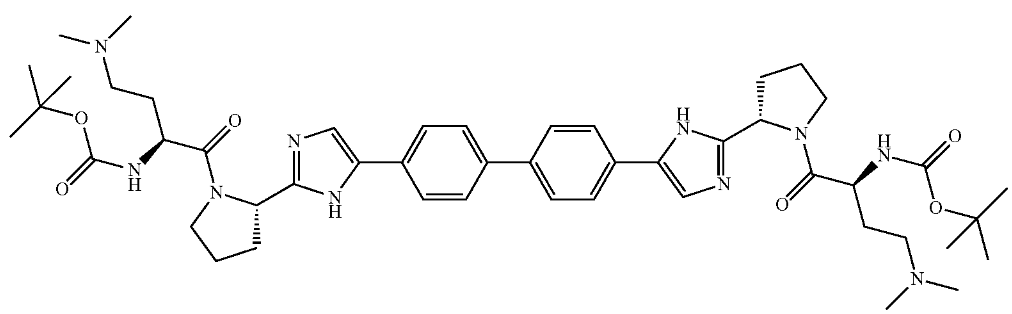 | 125 | LCMS: Anal. Calcd. for $C_{48}H_{68}N_{10}O_6$ 880; found: 881 $(M+H)^+$. |

-continued

| Example | Compound Name | Structure | Cap | LCMS |
|---|---|---|---|---|
| cj-141 | dimethyl (4,4'-biphenyldiylbis(1H-imidazole-5,2-diyl(2S)-2,1-pyrrolidinediyl-carbonyl(1R,2S)-2,1-cyclohexanediyl))bis-carbamate | 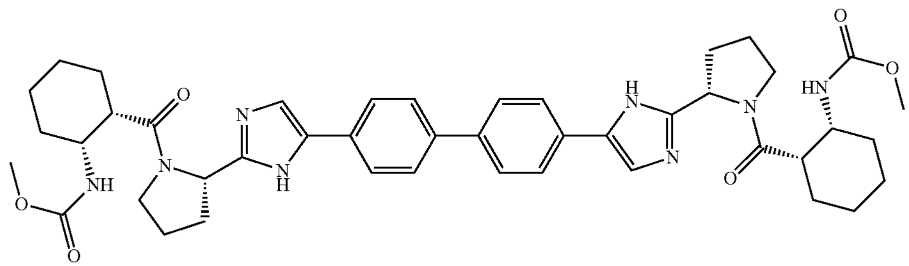 | 98 | LCMS: Anal. Calcd. for $C_{44}H_{54}N_8O_6$ 790; found: 791 $(M+H)^+$. |
| cj-142 | (3S,3'S)-4,4'-(4,4'-biphenyldiylbis(1H-imidazole-5,2-diyl(2S)-2,1-pyrrolidinediyl))bis(N-1-,-n-1-dimethyl-4-oxo-1,3-butanediamine | 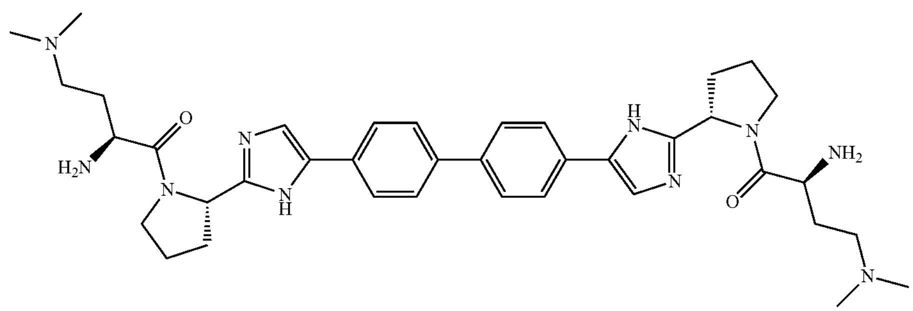 | see text | LCMS: Anal. Calcd. for $C_{38}H_{52}N_{10}O_2$ 680; found: 681 $(M+H)^+$. |

| Example | Compound Name | Structure | Cap | LCMS |
|---|---|---|---|---|
| cj-143 | dimethyl (4,4'-biphenyldiylbis(1H-imidazole-5,2-diyl(2S)-2,1-pyrrolidinediyl((2R)-4-oxo-1-phenyl-4,2-butanediyl)))-biscarbamate | 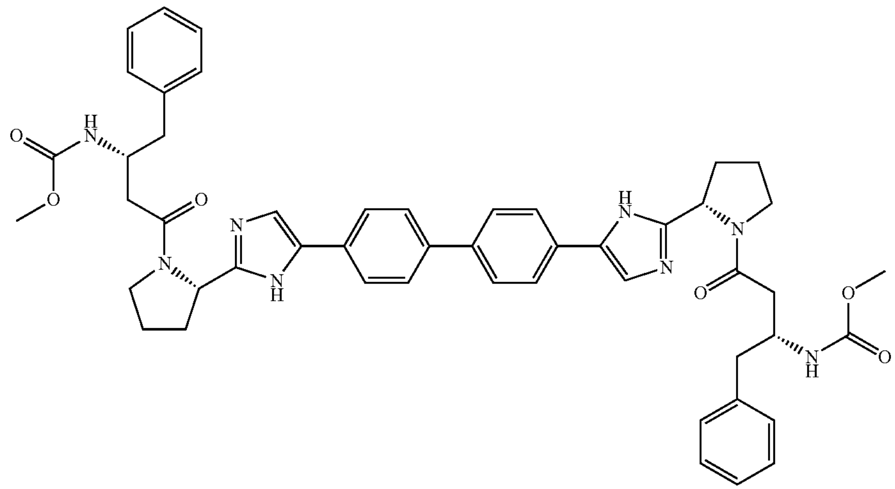 | 117 | LCMS: Anal. Calcd. for $C_{50}H_{54}N_8O_6$ 862; found: 863 $(M+H)^+$. |
| cj-144 | dimethyl (4,4'-biphenyldiylbis(1H-imidazole-5,2-diyl(2S)-2,1-pyrrolidinediyl-carbonyl(1R,3S)-3,1-cyclopentanediyl))bis-carbamate | 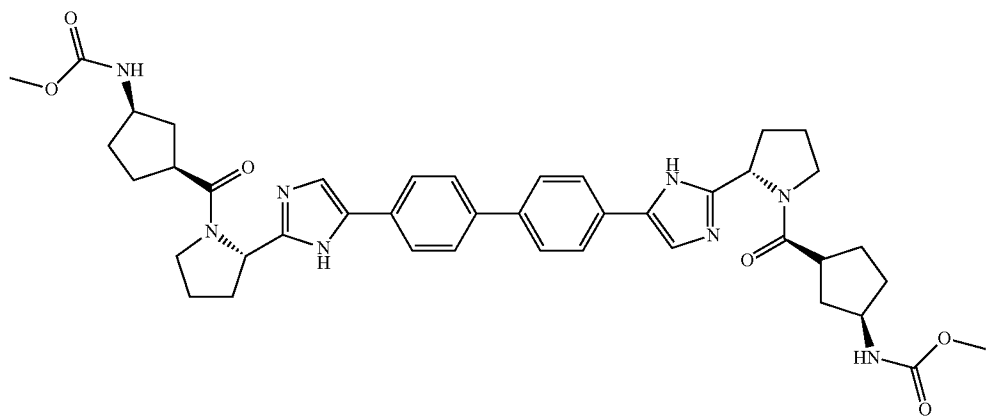 | 99 | LCMS: Anal. Calcd. for $C_{42}H_{50}N_8O_6$ 762; found: 763 $(M+H)^+$. |

| Example | Compound Name | Structure | Cap | LCMS |
|---|---|---|---|---|
| cj-145 | methyl ((1R)-1-benzyl-2-((2S)-2-(5-(4'-(2-((2S)-1-((2R)-2-((methoxycarbonyl)amino)-3-phenylpropanoyl)-2-pyrrolidinyl)-1H-imidazol-5-yl)-4-biphenylyl)-1H-imidazol-2-yl)-1-pyrrolidinyl)-2-oxoethyl)carbamate | 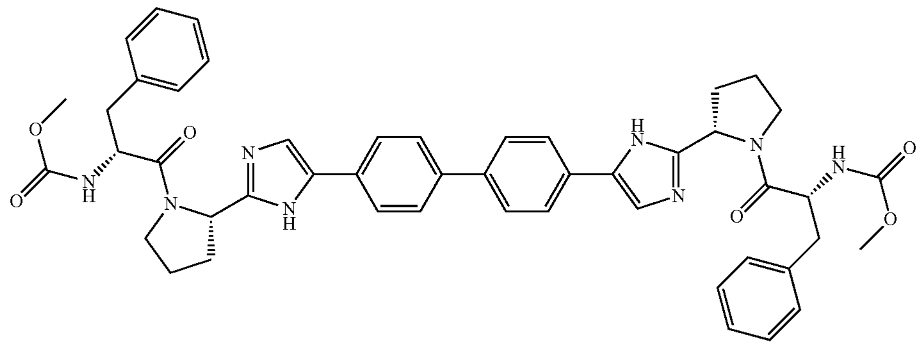 | 101 | LCMS: Anal. Calcd. for $C_{48}H_{50}N_8O_6$ 834; found: 835 $(M+H)^+$. |
| cj-146 | dimethyl (4,4'-biphenyldiylbis(1H-imidazole-5,2-diyl(2S)-2,1-pyrrolidinediyl((2S)-4-(dimethylamino))-1-oxo-1,2-butanediyl))-biscarbamate | 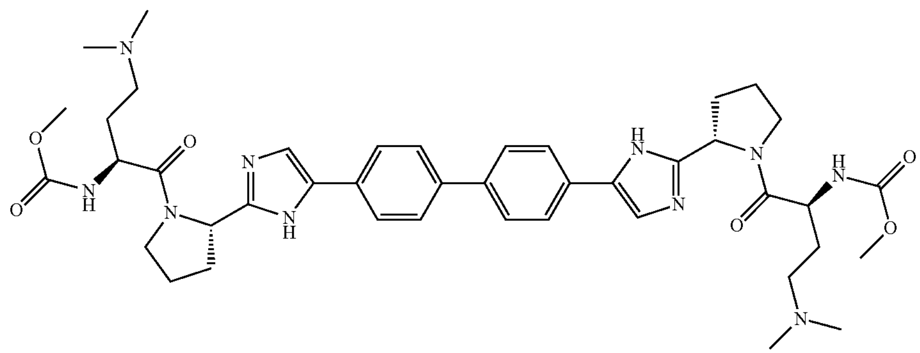 | see text | LCMS: Anal. Calcd. for $C_{42}H_{56}N_{10}O_6$ 796; found: 797 $(M+H)^+$. |
| cj-147 | (2R,2'R)-1,1'-(4,4'-biphenyldiylbis(1H-imidazole-5,2-diyl(2S)-2,1-pyrrolidinediyl))bis(N,N-dimethyl-1-oxo-3-phenyl-2-propanamine) | 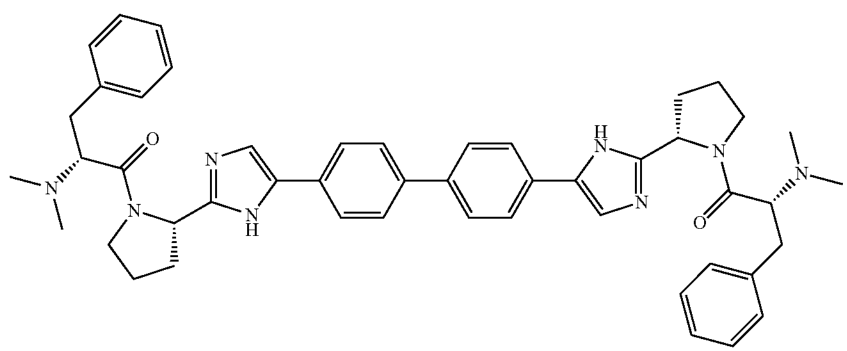 | 90 | LCMS: Anal. Calcd. for $C_{48}H_{54}N_8O_2$ 774; found: 775 $(M+H)^+$. |

| Example | Compound Name | Structure | Cap | LCMS |
|---|---|---|---|---|
| cj-148 | methyl ((1S)-1-benzyl-2-((2S)-2-(5-(4'-((2S)-1-((2S)-2-((methoxycarbonyl)amino)-3-phenylpropanoyl)-2-pyrrolidinyl)-1H-imidazol-5-yl)-4-biphenylyl)-1H-imidazol-2-yl)-1-pyrrolidinyl)-2-oxoethyl)carbamate | 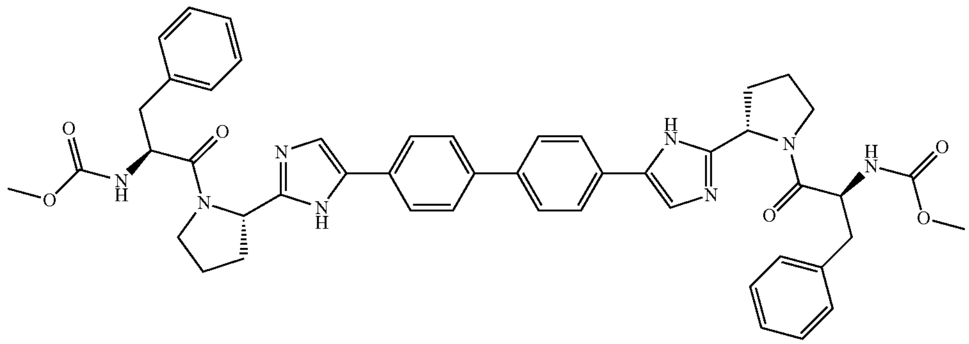 | 102 | LCMS: Anal. Calcd. for C₄₈H₅₀N₈O₆ 834; found: 835 (M+H)⁺. |
| cj-149 | dimethyl (4,4'-biphenyldiylbis(1H-imidazole-5,2-diyl(2S)-2,1-pyrrolidinediyl-carbonyl(1R,3S)-3,1-cyclopentanediyl))bis-carbamate | 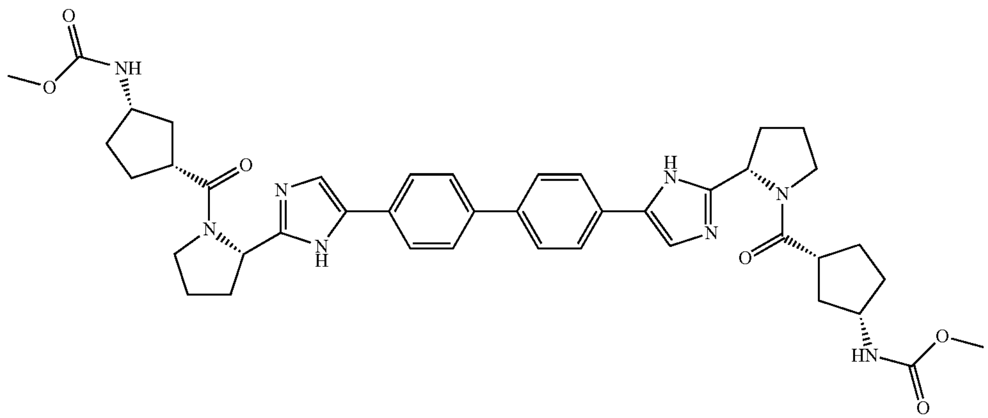 | 99a | LCMS: Anal. Calcd. for C₄₂H₅₀N₈O₆ 806; found: 807 (M+H)⁺. |
| cj-150 | dimethyl (4,4'-biphenyldiylbis(1H-imidazole-5,2-diyl(2S)-2,1-pyrrolidinediyl-carbonylcis-4,1-cyclohexanediyl))bis-carbamate | 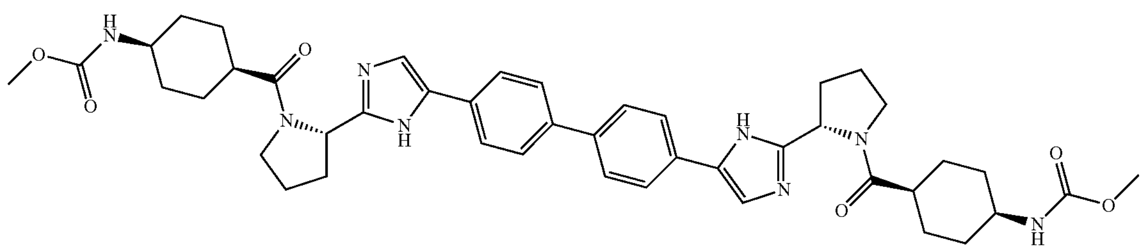 | 104 | LCMS: Anal. Calcd. for C₄₄H₅₄N₈O₆ 790; found: 791 (M+H)⁺. |

-continued

| Example | Compound Name | Structure | Cap | LCMS |
|---|---|---|---|---|
| cj-151 | dimethyl (4,4'-biphenyldiylbis(1H-imidazole-5,2-diyl(2S)-2,1-pyrrolidinediyl-carbonyltrans-4,1-cyclohexanediyl))bis-carbamate | 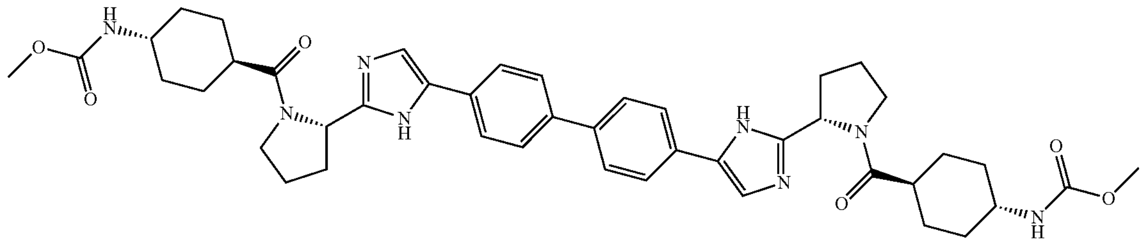 | 105 | LCMS: Anal. Calcd. for C₄₄H₅₄N₈O₆ 790; found: 791 (M + H)⁺. |
| cj-152 | ([cis)-4,4'-(4,4'-biphenyldiylbis(1H-imidazole-5,2-diyl(2S)-2,1-pyrrolidinediyl-carbonyl)bis(N,N-diethylcyclo-hexanamine) | 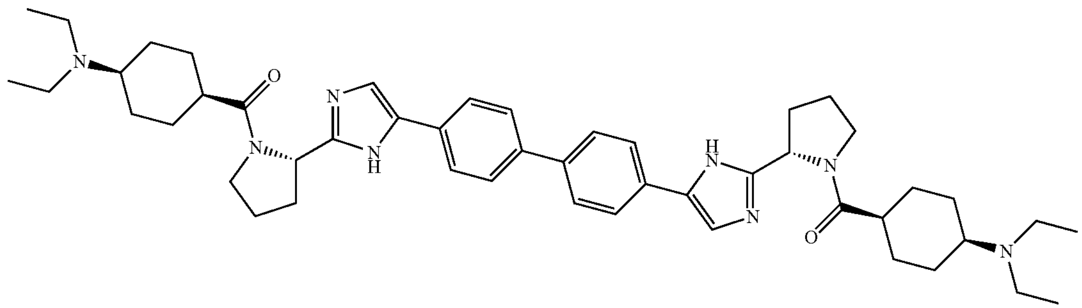 | 106 | LCMS: Anal. Calcd. for C₄₈H₆₆N₈O₂ 766; found: 777 (M + H)⁺. |
| cj-153 | methyl ((1S)-2-((2S)-2-(5-(4'-(2-((2S)-1-((2S)-2-((methoxycarbonyl) amino)-3-(1,3-thiazol-4-yl)propanoyl)-2-pyrrolidinyl)-1H-imidazol-5-yl)-4-biphenylyl)-1H-imidazol-2-yl)-1-pyrrolidinyl)-2-oxo-1-(1,3-thiazol-4-ylmethyl)ethyl)-carbamate | 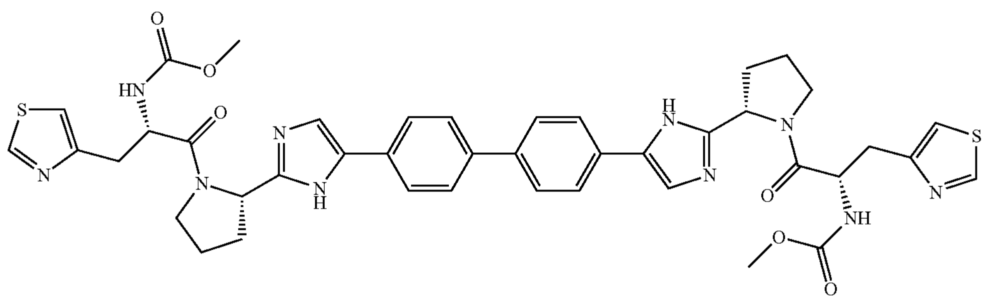 | 107 | LCMS: Anal. Calcd. for C₄₂H₄₄N₁₀O₆S₂ 848; found: 849 (M + H)⁺ |

| Example | Compound Name | Structure | Cap | LCMS |
|---|---|---|---|---|
| cj-154 | methyl ((1S)-2-((2S)-2-(5-(4'-(2-((2S)-1-((2S)-3-(1-benzyl-1H-imidazol-4-yl)-2-(((methoxycarbonyl)amino)propanoyl)-2-pyrrolidinyl)-1H-imidazol-5-yl)-4-biphenylyl)-1H-imidazol-2-yl)-1-pyrrolidinyl)-1-((1-benzyl-1H-imidazol-4-yl)methyl)-2-oxoethyl)carbamate | 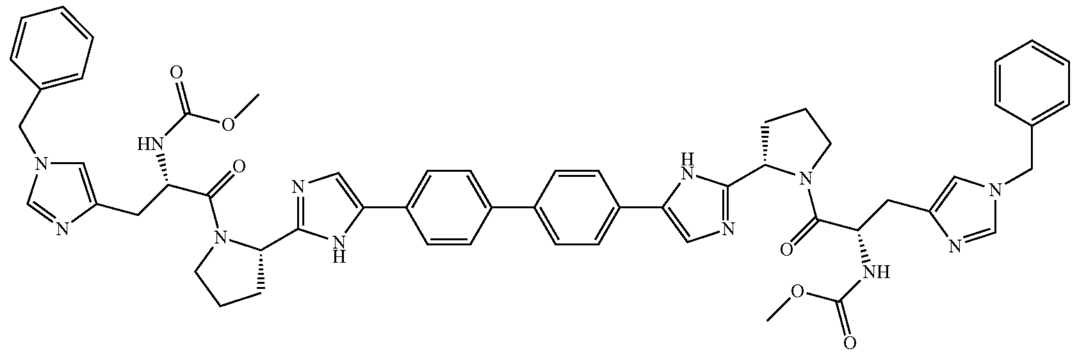 | 108 | LCMS: Anal. Calcd. for $C_{56}H_{58}N_{12}O_6$ 994; found: 995 $(M+H)^+$. |
| cj-155 | dimethyl (4,4'-biphenyldiylbis(1H-imidazole-5,2-diyl(2S)-2,1-pyrrolidinediyl-carbonyl(1S,2S)-2,1-cyclopentanediyl))bis-carbamate | 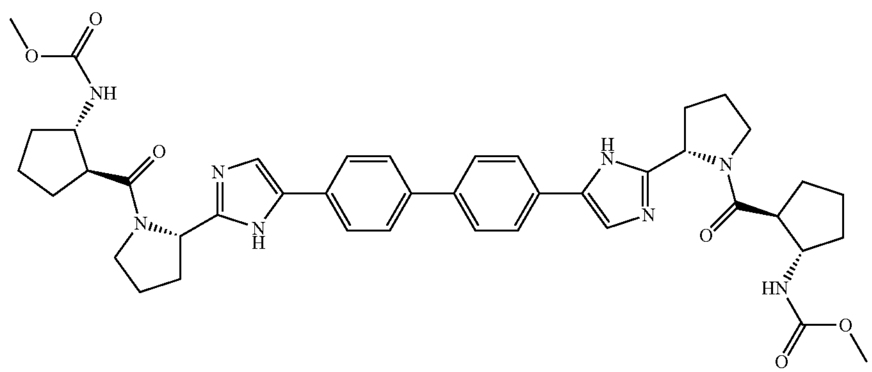 | 121 | LCMS: Anal. Calcd. for $C_{42}H_{50}N_8O_6$ 762; found: 763 $(M+H)^+$. |
| cj-156 | methyl ((1S)-3-methoxy-1-(((2S)-2-(5-(4'-(2-((2S)-1-(N-(methoxycarbonyl)-O-methyl-L-homoseryl)-2-pyrrolidinyl)-1H-imidazol-5-yl)-4-biphenylyl)-1H-imidazol-2-yl)-1-pyrrolidinyl)carbonyl)-propyl)carbamate | 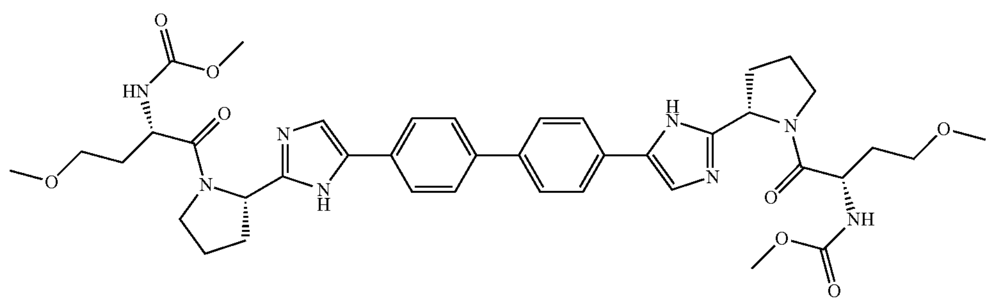 | 87 | LCMS: Anal. Calcd. for $C_{40}H_{50}N_8O_8$ 770; found: 771 $(M+H)^+$. |

Example cj-142

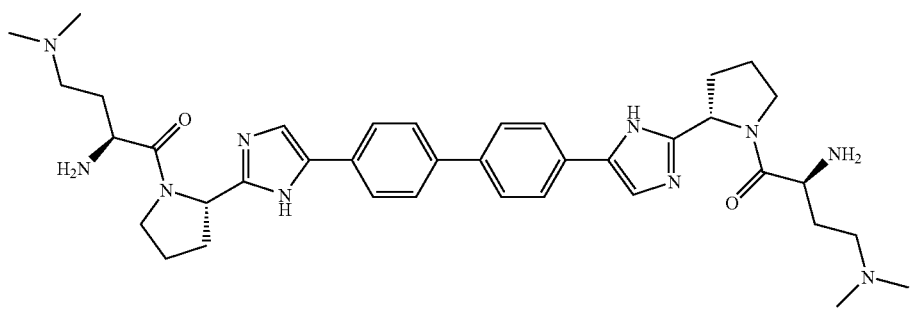

cj-142

Example cj-142 was prepared from the product obtained in Example cj-140 by treatment with 40% TFA in CH$_2$Cl$_2$. The mixture was allowed to stir for 3 h at room temperature and then concentrated in vacuo. The residue was purified by prep HPLC (YMC-Pack, C18 30×100 mm, CH$_3$CN—H$_2$O-TFA).

Example cj-156

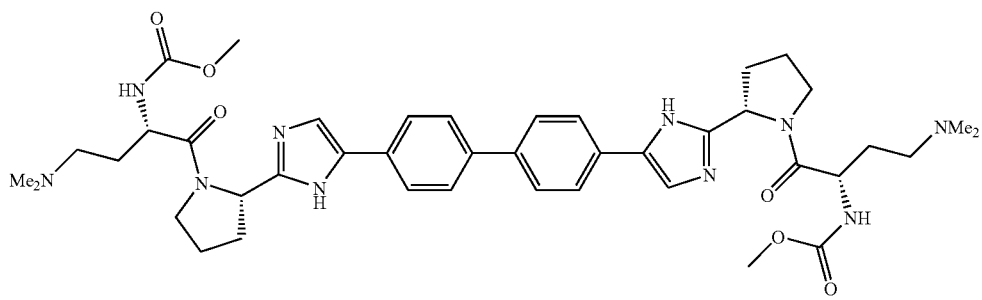

cj-156

The compound of Example-cj-156 was prepared by carbamoylation of the compound prepared in Example-cj-142 according to the method shown for Cap-51.

Section JG

Method A: LCMS—Xterra MS C-18 3.0×50 mm, 0 to 100% B over 30.0 minute gradient, 1 minute hold time, A=5% acetonitrile, 95% water, 10 mm ammonium acetate, B=95% acetonitrile, 5% water, 10 mm ammonium acetate.

Method B: HPLC—X-Terra C-18 4.6×50 mm, 0 to 100% B over 10.0 minute gradient, 1 minute hold time, A=10% methanol 90% water 0.1% TFA, B=90% methanol 10% water 0.1% TFA Method C: HPLC—YMC C-18 4.6×50 mm, 0 to 100% B over 10.0 minute gradient, 1 minute hold time, A=10% methanol 90% water 0.2% H$_3$PO$_4$, B=90% methanol 10% water 0.2% H$_3$PO$_4$.

Method D: HPLC—Phenomenex C-18 4.6×150 mm, 0 to 100% B over 10.0 minute gradient, 1 minute hold time, A=10% methanol 90% water 0.2% H$_3$PO$_4$, B=90% methanol 10% water 0.2% H$_3$PO$_4$ Method E: LCMS—Gemini C-18 4.6×50 mm, 0 to 100% B over 10.0 minute gradient, 1 minute hold time, A=5% acetonitrile, 95% water, 10 mm ammonium acetate, B=95% acetonitrile, 5% water, 10 mm ammonium acetate.

Method F: LCMS—Luna C-18 3.0×50 mm, 0 to 100% B over 7.0 minute gradient, 1 minute hold time, A=5% acetonitrile, 95% water, 10 mm ammonium acetate, B=95% acetonitrile, 5% water, 10 mm ammonium acetate.

Method G: HPLC—Phenomenex Gemini C-18 4.6×150 mm, 10 to 80% B over 35 minute gradient, 1 minute hold time, A=5% acetonitrile, 95% water, 10 mm ammonium acetate, B=95% acetonitrile, 5% water, 10 mm ammonium acetate Method H: HPLC—Phenomenex Gemini C-18 4.6×150 mm, 10 to 80% B over 25 minute gradient, 1 minute hold time, A=5% acetonitrile, 95% water, 10 mm ammonium acetate, B=95% acetonitrile, 5% water, 10 mm ammonium acetate Method I: HPLC—Waters-X-Bridge C-18 4.6×150 mm, 10 to 70% B over 30 minute gradient, 1 minute hold time, A=5% acetonitrile, 95% water, 10 mm ammonium acetate, B=95% acetonitrile, 5% water, 10 mm ammonium acetate

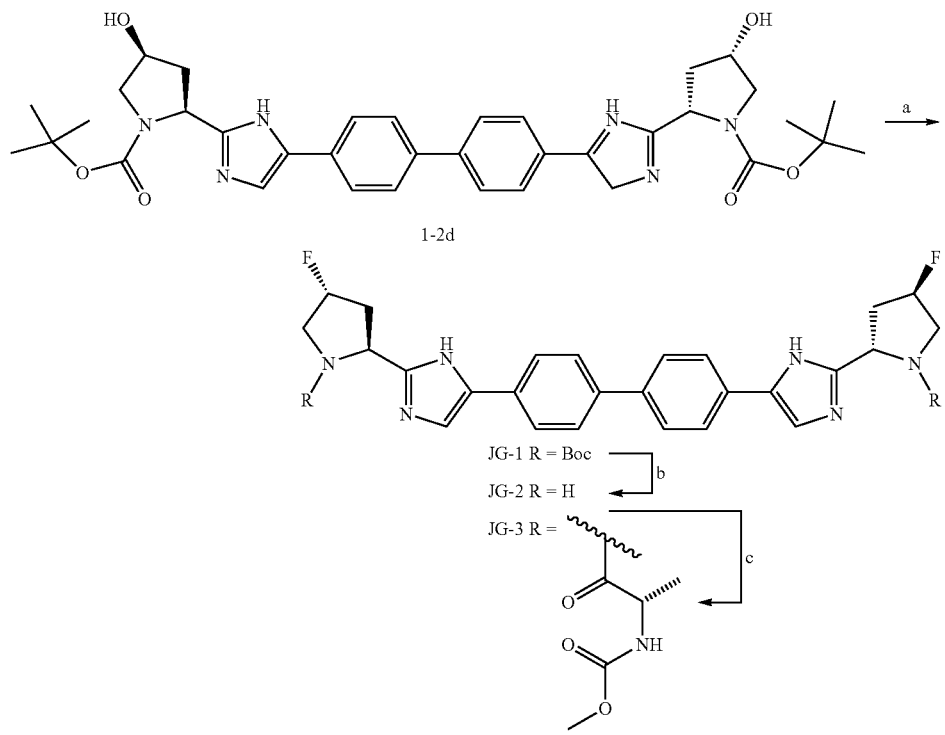

Step a:

(3S,3'S,5S,5'S)-tert-butyl 5,5'-(5,5'-(biphenyl-4,4'-diyl)bis(1H-imidazole-5,2-diyl))bis(3-hydroxypyrrolidine-1-carboxylate) (1.40 g, 2.13 mmol) was added as a solid to a solution of bis(2-methoxyethyl)aminosulfur trifluoride (0.87 mL, 4.69 mmol) in 14.0 mL $CH_2Cl_2$ cooled to −78° C. Reaction was stirred at −78° C. for two hours and then warmed to room temperature and stirred for 2 hours. Reaction was poured into saturated sodium bicarbonate solution and stirred until bubbling ceased. Layers were separated and aqueous layer washed one time with $CH_2Cl_2$. Combined organics were washed with brine, dried ($MgSO_4$), filtered, and concentrated to give a yellow oil. The oil was triturated with $CH_2Cl_2$ and pentane to yield (3R,3'R,5S,5'S)-tert-butyl 5,5'-(5,5'-(biphenyl-4,4'-diyl)bis(1H-imidazole-5,2-diyl))bis(3-fluoropyrrolidine-1-carboxylate) JG-1 as a tan solid (0.98 g, 71%).

$^1$H NMR (500 MHz, DMSO-$d_6$) δ ppm 12.10 (2H, m) 7.60-7.82 (8H, m) 7.35 (2H, m) 5.45 (1H, s) 5.35 (1H, s) 4.85-4.90 (2H, m) 3.69-3.79 (4H, m) 2.53-2.61 (2H, m) 2.28-2.37 (2H, m) 1.40 (8H, s) 1.12 (10H, s)

LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA, ($t_R$=3.04 min) Anal Calcd. for $C_{36}H_{42}F_2N_6O_4$ 660.70. found 661.68 (M+H)$^+$ Step b:

To a solution of (3R,3'R,5S,5'S)-tert-butyl 5,5'-(5,5'-(biphenyl-4,4'-diyl)bis(1H-imidazole-5,2-diyl))bis(3-hydroxypyrrolidine-1-carboxylate) (0.098 g, 1.48 mmol) in 4 mL dioxane was added 2.0 mL of a 4.0M solution of HCl in dioxane. The reaction was stirred for 2 hours at room temperature and concentrated under reduced pressure. The resulting tan solid was dried under vacuum to give 4,4'-bis(2-((2S,4S)-4-fluoropyrrolidin-2-yl)-1H-imidazol-5-yl)biphenyl tetrahydrochloride JG-2 (0.89 g, 100% yield). No further purification.

$^1$H NMR (500 MHz, DMSO-$d_6$) δ ppm 9.05 (2H, s), 8.18 (2H, s), 8.00-8.09 (4H, m) 7.89 (4H, d, J=7.63 Hz) 5.71 (1H, s) 5.61 (1H, s) 5.24-5.33 (2H, m) 3.92 (2H, d, J=10.68 Hz) 3.63-3.71 (2H, m) 2.79-2.89 (2H, m)

LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA, ($t_R$=2.12 min) Anal Calcd. for $C_{26}H_{26}F_2N_6$ 460.53. found 461.37 (M+H)$^+$ Step c:

To a stirred solution of 4,4'-bis(2-((2S,4R)-4-fluoropyrrolidin-2-yl)-1H-imidazol-5-yl)biphenyltetrahydrochloride (0.060 g, 0.10 mmol), (S)-2-(methoxycarbonylamino)propanoic acid (0.031 g, 0.21 mmol), and HATU (0.081 g, 0.21 mmol) in 3 mL DMF was added diisopropylethyl amine (0.11 mL, 0.61 mmol). The reaction was stirred at room temperature overnight (16 hours) and concentrated under reduced pressure. The crude product was purified by reverse-phase preparative HPLC and secondly by passing it through a Waters MCX extraction cartridge to provide Dimethyl (2S,2'S)-1,1'-((3R,3'R,5S,5'S)-5,5'-(5,5'-(biphenyl-4,4'-diyl)bis(1H-imidazole-5,2-diyl))bis(3-fluoropyrrolidine-5,1-diyl))bis(1-oxopropane-2,1-diyl)dicarbamate JG-3, free base (0.0097 g, 7.5%).

$^1$H NMR (500 MHz, DMSO-$d_6$) δ ppm 11.91 (2H, m), 7.76-7.84 (3H, m), 7.64-7.84 (5H, m), 7.48-7.58 (2H, m), 5.55 (1H, s), 5.11 (1H, s), 4.29-4.38 (2H, m), 4.13 (2H, d, J=12.51 Hz), 3.89-3.98 (2H, m), 3.53 (6H, s), 2.54-2.64 4H, m), 1.21 (6H, s)

LCMS—Luna C-18 3.0×50 mm, 0 to 100% B over 7.0 minute gradient, 1 minute hold time, A=5% acetonitrile, 95% water, 10 mm ammonium acetate, B=95% acetonitrile, 5% water, 10 mm ammonium acetate, ($t_R$=20.40 min)

Nominal/LRMS—Calcd. for $C_{36}H_{40}F_2N_8O_6$ 718.30. found 719.24 (M+H)$^+$

Accurate/HRMS—Calcd. for $C_{36}H_{41}F_2N_8O_6$ 719.3117. found 719.3114 (M+H)$^+$

| Structure | Compound Name | Data |
|---|---|---|
| JG-3 | methyl ((1S)-2-((2S,4R)-4-fluoro-2-(5-(4'-(2-((2S,4R)-4-fluoro-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-1-methyl-2-oxoethyl)carbamate | RT = 13.60 min, method I<br>LRMS: Anal. Calcd. for $C_{36}H_{40}F_2N_8O_6$ 718.30 found: 719.24 (M + H)$^+$<br>HRMS: Anal. Calcd. for $C_{36}H_{41}F_2N_8O_6$ 719.3117 found 719.3114 (M + H)$^+$ |
| JG-4<br>From 1-1e and Cap-12 | methyl ((1S)-2-((2S,4R)-4-hydroxy-2-(5-(4'-(2-((2S,4R)-4-hydroxy-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-1-methyl-2-oxoethyl)carbamate | RT = 9.27 min, method H<br>LRMS: Anal. Calcd. for $C_{36}H_{42}N_8O_8$ 714.77 found: 715.33 (M + H)$^+$<br>HRMS: Anal. Calcd. for $C_{36}H_{43}N_8O_8$ 715.3204 found: 715.3186 (M + H)$^+$ |
| JG-5<br>From 1-1e and Cap-51 | methyl ((1S)-1-(((2S,4R)-4-hydroxy-2-(5-(4'-(2-((2S,4R)-4-hydroxy-1-((2S)-2-((methoxy-carbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate | RT = 15.08 min, method G<br>LRMS: Anal. Calcd. for $C_{40}H_{50}N_8O_8$ 770.88 found: 771.76 (M + H)$^+$<br>HRMS: Anal. Calcd. for $C_{40}H_{51}N_8O_8$ 771.3830 found: 771.3798 (M + H)$^+$ |
| JG-6<br>From 1-1e and Cap-54b | dimethyl (4,4'-biphenyldiylbis(1H-imidazole-5,2-diyl((2S,4R)-4-hydroxy-2,1-pyrrolidinediyl)((1S)-1-cyclopropyl-2-oxo-2,1-ethane-diyl)))biscarbamate | RT = 13.67 min, method G<br>LRMS: Anal. Calcd. for $C_{40}H_{46}N_8O_8$ 766.85 found: 767.65 (M + H)$^+$<br>HRMS: Anal. Calcd. for $C_{40}H_{47}N_8O_8$ 767.3517 found: 767.3483 (M + H)$^+$ |

| Structure | Compound Name | Data |
|---|---|---|

JG-7

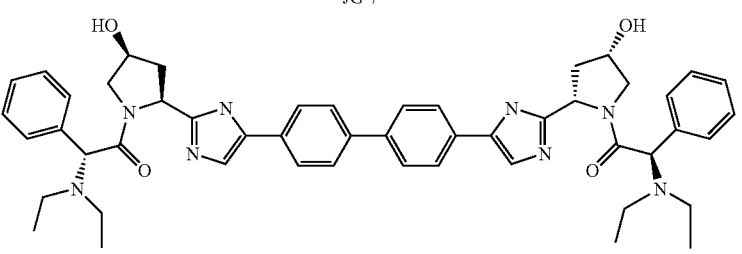

From 1-2e and Cap-2

(3S,5S,3'S,5'S)-5,5'-(4,4'-biphenyldiylbis(1H-imida-zole-5,2-diyl))-bis(1-((2R)-2-(diethyl-amino)-2-phenylacetyl)-3-pyrrolidinol)

RT = 15.88 min, method H
LRMS: Anal. Calcd. for $C_{50}H_{58}N_8O_4$ 834.45
found: 835.38 (M + H)$^+$
HRMS: Anal. Calcd. for $C_{50}H_{59}N_8O_4$ 835.4659
found: 835.4627 (M + H)$^+$

JG-8

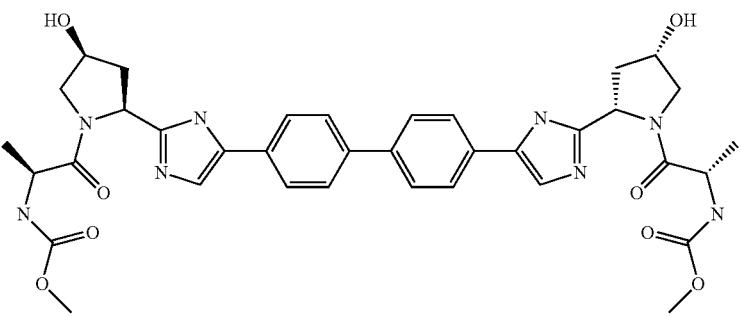

From 1-2e and Cap-52 methyl ((1S)-2-((2S,4S)-4-hydroxy-2-(5-(4'-(2-((2S,4S)-4-hydroxy-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-1-methyl-2-oxoethyl)carbamate RT = 9.99 min, method H
LRMS: Anal. Calcd. for $C_{36}H_{42}N_8O_8$ 714.77
found: 715.71 (M + H)$^+$
HRMS: Anal. Calcd. for $C_{36}H_{43}N_8O_8$ 715.3204
found: 715.3188 (M + H)$^+$

JG-9

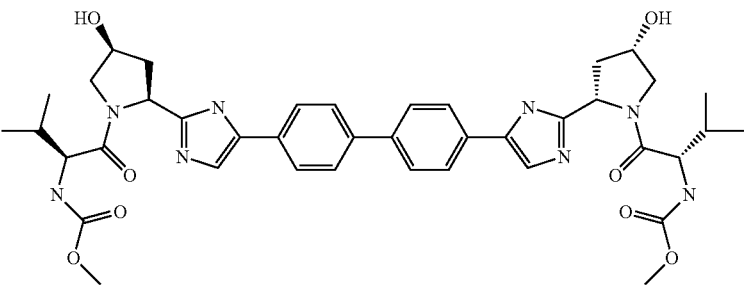

From 1-2e and Cap-51 methyl ((1S)-1-(((2S,4S)-4-hydroxy-2-(5-(4'-(2-((2S,4S)-4-hydroxy-1-((2S)-2-((methoxycarbonyl)-amino)-3-methyl-butanoyl)-2-pyrrolidinyl)-1H-imidazol-5-yl)-4-biphenylyl)-1H-imidazol-2-yl)-1-pyrrolidinyl)carbonyl)-2-methylpropyl)carbamate RT = 14.12 min, method H
LRMS: Anal. Calcd. for $C_{40}H_{50}N_8O_8$ 770.88
found: 771.74 (M + H)$^+$
HRMS: Anal. Calcd. for $C_{40}H_{51}N_8O_8$ 771.3830
found: 771.3799 (M + H)$^+$

JG-10

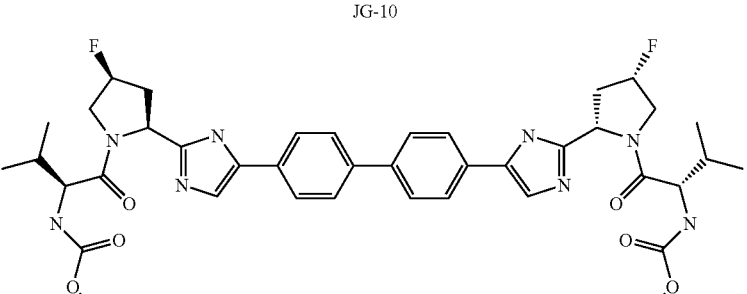

From 1-2e2 and Cap-51 methyl ((1S)-1-(((2S,4S)-4-fluoro-2-(5-(4'-(2-((2S,4S)-4-fluoro-1-((2S)-2-((methoxycarbonyl)-amino)-3-methyl-butanoyl)-2-pyrrolidinyl)-1H-imidazol-5-yl)-4-biphenylyl)-1H-imidazol-2-yl)-1-pyrrolidinyl)carbonyl)-2-methylpropyl)carbamate RT = 17.66 min, method I
LRMS: Anal. Calcd. for $C_{40}H_{48}F_2N_8O_6$ 774.86
found: 775.49 (M + H)$^+$
HRMS: Anal. Calcd. for $C_{40}H_{49}F_2N_8O_6$ 775.3743
found: 775.3717 (M + H)$^+$ -continued

| Structure | Compound Name | Data |
|---|---|---|
| JG-12<br>From (S)-2-(methoxycarbonylamino)-4-methylpentanoic acid and JG-2 | methyl ((1S)-1-(((2S,4R)-4-fluoro-2-(5-(4'-(2-((2S,4R)-4-fluoro-1-((2S)-2-((methoxycarbonyl)amino)-4-methylpentanoyl)-2-pyrrolidinyl)-1H-imidazol-5-yl)-4-biphenylyl)-1H-imidazol-2-yl)-1-pyrrolidinyl)carbonyl)-3-methylbutyl)carbamate | RT = 9.69 min, method I<br>LRMS: Anal. Calcd. for $C_{42}H_{52}F_2N_8O_6$ 802.92 found: 803.42 (M + H)$^+$<br>HRMS: Anal. Calcd. for $C_{42}H_{53}F_2N_8O_6$ 803.4056 found: 803.4018 (M + H)$^+$ |
| JG-13<br>From 1-2e2 and Cap-52 | methyl ((1S)-2-((2S,4S)-4-fluoro-2-(5-(4'-(2-((2S,4S)-4-fluoro-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-1-methyl-2-oxoethyl)carbamate | RT = 13.60 min, method I<br>LRMS: Anal. Calcd. for $C_{36}H_{40}F_2N_8O_6$ 718.30 found: 719.45 (M + H)$^+$<br>HRMS: Anal. Calcd. for $C_{36}H_{41}F_2N_8O_6$ 719.3117 found: 719.3090 (M + H)$^+$ |
| JG-14<br>From JG-25 and Cap-52 | methyl ((1S)-2-((2S,4S)-2-(5-(4'-(2-((2S,4S)-1-((2R)-2-(diethylamino)-2-phenylacetyl)-4-fluoro-2-pyrrolidinyl)-1H-imidazol-5-yl)-4-biphenylyl)-1H-imidazol-2-yl)-4-fluoro-1-pyrrolidinyl)-1-methyl-2-oxoethyl)carbamate | RT = 15.13 min, method I<br>LCMS: Anal. Calcd. for $C_{43}H_{48}F_2N_8O_4$ 778.91 found: 779.79 (M + H)$^+$ |
| JG-15<br>From JG-25 and Cap-51 | methyl ((1S)-1-(((2S,4S)-2-(5-(4'-(2-((2S,4S)-1-((2R)-2-(diethylamino)-2-phenylacetyl)-4-fluoro-2-pyrrolidinyl)-1H-imidazol-5-yl)-4-biphenylyl)-1H-imidazol-2-yl)-4-fluoro-1-pyrrolidinyl)carbonyl)-2-methylpropyl)carbamate | RT = 17.51 min, method I<br>LCMS: Anal. Calcd. for $C_{45}H_{52}F_2N_8O_4$ 806.96 found: 807.50 (M + H)$^+$ |

-continued

| Structure | Compound Name | Data |
|---|---|---|
| JG-16 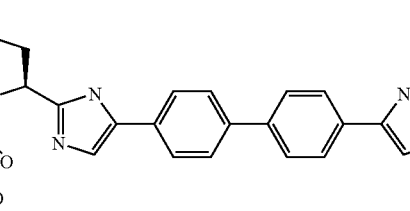 From JG-2 and Cap-51 | methyl ((1S)-1-(((2S,4R)-4-fluoro-2-(5-(4'-(2-((2S,4R)-4-fluoro-1-((2S)-2-((methoxycarbonyl)-amino)-3-methyl-butanoyl)-2-pyrrolidinyl)-1H-imidazol-5-yl)-4-biphenylyl)-1H-imidazol-2-yl)-1-pyrrolidinyl)carbonyl)-2-methylpropyl)carbamate | RT = 16.51 min, method I LRMS: Anal. Calcd. for $C_{40}H_{48}F_2N_8O_6$ 774.86 found: 775.39 (M + H)$^+$ HRMS: Anal. Calcd. for $C_{40}H_{49}F_2N_8O_6$ 775.3743 found: 775.3740 (M + H)$^+$ |
| JG-17 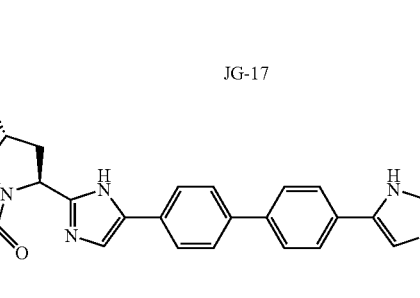 From JG-2 and Cap-2 | (1R,1'R)-2,2'-(4,4'-biphenyldiylbis(1H-imidazole-5,2-diyl((2S,4R)-4-fluoro-2,1-pyrrolidinediyl)))-bis(N,N-diethyl-2-oxo-1-phenylethanamine) | RT = 8.13 min, method I LCMS: Anal. Calcd. for $C_{50}H_{56}F_2N_8O_2$ 839.04 found: 839.46 (M + H)$^+$ HRMS: Anal. Calcd. for $C_{50}H_{57}F_2N_8O_2$ 839.4572 found: 839.4543 (M + H)$^+$ |

Synthesis of JG-18 as in Example 28 Step a Using Hydroxyproline in Place of Proline

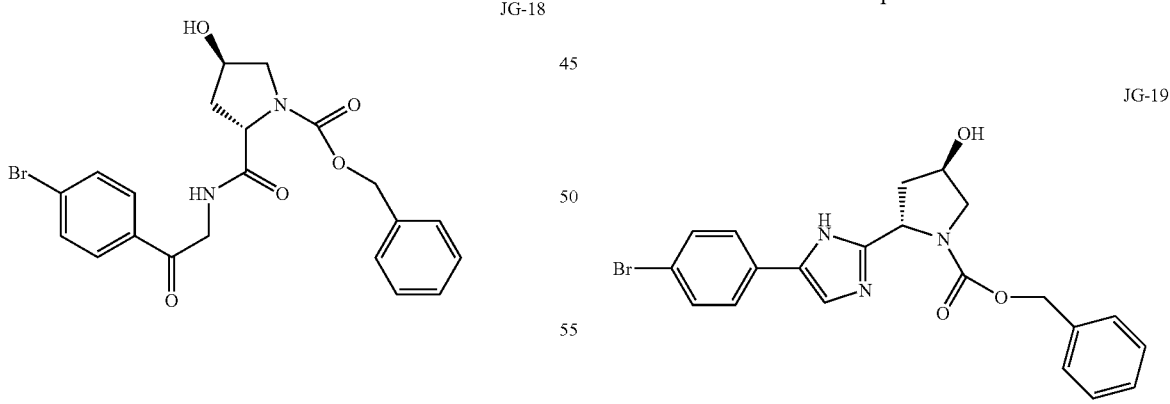

JG-18

$^1$H NMR (500 MHz, DMSO-$d_6$) δ ppm 7.89 (2H, t, J=8.39 Hz) 7.74 (2H, t, J=8.24 Hz) 7.28-7.37 (5H, m) 5.01-5.08 (3H, m) 4.27-4.57 (4H, m) 3.44-3.53 (1H, m) 3.37 (1H, d, J=10.99 Hz) 2.12 (1H, d, J=11.60 Hz) 1.93 (1H, dd, J=12.05 Hz, 6.56 Hz)

LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA mobile phase, $t_R$=3.62 min, Anal Calcd. for $C_{21}H_{21}BrN_2O_5$ 461.32. found 462.64 (M+H)$^+$.

Synthesis of JG-19 from JG-18 as in Example 28 Step b

JG-19

LCMS—Luna C-18 3.0×50 mm, 0 to 100% B over 4.0 minute gradient, 1 minute hold time, A=5% acetonitrile, 95% water, 10 mm ammonium acetate, B=95% acetonitrile, 5% water, 10 mm ammonium acetate, $t_R$=1.88 min, Anal. Calcd. for $C_{21}H_{20}BN_3O_3$ 441.07. found 442.22 (M+H)$^+$

JG-20

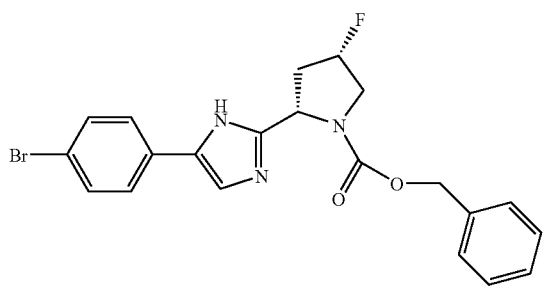

(2S,4R)-benzyl 2-(5-(4-bromophenyl)-1H-imidazol-2-yl)-4-hydroxypyrrolidine-1-carboxylate (1.5 g, 3.4 mmol) was added as a solid to a solution of bis(2-methoxyethyl)aminosulfur trifluoride (0.98 mL, 5.1 mmol) in 15 mL CH$_2$Cl$_2$ cooled to −78° C. Reaction was stirred at −78° C. for two hours and then warmed to room temperature and stirred for 2 hours. Reaction was poured into saturated sodium bicarbonate solution and stirred until bubbling ceased. Layers were separated and aqueous layer washed one time with CH$_2$Cl$_2$. Combined organics were washed with brine, dried (MgSO$_4$), filtered, and concentrated to give a yellow oil. The oil was triturated with CH$_2$Cl$_2$ and pentane to yield (2S,4S)-benzyl 2-(5-(4-bromophenyl)-1H-imidazol-2-yl)-4-fluoropyrrolidine-1-carboxylate JG-20 as a yellow solid (0.96 g, 62%).

$^1$H NMR (500 MHz, DMSO-d$_6$) δ ppm 7.70 (2H, d, J=7.02 Hz) 7.48-7.55 (3H, m) 7.41-7.35 (3H, m) 7.19-7.11 (2H, m) 5.15-5.02 (3H, m) 3.84-3.78 (2H, m) 3.33 (2H, s) 2.53-2.61 (1H, m) 2.33-2.42 (1H, m)

LCMS—Luna C-18 3.0×50 mm, 0 to 100% B over 4.0 minute gradient, 1 minute hold time, A=5% acetonitrile, 95% water, 10 mm ammonium acetate, B=95% acetonitrile, 5% water, 10 mm ammonium acetate, t$_R$=2.10 min, Anal. Calcd. for C$_{21}$H$_{19}$Br$_1$F$_1$N$_3$O$_2$ 443.06. found 444.05 (M+H)$^+$

JG-21

(2S,4R)-tert-butyl 4-hydroxy-2-(5-(4-(4,4,5,5-tetramethyl-1,3,2-dioxaborolan-2-yl)phenyl)-1H-imidazol-2-yl)pyrrolidine-1-carboxylate, 1-2c (1.5 g, 3.3 mmol) was added as a solid to a solution of bis(2-methoxyethyl)aminosulfur trifluoride (0.91 mL, 5.0 mmol) in 15 mL CH$_2$Cl$_2$ cooled to −78° C. Reaction was stirred at −78° C. for two hours and then warmed to room temperature and stirred for 2 hours. Reaction was poured into saturated sodium bicarbonate solution and stirred until bubbling ceased. Layers were separated and aqueous layer washed one time with CH$_2$Cl$_2$. Combined organics were washed with brine, dried (MgSO$_4$), filtered, and concentrated to give a brown oil. The oil was chromatographed on silica gel with 5% MeOH/CH$_2$Cl$_2$ to yield 4-(2-((2S,4S)-1-(tert-butoxycarbonyl)-4-fluoropyrrolidin-2-yl)-1H-imidazol-5-yl)phenylboronic acid as a tan solid (0.46 g, 37%).

LCMS—Luna C-18 3.0×50 mm, 0 to 100% B over 4.0 minute gradient, 1 minute hold time, A=5% acetonitrile, 95% water, 10 mm ammonium acetate, B=95% acetonitrile, 5% water, 10 mm ammonium acetate, t$_R$=1.46 min, Anal. Calcd. for C$_{18}$H$_{23}$B$_1$F$_1$N$_3$O$_4$ 375.18. found 376.12 (M+H)$^+$ JG-22 is synthesized from JG-20 and JG-21 as described in Example 28 step c.

JG-22

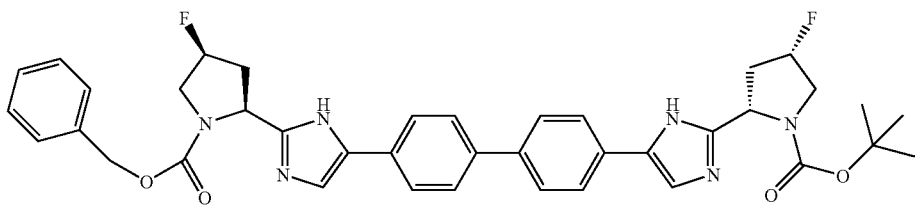

LCMS—Luna C-18 3.0×50 mm, 0 to 100% B over 4.0 minute gradient, 1 minute hold time, A=5% acetonitrile, 95% water, 10 mm ammonium acetate, B=95% acetonitrile, 5% water, 10 mm ammonium acetate, t$_R$=2.27 min, Anal. Calcd. for C$_{39}$H$_{40}$F$_2$N$_6$O$_4$ 694.31. found 695.35 (M+H)$^+$ JG-23 is synthesized from JG-22 as described in Example 28 step d.

JG-23

LCMS—Phenomenex C-18 3.0×50 mm, 0 to 100% B over 4.0 minute gradient, 1 minute hold time, A=10% methanol 90% water 0.1% TFA, B=90% methanol 10% water 0.1% TFA mobile phase, t$_R$=2.62 min, Anal Calcd. for C$_{31}$H$_{34}$F$_2$N$_6$O$_2$ 560.27. found 561.52 (M+H)$^+$.

JG-24 is synthesized from JG-22 and Cap-2 as in Example 28 step e.

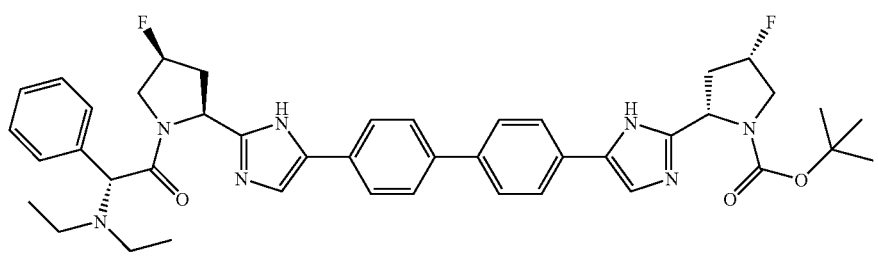
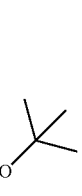

JG-24

LCMS—Luna C-18 3.0×50 mm, 0 to 100% B over 4.0 minute gradient, 1 minute hold time, A=5% acetonitrile, 95% water, 10 mm ammonium acetate, B=95% acetonitrile, 5% water, 10 mm ammonium acetate, $t_R$=2.30 min, Anal. Calcd. for $C_{41}H_{45}F_2N_7O_3$ 721.36. found 722.42 $(M+H)^+$ JG-25 is synthesized from JG-24 via reaction with methanolic HCl as described in Example LS14 step b.

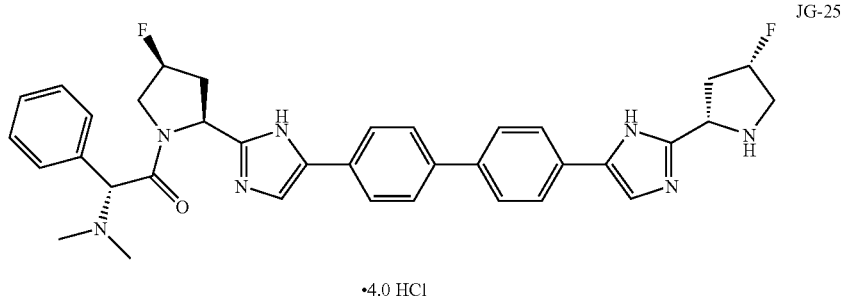

JG-25

•4.0 HCl

LCMS—Luna C-18 3.0×50 mm, 0 to 100% B over 4.0 minute gradient, 1 minute hold time, A=5% acetonitrile, 95% water, 10 mm ammonium acetate, B=95% acetonitrile, 5% water, 10 mm ammonium acetate, $t_R$=1.98 min, Anal. Calcd. for $C_{36}H_{37}F_2N_7O_1$ 621.30. found 622.48 $(M+H)^+$ Section OL LC Conditions:

Condition 1: Solvent A: 5% acetonitrile/95% water/10 mmol ammonium acetate; Solvent B: 95% acetonitrile/5% water/10 mmol ammonium acetate; Column: Phenomenex GEMINI 5u C18 4.6×5.0 mm; Wavelength: 220 nM; Flow rate: 4 ml/min; 0% B to 100% B over 3 min with a 1 min hold time.

Condition 2: Solvent A: 5% acetonitrile/95% water/10 mmol ammonium acetate; Solvent B: 95% acetonitrile/5% water/10 mmol ammonium acetate; Column: Phenomenex GEMINI 5u C18 4.6×5.0 mm; Wavelength: 220 nM; Flow rate: 4 ml/min; 0% B to 100% B over 2 min with a 1 min hold time Condition 3: Solvent A: 5% acetonitrile/95% water/10 mmol ammonium acetate; Solvent B: 95% acetonitrile/5% water/10 mmol ammonium acetate; Column: Phenomenex GEMINI 5u C18 4.6×5.0 mm; Wavelength: 220 nM; Flow rate: 4 ml/min; 0% B to 100% B over 4 min with a 1 min hold time Condition 4: Solvent A: 10% MeOH/90% water/0.1% TFA; Solvent B: 90% MeOH/10% water/0.1% TFA; Column: Phenomenex 10u C18 3.0×5.0 mm; Wavelength: 220 nM; Flow rate: 4 ml/min; 0% B to 100% B over 4 min with a 1 min hold time Condition 5: Solvent A: 5% acetonitrile/95% water/10 mmol ammonium acetate; Solvent B: 95% acetonitrile/5% water/10 mmol ammonium acetate; Column: Phenomenex GEMINI 5u C18 4.6×5.0 mm; Wavelength: 220 nM; Flow rate: 4 ml/min; 0% B to 100% B over 9 min with a 1 min hold time Condition 6: Solvent A: 10% MeOH/90% water/0.2% $H_3PO_4$; Solvent B: 90% MeOH/10% water/0.2% $H_3PO_4$; Column: Phenomenex 5u C-18 4.6×50 mm; Wavelength: 220 nM; Flow rate: 1.5 ml/min; 0% B to 100% B over 14 min with a 3 min hold time Condition 7: Solvent A: 10% MeOH/90% water/0.1% TFA; Solvent B: 90% MeOH/10% water/0.1% TFA; Column: Phenomenex 10u C18 3.0×5.0 mm; Wavelength: 220 nM; Flow rate: 4 ml/min; 0% B to 100% B over 3 min with a 1 min hold time Condition 8: Solvent A: 10% MeOH/90% water/0.1% TFA; Solvent B: 90% MeOH/10% water/0.1% TFA; Column: Phenomenex 10u C18 3.0×5.0 mm; Wavelength: 220 nM; Flow rate: 4 ml/min; 0% B to 100% B over 2 min with a 1 min hold time Experimentals Caps:

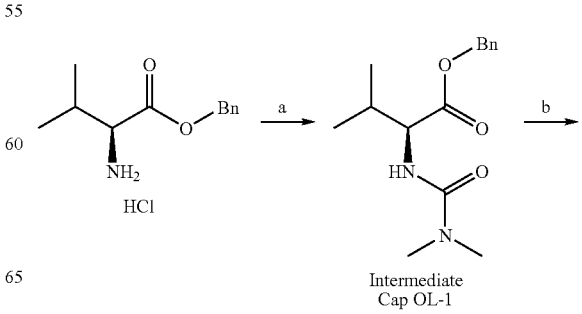

Intermediate
Cap OL-1

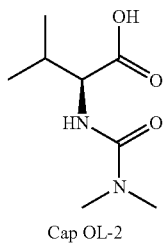

Cap OL-2

Step a: Dimethylcarbamoyl chloride (0.92 mL, 10 mmol) was added slowly to a solution of (S)-benzyl 2-amino-3-methylbutanoate hydrochloride (2.44 g; 10 mmol) and Hunig's base (3.67 mL, 21 mmol) in THF (50 mL). The resulting white suspension was stirred at room temperature overnight (16 hours) and concentrated under reduced pressure. The residue was partitioned between ethyl acetate and water. The organic layer was washed with brine, dried (MgSO₄), filtered, and concentrated under reduced pressure. The resulting yellow oil was purified by flash chromatography, eluting with ethyl acetate:hexanes (1:1). Collected fractions were concentrated under vacuum providing 2.35 g (85%) of Intermediate Cap OL-1 as a clear oil. $^1$H NMR (300 MHz, DMSO-$d_6$) δ ppm 0.84 (d, J=6.95 Hz, 3H) 0.89 (d, J=6.59 Hz, 3H) 1.98-2.15 (m, 1H) 2.80 (s, 6H) 5.01-5.09 (m, J=12.44 Hz, 1H) 5.13 (d, J=12.44 Hz, 1H) 6.22 (d, J=8.05 Hz, 1H) 7.26-7.42 (m, 5H). LC (Cond. 1): RT=1.76 min; MS: Anal. Calcd. for [M+H]$^+$ $C_{16}H_{22}N_2O_3$: 279.17. found 279.03.

Step b: To Intermediate Cap OL-1 (2.35 g; 8.45 mmol) in 50 ml MeOH was added Pd/C (10%; 200 mg) and the resulting black suspension was flushed with N₂ (3×) and placed under 1 atm of H₂. The mixture was stirred at room temperature overnight and filtered though a microfiber filter to remove the catalyst. The resulting clear solution was then concentrated under reduced pressure to obtain 1.43 g (89%) of Cap OL-2 as a white foam, which was used without further purification. $^1$H NMR (500 MHz, DMSO-$d_6$) δ ppm 0.87 (d, J=4.27 Hz, 3H) 0.88 (d, J=3.97 Hz, 3H) 1.93-2.11 (m, 1H) 2.80 (s, 6H) 3.90 (dd, J=8.39, 6.87 Hz, 1H) 5.93 (d, J=8.54 Hz, 1H) 12.36 (s, 1H).). LC (Cond. 1): RT=0.33 min; MS: Anal. Calcd. for [M+H]$^+$ $C_8H_{17}N_2O_3$: 1898.12. found 189.04.

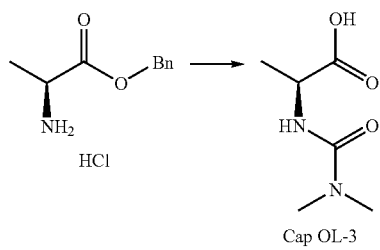

Cap OL-3

Cap OL-3 was prepared from (S)-benzyl 2-aminopropanoate hydrochloride according to the method described for Cap OL-2. $^1$H NMR (500 MHz, DMSO-$d_6$) δ ppm 1.27 (d, J=7.32 Hz, 3H) 2.80 (s, 6H) 4.06 (qt, 1H) 6.36 (d, J=7.32 Hz, 1H) 12.27 (s, 1H). LC (Cond. 1): RT=0.15 min; MS: Anal. Calcd. for [M+H]$^+$ $C_6H_{13}N_2O_3$: 161.09. found 161.00.

Cap OL-4

Cap OL-4 was prepared from (S)-tert-butyl 2-amino-3-methylbutanoate hydrochloride and 2-fluoroethyl chloroformate according to the method described for Cap-47. $^1$HNMR (500 MHz, DMSO-$d_6$) δ ppm 0.87 (t, J=6.71 Hz, 6H) 1.97-2.10 (m, 1H) 3.83 (dd, J=8.39, 5.95 Hz, 1H) 4.14-4.18 (m, 1H) 4.20-4.25 (m, 1H) 4.50-4.54 (m, 1H) 4.59-4.65 (m, 1H) 7.51 (d, J=8.54 Hz, 1H) 12.54 (s, 1H)

Cap OL-5

Cap OL-5 was prepared from (S)-diethyl alanine and methyl chloroformate according to the method described for Cap-51. $^1$H NMR (500 MHz, DMSO-$d_6$) δ ppm 0.72-0.89 (m, 6H) 1.15-1.38 (m, 4H) 1.54-1.66 (m, 1H) 3.46-3.63 (m, 3H) 4.09 (dd, J=8.85, 5.19 Hz, 1H) 7.24 (d, J=8.85 Hz, 1H) 12.55 (s, 1H). LC (Cond. 2): RT=0.66 min; MS: Anal. Calcd. for [M+H]$^+$ $C_9H_{18}NO_4$: 204.12. found 204.02.

New Examples

The following analogs were prepared from 1e in similar fashion to the preparation of Example 1 and employing the appropriate Cap.

| Example Number | Compound Name | Structure | Analytical Data |
|---|---|---|---|
| OL-1 | 3-((1S)-1-(((2S)-2-(4-(4'-(2-((2S)-1-((2S)-2-((dimethylcarbamoyl)-amino)-3-methyl-butanoyl)-2-pyrrolidinyl)-1H-imidazol-4-yl)-4-biphenylyl)-1H-imidazol-2-yl)-1-pyrrolidinyl)carbonyl)-2-methylpropyl)-1,1-dimethylurea | From 1e and Cap OL-2 | LC/MS: 2.16 min (Cond'n 3); Anal. Calcd. for [M + H]$^+$ $C_{42}H_{57}N_{10}O_4$: 765.45; found 765.47. |
| OL-2 | 3-((1S)-2-((2S)-2-(4-(4'-(2-((2S)-1-(N-(dimethylcarbamoyl)-L-alanyl)-2-pyrrolidinyl)-1H-imidazol-4-yl)-4-biphenylyl)-1H-imidazol-2-yl)-1-pyrrolidinyl)-1-methyl-2-oxoethyl)-1,1-dimethylurea | From 1e and Cap OL-3 | LC/MS: 1.86 min (Cond'n 3); Anal. Calcd. for [M + H]$^+$ $C_{38}H_{49}N_{10}O_4$: 709.39; found 709.43. |
| OL-3 | 2-fluoroethyl ((1S)-1-(((2S)-2-(4-(4'-(2-((2S)-1-((2S)-2-(((2-fluoroethoxy)carbonyl)-amino)-3-methylbutanoyl)-2-pyrrolidinyl)-1H-imidaozl-4-yl)-4-biphenylyl)-1H-imidazol-2-yl)-1-pyrrolidinyl)carbonyl)-2-methylpropyl)carbamate | From 1e and Cap OL-4 | LC/MS: 2.83 min (Cond'n 4); Anal. Calcd. for [M + H]$^+$ $C_{42}H_{53}F_2N_8O_6$: 803.40; found 803.47. |
| OL-4 | methyl ((1S)-2-ethyl-1-(((2S)-2-(4-(4'-(2-((2S)-1-((2S)-3-ethyl-2-((methoxycarobnyl)-amino)pentanoyl)-2-pyrrolidinyl)-1H-imidazol-4-yl)-4-biphenylyl)-1H-imidazol-2-yl)-1-pyrrolidinyl)carbonyl)-butyl)carbamate | From 1e and Cap OL-5 | LC/MS: 2.64 min (Cond'n 3); Anal. Calcd. for [M + H]$^+$ $C_{44}H_{59}N_8O_6$: 795.45; found 795.48. |

| Example Number | Compound Name | Structure | Analytical Data |
|---|---|---|---|
| OL-5 | 1,1'-(4,4'-biphenyldiylbis(1H-imidazole-4,2-diyl(2S)-2,1-pyrrolidinediyl((2S)-3-methyl-1-oxo-1,2-butanediyl)))ditetrahydro-2(1H)-pyrimidinone | 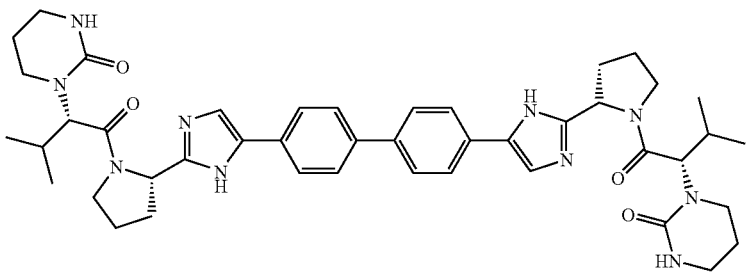 From 1e and (S)-3-methyl-2-(2-oxotetrahydropyrimidin-1(2H)-yl)butanoic acid | LC/MS: 2.95 min (Cond'n 4); Anal. Calcd. for [M + H]$^+$ $C_{44}H_{57}N_{10}O_6$: 789.46; found 789.52. |
| OL-6 | methyl ((1S)-1-(((2S)-2-(4-(4'-(2-((2S)-1-((2S)-2-((methoxycarbonyl)amino)-4-methylpentanoyl)-2-pyrrolidinyl)-1H-imidazol-4-yl)-4-biphenylyl)-1H-imidazol-2-yl)-1-pyrrolidinyl)carbonyl)-3-methylbutyl)carbamate | 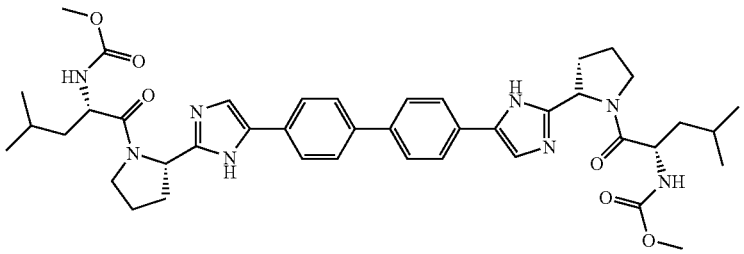 From 1e and (S)-2-(methoxycarbonylamino)-4-methylpentanoic acid which was prepared from L-Isoleucine and methylchloroformate in similar fashion to the preparation of Cap-51 | LC/MS: 2.95 min (Cond'n 3); Anal. Calcd. for [M + H]$^+$ $C_{42}H_{53}N_8O_6$: 767.42; found 767.43. |

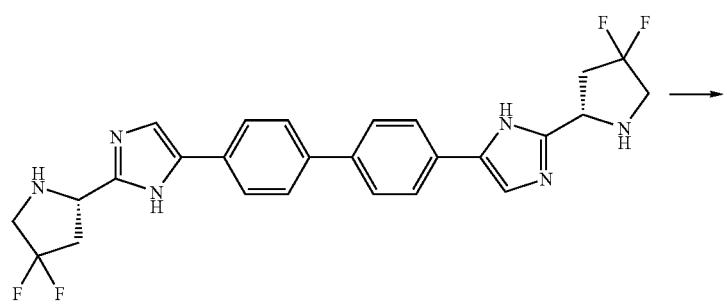

1-2e-3

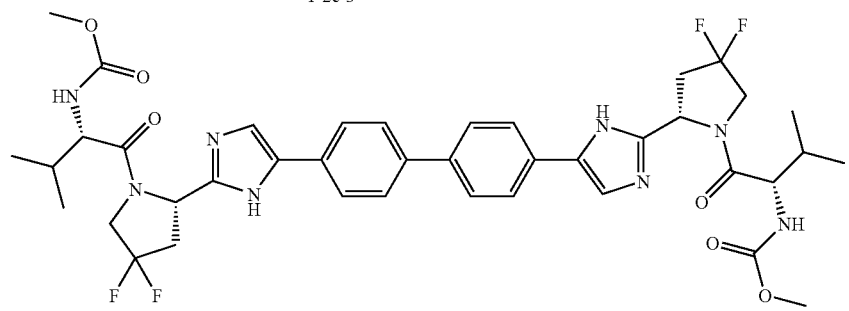

OL-7

Example OL-7 methyl ((1S)-1-(((2S)-2-(4-(4'-(2-((2S)-4,4-difluoro-1-((2S)-2-((methoxycarbonyl)amino)-3-methylbutanoyl)-2-pyrrolidinyl)-1H-imidazol-4-yl)-4-biphenylyl)-1H-imidazol-2-yl)-4,4-difluoro-1-pyrrolidinyl)carbonyl)-2-methylpropyl)carbamate Example OL-7 was prepared from 1-2e-3 in similar fashion to the preparation of Example 1, using Cap-51 as the coupling partner. $^1$H NMR (500 MHz, DMSO-d$_6$) δ ppm 0.80 (dd, J=6.41, 2.44 Hz, 12H) 1.87-1.98 (m, 2H) 2.79-2.91 (m, 2H) 3.01-3.13 (m, 2H) 3.54 (s, 6H) 3.98 (t, J=7.93 Hz, 2H) 4.22-4.37 (m, 2H) 4.52 (t, J=14.19 Hz, 2H) 5.31 (t, J=8.39 Hz, 2H) 7.50 (d, J=7.93 Hz, 2H) 7.82-7.87 (m, 4H) 7.88-7.97 (m, 6H) 8.08 (s, 2H). LC (Cond'n 6): 7.64 min; MS: Anal. Calcd. for [M+H]$^+$ C$_{40}$H$_{47}$F$_4$N$_8$O$_6$: 811.35. found 811.46. HRMS: Anal. Calcd. for (M+H)$^+$ C$_{40}$H$_{47}$F$_4$N$_8$O$_6$ 811.3549 found 811.3553.

The following analogs were prepared from 1-2e-3 in similar fashion to the preparation of Example 1 and employing the appropriate Cap.

| Example Number | Compound Name | Structure | Analytical Data |
|---|---|---|---|
| OL-8 | (1R,1'R)-2,2'-(4,4'-biphenyldiylbis(1H-imidazole-4,2-diyl((2S)-4,4-difluoro-2,1-pyrrolidinediyl)))-bis(N,N-dimethyl-2-oxo-1-phenylethanamine) | From 1-2e-3 and Cap-1 | LC/MS: 3.98 min (Cond'n 5); Anal. Calcd. for [M + H]$^+$ C$_{46}$H$_{47}$F$_4$N$_8$O$_2$: 819.37; found 819.78. |
| OL-9 | (1R,1'R)-2,2'-(4,4'-biphenyldiylbis(1H-imidazole-4,2-diyl((2S)-4,4-difluoro-2,1-pyrrolidinediyl)))-bis(N,N-diethyl-2-oxo-1-phenylethanamine) | From 1-2e-3 and Cap-2 | LC/MS: 4.58 min (Cond'n 5); Anal. Calcd. for [M + H]$^+$ C$_{50}$H$_{55}$F$_4$N$_8$O$_2$: 875.449; found 875.90. |
| OL-10 | methyl ((1S,2R)-1-(((2S)-2-(4-(4'-(2-((2S)-4,4-difluoro-1-(N-(methoxycarbonyl)-O-methyl-L-threonyl)-2-pyrrolidinyl)-1H-imidazol-4-yl)-4-biphenylyl)-1H-imidazol-2-yl)-4,4-difluoro-1-pyrrolidinyl)carbonyl)-2-methoxy propyl)-carbamate | From 1-2e-3 and Cap-86 | LC/MS: 2.18 min (Cond'n 7); Anal. Calcd. for [M + H]$^+$ C$_{40}$H$_{47}$F$_4$N$_8$O$_8$: 843.84; found 844.04. |

| Example Number | Compound Name | Structure | Analytical Data |
|---|---|---|---|
| OL-11 | methyl ((1S)-2-((2S)-2-(4-(4'-(2-((2S)-4,4-difluoro-1-(N-(methoxycarbonyl)-L-alanyl)-2-pyrrolidinyl)-1H-imidazol-4-yl)-4-biphenylyl)-1H-imidazol-2-yl)-4,4-difluoro-1-pyrrolidinyl)-1-methyl-2-oxoethyl)carbamate | 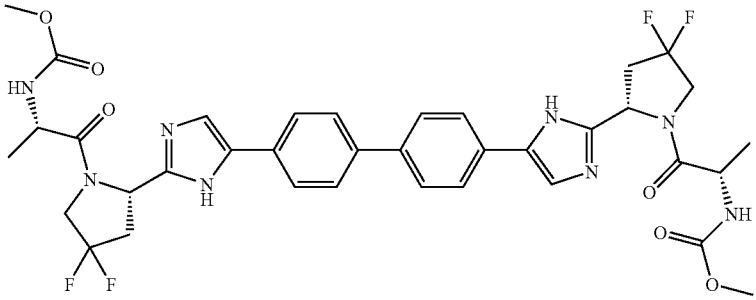<br>From 1-2e-3 and Cap-52 | LC/MS: 2.04 min (Cond'n 7); Anal. Calcd. for [M + H]+ C36H39F4N8O6: 755.29; found 755.78. |

The following analogs were prepared from 1-3e in similar fashion to the preparation of Example 1 and employing the appropriate Cap.

| Example Number | Compound Name | Structure | Analytical Data |
|---|---|---|---|
| OL-12 | methyl ((1S)-1-(((2S)-2-(4-(4'-(2-((2S)-4,4-difluoro-1-((2S)-2-((methoxycarbonyl)amino)-3-methylbutanoyl)-2-pyrrolidinyl)-1H-imidazol-4-yl)-4-biphenylyl)-1H-imidazol-2-yl)-1-pyrrolidinyl)-carbonyl)-2-methylpropyl) carbamate | 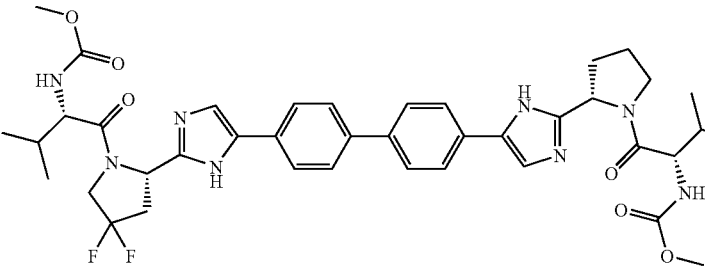<br>From 1-3e and Cap-51 | LC/MS: 2.33 min (Cond'n 3); Anal. Calcd. for [M + H]+ C40H49F2N8O2: 775.37; found 775.37. |
| OL-13 | rac-(1R)-2-((2S)-2-(4-(4'-(2-((2S)-1-((2R)-2-(diethylamino)-2-phenylacetyl)-4,4-difluoro-2-pyrrolidinyl)-1H-imidazol-4-yl)-4-biphenylyl)-1H-imidazol-2-yl)-1-pyrrolidinyl)-N,N-diethyl-2-oxo-1-phenylethanamine | 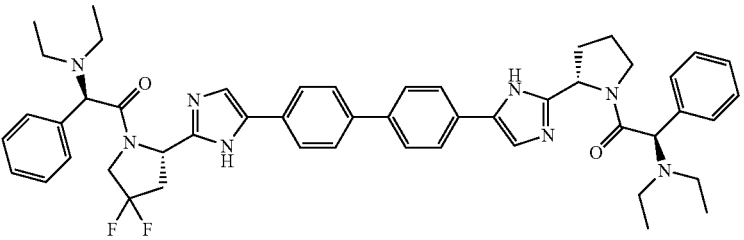<br>From 1-3e and Cap-2 | LC/MS: 3.93 min (Cond'n 5); Anal. Calcd. for [M + H]+ C50H57F2N8O2: 839.40; found 839.93. |

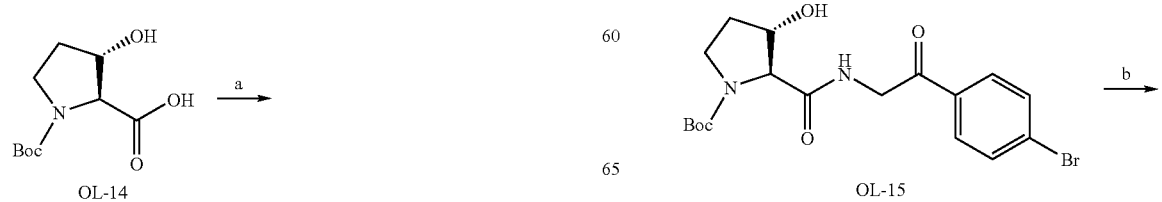

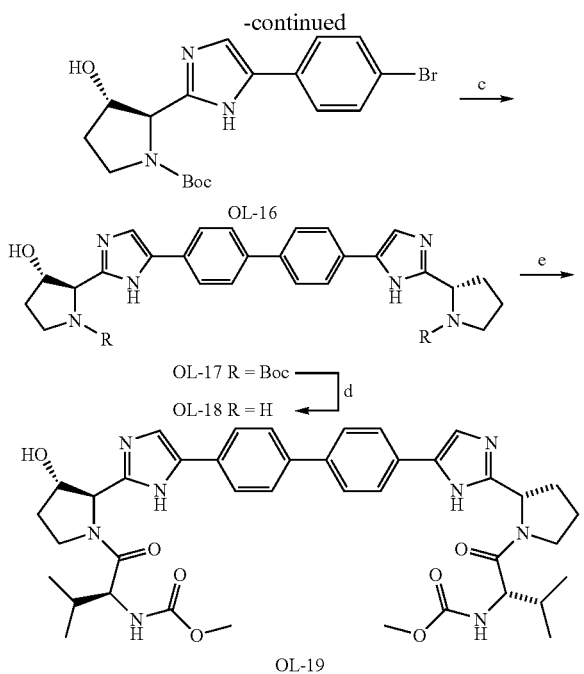

OL-16

OL-17 R = Boc
OL-18 R = H

OL-19

Example OL-19 methyl ((1S)-1-(((2R,3S)-3-hydroxy-2-(4-(4'-(2-
((2S)-1-((2S)-2-((methoxycarbonyl)amino)-3-meth-
ylbutanoyl)-2-pyrrolidinyl)-1H-imidazol-4-yl)-4-
biphenylyl)-1H-imidazol-2-yl)-1-pyrrolidinyl)
carbonyl)-2-methylpropyl)carbamate Step a: Intermediate OL-15 was prepared in similar fashion as intermediate 1a, where N-Boc-L-proline was substituted for N-Boc-trans-3-hydroxy-L-proline. $^1$H NMR (500 MHz, DMSO-d$_6$) δ ppm 1.34/1.4 (2 br. s., 9H) 1.65-1.77 (m, 1H) 1.83-1.95 (m, 1H) 3.33-3.42 (m, 1H) 3.43-3.51 (m, 1H) 3.96-4.07 (m, 1H) 4.16 (s, 1H) 4.44-4.65 (m, 2H) 5.22-5.28 (m, 1H) 7.74 (d, J=8.54 Hz, 2H) 7.86-7.94 (m, 2H) 8.15-8.32 (m, 1H). LC (Cond. 4): RT=3.33 min; MS: Anal. Calcd. for [2M+Na]$^+$ C$_{36}$H$_{46}$Br$_2$N$_4$NaO$_{10}$: 877.57. found 877.11.

Step b: Intermediate OL-16 was prepared from intermediate OL-15 in similar fashion as intermediate 1b. $^1$H NMR (500 MHz, DMSO-d$_6$) δ ppm 1.16/1.39 (2 br. s., 9H) 1.71-1.81 (m, J=6.10 Hz, 1H) 2.01-2.17 (m, 1H) 3.37-3.50 (m, 1H) 3.50-3.62 (m, 1H) 4.15 (s, 1H) 4.49-4.70 (m, 1H) 5.36 (dd, J=6.71, 3.66 Hz, 1H) 7.44-7.62 (m, 3H) 7.68 (d, J=7.02 Hz, 2H) 11.96/11.99/12.26/12.30 (m, 1H). LC (Cond. 8): RT=1.87 min; MS: Anal. Calcd. for [M+H]$^+$ C$_{18}$H$_{23}$BrN$_3$O$_3$: 408.08. found 408.09.

Step c: Intermediate OL-17 was prepared by coupling intermediate OL-16 with 1c in similar fashion to the preparation of 1d. $^1$H NMR (500 MHz, DMSO-d$_6$) δ ppm 1.09-1.49 (m, 18H) 1.71-2.04 (m, 4H) 2.06-2.28 (m, 2H) 3.33-3.40 (m, 1H) 3.41-3.65 (m, 3H) 4.18 (s, 1H) 4.52-4.69 (m, 1H) 4.70-4.88 (m, 1H) 5.38 (s, 1H) 6.64-7.35 (m, 1H) 7.39-7.96 (m, 9H) 11.71-12.0/12.10-12.36 (m, 2H). LC (Cond. 2): RT=1.36 min; MS: Anal. Calcd. for [M+H]$^+$ C$_{36}$H$_{45}$N$_6$O$_5$: 641.77. found 641.39.

Step d: Intermediate OL-18 was prepared by deprotection of intermediate OL-17 with HCl in similar fashion to the preparation of 1-1e. $^1$H NMR (500 MHz, DMSO-d$_6$) δ ppm 1.92-2.07 (m, 2H) 2.14-2.25 (m, 1H) 2.35-2.44 (m, 1H) 3.15 (s, 4H) 3.32-3.41 (m, J=7.02, 7.02, 7.02 Hz, 1H) 3.41-3.51 (m, J=7.32 Hz, 2H) 3.54-3.66 (m, 1H) 4.68 (d, J=4.27 Hz, 1H) 4.78-4.89 (m, J=4.88 Hz, 1H) 5.04 (s, 1H) 6.89/7.73 (2d, J=8.70 Hz, 1H) 7.89 (dd, J=8.24, 4.58 Hz, 4H) 7.96-8.07 (m, 4H) 8.15 (d, J=23.19 Hz, 2H) 9.62-10.12 (m, 2H) 10.21-10.74 (m, 2H).). LC (Cond. 8): RT=1.30 min; MS: Anal. Calcd. for [M+H]$^+$ C$_{26}$H$_{29}$N$_6$O: 441.24. found 441.18.

Step e: Example OL-19 was prepared by coupling of intermediate OL-18 with Cap-51 in similar fashion to the preparation of Example 1. $^1$H NMR (500 MHz, DMSO-d$_6$) δ ppm 0.78 (d, J=6.41 Hz, 6H) 0.83 (d, J=6.71 Hz, 6H) 1.92-2.12 (m, 5H) 2.12-2.21 (m, 1H) 2.31 (dd, J=12.21, 5.80 Hz, 1H) 2.35-2.43 (m, 1H) 3.54 (d, J=4.27 Hz, 6H) 3.78-3.89 (m, 3H) 3.91-4.02 (m, 1H) 4.07-4.19 (m, 2H) 4.36-4.50 (m, 1H) 4.81 (d, J=3.66 Hz, 1H) 5.13 (t, J=7.17 Hz, 1H) 5.79 (s, 1H) 7.34 (dd, J=11.29, 8.85 Hz, 2H) 7.83-7.90 (m, 4H) 7.90-8.01 (m, 4H) 8.12 (s, 2H) [Note: the signal for the imidazole NH was too broad to assign a chemical shift].). LC (Cond. 4): RT=2.76 min; MS: Anal. Calcd. for [M+H]$^+$ C$_{40}$H$_{51}$N$_8$O$_7$: 755.39. found 755.38. HRMS: Anal. Calcd. for (M+H)$^{+C}_{40}$H$_{51}$N$_8$O$_7$ 755.3881 found 755.3873.

The following analog was prepared from intermediate OL-18 in similar fashion to the preparation of Example 1 and employing Cap-52.

| Example Number | Compound Name | Structure | Analytical Data |
|---|---|---|---|
| OL-20 | methyl ((1S)-2-((2S)-2-(4-(4'-(2-((2R,3S)-3-hydroxy-1-(N-(methoxycarbonyl)-L-alanyl)-2-pyrrolidinyl)-1H-imidazol-4-yl)-4-biphenylyl)-1H-imidazol-2-yl)-1-pyrrolidinyl)-1-methyl-2-oxoethyl)carbamate | From OL-18 and Cap-52 | LC/MS: 2.32 min (Cond'n 4); Anal. Calcd. for [M + H]$^+$ C$_{36}$H$_{43}$N$_8$O$_7$: 699.78; found 699.32. |

The following analog was prepared in similar fashion to the preparation of OL-19 but using N-Boc-cis-3-hydroxy-L-proline as starting material.

| Example Number | Compound Name | Structure | Analytical Data |
|---|---|---|---|
| OL-21 | methyl ((1S)-1-(((2R)-3-hydroxy-2-(4-(4'-(2-((2S)-1-((2S)-2-((methoxycarbonyl)amino)-3-methylbutanoyl)-2-pyrrolidinyl)-1H-imidazol-4-yl)-4-biphenylyl)-1H-imidazol-2-yl)-1-pyrrolidinyl)carbonyl)-2-methylpropyl)carbamate | 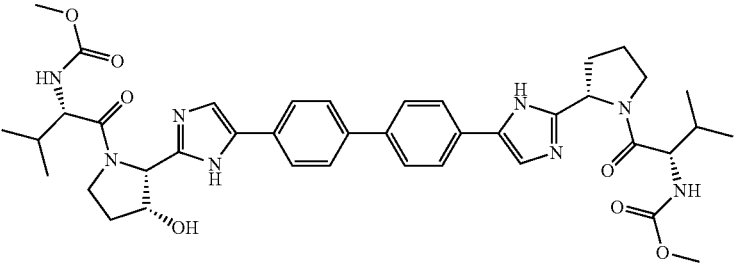<br>From N-Boc-cis-3-hydroxy-L-proline and Cap-51 | LC/MS: 2.74 min (Cond'n 4); Anal. Calcd. for [M + H]$^+$ $C_{40}H_{51}N_8O_7$: 755.39; found 755.34. |

| Example Number | Compound Name | Heterocycles with New Caps | Analytical Data (Cond 1: 3 min gradient, 4 min run; Cond 2: 2 min gradient, 3 min run) |
|---|---|---|---|
| D71 | tert-butyl (2S)-2-(5-(2-(4-(2-((2S)-1-((2R)-2-(diethylamino)-2-phenylacetyl)-2-pyrrolidinyl)-1H-imidazol-5-yl)phenyl)-5-pyrimidinyl)-1H-imidazol-2-yl)-1-pyrrolidinecarboxylate | 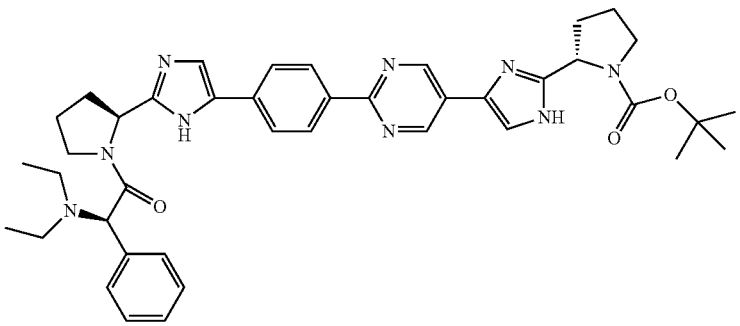<br>Prepared from 152i-1 (in lieu of 148e) and Cap-2 using experimental conditions outlined in Example 148 | $t_R$ = 1.82 min, (97.7%), (Cond 1) LRMS: Anal. Calcd. for $C_{41}H_{50}N_9O_3$ 716.40; found: 716.44 (M + H)$^+$. HRMS: Anal. Calcd. for $C_{41}H_{50}N_9O_3$ 716.4037; found: 716.4056 (M + H)$^+$. |
| D72 | (1R)-N,N-diethyl-2-oxo-1-phenyl-2-((2S)-2-(5-(4-(5-(2-((2S)-2-pyrrolidinyl)-1H-imidazol-5-yl)-2-pyrimidinyl)phenyl)-1H-imidazol-2-yl)-1-pyrrolidinyl)-ethanamine | 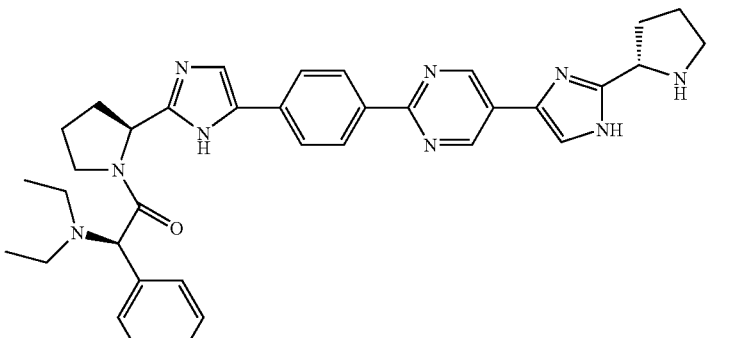<br>Prepared from entry 71 (in lieu of 152j-27) using experimental conditions outlined in Example 152k-1. | $t_R$ = 1.56 min, (~95.3%, has shoulder), (Cond 1) LRMS: Anal. Calcd. for $C_{36}H_{42}N_9O$ 616.35; found: 616.37 (M + H)$^+$. HRMS: Anal. Calcd. for $C_{36}H_{42}N_9O$ 616.3512; found: 616.3540 (M + H)$^+$. |

| | | | |
|---|---|---|---|
| D73 | methyl ((1S)-2-((2S)-2-(5-(4-(5-(2-((2S)-1-(N-(methoxycarbonyl)-L-alanyl)-2-pyrrolidinyl)-1H-imidazol-5-yl)-2-pyrimidinyl)phenyl)-1H-imidazol-2-yl)-1-pyrrolidinyl)-1-methyl-2-oxoethyl)carbamate | 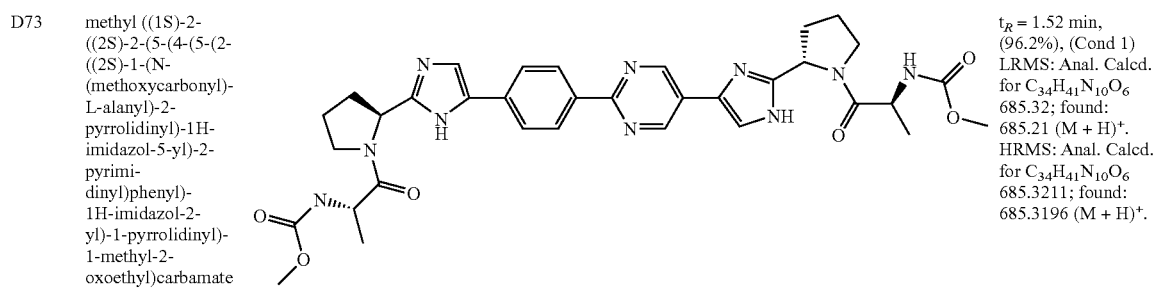 | $t_R$ = 1.52 min, (96.2%), (Cond 1) LRMS: Anal. Calcd. for $C_{34}H_{41}N_{10}O_6$ 685.32; found: 685.21 $(M + H)^+$. HRMS: Anal. Calcd. for $C_{34}H_{41}N_{10}O_6$ 685.3211; found: 685.3196 $(M + H)^+$. |

Prepared from 152h-1 (in lieu of 148e) and Cap-52 using experimental conditions outlined in Example 148

| | | | |
|---|---|---|---|
| D74 | methyl ((1S)-1-(((2S)-2-(5-(2-(4-(2-((2S)-1-((2S)-2-((methoxycarbonyl)amino)-3-methylbutanoyl)-2-pyrrolidinyl)-1H-imidazol-5-yl)phenyl)-5-pyrimidinyl)-1H-imidazol-2-yl)-1-pyrrolidinyl)carbonyl)-2-methylpropyl)carbamate | 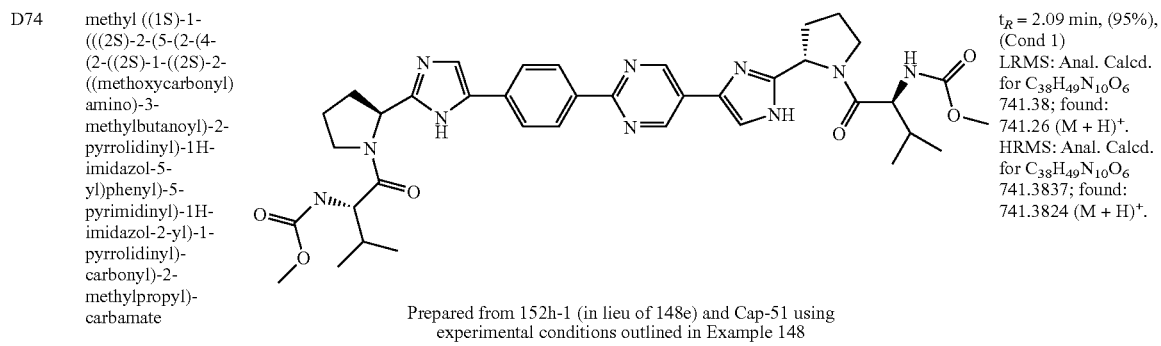 | $t_R$ = 2.09 min, (95%), (Cond 1) LRMS: Anal. Calcd. for $C_{38}H_{49}N_{10}O_6$ 741.38; found: 741.26 $(M + H)^+$. HRMS: Anal. Calcd. for $C_{38}H_{49}N_{10}O_6$ 741.3837; found: 741.3824 $(M + H)^+$. |

Prepared from 152h-1 (in lieu of 148e) and Cap-51 using experimental conditions outlined in Example 148

| | | | |
|---|---|---|---|
| D75 | methyl ((1S)-1-cyclopropyl-2-((2S)-2-(5-(2-(4-(2-((2S)-1-((2S)-2-cyclopropyl-2-((methoxycarbonyl)amino)acetyl)-2-pyrrolidinyl)-1H-imidazol-5-yl)phenyl)-5-pyrimidinyl)-1H-imidazol-2-yl)-1-pyrrolidinyl)-2-oxoethyl)carbamate | 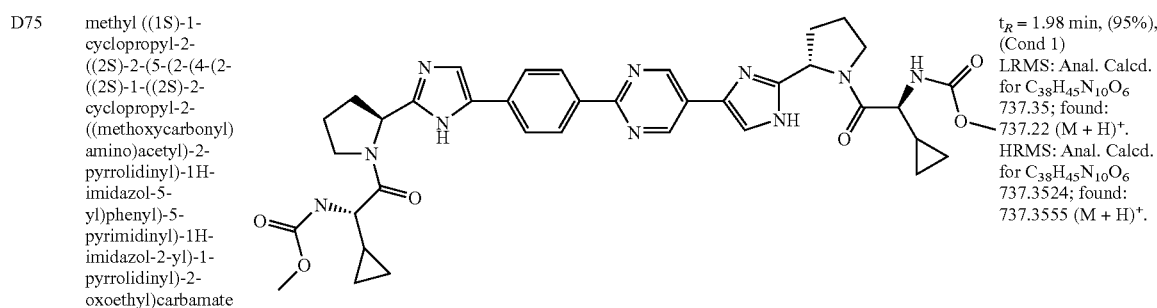 | $t_R$ = 1.98 min, (95%), (Cond 1) LRMS: Anal. Calcd. for $C_{38}H_{45}N_{10}O_6$ 737.35; found: 737.22 $(M + H)^+$. HRMS: Anal. Calcd. for $C_{38}H_{45}N_{10}O_6$ 737.3524; found: 737.3555 $(M + H)^+$. |

Prepared from 152h-1 (in lieu of 148e) and Cap-54b using experimental conditions outlined in Example 148

| | | | |
|---|---|---|---|
| D76 | methyl ((1S)-1-(((2S)-2-(5-(2-(4-(2-((2S)-1-((2R)-2-(diethylamino)-2-phenylacetyl)-2-pyrrolidinyl)-1H-imidazol-5-yl)-phenyl)-5-pyrimidinyl)-1H-imidazol-2-yl)-1-pyrrolidinyl)-carbonyl)-2-methyl-propyl)carbamate | 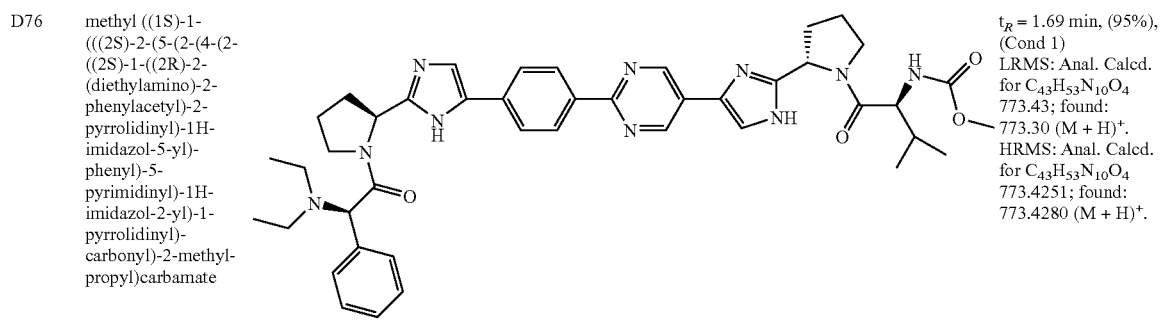 | $t_R$ = 1.69 min, (95%), (Cond 1) LRMS: Anal. Calcd. for $C_{43}H_{53}N_{10}O_4$ 773.43; found: 773.30 $(M + H)^+$. HRMS: Anal. Calcd. for $C_{43}H_{53}N_{10}O_4$ 773.4251; found: 773.4280 $(M + H)^+$. |

Prepared from entry D72 (in lieu of 148e) and Cap-51 using experimental conditions outlined in Example 148

| | | | |
|---|---|---|---|
| D77 | methyl ((1S)-2-((2S)-2-(5-(2-(4-(2-((2S)-1-((2R)-2-(diethylamino)-2-phenylacetyl)-2-pyrrolidinyl)-1H-imidazol-5-yl)phenyl)-5-pyrimidinyl)-1H-imidazol-2-yl)-1-pyrrolidinyl)-1-methyl-2-oxoethyl)carbamate | 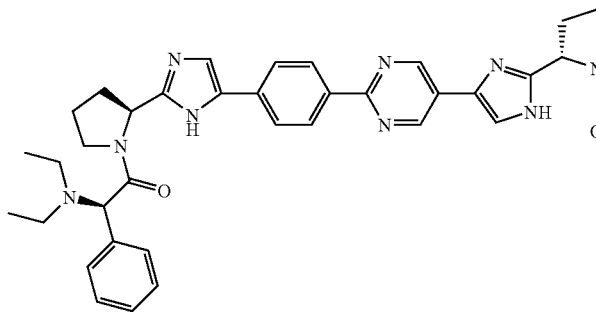 | $t_R$ = 1.81 min, (97.5%), (Cond 1) LRMS: Anal. Calcd. for $C_{41}H_{49}N_{10}O_4$ 745.39; found: 745.27 (M + H)$^+$. HRMS: Anal. Calcd. for $C_{41}H_{49}N_{10}O_4$ 745.3938; found: 745.3939 (M + H)$^+$. |

Prepared from entry D72 (in lieu of 148e) and Cap-52 using experimental conditions outlined in Example 148

Section J

| Example Number | Compound Name | Structure | Analytical Data |
|---|---|---|---|
| J.1a | | Prepared from 4-bromoacetophenone and dimethylcarbonate from Bioorg. Med. Chem. Lett (2001)11, 641 | $t_R$ = 1.7 min, (Cond 2); LCMS: $C_{10}H_9BrO_3$ found: 257 (M + H)$^+$. |
| J.1b | | Prepared from 4-bromoacetophenone and diethylcarbonate from Bioorg. Med. Chem. Lett (2001)11, 641. | $t_R$ = 1.9 min, (Cond 2); LCMS: $C_{11}H_{11}BrO_3$ found: 271 (M + H)$^+$. |
| J.1c | | Prepared from 4-bromoacetophenone and dibenzylcarbonate from Bioorg. Med. Chem. Lett (2001)11, 641. | $t_R$ = 2.1 min, (Cond 2); LCMS: $C_{16}H_{13}BrO_3$ found: 332 (M + H)$^+$. |

-continued

| Example Number | Compound Name | Structure | Analytical Data |
|---|---|---|---|
| J1 | | Prepared from entry J.1a (in lieu of J.1b) and proline using experimental conditions in Example J2. | $t_R$ = 2.2 min, (Cond 2); LCMS: $C_{20}H_{24}BrNO_7$ found: 470 (M + H)$^+$. |
| J2 | | Prepared from entry J.1b and proline using experimental conditions in Example J2. | $t_R$ = 2.2 min, (Cond 2); LCMS: $C_{21}H_{26}BrNO_7$ found: 484 (M + H)$^+$. |
| J3 | | Prepared from entry J.1c (in lieu of J.1b) and proline using experimental conditions in Example J2. | $t_R$ = 2.3 min, (Cond 2); LCMS: $C_{26}H_{28}BrNO_7$ found: 546 (M + H)$^+$. |
| J4 | | Prepared from entry J.1 and (in lieu of J.2) using experimental conditions in Example J2. | $t_R$ = 1.84 min, (100%) (Cond 2); LRMS: Anal. Calcd. for $C_{20}H_{24}BrN_3O_4$; 450.10; found: 450.13 and 452.13 (M + H)$^+$. |

| Example Number | Compound Name | Structure | Analytical Data |
|---|---|---|---|
| J5 | | Prepared from entry J2 using experimental conditions in J5. | $t_R$ = 1.93 min, (99%) (Cond 2); Reported in J5. |
| J6 | | Prepared from entry J3 (in lieu of entry J1) using experimental conditions in J5. | $t_R$ = 2.1 min, (93%) (Cond 2); LRMS: Anal. Calcd. for $C_{26}H_{29}BrN_3O_4$ 526.13; found: 526.16 and 528.16 $(M + H)^+$. |
| J7 | | Prepared from entry J5 using experimental in J7. | $t_R$ = 1.7 min, (100%) (Cond 2); Reported in J7. |

| Example Number | Compound Name | Structure | Analytical Data |
|---|---|---|---|
| J8 | methyl 2-((2S)-1-(tert-butoxycarbonyl)-2-pyrrolidinyl)-5-(4'-(2-((2S)-1-(tert-butoxocarbonyl)-2-pyrrolidinyl)-1H-imidazol-5-yl)-4-biphenylyl)-1H-imidazole-4-carboxylate | Prepared from entry J4 (in lieu of 152e-1) and 1c using experimental conditions outlined in Example 152g-1. | $t_R$ = 1.70 min, (95%) (Cond 2); LRMS: Anal. Calcd. for $C_{38}H_{47}N_6O_6$ 683.36; found: 683.42 $(M + H)^+$. |
| J9 | ethyl 2-((2S)-1-(tert-butoxycarbonyl)-2-pyrrolidinyl)-5-(4'-(2-((2S)-1-(tert-butoxycarbonyl)-2-pyrrolidinyl)-1H-imidazol-5-yl)-4-biphenylyl)-1H-imidazole-4-carboxylate | Prepared from entry J5 (in lieu of 152e-1) and 1c using experimental conditions outlined in Example 152g-1. | $t_R$ = 1.78 min, (97.5%) (Cond 2); LRMS: Anal. Calcd. for $C_{39}H_{49}N_6O_6$ 697.37; found: 697.38 $(M + H)^+$. |

| Example Number | Compound Name | Structure | Analytical Data |
|---|---|---|---|
| J10 | benzyl 2-((2S)-1-(tert-butoxycarbonyl)-2-pyrrolidinyl)-5-(4'-(2-((2S)-1-(tert-butoxycarbonyl)-2-pyrrolidinyl)-1H-imidazol-5-yl)-4-biphenylyl)-1H-imidazole-4-carboxylate | Prepared from entry J6 (in lieu of 152e-1) and 1c using experimental conditions outlined in Example 152g-1. | $t_R$ = 1.88 min, (85%) (Cond 2); LRMS: Anal. Calcd. for $C_{44}H_{51}N_6O_6$ 759.39; found: 759.48 $(M + H)^+$. |
| J11 | tert-butyl (2S)-2-(5-(4'-(2-((2S)-1-(tert-butoxycarbonyl)-2-pyrrolidinyl)-1H-imidazol-5-yl)-4-biphenylyl)-4-(methylcarbamoyl)-1H-imidazol-2-yl)-1-pyrrolidinecarboxylate | Prepared from entry J7 (in lieu of 152e-1) and 1c using experimental conditions outlined in Example 152g-1. | $t_R$ = 1.65 min, (90%) (Cond 2); LRMS: Anal. Calcd. for $C_{38}H_{48}N_7O_5$ 682.37; found: 682.42 $(M + H)^+$. |

| Example Number | Compound Name | Structure | Analytical Data |
|---|---|---|---|
| J11.a | | 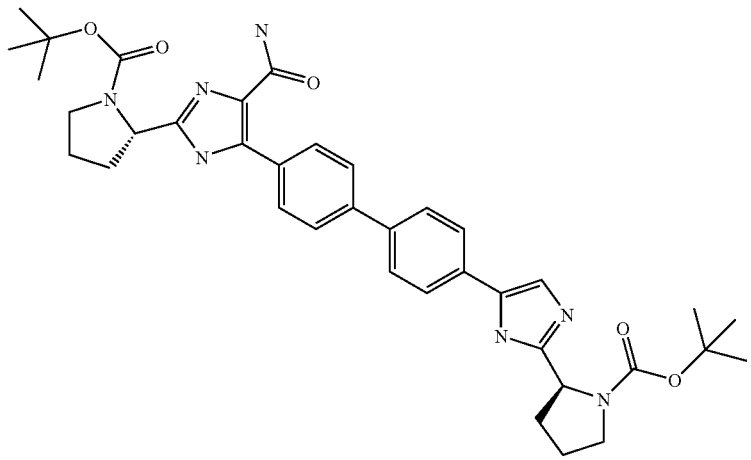<br>Prepared from entry J9 as described in J11.a. | $t_R$ = 1.60 min, (Cond 2);<br>LCMS: $C_{37}H_{46}N_7O_5$ found: 668 $(M + H)^+$. |
| J12 | | 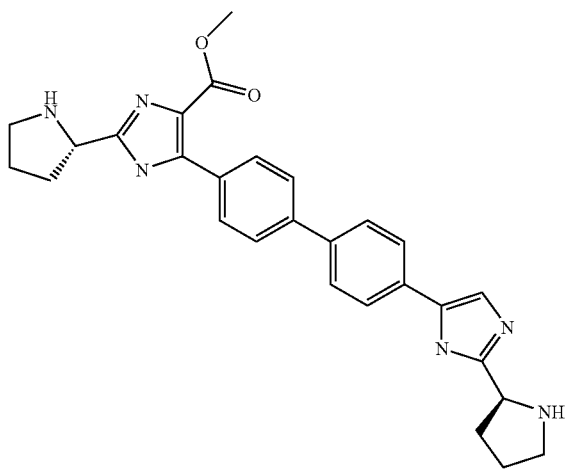<br>Prepared from entry J8 (in lieu of 152j-27) using experimental conditions outlined in Example 152k-1. | $t_R$ = 1.25 min, (97%) (Cond 2);<br>LCMS: $C_{28}H_{31}N_6O_2$ found: 483 $(M + H)^+$. |

| Example Number | Compound Name | Structure | Analytical Data |
|---|---|---|---|
| J13 | | 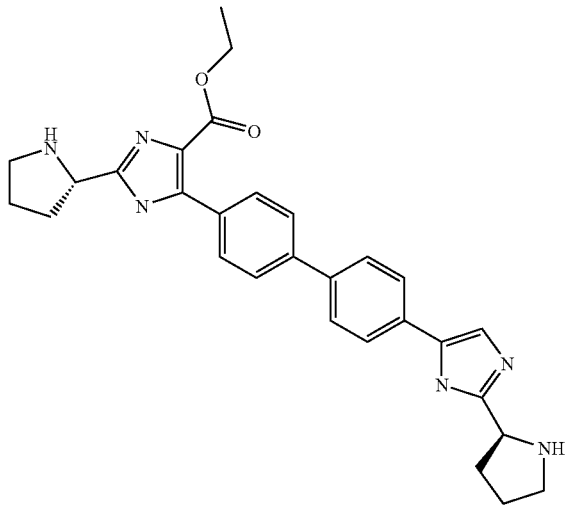 Prepared from entry J9 (in lieu of 152j-27) using experimental conditions outlined in Example 152k-1. | $t_R$ = 1.34 min, (Cond 2); LCMS: $C_{29}H_{33}N_6O_2$ found: 497 $(M + H)^+$. |
| J14 | | 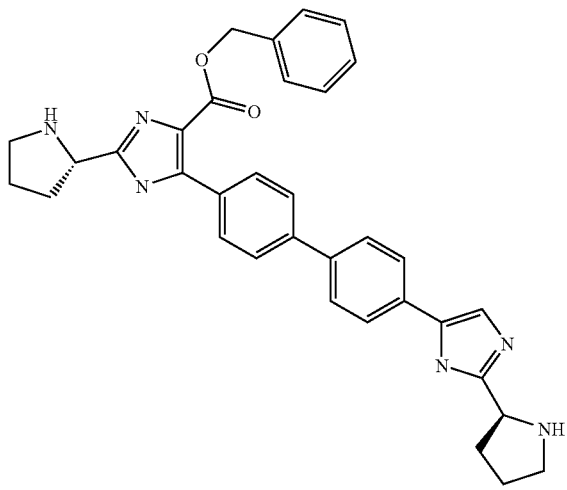 Prepared from entry J10 (in lieu of 152j-27) using experimental conditions outlined in Example 152k-1. | $t_R$ = 1.51 min, (90%) (Cond 2); LCMS: $C_{34}H_{35}N_6O_2$ found: 559 $(M + H)^+$. |

| Example Number | Compound Name | Structure | Analytical Data |
|---|---|---|---|
| J15 | | 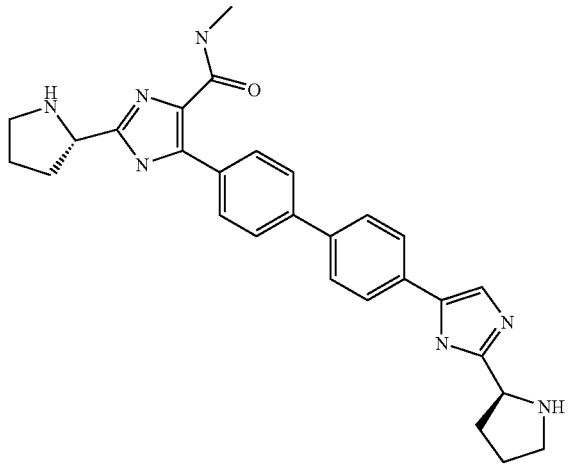<br>Prepared from entry J11 (in lieu of 152j-27) using experimental conditions outlined in Example 152k-1. | $t_R$ = 1.32 min, (99%) (Cond 2);<br>LCMS: $C_{28}H_{32}N_7O$ found: 482 $(M + H)^+$. |
| J15.a | | 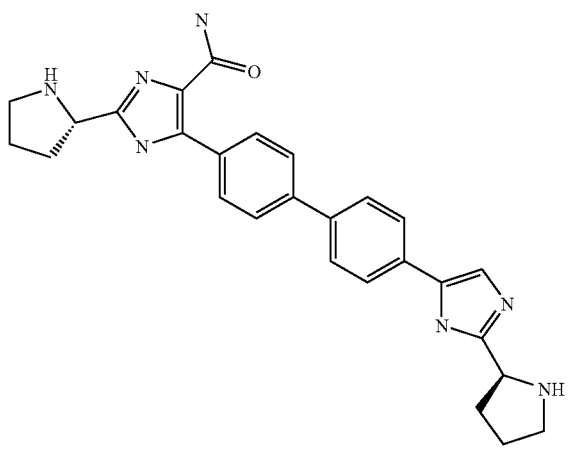<br>Prepared from entry J11.a (in lieu of 152j-27) using experimental conditions outlined in Example 152k-1. | $t_R$ = 1.07 min, (98%) (Cond 2);<br>LCMS: $C_{27}H_{30}N_7O$ found: 468 $(M + H)^+$. |

| Example Number | Compound Name | Structure | Analytical Data |
|---|---|---|---|
| J16 | methyl 2-((2S)-1-((2R)-2-((methoxycarbonyl)amino)-2-phenylacetyl)-2-pyrrolidinyl)-5-(4'-(2-((2S)-1-((2R)-2-((methoxycarbonyl)amino)-2-phenylacetyl)-2-pyrrolidinyl)-1H-imidazol-5-yl)-4-biphenylyl)-1H-imidazole-4-carboxylate | *Prepared from entry J12 (in lieu of 148e) and Cap-4 using experimental conditions outlined in Example 148.* | $t_R$ = 1.62 min, (99.5%) (Cond 2); LRMS: Anal. Calcd. for C48H49N8O8 865.37; found: 865.34 (M + H)+. HRMS: Anal. Calcd. for C48H49N8O8 865.3673; found: 865.3715 (M + H)+. |
| J17 | methyl 2-((2S)-1-((2R)-2-(dimethylamino)-2-phenylacetyl)-2-pyrrolidinyl)-5-(4'-(2-((2S)-1-((2R)-2-(dimethylamino)-2-phenylacetyl)-2-pyrrolidinyl)-1H-imidazol-5-yl)-4-biphenylyl)-1H-imidazole-4-carboxylate | *Prepared from entry J12 (in lieu of 148e) and Cap-1 using experimental conditions outlined in Example 148.* | $t_R$ = 1.37 min, (92%) (Cond 2); LRMS: Anal. Calcd. for C48H53N8O4 804.42; found: 805.51 (M + H)+. HRMS: Anal. Calcd. for C48H53N8O4 805.4190; found: 805.4211 (M + H)+. |

| Example Number | Compound Name | Structure | Analytical Data |
|---|---|---|---|
| J18 | methyl 2-((2S)-1-((2R)-2-phenyl-2-(1-piperidinyl)acetyl)-2-pyrrolidinyl)-5-(4'-(2-((2S)-1-((2R)-2-phenyl-2-(1-piperidinyl)acetyl)-2-pyrrolidinyl)-1H-imidazol-5-yl)-4-biphenylyl)-1H-imidazole-4-carboxylate | Prepared from entry J12 (in lieu of 148e) and Cap-14 using experimental conditions outlined in Example 148. | $t_R$ = 1.46 min, (94%) (Cond 2); LRMS: Anal. Calcd. for C54H61N8O6 885.48; found: 885.48 (M + H)+. HRMS: Anal. Calcd. for C54H61N8O6 885.4816; found: 885.4852 (M + H)+. |
| J19 | ethyl 2-((2S)-1-((2R)-2-((methoxycarbonyl)amino)-2-phenylacetyl)-2-pyrrolidinyl)-5-(4'-(2-((2S)-1-((2R)-2-((methoxycarbonyl)amino)-2-phenylacetyl)-2-pyrrolidinyl)-1H-imidazol-5-yl)-4-biphenylyl)-1H-imidazole-4-carboxylate | Prepared from entry J13 (in lieu of 148e) and Cap-4 using experimental conditions outlined in Example 148. | $t_R$ = 1.68 min, (99%) (Cond 2); LRMS: Anal. Calcd. for C49H51N8O8 879.38; found: 879.37 (M + H)+. HRMS: Anal. Calcd. for C49H51N8O8 879.3830; found: 879.3814 (M + H)+. |

| Example Number | Compound Name | Structure | Analytical Data |
|---|---|---|---|
| J20 | ethyl 2-((2S)-1-((2R)-2-(dimethylamino)-2-phenylacetyl)-2-pyrrolidinyl)-5-(4'-(2-((2S)-1-((2R)-2-(dimethylamino)-2-phenylacetyl)-2-pyrrolidinyl)-1H-imidazol-5-yl)-4-biphenylyl)-1H-imidazole-4-carboxylate | 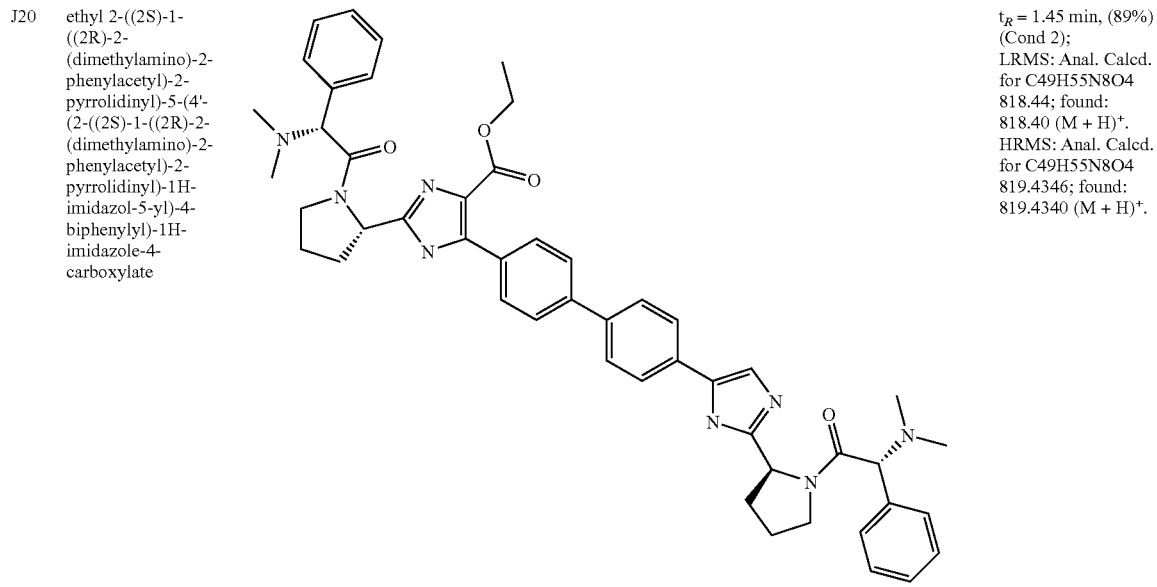 Prepared from entry J13 (in lieu of 148e) and Cap-1 using experimental conditions outlined in Example 148. | $t_R$ = 1.45 min, (89%) (Cond 2); LRMS: Anal. Calcd. for C49H55N8O4 818.44; found: 818.40 (M + H)+. HRMS: Anal. Calcd. for C49H55N8O4 819.4346; found: 819.4340 (M + H)+. |
| J21 | benzyl 2-((2S)-1-((2R)-2-((methoxycarbonyl)amino)-2-phenylacetyl)-2-pyrrolidinyl)-5-(4'-(2-((2S)-1-((2R)-2-((methoxycarbonyl)amino)-2-phenylacetyl)-2-pyrrolidinyl)-1H-imidazol-5-yl)-4-biphenylyl)-1H-imidazole-4-carboxylate | 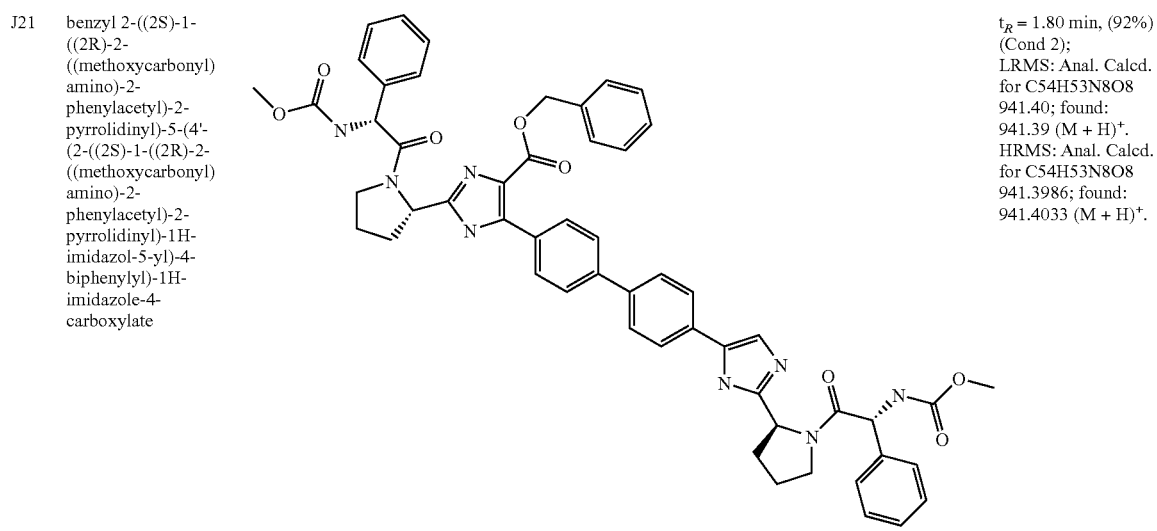 Prepared from entry J14 (in lieu of 148e) and Cap-4 using experimental conditions outlined in Example 148. | $t_R$ = 1.80 min, (92%) (Cond 2); LRMS: Anal. Calcd. for C54H53N8O8 941.40; found: 941.39 (M + H)+. HRMS: Anal. Calcd. for C54H53N8O8 941.3986; found: 941.4033 (M + H)+. |

| Example Number | Compound Name | Analytical Data |
|---|---|---|
| J22 | benzyl 2-((2S)-1-((2R)-2-(dimethylamino)-2-phenylacetyl)-2-pyrrolidinyl)-5-(4'-(2-((2S)-1-((2R)-2-(dimethylamino)-2-phenylacetyl)-2-pyrrolidinyl)-1H-imidazol-5-yl)-4-biphenylyl)-1H-imidazole-4-carboxylate | $t_R$ = 1.56 min, (96%) (Cond 2); LRMS: Anal. Calcd. for C54H57N8O4 881.45; found: 881.46 (M + H)+. HRMS: Anal. Calcd. for C54H57N8O4 881.4503; found: 881.4536 (M + H)+. |

Prepared from entry J14 (in lieu of 148e) and Cap-1 using experimental conditions outlined in Example 148.

| J23 | benzyl 2-((2S)-1-((2R)-2-phenyl-2-(1-piperidinyl)acetyl)-2-pyrrolidinyl)-5-(4'-(2-((2S)-1-((2R)-2-phenyl-2-(1-piperidinyl)acetyl)-2-pyrrolidinyl)-1H-imidazol-5-yl)-4-biphenylyl)-1H-imidazole-4-carboxylate | $t_R$ = 1.63 min, (96%) (Cond 2); LRMS: Anal. Calcd. for C60H65N8O4 961.51; found: 961.54 (M + H)+. HRMS: Anal. Calcd. for C60H65N8O4 961.5129; found: 961.5164 (M + H)+. |

Prepared from entry J14 (in lieu of 148e) and Cap-14 using experimental conditions outlined in Example 148.

| Example Number | Compound Name | Structure | Analytical Data |
|---|---|---|---|
| J24 | benzyl 2-((2S)-1-(N-(methoxycarbonyl)-L-alanyl)-2-pyrrolidinyl)-5-(4'-(2-((2S)-1-(N-(methoxycarbonyl)-L-alanyl)-2-pyrrolidinyl)-1H-imidazol-5-yl)-4-biphenylyl)-1H-imidazole-4-carboxylate | Prepared from entry J14 (in lieu of 148e) and Cap-52 using experimental conditions outlined in Example 148. | $t_R$ = 1.64 min, (94%) (Cond 2); LRMS: Anal. Calcd. for C44H49N8O8 817.37; found: 817.38 (M + H)+. HRMS: Anal. Calcd. for C44H49N8O8 817.3673; found: 817.3675 (M + H)+. |
| J25 | methyl ((1R)-2-((2S)-2-(5-(4'-(2-((2S)-1-((2R)-2-((methoxycarbonyl)amino)-2-phenylacetyl)-2-pyrrolidinyl)-1H-imidazol-5-yl)-4-biphenylyl)-4-(methylcarbamoyl)-1H-imidazol-2-yl)-1-pyrrolidinyl)-2-oxo-1-phenylethyl)carbamate | Prepared from entry J15 (in lieu of 148e) and Cap-4 using experimental conditions outlined in Example 148. | $t_R$ = 1.58 min, (99.6%) (Cond 2); LRMS: Anal. Calcd. for C48H50N9O7 864.38; found: 864.47 (M + H)+. HRMS: Anal. Calcd. for C48H50N9O7 864.3833; found: 864.3849 (M + H)+. |

| Example Number | Compound Name | Structure | Analytical Data |
|---|---|---|---|
| J26 | 2-((2S)-1-((2R)-2-(dimethylamino)-2-phenylacetyl)-2-pyrrolidinyl)-5-(4'-(2-((2S)-1-((2R)-2-(dimethylamino)-2-phenylacetyl)-2-pyrrolidinyl)-1H-imidazol-5-yl)-4-biphenylyl)-N-methyl-1H-imidazole-4-carboxamide | 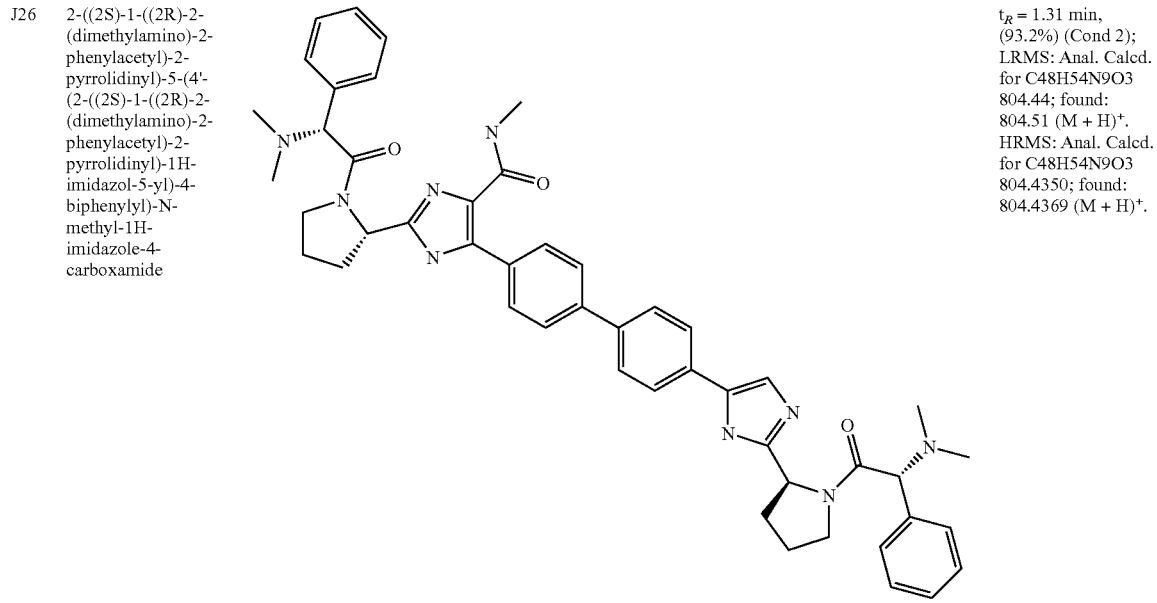 Prepared from entry J15 (in lieu of 148e) and Cap-1 using experimental conditions outlined in Example 148. | $t_R$ = 1.31 min, (93.2%) (Cond 2); LRMS: Anal. Calcd. for C48H54N9O3 804.44; found: 804.51 (M + H)+. HRMS: Anal. Calcd. for C48H54N9O3 804.4350; found: 804.4369 (M + H)+. |
| J27 | N-methyl-2-((2S)-1-((2R)-2-phenyl-2-(1-piperidinyl)acetyl)-2-pyrrolidinyl)-5-(4'-(2-((2S)-1-((2R)-2-phenyl-2-(1-piperidinyl)acetyl)-2-pyrrolidinyl)-1H-imidazol-5-yl)-4-biphenylyl)-1H-imidazole-4-carboxamide | 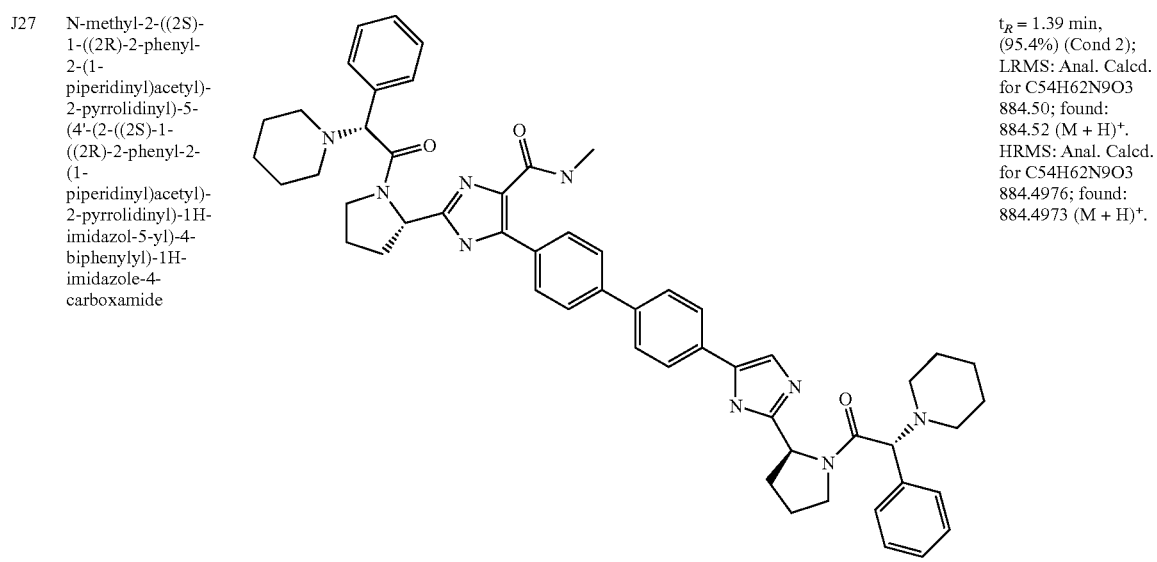 Prepared from entry J15 (in lieu of 148e) and Cap-14 using experimental conditions outlined in Example 148. | $t_R$ = 1.39 min, (95.4%) (Cond 2); LRMS: Anal. Calcd. for C54H62N9O3 884.50; found: 884.52 (M + H)+. HRMS: Anal. Calcd. for C54H62N9O3 884.4976; found: 884.4973 (M + H)+. |

| Example Number | Compound Name | Structure | Analytical Data |
|---|---|---|---|
| J28 | methyl ((1S)-2-((2S)-2-(5-(4'-(2-((2S)-1-(N-(methoxycarbonyl)-L-alanyl)-2-pyrrolidinyl)-4-(methylcarbamoyl)-1H-imidazol-5-yl)-4-biphenylyl)-1H-imidazol-2-yl)-1-pyrrolidinyl)-1-methyl-2-oxoethyl)carbamate | Prepared from entry J15 (in lieu of 148e) and Cap-52 using experimental conditions outlined in Example 148. | $t_R$ = 1.34 min, (89.3%) (Cond 2); LRMS: Anal. Calcd. for C38H46N9O7 740.35; found: 740.31 (M + H)+. HRMS: Anal. Calcd. for C38H46N9O7 740.3520; found: 740.3597 (M + H)+. |
| J29 | methyl ((1R)-2-((2S)-2-(4-carbamoyl-5-(4'-(2-((2S)-1-((2R)-2-((methoxycarbonyl)amino)-2-phenylacetyl)-2-pyrrolidinyl)-1H-imidazol-5-yl)-4-biphenylyl)-1H-imidazol-2-yl)-1-pyrrolidinyl)-2-oxo-1-phenylethyl)carbamate | Prepared from entry J15.a (in lieu of 148e) and Cap-4 using experimental conditions outlined in Example 148. | $t_R$ = 1.55 min, (96.4%) (Cond 2); LRMS: Anal. Calcd. for C47H48N9O7 740.35; found: 740.31 (M + H)+. HRMS: Anal. Calcd. for C47H48N9O7 740.3520; found: 740.3497 (M + H)+. |

| Example Number | Compound Name | Structure | Analytical Data |
|---|---|---|---|
| J30 | 2-((2S)-1-((2R)-2-((methoxycarbonyl)amino)-2-phenylacetyl)-2-pyrrolidinyl)-5-(4'-(2-((2S)-1-((2R)-2-((methoxycarbonyl)amino)-2-phenylacetyl)-2-pyrrolidinyl)-1H-imidazol-5-yl)-4-biphenylyl)-1H-imidazole-4-carboxylic acid | Prepared from entry 21 (in lieu of 28c) using experimental conditions outlined in Example 28 step d. | $t_R$ = 1.52 min, (92.8%) (Cond 2); LRMS: Anal. Calcd. for C47H47N8O8 851.35; found: 851.37 (M + H)+. HRMS: Anal. Calcd. for C47H47N8O8 851.3517; found: 851.3553 (M + H)+. |
| J31 | 2-((2S)-1-((2R)-2-phenyl-2-(1-piperidinyl)acetyl)-2-pyrrolidinyl)-5-(4'-(2-((2S)-1-((2R)-2-phenyl-2-(1-piperidinyl)acetyl)-2-pyrrolidinyl)-1H-imidazol-5-yl)-4-biphenylyl)-1H-imidazole-4-carboxylic acid | Prepared from entry 23 (in lieu of 28c) using experimental conditions outlined in Example 28 step d. | $t_R$ = 1.36 min, (96.5%) (Cond 2); LRMS: Anal. Calcd. for C53H59N8O4 871.147; found: 871.47 (M + H)+. HRMS: Anal. Calcd. for C53H59N8O4 871.4659; found: 871.4692 (M + H)+. |

| Example Number | Compound Name | Structure | Analytical Data |
|---|---|---|---|
| J32 | | 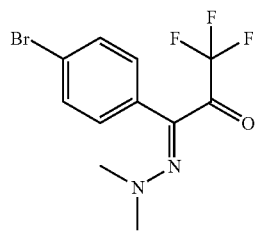<br>Prepared from 4-bromobenzaldehyde according to procedure described in J. Org. Chem. (1988), 53, 129. | $t_R$ = 1.96 min, (96%) (Cond 2);<br>LRMS: Anal. Calcd. for $C_{11}H_{11}BrF_3N_2O$ 323.00; found: 323.05 and 325.05 $(M + H)^+$.<br>$^1$H NMR (300 MHz, DMSO-$d_6$) δ 7.58 (d, J = 8.4 Hz, 2 H), 7.21 (d, J = 8.4 Hz, 2 H), 3.06 (s, 6 H). |
| J32.a | | 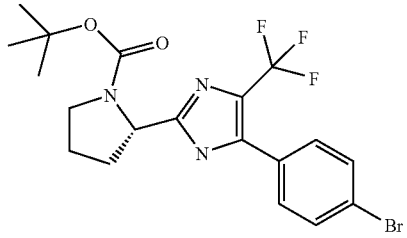<br>Prepared from entry J32 using experimental conditions in J32.a | $t_R$ = 2.19 min, (96%) (Cond 2);<br>Reported in J32.a |
| J32.b | | 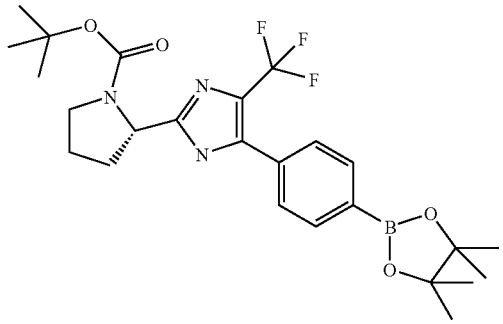<br>Prepared from entry J32.a (in lieu of 1b) using experimental conditions outlined in Example 1 step c. | $t_R$ = 2.3 min, (73%) (Cond 2);<br>LCMS: $C_{25}H_{34}BF_3N_3O_4$ found: 508 $(M + H)^+$. |

-continued

| Example Number | Compound Name | Structure | Analytical Data |
|---|---|---|---|
| J33 | tert-butyl (2S)-2-(5-(4'-(2-((2S)-1-(tert-butoxycarbonyl)-2-pyrrolidinyl)-1H-imidazol-5-yl)-4-biphenylyl)-4-(trifluoromethyl)-1H-imidazol-2-yl)-1-pyrrolidine-carboxylate | Prepared from entry J32.a (in lieu of 152e-1) and 1c using experimental conditions outlined in Example 152g-1. | $t_R$ = 2.7 min, (95%) (Cond 2); LRMS: Anal. Calcd. for $C_{37}H_{44}F_3N_6O_4$ 693.34; found: 693.33 $(M + H)^+$. HRMS: Anal. Calcd. for $C_{37}H_{44}F_3N_6O_4$ 693.3376; found: 693.3370 $(M + H)^+$. |
| J33.a | tert-butyl (2S)-2-(5-(4'-(2-((1S)-1-((tert-butoxycarbonyl)(methyl)amino)ethyl)-1H-imidazol-5-yl)-4-biphenylyl)-4-(trifluoromethyl)-1H-imidazol-2-yl)-1-pyrrolidine-carboxylate | Prepared from entry J32.a (in lieu of 152e-1) and 1-8c using experimental conditions outlined in Example 152g-1. | $t_R$ = 1.97 min, (97%) (Cond 2); LRMS: Anal. Calcd. for $C_{36}H_{44}F_3N_6O_4$ 681.34; found: 681.31 $(M + H)^+$. HRMS: Anal. Calcd. for $C_{36}H_{44}F_3N_6O_4$ 681.3376; found: 681.3383 $(M + H)^+$. |

| Example Number | Compound Name | Structure | Analytical Data |
|---|---|---|---|
| J34 | tert-butyl (2S)-2-(5-(4'-(2-((2S)-1-((benzyloxy)carbonyl)-2-pyrrolidinyl)-1H-imidazol-5-yl)-4-biphenylyl)-4-(trifluoromethyl)-1H-imidazol-2-yl)-1-pyrrolidinecarboxylate | Prepared from entry J32.a (in lieu of 152e-1) and 1-5c using experimental conditions outlined in Example 152g-1. | $t_R$ = 2.0 min, (95%) (Cond 2); LRMS: Anal. Calcd. for $C_{40}H_{42}F_3N_6O_4$ 727.32; found: 727.19 (M + H)$^+$. HRMS: Anal. Calcd. for $C_{40}H_{42}F_3N_6O_4$ 727.3220; found: 727.3251 (M + H)$^+$. |
| J34.a | tert-butyl (2S)-2-(5-(4-(5-(2-((2S)-1-(tert-butoxycarbonyl)-2-pyrrolidinyl)-1H-imidazol-5-yl)-2-pyrimidinyl)phenyl)-4-(trifluoromethyl)-1H-imidazol-2-yl)-1-pyrrolidinecarboxylate | Prepared from entry J32.b (in lieu of 152e-1) and 152d-1 using experimental conditions outlined in Example 152g-1. | $t_R$ = 1.97 min, (93%) (Cond 2); LRMS: Anal. Calcd. for $C_{35}H_{42}F_3N_8O_4$ 695.33; found: 695.28 (M + H)$^+$. |

| Example Number | Compound Name | Structure | Analytical Data |
|---|---|---|---|
| J35 | | 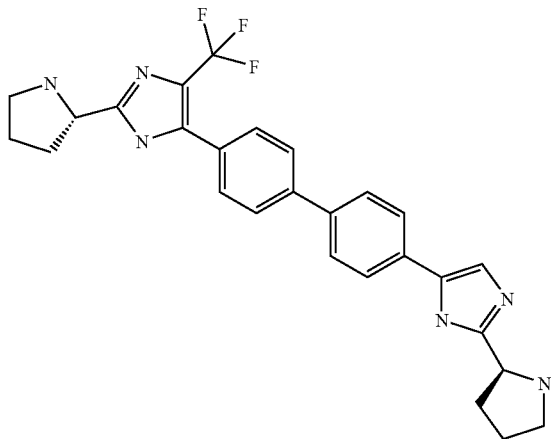 Prepared from entry J33 (in lieu of 152j-27) using experimental conditions outlined in Example 152k-1. | $t_R$ = 1.46 min, (92%) (Cond 2); LCMS: $C_{27}H_{28}F_3N_6O$ found: 493 $(M + H)^+$. |
| J35.a | | 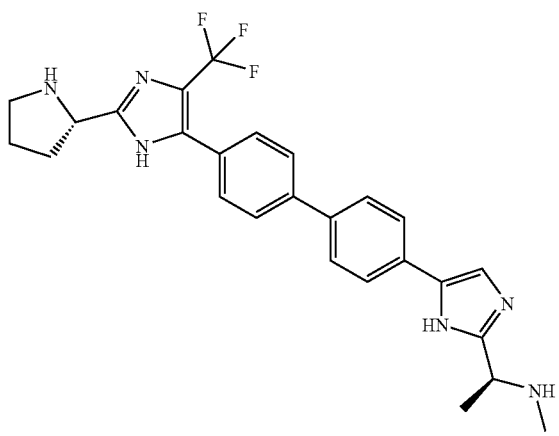 Prepared from entry J33.a (in lieu of 152j-27) using experimental conditions outlined in Example 152k-1. | LCMS: $C_{26}H_{28}F_3N_6$ found: 481 $(M + H)^+$. |

| Example Number | Compound Name | Structure | Analytical Data |
|---|---|---|---|
| J36 | | 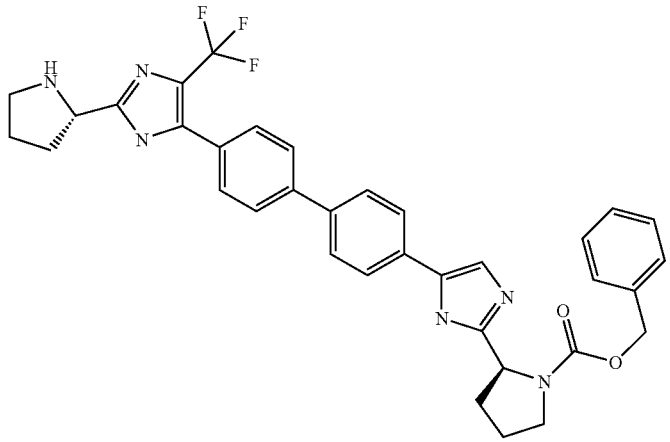 Prepared from entry J34 (in lieu of 152j-27) using experimental conditions outlined in Example 152k-1. | LCMS: $C_{35}H_{34}F_3N_6O_2$ found: 626 $(M + H)^+$. |
| J36.a | | 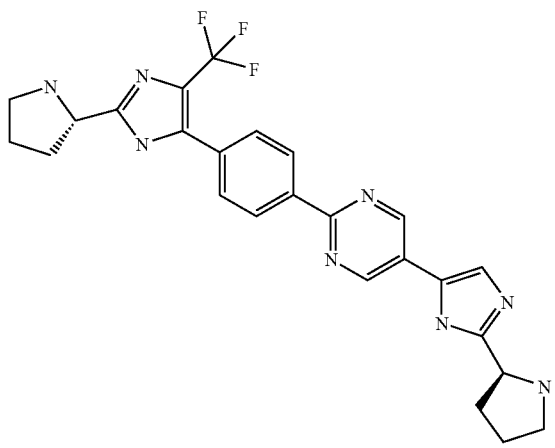 Prepared from entry J34.a (in lieu of 152j-27) using experimental conditions outlined in Example 152k-1. | $t_R$ = 1.45 min. (Cond 2); LCMS: $C_{25}H_{26}F_3N_8$ found: 495 $(M + H)^+$. |

| Example Number | Compound Name | Structure | Analytical Data |
|---|---|---|---|
| J37 | methyl ((1R)-2-((2S)-2-(5-(4'-(2-((2S)-1-((2R)-2-((methoxycarbonyl)amino)-2-phenylacetyl)-2-pyrrolidinyl)-1H-imidazol-5-yl)-4-biphenylyl)-4-(trifluoromethyl)-1H-imidazol-2-yl)-1-pyrrolidinyl)-2-oxo-1-phenylethyl)carbamate | 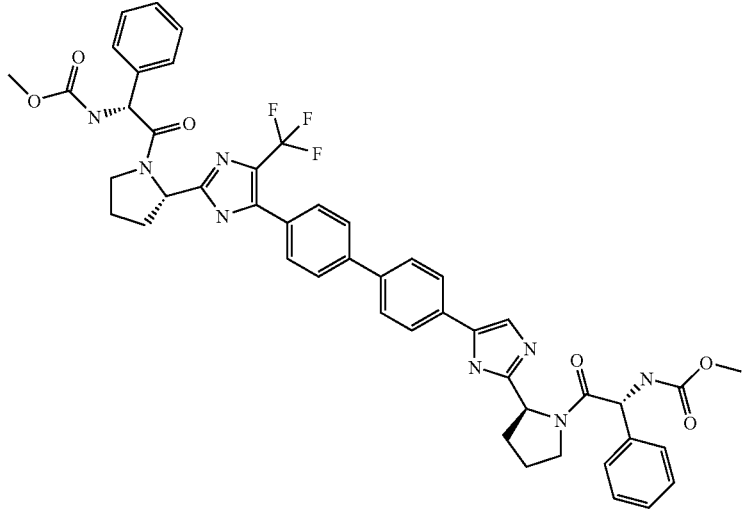 Prepared from entry J35 (in lieu of 148e) and Cap-4 using experimental conditions outlined in Example 148. | $t_R$ = 1.9 min, (95%) (Cond 2); LRMS: Anal. Calcd. for $C_{47}H_{46}F_3N_8O_4$ 875.35; found: 875.35 (M + H)$^+$. HRMS: Anal. Calcd. for $C_{47}H_{46}F_3N_8O_4$ 875.3492; found: 875.3504 (M + H)$^+$. |
| J38 | methyl ((1S)-2-((2S)-2-(5-(4'-(2-((2S)-1-(N-(methoxycarbonyl)-L-alanyl)-2-pyrrolidinyl)-4-(trifluoromethyl)-1H-imidazol-5-yl)-4-biphenylyl)-1H-imidazol-2-yl)-1-pyrrolidinyl)-1-methyl-2-oxoethyl)carbamate | 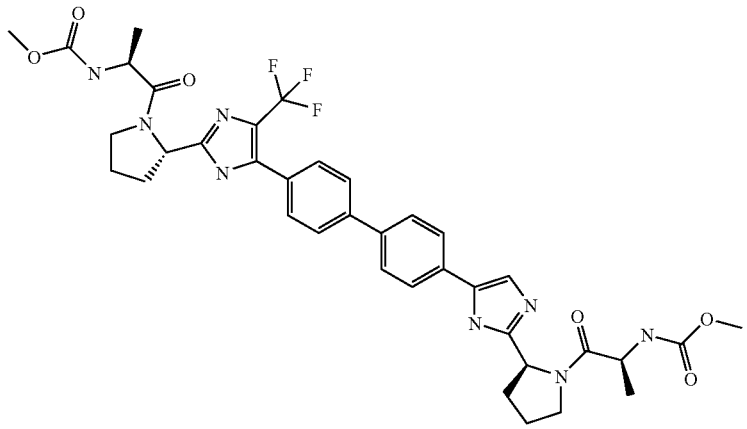 Prepared from entry J35 (in lieu of 148e) and Cap-52 using experimental conditions outlined in Example 148. | $t_R$ = 1.7 min, (95.5%) (Cond 2); LRMS: Anal. Calcd. for $C_{37}H_{42}F_3N_8O_6$ 751.32; found: 751.32 (M + H)$^+$. HRMS: Anal. Calcd. for $C_{37}H_{42}F_3N_8O_6$ 751.3179; found: 751.3163 (M + H)$^+$. |

| Example Number | Compound Name | Structure | Analytical Data |
| --- | --- | --- | --- |
| J39 | methyl ((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-4-(trifluoromethyl)-1H-imidaozl-2-yl)-1-pyrrolidinyl)carbonyl)-2-methylpropyl)carbamate | 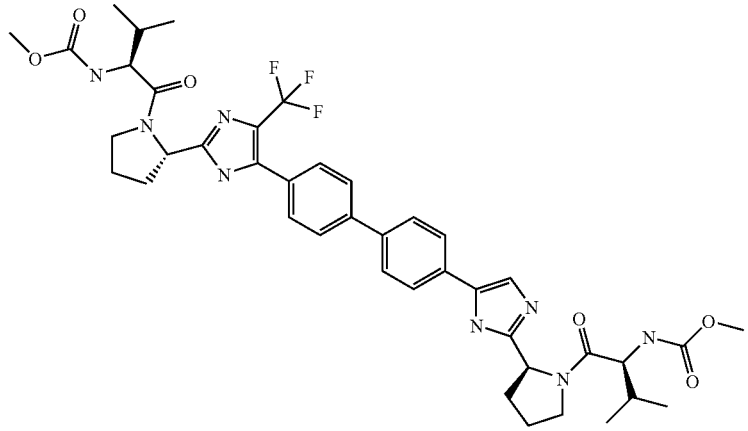<br>Prepared from entry J35 (in lieu of 148e) and Cap-51 using experimental conditions outlined in Example 148. | $t_R$ = 1.9 min, (96%) (Cond 2); LRMS: Anal. Calcd. for $C_{41}H_{50}F_3N_8O_6$ 807.38; found: 807.33 (M + H)$^+$. HRMS: Anal. Calcd. for $C_{41}H_{50}F_3N_8O_6$ 807.3805; found: 807.3773 (M + H)$^+$. |
| J40 | (1R)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-4-(trifluoromethyl)-1H-imidazol-2-yl)-1-pyrrolidinyl)-N,N-diethyl-2-oxo-1-phenylethanamine | 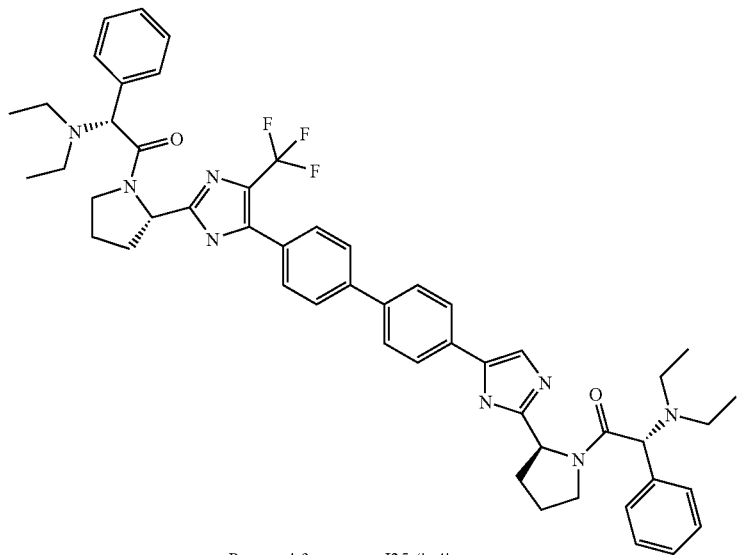<br>Prepared from entry J35 (in lieu of 148e) and Cap-2 using experimental conditions outlined in Example 148. | $t_R$ = 1.6 min, (95%) (Cond 2); LRMS: Anal. Calcd. for $C_{51}H_{58}F_3N_8O_2$ 871.46; found: 871.48 (M + H)$^+$. HRMS: Anal. Calcd. for $C_{51}H_{58}F_3N_8O_2$ 871.4635; found: 871.4647 (M + H)$^+$. |

| Example Number | Compound Name | Structure | Analytical Data |
|---|---|---|---|
| J41 | methyl ((1S)-1-cyclopropyl-2-((2S)-2-(5-(4'-(2-((2S)-1-((2S)-2-cyclopropyl-2-((methoxycarbonyl)amino)acetyl)-2-pyrrolidinyl)-1H-imidazol-5-yl)-4-biphenylyl)-4-(trifluoromethyl)-1H-imidazol-2-yl)-1-pyrrolidinyl)-2-oxoethyl)carbamate | Prepared from entry J35 (in lieu of 148e) and Cap-54b using experimental conditions outlined in Example 148. | $t_R$ = 1.8 min, (96.9%) (Cond 2); LRMS: Anal. Calcd. for $C_{41}H_{46}F_3N_8O_6$ 803.35; found: 803.35 (M + H)⁺. HRMS: Anal. Calcd. for $C_{41}H_{46}F_3N_8O_6$ 803.3492; found: 803.3507 (M + H)⁺. |
| J42 | methyl ((1S,2R)-2-methoxy-1-(((2S)-2-(5-(4'-(2-((2S)-1-(N-(methoxycarbonyl)-O-methyl-L-threonyl)-2-pyrrolidinyl)-4-(trifluoromethyl)-1H-imidazol-5-yl)-4-biphenylyl)-1H-imidazol-2-yl)-1-pyrrolidinyl)carbonyl)propyl)carbamate | Prepared from entry J35 (in lieu of 148e) and Cap-86 using experimental conditions outlined in Example 148. | $t_R$ = 1.8 min, (92%) (Cond 2); LRMS: Anal. Calcd. for $C_{41}H_{50}F_3N_8O_8$ 839.37; found: 839.30 (M + H)⁺. HRMS: Anal. Calcd. for $C_{41}H_{50}F_3N_8O_8$ 839.3704; found: 839.3677 (M + H)⁺. |

| Example Number | Compound Name | Structure | Analytical Data |
|---|---|---|---|
| J42.a | methyl ((1S)-2-((2S)-2-(5-(4'-(2-((1S)-1-((N-(methoxycarobnyl)-L-alanyl)(methyl)amino)ethyl)-1H-imidazol-5-yl)-4-biphenylyl)-4-(trifluoromethyl)-1H-imidazol-2-yl)-1-pyrrolidinyl)-1-methyl-2-oxoethyl)carbamate | 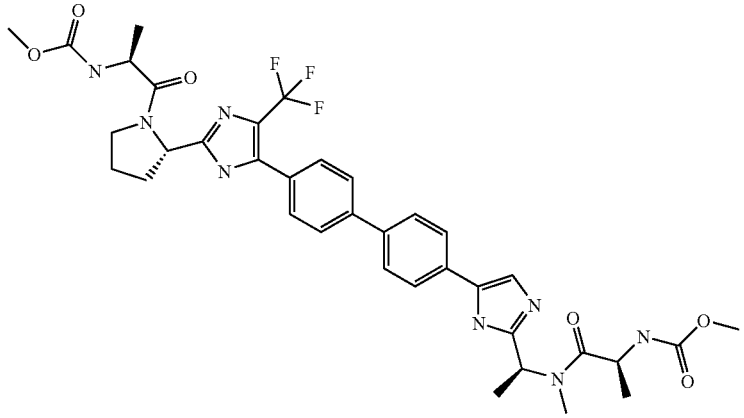<br>Prepared from entry J35.a (in lieu of 148e) and Cap-52 using experimental conditions outlined in Example 148. | $t_R$ = 1.69 min, (100%) (Cond 2); LRMS: Anal. Calcd. for $C_{36}H_{42}F_3N_8O_6$ 739.32; found: 739.31 $(M + H)^+$. HRMS: Anal. Calcd. for $C_{36}H_{42}F_3N_8O_6$ 739.3179; found: 739.3195 $(M + H)^+$. |
| J43 | benzyl (2S)-2-(5-(4'-(2-((2S)-1-(N-(methoxycarbonyl)-L-alanyl)-2-pyrrolidinyl)-4-(trifluoromethyl)-1H-imidazol-5-yl)-4-biphenylyl)-1H-imidazol-2-yl)-1-pyrrolidinecarboxylate | 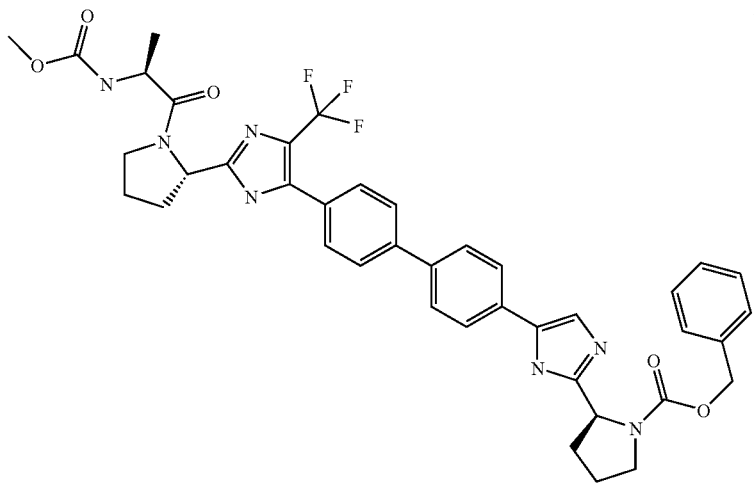<br>Prepared from entry J36 (in lieu of 148e) and Cap-52 using experimental conditions outlined in Example 148. | $t_R$ = 1.9 min, (95%) (Cond 2); LRMS: Anal. Calcd. for $C_{40}H_{41}F_3N_7O_5$ 756.31; found: 756.19 $(M + H)^+$. HRMS: Anal. Calcd. for $C_{40}H_{41}F_3N_7O_5$ 756.3121; found: 756.3127 $(M + H)^+$. |

| Example Number | Compound Name | Structure | Analytical Data |
|---|---|---|---|
| J44 | | 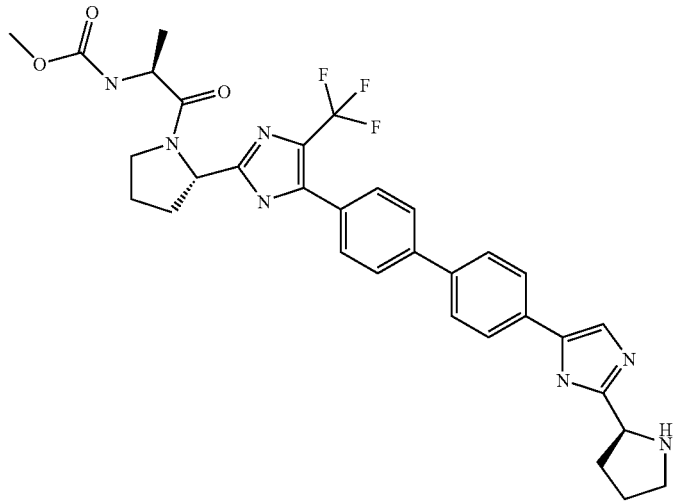 Prepared from entry J43 (in lieu of 152g-8) using experimental conditions outlined in Example 152i-1. | LCMS: $C_{32}H_{35}F_3N_7O_3$ found: 622 $(M + H)^+$. |
| J45 | methyl ((1S)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-4-(trifluoromethyl)-1H-imidazol-2-yl)-1-pyrrolidinyl)-1-methyl-2-oxoethyl)carbamate | 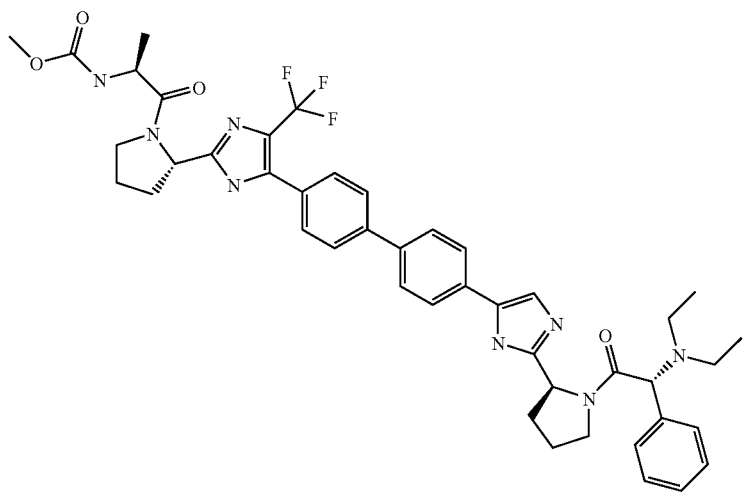 Prepared from entry J44 (in lieu of 148e) and Cap-2 using experimental conditions outlined in Example 148. | $t_R$ = 1.7 min, (93%) (Cond 2); LRMS: Anal. Calcd. for $C_{44}H_{50}F_3N_8O_4$ 811.39; found: 811.34 $(M + H)^+$. HRMS: Anal. Calcd. for $C_{44}H_{50}F_3N_8O_4$ 811.3907; found: 811.3913 $(M + H)^+$. |

| Example Number | Compound Name | Structure | Analytical Data |
|---|---|---|---|
| J46 | methyl ((1R)-2-((2S)-2-(5-(4-(5-(2-((2S)-1-((2R)-2-((methoxycarbonyl)amino)-2-phenylacetyl)-2-pyrrolidinyl)-1H-imidazol-5-yl)-2-pyrimidinyl)phenyl)-4-(trifluoromethyl)-1H-imidazol-2-yl)-1-pyrrolidinyl)-2-oxo-1-phenylethyl)carbamate | 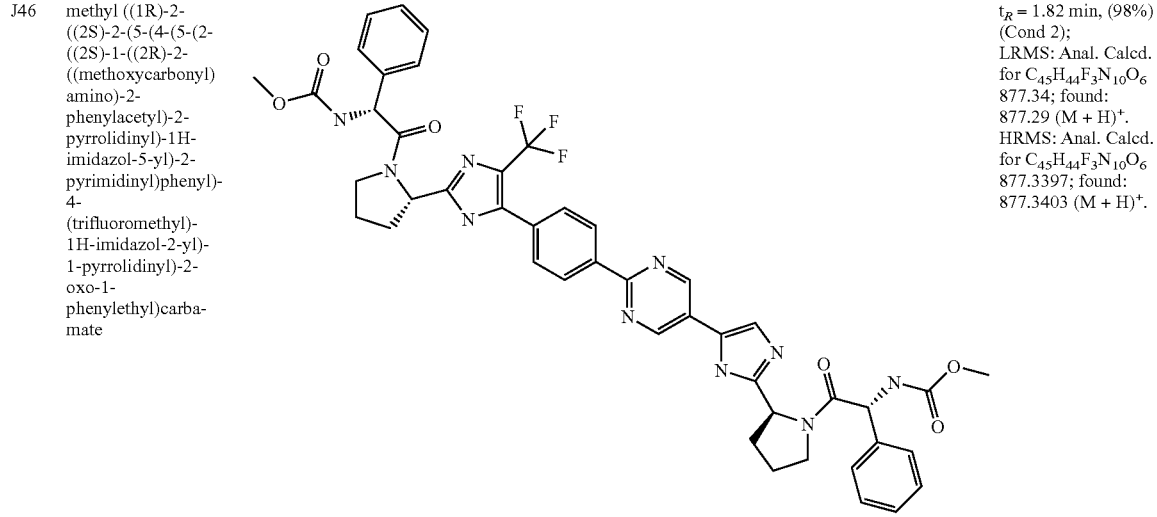<br>Prepared from entry J34.a (in lieu of 148e) and Cap-4 using experimental conditions outlined in Example 148 | $t_R$ = 1.82 min, (98%) (Cond 2);<br>LRMS: Anal. Calcd. for $C_{45}H_{44}F_3N_{10}O_6$ 877.34; found: 877.29 $(M + H)^+$.<br>HRMS: Anal. Calcd. for $C_{45}H_{44}F_3N_{10}O_6$ 877.3397; found: 877.3403 $(M + H)^+$. |
| J47 | (1R)-2-((2S)-2-(5-(4-(5-(2-((2S)-1-((2R)-2-(diethylamino)-2-phenylacetyl)-2-pyrrolidinyl)-1H-imidazol-5-yl)-2-pyrimidinyl)phenyl)-4-(trifluoromethyl)-1H-imidazol-2-yl)-1-pyrrolidinyl)-N,N-diethyl-2-oxo-1-phenylethanamine | 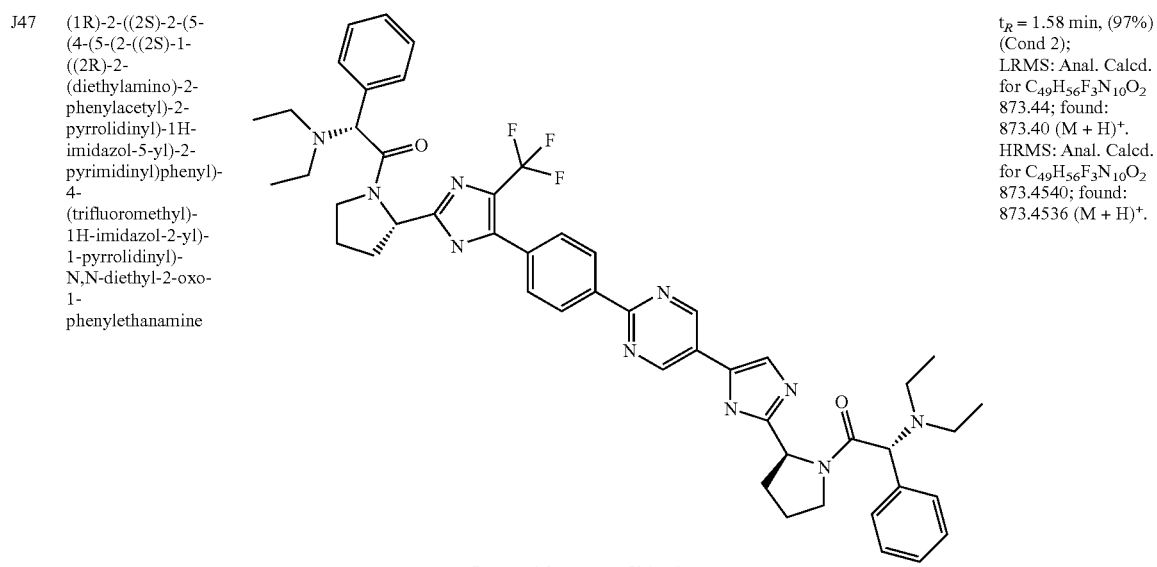<br>Prepared from entry J34.a (in lieu of 148e) and Cap-2 using experimental conditions outlined in Example 148 | $t_R$ = 1.58 min, (97%) (Cond 2);<br>LRMS: Anal. Calcd. for $C_{49}H_{56}F_3N_{10}O_2$ 873.44; found: 873.40 $(M + H)^+$.<br>HRMS: Anal. Calcd. for $C_{49}H_{56}F_3N_{10}O_2$ 873.4540; found: 873.4536 $(M + H)^+$. |

| Example Number | Compound Name | Structure | Analytical Data |
|---|---|---|---|
| J48 | methyl ((1S)-1-(((2S)-2-(5-(2-(4-(2-((2S)-1-((2S)-2-((methoxycarbonyl)amino)-3-methylbutanoyl)-2-pyrrolidinyl)-4-(trifluoromethyl)-1H-imidazol-5-yl)phenyl)-5-pyrimidinyl)-1H-imidazol-2-yl)-1-pyrrolidinyl)carbonyl)-2-methylpropyl)carbamate | 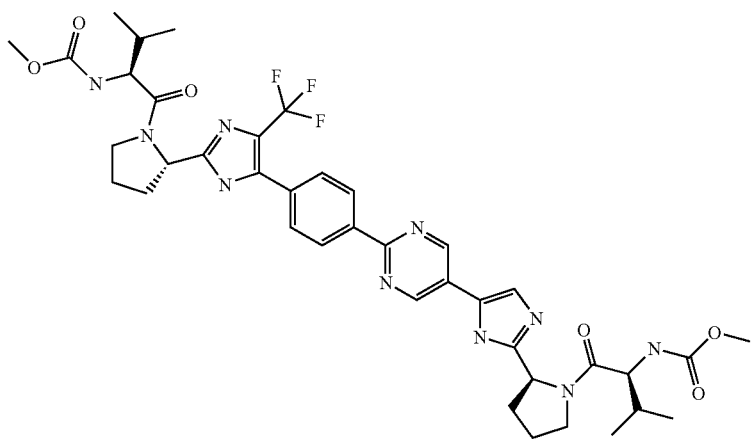<br>Prepared from entry J34.a (in lieu of 148e) and Cap-51 using experimental conditions outlined in Example 148 | $t_R$ = 1.85 min, (99%) (Cond 2); LRMS: Anal. Calcd. for $C_{39}H_{48}F_3N_{10}O_6$ 809.37; found: 809.37 (M + H)$^+$. HRMS: Anal. Calcd. for $C_{39}H_{48}F_3N_{10}O_6$ 809.3710; found: 809.3683 (M + H)$^+$. |
| J49 | methyl ((1S)-1-cyclopropyl-2-((2S)-2-(5-(4-(5-(2-((2S)-1-((2S)-2-cyclopropyl-2-((methoxycarbonyl)amino)acetyl)-2-pyrrolidinyl)-1H-imidazol-5-yl)-2-pyrimidinyl)phenyl)-4-(trifluoromethyl)-1H-imidazol-2-yl)-1-pyrrolidinyl)-2-oxoethyl)carbamate | 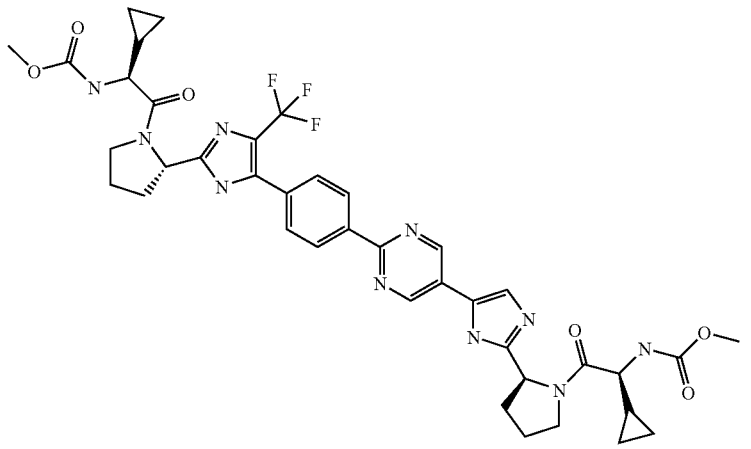<br>Prepared from entry J34.a (in lieu of 148e) and Cap-54b using experimental conditions outlined in Example 148 | $t_R$ = 1.75 min, (100%) (Cond 2); LRMS: Anal. Calcd. for $C_{39}H_{44}F_3N_{10}O_6$ 805.34; found: 805.34 (M + H)$^+$. HRMS: Anal. Calcd. for $C_{39}H_{44}F_3N_{10}O_6$ 805.3397; found: 805.3384 (M + H)$^+$. |

-continued

| Example Number | Compound Name | Structure | Analytical Data |
|---|---|---|---|
| J50 | methyl ((1S)-2-((2S)-2-(5-(4-(5-(2-((2S)-1-(N-(methoxycarbonyl)-L-alanyl)-2-pyrrolidinyl)-1H-imidazol-5-yl)-2-pyrimidinyl)phenyl)-4-(trifluoromethyl)-1H-imidazol-2-yl)-1-pyrrolidinyl)-1-methyl-2-oxoethyl)carbamate | Prepared from entry J34.a (in lieu of 148e) and Cap-52 using experimental conditions outlined in Example 148 | $t_R$ = 1.61 min, (94%) (Cond 2); LRMS: Anal. Calcd. for $C_{35}H_{40}F_3N_{10}O_6$ 753.31; found: 753.31 (M + H)$^+$. HRMS: Anal. Calcd. for $C_{35}H_{40}F_3N_{10}O_6$ 753.3084; found: 753.3099 (M + H)$^+$. |
| J51 | (2R)-1-((2S)-2-(5-(4-(5-(2-((2S)-1-((2R)-2-(diethylamino)propanoyl)-2-pyrrolidinyl)-1H-imidazol-5-yl)-2-pyrimidinyl)phenyl)-4-(trifluoromethyl)-1H-imidazol-2-yl)-1-pyrrolidinyl)-N,N-diethyl-1-oxo-2-propanamine | Prepared from entry J34.a (in lieu of 148e) and Cap-70b using experimental conditions outlined in Example 148 | $t_R$ = 1.41 min, (92%) (Cond 2); LRMS: Anal. Calcd. for $C_{39}H_{52}F_3N_{10}O_2$ 749.42; found: 749.37 (M + H)$^+$. HRMS: Anal. Calcd. for $C_{39}H_{52}F_3N_{10}O_2$ 749.4227; found: 749.4223 (M + H)$^+$. |

Cond 1: LCMS conditions: Phenomenex-Luna 4.6×50 mm S10 to 100% B over 3 min, 4 min stop time, 4 mL/min, 220 nm, A: 10% MeOH—90% H$_2$O—0.1% TFA; B: 90% MeOH—10% H$_2$O—0.1% TFA Cond 2: LCMS conditions: Phenomenex-Luna 4.6×50 mm S10, 0 to 100% B over 2 min, 3 min stop time, 4 mL/min, 220 nm, A: 10% MeOH—90% H$_2$O—0.1% TFA; B: 90% MeOH—10% H$_2$O—0.1% TFA Example J2

(2S)-2-(1-(4-bromophenyl)-3-ethoxy-1,3-dioxopropan-2-yl) 1-tert-butyl pyrrolidine-1,2-dicarboxylate

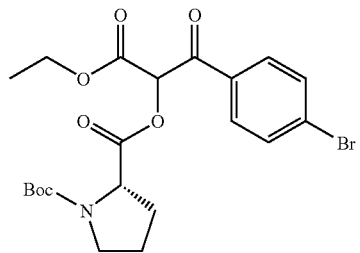

J2

The ethyl 3-(4-bromophenyl)-3-oxopropanoate (15 g, 55 mmol) was dissolved in CH$_2$Cl$_2$ (600 mL) and freshly recrystallized NBS (9.8 g, 55 mmol) was added and the solution stirred 18 hr. The reaction mixture was washed with NaHCO$_3$ solution, brine, and dried (MgSO$_4$), filtered, and concentrated to give a residue which was not purified. Ethyl 2-bromo-3-(4-bromophenyl)-3-oxopropanoate (16.5 g, 48 mmol) and N-Boc-L-proline (10 g, 48 mmol) were taken up in acetonitrile (450 mL) and Hunig's base (16 mL, 95 mmol) was added and the solution stirred 18 hr. The solvent was removed by rotary evaporation and the residue taken up in ethyl acetate, washed with 0.1 N HCl, and brine. $^1$H NMR (300 MHz, DMSO-d$_6$) δ 7.95 (d, J=8.4 Hz, 2H), 7.79 (d, J=8.4 Hz, 2H), 6.68-6.65 (m, 1H), 4.39-4.30 (m, 1H), 4.21-4.12 (m, 2H), 2.27-2.21 (m, 1H), 2.0-1.95 (m, 1H), 1.90-1.76 (m, 2H), 1.39 (s, 2H), 1.31 (s, 9H), 1.11 (t, J=7.3 Hz, 3H).

LRMS: Anal. Calcd. for C$_{21}$H$_{26}$BrNO$_7$ 484.09. found: 410.08 (M+H)$^+$.

Example J5

(S)-ethyl 5-(4-bromophenyl)-2-(1-(tert-butoxycarbonyl)pyrrolidin-2-yl)-1H-imidazole-4-carboxylate

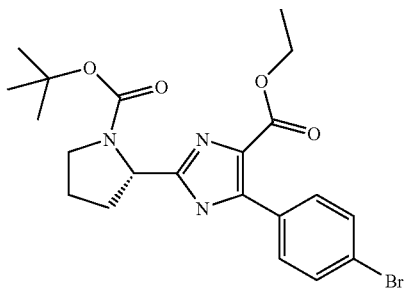

J5

A 1 L pressure bottle was charged with (2S)-2-(1-(4-bromophenyl)-3-ethoxy-1,3-dioxopropan-2-yl) 1-tert-butyl pyrrolidine-1,2-dicarboxylate J2 (7 g, 35 mmol) and 11 g of NH$_4$OAc in 125 mL of Xylene, and the reaction was heated at 140° C. for 3.5 hr. After being cooled, the solution was partition between ethyl acetate and water. The organic layer was concentrated and the resultant residue applied to a Biotage 40 m silica gel cartridge and eluted by 20-100% gradient, ethyl acetate/Hex to give 3 g (45%). $^1$H NMR (300 MHz, CDCl$_3$) δ 12.75 (br. s, 7.82), (br. s, 2H), 7.50 (d, J=8.4 Hz, 2H), 4.96-4.92 (m, 1H), 4.23 (q, J=6.6 Hz, 2H), 3.68-3.50 (m, 1H), 3.40-3.32 (m, 1H), 2.19-2.15 (m, 1H), 1.99-1.89 (m, 3H), 1.48/1.13 (s, 9H), 1.23 (t, J=7.3 Hz, 3H). LRMS: Anal. Calcd. for C$_{21}$H$_{26}$BrN$_3$O$_4$ 464.12. found: 464.15 and 466.15 (M+H)$^+$.

Example J7

(S)-tert-butyl 2-(5-(4-bromophenyl)-4-(methylcarbamoyl)-1H-imidazol-2-yl)pyrrolidine-1-carboxylate

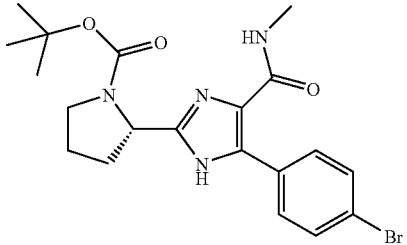

J7

(S)-ethyl 5-(4-bromophenyl)-2-(1-(tert-butoxycarbonyl)pyrrolidin-2-yl)-1H-imidazole-4-carboxylate (1 g, 2.1 mmol) was dissolved in 2M methylamine in MeOH (35 mL) and heated in a pressure vessel at 70° C. for 48 h. The reaction mixture was concentrated and the residue applied to a Biotage 25 m silica gel cartridge and eluted by 10-100% gradient, ethyl acetate/Hex to give 556 mg (57%). $^1$H NMR (300 MHz, DMSO-d$_6$) δ 12.5 (br.s, 1H), 7.86-7.82 (m, 1H), 7.77 (d, J=8.4 Hz, 2H), 7.61 (d, J=8.7 Hz, 2H), 4.83-4.70 (m, 1H), 3.69-3.52 (br.s, 1H), 3.42-3.32 (m, 1H), 2.71 (d, 4.8 Hz, 3H), 2.30-1.78 (m, 4H), 1.19-1.14 (m, 9H).

LRMS: Anal. Calcd. for C$_{20}$H$_{26}$BrN$_4$O$_3$ 449.12. found: 449.15 and 451.14 (M+H)$^+$.

Example J11.a

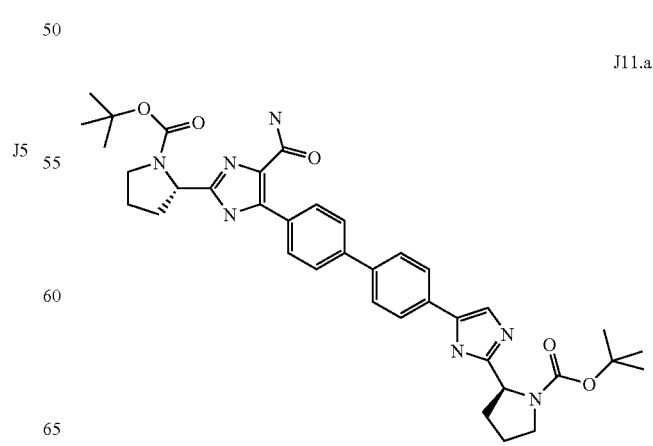

J11.a

Entry J9 (1.1 g, 1.58 mmol) was taken up in ethanol (60 mL), 28% concentrated ammonium hydroxide soln (10 mL) was added, and the reaction heated in a pressure vessel at 75° C. for 48 h. The solvent was removed by rotary evaporation and the residue taken up in ethyl acetate and washed with water, brine. Concentration and application to a 25 M Biotage cartridge, gradient elution with 10%-100% ethyl acetate/$CH_2Cl_2$, gave J11.a 90 mg (8.5%) and recovered starting material J9 696 mg (63%).

Example J32.a (S)-tert-butyl 2-(5-(4-bromophenyl)-4-(trifluoromethyl)-1H-imidazol-2-yl)pyrrolidine-1-carboxylate

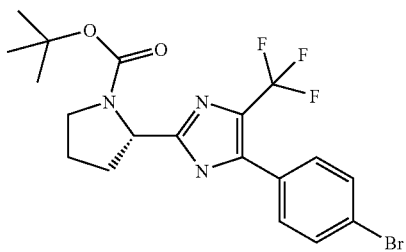

J32.a 3-(4-bromophenyl)-3-(2,2-dimethylhydrazono)-1,1,1-trifluoropropan-2-one (2.0 g, 6.2 mmol) was suspended in 5N sulfuric acid (60 mL) and heated at 45° C. for 6 h. The temperature was raised to 85° C. for 2 h, and upon cooling a precipitate formed. This material which was isolated by filtration to give 1-(4-bromophenyl)-3,3,3-trifluoropropane-1,2-dione 1.6 g (92%) as a yellow solid. The dione (1.6 g, 5.7 mmol) was taken up in methanol (30 mL), N-(tert-butoxycarbonyl)-L-prolinal (1 g, 5.0 mmol) was added, followed by addition of 28% ammonium hydroxide solution (10 mL). The reaction was stirred at room temperature for 18 h, poured onto dichloromethane (200 mL), washed with water and dried with $MgSO_4$. Filtration, concentration and application to a 40 M Biotage cartridge, gradient elution with 5%-30% ethyl acetate/Hexanes, gave J32.a 1.3 g (50%). $^1$H NMR (300 MHz, DMSO-$d_6$) δ 12.88 (br.s, 1H), 7.72 (d, J=8.4 Hz, 2H), 7.39 (d, J=8.0 Hz, 2H), 4.84-4.70 (m, 1H), 3.57-3.49 (m, 1H), 3.39-3.29 (m, 1H), 2.31-2.20 (m, 1H), 1.98-1.78 (m, 3H), 1.39/1.13 (m, 9H). LRMS: Anal. Calcd. for $C_{19}H_{20}BrF_3N_3O_2$ 458.07. found: 458.06 and 460.06 (M−H)$^-$. HRMS: Anal. Calcd. for $C_{19}H_{22}BrF_3N_3O_2$ 460.0847. found: 460.0866 and 462.0840 (M+H)$^+$.

Section D

| Entry | Compound Name | Structure | **Data |
|---|---|---|---|
| D1 | | 1-(4-bromo-2-fluorophenyl) structure with Br, F, and COCH₂Br groups. Prepared from 1-(4-bromo-2-fluorophenyl)ethanone (Vendor: Marshalton 50043) using bromination conditions outlined in D5. | $t_R$ = 2.65 min, (86.7%) LCMS: Anal. Calcd. for $C_8H_5BrFO$ 296.88; found: 296.91 $(M + H)^+$. |
| D2 | | 1-(4-chloro-2,5-difluorophenyl) structure with Cl, F, F, and COCH₂Br groups. Prepared from 1-(4-chloro-2,5-difluorophenyl)ethanone (Vendor: Oakwood products, 001626) using bromination conditions outlined in D5. | $t_R$ = 2.66 min, (80%) LCMS: Anal. Calcd. for $C_8H_4BrClFO$ 270.92; found: ND $(M + H)^+$. |
| D3 | | 2-bromo-1-(5-bromo-2-methoxyphenyl) structure with Br, OMe, and COCH₂Br groups. Prepared from 2-bromo-1-(5-bromo-2-methoxyphenyl)ethanone (Andersh et al., Synth. Comm. 2000, 30 (12), 2091-98) using bromination conditions outlined in D5. | $t_R$ = 2.57 min, (95%) LCMS: Anal. Calcd. for $C_9H_8BrO_2$ 228.99; found: 229.00 $(M + H)^+$. |

-continued

Section D

| Entry | Compound Name | Structure | **Data |
|---|---|---|---|
| D4 | Prepared from entry D1 and CBz-L-proline (in lieu of Boc-L-proline) using experimental conditions outlined in D5. | 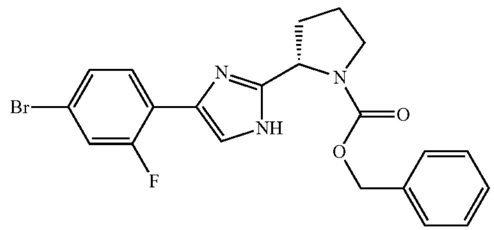 | $t_R$ = 2.38 min, (95.0%) LRMS: Anal. Calcd. for $C_{19}H_{20}{}^{79}BrFN_3O_2$ 444.07; found: 444.04 $(M + H)^+$. HRMS: Anal. Calcd. for $C_{19}H_{20}{}^{79}BrFN_3O_2$ 444.0721; found: 444.0736 $(M + H)^+$ |
| D5 | Experimental conditions in D5 | 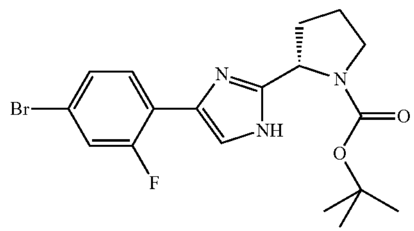 | $t_R$ = 2.27 min, (95%) LRMS: Anal. Calcd. for $C_{18}H_{22}{}^{79}BrFN_3O_2$ 410.09 and 412.08; found: 410.08 and 412.08 $(M + H)^+$. HRMS: Anal. Calcd. for $C_{18}H_{22}{}^{79}BrFN_3O_2$ 410.0879; found: 410.0893 $(M + H)^+$. |
| D6 | Prepared from entry D3 (in lieu of entry D1) using experimental conditions outlined in D5. | 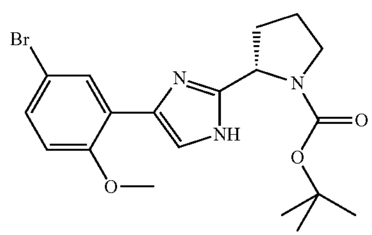 | $t_R$ = 2.26 min, (95%) LRMS: Anal. Calcd. for $C_{19}H_{25}{}^{79}BrN_3O_3$ 422.11 and 424.11; found: 422.10 and 424.10 $(M + H)^+$. HRMS: Anal. Calcd. for $C_{19}H_{25}{}^{79}BrN_3O_3$ 422.1079; found: 422.1089 $(M + H)^+$. |

-continued

Section D

| Entry | Compound Name | Structure | **Data |
|---|---|---|---|
| D7 | | Prepared from entry D2 (in lieu of entry D1) using experimental conditions outlined in enclosed experiment. | $t_R$ = 2.28 min, (95%) LRMS: Anal. Calcd. for $C_{18}H_{21}ClF_2N_3O_2$ 384.13; found: 384.13 $(M+H)^+$. HRMS: Anal. Calcd. for $C_{18}H_{21}ClF_2N_3O_2$ 384.1290; found: 384.1301 $(M+H)^+$. |
| D8 | | Prepared from entry D5 (in lieu of 1b) using experimental conditions outlined in Example 1, Step c. | $t_R$ = 2.62 min (~50%) and 1.95 min (~50%, boronic acid) LRMS: Anal. Calcd. for $C_{24}H_{34}BFN_3O_4$ 458.26; found: 458.23 $(M+H)^+$. HRMS: Anal. Calcd. for $C_{24}H_{34}BFN_3O_4$ 458.2626; found: 458.2610 $(M+H)^+$. |

-continued

Section D

| Entry | Compound Name | Structure | **Data |
|---|---|---|---|
| D9 | tert-butyl (2S)-2-(4-(4'-(2-((2S)-1-(tert-butoxycarbonyl)-2-pyrrolidinyl)-1H-imidazol-5-yl)-4-methoxy-3-biphenylyl)-1H-imidazol-2-yl)-1-pyrrolidine-carboxylate | Prepared from entry D6 (in lieu of 152e-1) and 1c using experimental conditions outlined in Example 152g-1. | $t_R$ = 2.28 min, (95%) LRMS: Anal. Calcd. for $C_{37}H_{47}N_6O_5$ 655.36; found: 655.37 (M + H)⁺. HRMS: Anal. Calcd. for $C_{37}H_{47}N_6O_5$ 655.3608; found: 655.3627 (M + H)⁺. |
| D10 | di-tert-butyl (2S,2'S)-2,2'-(3-fluoro-4,4'-biphenyl-diyl)bis(1H-imidazole-4,2-diyl)di(1-pyrrolidinecarboxylate) | Prepared from entry D5 (in lieu of 152e-1) and 1c using experimental conditions outlined in Example 152g-1. | $t_R$ = 2.21 min, (99.2%) LCMS: Anal. Calcd. for $C_{36}H_{44}FN_6O_4$ 643.34; found: 643.51 (M + H)⁺. HRMS: Anal. Calcd. for $C_{36}H_{44}FN_6O_4$ 643.3403; found: 643.3390 (M + H)⁺. |

-continued

Section D

| Entry | Compound Name | Structure | **Data |
|---|---|---|---|
| D11 | tert-butyl (2S)-2-(4-(4'-(2-((2S)-1-(tert-butoxycarbonyl)-2-pyrrolidinyl)-1H-imidazol-5-yl)-2,5-difluoro-4-biphenylyl)-1H-imidazol-2-yl)-1-pyrrolidinecarboxylate | 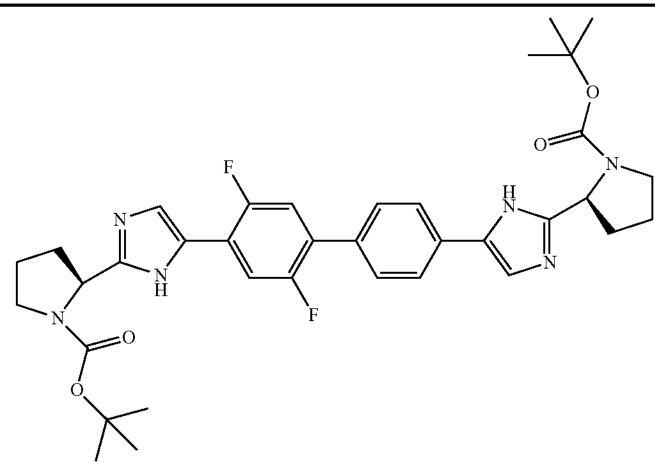 | $t_R$ = 2.24 min, (95%) LRMS: Anal. Calcd. for $C_{36}H_{43}F_2N_6O_4$ 661.33; found: 661.35 (M + H)+. HRMS: Anal. Calcd. for $C_{36}H_{43}F_2N_6O_4$ 661.3314; found: 661.3336 (M + H)+. |

Prepared from entry D7 (in lieu of 152e-1) and 1c using experimental conditions outlined in Example 152g-1.

| Entry | Compound Name | Structure | **Data |
|---|---|---|---|
| D12 | di-tert-butyl (2S,2'S)-2,2'-((3,3'-difluoro-4,4'-biphenyldiyl)bis(1H-imidazole-5,2-diyl))di(1-pyrrolidinecarboxylate) | 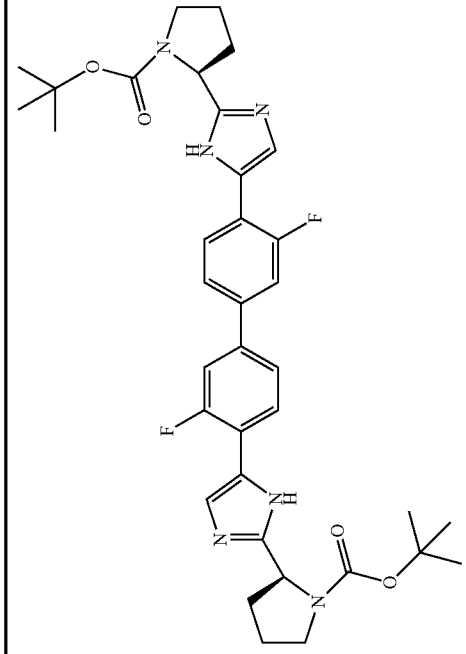 | $t_R$ = 2.20 min, (95%) LRMS: Anal. Calcd. for $C_{36}H_{43}F_2N_6O_4$ 661.33; found: 661.22 (M + H)+. HRMS: Anal. Calcd. for $C_{36}H_{43}F_2N_6O_4$ 661.3314; found: 661.3307 (M + H)+. |
Prepared from entry D5 (in lieu of 152e-1) using experimental conditions outlined in Example 153a-1.

-continued

Section D

| Entry | Compound Name | Structure | **Data |
|---|---|---|---|
| D13 | tert-butyl (2S)-2-(5-(2-(4-(2-((2S)-1-(tert-butoxycarbonyl)-2-pyrrolidinyl)-1H-imidazol-4-yl)-3-fluorophenyl)-5-pyrimidinyl)-1H-imidazol-2-yl)-1-pyrrolidinecarboxylate | 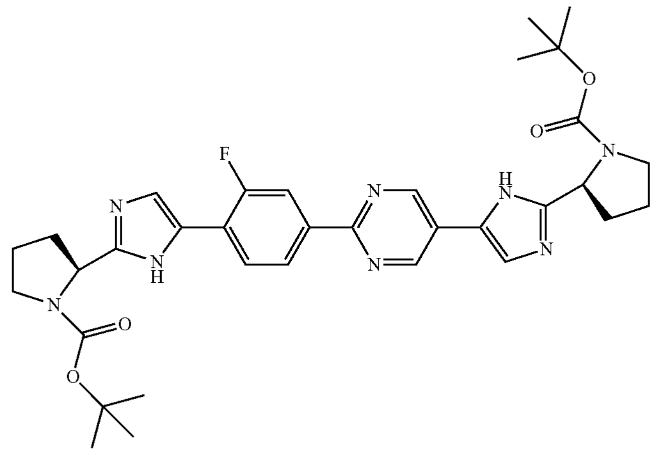 | $t_R$ = 2.27 min, (95%) LRMS: Anal. Calcd. for $C_{34}H_{42}FN_8O_4$ 645.33; found: 645.34 (M + H)$^+$. HRMS: Anal. Calcd. for $C_{34}H_{42}FN_8O_4$ 645.3313; found: 645.3323 (M + H)$^+$. |

Prepared from entry D8 (in lieu of 1c) and 152b-1 using experimental conditions outlined in Example 152g-1.

-continued

Section D

| Entry | Compound Name | Structure | **Data |
|---|---|---|---|
| D14 | tert-butyl (2S)-2-(4-(4'-(2-((2S)-1-((benzyloxy)carbonyl)-2-pyrrolidinyl)-1H-imidazol-5-yl)-3-fluoro-4-biphenylyl)-1H-imidazol-2-yl)-1-pyrrolidinecarboxylate | 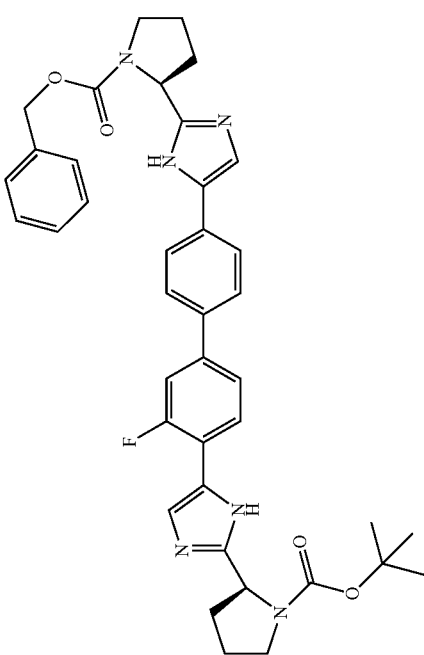 | $t_R$ = 2.26 min, (95%) LRMS: Anal. Calcd. for $C_{39}H_{42}FN_6O_4$ 677.33; found: 677.33 $(M+H)^+$. HRMS: Anal. Calcd. for $C_{39}H_{42}FN_6O_4$ 677.3252; found: 677.3278 $(M+H)^+$. |

Prepared from entry D5 (in lieu of 152e-1) and 1-5c using experimental conditions outlined in Example 152g-1.

| Entry | Compound Name | Structure | **Data |
|---|---|---|---|
| D15 | tert-butyl (2S)-2-(4-(4'-(2-((2S)-1-((benzyloxy)carbonyl)-2-pyrrolidinyl)-1H-imidazol-5-yl)-3,3'-difluoro-4-biphenylyl)-1H-imidazol-2-yl)-1-pyrrolidinecarboxylate | 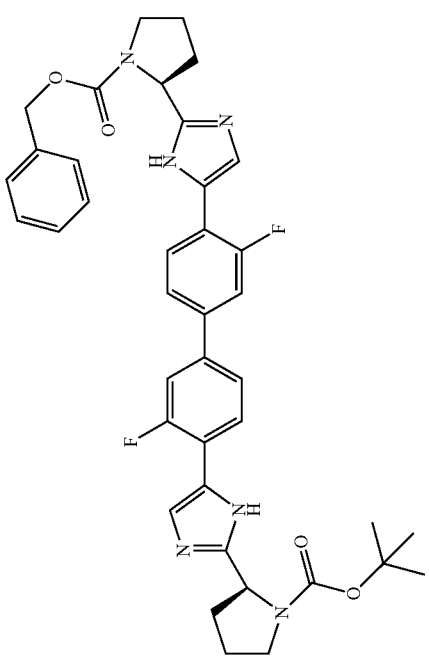 | $t_R$ = 2.36 min, (97.3%) LRMS: Anal. Calcd. for $C_{39}H_{41}F_2N_6O_4$ 695.32; found: 695.33 $(M + H)^+$. HRMS: Anal. Calcd. for $C_{39}H_{41}F_2N_6O_4$ 695.3157; found: 695.3151 $(M + H)^+$. |
Prepared from entry D8 (in lieu of 1c) and entry D4 using experimental conditions outlined in Example 152g-1.

| Entry | Compound Name | Structure | **Data |
|---|---|---|---|
| D16 | tert-butyl (2S)-2-(5-(3-fluoro-4'-(2-((2S)-1-((2R)-2-((methoxycarbonyl)amino)-2-phenylacetyl)pyrrolidinyl)-1H-imidaozl-5-yl)-4-biphenylyl)-1H-imidazol-2-yl)-1-pyrrolidinecarboxylate | 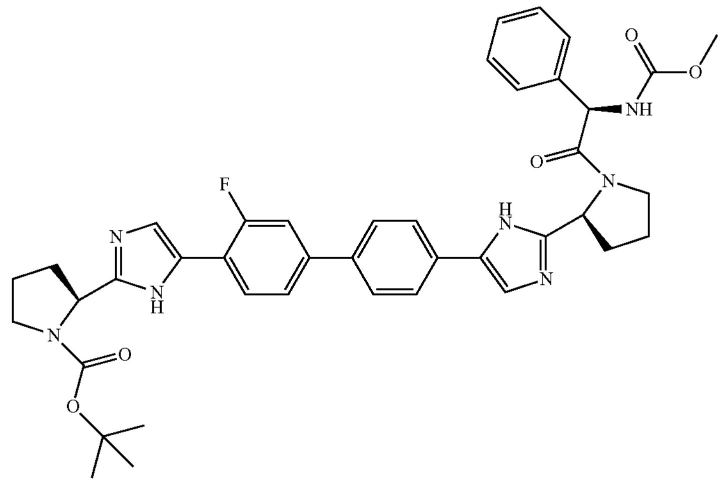 | $t_R$ = 2.16 min, (91.0%) LRMS: Anal. Calcd. for $C_{41}H_{45}FN_7O_5$ 734.35; found: 734.36 $(M + H)^+$. HRMS: Anal. Calcd. for $C_{41}H_{45}FN_7O_5$ 734.3466; found: 734.3474 $(M + H)^+$. |

Prepared from entry D21 (in lieu of 148e) and Cap-4 using experimental conditions outlined in Example 148.

| Entry | Section D Compound Name | Structure | **Data |
|---|---|---|---|
| D17 | tert-butyl (2S)-2-(5-(4'-(2-((2S)-1-((2R)-2-(diethylamino)-2-phenylacetyl)-2-pyrrolidinyl)-1H-imidazol-5-yl)-3-fluoro-4-biphenylyl)-1H-imidazol-2-yl)-1-pyrrolidinecarboxylate | 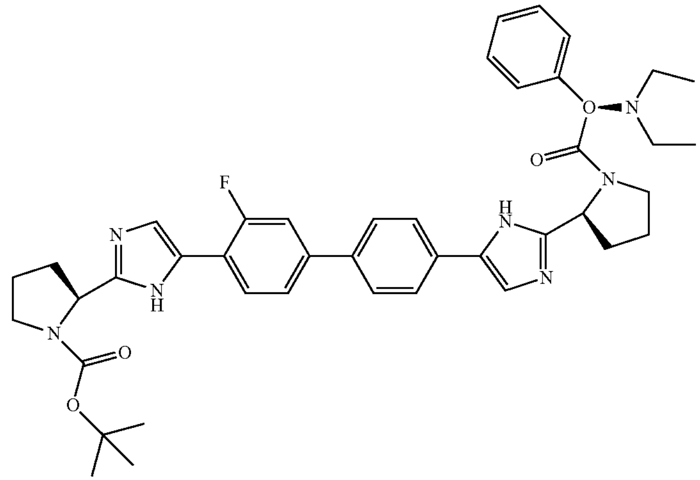 | $t_R$ = 1.95 min, (95%) LRMS: Anal. Calcd. for $C_{43}H_{51}FN_7O_3$ 732.40; found: 732.44 $(M + H)^+$. HRMS: Anal. Calcd. for $C_{43}H_{51}FN_7O_3$ 732.4037; found: 732.4065 $(M + H)^+$. |

Prepared from entry D21 (in lieu of 148e) and Cap-2 using experimental conditions outlined in Example 148.

-continued

Section D

| Entry | Compound Name | Structure | **Data |
|---|---|---|---|
| D18 | tert-butyl (2S)-2-(5-(3-fluoro-4'-(2'-((2S)-1-(N-(methoxycarbonyl)-L-valyl)-2-pyrrolidinyl)-1H-imidazol-5-yl)-4-biphenylyl)-1H-imidazol-2-yl)-1-pyrrolidinecarboxylate | 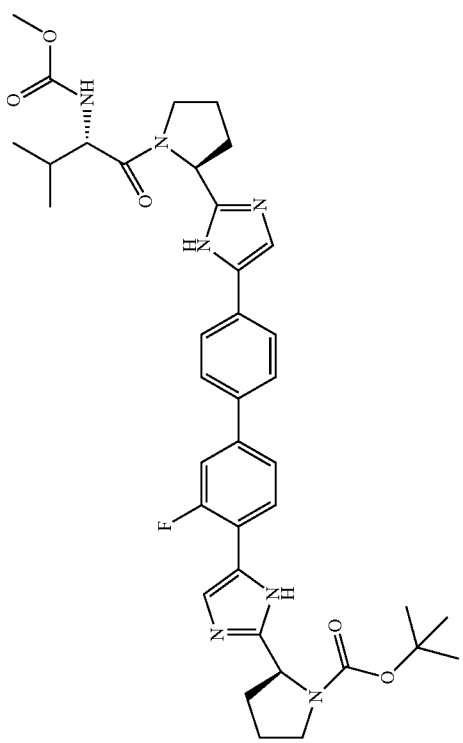 | $t_R$ = 2.14 min, (95%) LRMS: Anal. Calcd. for $C_{38}H_{47}FN_7O_5$ 700.36; found: 700.37 (M + H)$^+$. HRMS: Anal. Calcd. for $C_{38}H_{47}FN_7O_5$ 700.3623; found: 700.3596 (M + H)$^+$. |

Prepared from entry D21 (in lieu of 148e) and Cap-51 using experimental conditions outlined in Example 148.

| Entry | Compound Name | Structure | **Data |
|---|---|---|---|
| D19 | tert-butyl (2S)-2-(5-(3,3'-difluoro-4'-(2-((2S)-1-((2R)-2-(((methoxycarbonyl)-amino)-2-phenylacetyl)-2-pyrrolidinyl)-1H-imidazol-5-yl)-4-biphenylyl)-1H-imidaozl-2-yl)-1-pyrrolidinecarboxylate | 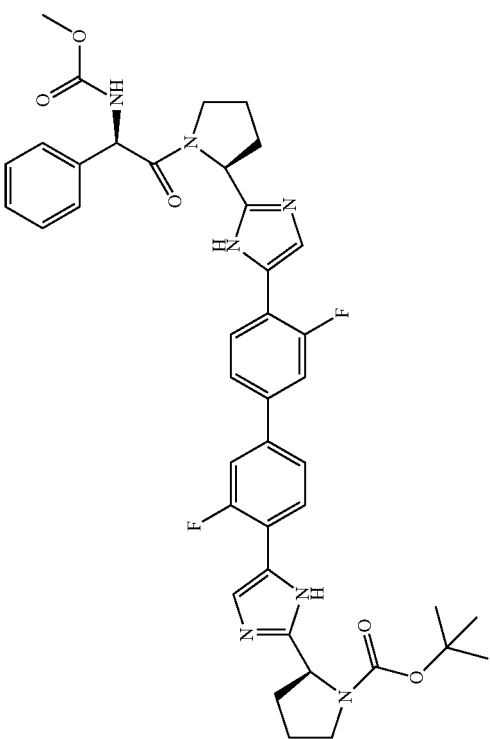 | $t_R$ = 2.23 min, (95%) LRMS: Anal. Calcd. for $C_{41}H_{44}F_2N_7O_5$ 752.34; found: 752.35 (M + H)+. HRMS: Anal. Calcd. for $C_{41}H_{44}F_2N_7O_5$ 752.3372; found: 752.3385 (M + H)+. |

Prepared from entry D22 (in lieu of 148e) and Cap-4 using experimental conditions outlined in Example 148.

-continued

Section D

| Entry | Compound Name | Structure | **Data |
|---|---|---|---|
| D20 | tert-butyl (2S)-2-(5-(3,3'-difluoro-4'-(2-((2S)-1-(N-(methoxycarbonyl)-L-valyl)-2-pyrrolidinyl)-1H-imidazol-5-yl)-4-biphenylyl)-1H-imidazol-2-yl)-1-pyrrolidinecarboxylate | 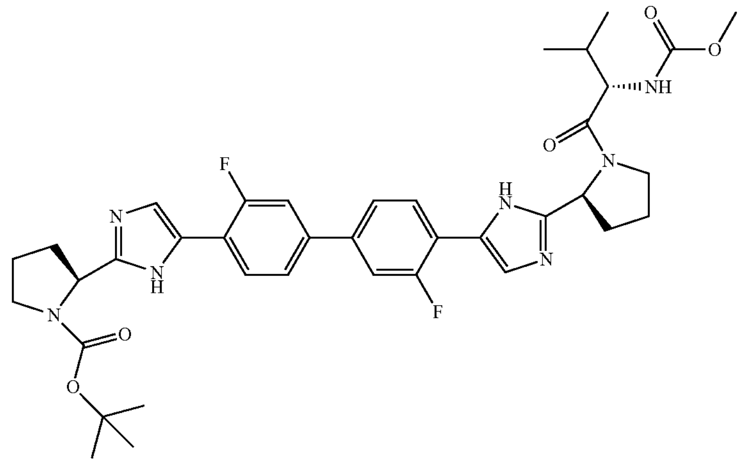 | $t_R$ = 2.16 min, (90%) LRMS: Anal. Calcd. for $C_{38}H_{46}F_2N_7O_5$ 718.35; found: 718.36 (M + H)$^+$. HRMS: Anal. Calcd. for $C_{38}H_{46}F_2N_7O_5$ 718.3528; found: 718.3505 (M + H)$^+$. |
| | | Prepared from entry D22 (in lieu of 148e) and Cap-51 using experimental conditions outlined in Example 148. | |
| D21 | tert-butyl (2S)-2-(5-(3-fluoro-4'-(2-((2S)-2-pyrrolidinyl)-1H-imidazol-5-yl)-4-biphenylyl)-1H-imidazol-2-yl)-1-pyrrolidinecarboxylate triacetate | 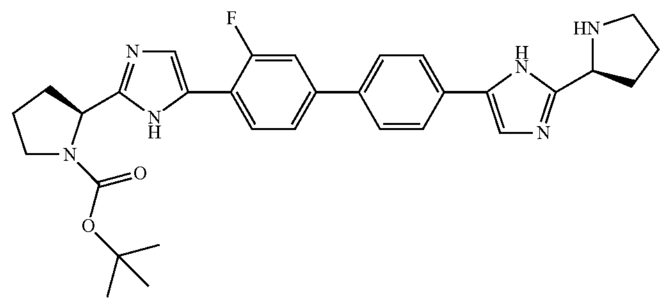 | $t_R$ = 1.94 min, (95%) LRMS: Anal. Calcd. for $C_{31}N_{36}FN_6O_2$ 543.29; found: 543.30. HRMS: Anal. Calcd. for $C_{31}H_{36}FN_6O_2$ 543.2884; found: 543.2872 (M + H)$^+$. |
| | | Prepared from entry D14 (in lieu of 152g-8) using experimental conditions outlined in Example 152i-1. | |

| Entry | Compound Name | Structure | **Data |
|---|---|---|---|
| D22 | tert-butyl (2S)-2-(5-(3,3'-difluoro-4'-(2-((2S)-2-pyrrolidinyl)-1H-imidazol-5-yl)-4-biphenylyl)-1H-imidazol-2-yl)-1-pyrrolidinecarboxylate | Prepared from entry D15 (in lieu of 152g-8) using experimental conditions outlined in Example 152i-1. | $t_R$ = 2.14 min, (95%) LRMS: Anal. Calcd. for $C_{31}H_{35}F_2N_6O_2$ 561.28; found: 561.29 (M + H)⁺. HRMS: Anal. Calcd. for $C_{31}H_{35}F_2N_6O_2$ 561.2790; found: 561.2766 (M + H)⁺. |
| D23 | methyl ((1R)-2-((2S)-2-(5-(3'-fluoro-4'-(2-((2S)-2-pyrrolidinyl)-1H-imidazol-5-yl)-4-biphenylyl)-1H-imidazol-2-yl)-1-pyrrolidinyl)-2-oxo-1-phenylethyl)carbamate | Prepared from entry D16 (in lieu of 152j-27) using experimental conditions outlined in Example 152k-1. | $t_R$ = 1.90 min, (94%) LRMS: Anal. Calcd. for $C_{36}H_{37}FN_7O_3$ 634.29; found: 634.29 (M + H)⁺. HRMS: Anal. Calcd. for $C_{36}H_{37}FN_7O_3$ 634.2942; found: 634.2948 (M + H)⁺. |

-continued

Section D

| Entry | Compound Name | Structure | **Data |
|---|---|---|---|
| D24 | methyl ((1S)-1-(((2S)-2-(5-(3'-fluoro-4'-(2-((2S)-2-pyrrolidinyl)-1H-imidazol-5-yl)-4-biphenylyl)-1H-imidazol-2-yl)-1-pyrrolidinyl)carbonyl)-2-methylpropyl)carbamate | 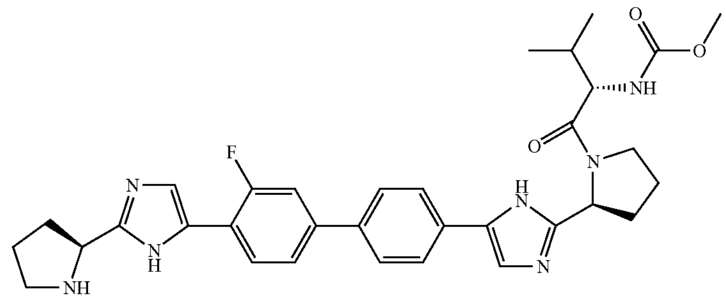 | $t_R$ = 1.89 min, (95%) LRMS: Anal. Calcd. for for $C_{33}H_{39}FN_7O_3$ 600.31; found: 600.32 (M + H)⁺. HRMS: Anal. Calcd. for $C_{33}H_{39}FN_7O_3$ 600.3098; found: 600.3121 (M + H)⁺. |
| | | Prepared from entry D18 (in lieu of [152j]-27) using experimental conditions outlined in Example 152k-l. | |
| D25 | (1R)-N,N-diethyl-2-((2S)-2-(5-(3'-fluoro-4'-(2-((2S)-2-pyrrolidinyl)-1H-imidazol-5-yl)-4-biphenylyl)-1H-imidazol-2-yl)-1-pyrrolidinyl)-2-oxo-1-phenylethanamine | 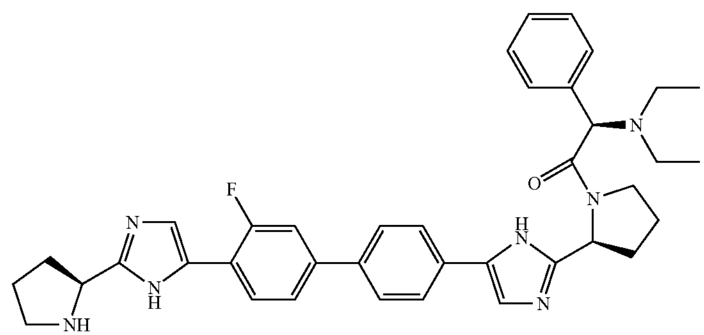 | $t_R$ = 1.72 min, (90%) LRMS: Anal. Calcd. for $C_{38}H_{43}FN_7O$ 632.35; found: 632.36 (M + H)⁺. HRMS: Anal. Calcd. for $C_{38}H_{43}FN_7O$ 632.3513; found: 632.3527 (M + H)⁺. |
| | | Prepared from entry D17 (in lieu of [152j]-27) using experimental conditions outlined in Example 152k-l. | |

| Entry | Compound Name | Structure | **Data |
|---|---|---|---|
| D26 | methyl ((1S)-1-(((2S)-2-(5-(3,3'-difluoro-4'-(2-((2S)-2-pyrrolidinyl)-1H-imidazol-5-yl)-4-biphenylyl)-1H-imidazol-2-yl)-1-pyrrolidinyl)carbonyl)-2-methylpropyl)carbamate | Prepared from entry D20 (in lieu of 152j-27) using experimental conditions outlined in Example 152k-1. | $t_R$ = 1.96 min, (95%) LRMS: Anal. Calcd. for $C_{33}H_{38}F_2N_7O_3$ 618.30; found: 618.31 (M + H)$^+$. HRMS: Anal. Calcd. for $C_{33}H_{38}F_2N_7O_3$ 618.3004; found: 618.3024 (M + H)$^+$. |
| D27 | methyl ((1R)-2-((2S)-2-(5-(3,3'-difluoro-4'-(2-((2S)-2-pyrrolidinyl)-1H-imidazol-5-yl)-4-biphenylyl)-1H-imidazol-2-yl)-1-pyrrolidinyl)-2-oxo-1-phenylethyl)carbamate | Prepared from entry D19 (in lieu of 152j-27) using experimental conditions outlined in Example 152k-1. | $t_R$ = 1.63 min, (95%) LRMS: Anal. Calcd. for $C_{36}H_{36}F_2N_7O_3$ 652.28; found: 652.29 (M + H)$^+$. HRMS: Anal. Calcd. for $C_{36}H_{36}F_2N_7O_3$ 652.2848; found: 652.2858 (M + H)$^+$. |

-continued

Section D

| Entry | Compound Name | Structure | **Data |
|---|---|---|---|
| D28 | 5,5'-(4-methoxy-3,4'-biphenyldiyl)bis(2-((2S)-2-pyrrolidinyl)-1H-imidazole) | Prepared from entry D9 (in lieu of 152j-27) using experimental conditions outlined in Example 152k-1 | $t_R$ = 1.53 min, (98.2%) LRMS: Anal. Calcd. for $C_{27}H_{31}N_6O$ 455.26; found: 455.26 $(M + H)^+$. HRMS: Anal. Calcd. for $C_{27}H_{31}N_6O$ 455.2559; found: 455.2576 $(M + H)^+$. |
| D29 | 5,5'-(3-fluoro-4,4'-biphenyldiyl)bis(2-((2S)-2-pyrrolidinyl)-1H-imidazole) tetraacetate | Prepared from entry 10 (in lieu of 152j-27) using experimental conditions outlined in Example 152k-1. | $t_R$ = 1.55 min, (95%) LRMS: Anal. Calcd. for $C_{26}H_{28}FN_6$ 443.24; found: 443.24 $(M + H)^+$. HRMS: Anal. Calcd. for $C_{26}H_{28}FN_6$ 443.2359; found: 443.2371 $(M + H)^+$. |
| D30 | | Prepared from entry D12 (in lieu of 152j-27) using experimental conditions outlined in Example 152k-1. | $t_R$ = 1.72 min, (77.5%) LRMS: Anal. Calcd. for $C_{26}H_{27}F_2N_6$ 461.23; found: 461.25 $(M + H)^+$. HRMS: Anal. Calcd. for $C_{26}H_{27}F_2N_6$ 461.2265; found: 461.2272 $(M + H)^+$. |

-continued

Section D

| Entry | Compound Name | Structure | **Data |
|---|---|---|---|
| D31 | 5,5'-(2,5-difluoro-4,4'-biphenyldiyl)bis(2-((2S)-2-pyrrolidinyl)-1H-imidazole) | Prepared from entry D11 (in lieu of 152j-27) using experimental conditions outlined in Example 152k-1. | $t_R$ = 1.67 min, (95%) LRMS: Anal. Calcd. for $C_{26}H_{27}F_2N_6$ 461.23; found: 461.23 (M + H)⁺. HRMS: Anal. Calcd. for $C_{26}H_{27}F_2N_6$ 461.2265; found: 461.2287 (M + H)⁺. |
| D32 | 2-(3-fluoro-4-(2-((2S)-2-pyrrolidinyl)-1H-imidazol-5-yl)phenyl)-5-(2-((2S)-2-pyrrolidinyl)-1H-imidazol-5-yl)pyrimidine | Prepared from entry D13 (in lieu of 152j-27) using experimental conditions outlined in Example 152k-1. | $t_R$ = 1.63 min, (95%) LRMS: Anal. Calcd. for $C_{24}H_{26}FN_8$ 445.23; found: 445.23 (M + H)⁺. HRMS: Anal. Calcd. for $C_{24}H_{26}FN_8$ 445.2264; found: 445.2268 (M + H)⁺. |
| D33 | (1R,1'R)-2,2'-((4-methoxy-3,4'-biphenyldiyl)bis(1H-imidazole-5,2-diyl(2S)-2,1-pyrrolidinediyl))bis(N,N-dimethyl-2-oxo-1-phenylethanamine) | Prepared from entry D28 (in lieu of 148e) and Cap-1 using experimental conditions outlined in Example 148. | $t_R$ = 1.71 min, (95%) LRMS: Anal. Calcd. for $C_{47}H_{53}N_8O_3$ 777.42; found: 777.41 (M + H)⁺. HRMS: Anal. Calcd. for $C_{47}H_{53}N_8O_3$ 777.4241; found: 777.4254 (M + H)⁺. |

-continued

Section D

| Entry | Compound Name | Structure | **Data |
|---|---|---|---|
| D34 | dimethyl ((4-methoxy-3,4'-biphenyldiyl)bis(1H-imidaozle-5,2-diyl(2S)-2,1-pyrrolidinediyl((1R)-2-oxo-1-phenyl-2,1-ethanediyl)))biscarbamate | Prepared from entry D28 (in lieu of 148e) and Cap-4 using experimental conditions outlined in Example 148. | $t_R$ = 2.09 min, (95%) LRMS: Anal. Calcd. for $C_{47}H_{49}N_8O_7$ 837.37; found: 837.34 (M + H)$^+$. HRMS: Anal. Calcd. for $C_{47}H_{49}N_8O_7$ 837.3724; found: 837.3690 (M + H)$^+$. |
| D35 | methyl ((1S)-1-(((2S)-2-(5-(4'-(2-((2S)-1-((2R)-2-(diethylamino)-2-phenylacetyl)-2-pyrrolidinyl)-1H-imidazol-5-yl)-3-fluoro-4-biphenylyl)-1H-imidazol-2-yl)-1-pyrrolidinyl)carbonyl)-2-methylpropyl)carbamate | Prepared from entry D25 (in lieu of 148e) and Cap-51 using experimental conditions outlined in Example 148. | $t_R$ = 1.85 min, (97.2%) LRMS: Anal. Calcd. for $C_{45}H_{54}FN_8O_4$ 789.43; found: 789.43 (M + H)$^+$. HRMS: Anal. Calcd. for $C_{45}H_{54}FN_8O_4$ 789.4252; found: 789.4225 (M + H)$^+$. |

-continued

Section D

| Entry | Compound Name | Structure | **Data |
|---|---|---|---|
| D36 | methyl ((1S)-2-((2S)-2-(5-(4'-(2-((2S)-1-((2R)-2-(diethylamino)-2-phenylacetyl)-1H-imidazol-5-yl)-3-fluoro-4-biphenylyl)-1H-imidazol-2-yl)-1-pyrrolidinyl)-1-methyl-2-oxoethyl)carbamate | Prepared from entry D25 (in lieu of 148e) and Cap-52 using experimental conditions outlined in Example 148. | $t_R$ = 1.76 min, (97.9%) LRMS: Anal. Calcd. for $C_{43}H_{50}FN_8O_4$ 761.39; found: 761.26 (M + H)$^+$. HRMS: Anal. Calcd. for $C_{43}H_{50}FN_8O_4$ 761.3939; found: 761.3967 (M + H)$^+$. |
| D37 | methyl ((1R)-2-((2S)-2-(5-(4'-(2-((2S)-1-((2R)-2-(diethylamino)-2-phenylacetyl)-1H-imidazol-5-yl)-3-fluoro-4-biphenylyl)-1H-imidazol-2-yl)-1-pyrrolidinyl)-2-oxo-1-phenylethyl)carbamate | Prepared from entry D25 (in lieu of 148e) and Cap-4 using experimental conditions outlined in Example 148. | $t_R$ = 1.90 min, (98.6%) LRMS: Anal. Calcd. for $C_{48}H_{52}FN_8O_4$ 823.41; found: 823.42 (M + H)$^+$. HRMS: Anal. Calcd. for $C_{48}H_{52}FN_8O_4$ 823.4096; found: 823.4102 (M + H)$^+$. |

-continued

Section D

| Entry | Compound Name | Structure | **Data |
|---|---|---|---|
| D38 | methyl ((1R)-2-((2S)-2-(5-(3'-fluoro-4'-(2-((2S)-1-(N-(methoxycarbonyl)-L-alanyl)-2-pyrrolidinyl)-1H-imidazol-5-yl)-1-biphenylyl)-1H-imidazol-2-yl)-1-pyrrolidinyl)-2-oxo-1-phenylethyl)carbamate | Prepared from entry D23 (in lieu of 148e) and Cap-52 using experimental conditions outlined in Example 148. | $t_R$ = 1.89 min, (98.2%) LRMS: Anal. Calcd. for $C_{47}H_{49}N_8O_7$, 763.34; found: 763.32 (M + H)⁺. HRMS: Anal. Calcd. for $C_{41}H_{44}FN_8O_6$ 763.3368; found: 763.3358 (M + H)⁺. |
| D39 | methyl ((1R)-2-((2S)-2-(5-(4'-(2-((2S)-1-(2R)-2-(diethylamino)-2-phenylacetyl)-1H-imidazol-5-yl)-3'-fluoro-4-biphenylyl)-1H-imidazol-2-yl)-1-pyrrolidinyl)-2-oxo-1-phenylethyl)carbamate | Prepared from entry D23 (in lieu of 148e) and Cap-2 using experimental conditions outlined in Example 148. | $t_R$ = 1.88 min, (98.7%) LRMS: Anal. Calcd. for $C_{48}H_{52}FN_8O_4$ 823.41; found: 823.39 (M + H)⁺. HRMS: Anal. Calcd. for $C_{48}H_{52}FN_8O_4$ 823.4096; found: 823.4127 (M + H)⁺. |

| Entry | Compound Name | Structure | **Data |
|---|---|---|---|
| D40 | methyl ((1S)-1-(((2S)-2-(5-(3'-fluoro-4'-(2-((2S)-1-((2S)-2-(((methoxycarbonyl)-amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate | 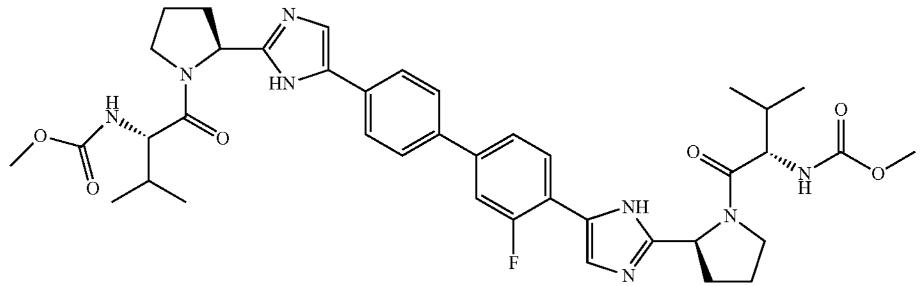 | $t_R$ = 1.97 min, (98.4%) LRMS: Anal. Calcd. for $C_{40}H_{50}FN_8O_6$ 757.38; found: 757.32 (M + H)⁺. HRMS: Anal. Calcd. for $C_{40}H_{50}FN_8O_6$ 757.3837; found: 757.3815 (M + H)⁺. Prepared from entry D29 (in lieu of 148e) and Cap-51 using experimental conditions outlined in Example 148. |
| D41 | methyl ((1S)-1-(((2S)-2-(5-(3'-fluoro-4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)carbonyl)-2-methylpropyl)carbamate | 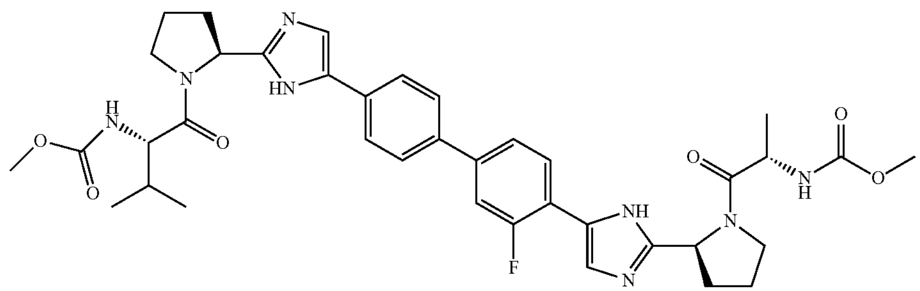 | $t_R$ = 1.82 min, (95.0%) LRMS: Anal. Calcd. for $C_{38}H_{46}FN_8O_6$ 729.35; found: 729.29 (M + H)⁺. HRMS: Anal. Calcd. for $C_{38}H_{46}FN_8O_6$ 729.3524; found: 729.3523 (M + H)⁺. Prepared from entry D24 (in lieu of 148e) and Cap-52 using experimental conditions outlined in Example 148. |

-continued

Section D

| Entry | Compound Name | Structure | **Data |
|---|---|---|---|
| D42 | methyl (((1S,2R)-1-(((2S)-2-(5-(3-fluoro-4'-(2-((2S)-1-(N-(methoxycarbonyl)-L-valyl)-2-pyrrolidinyl)-1H-imidazol-5-yl)-4-biphenylyl)-1H-imidazol-2-yl)-1-pyrrolidinyl)carbonyl)-2-methoxypropyl)carbamate | 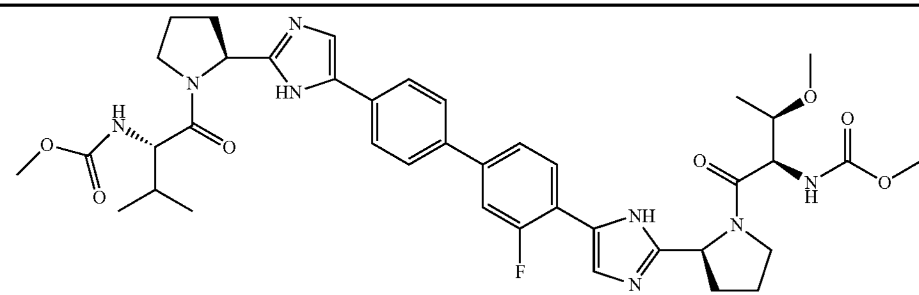 | $t_R$ = 1.91 min, (94.0%) LRMS: Anal. Calcd. for $C_{40}H_{50}FN_8O_7$ 773.38; found: 773.31 (M + H)⁺. HRMS: Anal. Calcd. for $C_{40}H_{50}FN_8O_7$ 773.3786; found: 773.3759 (M + H)⁺. Prepared from entry D24 (in lieu of 148e) and Cap-86 using experimental conditions outlined in Example 148. |
| D43 | methyl (((1S)-1-(((2S)-2-(5-(4'-(2-((2S)-1-(N,N-diethyl-D-alanyl)-2-pyrrolidinyl)-1H-imidazol-5-yl)-3'-fluoro-4-biphenylyl)-1H-imidazol-2-yl)-1-pyrrolidinyl)carbonyl)-2-methylpropyl)carbamate | 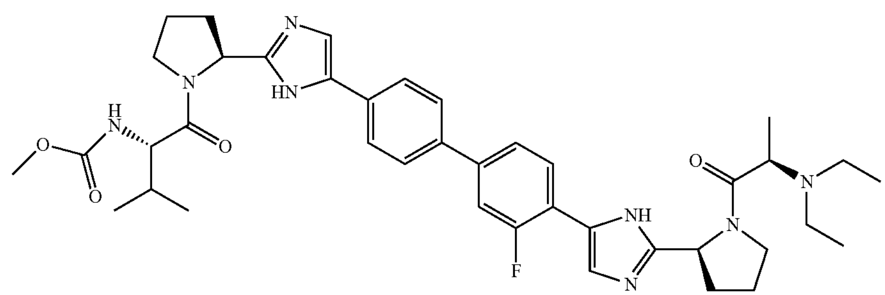 | $t_R$ = 1.72 min, (97.6%) LRMS: Anal. Calcd. for $C_{40}H_{52}FN_8O_4$ 727.41; found: 727.35 (M + H)⁺. HRMS: Anal. Calcd. for $C_{40}H_{52}FN_8O_4$ 727.4096; found: 727.4091 (M + H)⁺. Prepared from entry D24 (in lieu of 148e) and Cap-69b using experimental conditions outlined in Example 148. |

| Entry | Compound Name | Structure | **Data |
|---|---|---|---|
| D44 | methyl ((1S)-1-(((2S)-2-(5-(4'-(2-((2S)-1-((2R)-2-(diethylamino)-2-phenylacetyl)-2-pyrrolidinyl)-1H-imidazol-5-yl)-3'-fluoro-4-biphenylyl)-1H-imidazol-2-yl)-1-pyrrolidinyl)carbonyl)-2-methylpropyl)carbamate | 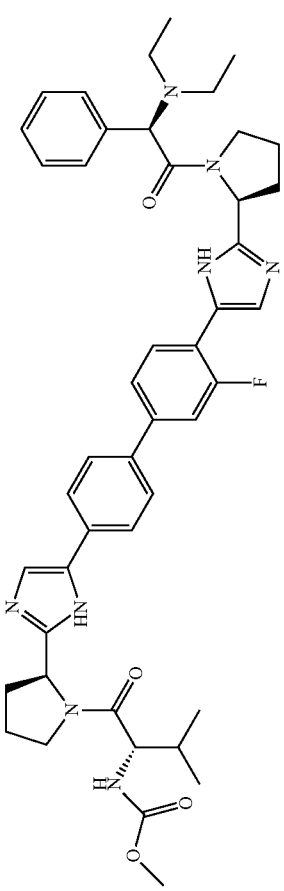 Prepared from entry D24 (in lieu of 148e) and Cap-2 using experimental conditions outlined in Example 148. | $t_R$ = 1.83 min, (96.9%) LRMS: Anal. Calcd. for $C_{45}H_{54}FN_8O_4$ 789.43; found: 789.36 (M + H)⁺. HRMS: Anal. Calcd. for $C_{45}H_{54}FN_8O_4$ 789.4252; found: 789.4225 (M + H)⁺. |
| D45 | methyl ((1S)-2-((2S)-2-(5-(3'-fluoro-4-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-1-methyl-2-oxoethyl)carbamate | 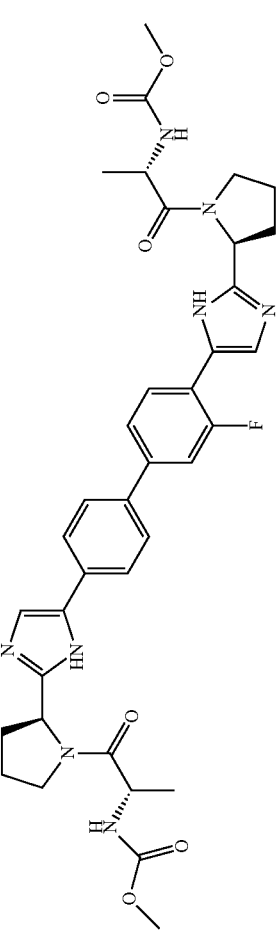 Prepared from entry D29 (in lieu of 148e) and Cap-52 using experimental conditions outlined in Example 148. | $t_R$ = 1.69 min, (97.7%) LRMS: Anal. Calcd. for $C_{36}H_{42}FN_8O_6$ 701.32; found: 701.30 (M + H)⁺. HRMS: Anal. Calcd. for $C_{36}H_{42}FN_8O_6$ 701.3222; found: 701.3211 (M + H)⁺. |

| Entry | Compound Name | Structure | **Data |
|---|---|---|---|
| D46 | dimethyl ((3-fluoro-4,4'-biphenyldiyl)bis(1H-imidazole-5,2-diyl(2S)-2,1-pyrrolidinediyl((1R)-2-oxo-1-phenyl-2,1-ethanediyl))biscarbamate | Prepared from entry D29 (in lieu of 148e) and Cap-4 using experimental conditions outlined in Example 148. | $t_R$ = 2.05 min, (99.9%) LRMS: Anal. Calcd. for for $C_{46}H_{46}FN_8O_6$ 825.35; found: 825.35 $(M+H)^+$. HRMS: Anal. Calcd. for $C_{46}H_{46}FN_8O_6$ 825.3524; found: 825.3522 $(M+H)^+$. |
| D47 | (1R,1'R)-2,2'-((3-fluoro-4,4'-biphenyldiyl)bis(1H-imidazole-5,2-diyl(2S)-2,1-pyrrolidinediyl))bis(N,N-diethyl-2-oxo-1-phenylethanamine) | Prepared from entry D29 (in lieu of 148e) and Cap-2 using experimental conditions outlined in Example 148. | $t_R$ = 1.72 min, (99.5%) LRMS: Anal. Calcd. for for $C_{50}H_{58}FN_8O_2$ 821.47; found: 821.44 $(M+H)^+$. HRMS: Anal. Calcd. for $C_{50}H_{58}FN_8O_2$ 821.4667; found: 821.4636 $(M+H)^+$. |

-continued

Section D

| Entry | Compound Name | Structure | **Data |
|---|---|---|---|
| D48 | methyl (((1R)-2-((2S)-2-(5-(4'-(2-((2S)-1-(N,N-diethyl-D-alanyl)-2-pyrrolidinyl)-1H-imidazol-5-yl)-3'-fluoro-4-biphenylyl)-1H-imidazol-2-yl)-1-pyrrolidinyl)-2-oxo-1-phenylethyl)carbamate | 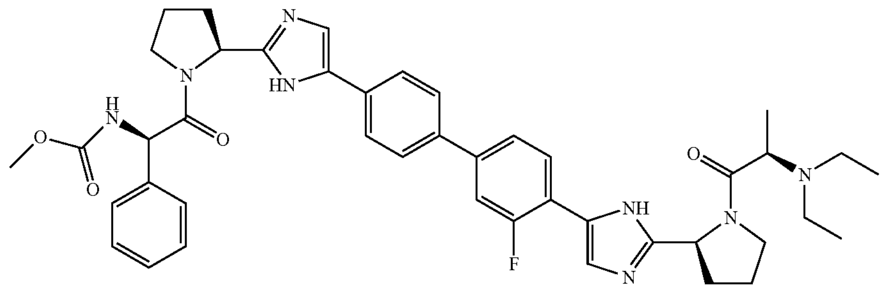 | $t_R$ = 1.76 min, (99.7%) LRMS: Anal. Calcd. for $C_{43}H_{50}FN_8O_4$ 761.39; found: 761.27 (M + H)⁺. HRMS: Anal. Calcd. for $C_{43}H_{50}FN_8O_4$ 761.3939; found: 761.3952 (M + H)⁺. |
| D49 | methyl ((1S)-1-cyclopropyl-2-((2S)-2-(5-(4'-(2-((2S)-1-((2R)-2-(diethylamino)-2-phenylacetyl)-1H-imidazol-5-yl)-3-fluoro-4-biphenylyl]-1H-imidazol-2-yl)-1-pyrrolidinyl)-2-oxoethyl)carbamate | 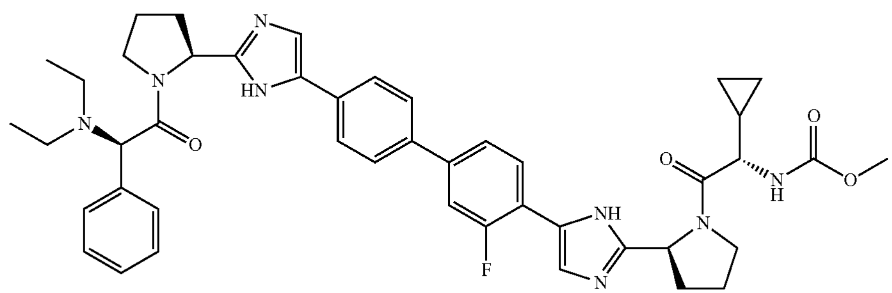 | $t_R$ = 1.92 min, (98.7%) LRMS: Anal. Calcd. for $C_{45}H_{52}FN_8O_4$ 787.41; found: 787.36 (M + H)⁺. HRMS: Anal. Calcd. for $C_{45}H_{52}FN_8O_4$ 787.4096; found: 787.4074 (M + H)⁺. |

Prepared from entry D23 (in lieu of 148e) and Cap-69b using experimental conditions outlined in Example 148.

Prepared from entry D25 (in lieu of 148e) and Cap-54b using experimental conditions outlined in Example 148.

-continued

Section D

| Entry | Compound Name | Structure | **Data |
|---|---|---|---|
| D50 | methyl ((1S)-1-cyclopropyl-2-((2S)-2-(5-(3-fluoro-4'-(2-((2S)-1-(N-(methoxycarbonyl)-L-valyl)-2-pyrrolidinyl)-1H-imidazol-5-yl)-4-biphenylyl)-1H-imidazol-2-yl)-1-pyrrolidinyl)-2-oxoethyl)carbamate | Prepared from entry D24 (in lieu of 148e) and Cap-54b using experimental conditions outlined in Example 148. | $t_R$ = 1.94 min, (99.0%) LRMS: Anal. Calcd. for $C_{40}H_{48}F_2N_8O_7$ 755.37; found: 755.32 $(M+H)^+$. HRMS: Anal. Calcd. for $C_{40}H_{48}FN_8O_6$ 755.3681; found: 755.3670 $(M+H)^+$. |
| D51 | methyl ((1R)-2-((2S)-2-(5-(4'-(2-((2S)-1-(N,N-diethyl-D-alanyl)-2-pyrrolidinyl)-1H-imidazol-5-yl)-3'-fluoro-4-biphenylyl)-1H-imidazol-2-yl)-1-pyrrolidinyl)-2-oxo-1-phenylethyl)carbamate | Prepared from entry D23 (in lieu of 148e) and Cap-69b using experimental conditions outlined in Example 148. | $t_R$ = 1.92 min, (98.3%) LRMS: Anal. Calcd. for $C_{43}H_{50}FN_8O_4$ 761.39; found: 761.35 $(M+H)^+$. HRMS: Anal. Calcd. for $C_{43}H_{50}FN_8O_4$ 761.3939; found: 761.3956 $(M+H)^+$. |

| Entry | Compound Name | Structure | **Data |
|---|---|---|---|
| D52 | methyl ((1S)-2-((2S)-2-(5-(2',5'-difluoro-4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-1-methyl-2-oxoethyl)carbamate | Prepared from entry D31 (in lieu of 148e) and Cap-52 using experimental conditions outlined in Example 148. | $t_R$ = 1.69 min, (99.2%) LRMS: Anal. Calcd. for $C_{36}H_{41}F_2N_8O_6$ 719.31; found: 719.29 $(M+H)^+$. HRMS: Anal. Calcd. for $C_{36}H_{41}F_2N_8O_6$ 719.3117; found: 719.3109 $(M+H)^+$. |
| D53 | dimethyl (2,5-difluoro-4,4'-biphenyldiyl)bis(1H-imidazole-5,2-diyl(2S)-2,1-pyrrolidinediyl((1R)-2-oxo-1-phenyl-2,1-ethanediyl))biscarbamate | Prepared from entry D31 (in lieu of 148e) and Cap-4 using experimental conditions outlined in Example 148 of 10889PSP. | $t_R$ = 2.08 min, (100.0%) LRMS: Anal. Calcd. for $C_{46}H_{45}F_2N_8O_6$ 843.34; found: 843.34 $(M+H)^+$. HRMS: Anal. Calcd. for $C_{46}H_{45}F_2N_8O_6$ 843.3430; found: 843.3458 $(M+H)^+$. |

-continued

Section D

| Entry | Compound Name | Structure | **Data |
|---|---|---|---|
| D54 | (1R,1'R)-2,2'-((2S)-difluoro-4,4'-biphenyldiyl)bis(1H-imidazole-5,2-diyl(2S)-2,1-pyrrolidinediyl)bis-(N,N-diethyl-2-oxo-1-phenylethanamine)<br><br>Prepared from entry D31 (in lieu of 148e) and Cap-2 using experimental conditions outlined in Example 148. | 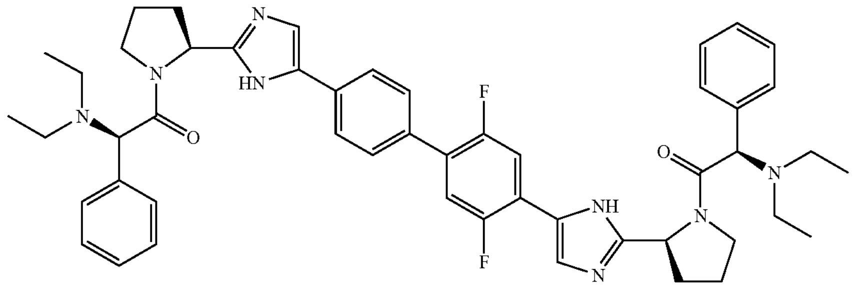 | $t_R$ = 1.76 min, (99.8%) LRMS: Anal. Calcd. for $C_{50}H_{57}F_2N_8O_2$ 839.46; found: 839.43 $(M+H)^+$.<br>HRMS: Anal. Calcd. for $C_{50}H_{57}F_2N_8O_2$ 839.45573; found: 839.4585 $(M+H)^+$. |
| D55 | methyl ((1S)-1-cyclopropyl-2-((2S)-2-(5-(3,3'-difluoro-4'-(2-((2S)-1-(N-(methoxycarbonyl)-L-valyl)-2-pyrrolidinyl)-1H-imidazol-5-yl)-4-biphenylyl)-1H-imidazol-2-yl)-1-pyrrolidinyl)-2-oxoethyl)carbamate<br><br>Prepared from entry D26 (in lieu of 148e) and Cap-54b using experimental conditions outlined in Example 148. | 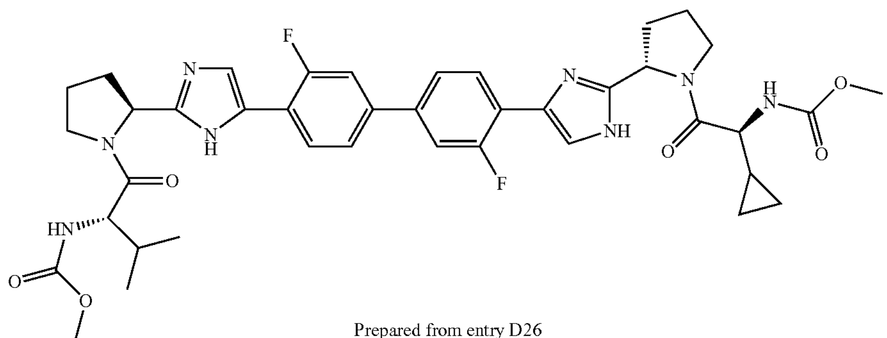 | $t_R$ = 1.93 min, (98.5%) LRMS: Anal. Calcd. for $C_{40}H_{47}F_2N_8O_6$ 773.36; found: 773.31 $(M+H)^+$.<br>HRMS: Anal. Calcd. for $C_{40}H_{47}F_2N_8O_6$ 773.3567; found: 773.3587 $(M+H)^+$. |

-continued

Section D

| Entry | Compound Name | Structure | **Data |
|---|---|---|---|
| D56 | methyl (((1S,2R)-1-(((2S)-2-(5-(3,3'-difluoro-4'-(2-((2S)-1-(N-(methoxycarbonyl)-L-valyl)-2-pyrrolidinyl)-1H-imidaozl-5-yl)-4-biphenylyl)-1H-imidazol-2-yl)-1-pyrrolidinyl)carbonyl)-2-methoxypropyl)carbamate | Prepared from entry D26 (in lieu of 148e) and Cap-86 using experimental conditions outlined in Example 148. | $t_R = 2.00$ min, (98.0%) LRMS: Anal. Calcd. for $C_{40}H_{49}F_2N_8O_7$ 791.37; found: 791.32 $(M+H)^+$. HRMS: Anal. Calcd. for $C_{40}H_{49}F_2N_8O_7$ 791.3692; found: 791.3682 $(M+H)^+$. |
| D57 | methyl (((1S)-1-(((2S)-2-(5-(3,3'-difluoro-4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)carbonyl)-2-methylpropyl)carbamate | Prepared from entry D26 (in lieu of 148e) and Cap-52 using experimental conditions outlined in Example 148. | $t_R = 1.86$ min, (95.6%) LRMS: Anal. Calcd. for $C_{38}H_{45}F_2N_8O_6$ 747.34; found: 747.30 $(M+H)^+$. HRMS: Anal. Calcd. for $C_{38}H_{45}F_2N_8O_6$ 747.3430; found: 747.3425 $(M+H)^+$. |

| Entry | Compound Name | Structure | **Data |
|---|---|---|---|
| D58 | methyl (((1S)-1-(((2S)-2-(5-(3,3'-difluoro-4'-(2-((2S)-1-((methoxycarbonyl)-amino)-3-methylbutanoyl)-1H-imidazol-5-yl)-4-biphenylyl)-1H-imidazol-2-yl)-1-pyrrolidinyl)carbonyl)-2-methylpropyl)carbamate | Prepared from entry D26 (in lieu of 148e) and Cap-51 using experimental conditions outlined in Example 148. | $t_R$ = 2.02 min, (96.3%) LRMS: Anal. Calcd. for $C_{40}H_{49}F_2N_8O_6$ 775.37; found: 775.31 (M + H)⁺. HRMS: Anal. Calcd. for $C_{40}H_{49}F_2N_8O_6$ 775.3743; found: 775.37.34 (M + H)⁺. |
| D59 | methyl (((1S)-1-(((2S)-2-(5-(4'-(2-((2S)-1-(N,N-diethyl-D-alanyl)-1H-imidazol-5-yl)-3,3'-difluoro-4-biphenylyl)-1H-imidazol-2-yl)-1-pyrrolidinyl)carbonyl)-2-methylpropyl)carbamate | Prepared from entry D26 (in lieu of 148e) and Cap-69b using experimental conditions outlined in Example 148. | $t_R$ = 1.78 min, (98.2%) LRMS: Anal. Calcd. for $C_{40}H_{51}F_2N_8O_4$ 745.40; found: 745.34 (M + H)⁺. HRMS: Anal. Calcd. for $C_{40}H_{51}F_2N_8O_4$ 745.4001; found: 745.4008 (M + H)⁺. |

-continued

Section D

| Entry | Compound Name | Structure | **Data |
|---|---|---|---|
| D60 | methyl ((1S)-1-(((2S)-2-(5-(3,3'-difluoro-4'-(2-((2S)-1-((methoxycarbonyl)-amino)-2-phenylacetyl)-pyrrolidinyl)-1H-imidazol-5-yl)-4-biphenylyl)-1H-imidazol-2-yl)-1-pyrrolidinyl)carbonyl)-2-methylpropyl)carbamate | 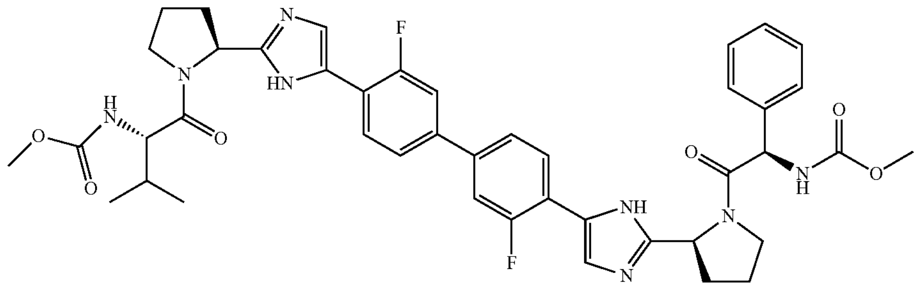 | $t_R$ = 2.08 min, (99.1%) LRMS: Anal. Calcd. for $C_{43}H_{47}F_2N_8O_6$ 809.36; found: 809.29 (M + H)+. HRMS: Anal. Calcd. for $C_{43}H_{47}F_2N_8O_6$ 809.3587; found: 809.3568 (M + H)+. Prepared from entry D26 (in lieu of 148e) and Cap-4 using experimental conditions outlined in Example 148. |
| D61 | methyl ((1S)-2-((2S)-2-(5-(3,3'-difluoro-4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-1-methyl-2-oxoethyl)carbamate | 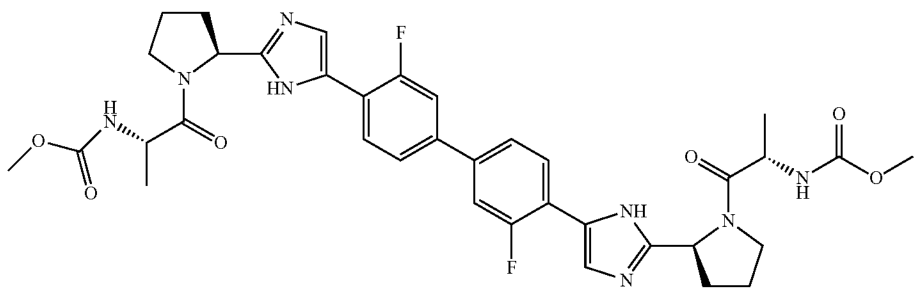 | $t_R$ = 1.71 min, (94.3%) LRMS: Anal. Calcd. for $C_{36}H_{41}F_2N_8O_6$ 719.31; found: 719.19 (M + H)+. HRMS: Anal. Calcd. for $C_{36}H_{41}F_2N_8O_6$ 719.3117; found: 719.3115 (M + H)+. Prepared from entry D30 (in lieu of 148e) and Cap-52 using experimental coditions outlined in Example 148. |

| Entry | Compound Name | Structure | **Data |
|---|---|---|---|
| D62 | methyl ((1R)-2-((2S)-2-(5-(3,3'-difluoro-4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-2-oxo-1-phenylethyl)carbamate | Prepared from entry D27 (in lieu of 148e) and Cap-52 using experimental conditions outlined in Example 148. | $t_R$ = 1.94 min, (98.3%) LRMS: Anal. Calcd. for $C_{41}H_{43}F_2N_8O_6$ 781.33; found: 781.26 (M + H)⁺. HRMS: Anal. Calcd. for $C_{41}H_{43}F_2N_8O_6$ 781.3274; found: 781.3264 (M + H)⁺. |
| D63 | methyl ((1R)-2-((2S)-2-(5-(4'-(2-((2S)-1-(N,N-diethyl-D-alanyl)-2-pyrrolidinyl)-1H-imidazol-5-yl)-3,3'-difluoro-4-biphenylyl)-1H-imidazol-2-yl)-1-pyrrolidinyl)-2-oxo-1-phenylethyl)carbamate | Prepared from entry D27 (in lieu of 148e) and Cap-69b using experimental conditions outlined in Example 148. | $t_R$ = 1.44 min, (99.0%) LRMS: Anal. Calcd. for $C_{43}H_{49}F_2N_8O_4$ 779.38; found: 779.32 (M + H)⁺. HRMS: Anal. Calcd. for $C_{43}H_{49}F_2N_8O_4$ 779.3845; found: 779.3842 (M + H)⁺. |

| Entry | Compound Name | Structure | **Data |
|---|---|---|---|
| D64 | methyl ((1R)-2-((2S)-2-(5-(4'-(2-((2S)-1-((2R)-2-(diethylamino)-2-phenylacetyl)-pyrrolidinyl)-1H-imidazol-5-yl)-3,3'-difluoro-4-biphenylyl)-1H-imidazol-2-yl)-1-pyrrolidinyl)-2-oxo-1-phenylethyl)carbamate | Prepared from entry D27 (in lieu of 148e) and Cap-2 using experimental conditions outlined in Example 148. | $t_R$ = 1.94 min, (95.3%) LRMS: Anal. Calcd. for $C_{48}H_{51}F_2N_8O_4$ 841.40; found: 841.33 $(M + H)^+$. HRMS: Anal. Calcd. for $C_{48}H_{51}F_2N_8O_4$ 841.4001; found: 841.3991 $(M + H)^+$. |
| D65 | methyl ((1S,2R)-1-(((2S)-2-(5-(3,3'-difluoro-4'-(2-((2S)-1-((2R)-2-((methoxycarbonyl)amino)-2-phenylacetyl)-pyrrolidinyl)-1H-imidazol-5-yl)-4-biphenylyl)-1H-imidazol-2-yl)-1-pyrrolidinyl)carbonyl)-2-methoxypropyl)carbamate bis(trifluoroacetate) | Prepared from entry D27 (in lieu of 148e) and Cap-86 using experimental conditions outlined in Example 148. | $t_R$ = 2.00 min, (96.2%) LRMS: Anal. Calcd. for $C_{43}H_{47}F_2N_9O_7$ 825.35; found: 825.28 $(M + H)^+$. HRMS: Anal. Calcd. for $C_{43}H_{47}F_2N_9O_7$ 825.3536; found: 825.3527 $(M + H)^+$. |

-continued

Section D

| Entry | Compound Name | Structure | **Data |
|---|---|---|---|
| D66 | methyl ((1S)-1-cyclopropyl-2-((2S)-2-(5-(3,3'-difluoro-4'-(2-((2S)-1-((2R)-2-((methoxycarbonyl)-amino)-2-phenylacetyl)-2-pyrrolidinyl)-1H-imidazol-5-yl)-4-biphenylyl)-1H-imidazol-2-yl)-1-pyrrolidinyl)-2-oxoethyl)carbamate | 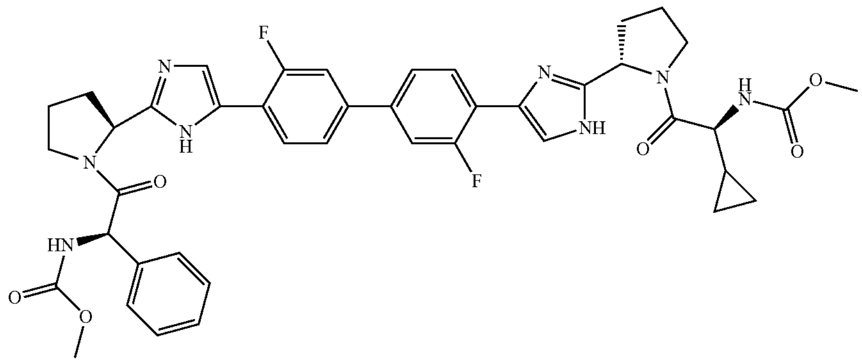 | $t_R$ = 2.01 min, (99.5%) LRMS: Anal. Calcd. for $C_{43}H_{45}F_2N_8O_6$ 807.34; found: 807.29 $(M + H)^+$. HRMS: Anal. Calcd. for $C_{43}H_{45}F_2N_8O_6$ 807.3430; found: 807.3409 $(M + H)^+$. Prepared from entry D27 (in lieu of 148e) and Cap-54b using experimental conditions outlined in Example 148. |
| D67 | methyl ((1S)-2-((2S)-2-(5-(2-fluoro-4-(5-(2-((2S)-1-(N-(methoxycarbonyl)-L-alanyl)-2-pyrrolidinyl)-1H-imidazol-5-yl)-2-pyrimidinyl)phenyl)-1H-imidazol-2-yl)-1-pyrrolidinyl)-1-methyl-2-oxoethyl)carbamate | 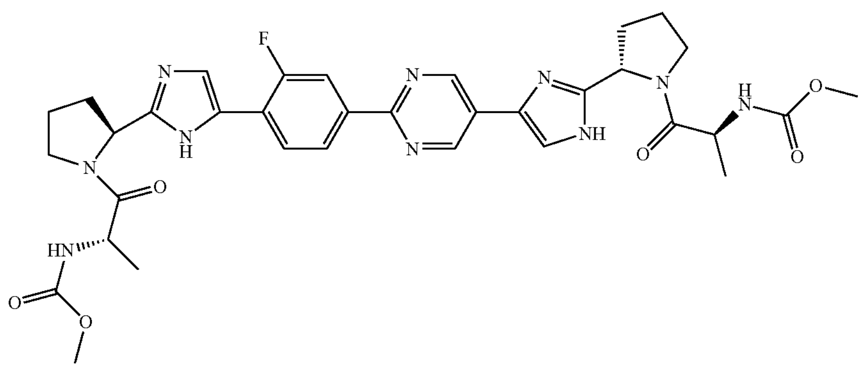 | $t_R$ = 1.58 min, (91.1%) LRMS: Anal. Calcd. for $C_{34}H_{40}FN_{10}O_6$ 703.31; found: 703.27 $(M + H)^+$. HRMS: Anal. Calcd. for $C_{34}H_{40}FN_{10}O_6$ 703.3116; found: 703.3101 $(M + H)^+$. Prepared from entry D32 (in lieu of 148e) and Cap-52 using experimental conditions outlined in Example 148. |

| Entry | Compound Name | Structure | **Data |
|---|---|---|---|
| D68 | methyl ((1S)-1-(((2S)-2-(5-(2-fluoro-4-(5-(2-((2S)-1-((2S)-2-((methoxycarbonyl)-amino)-3-methylbutanoyl)-pyrrolidinyl)-1H-imidazol-5-yl)-2-pyrimidinyl)phenyl)-1H-imidazol-2-yl)-1-pyrrolidinyl)carbonyl)-2-methylpropyl)carbamate | Prepared from entry D32 (in lieu of 148e) and Cap-51 using experimental conditions outlined in Example 148. | $t_R$ = 1.95 min, (99.3%) LRMS: Anal. Calcd. for $C_{38}H_{48}FN_{10}O_6$ 759.37; found: 759.30 (M + H)+. HRMS: Anal. Calcd. for $C_{38}H_{48}FN_{10}O_6$ 759.3742; found: 759.3715 (M + H)+. |
| D69 | methyl ((1R)-2-((2S)-2-(5-(2-(3-fluoro-4-(2-((2S)-1-((2R)-2-((methoxycarbonyl)-amino)-2-phenylacetyl)-pyrrolidinyl)-1H-imidazol-5-yl)phenyl)-5-pyrimidinyl)-1H-imidazol-2-yl)-1-pyrrolidinyl)-2-oxo-1-phenylethyl)carbamate | Prepared from entry D32 (in lieu of 148e) and Cap-4 using experimental conditions outlined in Example 148. | $t_R$ = 2.05 min, (99.3%) LRMS: Anal. Calcd. for $C_{44}H_{44}FN_{10}O_6$ 827.34; found: 827.27 (M + H)+. HRMS: Anal. Calcd. for $C_{44}H_{44}FN_{10}O_6$ 827.3429; found: 827.3407 (M + H)+. |

-continued

Section D

| Entry | Compound Name | Structure | **Data |
|---|---|---|---|
| D70 | methyl (((1S,2R)-1-(((2S)-2-(5-(2-fluoro-4-(5-(2-((2S)-1-((N-(methoxycarbonyl)-O-methyl-L-threonyl)-pyrrolidinyl)-1H-imidazol-5-yl)-2-pyrimidinyl)phenyl)-1H-imidazol-2-yl)-1-pyrrolidinyl)carbonyl)-2-methoxypropyl)carbamate | 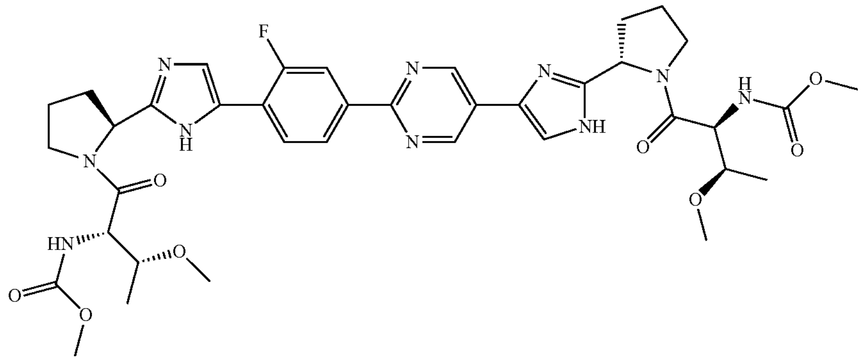 | $t_R$ = 1.79 min, (93.0%) LRMS: Anal. Calcd. for $C_{38}H_{48}FN_{10}O_8$ 791.36; found: 791.31 (M + H)+. HRMS: Anal. Calcd. for $C_{38}H_{45}FN_{10}O_8$ 791.3641; found: 791.3636 (M + H)+. |

Prepared from entry D32 (in lieu of 148e) and Cap-86 using experimental conditions outlined in Example 148.

**LCMS conditions: Phenomenex-Luna 4.6 × 50 mm S10, 0 to 100% B over 3 min, 4 min stop time, 4 mL/min, 220 nm, A: 10% MeOH-90% H2O - 0.1% TFA; B: 90% MeOH-10% H2O-0.1% TFA

Example D5

(S)-tert-butyl 2-(5-(4-bromo-2-fluorophenyl)-1H-imidazol-2-yl)pyrrolidine-1-carboxylate

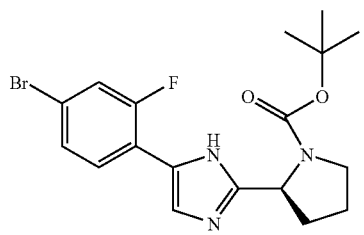

Bromine (0.54 mL, 10.6 mmol) was added dropwise to a cold (0° C.) solution of 4-bromo-2-fluoroacetophenone (2.30 g, 10.6 mmol) in dioxane (80 mL) and tetrahydrofuran (80 mL). The mixture was stirred for 1 h at 0° C. and warmed to RT for 15 h. The mixture was diluted with ethyl acetate, washed with saturated $NaHCO_3$ solution, 5% sodium thiosulfate solution and brine prior to drying ($Na_2SO_4$). 2-Bromo-1-(4-bromo-2-fluorophenyl)ethanone (D1) was isolated as a colorless film which solidified upon further concentration under high vacuum. This solid was dissolved into anhydrous acetonitrile (50 mL) and treated with N-Boc-L-proline (2.28 g, 10.6 mmol) and diisopropylethylamine (1.85 mL, 10.6 mmol). After being stirred for 3 h at RT, the solvent was removed in vacuo and the residue was partitioned into ethyl acetate and water. The organic phase was washed with 0.1N hydrochloric acid, saturated $NaHCO_3$ solution and brine prior to drying ($Na_2SO_4$), filtration, and concentration. This residue was taken up in xylenes (50 mL) and treated to solid $NH_4OAc$ (4.1 g, 53.0 mmol). The mixture was heated at 140° C. for 2 hr in a thick-walled, screw-top flask before it was cooled to ambient temperature, diluted with ethyl acetate and washed with saturated $NaHCO_3$ solution and brine prior to drying ($Na_2SO_4$) and concentration. Purification of the residue by Biotage™ flash chromatography on silica gel (65M column, preequilibration with 16% B for 1800 mL followed by gradient elution with 16% B to 16% B for 450 mL, 16% B to 50% B for 2199 ml and finally 50% B to 100% B for 2199 mL) afforded title compound (D5) (3.61 g, 83%) as a brownish/caramel-colored oil. A small portion (40 mg) of the title compound was further purified by preparative HPLC (20% B to 100% B over 14 min where B is 10 mM $NH_4OAc$ in 10:90 $H_2O$/ACN and A is 10 mM $NH_4OAc$ in 95:5 $H_2O$/CAN using a Phenomenex-Gemini 30×100 mm S10 column flowing at 40 mL/min) to afford pure title compound (31.8 mg) as a white solid.

$^1$H NMR (500 MHz, DMSO-$d_6$) δ 12.13-11.95 (m, 1H), 7.94 (br s, 1H), 7.54 (d, J=10.7 Hz, 1H), 7.42 (d, J=7.9 Hz, 1H), 7.36-7.34 (m, 1H), 4.86-4.77 (2m, 1H), 3.54 (m, 1H), 3.38-3.32 (m, 1H), 2.28-2.14 (2m, 1H), 2.05-1.78 (2m, 3H), 1.39 and 1.14 (2s, 9H).

HPLC Phenomenex LUNA C-18 4.6×50 mm, 0 to 100% B over 3 minutes, 1 minute hold time, A=90% water, 10% methanol, 0.1% TFA, B=10% water, 90% methanol, 0.1% TFA, RT=2.27 min, 95% homogeneity index.

LRMS: Anal. Calcd. for $C_{18}H_{22}BrFN_3O_2$ 410.09 and 412.09. found: 410.08 and 412.08 $(M+H)^+$.

HRMS: Anal. Calcd. for $C_{18}H_{22}BrFN_3O_2$ 410.0879. found: 410.0893 $(M+H)^+$.

Examples M1-M27

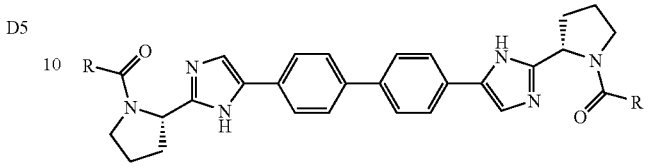

Example M1-M27 were prepared from 1e and the respective acids using the method described for Example 1. The products were prepared as TFA salts, unless noted otherwise. LC Conditions were as follows:

Condition 1
Column=Phenomenex-Luna 3.0×50 mm S10
Start % B=0
Final % B=100
Gradient time=2 min
Stop time=3 min
Flow Rate=4 mL/min
Wavelength=220 nm
Solvent A=0.1% TFA in 10% methanol/90% $H_2O$
Solvent B=0.1% TFA in 90% methanol/10% $H_2O$
Condition 2
Column=Phenomenex-Luna 4.6×50 mm S10
Start % B=0
Final % B=100
Gradient time=2 min
Stop time=3 min
Flow Rate=5 mL/min
Wavelength=220 nm
Solvent A=0.1% TFA in 10% methanol/90% $H_2O$
Solvent B=0.1% TFA in 90% methanol/10% $H_2O$
Condition 3
Column=HPLC XTERRA C18 3.0×50 mm S7
Start % B=0
Final % B=100
Gradient time=3 min
Stop time=4 min
Flow Rate=4 mL/min
Wavelength=220 nm
Solvent A=0.1% TFA in 10% methanol/90% $H_2O$
Solvent B=0.1% TFA in 90% methanol/10% $H_2O$
Condition M1
Column: Luna 4.6×50 mm S10
Start % B=0
Final % B=100
Gradient time=3 min
Stop time=4 min
Flow rate=4 mL/min
Solvent A:=95% $H_2O$: 5% $CH_3CN$, 10 mm Ammonium acetate
Solvent B:=5% $H_2O$: 95% $CH_3CN$; 10 mm Ammonium acetate

| Example | Compound Name | (Source) | RT (LC-Cond.); % homogeneity index; MS data; $^1$H NMR data |
|---|---|---|---|
| M1 | 7,7'-(4,4'-biphenyldiylbis(1H-imidazole-5,2-diyl(2S)-2,1-pyrrolidinediyl(2-oxo-1-phenyl-2,1-ethanediyl)))bis(7-azabicyclo[2.2.1]heptane) | 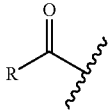<br>(Cap-77a) | 1.04 min (Cond. 1); >98%; LC/MS: Anal. Calcd. for [M + H]$^+$ C$_{54}$H$_{59}$N$_8$O$_2$: 851.48; found 851.55; HRMS: Anal. Calcd. for [M + H]$^+$ C$_{54}$H$_{59}$N$_8$O$_2$: 851.4761; found 851.4780 |
| M2 | 7,7'-(4,4'-biphenyldiylbis(1H-imidazole-5,2-diyl(2S)-2,1-pyrrolidinediyl(2-oxo-1-phenyl-2,1-ethanediyl)))bis(7-azabicyclo[2.2.1]heptane) | 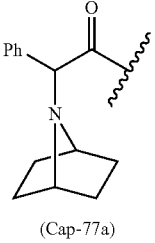<br>(Cap-77b) | 1.13 min (Cond. 1); >98%; LC/MS: Anal. Calcd. for [M + H]$^+$ C$_{54}$H$_{59}$N$_8$O$_2$: 851.48; found 851.57; HRMS: Anal. Calcd. for [M + H]$^+$ C$_{54}$H$_{59}$N$_8$O$_2$: 851.4761; found 851.4792 |
| M3 | N,N'-(4,4'-biphenyldiylbis(1H-imidazole-5,2-diyl(2S)-2,1-pyrrolidinediyl((1R)-2-oxo-1-phenyl-2,1-ethanediyl)))bis(N-ethylcyclopropanamine) | 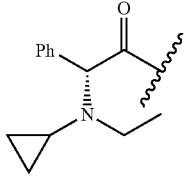<br>(Cap-78) | 1.13 min (Cond. 1); >95%; LC/MS: Anal. Calcd. for [M + H]$^+$ C$_{52}$H$_{59}$N$_8$O$_2$: 827.48; found 827.69; HRMS: Anal. Calcd. for [M + H]$^+$ C$_{52}$H$_{59}$N$_8$O$_2$: 827.4761; found 827.4782 |
| M4 | ethyl ((1R)-2-((2S)-2-(5-(4'-(2-((2S)-1-(N-(ethoxycarbonyl)-D-alanyl)-2-pyrrolidinyl)-1H-imidazol-5-yl)-4-biphenylyl)-1H-imidazol-2-yl)-1-pyrrolidinyl)-1-methyl-2-oxoethyl)carbamate | 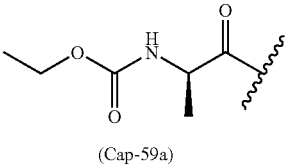<br>(Cap-59a) | 1.20 min (Cond. 1); >97%; LC/MS: Anal. Calcd. for [M + H]$^+$ C$_{38}$H$_{47}$N$_8$O$_6$: 711.36; found 711.46; HRMS: Anal. Calcd. for [M + H]$^+$ C$_{38}$H$_{47}$N$_8$O$_6$: 711.3619; found 711.3638 |
| M5 | ethyl ((1S)-2-((2S)-2-(5-(4'-(2-((2S)-1-(N-(ethoxycarbonyl)-L-alanyl)-2-pyrrolidinyl)-1H-imidazol-5-yl)-4-biphenylyl)-1H-imidazol-2-yl)-1-pyrrolidinyl)-1-methyl-2-oxoethyl)carbamate | 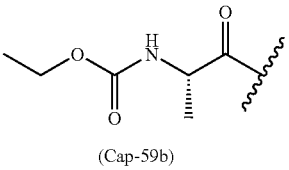<br>(Cap-59b) | 1.16 min (Cond. 1); 97%; LC/MS: Anal. Calcd. for [M + H]$^+$ C$_{38}$H$_{47}$N$_8$O$_6$: 711.36; found 711.48; HRMS: Anal. Calcd. for [M + H]$^+$ C$_{38}$H$_{47}$N$_8$O$_6$: 711.3619; found 711.3621 |
| M6 | dimethyl (4,4'-biphenyldiylbis(1H-imidazole-5,2-diyl(2S)-2,1-pyrrolidinediylcarbonyl-1,1-cyclopropanediyl))biscarbamate | 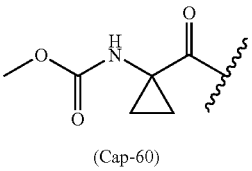<br>(Cap-60) | 1.12 min (Cond. 1); >98%; LC/MS: Anal. Calcd. for [M + H]$^+$ C$_{38}$H$_{43}$N$_8$O$_6$: 707.33; found 707.45; HRMS: Anal. Calcd. for [M + H]$^+$ C$_{38}$H$_{43}$N$_8$O$_6$: 707.3306; found 707.3309 |

-continued

| Example | Compound Name | (Source) | RT (LC-Cond.); % homogeneity index; MS data; ¹H NMR data |
|---|---|---|---|
| M7 | methyl (2-((2S)-2-(5-(4'-(2-((2S)-1-(2-((methoxycarbonyl)amino)-2-methylpropanoyl)-2-pyrrolidinyl)-1H-imidazol-5-yl)-4-biphenylyl)-1H-imidazol-2-yl)-1-pyrrolidinyl)-1,1-dimethyl-2-oxoethyl)carbamate | (Cap-61) | 1.21 min (Cond. 1); >98%; LC/MS: Anal. Calcd. for [M + H]⁺ $C_{38}H_{47}N_8O_6$: 711.36; found 711.53; HRMS: Anal. Calcd. for [M + H]⁺ $C_{38}H_{47}N_8O_6$: 711.3619; found 711.3652 |
| M8 | (2R,2'R)-1,1'-(4,4'-biphenyldiylbis(1H-imidazole-5,2-diyl(2S)-2,1-pyrrolidinediyl))bis(N,N-dimethyl-1-oxo-2-propanamine) | (Cap-83) | 0.91 min (Cond. 1); >80%; LC/MS: Anal. Calcd. for [M + H]⁺ $C_{36}H_{47}N_8O_2$: 623.38; found 623.46; HRMS: Anal. Calcd. for [M + H]⁺ $C_{36}H_{47}N_8O_2$: 623.3822; found 623.3819 |
| M9 | (2R,2'R)-1,1'-(4,4'-biphenyldiylbis(1H-imidazole-5,2-diyl(2S)-2,1-pyrrolidinediyl))bis(N,N-diethyl-1-oxo-2-propanamine) | (Cap-69a) | 1.00 min (Cond. 1); >95%; LC/MS: Anal. Calcd. for [M + H]⁺ $C_{40}H_{55}N_8O_2$: 623.38; found 679.67; HRMS: Anal. Calcd. for [M + H]⁺ $C_{40}H_{55}N_8O_2$: 679.4448; found 679.4432 |
| M10 | (2R,2'R)-1,1'-(4,4'-biphenyldiylbis(1H-imidazole-5,2-diyl(2S)-2,1-pyrrolidinediyl))bis(N,N-diethyl-3-methyl-1-oxo-2-butanamine) | (Cap-72) | 1.03 min (Cond. 1); >98%; LC/MS: Anal. Calcd. for [M + H]⁺ $C_{44}H_{63}N_8O_2$: 735.51; found 735.76; HRMS: Anal. Calcd. for [M + H]⁺ $C_{44}H_{63}N_8O_2$: 735.5074; found 735.5060 |
| M11 | methyl ((1S)-1-(((2S)-2-(5-(4'-(2-((2S)-1-((2S)-2-((methoxycarbonyl)(methyl)amino)-3-methylbutanoyl)-2-pyrrolidinyl)1H-imidazol-5-yl)-4-biphenylyl)-1H-imidazol-2-yl)-1-pyrrolidinyl)carbonyl)-2-methylpropyl)methylcarbamate | (Cap-62) | 1.46 min (Cond. 1); >98%; LC/MS: Anal. Calcd. for [M + H]⁺ $C_{42}H_{55}N_8O_2$: 767.42; found 767.38; HRMS: Anal. Calcd. for [M + H]⁺ $C_{42}H_{55}N_8O_2$: 767.4245; found 767.4252 |
| M12 | dimethyl (4,4'-biphenyldiylbis(1H-imidazole-5,2-diyl(2S)-2,1-pyrrolidinediyl((1S)-2-oxo-1-phenyl-2,1-ethanediyl)))biscarbamate | (Cap-82) | 1.32 min (Cond. 1); >98%; LC/MS: Anal. Calcd. for [M + H]⁺ $C_{46}H_{47}N_8O_6$: 807.36; found 807.32; HRMS: Anal. Calcd. for [M + H]⁺ $C_{46}H_{47}N_8O_6$: 807.3619; found 807.3651 |

-continued

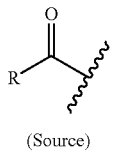

| Example | Compound Name | (Source) | RT (LC-Cond.); % homogeneity index; MS data; ¹H NMR data |
|---|---|---|---|
| M13 | N,N'-(4,4'-biphenyldiylbis(1H-imidazole-5,2-diyl(2S)-2,1-pyrrolidinediyl((2R)-1-oxo-1,2-propanediyl)))bis(N-propyl-1-propanamine) | 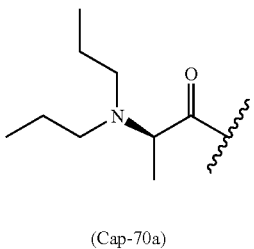 (Cap-70a) | 1.09 min (Cond. 1); >98%; LC/MS: Anal. Calcd. for [M + H]⁺ $C_{44}H_{63}N_8O_2$: 735.51; found 735.46; HRMS: Anal. Calcd. for [M + H]⁺ $C_{44}H_{63}N_8O_2$: 735.5074; found 735.5063 |
| M14 | methyl ((1S)-2-hydroxy-1-(((2S)-2-(5-(4'-(2-((2S)-1-((2S)-3-hydroxy-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate | 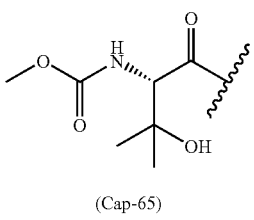 (Cap-65) | 1.13 min (Cond. 1); >98%; LC/MS: Anal. Calcd. for [M + H]⁺ $C_{40}H_{51}N_8O_8$: 771.38; found 771.21 |
| M15 | methyl ((1S,2R)-2-hydroxy-1-(((2S)-2-(5-(4'-(2-((2S)-1-((2S,3R)-3-hydroxy-2-((methoxycarbonyl)amino)butanoyl)-2-pyrrolidinyl)-1H-imidazol-5-yl)-4-biphenylyl)-1H-imidazol-2-yl)-1-pyrrolidinyl)carbonyl)propyl)carbamate | 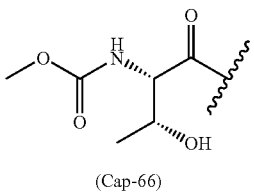 (Cap-66) | 1.10 min (Cond. 1); >98%; LC/MS: Anal. Calcd. for [M + H]⁺ $C_{38}H_{47}N_8O_8$: 743.35; found 753.23; ¹H NMR (DMSO-d₆, δ = 2.5 ppm, 400 MHz), ~14.5 (br s, 4 H), 8.15 (s, 2 H), 7.97 (d, J = 8.5, 4 H), 7.89 (d, J = 8.4, 4 H), 7.10/7.05 (two overlapping d, J = 8.0, 8.4, 1.82 H), 6.57 (app br s, 0.18 H), 5.78 (br d, J = 7.9, 0.18 H), 5.16 (m, 1.82 H), 4.27 (dd, J = 8.0, 5.3, 1.82 H), 4.10 (m, 0.18 H), 3.96-3.81 (m, 6 H), 3.55 (s, 5.46 H), 3.37 (s, 0.54 H), 2.41 (m, 2 H), 2.17-2.00 (m, 6 H), 1.10 (d, J = 6.3, 0.54 H), 1.04 (d, J = 6.3, 5.46 H). |
| M16 | methyl ((1S,2S)-2-hydroxy-1-(((2S)-2-(5-(4'-(2-((2S)-1-((2S,3S)-3-hydroxy-2-((methoxycarbonyl)amino)butanoyl)-2-pyrrolidinyl)-1H-imidazol-5-yl)-4-biphenylyl)-1H-imidazol-2-yl)-1-pyrrolidinyl)carbonyl)propyl)carbamate | 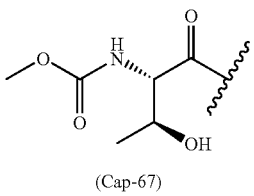 (Cap-67) | 1.11 min (Cond. 1); >98%; LC/MS: Anal. Calcd. for [M + H]⁺ $C_{38}H_{47}N_8O_8$: 743.35; found 743.23 |

| Example | Compound Name | (Source) | RT (LC-Cond.); % homogeneity index; MS data; ¹H NMR data |
|---|---|---|---|
| M17 | methyl ((1S)-2-((2S)-2-(5-(4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-1-methyl-2-oxoethyl)carbamate | (Cap-52) | 1.64 min (Cond. 2); 99%; LC/MS: Anal. Calcd. for $[M + H]^+$ $C_{36}H_{43}N_8O_6$: 683.33; found 683.30; HRMS: Anal. Calcd. for $[M + H]^+$ $C_{36}H_{43}N_8O_6$: 683.3306; found 683.3305. |
| M18 | methyl ((1R)-2-((2S)-2-(5-(4'-(2-((2S)-1-(N-(methoxycarbonyl)-D-alanyl)-2-pyrrolidinyl)-1H-imidazol-5-yl)-4-biphenylyl)-1H-imidazol-2-yl)-1-pyrrolidinyl)-1-methyl-2-oxoethyl)carbamate | (Cap-85) | 1.70 min (Cond. 2); 97%; LC/MS: Anal. Calcd. for $[M + H]^+$ $C_{36}H_{43}N_8O_6$: 683.33; found 683.32; HRMS: Anal. Calcd. for $[M + H]^+$ $C_{36}H_{43}N_8O_6$: 683.3306; found 683.3318. |
| M19 | (2S,2'S)-1,1'-(4,4'-biphenyldiylbis(1H-imidazole-5,2-diyl(2S)-2,1-pyrrolidinediyl)bis(N,N-dimethyl-1-oxo-2-propanamine) | (Cap-13) | 1.43 min (Cond. 2); >99%; LC/MS: Anal. Calcd. for $[M + H]^+$ $C_{36}H_{47}N_8O_2$: 623.38; found 623.43; HRMS: Anal. Calcd. for $[M + H]^+$ $C_{36}H_{47}N_8O_2$: 623.3822; found 623.3837. |
| M20 | dimethyl (4,4'-biphenyldiylbis(1H-imidazole-5,2-diyl(2S)-2,1-pyrrolidinediyl((2R)-1-oxo-1,2-butanediyl))biscarbamate | (Cap-53a) | 1.82 min (Cond. 2); >99%; LC/MS: Anal. Calcd. for $[M + H]^+$ $C_{38}H_{47}N_8O_6$: 711.36; found 711.35; HRMS: Anal. Calcd. for $[M + H]^+$ $C_{38}H_{47}N_8O_6$: 711.3619; found 711.3649. |
| M21 | dimethyl (4,4'-biphenyldiylbis(1H-imidazole-5,2-diyl(2S)-2,1-pyrrolidinediyl((2S)-1-oxo-1,2-butanediyl))biscarbamate | (Cap-53b) | 1.81 min (Cond. 2); >99%; LC/MS: Anal. Calcd. for $[M + H]^+$ $C_{38}H_{47}N_8O_6$: 711.36; found 711.35; HRMS: Anal. Calcd. for $[M + H]^+$ $C_{38}H_{47}N_8O_6$: 711.3619; found 711.3643. |
| M22 | dimethyl (4,4'-biphenyldiylbis(1H-imidazole-5,2-diyl(2S)-2,1-pyrrolidinediyl((1R)-1-cyclopropyl-2-oxo-2,1-ethandiyl)))biscarbamate | (Cap-54a) | 1.83 min (Cond. 2); >99%; LC/MS: Anal. Calcd. for $[M + H]^+$ $C_{40}H_{47}N_8O_6$: 735.36; found 735.44; HRMS: Anal. Calcd. for $[M + H]^+$ $C_{40}H_{47}N_8O_6$: 735.3619; found: 735.3614. |

-continued

| Example | Compound Name | (Source) | RT (LC-Cond.); % homogeneity index; MS data; $^1$H NMR data |
|---------|---------------|----------|-------------------------------------------------------------|
| M23 | dimethyl (4,4'-biphenyldiylbis(1H-imidazole-5,2-diyl(2S)-2,1-pyrrolidinediyl((1S)-1-cyclopropyl-2-oxo-2,1-ethandiyl)))biscarbamate | (Cap-54b) | 1.81 min (Cond. 2); >99%; LC/MS: Anal. Calcd. for [M + H]$^+$ C$_{40}$H$_{47}$N$_8$O$_6$: 735.36; found 735.43; HRMS: Anal. Calcd. for [M + H]$^+$ C$_{40}$H$_{47}$N$_8$O$_6$: 735.3619; found 735.3651. |
| M24 | methyl ((1S)-1-(((2S)-2-(5-(4'-(2-((2S)-1-((2S)-2-((methoxycarbonyl)amino)-3,3-dimethylbutanoyl)-2-pyrrolidinyl)-1H-imidazol-5-yl)-4-biphenylyl)-1H-imidazol-2-yl)-1-pyrrolidinyl)carbonyl)-2,2-dimethylpropyl)carbamate | | 2.11 min (Cond. 2); >99%; LC/MS: Anal. Calcd. for [M + H]$^+$ C$_{42}$H$_{55}$N$_8$O$_6$: 767.42; found 767.58; HRMS: Anal. Calcd. for C$_{42}$H$_{55}$N$_8$O$_6$: 767.4245; found 767.4230. |
| M25 | dimethyl (4,4'-biphenyldiylbis(1H-imidazole-5,2-diyl(2S)-2,1-pyrrolidinediyl((4S)-5-oxo-1-penten-5,4-diyl)))biscarbamate | (Cap-55) | 1.91 min (Cond. 2); 98% LC/MS: Anal. Calcd. for [M + H]$^+$ C$_{40}$H$_{47}$N$_8$O$_6$: 735.36; found 735.47; HRMS: Anal. Calcd. for [M + H]$^+$ C$_{40}$H$_{47}$N$_8$O$_6$: 735.3619; found 735.3630. |
| M26 | methyl ((1S)-2-((2S)-2-(5-(4'-(2-((2S)-1-(N-(methoxycarbonyl)-O-methyl-L-seryl)-2-pyrrolidinyl)-1H-imidazol-5-yl)-4-biphenylyl)-1H-imidazol-2-yl)-1-pyrrolidinyl)-1-(methoxymethyl)-2-oxoethyl)carbamate | (Cap-56) | 1.72 min (Cond. 2); 97%; LC/MS: Anal. Calcd. for [M + H]$^+$ C$_{38}$H$_{47}$N$_8$O$_8$: 743.35; found 743.49; HRMS: Anal. Calcd. for [M + H]$^+$ C$_{38}$H$_{47}$N$_8$O$_8$: 743.3517; found 743.3489. |
| M27 | methyl ((1S)-1-(((2S)-2-(5-(4'-(2-((2S)-1-((2S)-2-((methoxycarbonyl)amino)pentanoyl)-2-pyrrolidinyl)-1H-imidazol-5-yl)-4-biphenylyl)-1H-imidazol-2-yl)-1-pyrrolidinyl)carbonyl)butyl)carbamate | (Cap-57) | 1.98 min (Cond. 2); 98%; LC/MS: Anal. Calcd. for [M + H]$^+$ C$_{40}$H$_{51}$N$_8$O$_6$: 736.39; found 739.52; HRMS: Anal. Calcd. for [M + H]$^+$ C$_{40}$H$_{51}$N$_8$O$_6$: 739.3932; found 739.3904. |

Example M28 methyl ((1S)-1-(((2R)-2-(5-(4'-(2-((2R)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate

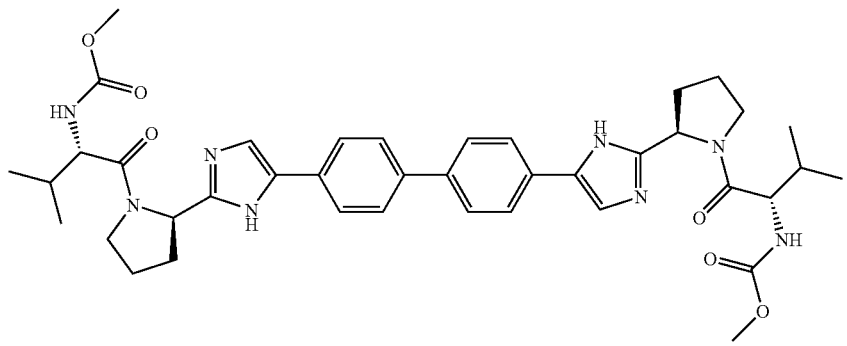

Example M28

Step a

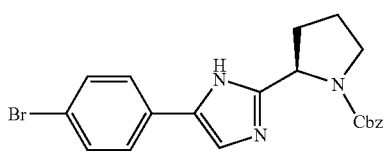

Bromide M28a was prepared from D-Proline according to the procedure described for its enantiomer 28b.

Example M28

Step b

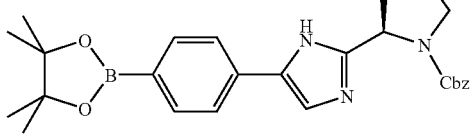

Boronate ester M28b was prepared from bromide M28a according to the procedure described for intermediate 1c. LC: RT=1.57 min (Cond. 1); LC/MS: Anal. Calcd. for [M+H]+ $C_{27}H_{33}BN_3O_4$: 474.26. found 474.24.

Example M28

Step c

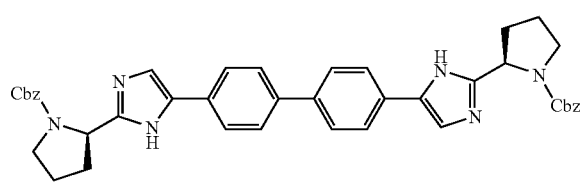

Biphenyl M28c was prepared from bromide M28a and boronate M28b according to the procedure described for intermediate 1d. LC: RT=1.43 min (Cond. 1); LC/MS: Anal. Calcd. for [M+H]+ $C_{42}H_{41}N_6O_4$: 693.32. found 693.38.

Example M28

Step d

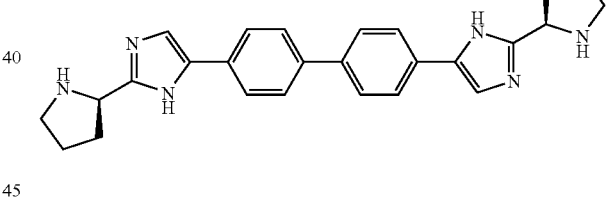

Pyrrolidine M28d was prepared from carbamate M28c according to the procedure described for intermediate 28d. $^1$H NMR (DMSO-$d_6$, δ=2.5 ppm, 400 MHz): δ 11.83 (br s, 2H), 7.80 (d, J=8.3, 4H), 7.66 (d, J=8.3, 4H), 7.46 (br s, 2H), 4.16 (app t, J=7.2, 2H), 3.00-2.94 (m, 2H), 2.88-2.82 (m, 2H), 2.10-2.01 (m, 2H), 1.94-1.85 (m, 2H), 1.82-1.66 (m, 4H). [Note: in the region between 3.2-2.6 ppm there is a broad base-line signal that is believed to be that of the pyrrolidine NH]. LC: RT=1.02 min (Cond. 1); LC/MS: Anal. Calcd. for [M+H]+ $C_{26}H_{29}N_6$: 425.25. found 425.27.

Example M28

Example M28 was prepared as TFA salt from intermediate M28d and Cap-51 according to the procedure described for Example 1. LC: RT=1.33 min (Cond. 1); 96% homogeneity index; LC/MS: Anal. Calcd. for [M+H]+ $C_{40}H_{51}N_8O_6$: 739.32. found 739.43; HRMS: Anal. Calcd. for [M+H]+ $C_{40}H_{51}N_8O_6$: 739.3932. found 739.3907.

Example M28-1

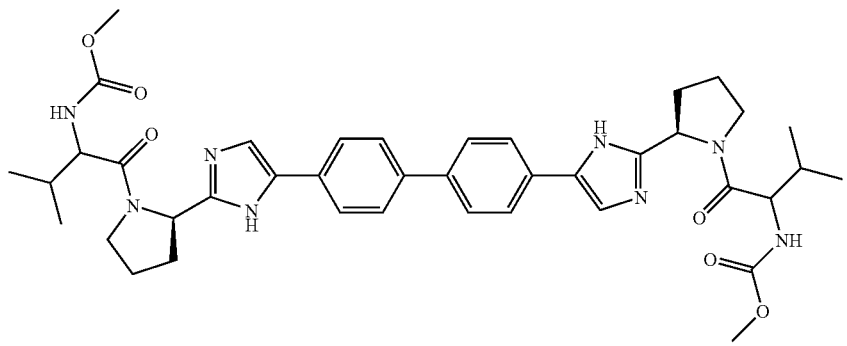

The TFA salt of Example M28-1 was prepared as a mixture of three stereoisomers from intermediate M28d and racemic version of Cap-51 according to the procedure described for Example 1. Three peaks with a retention time of 21.74 min, 22.62 min, and 23.40 min, and exhibiting the correct molecular weight, were observed when the sample was analyzed under the following condition:
Waters Acquity HPLC with Micromass ZQ MS (electrospray probe) and Waters 2996 PDA detection. (UV detection (315 nm)
Column: Acquity HPLC; BEH C18; 1.7 um; 100×2.1 mm ID; (at approx. 30 C)
Mobile phase A: water, 25 mM ammonium acetate at pH=5
Mobile phase B: acetonitrile
Flow rate: 0.50 ml/min
10-50% B 0-35.0 min
50-98% B 35.0-45.0 min
Hold 98% B 45.0-48.0 min
98% B-100% B 48.0-48.5 min
Hold 100% B 48.5-50.0 min

Example M28-2 methyl ((1S)-1-(((2S)-2-(5-(4'-(2-((2R)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate

Example M28-2

Step a

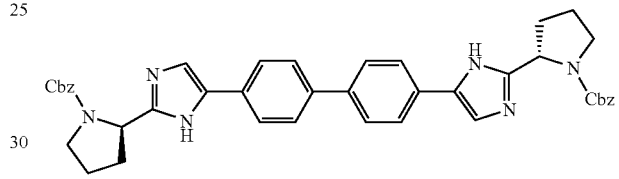

Carbamate M28-2a was prepared from boronate ester M28b and bromide 28b according to the procedure described for intermediate 1d. $^1$H NMR (DMSO-$d_6$, δ=2.5 ppm, 400 MHz): δ 12.25/12.01/11.93 (three br s, 2H), 7.86-6.98 (m, 20H), 5.13-4.88 (m, 6H), 3.63 (m, 2H), 3.47 (m, 2H), 2.35-1.84 (M, 8H). LC: RT=1.46 min (Cond. 1); LC/MS: Anal. Calcd. for [M+H]$^+$ $C_{42}H_{41}N_6O_4$: 693.32. found 693.34.

Example M28-2

Step b

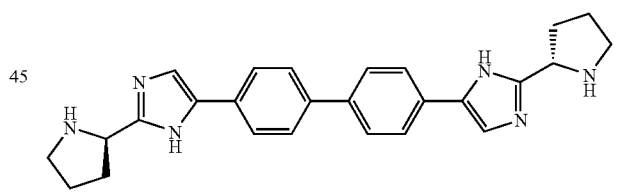

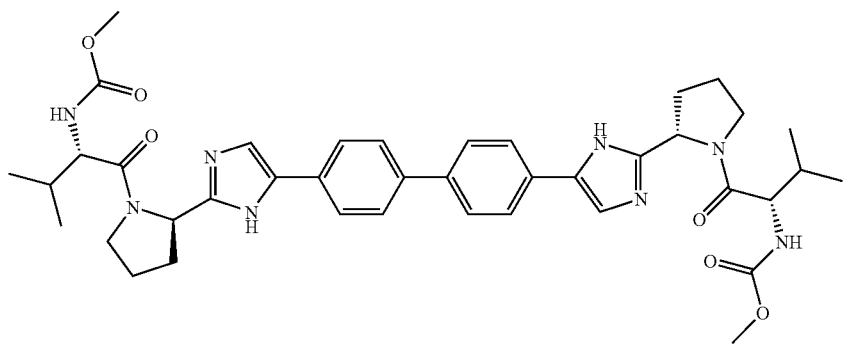

Pyrrolidine M28-2b was prepared from carbamate M28-2a according to the procedure described for intermediate 28d. $^1$H NMR (DMSO-$d_6$, δ=2.5 ppm, 400 MHz): δ 11.84 (br s, 2H), 7.80 (d, J=8.3, 4H), 7.66 (d, J=8.3, 4H), 7.46 (br s, 2H), 4.87 (m, 0.05H), 4.16 (app t, J=7.2, 1.95H), 3.00-2.94 (m, 2H), 2.88-2.82 (m, 2H), 2.10-2.01 (m, 2H), 1.94-1.85 (m, 2H), 1.82-1.66 (m, 4H). [Note: in the region between ~3.1-2.6 ppm there is a broad base-line signal that is believed to be that of the pyrrolidine NH]. LC: RT=0.96 min (Cond. 1); LC/MS: Anal. Calcd. for [M+H]$^+$ $C_{26}H_{29}N_6$: 425.25. found 425.28.

Example M28-2

Example M28-2 was prepared as TFA salt from intermediate M28-2b and Cap-51 according to the procedure described for Example 1. LC: RT=1.96 minutes (Cond. 2); 98% homogeneity index; LC/MS: Anal. Calcd. for [M+H]$^+$ $C_{40}H_{51}N_8O_6$ 739.39. found 739.47.

Example M28-3

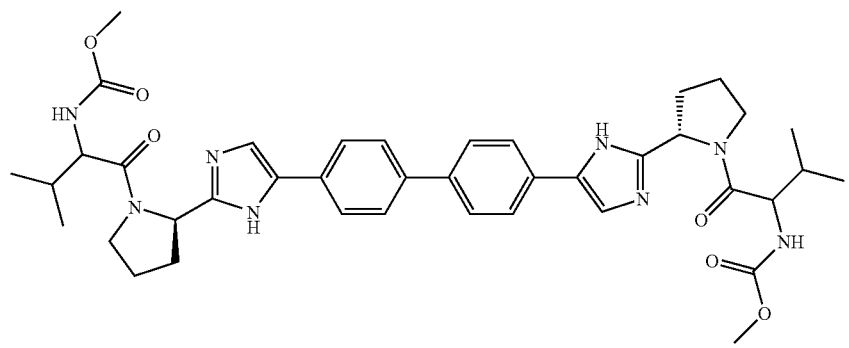

The TFA salt of Example M28-3 was prepared as a mixture of four stereoisomers from intermediate M28-2b and racemic version of Cap-51 according to the procedure described for Example 1. Three peaks with a retention time of 21.28 min, 22.19 min, and 23.01 min, and exhibiting the correct molecular weight, were observed when the sample was analyzed under the LC/MS condition described for Example M28-1.

Example M29 dimethyl (4,4'-biphenyldiylbis(1H-imidazole-5,2-diyl(2R)-2,1-pyrrolidinediyl((1R)-1-cyclopropyl-2-oxo-2,1-ethanediyl)))biscarbamate

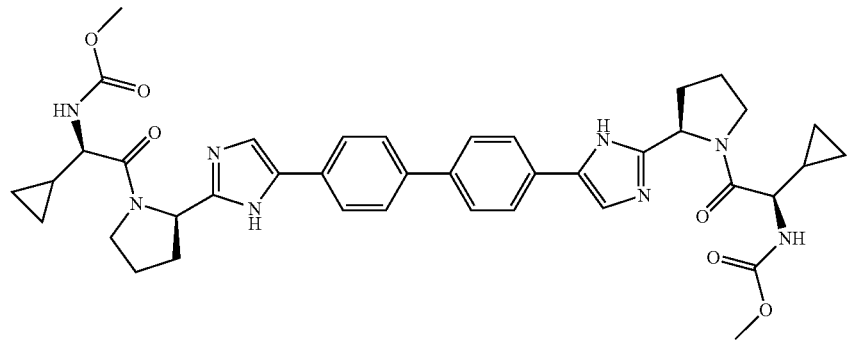

Example M29 was prepared as TFA salt from intermediate M28d and Cap-54a according to the procedure described for Example 1. LC: RT=1.21 min (Cond. 1); >98% homogeneity index; LC/MS: Anal. Calcd. for [M+H]$^+$ $C_{40}H_{47}N_8O_6$: 735.36. found 735.42; HRMS: Anal. Calcd. for [M+H]$^+$ $C_{40}H_{47}N_8O_6$: 735.3619. found 735.3598.

Example M30-M62

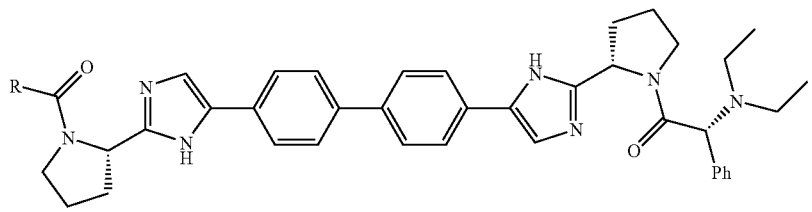

Example M30-M62 were prepared as TFA salts from CJ-24 and the respective caps using the same method described for Example 28.

| Example | Compound Name | (Source) | RT (LC-Cond.); % homogeneity index; MS data |
|---|---|---|---|
| M30 | ethyl ((1R)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-1-methyl-2-oxoethyl)carbamate | (Cap-59a) | 1.13 min (Cond. 1); >98%; LC/MS: Anal. Calcd. for [M + H]$^+$ C$_{44}$H$_{53}$N$_8$O$_4$: 757.42; found 757.50; HRMS: Anal. Calcd. for [M + H]$^+$ C$_{44}$H$_{53}$N$_8$O$_4$: 757.4190; found 757.4181 |
| M31 | ethyl ((1S)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-1-methyl-2-oxoethyl)carbamate | (Cap-59b) | 1.07 min (Cond. 1); >98%; LC/MS: Anal. Calcd. for [M + H]$^+$ C$_{44}$H$_{53}$N$_8$O$_4$: 757.42; found 757.55; HRMS: Anal. Calcd. for [M + H]$^+$ C$_{44}$H$_{53}$N$_8$O$_4$: 757.4190; found 757.4225 |
| M32 | (5S)-5-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)-2-pyrrolidinone | | 1.02 min (Cond. 1); >98%; LC/MS: Anal. Calcd. for [M + H]$^+$ C$_{43}$H$_{49}$N$_8$O$_3$: 725.39; found 725.48; HRMS: Anal. Calcd. for [M + H]$^+$ C$_{43}$H$_{49}$N$_8$O$_3$: 725.3928; found 725.3926 |
| M33 | methyl (1-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)cyclopropyl)carbamate | (Cap-60) | 1.12 min (Cond. 1); >98%; LC/MS: Anal. Calcd. for [M + H]$^+$ C$_{44}$H$_{51}$N$_8$O$_4$: 755.40; found 755.61; HRMS: Anal. Calcd. for [M + H]$^+$ C$_{44}$H$_{51}$N$_8$O$_4$: 755.4033; found 755.4066 |

-continued

| Example | Compound Name | (Source) | RT (LC-Cond.); % homogeneity index; MS data |
|---|---|---|---|
| M34 | methyl (2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-1,1-dimethyl-2-oxoethyl)carbamate | 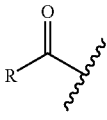<br>(Cap-61) | 1.16 min (Cond. 1); >98%; LC/MS: Anal. Calcd. for [M + H]$^+$ C$_{44}$H$_{53}$N$_8$O$_4$: 757.42; found 757.63; HRMS: Anal. Calcd. for [M + H]$^+$ C$_{44}$H$_{53}$N$_8$O$_4$: 757.4190; found 757.4164 |
| M35 | (2R)-1-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-N,N-diethyl-1-oxo-2-propanamine | 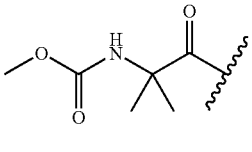<br>(Cap-69a) | 1.06 min (Cond. 1); >98%; LC/MS: Anal. Calcd. for [M + H]$^+$ C$_{45}$H$_{57}$N$_8$O$_2$: 741.46; found 741.64; HRMS: Anal. Calcd. for [M + H]$^+$ C$_{45}$H$_{57}$N$_8$O$_2$: 741.4604; found 741.4597 |
| M36 | (2S)-1-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-N,N-diethyl-1-oxo-2-propanamine | 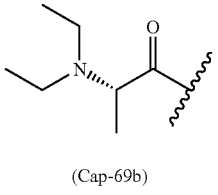<br>(Cap-69b) | 1.04 min (Cond. 1); >98%; LC/MS: Anal. Calcd. for [M + H]$^+$ C$_{45}$H$_{57}$N$_8$O$_2$: 741.46; found 741.63; HRMS: Anal. Calcd. for [M + H]$^+$ C$_{45}$H$_{57}$N$_8$O$_2$: 741.4604; found 741.4581 |
| M37 | (1R)-N,N-diethyl-2-((2S)-2-(5-(4'-(2-((2S)-1-(1,3-oxazol-2-ylcarbonyl)-2-pyrrolidinyl)-1H-imidazol-5-yl)-4-biphenylyl)-1H-imidazol-2-yl)-1-pyrrolidinyl)-2-oxo-1-phenylethanamine | 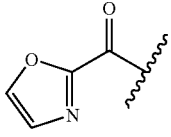 | 1.11 min (Cond. 1); >98%; LC/MS: Anal. Calcd. for [M + H]$^+$ C$_{42}$H$_{45}$N$_8$O$_3$: 709.36; found 709.51; HRMS: Anal. Calcd. for [M + H]$^+$ C$_{42}$H$_{45}$N$_8$O$_2$: 709.3615; found 709.3615 |
| M38 | (1R)-N,N-diethyl-2-oxo-1-phenyl-2-((2S)-2-(5-(4'-(2-((2S)-1-(3-pyridinylcarbonyl)-2-pyrrolidinyl)-1H-imidazol-5-yl)-4-biphenylyl)-1H-imidazol-2-yl)-1-pyrrolidinyl)ethanamine | 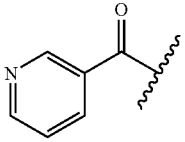 | 1.09 min (Cond. 1); >98%; LC/MS: Anal. Calcd. for [M + H]$^+$ C$_{44}$H$_{47}$N$_8$O$_3$: 719.38; found 719.51; HRMS: Anal. Calcd. for [M + H]$^+$ C$_{44}$H$_{47}$N$_8$O$_2$: 719.3822; found 719.3829 |
| M39 | (2R)-1-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-1-oxo-2-propanol | 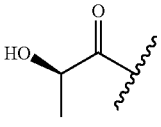 | 1.09 min (Cond. 1); >98%; LC/MS: Anal. Calcd. for [M + H]$^+$ C$_{41}$H$_{48}$N$_7$O$_3$: 686.38; found 686.58; HRMS: Anal. Calcd. for [M + H]$^+$ C$_{41}$H$_{48}$N$_7$O$_3$: 686.3819; found 686.3843 |

-continued

| Example | Compound Name | (Source) | RT (LC-Cond.); % homogeneity index; MS data |
|---------|---------------|----------|----------------------------------------------|
| M40 | (2S)-1-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-1-oxo-2-propanol | | 1.09 min (Cond. 1); >98%; LC/MS: Anal. Calcd. for [M + H]$^+$ C$_{41}$H$_{48}$N$_7$O$_3$: 686.38; found 686.57; HRMS: Anal. Calcd. for [M + H]$^+$ C$_{41}$H$_{48}$N$_7$O$_3$: 686.3819; found 686.3832 |
| M41 | methyl (1-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)cyclobutyl)carbamate | (Cap-64) | 1.19 min (Cond. 1); >98%; LC/MS: Anal. Calcd. for [M + H]$^+$ C$_{45}$H$_{53}$N$_8$O$_4$: 769.42; found 769.66; HRMS: Anal. Calcd. for [M + H]$^+$ C$_{45}$H$_{53}$N$_8$O$_4$: 769.419; found 469.4155 |
| M42 | methyl (1-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)cyclopentyl)carbamate | (Cap-63) | 1.25 min (Cond. 1); >98%; LC/MS: Anal. Calcd. for [M + H]$^+$ C$_{46}$H$_{55}$N$_8$O$_4$: 783.43; found 783.69; HRMS: Anal. Calcd. for [M + H]$^+$ C$_{46}$H$_{55}$N$_8$O$_4$: 783.4346; found 783.4357 |
| M43 | N-((1S)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-1-methyl-2-oxoethyl)-N-propyl-1-propanamine | (Cap-70b) | 1.10 min (Cond. 1); >98%; LC/MS: Anal. Calcd. for [M + H]$^+$ C$_{47}$H$_{61}$N$_8$O$_2$: 769.49; found 769.69; HRMS: Anal. Calcd. for [M + H]$^+$ C$_{47}$H$_{61}$N$_8$O$_2$: 769.4917; found 769.4925 |
| M44 | (4S)-4-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)-1,3-oxazolidin-2-one | (Cap-81) | 1.08 min (Cond. 1); >98%; LC/MS: Anal. Calcd. for [M + H]$^+$ C$_{42}$H$_{47}$N$_8$O$_4$: 727.37; found 727.56; HRMS: Anal. Calcd. for [M + H]$^+$ C$_{42}$H$_{47}$N$_8$O$_4$: 727.3720; found 727.3740 |
| M45 | (2R)-1-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-N,N-diethyl-3-methyl-1-oxo-2-butanamine | (Cap-72) | 1.08 min (Cond. 1); >98%; LC/MS: Anal. Calcd. for [M + H]$^+$ C$_{47}$H$_{61}$N$_8$O$_2$: 769.49; found 769.73; HRMS: Anal. Calcd. for [M + H]$^+$ C$_{47}$H$_{61}$N$_8$O$_2$: 769.4917; found 769.4898 |

-continued

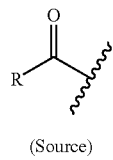

| Example | Compound Name | (Source) | RT (LC-Cond.); % homogeneity index; MS data |
|---|---|---|---|
| M46 | N-((1R)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-1-methyl-2-oxoethyl)-N-propyl-1-propanamine | 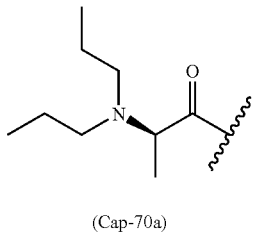<br>(Cap-70a) | 1.12 min (Cond. 1); >98%; LC/MS: Anal. Calcd. for [M + H]$^+$ $C_{47}H_{61}N_8O_2$: 769.49; found 769.45; HRMS: Anal. Calcd. for [M + H]$^+$ $C_{47}H_{61}N_8O_2$: 769.4917; found 769.4915 |
| M47 | methyl ((1R)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-2-oxo-1-phenylethyl)carbamate | 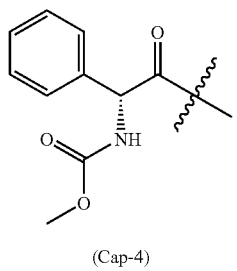<br>(Cap-4) | 1.85 min (Cond. 2); 97%; LC/MS: Anal. Calcd. for [M + H]$^+$ $C_{48}H_{53}N_8O_4$: 805.42; found 805.4; HRMS: Anal. Calcd. for [M + H]$^+$: $C_{48}H_{53}N_8O_4$ 805.4190; found 805.4196. |
| M48 | (1R)-N,N-diethyl-2-(2S)-2-(5-(4'-(2-((2S)-1-((2R)-2-(4-morpholinyl)-2-phenylacetyl)-2-pyrrolidinyl)-1H-imidazol-5-yl)-4-biphenylyl)-1H-imidazol-2-yl)-1-pyrrolidinyl)-2-oxo-1-phenylethanamine | 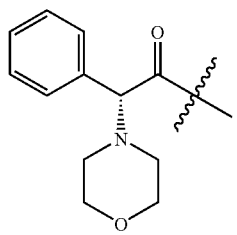<br>(Cap-6) | 1.69 min (Cond. 2); 98%; LC/MS: Anal. Calcd. for [M + H]$^+$ $C_{50}H_{57}N_8O_3$: 817.45; found 817.48; HRMS: Anal. Calcd. for [M + H]$^+$ $C_{50}H_{57}N_8O_3$: 817.4554; found 817.4589. |
| M49 | methyl ((1S)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-1-methyl-2-oxoethyl)carbamate | 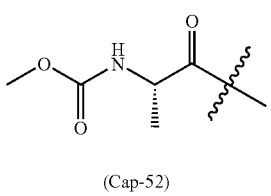<br>(Cap-52) | 1.67 min (Cond. 2); 92%; LC/MS: Anal. Calcd. for [M + H]$^+$ $C_{43}H_{51}N_8O_4$: 743.40; found 743.42; HRMS: Anal. Calcd. for [M + H]$^+$ $C_{43}H_{51}N_8O_4$: 743.4033; found 743.4053. |
| M50 | methyl (2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-2-oxoethyl)carbamate | 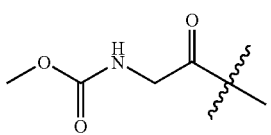 | 1.63 min (Cond. 2); 99%; LC/MS: Anal. Calcd. for [M + H]$^+$ $C_{42}H_{49}N_8O_4$: 729.39; found 729.39; HRMS: Anal. Calcd. for [M + H]$^+$ $C_{42}H_{49}N_8O_4$: 729.3877; found 729.3888. |

-continued

| Example | Compound Name | (Source) | RT (LC-Cond.); % homogeneity index; MS data |
|---|---|---|---|
| M51 | (1R)-N,N-diethyl-2-((2S)-2-(5-(4'-(2-((2S)-1-(4-morpholinylcarbonyl)-2-pyrrolidinyl)-1H-imidazol-5-yl)-4-biphenylyl)-1H-imidazol-2-yl)-1-pyrrolidinyl)-2-oxo-1-phenylethanamine | | 1.67 min (Cond. 2); 99%; LC/MS: Anal. Calcd. for [M + H]$^+$ $C_{43}H_{51}N_8O_3$: 727.41; found 727.40; HRMS: Anal. Calcd. for [M + H]$^+$ $C_{43}H_{51}N_8O_3$: 727.4084; found 727.4117. |
| M52 | (1R)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-N,N-dimethyl-2-oxo-1-phenylethanamine | (Cap-1) | 1.65 min (Cond. 2); 92%; LC/MS: Anal. Calcd. for [M + H]$^+$ $C_{48}H_{55}N_8O_2$: 775.44; found 775.48; HRMS: Anal. Calcd. for [M + H]$^+$ $C_{48}H_{55}N_8O_2$: 775.4448; found 775.4433. |
| M53 | methyl ((1R)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-1-methyl-2-oxoethyl)carbamate | (Cap-85) | 1.68 min (Cond. 2); 98%; LC/MS: Anal. Calcd. for [M + H]$^+$ $C_{43}H_{51}N_8O_4$: 743.40; found 743.42; HRMS: Anal. Calcd. for [M + H]$^+$ $C_{43}H_{51}N_8O_4$: 743.4033; found 743.4055. |
| M54 | methyl ((1R)-1-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)propyl)carbamate | (Cap-53a) | 1.78 min (Cond. 2); >99%; LC/MS: Anal. Calcd. for [M + H]$^+$ $C_{44}H_{53}N_8O_4$: 757.42; found 757.42; HRMS: Anal. Calcd. for [M + H]$^+$ $C_{44}H_{53}N_8O_4$: 757.4190; found 757.4216. |
| M55 | methyl ((1S)-1-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)propyl)carbamate | (Cap-53b) | 1.74 min (Cond. 2); >99%; LC/MS: Anal. Calcd. for [M + H]$^+$ $C_{44}H_{53}N_8O_4$: 757.42; found 757.41; HRMS: Anal. Calcd. for [M + H]$^+$ $C_{44}H_{53}N_8O_4$: 757.4190; found 757.4212. |
| M56 | methyl ((1R)-1-cyclopropyl-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-2-oxoethyl)carbamate | (Cap-54a) | 1.74 min (Cond. 2); >99%; LC/MS: Anal. Calcd. for [M + H]$^+$ $C_{45}H_{53}N_8O_4$: 769.42; found 769.52; HRMS: Anal. Calcd. for [M + H]$^+$ $C_{45}H_{53}N_8O_4$: 769.4190; found 769.4188. |

-continued

| Example | Compound Name | (Source) | RT (LC-Cond.); % homogeneity index; MS data |
|---------|---------------|----------|----------------------------------------------|
| M57 | methyl ((1S)-1-cyclopropyl-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-2-oxoethyl)carbamate | (Cap-54b) | 1.72 min (Cond. 2); >99%; LC/MS: Anal. Calcd. for [M + H]$^+$ $C_{45}H_{53}N_8O_4$: 769.42; found 769.53; HRMS: Anal. Calcd. for [M + H]$^+$ $C_{45}H_{53}N_8O_4$: 769.4190; found 769.4218. |
| M58 | methyl ((1S)-1-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)-2-methylpropyl)carbamate | (Cap-51) | 1.76 min (Cond. 2); >99%; LC/MS: Anal. Calcd. for [M + H]$^+$ $C_{45}H_{55}N_8O_4$: 771.43; found 771.54; HRMS: Anal. Calcd. for [M + H]$^+$ $C_{45}H_{53}N_8O_4$: 771.4346; found 771.4379. |
| M59 | methyl ((1S)-1-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)-2,2-dimethylpropyl)carbamate | | 1.92 min (Cond. 2); 99%; LC/MS: Anal. Calcd. for [M + H]$^+$ $C_{46}H_{57}N_8O_6$: 785.45; found 785.63; HRMS: Anal. Calcd. for [M + H]$^+$ $C_{42}H_{57}N_8O_4$: 785.4503; found 785.4515. |
| M60 | methyl ((1S)-1-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)-3-buten-1-yl)carbamate | (Cap-55) | 1.81 min (Cond. 2); 99%; LC/MS: Anal. Calcd. for [M + H]$^+$ $C_{45}H_{53}N_8O_4$: 769.42; found 769.55; HRMS: Anal. Calcd. for [M + H]$^+$ $C_{45}H_{53}N_8O_4$: 769.4190; found 769.4157. |
| M61 | methyl ((1S)-2-((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)-1-(methoxymethyl)-2-oxoethyl)carbamate | (Cap-56) | 1.73 min (Cond. 2); 99%; LC/MS: Anal. Calcd. for [M + H]$^+$ $C_{44}H_{53}N_8O_5$: 773.41; found 773.55; HRMS: Anal. Calcd. for [M + H]$^+$ $C_{44}H_{53}N_8O_5$: 773.4139; found 773.4107. |
| M62 | methyl ((1S)-1-(((2S)-2-(5-(4'-(2-((2S)-1-((2R)-2-(diethylamino)-2-phenylacetyl)-2-pyrrolidinyl)-1H-imidazol-5-yl)-4-biphenylyl)-1H-imidazol-2-yl)-1-pyrrolidinyl)carbonyl)butyl)carbamate | (Cap-57) | 1.73 min (Cond. 2); 99%; LC/MS: Anal. Calcd. for [M + H]$^+$ $C_{45}H_{55}N_8O_4$: 771.43; found 771.56 (M + H)$^+$; HRMS: Anal. Calcd. for [M + H]$^+$ $C_{45}H_{55}N_8O_4$: 771.4346; found 771.4315. |

Example M63-M66

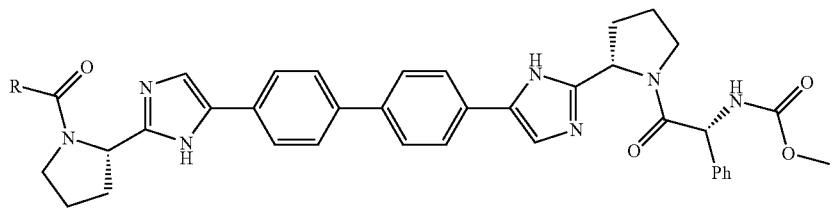

Example M63-M66x were prepared from 28f and the respective acids using the method described for Example 28. Products were prepared as TFA salts unless noted otherwise.

| Example | Compound Name | (Source) | RT (LC-Cond.); % homogeneity index; MS data |
|---|---|---|---|
| M63 | methyl ((1R)-2-((2S)-2-(5-(4'-(2-((2S)-1-(N,N-diethyl-D-alanyl)-2-pyrrolidinyl)-1H-imidazol-5-yl)-4-biphenylyl)-1H-imidazol-2-yl)-1-pyrrolidinyl)-2-oxo-1-phenylethyl)carbamate | (Cap-69a) | 1.17 min (Cond. 1); >98%; LC/MS: Anal. Calcd. for [M + H]$^+$ $C_{43}H_{51}N_8O_4$: 743.40; found 743.41; HRMS: Anal. Calcd. for [M + H]$^+$ $C_{43}H_{51}N_8O_4$: 743.4033; found 743.4017 |
| M64 | methyl ((1R)-2-((2S)-2-(5-(4'-(2-((2S)-1-(N,N-dipropyl-D-alanyl)-2-pyrrolidinyl)-1H-imidazol-5-yl)-4-biphenylyl)-1H-imidazol-2-yl)-1-pyrrolidinyl)-2-oxo-1-phenylethyl)carbamate | (Cap-70a) | 1.22 min (Cond. 1); >98%; LC/MS: Anal. Calcd. for [M + H]$^+$ $C_{45}H_{55}N_8O_4$: 771.43; found 771.39; HRMS: Anal. Calcd. for [M + H]$^+$ $C_{45}H_{55}N_8O_4$: 771.4346; found 771.4361 |
| M65 | methyl ((1R)-2-((2S)-2-(5-(4'-(2-((2S)-1-(1H-imidazol-5-ylcarbonyl)-2-pyrrolidinyl)-1H-imidazol-5-yl)-4-biphenylyl)-1H-imidazol-2-yl)-1-pyrrolidinyl)-2-oxo-1-phenylethyl)carbamate | | 1.15 min (Cond. 1); >90%; LC/MS: Anal. Calcd. for [M + H]$^+$ $C_{40}H_{40}N_9O_4$: 710.32; found 710.31; HRMS: Anal. Calcd. for [M + H]$^+$ $C_{40}H_{40}N_9O_4$: 710.3203; found 710.3180 |

-continued

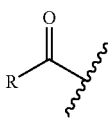
(Source)

| Example | Compound Name | (Source) | RT (LC-Cond.); % homogeneity index; MS data |
|---|---|---|---|
| M66a & M66b | M66a: methyl ((1R)-2-((2S)-2-(5-(4'-(2-((2S)-1-(4-(diethylamino)-2-((methoxycarbonyl)amino)butanoyl)-2-pyrrolidinyl)-1H-imidazol-5-yl)-4-biphenylyl)-1H-imidazol-2-yl)-1-pyrrolidinyl)-2-oxo-1-phenylethyl)carbamate | 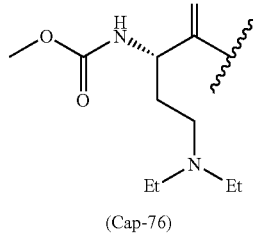<br>(Cap-76) | Two fractions enriched with one of two compounds exhibiting very similar spectral data were isolated. M66a: 1.19 min (Cond. 1); 97%; LC/MS: Anal. Calcd. for [M + H]+ $C_{46}H_{56}N_9O_6$: 830.44; found 830.39 M66b: 1.21 min (Cond. 1); >97%; LC/MS: Anal. Calcd. for [M + H]+ $C_{46}H_{56}N_9O_6$: 830.44; found 830.39; HRMS: Anal. Calcd. for [M + H]+ $C_{46}H_{56}N_9O_6$: 830.4354; found 830.4316 |
| M66x (AcOH) | methyl ((1R)-2-((2S)-2-(5-(4'-(2-((2S)-1-((2R)-2-(diethylamino)butanoyl)-2-pyrrolidinyl)-1H-imidazol-5-yl)-4-biphenylyl)-1H-imidazol-2-yl)-1-pyrrolidinyl)-2-oxo-1-phenylethyl)carbamate | 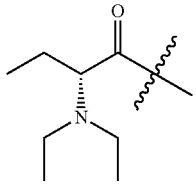 | 1.80 minutes (Cond. 2); (98%); LC/MS: Anal. Calcd. for [M + H]+ $C_{44}H_{53}N_8O_4$ 757.42; found 757.48; HRMS: Anal. Calcd for [M + H]+ $C_{44}H_{53}N_8O_4$: 757.4190; found 757.4156 |

Example M67-M91

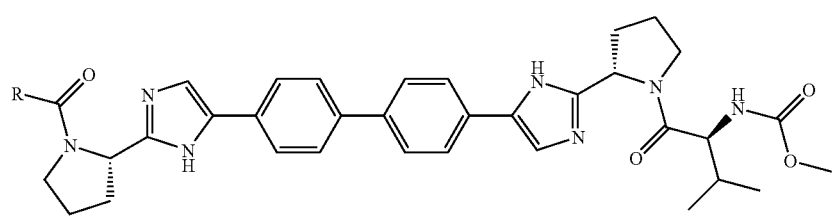

Example M67-M91y were prepared from 28d and the respective acids using the method described for Example 28. Final products were prepared as TFA salts, unless noted otherwise.

| Example | Compound Name | (Source) | RT (LC-Cond.); % homogeneity index; MS data |
|---|---|---|---|
| M67a & M67b | M67a: methyl ((1S)-1-(((2S)-2-(5-(4'-(2-((2S)-1-(4-(diethylamino)-2-((methoxycarbonyl)amino)butanoyl)-2-pyrrolidinyl)-1H-imidazol-5-yl)-4-biphenylyl)-1H-imidazol-2-yl)-1-pyrrolidinyl)carbonyl)-2-methylpropyl)carbamate | 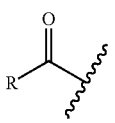 (Cap-76) | Two fractions enriched with one of two compounds exhibiting very similar spectral data were isolated M67a: 1.16 min (Cond. 1); >98%; LC/MS: Anal. Calcd. for [M + H]$^+$ $C_{43}H_{58}N_9O_6$: 796.45; found 796.40 M67b: 1.17 min (Cond. 1); >96%; LC/MS: Anal. Calcd. for [M + H]$^+$ $C_{43}H_{58}N_9O_6$: 796.45; found 796.40; HRMS: Anal. Calcd. for [M + H]$^+$ $C_{43}H_{58}N_9O_6$: 796.4510; found 796.4537 |
| M68 (•AcOH) | methyl ((1S)-1-(((2S)-2-(5-(4'-2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-3-(4-morpholinyl)propyl)carbamate | 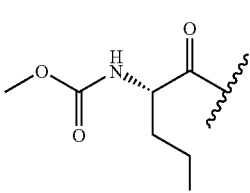 (Cap-79) | 1.10 min (Cond. 1); >96%; LC/MS: Anal. Calcd. for [M + H]$^+$ $C_{43}H_{56}N_9O_7$: 810.43; found 810.44; HRMS: Anal. Calcd. for [M + H]$^+$ $C_{43}H_{56}N_9O_7$: 810.4303; found 810.4333 |
| M69 | methyl ((1S)-1-(((2S)-2-(5-(4'-(2-((2S)-1-(N,N-diethyl-L-alanyl)-2-pyrrolidinyl)-1H-imidazol-5-yl)-4-biphenylyl)-1H-imidazol-2-yl)-1-pyrrolidinyl)carbonyl)-2-methylpropyl)carbamate | 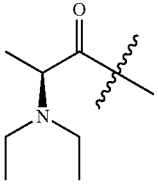 (Cap-69b) | 1.72 min (Cond. 2); 98%; LC/MS: Anal. Calcd. for [M + H]$^+$ $C_{40}H_{53}N_8O_4$: 709.42; found 709.56; HRMS: Anal. Calcd. for [M + H]$^+$ $C_{40}H_{53}N_8O_4$: 709.4190; found 709.4219. |
| M70 | methyl ((1S)-1-(((2S)-2-(5-(4'-(2-((2S)-1-(N,N-diethyl-D-alanyl)-2-pyrrolidinyl)-1H-imidazol-5-yl)-4-biphenylyl)-1H-imidazol-2-yl)-1-pyrrolidinyl)carbonyl)-2-methylpropyl)carbamate | 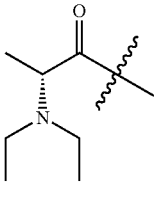 (Cap-69a) | 1.75 min (Cond. 2); 99%; LC/MS: Anal. Calcd. for [M + H]$^+$ $C_{40}H_{53}N_8O_4$: 709.42; found 709.55; HRMS: Anal. Calcd. for [M + H]$^+$ $C_{40}H_{53}N_8O_4$: 709.4190; found 709.4184. |

-continued

| Example | Compound Name | (Source) | RT (LC-Cond.); % homogeneity index; MS data |
|---|---|---|---|
| M71 | methyl ((1S)-2-((2S)-2-(5-(4'-(2-((2S)-1-(N-(methoxycarbonyl)-L-valyl)-2-pyrrolidinyl)-1H-imidazol-5-yl)-4-biphenylyl)-1H-imidazol-2-yl)-1-pyrrolidinyl)-1-(methoxymethyl)-2-oxoethyl)carbamate | (Cap-56) | 1.81 min (Cond. 2); 97%; LC/MS: Anal. Calcd. for [M + H]$^+$ C$_{39}$H$_{49}$N$_8$O$_7$: 741.37; found 741.48; HRMS: Anal. Calcd. for [M + H]$^+$ C$_{39}$H$_{49}$N$_8$O$_7$: 741.3724; found 741.3738. |
| M72 | methyl ((1S)-1-(((2S)-2-(5-(4'-(2-((2S)-1-((2S)-2-((methoxycarbonyl)amino)-3,3-dimethylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate |  | 2.07 min (Cond. 2); 97%; LC/MS: Anal. Calcd. for [M + H]$^+$ C$_{41}$H$_{53}$N$_8$O$_6$: 753.41; found 753.53; HRMS: Anal. Calcd. for [M + H]$^+$ C$_{41}$H$_{53}$N$_8$O$_6$: 753.4088; found 753.4111. |
| M73 | methyl (2-((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)-2-oxoethyl)carbamate |  | 1.80 min (Cond. 2); 97%; LC/MS: Anal. Calcd. for [M + H]$^+$ C$_{37}$H$_{45}$N$_8$O$_6$: 697.35; found 697.32; HRMS: Anal. Calcd. for [M + H]$^+$ C$_{37}$H$_{45}$N$_8$O$_6$: 697.3462; found 697.3443. |
| M74 | methyl ((1S)-1-(((2S)-2-(5-(4'-(2-((2S)-1-((2S)-2-((methoxycarbonyl)amino)butanoyl)-2-pyrrolidinyl)-1H-imidazol-5-yl)-4-biphenylyl)-1H-imidazol-2-yl)-1-pyrrolidinyl)carbonyl)-2-methylpropyl)carbamate | (Cap-53b) | 1.90 min (Cond. 2); 98%; LC/MS: Anal. Calcd. for [M + H]$^+$ C$_{39}$H$_{49}$N$_8$O$_6$: 725.37; found 725.36; HRMS: Anal. Calcd. for [M + H]$^+$ C$_{39}$H$_{49}$N$_8$O$_6$: 725.3775; found 725.3742. |
| M75 | methyl ((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)butyl)carbamate | (Cap-57) | 1.96 min (Cond. 2); 98%; LC/MS: Anal. Calcd. for [M + H]$^+$ C$_{40}$H$_{51}$N$_8$O$_6$: 739.39; found 739.37; HRMS: Anal. Calcd. for [M + H]$^+$ C$_{40}$H$_{51}$N$_8$O$_6$: 739.3932; found 739.3953. |
| M76 | methyl ((1S)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-3-buten-1-yl)carbamate | (Cap-55) | 1.91 min (Cond. 2); 98%; LC/MS: Anal. Calcd. for [M + H]$^+$ C$_{40}$H$_{49}$N$_8$O$_6$: 737.38; found 737.38; HRMS: Anal. Calcd. C$_{40}$H$_{49}$N$_8$O$_6$: 737.3775; found 737.3744. |

| Example | Compound Name | (Source) | RT (LC-Cond.); % homogeneity index; MS data |
|---|---|---|---|
| M77 | methyl ((1S)-1-(((2S)-2-(5-(4'-(2-((2S)-1-((2S)-2-cyclopropyl-2-((methoxycarbonyl)amino)acetyl)-2-pyrrolidinyl)-1H-imidazol-5-yl)-4-biphenylyl)-1H-imidazol-2-yl)-1-pyrrolidinyl)carbonyl)-2-methylpropyl)carbamate | (Cap-54b) | 1.90 min (Cond. 2); 98%; LC/MS: Anal. Calcd. for [M + H]$^+$ C$_{40}$H$_{49}$N$_8$O$_6$ 737.38; found 737.34; HRMS: Anal. Calcd. for [M + H]$^+$ C$_{40}$H$_{49}$N$_8$O$_6$ 737.3775; found 737.3764. |
| M78 | methyl ((1S)-1-(((2S)-2-(5-(4'-(2-((2S)-1-((2R)-2-(ethyl(methyl)amino)-2-phenylacetyl)-2-pyrrolidinyl)-1H-imidazol-5-yl)-4-biphenylyl)-1H-imidazol-2-yl)-1-pyrrolidinyl)carbonyl)-2-methylpropyl)carbamate | (Cap-3) | 1.82 min (Cond. 2); 98%; LC/MS: Anal. Calcd. for [M + H]$^+$ C$_{44}$H$_{53}$N$_8$O$_4$ 757.42; found 757.42; HRMS: Anal. Calcd. for [M + H]$^+$ C$_{44}$H$_{53}$N$_8$O$_4$ 757.4190; found 757.4188. |
| M79 | methyl ((1S)-1-(((2S)-2-(5-(4'-(2-((2S)-1-(N,N-diethyl-D-valyl)-2-pyrrolidinyl)-1H-imidazol-5-yl)-4-biphenylyl)-1H-imidazol-2-yl)-1-pyrrolidinyl)carbonyl)-2-methylpropyl)carbamate | (Cap-72) | 1.78 min (Cond. 2); 94%; LC/MS: Anal. Calcd. for [M + H]$^+$ C$_{42}$H$_{57}$N$_8$O$_4$ 737.45; found 737.45; HRMS: Anal. Calcd. for [M + H]$^+$ C$_{42}$H$_{57}$N$_8$O$_4$ 737.4503; found 737.4488. |
| M80 | methyl ((1S)-1-(((2S)-2-(5-(4'-(2-((2S)-1-((2R)-2-((methoxycarbonyl)amino)-2-phenylacetyl)-2-pyrrolidinyl)-1H-imidazol-5-yl)-4-biphenylyl)-1H-imidazol-2-yl)-1-pyrrolidinyl)carbonyl)-2-methylpropyl)carbamate | (Cap-4) | 2.05 min (Cond. 2); 99%; LC/MS: Anal. Calcd. for [M + H]$^+$ C$_{43}$H$_{49}$N$_8$O$_6$ 773.37; found 773.40; HRMS: Anal. Calcd. for [M + H]$^+$ C$_{43}$H$_{49}$N$_8$O$_6$ 773.375; found 773.3759. |
| M81 | methyl ((1S)-2-methyl-1-(((2S)-2-(5-(4'-(2-((2S)-1-(3-methylbutanoyl)-2-pyrrolidinyl)-1H-imidazol-5-yl)-4-biphenylyl)-1H-imidazol-2-yl)-1-pyrrolidinyl)carbonyl)propyl)carbamate | | 2.05 min (Cond. 2); 99%; LC/MS: Anal. Calcd. for [M + H]$^+$ C$_{38}$H$_{48}$N$_7$O$_4$ 666.38; found 666.37; HRMS: Anal. Calcd. for [M + H]$^+$ C$_{38}$H$_{48}$N$_7$O$_4$ 666.3768; found 666.3785. |

-continued

| Example | Compound Name | 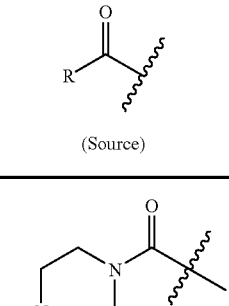 (Source) | RT (LC-Cond.); % homogeneity index; MS data |
|---------|---------------|---------|---------|
| M82 | methyl ((1S)-2-methyl-1-(((2S)-2-(5-(4'-(2-((2S)-1-((4-methyl-1-piperazinyl)carbonyl)-2-pyrrolidinyl)-1H-imidazol-5-yl)-4-biphenylyl)-1H-imidazol-2-yl)-1-pyrrolidinyl)carbonyl)propyl)carbamate | | 1.75 min (Cond. 2); 98%; LC/MS: Anal. Calcd. for [M + H]$^+$ C$_{39}$H$_{50}$N$_9$O$_4$ 708.40; found 708.38; HRMS: Anal. Calcd. for [M + H]$^+$ C$_{39}$H$_{50}$N$_9$O$_4$ 708.3986; found 708.3974. |
| M83 | methyl ((1S)-1-(((2S)-2-(5-(4'-(2-((2S)-1-(N,N-dipropyl-D-alanyl)-2-pyrrolidinyl)-1H-imidazol-5-yl)-4-biphenylyl)-1H-imidazol-2-yl)-1-pyrrolidinyl)carbonyl)-2-methylpropyl)carbamate | 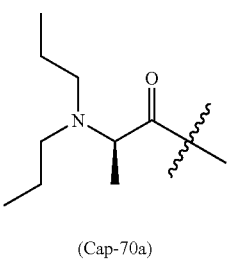 (Cap-70a) | 1.81 min (Cond. 2); 98%; LC/MS: Anal. Calcd. for [M + H]$^+$ C$_{42}$H$_{57}$N$_8$O$_4$ 737.45; found 737.47; HRMS: Anal. Calcd. for [M + H]$^+$ C$_{42}$H$_{57}$N$_8$O$_4$ 737.4503; found 737.4480. |
| M84 | methyl ((1S)-1-(((2S)-2-(5-(4'-(2-((2S)-1-(N,N-dipropyl-L-alanyl)-2-pyrrolidinyl)-1H-imidazol-5-yl)-4-biphenylyl)-1H-imidazol-2-yl)-1-pyrrolidinyl)carbonyl)-2-methylpropyl)carbamate | 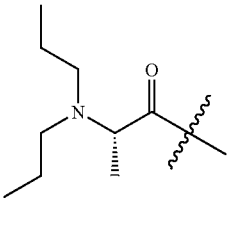 (Cap-70b) | 1.78 min (Cond. 2); 99%; LC/MS: Anal. Calcd. for [M + H]$^+$ C$_{42}$H$_{57}$N$_8$O$_4$ 737.45; found 737.47; HRMS: Anal. Calcd. for [M + H]$^+$ C$_{42}$H$_{57}$N$_8$O$_4$ 737.4503; found 737.4491. |
| M85 | methyl ((1S)-1-(((2S)-2-(5-(4'-(2-((2S)-1-((2R)-2-(diethylamino)butanoyl)-2-pyrrolidinyl)-1H-imidazol-5-yl)-4-biphenylyl)-1H-imidazol-2-yl)-1-pyrrolidinyl)carbonyl)-2-methylpropyl)carbamate | 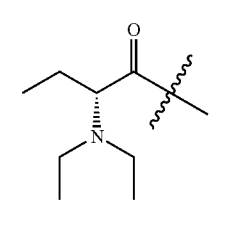 (Cap-71a) | 1.76 min (Cond. 2); 98%; LC/MS: Anal. Calcd. for [M + H]$^+$ C$_{41}$H$_{55}$N$_8$O$_4$ 723.43; found 723.47; HRMS: Anal. Calcd. for [M + H]$^+$ C$_{41}$H$_{55}$N$_8$O$_4$ 723.4346; found 723.4335. |
| M86 | methyl ((1S)-1-(((2S)-2-(5-(4'-(2-((2S)-1-((2S)-2-(diethylamino)butanoyl)-2-pyrrolidinyl)-1H-imidazol-5-yl)-4-biphenylyl)-1H-imidazol-2-yl)-1-pyrrolidinyl)carbonyl)-2-methylpropyl)carbamate | 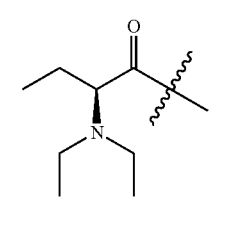 (Cap-71b) | 1.73 min (Cond. 2); 98%; LC/MS: Anal. Calcd. for [M + H]$^+$ C$_{41}$H$_{55}$N$_8$O$_4$ 723.43; found 723.47; HRMS: Anal. Calcd. for [M + H]$^+$ C$_{41}$H$_{55}$N$_8$O$_4$ 723.4346; found 723.4343. |

-continued

| Example | Compound Name | (Source) | RT (LC-Cond.); % homogeneity index; MS data |
|---|---|---|---|
| M87 | methyl ((1S)-1-(((2S)-2-(5-(4'-(2-((2S)-1-(1H-imidazol-4-ylcarbonyl)-2-pyrrolidinyl)-1H-imidazol-5-yl)-4-biphenylyl)-1H-imidazol-2-yl)-1-pyrrolidinyl)carbonyl)-2-methylpropyl)carbamate | (no Cap label) | 1.67 min (Cond. 2); 99%; LC/MS: Anal. Calcd. for [M + H]$^+$ C$_{37}$H$_{42}$N$_9$O$_4$ 676.34; found 676.45; HRMS: Anal. Calcd. for [M + H]$^+$ C$_{37}$H$_{42}$N$_9$O$_4$ 676.3360; found 676.3344. |
| M88 | methyl ((1S)-1-(((2S)-2-(5-(4'-(2-((2S)-1-(N,N-diethyl-O-methyl-L-seryl)-2-pyrrolidinyl)-1H-imidazol-5-yl)-4-biphenylyl)-1H-imidazol-2-yl)-1-pyrrolidinyl)carbonyl)-2-methylpropyl)carbamate | (Cap-73) | 1.67 min (Cond. 2); 97%; LCMS: Anal. Calcd. for [M + H]$^+$ C$_{41}$H$_{55}$N$_8$O$_5$ 739.43; found 739.54; HRMS: Anal. Calcd. for [M + H]$^+$ C$_{41}$H$_{55}$N$_8$O$_5$ 739.4295; found 739.4327. |
| M89 | methyl ((1S)-1-(((2S)-2-(5-(4'-(2-((2S)-1-(N$^2$,N$^2$-diethyl-D-asparaginyl)-2-pyrrolidinyl)-1H-imidazol-5-yl)-4-biphenylyl)-1H-imidazol-2-yl)-1-pyrrolidinyl)carbonyl)-2-methylpropyl)carbamate | (Cap-74) | 1.76 min (Cond. 2); 97%; LCMS: Anal. Calcd. for for [M + H]$^+$ C$_{41}$H$_{54}$N$_9$O$_5$ 752.42; found 752.43; HRMS: Anal. Calcd. for [M + H]$^+$ C$_{41}$H$_{54}$N$_9$O$_5$ 752.4248; found 752.4263. |
| M90 | methyl ((1S)-1-(((2S)-2-(5-(4'-(2-((2R)-1-((2R)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate | (Cap-84) | 2.00 min (Cond. 2); 98%; LC/MS: Anal. Calcd. for [M + H]$^+$ C$_{40}$H$_{51}$N$_8$O$_6$ 739.39; found 739.46; HRMS: Anal. Calcd. for [M + H]$^+$ C$_{40}$H$_{51}$N$_8$O$_6$ 739.3932; found 739.3901. |
| M91 | methyl ((1S)-1-(((2S)-2-(5-(4'-(2-((2S)-1-(N,N-diethyl-O-methyl-D-seryl)-2-pyrrolidinyl)-1H-imidazol-5-yl)-4-biphenylyl)-1H-imidazol-2-yl)-1-pyrrolidinyl)carbonyl)-2-methylpropyl)carbamate | (Cap-75) | 1.73 min (Cond. 2); 99%; LC/MS: Anal. Calcd. for [M + H]$^+$ C$_{41}$H$_{55}$N$_8$O$_5$ 739.43; found 739.39; HRMS: Anal. Calcd. for [M + H]$^+$ C$_{41}$H$_{55}$N$_8$O$_5$ 739.4295; found 739.4277. |
| M91x | methyl ((1S)-1-(((2S)-2-(5-(4'-(2-((2S)-1-(N,N-diethyl-3-methyl-D-valyl)-2-pyrrolidinyl)-1H-imidazol-5-yl)-4-biphenylyl)-1H-imidazol-2-yl)-1-pyrrolidinyl)carbonyl)-2-methylpropyl)carbamate | (no Cap label) | 1.78 minutes (Cond. 2); (97%); LC/MS: Anal. Calcd.for [M + H]$^+$ C$_{43}$H$_{59}$N$_8$O$_4$ 751.47; found 751.50; HRMS: Anal. Calcd for [M + H]$^+$ C$_{43}$H$_{59}$N$_8$O$_4$: 751.4659; found 751.4648. |

-continued

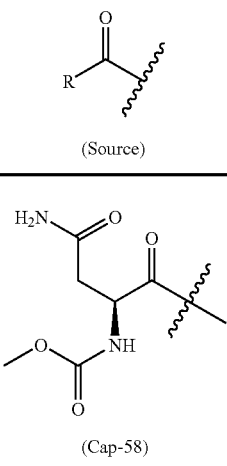

| Example | Compound Name | (Source) | RT (LC-Cond.); % homogeneity index; MS data |
|---|---|---|---|
| M91y | methyl ((1S)-3-amino-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-3-oxopropyl)carbamate (non-preferred name) | (Cap-58) | 1.92 min (Cond. 2); (>97%); LC/MS: Anal. Calcd. for [M + H]$^+$ C$_{39}$H$_{48}$N$_9$O$_7$ 754.37; found 754.42; HRMS: Anal. Calcd. for [M + H]$^+$ C$_{39}$H$_{48}$N$_9$O$_7$: 754.3677; found 754.3676. |

Example M92-M103

Example M92-M103 were prepared from 28d and the respective acids using the method described for Example 28. Final products were prepared as TFA salts, unless noted otherwise.

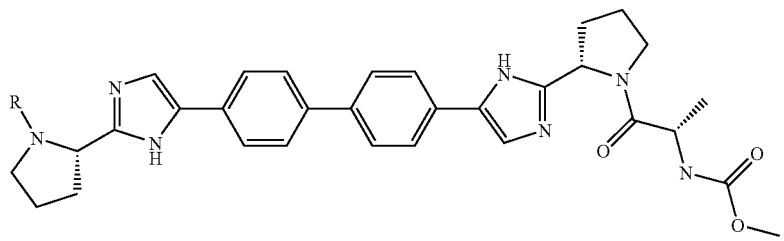

| Example | Compound Name | R (Source) | Analytical Data |
|---|---|---|---|
| M92 | methyl ((1S)-1-methyl-2-((2S)-2-(5-(4'-(2-((2S)-1-(1,3-oxazol-2-ylcarbonyl)-2-pyrrolidinyl)-1H-imidazol-5-yl)-4-biphenylyl)-1H-imidazol-2-yl)-1-pyrrolidinyl)-2-oxoethyl)carbamate | | 1.70 min (Cond. 2); 95%; LC/MS: Anal. Calcd. for [M + H]$^+$ C$_{35}$H$_{37}$N$_8$O$_5$ 649.29; found 649.41; HRMS: Anal. Calcd for [M + H]$^+$ C$_{35}$H$_{37}$N$_8$O$_5$ 649.2887; found 649.2867 |
| M93 | methyl ((1S)-1-cyclopropyl-2-((2S)-2-(5-(4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-2-oxoethyl)carbamate | (Cap-54b) | 1.76 min (Cond. 2); 98%; LC/MS: Anal. Calcd. for [M + H]$^+$ C$_{38}$H$_{45}$N$_8$O$_6$ 709.35; found 709.50; HRMS: Anal. Calcd for [M + H]$^+$ C$_{38}$H$_{47}$N$_8$O$_6$ 709.3462; found 709.3478 |

-continued

| Example | Compound Name | R (Source) | Analytical Data |
|---|---|---|---|
| M94 | methyl ((1S)-1-(((2S)-2-(5-(4'-(2-((2S)-1-((2S)-2-((methoxycarbonyl)amino)propanoyl)-2-pyrrolidinyl)-1H-imidazol-5-yl)-4-biphenylyl)-1H-imidazol-2-yl)-1-pyrrolidinyl)carbonyl)butyl)carbamate | (Cap-57) | 1.84 min (Cond. 2); 99%; LC/MS: Anal. Calcd. for [M + H]$^+$ C$_{38}$H$_{47}$N$_8$O$_6$ 711.36; found 711.54; HRMS: Anal. Calcd for [M + H]$^+$ C$_{38}$H$_{47}$N$_8$O$_6$ 711.3619; found 711.3590. |
| M95 | methyl ((1S)-1-(((2S)-2-(5-(4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)carbonyl)-2,2-dimethylpropyl)carbamate | | 1.91 min (Cond. 2); 99%; LC/MS: Anal. Calcd. for [M + H]$^+$ C$_{39}$H$_{49}$N$_8$O$_6$ 725.37; found 725.54; HRMS: Anal. Calcd for [M + H]$^+$ C$_{39}$H$_{49}$N$_8$O$_6$ 725.3775; found 725.3809. |
| M96 | methyl ((1S)-2-((2S)-2-(5-(4'-(2-((2S)-1-(N,N-diethyl-D-alanyl)-2-pyrrolidinyl)-1H-imidazol-5-yl)-4-biphenylyl)-1H-imidazol-2-yl)-1-pyrrolidinyl)-1-methyl-2-oxoethyl)carbamate | (Cap-69a) | 1.61 min (Cond. 2); 99%; LC/MS: Anal. Calcd. for [M + H]$^+$ C$_{38}$H$_{49}$N$_8$O$_4$ 681.39; found 681.54; HRMS: Anal. Calcd for [M + H]$^+$ C$_{38}$H$_{49}$N$_8$O$_4$ 681.3877; found 681.3867. |
| M97 | methyl ((1S)-2-((2S)-2-(5-(4'-(2-((2S)-1-(7-azabicyclo[2.2.1]hept-7-yl(phenyl)acetyl)-2-pyrrolidinyl)-1H-imidazol-5-yl)-4-biphenylyl)-1H-imidazol-2-yl)-1-pyrrolidinyl)-1-methyl-2-oxoethyl)carbamate | (Cap-77b) | 1.72 min (Cond. 2); 98%; LC/MS: Anal. Calcd. for [M + H]$^+$ C$_{45}$H$_{51}$N$_8$O$_4$ 767.40; found 767.59; HRMS: Anal. Calcd for [M + H]$^+$ C$_{45}$H$_{51}$N$_8$O$_4$ 767.4033; found 767.4067. |
| M98 | methyl ((1S)-2-((2S)-2-(5-(4'-(2-((2S)-1-((2R)-2-hydroxy-2-phenylacetyl)-2-pyrrolidinyl)-1H-imidazol-5-yl)-4-biphenylyl)-1H-imidazol-2-yl)-1-pyrrolidinyl)-1-methyl-2-oxoethyl)carbamate | | 1.80 min (Cond. 2); 99%; LC/MS: Anal. Calcd. for [M + H]$^+$ C$_{39}$H$_{42}$N$_7$O$_5$ 688.32; found 688.48; HRMS: Anal. Calcd for [M + H]$^+$ C$_{39}$H$_{42}$N$_7$O$_5$ 688.3247; found 688.3263. |
| M99 | methyl ((1S)-2-((2S)-2-(5-(4'-(2-((2S)-1-((2R)-2-(ethyl(methyl)amino)-2-phenylacetyl)-2-pyrrolidinyl)-1H-imidazol-5-yl)-4-biphenylyl)-1H-imidazol-2-yl)-1-pyrrolidinyl)-1-methyl-2-oxoethyl)carbamate | (Cap-3) | 1.70 min (Cond. 2); 99%; LC/MS: Anal. Calcd. for [M + H]$^+$ C$_{42}$H$_{49}$N$_8$O$_4$ 729.39; found 729.56; HRMS: Anal. Calcd for [M + H]$^+$ C$_{42}$H$_{49}$N$_8$O$_4$ 729.3877; found 729.3887. |

| Example | Compound Name | R (Source) | Analytical Data |
|---|---|---|---|
| M100 | methyl ((1S)-2-((2S)-2-(5-(4'-(2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-1-(methoxymethyl)-2-oxoethyl)carbamate | (Cap-56) | 1.75 min (Cond. 2); 99%; LC/MS: Anal. Calcd. for [M + H]$^+$ C$_{37}$H$_{45}$N$_8$O$_7$ 713.34; found 713.34. HRMS: Anal. Calcd for [M + H]$^+$ C$_{37}$H$_{45}$N$_8$O$_7$ 713.3411; found 713.3386. |
| M101 | methyl ((1S)-2-((2S)-2-(5-(4'-(2-((2S)-1-(N,N-diethyl-D-valyl)-2-pyrrolidinyl)-1H-imidazol-5-yl)-4-biphenylyl)-1H-imidazol-2-yl)-1-pyrrolidinyl)-1-methyl-2-oxoethyl)carbamate | (Cap-72) | 1.66 min (Cond. 2); 94%; LC/MS: Anal. Calcd. for [M + H]$^+$ C$_{40}$H$_{53}$N$_8$O$_4$ 709.42; found: 709.42; HRMS: Anal. Calcd for [M + H]$^+$ C$_{40}$H$_{53}$N$_8$O$_4$ 709.4190; found 709.4166. |
| M102 | methyl ((1S)-2-((2S)-2-(5-(4'-(2-((2S)-1-(N,N-dipropyl-D-alanyl)-2-pyrrolidinyl)-1H-imidazol-5-yl)-4-biphenylyl)-1H-imidazol-2-yl)-1-pyrrolidinyl)-1-methyl-2-oxoethyl)carbamate | (Cap-70a) | 1.71 min (Cond. 2); 98%; LC/MS: Anal. Calcd. for [M + H]$^+$ C$_{40}$H$_{53}$N$_8$O$_4$ 709.42; found 709.48; HRMS: Anal. Calcd for [M + H]$^+$ C$_{40}$H$_{53}$N$_8$O$_4$ 709.4190; found 709.4191. |
| M103 | methyl ((1S)-2-((2S)-2-(5-(4'-(2-((2S)-1-(N,N-dipropyl-L-alanyl)-2-pyrrolidinyl)-1H-imidazol-5-yl)-4-biphenylyl)-1H-imidazol-2-yl)-1-pyrrolidinyl)-1-methyl-2-oxoethyl)carbamate | (Cap-70b) | 1.66 min (Cond. 2); 98%; LC/MS: Anal. Calcd. for [M + H]$^+$ C$_{40}$H$_{53}$N$_8$O$_4$ 709.42; found 709.42; HRMS: Anal. Calcd for [M + H]$^+$ C$_{40}$H$_{53}$N$_8$O$_4$ 709.4190; found 709.4198. |

Example M104 methyl ((1S)-1-(((2S)-2-(5-(4'-(2-((2S)-1-(3-hydroxy-L-valyl)-2-pyrrolidinyl)-1H-imidazol-5-yl)-4-biphenylyl)-1H-imidazol-2-yl)-1-pyrrolidinyl)carbonyl)-2-methylpropyl)carbamate

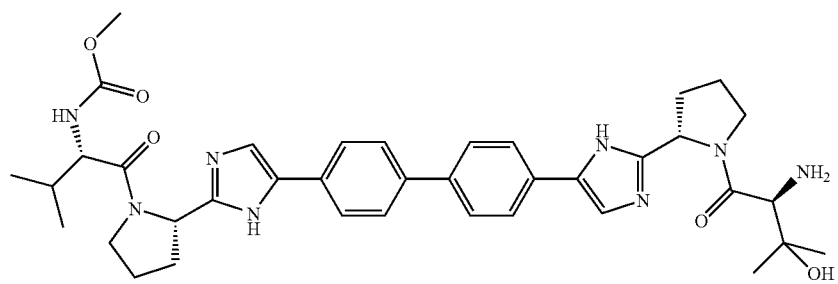

Example M104

Step a

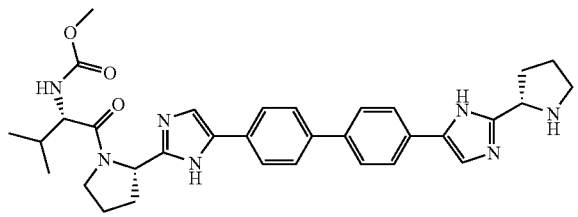

Pyrrolidine M104a was prepared from intermediate 28d and Cap-51 according to the procedure described for the synthesis of pyrrolidine 28f

Example M104

HATU (96.3 mg, 0.253 mmol) was added to a DMF (5.0 mL) solution of pyrrolidine M104a (150 mg, 0.217 mmol), (S)-2-(tert-butoxycarbonylamino)-3-hydroxy-3-methylbutanoic acid (65.8 mg, 0.282 mmol) and i-Pr$_2$EtN (180 uL, 1.03 mmol), and the reaction mixture was stirred at ambient condition for 35 min. The volatile component was removed in vacuo, and the residue was purified with a reverse phase HPLC (MeOH/H$_2$O/TFA), and the fractions were concentrated in vacuo. The resultant residue was treated with 25% TFA/CH$_2$Cl$_2$ (6.0 mL) and stirred for 3.25 hr. The volatile component was removed in vacuo and the residue was free-based (MCX; MeOH wash; 2.0 M NH$_3$/MeOH elution) to afford Example M104 as an off-white foam (107 mg). LC (Cond. 2): RT=1.03 min; >95% homogeneity index; LC/MS: Anal. Calcd. for [M+H]$^+$ C$_{38}$H$_{49}$N$_8$O$_5$=697.38. found 697.28.

Example M105 methyl ((1S)-1-(((2S)-2-(5-(4'-(2-((2S)-1-((2S)-3-hydroxy-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate

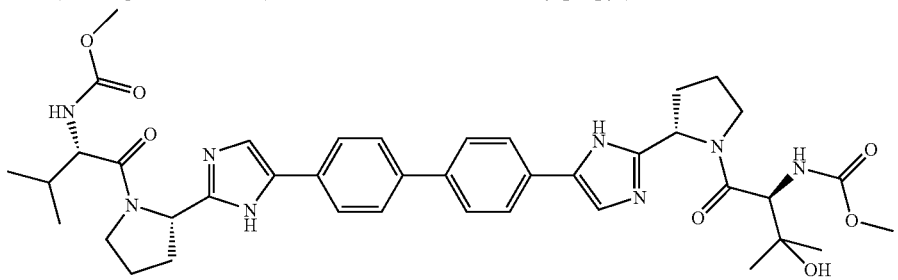

Methyl chloroformate (20 μL, 0.258 mmol) was added to a THF (2.0 mL) solution of Example M104 (82.9 mg, 0.119 mmol) and i-Pr$_2$EtN (50 uL, 0.287 mmol) and stirred for 65 min. The mixture was then treated with 2.0 M NH$_3$/MeOH (3 mL), stirred for 2.75 hr, and the volatile component was removed in vacuo. The resultant residue was purified with a reverse phase HPLC (MeOH/H$_2$O/TFA) to afford the TFA salt of Example M105 as a white foam (64.1 mg). LC (Cond. 2): RT=1.17 min; >98% homogeneity index; LC/MS: Anal. Calcd. for [M+H]$^+$ C$_{40}$H$_{51}$N$_8$O$_7$=755.39. found 755.25.

Example M106 methyl ((1S)-1-(((2S)-2-(5-(4'-(2-((2S)-1-((2S,3R)-4-hydroxy-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate

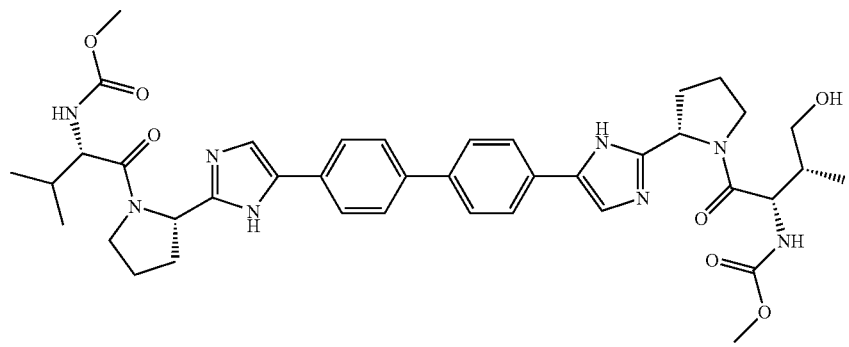

HATU (69 mg, 0.181 mmol) was added to a DMF (3.0 mL) solution of pyrrolidine M104a (101 mg, 0.173 mmol), Cap-80b (55.9 mg, ~0.183 mmol) and i-Pr$_2$EtN (90 μL, 0.515 mmol), and the reaction mixture was stirred at ambient condition for 70 min. The volatile component was removed in vacuo and the residue was purified with a reverse phase HPLC (H$_2$O/MeOH/TFA) to retrieve the dominant signal. The collected fraction was allowed to stand at ambient condition for a few hours and then the volatile component was removed in vacuo, at which time total desilylation of the coupled product was achieved. The resultant product was submitted to a reverse phase HPLC purification (ACN/H$_2$O/NH$_4$OAc) to afford Example M106 as an off-white foam (32.2 mg). LC (Cond. 2): RT=1.19 min; >95% homogeneity index; LC/MS: Anal. Calcd. for [M+H]$^+$ C$_{40}$H$_{51}$N$_8$O$_7$=755.39. found 755.85.

Example M107 methyl ((1S)-1-(((2S)-2-(5-(4'-(2-((2S)-1-((2S,3S)-4-hydroxy-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate

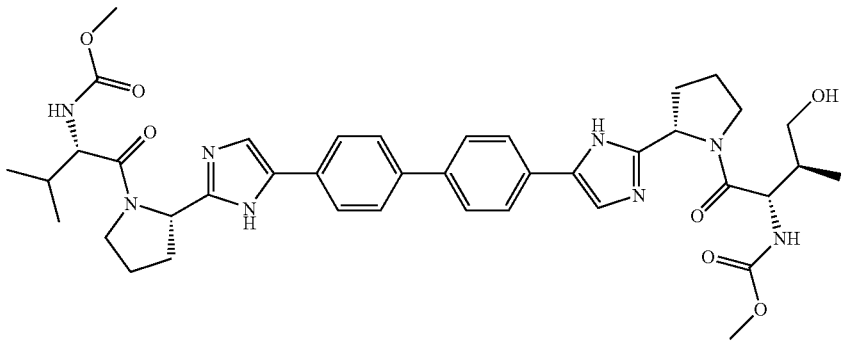

Example M107 was prepared from pyrrolidine M104a and Cap-80a according to the procedure described for the synthesis of Example M106. LC (Cond. 2): RT=1.20 min; ~95% homogeneity index; LC/MS: Anal. Calcd. for [M+H]$^+$ C$_{40}$H$_{51}$N$_8$O$_7$=755.39. found 755.78.

Example M108 methyl ((1S)-2-methyl-1-(((2S)-2-(5-(4'-(2-((2S)-1-L-valyl-2-pyrrolidinyl)-1H-imidazol-5-yl)-4-biphenylyl)-1H-imidazol-2-yl)-1-pyrrolidinyl)carbonyl)propyl)carbamate

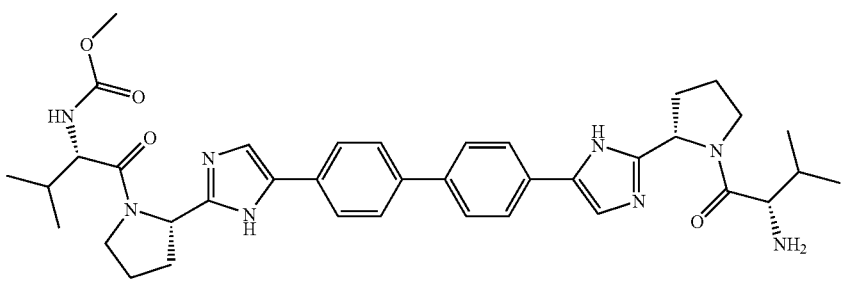

HATU (70.1 mg, 0.184 mmol) was added to a DMF (3.0 mL) solution of pyrrolidine M104a (100.7 mg, 0.173 mmol), (L)-Boc-Valine (49.6 mg, 0.228 mmol) and i-Pr$_2$EtN (70 uL, 0.40 mmol), and the reaction mixture was stirred at ambient condition for 65 min. The volatile component was removed in vacuo and the residue was purified with a Biotage (60-100% EtOAc/hexanes) to afford 116.6 mg of the coupled product.
The above product (112 mg) was treated with 25% TFA/CH$_2$Cl$_2$ (2 mL) and the reaction mixture was stirred for 6 hr. The volatile component was removed in vacuo and the crude material was purified with a combination of MCX resin (MeOH wash; 2.0 M NH$_3$/MeOH elution) and reverse phase HPLC (H$_2$O/MeOH/TFA) to afford the TFA salt of Example M108 as a white foam (98.5 mg). LC (Cond. 2): RT=1.14 min; >98% homogeneity index; LC/MS: Anal. Calcd. for [M+H]$^+$ C$_{38}$H$_{49}$N$_8$O$_4$=681.39. found 681.36. HRMS Calcd. for [M+H]$^+$ C$_{38}$H$_{49}$N$_8$O$_4$: 681.3877. found 681.3865.

Example M109 (R=Bn) & M110 (R=Me)

M109: benzyl (3S)-3-((methoxycarbonyl)amino)-4-((2S)-2-(5-(4'-(2-((2S)-1-(N-(methoxycarbonyl)-L-valyl)-2-pyrrolidinyl)-1H-imidazol-5-yl)-4-biphenylyl)-1H-imidazol-2-yl)-1-pyrrolidinyl)-4-oxobutanoate M110: methyl (3S)-3-((methoxycarbonyl)amino)-4-((2S)-2-(5-(4'-(2-((2S)-1-(N-(methoxycarbonyl)-L-valyl)-2-pyrrolidinyl)-1H-imidazol-5-yl)-4-biphenylyl)-1H-imidazol-2-yl)-1-pyrrolidinyl)-4-oxobutanoate

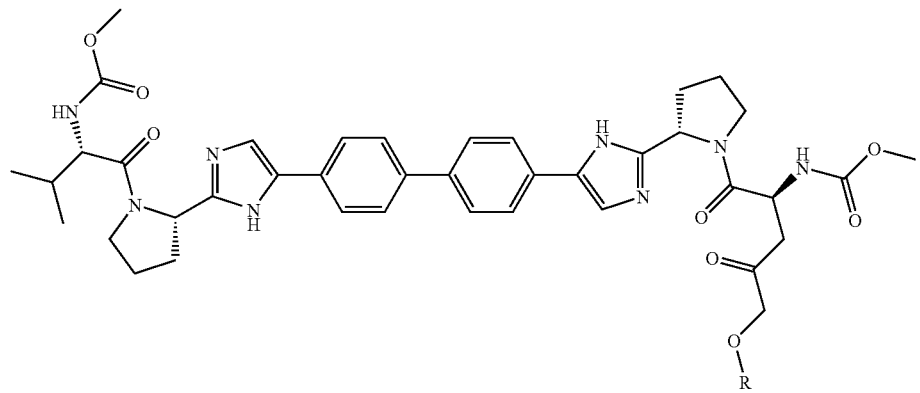

HATU (109 mg, 0.287 mmol) was added to DMF (1.5 ml) solution of pyrrolidine M104a (151 mg, 0.260 mmol), Cap-68 (109 mg, 387 mmol), and i-Pr$_2$EtN (100 µl, 0.574 mmol), and the reaction mixture was stirred at ambient condition for 3 hr. The volatile component was removed in vacuo and crude material was purified with a combination of MCX resin (MeOH wash; 2.0 M NH$_3$/MeOH elution) and reverse phase HPLC (H$_2$O/MeOH/TFA) to afford the TFA salt Example M109 (88.0 mg) and Example M110 (90.2 mg). Example M109: LC (Cond. 2): RT=2.16; 97% homogenity index; LC/MS: Anal. Calcd. for [M+H]$^+$ C$_{46}$H$_{53}$N$_8$O$_8$: 845.40. found 845.51. HRMS Calcd. for [M+H]$^+$ C$_{46}$H$_{53}$N$_8$Os: 845.3986. found 845.3983. Example M110: LC (Cond. 2): RT=1.92; 97% homogenity index; LC/MS: Anal. Calcd. for [M+H]$^+$ C$_{40}$H$_{49}$N$_8$O$_4$: 769.47. found 769.46. HRMS Calcd. for [M+H]$^+$ C$_{40}$H$_{49}$N$_8$O$_4$: 769.3673. found 769.3682.

Example M111

(3S)-3-((methoxycarbonyl)amino)-4-((2S)-2-(5-(4'-(2-((2S)-1-(N-(methoxycarbonyl)-L-valyl)-2-pyrrolidinyl)-1H-imidazol-5-yl)-4-biphenylyl)-1H-imidazol-2-yl)-1-pyrrolidinyl)-4-oxobutanoic acid

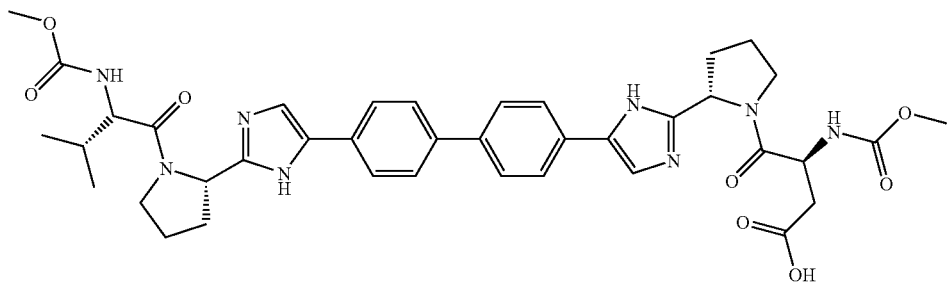

A mixture of Example M109 (69.7 mg, 0.082 mmol) and 10% Pd/C (10 mg) in methanol (5 ml) was stirred at room temperature under a balloon of H$_2$ for 1.5 h. The reaction was filtered through diatomaceous earth (Celite®) and concentrated in vacuo, and the resultant material was purified with a reverse phase HPLC (H$_2$O/MeOH/TFA) to afford the TFA salt of Example M111 as an off-white foam (54.0 mg). LC (Cond. 2): RT=1.18; 99% homogenity index; LC/MS: Anal. Calcd. for [M+H]$^+$ C$_{39}$H$_{47}$N$_8$O$_8$: 755.35. found 755.32. HRMS Calcd. for [M+H]$^+$ C$_{39}$H$_{47}$N$_8$O$_8$: 755.3517. found 755.3525.

Example M112 methyl ((1S)-1-(((2S)-2-(5-(4'-(2-((2S)-1-((2S)-2-((methoxycarbonyl)amino)-4-(4-methyl-1-piperazinyl)-4-oxobutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate

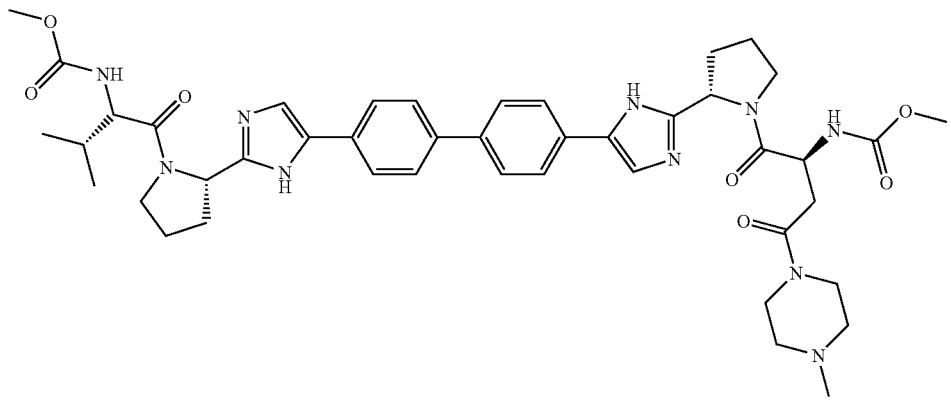

HATU (30.6 mg, 0.080 mmol) was added to a DMF (1.5 ml) solution of Example M111 (55.3 mg, 0.0733 mmol), N-methyl piperazine (11.0 mg, 0.11 mmol) and i-Pr$_2$EtN (25 μl, 0.14 mmol), and the reaction mixture was stirred at ambient condition for 1.5 h. All volatile components were removed in vacuo, and the residue was purified with a combination of MCX resin and a reverse phase HPLC (H$_2$O/MeOH/TFA) to afford the TFA salt of Example M112 as an off-white foam (51.4 mg). LC (Cond. 2): RT=1.75; 91% homogenity index; LC/MS: Anal. Calcd. for [M+H]$^+$ C$_{44}$H$_{57}$N$_{10}$O$_7$: 837.44. found 837.59. HRMS Calcd. for [M+H]$^+$ C$_{44}$H$_{57}$N$_{10}$O$_7$: 837.4412. found 837.4453.

Example M113 methyl ((1S)-3-(dimethylamino)-1-(((2S)-2-(5-(4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-3-oxopropyl)carbamate Example M118 was prepared from Example M111 and Me$_2$N.HCl according to the procedure described for Example M112. LC (Cond. 2): RT=1.89; 99% homogenity index. LC/MS: Anal. Calcd. for [M+H]$^+$ C$_{41}$H$_{52}$N$_9$O$_7$: 782.40. found 782.47. HRMS Calcd. for [M+H]$^+$ C$_{41}$H$_{52}$N$_9$O$_7$: 782.3990. found 782.4008.

Example M114

4,4'-bis(2-((2S)-1-(N-(methoxycarbonyl)-L-valyl)-2-pyrrolidinyl)-1H-imidazol-5-yl)-2-biphenylcarboxylic acid

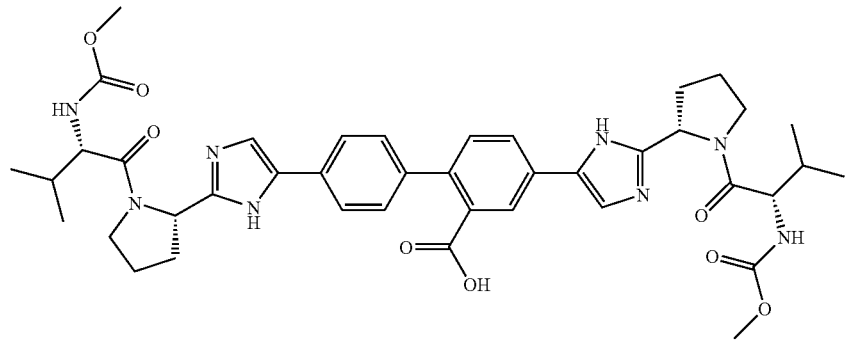

Example M114

Step a

DMF (20 mL) was added to mixture of KHCO$_3$ (1.84 g, 18.4 mmol) and 2-bromo-5-iodobenzoic acid (4.99 g, 15.3 mmol) and the resulting mixture was stirred for 15 min. Benzyl bromide (2.4 mL, 20.2 mmol) was added drop-wise over 5 min and stirring was continued at ambient condition for ~20 hr. Most of the volatile component was removed in vacuo and the residue was partitioned between CH$_2$Cl$_2$ (50 mL) and water (50 mL), and the organic layer was washed with water (50 mL), dried (MgSO$_4$), filtered, and concentrated. The resulting crude material was purified with flash chromatography (7% EtOAc/hexanes) to afford ester M114a as a colorless viscous oil (6.01 g). $^1$H NMR (DMSO-d$_6$, δ=2.5 ppm, 400 MHz): δ 8.07 (d, J=2.0, 1H), 7.81 (dd, J=8.4, 2.1, 1H), 7.53 (d, J=8.4, 1H), 7.48 (m, 2H), 7.43-7.34 (m, 3H), 5.34 (s, 2H). LC (Cond. 1): RT=2.1 min; LC/MS: Anal. Calcd. for [M+Na]$^+$ C$_{14}$H$_{10}$BrINaO$_2$: 438.88. found 438.83.

Example M114

Step b-d

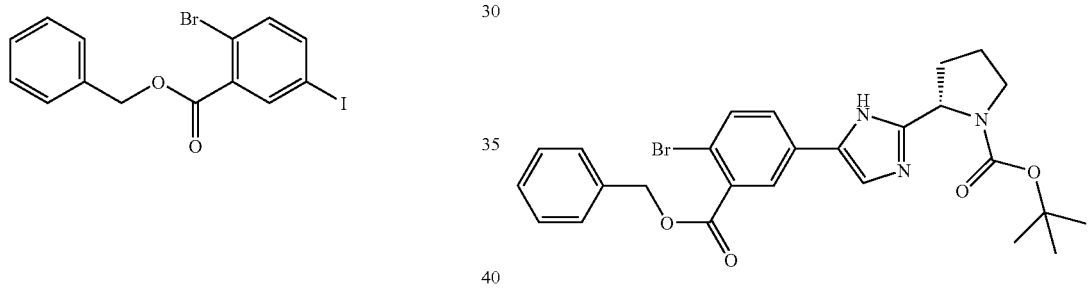

Ester M114a was elaborated to ester M114d by employing a three step protocol employed in the synthesis of bromide 121c from 1-bromo-4-iodo-2-methylbenzene. M114d: $^1$H NMR (DMSO-d$_6$, δ=2.5 ppm, 400 MHz): δ 12.04/11.97 (br s, 1H), 8.12 (d, J=2.0, 0.92H), 7.99 (app br s, 0.08H), 7.81 (dd, J=8.3, 2.0, 0.92H), 7.74-7.62 (m, 2.08H), 7.50 (app br d, J=7.0, 2H), 7.44-7.35 (m, 3H), 5.38 (s, 2H), 4.79 (m, 1H), 3.52 (app br s, 1H), 3.36 (m, 1H), 2.24-1.79 (m, 4H), 1.39/5.11 (two s, 9H). LC (Cond. 1): RT=1.66 min; LC/MS: Anal. Calcd. for [M+H]$^+$ C$_{26}$H$_{29}$BrN$_3$O$_4$: 526.13. found 526.16.

Example M114

Step e

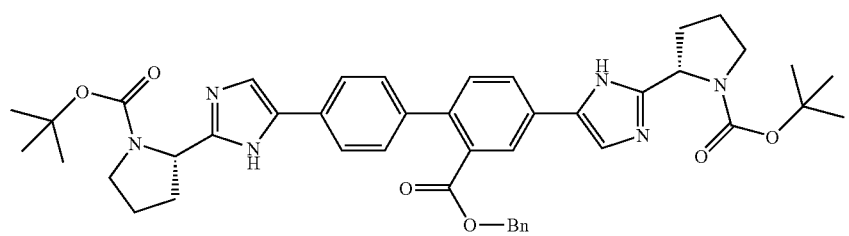

Ester M114e was prepared from bromide M114d and boronate 1c according to the preparation of dimer 1d. $^1$H NMR (DMSO-$d_6$, δ=2.5 ppm, 400 MHz): δ 12.18/12.00/11.91/11.83 (four br s, 2H), 8.11-7.03 (m, 14H), 5.10 (s, 2H), 4.85-4.78 (m, 2H), 3.55 (app br s, 2H), 3.37 (m, 2H), 2.29-1.80 (m, 8H), 1.41/1.16 (two s, 18H). LC (Cond. 1): RT=1.54 min; LC/MS: Anal. Calcd. for [M+H]$^+$ C$_{44}$H$_{51}$N$_6$O$_6$: 759.39. found 759.63.

Example M114

Step f

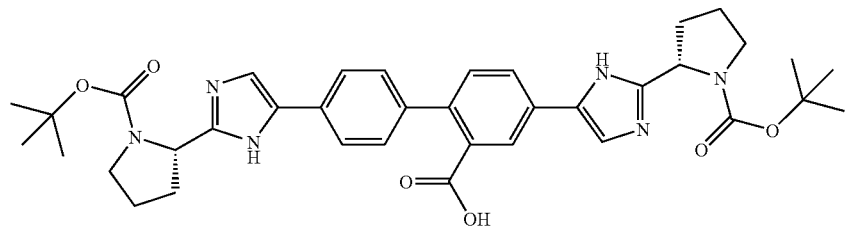

A mixture of benzyl ester M114e (1.005 g, 1.325 mmol) and 10% Pd/C (236 mg) in MeOH (20 mL) was stirred under a balloon of H$_2$ for 5 hr. The reaction mixture was then treated with a 1:1 mixture of MeOH and CH$_2$Cl$_2$, filtered through a pad of diatomaceous earth (Celite®-521), and the filtrate was rotervaped to afford acid M114f (840 mg), contaminated with Ph$_3$PO which was a carryover from the Suzuki coupling step. $^1$H NMR (DMSO-$d_6$, δ=2.5 ppm, 400 MHz): δ 12.17/11.98/11.89/11.81 (four app br s, 2H), 8.04-7.31 (m, 9H), 4.85-4.78 (m, 2H), 3.55 (app br s, 2H), ~3.37 (m, 2H, overlapped with water signal) 2.27-1.84 (m, 8H), 1.41/1.16 (two s, 18H). LC (Cond. 1): RT=1.37 min; LC/MS: Anal. Calcd. for [M+H]$^+$ C$_{37}$H$_{45}$N$_6$O$_6$: 669.34. found 669.53.

Example M114

Step g

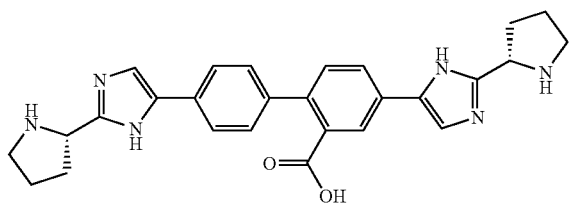

4N HCl/dioxane (8.0 mL) and CH$_2$Cl$_2$ (2.0 mL) were sequentially added to carbamate M114f (417 mg, 0.623 mmol), the mixture was vigorously stirred 5.5 hr, and then the volatile component was removed in vacuo to afford the HCl (0.4x) salt of pyrrolidine M114g (487 mg), contaminated with Ph$_3$PO impurity. $^1$H NMR (DMSO-$d_6$, δ=2.5 ppm, 400 MHz) after D$_2$O exchange: δ 8.23 (d, J=1.7, 1H), 8.09-8.04 (m, 3H), 7.92 (d, J=8.3, 2H), 7.53 (d, J=8.1, 1H), 7.48 (d, J=8.3, 2H), 5.00 (app br t, J=8.3, 1H), 4.90 (app br t, J=8.4, 1H), 3.6-3.3 (m, 4H), 2.5-1.99 (m, 8H). LC (Cond. 1): RT=0.92 min; LC/MS: Anal. Calcd. for [M+H]$^+$ C$_{27}$H$_{29}$N$_6$O$_2$: 469.24. found 469.31.

Example M114

HATU (79.9 mg, 0.21 mmol) was added to a DMF (3.0 mL) solution of pyrrolidine M114g. 4HCl (80 mg, 0.13 mmol), Cap-51 (92.4 mg, 0.527 mmol) and i-Pr$_2$EtN (160 μL, 0.919 mmol), and the reaction mixture was stirred at ambient condition for 2 hr. The volatile component was removed in vacuo and the residue was purified with a combination of MCX (MeOH wash; 2.0 M NH$_3$/MeOH elution) and a reverse phase HPLC (CH$_3$CN/H$_2$O/NH$_4$OAc) to afford the acetic acid salt of Example M114. LC (Cond. 1): RT=1.20 min; >98 homogeneity index. LC/MS: Anal. Calcd. for [M+H]$^+$ C$_{41}$H$_{51}$N$_8$O$_8$: 783.38. found 783.34. HRMS Calcd. for [M+H]$^+$ C$_{41}$H$_{51}$N$_8$O$_8$: 783.3830. found 783.3793.

Example M115-M116

Examples M115-M116 were prepared using the same method as described for Example M114 and by substituting the appropriate acids for Cap-51. The products were isolated as either the acetic acid or TFA salt depending on the nature of the mobile phase of the HPLC purification step.

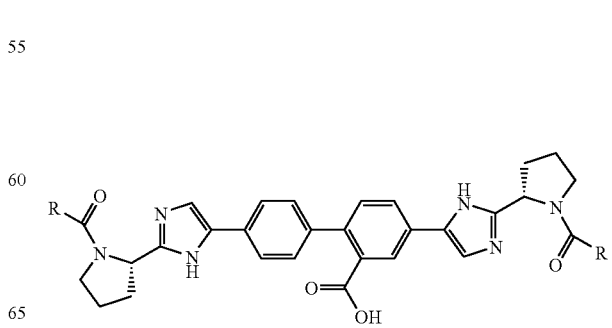

| Example | Compound Name | (Source) | RT (LC-Cond.); % homogeneity index; MS data |
|---|---|---|---|
| M115 (AcOH) | 4,4'-bis(2-((2S)-1-((2R)-2-cyclopropyl-2-((methoxycarbonyl)amino)acetyl)-2-pyrrolidinyl)-1H-imidazol-5-yl)-2-biphenylcarboxylic acid | (Cap-54a) | 1.17 min (Cond. 1); >98%; LC/MS: Anal. Calcd. for [M + H]$^+$ C$_{41}$H$_{47}$N$_8$O$_8$: 779.35; found 779.33; HRMS: Anal. Calcd. for [M + H]$^+$ C$_{41}$H$_{47}$N$_8$O$_8$: 779.3517; found 779.3498 |
| M116 (2.TFA) | 4,4'-bis(2-((2S)-1-((2S)-2-cyclopropyl-2-((methoxycarbonyl)amino)acetyl)-2-pyrrolidinyl)-1H-imidazol-5-yl)-2-biphenylcarboxylic acid | (Cap-54b) | 1.13 min (Cond. 1); >98%; LC/MS: Anal. Calcd. for [M + H]$^+$ C$_{41}$H$_{47}$N$_8$O$_8$: 779.35; found 779.33; HRMS: Anal. Calcd. for [M + H]$^+$ C$_{41}$H$_{47}$N$_8$O$_8$: 779.3517; found 779.3551 |
| M117 (2.TFA) | 4,4'-bis(2-((2S)-1-((2R)-2-((methoxycarbonyl)amino)-2-phenylacetyl)-2-pyrrolidinyl)-1H-imidazol-5-yl)-2-biphenylcarboxylic acid | (Cap-4) | 1.29 min (Cond. 1); >98%; LC/MS: Anal. Calcd. for [M + H]$^+$ C$_{47}$H$_{47}$N$_8$O$_8$: 851.35; found 851.33; HRMS: Anal. Calcd. for [M + H]$^+$ C$_{47}$H$_{47}$N$_8$O$_8$: 851.3517; found 851.3480 |

Example M18 methyl ((1S)-1-(((2S)-2-(5-(2'-carbamoyl-4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate

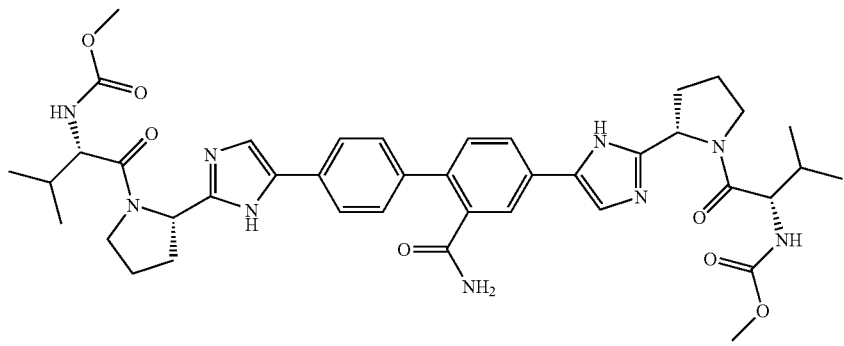

Example M118, Step a

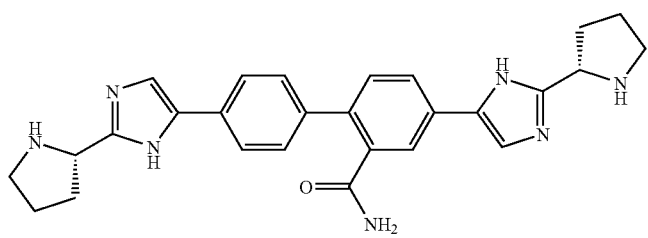

Et₃N (300 µL, 2.15 mmol) was added to a mixture of acid M114f (198.3 mg, 0.297 mmol), HOBt (94.2 mg, 0.697 mmol), EDCI (0.66 mmol), NH₄Cl (101 mg, 1.89 mmol) in DMF (8.0 mL) and stirred for 17 hr at ambient condition. The reaction mixture was filtered through 0.45 µm filter, the volatile component was removed in vacuo and the residue was partitioned between CH₂Cl₂ and water. The organic layer was concentrated and the resulting crude material was purified with a reverse phase HPLC (MeOH/H₂O/TFA).

The above product was treated with 25% TFA/CH₂Cl₂ (4.0 mL) and the reaction mixture was stirred for 2.5 hr at ambient condition. The volatile component was removed in vacuo and the residue was free-based (MCX; MeOH wash; 2.0 M NH₃/MeOH elution) to afford amide M118a (67.2 mg). $^1$H NMR (DMSO-$d_6$, δ=2.5 ppm, 400 MHz): δ 11.83 (br s, 2H), 7.81-7.80 (m, 2H), 7.73 (d, J=8.3, 2H), 7.65 (br s, 1H), 7.52 (br S, 1H), 7.44 (br s, 1H), 7.41 (d, J=8.3, 2H), 7.36 (d, J=8.3, 1H), 7.31 (br s, 1H), 4.16 (app t, J=7.2, 2H), 3.00-2.94 (m, 2H), 2.88-2.82 (m, 2H), 2.10-2.01 (m, 2H), 1.94-1.85 (m, 2H), 1.83-1.66 (m, 4H). LC (Cond. 1): RT=0.89 min; >95 homogeneity index. LC/MS: Anal. Calcd. for [M+H]⁺ $C_{27}H_{30}N_7O$: 468.25. found 468.24.

Example M118

The TFA salt of Example 118 was prepared from intermediate M118a and Cap-51 according to the procedure described for Example 1. LC (Cond. 1): RT=1.16 min; 97% homogeneity index. LC/MS: Anal. Calcd. for [M+H]⁺ $C_{41}H_{52}N_9O_7$: 782.40. found 782.40. HRMS: Anal. Calcd. for [M+H]⁺ $C_{41}H_{52}N_9O_7$: 782.3990. found 782.3979.

Example M19 methyl ((1S)-1-(((2S)-2-(5-(2-(hydroxymethyl)-4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate

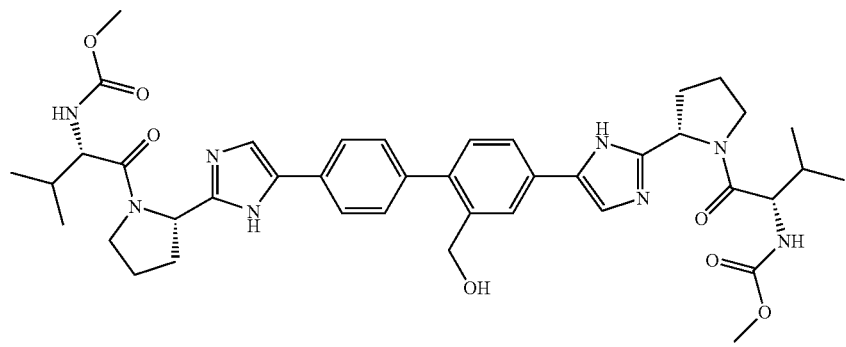

Example M119

Step a

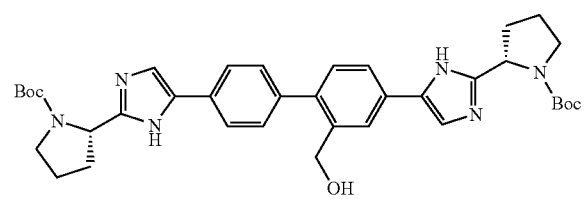

DIBAL-H (8.0 mL of 1.0 M/CH₂Cl₂, 8.0 mmol) was added drop-wise to an ice-water cooled CH₂Cl₂ (20 mL) solution of benzyl ester M114e (1.216 g, 1.60 mmol), and the reaction mixture was stirred for 1 hr and an additional DIBAL-H (0.5 mL of 1.0 M/CH₂Cl₂, 0.5 mmol) was added and stirring was continued for ~2.5 hr. The reaction was quenched with excess saturated NH₄Cl solution and the mixture was diluted with water and extracted with CH₂Cl₂ (3×). The combined organic phase was dried (MgSO₄), filtered, and concentrated in vacuo. The resulting crude material was purified with a Biotage (100 g silica gel; 2-6% MeOH/EtOAc) to afford alcohol M119a as an off-white foam (610 mg). $^1$H NMR (DMSO-$d_6$, δ=2.5 ppm, 400 MHz): δ 12.23 (br s, 0.19H), 12.17 (br s, 0.19H), 11.89 (br s, 0.81H), 11.82 (br s, 0.81H), 7.97 (s, 0.81H), 7.84 (s, 0.19H), 7.78 (d, J=8.1, 1.62H), 7.69-7.20 (m, 6.38H), 5.21-5.15 (m, 1H), 4.86-4.78 (m, 2H), 4.49-4.45 (m, 2H), ~3.54 (m, 2H), 3.40-3.34 (m, 2H), 2.30-1.80 (m, 8H), 1.41/1.17 (two s, 18H). LC (Cond. 1): RT=1.36 min. LC/MS: Anal. Calcd. for [M+H]⁺ $C_{37}H_{47}N_6O_5$: 655.36. found 655.34.

Example M119

Step b

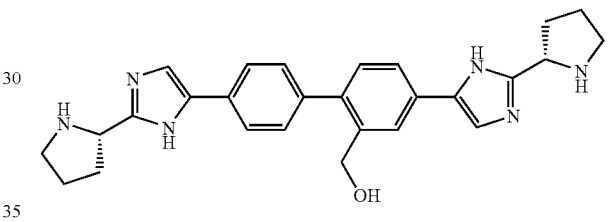

25% TFA/CH₂Cl₂ (3.0 mL) was added to carbamate M119a (105 mg, 0.160 mmol) and the mixture was stirred at ambient condition for 4.5 hr. The volatile component was removed in vacuo and the residue was free-based (MCX; MeOH wash; 2.0 M NH3/MeOH elution) to afford pyrrolidine M119b, contaminated with its trifluoroacetylated derivative of unknown regiochemistry. The sample was dissolved in MeOH (1.5 mL) and treated with 1.0 M NaOH/H₂O (300 µL, 0.3 mmol) and the mixture was stirred for 2.75 hr. It was then directly submitted to MCX purification (MeOH wash; 2.0 M NH₃/MeOH elution) to afford M119b as a film of white solid (63.8 mg). $^1$H NMR (DMSO-$d_6$, δ=2.5 ppm, 400 MHz): δ 11.82 (br s, 2H), 7.96 (s, 1H), 7.77 (d, J=8.0, 2H), 7.66 (d, J=8.0, 1H), 7.46 (br s, 1H), 7.42 (br s, 1H), 7.36 (d, J=8.0, 2H), 7.21 (d, J=8.0, 1H), 5.16 (app br s, 1H), 4.46 (s, 2H), 4.16 (app t, J=7.1, 2H), 3.00-2.82 (two m, 4H; there is a broad base line signal in this region from the pyrrolidine NH that was not included in the integration), 2.10-2.01 (m, 2H), 1.94-1.85 (m, 2H), 1.83-1.67 (m, 4H). LC (Cond. 1): RT=0.78 min. LC/MS: Anal. Calcd. for [M+H]+ C27H31N6O: 455.26. found 455.27.

Example M119

Example M119 was prepared from M119b and Cap-51 according to the procedure described for Example 1, with the exception that a reverse phase HPLC with ACN/H2O/NH4OAC solvent system was employed for the purification step. LC (Cond. 1): RT=1.15 min; 98% homogeneity index. LC/MS: Anal. Calcd. for [M+H]+ C41H53N8O7: 769.40. found 769.40. HRMS: Anal. Calcd. for [M+H]+ C41H53N8O7: 769.4037. found 769.4023.

Example M120 methyl ((1S)-1-(((2S)-2-(5-(2-((dimethylamino)methyl)-4'-(2-((2S)-1-((2S)-2-((methoxycarbonyl)amino)-3-methylbutanoyl)-2-pyrrolidinyl)-1H-imidazol-5-yl)-4-biphenylyl)-1H-imidazol-2-yl)-1-pyrrolidinyl)carbonyl)-2-methylpropyl)carbamate

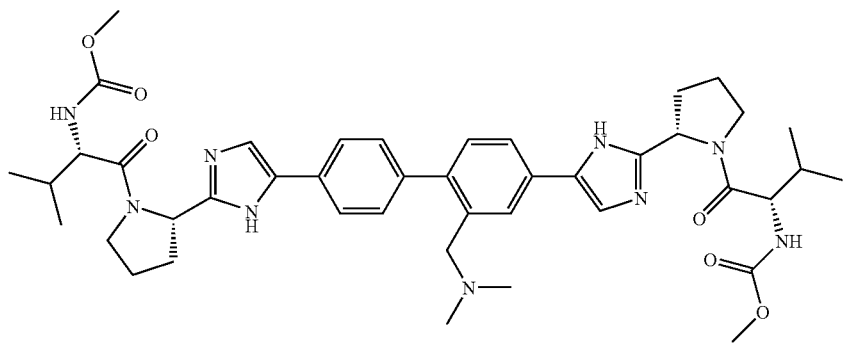

Example M120

Step a

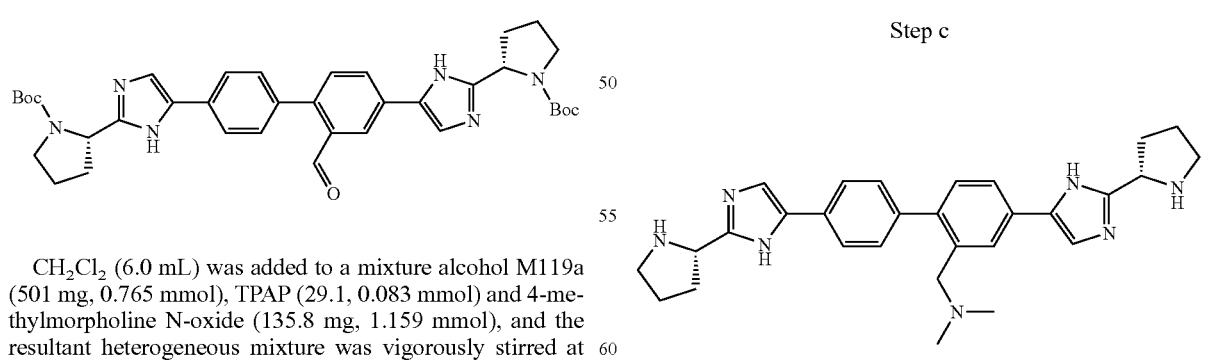

CH2Cl2 (6.0 mL) was added to a mixture alcohol M119a (501 mg, 0.765 mmol), TPAP (29.1, 0.083 mmol) and 4-methylmorpholine N-oxide (135.8 mg, 1.159 mmol), and the resultant heterogeneous mixture was vigorously stirred at ambient condition for 14.5 hr. Additional TPAP (11.0 mg, 0.031 mmol) and 4-methylmorpholine N-oxide (39 mg, 0.33 mmol) were added and stirring was continued for an additional 24 hr. The mixture was filtered through diatomaceous earth (Celite®), the filtrate was rotervaped and the resulting crude material was purified with a Biotage (2% MeOH/EtOAc) to afford aldehyde M120a as a yellow viscous oil (195.6 mg). LC (Cond. 1): RT=1.37 min. LC/MS: Anal. Calcd. for [M+H]+ C37H45N6O5: 653.35. found 653.40.

Example M120

Step b

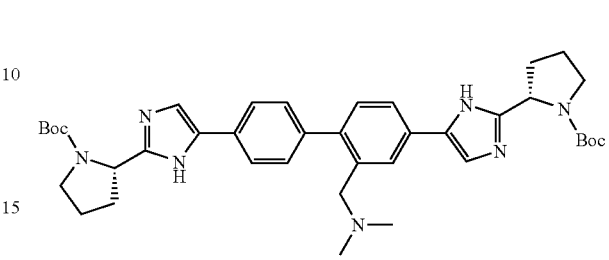

NaCNBH3 (33 mg, 0.50 mmol) was added in one batch to a MeOH (3.0 mL) solution of aldehyde M120a (195.6 mg, 0.30 mmol) and Me2NH (200 μL of 40% solution in H2O), and the reaction mixture was stirred for 4 hr. The volatile component was removed in vacuo and the residue was purified with a flash chromatography (sample was loaded as a silica gel mesh; 3-15% MeOH/CH2Cl2) to afford amine M120b as an off-white foam (120 mg). LC (Cond. 1): RT=1.32 min. LC/MS: Anal. Calcd. for [M+H]+ C39H52N7O4: 682.41. found 682.42.

Example M120

Step c

Carbamate M120b was converted to M120c by employing the protocol described for the preparation of 1e from 1d. 1H NMR (DMSO-d6, δ=2.5 ppm, 400 MHz): δ 11.82 (br s, 2H), 7.87 (s, 1H), 7.77 (d, J=8.0, 2H), 7.65 (d, J=7.8, 1H), 7.45/7.43 (overlapping two br s, 2H), 7.37 (d, J=7.8, 2H), 7.21 (d, J=7.8, 1H), 4.87 (m, 0.1H), 4.17 (m, 1.90H), ~3.3 (signal of Me$_2$NCH$_2$ overlapped with that of water), 3.01-2.94 (m, 2H), 2.89-2.83 (m, 2H), 2.10 (s, 6H), 2.10-2.01 (m, 2H), 1.94-1.85 (m, 2H), 1.81-1.67 (m, 4H). LC (Cond. 1): RT=0.79 min. LC/MS: Anal. Calcd. for [M+H]$^+$ C$_{29}$H$_{36}$N$_7$: 482.30. found 482.35.

Example M120

The TFA salt of Example M120 was prepared from pyrrolidine M120c and Cap-51 according to the procedure described for Example 1. LC (Cond. 1): RT=1.06 min; 96% homogeneity index. LC/MS: Anal. Calcd. for [M+H]$^+$ C$_{43}$H$_{58}$N$_9$O$_6$: 796.45. found 796.48. HRMS: Anal. Calcd. for [M+H]$^+$ C$_{43}$H$_{58}$N$_9$O$_6$: 796.4510. found 796.4515.

Example M121 dimethyl ((2-((dimethylamino)methyl)-4,4'-biphenyldiyl)bis(1H-imidazole-5,2-diyl(2S)-2,1-pyrrolidinediyl((1R)-2-oxo-1-phenyl-2,1-ethanediyl))) biscarbamate

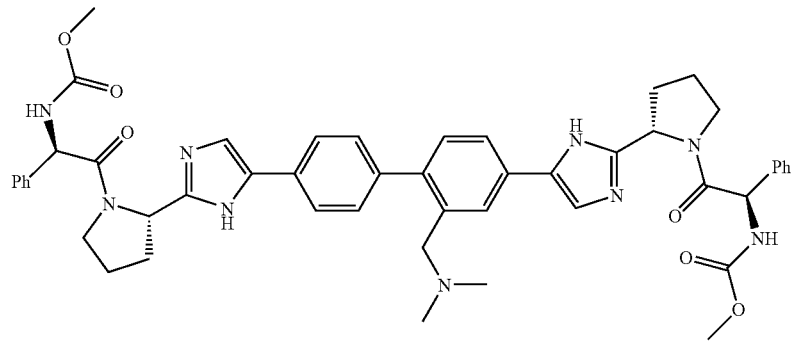

The TFA salt of Example M121 was prepared from M120c and Cap-4 according to the procedure described for Example 1. LC (Cond. 1): RT=1.15 min; >98% homogeneity index. LC/MS: Anal. Calcd. for [M+H]$^+$ C$_{49}$H$_{54}$N$_9$O$_6$: 796.45. found 864.46. HRMS: Anal. Calcd. for [M+H]$^+$ C$_{49}$H$_{54}$N$_9$O$_6$: 864.4197. found 864.4222.

Example M122 methyl ((1S)-1-(((1S,3S,5S)-3-(5-(4'-(2-((1S,3S,5S)-2-((2S)-2-((methoxycarbonyl)amino)-3-methylbutanoyl)-2-azabicyclo[3.1.0]hex-3-yl)-1H-imidazol-5-yl)-4-biphenylyl)-1H-imidazol-2-yl)-2-azabicyclo[3.1.0]hex-2-yl)carbonyl)-2-methylpropyl)carbamate

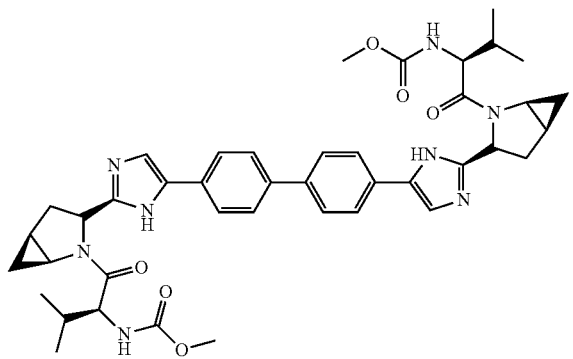

Example M122

Step a

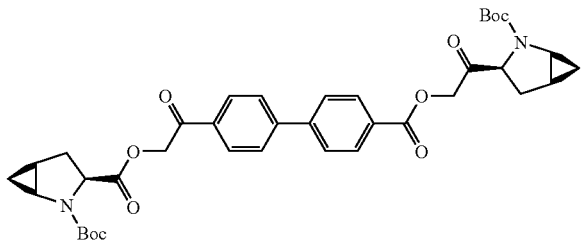

Diisopropyl ethylamine (1.81 mL, 10.4 mmol) was slowly added to acetonitrile (20 mL) solution of (1S,3S,5S)-2-(tert-butoxycarbonyl)-2-azabicyclo[3.10]hexane-3-carboxylic acid (2.36 g, 10.4 mmol) and (2-(4'-(2-bromoacetyl)biphenyl-4-yl)-2-oxoethyl)bromonium (2.0 g, 5.05 mmol), and the reaction mixture was stirred at ambient conditions for 16 hr. The solvent was evaporated and the residue was partitioned between ethyl acetate and water (1:1, 40 mL each). The organic layer was washed with Sat. NaHCO$_3$ (2×10 mL), brine, dried (Na$_2$SO$_4$), filtered, and concentrated in vacuo to afford ketoester M122a (3.58 g) as a viscous amber oil, which solidified upon storage in a refrigerator. $^1$H NMR (DMSO-d$_6$, δ=2.5 ppm, 400 MHz): δ 8.20 (m, 4H), 7.97 (d, J=8.5, 4H), 5.71-5.48 (m, 4H), 4.69 (m, 2H), 3.44 (m, 2H), 3.3 (m, 2H), 2.76-2.67 (m, 2H), 2.27 (m, 2H), 1.60 (m, 2H), 1.44/1.38 (two s, 18H), 0.78 (m, 2H), 0.70 (m, 2H). LC (Cond. 1): RT=1.70 min; LC/MS: the molecular ion was not picked up.

Example M122

Step b

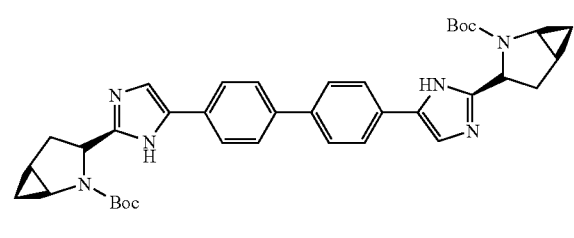

Ammonium acetate (2.89 g, 37.5 mmol) was added to a toluene (20 mL) solution of ketoester M122a (2.58 g, 3.75 mmol), and the resulting mixture was heated at 120° C. for 4.5 hr, while azaetroping the water that is formed with a Dean-Stark set-up. The reaction mixture was cooled to room temperature and the volatile component was removed in vacuo. Sat. NaHCO$_3$ solution (10 mL) was added to the solid and the mixture was stirred for 30 min, and the solid was filtered, dried in vacuo and submitted to a Biotage purification (28-100% EtOAc/hexanes) to afford imidazole M122b as light yellow solid (0.6 g). LC (Cond. 1): RT=1.52 min; LC/MS: Anal. Calcd. for [M+H]$^+$ C$_{38}$H$_{45}$N$_6$O$_4$: 649.35. found 649.78.

Example M122

Step c

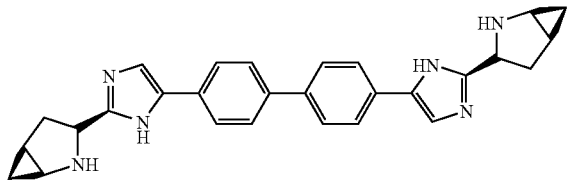

4 N HCl in dioxane (5 mL) was added to a ice-water cooled dioxane (16 mL) solution of carbamate M122b (0.8 g, 1.2 mmol), the ice-water bath was removed and the mixture was stirred at ambient condition for 4 hr. Big chunks of solid that formed during the reaction were broken up with a spatula. Removal of the volatile component in vacuo afforded pyrrolidine M122c (0.4HCl) as yellow solid (0.73 g).

$^1$H NMR (DMSO-d$_6$, δ=2.5 ppm, 400 MHz): δ 7.90 (d, J=8.3, 4H), 7.84 (br s, 2H), 7.79 (d, J=8.3, 4H), 5.24 (m, 2H), 3.38 (m, 2H), 2.71 (m, 2H), ~2.50 (2H, overlapped with solvent signal), 1.93 (m, 2H), 1.38 (m, 2H), 0.96 (m, 2H). LC (Cond. 1): RT=1.03 min; LC/MS: Anal. Calcd. for [M+H]$^+$ C$_{28}$H$_{29}$N$_6$: 449.25. found 449.59.

Example M122

The TFA salt of Example M122 was prepared from M122c and Cap-51 according to the procedure described for Example 1. LC (Cond. 1): RT=1.34 min; LC/MS: Anal. Calcd. for [M+H]$^+$ C$_{42}$H$_{51}$N$_8$O$_6$: 763.39. found 763.73.

Example M123-M130

Example M123-M130 were prepared according to the procedure described for Example M122. Example M123-M129 were prepared as TFA salts, where as Example M130 was prepared as a free base.

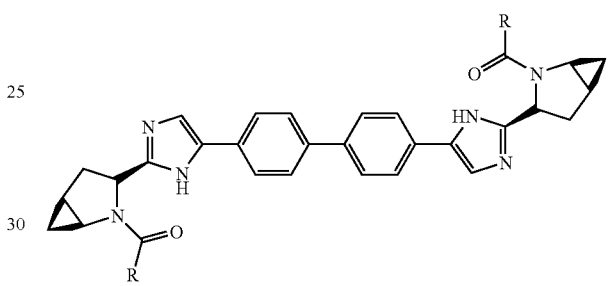

| Example | Compound Name | (Source) 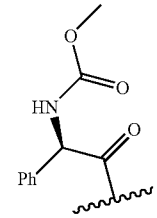 | RT (LC-Cond.); % homogeneity index; MS data |
|---|---|---|---|
| M123 | methyl ((1R)-1-(((1S,3S,5S)-3-(5-(4'-(2-((1S,3S,5S)-2-((2R)-2-((methoxycarbonyl)amino)-3-methylbutanoyl)-2-azabicyclo[3.1.0]hex-3-yl)-1H-imidazol-5-yl)-4-biphenylyl)-1H-imidazol-2-yl)-2-azabicyclo[3.1.0]hex-2-yl)carbonyl)-2-methylpropyl)carbamate | (Cap-84) | 1.372 minutes (Cond. 1); >98%; LC/MS: Anal. Calcd. for [M + H]$^+$ C$_{42}$H$_{51}$N$_8$O$_6$: 763.39; found 763.73 |
| M124 | dimethyl (4,4'-biphenyldiylbis(1H-imidazole-5,2-diyl(1S,3S,5S)-2-azabicyclo[3.1.0]hexane-3,2-diyl((1R)-2-oxo-1-phenyl-2,1-ethanediyl)))biscarbamate | (Cap-4) | 2.28 minutes (Cond. M1); >98%; LC/MS: Anal. Calcd. for [M + H]$^+$ C$_{48}$H$_{47}$N$_8$O$_6$: 831.36; found 831.36 |

| Example | Compound Name | (Source) | RT (LC-Cond.); % homogeneity index; MS data |
|---|---|---|---|
| | | 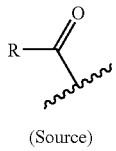 | |
| M125 | methyl ((1S)-2-hydroxy-1-((((1S,3S,5S)-3-(5-(4'-(2-((1S,3S,5S)-2-((2S)-3-hydroxy-2-((methoxycarbonyl)amino)-3-methylbutanoyl)-2-azabicyclo[3.1.0]hex-3-yl)-1H-imidazol-5-yl)-4-biphenylyl)-1H-imidazol-2-yl)-2-azabicyclo[3.1.0]hex-2-yl)carbonyl)-2-methylpropyl)carbamate | 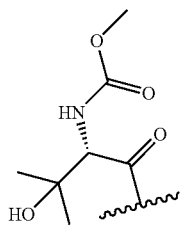<br>(Cap-65) | 1.76 minutes (Cond. M1); >98%; LC/MS: Anal. Calcd. for [M + H]$^+$ $C_{42}H_{51}N_8O_8$: 795.38; found 795.37 |
| M126 | dimethyl (4,4'-biphenyldiylbis(1H-imidazole-5,2-diyl(1S,3S,5S)-2-azabicyclo[3.1.0]hexane-3,2-diyl((2S)-1-oxo-1,2-butanediyl)))biscarbamate | 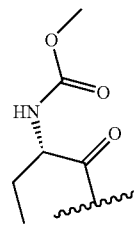<br>(Cap-53b) | 1.25 minutes (Cond. 1); >98%; LC/MS: Anal. Calcd. for [M + H]$^+$ $C_{40}H_{47}N_8O_6$: 735.36; found 735.68 |
| M127 | dimethyl (4,4'-biphenyldiylbis(1H-imidazole-5,2-diyl(1S,3S,5S)-2-azabicyclo[3.1.0]hexane-3,2-diyl((1S)-1-cyclopropyl-2-oxo-2,1-ethanediyl))) biscarbamate | 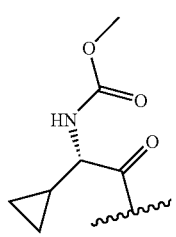<br>(Cap-54b) | 1.27 minutes (Cond. 1); >98%; LC/MS: Anal. Calcd. for [M + H]$^+$ $C_{42}H_{47}N_8O_6$: 759.36; found 759.72 |
| M128 | methyl ((1S)-1-((((1S,3S,5S)-3-(5-(4'-(2-((1S,3S,5S)-2-((2S)-2-((methoxycarbonyl)amino)-3,3-dimethylbutanoyl)-2-azabicyclo[3.1.0]hex-3-yl)-1H-imidazol-5-yl)-4-biphenylyl)-1H-imidazol-2-yl)-2-azabicyclo[3.1.0]hex-2-yl)carbonyl)-2,2-dimethylpropyl)carbamate | 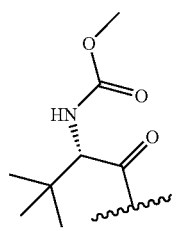 | 2.48 minutes (Cond. M1); >98%; LC/MS: Anal. Calcd. for [M + H]$^+$ $C_{44}H_{55}N_8O_6$: 791.42; found 791.41 |
| M129 | methyl (2-((1S,3S,5S)-3-(5-(4'-(2-((1S,3S,5S)-2-(((methoxycarbonyl)amino)acetyl)-2-azabicyclo[3.1.0]hex-3-yl)-1H-imidazol-5-yl)-4-biphenylyl)-1H-imidazol-2-yl)-2-azabicyclo[3.1.0]hex-2-yl)-2-oxoethyl)carbamate | 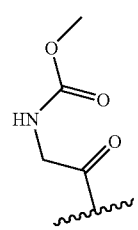 | 1.10 minutes (Cond. 1); >98%; LC/MS: Anal. Calcd. for [M + H]$^+$ $C_{36}H_{39}N_8O_6$: 679.74; found 679.77 |

-continued

| Example | Compound Name | 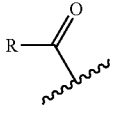 (Source) | RT (LC-Cond.); % homogeneity index; MS data |
|---|---|---|---|
| M130 | methyl ((1S)-2-((1S,3S,5S)-3-(5-(4'-(2-((1S,3S,5S)-2-(N-(methoxycarbonyl)-L-alanyl)-2-azabicyclo[3.1.0]hex-3-yl)-1H-imidazol-5-yl)-4-biphenylyl)-1H-imidazol-2-yl)-2-azabicyclo[3.1.0]hex-2-yl)-1-methyl-2-oxoethyl)carbamate | (Cap-52) | 1.16 minutes (Cond. 1); >98%; LC/MS: Anal. Calcd. for [M + H]+ $C_{38}H_{43}N_8O_6$: 707.33; found 707.69 |

Example M131 methyl ((1S)-1-(((1R,3R,5R)-3-(5-(4'-(2-((1R,3R,5R)-2-((2S)-2-((methoxycarbonyl)amino)-3-methylbutanoyl)-2-azabicyclo[3.1.0]hex-3-yl)-1H-imidazol-5-yl)-4-biphenylyl)-1H-imidazol-2-yl)-2-azabicyclo[3.1.0]hex-2-yl)carbonyl)-2-methylpropyl)carbamate

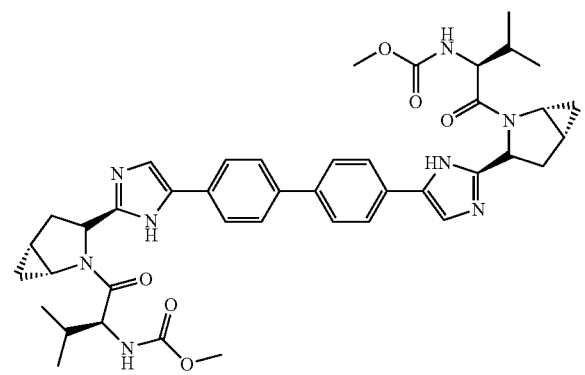

Example M131 was prepared according to the procedure described for its diastereomer Example M122 starting from (1R,3S,5R)-2-(tert-butoxycarbonyl)-2-azabicyclo[3.1.0] hexane-3-carboxylic acid, which was in turn synthesized by employing a literature protocol (Hanessian et al., *Angew. Chem., Int. Ed. Engl.* 1997, 36, 1881-1884). LC (Cond. I): RT=1.273 min; LC/MS: Anal. Calcd. for [M+H]+ $C_{42}H_{50}N_8O_6$: 763.39. found 763.94.

Example M132 methyl ((1S)-2-((1R,3S,5R)-3-(4-(4'-(2-((1R,3S,5R)-2-(N-(methoxycarbonyl)-L-alanyl)-2-azabicyclo[3.1.0]hex-3-yl)-1H-imidazol-4-yl)-4-biphenylyl)-1H-imidazol-2-yl)-2-azabicyclo[3.1.0]hex-2-yl)-1-methyl-2-oxoethyl)carbamate

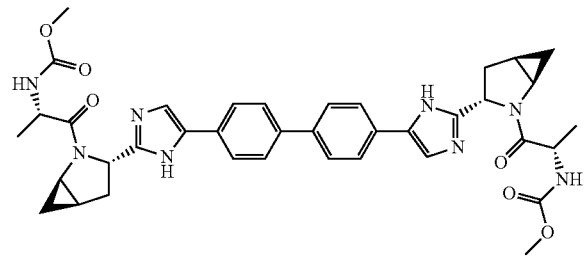

Example M132

Step a

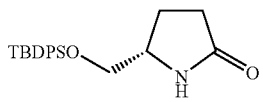

To a solution of (S)-5-(hydroxymethyl)pyrrolidin-2-one (10 g, 87 mmol) in $CH_2Cl_2$ (50 mL) was added tert-butylchlorodiphenylsilane (25.6 g, 93 mmol), triethylamine (12.1 mL, 87 mmol) and DMAP (1.06 g, 8.7 mmol). The mixture was stirred at room temperature for 5 hours, treated with $CH_2Cl_2$ (50 mL) and washed with water (50 mL). The organic layer was dried ($Na_2SO_4$), filtered, and concentrated in vacuo. The crude product was purified with a flash chromatography (30 to 100% of EtOAc/hexanes) to afford ether M132a as colorless oil (22.7 g, 74% yield). $^1$H NMR (DMSO-$d_6$, δ=2.50, 400 MHz): 7.69 (br s, 1H), 7.64-7.61 (m, 4H), 7.50-7.42 (m, 6H), 3.67-3.62 (m, 1H), 3.58-3.51 (m, 2H), 2.24-2.04 (m, 3H), 1.89-1.78 (m, 1H), 1.00 (s, 9H).

Example M132

Step b

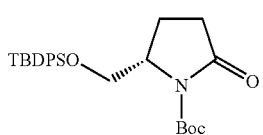

Di-tert-butyl dicarbonate (28.0 g, 128 mmol) was added slowly to a cooled (ice/water) $CH_2Cl_2$ (120 mL) solution of ether M132a (22.7 g, 64.2 mmol), triethylamine (8.95 mL, 64.2 mmol), and DMAP (7.84 g, 64.2 mmol). At the end of addition, the cooling bath was removed and stirring continued at ambient condition for 20 hours. The volatile component was removed in vacuo, and the crude material was submitted to a flash chromatography (20 to 50% EtOAc/hexanes) to afford carbamate M132b as off-white solid (29 g, 99% yield). $^1$H NMR (DMSO-d$_6$, δ=2.50, 400 MHz): 7.61-7.54 (m, 4H), 7.50-7.38 (m, 6H), 4.19-4.16 (m, 1H), 3.90 (dd, J=10.4, 3.6, 1H), 3.68 (dd, J=10.4, 2.1, 1H), 2.68-2.58 (m, 1H), 2.40-2.33 (m, 1H), 2.22-2.12 (m, 1H), 2.01-1.96 (m, 1H), 1.35 (s, 9H), 0.97 (s, 9H).

Example M132

Step c

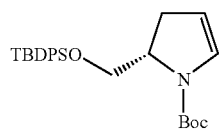

A three-necked flask equipped with a thermometer and a nitrogen inlet was charged with carbamate M132b (10.054 g, 22.16 mmol) and toluene (36 mL), and lowered into −55° C. cooling bath. When the internal temperature of the mixture reached ~−50° C., Superhydride (23 mL of 1.0 M in THF, 23.00 mmol) was added dropwise over 30 minutes while maintaining the internal temperature between −50 and −45° C., and stirred for 35 minutes while maintaining the temperature between −50 and −45° C. Hunig's Base (16.5 mL, 94 mmol) was added dropwise over 10 minutes. Then DMAP (34 mg, 0.278 mmol) was added in one batch, followed by the addition of trifluoroacetic anhydride (3.6 mL, 25.5 mmol) over 15 minutes, while maintaining the internal temperature between −50 and −45° C. The bath was removed 10 minutes later, and the reaction mixture was stirred for 14 hours while allowing it to thaw to ambient temperature. It was then diluted with toluene (15 mL), cooled with ice-water bath, and treated slowly with water (55 mL) over 5 minutes. At the end of addition, the phases were separated, and the organic layer was washed with water (50 mL, 2×) and then concentrated in vacuo. The crude material was purified with a flash chromatography (5% EtOAc/hexanes) to afford carbamate M132c as a colorless viscous oil (7.947 g, 82%). $^1$H NMR (DMSO-d$_6$, δ=2.50, 400 MHz): 7.62-7.58 (m, 4H), 7.49-7.40 (m, 6H), 6.47 (br m, 1H), 5.07-5.01 (br m, 1H), 4.18 (br m, 1H), 3.89 (br m, 0.48H), 3.69 (br m, 1.52H), 2.90-2.60 (br m, 2H), 1.40/1.26 (two overlapping s, 9H), 0.98 (s, 9H).

Example M132

Step d

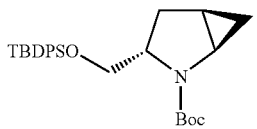

M132d-i

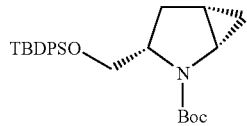

M132d-ii

Diethylzinc (19 mL of ~1.1 M in toluene, 20.90 mmol) was added dropwise over 15 minutes to a cooled (−30° C.) toluene (27 mL) solution of carbamate M132c (3.94 g, 9.0 mmol). Then chloroiodomethane (97%, stabilized over copper; 3 mL, 41.2 mmol) was added dropwise over 10 minutes, and stirred while maintaining the bath temperature around −25° C. for 1 hour and around −21° C. for 18.5 hours. The reaction was then opened to air and quenched by a slow addition of 50% saturated NaHCO$_3$ solution (40 mL), and then removed from the cooling bath and stirred at ambient condition for 20 minutes. It was filtered through a filter paper and the white cake was washed with 50 mL of toluene. The organic phase of the filtrate was separated, and washed with water (40 mL, 2×), dried (MgSO$_4$), filtered, and concentrated in vacuo. The resulting crude material was purified with a Biotage system (350 g silica gel; sample was loaded with 7% EtOAc/hexanes; eluted with 7-20% EtOAc/hexanes) to afford methanopyrrolidine M132d as a colorless viscous oil, mainly as the trans isomer (3.691 g, 90.7%). [Note: the exact trans/cis ratio has not been determined yet at this stage]. $^1$H NMR (DMSO-d$_6$, δ=2.50, 400 MHz) of M132d-i: 7.62-7.60 (m, 4H), 7.49-7.40 (m, 6H), 3.76 (br m, 1H), 3.67 (br m, 2H), 3.11-3.07 (m, 1H), 2.23 (br m, 1H), 2.03 (br m, 1H), 1.56-1.50 (m, 1H), 1.33 (br s, 9H), 1.00 (s, 9H), 0.80-0.75 (m, 1H), 0.30 (br m, 1H).

Example M132

Step e

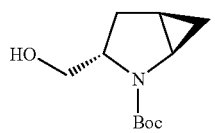

M132e-i

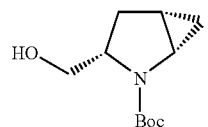

M132e-ii

TBAF (7.27 mL of 1.0 M in THF, 7.27 mmol) was added dropwise over 5 minutes to a THF (30 mL) solution of the ether M132d (3.13 g, 6.93 mmol) and the mixture was stirred at ambient condition for 4.75 hours. After it was treated with saturated NH$_4$Cl solution (5 mL), most of the volatile component was removed in vacuo, and the residue was partitioned between CH$_2$Cl$_2$ (70 mL) and 50% saturated NH$_4$Cl solution (30 mL). The aqueous phase was extracted with CH$_2$Cl$_2$ (30 mL), and the combined organic phase was dried (MgSO$_4$), filtered, concentrated in vacuo, and then exposed to high vacuum overnight. The resulting crude material was purified with a Biotage (40-50% EtOAc/hexanes) to afford alcohol M132e as colorless oil, mainly as the trans isomer, contaminated with traces of lower Rf impurities (1.39 g, 94%). [Note: the exact trans/cis ratio has not been determined yet at this stage]. $^1$H NMR (DMSO-d$_6$, δ=2.50, 400 MHz) of M132e-i: 4.70 (app t, J=5.7, 1H), 3.62-3.56 (m, 1H), 3.49-3.44 (m, 1H), 3.33-3.27 (m, 1H), 3.08-3.04 (m, 1H), 2.07 (br m, 1H), 1.93-1.87 (m, 1H), 1.51-144 (m, 1H), 1.40 (s, 9H), 0.76-0.71 (m, 1H), 0.26 (br m, 1H).

Example M132

Step f

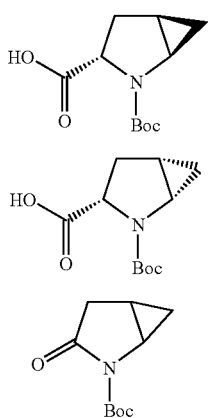

A semi-solution of NaIO$_4$ (6.46 g, 30.2 mmol) in H$_2$O (31 mL) was added to CH$_3$CN (20 mL) and CCl$_4$ (20 mL) solution of alcohol M132e (2.15 g, 10.08 mmol) prepared above, and RuCl$_3$ (0.044 g, 0.212 mmol) was added immediately and the heterogeneous reaction mixture was vigorously stirred for 75 minutes. The reaction mixture was diluted H$_2$O (60 mL) and extracted with CH$_2$Cl$_2$ (50 mL, 3×). The combined organic phase was treated with 1 mL CH$_3$OH, allowed to stand for about 5 minutes, and then filtered through a pad of diatomaceous earth (Celite®). The pad was washed with CH$_2$Cl$_2$ (50 mL), and the filtrate was rotervaped to afford a light charcoal-colored solid. $^1$H NMR of the crude material indicated a 1.00:0.04:0.18 mole ratio among trans acid M132f-i: presumed cis acid M132f-ii: side product M132f-iii. The crude material was dissolved in EtOAc (~10 mL) with heating, and allowed to stand at ambient condition with seeding. About 15 minutes into the cooling phase, a rapid crystal formation was observed. About 1 hour later, hexanes (~6 mL) was added and the mixture was refrigerated overnight (it does not appear that additional compound has precipitated out). The mixture was filtered and washed with ice/water cooled hexanes/EtOAc (2:1 ratio; 20 mL) and dried under high vacuum to afford the first crop of acid M132f-i (off-white crystals, 1.222 g). The mother liquor was rotervaped, and the residue was dissolved in ~3 ml of EtOAc (with heating), allowed to stand at ambient condition for 1 hour, and then 3 mL hexanes was added and stored in a refrigerator for ~15 hours. A second crop of acid M132f-i (grey crystals, 0.133 g) was retrieved similarly. $^1$H NMR (DMSO-d$_6$, δ=2.50, 400 MHz): 12.46 (br s, 1H), 3.88 (br m, 1H), 3.27 (br m, 1H; partially overlapped with the signal of water), 2.28 (br m, 1H), 2.08 (br m, 1H), 1.56 (br m, 1H), 1.40/1.34 (two overlapped br s, 9H), 0.73-0.68 (m, 1H), 0.46-0.43 (m, 1H). Optical rotation (10 mg/mL of CHCl$_3$): $[\alpha]_D$=−216 for first crop & −212 for the second crop.

Example M132

Step g

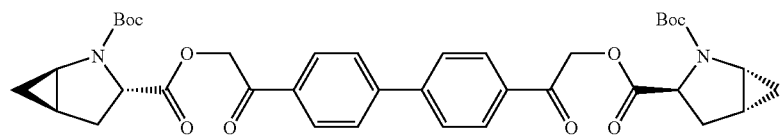

Ketoester M132g was prepared from acid M132f-i and 1,1'-(biphenyl-4,4'-diyl)bis(2-bromoethanone) by employing the procedure described for the preparation of ketoester M122a. LC (Cond. I): RT=2.09 minutes. LC/MS: Anal. Calcd. for [M+H-Boc]$^+$ C$_{33}$H$_{37}$N$_2$O$_8$: 589.26. found 589.29.

Example M132

Step h

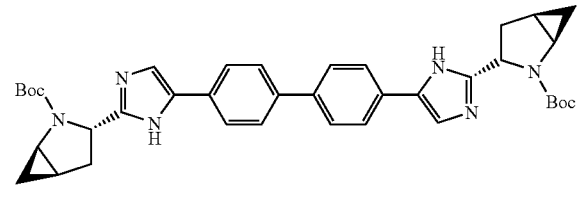

Carbamate M132h was prepared from ketoester M132g according to the procedure described for the preparation of imidazole 1b from ketoamide 1a, with the exception that 20 mol equiv of NH$_4$OAc was employed for the thermal cyclization, and that CH$_2$Cl$_2$ was employed during the work up step. LC (Cond. I): RT=1.48 minutes. LC/MS: Anal. Calcd. for [M+H]$^+$ C$_{38}$H$_{45}$N$_6$O$_4$: 649.35. found 649.40.

Example M132

Step i

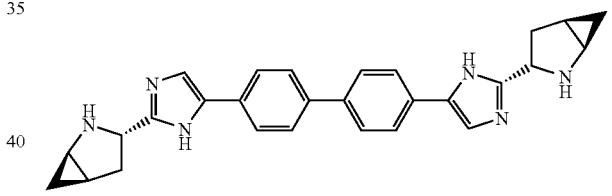

Pyrrolidine M132i (0.4HCl) was prepared from carbamate M132h according to the procedure described for the preparation of pyrrolidine M122c. The crude material was submitted to subsequent acylation step without purification. $^1$H NMR (DMSO-d$_6$, δ=2.50, 400 MHz): 10.5-10.0 (br signal, not integratable), 8.02 (s, 2H), 7.95 (d, J=8.6, 4H), 7.85 (d, J=8.3, 4H), 4.75 (m, 2H), 3.43 (m, 2H), 2.67-2.50 (m, 4H), 1.95 (m, 2H), 1.11 (m, 2H), 0.86 (m, 2H). RT=1.00 minutes. LC/MS: Anal. Calcd. for [M+H]$^+$ C28H20N6: 449.25. found 49.27.

Example M132

Example M132, along with its analogs Example M133-M137 highlighted in the table below, were prepared as TFA salts from pyrrolidine M132i (0.4HCl) by employing the procedure described for the synthesis of Example M122 and appropriate acids. Example M132: LC (Cond. I): RT=1.14 min; >95% homogeneity index. LC/MS: Anal. Calcd. for [M+H]$^+$ C$_{38}$H$_{43}$N$_8$O$_6$: 707.33. found 707.43.

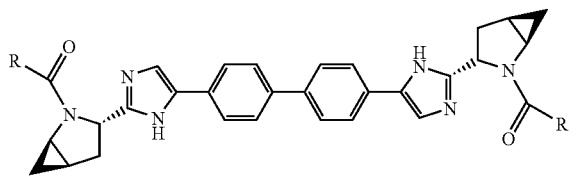

| Example | Compound Name | R (structure) | RT (LC-Cond.); % homogeneity index; MS data |
|---|---|---|---|
| M133 | dimethyl (4,4'-biphenyldiyl-bis(1H-imidazole-4,2-diyl(1R,3S,5R)-2-azabicyclo[3.1.0]hexane-3,2-diyl((2S)-1-oxo-1,2-butanediyl)))biscarbamate | | 1.22 minutes (Cond. I); >98%; LC/MS: Anal. Calcd. for [M + H]$^+$ C$_{40}$H$_{47}$N$_8$O$_6$: 735.36; found 735.48 |
| M134 | methyl (2-((1R,3S,5R)-3-(4-(4'-(2-((1R,3S,5R)-2-(((methoxycarbonyl)amino)acetyl)-2-azabicyclo[3.1.0]hex-3-yl)-1H-imidazol-4-yl)-4-biphenylyl)-1H-imidazol-2-yl)-2-azabicyclo[3.1.0]hex-2-yl)-2-oxoethyl)carbamate | | 1.12 minutes (Cond. I); >98%; LC/MS: Anal. Calcd. for [M + H]$^+$ C$_{36}$H$_{39}$N$_8$O$_6$: 679.30; found 679.38 |
| M135 | dimethyl (4,4'-biphenyldiylbis(1H-imidazole-4,2-diyl(1R,3S,5R)-2-azabicyclo[3.1.0]hexane-3,2-diyl((1S)-1-cyclopropyl-2-oxo-2,1-ethanediyl)))biscarbamate | | 1.25 minutes (Cond. I); >98%; LC/MS: Anal. Calcd. for [M + H]$^+$ C$_{42}$H$_{47}$N$_8$O$_6$: 759.36; found 759.45 |
| M136 | methyl ((1R)-1-(((1R,3S,5R)-3-(4-(4'-(((1R,3S,5R)-2-((2R)-2-((methoxycarbonyl)amino)-3-methylbutanoyl)-2-azabicyclo[3.1.0]hex-3-yl)-1H-imidazol-4-yl)-4-biphenylyl)-1H-imidazol-2-yl)-2-azabicyclo[3.1.0]hex-2-yl)carbonyl)-2-methylpropyl)carbamate | | 1.34 minutes (Cond. I); >98%; LC/MS: Anal. Calcd. for [M + H]$^+$ C$_{42}$H$_{50}$N$_8$O$_6$: 763.39; found 763.46 |
| M137 | dimethyl (4,4'-biphenyldiylbis(1H-imidazole-4,2-diyl(1R,3S,5R)-2-azabicyclo[3.1.0]hexane-3,2-diyl((1R)-2-oxo-1-phenyl-2,1-ethanediyl)))biscarbamate | | 1.38 minutes (Cond. I); >98%; LC/MS: Anal. Calcd. for [M + H]$^+$ C$_{48}$H$_{47}$N$_8$O$_6$: 831.36; found 831.37 |

Example M138 methyl ((1S)-1-(((1R,3S,5R)-3-(4-(4'-(2-((1R,3S,5R)-2-acetyl-2-azabicyclo[3.1.0]hex-3-yl)-1H-imidazol-4-yl)-4-biphenylyl)-1H-imidazol-2-yl)-2-azabicyclo[3.1.0]hex-2-yl)carbonyl)-2-methylpropyl)carbamate

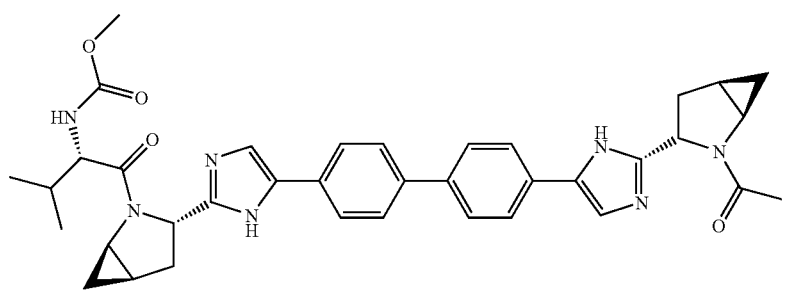

Example M138

Step a

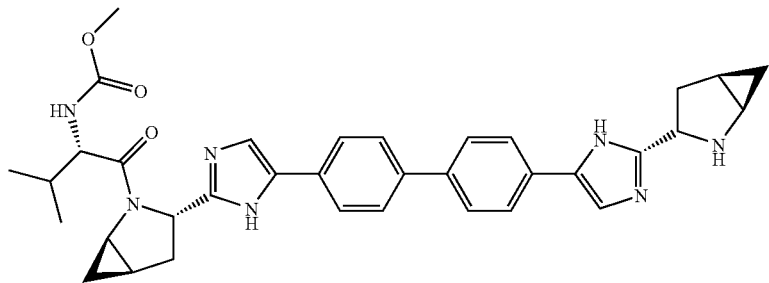

To a slurry of pyrrolidine M132i (0.4HCl) (0.3 g, 0.32 mmol) in DMF (4 mL), (S)-2-(methoxycarbonylamino)-3-methylbutanoic acid (97 mg, 0.55 mmol) and i-Pr$_2$EtN (0.26 mL, 1.5 mmol) were added. After the mixture became a clear solution, HATU (0.2 g, 0.53 mmol) was added, and it was stirred at room temperature for 3 hours. The volatile component was removed in vacuo, and the resulting residue (which was a mixture of starting material, and mono- and bis-acylated products) was dissolved in methanol and purified with a reverse phase HPLC (CH$_3$OH/H$_2$O/TFA) to isolate the TFA salt of pyrrolidine M138a as white foam (80 mg). LC (Cond. I): RT=1.17 minutes. LC/MS: Anal. Calcd. for [M+H]$^+$ C$_{35}$H$_{40}$N$_7$O$_3$: 606.32. found 606.36.

Example M138

Acetic acid (7.6 mg, 0.13 mmol), i-Pr$_2$EtN (32 mg, 0.25 mmol), and HATU (53 mg, 0.14 mmol) were sequentially added to a DMF (2 mL) solution of the TFA salt of pyrrolidine M138a (40 mg, 0.04 mmol), and the reaction mixture was stirred at room temperature for 3 hours. The volatile component was removed in vacuo, and the residue was dissolved in methanol and purified with a reverse phase HPLC (CH$_3$OH/H$_2$O/TFA) to afford the TFA salt of Example M138 as white foam (8 mg). LC (Cond. I): RT=1.20 min; >95% homogeneity index. LC/MS: Anal. Calcd. for [M+H]$^+$ C$_{37}$H$_{42}$N$_7$O$_4$: 648.33. found 648.36.

Example M139 methyl ((1S)-2-methyl-1-(((1R,3S,5R)-3-(4-(4'-(2-((1R,3S,5R)-2-(5-((3aS,4S,6aR)-2-oxohexahydro-1H-thieno[3,4-d]imidazol-4-yl)pentanoyl)-2-azabicyclo[3.1.0]hex-3-yl)-1H-imidazol-4-yl)-4-biphenylyl)-1H-imidazol-2-yl)-2-azabicyclo[3.1.0]hex-2-yl)carbonyl-2-methylpropyl)carbamate

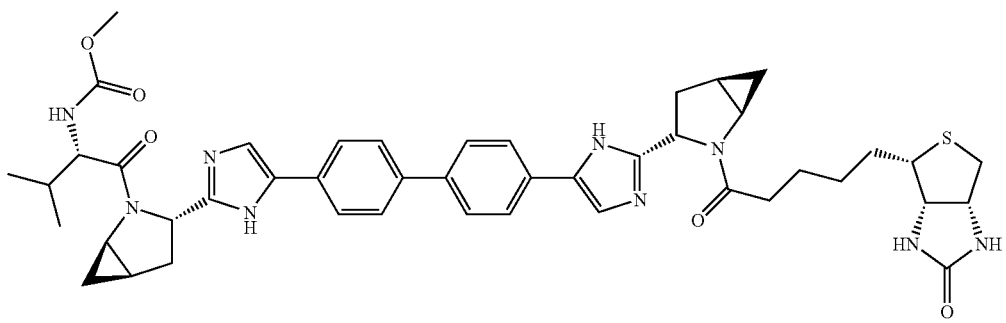

HATU (53 mg) was added to a mixture of the TFA salt of pyrrolidine M138a (40 mg, 0.042 mmol), d-Biotin (10.3 mg, 0.042 mmol) and i-Pr$_2$EtN (0.044 mL, 0.253 mmol), and the reaction mixture was stirred at room temperature for 3 hours. The volatile component was removed in vacuo, and the residue was dissolved in methanol and purified with a reverse phase HPLC (CH$_3$OH/H$_2$O/TFA) to afford the TFA salt of Example M139 as a light yellow solid (7 mg). LC (Cond. I): RT=1.28 min; >95% homogeneity index. LC/MS: Anal. Calcd. for [M+H]$^+$ C$_{45}$H$_{54}$N$_9$O$_5$S: 832.40. found 832.34.

Example M140

N-((1S)-1-(((1R,3S,5R)-3-(4-(4'-(2-((1R,3S,5R)-2-((2S)-2-acetamido-3-methylbutanoyl)-2-azabicyclo[3.1.0]hex-3-yl)-1H-imidazol-4-yl)-4-biphenylyl)-1H-imidazol-2-yl)-2-azabicyclo[3.1.0]hex-2-yl)carbonyl)-2-methylpropyl)acetamide

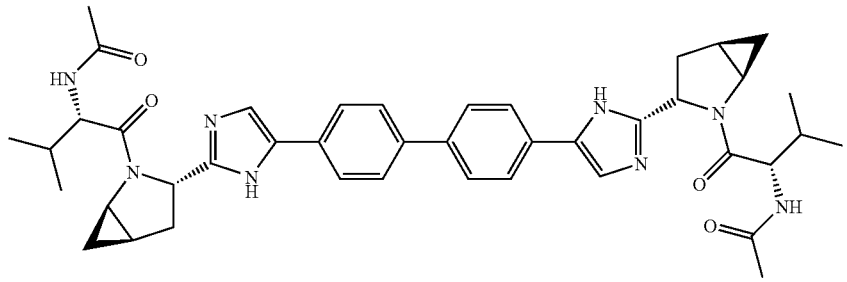

Example M140

Step a

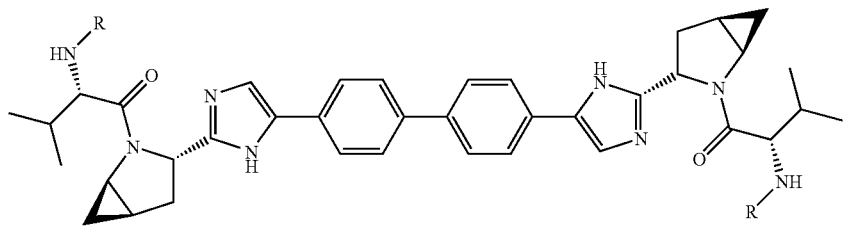

M140a-i: R = Boc
M140a-ii: R = H

HATU (852 mg, 2.24 mmol) was added to a DMF (20 mL) solution of pyrrolidine M132i (0.4HCL) (650 mg, 1.09 mmol), Boc-L-Valine (523 mg, 2.41 mmol), i-Pr$_2$EtN (1.15 mL, 6.56 mmol), and the reaction mixture was stirred at room temperature for 1 hour. The volatile component was removed in vacuo, and the crude was dissolved in CH$_3$OH and purified with a reverse phase HPLC (CH$_3$OH/H$_2$O/TFA) to afford 0.96 g of acylated product. A portion of the product (0.72 g) was dissolved in CH$_2$Cl$_2$ (4 mL), treated with TFA (0.26 mL, 3.35 mmol), and the resulting mixture was stirred at ambient condition for 4 hours. The volatile component was removed in vacuo to afford the TFA salt of M140a-ii, tert-butyl ((1S)-1-(((1R,3S,5R)-3-(4-(4'-(2-((1R,3S,5R)-2-((2S)-2-((tert-butoxycarbonyl)amino)-3-methylbutanoyl)-2-azabicyclo[3.1.0]hex-3-yl)-1H-imidazol-4-yl)-4-biphenylyl)-1H-imidazol-2-yl)-2-azabicyclo[3.1.0]hex-2-yl)carbonyl)-2-methylpropyl)carbamate, which was used in the next step without purification. LC (Cond. I): RT=0.93 minutes. LC/MS: Anal. Calcd. for [M+H]$^+$ C$_{38}$H$_{47}$N$_8$O$_2$: 647.38. found 647.26.

The free base form of carbamate M140a-i could be isolated at the coupling stage as follows: the HPLC fraction was neutralized with excess 2.0 N NH$_3$/CH$_3$OH, the volatile component was removed in vacuo and the residue was partitioned between CH$_2$Cl$_2$ and ~5% saturated NaHCO$_3$ solution. The organic layer was dried (Na$_2$SO$_4$), filtered, and concentrated in vacuo to afford M140a-i, (2S)-1-((1R,3S,5R)-3-(4-(4'-(2-((1R,3S,5R)-2-((2S)-2-amino-3-methylbutanoyl)-2-azabicyclo[3.1.0]hex-3-yl)-1H-imidazol-5-yl)-4-biphenylyl)-1H-imidazol-2-yl)-2-azabicyclo[3.1.0]hex-2-yl)-3-methyl-1-oxo-2-butanamine, as a light yellow foam. LC (Cond. I): RT=1.64 min; >95% homogeneity index. LC/MS: Anal. Calcd. for [M+H]$^+$ C$_{48}$H$_{63}$N$_8$O$_6$: 847.49. found 847.54.

Example M140

Acetic anhydride (21 mg, 0.204 mmol) and i-Pr$_2$EtN (0.083 mL, 0.476 mmol) were sequentially added to a DMF (3 mL) solution of the TFA salt of M140a-ii (75 mg, 0.068 mmol), and the reaction mixture was stirred at ambient condition until completion, as determined by LC/MS analysis. The volatile component was removed in vacuo, and the residue was dissolved in CH$_3$OH and submitted to a reverse phase HPLC (CH$_3$OH/H$_2$O/TFA) to afford the TFA salt of Example M140 as white foam (35 mg). LC (Cond. I): RT=1.18 min; >98% homogeneity index. LC/MS: Anal. Calcd. for [M+H]$^+$ C$_{42}$H$_{51}$N$_8$O$_4$: 731.40. found 731.34.

Example M141

N-((1S)-1-(((1R,3S,5R)-3-(4-(4'-(2-((1R,3S,5R)-2-((2S)-2-((cyclopropylcarbonyl)amino)-3-methylbutanoyl)-2-azabicyclo[3.1.0]hex-3-yl)-1H-imidazol-4-yl)-4-biphenylyl)-1H-imidazol-2-yl)-2-azabicyclo[3.1.0]hex-2-yl)carbonyl)-2-methylpropyl)cyclopropanecarbamate

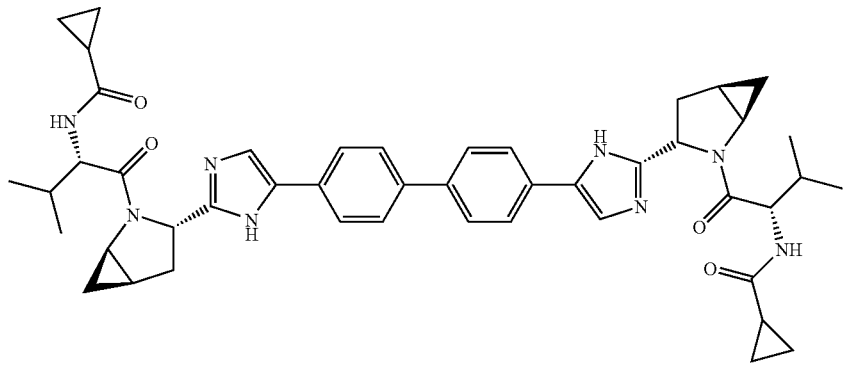

Example M141 was prepared as a TFA salt from amine M140a-ii (TFA salt) and cyclopropanecarboxylic acid according to the coupling procedure described for the synthesis of carbamate M140a-i. LC (Cond. I): RT=1.33 min; >95% homogeneity index. LC/MS: Anal. Calcd. for [M+H]$^+$ $C_{46}H_{55}N_8O_4$: 783.42. found 783.36.

Example M142-M143

Example M142 (free base) and Example M143 (TFA salt) were prepared by employing the procedures described for the synthesis of Example M140 and appropriate materials.

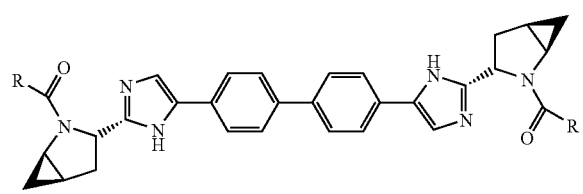

| Example | Compound Name | R | RT (LC-Cond.); % homogeneity index; MS data |
|---|---|---|---|
| M142 | tert-butyl ((1R)-1-(((1R,3S,5R)-3-(4-(4'-(2-((1R,3S,5R)-2-((2R)-2-((tert-butoxycarbonyl)amino)-3-methylbutanoyl)-2-azabicyclo[3.1.0]hex-3-yl)-1H-imidazol-4-yl)-4-biphenylyl)-1H-imidazol-2-yl)-2-azabicyclo[3.1.0]hex-2-yl)carbonyl)-2-methylpropyl)carbamate | 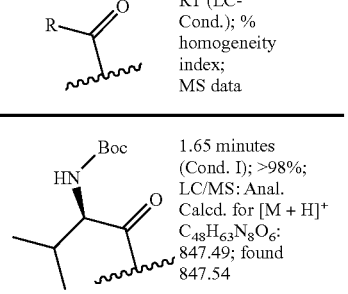 | 1.65 minutes (Cond. I); >98%; LC/MS: Anal. Calcd. for [M + H]$^+$ $C_{48}H_{63}N_8O_6$: 847.49; found 847.54 |
| M143 | N-((1R)-1-(((1R,3S,5R)-3-(4-(4'-(2-((1R,3S,5R)-2-((2R)-2-acetamido-3-methylbutanoyl)-2-azabicyclo[3.1.0]hex-3-yl)-1H-imidazol-4-yl)-4-biphenylyl)-1H-imidazol-2-yl)-2-azabicyclo[3.1.0]hex-2-yl)carbonyl)-2-methylpropyl)acetamide | 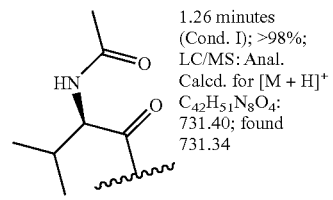 | 1.26 minutes (Cond. I); >98%; LC/MS: Anal. Calcd. for [M + H]$^+$ $C_{42}H_{51}N_8O_4$: 731.40; found 731.34 |

Example M144

N,N'-(4,4'-biphenyldiylbis(1H-imidazole-4,2-diyl(1R,3S,5R)-2-azabicyclo[3.1.0]hexane-3,2-diyl((2S)-3-methyl-1-oxo-1,2-butanediyl)))di(2-pyrimidinamine)

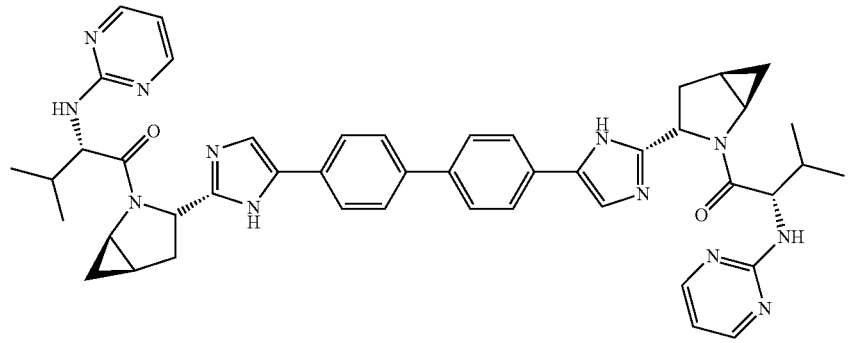

A mixture of the TFA salt of amine M140a-ii (75 mg, 0.068 mmol), 2-bromopyrimidine (32.4 mg, 0.204 mmol), and i-Pr$_2$EtN (0.048 mL, 0.272 mmol) in DMSO (0.2 mL)/toluene (1.2 mL) was heated at 90° C. for 20 hours. Additional 2-bromopyrimidine (32.4 mg, 0.204 mmol) was added and heating continued for 8 hours. Most of the volatile component was removed in vacuo and the residue was purified twice by a reverse phase HPLC system, (CH$_3$OH/H$_2$O/TFA) followed by (ACN/H$_2$O/TFA), to afford the TFA salt of Example M144, contaminated with unknown minor impurities, as a yellow foam (10 mg). RT=20.9 minutes (see the LC method detail below); >95% homogeneity index. LC/MS: Anal. Calcd. for [M+H]$^+$ C$_{46}$H$_{51}$N$_{12}$O: 803.43. found 803.70.

Method Details for Analysis of Example M144:
Instrument: Waters Acquity HPLC with Waters PDA UV-Vis detection and Waters SQ MS (ESCI probe)
Column: Waters Acquity BEH C18; 1.7 um; 150×2.1 mm ID; (at 35 C)
Mobile phase A: Water/acetonitrile (97.5/2.5) with 5 mM ammonium formate;
0.05% formic acid at pH 3.3
Mobile phase B: Acetonitrile/Water (97.5/2.5) with 5 mM ammonium formate;
0.05% formic acid
Flow: 0.35 ml/min
Hold 10% B 0-1 min
10-35% B 1-20 min
35-98% B 20-32 min
hold 98% 32-35 min
98-10% B 35-35.5 min
hold 10% B 35.5-40.0 min
UV detection: @260 nm

Example M145 methyl ((1S)-1-(((6S)-6-(4-(4'-(2-((6S)-5-((2S)-2-((methoxycarbonyl)amino)-3-methylbutanoyl)-5-azaspiro[2.4]hept-6-yl)-1H-imidazol-4-yl)-4-biphenylyl)-1H-imidazol-2-yl)-5-azaspiro[2.4]hept-5-yl)carbonyl)-2-methylpropyl)carbamate

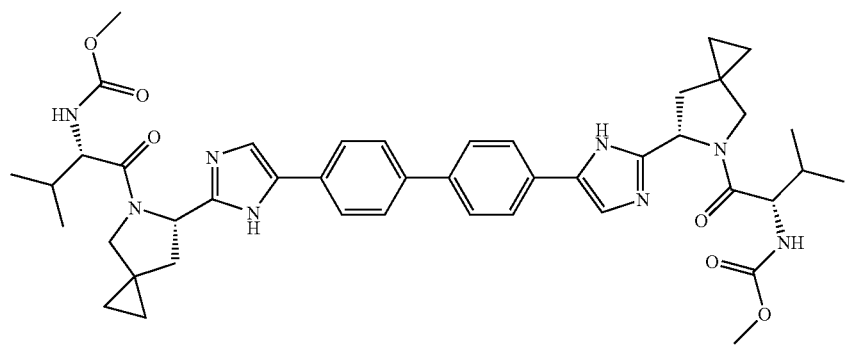

Example M145

Step a

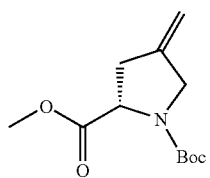

TMSCHN$_2$ (3.63 mL of 2.0 M/ether, 7.26 mmol) was added dropwise to a CH$_3$OH (33 mL)/benzene (33 mL) solution of(S)-1-tert-butyl 4-methylenepyrrolidine-1,2-dicarboxylate (1.5 g, 6.60 mmol), and the reaction mixture was stirred at ambient condition for 3.5 hours. Removal of the volatile component in vacuo afforded ester M145a as a tan oil (1.57 g). $^1$H NMR (CDCl$_3$, δ=7.26 ppm, 500 MHz): 5.01-4.98 (m, 2H), 4.50-4.48 (m, 0.5H), 4.39-4.37 (m, 0.5H), 4.07-4.04 (m, 2H), 3.71 (s, 3H), 3.01-2.87 (m, 1H), 2.66-2.55 (m, 1H), 1.46/1.41 (two overlapping s, 9H).

Example M145

Step b

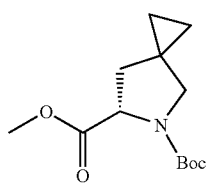

Diethylzinc (5.65 mL of 1.1 M in toluene, 6.22 mmol) was added dropwise over 20 minutes to a cooled (−22° C.) toluene (4 mL) solution of ester M145a (0.50 g, 2.07 mmol). Cloroiodomethane (0.90 mL, 12.4 mmol) was added dropwise over 10 minutes, and the reaction mixture was stirred at −22° C. for 18 hours. The reaction was quenched with saturated solution of NaHCO$_3$ (aq.) (5 mL) at similar temperature and was then allowed to thaw to ambient temperature. The mixture was filtered, and the precipitate was washed with EtOAc (100 mL). The layers of the filtrate were separated, and the organic phase was dried (MgSO$_4$), filtered, and concentrated in vacuo. The resulting crude material was purified with a Biotage (10-20% EtOAc/hexanes) to afford ester M145b as colorless oil (0.139 g). $^1$H NMR (CDCl$_3$, δ=7.26 ppm, 500 MHz): 4.47-4.44 (m, 0.5H), 4.47-4.34 (m, 0.5H), 3.73 (s, 3H), 3.39-3.27 (m, 2H), 2.25-2.18 (m, 1H), 1.86-1.84 (m, 0.5H), 1.78-1.75 (m, 0.5H), 1.44/1.40 (two overlapping s, 9H), 0.63-0.48 (m, 4H). LC (Cond. II): RT=2.26 minutes. LC/MS: Anal. Calcd. for [M+Na]$^+$ C$_{12}$H$_{19}$NNaO$_4$: 264.12. found 264.22.

Example M145

Step c

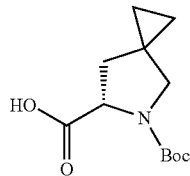

A water (0.61 mL) solution of LiOH (0.016 g, 0.65 mmol) was added to an ethanol (1.2 mL) solution of ester M145b (0.139 g, 0.544 mmol), and the reaction mixture was stirred at ambient condition for 19 hours. The volatile component was removed in vacuo, and the residue was dissolved in water (5 mL), cooled (ice/water), acidified to a pH region of 3.0 with 1N HCl (aq.), and then extracted with EtOAc (50 mL, 3×). The combined organic layer was dried (MgSO$_4$), filtered, and concentrated in vacuo to afford acid M145c as viscous oil which solidified upon standing (0.129 g). $^1$H NMR (CDCl$_3$, δ=7.26 ppm, 500 MHz): 4.48-4.40 (m, 1H), 3.55-3.05 (m, 2H), 2.37-1.87 (m, 2H), 1.47/1.44 (two overlapping s, 9H), 0.78-0.50 (m, 4H). LC (Cond. II): RT=2.26 minutes. LC/MS: Anal. Calcd. for [M+Na]$^+$ C$_{12}$H$_{19}$NNaO$_4$: 264.12. found 264.22.

Example M145

Step d

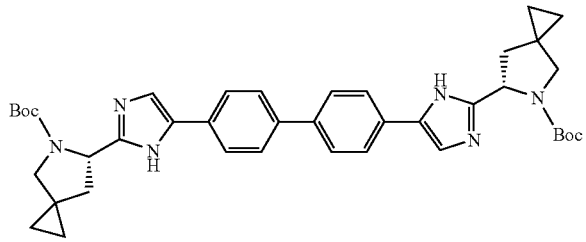

Carbamate M145d was prepared starting from acid M145c and 1,1'-(biphenyl-4,4'-diyl)bis(2-bromoethanone) and employing the general procedure described for the synthesis of M122b with the exception that the ketoester-cyclization step was conducted under microwave conditions (140° C.; 90 min). LC (Cond. II): RT=2.54 minutes. LC/MS: Anal. Calcd. for [M+H]$^+$ C$_{40}$H$_{49}$N$_6$O$_4$: 677.38. found 677.45.

Example M145

Step e

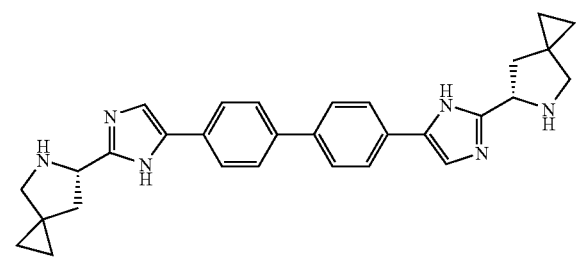

25% TFA/CH$_2$Cl$_2$ (5.3 mL) was added to carbamate M145d (0.718 g, 1.06 mmol) and the resultant mixture was stirred at ambient condition for 5 hours. The volatile component was removed in vacuo, and the residue was free-based with MCX (6 g, CH$_3$OH washing; 1:1 CHCl$_3$/2 N NH$_3$/CH$_3$OH elution) to afford pyrrolidine M145e as a light yellow solid (406 mg). $^1$H NMR (DMSO-d$_6$, δ=2.5 ppm, 500 MHz): 11.89 (br s, 2H), 7.82 (d, J=7.9, 4H), 7.67 (d, J=7.9, 4H), 7.50 (br s, 2H), 4.37 (m, 2H), 2.92 (app d, J=9.8, 2H), 2.81 (app d, J=10.1, 2H), 2.09-2.05 (m, 2H), 1.98-1.94 (m, 2H), 0.62-0.49 (m, 8H). LC (Cond. II): RT=1.75 minutes. LC/MS: Anal. Calcd. for [M+H]$^+$ C$_{30}$H$_{33}$N$_6$: 477.28. found 477.35.

Example M145

Example M145, along with its analogs Example M146-M147 highlighted in the table below, were prepared as TFA salts starting from pyrrolidine M145 and appropriate acids, by employing the general HATU coupling condition outlined for Example-1, with the exception that the reaction mixture was diluted with CH$_3$OH and directly submitted to a reverse phase HPLC (CH$_3$OH/H$_2$O/TFA) purification. Example M145: LC (Cond. II), RT=2.27 min); >95% homogeneity index. LC/MS: Anal. Calcd. for [M+H]$^+$=C$_{44}$H$_{55}$N$_8$O$_6$: 791.42. found 791.44.

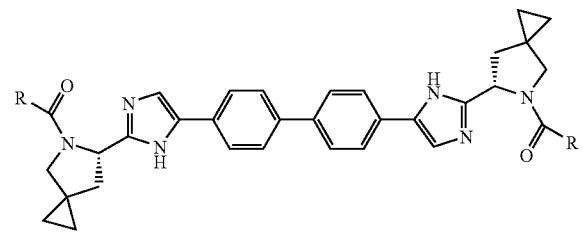

| Example | Compound Name | R | RT (LC-Cond.); % homogeneity index; MS data |
|---|---|---|---|
| M146 | methyl (2-((6S)-6-(4-(4'-(2-((6S)-5-(((methoxycarbonyl)amino)acetyl)-5-azaspiro[2.4]hept-6-yl)-1H-imidazol-4-yl)-4-biphenylyl)-1H-imidazol-2-yl)-5-azaspiro[2.4]hept-5-yl)-2-oxoethyl)carbamate | | 1.97 minutes (Cond. II); >95%; LC/MS: Anal. Calcd. for [M + H]$^+$ C$_{38}$H$_{43}$N$_8$O$_6$: 707.33; found 707.36 |
| M147 | methyl ((1S)-2-((6S)-6-(4-(4'-(2-((6S)-5-(N-(methoxycarbonyl)-L-alanyl)-5-azaspiro[2.4]hept-6-yl)-1H-imidazol-4-yl)-4-biphenylyl)-1H-imidazol-2-yl)-5-azaspiro[2.4]hept-5-yl)-1-methyl-2-oxoethyl)carbamate | | 2.01 minutes (Cond. II); >95%; LC/MS: Anal. Calcd. for [M + H]$^+$ C$_{40}$H$_{47}$N$_8$O$_6$: 735.36; found 735.41 |
| M148 | dimethyl (4,4'-biphenyldiylbis(1H-imidazol-4,2-diyl(6S)-5-azaspiro[2.4]heptane-6,5-diyl((2S)-1-oxo-1,2-butanediyl)))biscarbamate | | 2.14 minutes (Cond. II); >95%; LC/MS: Anal. Calcd. for [M + H]$^+$ C$_{42}$H$_{51}$N$_8$O$_6$: 763.39; found 763.46 |
| M149 | methyl ((1R)-1-(((6S)-6-(4-(4'-(2-((6S)-5-((2R)-2-((methoxycarbonyl)amino)-3-methylbutanoyl)-5-azaspiro[2.4]hept-6-yl)-1H-imidazol-4-yl)-4-biphenylyl)-1H-imidazol-2-yl)-5-azaspiro[2.4]hept-5-yl)carbonyl)-2-methylpropyl)carbamate | | 2.44 minutes (Cond. II); >95%; LC/MS: Anal. Calcd. for [M + H]$^+$ C$_{44}$H$_{55}$N$_8$O$_6$: 791.42; found 791.44 |
| M150 | dimethyl (4,4'-biphenyldiylbis(1H-imidazol-4,2-diyl(6S)-5-azaspiro[2.4]heptane-6,5-diyl((1R)-2-oxo-1-phenyl-2,1-ethanediyl)))biscarbamate | | 2.52 minutes (Cond. II); >95%; LC/MS: Anal. Calcd. for [M + H]$^+$ C$_{50}$H$_{51}$N$_8$O$_6$: 859.39; found 859.42 |

Example M151 methyl ((1S)-1-(((2S,5S)-2-(4-(4'-(2-((2S,5S)-1-((2S)-2-((methoxycarbonyl)amino)-3-methylbutanoyl)-5-methyl-2-pyrrolidinyl)-1H-imidazol-4-yl)-4-biphenylyl)-1H-imidazol-2-yl)-5-methyl-1-pyrrolidinyl)carbonyl)-2-methylpropyl)carbamate

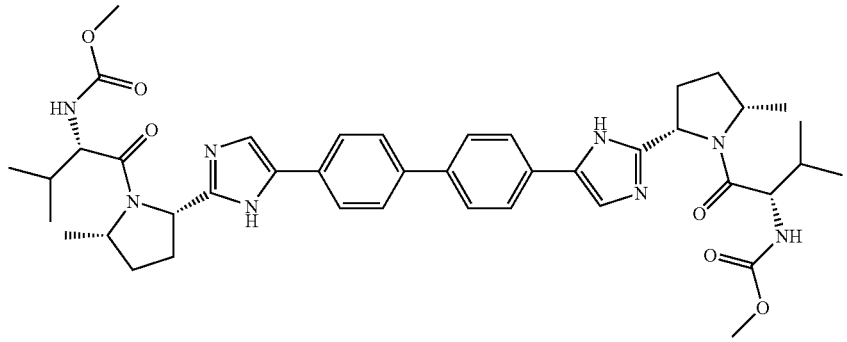

Example M151

Step a

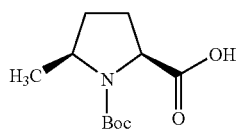

The title compound was synthesized according to a literature protocol (*J. Med. Chem.*, 2006, 49, 3520) with the following purification modifications: the crude material (2.7 g) was recrystallized from EtOAc/hexanes at ambient temperature to afford acid M151a as a white crystal (2.2 g). $^1$H NMR (CDCl$_3$, δ=7.24 ppm, 400 MHz): 4.32 (br m, 1H), 3.89 (br m, 1H), 2.40 (br m, 1H), 2.00 (m, 2H), 1.65 (m, 1H), 1.45 (s, 9H), 1.20 (d, J=5.6, 3H). LC (Cond. I): RT=1.40 minutes. LC/MS: Anal. Calcd. for [M+Na]$^+$ C$_{11}$H$_{20}$NO$_4$Na: 252.12. found 252.21.

Example M151

Step b

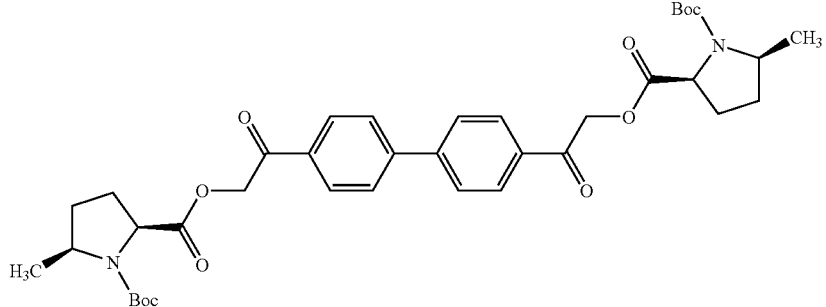

To a mixture of acid M151a and 1,1'-(biphenyl-4,4'-diyl)bis(2-bromoethanone) (1.85 g, 4.66 mmol) in acetonitrile (50 mL), i-Pr$_2$EtN (1.24 g, 9.6 mmol) was added dropwise, and the reaction was stirred at room temperature for 7 hr. The volatile component was removed in vacuo and the residue was partitioned between ethyl acetate and water (1:1, 100 mL). The organic layer was separated and washed with saturated NaHCO$_3$ and brine, dried (Na$_2$SO$_4$), filtered, and concentrated in vacuo to afford ketoester M151b as white foam (3.19 g), which was used in the next step without purification. $^1$H NMR (DMSO-d$_6$, δ=2.5 ppm, 400 MHz): 8.10 (d, J=8.5, 4H), 7.95 (d, J=8.5, 4H), 5.70-5.50 (br m, 4H), 4.40 (br m, 2H), 3.90 (br m, 2H), 2.25 (m, 2H), 2.15 (m, 4H), 1.60 (m, 2H), 1.41 (s, 8H), 1.39 (s, 10H), 1.20 (m, 6H). LC (Cond. I): RT=2.15 minutes. LC/MS: parent ion was not observed.

Example M151

Step c

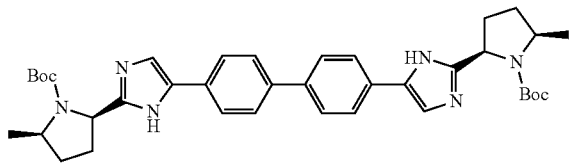

A mixture of ketoester M151b (2.94 g, 4.24 mmol) and ammonium acetate (6.54 g, 85 mmol) in xylene (40 mL) was heated in a sealed tube at 140° C. for 2 hours. The volatile component was removed in vacuo and the residue was partitioned between CH$_2$Cl$_2$ (100 mL) and water (50 mL). The organic layer was washed with saturated NaHCO$_3$ (20 mL), dried (Na$_2$SO$_4$), concentrated in vacuo. The resultant crude material was purified with a Biotage (0-100% EtOAc/hexanes) to afford imidazole M151c as light brown solid (1.72 g). LC (Cond. I): RT=1.03 minutes. LC/MS: Anal. Calcd. for [M+H]$^+$ C$_{38}$H$_{49}$N$_6$O$_4$: 653.37. found 653.40.

Example M151

Step d

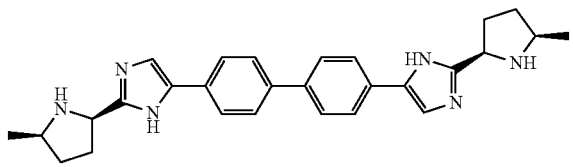

4 N HCl in dioxane (14 mL, 56 mmol) was added dropwise to a dioxane (70 mL) solution of carbamate M151c (1.72 g, 2.63 mmol), and the reaction mixture was stirred at room temperature for 4 hours. Removal of the volatile component in vacuo afforded the HCl salt of pyrrolidine M151d as a yellow solid (1.58 g). $^1$HNMR (DMSO-d$_6$, δ=2.5 ppm, 400 MHz): δ 9.85 (br s, 1H), 8.80 (br s, 1H), 7.89 (d, J=8.3, 4H), 7.77 (s, 2H), 7.75 (d, J=8.6, 4H), 4.70 (br m, 2H), 3.75 (br m, 2H), 2.45-2.35 (m, 4H), 2.25 (m, 2H), 1.75 (m, 2H), 1.50 (d, J=6.6, 6H). LC (Cond. I): RT=1.03 minutes. LC/MS: Anal. Calcd. for [M+H]$^+$ C$_{28}$H$_{33}$N$_6$: 453.28. found 453.28.

Example M151

Example M151, along with its analogs Example M152-M161 highlighted in the table below, were prepared as TFA salts starting from pyrrolidine M151d and appropriate acids, by employing the general HATU coupling condition outlined for Example-1, with the exception that the reaction mixture was diluted with CH$_3$OH and directly submitted to a reverse phase HPLC purification (CH$_3$OH/H$_2$O/TFA). Example M151: LC (Cond. I): RT=1.41 min; >95% homogeneity index. LC/MS: Anal. Calcd. for [M+H]$^+$ C$_{42}$H$_{55}$N$_8$O$_6$: 767.42. found 767.40.

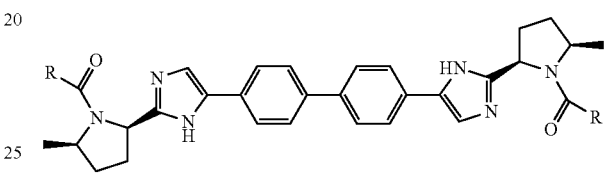

| Example | Compound Name | R—C(=O)— | RT (LC-Cond.); % homogeneity index; MS data |
|---|---|---|---|
| M152 | methyl ((1R)-1-(((2S,5S)-2-(4-(4'-(2-((2S,5S)-1-((2R)-2-((methoxycarbonyl)amino)-3-methylbutanoyl)-5-methyl-2-pyrrolidinyl)-1H-imidazol-4-yl)-4-biphenylyl)-1H-imidazol-2-yl)-5-methyl-1-pyrrolidinyl)carbonyl)-2-methylpropyl)carbamate | | 1.38 minutes (Cond. I); >98% LC/MS: Anal. Calcd. for [M + H]$^+$ C$_{42}$H$_{55}$N$_8$O$_6$: 767.42; found 767.33 |
| M153 | dimethyl (4,4'-biphenyldiylbis(1H-imidazol-4,2-diyl((2S,5S)-5-methyl-2,1-pyrrolidinediyl)((1R)-2-oxo-1-phenyl-2,1-ethanediyl)))biscarbamate | | 1.46 minutes (Cond. I); >98%; LC/MS: Anal. Calcd. for [M + H]$^+$ C$_{48}$H$_{51}$N$_8$O$_6$: 835.39; found 835.31 |
| M154 | dimethyl (4,4'-biphenyldiylbis(1H-imidazol-4,2-diyl((2S,5S)-5-methyl-2,1-pyrrolidinediyl)((2S)-1-oxo-1,2-butanediyl)))biscarbamate | | 1.27 minutes (Cond. I); >98%; LC/MS: Anal. Calcd. for [M + H]$^+$ C$_{40}$H$_{51}$N$_8$O$_6$: 739.39; found 739.28 |

-continued

| Example | Compound Name | R group structure | RT (LC-Cond.); % homogeneity index; MS data |
|---|---|---|---|
| M155 | methyl (2-((2S,5S)-2-(4-(4'-(2-((2S,5S)-1-(((methoxycarbonyl)amino)acetyl)-5-methyl-2-pyrrolidinyl)-1H-imidazol-4-yl)-4-biphenylyl)-1H-imidazol-2-yl)-5-methyl-1-pyrrolidinyl)-2-oxoethyl)carbamate | | 1.19 minutes (Cond. I); >98%; LC/MS: Anal. Calcd. for $[M+H]^+$ $C_{36}H_{43}N_8O_6$: 683.33; found 683.32 |
| M156 | methyl (2-((2S,5S)-2-(4-(4'-(2-((2S,5S)-1-(2-((methoxycarbonyl)amino)-2-methylpropanoyl)-5-methyl-2-pyrrolidinyl)-1H-imidazol-4-yl)-4-biphenylyl)-1H-imidazol-2-yl)-5-methyl-1-pyrrolidinyl)-1,1,-dimethyl-2-oxoethyl)carbamate | | 1.33 minutes (Cond. I); >98%; LC/MS: Anal. Calcd. for $[M+H]^+$ $C_{40}H_{51}N_8O_6$: 739.39; found 739.28 |
| M157 | methyl ((1S)-2-((2S,5S)-2-(4-(4'-2-((2S,5S)-1-(N-(methoxycarbonyl)-L-alanyl)-5-methyl-2-pyrrolidinyl)-1H-imidazol-4-yl)-4-biphenylyl)-1H-imidazol-2-yl)-5-methyl-1-pyrrolidinyl)-1-methyl-2-oxoethyl)carbamate | | 1.21 minutes (Cond. I); >98%; LC/MS: Anal. Calcd. for $[M+H]^+$ $C_{38}H_{47}N_8O_6$: 711.36; found 711.23 |
| M158 | 4,4'-(4,4'-biphenyldiyl)bis(2-((2S,5S)-5-methyl-1-(3-methylbutanoyl)-2-pyrrolidinyl)-1H-imidazole) | | 1.42 minutes (Cond. I); >98%; LC/MS: Anal. Calcd. for $[M+H]^+$ $C_{38}H_{49}N_6O_2$: 621.39; found 621.28 |
| M159 | 4,4'-(4,4'-biphenyldiyl)bis(2-((2S,5S)-5-methyl-1-(phenylacetyl)-2-pyrrolidinyl)-1H-imidazole) | | 1.46 minutes (Cond. I); >98%; LC/MS: Anal. Calcd. for $[M+H]^+$ $C_{44}H_{45}N_6O_2$: 689.36; found 689.26 |
| M160 | (2R,2'R)-1,1'-(4,4'-biphenyldiylbis(1H-imidazole-4,2-diyl((2S,5S)-5-methyl-2,1-pyrrolidinediyl)))bis(3-methyl-1-oxo-2-butanol) | | 1.27 minutes (Cond. I); >98%; LC/MS: Anal. Calcd. for $[M+H]^+$ $C_{38}H_{49}N_6O_4$: 653.38; found 653.27 |
| M161 | (2S,2'S)-1,1'-(4,4'-biphenyldiylbis(1H-imidazole-4,2-diyl((2S,5S)-5-methyl-2,1-pyrrolidinediyl)))bis(3-methyl-1-oxo-2-butanol) | | 1.267 minutes (Cond. I); >98%; LC/MS: Anal. Calcd. for $[M+H]^+$ $C_{38}H_{49}N_6O_4$: 653.38; found 653.34 |

Example M162

2-((2S,5S)-1-acetyl-5-methyl-2-pyrrolidinyl)-4-(4'-(2-((2S,5S)-1-acetyl-5-methyl-2-pyrrolidinyl)-1H-imidazol-5-yl)-4-biphenylyl)-1H-imidazole

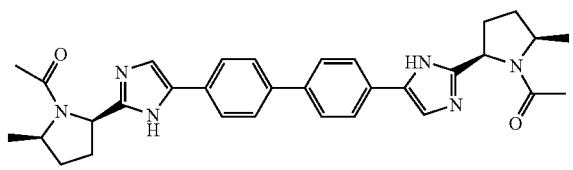

Acetic anhydride (38.4 mg, 0.376 mmol) and i-Pr$_2$EtN (0.153 mL, 0.877 mmol) were added to a DMF (3 mL) solution of the HCl salt of pyrrolidine M151d (75 mg, 0.125 mmol), and the mixture was stirred at room temperature for 2 hours. The volatile component was removed in vacuo, and the residue was dissolved in CH$_3$OH and purified with a reverse phase HPLC (CH$_3$OH/H$_2$O/TFA) to afford the TFA salt of M162 as a white foam (55 mg). LC (Cond. I): RT=1.13 min; >95% homogeneity index. LC/MS: Anal. Calcd. for [M+H]$^+$ C$_{32}$H$_{37}$N$_6$O$_2$: 537.30. found 537.21.

Examples J1-J14.f and E1-E5m

LCMS conditions 1: Phenomenex-Luna 4.6×50 mm S10, 0 to 100% B over 2 min, 3 min stop time, 4 mL/min, 220 nm, A: 10% CH$_3$OH—90% H2O—0.1% TFA; B: 90% CH$_3$OH—10% H2O—0.1% TFA.

LCMS conditions 2: Phenomenex-Luna 4.6×50 mm S10, 0 to 100% B over 3 min, 4 min stop time, 4 mL/min, 220 nm, A: 10% CH$_3$OH—90% H2O—0.1% TFA; B: 90% CH$_3$OH—10% H2O—0.1% TFA.

LCMS conditions 3: Luna 4.6×30 mm C18, 0 to 100% B over 2 min, 3 min stop time, 5 mL/min, 220 nm, A: 5% Acetonitrile-90% H2O—10 Mm NH$_4$OAc; B: 90% Acetonitrile –10% H2O—0.1% 10 Mm NH$_4$OAc.

Reference: *J. Org. Chem.* (1992) 57, 1784.

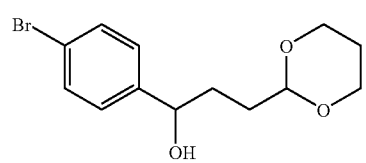

J1

108 mL of (1,3-dioxan-2-ylethyl) magnesium bromide (0.5M) was added to a solution of 4-bromobenzaldehyde (10 g, 54.0 mmol) in THF (350 mL) at –78° C. under nitrogen and stirred for 2 hours before warming to 0° C. The reaction was quenched with sat NH$_4$Cl soln, diluted with diethyl ether and Synthetic Scheme 1

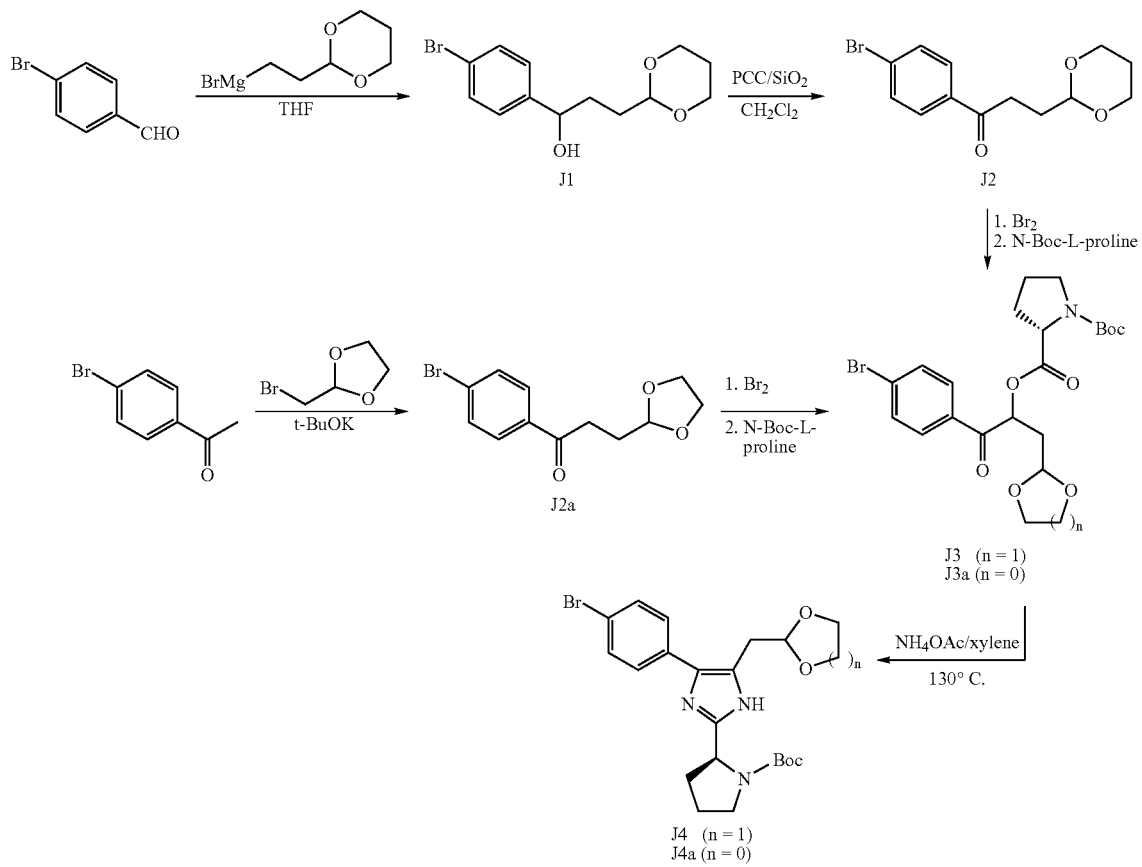

washed with brine. The crude product was charged (CH₂Cl₂) to a 40M Biotage silica gel cartridge; Gradient elution 15-100% B over 750 mL (A=Hexanes; B=ethyl acetate) to give Example J1, 1-(4-bromophenyl)-3-(1,3-dioxan-2-yl)propan-1-ol (quantitative yield). ¹H NMR (500 MHz, CDCl₃) δ 7.44 (d, J=8.5 Hz, 2H), 7.22 (d, J=8.5 Hz, 2H), 4.70-4.66 (m, 1H), 4.57 (t, J=4.9 Hz, 1H), 4.12-4.19 (m, 2H), 3.76 (tt, J=11.9, 2.7 Hz, 2H), 2.87 (d, J=3.7 Hz, 1H), 2.12-2.03 (m, 1H), 1.86-1.87 (m, 2H), 1.74-1.68 (m, 2H), 1.36-1.32 (m, 1H). RT=1.8 minutes (condition 1); LRMS: No parent ion evident.

Reference: *JOC* (1989) 54 5387.

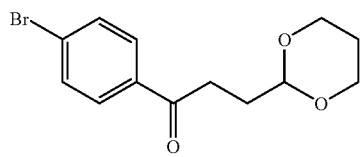

J2

PCC (8.16 g, 59.8 mmol) was admixed with 9 g SiO₂ and ground (mortar & pestle) and suspended in Dichloromethane (360 mL). To the suspension was added in one portion Example J1, 1-(4-bromophenyl)-3-(1,3-dioxan-2-yl)propan-1-ol (9 g, 29.9 mmol) dissolved in 5 mL of the same solvent. The reaction mixture was stirred for 2 hours an filtered through celite (rinse with (CH₂Cl₂). After being concentrated the residue was charged (CH₂Cl₂) to a 40 M Biotage silica gel cartridge. Gradient elution 15-70% B over 750 mL (A=Hexanes; B=ethyl acetate) gave Example J2, 1-(4-bromophenyl)-3-(1,3-dioxan-2-yl)propan-1-one 7.7 g (86%). ¹H NMR (500 MHz, CDCl₃) δ 7.84 (d, J=8.7 Hz, 2H), 7.59 (d, J=8.5 Hz, 2H), 4.65 (t, J=4.9 Hz, 1H), 4.09-4.06 (m, 2H), 3.74 (dt, J=11.0, 2.4 Hz, 2H), 3.06 (t, J=7.3 Hz, 2H), 2.07-2.01 (m, 3H), 1.35-1.31 (m, 1H). LCMS: RT=1.9 minutes (condition 1); C13H15BrO3 Calcd.: 299. found: 299 (M+H)⁺.

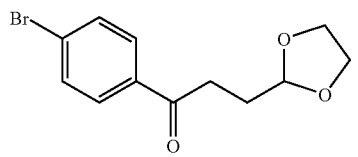

J2a

The potassium tert-butoxide (15 mL, 1M in THF) was added dropwise to a solution of 1-(4-bromophenyl)ethanone (3 g, 15.07 mmol) in DMSO (60 mL) at 0° C. and stirred for 30 min under nitrogen. The enolate was cannulated into a solution of 2-(bromomethyl)-1,3-dioxolane (2.52 g, 15.07 mmol) in DMSO (10 mL) at 0° C. and the reaction allowed to warm to 24° C. and stirred 6 hours. Concentrate to remove solvent (high vacuum rotory evaporation) and charge (CH₂Cl₂) of residue to a 40 (M) Biotage silica gel cartridge and gradient elution 5-35% B over 1 L (A=Hexanes; B=ethyl acetate) gave Example J2a, 1-(4-bromophenyl)-3-(1,3-dioxolan-2-yl)propan-1-one 327 mg (7.6%) and 571 mg of a bis addition product. ¹H NMR (500 MHz, CDCl₃) δ 7.83 (d, J=8.5 Hz, 2H), 7.58 (d, J=8.5 Hz, 2H), 4.97 (t, J=4.3 Hz, 1H), 3.96-3.94 (m, 2H), 3.87-3.84 (m, 2H), 3.08-3.05 (m, 2H), 2.15-2.11 (m, 2H).

Reference: Bromination *JACS* (1952) 74 6263. Displacement/Cyclization *J. Med. Chem.* (2001) 44 2990.

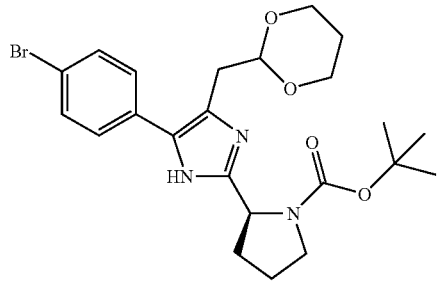

J4

Bromine (1.3 mL, 25.2 mmol) was added to a solution of Example J2, 1-(4-bromophenyl)-3-(1,3-dioxan-2-yl)propan-1-one (7.7 g, 25.7 mmol) in diethyl ether (60 mL) and 1,4-dioxane (40 mL) and the solution stirred 30 min at 24° C. (Until TLC indicated reaction complete). The solvent was removed by rotory evaporation and the residue was taken up in acetonitrile (350 mL). (S)—N-Boc-Proline (5.54 g, 25.7 mmol) was added followed by dropwise addition of Hunig's base (8.5 mL, 51.5 mmol) and the reaction was stirred 6 hours before being concentrated. The crude product was taken up in CH₂Cl₂ and charged to a 40 (M) Biotage silica gel cartridge. Gradient elution 15-100% B over 1 L (A=hexanes; B=ethyl acetate) gave Example J3, 2-(1-(4-bromophenyl)-3-(1,3-dioxan-2-yl)-1-oxopropan-2-yl) 1-tert-butyl pyrrolidine-1,2-dicarboxylate 13 g (100%).). RT=2.2 minutes (condition 1); LCMS: Anal. C23H30BrNO7 Calcd. 534. found: 534 (M+Na)⁺.

Ammonium acetate (6.45 g, 107 mmol) was added to a solution of Example J3, 2-(1-(4-bromophenyl)-3-(1,3-dioxan-2-yl)-1-oxopropan-2-yl) 1-tert-butyl pyrrolidine-1,2-dicarboxylate (5.5 g, 10.7 mmol) in xylene (120 mL) and stirred for 3 hours at 130° C. in a screw capped 500 mL pressure vessel. After being cooled, the reaction mixture was diluted with ethyl acetate (600 mL) and washed with sat NaHCO₃ and brine before being concentrated by rotory evaporation under high vacuum. The crude product was taken up in CH₂Cl₂ and charged to a 40 (M) Biotage silica gel cartridge. Gradient elution 15-100% B over 2 L (A=CH₂Cl₂; B=ethyl acetate) gave Example J4, (S)-tert-butyl 2-(4-((1,3-dioxan-2-yl)methyl)-5-(4-bromophenyl)-1H-imidazol-2-yl)pyrrolidine-1-carboxylate 2.22 g (40%). ¹H NMR (500 MHz, CDCl₃) δ 7.46 (s, 4H), 4.94-4.92 (m, 1H), 4.77 (t, J=4.9 Hz, 1H), 4.15-4.12 (m, 2H), 3.81-3.75 (m, 2H), 3.3-3.37 (m, 2H), 3.0-2.90 (m, 2H), 2.10-2.05 (m, 4H), 1.94-1.91 (m, 1H), 1.49 (s, 9H) 1.36-1.34 (m, 1H). RT=1.8 minutes (condition 1); HRMS: Anal. C23H30BrN3O4 Calcd. 492.1492. found: 492.1505 (M+H)⁺.

| | | |
|---|---|---|
| J4a<br>Derived from<br>example J2a | 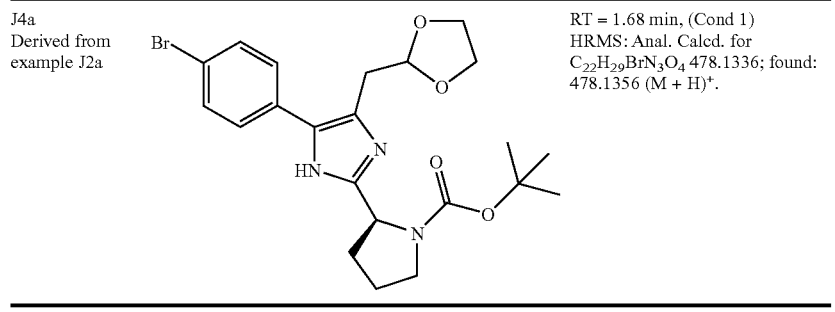 | RT = 1.68 min, (Cond 1)<br>HRMS: Anal. Calcd. for<br>$C_{22}H_{29}BrN_3O_4$ 478.1336; found:<br>478.1356 $(M + H)^+$. |

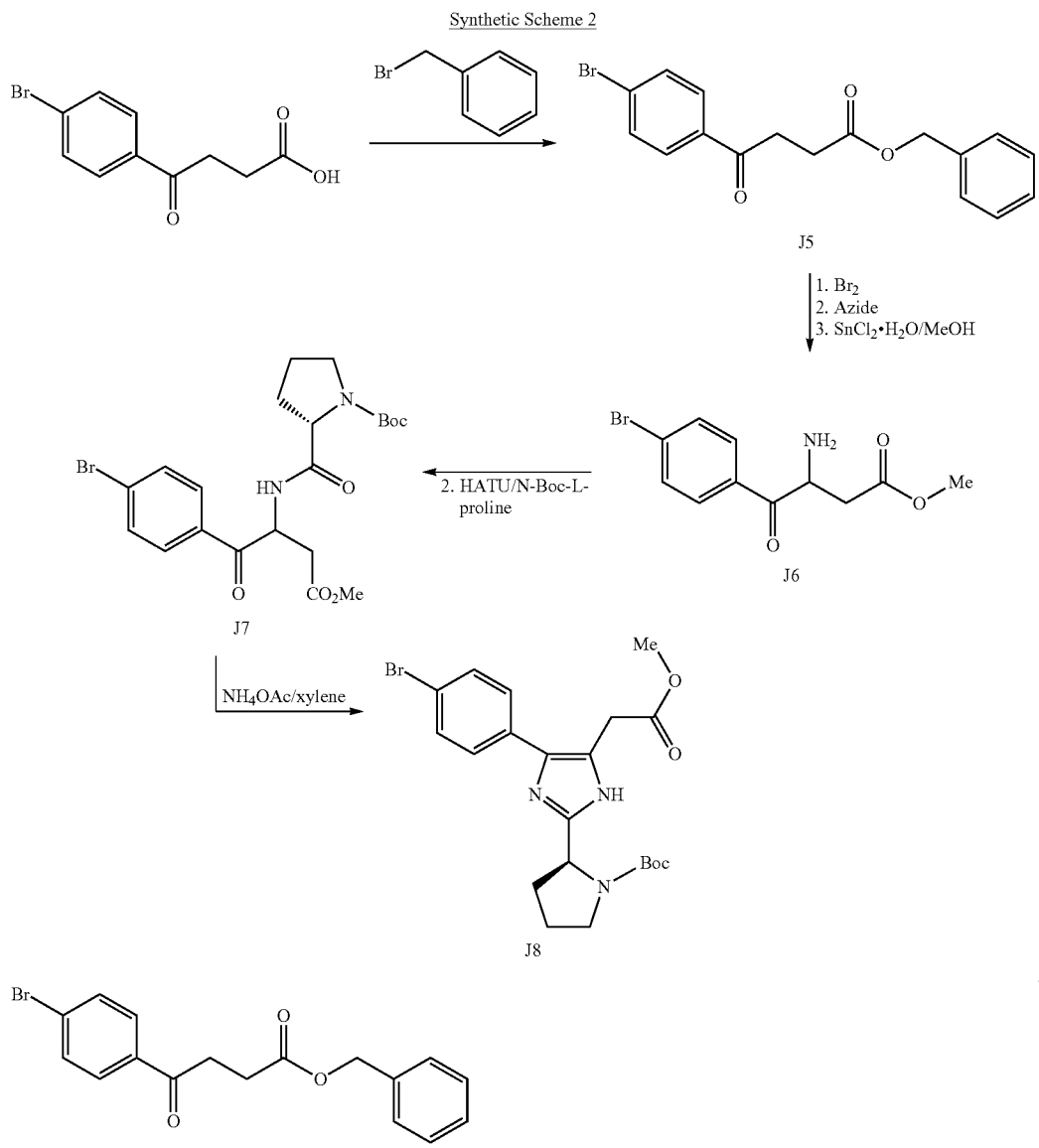

Synthetic Scheme 2

Benzyl bromide (9.98 g, 58.3 mmol) was added to a solution of 4-(4-bromophenyl)-4-oxobutanoic acid (15.0 g, 58.3 mmol) and $K_2CO_3$ (3.5 g, 58.3 mmol) in DMF (300 mL) and stirred for 18 hours. The reaction mixture was partitioned between water (200 mL) and ethyl acetate (500 mL). Sat'd NaHCO$_3$ soln (20 mL) was added and the aqueous layer extracted with ethyl acetate (2×) and the combined organic layers were washed with brine and dried and filtered. Concentration gave Example J5, benzyl 4-(4-bromophenyl)-4-oxobutanoate 16 g (79%) which was used without further purification. ¹H NMR (500 MHz, CDCl₃) δ 7.83 (d, J=8.6 Hz, 2H), 7.61 (d, J=8.5 Hz, 2H), 7.35-7.34 (m, 5H), 5.14 (s, 2H), 3.27 (t, J=6.7 Hz, 2H), 2.81 (t, J=6.7 Hz, 2H). HRMS: Anal. C17H16BrNO3 Calcd. 347.0277. found: 347.0283 (M+H)⁺.

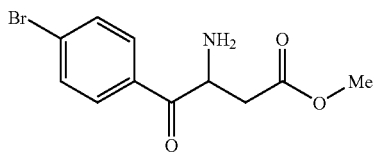

J6

Bromine (2.5 mL, 46.1 mmol) was added to a solution of Example J5, benzyl 4-(4-bromophenyl)-4-oxobutanoate (16 g, 46.1 mmol) in ether (200 mL) and 1,4-Dioxane (50 mL) and the solution was stirred for 6 hours before being concentrated by rotory evaporation and taken up in acetonitrile (450 mL). Sodium azide (3.0 g, 46.1 mmol) was added and the reaction mixture stirred 18 hours. The solvent was removed upon concentration and the residue taken up in ethyl acetate and wash with water, brine, dried Na₂SO₄, and filtered. Concentration gave benzyl 3-azido-4-(4-bromophenyl)-4-oxobutanoate 17 g (95%) which was carried forward without further purification. Tin (II) chloride dehydrate (24.9 g, 131 mmol) was added to a solution of benzyl 3-azido-4-(4-bromophenyl)-4-oxobutanoate (17 g, 43.8 mmol) in CH₃OH (550 mL) and stirred for 14 hours at 65° C. The reaction was concentrated by rotory evaporation and dried under high vacuum for 18 hours to give a mixture of benzyl and Example J6, methyl 3-amino-4-(4-bromophenyl)-4-oxobutanoate, (transesterification had occurred) and carried forward with purification. RT=1.3 minutes (condition 1); LCMS: Anal. C11H12BrNO3 Calcd. 286.0. found: 286.14 (M+H)⁺.

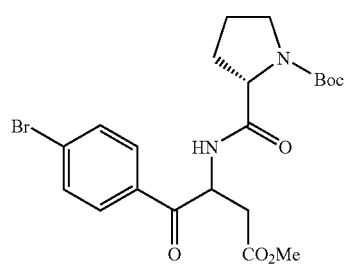

J7

HATU (10.5 g, 27.6 mmol) was added to a solution of Example J6, methyl 3-amino-4-(4-bromophenyl)-4-oxobutanoate (10 g, 27.6 mmol), (S)—N-Boc-proline (7.13 g, 33.1 mmol), and Hunig's Base (45 mL, 276 mmol) in DMF (150 mL) and stirred for 18 hours at 24° C. The reaction was diluted with ethyl acetate (2 vol) and H2O (¼ vol) and sat NaHCO₃ (⅛ vol). Filter through diatomaceous earth (Celite®) to remove tin salts. Extract aqueous layer (2×) with ethyl acetate, and concentrate combined organic to remove solvents (high vacuum on rotory evaporator). The residue was subject to a short silica gel chromatography to remove by-products, and the resultant crude product was charged (CH₂Cl₂) a 65 (M) Biotage silica gel cartridge. Gradient elution 15-70% B over 2 L (A=Hexanes; B=ethyl acetate) gave a less polar band of (2S)-tert-butyl 2-(4-(benzyloxy)-1-(4-bromophenyl)-1,4-dioxobutan-2-ylcarbamoyl)pyrrolidine-1-carboxylate 1.35 g (8.7%) and more polar Example J7, (2S)-tert-butyl 2-(4-(methoxy)-1-(4-bromophenyl)-1,4-dioxobutan-2-ylcarbamoyl)pyrrolidine-1-carboxylate 7.6 g (49%). RT=2.0 minutes (condition 1); LCMS: Anal. C21H27BrN2O6 Calcd. 383. found: 383 (M-Boc).

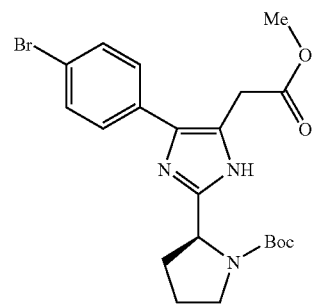

J8

Ammonium acetate (9.4 g, 157 mmol) was added to a solution of Example J7, (2S)-tert-butyl 2-(4-(methoxy)-1-(4-bromophenyl)-1,4-dioxobutan-2-ylcarbamoyl)pyrrolidine-1-carboxylate (7.6 g, 15.7 mmol) in xylene (80 mL) and stirred for 4 hours at 140° C. in a screw capped 150 mL pressure vessel. After being cooled, the reaction mixture was diluted with ethyl acetate and washed with sat NaHCO₃ and brine before being concentrated by rotory evaporation under high vacuum. The crude product was taken up in CH₂Cl₂ and charged to a 40 (M) Biotage silica gel cartridge. Gradient elution 15-100% B over 2 L (A=CH₂Cl₂; B=ethyl acetate) gave Example J8, (S)-tert-butyl 2-(4-(4-bromophenyl)-5-(2-methoxy-2-oxoethyl)-1H-imidazol-2-yl)pyrrolidine-1-carboxylate 3.38 g (46%). ¹H NMR (500 MHz, DMSO-d₆) δ 7.54 (s, 4H), 4.83-4.73 (m, 1H), 3.81 (br. s, 1H), 3.62 (s, 3H), 3.53-3.51 (m, 1H), 3.38-3.31 (m, 2H), 2.25-2.15 (m, 1H), 1.99-1.83 (m, 3H), 1.41/1.16 (s, 9H). RT=1.6 minutes (Condition 1). LCMS: Anal. Calcd. for C21H26BrN3O4 464.11. found: 464.40 (M+H)⁺.

Synthetic Scheme 3

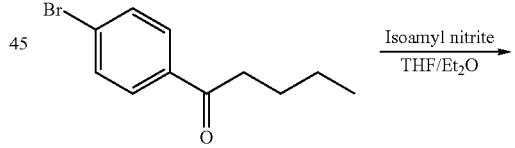

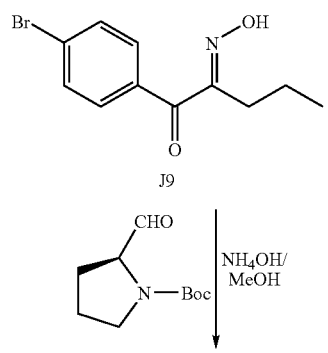

J9

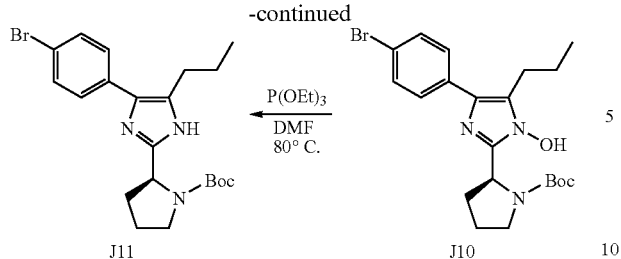

Reference: *J. Med. Chem.* (84), 27, 20. *Syn. Lett.* (2004) 2315.

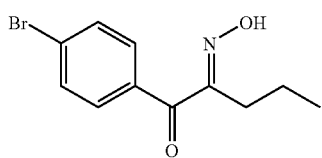

J9

The conc. HCl (40 mL) was added dropwise to a solution of 1-(4-bromophenyl)pentan-1-one (4.68 g, 19.41 mmol) and sodium nitrite (4.02 g, 58.2 mmol) in THF (80 ml) at 0° C. and allowed to warm to room temperature and stirred 18 hours. The reaction mixture was diluted with diethyl ether and the organic phase washed with sat'd $NaHCO_3$ and brine. Concentration gave (Z)-1-(4-bromophenyl)-2-(hydroxyimino) pentan-1-one 3.1 g (33%) as an oil which was used without further purification.). RT=2.1 min, (Condition 1) LCMS: Anal. Calcd. for C11H12BrN1O2 270.01. found: 270.15 $(M+H)^+$.

Reference: *Bioorg. Med. Chem. Lett* (2002) 1009.

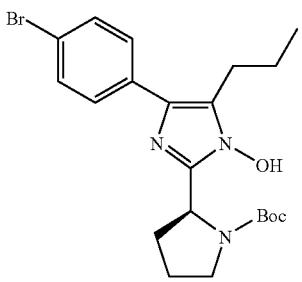

J10

The 28% ammonium hydroxide (15 mL) was added to a solution of (Z)-1-(4-bromophenyl)-2-(hydroxyimino)pentan-1-one (1.5 g, 5.55 mmol) and (S)—N—BOC-prolinal (1.1 g, 5.55 mmol) in methanol (60 mL) and stirred for 18 hours at 24° C. The reaction mixture was partitioned between $CH_2Cl_2$ and water and the organic phase concentrated and applied ($CH_2Cl_2$) to a 40 (M) Biotage silica gel column. Gradient elution, 5-100%, over 1 L (A=Hexanes; B=ethyl acetate) gave (S)-tert-butyl 2-(4-(4-bromophenyl)hydroxy-5-propyl-1H-imidazol-2-yl)pyrrolidine-1-carboxylate (863 mg, 34.5% yield). $^1H$ NMR (500 MHz, DMSO-$d_6$) δ 7.54 (m, 4H), 5.0-4.88 (m, 1H), 3.53-3.41 (m, 1H), 3.41-3.36 (m, 1H), 2.72 (t, J=7.0 Hz, 2H), 2.24-2.03 (m, 2H), 1.96-1.91 (m, 1H), 1.89-1.81 (m, 1H), 1.60 (h, J=7.6 Hz, 2H), 1.39/1.17 (s, 9H). 0.92 (t, J=7.0 Hz, 3H). RT=1.9 min, (Condition 1) LCMS: Anal. Calcd. for $C_{21}H_{28}BrN_3O_3$ 450.13. found: 450.33 $(M+H)^+$.

Reference: *Chem. Pharm. Bull* (1994) 42, 560.

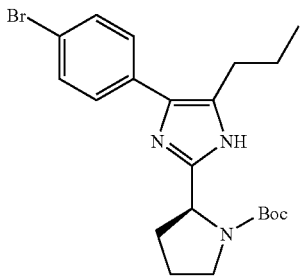

J11

The triethyl phosphite (0.9 mL, 5.33 mmol) was added to a solution of (S)-tert-butyl 2-(4-(4-bromophenyl)hydroxy-5-propyl-1H-imidazol-2-yl)pyrrolidine-1-carboxylate (800 mg, 1.776 mmol) in DMF (2 mL) and stirred for 18 hours at 80° C. Add second 0.8 mL and the reaction was continued an additional 8 hours, cooled, and taken up in ethyl acetate (400 mL) and washed with water and brine. Apply in $CH_2Cl_2$ to a 25 (M) Biotage silica gel column. Gradient elution, 15-100%, over 750 mL (A=Hexanes; B=ethyl acetate) gave (S)-tert-butyl 2-(4-(4-bromophenyl)-5-propyl-1H-imidazol-2-yl) pyrrolidine-1-carboxylate 585 mg (76%). $^1H$ NMR (500 MHz, DMSO-$d_6$) δ 7.55-7.53 (m, 4H), 4.80-4.69 (m, 1H), 3.53-3.51 (m, 1H), 3.38-3.32 (m, 1H), 2.71 (t, J=7.0 Hz, 2H), 2.24-2.11 (m, 1H), 2.0-1.79 (m, 1H), 1.89-1.79 (m, 2H), 1.63-1.59 (m, 2H), 1.41/1.17 (s, 9H). 0.91 (t, J=7.6 Hz, 3H). RT=1.8 min, (Condition 1) LRMS: Anal. Calcd. for $C_{21}H_{28}BrN_3O_2$ 434.14. found: 434.0 $(M+H)^+$.

Synthetic Scheme 4

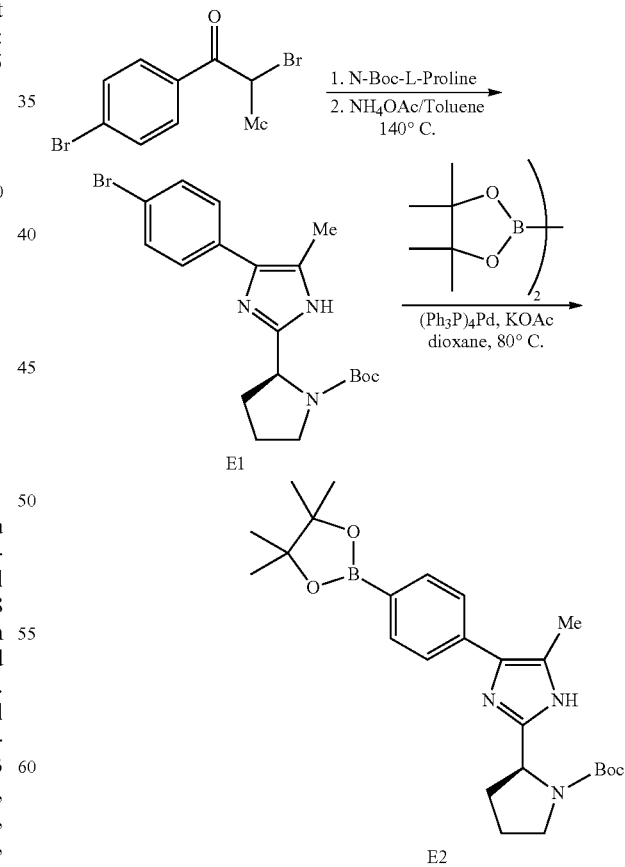

To a mixture of 2,4'-dibromopropiophenone (4.96 g, 0.017 mol) and N-Boc-L-proline (4.09 g, 0.019 mol) in dry $CH_3CN$ (75 mL) was added DIEA (3.30 mL, 0.019 mol) and the mixture was stirred at room temperature under Ar for 16 hours. The mixture was then concentrated under reduced pressure and the concentrate was partitioned with $CH_2Cl_2$-10% saturated $NaHCO_3$. The organic phase was washed (brine), dried ($Na_2SO_4$), filtered, and concentrated to give the proline ester (7.28 g, >100%) as a colorless gum which was used as such in the next step. LCMS: Anal. Calcd. for C19H24BrNO5: 426. found: 426 (M+H)+.

A mixture of the proline ester (0.435 g, 1.0 mmol) and ammonium acetate (0.308 g, 4.0 mmol) in toluene (5 mL) was heated at 140° C. (bath temperature) in a sealed tube for 5 hours. The cooled reaction mixture was evaporated and the residue was chromatographed ($SiO_2$/ethyl acetate-hexane, 3:2) to give Example E1 (0.320 g, 79%) as a nearly colorless foam. $^1$HNMR (400 MHz, $CDCl_3$) δ 7.53 (s, 4H), 4.98 (m, 0.3H), 4.87 (m, 0.7H), 3.65 (m, 1H), 3.4-3.6 (m, 1H), 2.50 (s, 3H), 2.32 (m, 1H), 2.13 (m, 2H), 1.94 (m, 1H), 1.47 (s, 3H), 1.31 (s, 6H). LCMS: Anal. Calcd. for C19H24BrN3O2: 405, 407. found: 406, 408 (M+H)+.

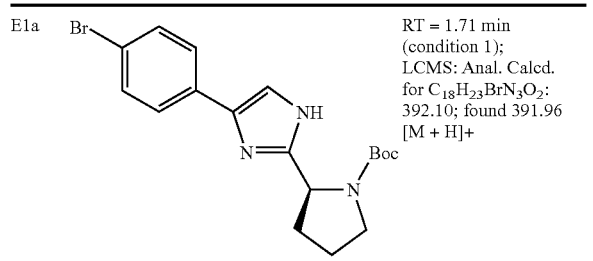

E1a: RT = 1.71 min (condition 1); LCMS: Anal. Calcd. for $C_{18}H_{23}BrN_3O_2$: 392.10; found 391.96 [M + H]+

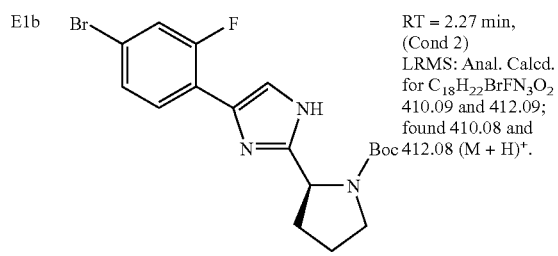

E1b: RT = 2.27 min, (Cond 2) LRMS: Anal. Calcd. for $C_{18}H_{22}BrFN_3O_2$ 410.09 and 412.09; found 410.08 and 412.08 (M + H)+.

-continued

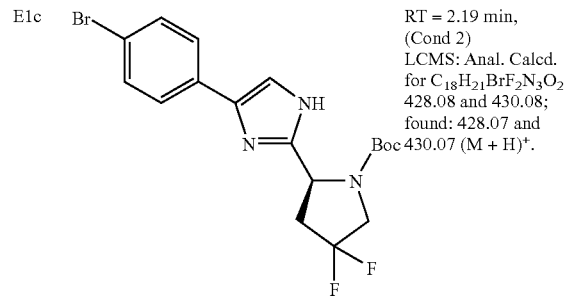

E1c: RT = 2.19 min, (Cond 2) LCMS: Anal. Calcd. for $C_{18}H_{21}BrF_2N_3O_2$ 428.08 and 430.08; found: 428.07 and 430.07 (M + H)+.

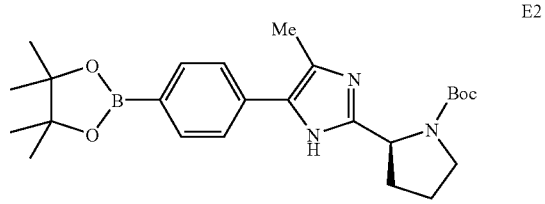

E2

A mixture of Example E1, (S)-tert-butyl 2-(4-(4-bromophenyl)-5-methyl-1H-imidazol-2-yl)-pyrrolidine-1-carboxylate (1.568 g, 3.86 mmol), bis(pinacolato)diboron (2.058 g, 8.10 mmol) and potassium acetate (0.947 g, 9.65 mmol) in dioxane (25 mL) was purged with a stream of Ar bubbles for 10 min and then $(Ph_3P)_4Pd$ (0.223 g, 0.19 mmol) was added and purging with Ar was continued for another 10 min. The reaction vessel was then sealed and heated at 80° C. (bath temperature) for 18 hours. The cooled mixture was diluted with dichloromethane and then it was washed ($H_2O$, brine), dried ($Na_2SO_4$), filtered, and concentrated. The residue was triturated with ethyl acetate and the resulting solid was filtered, washed with a little ethyl acetate and dried in vacuo to give the title compound (quantitative) as a solid. It was used as such in the next step without further purification. $^1$HNMR (400 MHz, DMSO-$d_6$) δ 11.93 (br s, 0.3H), 11.71 (br s, 0.7H), 7.65 (br s, 4H), 4.79 (m, 0.4H), 4.69 (m, 0.6H), 3.52 (m, 1H), 3.36 (m, 2H), 2.38 (s, 3H), 1.78-2.26 (m, 4H), 1.41 (s, 4H), 1.30 (s, 10H), 1.17 (m, 6H). LCMS: Anal. Calcd. for C25H36BN3O4: 453. found: 454 (M+H)+.

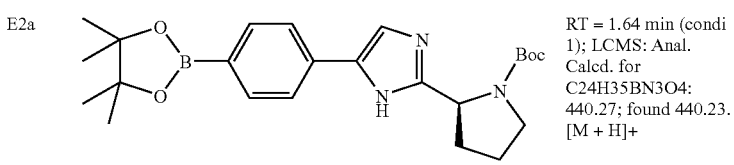

E2a: RT = 1.64 min (condi 1); LCMS: Anal. Calcd. for C24H35BN3O4: 440.27; found 440.23. [M + H]+

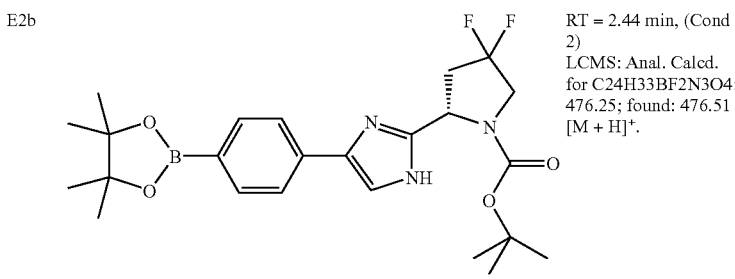

E2b: RT = 2.44 min, (Cond 2) LCMS: Anal. Calcd. for C24H33BF2N3O4: 476.25; found: 476.51 [M + H]+.

Synthetic Scheme 5

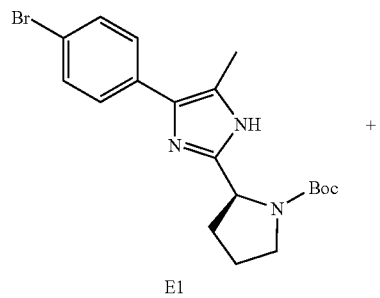

+

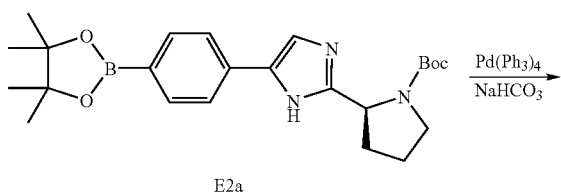

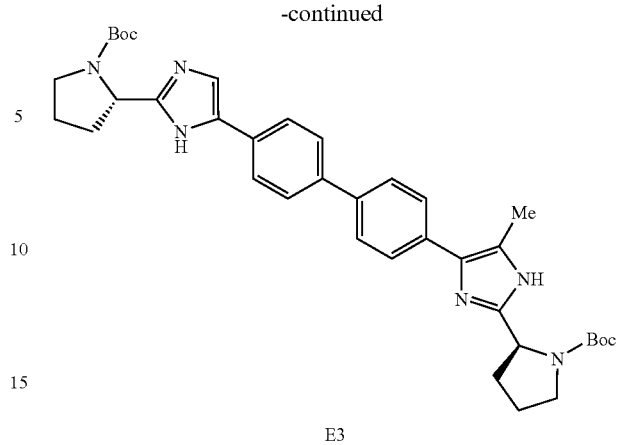

A mixture of Example E1, (S)-tert-butyl 2-(4-(4-bromophenyl)-5-methyl-1H-imidazol-2-yl)-pyrrolidine-1-carboxylate (0.682 g, 1.68 mmol), Example E2a, (S)-tert-butyl 2-(4-(4-(4,4,5,5-tetramethyl-1,3,2-dioxaborolan-2-yl)phenyl)-1H-imidazol-2-yl)pyrrolidine-1-carboxylate (0.764 g, 1.74 mmol) and NaHCO$_3$ (0.465 g, 5.53 mmol) in a mixture of DME (20 mL) and H$_2$O (5 mL) was purged with a stream of Ar bubbles for 10 min. To this mixture was added (Ph$_3$P)$_4$Pd (0.091 g, 0.08 mmol) and purging with Ar was continued for another 10 min. The reaction vessel was then sealed and heated at 80° C. (bath temperature) for 18 hours. The cooled mixture was concentrated under reduced pressure and the concentrate was diluted with ethyl acetate and washed with H$_2$O. The aqueous phase was back-extracted with ethyl acetate and the combined organic phase was washed (brine), dried (Na$_2$SO$_4$), filtered, and concentrated to give a gum. The residue was chromatographed (SiO$_2$/ethyl acetate-hexane, 7:3) to give Example E3 (0.592 g, 59%) as a foam. $^1$HNMR (400 MHz, CDCl$_3$) δ 7.37-7.88 (m, 8H), 7.27 (s, 1H), 5.10 (t, J=7.65 Hz, 2H), 3.45 (m, 4H), 3.00 (m, 2H), 2.44 (s, 3H), 2.20 (br s, 4H), 1.99 (m, 2H), 1.53 (s, 18H). LCMS: Anal. Calcd. for C37H46N6O4: 638. found: 639 (M+H)$^+$.

| | | |
|---|---|---|
| E3a<br>Derived<br>from<br>example<br>E2 and E3 | 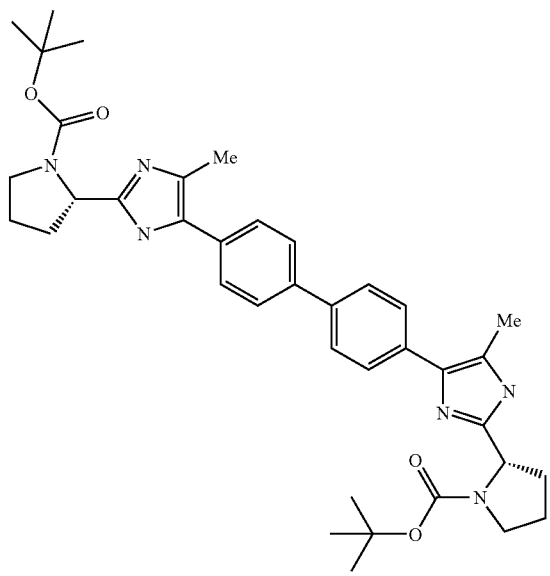 | LCMS: Anal.<br>Calcd. for<br>C38H48N6O4:<br>652; found:<br>653 (M + H)$^+$. |

| | | | |
|---|---|---|---|
| J12 Derived from example E2a and J4 | tert-butyl (2S)-2-(4-(4'-(2-((2S)-1-(tert-butoxycarbonyl)-2-pyrrolidinyl)-4-(1,3-dioxan-2-ylmethyl)-1H-imidazol-5-yl)-4-biphenylyl)-1H-imidazol-2-yl)-1-pyrrolidinecarboxylate | 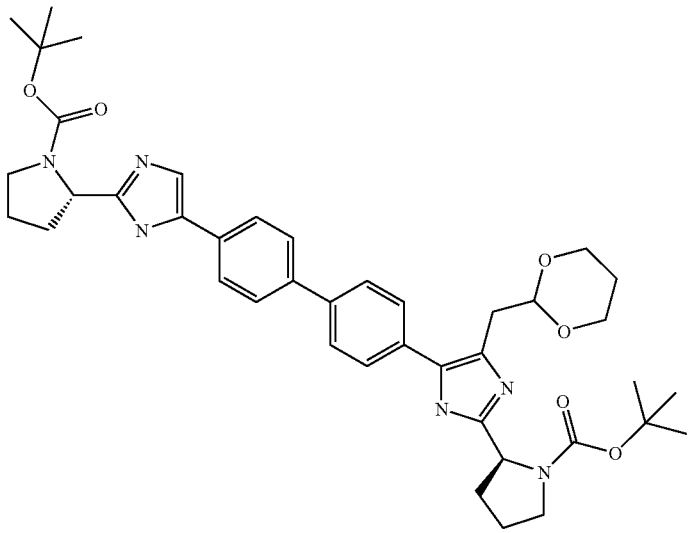 | RT = 1.65 min, (cond 3) HRMS: Anal. Calcd. for $C_{41}H_{53}N_6O_6$ 725.4021; found: 725.4026 $(M + H)^+$. |
| J12a Derived from example E2a and J4a | tert-butyl (2S)-2-(4-(4'-(2-((2S)-1-(tert-butoxycarbonyl)-2-pyrrolidinyl)-4-(1,3-dioxolan-2-ylmethyl)-1H-imidazol-5-yl)-4-biphenylyl)-1H-imidazol-2-yl)-1-pyrrolidinecarboxylate | 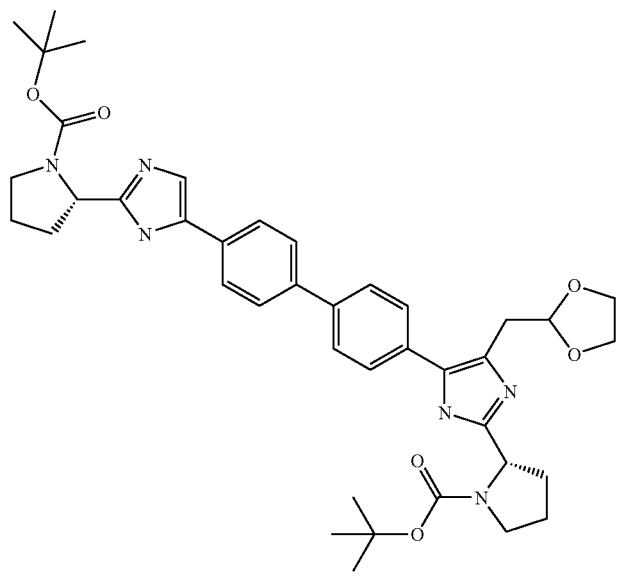 | RT = 1.62 min, (cond 1) HRMS: Anal. Calcd. for $C_{40}H_{51}N_6O_6$ 711.3865; found: 711.3874 $(M + H)^+$. |

| | | | |
|---|---|---|---|
| J12b Derived from example E2a and J8 | tert-butyl (2S)-2-(4-(4'-(2-((2S)-1-(tert-butoxycarbonyl)-2-pyrrolidinyl)-1H-imidazol-4-yl)-4-biphenylyl)-5-(2-methoxy-2-oxoethyl)-1H-imidazol-2-yl)-1-pyrrolidinecarboxylate | 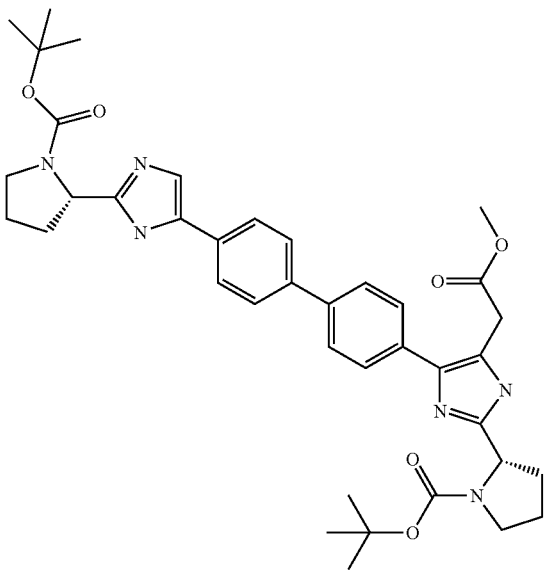 | RT = 1.72 min, (cond 1) HRMS: Anal. Calcd. for $C_{39}H_{48}N_6O_6$ 697.3087; found: 697.3721 (M + H)+. |
| J12c Derived from example E2a and J11 | tert-butyl (2S)-2-(4-(4'-(2-((2S)-1-(tert-butoxycarbonyl)-2-pyrrolidinyl)-1H-imidazol-4-yl)-4-biphenylyl)-5-propyl-1H-imidazol-2-yl)-1-pyrrolidinecarboxylate | 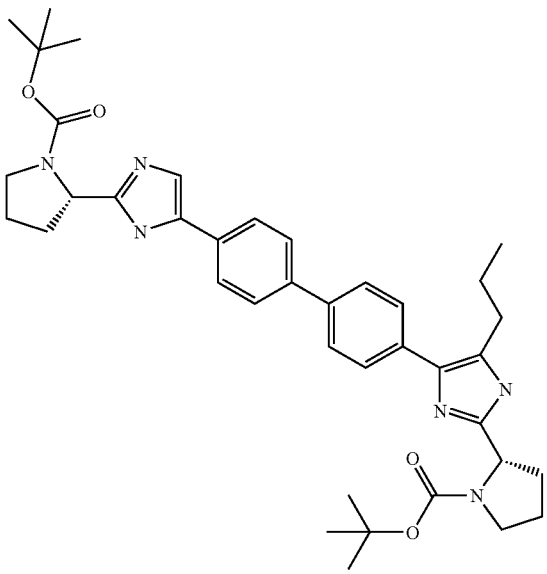 | RT = 1.72 min, (cond 1) LCMS: Anal. Calcd. for $C_{39}H_{50}N_6O_4$ 667.40; found: 667.30 (M + H)+. |

-continued

| | | | |
|---|---|---|---|
| J12d | ethyl 2-((2S)-1-(tert-butoxycarbonyl)-2-pyrrolidinyl)-5-(4'-(2-((2S)-1-(tert-butoxycarbonyl)-2-pyrrolidinyl)-1H-imidazol-5-yl)-4-biphenylyl)-1H-imidazole-4-carboxylate | 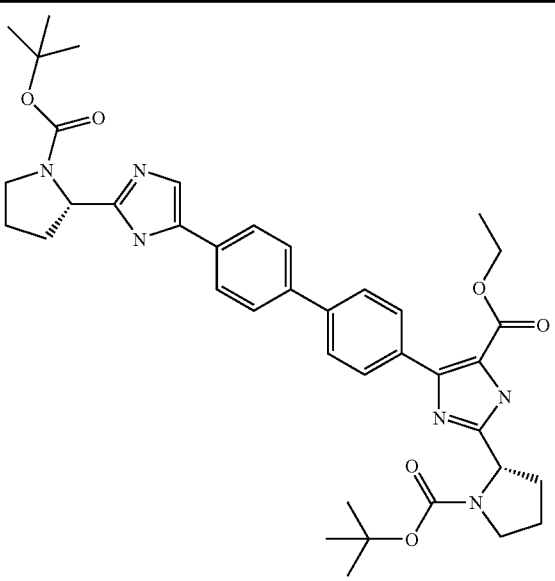 | RT = 1.70 min, (95%) (Cond 2); LRMS: Anal. Calcd. for C38H47N6O6 683.36; found: 683.42 (M + H)+ |
| J12e Derived from example E2b and E1b | tert-butyl (2S)-2-(4-(4'-(2-((2S)-1-(tert-butoxycarbonyl)-2-pyrrolidinyl)-1H-imidazol-4-yl)-3'-fluoro-4-biphenylyl)-1H-imidazol-2-yl)-4,4-difluoro-1-pyrrolidinecarboxylate | 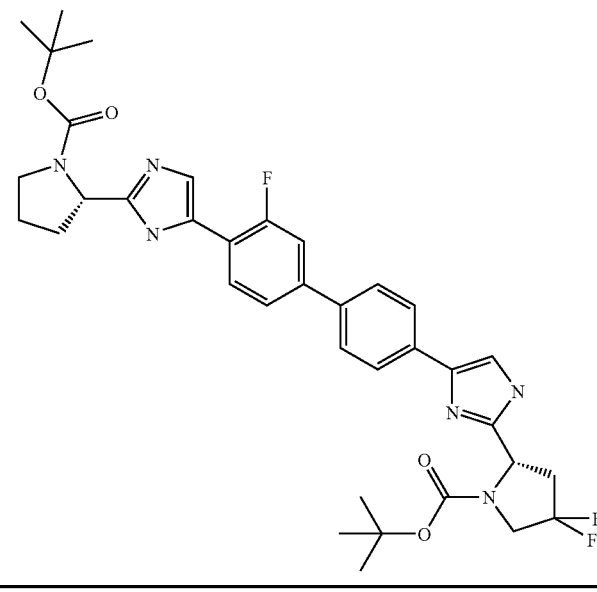 | RT = 2.24 min, (cond 2) LCMS: Anal. Calcd. for C36H42F3N6O4 679.32; found: 679.57 (M + H)+. |

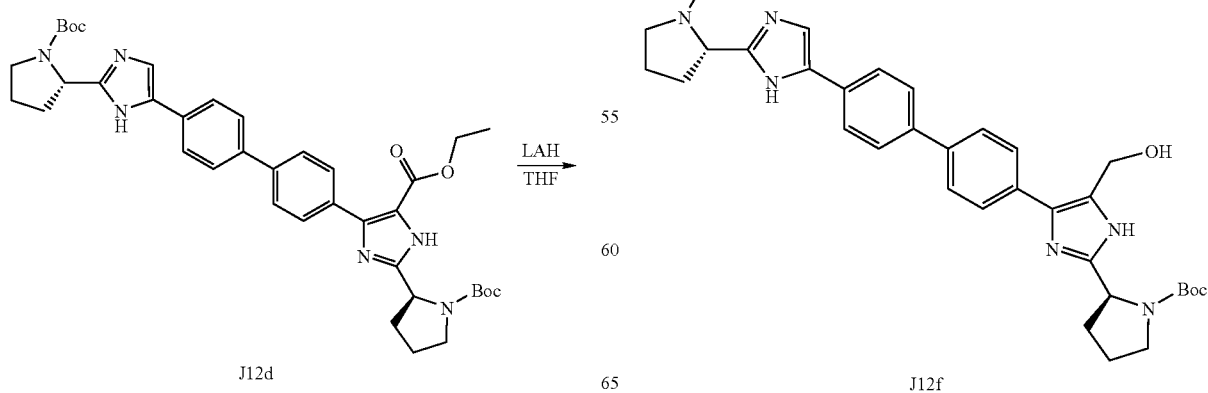

The LAH (0.7 mL, 1M in THF) was added to a solution of Example J12d, (466 mg, 0.669 mmol) in THF (50 mL) and stirred at 0° C. for 1.5 hours before slowly allowing to warm to room temperature. After 3 hours the reaction was quenched with water (0.4 mL), 15% NaOH (0.4 mL) and water (0.4 mL) and the aluminum salts removed by filtration. The salts were rinsed with THF, the combined filtrates were concentrated, and the residue charged ($CH_2Cl_2$) to a 25 (S) Biotage silica gel cartridge and gradient eluted 15-100% over 1 L solvent (A=$CH_2Cl_2$; B=10% $CH_3OH$/ethyl acetate) to give Example J12f, tert-butyl (2S)-2-(4-(4'-(2-((2S)-1-(tert-butoxycarbonyl)-2-pyrrolidinyl)-4-(hydroxymethyl)-1H-imidazol-5-yl)-4-biphenylyl)-1H-imidazol-2-yl)-1-pyrrolidinecarboxylate, 88 mg (20%) in addition to recovered J12d and over reduction. RT=1.7 minutes (Condition 1); LCMS Anal. Calcd. for C37H46N6O5 665.36. found: 665.46 $(M+H)^+$.

Synthetic Scheme 7

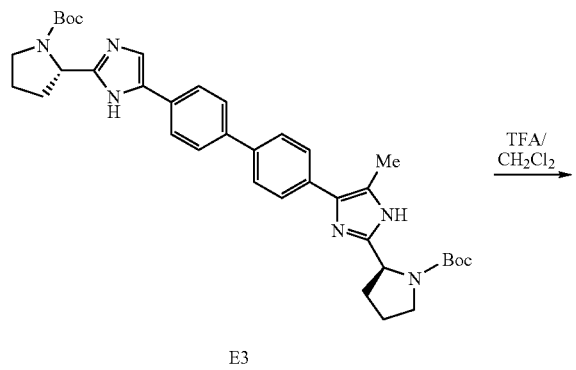

E3

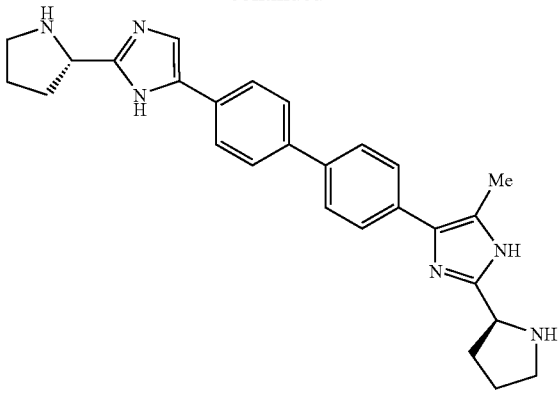

E4

A solution of Example E3 (0.240 g, 0.376 mmol) in 5 mL of TFA-$CH_2Cl_2$ (4:1) was stirred at room temperature for 2 hours and then the volatiles were removed under reduced pressure. The resulting gum was taken up in a minimum volume of $CH_3OH$ and adsorbed on an MCX LP cartridge (6 g, pre-conditioned with $CH_3OH$). The cartridge was washed with $CH_3OH$ and then eluted with 2M $NH_3$ in $CH_3OH$. The product-containing fractions were combined and evaporated to give E4 (quantitative) as a gum which was used as such in the next step. LCMS: Anal. Calcd. for C27H30N6: 438. found: 439 $(M+H)^+$.

E4a

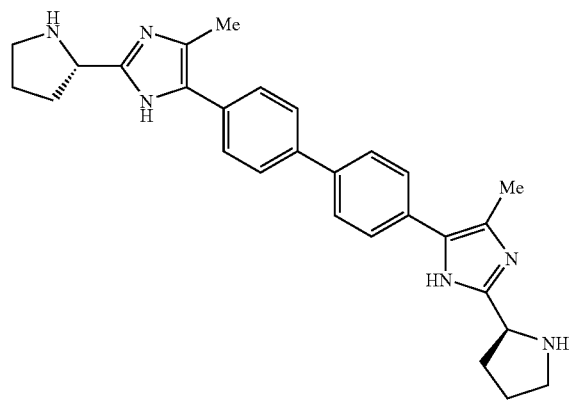

LCMS: Anal. Calcd. for $C_{28}H_{32}N_6$: 452; found: 453 $(M+H)^+$.

| | | | |
|---|---|---|---|
| J13 Derived from example J12 | 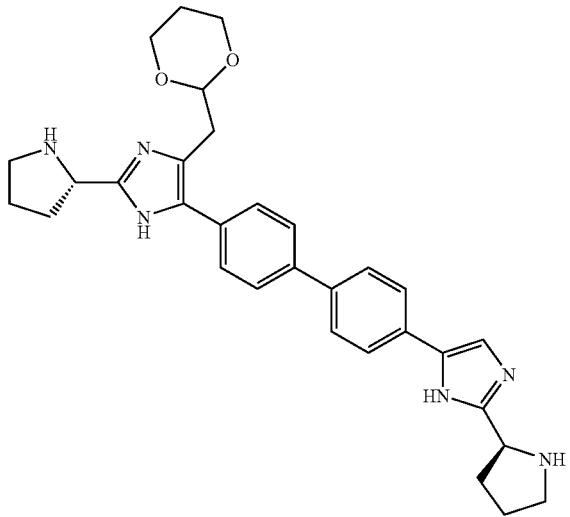 | RT = 1.18 min, (cond 1) LCMS: Anal. Calcd. for $C_{31}H_{36}N_6O_2$ 525.29; found: 525.31 $(M + H)^+$. | Prepared using experimental conditions from example 152k-1. |
| J13a Derived from example J12a | 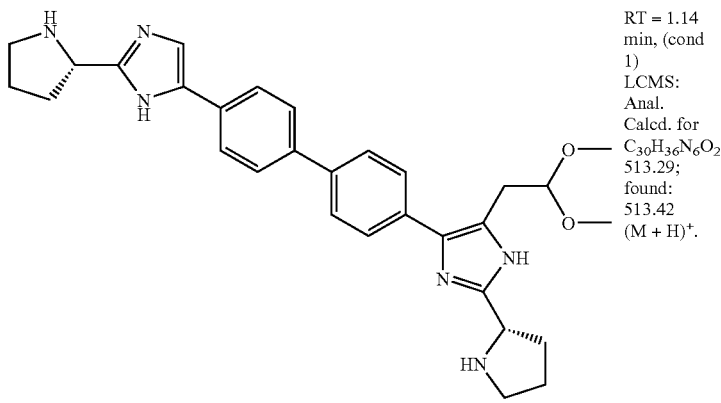 | RT = 1.14 min, (cond 1) LCMS: Anal. Calcd. for $C_{30}H_{36}N_6O_2$ 513.29; found: 513.42 $(M + H)^+$. | Prepared using experimental conditions in example 152k-1. |
| J13b Derived from example J12b | 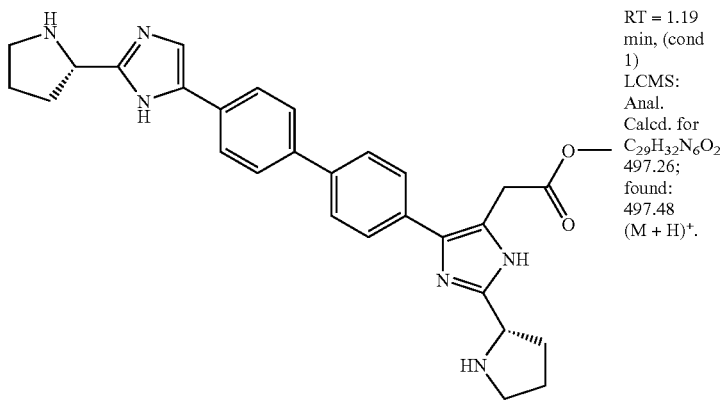 | RT = 1.19 min, (cond 1) LCMS: Anal. Calcd. for $C_{29}H_{32}N_6O_2$ 497.26; found: 497.48 $(M + H)^+$. | Prepared using experimental conditions as outlined in example 152k-1. |

-continued

| | | | |
|---|---|---|---|
| J13c Derived from example J12c | | 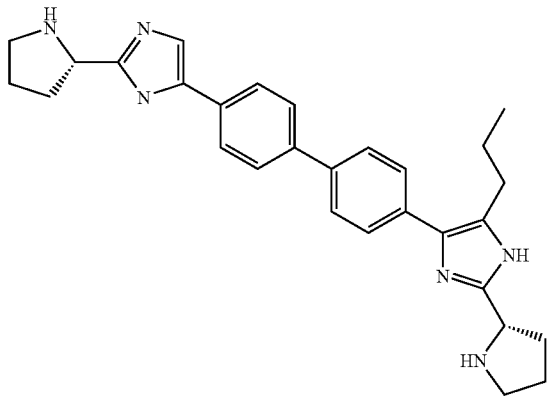 | RT = 1.26 min, (cond 1) LCMS: Anal. Calcd. for C₃₉H₅₀N₆O₄ 467.28; found: 467.55 (M + H)⁺. | Prepared using experimental conditions from example 152k-1. |
| J13e Derived from example J12e | 2-((2S)-4,4-difluoro-2-pyrrolidinyl)-4-(3'-fluoro-4'-(2-((2S)-2-pyrrolidinyl)-1H-imidazol-4-yl)-4-biphenylyl)-1H-imidazole | 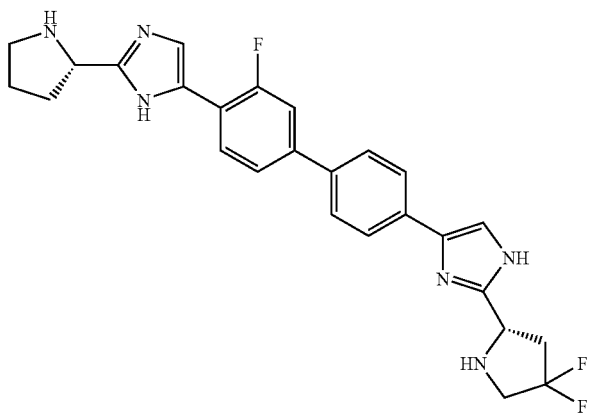 | RT = 1.77 min, (Cond 2) LCMS: Anal. Calcd. for C₂₆H₂₆F₃N₆₈ 479.22; found: 479.39 (M + H)⁺. | Prepared using experimental conditions from example 152k-1. |
| J13f Derived from example J12f | | 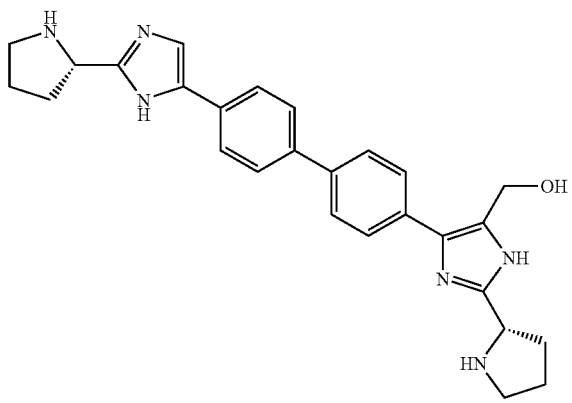 | RT = 1.02 min, (cond 1) LCMS: Anal. Calcd. for C₂₇H₃₀N₆O 455.25; found: 455.47 (M + H)⁺. | Prepared using experimental conditions from example 152k-1. |

Synthetic Scheme 8

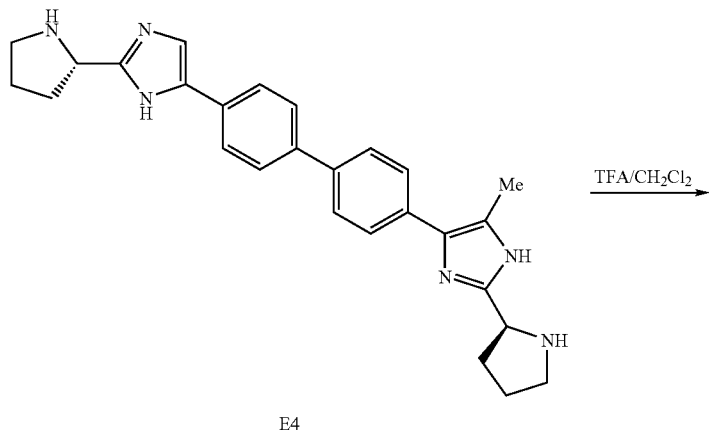

E4

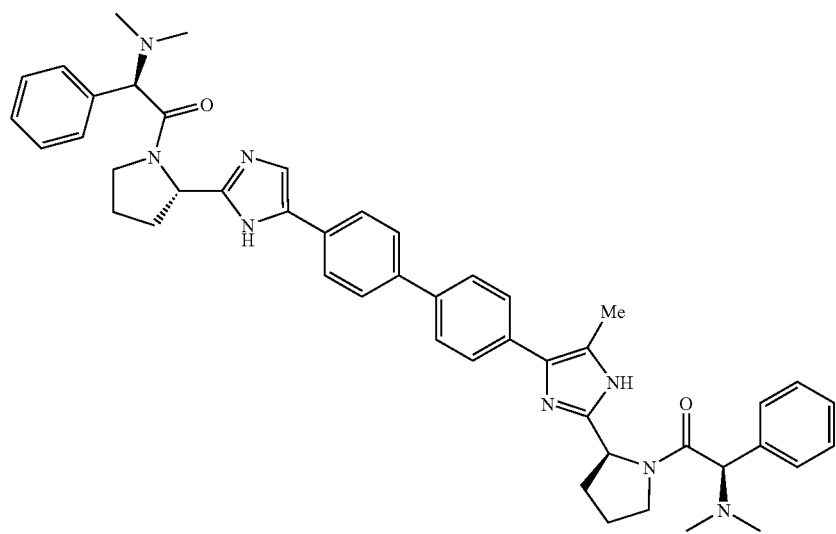

E5

A solution of (R)-2-(dimethylamino)-2-phenylacetic acid hydrochloride (0.047 g, 0.220 mmol), HATU (0.084 g, 0.220 mmol) and DIEA (0.17 mL, 0.70 mmol) in dry DMF (1 mL) was stirred at room temperature for 5 min and then a solution of E4 (0.041 g, 0.094 mmol) in dry DMF (0.5 mL) was added. The mixture was stirred at room temperature for 18 hours and then it was quenched with AcOH (0.2 mL) and a few drops of TFA. This solution was submitted directly to preparative HPLC (C-18/CH$_3$CN—H2O+0.1% TFA) to give the TFA salt of Example E5, (1R)-2-((2S)-2-(4-(4'-(2-((2S)-1-((2R)-2-(dimethylamino)-2-phenylacetyl)-2-pyrrolidinyl)-1H-imidazol-4-yl)-4-biphenylyl)-5-methyl-1H-imidazol-2-yl)-1-pyrrolidinyl)-N,N-dimethyl-2-oxo-1-phenylethanamine (0.011 g, 10%) as a white solid. $^1$HNMR (400 MHz, CH$_3$OH-d$_4$) δ 7.80-7.93 (m, 6H), 7.71-7.74 (m, 2H), 7.50-7.67 (m, 10H), 5.37-5.51 (m, 2H), 5.30 (m, 2H), 4.04 (br s, 3H), 3.00-3.13 (m, 4H), 2.81 (br s, 8H), 2.55 (s, 2H), 2.49 (s, 1H), 2.36 (m, 2H), 2.12-2.25 (m, 5H), 1.96 (br s, 2H). LCMS: Anal. Calcd. for C47H52N8O2: 760. found: 761 (M+H)$^+$.

| | | | |
|---|---|---|---|
| E5a Derived from example E4 | (1R)-2-((2S)-2-(4-(4'-(2-((2S)-1-((2R)-2-(diethylamino)-2-phenylacetyl)-2-pyrrolidinyl)-1H-imidazol-4-yl)-4-biphenylyl)-5-methyl-1H-imidazol-2-yl)-1-pyrrolidinyl)-N,N-diethyl-2-oxo-1-phenylethanamine | 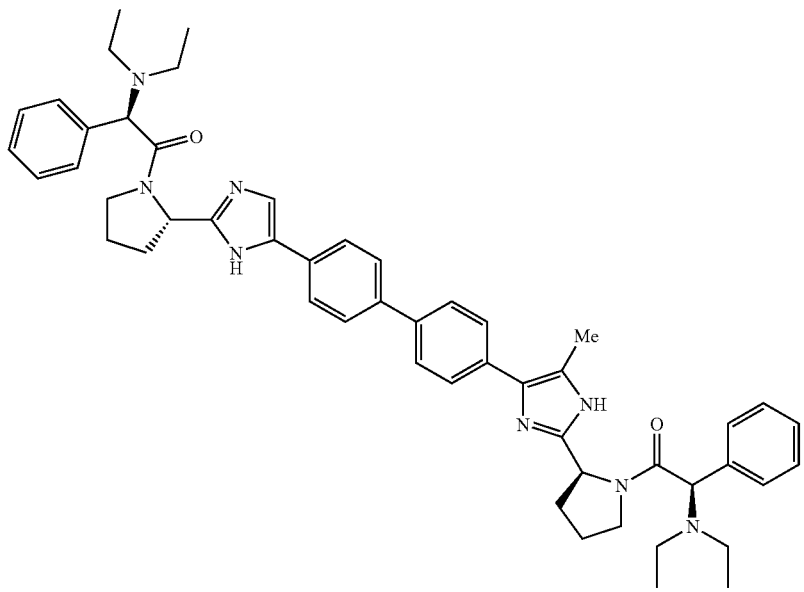 | LCMS: Anal. Calcd. for $C_{51}H_{60}N_8O_2$: 816; found: 817 $(M + H)^+$. |
| E5b Derived from example E4 | 1-((1R)-2-((2S)-2-(4-(4'-(4-methyl-2-((2S)-1-((2R)-2-phenyl-2-(1-piperidinyl)acetyl)-2-pyrrolidinyl)-1H-imidazol-5-yl)-4-biphenylyl)-1H-imidazol-2-yl)-1-pyrrolidinyl)-2-oxo-1-phenylethyl)piperidine | 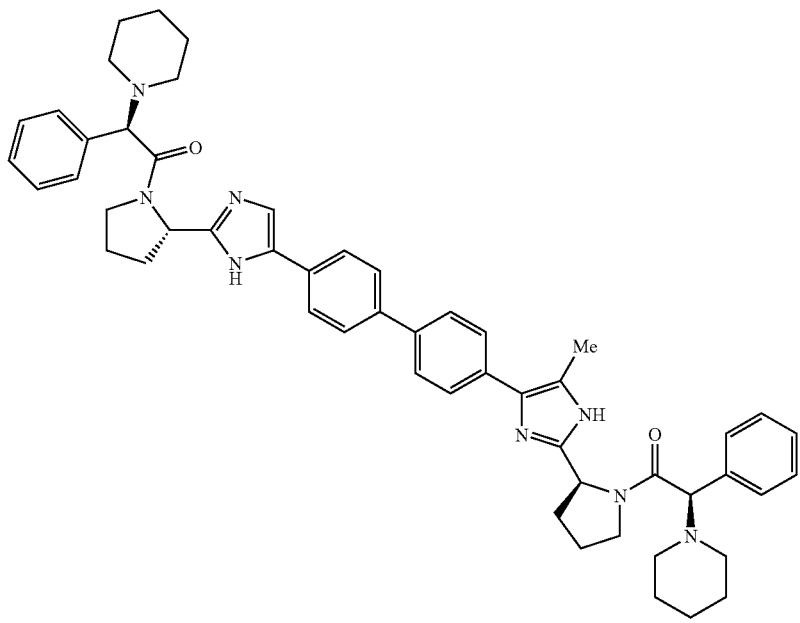 | LCMS: Anal. Calcd. for $C_{53}H_{60}N_8O_2$: 840; found: 841 $(M + H)^+$. |

| | | | |
|---|---|---|---|
| E5c Derived from example E4 | methyl ((1R)-2-((2S)-2-(4-(4'-(2-((2S)-1-((2R)-2-((methoxycarbonyl)amino)-2-phenylacetyl)-2-pyrrolidinyl)-1H-imidazol-4-yl)-4-biphenylyl)-5-methyl-1H-imidazol-2-yl)-1-pyrrolidinyl)-2-oxo-1-phenylethyl)carbamate | 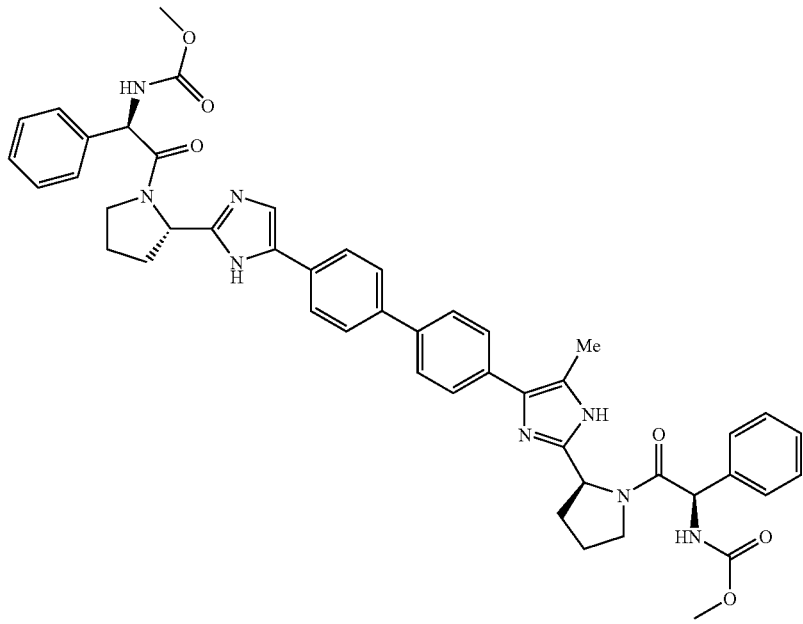 | LCMS: Anal. Calcd. for $C_{47}H_{48}N_8O_6$: 820; found: 821 $(M + H)^+$. |
| E5d Derived from example E4 | methyl ((1S)-2-((2S)-2-(4-(4'-(2-((2S)-1-(N-(methoxycarbonyl)-L-alanyl)-2-pyrrolidinyl)-4-methyl-1H-imidazol-5-yl)-4-biphenylyl)-1H-imidazol-2-yl)-1-pyrrolidinyl)-1-methyl-2-oxoethyl)carbamate | 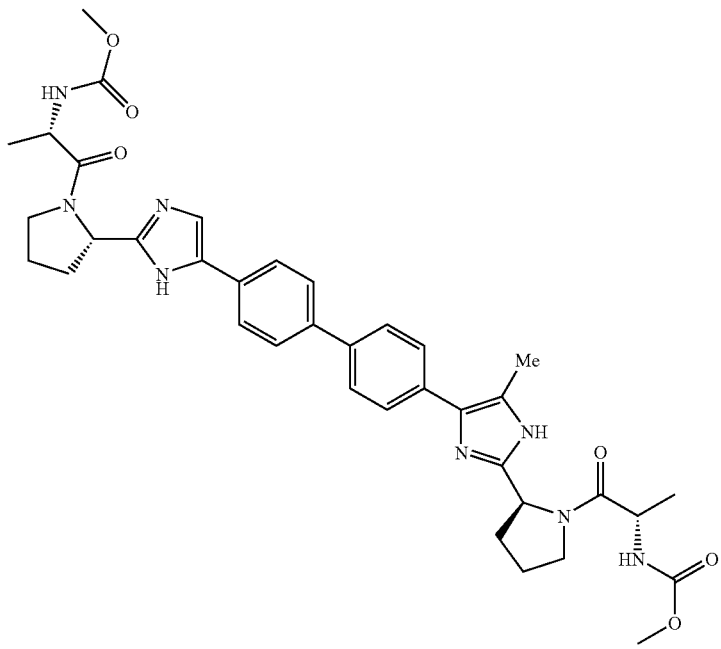 | LCMS: Anal. Calcd. for $C_{37}H_{44}N_8O_6$: 696; found: 697 $(M + H)^+$. |

| | | | |
|---|---|---|---|
| E5e Derived from example E4 | methyl ((1S)-1-(((2S)-2-(4-(4'-(2-((2S)-1-((2S)-2-((methoxycarbonyl) amino)-3-methylbutanoyl)-2-pyrrolidinyl)-1H-imidazol-4-yl)-4-biphenylyl)-5-methyl-1H-imidazol-2-yl)-1-pyrrolidinyl)carbonyl)-2-methyl-propyl)carbamate | 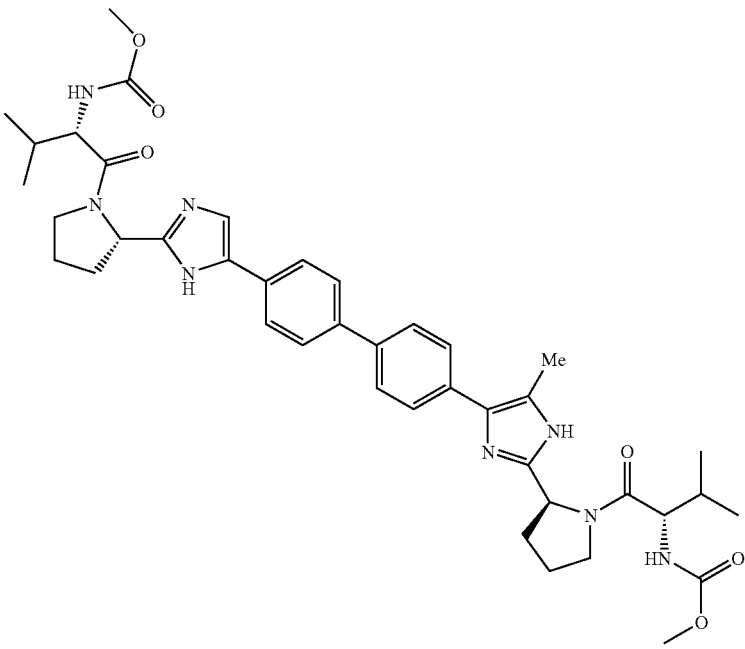 | LCMS: Anal. Calcd. for $C_{41}H_{52}N_8O_6$: 752; found: 753 $(M + H)^+$. |
| E5f Derived from example E4 | methyl ((1S,2R)-2-methoxy-1-(((2S)-2-(4-(4'-(2-((2S)-1-(N-methoxycarbonyl)-O-methyl-L-threonyl)-2-pyrrolidinyl)-4-methyl-1H-imidazol-5-yl)-4-biphenylyl)-1H-imidazol-2-yl)-1-pyrrolidinyl)carbonyl)propyl)carbamate | 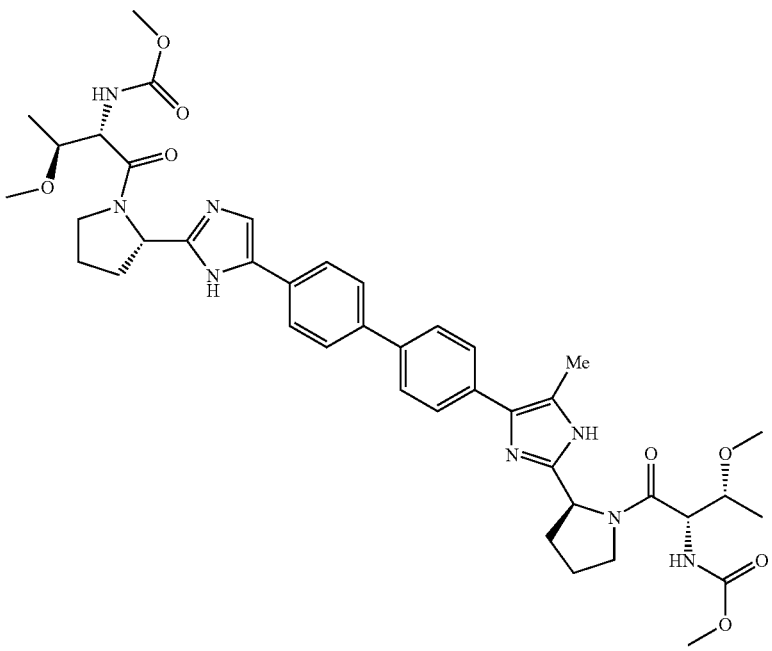 | LCMS: Anal. Calcd. for $C_{41}H_{52}N_8O_8$: 784; found: 785 $(M + H)^+$. |

| | | | |
|---|---|---|---|
| E5g Derived from example E4a | (1R,1'R)-2,2'-(4,4'-biphenyldiylbis((4-methyl-1H-imidazole-5,2-diyl)(2S)-2,1-pyrrolidinediyl))bis(N,N-dimethyl-2-oxo-1-phenylethanamine) | 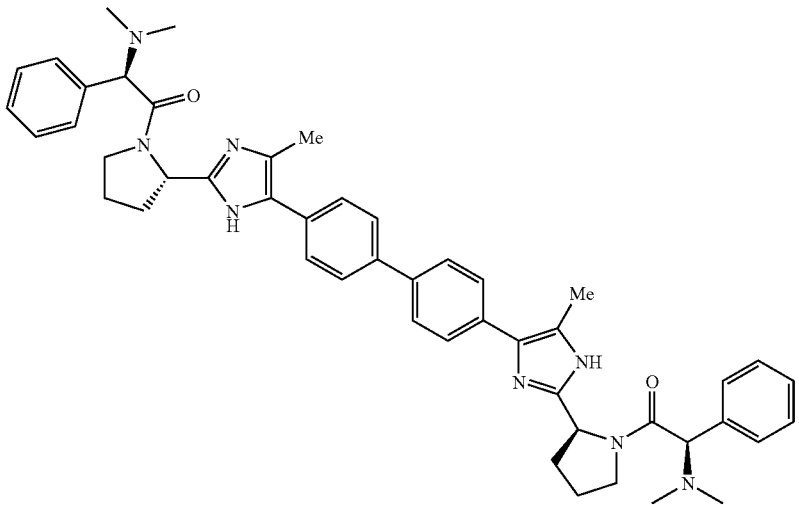 | LCMS: Anal. Calcd. for $C_{48}H_{54}N_8O_2$: 774; found: 775 $(M + H)^+$. |
| E5h Derived from example E4a | (1R,1'R)-2,2'-(4,4'-biphenyldiylbis((4-methyl-1H-imidazole-5,2-diyl)(2S)-2,1-pyrrolidinediyl))bis(N,N-diethyl-2-oxo-1-phenylethanamine) | 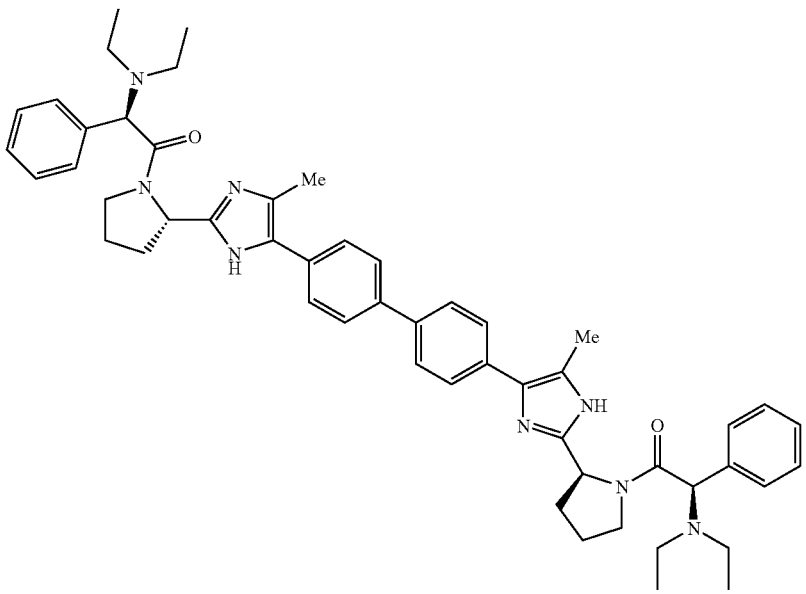 | LCMS: Anal. Calcd. for $C_{52}H_{62}N_8O_2$: 830; found: 831 $(M + H)^+$. |

| | | | |
|---|---|---|---|
| E5i Derived from example E4a | 1,1'-(4,4'-biphenyldiylbis((4-methyl-1H-imidazole-5,2-diyl)(2S)-2,1-pyrrolidine-diyl((1R)-2-oxo-1-phenyl-2,1-ethanediyl)))dipiperidine | 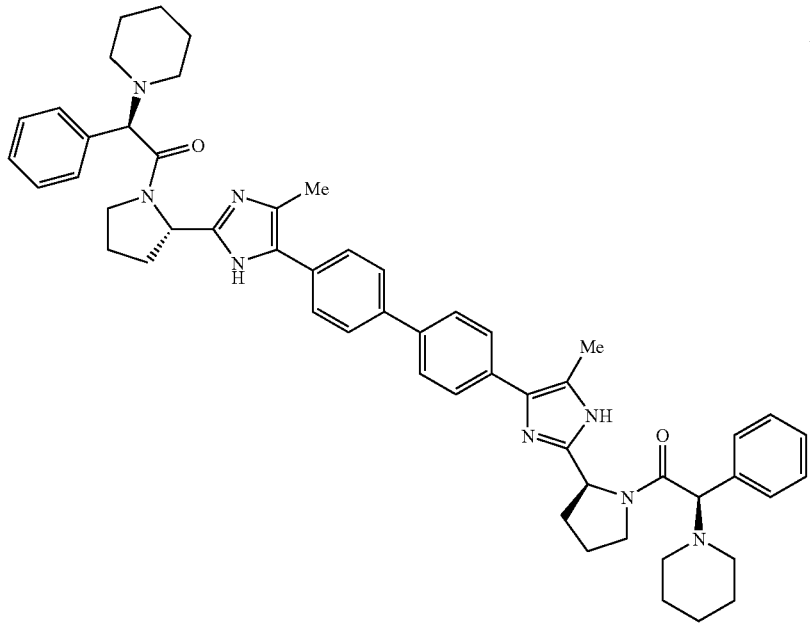 | LCMS: Anal. Calcd. for C54H62N8O2: 854; found: 855 (M + H)+. |
| E5j Derived from example E4a | dimethyl (4,4'-biphenyldiylbis((4-methyl-1H-imidazole-5,2-diyl)(2S)-2,1-pyrrolidine-diyl((1R)-2-oxo-1-phenyl-2,1-ethanediyl)))bis-carbamate | 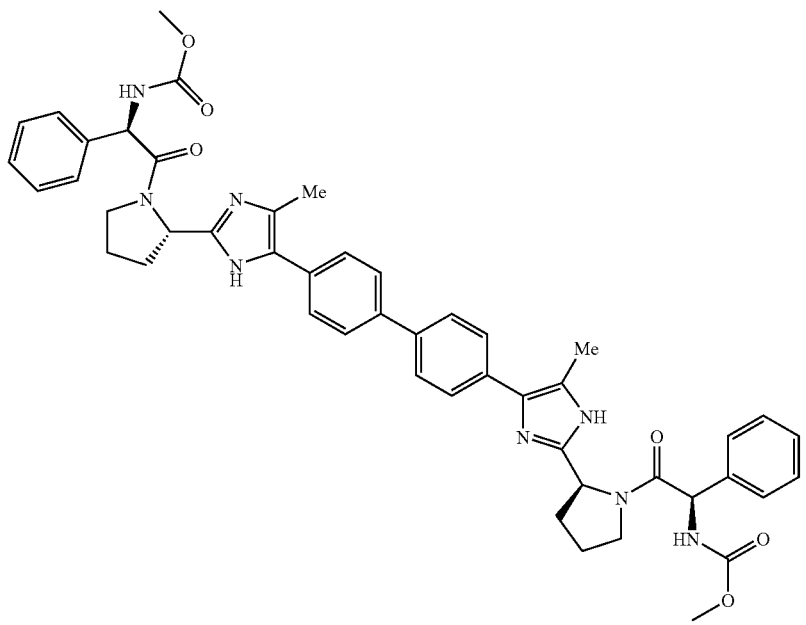 | LCMS: Anal. Calcd. for C48H50N8O6: 834; found: 835 (M + H)+. |

| | | | |
|---|---|---|---|
| E5k Derived from example E4a | methyl ((1S)-2-((2S)-2-(4-(4'-(2-((2S)-1-(N-(methoxycarbonyl)-L-alanyl)-2-pyrrolidinyl)-5-methyl-1H-imidazol-4-yl)-4-biphenylyl)-5-methyl-1H-imidazol-2-yl)-1-pyrrolidinyl)-1-methyl-2-oxoethyl)carbamate | 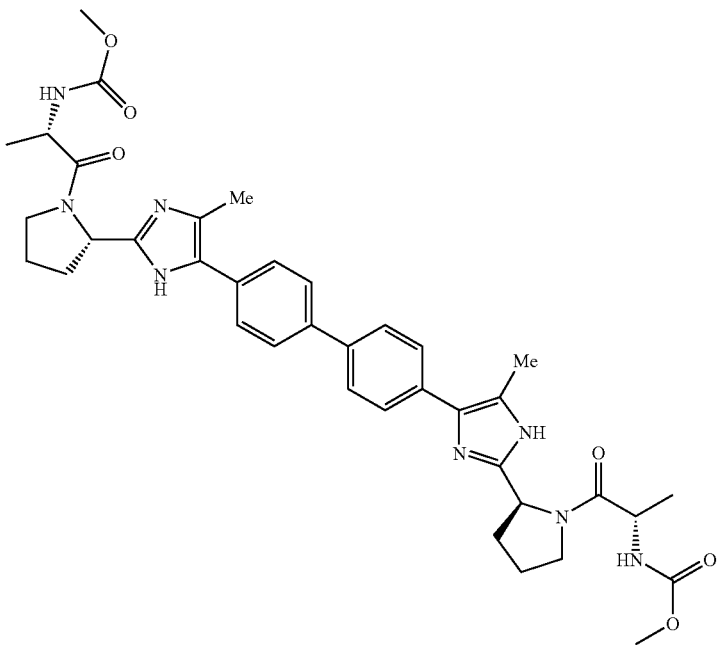 | LCMS: Anal. Calcd. for C38H46N8O6: 710; found: 711 (M + H)+. |
| E5l Derived from example E4a | methyl ((1S)-1-(((2S)-2-(4-(4'-(2-((2S)-1-((2S)-2-((methoxycarbonyl)amino)-3-methylbutanoyl)-2-pyrrolidinyl)-4-methyl-1H-imidazol-5-yl)-4-biphenylyl)-5-methyl-1H-imidazol-2-yl)-1-pyrrolidinyl)carbonyl)-2-methylpropyl)carbamate | 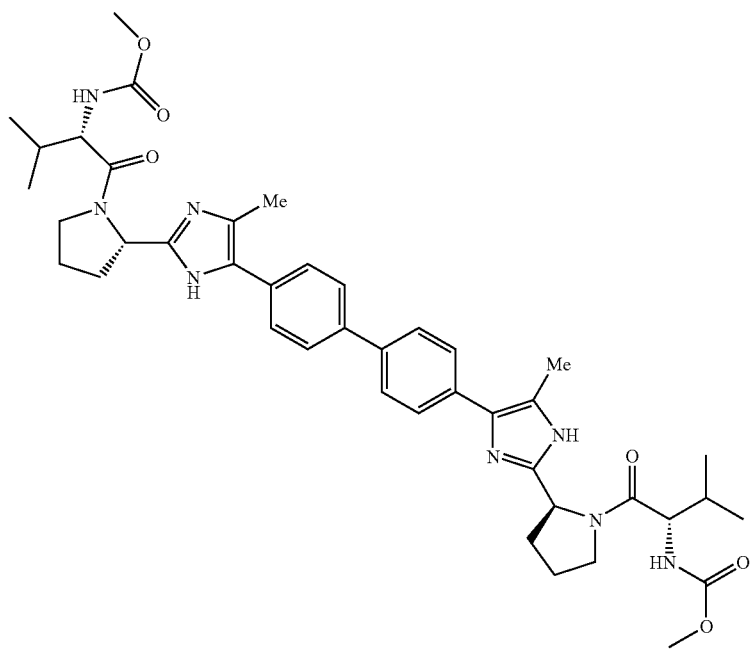 | LCMS: Anal. Calcd. for C42H54N8O6: 766; found: 767 (M + H)+. |

| | | | |
|---|---|---|---|
| E5m Derived from example E4a | methyl ((1S,2R)-2-methoxy-1-(((2S)-2-(4-(4'-(2-((2S)-1-(N-(methoxycarbonyl)-O-methyl-L-threonyl)-2-pyrrolidinyl)-5-methyl-1H-imidazol-4-yl)-4-biphenylyl)-5-methyl-1H-imidazol-2-yl)-1-pyrrolidinyl)carbonyl)propyl)carbamate | 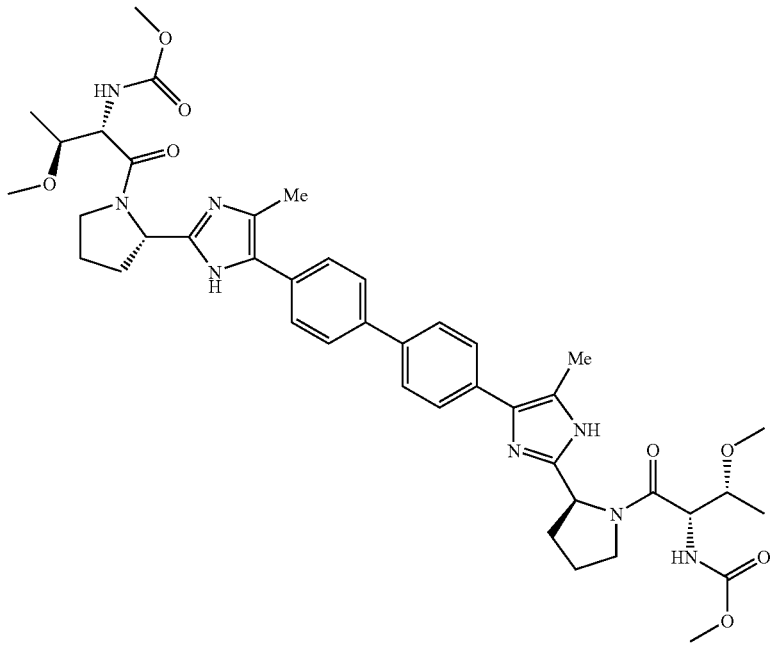 | LCMS: Anal. Calcd. for C42H54N8O8: 798; found: 799 (M + H)+. |
| J14 Derived from example J13 | methyl ((1S)-1-(((2S)-2-(4-(1,3-dioxan-2-ylmethyl)-5-(4'-(2-((2S)-1-((2S)-2-((methoxycarbonyl)amino)-3-methylbutanoyl)-2-pyrrolidinyl)-1H-imidazol-4-yl)-4-biphenylyl)-1H-imidazol-2-yl)-1-pyrrolidinyl) carbonyl)-2-methylpropyl)carbamate | 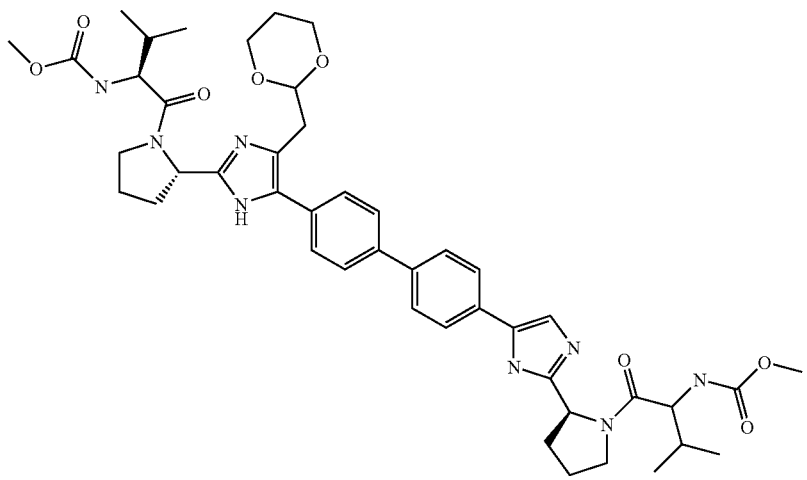 | RT = 1.37 min, (Cond 1); HRMS: Anal. Calcd. for C45H58N8O8 839.4450; found: 839.4456 (M + H)+. |

-continued

| | | | |
|---|---|---|---|
| J14a Derived from example J13a | methyl ((1S,2R)-1-(((2S)-2-(4-(2,2-dimethoxyethyl)-5-(4'-(2-((2S)-1-(N-(methoxycarbonyl)-O-methyl-L-threonyl)-2-pyrrolidinyl)-1H-imidazol-4-yl)-4-biphenylyl)-1H-imidazol-2-yl)-1-pyrrolidinyl)carbonyl)-2-methoxypropyl)carbamate | 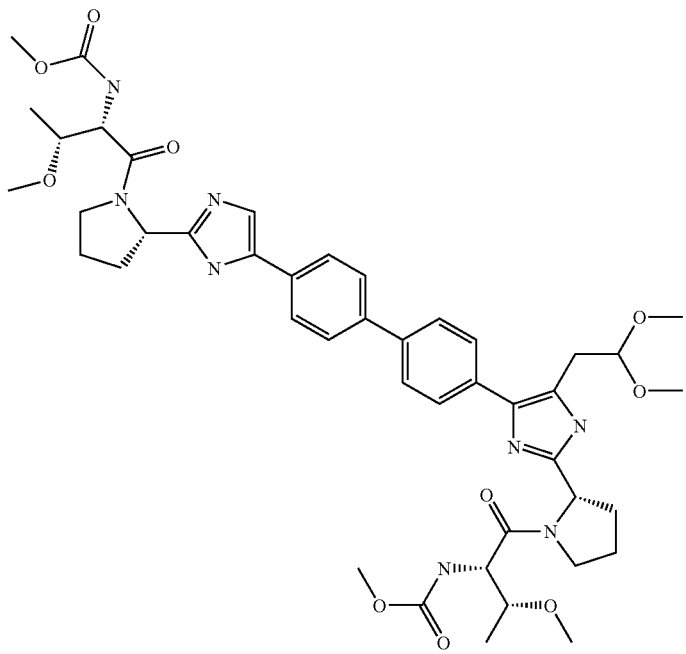 | RT = 1.44 min, (Cond 1); HRMS: Anal. Calcd. for $C_{44}H_{58}N_8O_{10}$ 859.4349; found: 859.4352 $(M + H)^+$. |
| J14a.1 Derived from example J13a | methyl ((1S)-1-(((2S)-2-(4-(2,2-dimethoxyethyl)-5-(4'-(2-((2S)-2-((methoxycarbonyl)amino)-3-methylbutanoyl)-2-pyrrolidinyl)-1H-imidazol-4-yl)-4-biphenylyl)-1H-imidazol-2-yl)-1-pyrrolidinyl)carbonyl)-2-methylpropyl)carbamate | 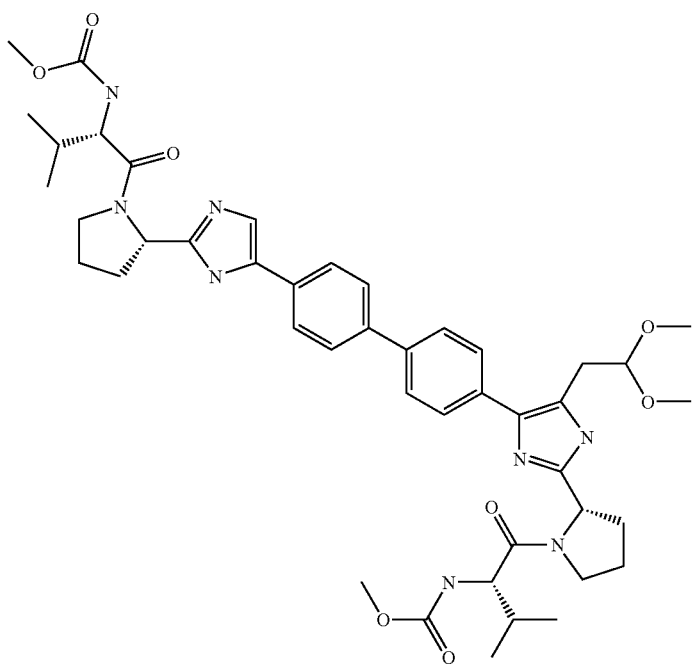 | RT = 1.44 min, (Cond 1); HRMS: Anal. Calcd. for $C_{44}H_{58}N_8O_8$ 827.4450; found: 827.4449 $(M + H)^+$. |

| | | | |
|---|---|---|---|
| J14b Derived from example J13b | methyl (2-((2S)-1-(N-(methoxycarbonyl)-O-methyl-L-threonyl)-2-pyrrolidinyl)-4-(4'-(2-((2S)-1-(N-(methoxycarbonyl)-O-methyl-L-threonyl)-2-pyrrolidinyl)-1H-imidazol-4-yl)-4-biphenylyl)-1H-imidazol-5-yl)acetate | 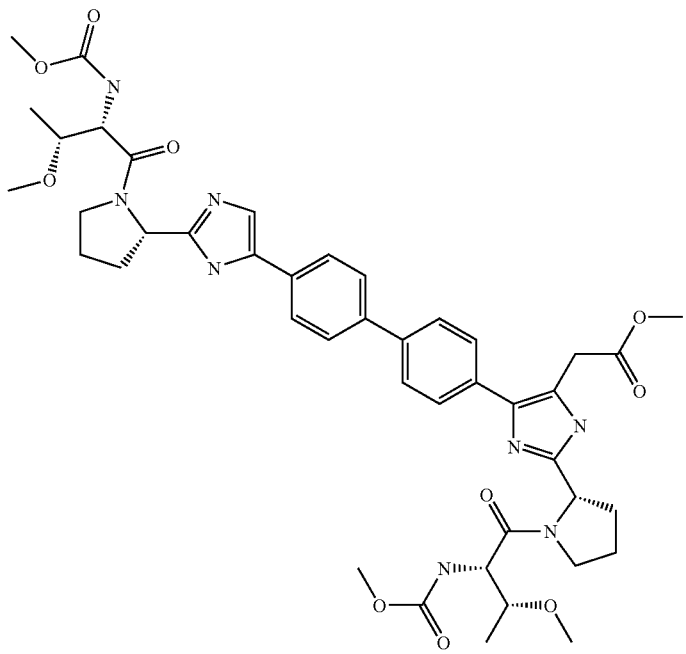 | HRMS: Anal. Calcd. for $C_{43}H_{54}N_8O_{10}$ 843.4036; found: 843.4046 $(M + H)^+$. |
| J14b.1 Derived from example J13b | methyl (2-((2S)-1-(N-(methoxycarbonyl)-L-valyl)-2-pyrrolidinyl)-4-(4'-(2-((2S)-1-(N-(methoxycarbonyl)-L-valyl)-2-pyrrolidinyl)-1H-imidazol-4-yl)-4-biphenylyl)-1H-imidazol-5-yl)acetate | 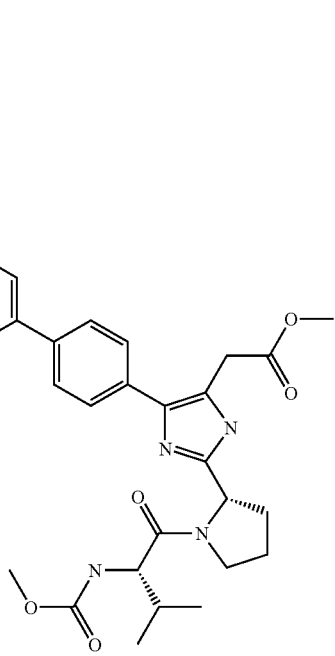 | RT = 1.42 min, (Cond 1); HRMS: Anal. Calcd. for $C_{43}H_{54}N_8O_8$ 811.4137; found: 811.4154 $(M + H)^+$. |

| | | | |
|---|---|---|---|
| J14c Derived from example J13c | methyl ((1S)-2-((2S)-2-(4-(4'-(2-((2S)-1-(N-(methoxycarbonyl)-L-alanyl)-2-pyrrolidinyl)-4-propyl-1H-imidazol-5-yl)-4-biphenylyl)-1H-imidazol-2-yl)-1-pyrrolidinyl)-1-methyl-2-oxoethyl)carbamate | 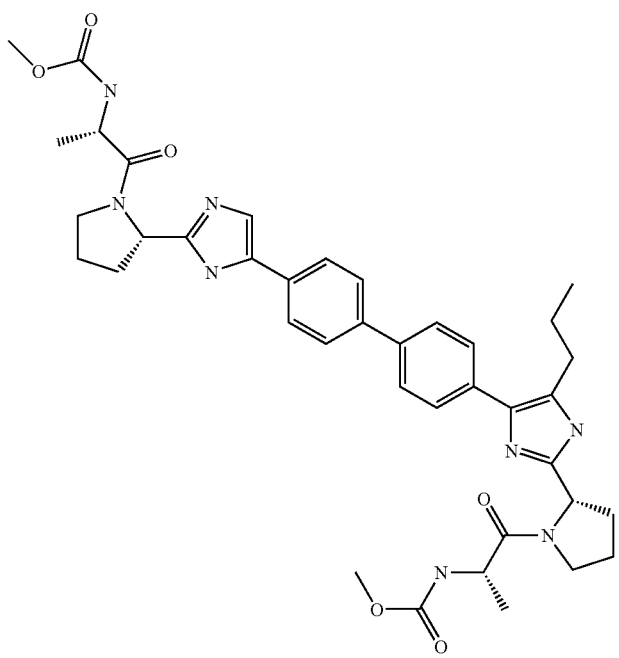 | RT = 1.42 min, (Cond 1); HRMS: Anal. Calcd. for $C_{39}H_{49}N_8O_6$ 725.3775; found: 725.3758 $(M + H)^+$. |
| J14c.1 Derived from example J13c | (1R)-2-((2S)-2-(4-(4'-(2-((2S)-1-((2R)-2-(diethylamino)-2-phenylacetyl)-2-pyrrolidinyl)-1H-imidazol-4-yl)-4-biphenylyl)-5-propyl-1H-imidazol-2-yl)-1-pyrrolidinyl)-N,N-diethyl-2-oxo-1-phenylethanamine | 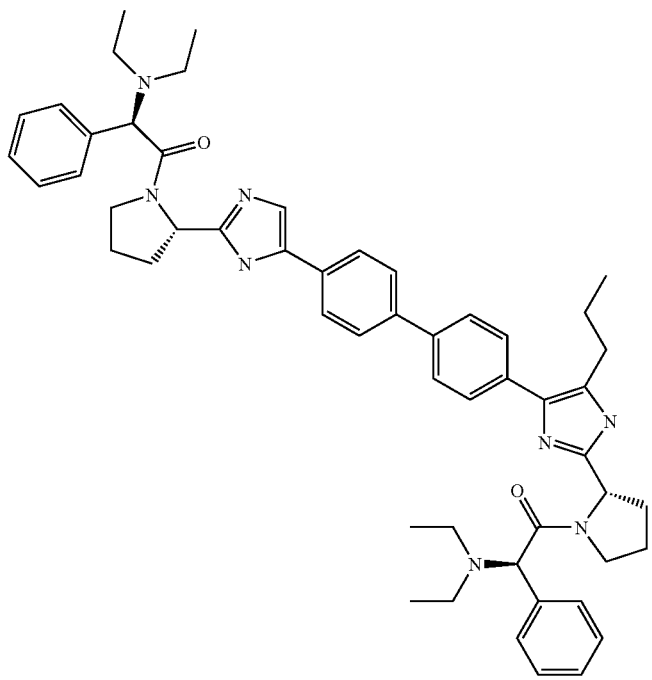 | RT = 1.39 min, (Cond 1); HRMS: Anal. Calcd. for $C_{53}H_{65}N_8O_2$ 845.5225; found: 845.5207 $(M + H)^+$. |

| | | | |
|---|---|---|---|
| J14c.2 Derived from example J13c | methyl ((1S)-1-(((2S)-2-(4-(4'-(2-((2S)-1-((2S)-2-((methoxycarbonyl) amino)-3-methylbutanoyl)-2-pyrrolidinyl)-1H-imidazol-4-yl)-4-biphenylyl)-5-propyl-1H-imidazol-2-yl)-1-pyrrolidinyl)car-bonyl)-2-methyl-propyl)carbamate | 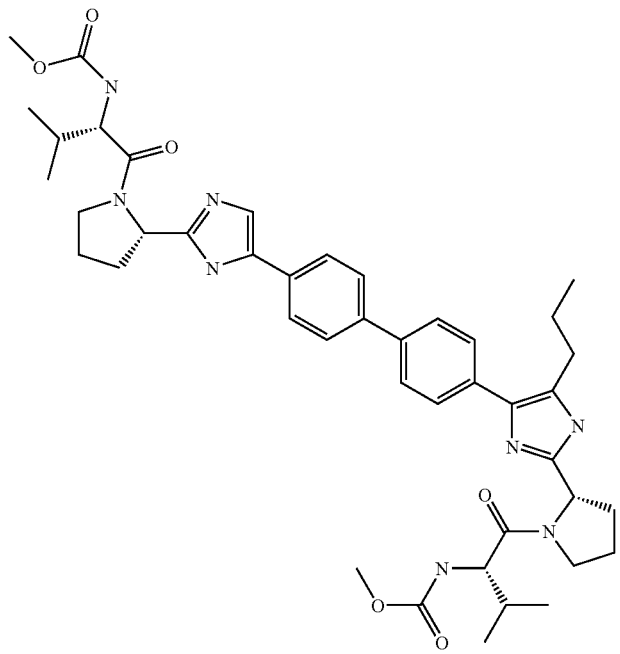 | RT = 1.59 min, (Cond 1); HRMS: Anal. Calcd. for $C_{43}H_{57}N_8O_6$ 781.4317; found: 781.4377 $(M + H)^+$. |
| J14e Derived from example J13e | methyl ((1S)-1-(((2S)-4,4-difluoro-2-(4-(3'-fluoro-4'-(2-((2S)-1-((2S)-2-((methoxycarbonyl) amino)-3-methylbutanoyl)-2-pyrrolidinyl)-1H-imidazol-4-yl)-4-biphenylyl)-1H-imidazol-2-yl)-1-pyrrolidinyl)car-bonyl)-2-methyl-propyl)carbamate | 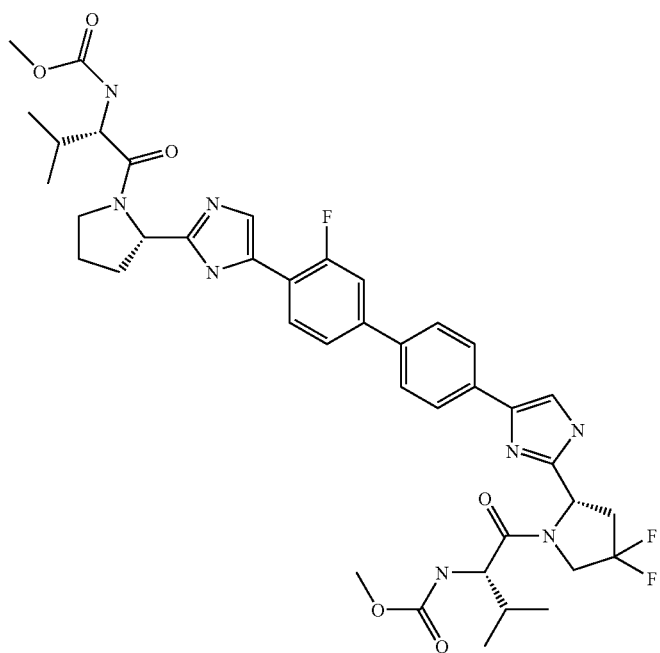 | RT = 1.99 min, (Cond 2) HRMS: Anal. Calcd. for $C_{40}H_{48}F_3N_8O_6$ 793.3643; found: 793.3653 $(M + H)^+$. |

| | | | |
|---|---|---|---|
| J14e.1 Derived from example J13e | (1R)-2-((2S)-2-(4-(4'-(2-((2S)-1-((2R)-2-(diethylamino)-2-phenylacetyl)-4,4-difluoro-2-pyrroldinyl)-1H-imidazol-4-yl)-3-fluoro-4-biphenylyl)-1H-imidazol-2-yl)-1-pyrrolidinyl)-N,N-diethyl-2-oxo-1-phenylethanamine | 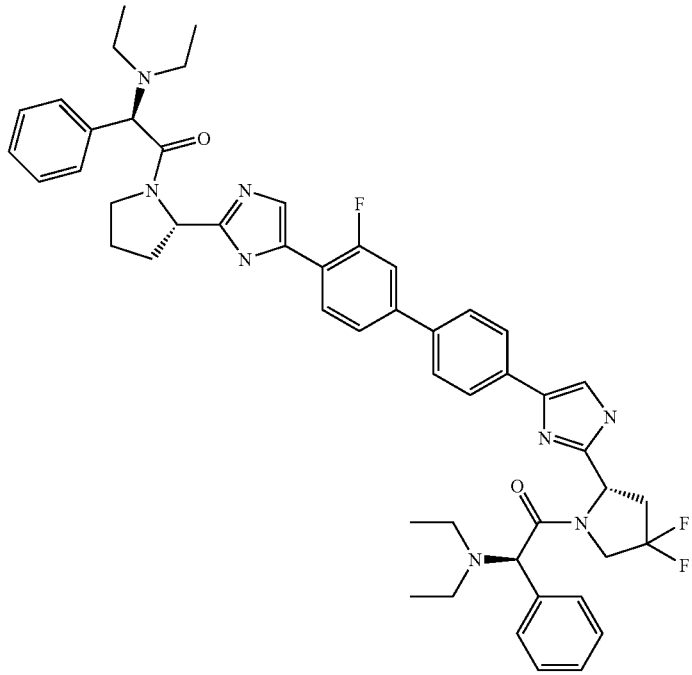 | RT = 1.79 min, (Cond 2) HRMS: Anal. Calcd. for $C_{50}H_{56}F_3N_8O_2$ 857.4473; found: 857.4478 $(M + H)^+$. |
| J14f Derived from example J13f | methyl ((1S)-1-(((2S)-2-(4-(hydroxymethyl)-5-(4'-(2-((2S)-1-((2S)-2-((methoxycarbonyl)amino)-3-methylbutanoyl)-2-pyrrolidinyl)-1H-imidazol-4-yl)-4-biphenylyl)-1H-imidazol-2-yl)-1-pyrrolidinyl)carbonyl)-2-methylpropyl)carbamate | 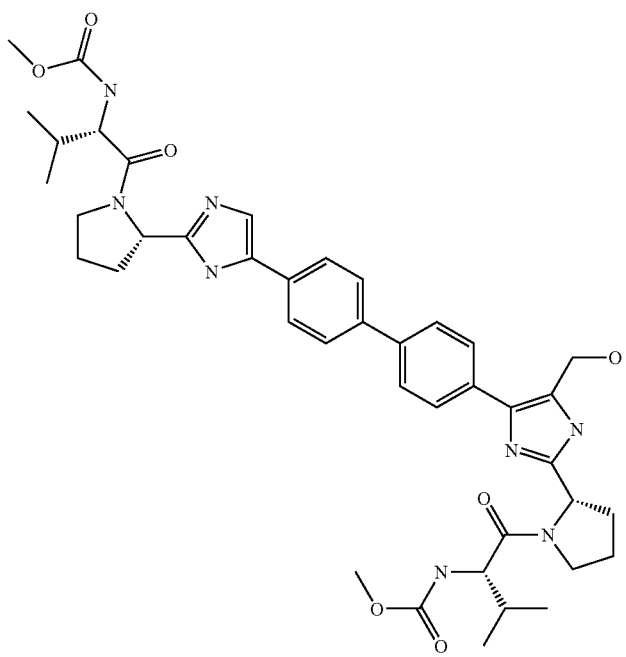 | RT = 1.40 min, (Cond 1); HRMS: Anal. Calcd. for $C_{41}H_{53}N_8O_7$ 769.4037; found: 769.4020 $(M + H)^+$. |

| | | | |
|---|---|---|---|
| J14f.1 Derived from example J13f | methyl ((1S)-2-((2S)-2-(4-(4'-(4-(hydroxymethyl)-2-((2S)-1-(N-(methoxycarbonyl)-L-alanyl)-2-pyrrolidinyl)-1H-imidazol-5-yl)-4-biphenylyl)-1H-imidazol-2-yl)-1-pyrrolidinyl)-1-methyl-2-oxoethyl)carbamate | 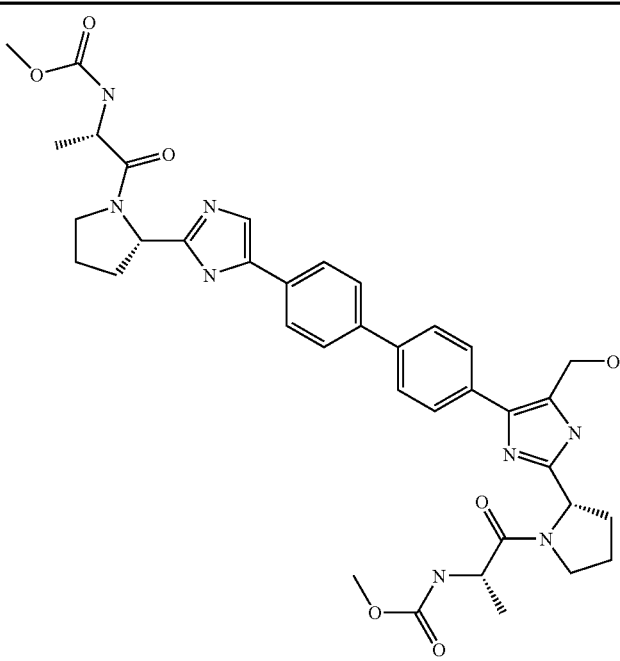 | RT = 1.21 min, (Cond 1); HRMS: Anal. Calcd. for $C_{37}H_{45}N_8O_7$ 713.3411; found: 713.3391 $(M + H)^+$. |
Section PY
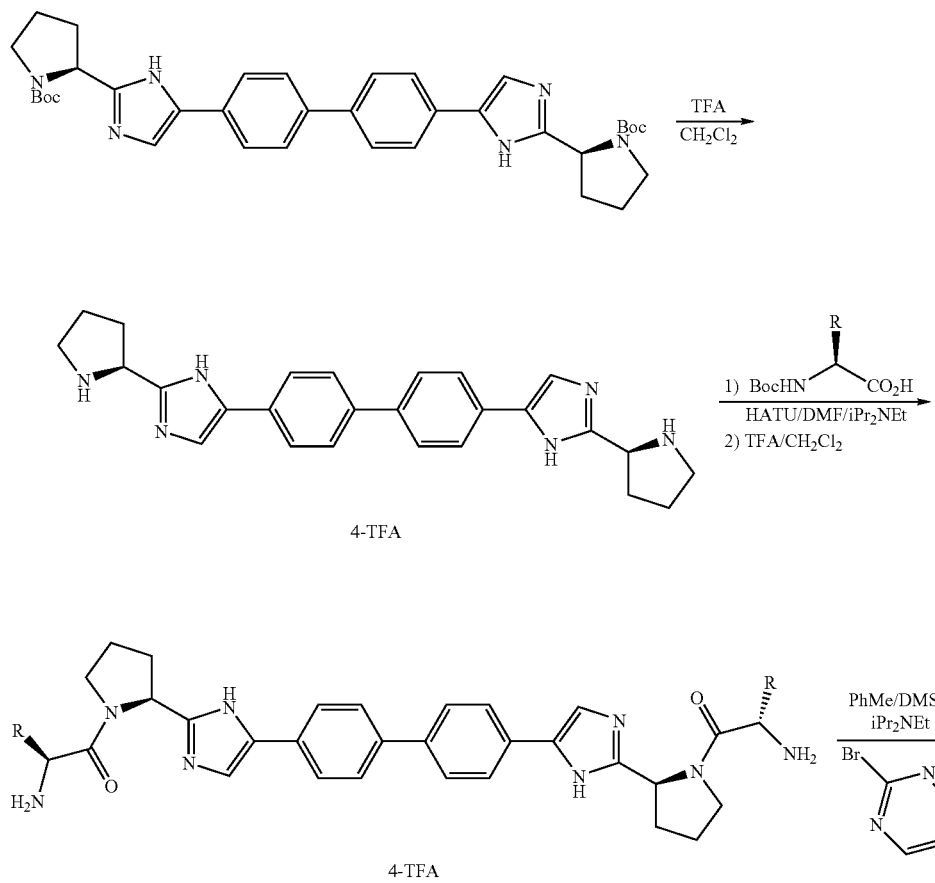

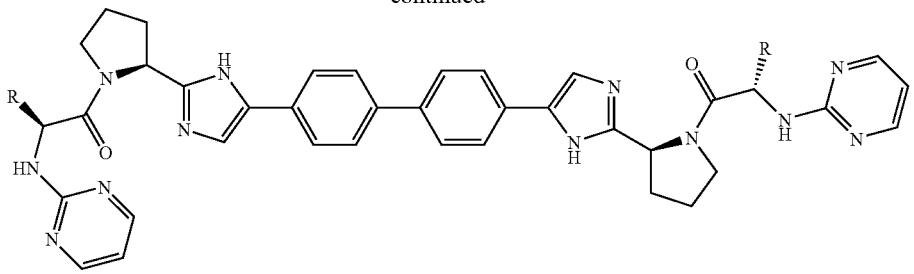

Example PY1

4,4'-bis(2-((S)-pyrrolidin-2-yl)-1H-imidazol-5-yl)biphenyl trifluoroacetic acid salt

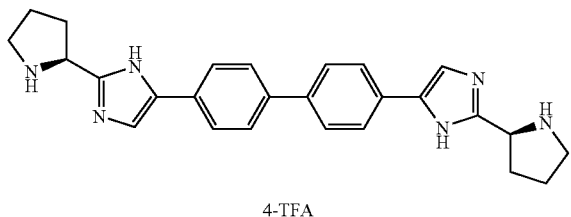

4-TFA

To a solution of (2S,2'S)-tert-butyl 2,2'-(5,5'-(biphenyl-4,4'-diyl)bis(1H-imidazole-5,2-diyl))dipyrrolidine-1-carboxylate (2.61 g, 4.18 mmol) in CH$_2$Cl$_2$ (25 mL) was added TFA (12 mL) and the mixture was allowed to stir at room temperature. After allowing the reaction to stir for 2 hours it was concentrated to dryness in vacuo. The material was used without further purification in subsequent steps. LCMS: Anal. Calcd. for C$_{26}$H$_{28}$N$_6$: 424. found: 425 (M+H)$^+$.

Example PY2

(2S,2'S)-1,1'-((2S,2'S)-2,2'-(5,5'-(biphenyl-4,4'-diyl)bis(1H-imidazole-5,2-diyl))bis(pyrrolidine-2,1-diyl))bis(2-amino-3-methylbutan-1-one)

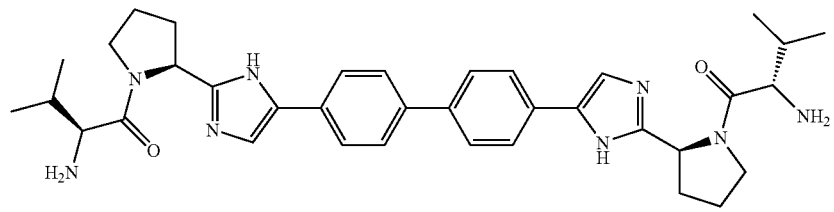

To a solution of 4,4'-bis(2-((S)-pyrrolidin-2-yl)-1H-imidazol-5-yl)biphenyl tetrakis(2,2,2-trifluoroacetate) (2.695 g, 3.06 mmol), (S)-2-(tert-butoxycarbonylamino)-3-methylbutanoic acid (1.60 g, 7.34 mmol) and DIEA (5.3 mL, 30.6 mmol) in DMF (15 mL) was added HATU (2.39 g, 6.27 mmol) and the mixture was allowed to stir at room temperature for 14 h. MeOH (5 mL) was added and the mixture was allowed to stir for 4 h. It was then poured into ca. 150 mL of cold water and allowed to stand for 20 min. The solid was filtered and dried under vacuum overnight and then purified by biotage (40+M, 0 to 25% MeOH in EtOAc) to give a yellow brown foam (1.76 g, 70%). $^1$HNMR (300 MHz, DMSO-d$_6$) δ 12.11-12.17 (m, 1H), 11.76 (s, 1H), 7.73-7.94 (m, 4H), 7.62-7.70 (m, 4H), 7.49 (d, J=1.8 Hz, 1H), 6.76 (d, J=8.5 Hz, 1H), 5.06 (dd, J=2.7, 6.3 Hz, 2H), 4.00-4.07 (m, 2H), 3.77 (s, br, 3H), 2.07-2.15 (m, 4H), 1.88-2.00 (m, 6H), 1.37 (s, 18H), 0.88 (d, J=6.6 Hz, 6H), 0.82 (d, J=6.6 Hz, 6H). LCMS: Anal. Calcd. for C$_{46}$H$_{62}$N$_8$O$_6$: 822. found: 823 (M+H)$^+$. The material was suspended in CH$_2$Cl$_2$ (15 mL) and TFA (6 mL) was added. After stirring for 2 h the solvents were removed in vacuo giving a yellow orange solid. The solid was partitioned between sat NaHCO$_3$ and EtOAc however the material was insoluble in EtOAc. Therefore the volatiles were removed in vacuo and the residue was loaded on to an SCX cation exchange cartridge and eluted with MeOH and then NH$_3$ in MeOH (2M). The appropriate fractions were concentrated in vacuo to give a yellow foam (1.24 g, 65%). LCMS: Anal. Calcd. for C$_{36}$H$_{46}$N$_8$O$_2$: 622. found: 623 (M+H)$^+$. The material was used as is in subsequent steps.

The following were prepared similarly. Note that in some cases the TFA salt obtained from the Boc deprotection was carried forward directly.

| Example | Structure | Analytical Data |
|---|---|---|
| Example PY3 | 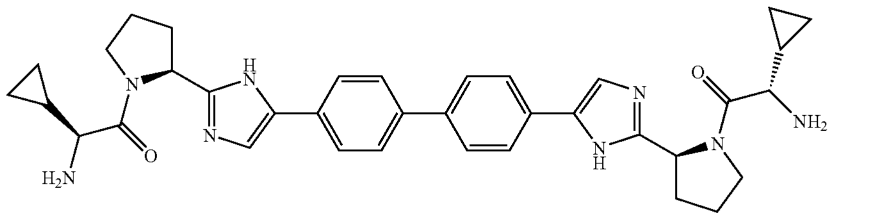 | LCMS: Anal. Calcd. for $C_{36}H_{42}N_8O_2$: 618; found: 619 $(M + H)^+$. |
| Example PY4 | 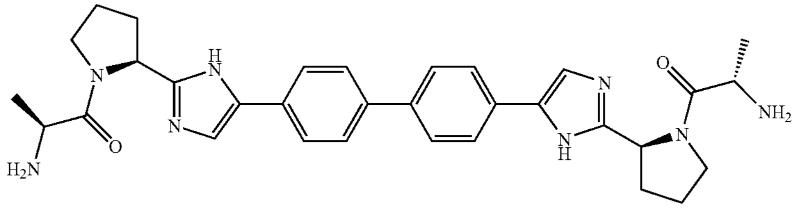 | LCMS: Anal. Calcd. for $C_{32}H_{38}N_8O_2$: 566; found: 567 $(M + H)^+$. |
| Example PY5 | 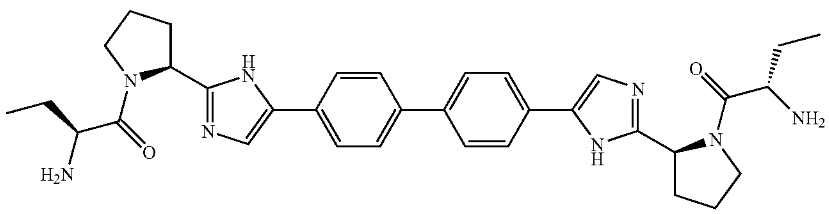 | LCMS: Anal. Calcd. for $C_{34}H_{42}N_8O_2$: 594; found: 595 $(M + H)^+$. |
| Example PY6 | 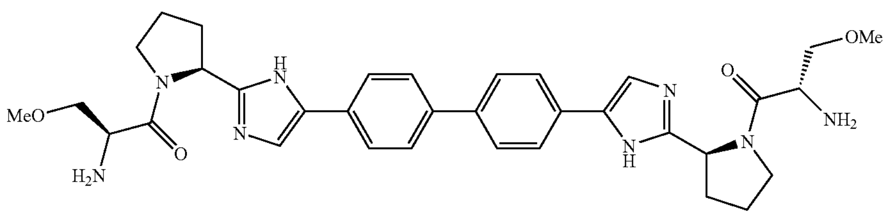 | LCMS: Anal. Calcd. for $C_{34}H_{42}N_8O_4$: 626; found: 627 $(M + H)^+$. |
| Example PY7 | 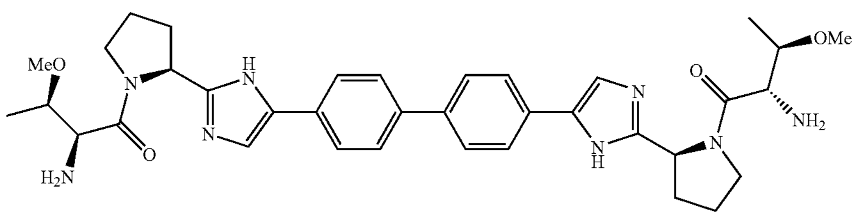 | LCMS: Anal. Calcd. for $C_{36}H_{42}N_8O_2$: 618; found: 619 $(M + H)^+$. |

Example PY8

(N,N'-(4,4'-biphenyldiylbis(1H-imidazole-4,2-diyl (2S)-2,1-pyrrolidinediyl((2S)-3-methyl-1-oxo-1,2-butanediyl)))di(2-pyrimidinamine)

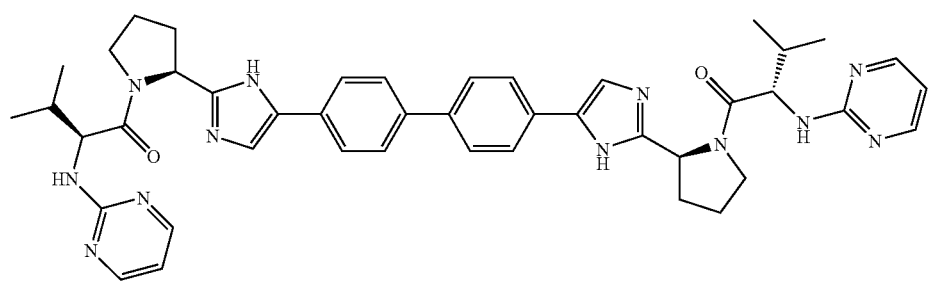

A mixture of (2S,2'S)-1,1'-((2S,2'S)-2,2'-(5,5'-(biphenyl-4,4'-diyl)bis(1H-imidazole-5,2-diyl))bis(pyrrolidine-2,1-diyl))bis(2-amino-3-methylbutan-1-one) (222 mg, 0.36 mmol), 2-bromopyrimidine (0.170 g, 1.07 mmol) and iPr$_2$NEt (0.25 mL, 1.432 mmol) in toluene (3 mL) and DMSO (0.5 mL) was heated at 90° C. overnight. LCMS indicated the reaction to be incomplete therefore heating was continued for a further 12 hours. The volatiles were removed in vacuo and the residue was diluted with MeOH and purified by prep HPLC (CH$_3$CN—H$_2$O—NH$_4$OAc). The appropriate fractions were concentrated in vacuo and subsequently re-purified by prep HPLC (CH$_3$CN—H$_2$O-TFA). The appropriate fractions were adsorbed onto an MCX cation exchange resin cartridge (Oasis) and the resin was washed with MeOH and eluted with 2M NH3 in MeOH. The solvent was removed in vacuo and the residue was lyophilized to give a colorless solid (17.2 mg, 6%). $^1$HNMR (300 MHz, DMSO-d$_6$) δ 12.15, 12.28 (s, 1H, rotamers, 1:1 ratio), 8.28 (d, J=4.8 Hz, 4H), 7.79 (app d, J=8.1 Hz, 4H), 7.62-7.70 (m, 4H), 7.49 (d, J=1.5 Hz, 2H), 6.85 (d, J=8.4 Hz, 2H), 6.60 (t, J=4.8 Hz, 2H), 5.05 (dd, J=6.9, 4.0 Hz, 2H), 4.50 (app t, unresolved dd, J=8.5, 8.0 Hz, 2H), 3.98-4.06 (m, 2H), 3.78-3.85 (m, 2H), 1.98-2.23 (m, 10H), 0.96 (d, J=6.6 Hz, 6H), 0.92 (d, J=6.6 Hz, 6H). LCMS: Anal. Calcd. for C$_{44}$H$_{50}$N$_{12}$O$_2$: 778. found: 779 (M+H)$^+$.

The following were prepared similarly:

Note that in some cases the TFA salt obtained from the Boc deprotection was carried forward directly and an appropriate amount of iPr$_2$NEt was added to the reaction mixture.

| Compound Name | Example | Structure | Analytical Data |
|---|---|---|---|
| N,N'-(4,4'-biphenyl-diyl bis(1H-imidazole-4,2-diyl (2S)-2,1-pyrrolidinediyl ((1S)-1-cyclopropyl-2-oxo-2,1-ethanediyl))) di(2-pyrimidinamine) | Example PY9 | | LCMS: Anal. Calcd. for C$_{36}$H$_{42}$N$_8$O$_2$: 618; found: 619 (M + H)$^+$. |
| N,N'-(4,4'-biphenyl-diyl bis(1H-imidazole-4,2-diyl (2S)-2,1-pyrrolidinediyl ((2S)-1-oxo-1,2-propanediyl))) di(2-pyrimidineamine) | Example PY10 | | LCMS: Anal. Calcd. for C$_{32}$H$_{38}$N$_8$O$_2$: 566; found: 567 (M + H)$^+$. |
| N,N'-(4,4'-biphenyl-diyl bis(1H-imidazole-4,2-diyl (2S)-2,1-pyrrolidinediyl ((2S)-1-oxo-1,2-butanediyl))) di(2-pyrimidinamine) | Example PY11 | | LCMS: Anal. Calcd. for C$_{34}$H$_{42}$N$_8$O$_2$: 594; found: 595 (M + H)$^+$. |

| Compound Name | Example | Structure | Analytical Data |
|---|---|---|---|
| N,N'-(4,4'-biphenyl-diyl bis(1H-imidazole-4,2-diyl (2S)-2,1-pyrrolidinediyl ((2S)-3-methoxy-1-oxo-1,2-propanediyl))) di(2-pyrimidinamine) | Example PY12 | | LCMS: Anal. Calcd. for $C_{34}H_{42}N_8O_4$: 626; found: 627 $(M+H)^+$. |
| N,N'-(4,4'-biphenyl-diyl bis(1H-imidazole-4,2-diyl (2S)-2,1-pyrrolidinediyl ((2S,3R)-3-methoxy-1-oxo-1,2-butanediyl))) di(2-pyrimidinamine) | Example PY13 | | LCMS: Anal. Calcd. for $C_{36}H_{42}N_8O_2$: 618; found: 619 $(M+H)^+$. |

Example PY14

Modified Method

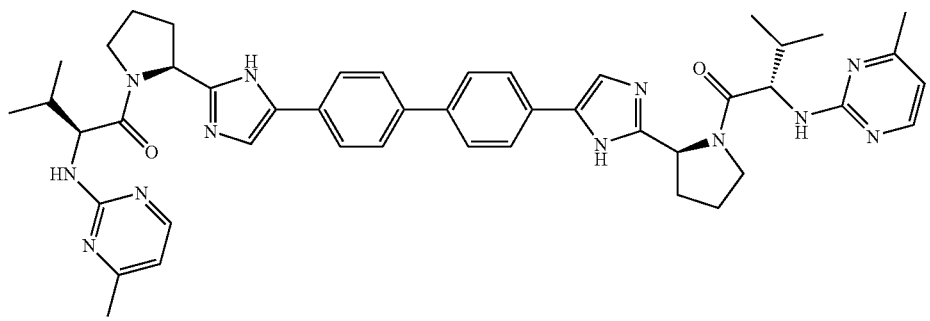

A mixture of (2S,2'S)-1,1'-((2S,2'S)-2,2'-(5,5'-(biphenyl-4,4'-diyl)bis(1H-imidazole-5,2-diyl))bis(pyrrolidine-2,1-diyl))bis(2-amino-3-methylbutan-1-one) (50 mg, 0.080 mmol), 2-chloro-4-methylpyrimidine (103 mg, 0.803 mmol), and DIPEA (0.140 mL, 0.803 mmol) in NMP (3 mL) was heated in a sealed tube for 4 h at 140° C. using a Microwave. The volatiles were removed in vacuo and the residue was diluted with MeOH and filtered through a Strata XC MCX cartridge. The cartridge was washed with methanol. The compound was release from the cartridge by washing with a solution of 2M of Ammonia/Methanol. The filtrate was evaporated under reduced pressure to give an orange oil. The crude material was purified HPLC ($CH_3CN$—$H_2O$—$NH_4OAc$). The appropriate fractions were concentrated in vacuo and subsequently re-purified by prep HPLC ($CH_3CN$—$H_2O$-TFA). The appropriate fractions were concentrated in vacuo to give a Yellow solid (21.5 mg, 31.9%). LCMS: Anal. Calcd. for $C_{46}H_{54}N_{12}O_2$: 807. found: 807.5 $(M+H)^+$.

| Example | Structure | Analytical Data |
|---|---|---|
| Example PY15 | 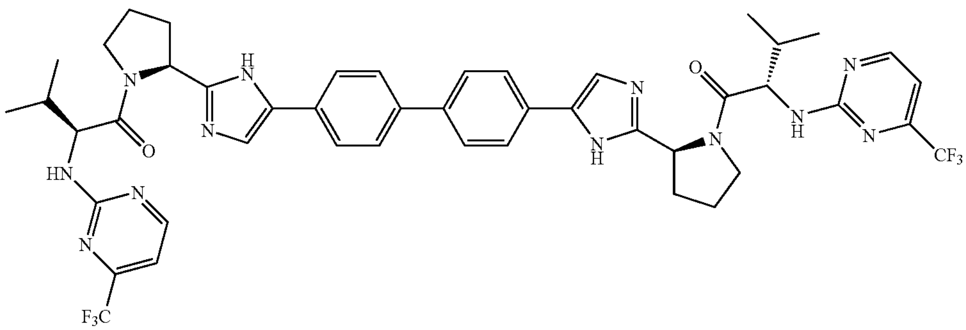 | LCMS: Anal. Calcd. for $C_{46}H_{48}F_6N_6O_2$: 914; found: 915.16 $(M + H)^+$. |
| Example PY16 | 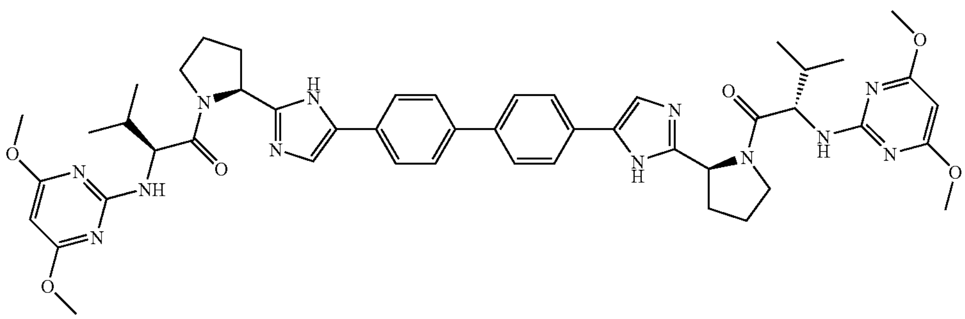 | LCMS: Anal. Calcd. for $C_{48}H_{58}N_{12}O_6$: 898; found: $(M + H)^+$ 899.21.16 |
| Example PY17 | 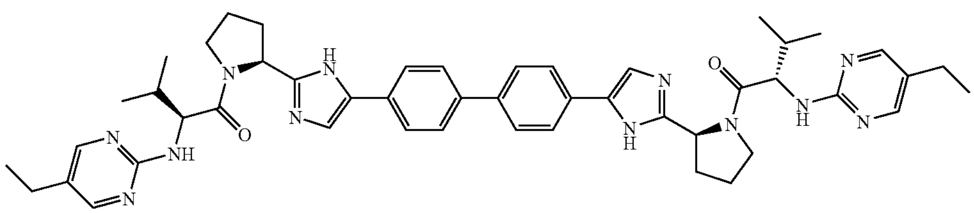 | LCMS: Anal. Calcd. for $C_{48}H_{58}N_{12}O_2$: 834; found: $(M + H)^+$ 835.45. |
| Example PY18 | 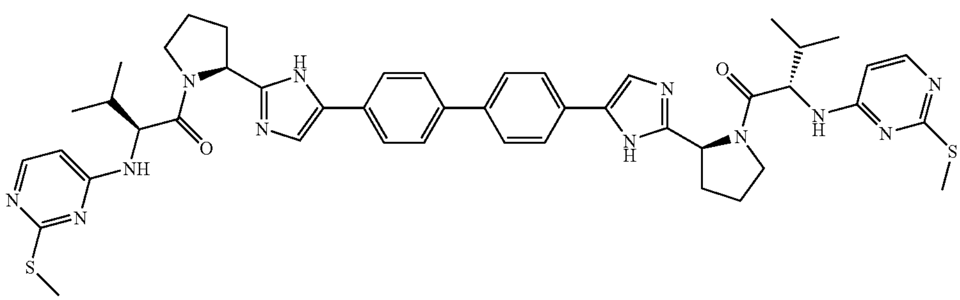 | LCMS: Anal. Calcd. for $C_{46}H_{54}N_{12}O_4S_2$: 870; found: $(M + H)^+$ 871.24. |
Scheme 2
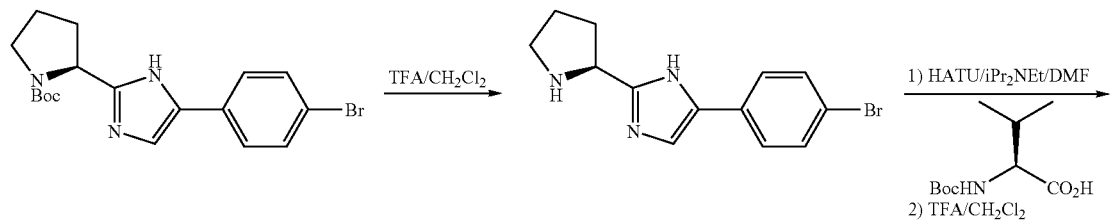

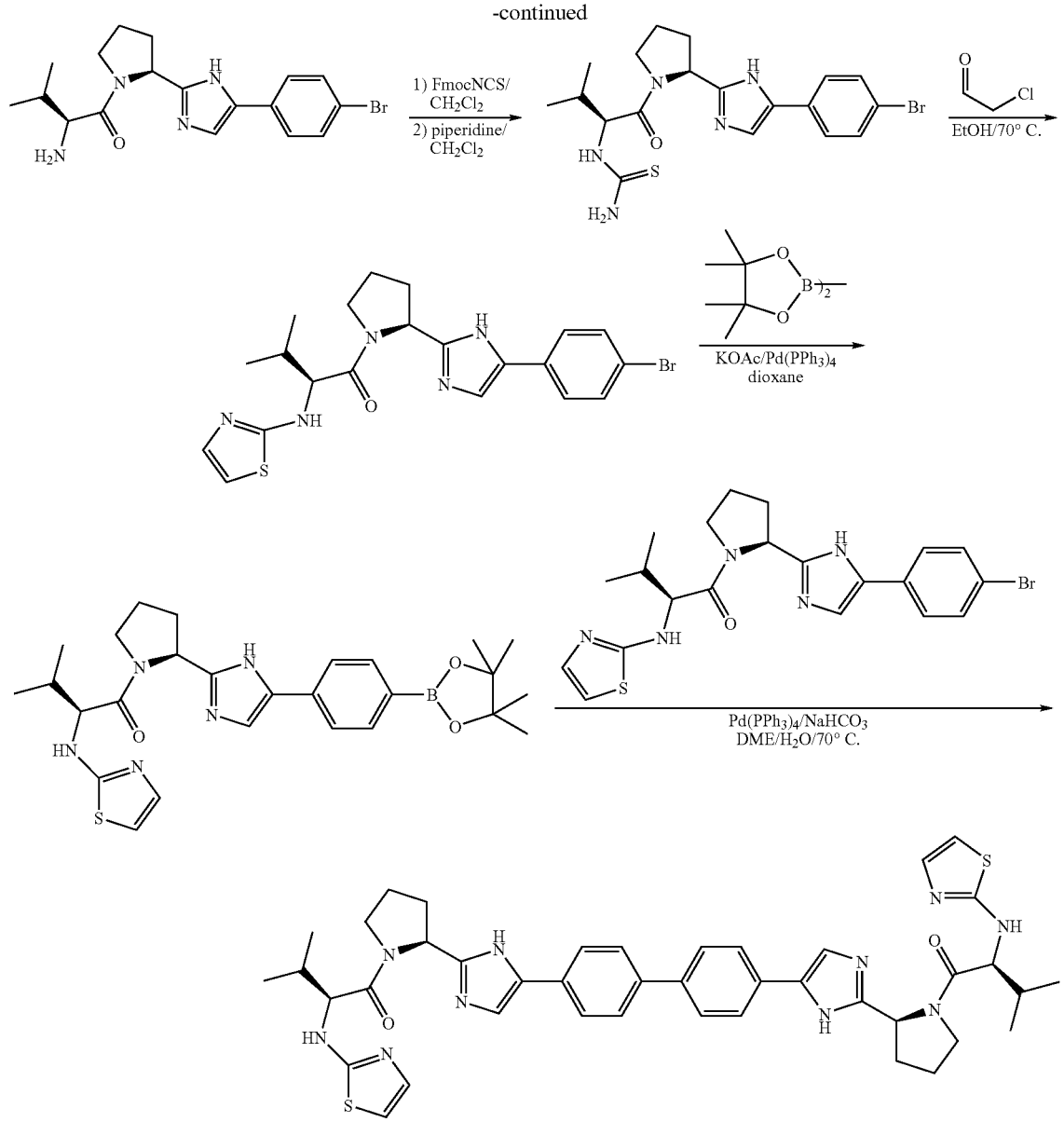

Example PY19

(S)-2-amino-1-((S)-2-(5-(4-bromophenyl)-1H-imidazol-2-yl)pyrrolidin-1-yl)-3-methylbutan-1-one

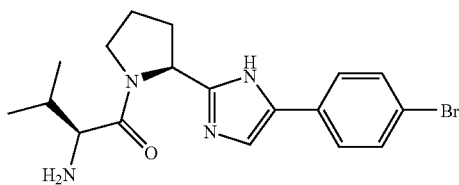

The title compound was prepared from (S)-tert-butyl 2-(5-(4-bromophenyl)-1H-imidazol-2-yl)pyrrolidine-1-carboxylate and (S)-2-amino-3-methylbutanoic acid by the procedures detailed in Examples 1 and 2. $^1$HNMR (300 MHz, DMSO-$d_6$) δ 11.73 (s, 1H), 7.68 (d, J=5.9 Hz, 1H), 7.65 (d, J=5.9 Hz, 1H), 7.46-7.58 (m, 3H), 5.14, 5.05 (dd, J=7.0, 3.0 Hz, 1H, rotamers, 1:1 ratio), 3.66 (app t, J=6.5 Hz, 1H), 3.53-3.61 and 3.38-3.47 (m, 1H, rotamers, 1:1 ratio), 3.28 (s, 2H), 1.70-2.21 (m, 6H), 0.75-0.88 (m, 6H). LCMS: Anal. Calcd. for $C_{18}H_{23}BrN_4O$: 390, 392. found: 391, 393 (M+H)$^+$.

Example PY20

1-((S)-1-((S)-2-(5-(4-bromophenyl)-1H-imidazol-2-yl)pyrrolidin-1-yl)-3-methyl-1-oxobutan-2-yl)thiourea

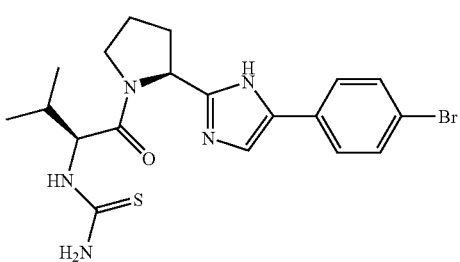

To a solution of (S)-2-amino-1-((S)-2-(5-(4-bromophenyl)-1H-imidazol-2-yl)pyrrolidin-1-yl)-3-methylbutan-1-one (1.530 g, 3.91 mmol) in $CH_2Cl_2$ (10 mL) was added O-(9H-fluoren-9-yl)methyl carbonisothiocyanatidate (1.100 g, 3.91 mmol) as a solid in one portion. The mixture was allowed to stir at room temperature for 12 h. Piperidine (2 mL) was added to the mixture and it was allowed to stir at room temperature for 1 h. A further portion of piperidine (2 mL) was added and the solution allowed to stir 1 h. The solution was concentrated to dryness and the residue was purified by column chromatography (biotage, eluting with 5:4.5:0.5 hex:EtOAc:MeOH, and then 5% MeOH in EtOAc). The title compound as obtained as a light yellow glass (1.30 g, 74%). $^1$HNMR (300 MHz, DMSO-$d_6$) δ 11.81 (s, H), 7.65 (d, J=8.8 Hz), 7.63-7.71 (m, overlap with previous peak, 2H total), 7.42-7.56 (m, 2H), 7.10-7.14 (m, 1H), 5.06 (dd, J=7.0, 3.0 Hz, 1H), 4.94 (app t, J=8.0 Hz, 1H), 4.72-4.76 and 4.56-4.62 (m, 1H, rotamers, 1:1 ratio), 3.77-3.90 (m, 1H), 2.07-2.14 (m, 2H), 1.90-1.98 (m, 3H), 0.93 (d, J=7.0 Hz, 3H), 0.84 (d, J=7.0 Hz, 3H). LCMS: Anal. Calcd. for $C_{19}H_{24}BrN_5OS$: 449, 451. found: 450, 452 (M+H)$^+$.

Example PY21

(S)-1-((S)-2-(5-(4-bromophenyl)-1H-imidazol-2-yl)pyrrolidin-1-yl)-3-methyl-2-(thiazol-2-ylamino)butan-1-one

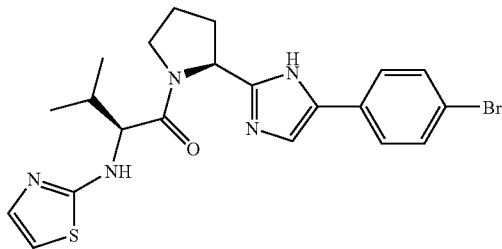

A solution of 1-((S)-1-((S)-2-(5-(4-bromophenyl)-1H-imidazol-2-yl)pyrrolidin-1-yl)-3-methyl-1-oxobutan-2-yl)thiourea (1.29 g, 2.86 mmol) was dissolved in EtOH (50 mL) and 2-chloroacetaldehyde (0.4 mL, 3.15 mmol) was added. The mixture was heated at 70° C. overnight. A further portion of 2-chloroacetaldehyde (0.4 mL, 3.15 mmol) was added and heating continued for a further 12 h. The solution was concentrated in vacuo and the residue was purified by column chromatography (biotage), eluting with 50% EtOAc in hexanes and then 10% MeOH in EtOAc. The desired product was isolated as a orange-brown foam (557.2 mg). LCMS ($NH_4OAc$) shows this to be of sufficient purity. Eluting further with 100% MeOH gave a second fraction (980.8 mg) which was shown to contain the product by TLC (5:4.5:0.5 hex:EtOAc:MeOH). This second fraction from the column was re-purified to give a light orange-brown foam (426.6 mg). The two fractions were combined to afford the title compound as a orange brown foam (983.8 mg, 72%).
$^1$HNMR (300 MHz, CD$_3$OD) δ 7.57 (app d, J=8.0 Hz, 2H), 7.47 (app d, J=8.0 Hz, 2H), 7.32 (s, 1H), 6.98 (d, J=3.6 Hz, 1H), 6.55 (d, J=3.6 Hz, 1H), 5.32-5.35 and 5.10-5.15 (m, 1H, rotamers, 1:3 ratio), 4.08-4.15 (m, 1H), 3.82-3.90 (m, 1H), 3.03-3.15 (m, 1H), 2.03-2.33 (m, 4H), 1.06 and 0.99 (d, J=7.0 Hz, 3H, rotamers 1:3 ratio), 1.04 and 0.94 (d, J=7.0 Hz, 3H, rotamers 1:3 ratio). LCMS: Anal. Calcd. for $C_{21}H_{24}BrN_5OS$: 473, 475. found: 474, 476 (M+H)$^+$.

Example PY22

(S)-3-methyl-1-((S)-2-(5-(4-(4,4,5,5-tetramethyl-1,3,2-dioxaborolan-2-yl)phenyl)-1H-imidazol-2-yl)pyrrolidin-1-yl)-2-(thiazol-2-ylamino)butan-1-one

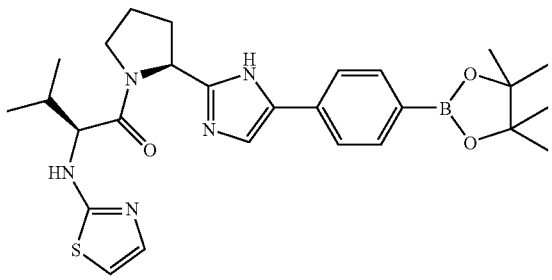

A mixture of (S)-1-((S)-2-(5-(4-bromophenyl)-1H-imidazol-2-yl)pyrrolidin-1-yl)-3-methyl-2-(thiazol-2-ylamino)butan-1-one (87.5 mg, 0.184 mmol), 4,4,4',4',5,5,5',5'-octamethyl-2,2'-bi(1,3,2-dioxaborolane) (141 mg, 0.553 mmol), potassium acetate (91 mg, 0.922 mmol) and Pd(Ph$_3$P)$_4$ (21.31 mg, 0.018 mmol) was suspended in dioxane and degassed by bubbling N$_2$ through the mixture. It was then heated at 85° C. After heating for 4 h the mixture was concentrated and purified by passing through a pad of silica gel eluting with 1:1 hex:EtOAc, and then EtOAc (neat) to give afforded the desired product as a light yellow film (101 mg). LCMS (CH$_3$CN—H$_2$O—NH$_4$OAc) showed that the product was contaminated with ca. 10% PPh$_3$O. The material was used as is in subsequent steps. LCMS: Anal. Calcd. for $C_{27}H_{36}BN_5O_3S$: 521. found: 522 (M+H)$^+$.

Example PY23

(N,N'-(4,4'-biphenyldiylbis(1H-imidazole-4,2-diyl(2S)-2,1-pyrrolidinediyl((2S)-3-methyl-1-oxo-1,2-butanediyl)))bis(1,3-thiazol-2-amine)

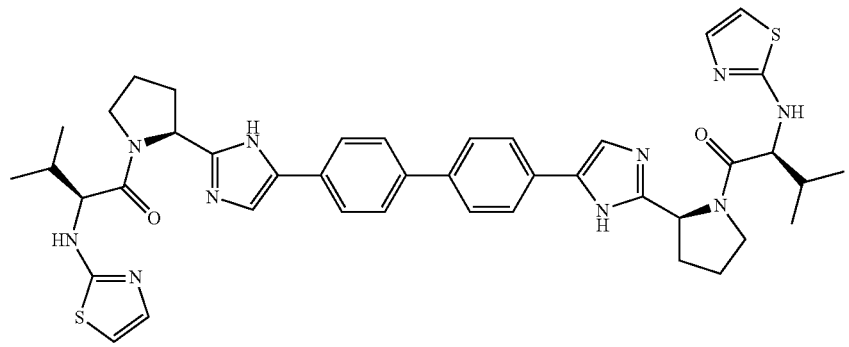

A mixture of (S)-3-methyl-1-((S)-2-(5-(4-(4,4,5,5-tetramethyl-1,3,2-dioxaborolan-2-yl)phenyl)-1H-imidazol-2-yl)pyrrolidin-1-yl)-2-(thiazol-2-ylamino)butan-1-one (275 mg, 0.527 mmol), (S)-1-((S)-2-(5-(4-bromophenyl)-1H-imidazol-2-yl)pyrrolidin-1-yl)-3-methyl-2-(thiazol-2-ylamino)butan-1-one (250 mg, 0.527 mmol), NaHCO$_3$ (133 mg, 1.582 mmol) and Pd(Ph$_3$P)$_4$ (60.9 mg, 0.053 mmol) in DME (3 mL) and Water (1 mL) was degassed by passing a stream of N$_2$ through the mixture. The vessel was sealed and the reaction was heated at 80° C. overnight. The reaction mixture was diluted with H$_2$O and extracted with EtOAc containing ca. 5% MeOH (×3). The combined org layers were concentrated, dissolved in MeOH and loaded onto an MCX cartridge. The cartridge was washed with MeOH and then NH$_3$ in MeOH (2M). The appropriate fractions were concentrated in vacuo and the residue was purified by prep HPLC (CH$_3$CN—H$_2$O—NH$_4$OAc). The material was purified by column chromatography (biotage) eluting with 0 to 20% MeOH in EtOAc. Further purification by prep HPLC (CH$_3$CN—H$_2$O—NH$_4$OAc) followed by lyophilization afforded the title compound as a colorless solid (6.9 mg, 2%).

$^1$HNMR (300 MHz, DMSO-d$_6$) δ 13.41 (s, 1H), 11.75 (s, 2H), 7.75-7.80 (m, 4H), 7.68-7.71 (m, 4H), 7.49 (s, 2H), 6.99 (d, J=3.7 Hz, 2H), 6.57 (d, J=3.7 Hz, 2H), 5.34-5.36 (m, 1H), 5.07 (app dd, J=3.7, 7.0 Hz, 2H), 4.42 (t, J=8.4 Hz, 2H), 3.98-4.05 (m, 2H), 3.79-3.85 (m, 2H), 3.44-3.56 (m, 1H), 1.97-2.21 (m, 8H), 1.01 and 0.95 (d, J=7.0 Hz, 6H, rotamers, 1:3 ratio), 0.99 and 0.92 (d, J=7.0 Hz, 6H, rotamers, 1:3 ratio). LCMS: Anal. Calcd. for C$_{42}$H$_{48}$N$_{10}$O$_2$S$_2$: 788. found: 789 (M+H)$^+$.

Examples FY1-FY3

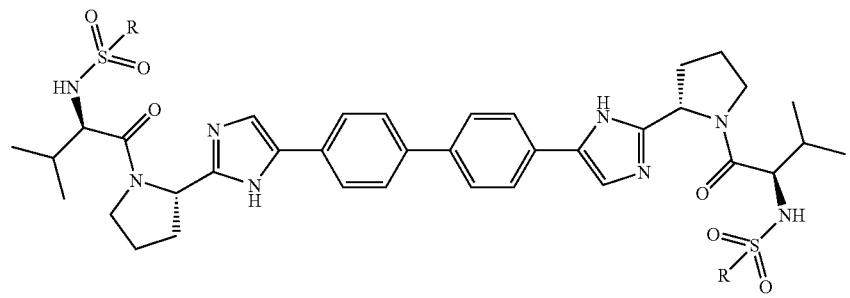

| Example | R | RT (LC-Cond. is noted above); % homogeneity index; MS data |
|---|---|---|
| FY1 | | 2.03 min; >95%; LC/MS: Anal. Calcd. for [M + H]$^+$ C$_{38}$H$_{51}$N$_8$O$_6$S$_2$ 779.34; found: 779.72 |
| FY2 | | 2.19 min; >95%; LC/MS: Anal. Calcd. for [M + H]$^+$ C$_{40}$H$_{55}$N$_8$O$_6$S$_2$ 807.37; found: 807.78 |
| FY3 | | 2.24 min; >95%; LC/MS: Anal. Calcd. for [M + H]$^+$ C$_{42}$H$_{55}$N$_8$O$_6$S$_2$ 831.37; found: 832.02 |

BIOLOGICAL ACTIVITY

An HCV Replion assay was utilized in the present disclosure, and was prepared, conducted and validated as described in commonly owned PCT/US2006/022197 and in O'Boyle et. al. *Antimicrob Agents Chemother.* 2005 April; 49(4): 1346-53.

HCV 1b-377-neo replicon cells were used to test the currently described compound series as well as cells resistant to compound A due to a Y2065H mutation in NS5A (described in application PCT/US2006/022197). The compounds tested were determined to have more than 10-fold less inhibitory activity on cells resistant to compound A than wild-type cells indicating a related mechanism of action between the two compound series. Thus, the compounds of the present disclosure can be effective to inhibit the function of the HCV NS5A protein and are understood to be as effective in combinations as previously described in application PCT/US2006/022197 and commonly owned WO/04014852. Further, the compounds of the present disclosure can be effective against the HCV 1b genotype. It should also be understood that the compounds of the present disclosure can inhibit multiple genotypes of HCV. Table 2 shows the EC50 values of representative compounds of the present disclosure against the HCV 1b genotype. In one embodiment compounds of the present disclosure are active against the 1a, 1b, 2a, 2b, 3a, 4a, and 5a genotypes. EC50 ranges against HCV 1b are as follows: A=1-10 μM; B=100-999 nM; C=1-99 nM; and D=1-999 pM.

Examples FY1-FY3 were prepared according to the protocols described for the synthesis of Example F66 and by employing appropriate materials.

LC/MS Condition:
Column: Phenomenex 10u 3.0×50 mm
Start % B=0
Final % B=100
Gradient Time=3 min
Flow Rate=4 mL/Min
Wavelength=220
Solvent A=10% MeOH—90% H$_2$O—0.1% TFA
Solvent B=90% MeOH—10% H$_2$O—0.1% TFA The compounds of the present disclosure may inhibit HCV by mechanisms in addition to or other than NS5A inhibition. In one embodiment the compounds of the present disclosure inhibit HCV replicon and in another embodiment the compounds of the present disclosure inhibit NS5A.

TABLE 2

| Example | Range |
|---|---|
| 1 | D |
| 24-4e | C |
| 24-4f | B |
| 24-4g | A |
| 25-1 | D |
| 25-2 | D |
| 25-3 | D |
| 25-4 | D |
| 25-5 | D |
| 25-6 | C |
| 25-7 | C |
| 25-8 | D |
| 24-4h | D |
| 120-9 | D |
| 120 | D |
| 120-5 | C |
| 120-6 | C |
| 120-7 | D |
| 120-8 | C |
| 103-3 | D |
| 103-4 | D |
| 103-1 | D |
| 103-2 | D |
| 103-5 | D |
| 103-6 | C |
| 103-8 | D |
| 103-7 | D |
| 151 isomer 1 | C |
| 151 isomer 2 | B |
| 152j-9 | C |
| 152j-10 | C |
| 152j-1 | C |
| 152j-2 | D |
| 153c-5 | C |
| 153c-6 | C |
| 153c-2 | C |
| 153c-1 | C |
| 152j-7 | C |
| 152j-8 | D |
| 153c-3 | A |
| 153c-4 | A |
| 152j-11 | D |
| 152j-12 | D |
| 152j-15 | D |
| 152j-28 | D |
| 152j-13 | C |
| 152j-14 | C |
| 152j-19 | D |
| 152j-16 | D |
| 152j-3 | D |
| 152j-20 | C |
| 152j-17 | D |
| 152j-18 | D |
| 152j-3 | D |
| 152j-5 | D |
| 152j-6 | D |
| 152l-2 | D |
| 152l-1 | D |
| 152j-24 | D |
| 152j-23 | D |
| 153c-7 | C |
| 152j-22 | D |
| 24-18-2 | D |
| 24-18-1 | D |
| 24-18-4 | D |
| 24-18-5 | D |
| 24-18-6 | D |
| 24-18-3 | D |
| 152j-21 | D |
| 152l-3 | D |

TABLE 2-continued

| Example | Range |
|---|---|
| 131.1-2 | D |
| 131.1-1 | D |
| 24-4a | D |
| 120-1 | D |
| 120-2 | D |
| 120-3 | D |
| 120-4 | D |
| 24-10 | D |
| 24-9 | D |
| 24-8 | D |
| 24-11 | C |
| 24-12 | C |
| 11 | C |
| 24-16 | D |
| 24-18 | D |
| 24-17 | D |
| 24-15 | C |
| 24-13 | B |
| 24-14 | C |
| 24-4b | C |
| 24-4c | D |
| 24-4d | D |
| 148 | C |
| 149 | D |
| 150 | C |
| 24-5 | D |
| 24-6 | D |
| 24-7 | D |
| 24-1 | D |
| 24-2 | D |
| 24-3 | D |
| 28-1 | D |
| 28-2 | D |
| 28-3 | D |
| 28-4 | D |
| 28-5 | D |
| 84-1 | D |
| 84-2 | D |
| 84-3 | D |
| 84-4 | D |
| 84-7 | C |
| 84-10 | C |
| 84-12 | D |
| 84-14 | C |
| 84-15 | C |
| 84-17 | D |
| 84-18 | C |
| 84-19 | C |
| 84-20 | C |
| 84-24 | D |
| 84-26 | D |
| 84-27 | D |
| 84-28 | D |
| 84-32 | D |
| 84-33 | D |
| 84-34 | C |
| 84-35 | D |
| 84-36 | D |
| 84-38 | D |
| 84-39 | D |
| 84-40 | D |
| 84-44 | D |
| 84-46 | D |
| 84-47 | D |
| 84-48 | D |
| 84-49 | D |
| 84-50 | D |
| 84-51 | D |
| 84-52 | D |
| 84-53 | D |
| 84-54 | D |
| 84-55 | D |
| 84-56 | D |
| 84-57 | D |
| 84-58 | D |
| 84-59 | D |
| 84-60 | D |
| 84-61 | D |

TABLE 2-continued

| Example | Range |
|---|---|
| 84-62 | D |
| 84-63 | D |
| 84-64 | D |
| 84-65 | C-D |
| 84-66 | C-D |
| 84-67 | D |
| 84-68 | C |
| 84-69 | D |
| 84-70 | C |
| 84-71 | C |
| 84-72 | C |
| 84-73 | C |
| 84-74 | D |
| 84-75 | C |
| 84-76 | D |
| 84-77 | D |
| 84-78 | D |
| 84-79 | D |
| 84-80 | D |
| 84-81 | D |
| 84-82 | D |
| 84-83 | D |
| 84-84 | D |
| 84-85 | D |
| 84-86 | D |
| 84-87 | D |
| 94-1 | D |
| 94-2 | C |
| 94-3 | D |
| 94-6 | C-D |
| 94-9 | D |
| 94-10 | D |
| 94-12 | C |
| 94-13 | D |
| 94-17 | D |
| 94-19 | D |
| 94-20 | C |
| 94-24 | D |
| 94-25 | D |
| 94-26 | D |
| 94-27 | C |
| 94-30 | D |
| 94-32 | C |
| 94-33 | C |
| 94-34 | C |
| 94-36 | D |
| 94-37 | C |
| 94-38 | D |
| 94-42 | D |
| 94-44 | D |
| 94-45 | D |
| 94-46 | D |
| 94-47 | D |
| 94-48 | D |
| 94-49 | D |
| 94-50 | D |
| 94-51 | D |
| 94-52 | D |
| 94-53 | D |
| 94-54 | D |
| 94-55 | D |
| 94-56 | D |
| 107-1 | D |
| 107-2 | D |
| 107-3 | D |
| 107-4 | D |
| 107-5 | D |
| 107-6 | D |
| 107-7 | D |
| 107-8 | D |
| 107-9 | D |
| 107-10 | D |
| 107-11 | D |
| 107-12 | D |
| 107-13 | D |
| 107-14 | D |
| 107-15 | D |
| 107-16 | D |
| 107-17 | D |
| 107-18 | D |
| 107-19 | D |
| 107-20 | D |
| 107-21 | D |
| 107-22 | D |
| 107-23 | D |
| 107-24 | D |
| 107-25 | D |
| 107-26 | D |
| 107-27 | D |
| 107-28 | D |
| 107-29 | D |
| 107-30 | D |
| 107-31 | D |
| 107-32 | D |
| 107-33 | D |
| 107-34 | D |
| 107-35 | D |
| 107-36 | D |
| 107-37 | D |
| 107-38 | D |
| 107-39 | D |
| 107-40 | D |
| 107-41 | D |
| 107-42 | D |
| 107-43 | D |
| 107-44 | D |
| 2 | D |
| 3 | D |
| 4 | D |
| 5 | C |
| 6 | C |
| 7 | D |
| 8 | D |
| 24-23 | D |
| 9 | C |
| 10 | C |
| 11 | C |
| 12 | C |
| 13 | C |
| 14 | B |
| 15 | C |
| 16 | C |
| 17 | D |
| 18 | D |
| 19 | D |
| 20 | C |
| 21 | D |
| 22 | D |
| 23 | D |
| 24 | C |
| 25 | D |
| 26 | C |
| 27 | C |
| 28 | C |
| 29 | D |
| 30 | C |
| 31 | D |
| 32 | C |
| 33 | D |
| 34 | D |
| 35 | D |
| 36 | D |
| 37 | D |
| 38 | D |
| 39 | D |
| 40 | D |
| 41 | D |
| 42 | D |
| 43 | D |
| 44 | D |
| 45 | D |
| 46 | D |
| 47 | D |
| 48 | D |
| 49 | D |
| 50 | B |

TABLE 2-continued

| Example | Range |
|---|---|
| 51 | D |
| 52 | D |
| 53 | D |
| 54 | D |
| 55 | D |
| 56 | D |
| 57 | D |
| 58 | D |
| 59 | D |
| 60 | D |
| 61 | D |
| 62 | D |
| 63 | D |
| 64 | D |
| 65 | C |
| 67 | D |
| 68 | D |
| 69 | D |
| 70 | C |
| 71 | D |
| 72 | C |
| 73 | D |
| 74 | D |
| 75 | D |
| 76 | D |
| 77 | D |
| 78 | D |
| 79 | D |
| 80 | D |
| 81 | D |
| 82 | D |
| 83 | D |
| 84 | D |
| 85 | D |
| 86 | D |
| 87 | D |
| 88 | D |
| 89 | D |
| 90 | D |
| 91 | D |
| 92 | D |
| 93 | D |
| 94 | D |
| 95 | D |
| 96 | D |
| 97 | D |
| 98 | D |
| 99 | D |
| 100 | D |
| 101 | D |
| 102 | D |
| 103 | D |
| 104 | D |
| 105 | D |
| 106 | D |
| 107 | D |
| 108 | D |
| 109 | C |
| 110 | D |
| 111 | D |
| 112 | D |
| 113 | D |
| 114 | D |
| 115 | D |
| 116 | D |
| 117 | D |
| 118 | D |
| 119 | D |
| 120 | D |
| 121 | D |
| 122 | D |
| 123 | D |
| 124 | D |
| 125 | D |
| 126 | D |
| 127 | D |
| 128 | D |
| 129 | D |

TABLE 2-continued

| Example | Range |
|---|---|
| 130 | D |
| 131 | D |
| 132 | D |
| 133 | C |
| 134 | D |
| 135 | D |
| 136 | D |
| 138 | D |
| 139 | D |
| 140 | D |
| 141 | D |
| 142 | C |
| 143 | D |
| 144 | D |
| 145 | D |
| 146 | D |
| 147 | D |
| LS2 | C |
| LS3 | C |
| LS4 | C |
| LS16 | C |
| LS6 | B |
| LS11 | A |
| LS14 | D |
| LS20 | D |
| LS21 | D |
| LS22 | D |
| LS23 | D |
| LS24 | D |
| LS25 | D |
| LS26 | D |
| LS27 D'mer 1 | D |
| LS27 D'mer 2 | D |
| LS36 | D |
| LS37 | D |
| F5 | D |
| F6 | D |
| F7 | D |
| F8 | D |
| F14 | D |
| F15 | D |
| F16 | D |
| F17 | D |
| F20 | B |
| F21 | B |
| F22 | B |
| F25 | D |
| F26 | C |
| F27 | C |
| F28 | C |
| F29 | C |
| F30 | C |
| F32 | B |
| F33 | B |
| F34 | C |
| F35 | B |
| F37 | B |
| F38 | D |
| F39 | D |
| Diastereomer | |
| F41 | D |
| F43 | D |
| F48 | D |
| F49 | C |
| F51 | D |
| F52 | D |
| F53 | D |
| F54 | D |
| F55 | D |
| F56 | D |
| F57 | D |
| F58 | D |
| F60 | D |
| F61 | C |
| F62 | C |
| F63 | D |
| F64 | C |
| F65 | B |

TABLE 2-continued

| Example | Range |
|---|---|
| F66 | C |
| F67 | C |
| F69 | B |
| F70 | B |
| F71 | D |
| cj-48 | B |
| cj-49 | C |
| cj-50 | D |
| cj-51 | D |
| cj-52 | D |
| cj-53 | D |
| cj-54 | D |
| cj-55 | D |
| cj-56 | D |
| cj-57 | D |
| cj-58 | D |
| cj-59 | D |
| cj-60 | D |
| cj-61 | D |
| cj-62 | D |
| cj-63 | D |
| cj-64 | D |
| cj-65 | D |
| cj-66 | D |
| cj-67 | D |
| cj-68 | D |
| cj-69 | D |
| cj-70 | D |
| cj-71 | D |
| cj-72 | D |
| cj-73 | D |
| cj-74 | C |
| cj-75 | D |
| cj-76 | D |
| cj-77 | D |
| cj-78 | D |
| cj-79 | D |
| cj-80 | D |
| cj-81 | D |
| cj-82 | D |
| cj-83 | D |
| cj-84 | D |
| cj-85 | D |
| cj-86 | D |
| cj-87 | D |
| cj-88 | D |
| cj-89 | D |
| cj-90 | D |
| cj-91 | D |
| cj-92 | C |
| cj-93 | D |
| cj-94 | D |
| cj-95 | D |
| cj-96 | D |
| cj-97 | D |
| cj-98 | D |
| cj-99 | D |
| cj-100 | D |
| cj-101 | D |
| cj-102 | D |
| cj-103 | D |
| cj-104 | D |
| cj-105 | D |
| cj-106 | D |
| cj-107 | D |
| cj-108 | D |
| cj-109 | D |
| cj-110 | D |
| cj-111 | D |
| cj-112 | D |
| cj-113 | D |
| cj-114 | D |
| cj-115 | D |
| cj-116 | D |
| cj-117 | D |
| cj-118 | D |
| cj-119 | D |
| cj-120 | D |

TABLE 2-continued

| Example | Range |
|---|---|
| cj-121 | D |
| cj-122 | D |
| cj-45 | D |
| cj-41 | D |
| cj-47 | C |
| cj-43 | D |
| cj-44 | D |
| cj-40 | D |
| cj-46 | D |
| cj-42 | D |
| cj-36 | D |
| cj-37 | D |
| cj-38 | D |
| cj-39 | D |
| cj-32 | D |
| cj-33 | D |
| cj-34 | D |
| cj-35 | C |
| cj-136 | D |
| cj-137 | C |
| cj-138 | A |
| cj-139 | C |
| cj-140 | B |
| cj-141 | A |
| cj-142 | A |
| cj-143 | A |
| cj-144 | D |
| cj-145 | C |
| cj-146 | B |
| cj-147 | C |
| cj-148 | C |
| cj-149 | C |
| cj-150 | C |
| cj-151 | C |
| cj-152 | C |
| cj-153 | D |
| cj-154 | D |
| cj-155 | C |
| cj-156 | D |
| cj-126 | D |
| cj-127 | C |
| cj-128 | D |
| cj-129 | D |
| cj-130 | D |
| cj-131 | C |
| cj-132 | B |
| cj-133 | C |
| cj-134 | C |
| cj-135 | C |
| cj-125 | C |
| cj-15c | D |
| cj-20c | D |
| cj-20b | D |
| cj-20a | D |
| cj-17 | D |
| cj-16 | D |
| cj-20d | D |
| cj-20 | D |
| cj-15a | D |
| cj-15 | D |
| cj-15d | D |
| cj-11n | C |
| cj-11o | C |
| cj-11p | D |
| cj-11m | C |
| cj-11h | D |
| cj-11i | D |
| cj-11j | D |
| cj-11k | D |
| cj-11e | A |
| cj-11f | C |
| cj-11g | C |
| cj-11d | D |
| cj-11b | D |
| cj-11 | D |
| cj-11a | D |
| cj-11c | D |
| JG-3 | D |

TABLE 2-continued

| Example | Range |
|---|---|
| JG-4 | C |
| JG-5 | D |
| JG-6 | C |
| JG-7 | D |
| JG-8 | D |
| JG-9 | D |
| JG-10 | C |
| JG-12 | D |
| JG-13 | C |
| JG-14 | D |
| JG-15 | D |
| JG-16 | D |
| JG-17 | D |
| OL-1 | D |
| OL-2 | D |
| OL-3 | C |
| OL-4 | D |
| OL-5 | D |
| OL-6 | D |
| OL-7 | D |
| OL-8 | D |
| OL-9 | D |
| OL-10 | D |
| OL-11 | D |
| OL-12 | D |
| OL-13 | D |
| OL-19 | D |
| OL-20 | C |
| OL-21 | D |
| D73 | D |
| D74 | D |
| D75 | D |
| D76 | D |
| D77 | D |
| J16 | D |
| J17 | D |
| J18 | D |
| J19 | D |
| J20 | D |
| J21 | D |
| J22 | D |
| J23 | D |
| J24 | D |
| J25 | D |
| J26 | D |
| J27 | D |
| J28 | C |
| J29 | D |
| J30 | C |
| J31 | D |
| J37 | D |
| J38 | D |
| J39 | D |
| J40 | D |
| J41 | D |
| J42 | D |
| J42.a | D |
| J45 | D |
| J46 | D |
| J47 | D |
| J48 | D |
| J49 | D |
| J50 | D |
| J51 | C |
| D33 | D |
| D34 | D |
| D35 | D |
| D36 | D |
| D37 | D |
| D38 | D |
| D39 | D |
| D40 | D |
| D41 | D |
| D42 | D |
| D43 | D |
| D44 | D |
| D45 | D |
| D46 | D |

TABLE 2-continued

| Example | Range |
|---|---|
| D47 | D |
| D48 | D |
| D49 | D |
| D50 | D |
| D51 | D |
| D52 | D |
| D53 | D |
| D54 | D |
| D55 | D |
| D56 | D |
| D57 | D |
| D58 | D |
| D59 | D |
| D60 | D |
| D61 | D |
| D62 | D |
| D63 | D |
| D64 | D |
| D65 | D |
| D66 | D |
| D67 | D |
| D68 | D |
| D69 | D |
| D70 | D |
| M1 | >A |
| M2 | C |
| M3 | C |
| M4 | B |
| M5 | A |
| M6 | A |
| M7 | >A |
| M8 | A |
| M9 | B |
| M10 | >A |
| M11 | C |
| M12 | C |
| M13 | B |
| M14 | B |
| M15 | B |
| M16 | A |
| M17 | B |
| M18 | A |
| M19 | >A |
| M21 | C |
| M22 | A |
| M23 | C |
| M24 | C |
| M25 | C |
| M26 | B |
| M27 | C |
| M28 | A |
| M28-2 | B |
| M29 | >A |
| M30 | C |
| M31 | C |
| M32 | B |
| M33 | C |
| M34 | C |
| M35 | C |
| M36 | C |
| M37 | C |
| M38 | C |
| M39 | C |
| M40 | C |
| M41 | C |
| M42 | C |
| M43 | C |
| M44 | B |
| M45 | C |
| M46 | C |
| M47 | C |
| M48 | C |
| M49 | C |
| M50 | C |
| M51 | C |
| M52 | C |
| M53 | C |
| M54 | C |

TABLE 2-continued

| Example | Range |
| --- | --- |
| M55 | C |
| M56 | C |
| M57 | C |
| M58 | C |
| M59 | C |
| M60 | C |
| M61 | C |
| M62 | C |
| M63 | C |
| M64 | C |
| M65 | C |
| M66a | B |
| M66b | B |
| M66x | C |
| M67a | B |
| M67b | B |
| M68 | B |
| M69 | B |
| M70 | C |
| M71 | C |
| M72 | C |
| M73 | B |
| M74 | C |
| M75 | C |
| M76 | C |
| M77 | C |
| M78 | C |
| M79 | C |
| M80 | C |
| M81 | B |
| M82 | C |
| M83 | C |
| M84 | C |
| M85 | C |
| M86 | C |
| M87 | C |
| M88 | C |
| M89 | C |
| M90 | A |
| M91 | C |
| M91x | C |
| M91y | B |
| M92 | A |
| M93 | C |
| M94 | C |
| M95 | C |
| M96 | B |
| M97 | C |
| M98 | C |
| M99 | C |
| M100 | C |
| M101 | B |
| M102 | C |
| M103 | B |
| M104 | B |
| M105 | C |
| M106 | C |
| M107 | C |
| M108 | C |
| M109 | C |
| M110 | C |
| M111 | A |
| M112 | C |
| M113 | C |
| M114 | >A |
| M115 | >A |
| M116 | >A |
| M117 | >A |
| M118 | >A |
| M119 | B |
| M120 | B |
| M121 | B |
| M122 | C |
| M123 | A |
| M124 | C |
| M125 | C |
| M126 | C |
| M127 | C |
| M128 | C |
| M129 | A |
| M130 | C |
| M131 | D |
| M132 | D |
| M133 | D |
| M134 | C |
| M135 | D |
| M136 | C |
| M137 | D |
| M138 | D |
| M139 | D |
| M140 | D |
| M140a-ii | C |
| M140a-i | C |
| M141 | C |
| M142 | C |
| M143 | C |
| M144 | D |
| M145 | D |
| M146 | D |
| M147 | D |
| M148 | D |
| M149 | C |
| M150 | D |
| M151 | D |
| M152 | |
| M153 | D |
| M154 | D |
| M155 | C |
| M156 | C |
| M157 | D |
| M158 | C |
| M159 | D |
| M160 | C |
| M161 | C |
| M162 | C |
| E5 | D |
| E5a | D |
| E5b | D |
| E5c | D |
| E5d | D |
| E5e | D |
| E5f | D |
| E5g | D |
| E5h | D |
| E5i | D |
| E5j | D |
| E5k | D |
| E5l | D |
| E5m | D |
| J14 | D |
| J14a | D |
| J14a.1 | D |
| J14b | D |
| J14b.1 | D |
| J14c | D |
| J14c.1 | D |
| J14c.2 | D |
| J14e | D |
| J14e.1 | D |
| J14f | D |
| J14f.1 | C |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The compounds of the present disclosure may inhibit HCV by mechanisms in addition to or other than NS5A inhibition.

In one embodiment the compounds of the present disclosure inhibit HCV replicon and in another embodiment the compounds of the present disclosure inhibit NS5A. Compounds of the present disclosure may inhibit multiple genotypes of HCV.

What is claimed is:

1. A compound selected from methyl ((1S)-2-((1R,3S,5R)-3-(4-(4'-(2-((1R,3S,5R)-2-(N-(methoxycarbonyl)-L-alanyl)-2-azabicyclo[3.1.0]hex-3-yl)-1H-imidazol-4-yl)-4-biphenylyl)-1H-imidazol-2-yl)-2-azabicyclo[3.1.0]hex-2-yl)-1-methyl-2-oxoethyl)carbamate;

dimethyl (4,4'-biphenyldiylbis(1H-imidazole-4,2-diyl(1R,3S,5R)-2-azabicyclo[3.1.0]hexane-3,2-diyl((2S)-1-oxo-1,2-butanediyl)))biscarbamate;

methyl (2-((1R,3S,5R)-3-(4-(4'-(2-((1R,3S,5R)-2-(((methoxycarbonyl)amino)acetyl)-2-azabicyclo[3.1.0]hex-3-yl)-1H-imidazol-4-yl)-4-biphenylyl)-1H-imidazol-2-yl)-2-azabicyclo[3.1.0]hex-2-yl)-2-oxoethyl)carbamate;

dimethyl (4,4'-biphenyldiylbis(1H-imidazole-4,2-diyl(1R,3S,5R)-2-azabicyclo[3.1.0]hexane-3,2-diyl((1S)-1-cyclopropyl-2-oxo-2,1-ethanediyl)))biscarbamate;

dimethyl (4,4'-biphenyldiylbis(1H-imidazole-4,2-diyl(1R,3S,5R)-2-azabicyclo[3.1.0]hexane-3,2-diyl((1R)-2-oxo-1-phenyl-2,1-ethanediyl)))biscarbamate;

methyl ((1S)-1-(((1R,3S,5R)-3-(4-(4'-(2-((1R,3S,5R)-2-acetyl-2-azabicyclo[3.1.0]hex-3-yl)-1H-imidazol-4-yl)-4-biphenylyl)-1H-imidazol-2-yl)-2-azabicyclo[3.1.0]hex-2-yl)carbonyl)-2-methylpropyl)carbamate;

methyl ((1S)-2-methyl-1-(((1R,3S,5R)-3-(4-(4'-(2-((1R,3S,5R)-2-(5-((3aS,4S,6aR)-2-oxohexahydro-1H-thieno[3,4-d]imidazol-4-yl)pentanoyl)-2-azabicyclo[3.1.0]hex-3-yl)-1H-imidazol-4-yl)-4-biphenylyl)-1H-imidazol-2-yl)-2-azabicyclo[3.1.0]hex-2-yl)carbonyl)-2-methylpropyl)carbamate;

tert-butyl ((1S)-1-(((1R,3S,5R)-3-(4-(4'-(2-((1R,3S,5R)-2-((2S)-2-((tert-butoxycarbonyl)amino)-3-methylbutanoyl)-2-azabicyclo[3.1.0]hex-3-yl)-1H-imidazol-4-yl)-4-biphenylyl)-1H-imidazol-2-yl)-2-azabicyclo[3.1.0]hex-2-yl)carbonyl)-2-methylpropyl)carbamate;

N-((1S)-1-(((1R,3S,5R)-3-(4-(4'-(2-((1R,3S,5R)-2-((2S)-2-((cyclopropylcarbonyl)amino)-3-methylbutanoyl)-2-azabicyclo[3.1.0]hex-3-yl)-1H-imidazol-4-yl)-4-biphenylyl)-1H-imidazol-2-yl)-2-azabicyclo[3.1.0]hex-2-yl)carbonyl)-2-methylpropyl) cyclopropanecarbamate;

tert-butyl ((1R)-1-(((1R,3S,5R)-3-(4-(4'-(2-((1R,3S,5R)-2-((2R)-2-((tert-butoxycarbonyl)amino)-3-methylbutanoyl)-2-azabicyclo[3.1.0]hex-3-yl)-1H-imidazol-4-yl)-4-biphenylyl)-1H-imidazol-2-yl)-2-azabicyclo[3.1.0]hex-2-yl)carbonyl)-2-methylpropyl)carbamate;

and

N,N'-(4,4'-biphenyldiylbis(1H-imidazole-4,2-diyl(1R,3S,5R)-2-azabicyclo[3.1.0]hexane-3,2-diyl((2S)-3-methyl-1-oxo-1,2-butanediyl)))di(2-pyrimidinamine);

or a pharmaceutically acceptable salt thereof.

2. A composition comprising a compound of claim 1, or a pharmaceutically acceptable salt thereof, and a pharmaceutically acceptable carrier.

3. The composition of claim 2 further comprising one or two additional compounds having anti-HCV activity.

4. The composition of claim 3 wherein at least one of the additional compounds is an interferon or a ribavirin.

5. The composition of claim 4 wherein the interferon is selected from interferon alpha 2B, pegylated interferon alpha, consensus interferon, interferon alpha 2A, and lymphoblastiod interferon tau.

6. The composition of claim 3 wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

7. The composition of claim 3 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

8. A method of relieving or causing regression of an HCV infection in a patient, comprising administering to the patient a therapeutically effective amount of a compound of claim 1, or a pharmaceutically acceptable salt thereof.

9. The method of claim 8 further comprising administering one or two additional compounds having anti-HCV activity prior to, after or simultaneously with the compound of claim 2, or a pharmaceutically acceptable salt thereof.

10. The method of claim 9 wherein at least one of the additional compounds is an interferon or a ribavirin.

11. The method of claim 10 wherein the interferon is selected from interferon alpha 2B, pegylated interferon alpha, consensus interferon, interferon alpha 2A, and lymphoblastiod interferon tau.

12. The method of claim 9 wherein at least one of the additional compounds is selected from interleukin 2, interleukin 6, interleukin 12, a compound that enhances the development of a type 1 helper T cell response, interfering RNA, anti-sense RNA, Imiqimod, ribavirin, an inosine 5'-monophosphate dehydrogenase inhibitor, amantadine, and rimantadine.

13. The method of claim 9 wherein at least one of the additional compounds is effective to inhibit the function of a target selected from HCV metalloprotease, HCV serine protease, HCV polymerase, HCV helicase, HCV NS4B protein, HCV entry, HCV assembly, HCV egress, HCV NS5A protein, and IMPDH for the treatment of an HCV infection.

* * * * *

UNITED STATES PATENT AND TRADEMARK OFFICE
CERTIFICATE OF CORRECTION

PATENT NO. : 8,303,944 B2
APPLICATION NO. : 12/030232
DATED : November 6, 2012
INVENTOR(S) : Carol Bachand et al.

It is certified that error appears in the above-identified patent and that said Letters Patent is hereby corrected as shown below:

In the Specification:

Column 6, line 20, change "Imiqimod," to -- Imiquimod, --.

Column 6, line 20, change "5'-monophospate" to -- 5'-monophosphate --.

Column 6, line 52, change "Imiqimod," to -- Imiquimod, --.

Column 6, line 53, change "5'-monophospate" to -- 5'-monophosphate --.

In the Claims:

Claim 5:

Column 944, lines 14 and 15, change "lymphoblastiod" to -- lymphoblastoid --.

Claim 6:

Column 944, line 20, change "Imiqimod," to -- Imiquimod, --.

Column 944, lines 20 and 21, change "5'-monophospate" to -- 5'-monophosphate --.

Claim 9:

Column 944, lines 34 and 35, change "claim 2," to -- claim 1, --.

Claim 11:

Column 944, lines 40 and 41, change "lymphoblastiod" to -- lymphoblastoid --.

Claim 12:

Column 944, line 46, change "Imiqimod," to -- Imiquimod, --.

Column 944, lines 46 and 47, change "5'-monophospate" to -- 5'-monophosphate --.

Signed and Sealed this
Twenty-second Day of April, 2014

Michelle K. Lee
*Deputy Director of the United States Patent and Trademark Office*